(12) United States Patent
Borchardt et al.

(10) Patent No.: US 11,510,992 B1
(45) Date of Patent: *Nov. 29, 2022

(54) COMPOSITIONS AND METHODS FOR THE TREATMENT OF VIRAL INFECTIONS

(71) Applicant: Cidara Therapeutics, Inc., San Diego, CA (US)

(72) Inventors: Allen Borchardt, San Diego, CA (US); Thomas P. Brady, San Diego, CA (US); Zhi-Yong Chen, La Jolla, CA (US); Thanh Lam, San Diego, CA (US); Leslie W. Tari, Solana Beach, CA (US)

(73) Assignee: Cidara Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/236,745

(22) Filed: Apr. 21, 2021

Related U.S. Application Data

(63) Continuation of application No. 17/194,093, filed on Mar. 5, 2021, now abandoned, which is a continuation of application No. PCT/US2020/049772, filed on Sep. 8, 2020.

(60) Provisional application No. 63/062,377, filed on Aug. 6, 2020, provisional application No. 63/032,488, filed on May 29, 2020, provisional application No. 62/988,304, filed on Mar. 11, 2020, provisional application No. 62/984,705, filed on Mar. 3, 2020, provisional application No. 62/970,491, filed on Feb. 5, 2020, provisional application No. 62/966,500, filed on Jan. 27, 2020, provisional application No. 62/959,857, filed on Jan. 10, 2020, provisional application No. 62/948,143, filed on Dec. 13, 2019, provisional application No. 62/941,405, filed on Nov. 27, 2019, provisional application No. 62/897,036, filed on Sep. 6, 2019.

(51) Int. Cl.
*A61K 47/68* (2017.01)
*A61P 31/16* (2006.01)
*C07D 309/28* (2006.01)

(52) U.S. Cl.
CPC .......... *A61K 47/6803* (2017.08); *A61P 31/16* (2018.01); *C07D 309/28* (2013.01)

(58) Field of Classification Search
CPC .... A61K 47/6803; C07D 309/28; A61P 31/16
USPC .......................................... 549/415; 424/809
See application file for complete search history.

(56) References Cited

U.S. PATENT DOCUMENTS

| | | | |
|---|---|---|---|
| 6,548,476 B1 | 4/2003 | Wu et al. | |
| 6,680,054 B1 | 1/2004 | Reece et al. | |
| 7,214,707 B2 | 5/2007 | Demaine et al. | |
| 2011/0243966 A1 | 10/2011 | Farrington et al. | |
| 2017/0102387 A1 | 4/2017 | Wong et al. | |
| 2017/0320926 A1 | 11/2017 | Scheer et al. | |
| 2019/0233525 A1 | 8/2019 | Igawa et al. | |

FOREIGN PATENT DOCUMENTS

| | | |
|---|---|---|
| WO | WO-2010/093706 A2 | 8/2010 |
| WO | WO-2017/046625 A1 | 3/2017 |
| WO | WO-2018/128826 A1 | 7/2018 |
| WO | WO-2020/051498 A1 | 3/2020 |

OTHER PUBLICATIONS

Macdonald, Simon J. F. et al., "Dimeric Zanamivir Conjugates with Various Linking Groups Are Potent, Long-Lasting Inhibitors of Influenza Neuraminidase Including H5N1 Avian Influenza", J. Med. Chem. 2005, 48, pp. 2964-2971. (Year: 2005).*
Shtyrya et al., "Influenza Virus Neuraminidase: Structure and Function," Acta Naturae. 1 (2): 26-32 (2009).
International Search Report and Written Opinion for International Application No. PCT/US2020/49772, dated Feb. 4, 2021 (13 pages).
Devanaboyina et al., "Engineered clearing agents for the selective depletion of antigen-specific antibodies," Nat Commun. 8:15314 (2017) (6 pages).
International Search Report and Written Opinion for International Application No. PCT/US2020/47490, dated Mar. 18, 2021 (18 pages).
U.S. Appl. No. 17/193,923, Balkovec et al.
U.S. Appl. No. 17/194,093, Balkovec et al.
U.S. Appl. No. 17/236,722, Balkovec et al.
Ali et al., "A Phase 2a Study to Evaluate the Safety of MEDI8852 in Outpatient Adults with Acute, Uncomplicated Influenza A," Open Forum Infectious Diseases. 4:S519, 1656 1(2017) (1 page Abstract).
Borrok et al., "pH-dependent Binding Engineering Reveals an FcRn Affinity Threshold That Governs IgG Recycling," J Biol Chem. 290(7):4282-4290 (2015) (10 pages).
Greengard et al., "The Anti-Influenza Virus Agent 4-GU-DANA (Zanamivir) Inhibits Cell Fusion Mediated by Human Parainfluenza Virus and Influenza Virus HA," J Virol. 74(23)11108-11114 (2000) (7 pages).
Guillon et al., "Structure-guided discovery of potent and dual-acting human parainfluenza virus haemagglutinin-neuraminidase inhibitors," Nat Commun. 5:5268-5279 (2014) (11 pages).
Hadhazi et al., "A Sulfonozanamivir Analogue Has Potent Anti-influenza Virus Activity," ChemMedChem. 13:785-789 (2018).

(Continued)

*Primary Examiner* — Joseph R Kosack
*Assistant Examiner* — Sagar Patel
(74) *Attorney, Agent, or Firm* — Clark & Elbing LLP

(57) ABSTRACT

Compositions and methods for the treatment of viral infections include conjugates containing inhibitors of viral neuraminidase (e.g., zanamivir, peramivir, or analogs thereof) linked to an Fc monomer, an Fc domain, and Fc-binding peptide, an albumin protein, or albumin-binding peptide. In particular, conjugates can be used in the treatment of viral infections (e.g., influenza viral infections).

35 Claims, 149 Drawing Sheets

Specification includes a Sequence Listing.

(56) References Cited

OTHER PUBLICATIONS

Hanessian et al., "Total Synthesis of A-315675: A Potent Inhibitor of Influenza Neuraminidase," J Am Chem Soc. 124(17):4716-4721 (2002).
Hayakawa et al., "Chemically Programmed Antibody is a Long-lasting and Potent Inhibitor of Influenza Neuraminidase," Chembiochem. 13(15):2191-2195 (2013).
International Search Report and Written Opinion for International Application No. PCT/US2019/050018, dated Feb. 19, 2020 (24 pages).
Kallewaard et al., "Structure and Function Analysis of an Antibody Recognizing All Influenza A Subtypes," Cell. 166(3):596-608 (2016) (34 Pages).
Kati et al., "In Vitro Characterization of A-315675, a Highly Potent Inhibitor of A and B Strain Influenza Virus Neuraminidases and Influenza Virus Replication," Antimicrob Agents Chemother. 46(4):1014-1021 (2002).
Mallory et al., "A phase 1 study to evaluate the safety and pharmacokinetics of MEDI8852, an anti-influenza A monoclonal antibody, in healthy adult volunteers," Biologicals. 50:81-86 (2017) (6 pages).
McKimm-Breschkin et al., "Structural and Functional Analysis of Anti-Influenza Activity of 4?,7?, 8- and 9?Deoxygenated 2,3-Difluoro?N?acetylneuraminic Acid Derivatives," J Med Chem. 61(5):1921-1933 (2018) (13 pages).
Meng et al., "Multivalent neuraminidase hydrolysis resistant triazole-sialoside protein conjugates as influenza-adsorbents," Chinese Chemical Letters. 29: 76-80 (2018) (5 pages).
Moscona., "Entry of parainfluenza virus into cells as a target for interrupting childhood respiratory disease," J Clin Invest. 115(7):1688-1698 (2005) (11 pages).
Paules et al., "The Hemagglutinin A Stem Antibody MEDI8852 Prevents and Controls Disease and Limits Transmission of Pandemic Influenza Viruses," J Infect Dis. 216(3):356-65 (2017) (10 pages).
Rota et al., "Potent Inhibitors against Newcastle Disease Virus Hemagglutinin-Neuraminidase," ChemMedChem. 13:236-240 (2018) (5 pages).
Wang et al., "Peramivir conjugates as orally available agents against influenza H275Y mutant," Eur J Med Chem. 145:224-34 (2018).
Weight et al., "Zanamivir conjugated to poly-L-glutamine is much more active against influenza viruses in mice and ferrets than the drug itself," Pharm Res. 31(2):466-474 (2014).
Zhao et al., "Multivalent zanamivir-bovine serum albumin conjugate as a potent influenza neuraminidase inhibitor," Journal of Carbohydrate Chemistry. 36:4-6, 235-246 (2017).
Tarbet et al., "A Zanamivir Dimer with Prophylactic and Enhanced Therapeutic Activity against Influenza viruses," J Antimicrob Chemother. 69(8): 2164-74 (2014).
Macdonald et al., "Dimeric Zanamivir Conjugates with Various Linking Groups are Potent, Long-Lasting Inhibitors of Influenza Neuraminidase Including H5N1 Avian Influenza," J Med Chem. 48(8):2964-2971 (2005).
Cheng et al., "From Neuraminidase Inhibihors to Conjugates: a Step Towards Better Anti-Influenza Drugs?" Future Med Chem. 6(7): 757-774 (2014).
Laborda et al., "Influenza Neuraminidase Inhibitors: Synthetic Approaches, Derivatives and Biological Activity," Molecules. 21(11): 1513 (2016).
Lin et al., "Synthesis of Acylguanidine Zanamivir Derivatives as Neuraminidase Inhibitors are the Evaluation of their Bio-Activities," Org Biomol Chem. 11(24): 3943-8 (2013).
Fu et al., "Structure-Based Tetravalent Zanamivir with Potent Inhibitory Activity against Drug-Resistant Influenza Viruses," J Med Chem. 59(13): 6303-6312 (2016).
Macdonald et al., "Potent and Long-Acting Dimeric Inhibitors of Influenza Virus Neuraminidase are Effective at a Once-Weekly Dosing Regimen," Antimicrob Agents Chemother. 48(12): 4542-9 (2004).
Almaguer et al., "CD377, a Novel Antiviral Fc-Conjugate, Demonstrates a Lower Resistance Potential than Baloxavir and Oseltamivir against Pandemic Influenza A (H1N1)," Abstract Book—30th ECCMID Apr. 18-21, 2020. p. 2766. Abstract 5707 (2020) (1 page).
Borchardt et al., "CB-012—A Novel Antiviral-Fc Conjugate for Treatment and Prevention of Influenza Virus," ASM Microbe, Jun. 20-24, San Francisco, California. Poster HMB-385 (2019) (1 page).
Döhrmann et al., "Fc-Mediated Effector Function Contributes to Potency of Novel Cloudbreak Antiviral Fc-Conjugate (AVC) CB-012," Options X, Aug. 28-Sep. 1, Singapore (2019) (1 page).
Döhrmann et al., "CD377, a Novel Antiviral Fc-Conjugate, Demonstrates Potent Broad-Spectrum Activity in Multiple in vitro Assays Against Influenza A and B," Abstract Book—30th ECCMID Apr. 18-21, 2020. p. 4170. Abstract 8832 (2020) (1 page).
Döhrmann et al., "Fc-Mediated Fcgamma Receptor Engagement of CD377, a Novel Antiviral Fc-Conjugate, Translates Into Potent Antibody-Dependent Cellular Phagocytosis and Antibody-Dependent Cellular Cytotoxicity Activity," Abstract Book—30th ECCMID Apr. 18-21, 2020. p. 4169. Abstract 8820 (2020) (1 page).
Döhrmann et al., "CD377, A Novel Antiviral Fc-Conjugate, Demonstrates Superior Reduction of Viral Burden and Cytokine Levels Compared to Oseltamivir in a Lethal Mouse Model of Influenza A (H1N1) Infection," Abstract Book—30th ECCMID Apr. 18-21, 2020. p. 4172. Abstract 8839. (2020) (1 page).
Gubareva et al., "Antivirals Targeting the Neuraminidase," Cold Spring Harb Perspect Med. 12(1):a038455 (2022) (21 pages).
Levin et al., "Efficacy of CB-012, A Novel Antiviral Fc-Conjugate, in Lethal Mouse Models of Oseltamivir-Sensitive and -Resistant Influenza A H1N1 and H3N2 Isolates," Options X, Aug. 28-Sep. 1, Singapore (2019) (1 page).
Levin et al., "Efficacy of CD377, A Novel Antiviral Fc-Conjugate Against Seasonal Influenza in Lethal Mouse Models," Abstract Book—30th ECCMID Apr. 18-21, 2020. p. 2804. Abstract 5793 (2020) (1 page).
Levin et al., "Efficacy of CD377, a Novel Antiviral Fc-Conjugate, Against Influenza A (H1N1) in a Lethal Mouse Model of Severe Combined Immunodeficiency (SCID)," Abstract Book—30th ECCMID Apr. 18-21, 2020. p. 2871. Abstract 6009 (2020) (1 page).
Levin et al., "Efficacy of CB-012, A Novel Antiviral Fc-Conjugate, against Influenza A (H1N1) In a Lethal Mouse Model of Severe Combined Immunodeficiency (SCID)," Options X, Aug. 28-Sep. 1, Singapore (2019) (1 page).
Levin et al., "Therapeutic Efficacy of CB-012, a Novel Cloudbreak Antiviral Fc-Conjugate (AVC) in Lethal Mouse Models of Influenza A (H1N1) and Influenza B (Victoria)," IDWeek, Oct. 2-6, Washington, D.C. Poster 689 (2019) (1 page).
Locke et al., "Novel Antiviral Fc-Conjugate CB-012 Demonstrates Potent Activity in Cytopathic Effect (CPE) and Viral Growth Inhibition Assays against Influenza A and B Strains," Options X, Aug. 28-Sep. 1, Singapore (2019) (1 page).
Ong et al., "Preclinical efficacy, pharmacokinetics and safety of CD377, a novel antiviral Fc-conjugate against influenza," Abstract Book—30th ECCMID Apr. 18-21, 2020. p. 2489. Abstract 5126 (2020) (1 page).
Ong et al., "Preclinical Efficacy, Pharmacokinetics, and Safety of CB-012, A Novel Antiviral Fc-Conjugate against Influenza," Options X, Aug. 28-Sep. 1, Singapore (2019) (1 page).
Tari, "Cloudbreak Influenza," EECMID 2019, Apr. 13-16, Amsterdam, Netherlands (2019) (22 pages).

* cited by examiner (SEQ ID NO: 1: murine Fc-IgG2a with IL2 signal sequence at the N-terminus)

(SEQ ID NO: 3: human Fc-IgG1 with IL2 signal sequence at the N-terminus)

(SEQ ID NO: 5: murine Fc-IgG2a with IL2 signal sequence at the N-terminus and hexa-histidine peptide at the C-terminus)

(SEQ ID NO: 7: human Fc-IgG1 with IL2 signal sequence at the N-terminus and hexa-histidine peptide at the C-terminus)

(SEQ ID NO: 9: human Fc-IgG1 with IL2 signal sequence at the N-terminus, two additional cysteines in the hinge region, and hexa-histidine peptide at the C-terminus)

(SEQ ID NO: 12: murine Fc-IgG2a with IL2 signal sequence at the N-terminus, Asn to Ala substitution, and hexa-histidine peptide at the C-terminus)

(SEQ ID NO: 14: human Fc-IgG1 with IL2 signal sequence at the N-terminus, Asn to Ala substitution, and hexa-histidine peptide at the C-terminus)

Conjugate 1

Conjugate 2

Conjugate 3

Conjugate 4

Conjugate 5

Conjugate 6

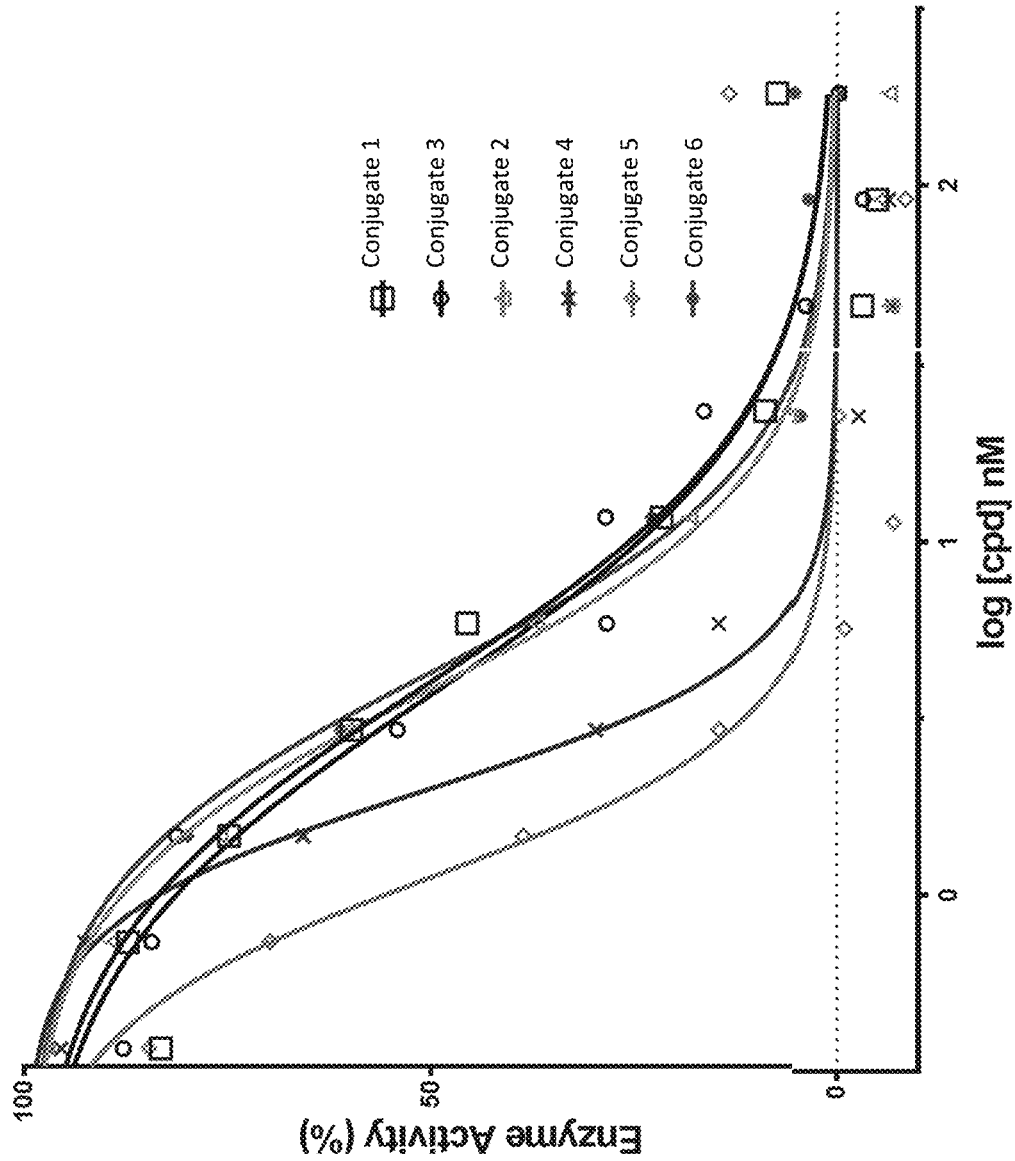

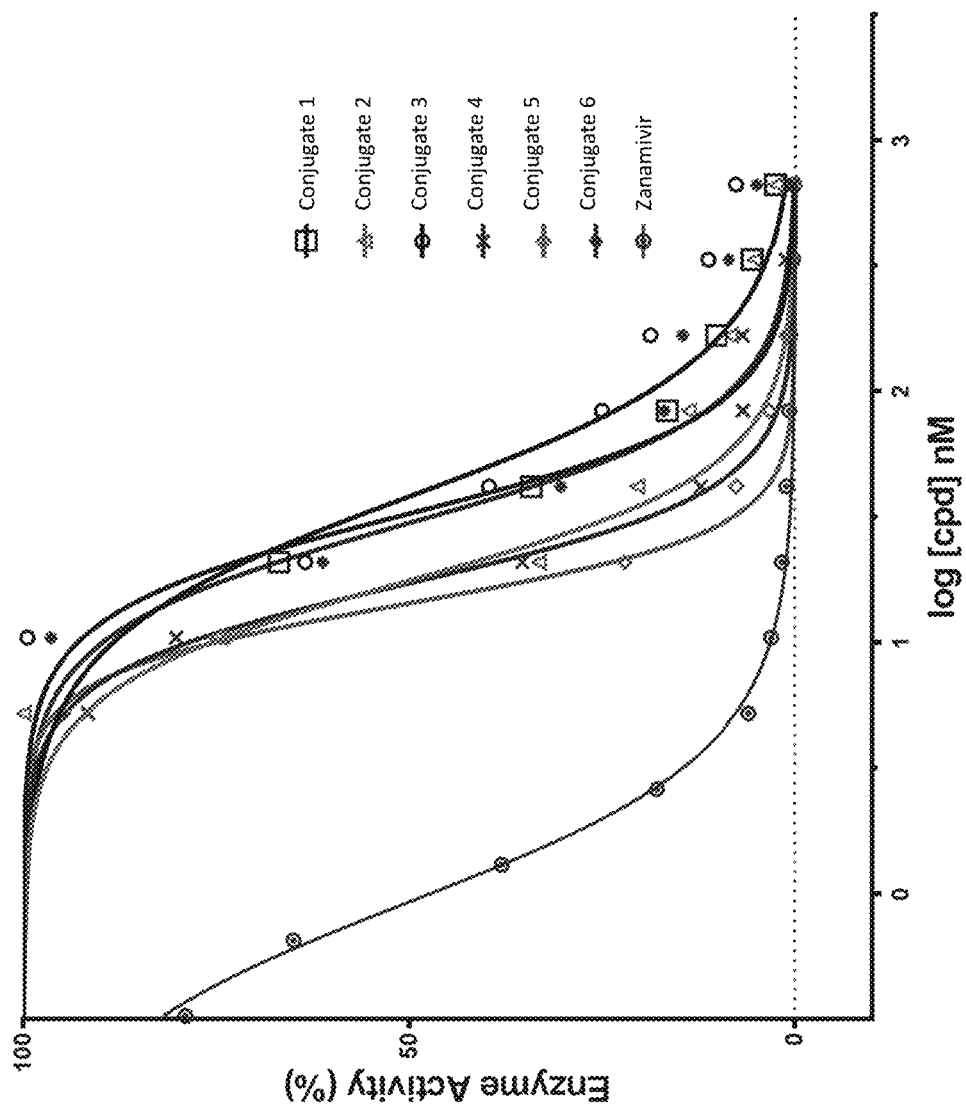

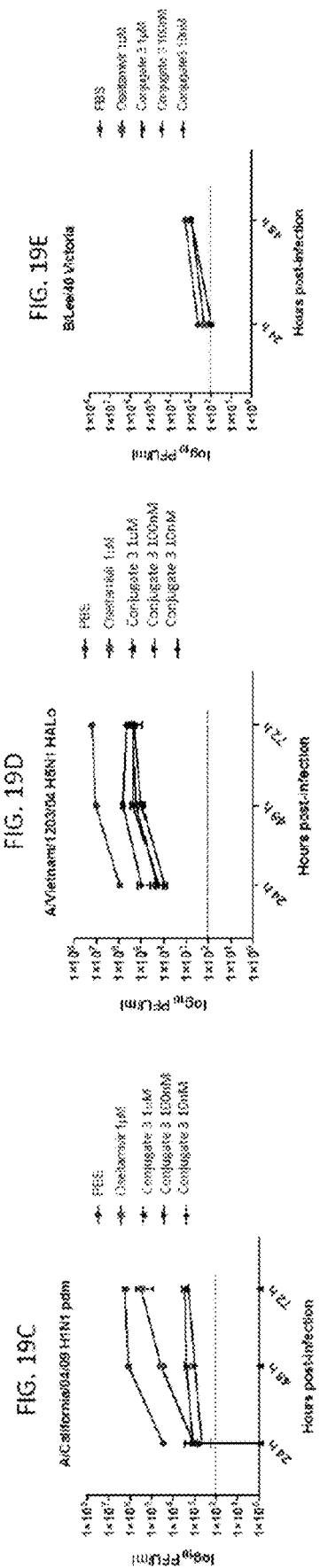

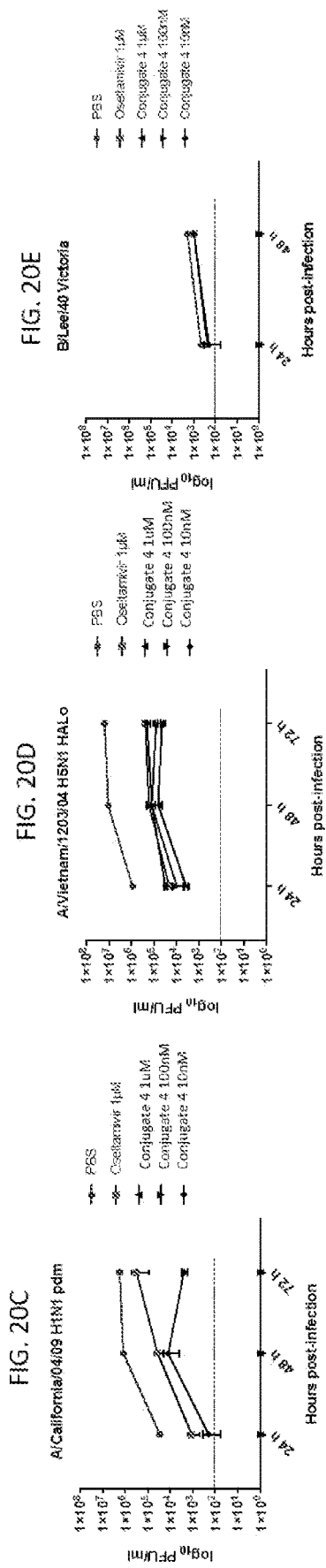

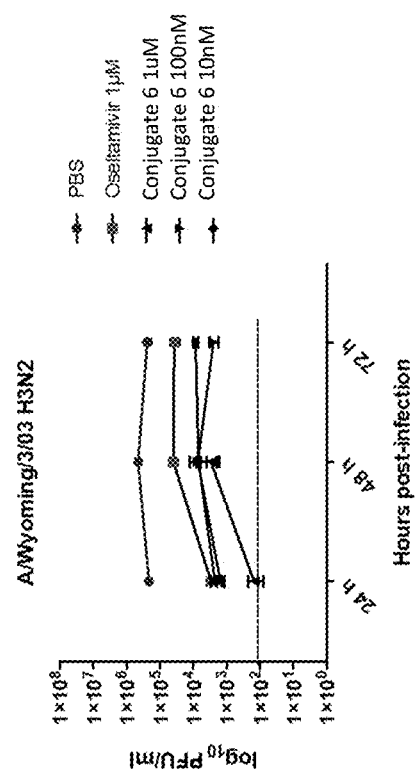
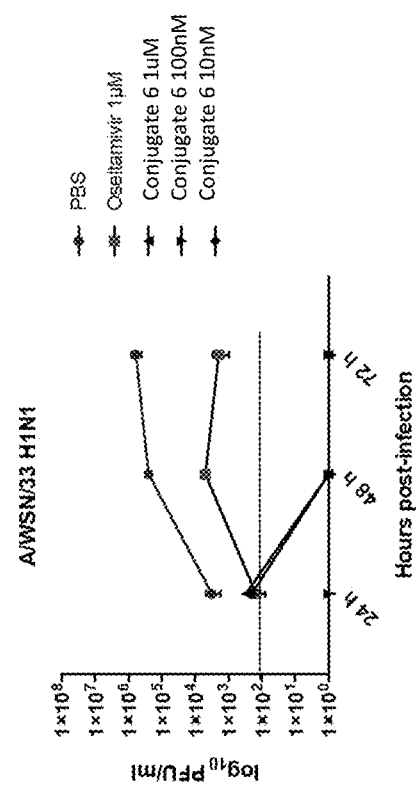

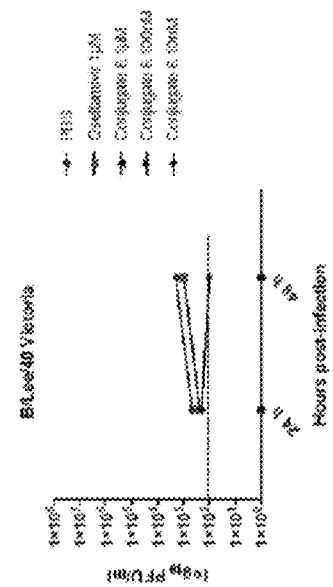
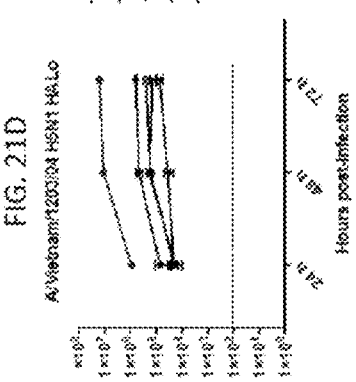
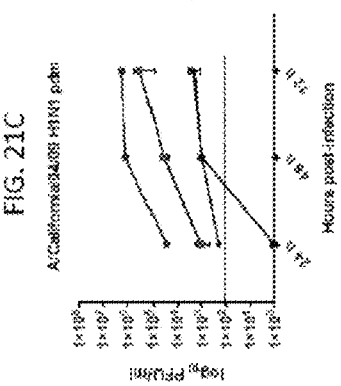
FIG. 21C
FIG. 21D
FIG. 21E

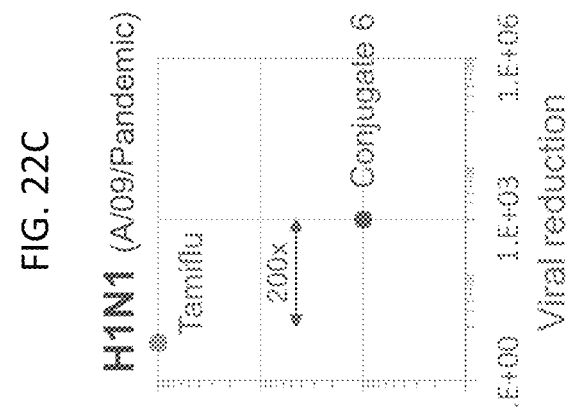
FIG. 22A  FIG. 22B  FIG. 22C
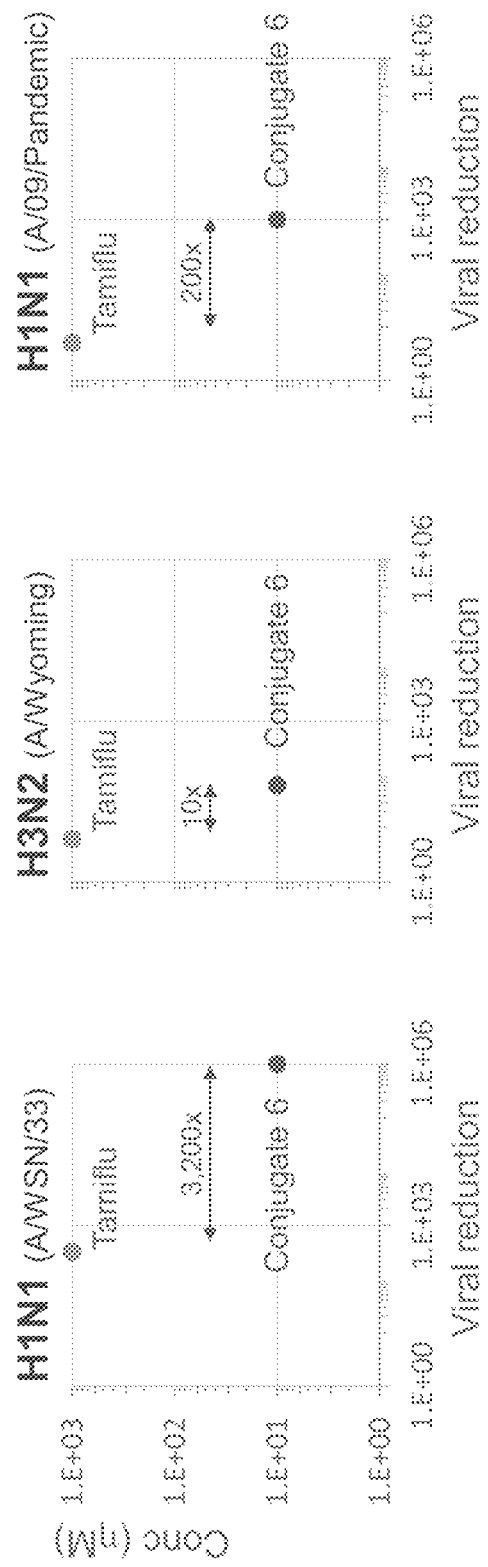

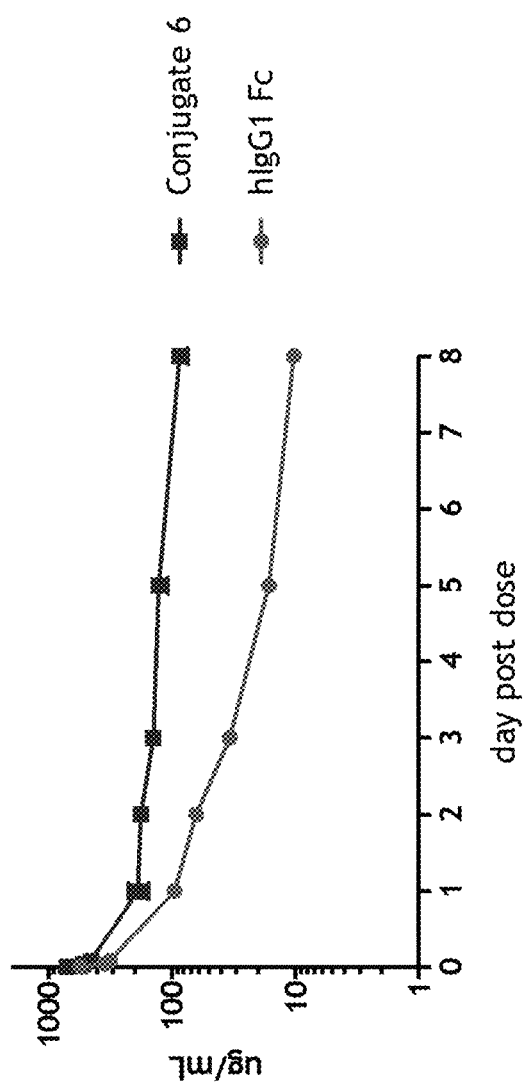

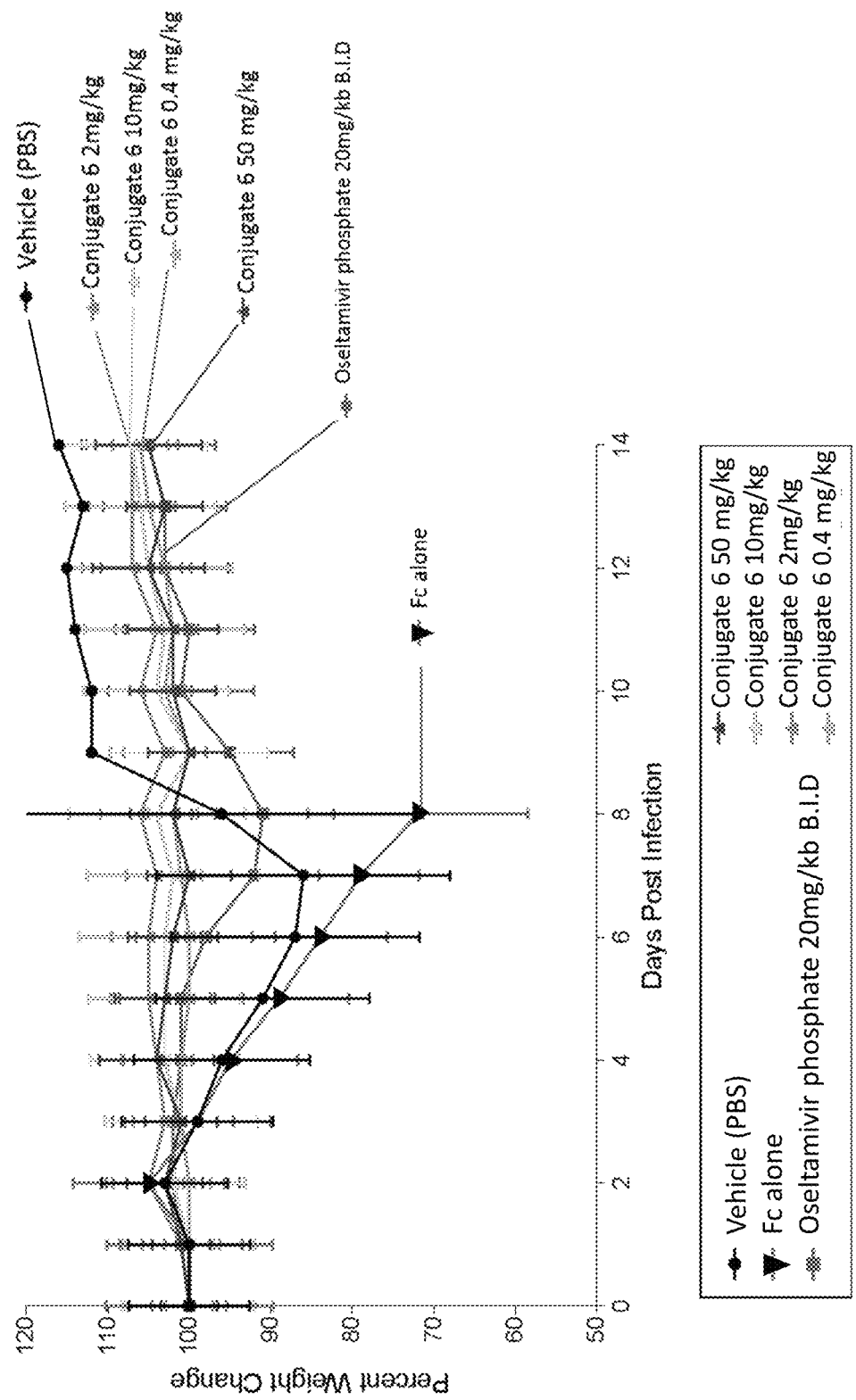

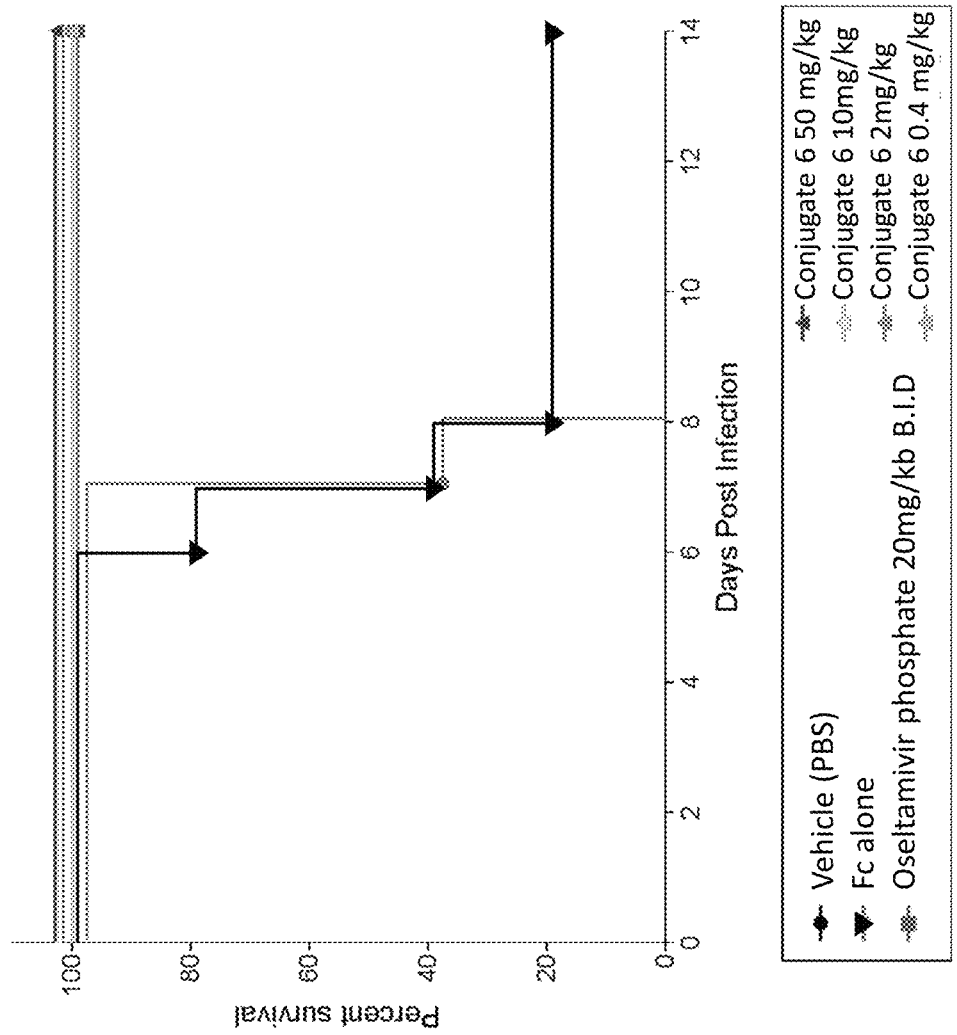

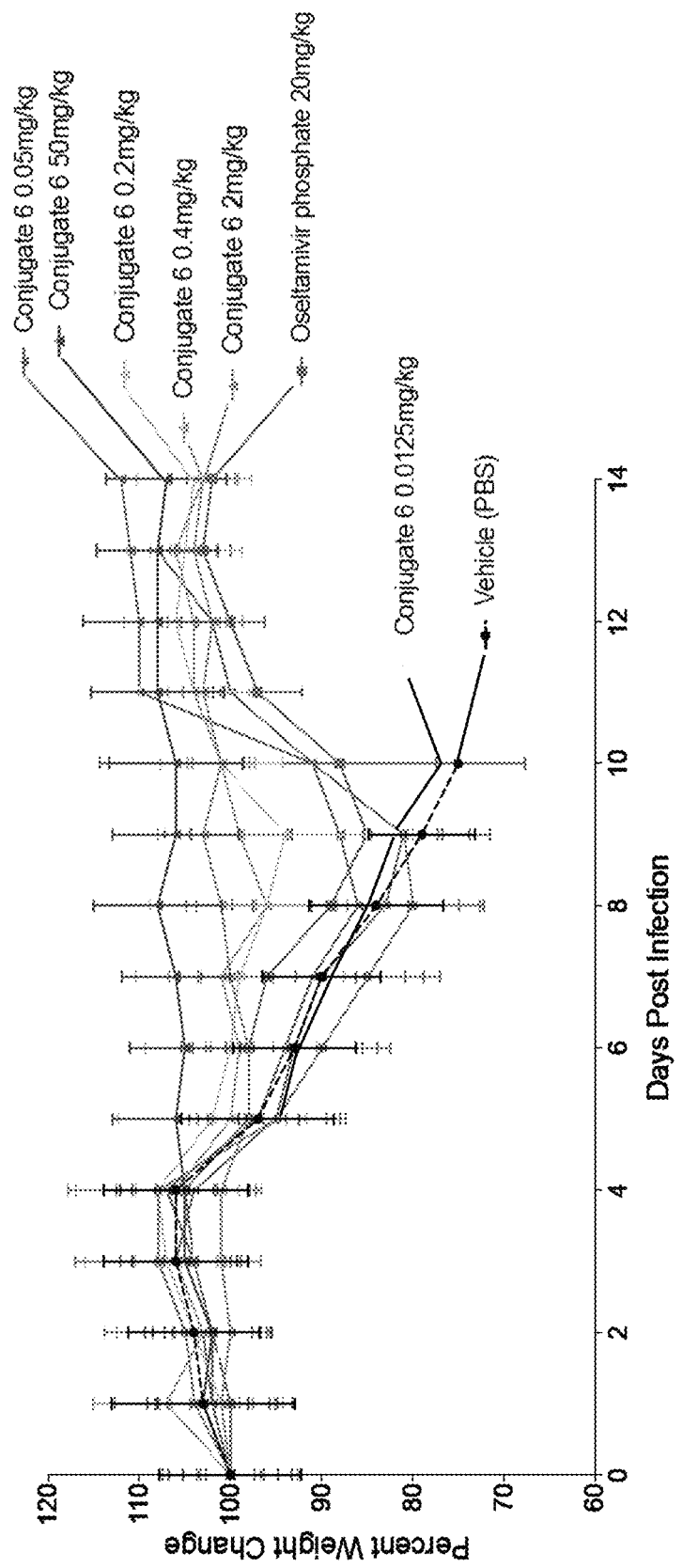

Mouse Survival

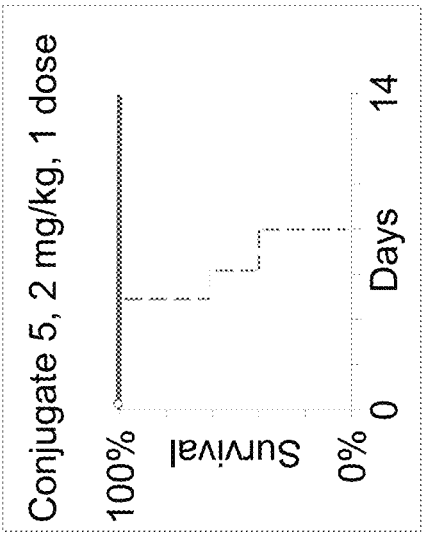
FIG. 34A
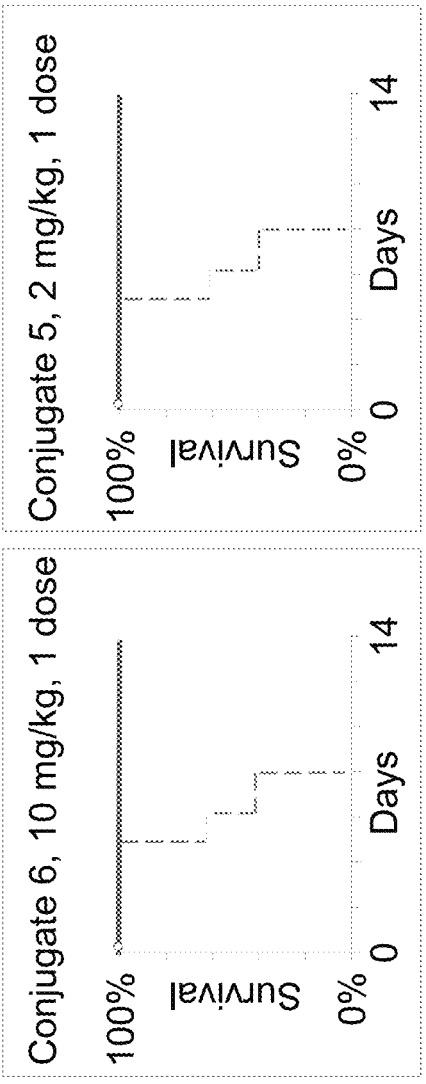
FIG. 34B
FIG. 34C
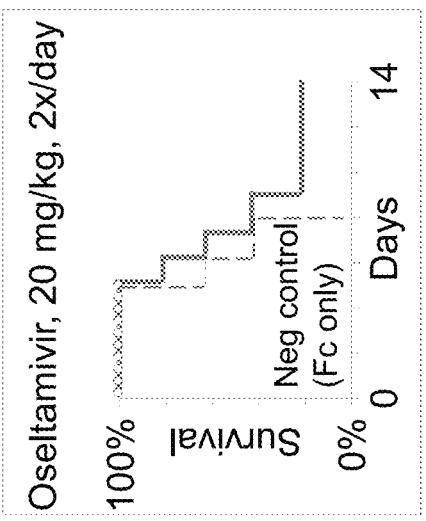
FIG. 34D
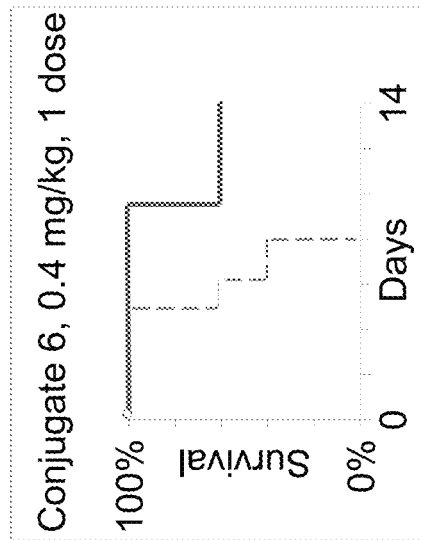

Mouse Weight

Conjugate 6 IV, SC, and IM administration

Conjugate 8

Conjugate 6

Conjugate 6 in vitro mouse plasma

Conjugate 6 in vitro human plasma

Conjugate 6 and Conjugate 12 *in vivo* efficacy

Conjugate 6 and Conjugate 12 *in vivo* efficacy

Conjugate 6 and Conjugate 12 in vitro Fcγ receptor IIIA binding

Conjugate 6 and Conjugate 12 in vitro Fcγ receptor IIIA binding

Toxicokinetics on days 1 and 8

FIG. 54 Conjugate 12

Conjugates 13a-13g

Conjugate 6 *in vivo* efficacy in immune compromised mice

Conjugate 6 *in vivo* efficacy in immune compromised mice

Conjugate 6 dose-dependent viral clearance in lungs

Conjugate 6 dose-dependent reduction in inflammatory cytokines in lungs

Pharmacokinetics of Conjugate 6 in BALB/c SCID mice and CD-1 mice
5 mg/kg IV, single dose Conjugate 33
SEQ ID NO: 73

ADCP

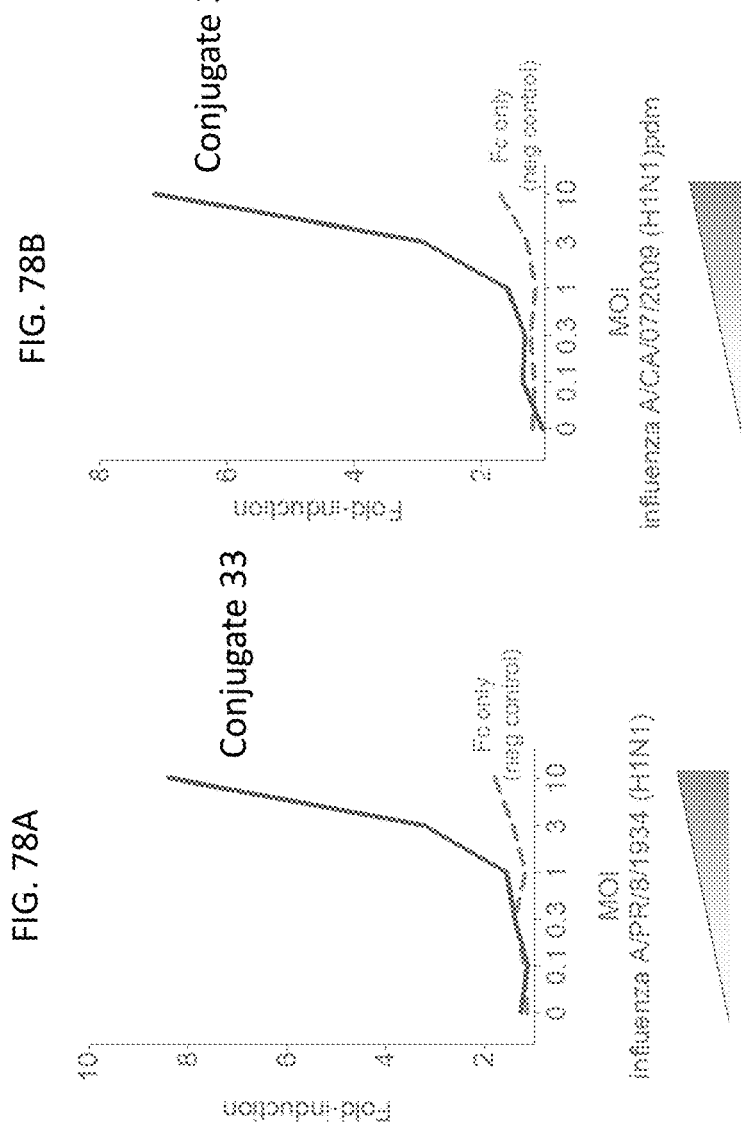

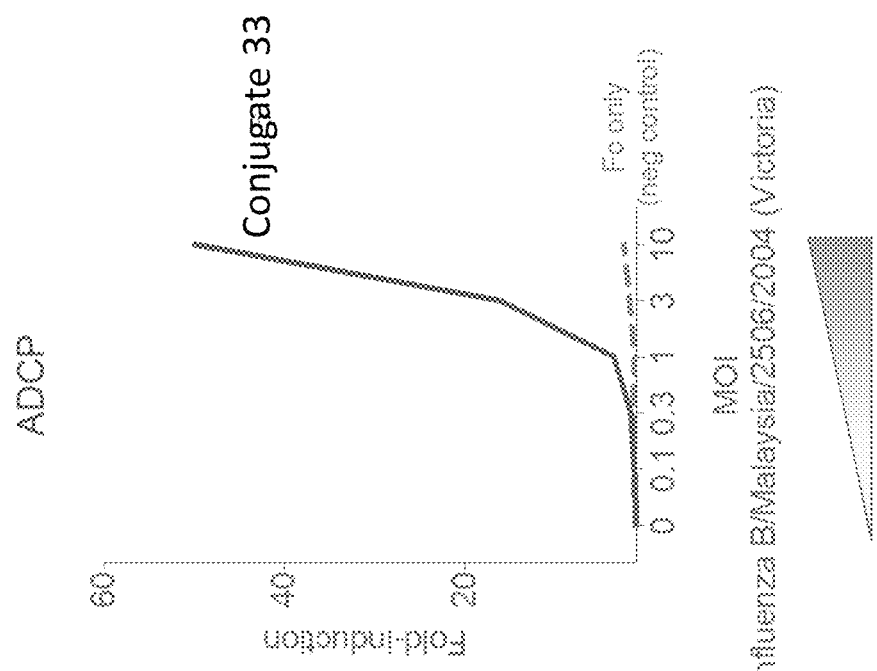

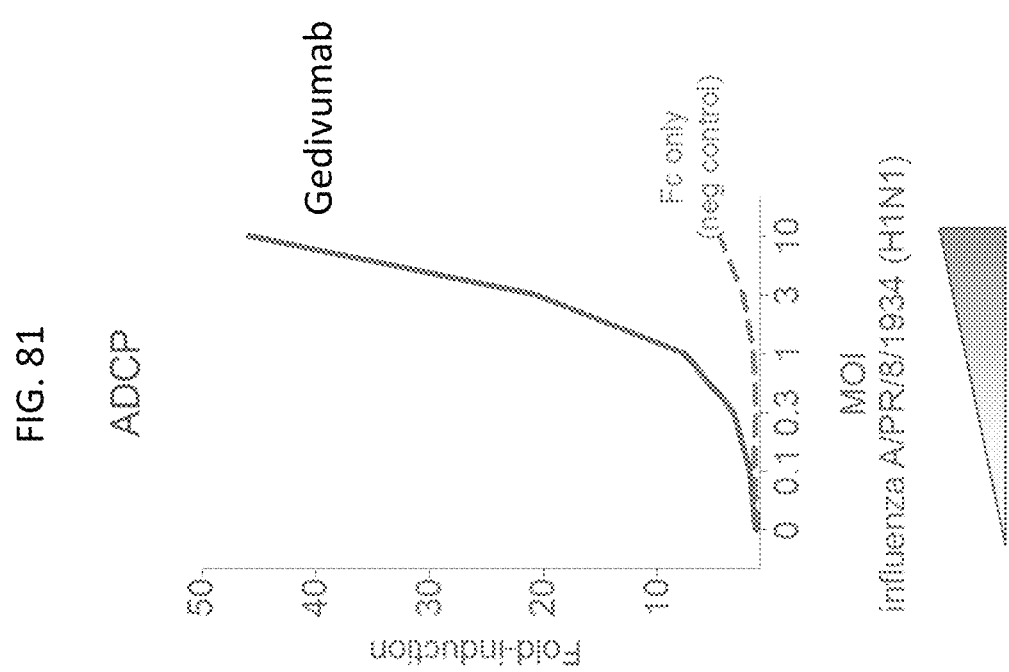

Conjugates 45 and 46

SEQ ID NO: 72 (Conjugate 45a)
SEQ ID NO: 73 (Conjugate 45b)
SEQ ID NO: 76 (Conjugate 46)

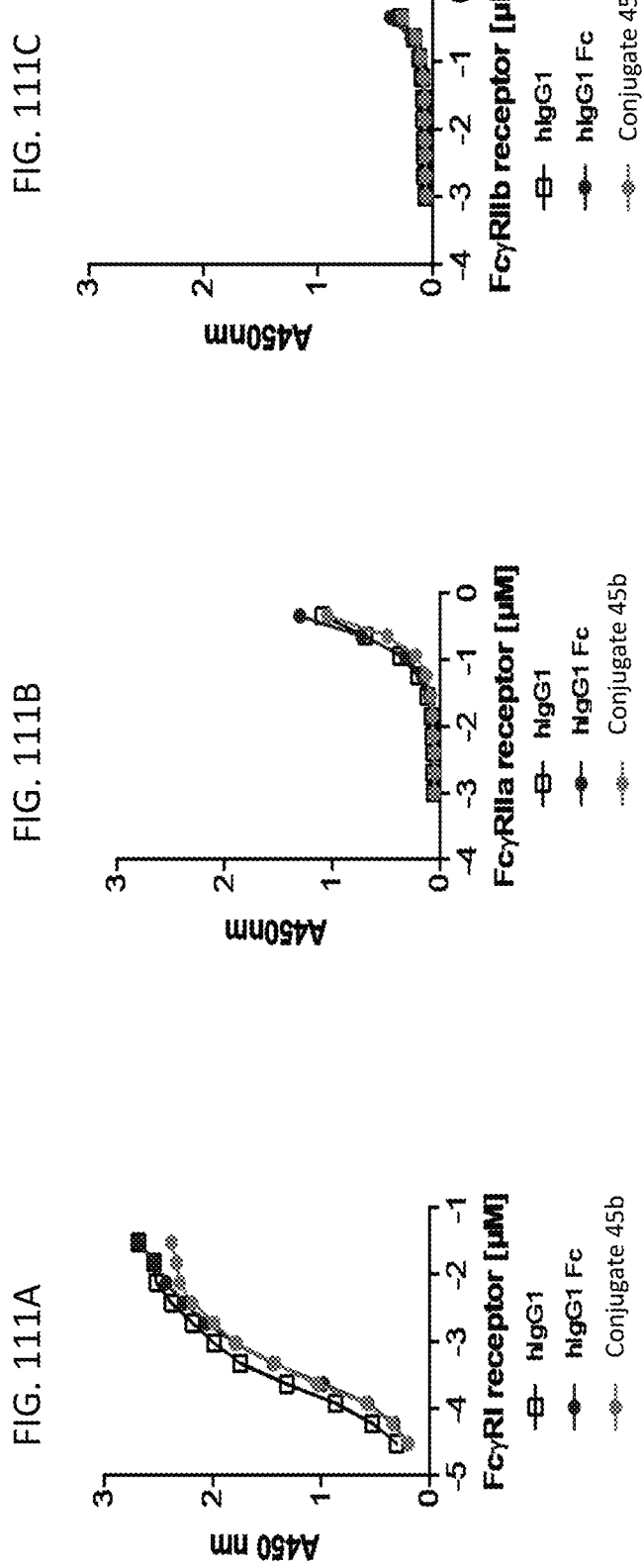

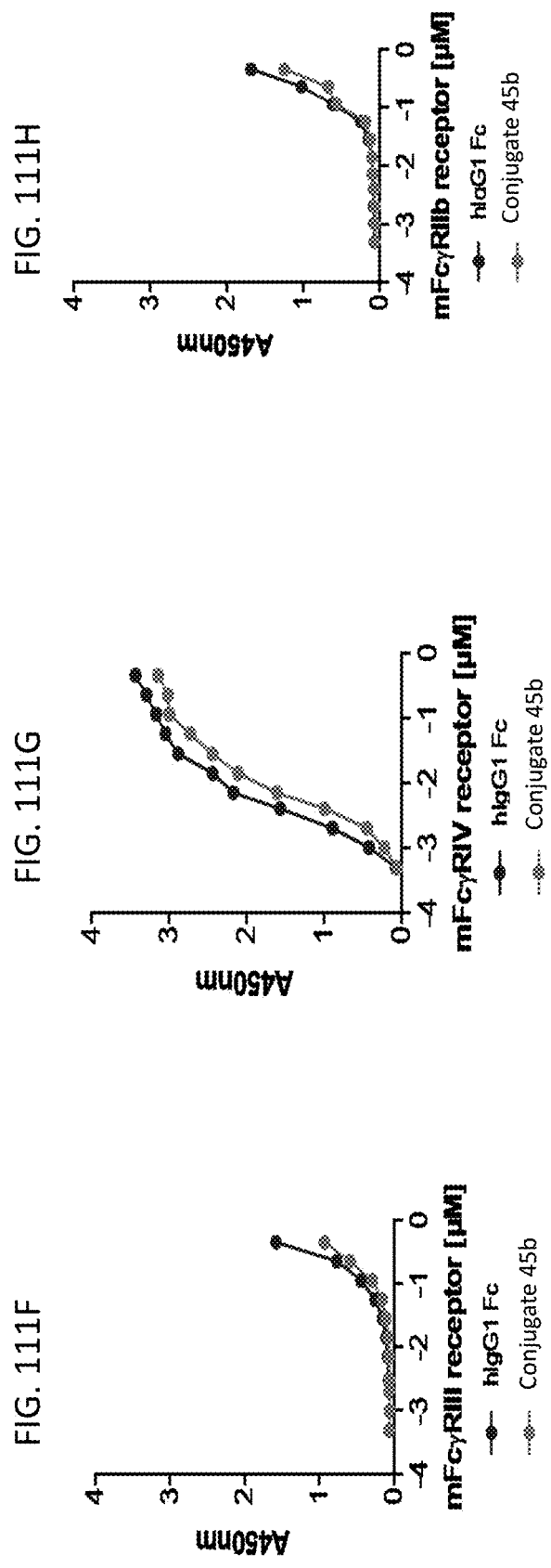

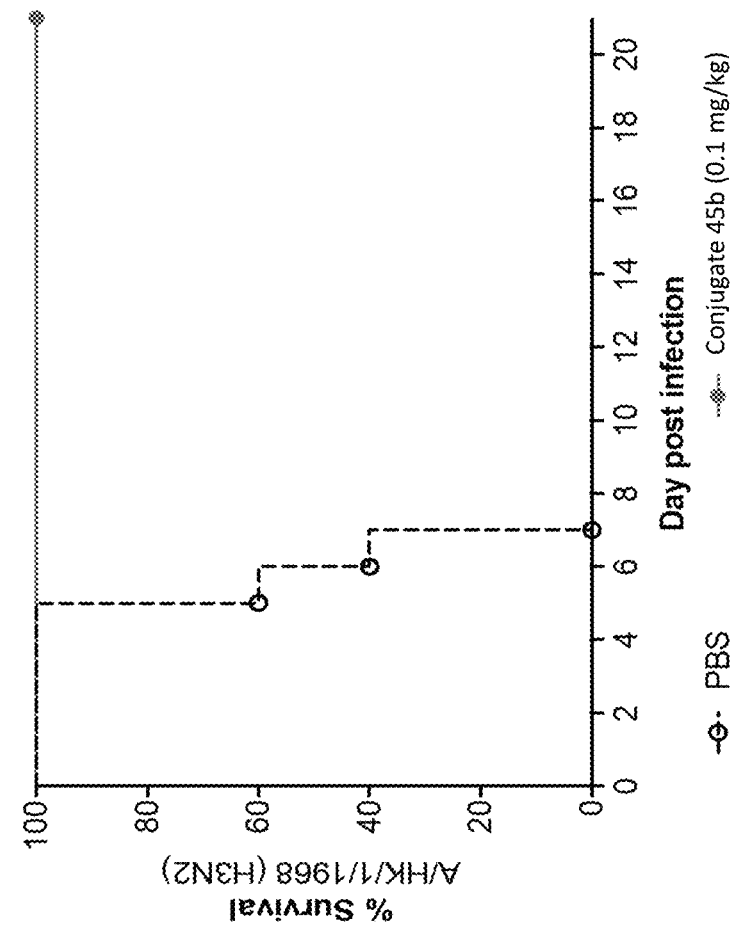

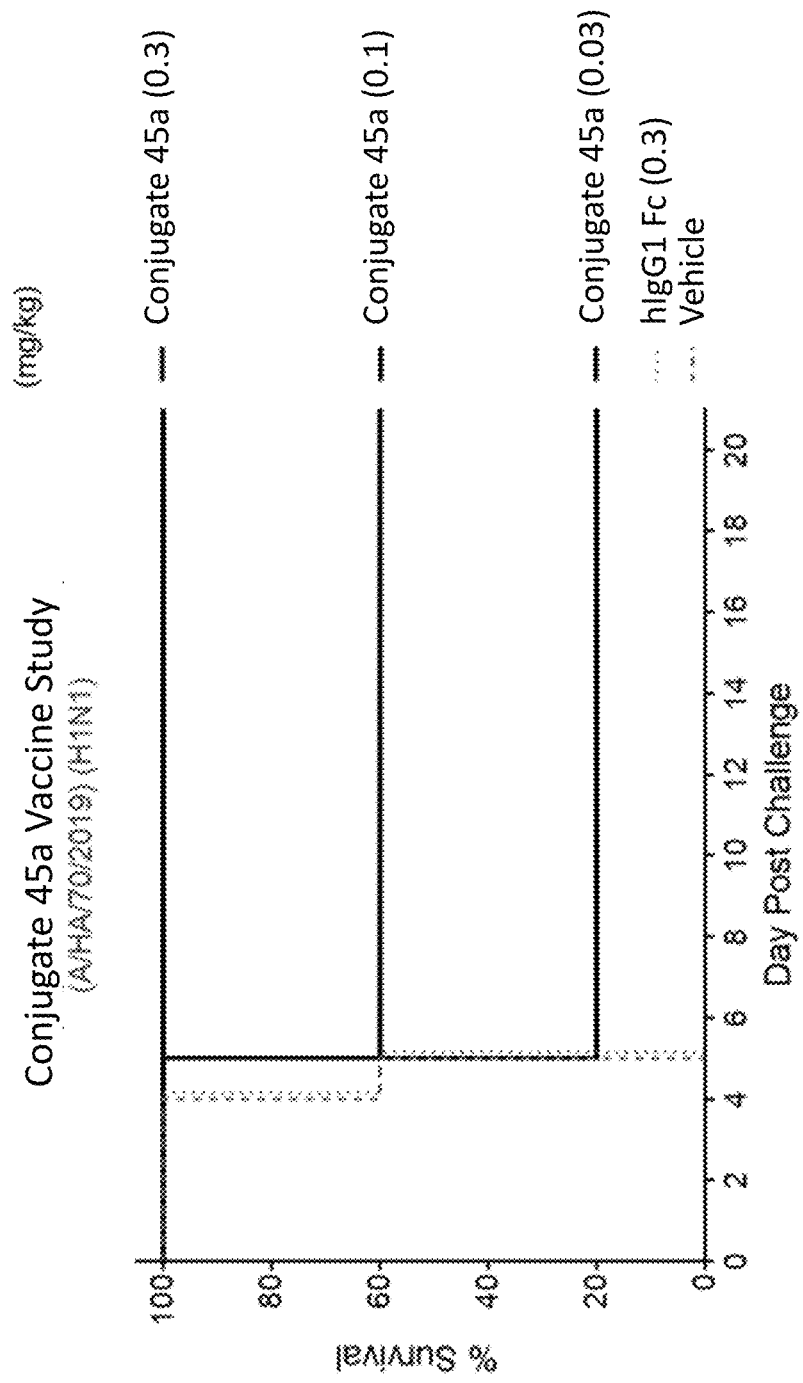

COMPOSITIONS AND METHODS FOR THE TREATMENT OF VIRAL INFECTIONS

BACKGROUND

The need for novel antiviral treatments for influenza is significant and especially critical in the medical field. Influenza virus, the causative agent of influenza, or the flu, is responsible for three to five million cases of severe illness annually, and approximately 500,000 deaths worldwide. While most people recover completely from influenza in about one to two weeks, others develop life-threatening complications, such as pneumonia. Thus, influenza can be deadly, especially for the young, old, or chronically ill. People with weak or compromised immune systems, such as people with advanced HIV infection or transplant patients, whose immune systems are medically suppressed to prevent transplant organ rejection, are at greater risk for complications relating to influenza. Pregnant women and young children are also at a high risk for complications.

The development of antiviral treatments for influenza has been a continuing challenge. Several influenza antiviral agents have been approved for use in the clinic, and these agents play important roles in modulating disease severity and controlling pandemics while vaccines are prepared. However, drug-resistant strains have emerged to the most commonly used inhibitors.

Influenza Antiviral agents largely target proteins presented on the surface of the influenza virus particle. The envelope of the influenza virus contains two immunodominant glycoproteins, hemagglutinin and neuraminidase, that play key roles in viral infection and spread. Hemagglutinin effects attachment of the virus to the host cell through its interaction with surface sialic acids, thereby initiating entry.

Neuraminidase is an exo-glycosidase enzyme that cleaves sialic acids (terminal neuraminic acid residues) from glycan structures on the surface of infected host cells, releasing progeny viruses and allowing the spread of the virus from the host cell to uninfected surrounding cells. Inhibition of neuraminidase therefore serves as a pharmacological target for antiviral drugs. Viral neuraminidase inhibitors used to reduce viral spread have been identified, including oseltamivir (Tamiflu™), zanamivir (Relenza™), and peramivir (Rapivab™)

However, influenza in transplant recipients remains characterized by prolonged viral shedding, increasing the likelihood of developing drug resistant strains. New, more effective therapies for treating influenza are needed.

SUMMARY

The disclosure relates to conjugates, compositions, and methods for inhibiting viral growth, and methods for the treatment of viral infections. In particular, such conjugates contain monomers or dimers of a moiety that inhibits influenza virus neuraminidase (e.g., zanamivir, peramivir, or analogs thereof) conjugated to Fc monomers, Fc domains, Fc-binding peptides, albumin proteins, or albumin protein-binding peptides. The neuraminidase inhibitor (e.g., zanamivir, peramivir, or analogs thereof) in the conjugates targets neuraminidase on the surface of the viral particle. The Fc monomers or Fc domains in the conjugates bind to FcγRs (e.g., FcRn, FcγRI, FcγRIIa, FcγRIIc, FcγRIIIa, and FcγRIIIb) on immune cells, e.g., neutrophils, to activate phagocytosis and effector functions, such as antibody-dependent cell-mediated cytotoxicity (ADCC), thus leading to the engulfment and destruction of viral particles by immune cells and further enhancing the antiviral activity of the conjugates. The albumin or albumin-binding peptide may extend the half-life of the conjugate, for example, by binding of albumin to the recycling neonatal Fc receptor. Such compositions are useful in methods for the inhibition of viral growth and in methods for the treatment of viral infections, such as those caused by an influenza virus A, influenza virus B and influenza virus C.

In a first aspect, the invention features a conjugate described by any one of formulas (D-I), (M-I), (1), or (2):

$$(A_1-\overset{(E)_n}{\underset{L}{|}}-A_2)_T, \quad (D\text{-}I)$$

$$(A_1-\overset{(E)_n}{\underset{L}{|}})_T, \quad (M\text{-}I)$$

$$\left\{ E \underset{E}{\overset{}{\underset{}{\bigg\langle}}} L \underset{A_2}{\overset{A_1}{\bigg\rangle}} \right\}_T, \text{ or} \quad (1)$$

$$\left\{ E \underset{E}{\overset{}{\underset{}{\bigg\langle}}} L-A_1 \right\}_T; \quad (2)$$

wherein each $A_1$ and each $A_2$ is independently selected from any one of formulas (A-I)-(A-XII):

(A-I)

(A-II)

(A-III)
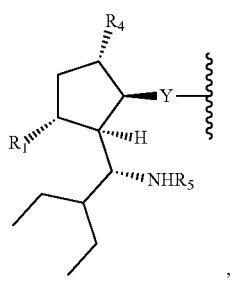
(A-IV)
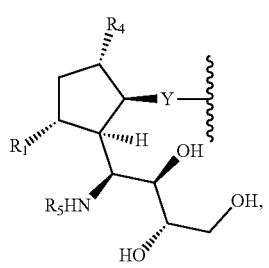
(A-V)
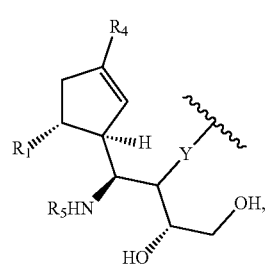
(A-VI)
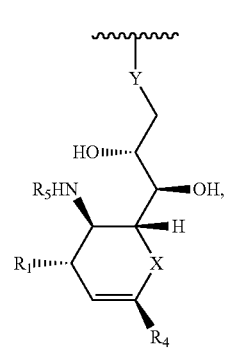
(A-VII)
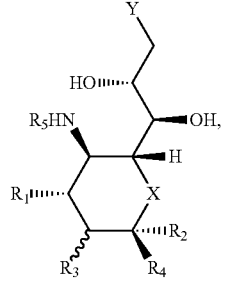
(A-VIII)
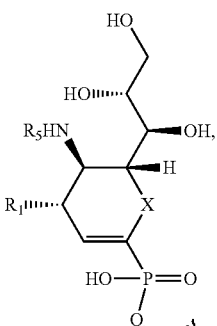
(A-IX)
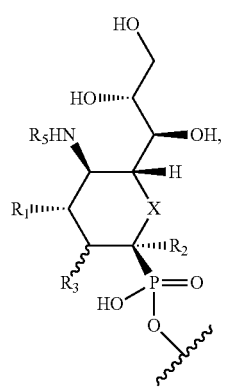
(A-X)
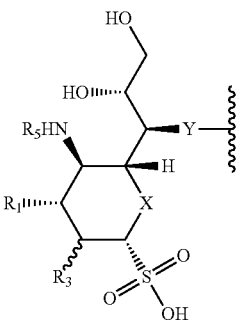
(A-XI)
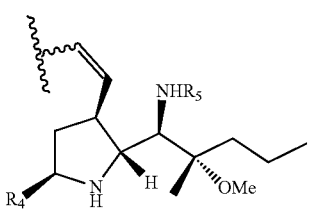
(A-XII)
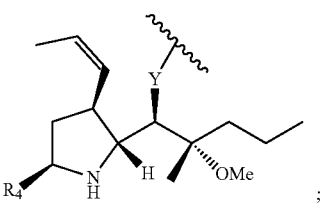
wherein $R_1$ is selected from —OH, —NH$_2$, —NHC(=NH)NH$_2$, and —NHC(=NH)NHR$_6$; $R_2$ and $R_3$ are each independently selected from —H, —OH, —F, —Cl, and —Br; $R_4$ is selected from —CO$_2$H, —P(=O)(OH)$_2$, —SO$_3$H; $R_5$ is selected from —COCH₃, —COCF₃, —SO₂CH₃; X is selected from —O— and —S—; Y is selected from
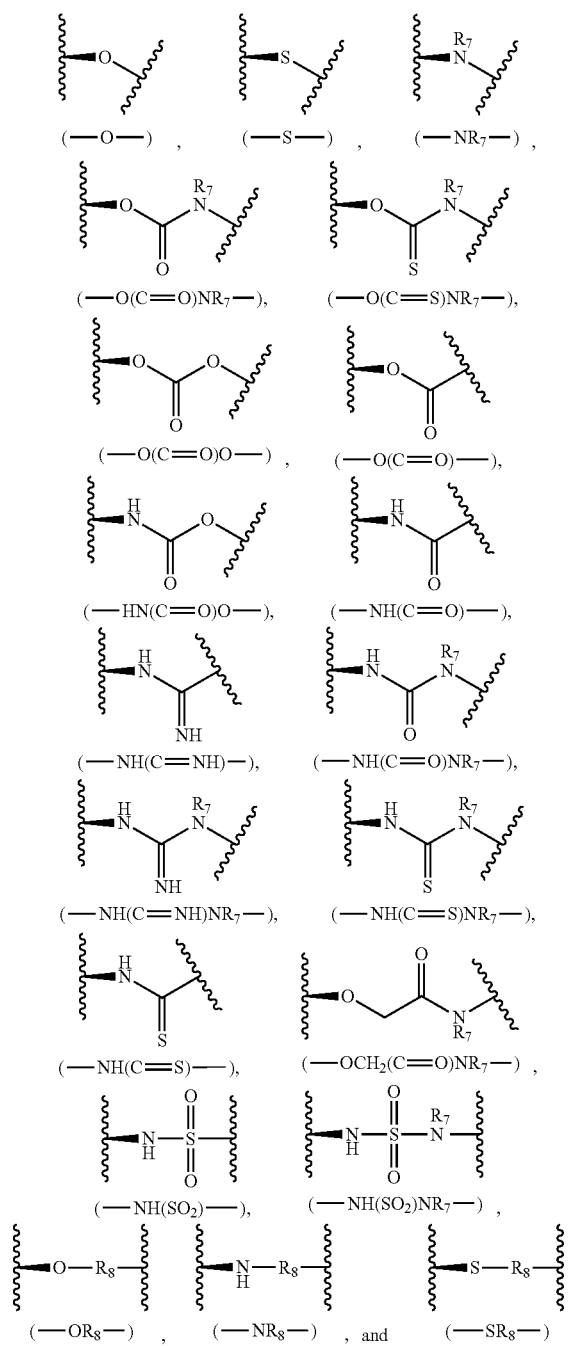
(—O—), (—S—), (—NR₇—),
(—O(C=O)NR₇—), (—O(C=S)NR₇—),
(—O(C=O)O—), (—O(C=O)—),
(—HN(C=O)O—), (—NH(C=O)—),
(—NH(C=NH)—), (—NH(C=O)NR₇—),
(—NH(C=NH)NR₇—), (—NH(C=S)NR₇—),
(—NH(C=S)—), (—OCH₂(C=O)NR₇—),
(—NH(SO₂)—), (—NH(SO₂)NR₇—),
(—OR₈—), (—NR₈—), and (—SR₈—);
R₆ is selected from
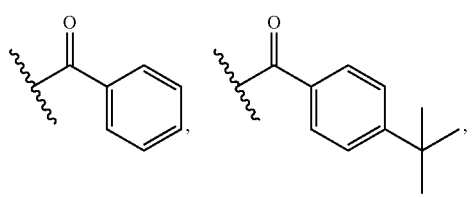
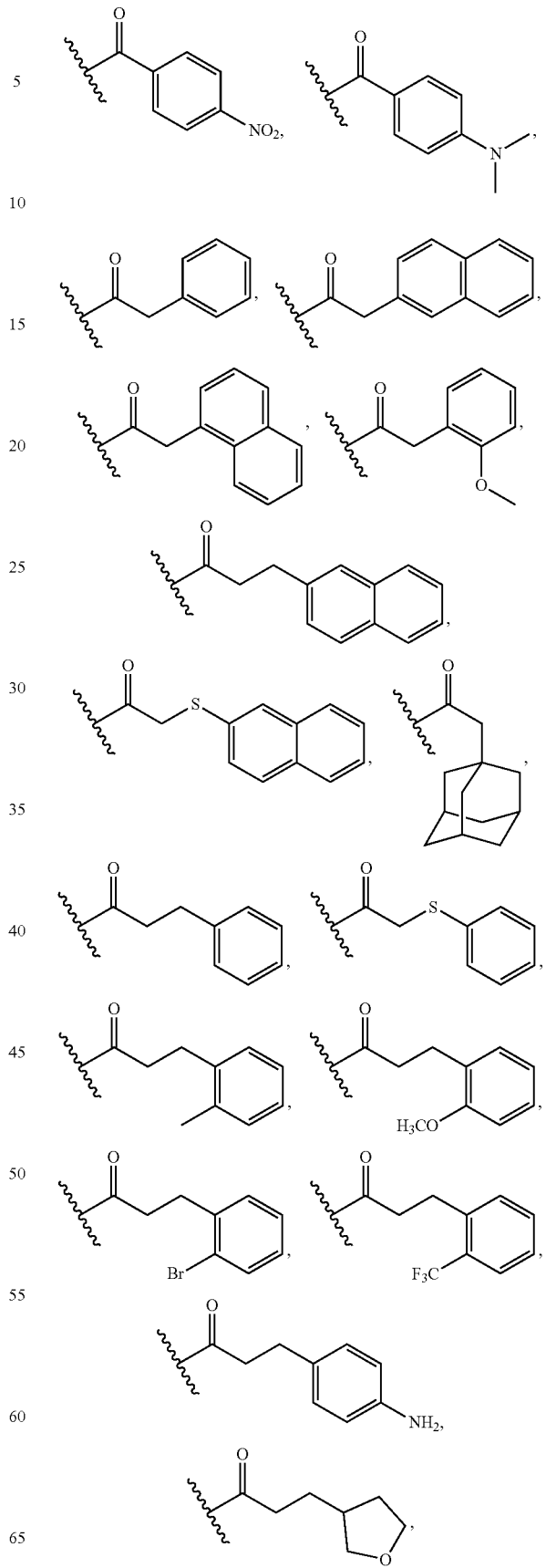

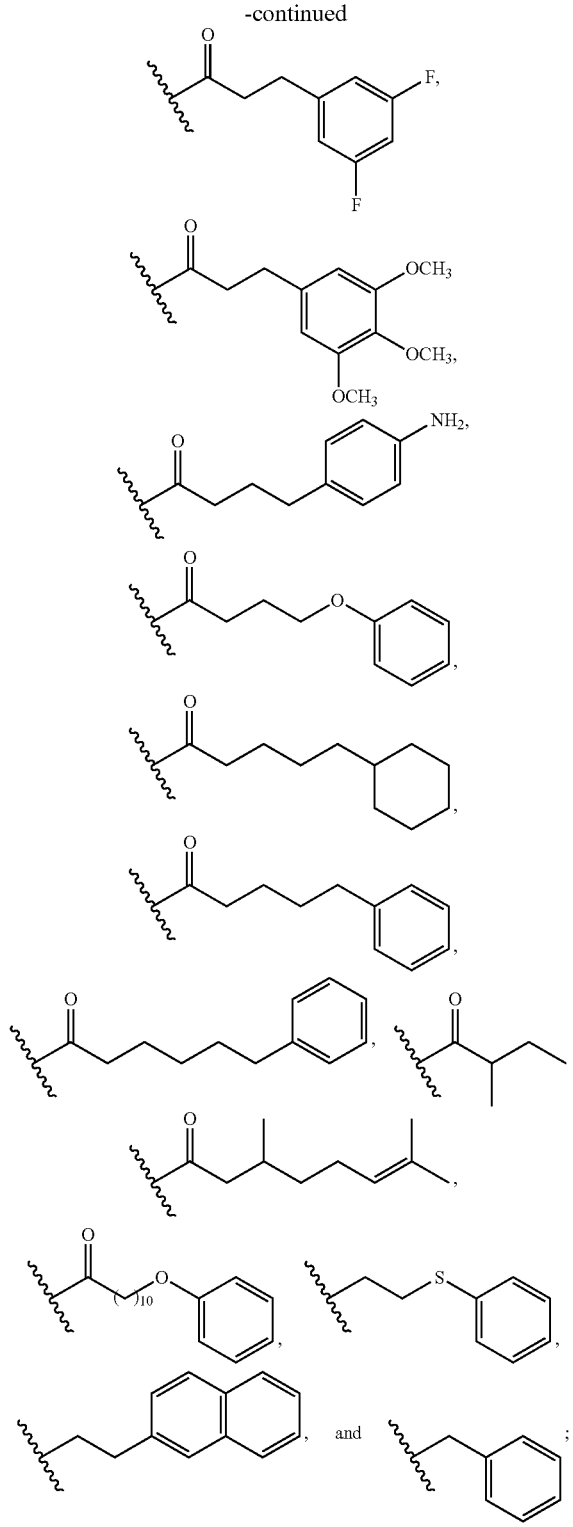

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl;

n is 1 or 2;

each E comprises an Fc domain monomer, an albumin protein, an albumin protein-binding peptide, or an Fc-binding peptide;

L is a linker covalently attached to E and to each Y of each $A_1$ or each $A_1$ and $A_2$;

T is an integer from 1 to 20, and each squiggly line in formulas (D-I), (M-I), (1), or (2) indicates that L is covalently attached to each E;

or a pharmaceutically acceptable salt thereof.

In some embodiments, n is 1 and each E includes an Fc domain monomer (e.g., an Fc domain monomer having the sequence of any one of SEQ ID NOs: 1-138), an albumin protein (e.g., an albumin protein having the sequence of any one of SEQ ID NOs: 139-141), an albumin protein-binding peptide, or an Fc-binding peptide;

In some embodiments, n is 2 and each E includes an Fc domain monomer (e.g., an Fc domain monomer having the sequence of any one of SEQ ID NOs: 1-138), wherein the Fc domain monomers dimerize to form and Fc domain;

L is a linker covalently attached to each E and to each Y or each $A_1$ and/or $A_2$;

T is an integer from 1 to 20 (e.g., 1, 2, 3, 4, 5, 6, 7, 8, 9, 10, 11, 12, 13, 14, 15, 16, 17, 18, 19, or 20), and each squiggly line in formulas (D-I), (M-I), (1), or (2) indicates that L is covalently attached (e.g., by way of a covalent bond or linker) to each E; or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L or each $A_1$-L-$A_2$ may be independently selected (e.g., independently selected from any of the $A_1$-L or $A_1$-L-$A_2$ structures described herein).

In preferred embodiments of any of the aspects described herein, n is 2 and each E includes an Fc domain monomer (e.g., an Fc domain monomer having the sequence of any one of SEQ ID NOs: 1-138). In a conjugate having two Fc domain monomers (e.g., a conjugate of formula (1), formula (2), formula (D-I) where n equals 2, or (M-I) where n equals 2), the Fc domain monomers dimerize to form an Fc domain.

In another aspect, the invention features a conjugate described by formula (D-I):

(D-I)

wherein each E includes an Fc domain monomer (e.g., an Fc domain monomer having the sequence of any one of SEQ ID NOs: 1-138); L in each $A_1$-L-$A_2$ is a linker covalently attached to a sulfur atom of a hinge cysteine in E and to each of $A_1$ and $A_2$; n is 1 or 2 (e.g., when n is 2, the two Fc domain monomers dimerize to form and Fc domain); T is an integer from 1 to 20 (e.g., 1, 2, 3, 4, 5, 6, 7, 8, 9, 10, 11, 12, 13, 14, 15, 16, 17, 18, 19, or 20), and the squiggly line connected to the E indicates that each $A_1$-L-$A_2$ is covalently attached (e.g., by way of a covalent bond or linker) to a sulfur atom of a hinge cysteine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In another aspect, the invention features a conjugate described by formula (D-I):

(D-I)

wherein each E includes an Fc domain monomer (e.g., an Fc domain monomer having the sequence of any one of SEQ ID NOs: 1-138); L in each $A_1$-L-$A_2$ is a linker covalently attached to a nitrogen atom of a surface exposed lysine in E and to each of $A_1$ and $A_2$; n is 1 or 2 (e.g., when n is 2, the two Fc domain monomers dimerize to form and Fc domain); T is an integer from 1 to 20 (e.g., 1, 2, 3, 4, 5, 6, 7, 8, 9, 10, 11, 12, 13, 14, 15, 16, 17, 18, 19, or 20), and the squiggly line connected to the E indicates that each $A_1$-L-$A_2$ is covalently attached (e.g., by way of a covalent bond or linker) to the nitrogen atom of a surface exposed lysine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein). In some embodiments, each of $A_1$ and $A_2$ may be independently selected from any one of formulas (A-I), (A-II), (A-VI), or (A-VII). In other embodiments, each of $A_1$ and $A_2$ may be independently selected from formula (A-I).

In another aspect, the invention features a conjugate described by formula (M-I):

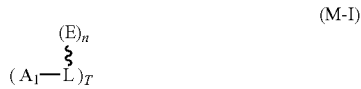

(M-I)

wherein each E includes an Fc domain monomer (e.g., an Fc domain monomer having the sequence of any one of SEQ ID NOs: 1-138); L in each L-$A_1$ is a linker covalently attached to a sulfur atom of a hinge cysteine in E and to $A_1$; n is 1 or 2 (e.g., when n is 2, the two Fc domain monomers dimerize to form and Fc domain); T is an integer from 1 to 20 (e.g., 1, 2, 3, 4, 5, 6, 7, 8, 9, 10, 11, 12, 13, 14, 15, 16, 17, 18, 19, or 20); and the squiggly line connected to E indicates that each L-$A_1$ is covalently attached (e.g., by way of a covalent bond or linker) to the sulfur atom of the hinge cysteine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any structure described by formula (A-I)-(A-XII). In some embodiments, each $A_1$ may be independently selected from any one of formulas (A-I), (A-II), (A-VI), or (A-VII). In other embodiments, each $A_1$ may be independently selected from formula (A-I).

In another aspect, the invention features a conjugate described by formula (M-I):

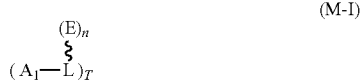

(M-I)

wherein each E includes an Fc domain monomer (e.g., an Fc domain monomer having the sequence of any one of SEQ ID NOs: 1-138); L in each L-$A_1$ is a linker covalently attached to a nitrogen atom of a surface exposed lysine in E and to $A_1$; n is 1 or 2 (e.g., when n is 2, the two Fc domain monomers dimerize to form and Fc domain); T is an integer from 1 to 20 (e.g., 1, 2, 3, 4, 5, 6, 7, 8, 9, 10, 11, 12, 13, 14, 15, 16, 17, 18, 19, or 20), the squiggly line connected to E indicates that each L-$A_1$ is covalently attached (e.g., by way of a covalent bond or linker) to the nitrogen atom of a surface exposed lysine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any structure described by formula (A-I)-(A-XII). In some embodiments, each $A_1$ may be independently selected from any one of formulas (A-I), (A-II), (A-VI), or (A-VII). In other embodiments, each $A_1$ may be independently selected from formula (A-I).

In one aspect, the disclosure features a conjugate described by formula (1):

(1)

wherein each $A_1$ and each $A_2$ is independently selected from any one of formulas (A-I)-(A-XII); each E comprises an Fc domain monomer (e.g., an Fc domain monomer having the sequence of any one of SEQ ID NOs: 1-138); L in each $A_1$-L-$A_2$ is a linker covalently attached to a sulfur atom of a hinge cysteine in each E and to each of $A_1$ and $A_2$; T is an integer from 1 to 20 (e.g., 1, 2, 3, 4, 5, 6, 7, 8, 9, 10, 11, 12, 13, 14, 15, 16, 17, 18, 19, or 20), and the two squiggly lines connected to the two Es indicate that each $A_1$-L-$A_2$ is covalently attached (e.g., by way of a covalent bond or a linker) to a pair of sulfur atoms of two hinge cysteines in the two Es, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In some embodiments, each of $A_1$ and $A_2$ may be independently selected from any one of formulas (A-I), (A-II), (A-VI), or (A-VII). In other embodiments, each of $A_1$ $A_2$ may be independently selected from formula (A-I).

In another aspect, the disclosure features a conjugate described by formula (1):

(1)

wherein each $A_1$ and each $A_2$ is independently selected from any one of formulas (A-I)-(A-V); each E comprises an Fc domain monomer (e.g., an Fc domain monomer having the sequence of any one of SEQ ID NOs: 1-138); L in each $A_1$-L-$A_2$ is a linker covalently attached to a sulfur atom of a hinge cysteine in each E and to each of $A_1$ and $A_2$; T is an integer from 1 to 20 (e.g., 1, 2, 3, 4, 5, 6, 7, 8, 9, 10, 11, 12, 13, 14, 15, 16, 17, 18, 19, or 20), and the two squiggly lines connected to the two Es indicate that each $A_1$-L-$A_2$ is covalently attached (e.g., by way of a covalent bond or a linker) to a pair of sulfur atoms of two hinge cysteines in the two Es, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In another aspect, the disclosure features a conjugate described by formula (1):

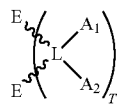

(1)

wherein each $A_1$ and each $A_2$ is independently selected from any one of formulas (A-VI)-(A-IX); each E comprises an Fc domain monomer (e.g., an Fc domain monomer having the sequence of any one of SEQ ID NOs: 1-138); L in each $A_1$-L-$A_2$ is a linker covalently attached to a sulfur atom of a hinge cysteine in each E and to each of $A_1$ and $A_2$; T is an integer from 1 to 20 (e.g., 1, 2, 3, 4, 5, 6, 7, 8, 9, 10, 11, 12, 13, 14, 15, 16, 17, 18, 19, or 20), and the two squiggly lines connected to the two Es indicate that each $A_1$-L-$A_2$ is covalently attached (e.g., by way of a covalent bond or a linker) to a pair of sulfur atoms of two hinge cysteines in the two Es, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In another aspect, the invention features a conjugate described by formula (2):

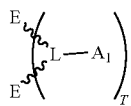

(2)

wherein each $A_1$ is independently selected from any one of formulas (A-I)-(A-XII); each E comprises an Fc domain monomer (e.g., an Fc domain monomer having the sequence of any one of SEQ ID NOs: 1-138); L in each L-$A_1$ is a linker covalently attached to a sulfur atom in a hinge cysteine in E and to $A_1$; T is an integer from 1 to 20 (e.g., 1, 2, 3, 4, 5, 6, 7, 8, 9, 10, 11, 12, 13, 14, 15, 16, 17, 18, 19, or 20), and the two squiggly lines connected to the two sulfur atoms indicate that each L-$A_1$ is covalently (e.g., by way of a covalent bond or a linker) attached to a pair of sulfur atoms of two hinge cysteines in the two Es, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any one of formulas (A-I)-(A-XII). In some embodiments, each of $A_1$ and $A_2$ may be independently selected from any one of formulas (A-I), (A-II), (A-VI), or (A-VII). In other embodiments, each of $A_1$ $A_2$ may be independently selected from formula (A-I).

In another aspect, the invention features a conjugate described by formula (2):

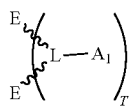

(2)

wherein each $A_1$ is independently selected from any one of formulas (A-I)-(A-V); each E comprises an Fc domain monomer (e.g., an Fc domain monomer having the sequence of any one of SEQ ID NOs: 1-138); L in each L-$A_1$ is a linker covalently attached to a sulfur atom in a hinge cysteine in E and to $A_1$; T is an integer from 1 to 20 (e.g., 1, 2, 3, 4, 5, 6, 7, 8, 9, 10, 11, 12, 13, 14, 15, 16, 17, 18, 19, or 20), and the two squiggly lines connected to the two sulfur atoms indicate that each L-$A_1$ is covalently attached (e.g., by way of a covalent bond or a linker) to a pair of sulfur atoms of two hinge cysteines in the two Es, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any one of formulas (A-I)-(A-V).

In another aspect, the invention features a conjugate described by formula (2):

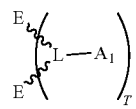

(2)

wherein each $A_1$ is independently selected from any one of formulas (A-VI)-(A-IX); each E comprises an Fc domain monomer (e.g., an Fc domain monomer having the sequence of any one of SEQ ID NOs: 1-138); L in each L-$A_1$ is a linker covalently attached to a sulfur atom in a hinge cysteine in E and to $A_1$; T is an integer from 1 to 20 (e.g., 1, 2, 3, 4, 5, 6, 7, 8, 9, 10, 11, 12, 13, 14, 15, 16, 17, 18, 19, or 20), and the two squiggly lines connected to the two sulfur atoms indicate that each L-$A_1$ is covalently attached (e.g., by way of a covalent bond or a linker) to a pair of sulfur atoms of two hinge cysteines in the two Es, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any one of formulas (A-VI)-(A-IX).

In some embodiments of any of the foregoing embodiments, each E includes an Fc domain monomer having the sequence of any one of SEQ ID NOs: 1-138.

In some embodiments, at least one of the pair of sulfur atoms is the sulfur atom corresponding to (e.g., the sulfur atom of) a hinge cysteine of SEQ ID NO: 10 or SEQ ID NO: 11, i.e., Cys10, Cys13, Cys16, or Cys18 of SEQ ID NO: 10 or SEQ ID NO: 11. In some embodiments, the pair of sulfur atoms are the sulfur atoms corresponding to (e.g., the sulfur atoms of) Cys10 and Cys13 in SEQ ID NO: 10 or SEQ ID NO: 11, Cys10 and Cys16 in SEQ ID NO: 10 or SEQ ID NO: 11, Cys 30 and Cys18 in SEQ ID NO: 10 or SEQ ID NO: 11, Cys13 and Cys 36 in SEQ ID NO: 10 or SEQ ID NO: 11, Cys13 and Cys 38 in SEQ ID NO: 10 or SEQ ID NO: 11, and/or Cys 36 and Cys 38 in SEQ ID NO: 10 or SEQ ID NO: 11. In some embodiments, when T is 2, the pair of sulfur atoms are (e.g., the sulfur atoms corresponding to) Cys10 and Cys13 in SEQ ID NO: 10 or SEQ ID NO: 11 or Cys 36 and Cys 38 in SEQ ID NO: 10 or SEQ ID NO: 11.

In some embodiments, the pair of sulfur atoms include one sulfur atom of a cysteine from each E, i.e., L-A along with the sulfur atoms to which it is attached forms a bridge between two Fc domains (e.g., two Fc domains comprising the sequence of SEQ ID NO: 10 or SEQ ID NO: 11). In some embodiments, the pair of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E. In some embodiments, the pair of sulfur atoms are the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E. In some embodiments, the pair of sulfur atoms are the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E. In some embodiments, the pair of sulfur atoms are the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E.

In some embodiments, when T is 2, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E and the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E. In some embodiments, when T is 2, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E and the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E. In some embodiments, when T is 2, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E and the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E.

In some embodiments, when T is 2, the pairs of sulfur atoms are the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E and the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E. In some embodiments, when T is 2, the pairs of sulfur atoms are the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E and the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E.

In some embodiments, when T is 2, the pairs of sulfur atoms are the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E and the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E.

In some embodiments, when T is 3, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E; the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E; and the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E. In some embodiments, when T is 3, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E; the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E; and the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E. In some embodiments, when T is 3, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E; the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E; and the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E. In some embodiments, when T is 3, the pairs of sulfur atoms are the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E; the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E; and the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E.

In some embodiments, when T is 3, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E; the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E; the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E; and the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E.

In some embodiments, the conjugate has the structure:

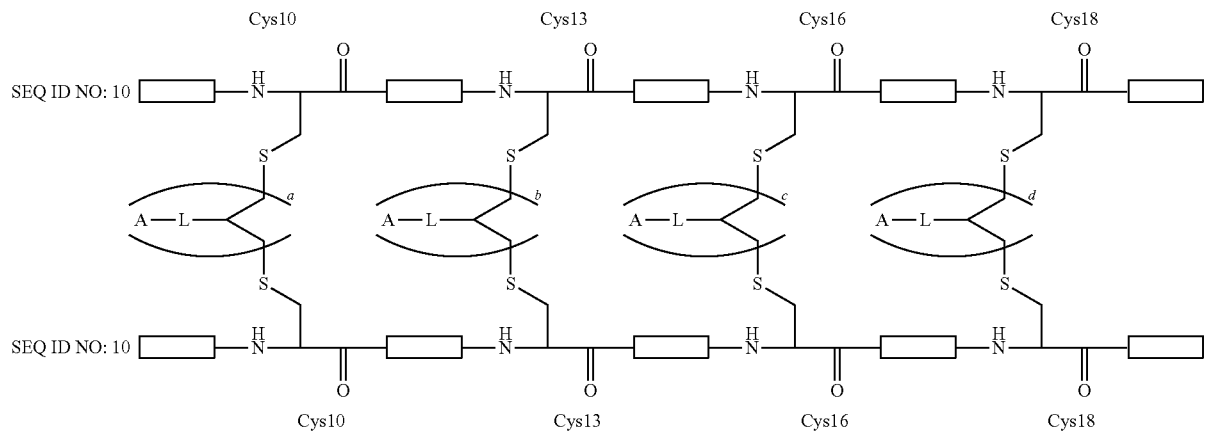

wherein each of a, b, c, and d is, independently, 0 or 1 and wherein when a, b, c, or d is 0, the two sulfur atoms form a disulfide bond.

In some embodiments, a is 1 and b, c, and d are 0. In some embodiments, a and b are 1 and c and d are 0. In some embodiments, a and c are 1 and b and d are 0. In some embodiments, a and d are 1 and b and c are 0. In some embodiments, a, b, and c are 1 and d is 0. In some embodiments, a, b, and d are 1 and c is 0. In some embodiments, a, c, and d are 1 and b is 0. In some embodiments, b and c are 1 and a and d are 0. In some embodiments, b and d are 1 and a and c are 0. In some embodiments, b, c, and d are 1 and a is 0. In some embodiments, c and d are 1 and a and b are 0. In some embodiments, a, b, c, and d are 1.

In some embodiments, each E comprises the sequence MVRSDKTHTCPPCPAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKGQPREPQVYTLPPSR EEMTKNQVSLTCLVKGFYPSDIAVEWESNGQPENNYKTTPPVLDSDGSFFLYSK-LTVDKSRWQQGNVFS CSVMHEALHNHYTQKSLSLSPGK (SEQ ID NO: 4).

In some embodiments, each E comprises the sequence MVRSDKTHTCPPCPAPELLGGPSVFLFPPKPKDTLYITREPEVTCVVVDVSHEDPEVKFNWYVDGVEVH NAKTKPREEQYNSTYRVVSVLTVLHQDWLNGKEYKCKVSNKALPAPIEKTISKAKGQPREPQVYTLPPSR EEMTKNQVSLTCLVKGFYPSDIAVEWESNGQPENNYKTTPPVLDSDGSFFLYSK-LTVDKSRWQQGNVFS CSVMHEALHNHYTQKSLSLSPGK (SEQ ID NO: 33).

In some embodiments, at least one of the pair of sulfur atoms is the sulfur atom corresponding to (e.g., the sulfur atom of) a hinge cysteine of SEQ ID NO: 4 or SEQ ID NO: 33, i.e., Cys10 and/or Cys13. In some embodiments, the pair of sulfur atoms are the sulfur atoms corresponding to (e.g., the sulfur atoms of) Cys10 and Cys13 in SEQ ID NO: 4 or SEQ ID NO: 33.

In some embodiments, the pair of sulfur atoms include one sulfur atom of a cysteine from each E, i.e., L-A along with the sulfur atoms to which it is attached forms a bridge between two Fc domains (e.g., two Fc domains comprising the sequence of SEQ ID NO: 4 or SEQ ID NO: 33). In some embodiments, the pair of sulfur atoms are the sulfur atom corresponding to (e.g., the sulfur atom of) Cys10 of SEQ ID NO: 4 or SEQ ID NO: 33 from one E and the sulfur atom corresponding to (e.g., the sulfur atom of) Cys10 of SEQ ID NO: 4 or SEQ ID NO: 33 from another E. In some embodiments, the pair of sulfur atoms are the sulfur atom corresponding to (e.g., the sulfur atom of) Cys13 of SEQ ID NO: 4 or SEQ ID NO: 33 from one E and the sulfur atom corresponding to (e.g., the sulfur atom of) Cys13 of SEQ ID NO: 4 or SEQ ID NO: 33 from another E. In some embodiments, when T is 2, the pairs of sulfur atoms are the sulfur atom corresponding to (e.g., the sulfur atom of) Cys10 of SEQ ID NO: 4 or SEQ ID NO: 33 from one E and the sulfur atom corresponding to (e.g., the sulfur atom of) Cys10 of SEQ ID NO: 4 or SEQ ID NO: 33 from another E and the sulfur atom corresponding to (e.g., the sulfur atom of) Cys13 of SEQ ID NO: 4 or SEQ ID NO: 33 from one E and the sulfur atom corresponding to (e.g., the sulfur atom of) Cys13 of SEQ ID NO: 4 or SEQ ID NO: 33 from another E.

In some embodiments, the conjugate has the structure:

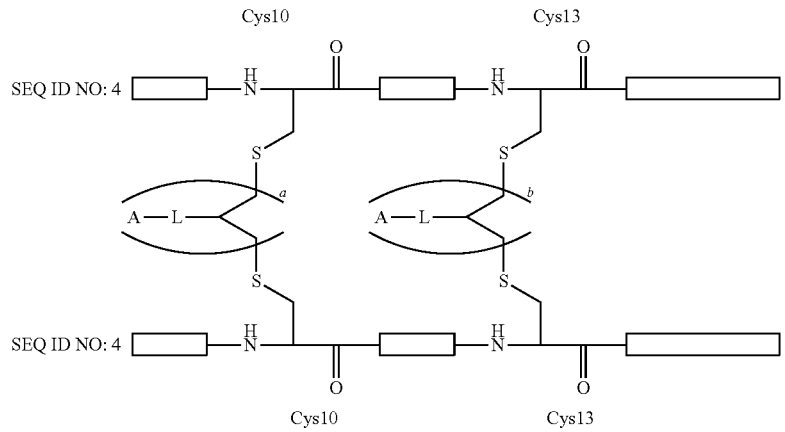

wherein each of a and b is, independently, 0 or 1 and wherein when a or b is 0, the two sulfur atoms form a disulfide bond. In some embodiments, a is 1 and b is 0. In some embodiments, a is 0 and b is 1. In some embodiments, a and b are 1.

In some embodiments, at least one of the pair of sulfur atoms is the sulfur atom corresponding to (e.g., the sulfur atom of) a hinge cysteine of SEQ ID NO: 8, i.e., Cys10 and/or Cys13. In some embodiments, the pair of sulfur atoms are the sulfur atoms corresponding to (e.g., the sulfur atoms of) Cys10 and Cys13 in SEQ ID NO: 8.

In some embodiments, the pair of sulfur atoms include one sulfur atom of a cysteine from each E, i.e., L-A along with the sulfur atoms to which it is attached forms a bridge between two Fc domains (e.g., two Fc domains comprising the sequence of SEQ ID NO: 8). In some embodiments, the pair of sulfur atoms are the sulfur atom corresponding to (e.g., the sulfur atom of) Cys10 of SEQ ID NO: 8 from one E and the sulfur atom corresponding to (e.g., the sulfur atom of) Cys10 of SEQ ID NO: 8 from another E. In some embodiments, the pair of sulfur atoms are the sulfur atom corresponding to (e.g., the sulfur atom of) Cys13 of SEQ ID NO: 8 from one E and the sulfur atom corresponding to (e.g., the sulfur atom of) Cys13 of SEQ ID NO: 8 from another E.

In some embodiments, when T is 2, the pairs of sulfur atoms are the sulfur atom corresponding to (e.g., the sulfur atom of) Cys10 of SEQ ID NO: 8 from one E and the sulfur atom corresponding to (e.g., the sulfur atom of) Cys10 of SEQ ID NO: 8 from another E and the sulfur atom corresponding to (e.g., the sulfur atom of) Cys13 of SEQ ID NO: 8 from one E and the sulfur atom corresponding to (e.g., the sulfur atom of) Cys13 of SEQ ID NO: 8 from another E.

In some embodiments, the conjugate has the structure:

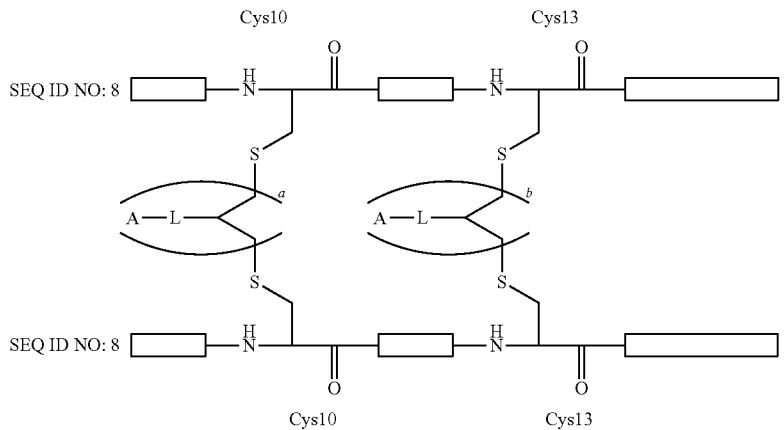

wherein each of a and b is, independently, 0 or 1 and wherein when a or b is 0, the two sulfur atoms form a disulfide bond. In some embodiments, a is 1 and b is 0. In some embodiments, a is 0 and b is 1. In some embodiments, a and b are 1.

In some embodiments, the conjugate has the structure:

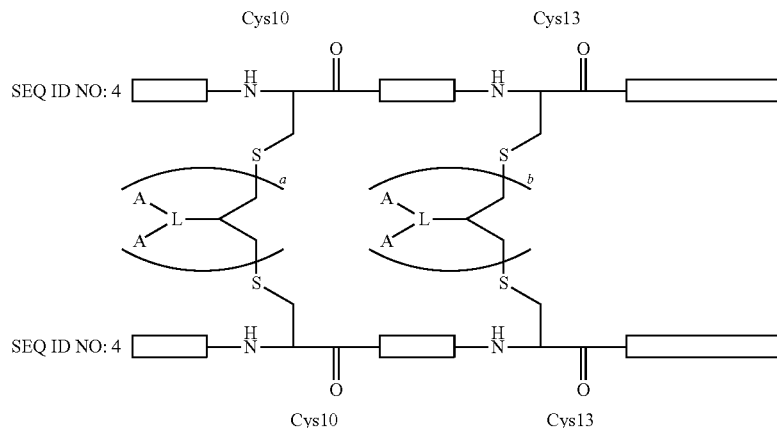

wherein each of a and b is, independently, 0 or 1 and wherein when a or b is 0, the two sulfur atoms form a disulfide bond. In some embodiments, a is 1 and b is 0. In some embodiments, a is 0 and b is 1. In some embodiments, a and b are 1.

In some embodiments, the conjugate has the structure:

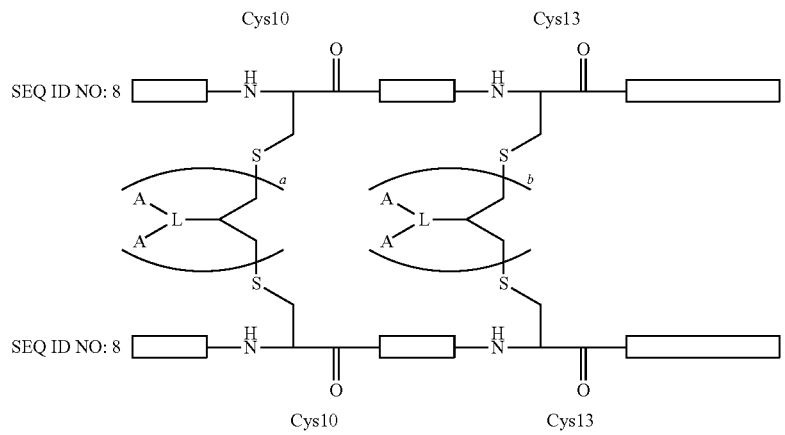

wherein each of a and b is, independently, 0 or 1 and wherein when a or b is 0, the two sulfur atoms form a disulfide bond. In some embodiments, a is 1 and b is 0. In some embodiments, a is 0 and b is 1. In some embodiments, a and b are 1.

In some embodiments, the conjugate has the structure:

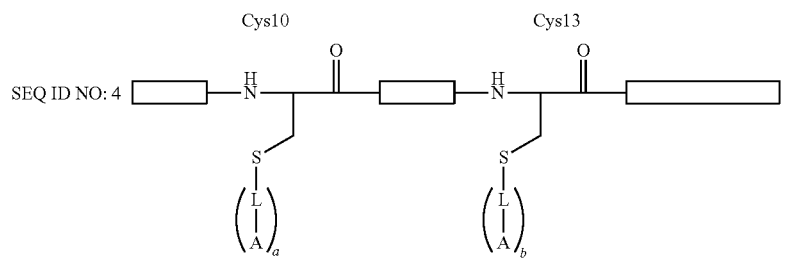

wherein each of a and b is, independently, 0 or 1 and wherein when a or b is 0, the sulfur atoms is a thiol.

In some embodiments, a is 1 and b is 0. In some embodiments, a is 0 and b is 1. In some embodiments, a and b are 1.

In some embodiments of the previous three aspects, the nitrogen atom is the nitrogen of a surface exposed lysine, e.g., the nitrogen atom corresponding to (e.g., the nitrogen atom of) Lys35, Lys63, Lys77, Lys79, Lys106, Lys123, Lys129, Lys181, Lys203, Lys228, or Lys236 of SEQ ID NO: 10 or SEQ ID NO: 11. In some embodiments, the nitrogen atom is the nitrogen atom corresponding to (e.g., the nitrogen atom of) Lys65, Lys79, Lys108, Lys230, and/or Lys238 of SEQ ID NO: 10 or SEQ ID NO: 11.

In some embodiments, the conjugate has the structure:

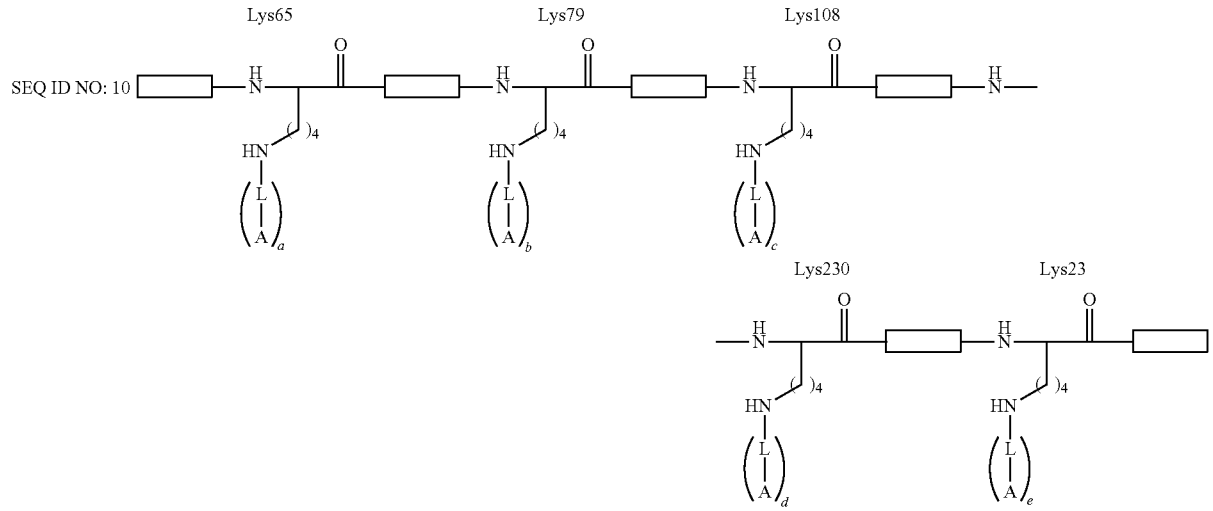

wherein each of a, b, c, d, and e is, independently, 0 or 1 and wherein when a, b, c, d, or e is 0, the two nitrogen atom is NH$_2$. In some embodiments, a is 1 and b, c, d, and e are 0. In some embodiments, b is 1 and a, c, d, and e are 0. In some embodiments, c is 1 and a, b, d, and e are 0. In some embodiments, d is 1 and a, b, c, and e are 0. In some embodiments, e is 1 and a, b, c, and d are 0. In some embodiments, a and b are 1 and c, d, and e are 0. In some embodiments, a and c are 1 and b, d, and e are 0. In some embodiments, a and d are 1 and b, c, and e are 0. In some embodiments, a and e are 1 and b, c, and d are 0. In some embodiments, b and c are 1 and a, d, and e are 0. In some embodiments, b and d are 1 and a, c, and e are 0. In some embodiments, b and e are 1 and a, c, and d are 0. In some embodiments, c and d are 1 and a, b, and e are 0. In some embodiments, c and e are 1 and a, b, and d are 0. In some embodiments, d and e are 1 and a, b, and c are 0. In some embodiments, a, b, and c are 1 and d and e are 0. In some embodiments, a, b, and d are 1 and c and e are 0. In some embodiments, a, b, and e are 1 and c and d are 0. In some embodiments, a, c, and d are 1 and b and e are 0. In some embodiments, a, c, and e are 1 and b and d are 0. In some embodiments, a, d, and e are 1 and b and c are 0. In some embodiments, b, c, and d are 1 and a and e are 0. In some embodiments, b, d, and e are 1 and a and c are 0. In some embodiments, c, d, and e are 1 and a and b are 0.

In some embodiments of any of the conjugates described herein, the conjugate forms a homodimer including an Fc domain. In some embodiments of the conjugates described herein, E homodimerizes with another E to form an Fc domain.

In another aspect, the invention features a conjugate described by (D-I):

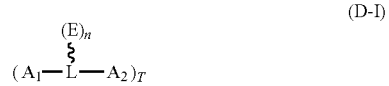

wherein E includes an albumin protein (e.g., an albumin protein having the sequence of any one of SEQ ID NOs: 139-141), an albumin protein-binding peptide, or an Fc-binding peptide; L in each A$_1$-L-A$_2$ is a linker independently covalently attached to a sulfur atom of a surface exposed cysteine or a nitrogen atom of a surface exposed lysine in E and to each of A$_1$ and A$_2$; n is 1; T is an integer from 1 to 20 (e.g., 1, 2, 3, 4, 5, 6, 7, 8, 9, 10, 11, 12, 13, 14, 15, 16, 17, 18, 19, or 20), and the squiggly line connected to the E indicates that each A$_1$-L-A$_2$ is independently covalently attached to the sulfur atom of a solvent-exposed cysteine or the nitrogen atom of a solvent-exposed lysine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each A$_1$-L-A$_2$ may be independently selected (e.g., independently selected from any of the A$_1$-L-A$_2$ structures described herein). In some embodiments, each of A$_1$ A$_2$ may be independently selected from any one of formulas (A-I), (A-II), (A-VI), or (A-VII). In other embodiments, each of A$_1$ A$_2$ may be independently selected from formula (A-I).

In a preferred embodiment of the above, x is 2.

In another aspect, the invention features a conjugate described by formula (M-I):

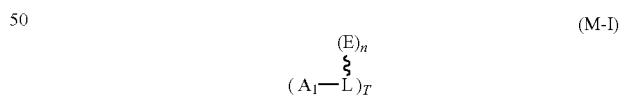

wherein E includes an albumin protein (e.g., an albumin protein having the sequence of any one of SEQ ID NOs: 139-141), an albumin protein-binding peptide, or an Fc-binding peptide; L in each L-A$_1$ is a linker independently covalently attached to a sulfur atom of a surface exposed cysteine or a nitrogen atom of a surface exposed lysine in E and to A$_1$; n is 1; T is an integer from 1 to 20 (e.g., 1, 2, 3, 4, 5, 6, 7, 8, 9, 10, 11, 12, 13, 14, 15, 16, 17, 18, 19, or 20); and the squiggly line connected to E indicates that each L-A$_1$ is independently covalently attached to the sulfur atom of the solvent-exposed cysteine or the nitrogen atom of the solvent-exposed lysine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any structure described by formula (A-I)-(A-XII). In some embodiments, each $A_1$ may be independently selected from any one of formulas (A-I), (A-II), (A-VI), or (A-VII). In other embodiments, each $A_1$ may be independently selected from formula (A-I). In a preferred embodiment of the above, x is 2.

In some embodiments, each E includes an albumin protein having the sequence of any one of SEQ ID NOs: 139-141.

In some embodiments, T is 1 and L-$A_1$ is covalently attached to the sulfur atom corresponding to Cys34 of SEQ ID NO: 139.

Intermediates of Table 1a may be conjugated to an Fc domain or Fc domain monomer (e.g., by way of a linker) by any suitable methods known to those of skill in the art, including any of the methods described or exemplified herein. In some embodiments, the conjugate (e.g., a conjugate described by any one of formulas (1), (2), (D-I)-(D-XI), or (M-I)-(M-XI)) includes E, wherein E is an Fc domain monomer or an Fc domain (e.g., an Fc domain monomer or an Fc domain, each Fc domain monomer having, independently, the sequence of any one of SEQ ID NOs: 1-138). In preferred embodiments, one or more nitrogen atoms of one or more surface exposed lysine residues of E or one or more sulfur atoms of one or more surface exposed cysteines in E is covalently conjugated to a linker (e.g., a $PEG_2$-$PEG_{20}$ linker). The linker conjugated to E may be functionalized such that it may react to form a covalent bond with any of the Ints described herein (e.g., an Int of Table 1a). In preferred embodiments, E is conjugated to a linker functionalized with an azido group and the Int (e.g., an Int of Table 1a) is functionalized with an alkyne group. Conjugation (e.g., by click chemistry) of the linker-azido of E and linker-alkyne of the Int forms a conjugate of the invention, for example a conjugate described by formula (5). In yet other embodiments, E is conjugated to a linker functionalized with an alkyne group and the Int (e.g., an Int of Table 1a) is functionalized with an azido group. Conjugation (e.g., by click chemistry; see, e.g., FIG. 103) of the linker-alkyne of E and linker-azido of the Int forms a conjugate of the invention, for example a conjugate described by any one of formulas (1), (2), (D-I)-(D-XI), or (M-I)-(M-XI).

TABLE 1a
Intermediates
| Intermediate | Structure |
|---|---|
| Int-1 | 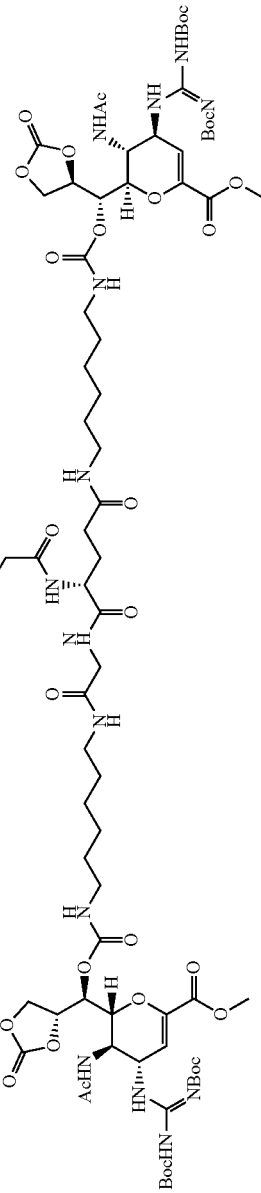 |
| Int-2 | 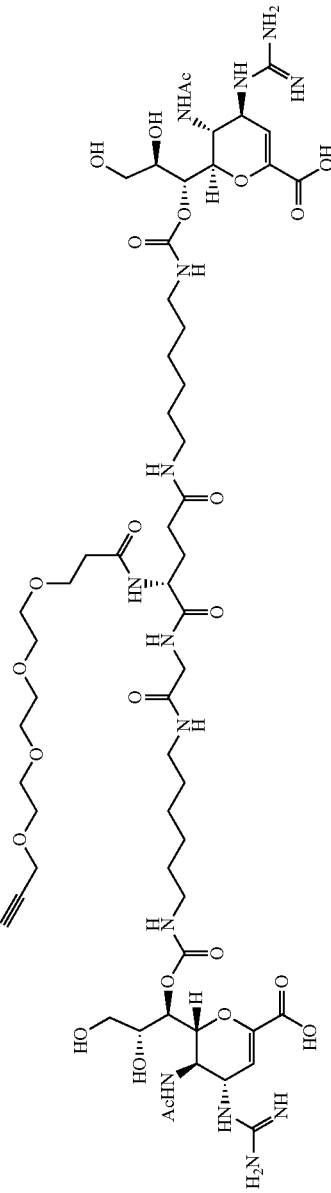 |

TABLE 1a-continued

Intermediates

| Intermediate | Structure |
|---|---|
| Int-3 | (structure) |
| Int-4 | (structure) |
| Int-5 | (structure) |

TABLE 1a-continued
Intermediates
| Intermediate | Structure |
|---|---|
| Int-6 | 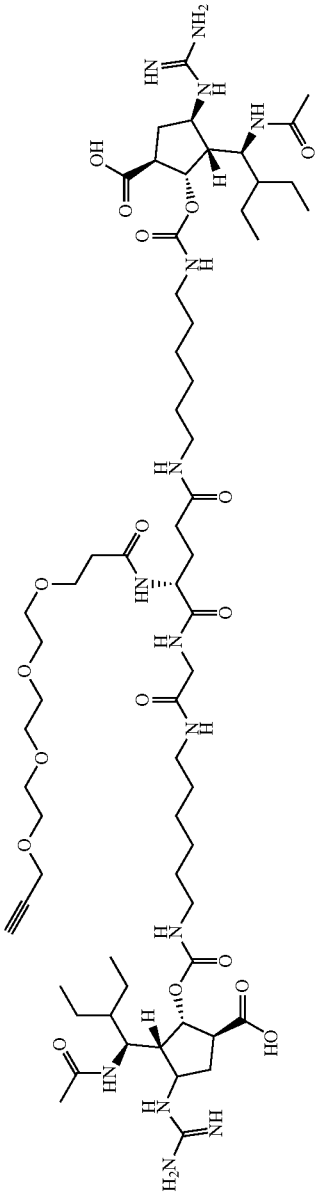 |
| Int-7 | 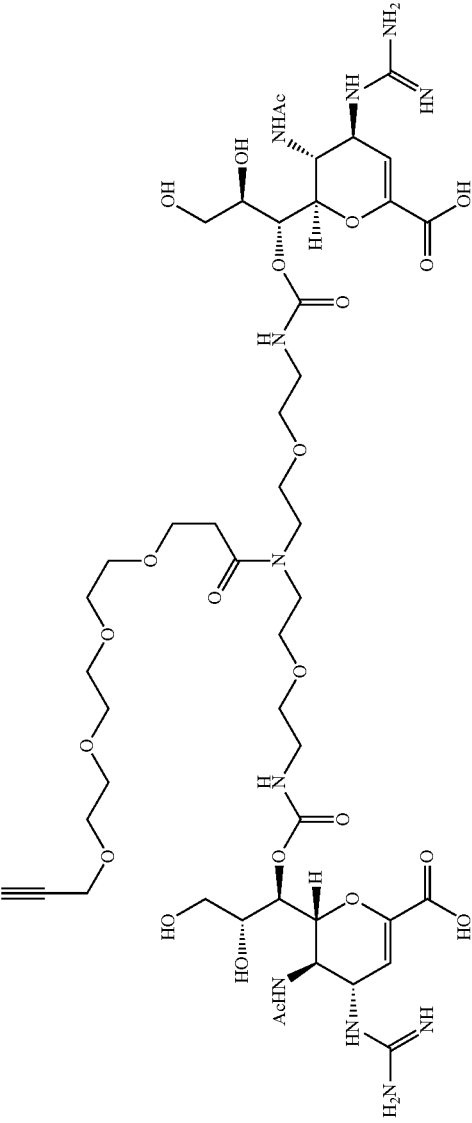 |

TABLE 1a-continued
Intermediates
| Intermediate | Structure |
|---|---|
| Int-9 | 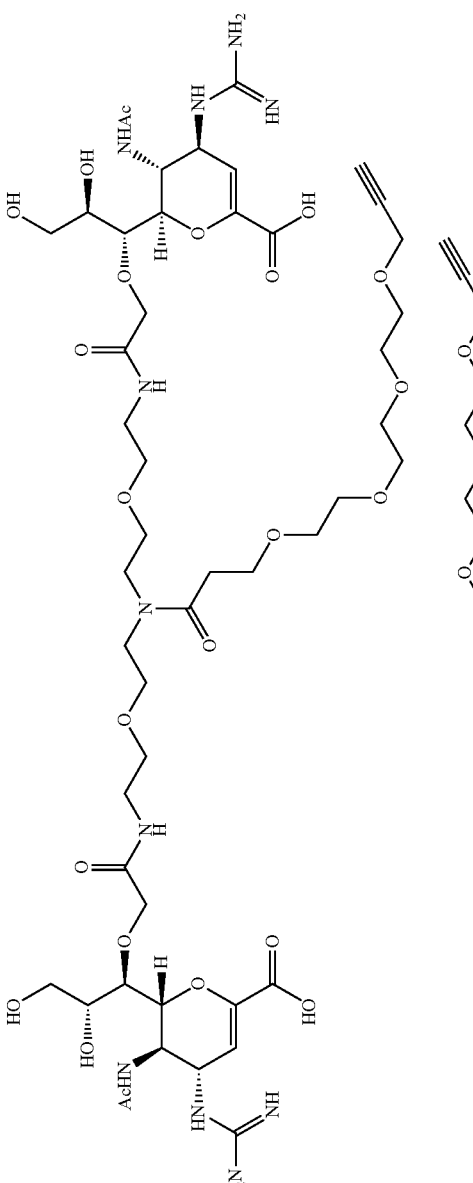 |
| Int-12 | 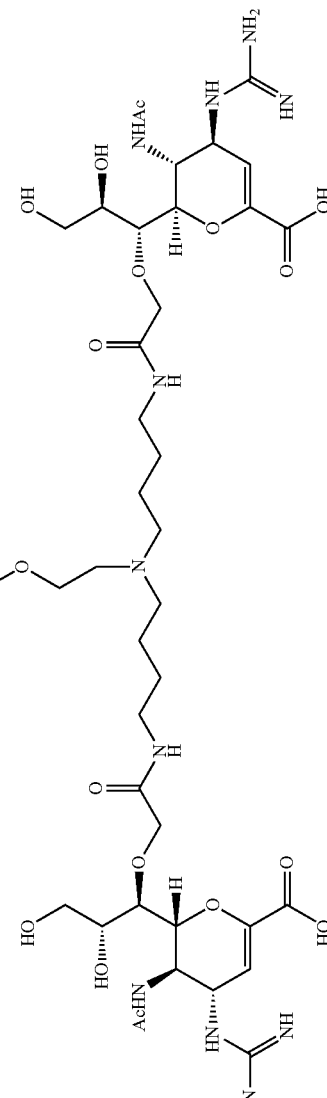 |

TABLE 1a-continued
Intermediates
| Intermediate | Structure |
|---|---|
| Int-13 | 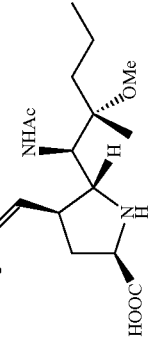 |
| Int-14 | 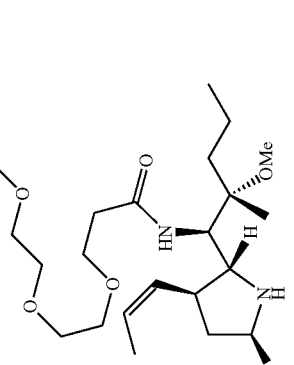 |

TABLE 1a-continued
Intermediates
| Intermediate | Structure |
|---|---|
| Int-15 | 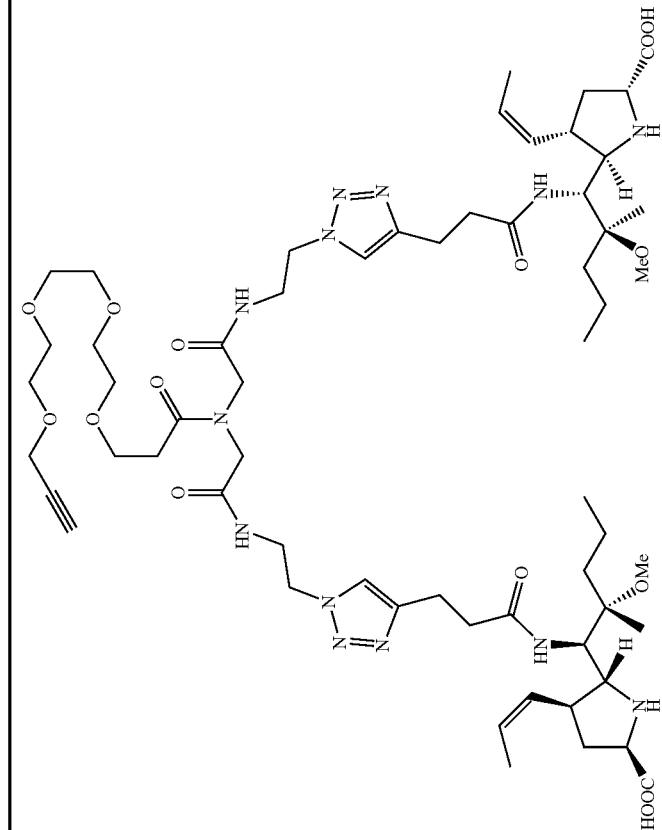 |

TABLE 1a-continued

Intermediates

| Intermediate | Structure |
|---|---|
| Int-16 | *(structure shown)* |

TABLE 1a-continued

Intermediates

| Intermediate | Structure |
|---|---|
| Int-17 | 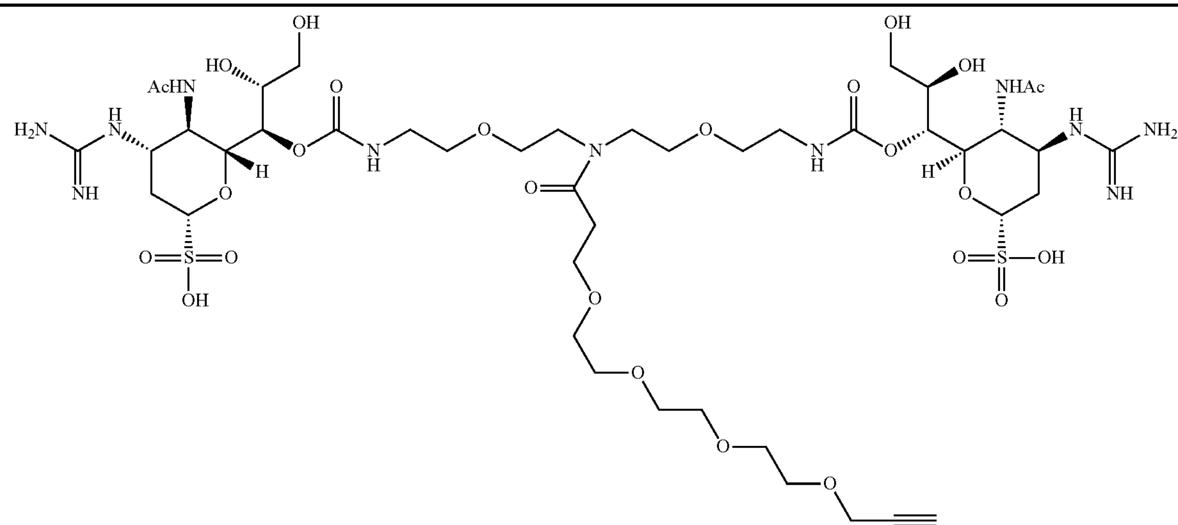 |

TABLE 1a-continued
Intermediates
| Intermediate | Structure |
|---|---|
| Int-18 | 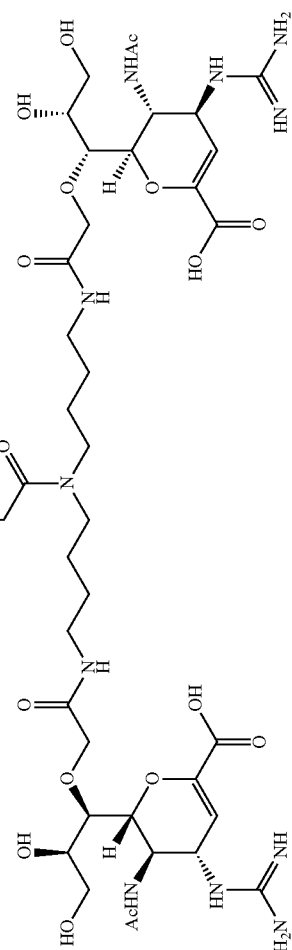 |

TABLE 1a-continued
Intermediates
| Intermediate | Structure |
|---|---|
| Int-19 | 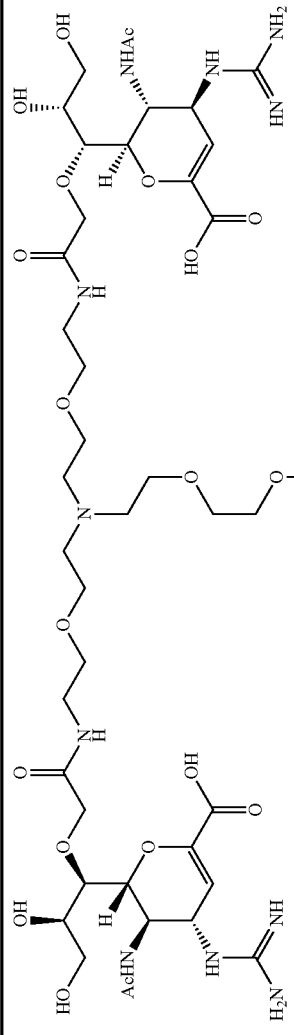 |
| Int-20 | 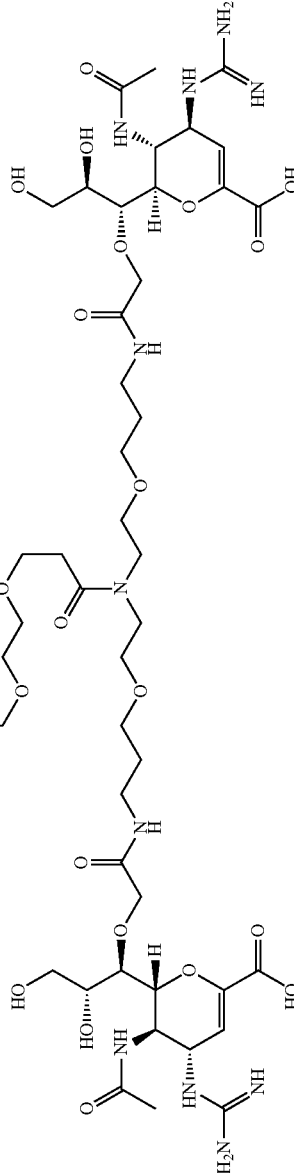 |

TABLE 1a-continued
Intermediates
| Intermediate | Structure |
|---|---|
| Int-21 | 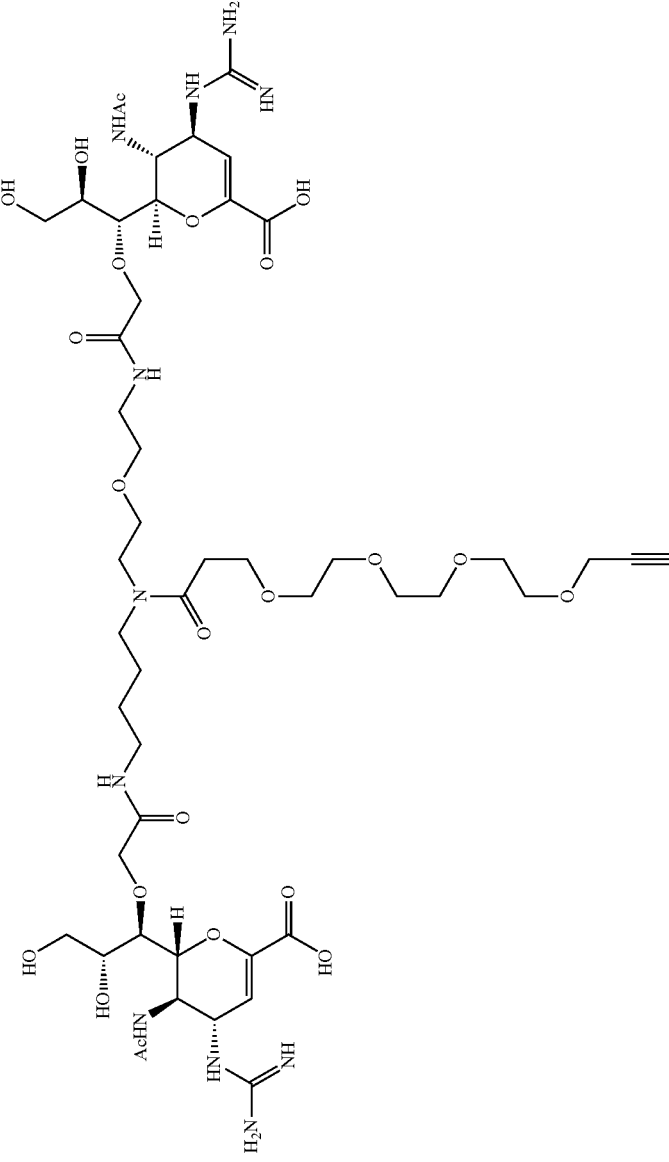 |
| Int-22 | 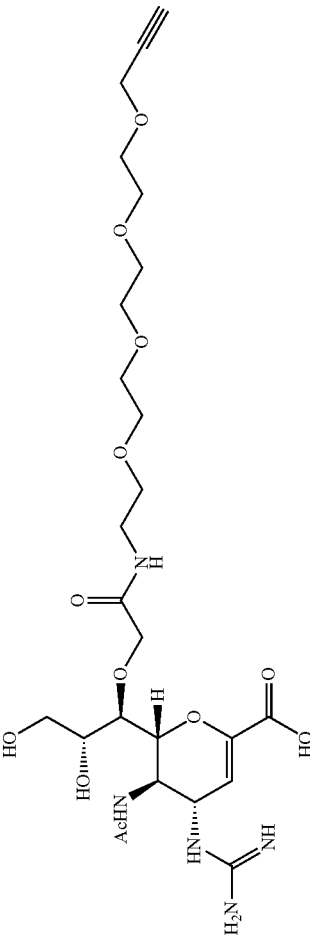 |

TABLE 1a-continued
Intermediates
| Intermediate | Structure |
|---|---|
| Int-23 | 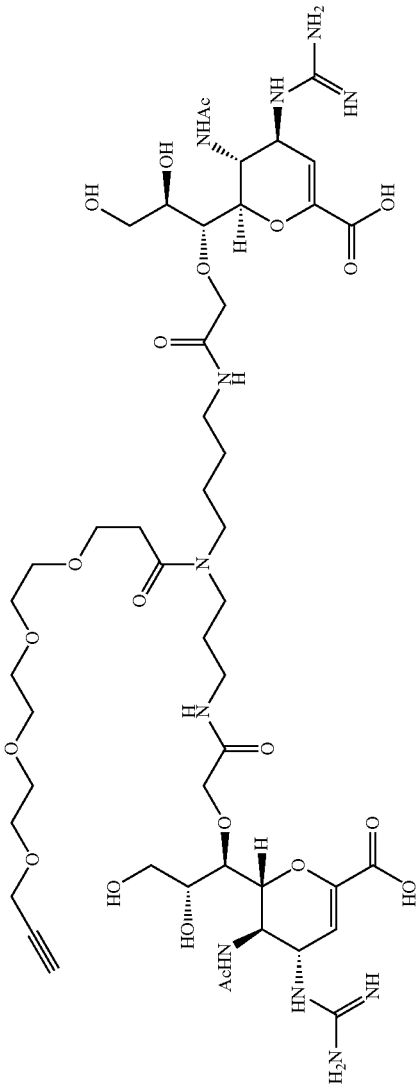 |
| Int-24 | 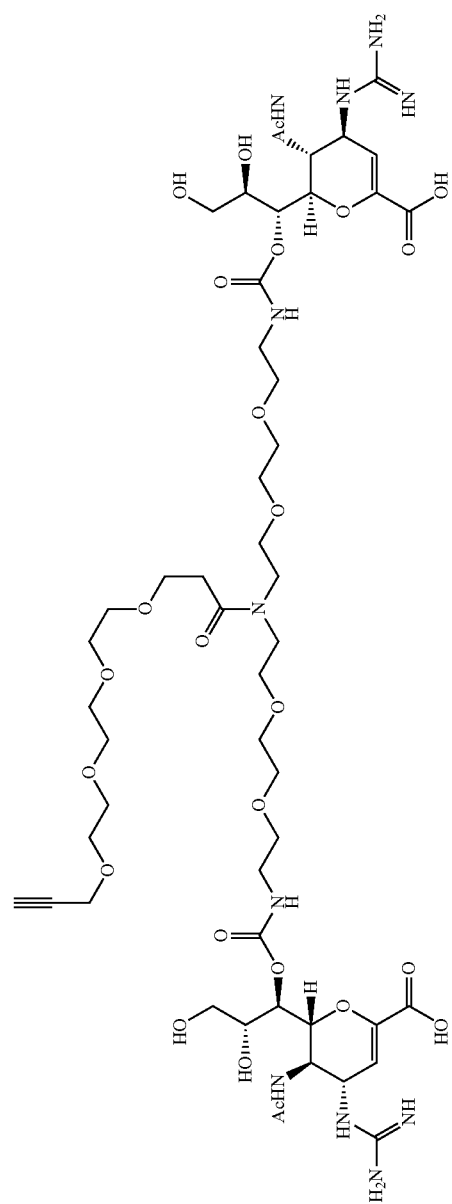 |

TABLE 1a-continued
Intermediates
| Intermediate | Structure |
|---|---|
| Int-25 | 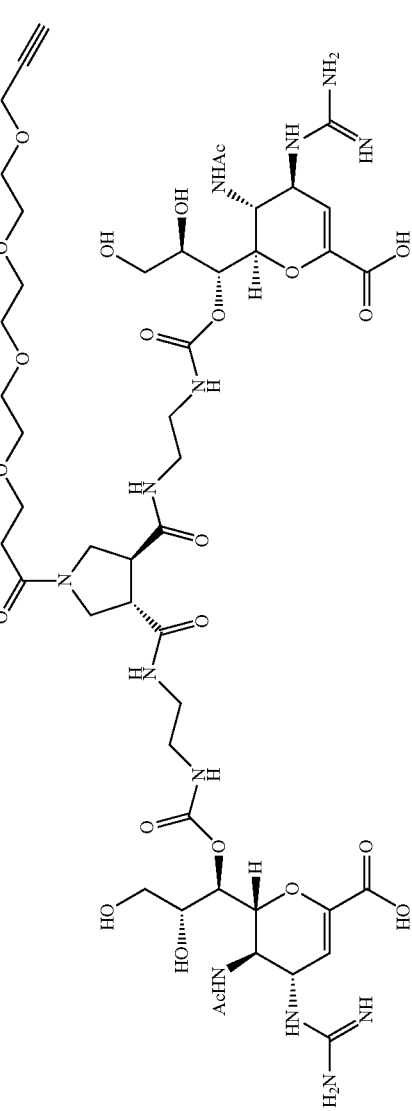 |
| Int-26 | 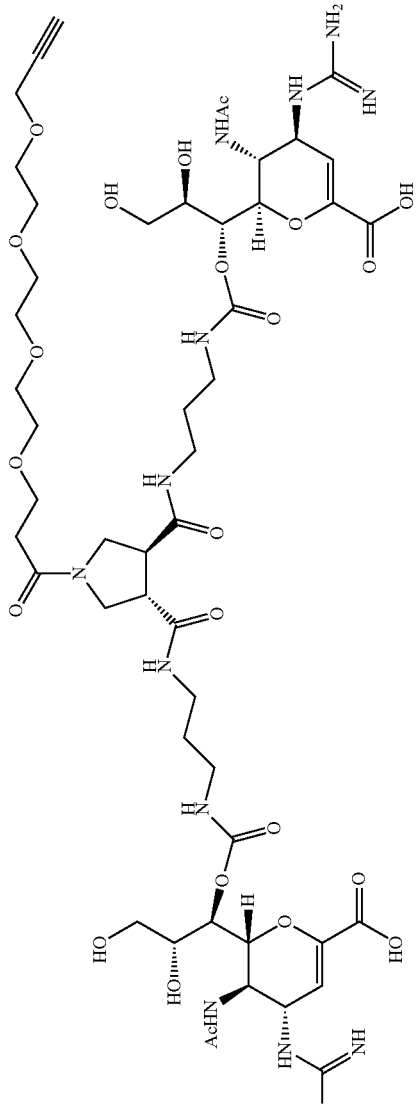 |

TABLE 1a-continued
Intermediates
| Intermediate | Structure |
|---|---|
| Int-27 | 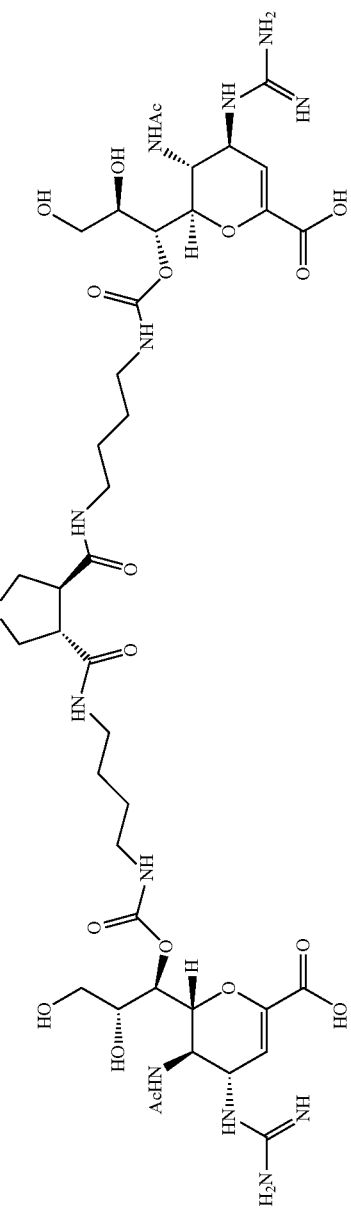 |
| Int-28 | 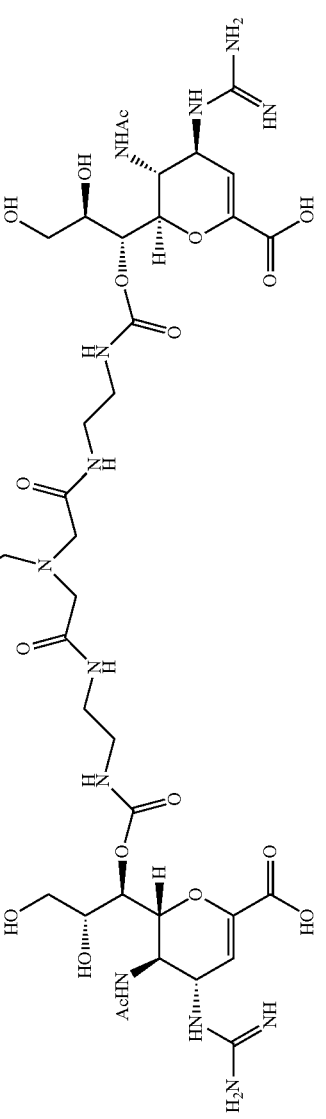 |

TABLE 1a-continued

Intermediates

| Intermediate | Structure |
|---|---|
| Int-30 | (structure) |
| Int-31 | (structure) |

TABLE 1a-continued

Intermediates

| Intermediate | Structure |
|---|---|
| Int-34 | (structure) |

TABLE 1a-continued
Intermediates
| Intermediate | Structure |
|---|---|
| Int-38 | 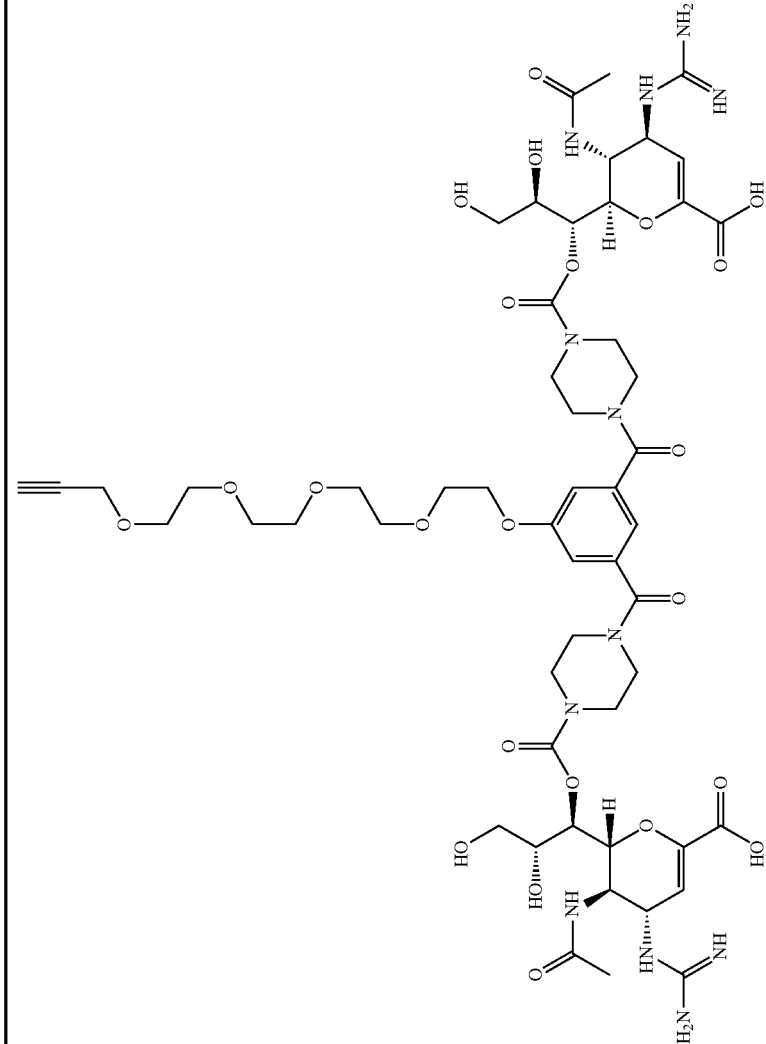 |

TABLE 1a-continued
Intermediates
| Intermediate | Structure |
|---|---|
| Int-39 | 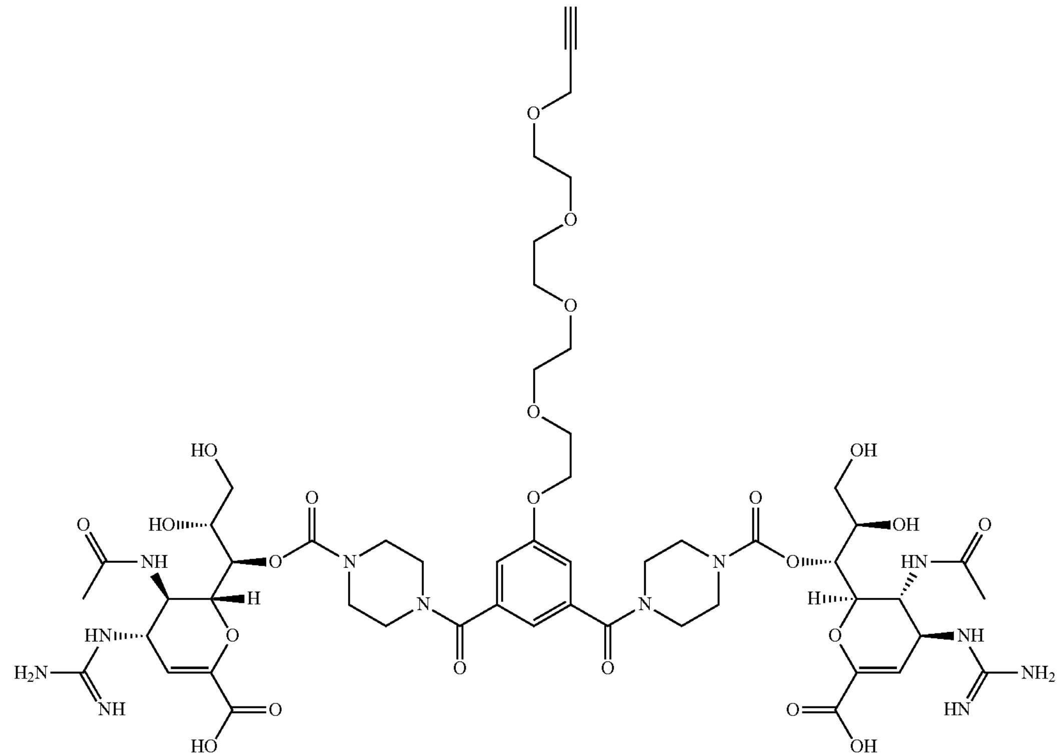 [SMILES: C#CCOCCOCCOCCOCCOc1cc(C(=O)N2CCN(C(=O)O[C@@H]([C@@H]3OC(C(=O)O)=C[C@H](NC(=N)N)[C@H]3NC(C)=O)[C@H](O)CO)CC2)cc(C(=O)N2CCN(C(=O)O[C@@H]([C@@H]3OC(C(=O)O)=C[C@H](NC(=N)N)[C@H]3NC(C)=O)[C@H](O)CO)CC2)c1] |
| Int-40 | 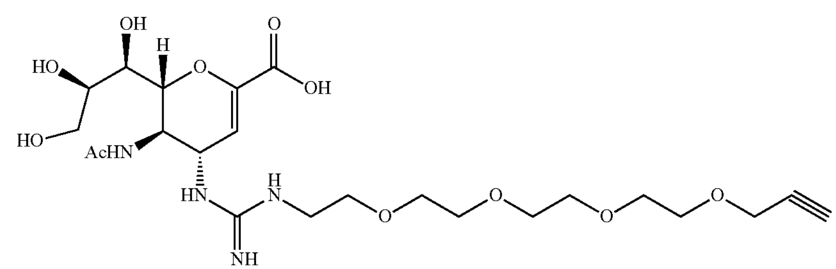 [SMILES: C#CCOCCOCCOCCOCCNC(=N)N[C@H]1C=C(C(=O)O)O[C@@H]([C@H](O)[C@H](O)CO)[C@@H]1NC(C)=O] |
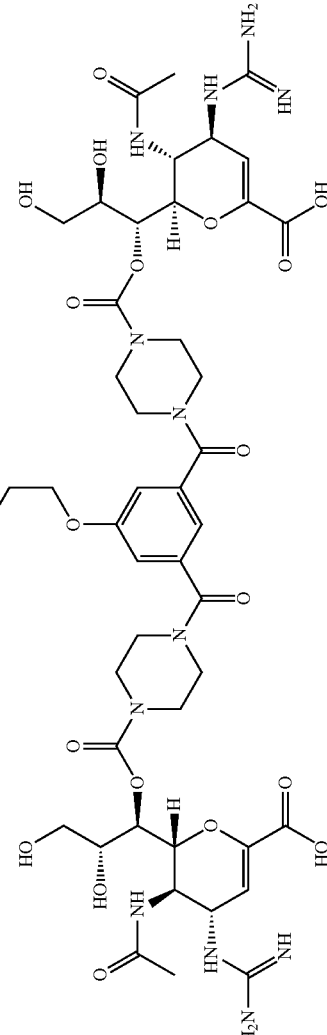

TABLE 1a-continued
Intermediates
| Intermediate | Structure |
|---|---|
| Int-42 | 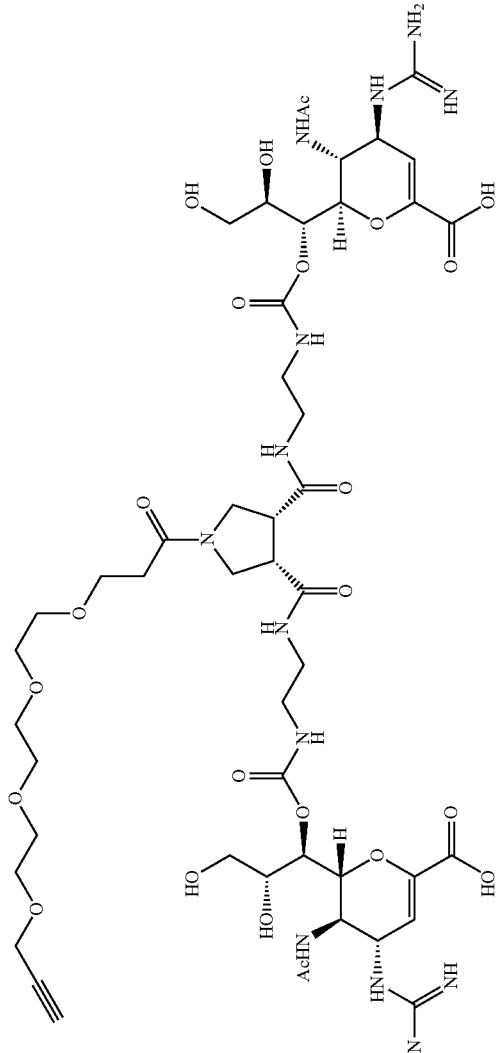 |
| Int-43 | 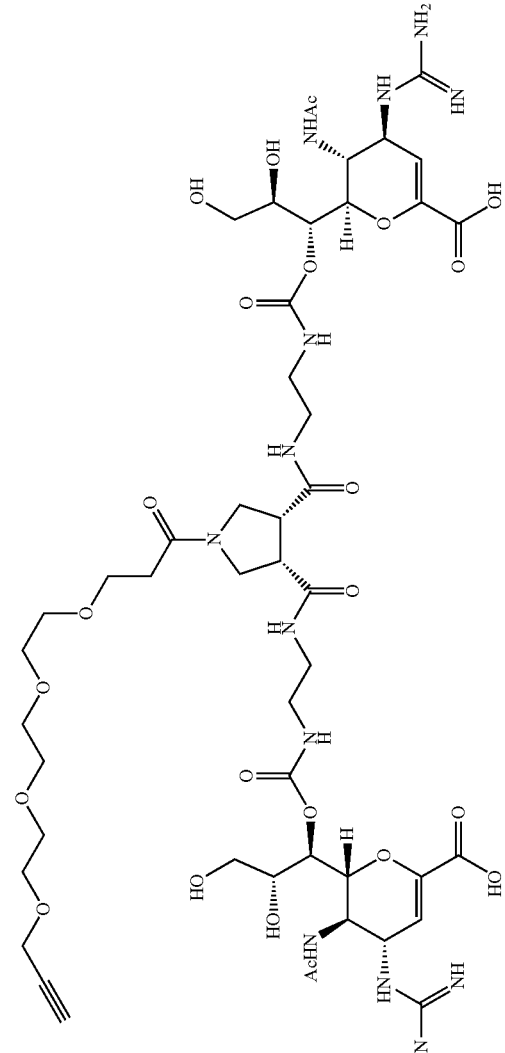 |

TABLE 1a-continued
Intermediates
| Intermediate | Structure |
|---|---|
| Int-44 | 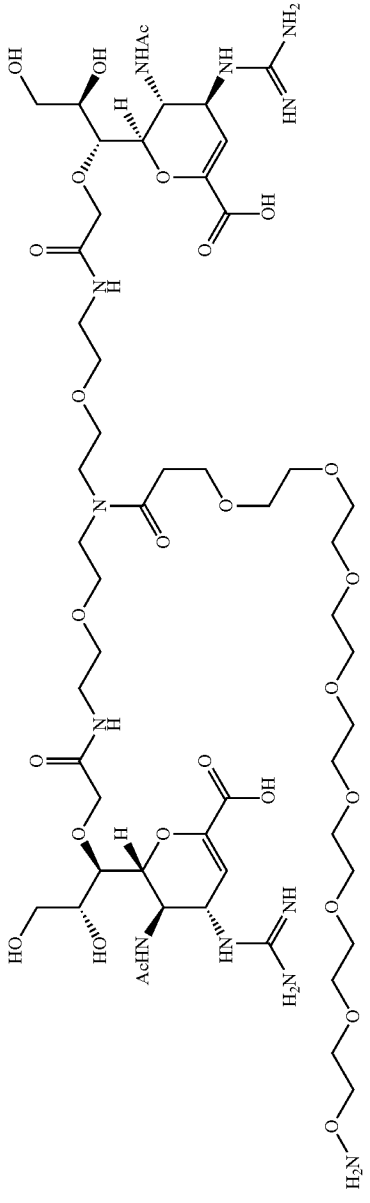 |
| Int-45 | 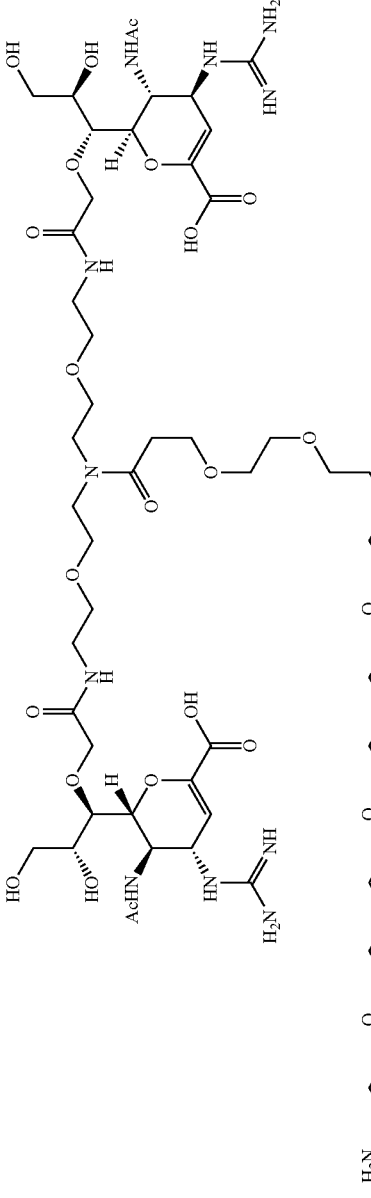 |

TABLE 1a-continued

Intermediates

| Intermediate | Structure |
|---|---|
| Int-46 | (structure) |
| Int-47 | (structure) |

TABLE 1a-continued
Intermediates
| Intermediate | Structure |
|---|---|
| Int-48 | 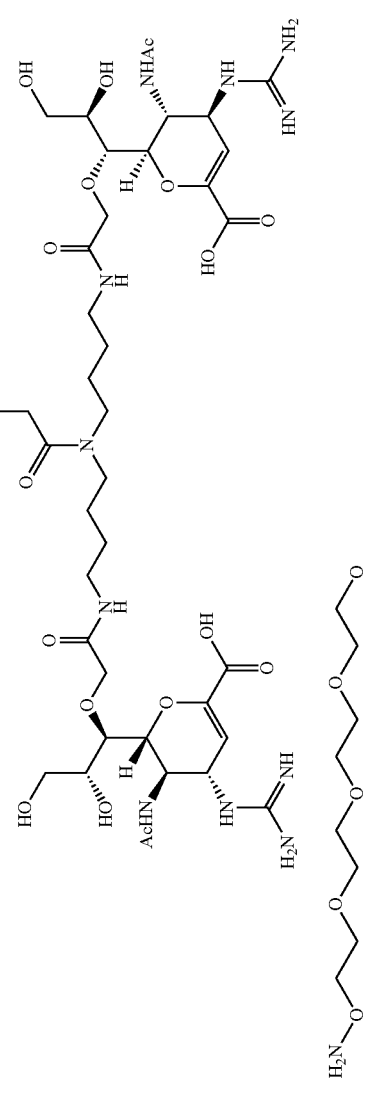 |
| Int-49 | 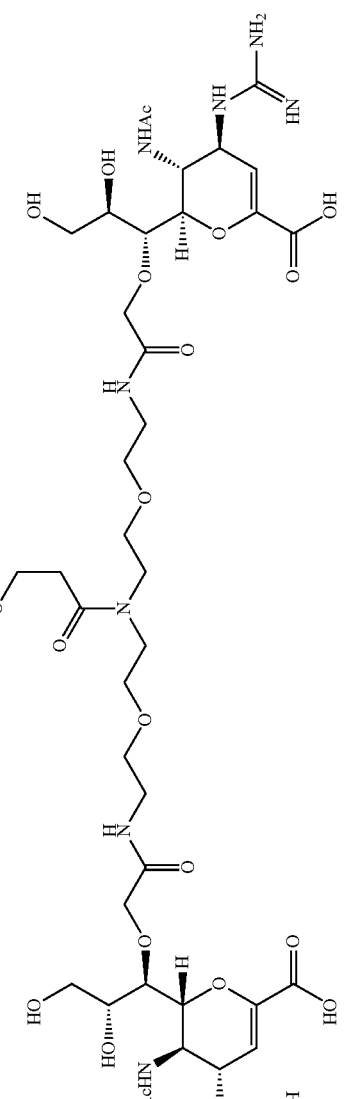 |

TABLE 1a-continued
Intermediates
| Intermediate | Structure |
|---|---|
| Int-50 | 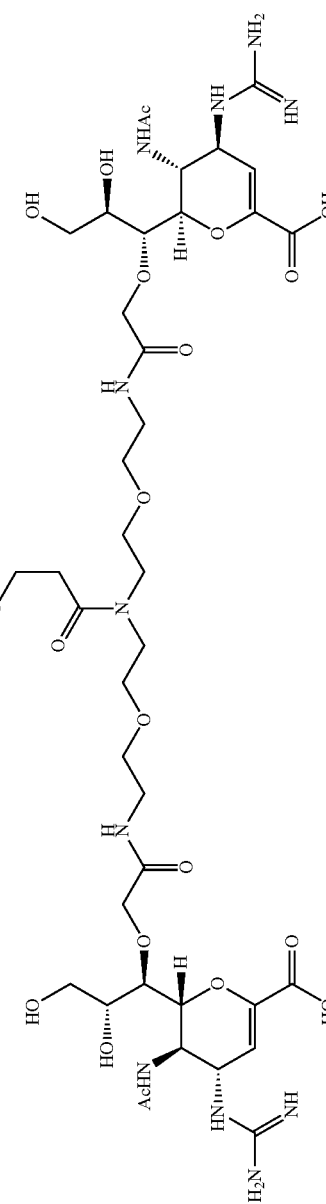 |
| Int-52 | 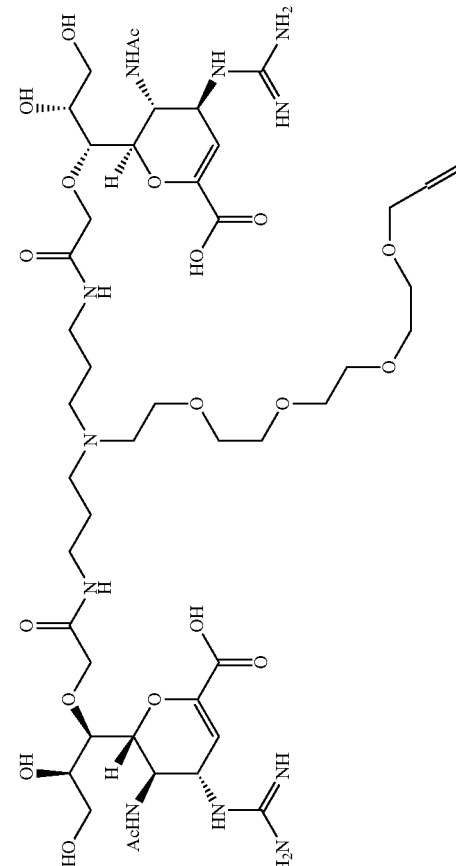 |

TABLE 1a-continued

Intermediates

| Intermediate | Structure |
|---|---|
| Int-53 | 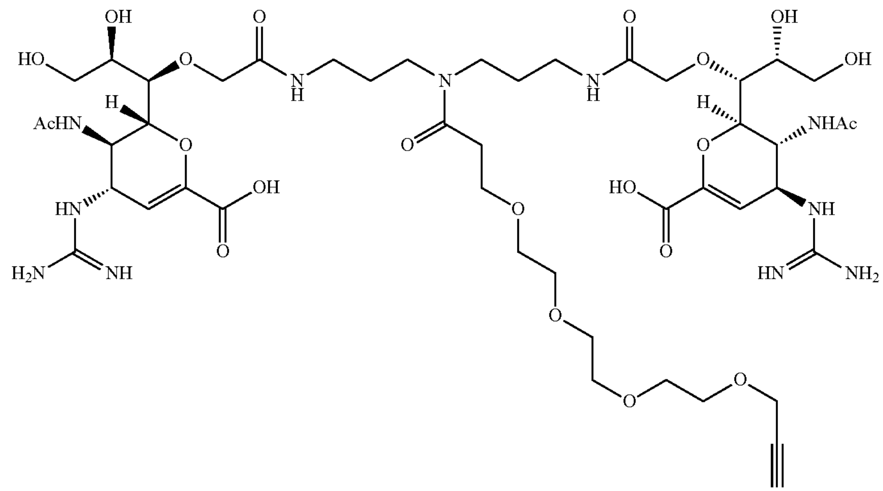 [SMILES: C#CCOCCOCCOCCOCCC(=O)N(CCCNC(=O)CO[C@@H]([C@@H]1OC(C(=O)O)=C[C@H](NC(=N)N)[C@H]1NC(C)=O)[C@H](O)CO)CCCNC(=O)CO[C@@H]([C@@H]1OC(C(=O)O)=C[C@H](NC(=N)N)[C@H]1NC(C)=O)[C@H](O)CO] |

TABLE 1a-continued
Intermediates
| Intermediate | Structure |
|---|---|
| Int-54 | 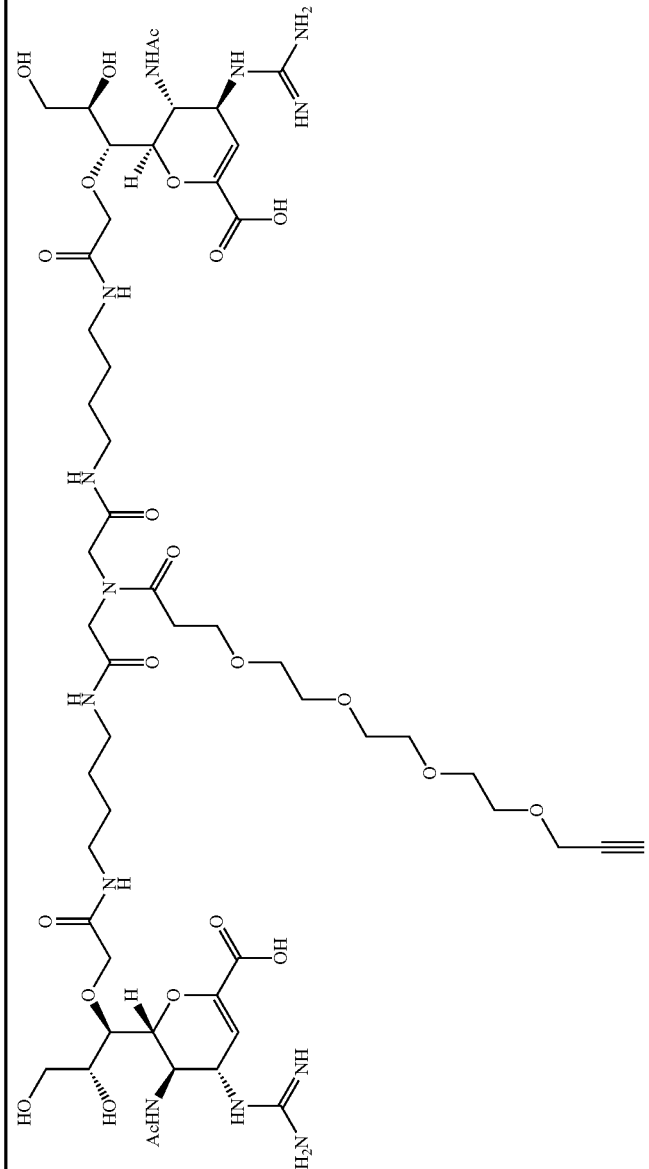 |

TABLE 1a-continued
Intermediates
| Intermediate | Structure |
|---|---|
| Int-55 | 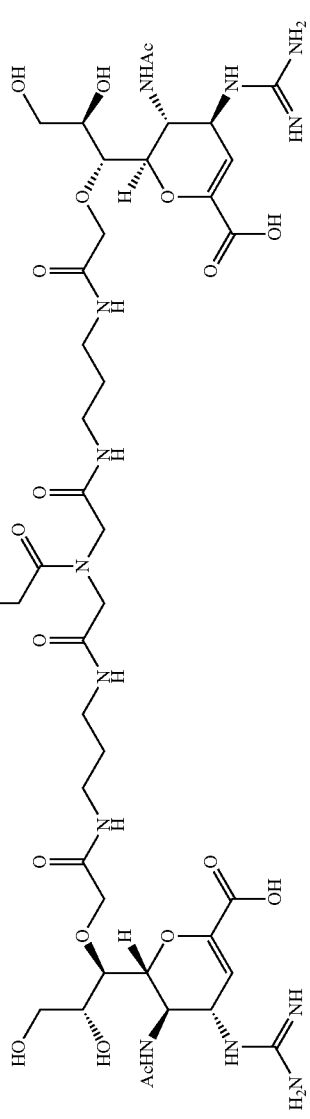 |

TABLE 1a-continued

Intermediates

| Intermediate | Structure |
|---|---|
| Int-57 | (structure) |

TABLE 1a-continued
Intermediates
| Intermediate | Structure |
|---|---|
| Int-58 | 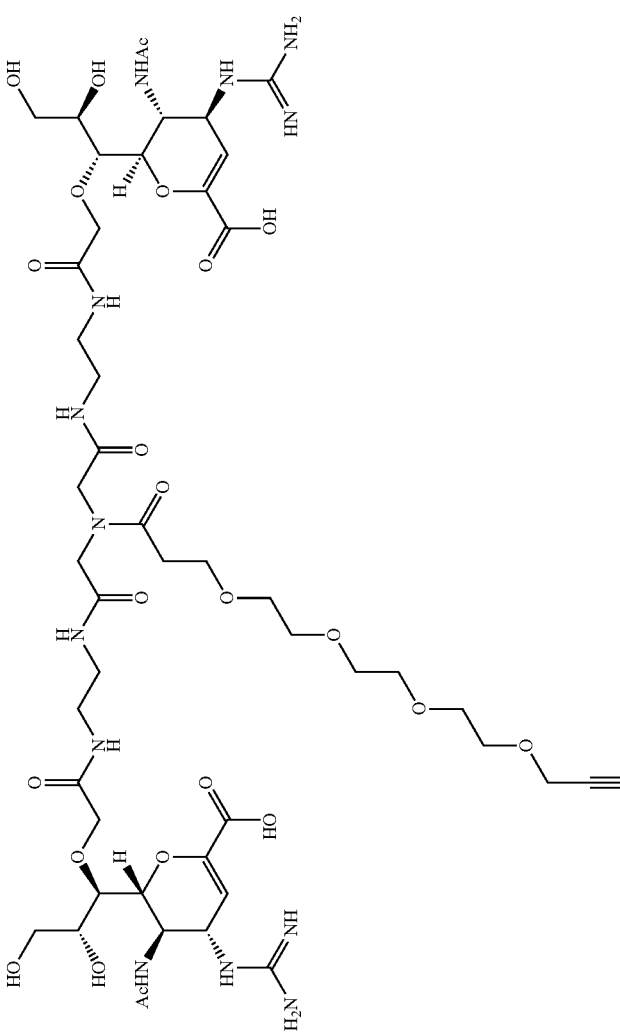 |

TABLE 1a-continued

Intermediates

| Intermediate | Structure |
|---|---|
| Int-59 | (structure) |
| Int-60 | (structure) |

TABLE 1a-continued

Intermediates

| Intermediate | Structure |
|---|---|
| Int-61 | 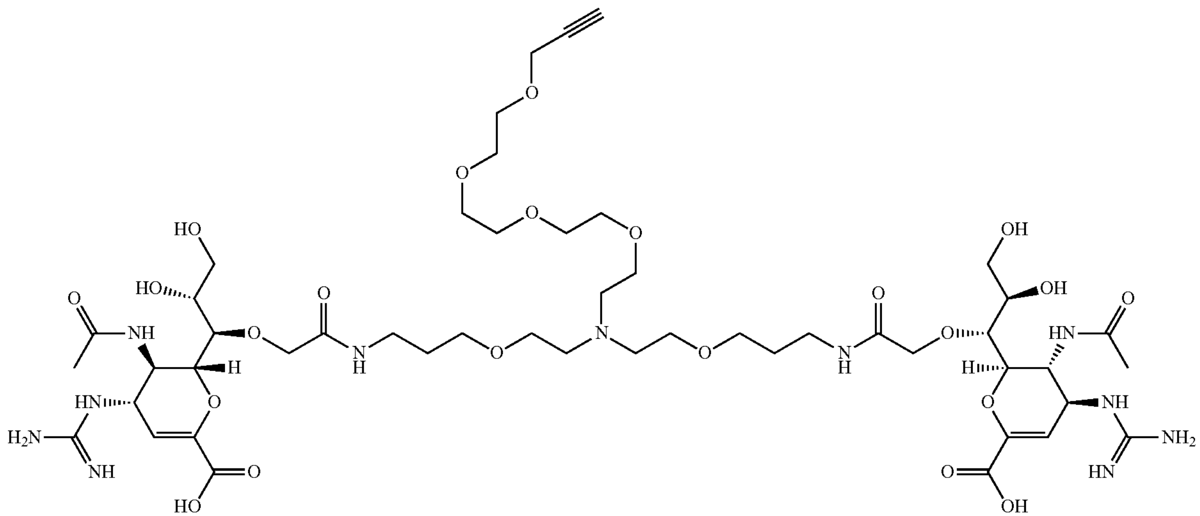 [SMILES: C#CCOCCOCCOCCOCCN(CCOCCCNC(=O)CO[C@@H]([C@@H]1OC(C(=O)O)=C[C@H](NC(=N)N)[C@H]1NC(C)=O)[C@H](O)CO)CCOCCCNC(=O)CO[C@@H]([C@@H]1OC(C(=O)O)=C[C@H](NC(=N)N)[C@H]1NC(C)=O)[C@H](O)CO] |
| Int-62 | 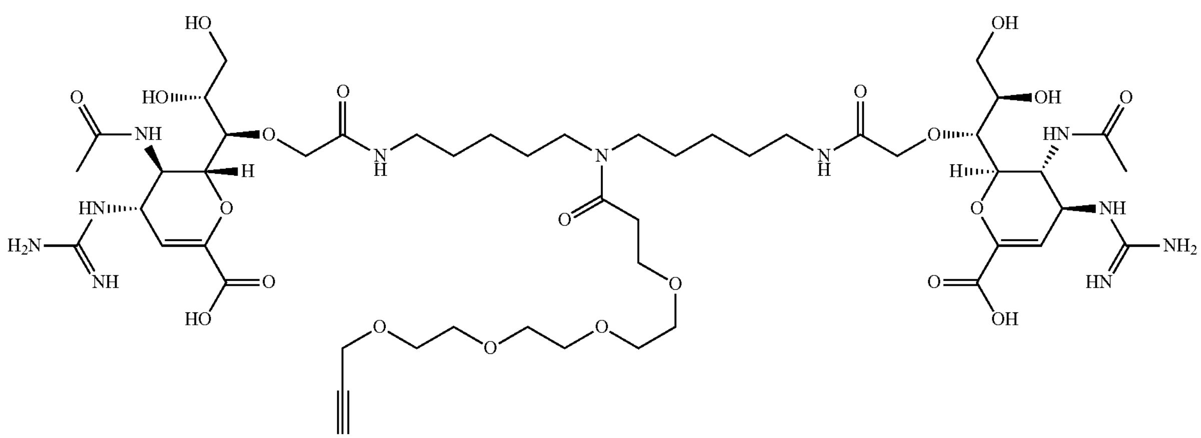 [SMILES: C#CCOCCOCCOCCOCCC(=O)N(CCCCCNC(=O)CO[C@@H]([C@@H]1OC(C(=O)O)=C[C@H](NC(=N)N)[C@H]1NC(C)=O)[C@H](O)CO)CCCCCNC(=O)CO[C@@H]([C@@H]1OC(C(=O)O)=C[C@H](NC(=N)N)[C@H]1NC(C)=O)[C@H](O)CO] |

TABLE 1a-continued
Intermediates
| Intermediate | Structure |
|---|---|
| Int-63 | 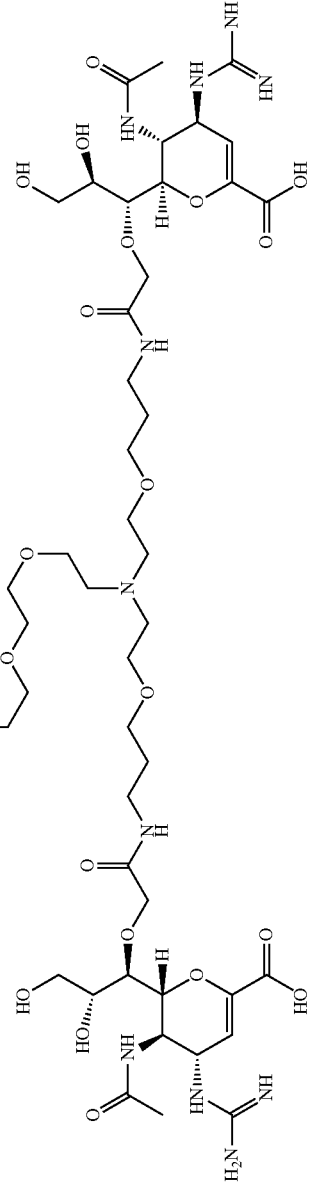 |
| Int-64 | 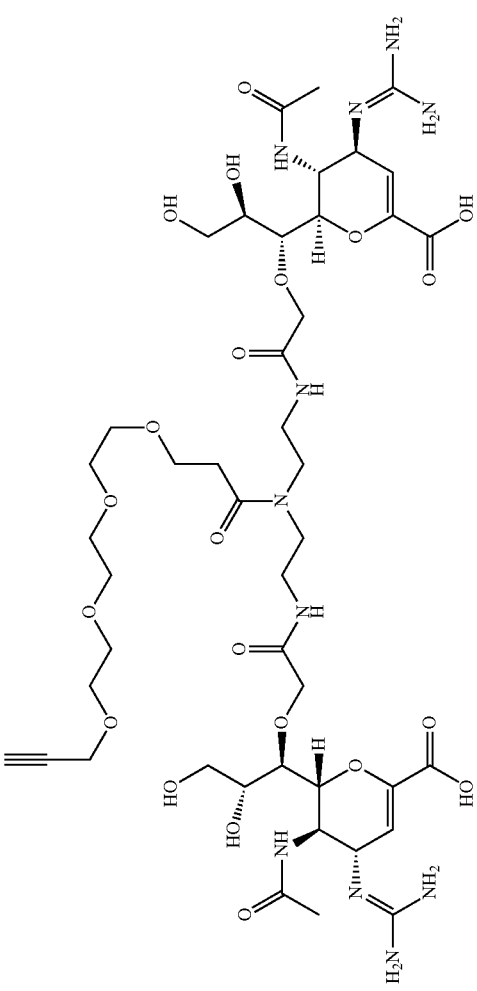 |

TABLE 1a-continued
Intermediates
| Intermediate | Structure |
|---|---|
| Int-65 | 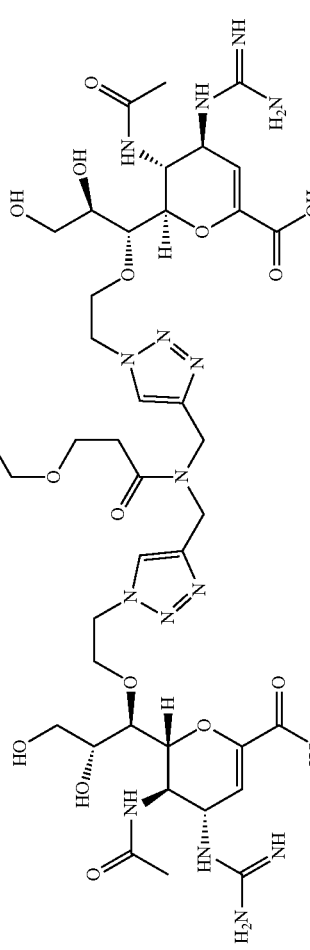 |
| Int-67 | 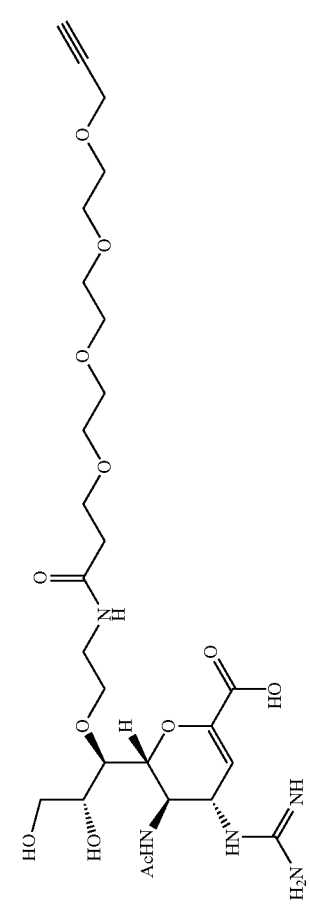 |

TABLE 1a-continued
Intermediates
| Intermediate | Structure |
|---|---|
| Int-68 | 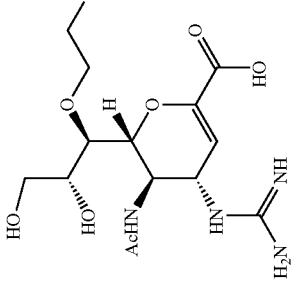 |
| Int-69 | 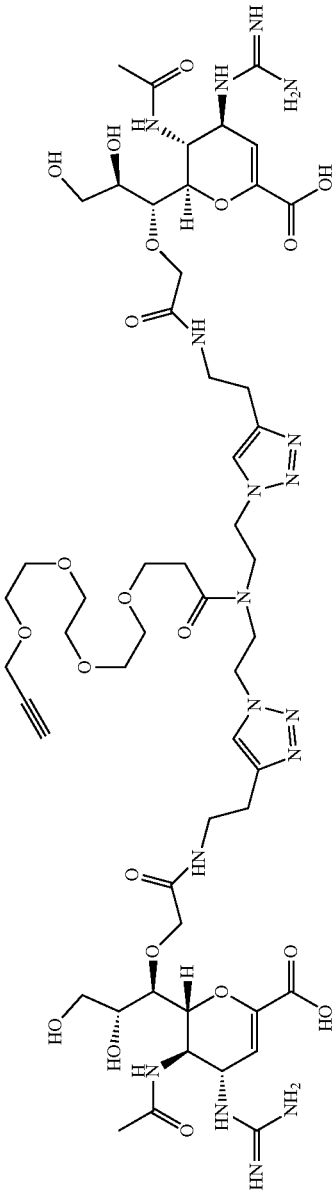 |

TABLE 1a-continued
Intermediates
| Intermediate | Structure |
|---|---|
| Int-70 | 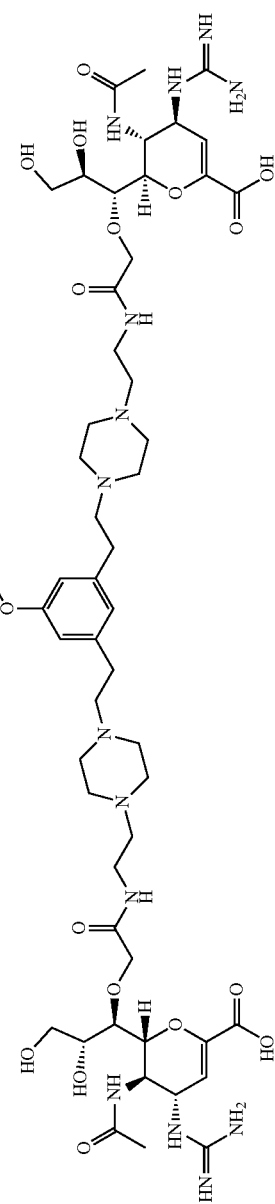 |

TABLE 1a-continued
Intermediates
| Intermediate | Structure |
|---|---|
| Int-71 | 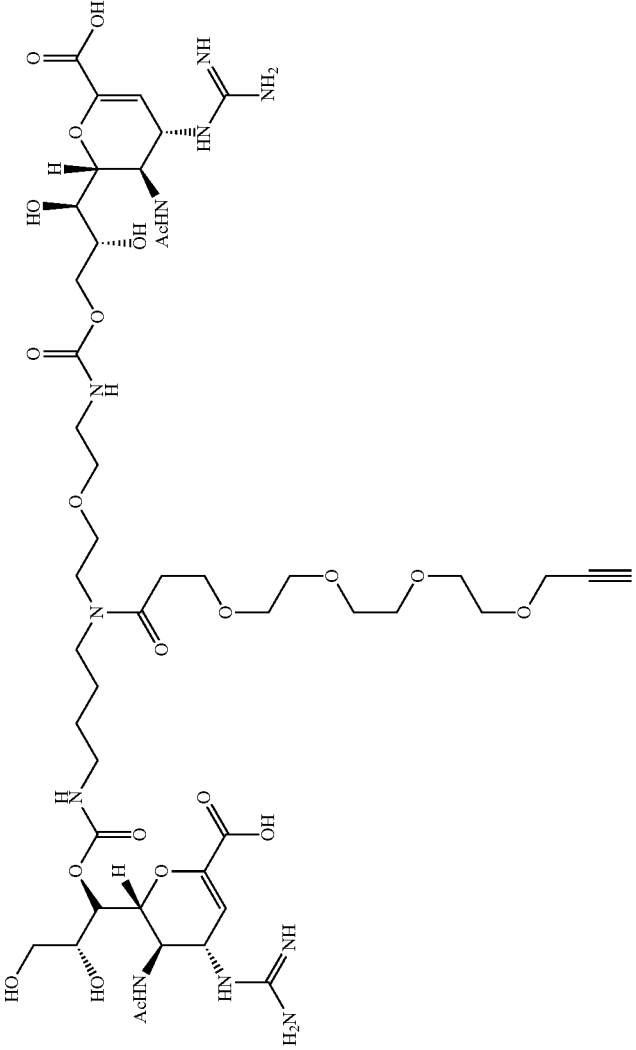 |

TABLE 1a-continued
Intermediates
| Intermediate | Structure |
|---|---|
| Int-72 | 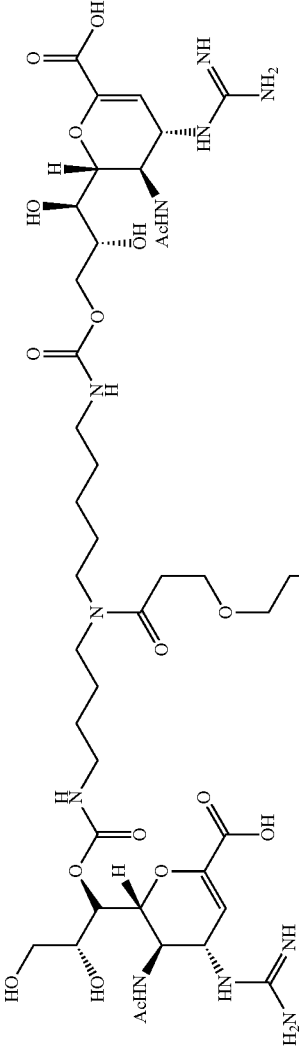 |

TABLE 1a-continued

Intermediates

| Intermediate | Structure |
|---|---|
| Int-73 | (chemical structure) |
| Int-74 | (chemical structure) |

TABLE 1a-continued

Intermediates

| Intermediate | Structure |
|---|---|
| Int-75 | (chemical structure) |
| Int-76 | (chemical structure) |

TABLE 1a-continued
Intermediates
Structure
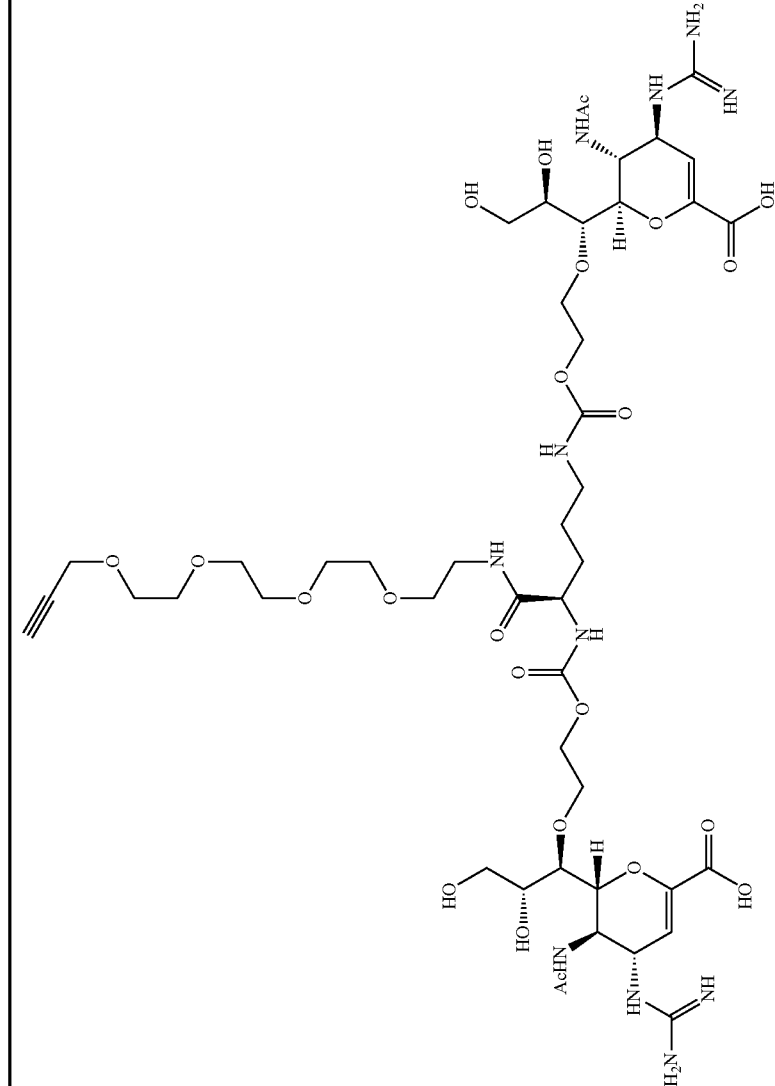
Intermediate
Int-77

TABLE 1a-continued

Intermediates

| Intermediate | Structure |
|---|---|
| Int-78 | 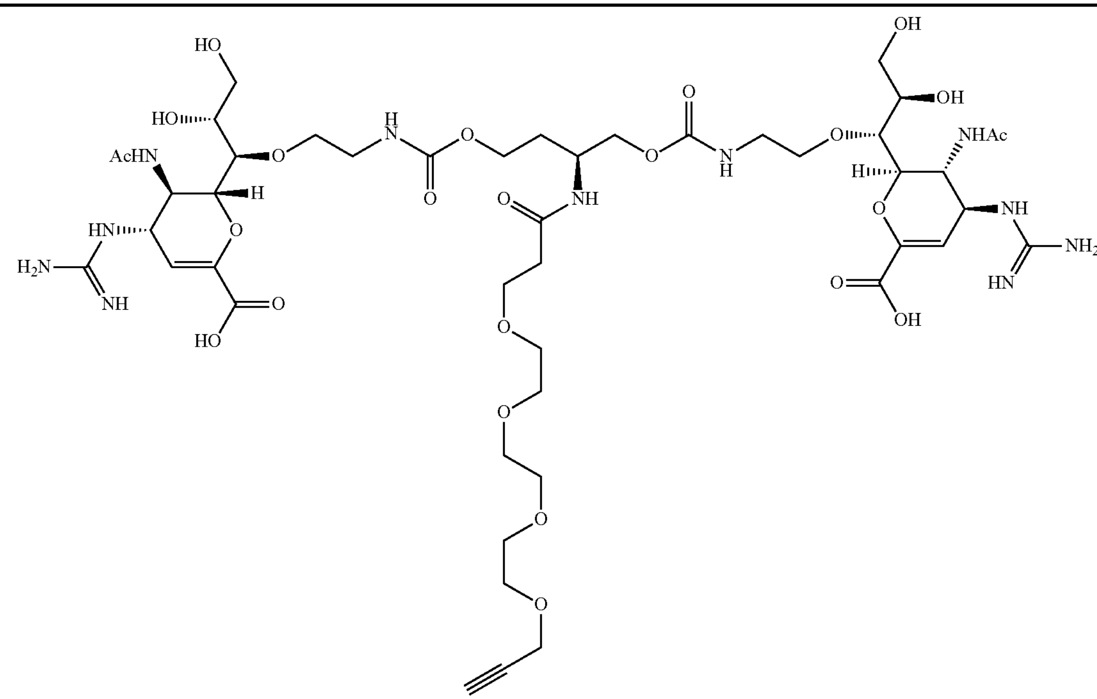 |

TABLE 1a-continued
Intermediates
| Intermediate | Structure |
|---|---|
| Int-79 | 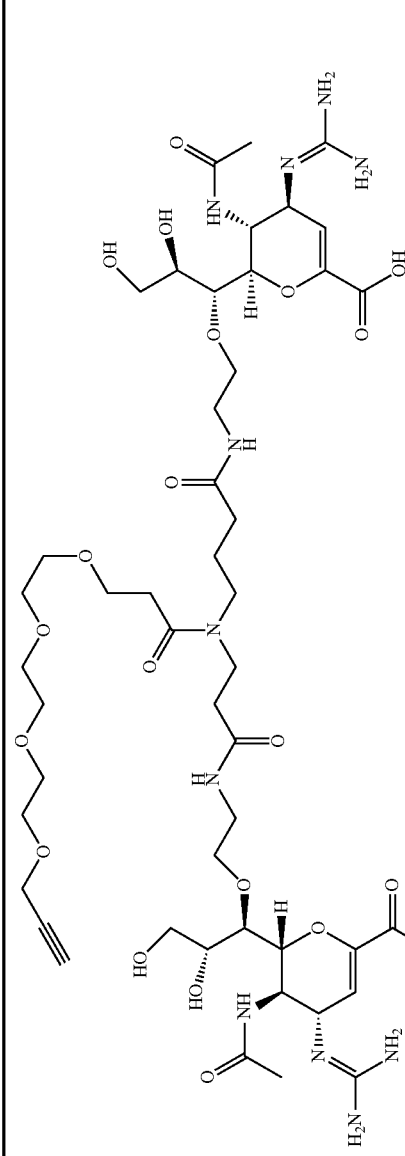 |
| Int-80 | 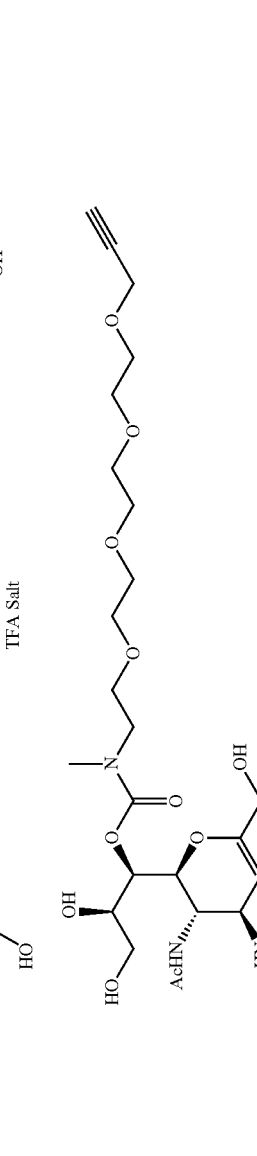 TFA Salt |

TABLE 1a-continued

Intermediates

| Intermediate | Structure |
|---|---|
| Int-81 | 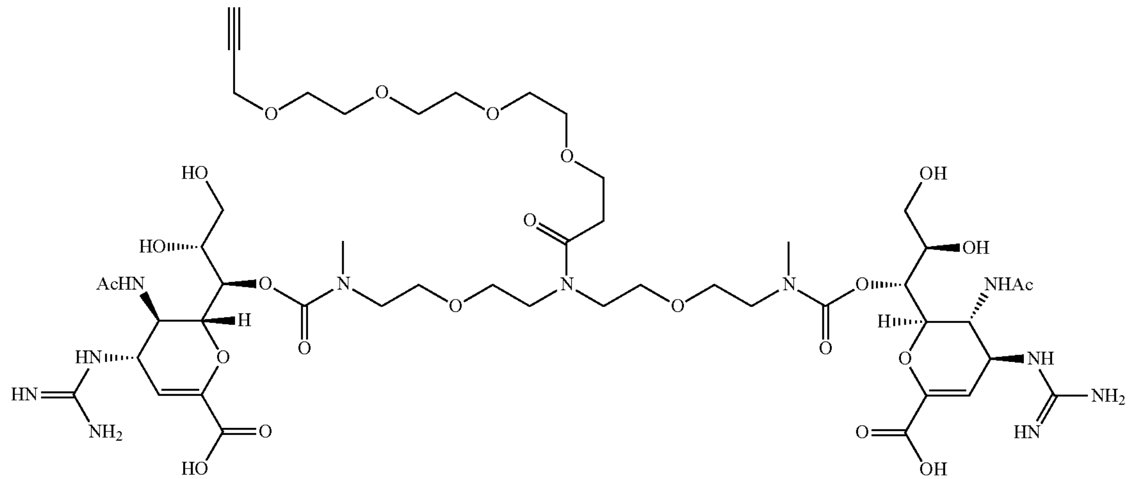 [SMILES: C#CCOCCOCCOCCOCCC(=O)N(CCOCCN(C)C(=O)O[C@@H]([C@@H]1OC(C(=O)O)=C[C@H](NC(=N)N)[C@H]1NC(C)=O)[C@H](O)CO)CCOCCN(C)C(=O)O[C@@H]([C@@H]1OC(C(=O)O)=C[C@H](NC(=N)N)[C@H]1NC(C)=O)[C@H](O)CO] |
| Int-82 | 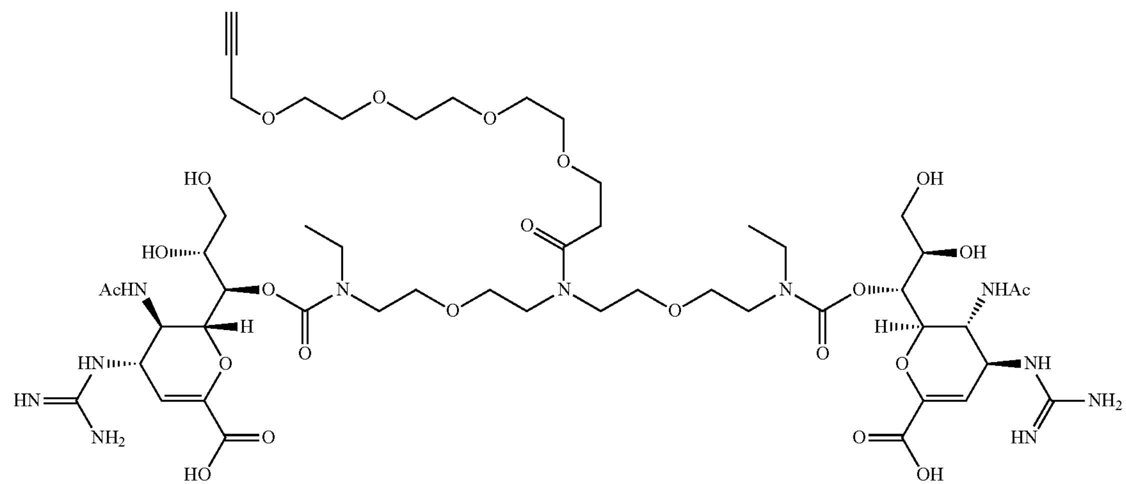 [SMILES: C#CCOCCOCCOCCOCCC(=O)N(CCOCCN(CC)C(=O)O[C@@H]([C@@H]1OC(C(=O)O)=C[C@H](NC(=N)N)[C@H]1NC(C)=O)[C@H](O)CO)CCOCCN(CC)C(=O)O[C@@H]([C@@H]1OC(C(=O)O)=C[C@H](NC(=N)N)[C@H]1NC(C)=O)[C@H](O)CO] |

TABLE 1a-continued

Intermediates

| Intermediate | Structure |
|---|---|
| Int-83 | (structure shown) |

TABLE 1a-continued

Intermediates

| Intermediate | Structure |
|---|---|
| Int-84 | (structure) |
| Int-85 | (structure) |

TABLE 1a-continued

Intermediates

| Intermediate | Structure |
|---|---|
| Int-86 | (chemical structure) |
| Int-87 | (chemical structure) |

TABLE 1a-continued

Intermediates

| Intermediate | Structure |
|---|---|
| Int-88 | (structure) |
| Int-89 | (structure) |

TABLE 1a-continued
Intermediates
| Intermediate | Structure |
|---|---|
| Int-90 | 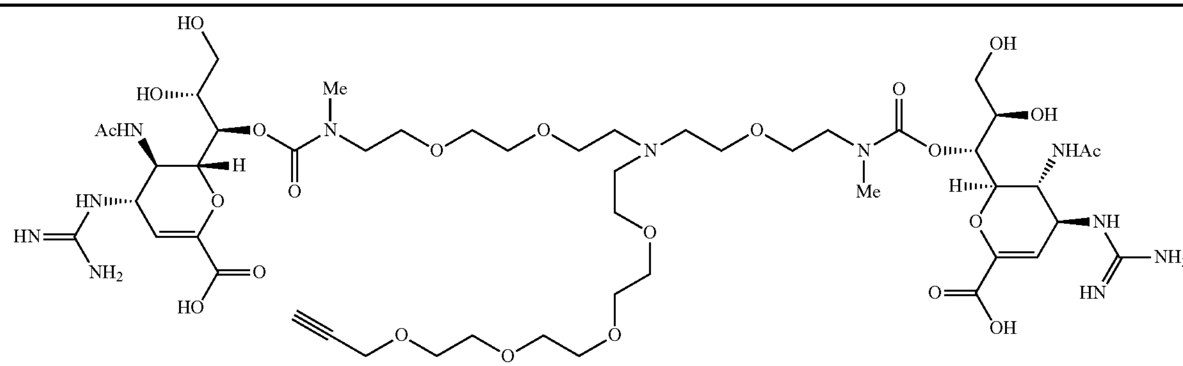 |
| Int-91 | 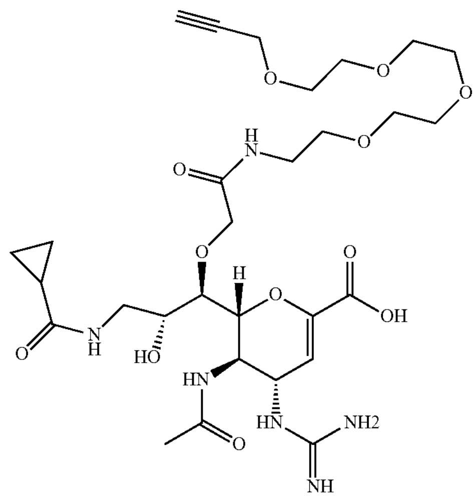 [SMILES: C#CCOCCOCCOCCOCCNC(=O)CO[C@@H]([C@@H]1OC(C(=O)O)=C[C@H](NC(=N)N)[C@H]1NC(C)=O)[C@H](O)CNC(=O)C1CC1] |
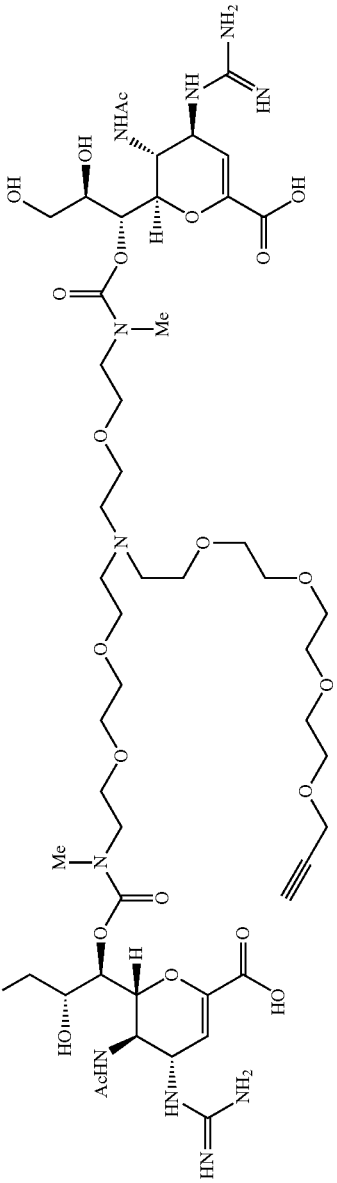

TABLE 1a-continued
Intermediates
| Intermediate | Structure |
|---|---|
| Int-92 | 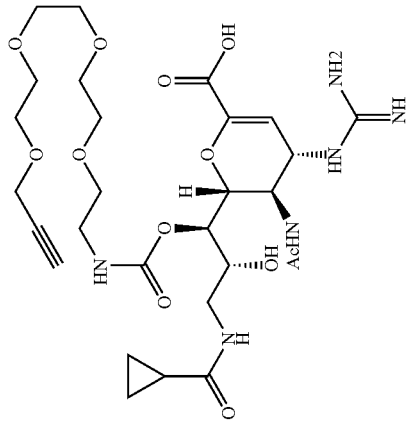 |

In another aspect, the invention features conjugates of Table 1b. Each conjugate of Table 1b corresponds to a conjugate of either formula (M-I) or formula (D-I), as indicated. Conjugates of Table 1b include conjugates formed by the covalent reaction of an Int of Table 1a with a linker which is in turn conjugated to E (e.g., an Fc domain monomer, an albumin protein, an albumin protein-binding peptide, or an Fc-binding peptide). In some embodiments, the reactive moiety of the Int (e.g., the alkyne or azido group) reacts with a corresponding reactive group (e.g., an alkyne or azido group) of a linker (represented by L') covalently attached to E, such that an Int of Table 1a is covalently attached to E. As represented in Table 1b, L' corresponds to the remainder of L as defined in (M-I) or (D-I) (e.g., L' is a linker that covalently joins the Int and E). For example, L' may include a triazole (formed by the click chemistry reaction between the Int and a linker conjugated to E) and a linker (e.g., a $PEG_2$-$PEG_{20}$ linker) which in turn is conjugated to an amino acid side chain of E (see, e.g., FIG. 103).

In some embodiments the conjugate of Table 1b, n is 1 or 2. When n is 1, each E includes an Fc domain monomer (e.g., an Fc domain monomer having the sequence of any one of SEQ ID NOs: 1-138), an albumin protein (e.g., an albumin protein having a sequence of any one of SEQ ID NOs: 139-141), an albumin protein-binding peptide, or an Fc-binding peptide. When n is 2, each E includes an Fc domain monomer (e.g., an Fc domain monomer having the sequence of any one of SEQ ID NOs: 1-138), and the Fc domain monomers dimerize to form an Fc domain.

In some embodiments of any conjugate of Table 1b, T is an integer from 1 to 20 (e.g., 1, 2, 3, 4, 5, 6, 7, 8, 9, 10, 11, 12, 13, 14, 15, 16, 17, 18, 19, or 20). The disclosure also provides a population of any of the conjugates of Table 2 wherein the average value of T is 1 to 20 (e.g., the average value of T is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5). In some embodiments, the average value of T is 1, 2, 3, 4, 5, 6, 7, 8, 9, 10, 11, 12, 13, 14, 15, 16, 17, 18, 19, or 20. In certain embodiments, the average T is 1 to 10 (e.g., 1.5, 2, 2.5, 3, 3.5, 4, 4.5, 5, 5.5, 6, 6.5, 7, 7.5, 8, 8.5, 9, 9.5, or 10). In certain embodiments, the average T is 1 to 5 (e.g., 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5). In some embodiment, the average T is 5 to 10 (e.g., 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10). In some embodiments, the average T is 2.5 to 7.5 (e.g., 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, or 7.5).

The squiggly line in the conjugates of Table 1b indicates that each L'-Int is covalently attached to an amino acid side chain in E (e.g., the nitrogen atom of a surface exposed lysine or the sulfur atom of a surface exposed cysteine in E), or a pharmaceutically acceptable salt thereof.

TABLE 1b
Conjugates Corresponding to Intermediates of Table 1a
| Corresponding Intermediate of Table 1a | Described by Formula | Conjugate Structure |
|---|---|---|
| Int-1 | (D-I) | 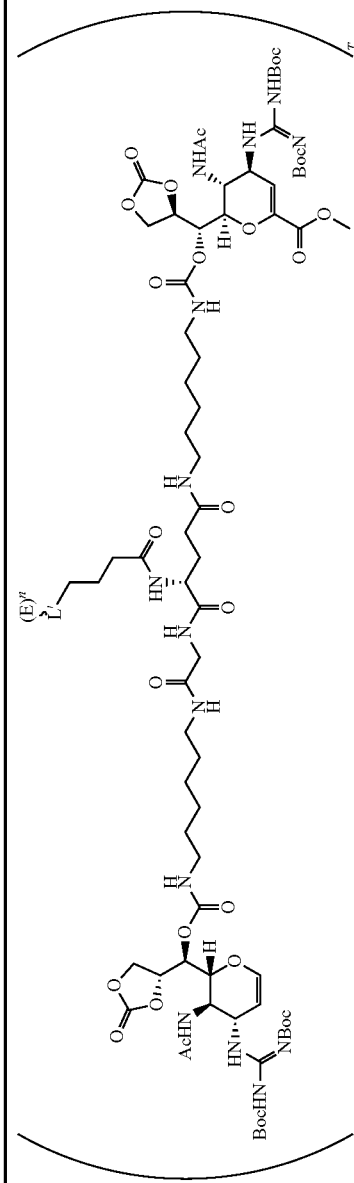 |
| Int-2 | (D-I) | 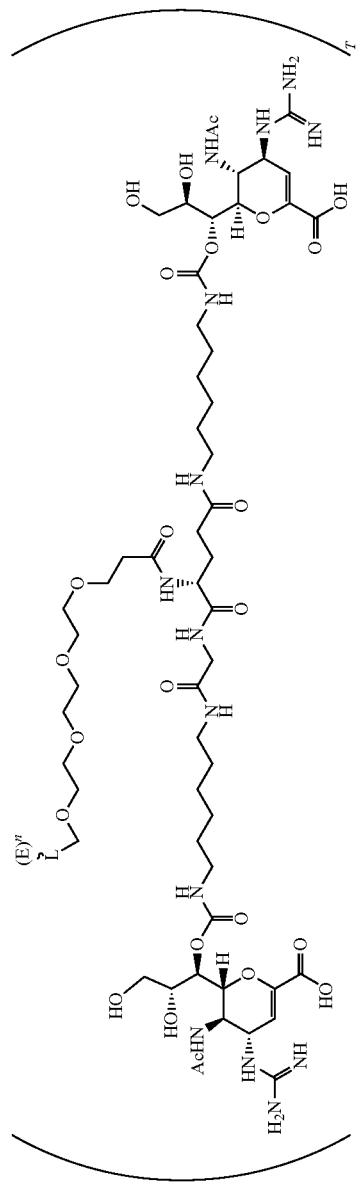 |

TABLE 1b-continued

Conjugates Corresponding to Intermediates of Table 1a

| Corresponding Intermediate of Table 1a | Described by Formula | Conjugate Structure |
|---|---|---|
| Int-3 | (D-I) | |
| Int-4 | (M-I) | |

TABLE 1b-continued
Conjugates Corresponding to Intermediates of Table 1a
| Corresponding Intermediate of Table 1a | Described by Formula | Conjugate Structure |
|---|---|---|
| Int-5 | (M-I) | 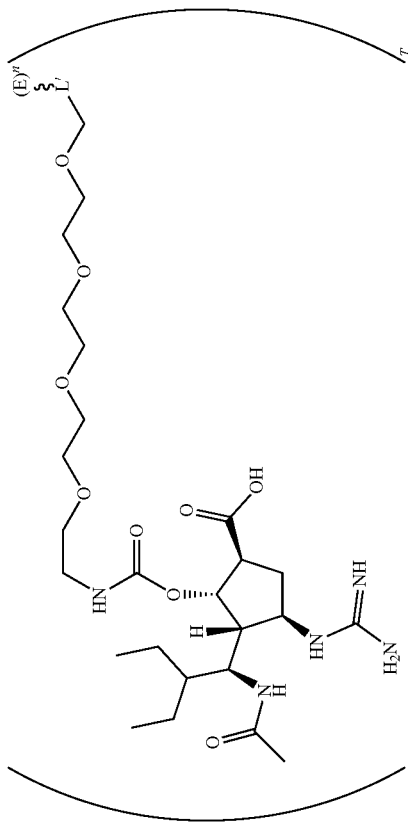 |
| Int-6 | (D-I) | 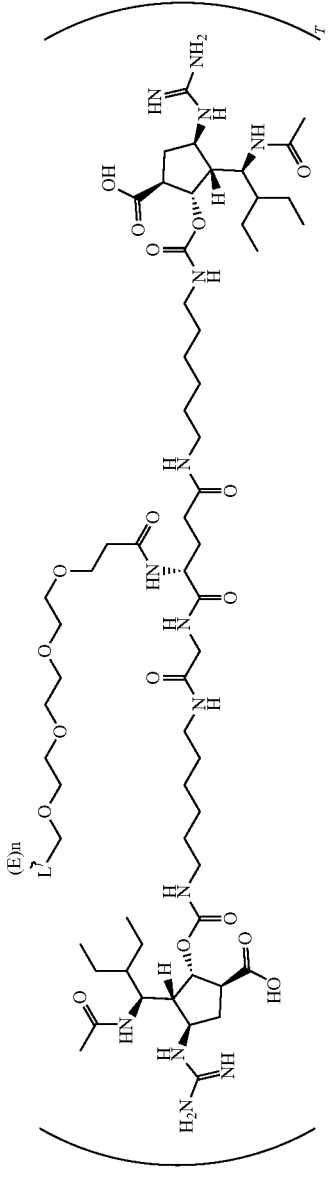 |

TABLE 1b-continued
Conjugates Corresponding to Intermediates of Table 1a
| Corresponding Intermediate of Table 1a | Described by Formula | Conjugate Structure |
|---|---|---|
| Int-7 | (D-I) | 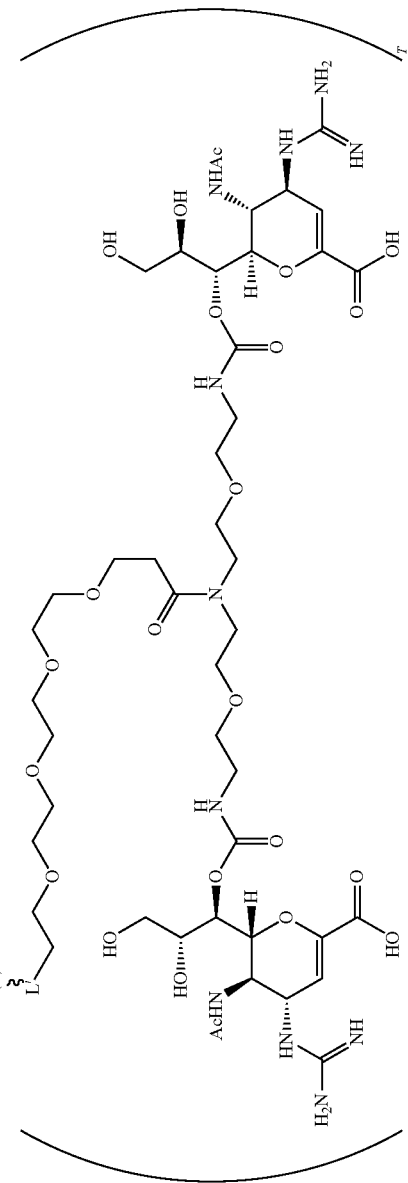 |
| Int-9 | (D-I) | 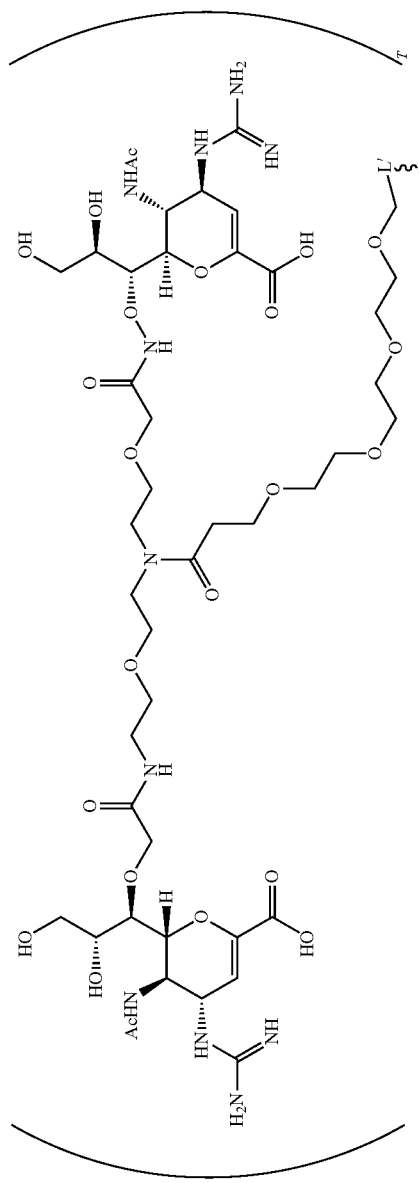 |

TABLE 1b-continued
Conjugates Corresponding to Intermediates of Table 1a
| Corresponding Intermediate of Table 1a | Described by Formula | Conjugate Structure |
|---|---|---|
| Int-12 | (D-I) | 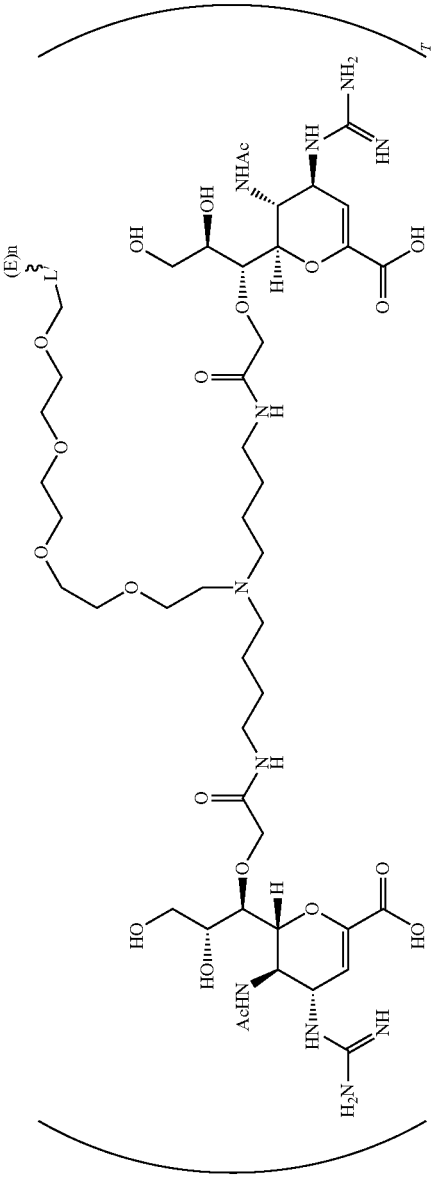 |
| Int-13 | (M-I) | 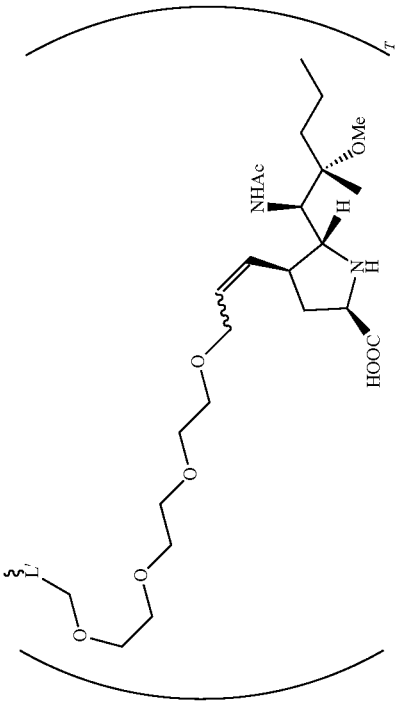 |

TABLE 1b-continued
Conjugates Corresponding to Intermediates of Table 1a
| Corresponding Intermediate of Table 1a | Described by Formula | Conjugate Structure |
|---|---|---|
| Int-14 | (M-I) | 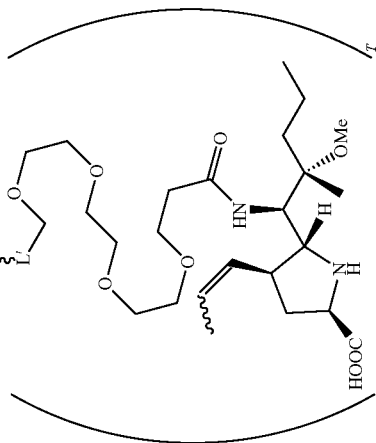 |

TABLE 1b-continued
Conjugates Corresponding to Intermediates of Table 1a
| Corresponding Intermediate of Table 1a | Described by Formula | Conjugate Structure |
|---|---|---|
| Int-15 | (D-I) | 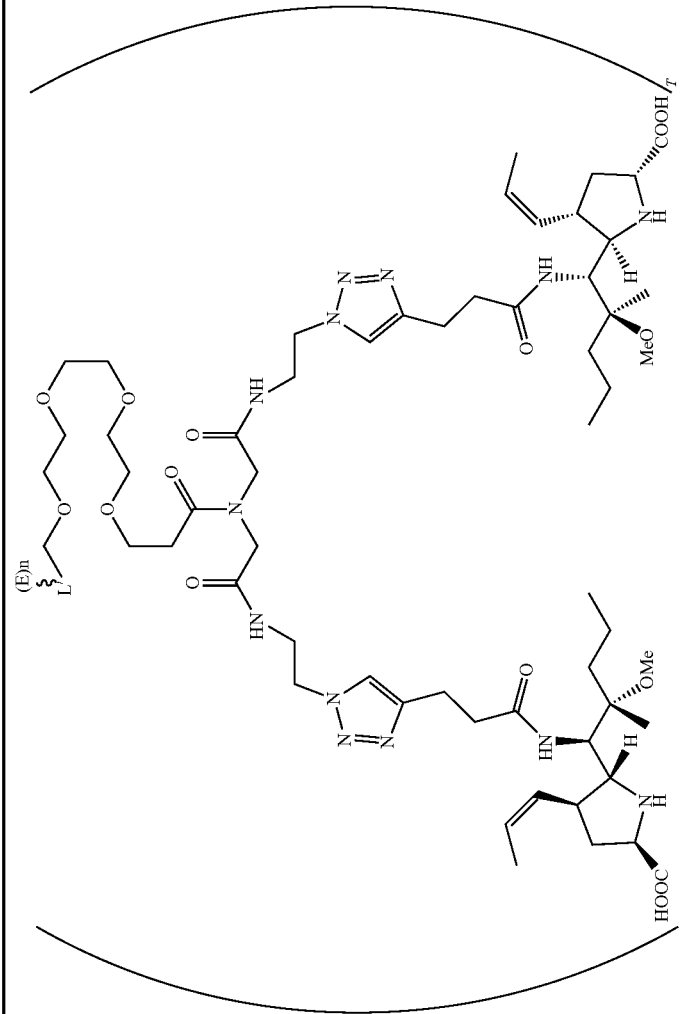 |

TABLE 1b-continued

Conjugates Corresponding to Intermediates of Table 1a

| Corresponding Intermediate of Table 1a | Described by Formula | Conjugate Structure |
|---|---|---|
| Int-16 | (M-I) | ![structure with PEG linker attached to sulfated sugar with guanidine and AcHN groups, terminated by T] |

TABLE 1b-continued
Conjugates Corresponding to Intermediates of Table 1a
| Corresponding Intermediate of Table 1a | Described by Formula | Conjugate Structure |
|---|---|---|
| Int-17 | (D-I) | 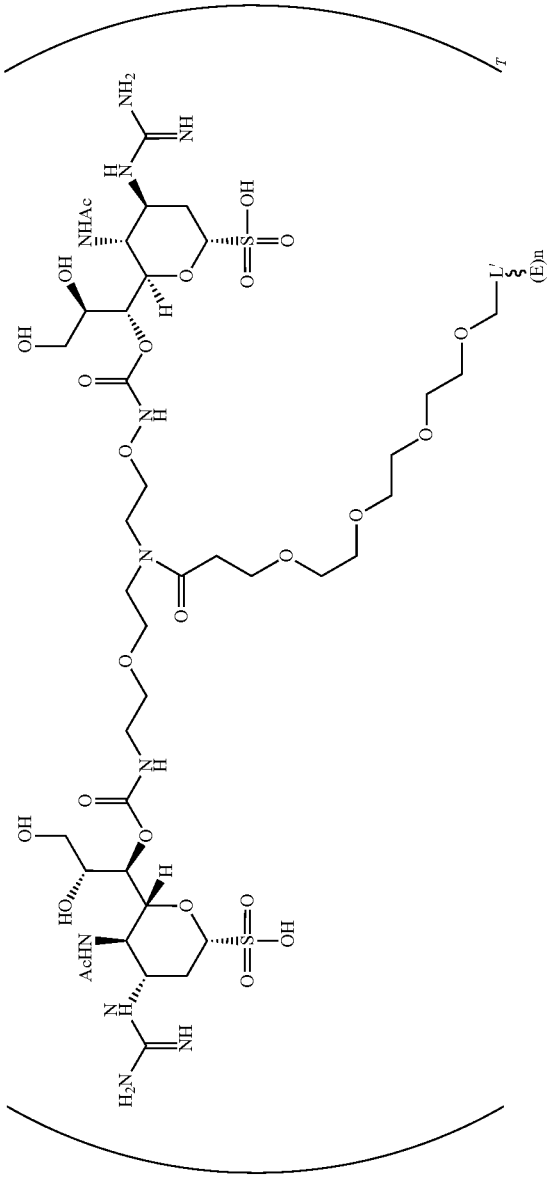 |

TABLE 1b-continued
Conjugates Corresponding to Intermediates of Table 1a
| Corresponding Intermediate of Table 1a | Described by Formula | Conjugate Structure |
|---|---|---|
| Int-18 | (D-I) | 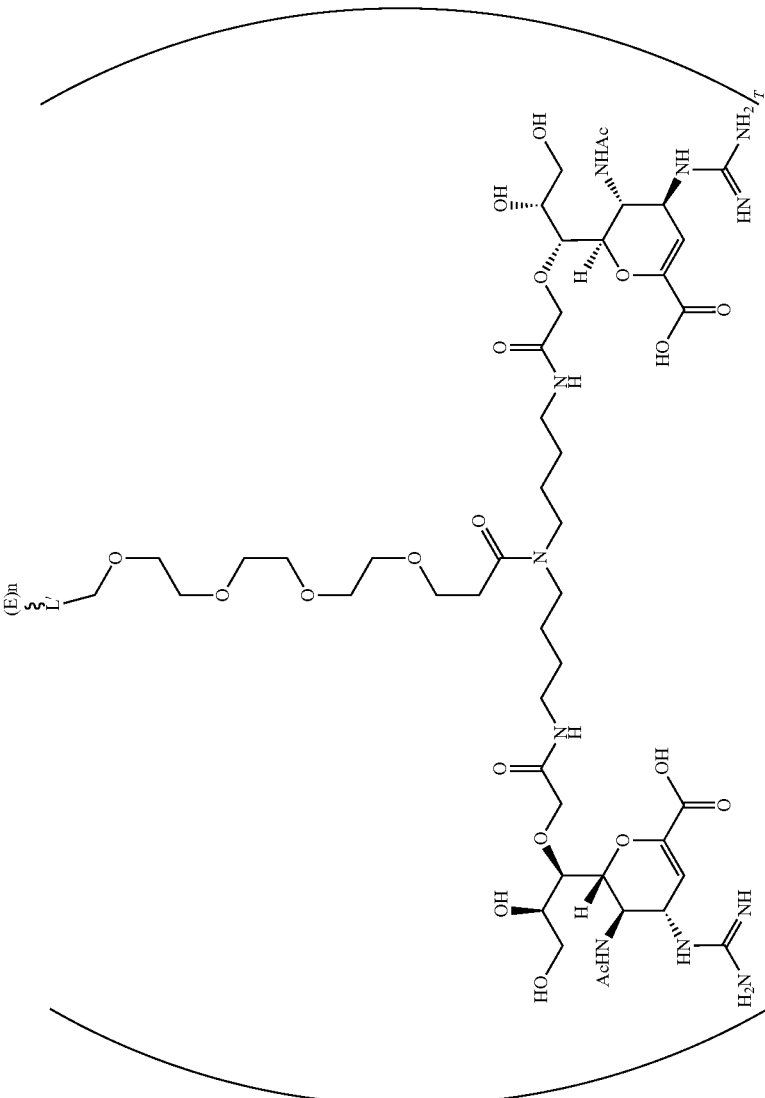 |

TABLE 1b-continued
Conjugates Corresponding to Intermediates of Table 1a
| Corresponding Intermediate of Table 1a | Described by Formula | Conjugate Structure |
|---|---|---|
| Int-19 | (D-I) | 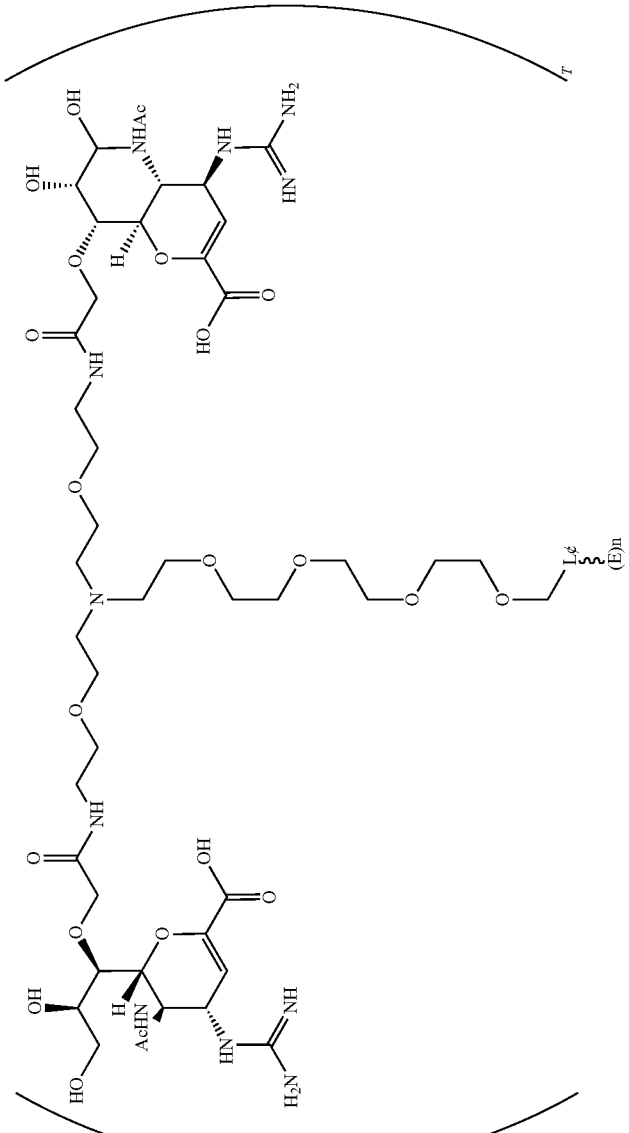 |

TABLE 1b-continued
Conjugates Corresponding to Intermediates of Table 1a
| Corresponding Intermediate of Table 1a | Described by Formula | Conjugate Structure |
|---|---|---|
| Int-20 | (D-I) | 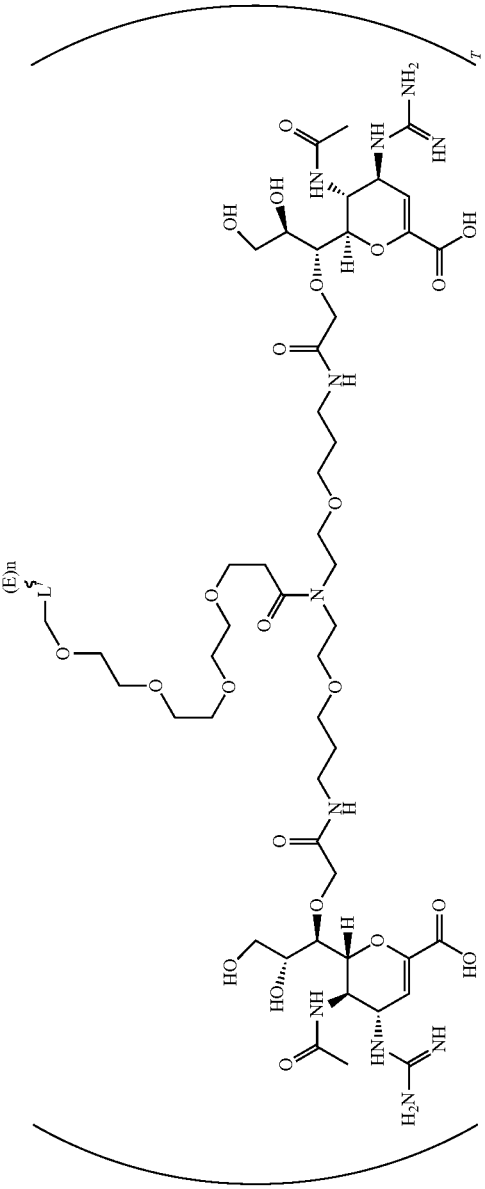 |

TABLE 1b-continued
Conjugates Corresponding to Intermediates of Table 1a
| Corresponding Intermediate of Table 1a | Described by Formula | Conjugate Structure |
|---|---|---|
| Int-21 | (D-I) | 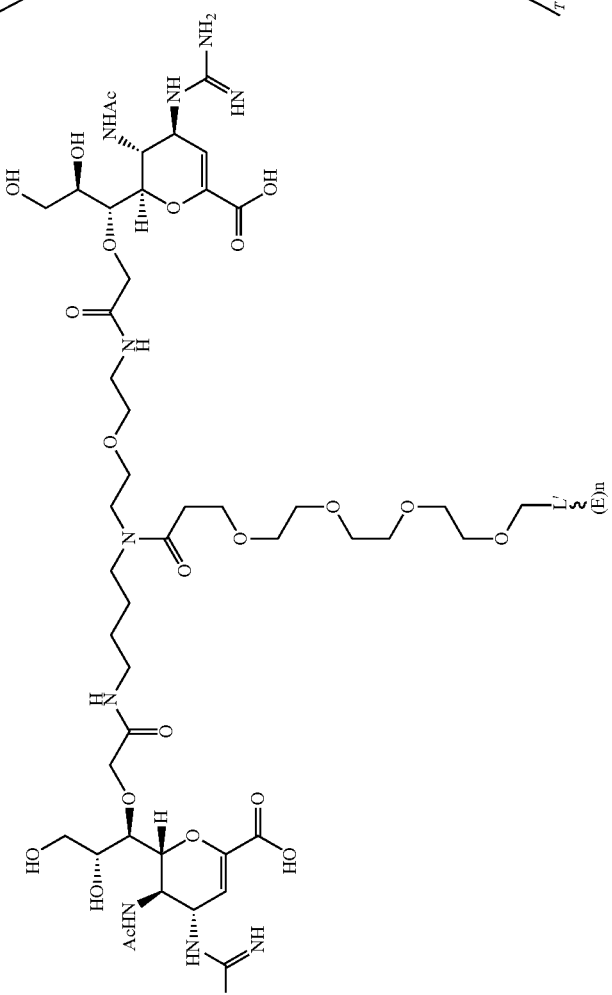 |

TABLE 1b-continued
Conjugates Corresponding to Intermediates of Table 1a
| Corresponding Intermediate of Table 1a | Described by Formula | Conjugate Structure |
|---|---|---|
| Int-22 | (M-I) | 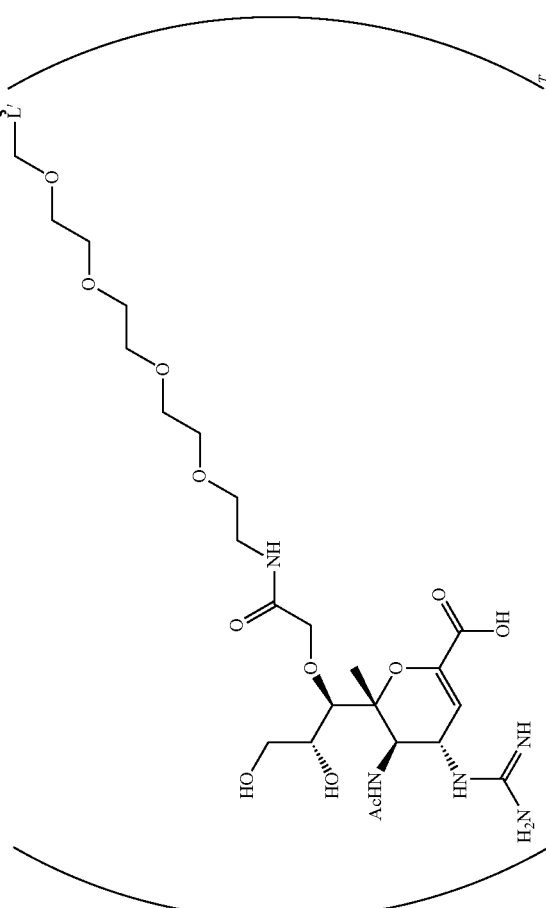 |

TABLE 1b-continued
Conjugates Corresponding to Intermediates of Table 1a
| Corresponding Intermediate of Table 1a | Described by Formula | Conjugate Structure |
|---|---|---|
| Int-23 | (D-I) | 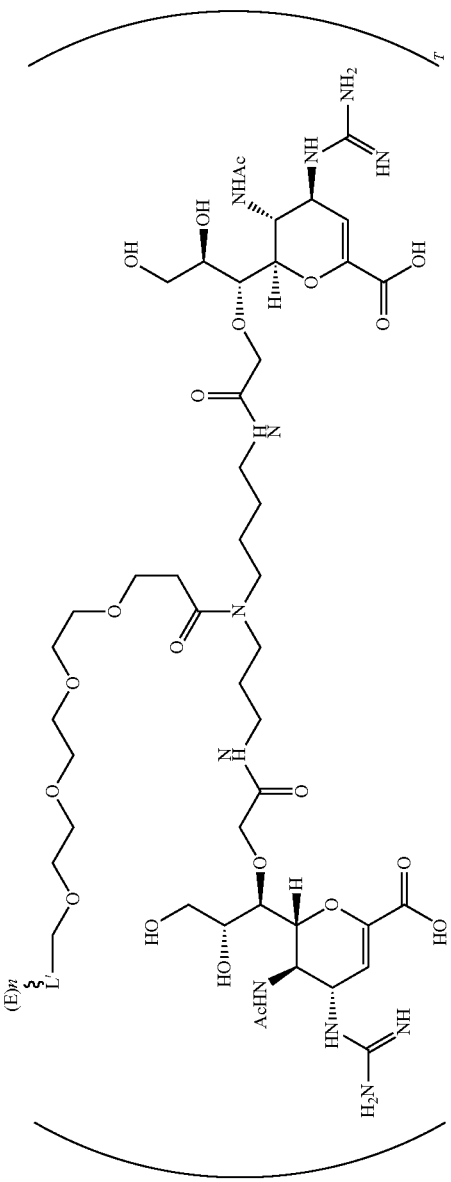 |
| Int-24 | (D-I) | 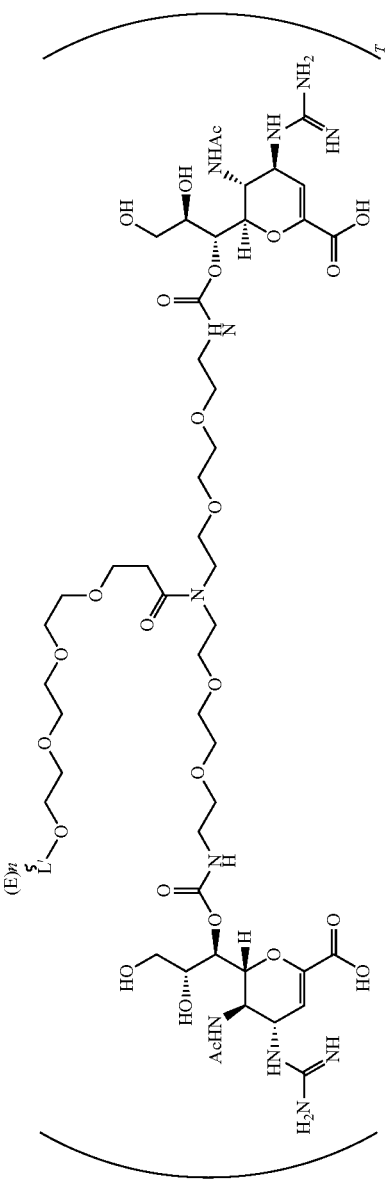 |

TABLE 1b-continued
Conjugates Corresponding to Intermediates of Table 1a
| Corresponding Intermediate of Table 1a | Described by Formula | Conjugate Structure |
|---|---|---|
| Int-25 | (D-I) | 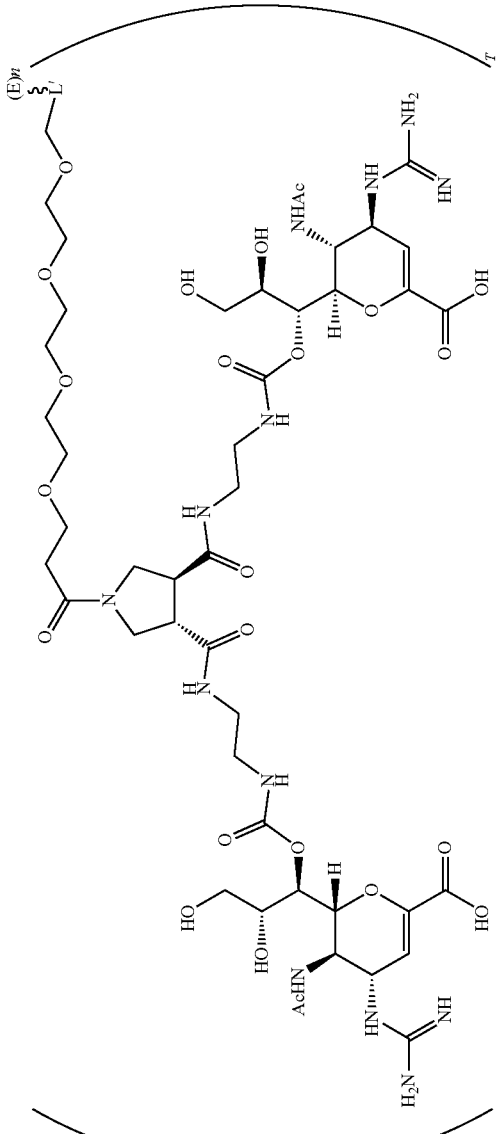 |
| Int-26 | (D-I) | 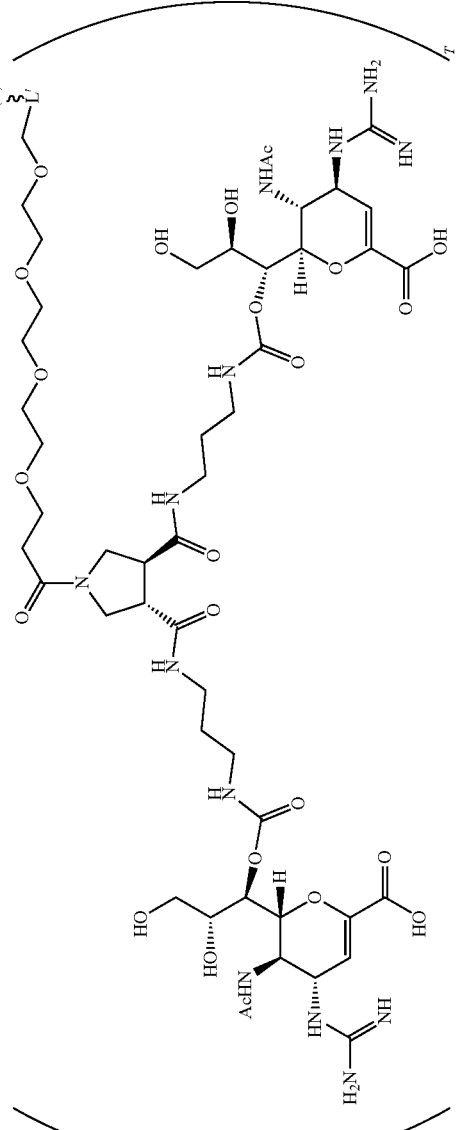 |

TABLE 1b-continued
Conjugates Corresponding to Intermediates of Table 1a
| Corresponding Intermediate of Table 1a | Described by Formula | Conjugate Structure |
|---|---|---|
| Int-27 | (D-I) | 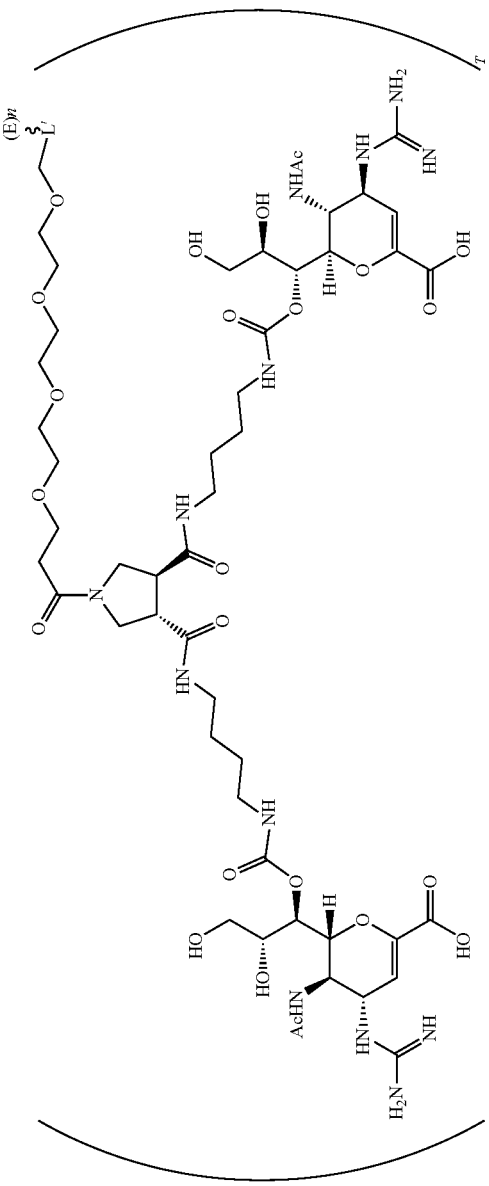 |
| Int-28 | (D-I) | 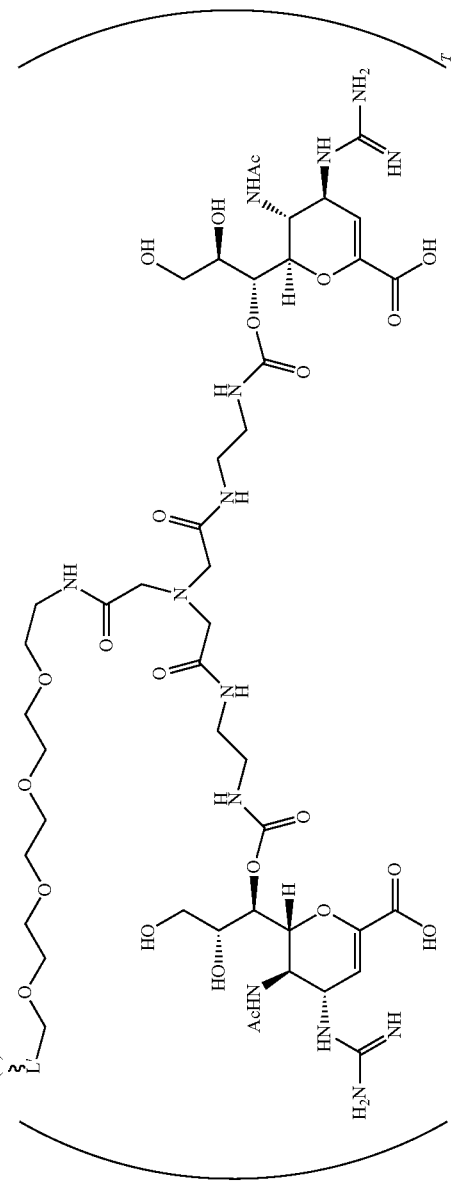 |

TABLE 1b-continued

Conjugates Corresponding to Intermediates of Table 1a

| Corresponding Intermediate of Table 1a | Described by Formula | Conjugate Structure |
|---|---|---|
| Int-30 | (M-I) | |
| Int-31 | (D-I) | |

TABLE 1b-continued
Conjugates Corresponding to Intermediates of Table 1a
| Corresponding Intermediate of Table 1a | Described by Formula | Conjugate Structure |
|---|---|---|
| Int-34 | (D-I) | 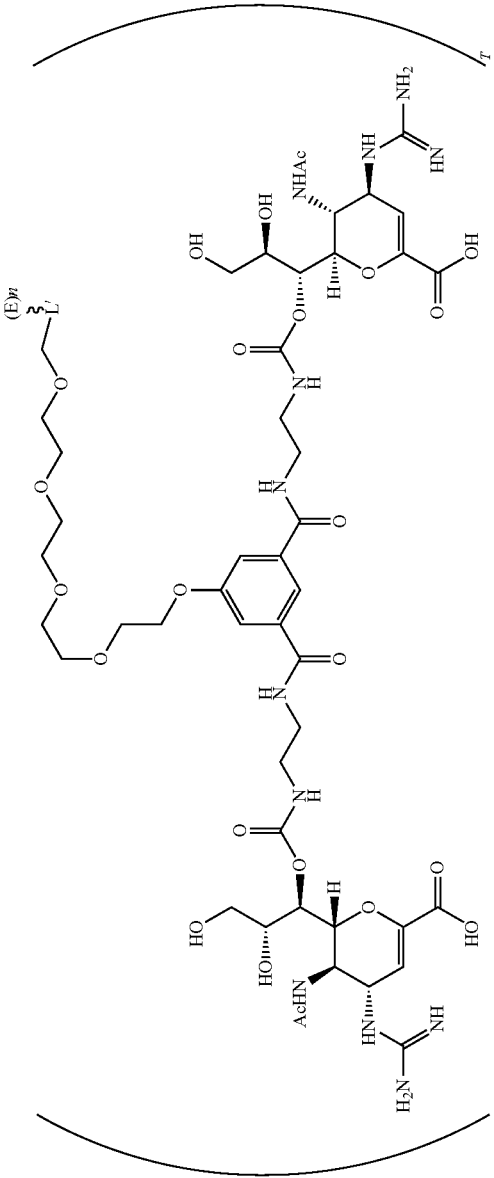 |

TABLE 1b-continued
Conjugates Corresponding to Intermediates of Table 1a
| Corresponding Intermediate of Table 1a | Described by Formula | Conjugate Structure |
|---|---|---|
| Int-38 | (D-I) | 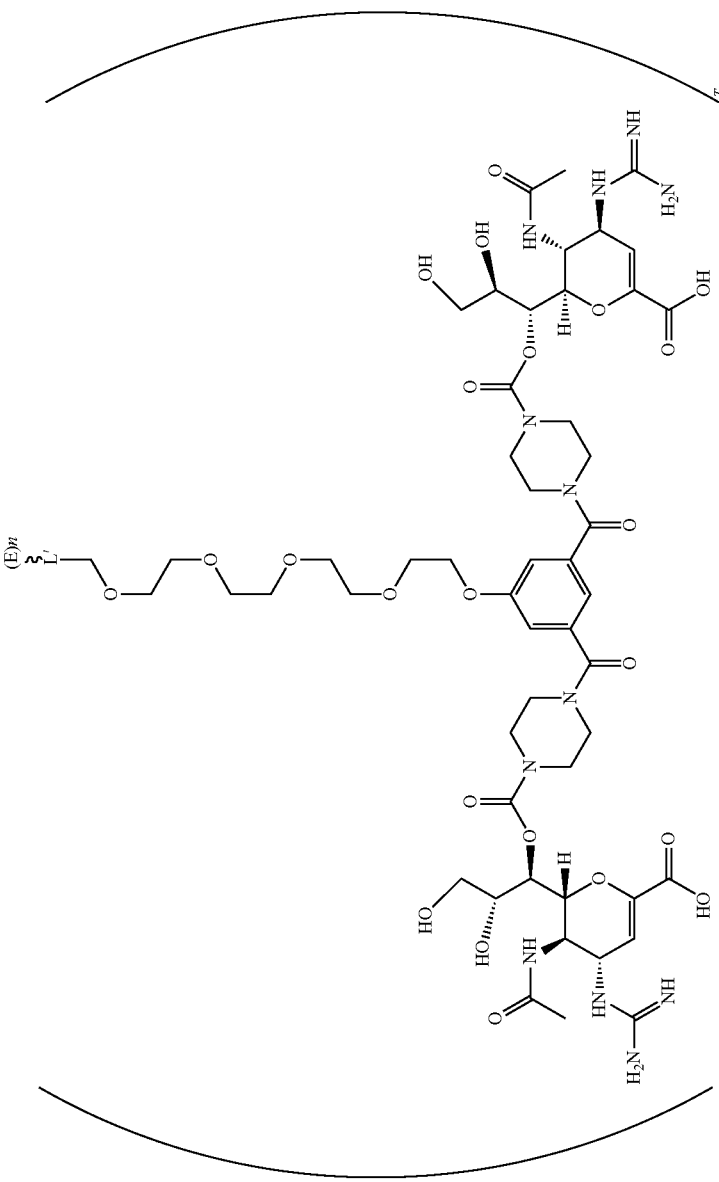 |

TABLE 1b-continued
Conjugates Corresponding to Intermediates of Table 1a
| Corresponding Intermediate of Table 1a | Described by Formula | Conjugate Structure |
|---|---|---|
| Int-39 | (D-I) | 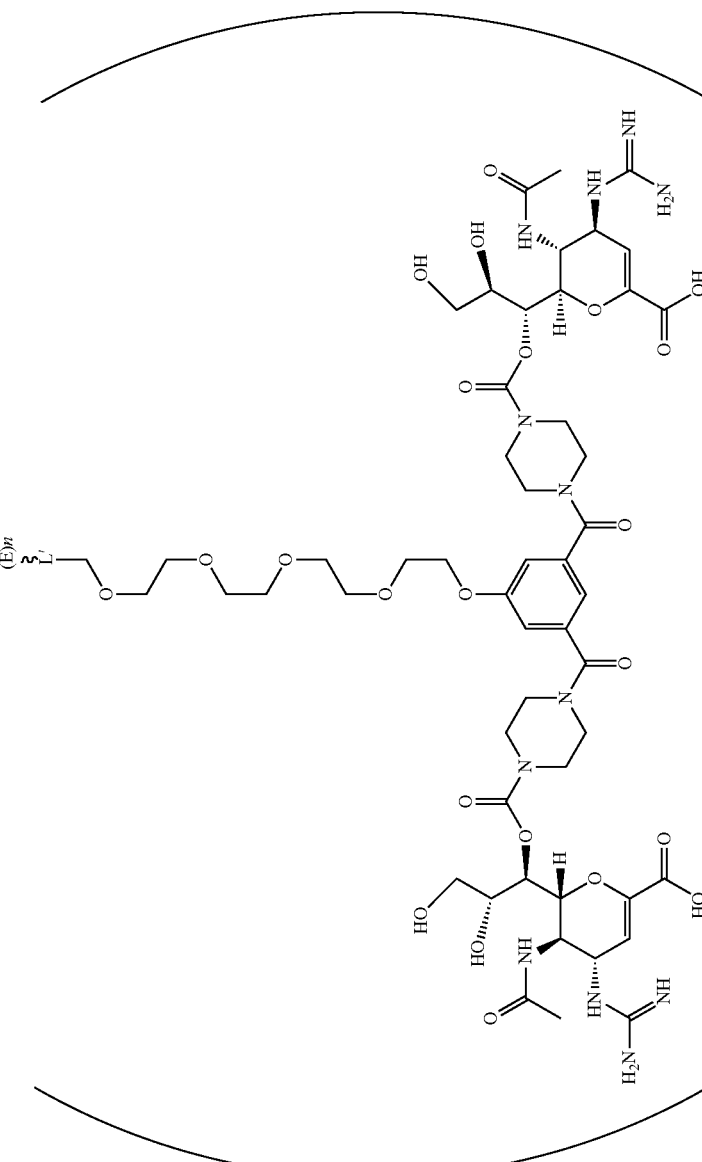 |

TABLE 1b-continued
Conjugates Corresponding to Intermediates of Table 1a
| Corresponding Intermediate of Table 1a | Described by Formula | Conjugate Structure |
|---|---|---|
| Int-40 | (D-I) | 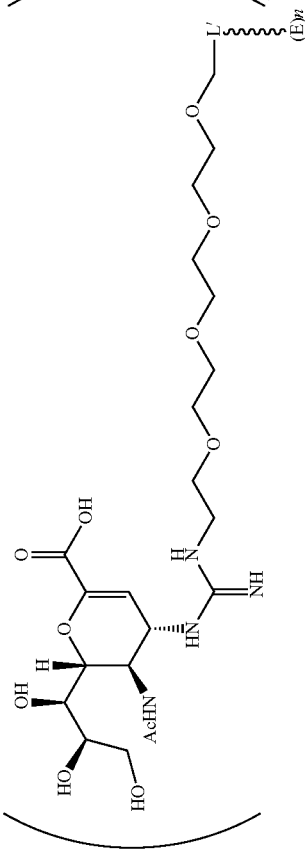 |
| Int-42 | (D-I) | 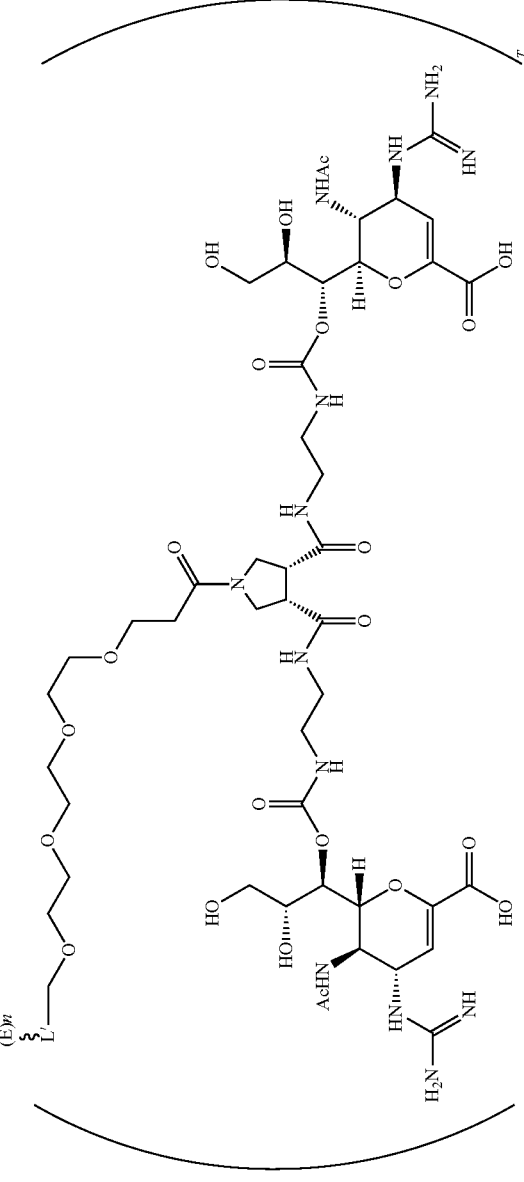 |

TABLE 1b-continued
Conjugates Corresponding to Intermediates of Table 1a
| Corresponding Intermediate of Table 1a | Described by Formula | Conjugate Structure |
|---|---|---|
| Int-43 | (D-I) | 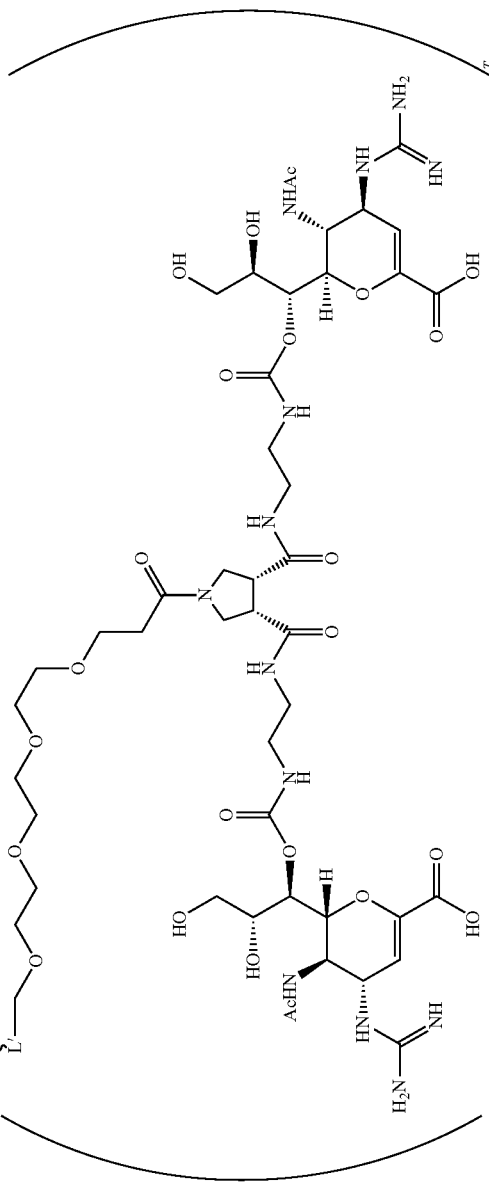 |
| Int-44 | (D-I) | 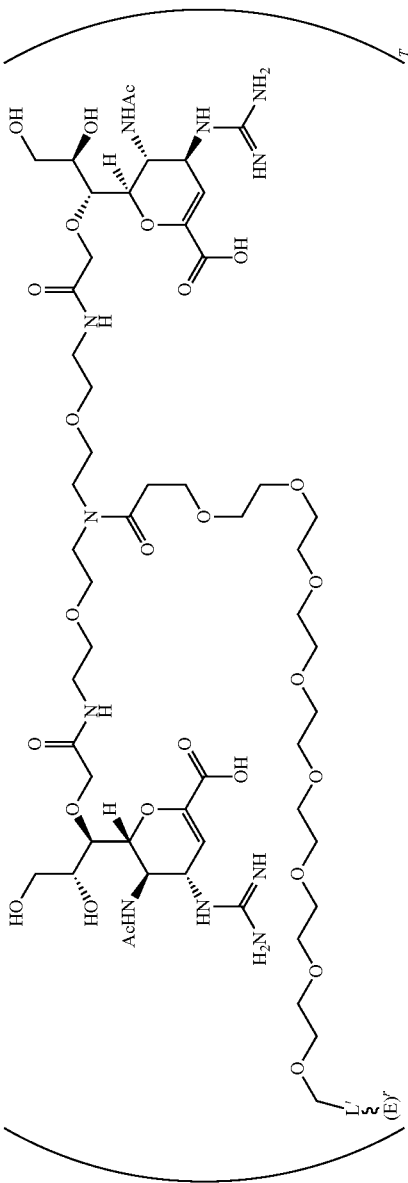 |

TABLE 1b-continued
Conjugates Corresponding to Intermediates of Table 1a
| Corresponding Intermediate of Table 1a | Described by Formula | Conjugate Structure |
|---|---|---|
| Int-45 | (D-I) | 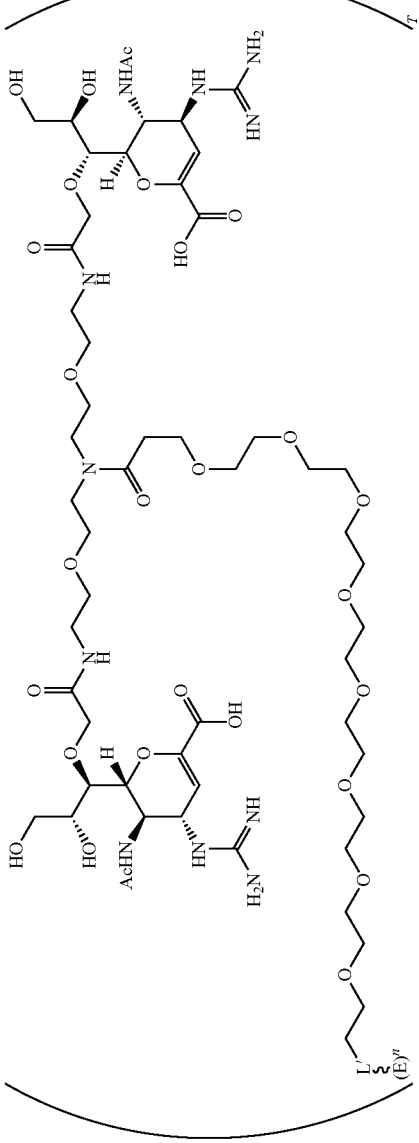 |
| Int-46 | (D-I) | 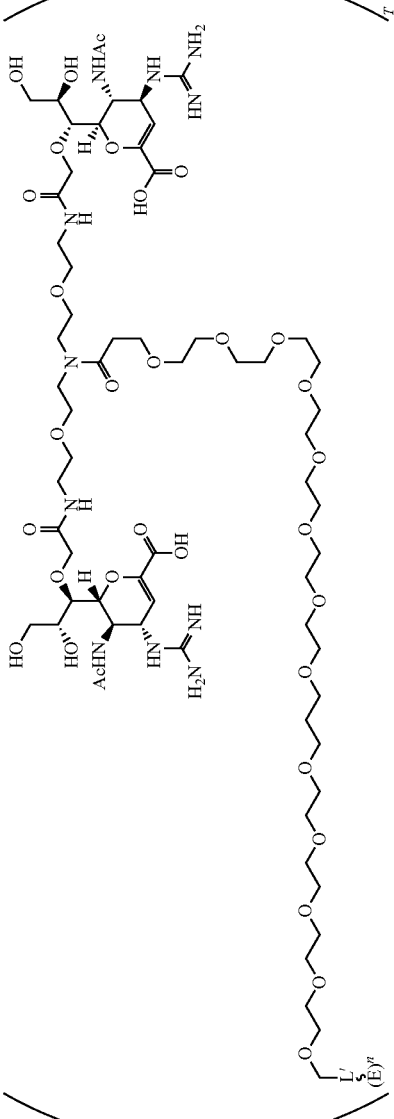 |

TABLE 1b-continued
Conjugates Corresponding to Intermediates of Table 1a
| Corresponding Intermediate of Table 1a | Described by Formula | Conjugate Structure |
|---|---|---|
| Int-47 | (D-I) | 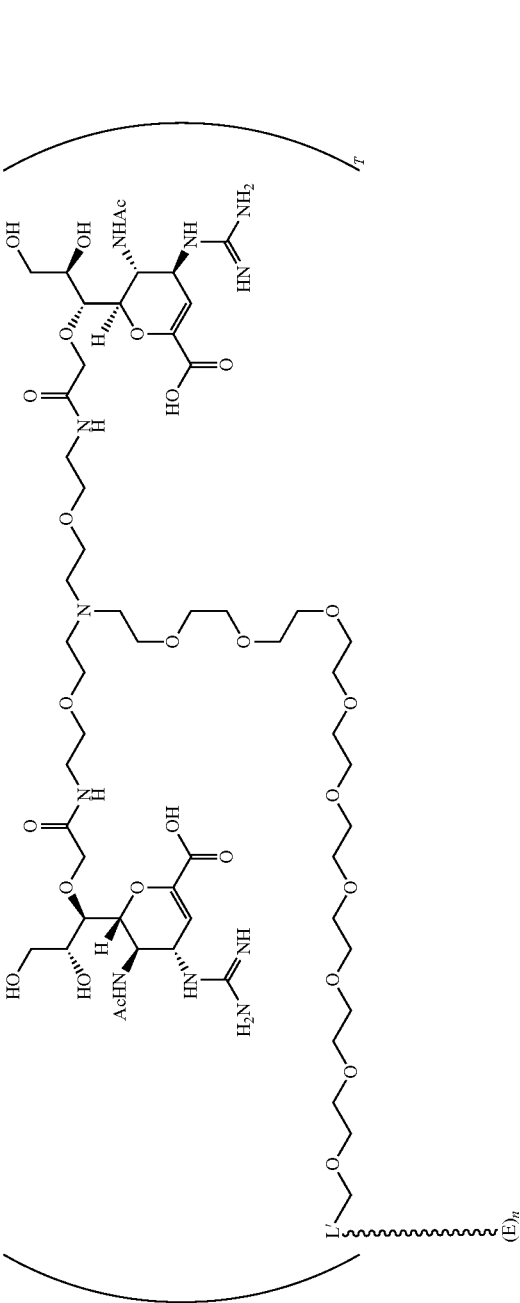 |

TABLE 1b-continued
Conjugates Corresponding to Intermediates of Table 1a
| Corresponding Intermediate of Table 1a | Described by Formula | Conjugate Structure |
|---|---|---|
| Int-48 | (D-I) | 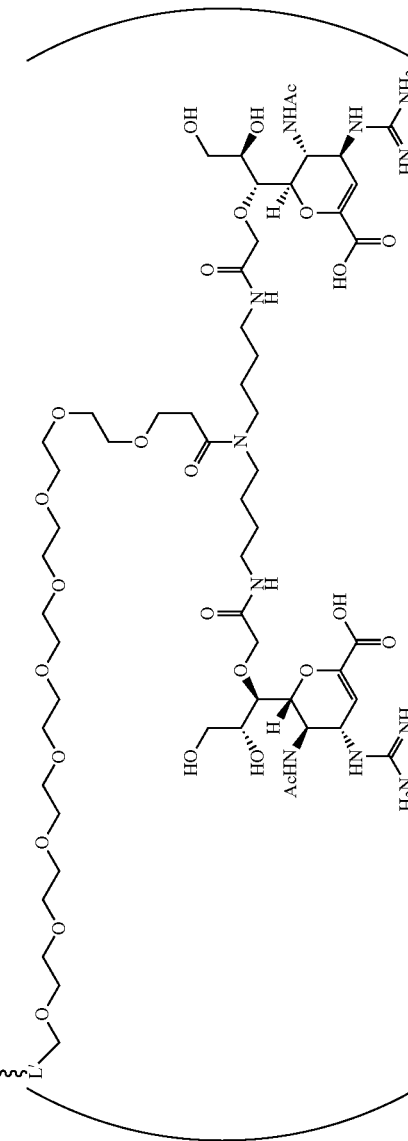 |

TABLE 1b-continued
Conjugates Corresponding to Intermediates of Table 1a
| Corresponding Intermediate of Table 1a | Described by Formula | Conjugate Structure |
|---|---|---|
| Int-49 | (D-I) | 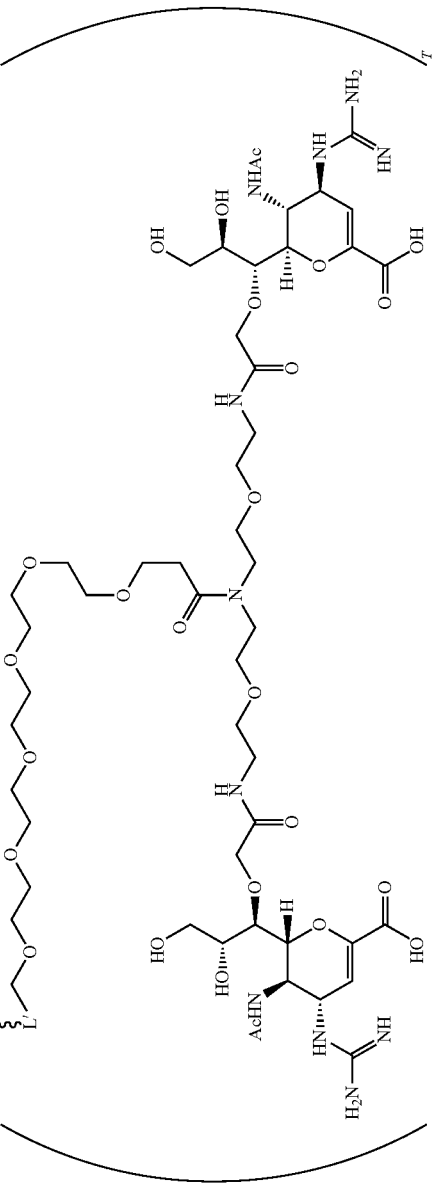 |

TABLE 1b-continued
Conjugates Corresponding to Intermediates of Table 1a
| Corresponding Intermediate of Table 1a | Described by Formula | Conjugate Structure |
|---|---|---|
| Int-50 | (D-I) | 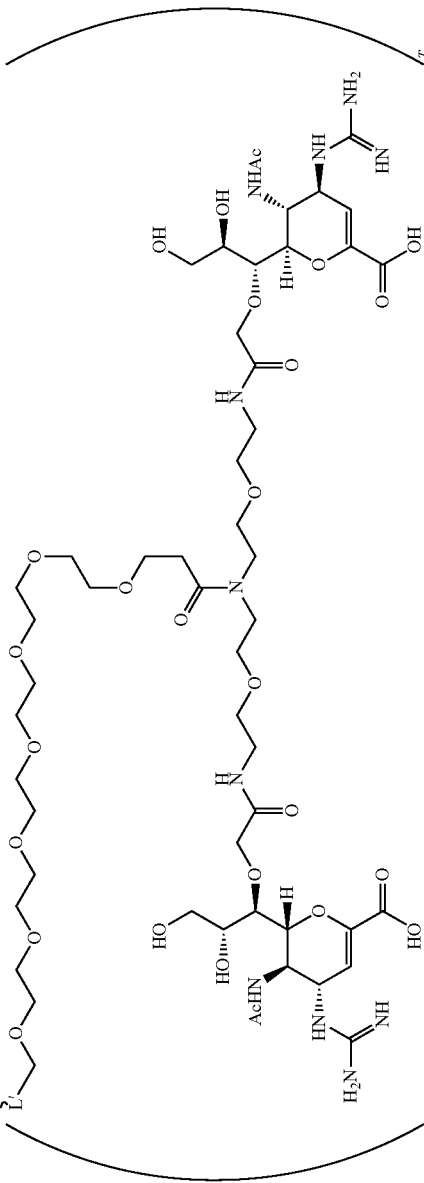 |

TABLE 1b-continued
Conjugates Corresponding to Intermediates of Table 1a
| Corresponding Intermediate of Table 1a | Described by Formula | Conjugate Structure |
|---|---|---|
| Int-52 | (D-I) | 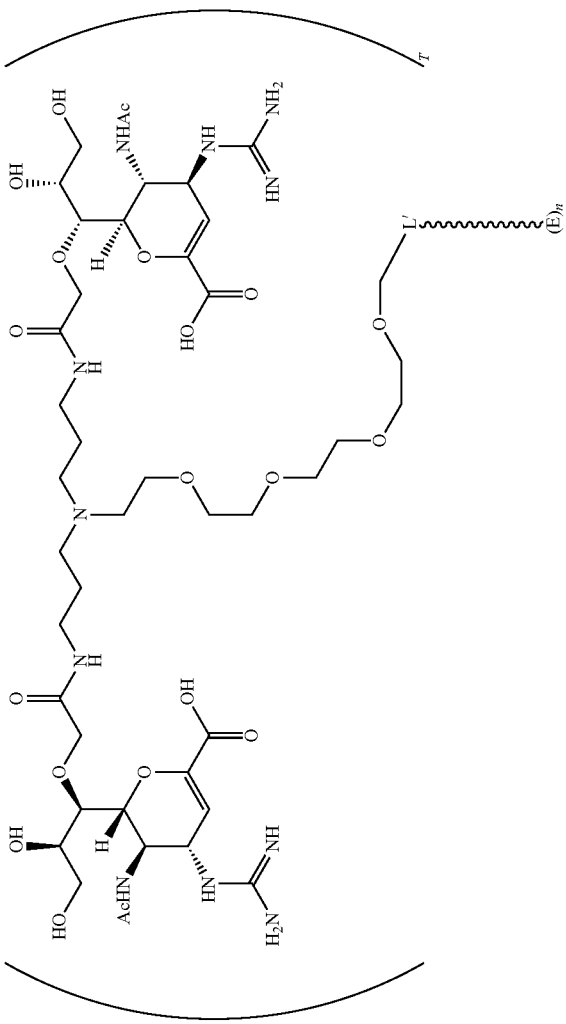 |

TABLE 1b-continued

Conjugates Corresponding to Intermediates of Table 1a

| Corresponding Intermediate of Table 1a | Described by Formula | Conjugate Structure |
|---|---|---|
| Int-53 | (D-I) | |

TABLE 1b-continued

Conjugates Corresponding to Intermediates of Table 1a

| Corresponding Intermediate of Table 1a | Described by Formula | Conjugate Structure |
|---|---|---|
| Int-54 | (D-I) | |

TABLE 1b-continued

Conjugates Corresponding to Intermediates of Table 1a

| Corresponding Intermediate of Table 1a | Described by Formula | Conjugate Structure |
|---|---|---|
| Int-55 | (D-I) | |

TABLE 1b-continued
Conjugates Corresponding to Intermediates of Table 1a
| Corresponding Intermediate of Table 1a | Described by Formula | Conjugate Structure |
|---|---|---|
| Int-57 | (D-I) | 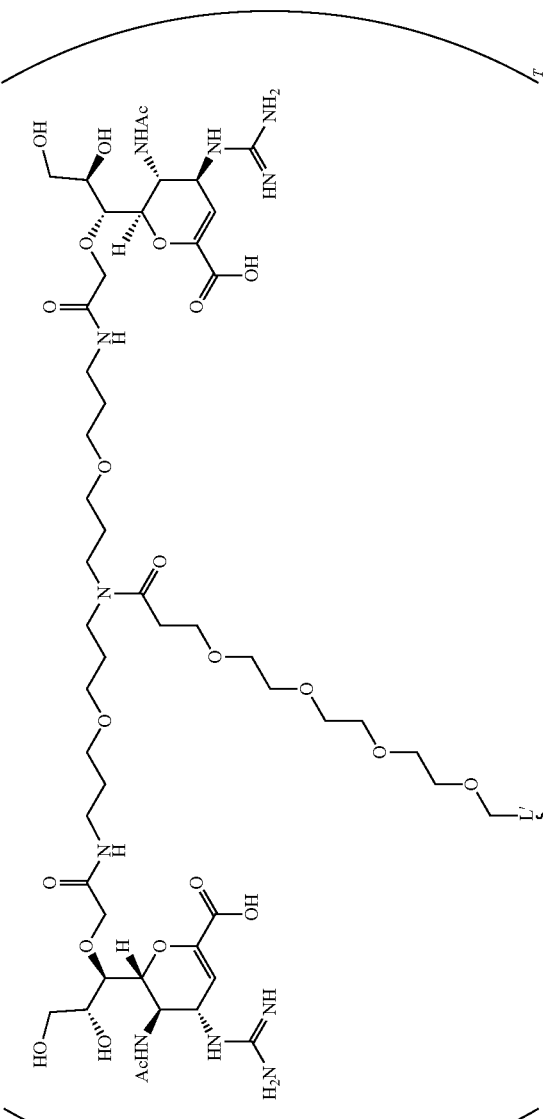 |

TABLE 1b-continued
Conjugates Corresponding to Intermediates of Table 1a
| Corresponding Intermediate of Table 1a | Described by Formula | Conjugate Structure |
|---|---|---|
| Int-58 | (D-I) | 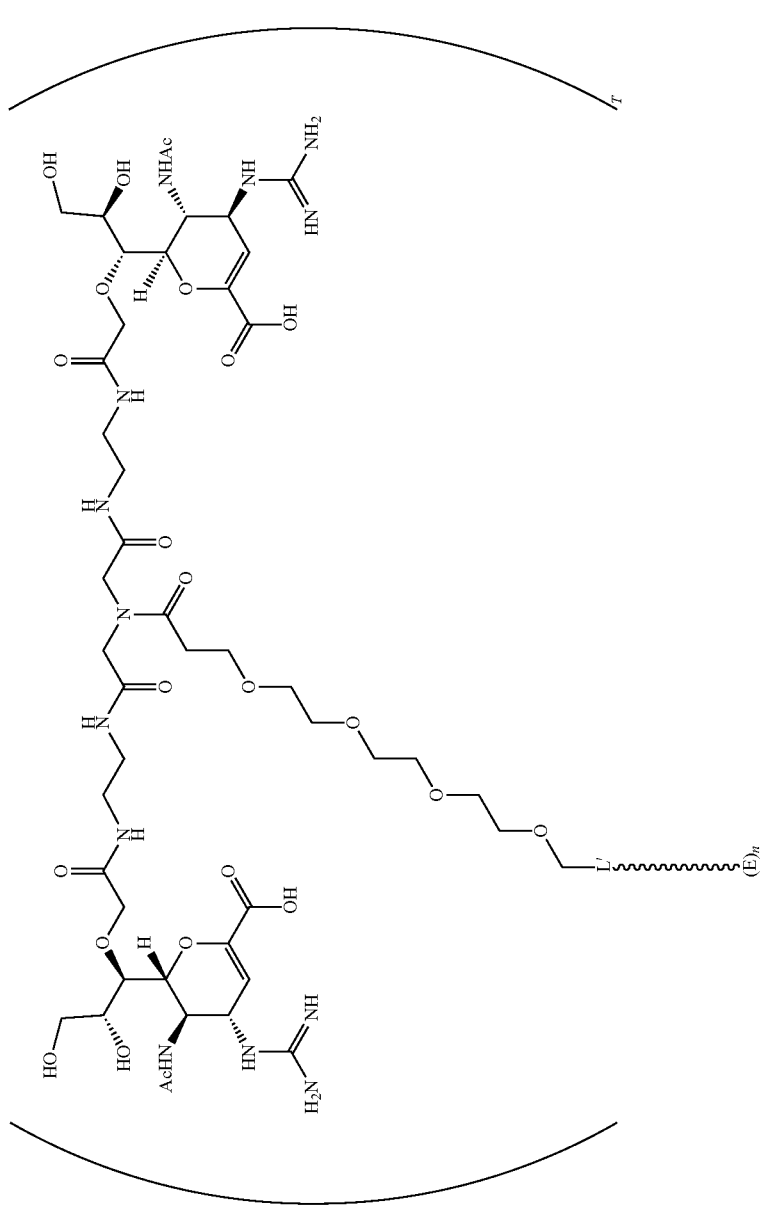 |

TABLE 1b-continued
Conjugates Corresponding to Intermediates of Table 1a
| Corresponding Intermediate of Table 1a | Described by Formula | Conjugate Structure |
|---|---|---|
| Int-59 | (D-I) | 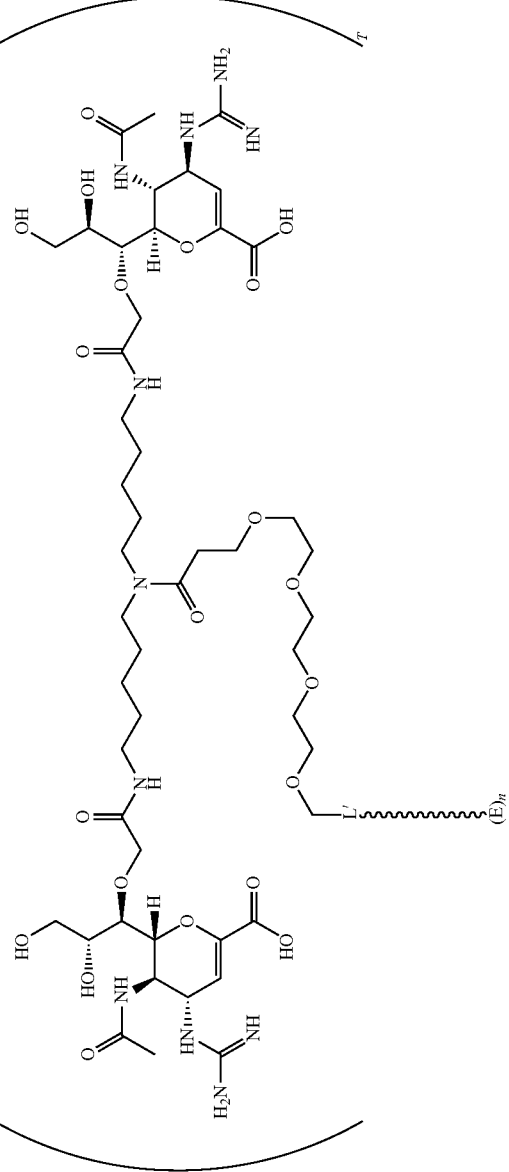 |

TABLE 1b-continued
Conjugates Corresponding to Intermediates of Table 1a
| Corresponding Intermediate of Table 1a | Described by Formula | Conjugate Structure |
|---|---|---|
| Int-60 | (D-I) | 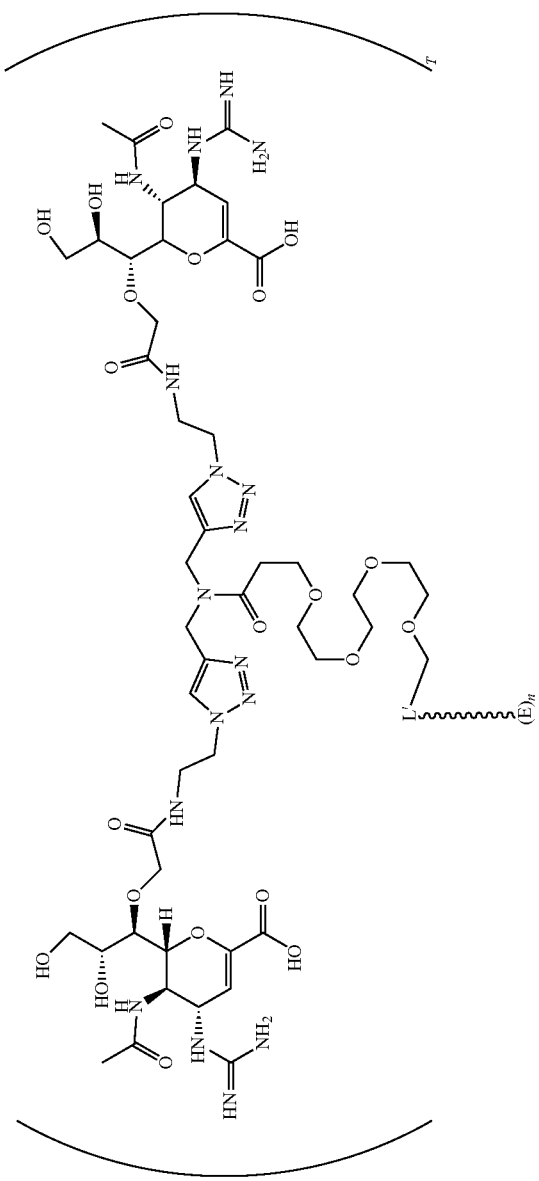 |

TABLE 1b-continued
Conjugates Corresponding to Intermediates of Table 1a
| Corresponding Intermediate of Table 1a | Described by Formula | Conjugate Structure |
|---|---|---|
| Int-61 | (D-I) | 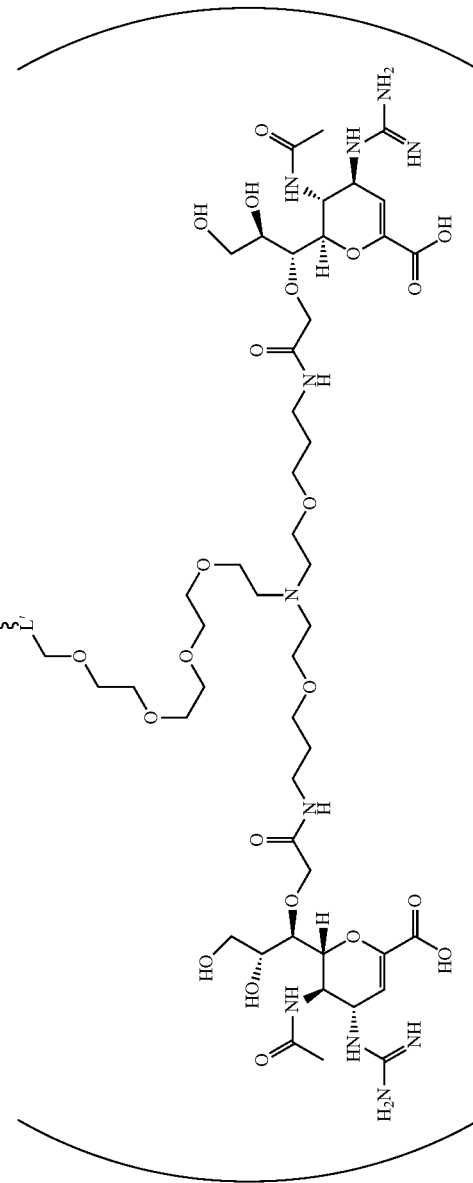 |
| Int-62 | (D-I) | 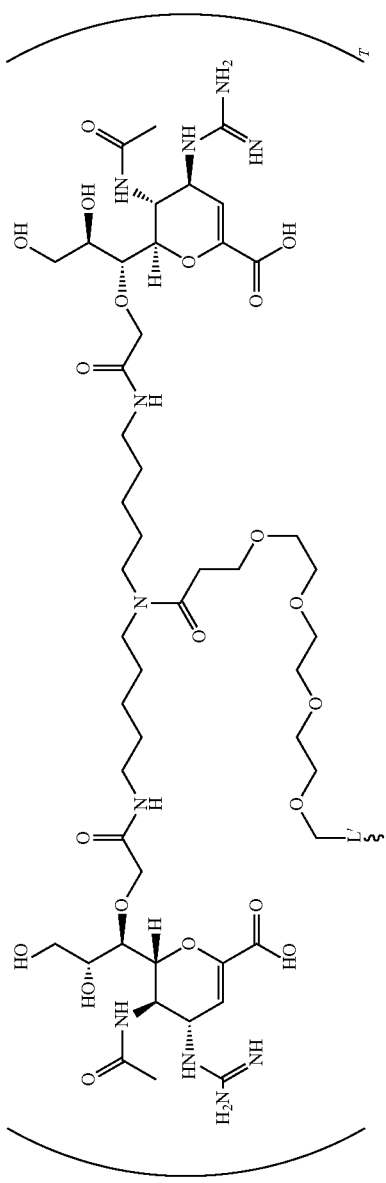 |

TABLE 1b-continued
Conjugates Corresponding to Intermediates of Table 1a
| Corresponding Intermediate of Table 1a | Described by Formula | Conjugate Structure |
|---|---|---|
| Int-63 | (D-I) | 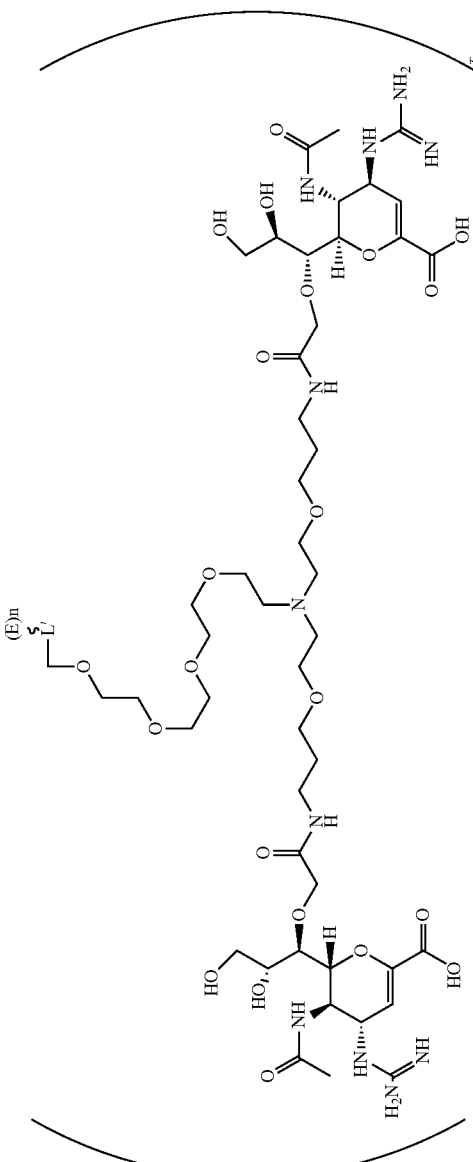 |
| Int-64 | (D-I) | 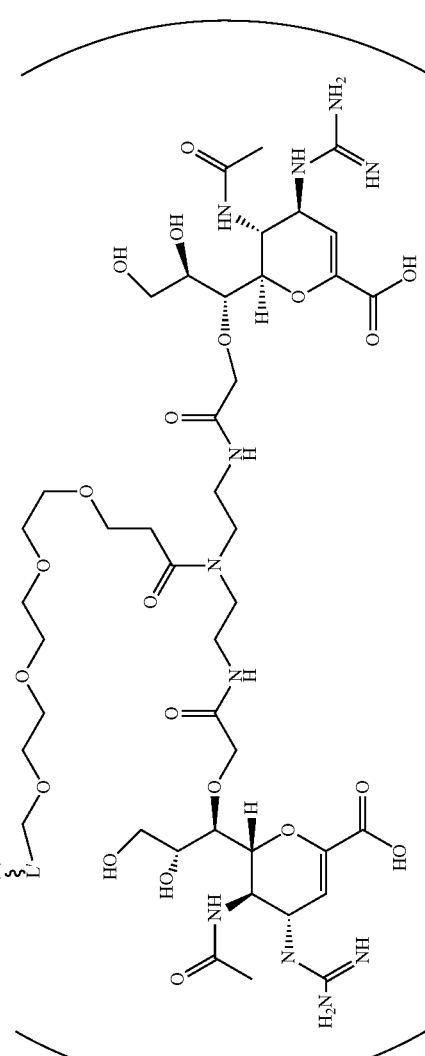 |

TABLE 1b-continued
Conjugates Corresponding to Intermediates of Table 1a
| Corresponding Intermediate of Table 1a | Described by Formula | Conjugate Structure |
|---|---|---|
| Int-65 | (D-I) | 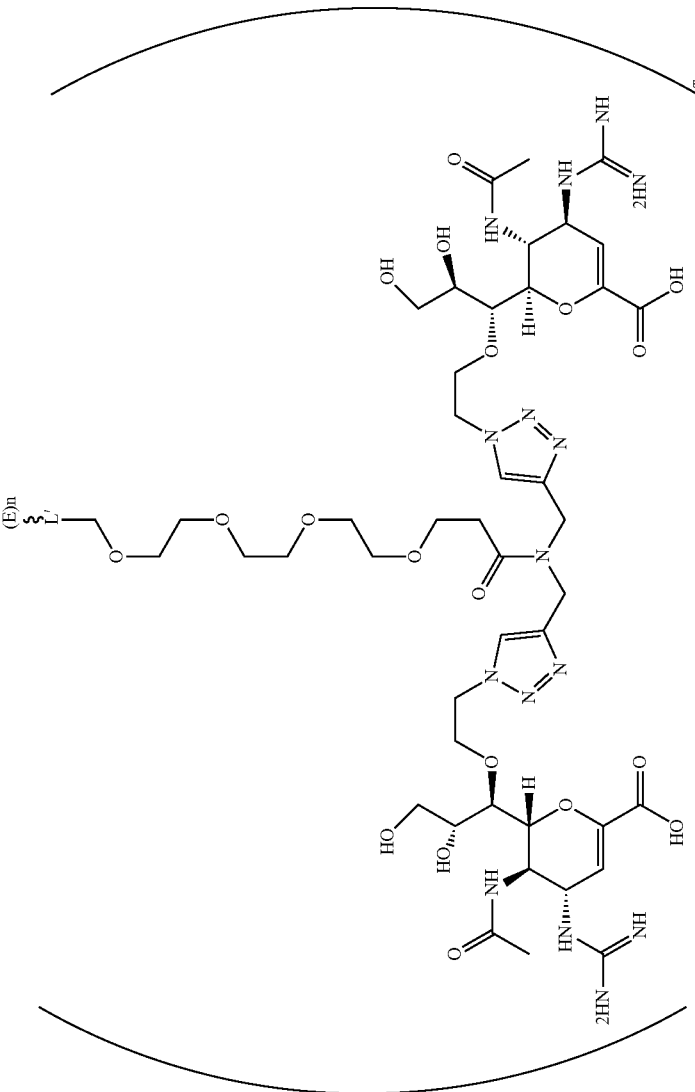 |

TABLE 1b-continued
Conjugates Corresponding to Intermediates of Table 1a
| Corresponding Intermediate of Table 1a | Described by Formula | Conjugate Structure |
|---|---|---|
| Int-67 | (D-I) | 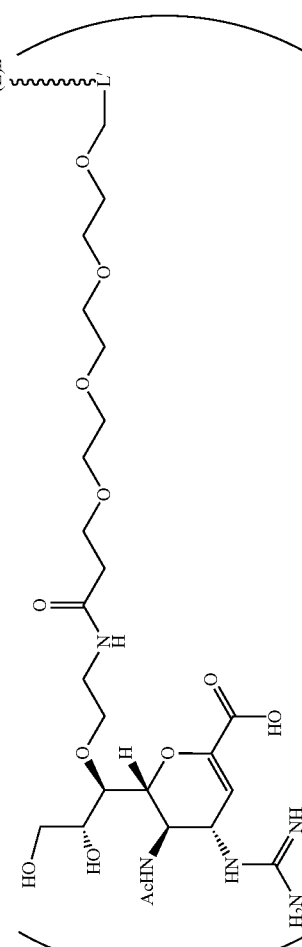 |
| Int-68 | (D-I) | 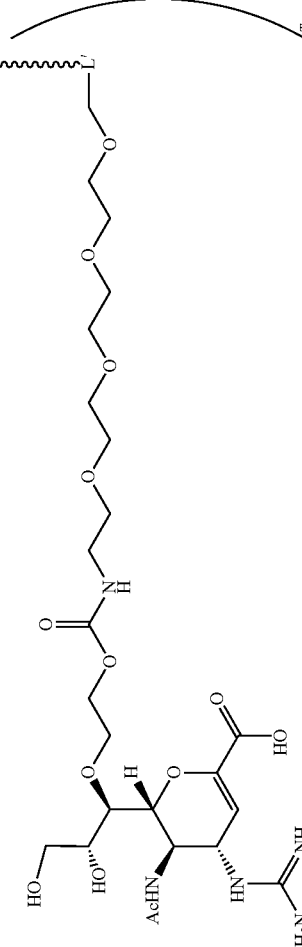 |

TABLE 1b-continued

Conjugates Corresponding to Intermediates of Table 1a

| Corresponding Intermediate of Table 1a | Described by Formula | Conjugate Structure |
|---|---|---|
| Int-69 | (D-I) | |
| Int-70 | (D-I) | |

TABLE 1b-continued
Conjugates Corresponding to Intermediates of Table 1a
| Corresponding Intermediate of Table 1a | Described by Formula | Conjugate Structure |
|---|---|---|
| Int-71 | (D-I) | 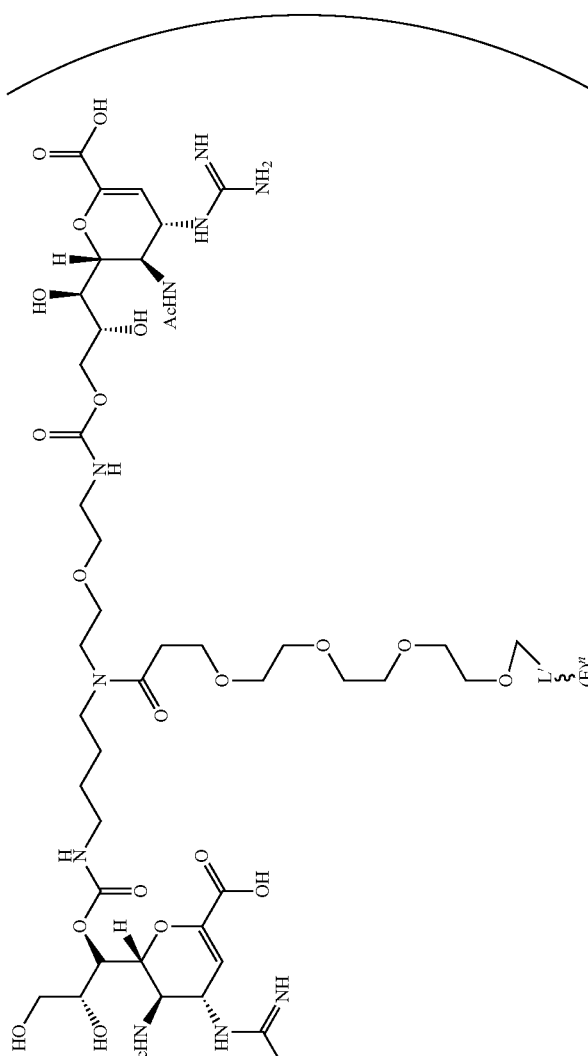 |

TABLE 1b-continued

Conjugates Corresponding to Intermediates of Table 1a

| Corresponding Intermediate of Table 1a | Described by Formula | Conjugate Structure |
|---|---|---|
| Int-72 | (D-I) | |

TABLE 1b-continued
Conjugates Corresponding to Intermediates of Table 1a
| Corresponding Intermediate of Table 1a | Described by Formula | Conjugate Structure |
|---|---|---|
| Int-73 | (D-I) | 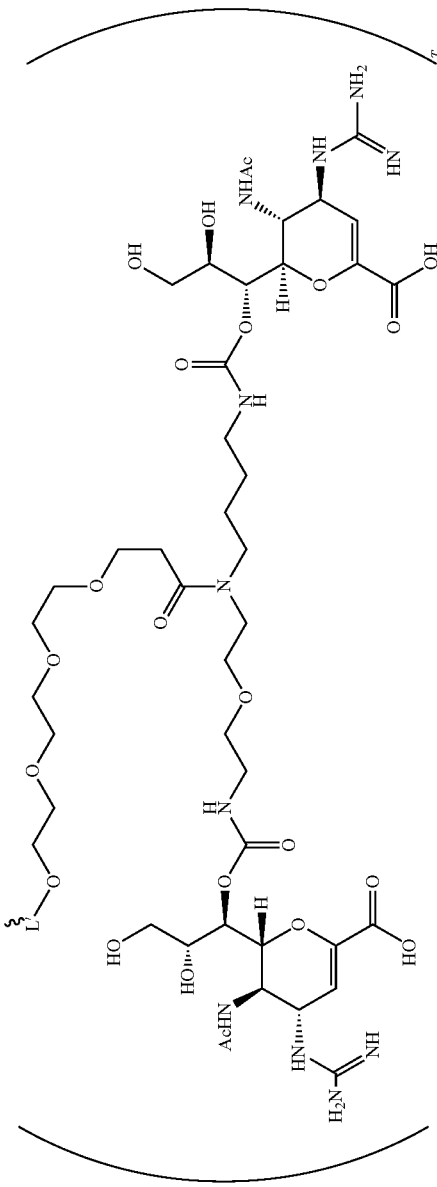 |
| Int-74 | (D-I) | 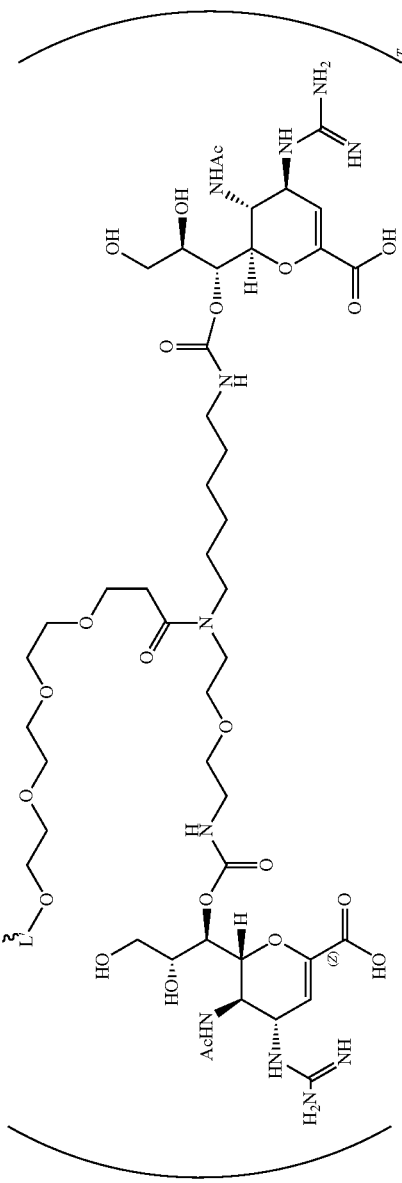 |

TABLE 1b-continued

Conjugates Corresponding to Intermediates of Table 1a

| Corresponding Intermediate of Table 1a | Described by Formula | Conjugate Structure |
|---|---|---|
| Int-75 | (D-I) | |
| Int-76 | (D-I) | |

TABLE 1b-continued
Conjugates Corresponding to Intermediates of Table 1a
| Corresponding Intermediate of Table 1a | Described by Formula | Conjugate Structure |
|---|---|---|
| Int-77 | (D-I) | 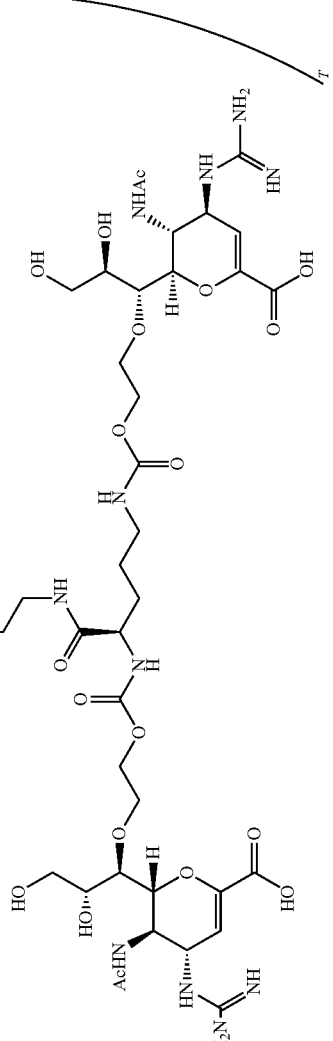 |

TABLE 1b-continued
Conjugates Corresponding to Intermediates of Table 1a
| Corresponding Intermediate of Table 1a | Described by Formula | Conjugate Structure |
|---|---|---|
| Int-78 | (D-I) | 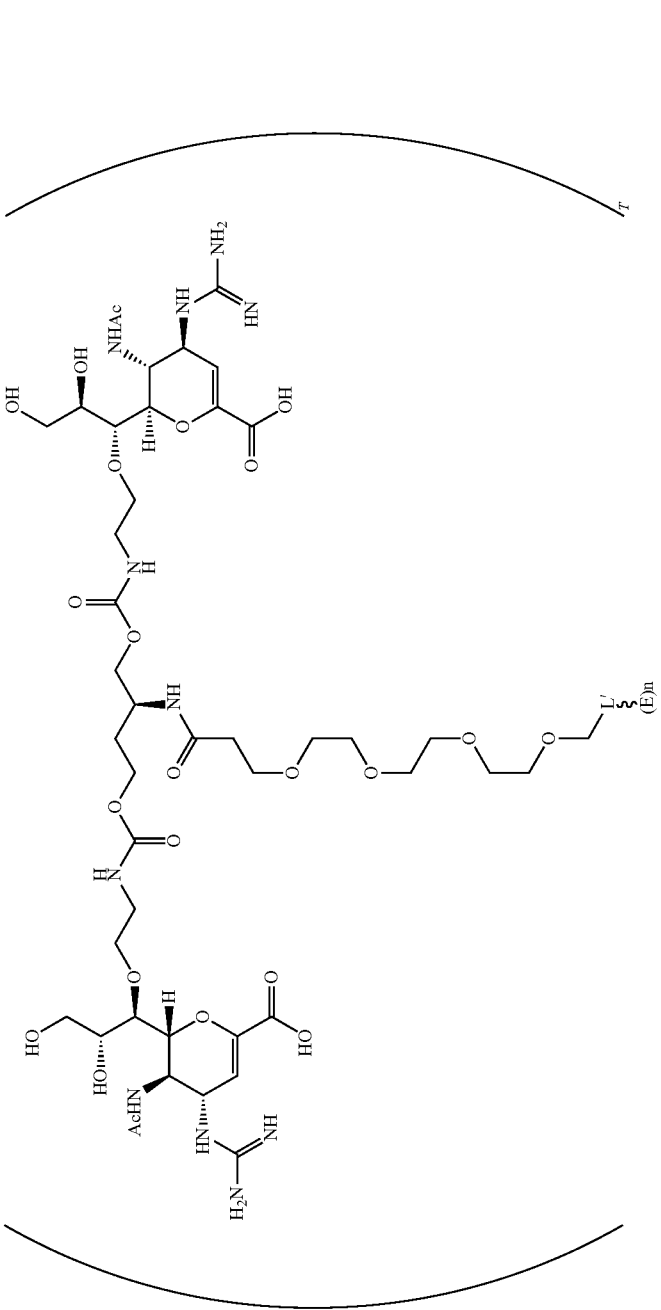 |

TABLE 1b-continued
Conjugates Corresponding to Intermediates of Table 1a
| Corresponding Intermediate of Table 1a | Described by Formula | Conjugate Structure |
|---|---|---|
| Int-79 | (D-I) | 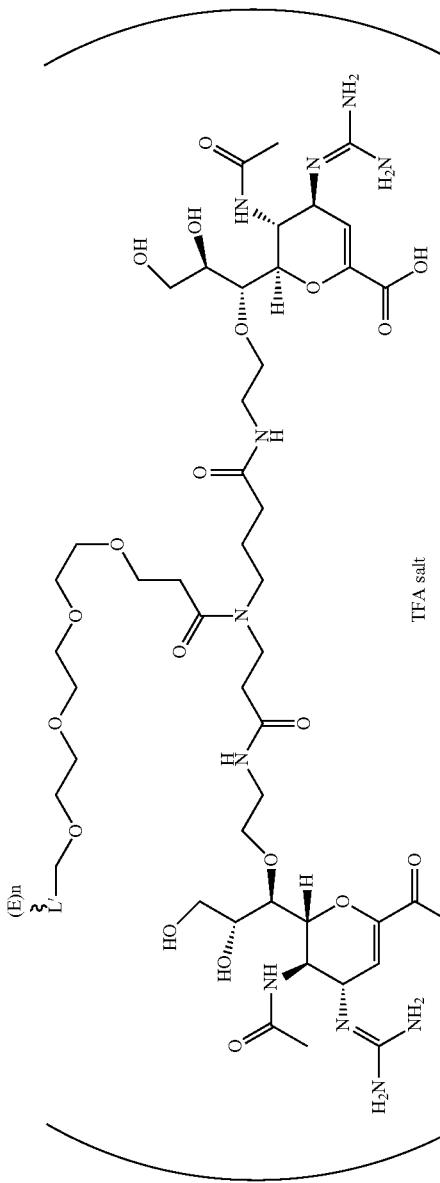 TFA salt |
| Int-80 | (D-I) | 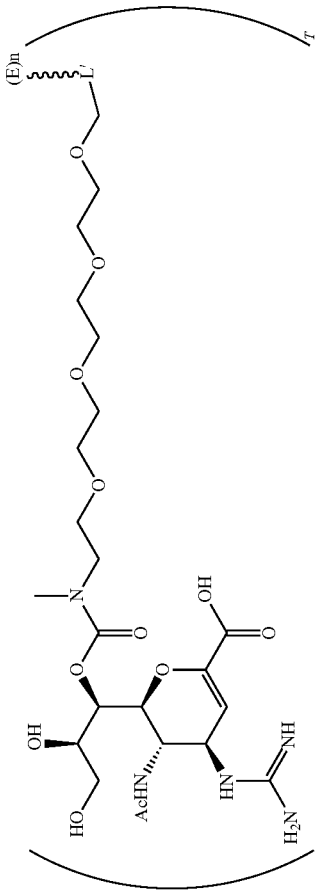 |

TABLE 1b-continued

Conjugates Corresponding to Intermediates of Table 1a

| Corresponding Intermediate of Table 1a | Described by Formula | Conjugate Structure |
|---|---|---|
| Int-81 | (D-I) | |
| Int-82 | (D-I) | |

TABLE 1b-continued
Conjugates Corresponding to Intermediates of Table 1a
| Corresponding Intermediate of Table 1a | Described by Formula | Conjugate Structure |
|---|---|---|
| Int-83 | (D-I) | 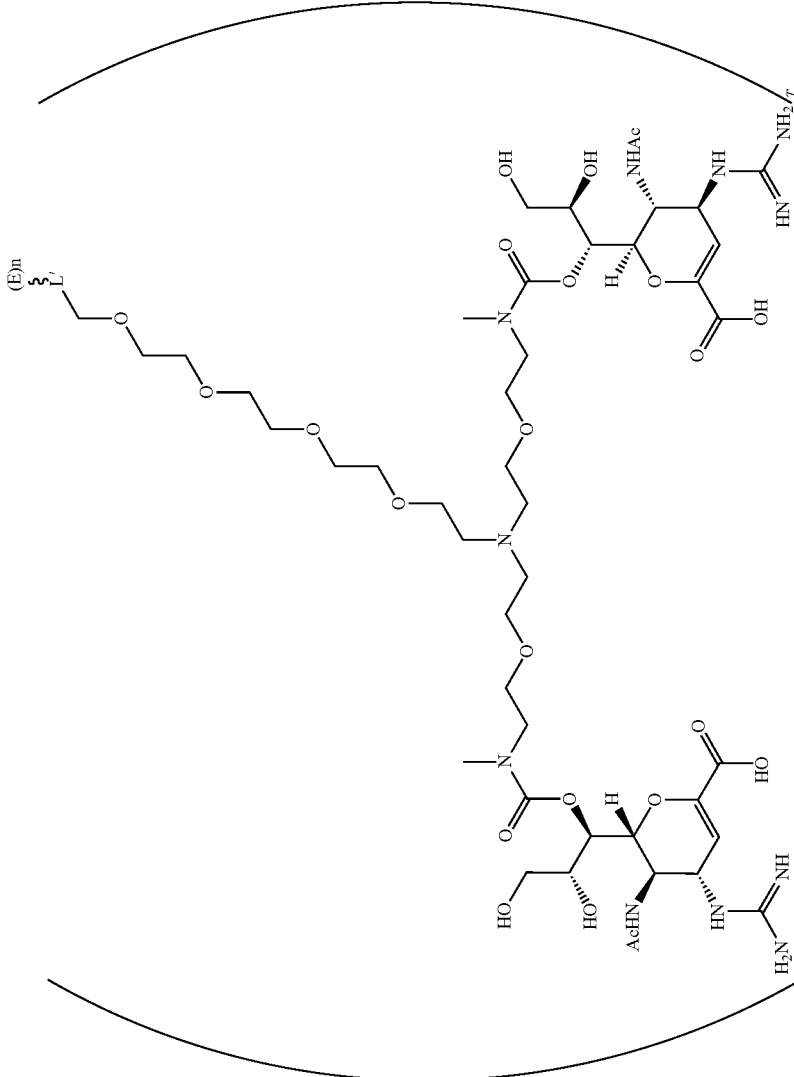 |

TABLE 1b-continued

Conjugates Corresponding to Intermediates of Table 1a

| Corresponding Intermediate of Table 1a | Described by Formula | Conjugate Structure |
|---|---|---|
| Int-84 | (D-I) | |
| Int-85 | (D-I) | |

TABLE 1b-continued
Conjugates Corresponding to Intermediates of Table 1a
| Corresponding Intermediate of Table 1a | Described by Formula | Conjugate Structure |
|---|---|---|
| Int-86 | (D-I) | 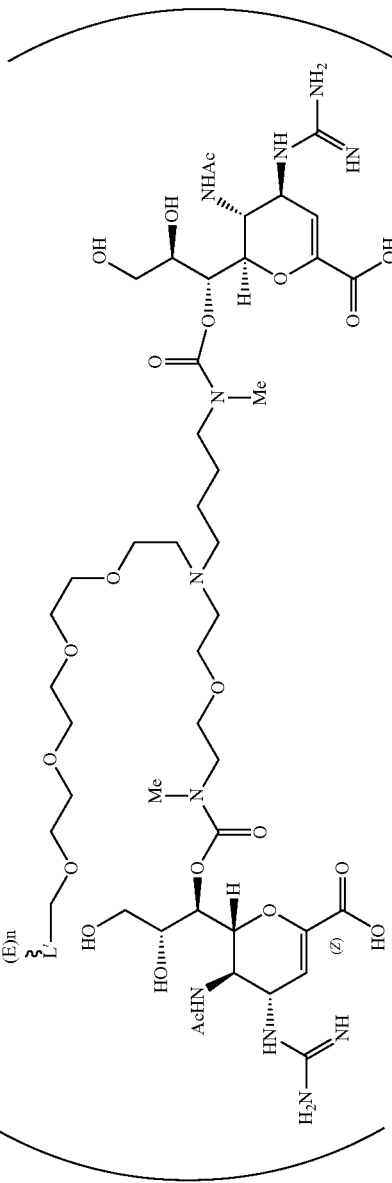 |
| Int-87 | (D-I) | 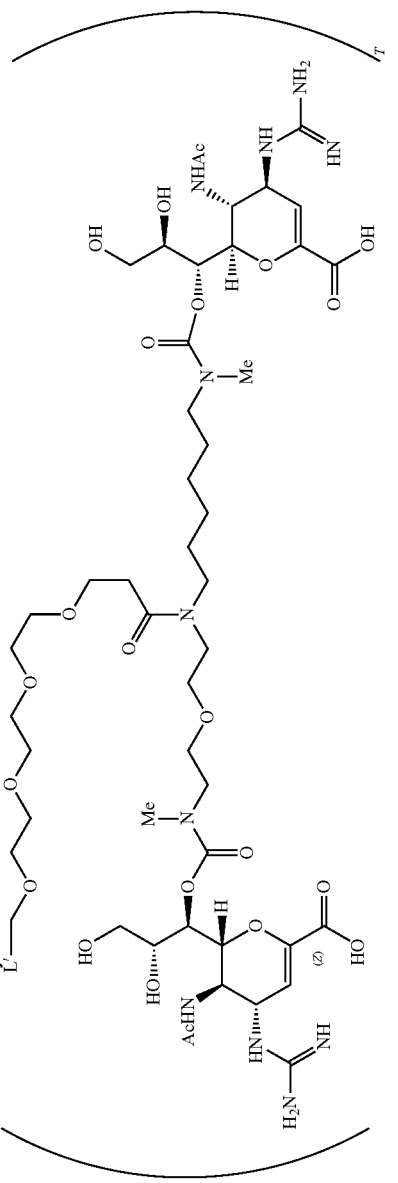 |

TABLE 1b-continued
Conjugates Corresponding to Intermediates of Table 1a
| Corresponding Intermediate of Table 1a | Described by Formula | Conjugate Structure |
|---|---|---|
| Int-88 | (D-I) | 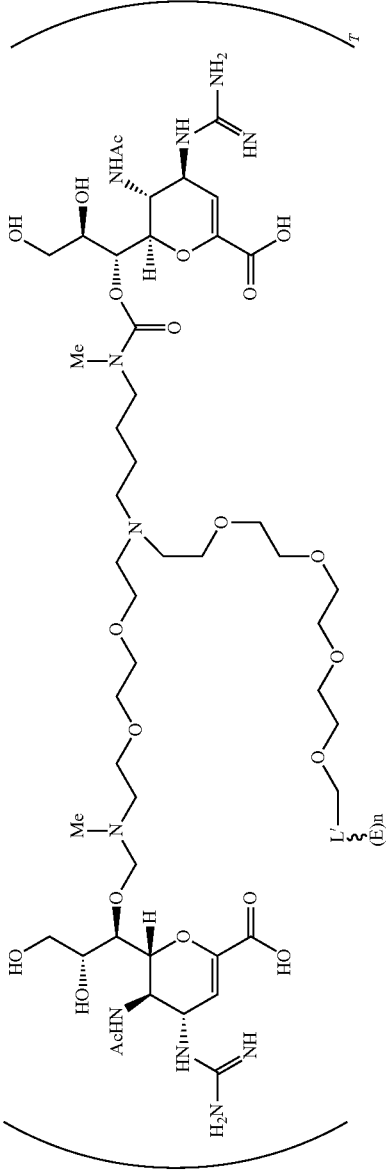 |
| Int-89 | (D-I) | 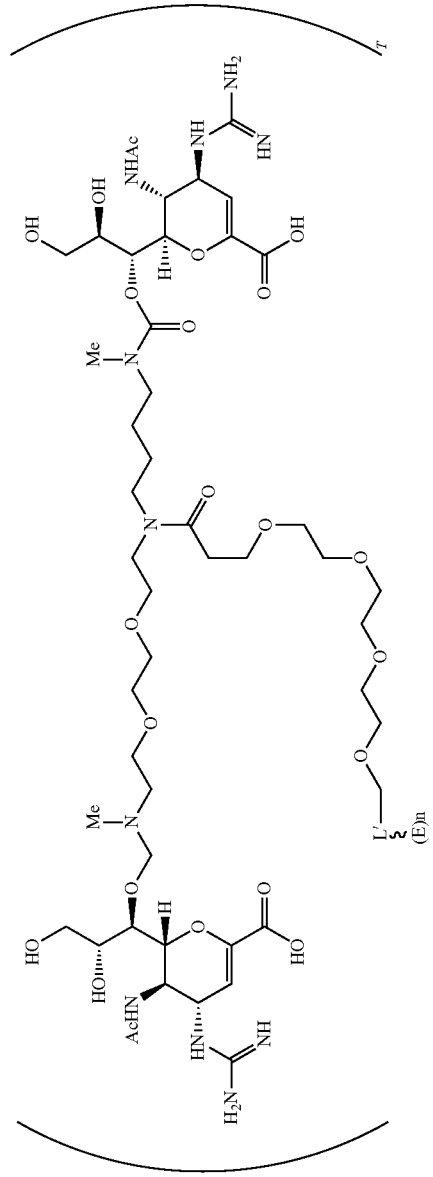 |

TABLE 1b-continued

Conjugates Corresponding to Intermediates of Table 1a

| Corresponding Intermediate of Table 1a | Described by Formula | Conjugate Structure |
|---|---|---|
| Int-90 | (D-I) | |
| Int-91 | (M-I) | |

TABLE 1b-continued
Conjugates Corresponding to Intermediates of Table 1a
| Corresponding Intermediate of Table 1a | Described by Formula | Conjugate Structure |
|---|---|---|
| Int-92 | (M-I) | 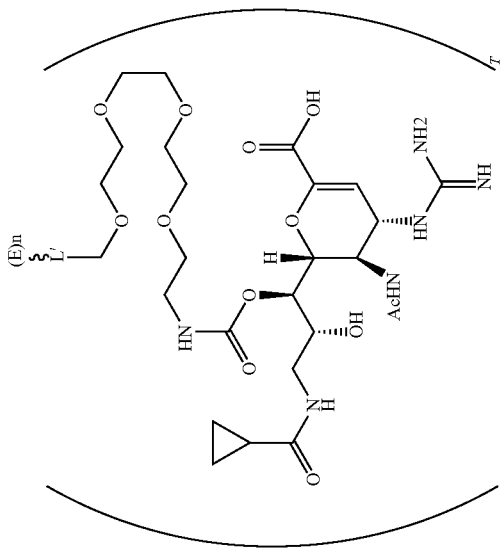 |

In some embodiments, each E includes an Fc domain monomer having the sequence of any one of SEQ ID NOs: 1-138. In other embodiments, each E includes an Fc domain monomer having a sequence at least 95% identical to the amino acid sequence of SEQ ID NO: 63 or SEQ ID NO: 64. In other embodiments, each E includes an Fc domain monomer having the amino acid sequence of SEQ ID NO: 63 or SEQ ID NO: 64. In other embodiments, each E includes an Fc domain monomer having a sequence at least 95% identical to the amino acid sequence of SEQ ID NO: 67 or SEQ ID NO: 68. In other embodiments, each E includes an Fc domain monomer having the amino acid sequence of SEQ ID NO: 67 or SEQ ID NO: 68. In other embodiments, each E includes an Fc domain monomer having a sequence at least 95% identical to the amino acid sequence of SEQ ID NO: 72 or SEQ ID NO: 73. In other embodiments, each E includes an Fc domain monomer having the amino acid sequence of SEQ ID NO: 72 or SEQ ID NO: 73. In other embodiments, each E includes an Fc domain monomer having a sequence at least 95% identical to the amino acid sequence of SEQ ID NO: 76 or SEQ ID NO: 77. In other embodiments, each E includes an Fc domain monomer having the amino acid sequence of SEQ ID NO: 76 or SEQ ID NO: 77. In other embodiments, each E includes an Fc domain monomer having a sequence at least 95% identical to the amino acid sequence of SEQ ID NO: 81 or SEQ ID NO: 82. In other embodiments, each E includes an Fc domain monomer having the amino acid sequence of SEQ ID NO: 81 or SEQ ID NO: 82. In other embodiments, each E includes an Fc domain monomer having a sequence at least 95% identical to the amino acid sequence of SEQ ID NO: 85 or SEQ ID NO: 86. In other embodiments, each E includes an Fc domain monomer having the amino acid sequence of SEQ ID NO: 85 or SEQ ID NO: 86.

In another aspect, the invention features a conjugate including (i) a first moiety, $A_1$; (ii) a second moiety, $A_2$; (iii) an Fc domain monomer or an Fc domain; and (iv) a linker covalently attached to $A_1$ and $A_2$, and to the Fc domain monomer or the Fc domain; wherein each $A_1$ and each $A_2$ is independently selected from any one of formulas (A-I)-(A-XII). In some embodiments, each of $A_1$ and $A_2$ may be independently selected from any one of formulas (A-I), (A-II), (A-VI), or (A-VII). In other embodiments, each of $A_1$ and $A_2$ may be independently selected from formula (A-I). In a preferred embodiment of the above, x is 2.

In another aspect, the invention features a conjugate including (i) a first moiety, Int; (ii) an Fc domain monomer or an Fc domain; and (iv) a linker covalently attached to Int, and to the Fc domain monomer or the Fc domain; wherein each Int is independently selected from any one of the intermediates of Table 1a.

In another aspect, the invention features a conjugate including (i) a first moiety, $A_1$; (ii) a second moiety, $A_2$; (iii) an albumin protein, an albumin protein-binding peptide, or an Fc-binding peptide; and (iv) a linker covalently attached to $A_1$ and $A_2$, and to the albumin protein, the albumin protein-binding peptide, or the Fc-binding peptide; wherein each $A_1$ and each $A_2$ is independently selected from any one of formulas (A-I)-(A-XII). In some embodiments, each of $A_1$ and $A_2$ may be independently selected from any one of formulas (A-I), (A-II), (A-VI), or (A-VII). In other embodiments, each of $A_1$ and $A_2$ may be independently selected from formula (A-I). In a preferred embodiment of the above, x is 2.

In another aspect, the invention features a conjugate described by formula (D-I):

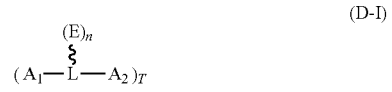

wherein each $A_1$ and each $A_2$ is independently selected from any one of formulas (A-I)-(A-XII); each E comprises an Fc domain monomer (e.g., an Fc domain monomer having the sequence of any one of SEQ ID NOs: 1-138), an albumin protein (e.g., an albumin protein having the sequence of any one of SEQ ID NOs: 139-141), an albumin protein-binding peptide, or an Fc-binding peptide; n is 1 or 2; T is an integer from 1 to 20 (e.g., T is 1, 2, 3, 4, 5, 6, 7, 8, 9, 10, 11, 12, 13, 14, 15, 16, 17, 18, 19, or 20); and L is a linker covalently attached to each of E, $A_1$, and $A_2$, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein). In some embodiments, each of $A_1$ and $A_2$ may be independently selected from any one of formulas (A-I), (A-II), (A-VI), or (A-VII). In other embodiments, each of $A_1$ and $A_2$ may be independently selected from formula (A-I).

In another aspect, the invention features a conjugate described by formula (D-I):

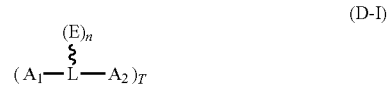

wherein each $A_1$ and each $A_2$ is independently selected from any one of formulas (A-I)-(A-V); each E comprises an Fc domain monomer (e.g., an Fc domain monomer having the sequence of any one of SEQ ID NOs: 1-138), an albumin protein (e.g., an albumin protein having the sequence of any one of SEQ ID NOs: 139-141), an albumin protein-binding peptide, or an Fc-binding peptide; n is 1 or 2; T is an integer from 1 to 20 (e.g., T is 1, 2, 3, 4, 5, 6, 7, 8, 9, 10, 11, 12, 13, 14, 15, 16, 17, 18, 19, or 20); and L is a linker covalently attached to each of E, $A_1$, and $A_2$, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In another aspect, the invention features a conjugate described by formula (D-I):

wherein each $A_1$ and each $A_2$ is independently selected from any one of formulas (A-VI)-(A-IX); each E comprises an Fc domain monomer (e.g., an Fc domain monomer having the sequence of any one of SEQ ID NOs: 1-138), an albumin protein (e.g., an albumin protein having the sequence of any one of SEQ ID NOs: 139-141), an albumin protein-binding peptide, or an Fc-binding peptide; n is 1 or 2; T is an integer from 1 to 20 (e.g., T is 1, 2, 3, 4, 5, 6, 7, 8, 9, 10, 11, 12, 13, 14, 15, 16, 17, 18, 19, or 20); and L is a linker covalently attached to each of E, $A_1$, and $A_2$, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In some embodiments, the conjugate is described by formula (D-I1):

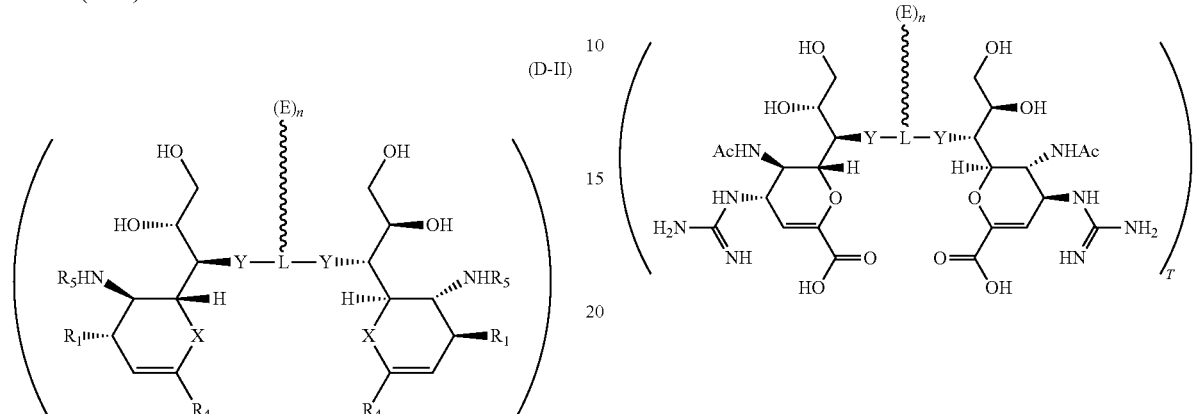

or a pharmaceutically acceptable salt thereof.

In some embodiments, the conjugate is described by formula (D-II-1):

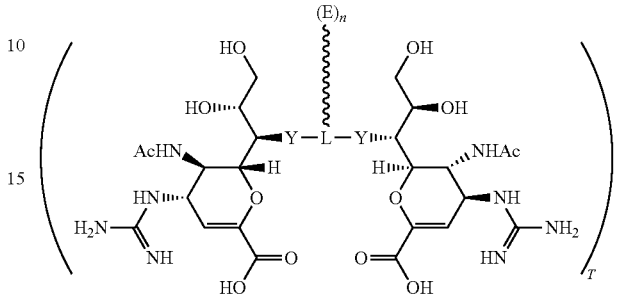

or a pharmaceutically acceptable salt thereof.

In some embodiments, the conjugate is described by formula (D-II-2):

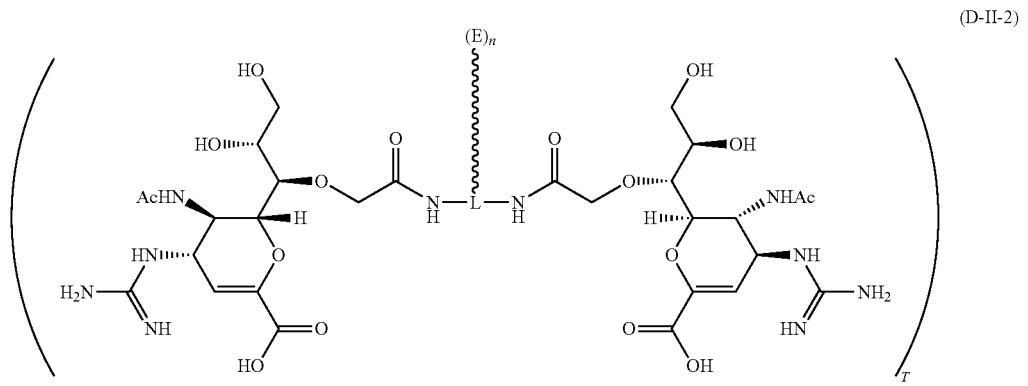

or a pharmaceutically acceptable salt thereof.

In some embodiments, the conjugate is described by formula (D-II-3):

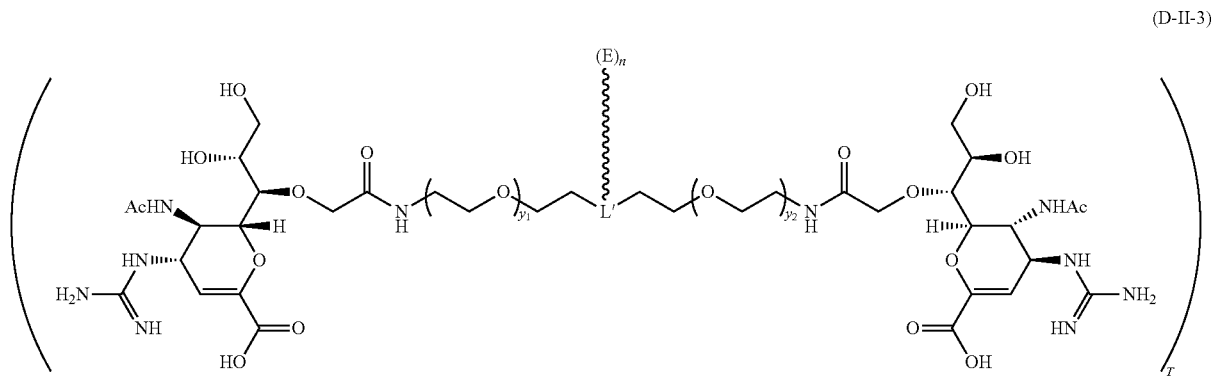

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.
In some embodiments, the conjugate has the structure selected from:
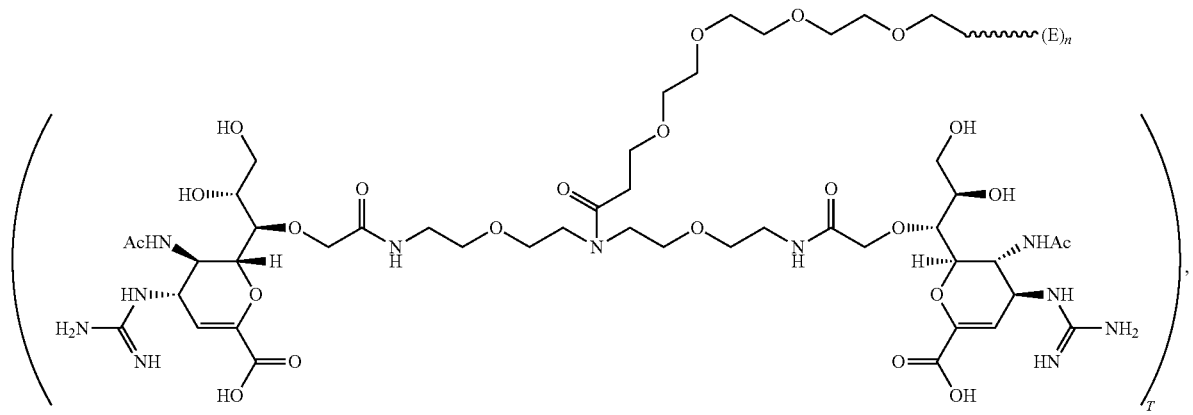
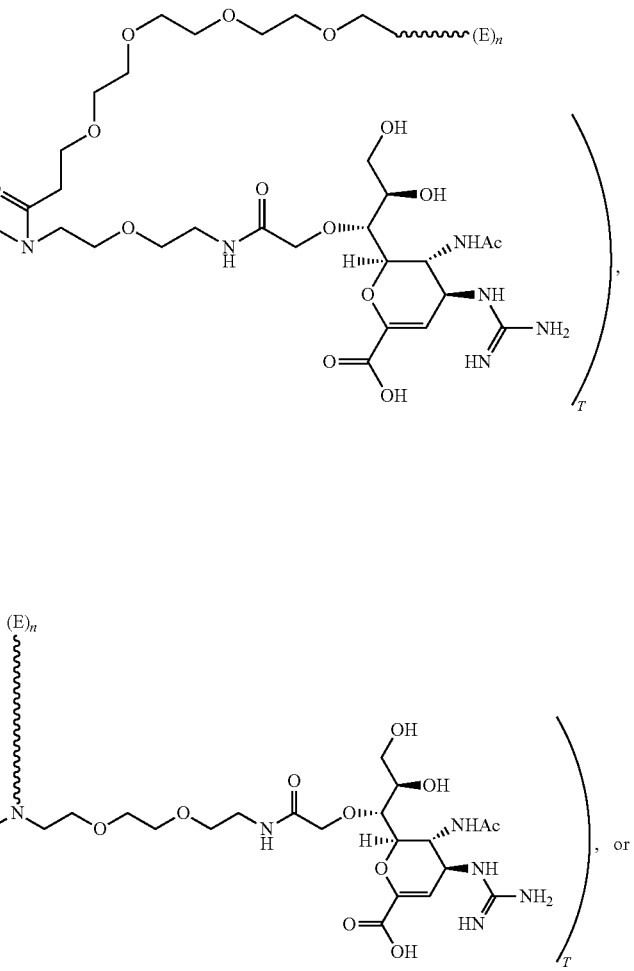
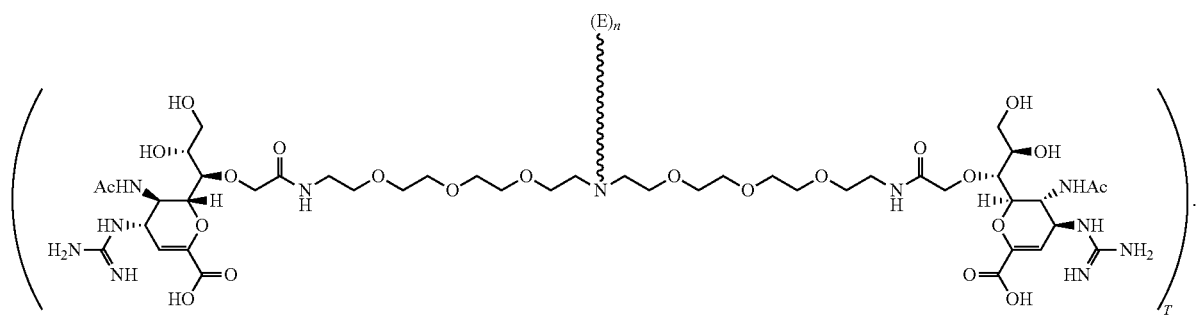

In some embodiments, the conjugate is described by formula (D-II-4):

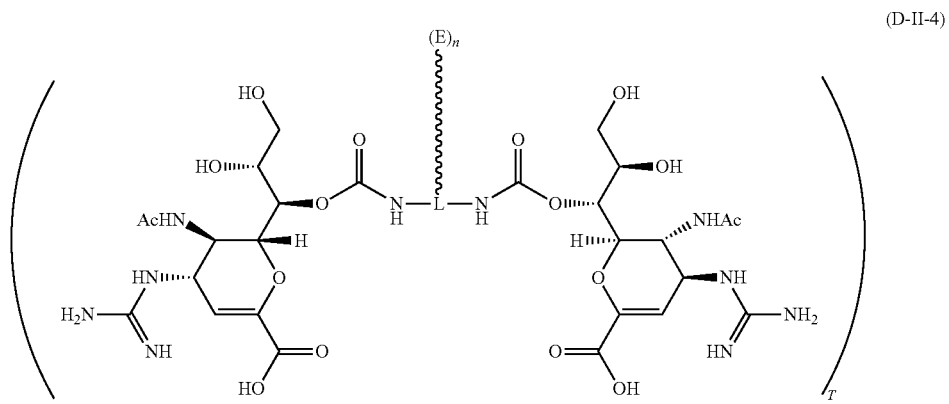

or a pharmaceutically acceptable salt thereof.

In some embodiments, the conjugate is described by formula (D-II-5):

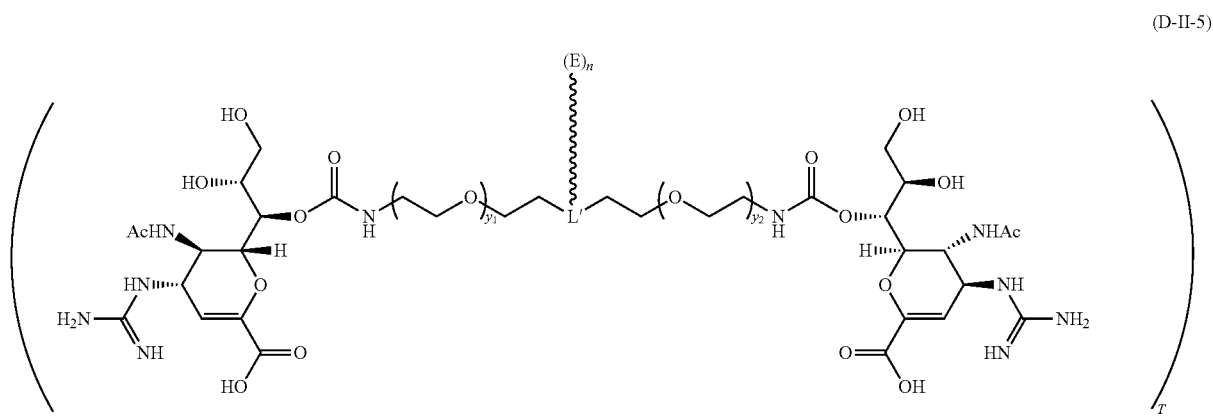

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate has the structure selected from:

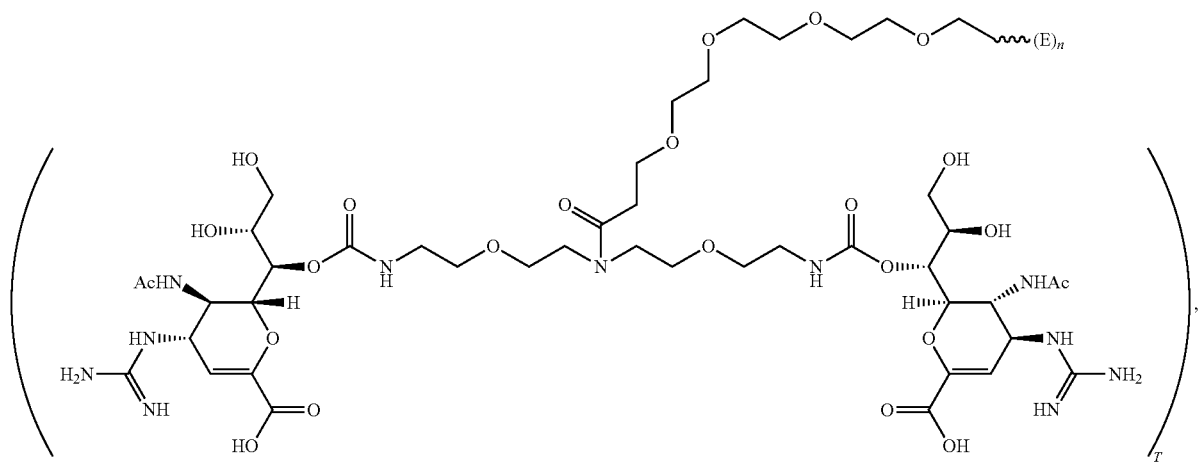

-continued
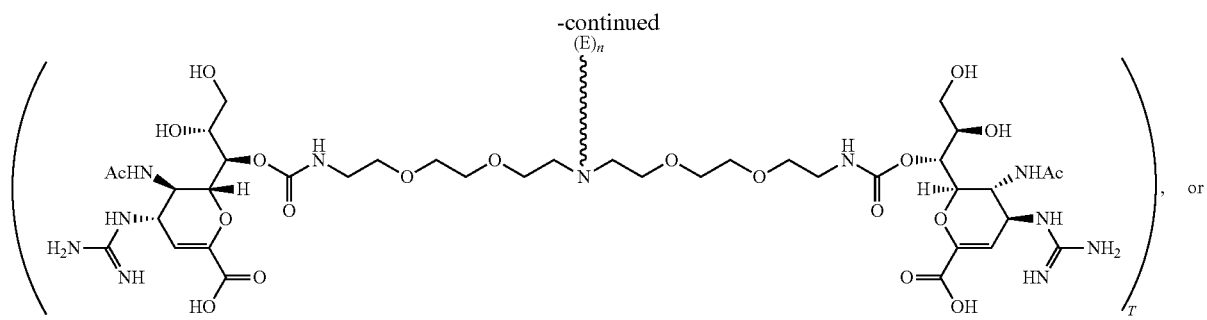
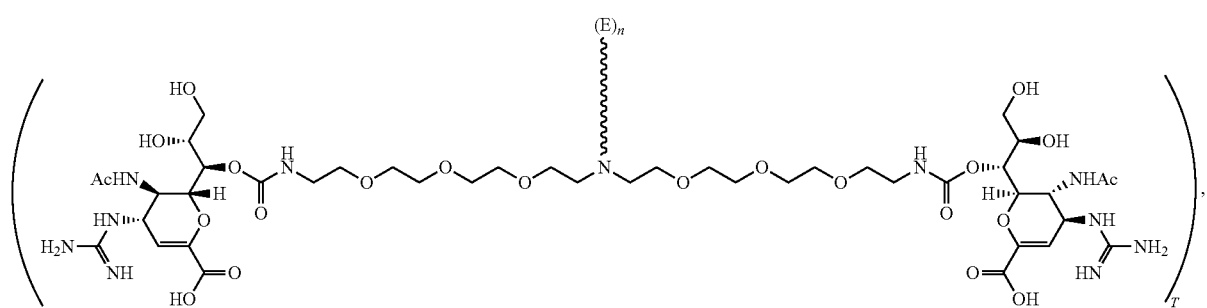
or a pharmaceutically acceptable salt thereof.
In some embodiments, the conjugate has the structure selected from:
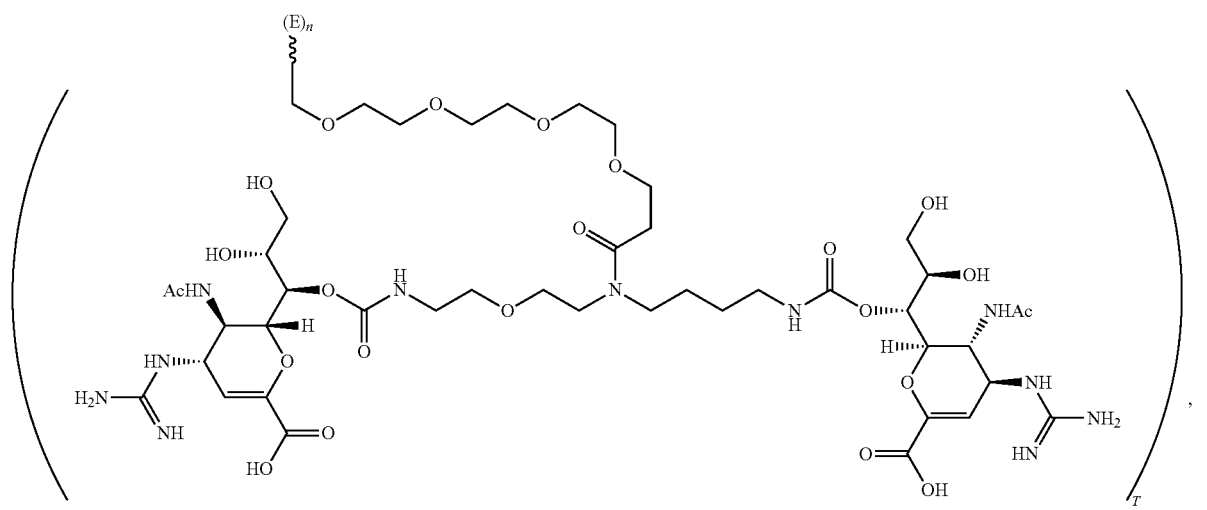

-continued
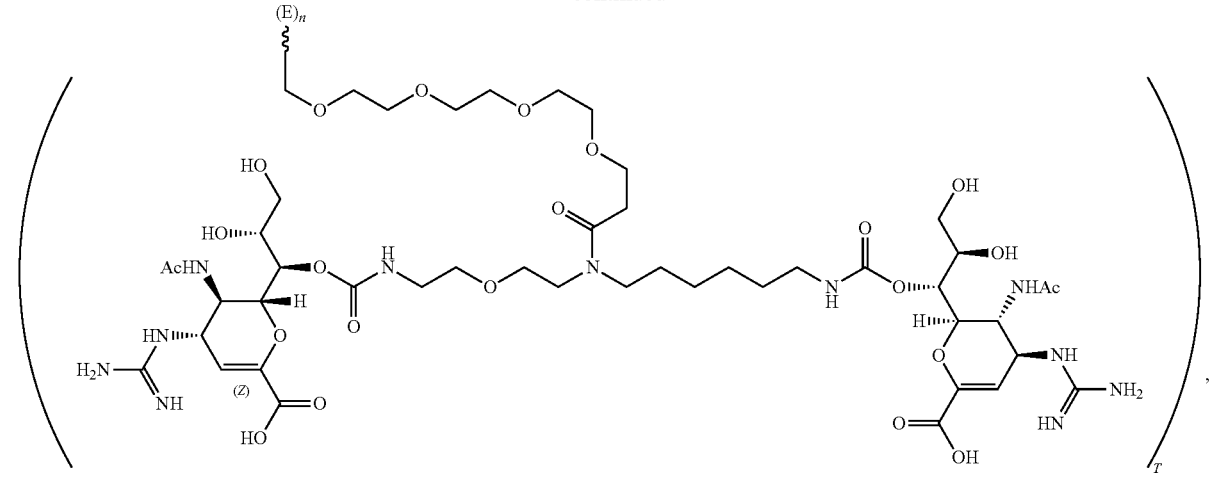
,
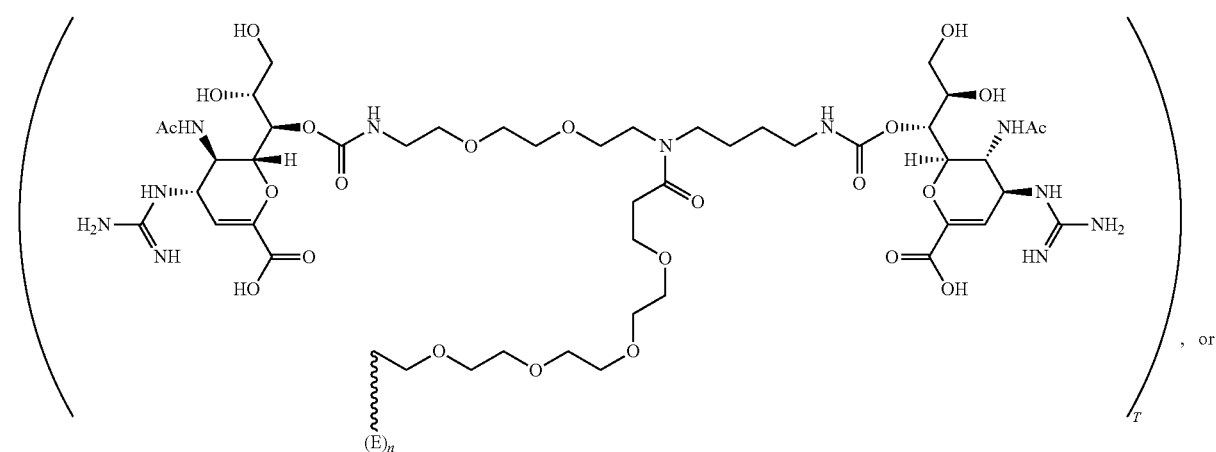
, or
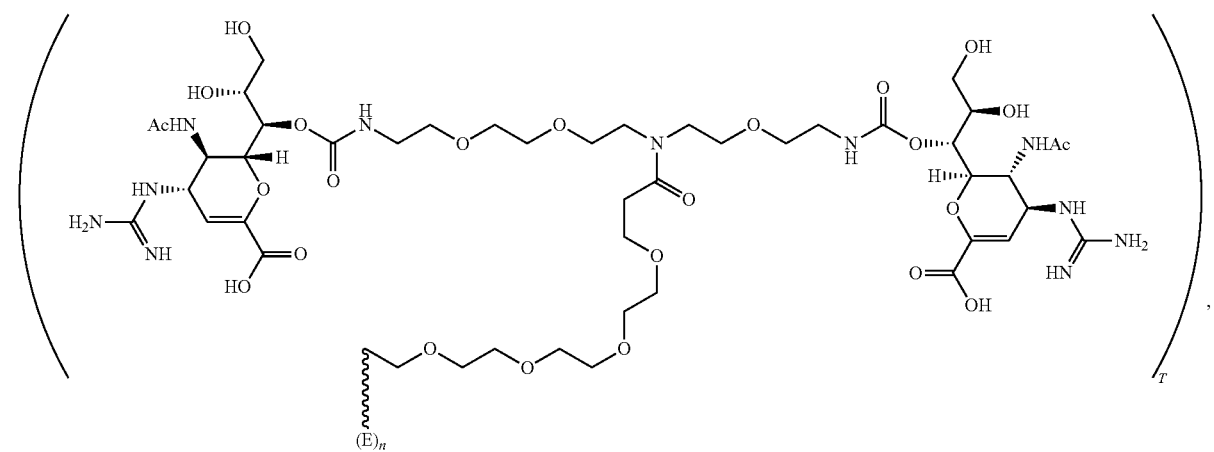
,
or a pharmaceutically acceptable salt thereof.

In some embodiments, the conjugate is described by formula (D-II-6):

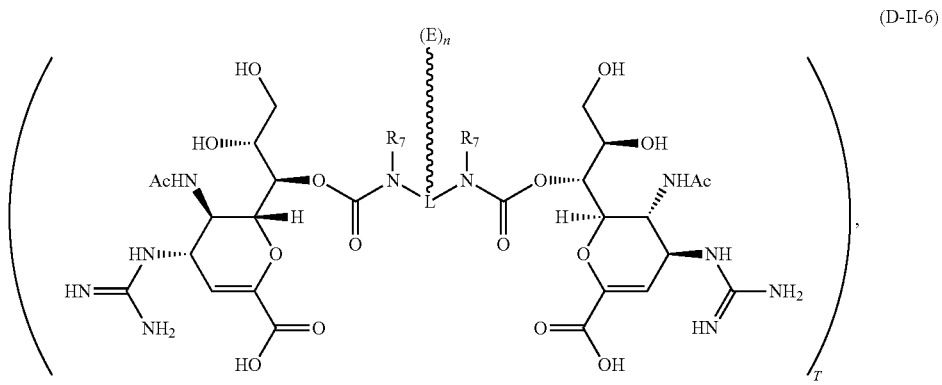

(D-II-6)

wherein $R_7$ is selected from H, C1-C20 alkyl, C3-C20 cycloalkyl, C3-C20 heterocycloalkyl; C5-C15 aryl, and C2-C15 heteroaryl; or a pharmaceutically acceptable salt thereof. In some embodiments, $R_7$ is selected from C1-C20 alkyl (e.g., methyl, ethyl, propyl, or butyl).

In some embodiments, the conjugate is described by formula (D-II-7):

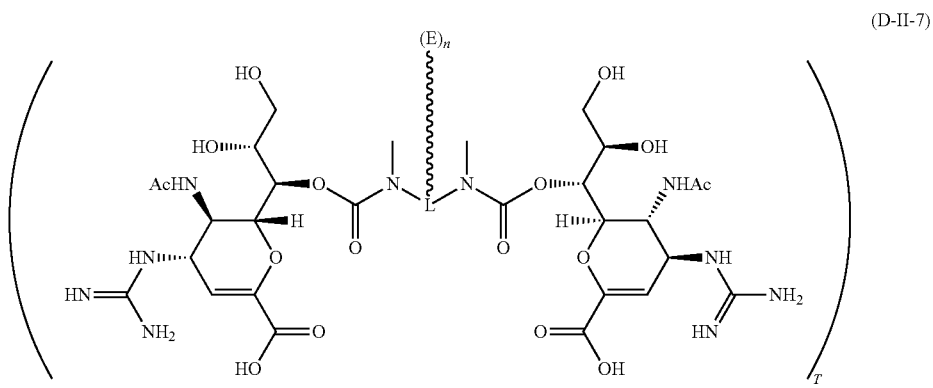

(D-II-7)

or a pharmaceutically acceptable salt thereof.

In some embodiments, the conjugate is described by formula (D-II-8):

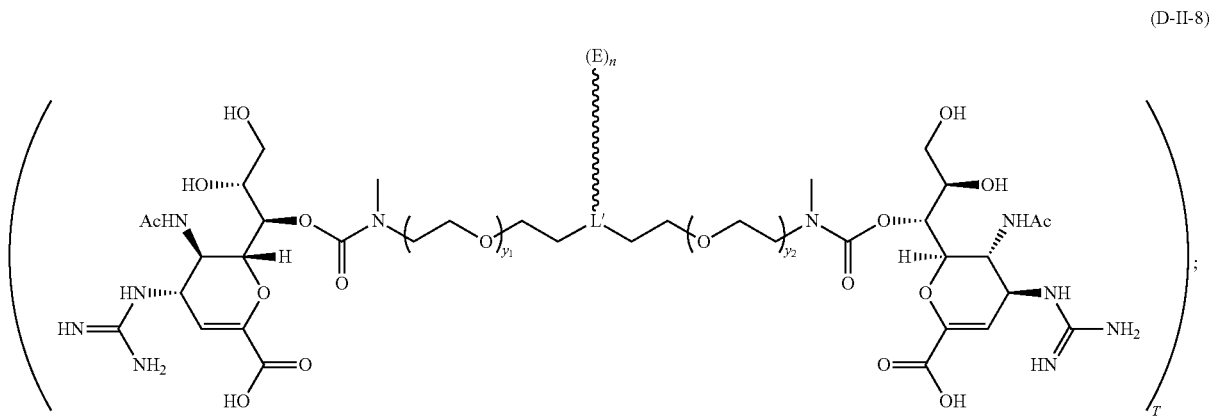

(D-II-8)

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.
In some embodiments, the conjugate has the structure
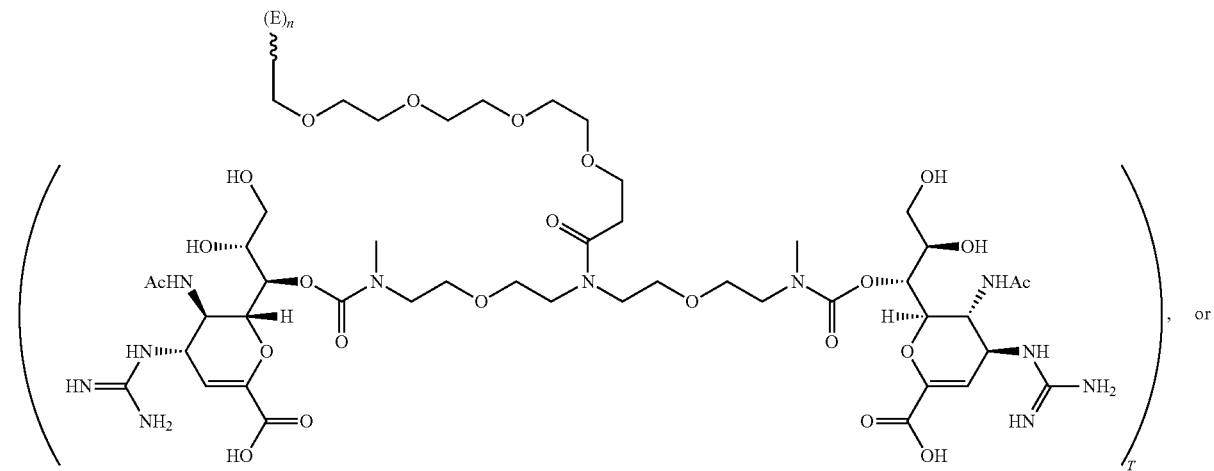
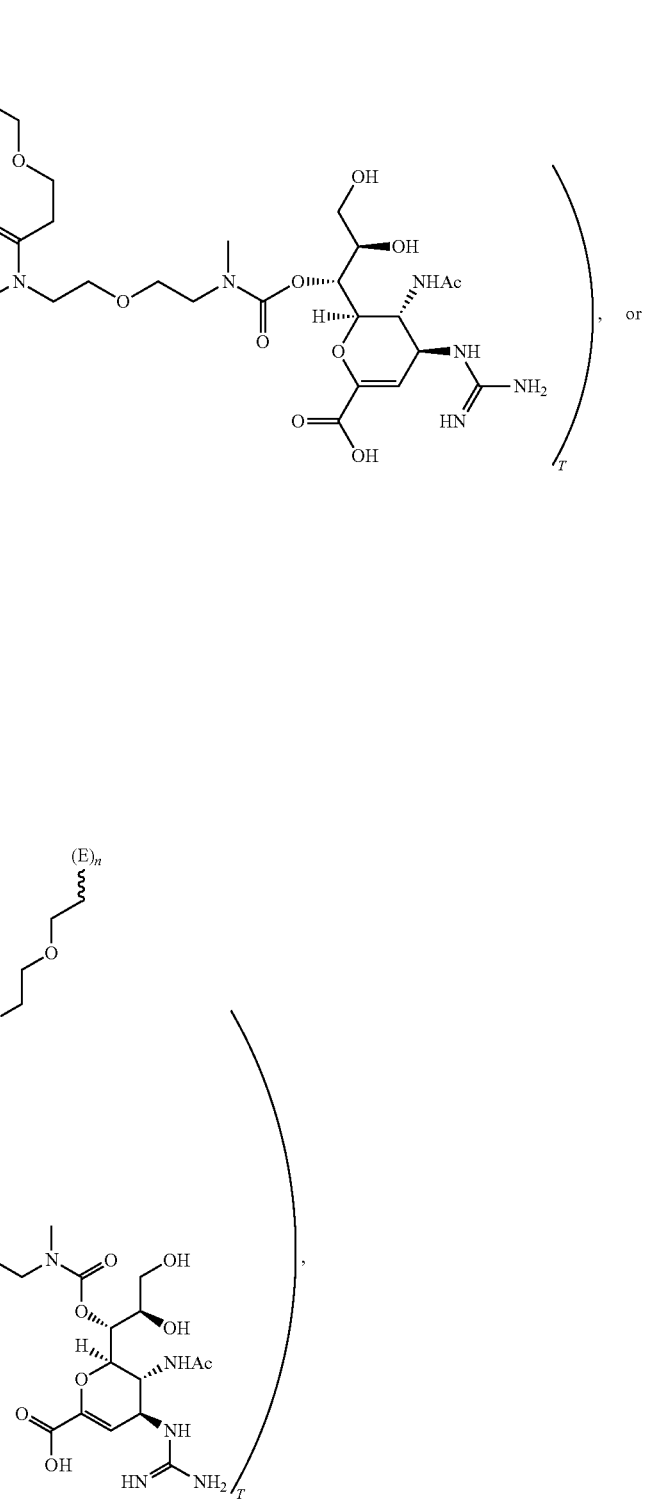
or a pharmaceutically acceptable salt thereof.

In some embodiments, the conjugate has the structure
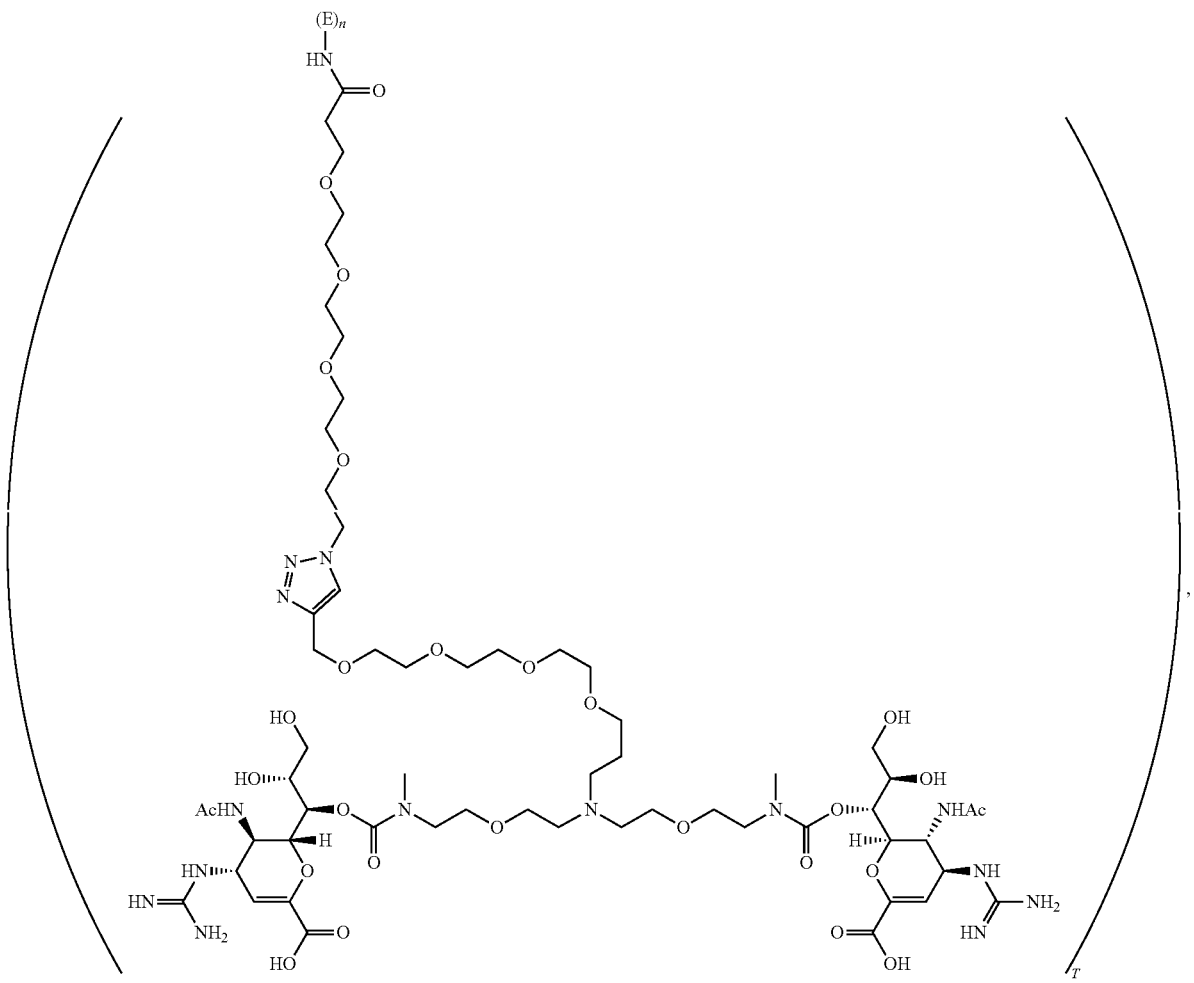
or a pharmaceutically acceptable salt thereof.
In some embodiments, the conjugate has the structure
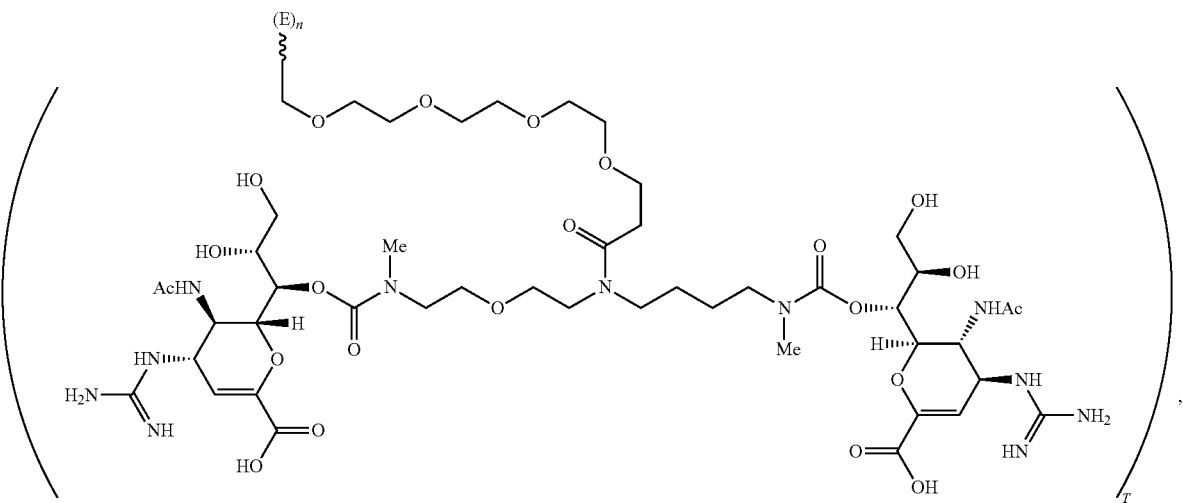

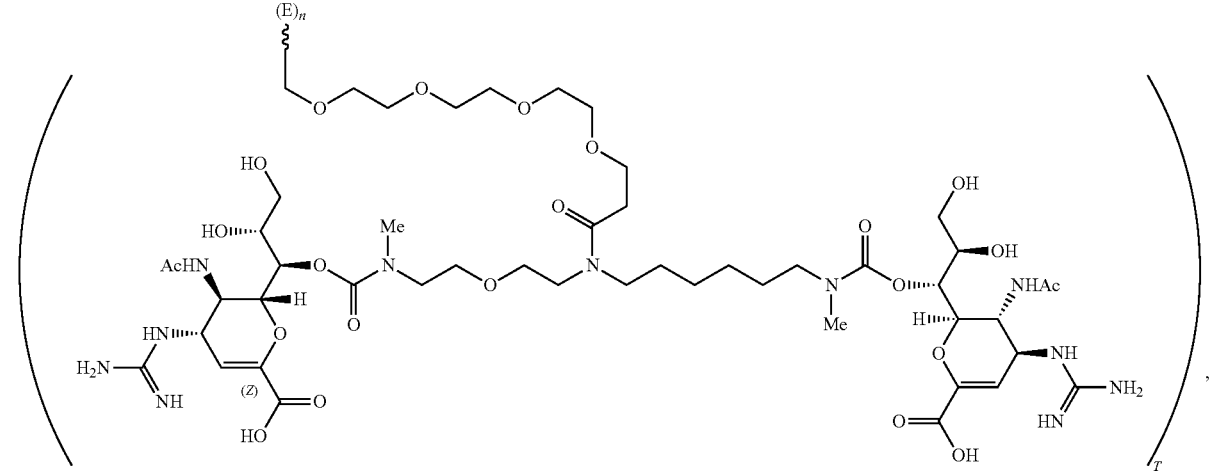
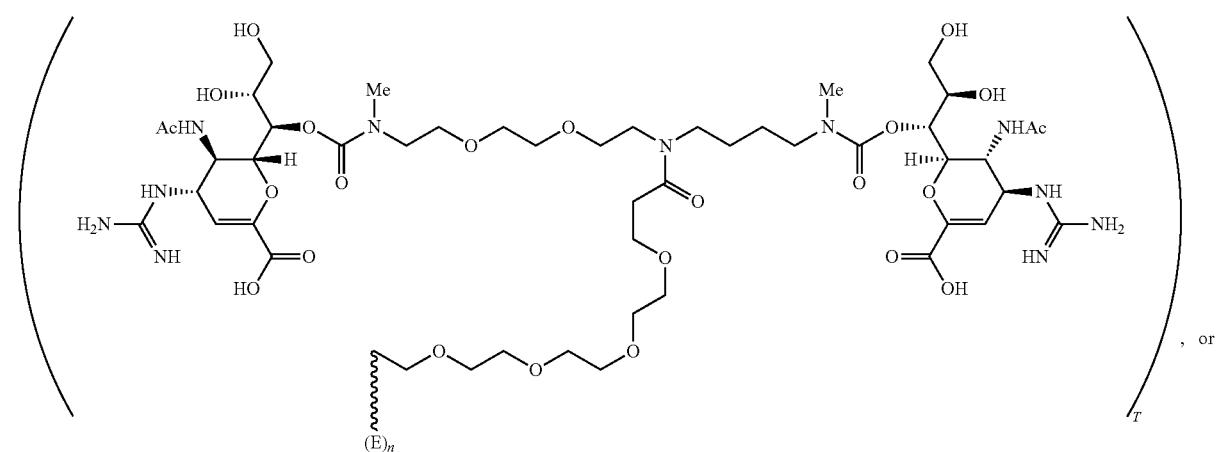
, or
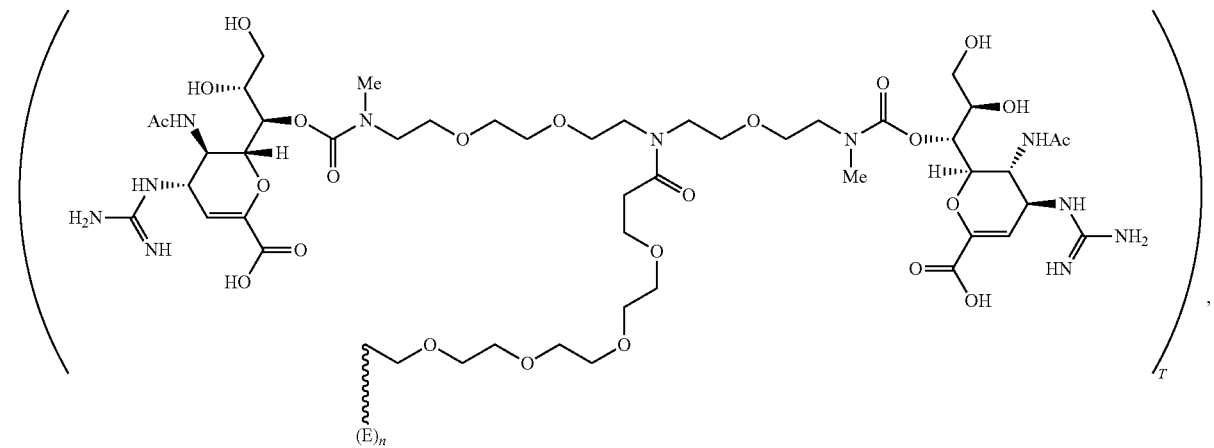
,
or a pharmaceutically acceptable salt thereof.

In some embodiments, the conjugate has the structure
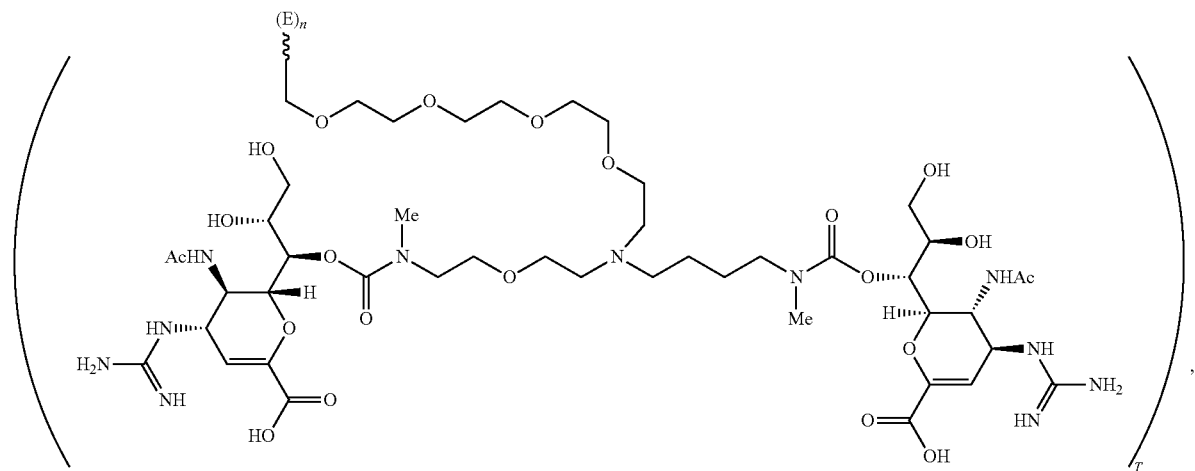
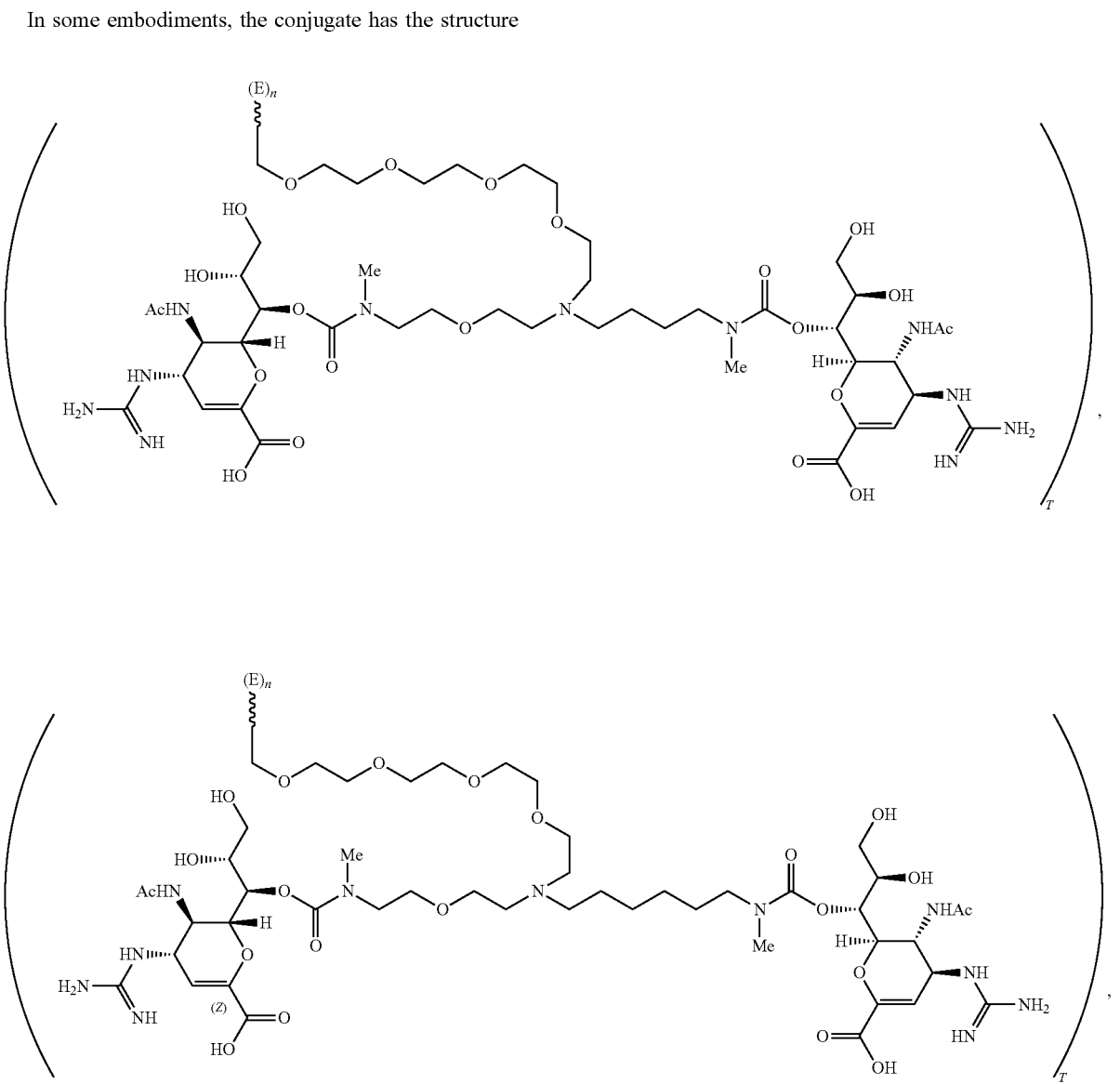
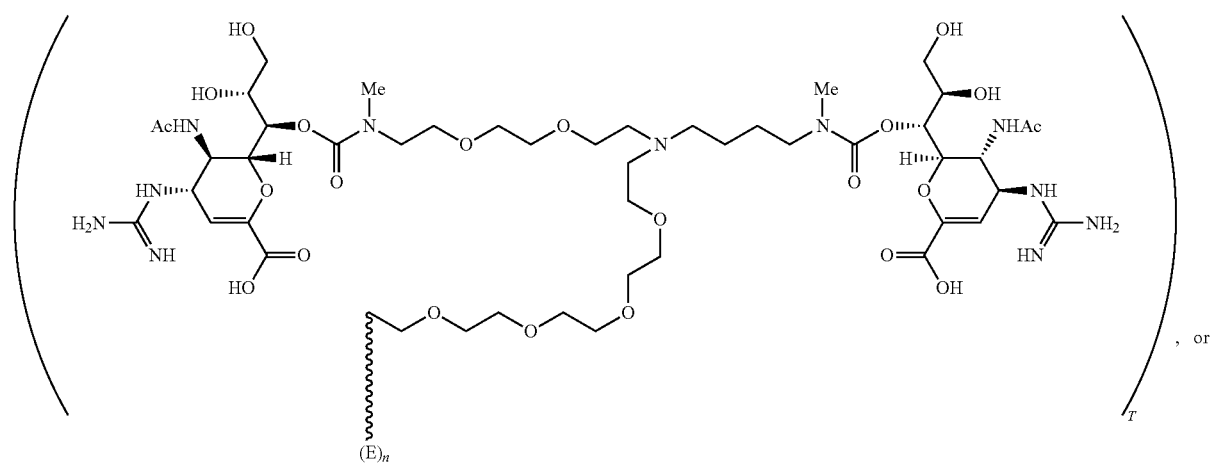
, or

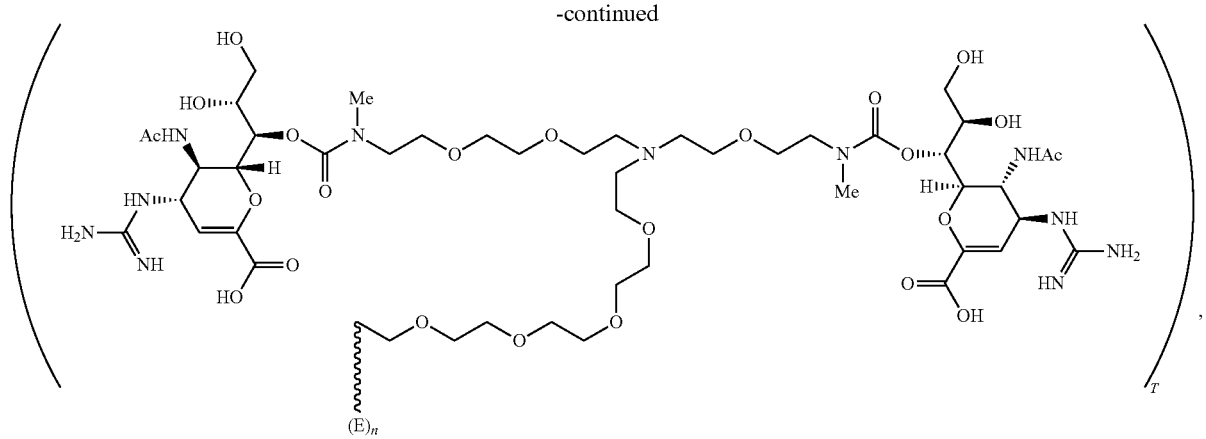

or a pharmaceutically acceptable salt thereof.

In some embodiments, the conjugate is described by formula (D-II-9):

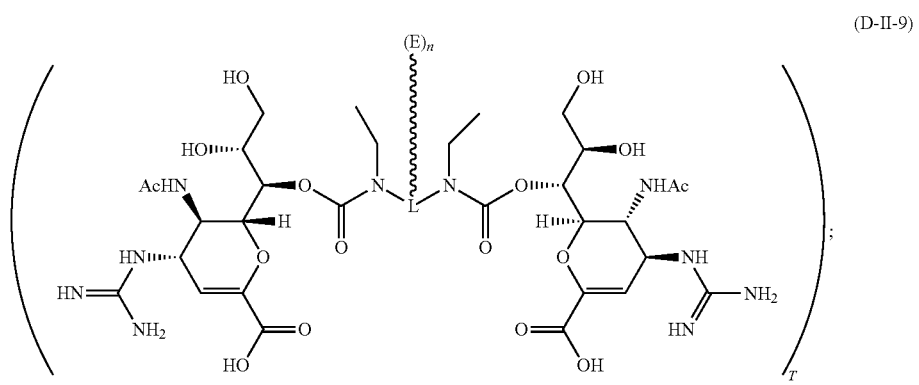

(D-II-9)

or a pharmaceutically acceptable salt thereof.

In some embodiments, the conjugate is described by formula (D-II-10):

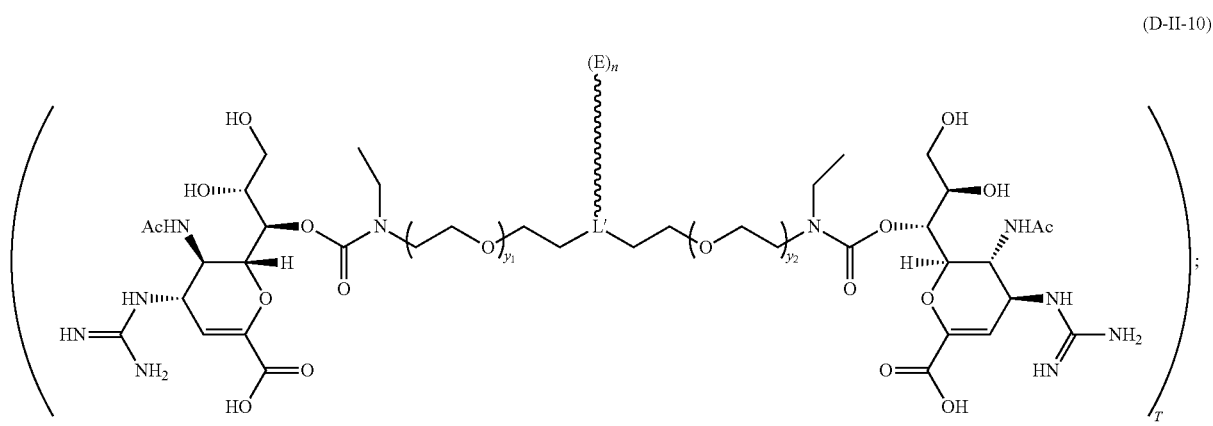

(D-II-10)

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate has the structure

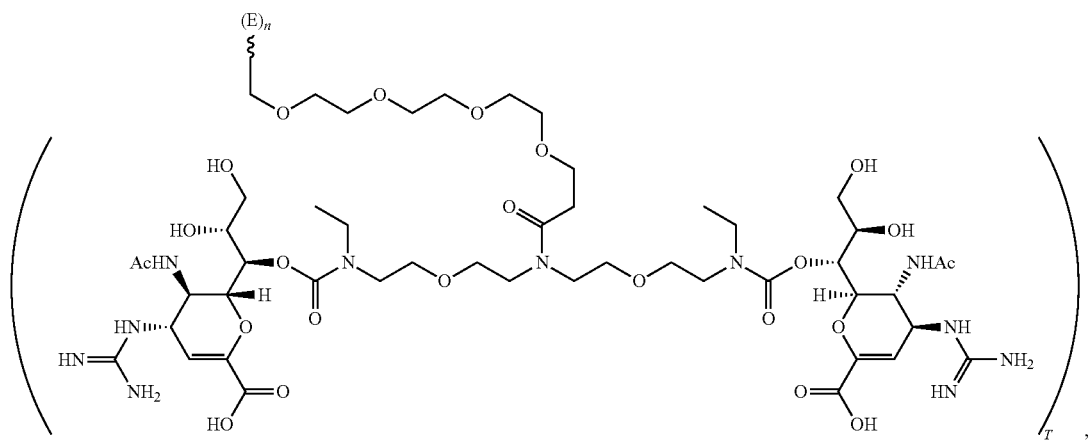

or a pharmaceutically acceptable salt thereof.

In some embodiments, the conjugate has the structure of

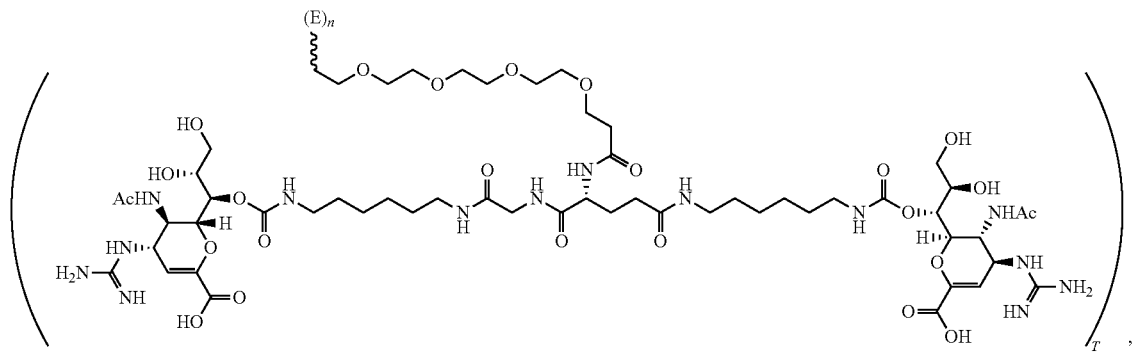

or a pharmaceutically acceptable salt thereof.

In some embodiments, the conjugate is described by formula (D-III):

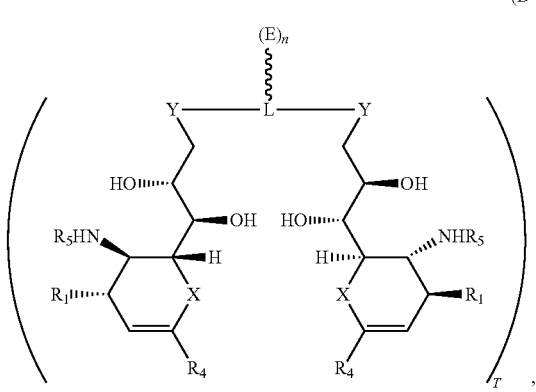

or a pharmaceutically acceptable salt thereof.

In some embodiments, the conjugate is described by formula (D-III-1):

(D-III-1)

or a pharmaceutically acceptable salt thereof.

In some embodiments, the conjugate is described by formula (D-III-2):

(D-III-2)

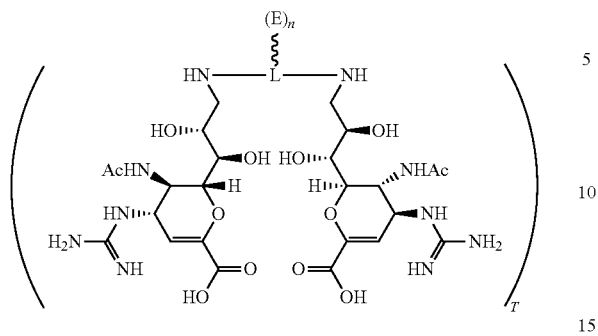

or a pharmaceutically acceptable salt thereof.

In some embodiments, the conjugate is described by formula (D-III-3):

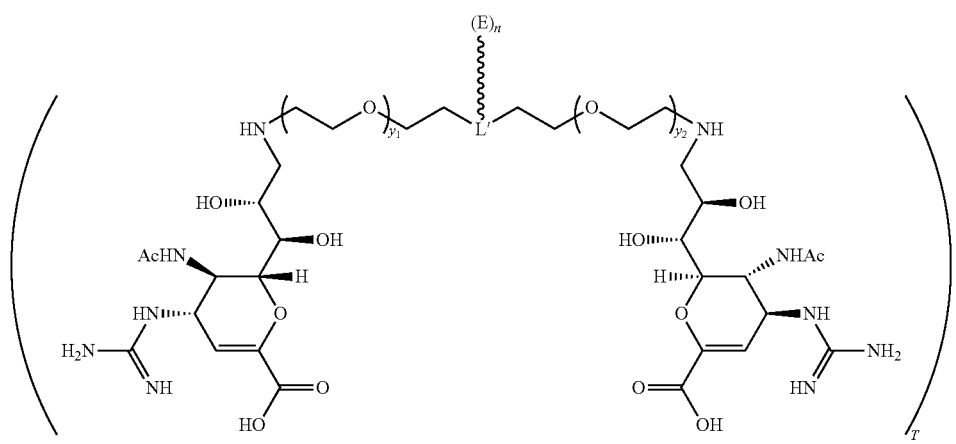

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate is described by formula (D-III-4):

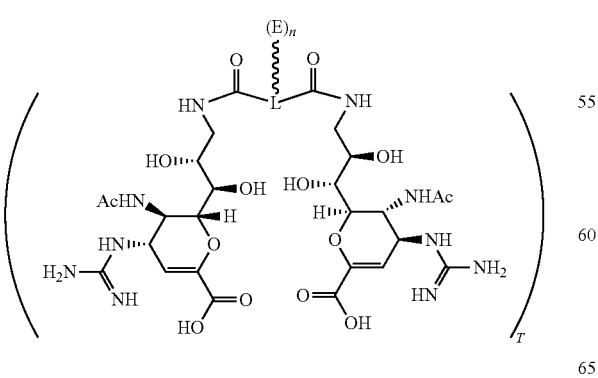

or a pharmaceutically acceptable salt thereof.

In some embodiments, the conjugate is described by formula (D-III-5):

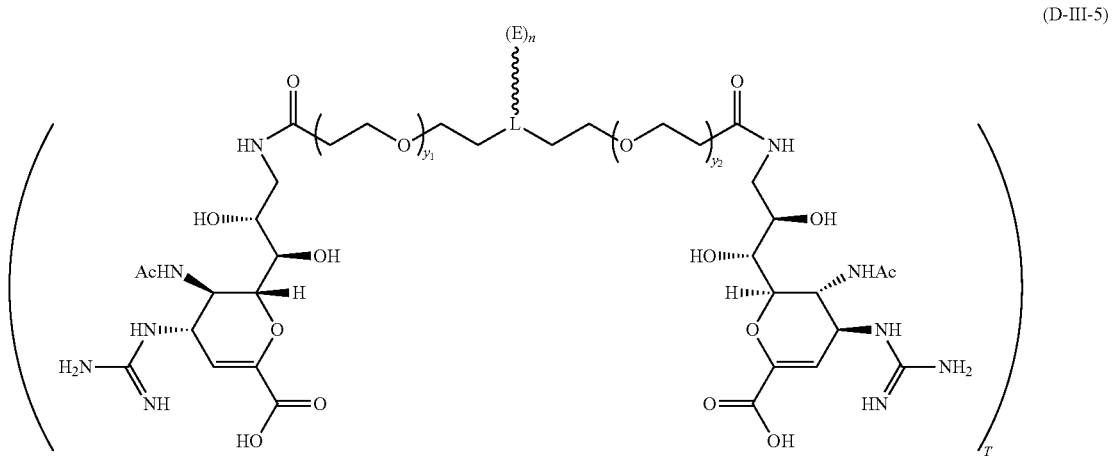

(D-III-5)

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate is described by formula (D-III-6):

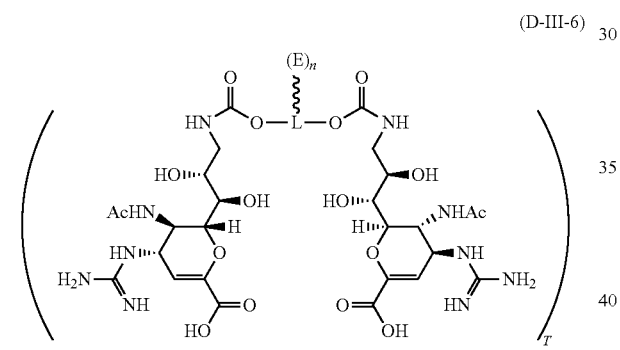

(D-III-6)

or a pharmaceutically acceptable salt thereof.

In some embodiments, the conjugate is described by formula (D-III-7):

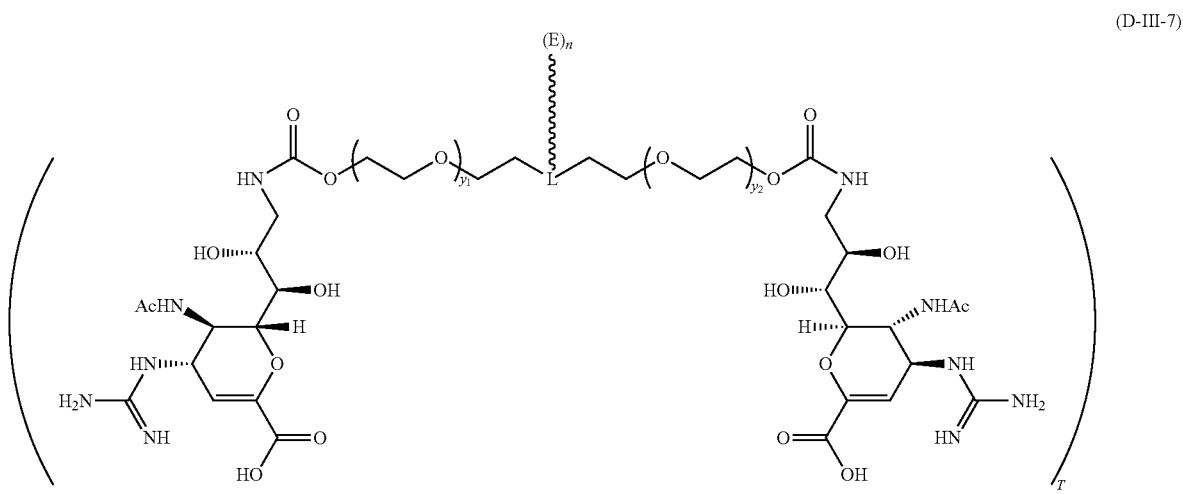

(D-III-7)

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate is described by formula (D-III-8):

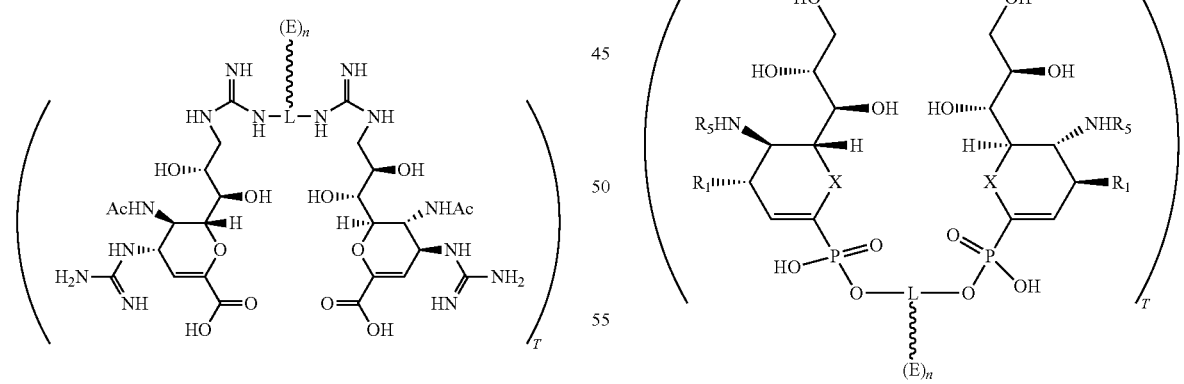

(D-III-8)

or a pharmaceutically acceptable salt thereof.

In some embodiments, the conjugate is described by formula (D-III-9):

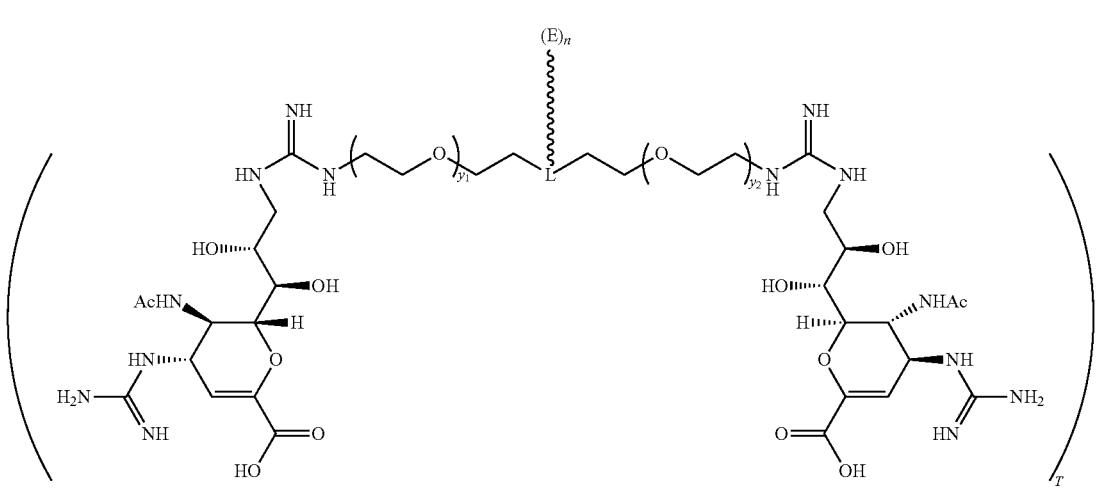

(D-III-9)

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate is described by formula (D-IV):

(D-IV)

or a pharmaceutically acceptable salt thereof.

In some embodiments, the conjugate is described by formula (D-IV-1):

(D-IV-1)

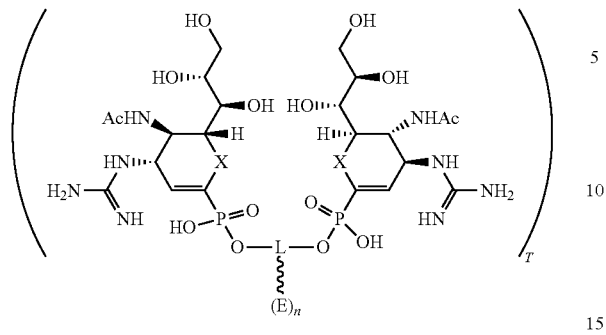

or a pharmaceutically acceptable salt thereof.

In some embodiments, the conjugate is described by formula (D-IV-2):

(D-IV-2)

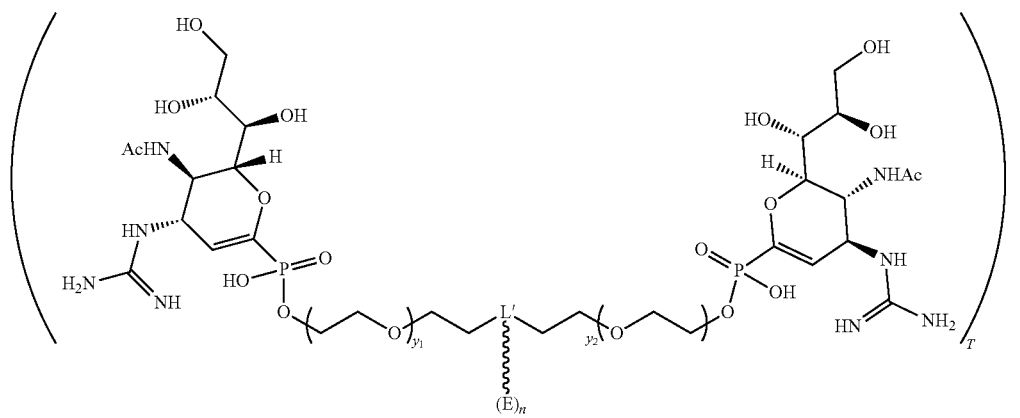

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate is described by formula (D-V):

(D-V)

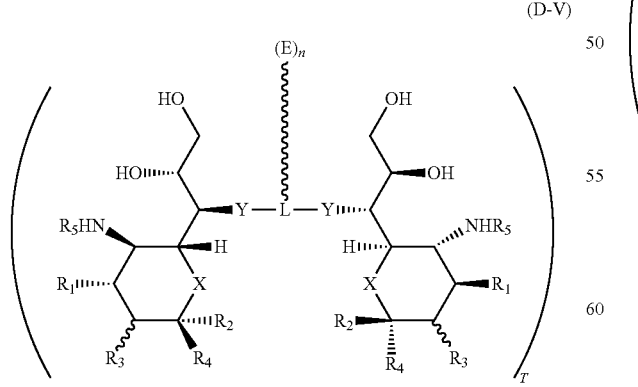

or a pharmaceutically acceptable salt thereof.

In some embodiments, the conjugate is described by formula (D-V-1):

(D-V-1)

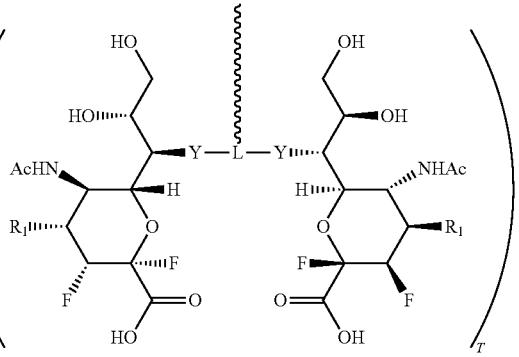

or a pharmaceutically acceptable salt thereof.

In some embodiments, the conjugate is described by formula (D-V-2):

(D-V-2)

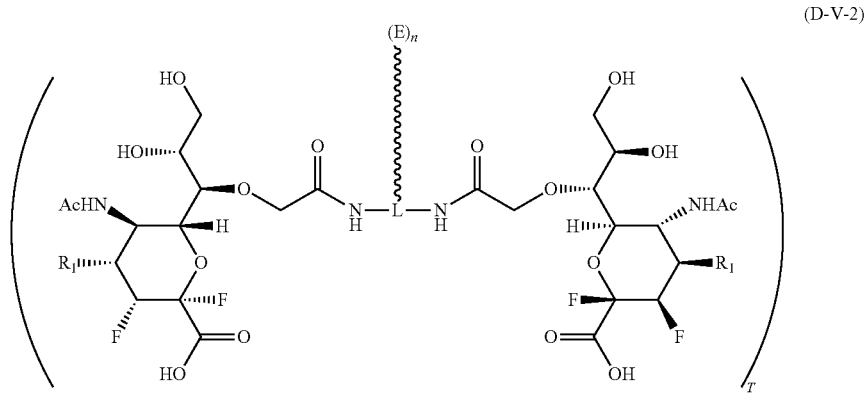

or a pharmaceutically acceptable salt thereof.

In some embodiments, the conjugate is described by formula (D-V-3):

(D-V-3)

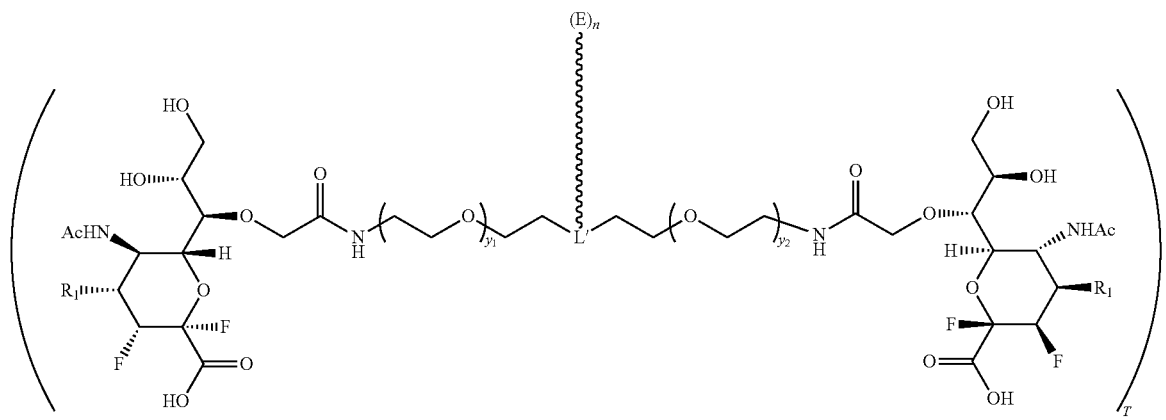

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom. In some embodiments, $y_1$ and $y_2$ are each 1, $y_1$ and $y_2$ are each 2, or $y_1$ and $y_2$ are each 3.

In some embodiments, the conjugate is described by formula (D-V-4):

(D-V-4)

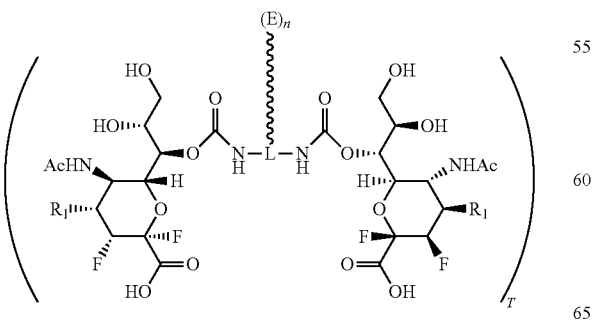

or a pharmaceutically acceptable salt thereof.

In some embodiments, the conjugate is described by formula (D-V-5):

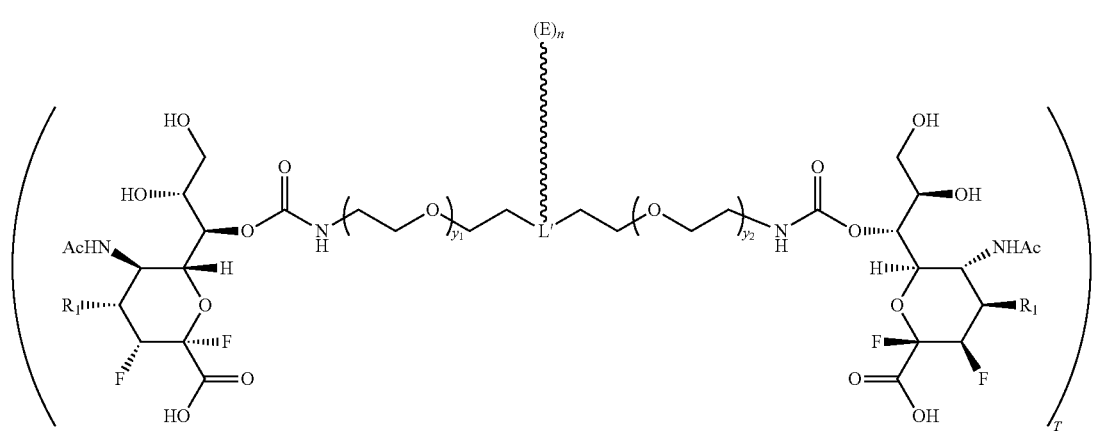

(D-V-5)

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom. In some embodiments, $y_1$ and $y_2$ are each 1, $y_1$ and $y_2$ are each 2, or $y_1$ and $y_2$ are each 3.

In some embodiments, the conjugate is described by formula (D-V-6):

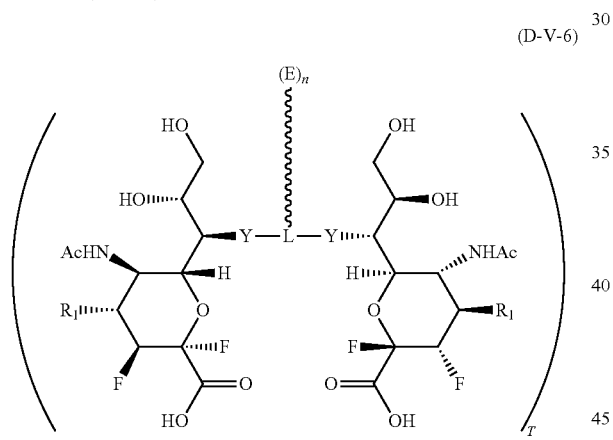

(D-V-6)

or a pharmaceutically acceptable salt thereof.

In some embodiments, the conjugate is described by formula (D-V-7):

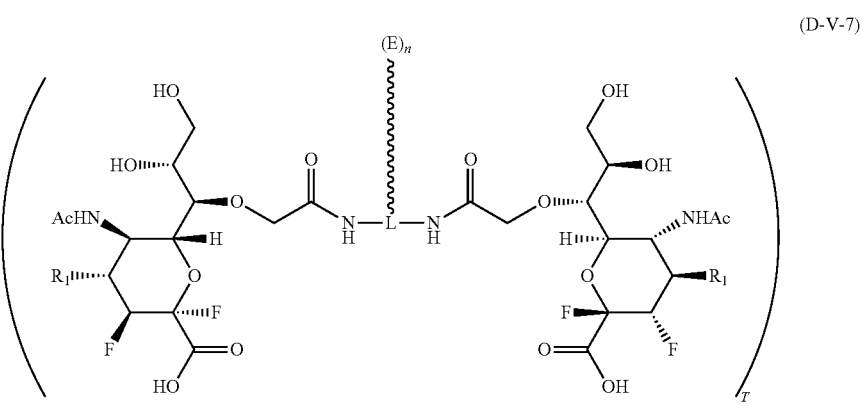

(D-V-7)

or a pharmaceutically acceptable salt thereof.

In some embodiments, the conjugate is described by formula (D-V-8):

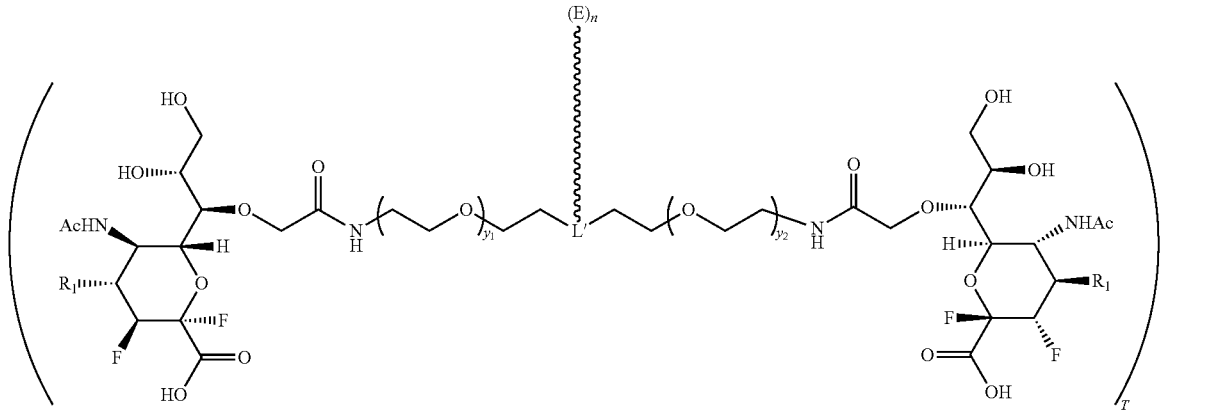

(D-V-8)

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom. In some embodiments, $y_1$ and $y_2$ are each 1, $y_1$ and $y_2$ are each 2, or $y_1$ and $y_2$ are each 3.

In some embodiments, the conjugate is described by formula (D-V-9):


(D-V-9)

or a pharmaceutically acceptable salt thereof.

In some embodiments, the conjugate is described by formula (D-V-10):

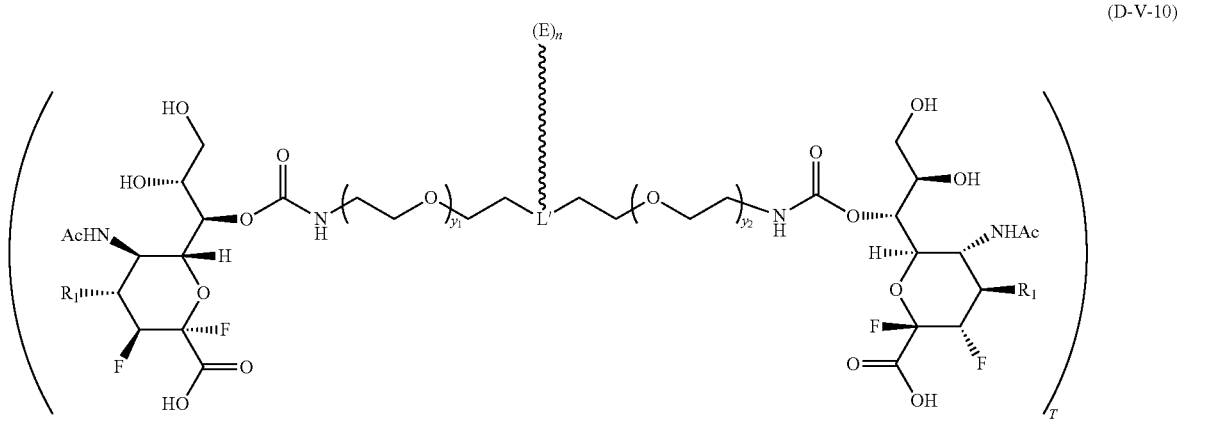

(D-V-10)

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom. In some embodiments, $y_1$ and $y_2$ are each 1, $y_1$ and $y_2$ are each 2, or $y_1$ and $y_2$ are each 3.

In some embodiments, the conjugate is described by formula (D-VI):

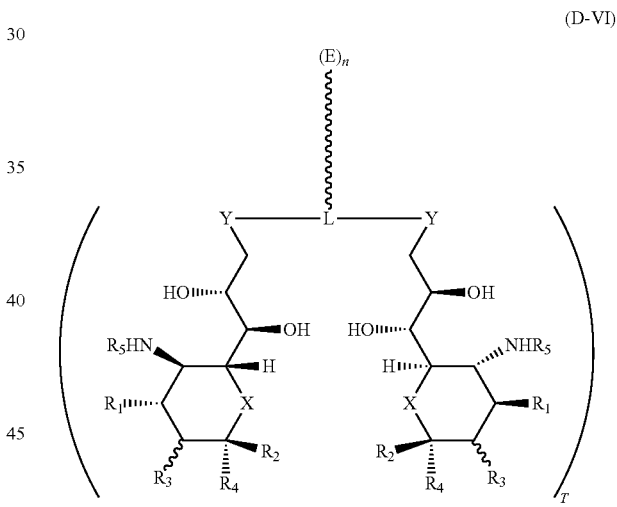

(D-VI)

or a pharmaceutically acceptable salt thereof.

In some embodiments, the conjugate is described by formula (D-VI-1):

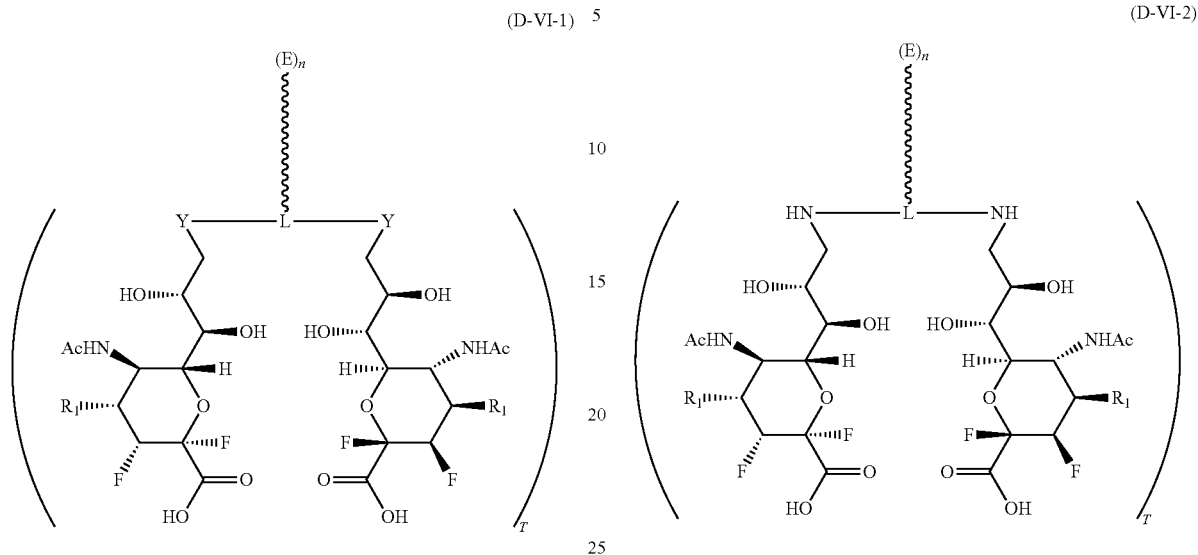

(D-VI-1)

or a pharmaceutically acceptable salt thereof.

In some embodiments, the conjugate is described by formula (D-VI-2):

(D-VI-2)

or a pharmaceutically acceptable salt thereof.

In some embodiments, the conjugate is described by formula (D-VI-3):

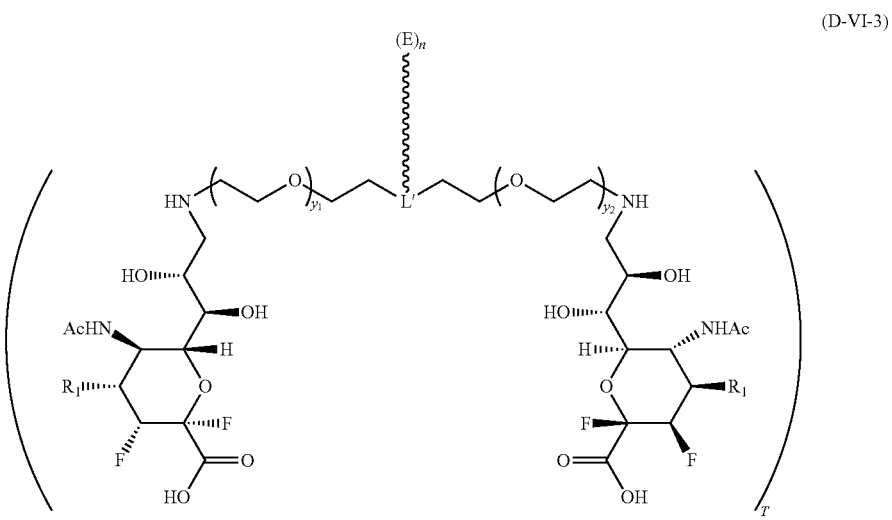

(D-VI-3)

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom. In some embodiments, $y_1$ and $y_2$ are each 1, $y_1$ and $y_2$ are each 2, or $y_1$ and $y_2$ are each 3.

In some embodiments, the conjugate is described by formula (D-VI-4):

(D-VI-4)

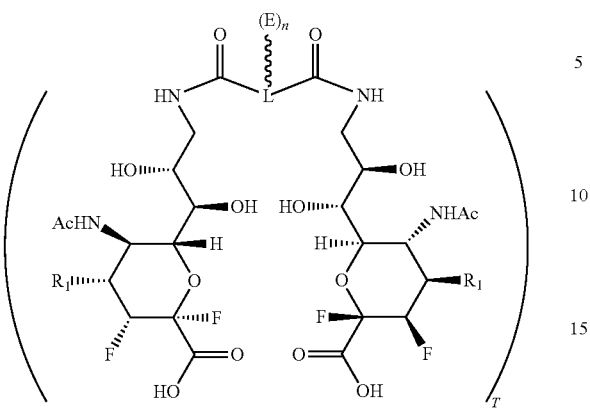

or a pharmaceutically acceptable salt thereof.

In some embodiments, the conjugate is described by formula (D-VI-5):

(D-VI-5)

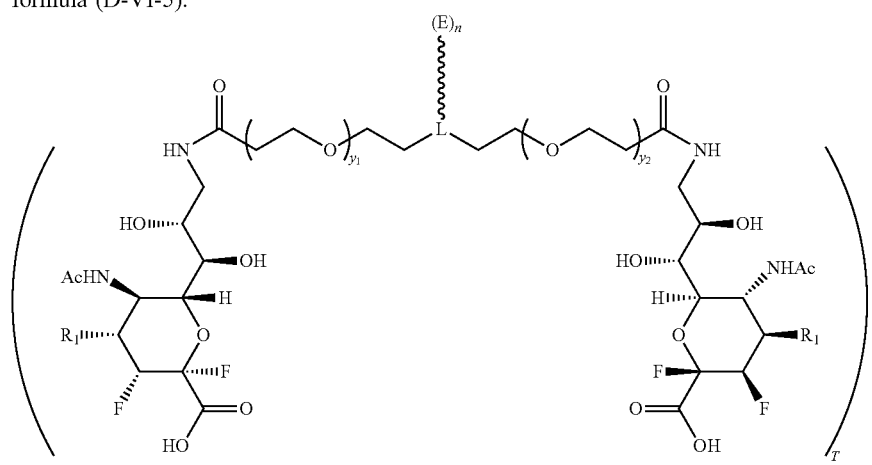

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom. In some embodiments, $y_1$ and $y_2$ are each 1, $y_1$ and $y_2$ are each 2, or $y_1$ and $y_2$ are each 3.

In some embodiments, the conjugate is described by formula (D-VI-6):

(D-VI-6)

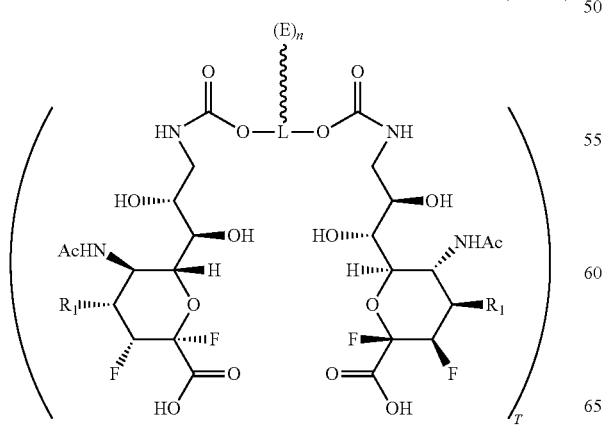

or a pharmaceutically acceptable salt thereof.

In some embodiments, the conjugate is described by formula (D-VI-7):

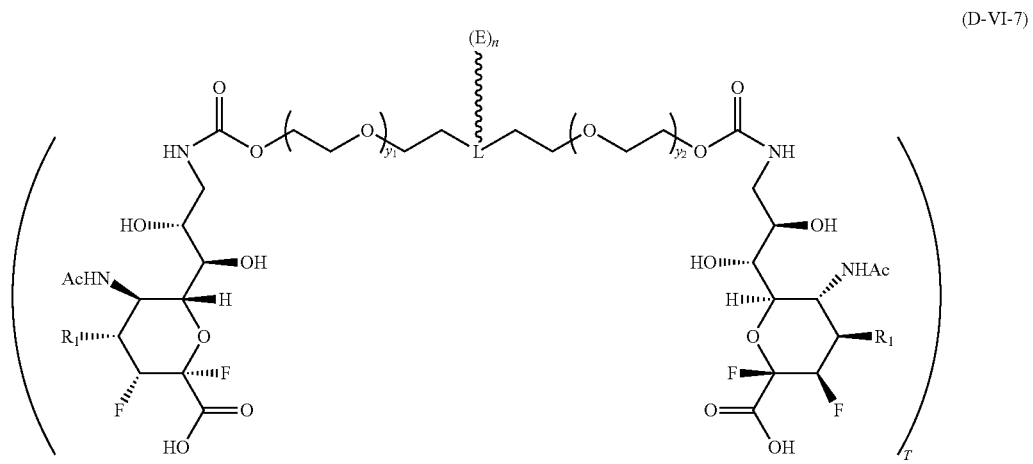

(D-VI-7)

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom. In some embodiments, $y_1$ and $y_2$ are each 1, $y_1$ and $y_2$ are each 2, or $y_1$ and $y_2$ are each 3.

In some embodiments, the conjugate is described by formula (D-VI-8):

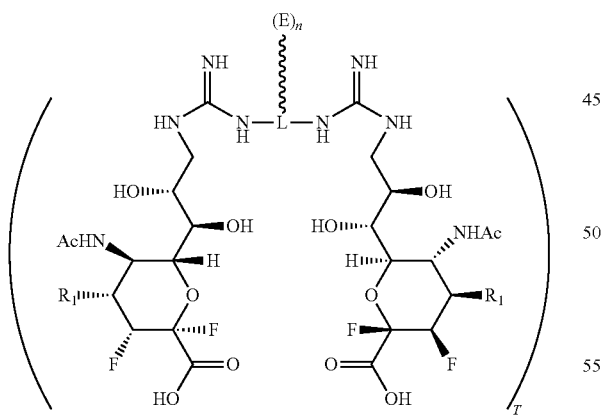

(D-VI-8)

or a pharmaceutically acceptable salt thereof.

In some embodiments, the conjugate is described by formula (D-VI-9):

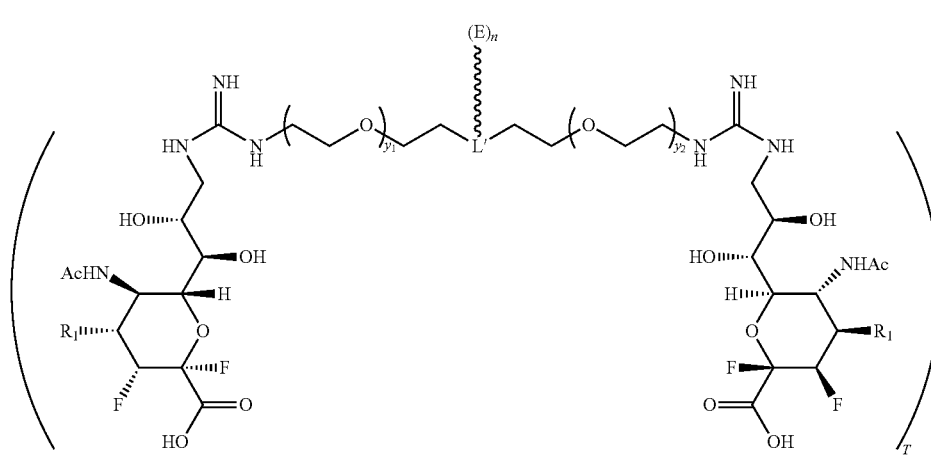

(D-VI-9)

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom. In some embodiments, $y_1$ and $y_2$ are each 1, $y_1$ and $y_2$ are each 2, or $y_1$ and $y_2$ are each 3.

In some embodiments, the conjugate is described by formula (D-VII):

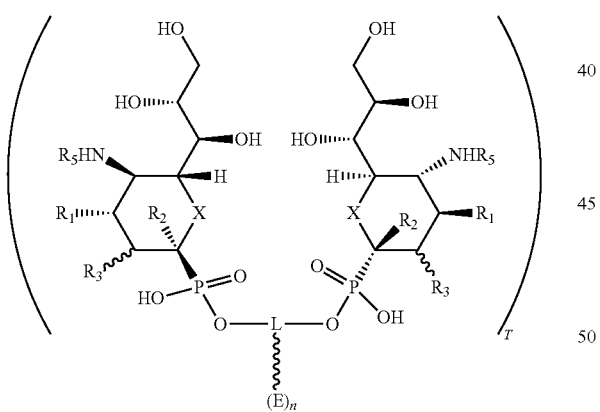

(D-VII)

or a pharmaceutically acceptable salt thereof.

In some embodiments of any of the aspects described herein, $R_1$ is OH. In some embodiments of any of the aspects described herein, $R_1$ is $NH_2$. In some embodiments of any of the aspects described herein, $R_1$ is —NHC(=NH)$NH_2$.

In some embodiments, the conjugate is described by formula (D-VIII):

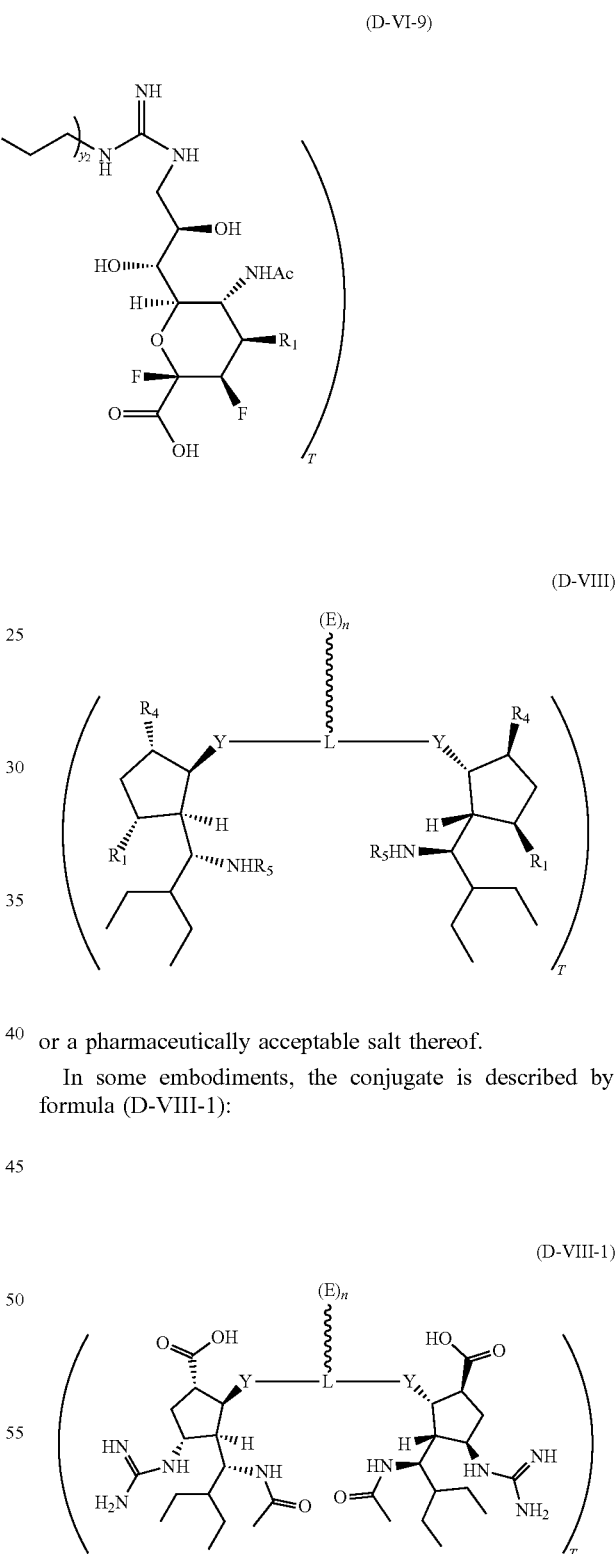

or a pharmaceutically acceptable salt thereof.

In some embodiments, the conjugate is described by formula (D-VIII-2):

(D-VIII-2)

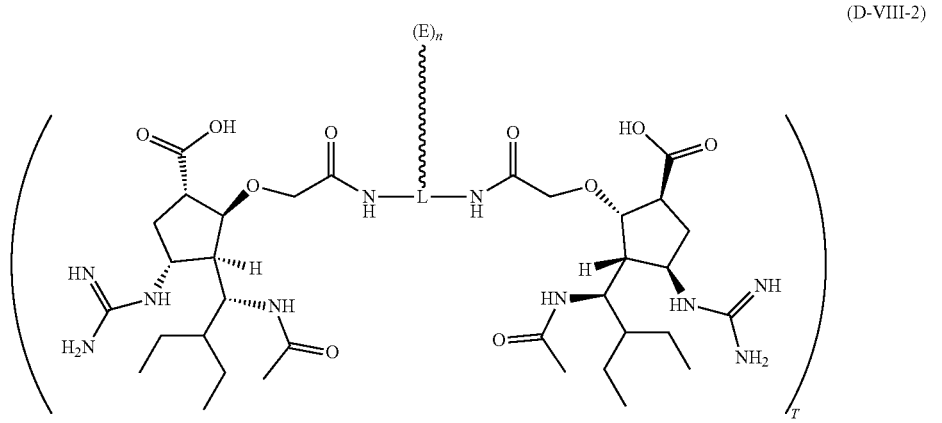

or a pharmaceutically acceptable salt thereof.

In some embodiments, the conjugate is described by formula (D-VIII-3):

(D-VIII-3)

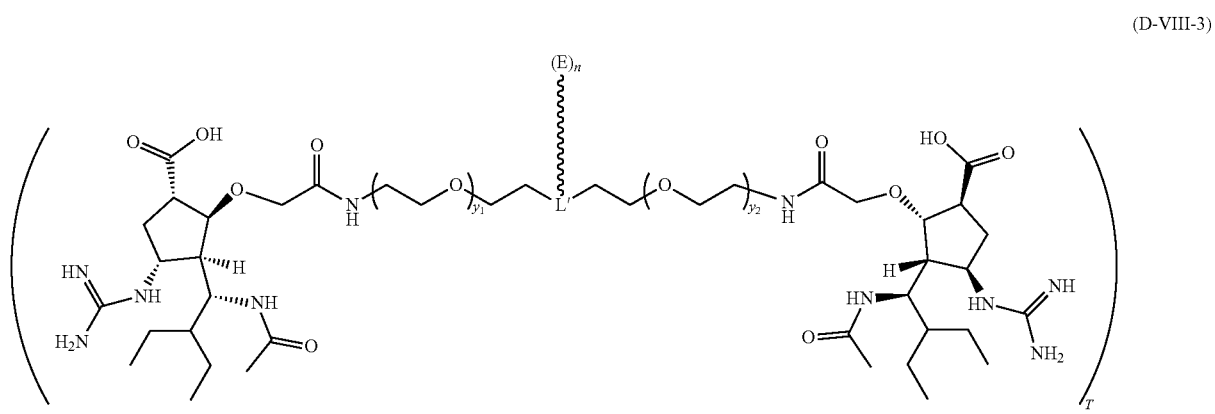

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate has the structure selected from

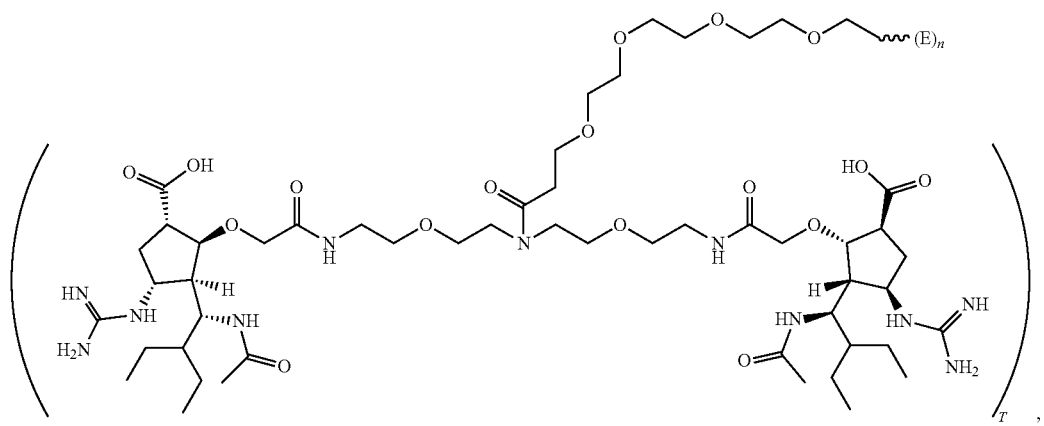

-continued
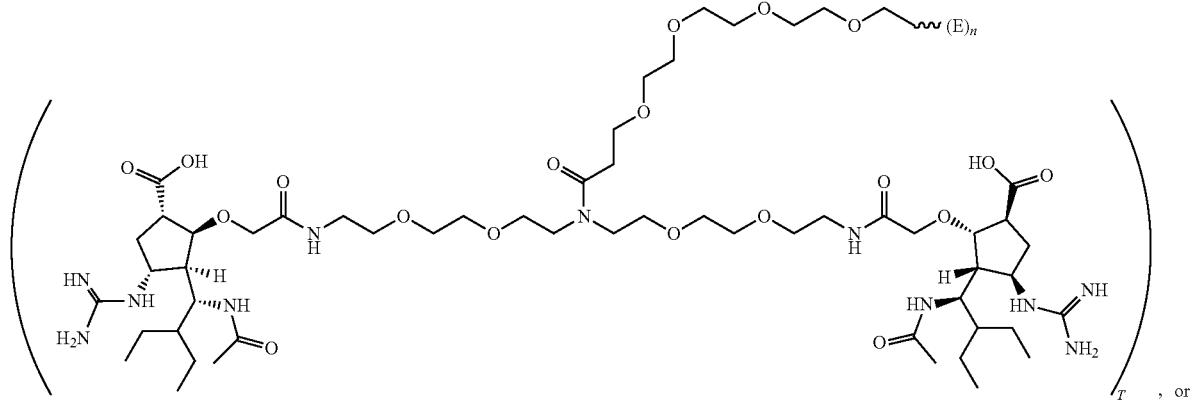
, or
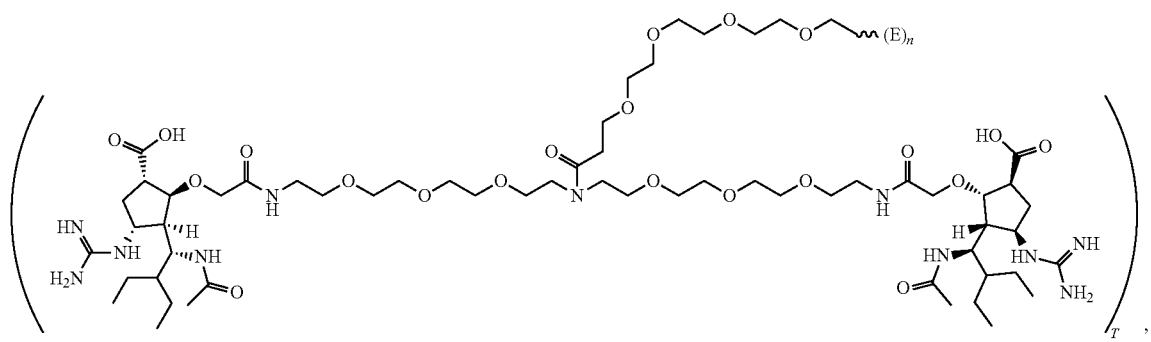
,
or a pharmaceutically acceptable salt thereof.
In some embodiments, the conjugate is described by formula (D-VIII-4):
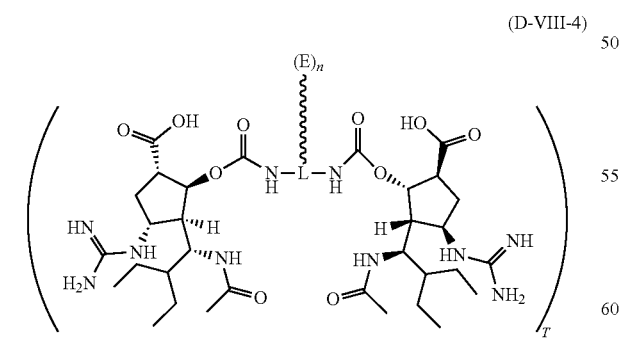
(D-VIII-4)
or a pharmaceutically acceptable salt thereof.
In some embodiments, the conjugate is described by formula (D-VIII-5):

(D-VIII-5)
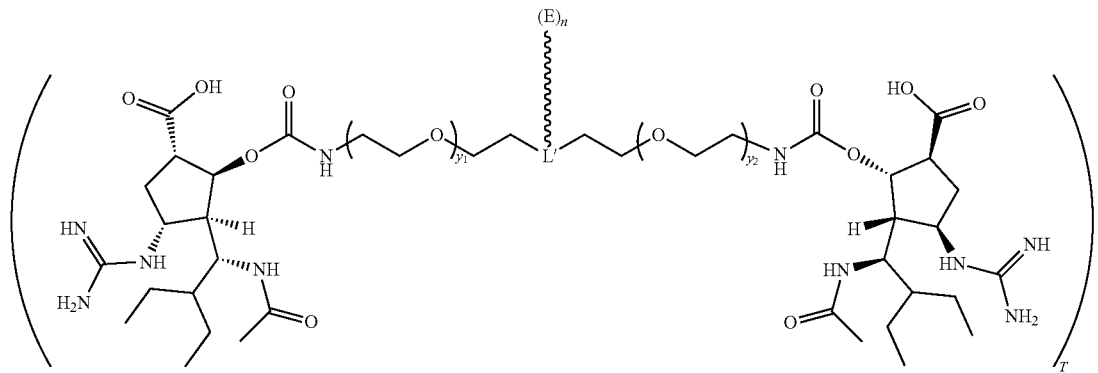
wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.
In some embodiments, the conjugate has the structure selected from:
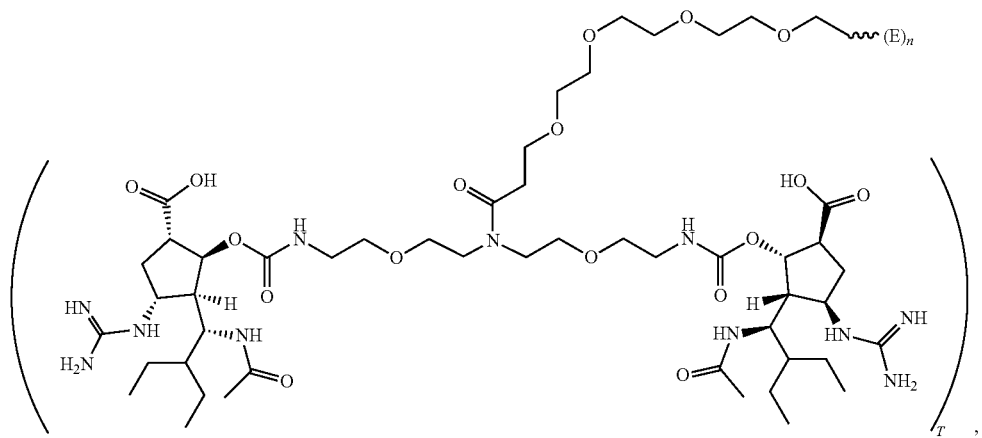
,
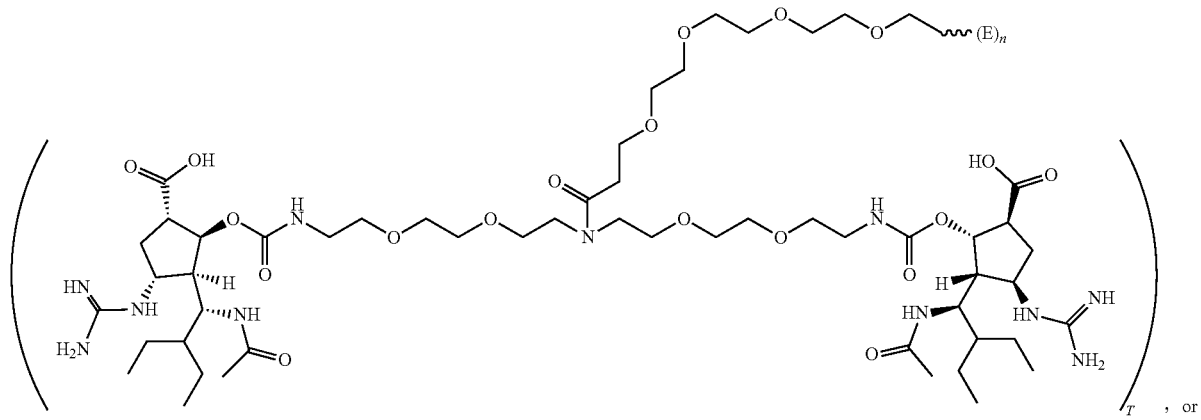
, or -continued
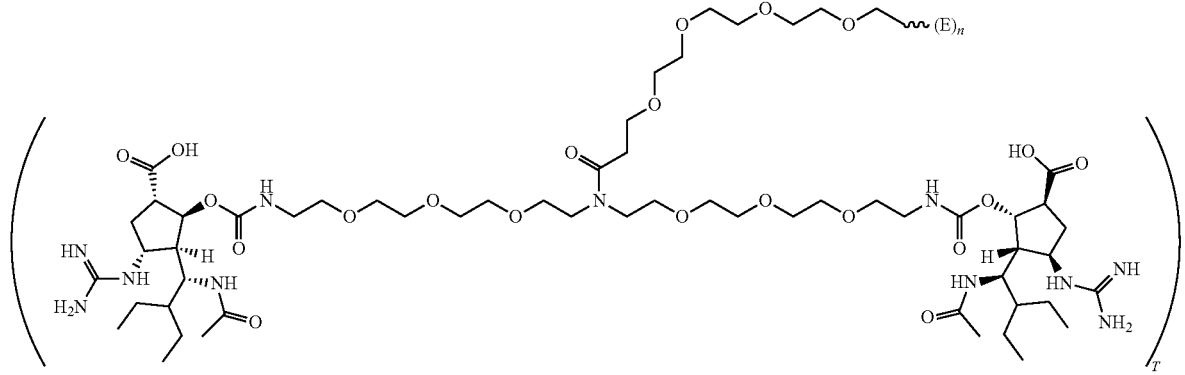
or a pharmaceutically acceptable salt thereof.
In some embodiments, the conjugate is described by the structure
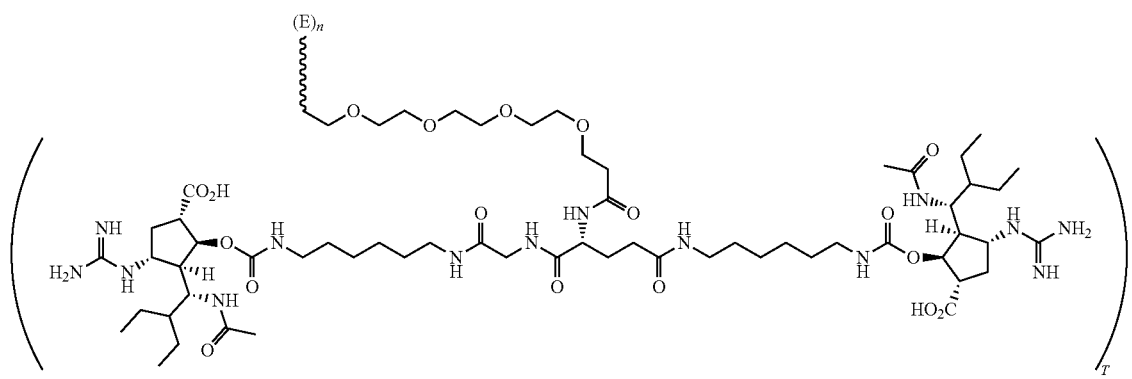
or a pharmaceutically acceptable salt thereof.
In some embodiments, the conjugate is described by formula (D-VIII-6):
(D-VIII-6)
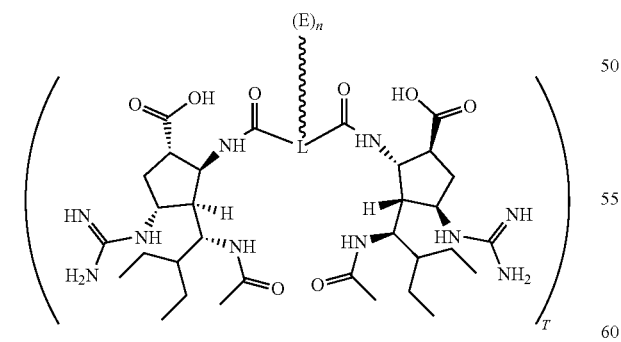
or a pharmaceutically acceptable salt thereof.
In some embodiments, the conjugate is described by formula (D-VIII-7):

(D-VIII-7)

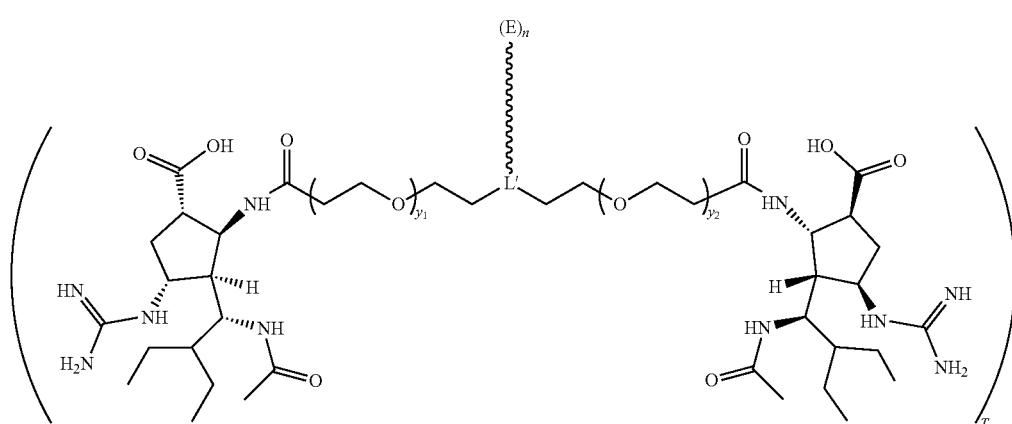

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate is described by formula (D-VIII-8):

(D-VIII-8)

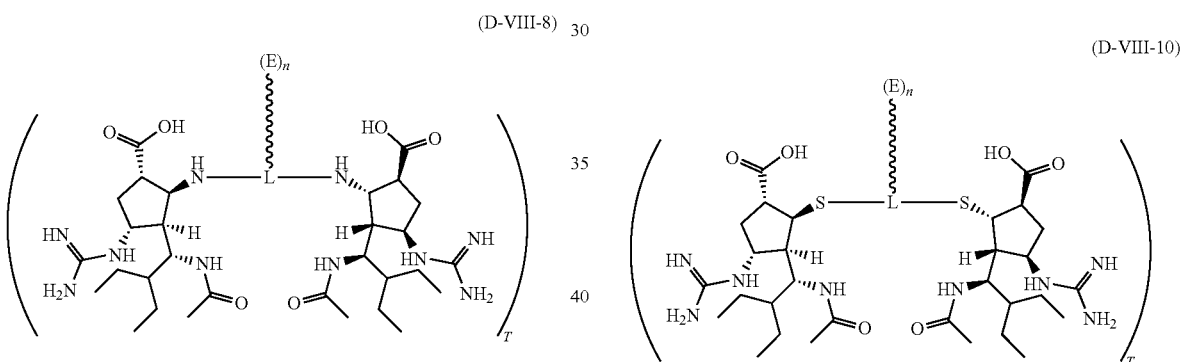

or a pharmaceutically acceptable salt thereof.

In some embodiments, the conjugate is described by formula (D-VIII-9):

(D-VIII-9)

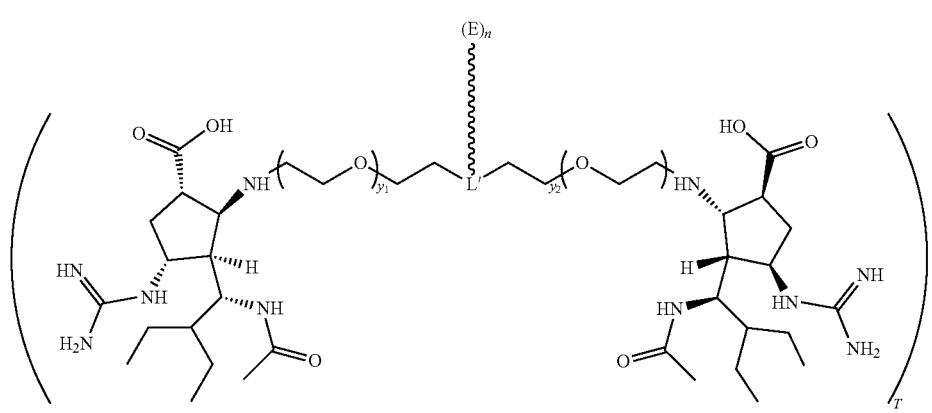

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate is described by formula (D-VIII-10):

(D-VIII-10)

or a pharmaceutically acceptable salt thereof.

In some embodiments, the conjugate is described by formula (D-VIII-11):

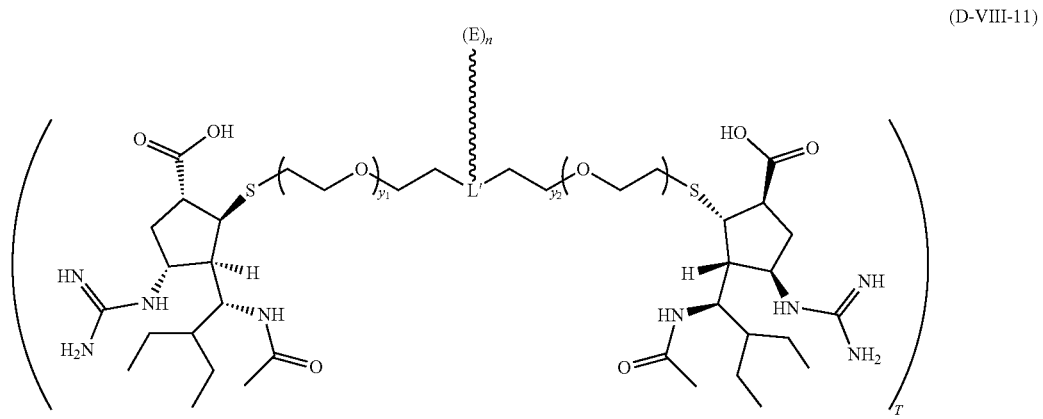

(D-VIII-11)

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate is described by formula (D-IX):

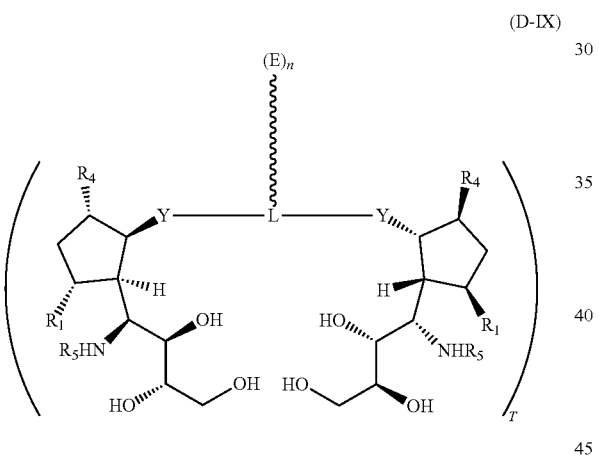

(D-IX)

or a pharmaceutically acceptable salt thereof.

In some embodiments, the conjugate is described by formula (D-IX-1):

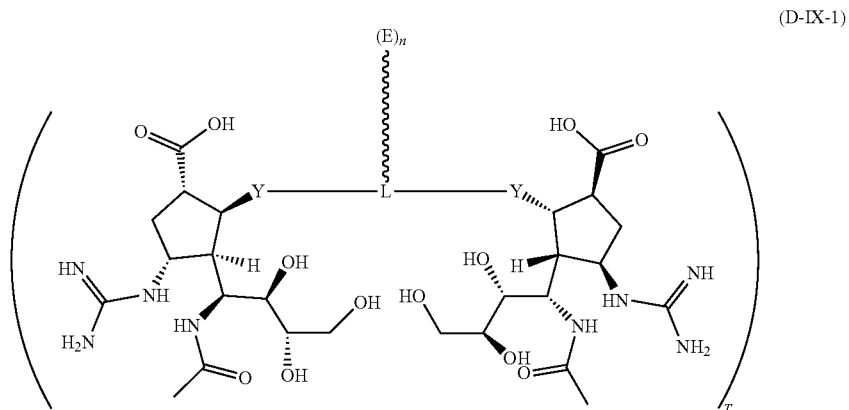

(D-IX-1)

or a pharmaceutically acceptable salt thereof.

In some embodiments, the conjugate is described by formula (D-IX-2):

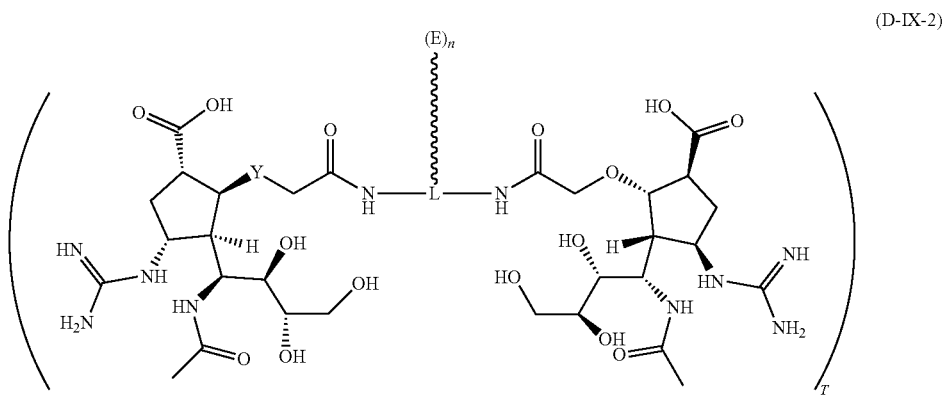

(D-IX-2)

or a pharmaceutically acceptable salt thereof.

In some embodiments, the conjugate is described by formula (D-IX-3):

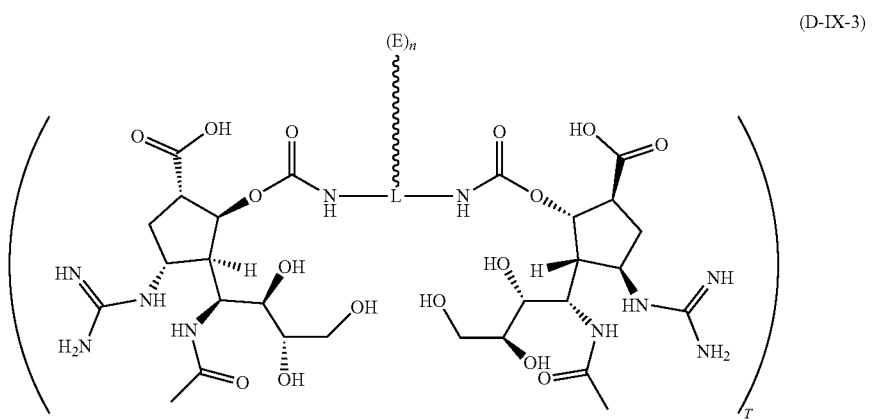

(D-IX-3)

or a pharmaceutically acceptable salt thereof.

In some embodiments, the conjugate is described by formula (D-IX-4):

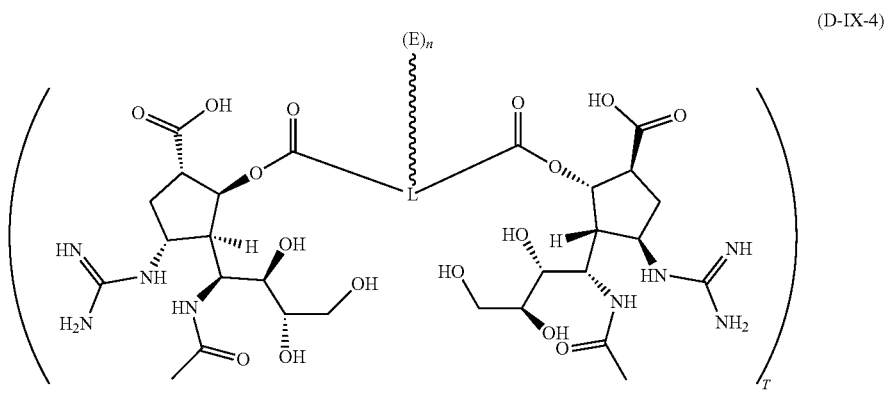

(D-IX-4)

or a pharmaceutically acceptable salt thereof.

In some embodiments, the conjugate is described by formula (D-IX-5):

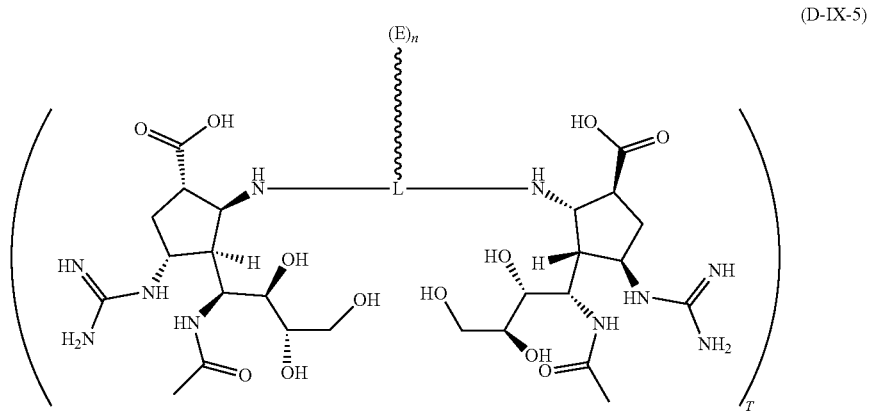

or a pharmaceutically acceptable salt thereof.

In some embodiments, the conjugate is described by formula (D-IX-6):

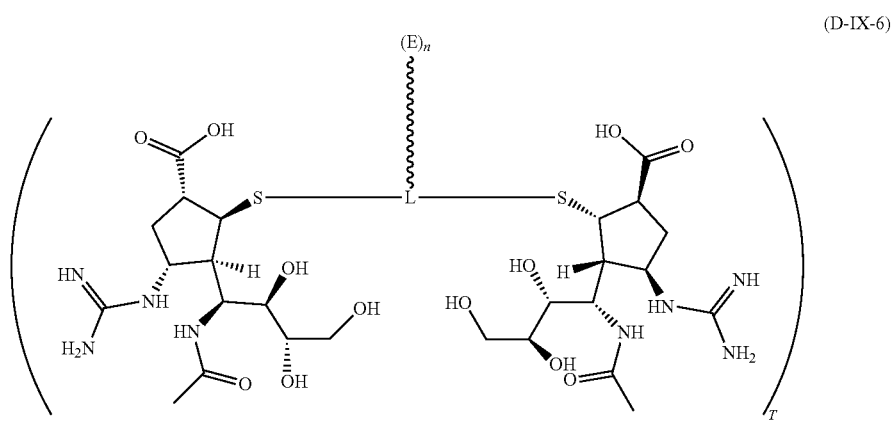

or a pharmaceutically acceptable salt thereof.

In some embodiments, the conjugate is described by formula (D-X):

In some embodiments, the conjugate is described by formula (D-X-1):

or a pharmaceutically acceptable salt thereof.

In some embodiments, the conjugate is described by formula (D-X-2):

(D-X-2)

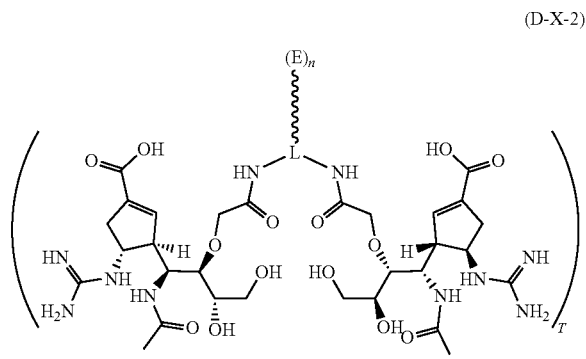

or a pharmaceutically acceptable salt thereof.

In some embodiments, the conjugate is described by formula (D-X-3):

(D-X-3)

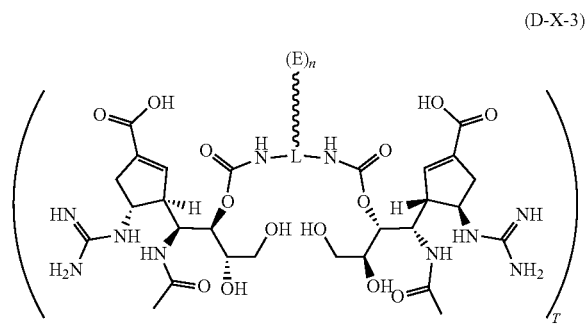

or a pharmaceutically acceptable salt thereof.

In some embodiments of any of the aspects described herein, L or L' includes one or more optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, optionally substituted C2-C15 heteroarylene, O, S, $NR^i$, P, carbonyl, thiocarbonyl, sulfonyl, phosphate, phosphoryl, or imino, wherein $R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl.

In some embodiments, the backbone of L or L' consists of one or more optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, optionally substituted C2-C15 heteroarylene, O, S, $NR^i$, P, carbonyl, thiocarbonyl, sulfonyl, phosphate, phosphoryl, or imino, wherein $R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl.

In some embodiments of any of the aspects described herein, L or L' is oxo substituted. In some embodiments, the backbone of L or L' comprises no more than 250 atoms. In some embodiments, L or L' is capable of forming an amide, a carbamate, a sulfonyl, or a urea linkage. In some embodiments L or L' is a bond. In some embodiments, L or L' is an atom.

In some embodiments of any of the aspects described herein, each L is described by formula (D-L-I)

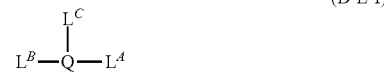

(D-L-I)

wherein $L^A$ is described by formula $G^{A1}\text{-}(Z^{A1})_{g1}\text{—}(Y^{A1})_{h1}\text{—}(Z^{A2})_{i1}\text{—}(Y^{A2})_{j1}\text{—}(Z^{A3})_{k1}\text{—}(Y^{A3})_{l1}\text{—}(Z^{A4})_{m1}\text{—}(Y^{A4})_{n1}\text{—}(Z^{A5})_{o1}\text{-}G^{A2}$; $L^B$ is described by formula $G^{B1}\text{-}(Z^{B1})_{g2}\text{—}(Y^{B1})_{h2}\text{—}(Z^{B2})_{i2}\text{—}(Y^{B2})_{j2}\text{—}(Z^{B3})_{k2}\text{—}(Y^{B3})_{l2}\text{—}(Z^{B4})_{m2}\text{—}(Y^{B4})_{n2}\text{—}(Z^{B5})_{o2}\text{-}G^{B2}$; $L^C$ is described by formula $G^{C1}\text{-}(Z^{C1})_{g3}\text{—}(Y^{C1})_{h3}\text{—}(Z^{C2})_{i3}\text{—}(Y^{C2})_{j3}\text{—}(Z^{C3})_{k3}\text{—}(Y^{C3})_{l3}\text{—}(Z^{C4})_{m3}\text{—}(Y^{C4})_{n3}\text{—}(Z^{C5})_{o3}\text{-}G^{C2}$; $G^{A1}$ is a bond attached to Q; $G^{B1}$ is a bond attached to $A_1$; $G^{B1}$ is a bond attached to Q); $G^{B2}$ is a bond attached to $A_2$; $G^{G1}$ is a bond attached to Q; $G^{C2}$ is a bond attached to E or a functional group capable of reacting with a functional group conjugated to E (e.g., maleimide and cysteine, amine and activated carboxylic acid, thiol and maleimide, activated sulfonic acid and amine, isocyanate and amine, azide and alkyne, and alkene and tetrazine); each of $Z^{A1}$, $Z^{A2}$, $Z^{A3}$, $Z^{A4}$, $Z^{A5}$, $Z^{B1}$, $Z^{B2}$, $Z^{B3}$, $Z^{B4}$, $Z^{B5}$, $Z^{C1}$, $Z^{C2}$, $Z^{C3}$, $Z^{C4}$ and $Z^{C5}$ is, independently, optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, or optionally substituted C2-C15 heteroarylene; each of $Y^{A1}$, $Y^{A2}$, $Y^{A3}$, $Y^{A4}$, $Y^{B1}$, $Y^{B2}$, $Y^{B3}$, $Y^{B4}$, $Y^{C1}$, $Y^{C2}$, $Y^{C3}$ and $Y^{C4}$ is, independently, O, S, $NR^i$, P, carbonyl, thiocarbonyl, sulfonyl, phosphate, phosphoryl, or imino; $R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl; each of g1, h1, i1, j1, k1, l1, m1, n1, o1, g2, h2, i2, j2, k2, l2, m2, n2, o2, g3, h3, i3, j3, k3, l3, m3, n3, and o3 is, independently, 0 or 1; Q is a nitrogen atom, optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, or optionally substituted C2-C15 heteroarylene.

In some embodiments, $L^c$ may have two points of attachment to the Fc domain, Fc-binding peptide, albumin protein, or albumin protein-binding peptide (e.g., two $G^{C2}$) In some embodiments of any of the aspects described herein, L includes a polyethylene glycol (PEG) linker. A PEG linker includes a linker having the repeating unit structure $(—CH_2CH_2O—)_n$, wherein n is an integer from 2 to 100. A polyethylene glycol linker may covalently join a neuraminidase inhibitor and E (e.g., in a conjugate of any one of formulas (M-I)-(M-XI)). A polyethylene glycol linker may covalently join a first neuraminidase inhibitor and a second neuraminidase inhibitor (e.g., in a conjugate of any one of formulas (D-I)-(D-XI)). A polyethylene glycol linker may covalently join a neuraminidase inhibitor dimer and E (e.g., in a conjugate of any one of formulas (D-I)-(D-XI)). A polyethylene glycol linker may be selected any one of $PEG_2$ to $PEG_{100}$ (e.g., $PEG_2$, $PEG_3$, $PEG_4$, $PEG_5$, $PEG_5$-$PEG_{10}$, $PEG_{10}$-$PEG_{20}$, $PEG_{20}$-$PEG_{30}$, $PEG_{30}$-$PEG_{40}$, $PEG_{50}$-$PEG_{60}$, $PEG_{60}$-$PEG_{70}$, $PEG_{70}$-$PEG_{80}$, $PEG_{80}$-$PEG_{90}$, $PEG_{90}$-$PEG_{10}$). In some embodiments, $L^c$ includes a PEG linker, where $L^c$ is covalently attached to each of Q and E.

In some embodiments, L is

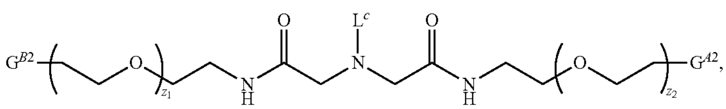

,

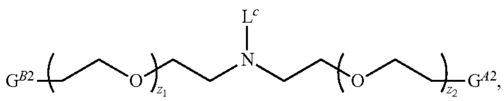

,

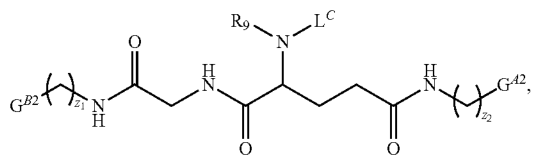

,

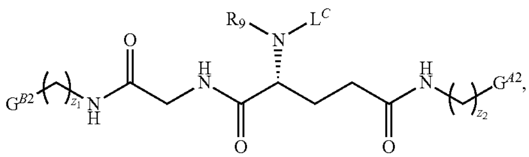

,

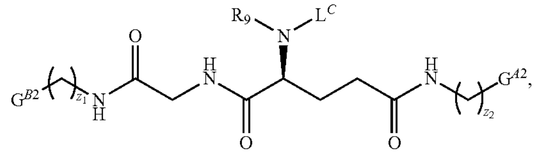

,

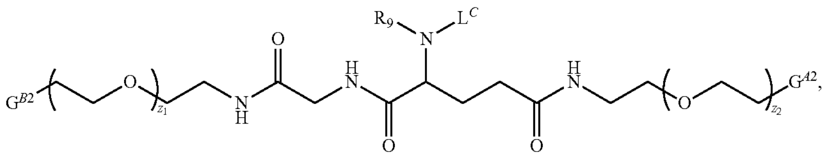

,

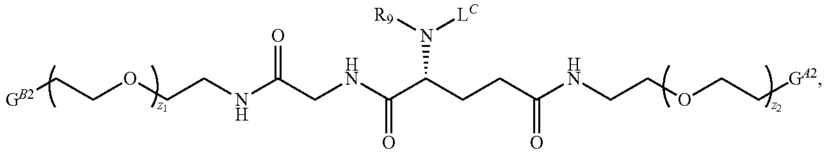

,

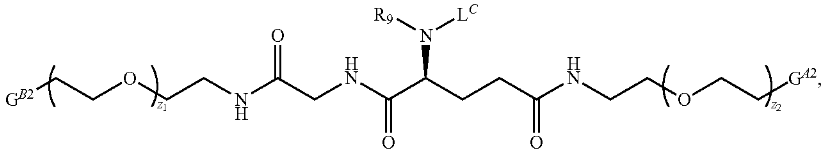

,

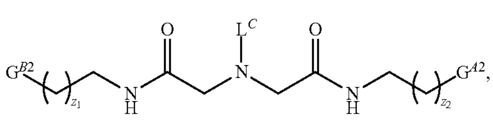

,

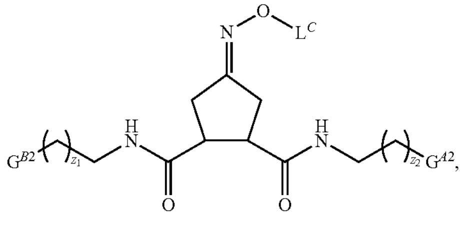

,

301
-continued
302
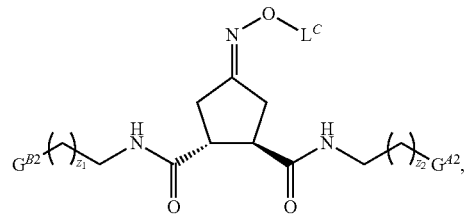
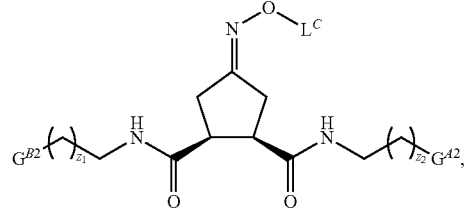
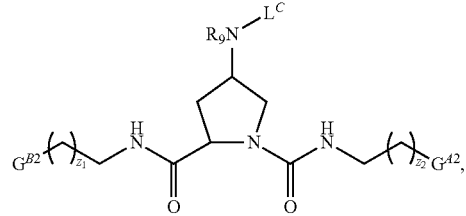
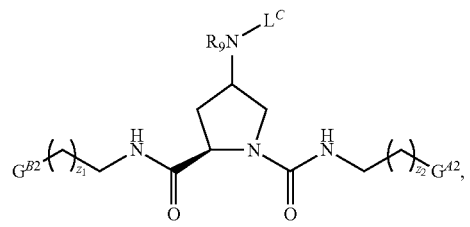
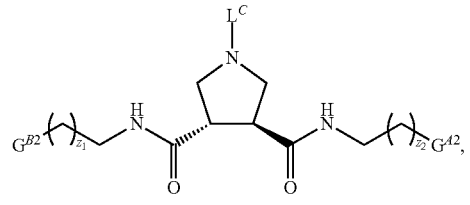
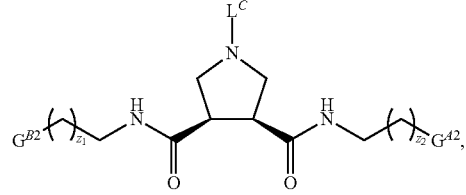
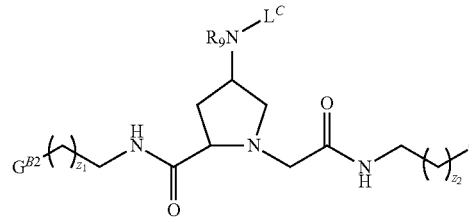
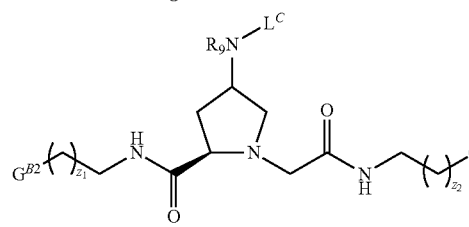
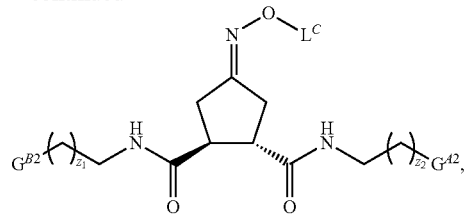

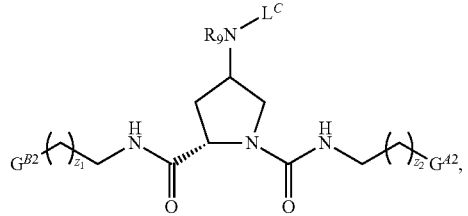
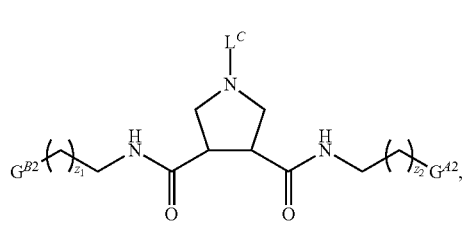
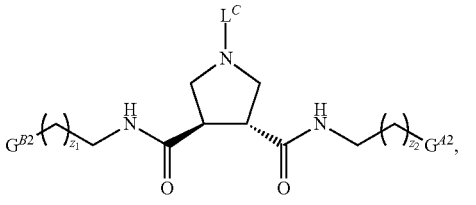
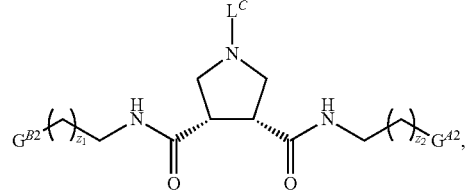
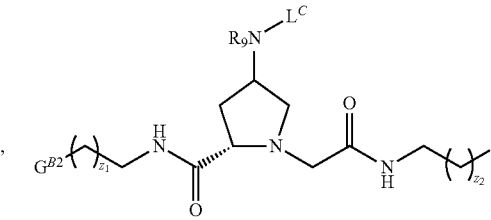
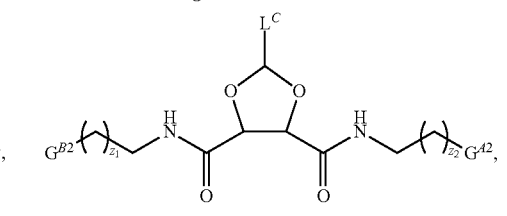

-continued
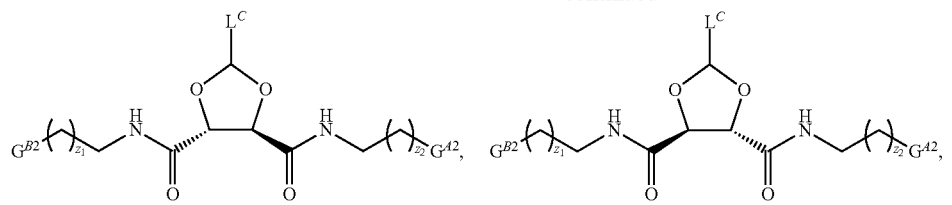
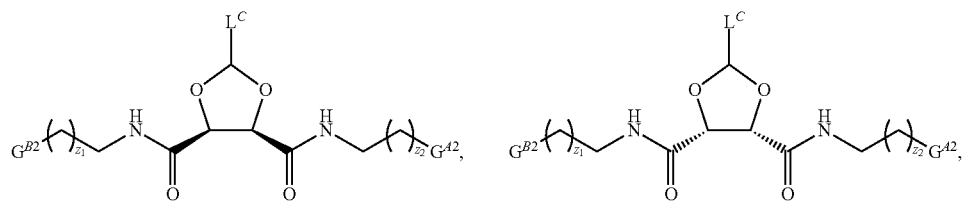
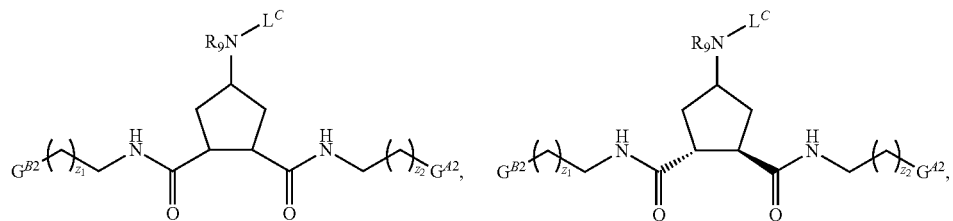
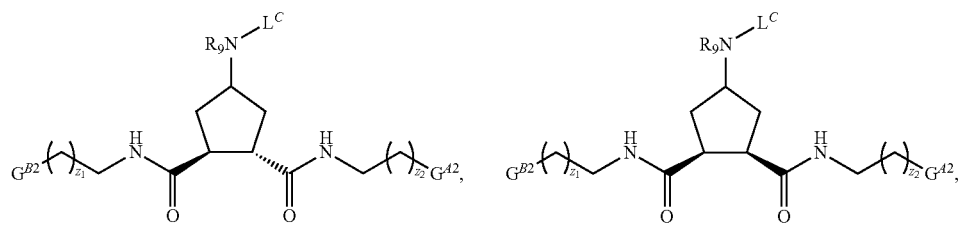
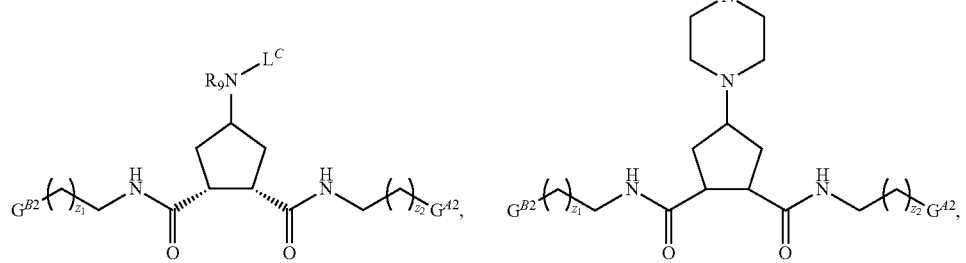
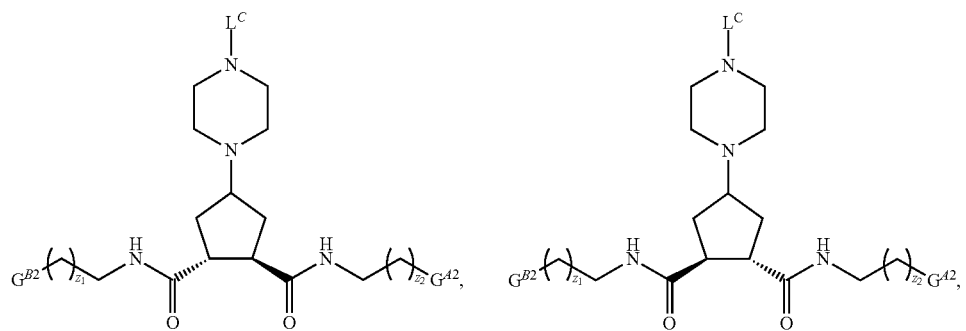

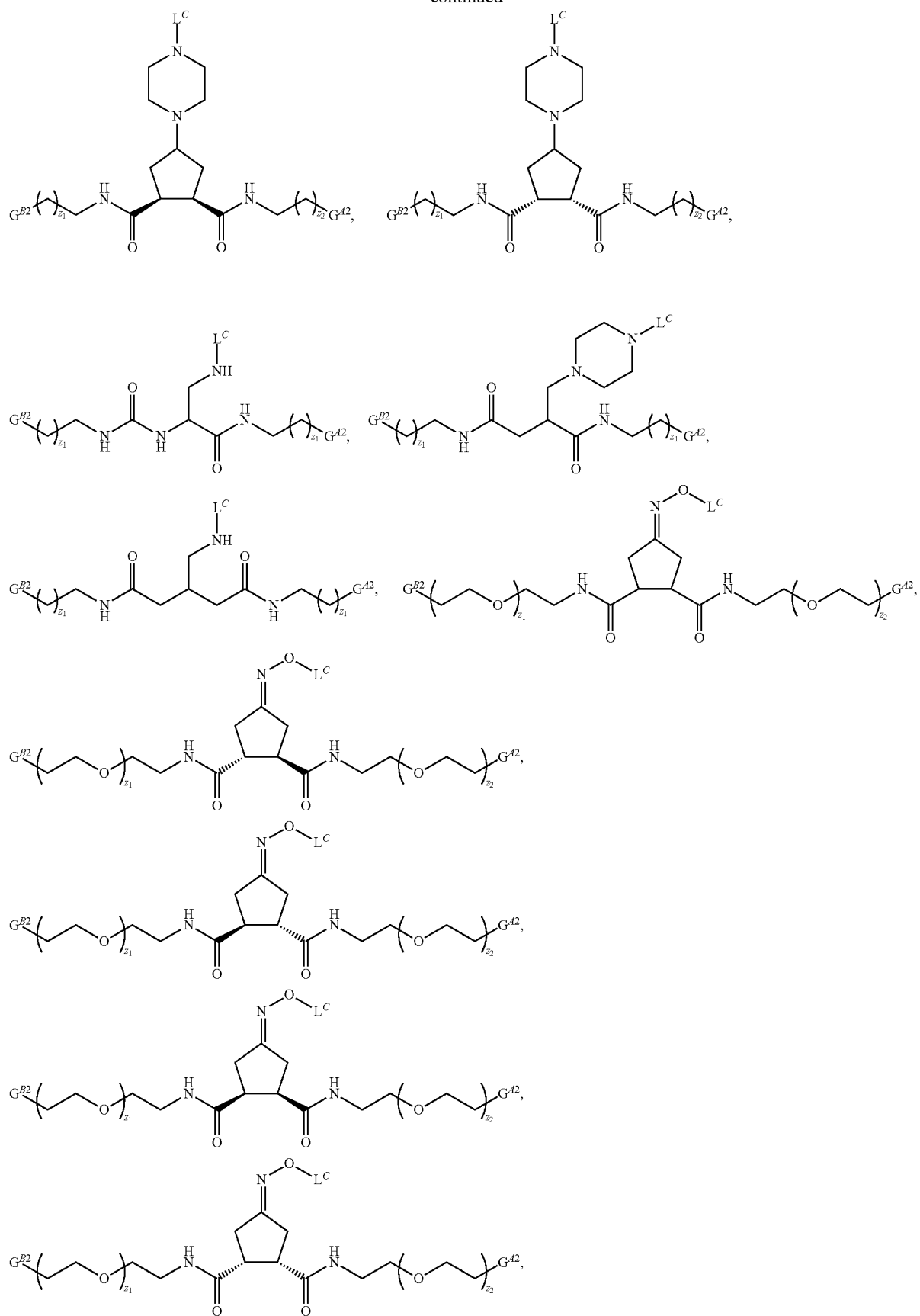

-continued
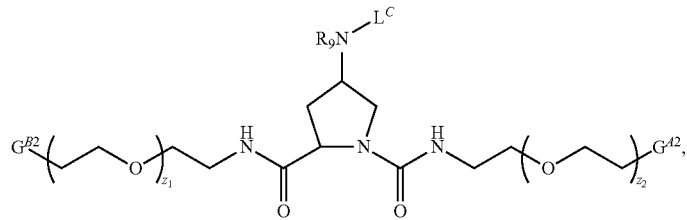
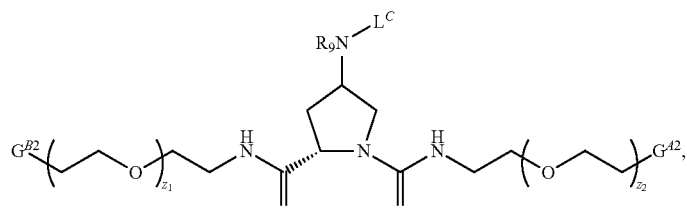
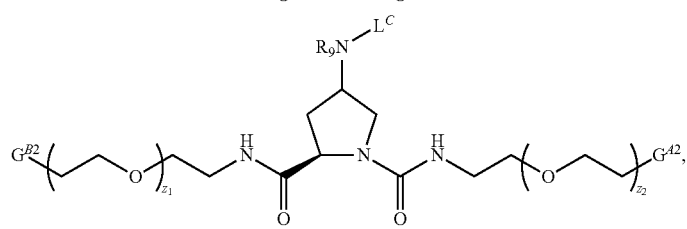
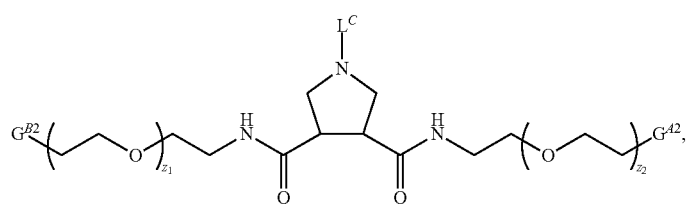
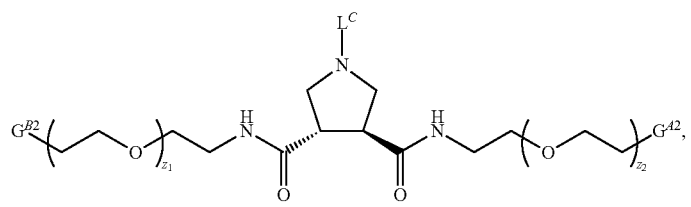
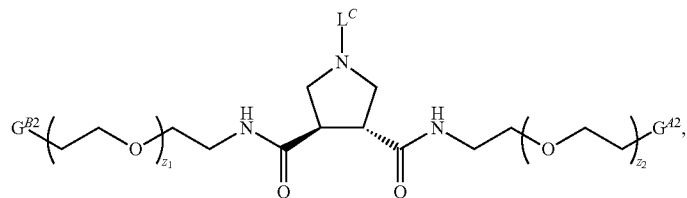
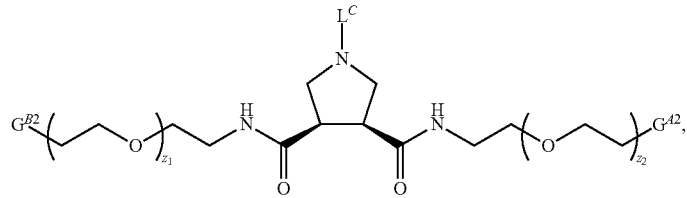
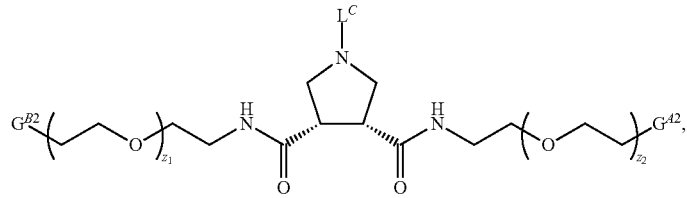

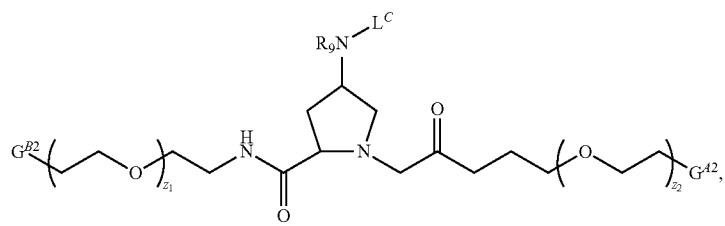
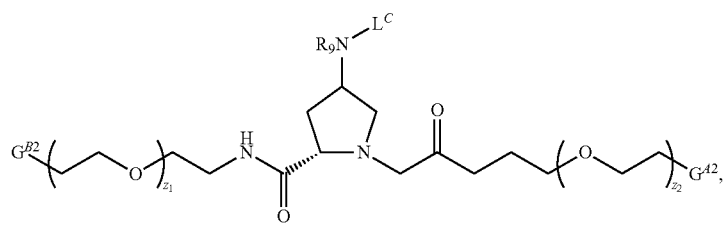
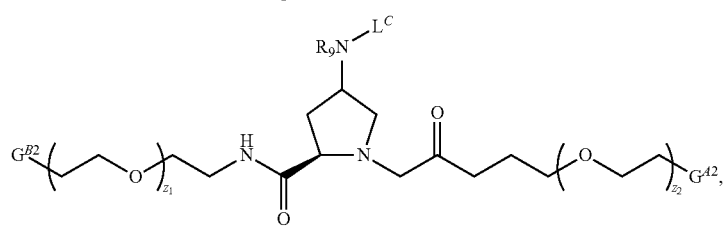
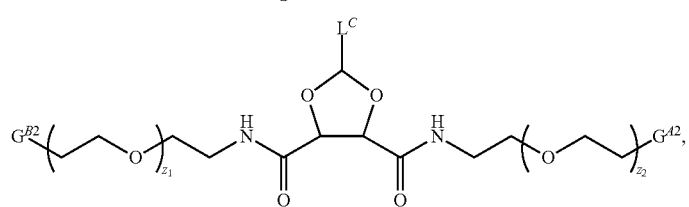
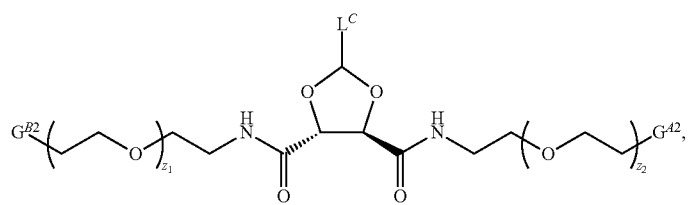
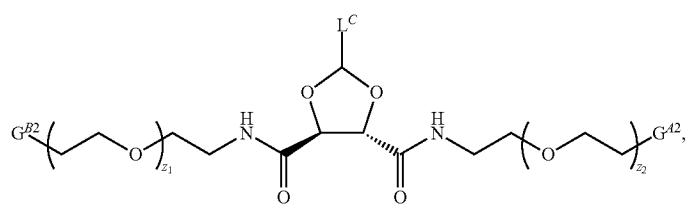
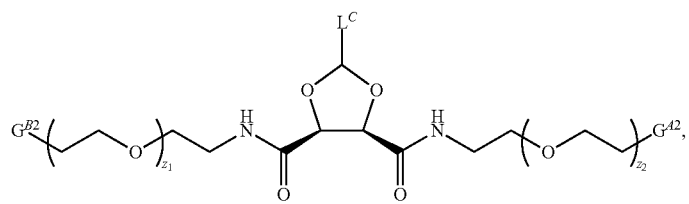
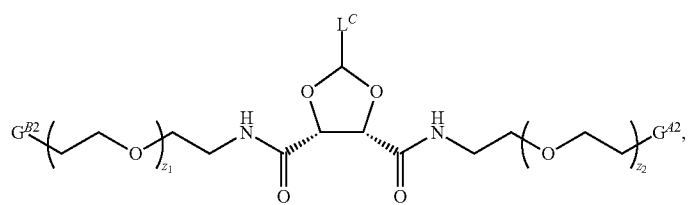

-continued
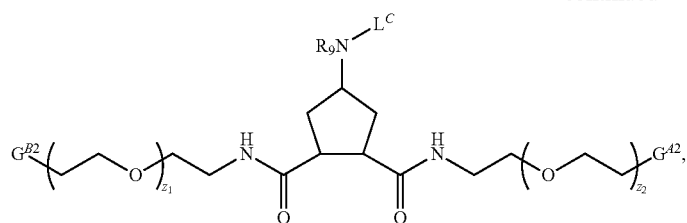
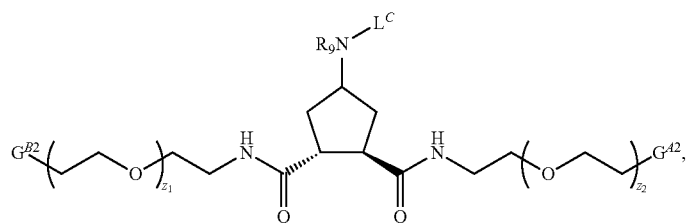
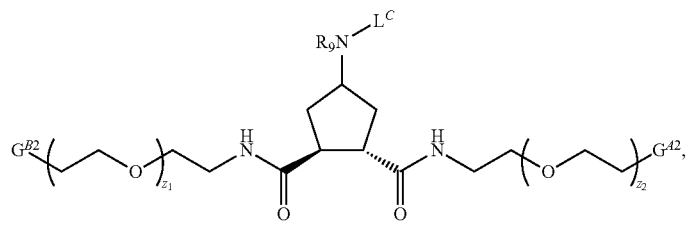
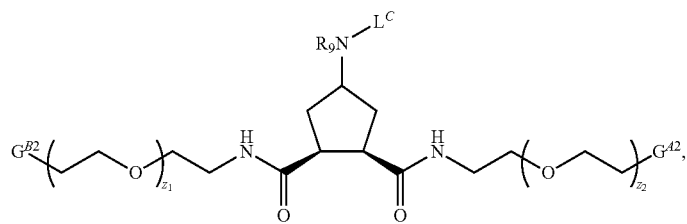
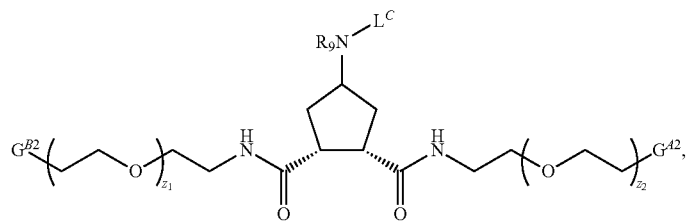
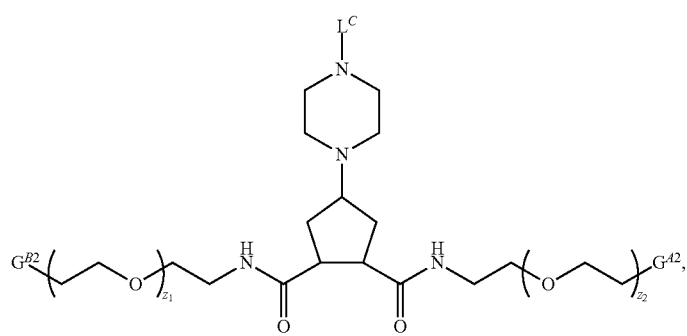

-continued
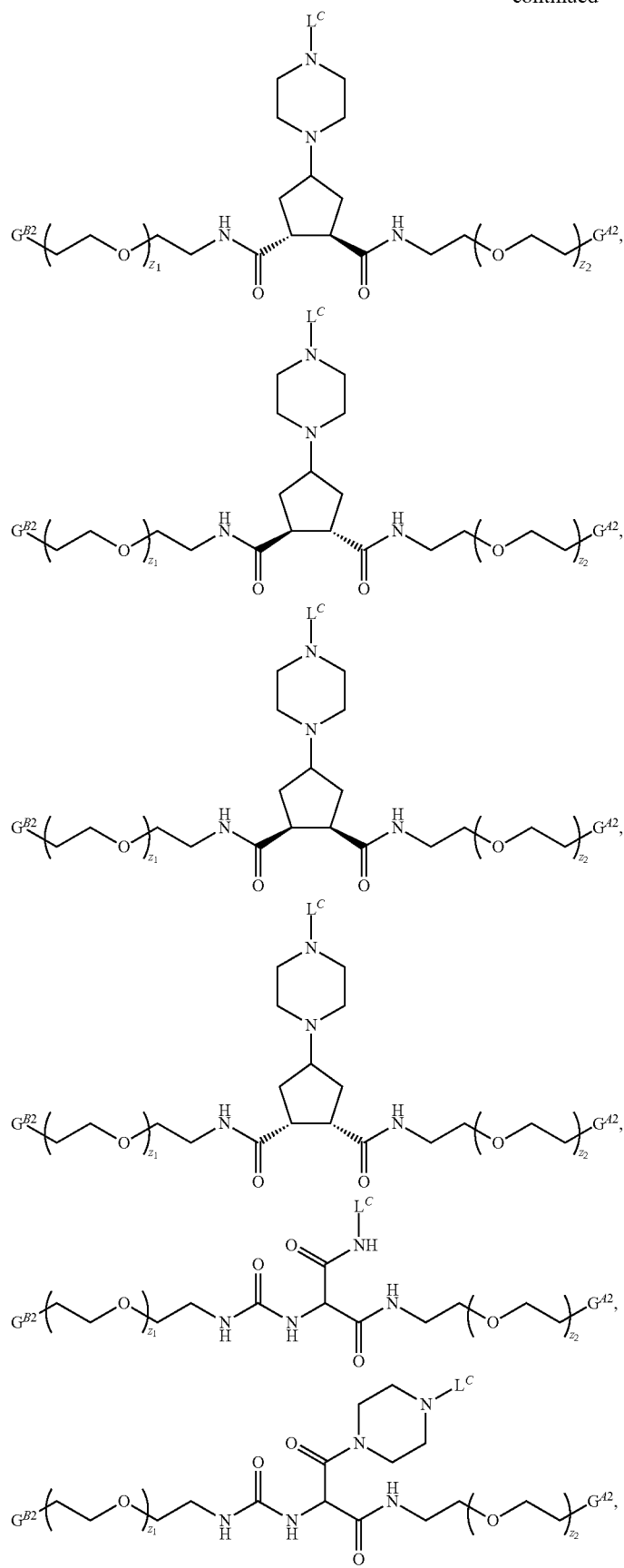

-continued
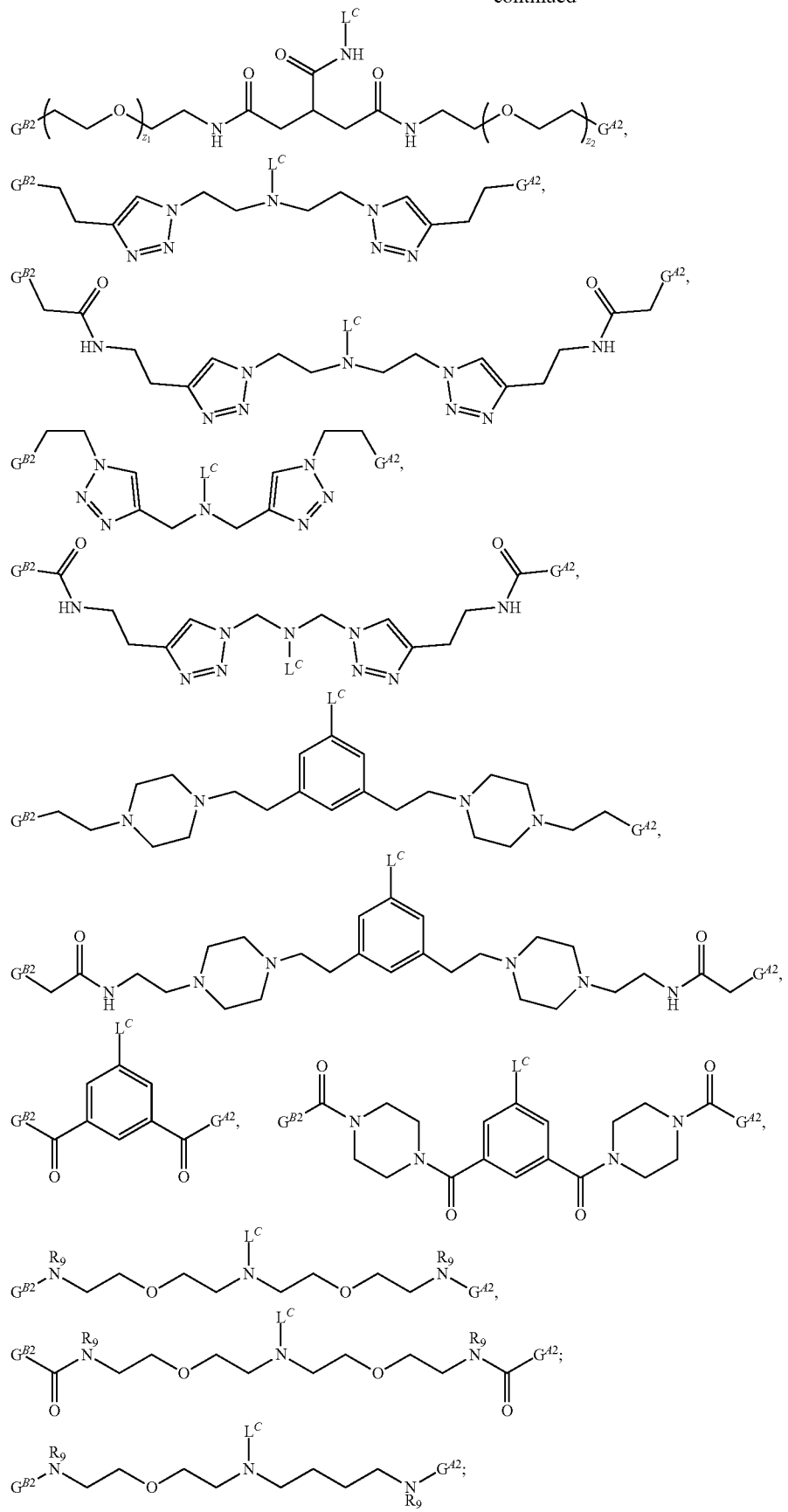

-continued
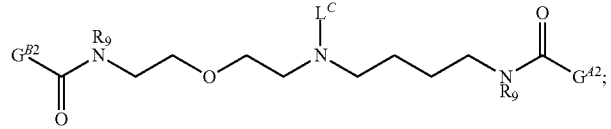
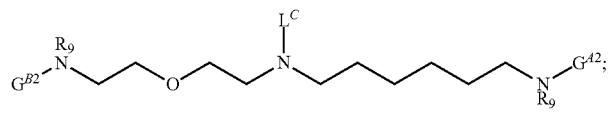
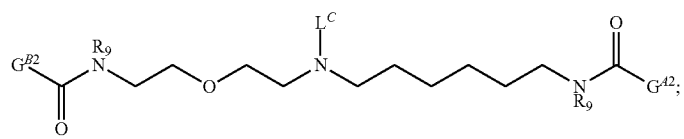
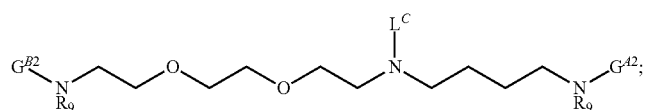
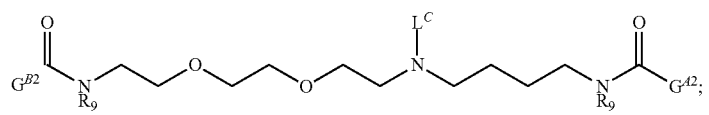
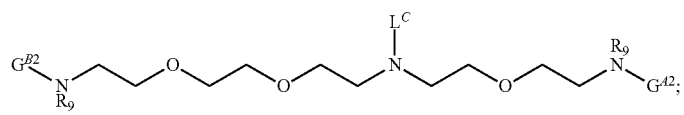
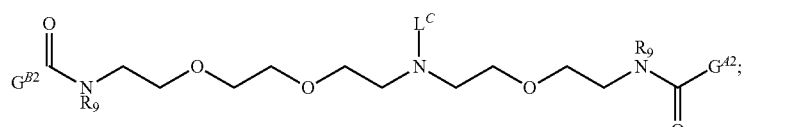
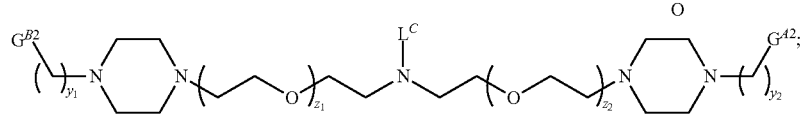
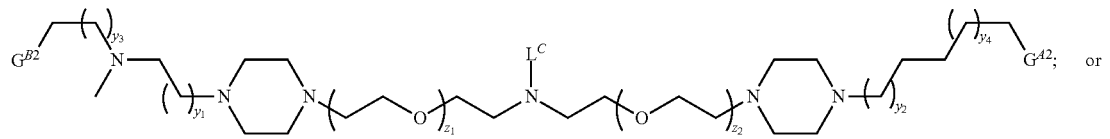
or
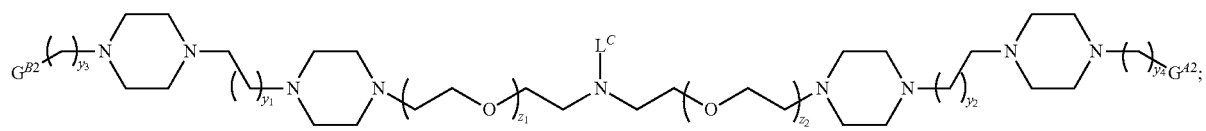
wherein $z_1$ and $z_2$ are each, independently, and integer from 1 to 20; and $R_9$ is selected from H, C1-C20 alkyl, C3-C20 cycloalkyl, C3-C20 heterocycloalkyl; C5-C15 aryl, and C2-C15 heteroaryl.

In some embodiments, L is
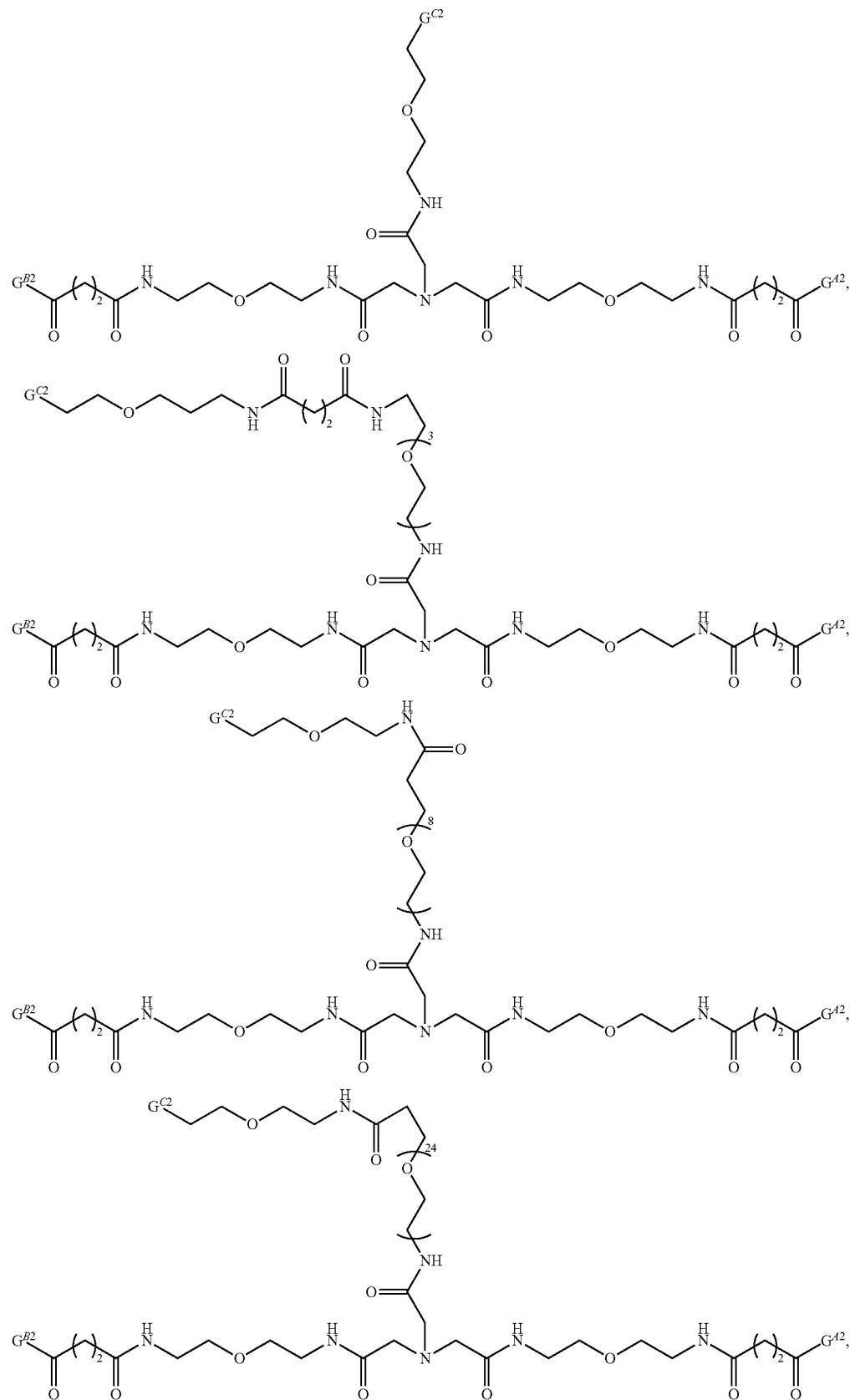

321 322
-continued
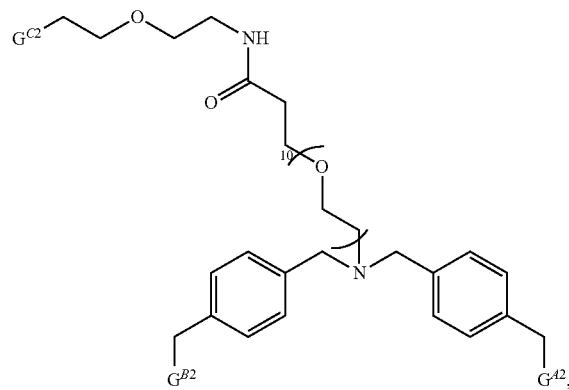
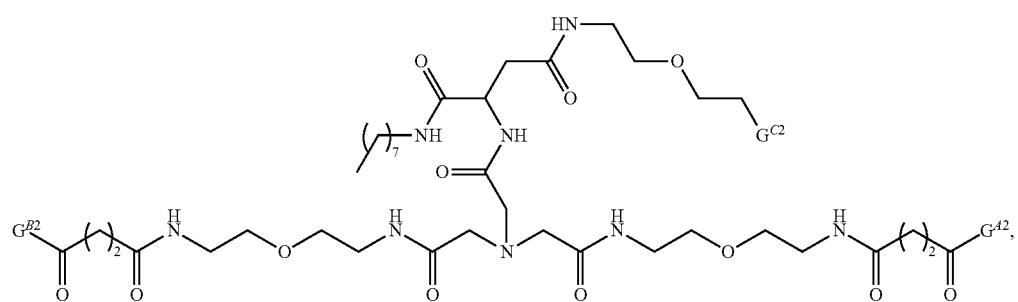
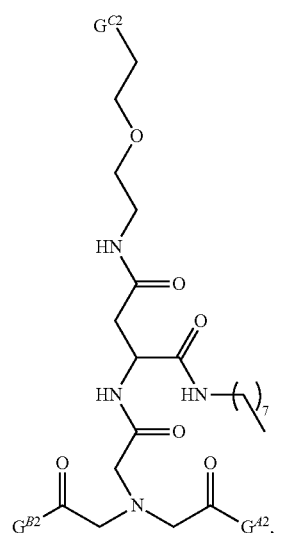
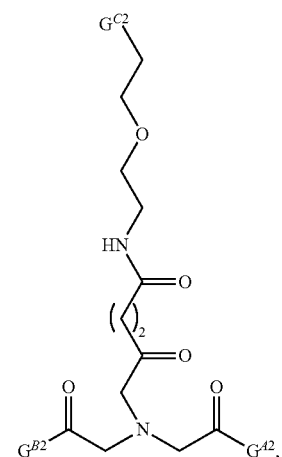
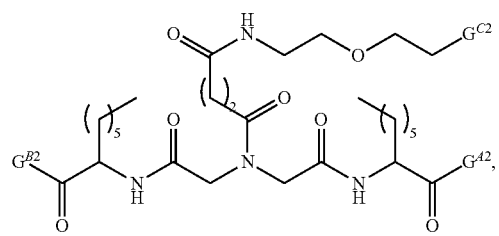

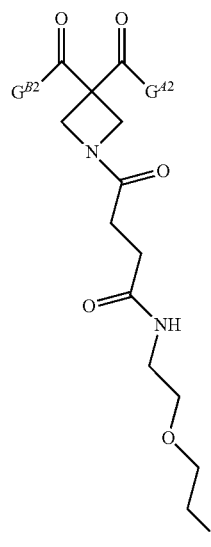
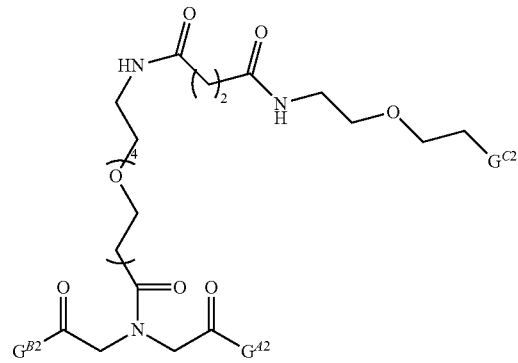
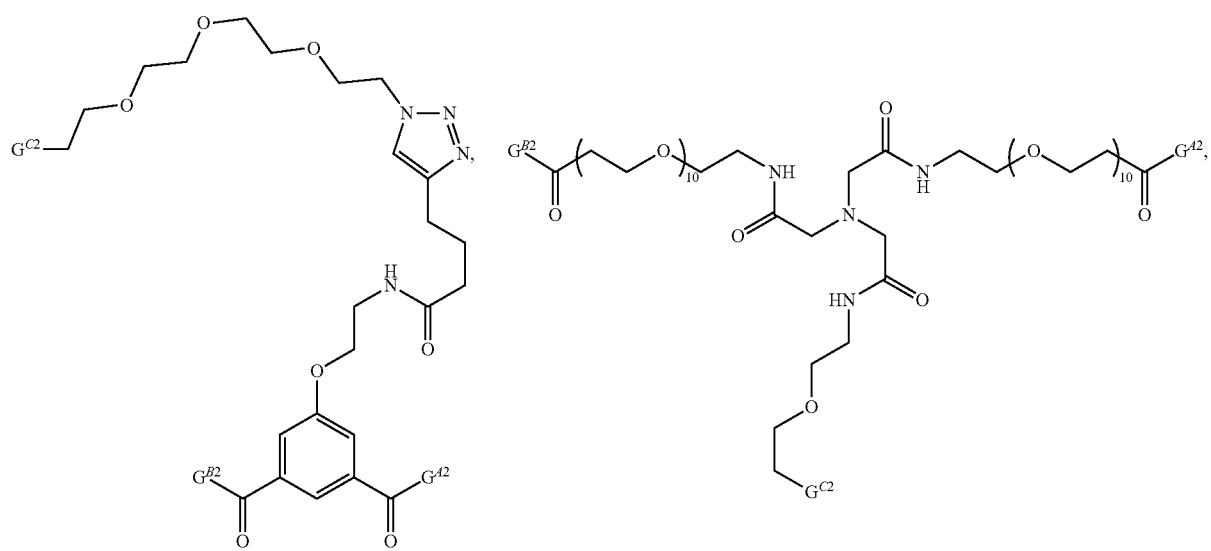
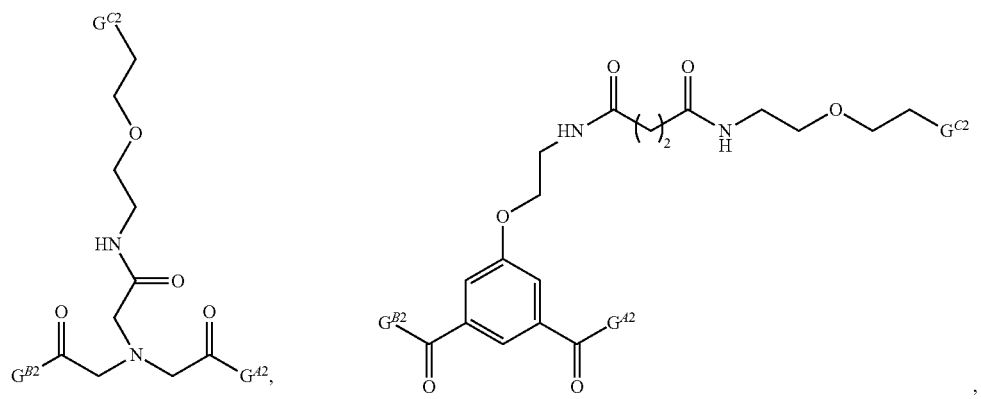

-continued
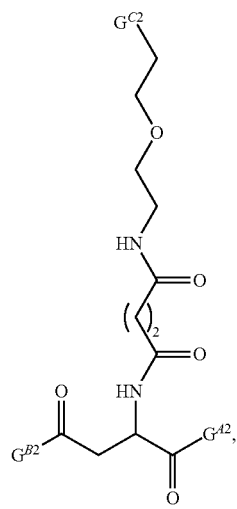 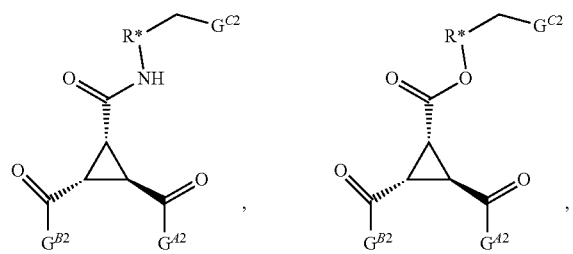
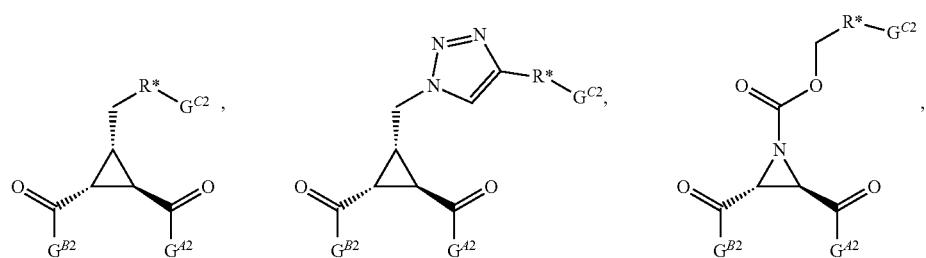
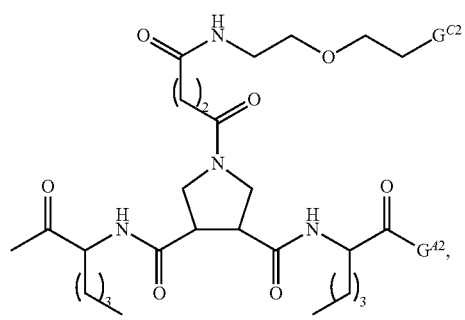 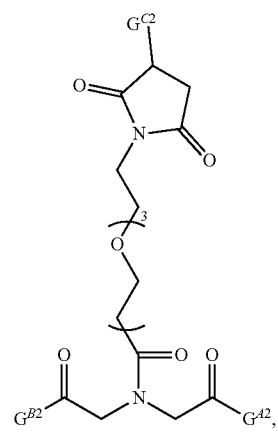

-continued
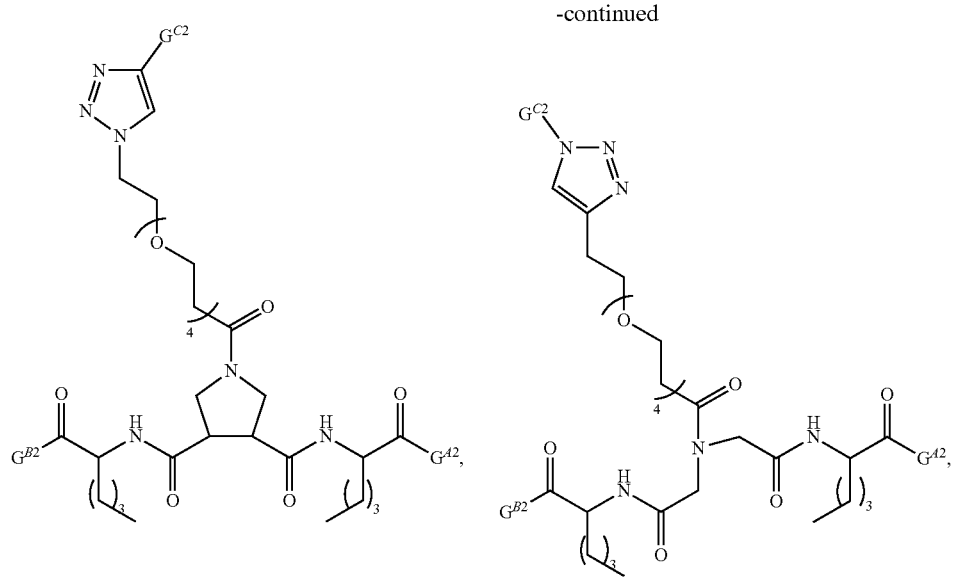
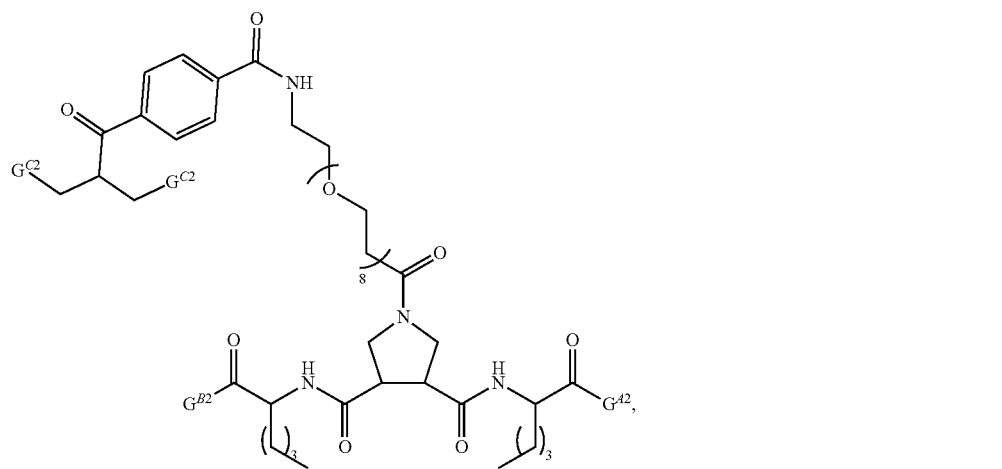
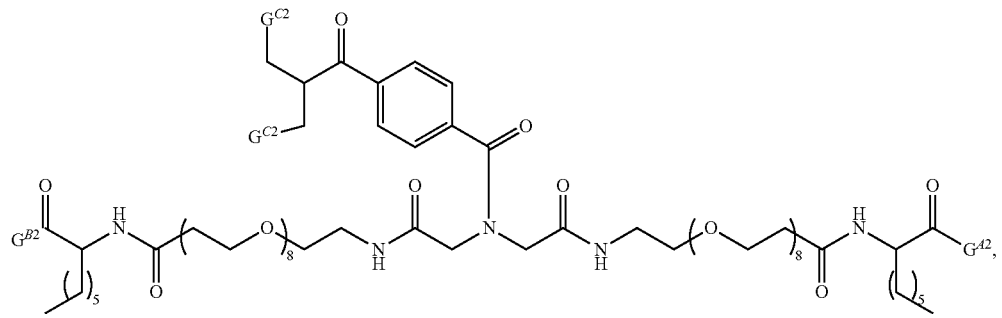
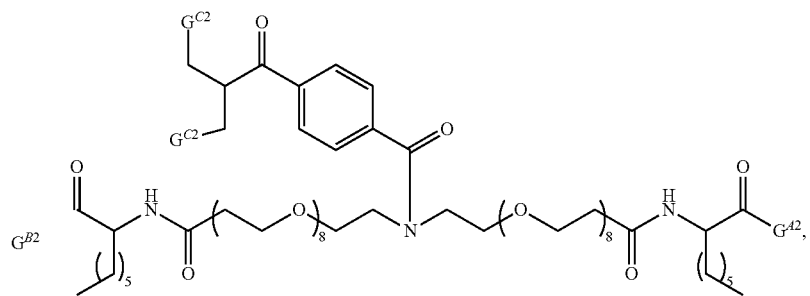

-continued
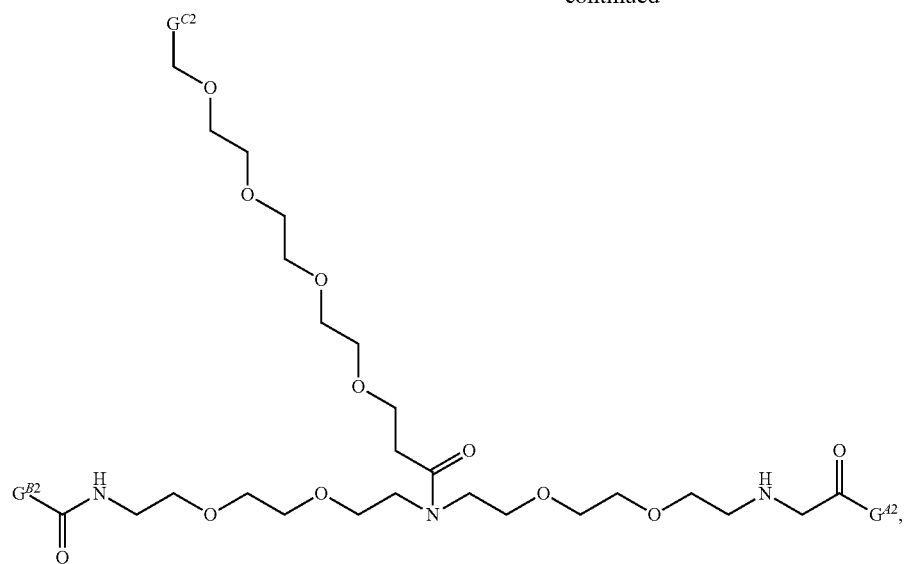
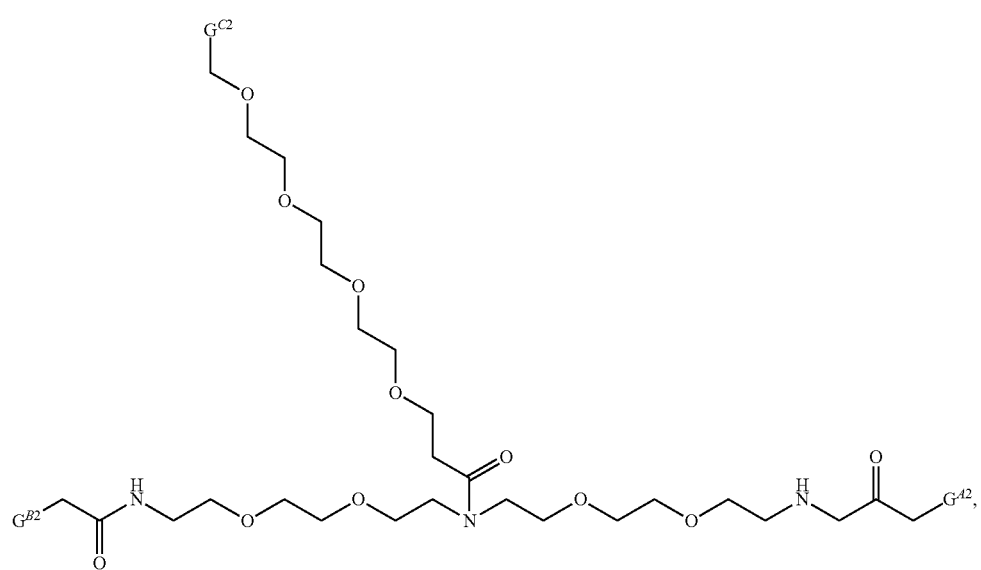
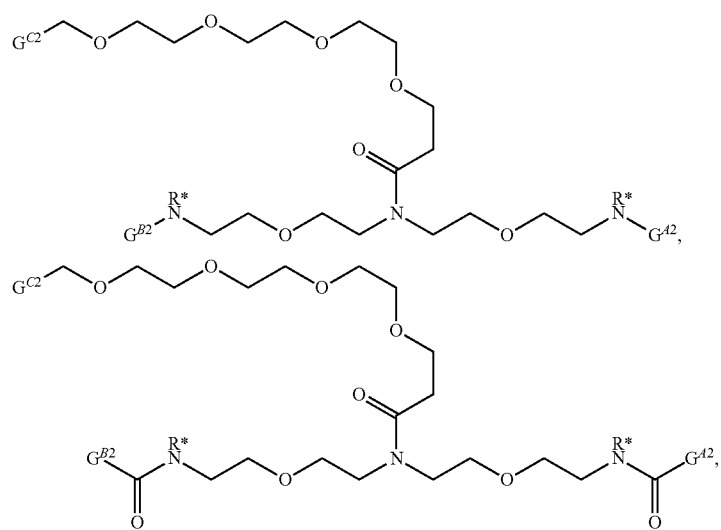

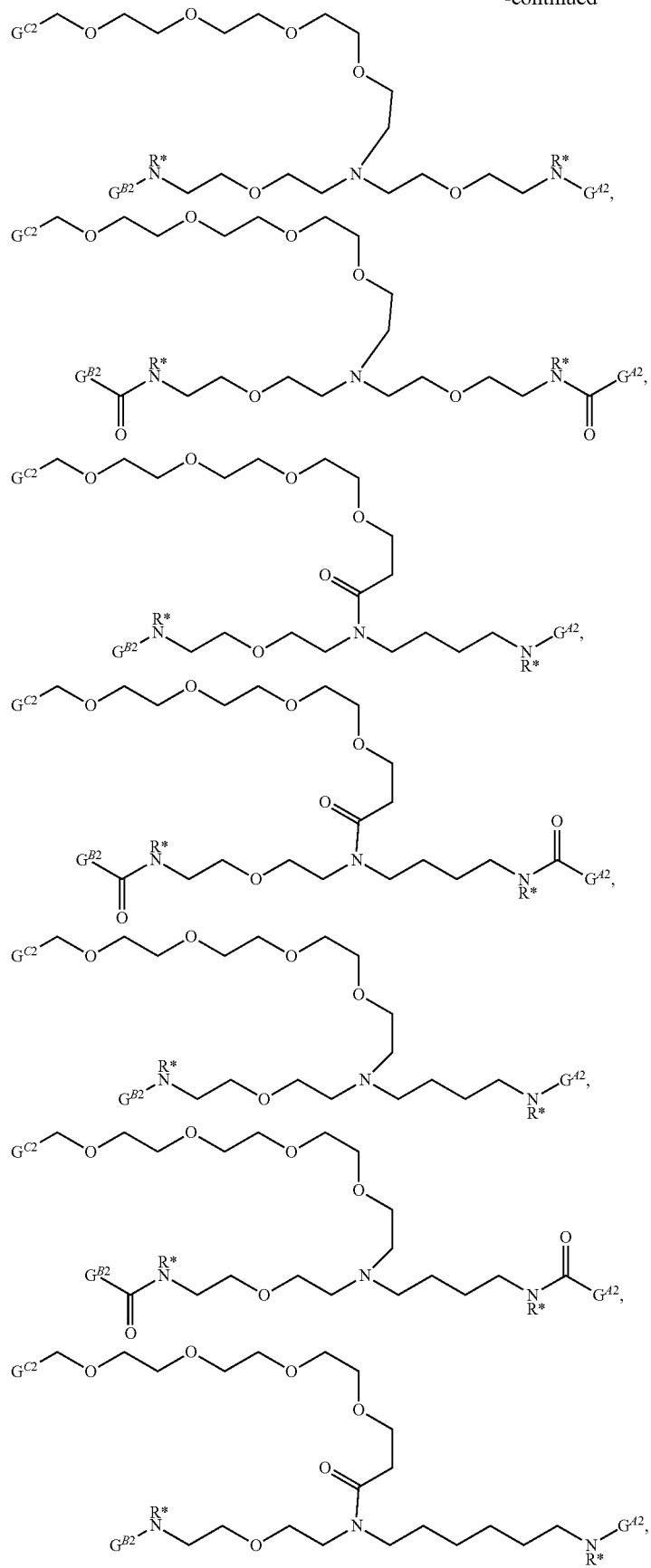

-continued
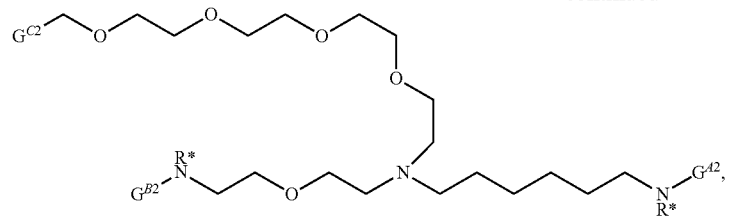
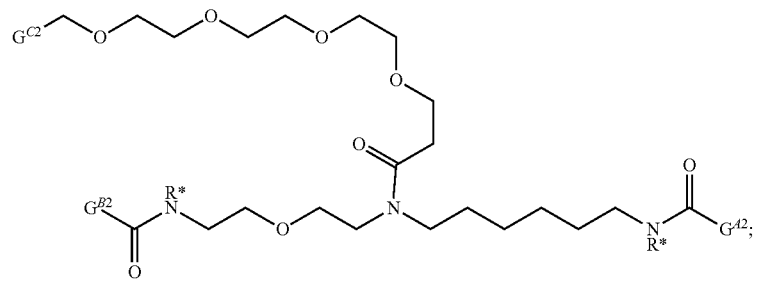
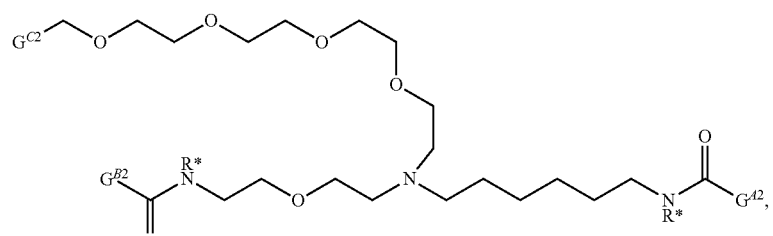
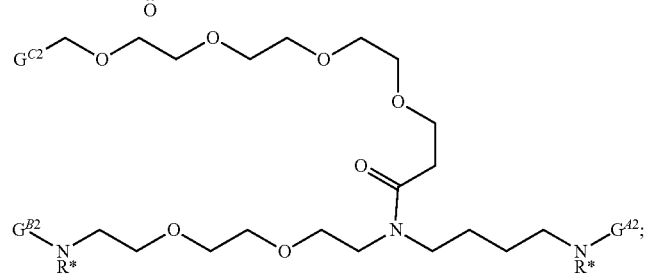
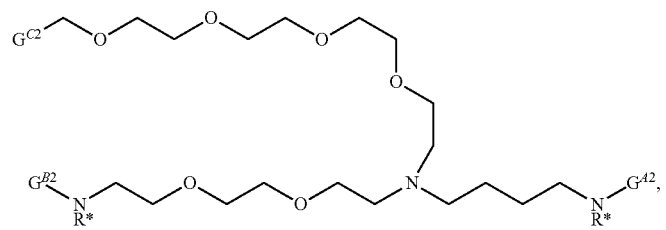
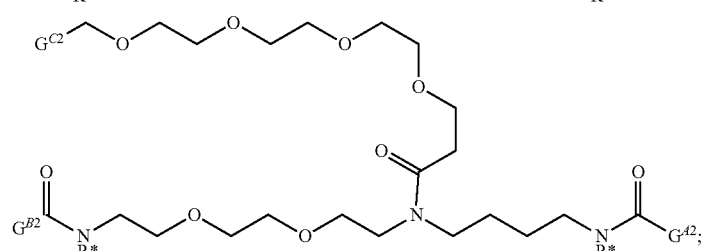
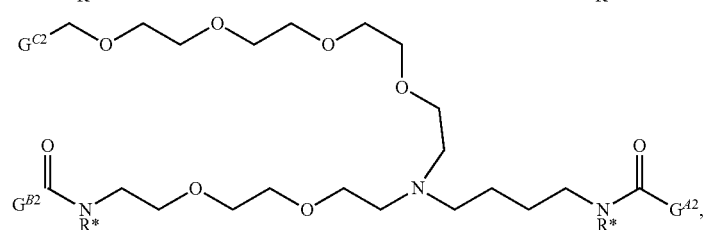

-continued wherein R* is a bond or includes one or more of optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, optionally substituted C2-C15 heteroarylene, O, S, $NR^i$, P, carbonyl, thiocarbonyl, sulfonyl, phosphate, and imino, and wherein $R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl.

In some embodiments, Y is:

(—NH(C═O)O—) and L is:

In some embodiments, Y is:

(—NH(C=O)O—) and L is:

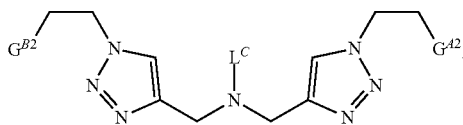

In some embodiments, Y is:

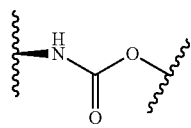

(—NH(C=O)O—) and L is:

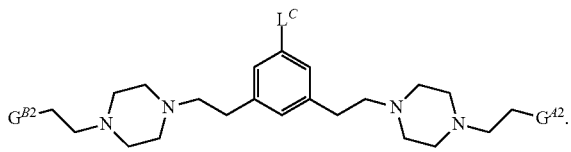

In some embodiment, Y is:

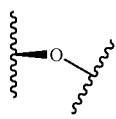

(—O—) and L is:

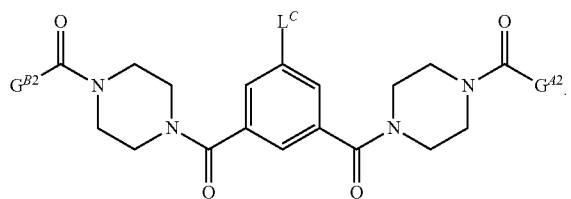

In another aspect, the invention features a conjugate described by formula (M-I):

wherein each $A_1$ is independently selected from any one of formulas (A-I)-(A-XII); each E comprises an Fc domain monomer (e.g., an Fc domain monomer having the sequence of any one of SEQ ID NOs: 1-138), an albumin protein (e.g., an albumin protein having the sequence of any one of SEQ ID NOs: 139-141), an albumin protein-binding peptide, or an Fc-binding peptide; n is 1 or 2; T is an integer from 1 to 20 (e.g., T is 1, 2, 3, 4, 5, 6, 7, 8, 9, 10, 11, 12, 13, 14, 15, 16, 17, 18, 19, or 20); and L is a linker covalently attached to each of E and $A_1$, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any one of formulas (A-I)-(A-XII). In some embodiments, each $A_1$ may be independently selected from any one of formulas (A-I), (A-II), (A-VI), or (A-VII). In other embodiments, each $A_1$ may be independently selected from formula (A-I).

In another aspect, the invention features a conjugate described by formula (M-I):

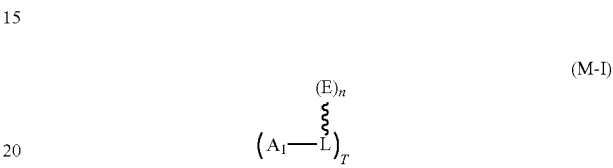

wherein each $A_1$ is independently selected from any one of formulas (A-I)-(A-V); each E comprises an Fc domain monomer (e.g., an Fc domain monomer having the sequence of any one of SEQ ID NOs: 1-138), an albumin protein (e.g., an albumin protein having the sequence of any one of SEQ ID NOs: 139-141), an albumin protein-binding peptide, or an Fc-binding peptide; n is 1 or 2; T is an integer from 1 to 20 (e.g., T is 1, 2, 3, 4, 5, 6, 7, 8, 9, 10, 11, 12, 13, 14, 15, 16, 17, 18, 19, or 20); and L is a linker covalently attached to each of E and $A_1$, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any one of formulas (A-I)-(A-V).

In another aspect, the invention features a conjugate described by formula (M-I):

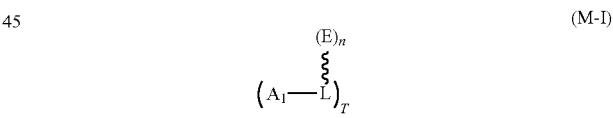

wherein each $A_1$ is independently selected from any one of formulas (A-VI)-(A-IX); each E comprises an Fc domain monomer (e.g., an Fc domain monomer having the sequence of any one of SEQ ID NOs: 1-138), an albumin protein (e.g., an albumin protein having the sequence of any one of SEQ ID NOs: 139-141), an albumin protein-binding peptide, or an Fc-binding peptide; n is 1 or 2; T is an integer from 1 to 20 (e.g., T is 1, 2, 3, 4, 5, 6, 7, 8, 9, 10, 11, 12, 13, 14, 15, 16, 17, 18, 19, or 20); and L is a linker covalently attached to each of E and $A_1$, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any one of formulas (A-VI)-(A-IX).

In some embodiments, the conjugate is described by formula (M-II):

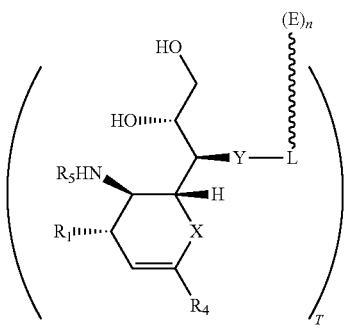

(M-II)

or a pharmaceutically acceptable salt thereof.

In some embodiments, the conjugate is described by formula (M-II-1):

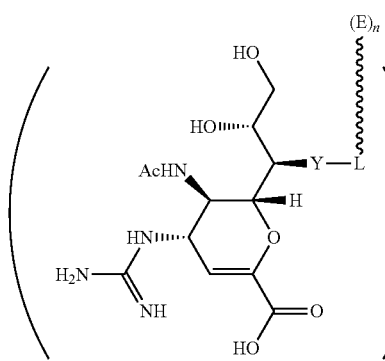

(M-II-1)

or a pharmaceutically acceptable salt thereof.

In some embodiments, the conjugate is described by formula (M-II-2):

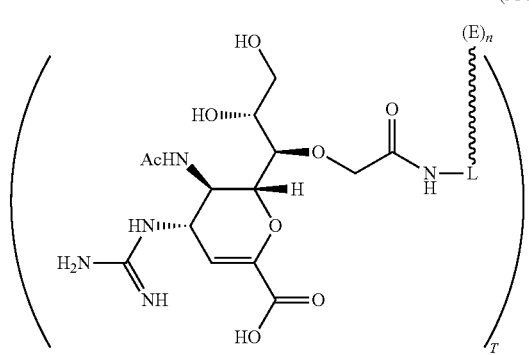

(M-II-2)

or a pharmaceutically acceptable salt thereof.

In some embodiments, the conjugate is described by formula (M-II-3):

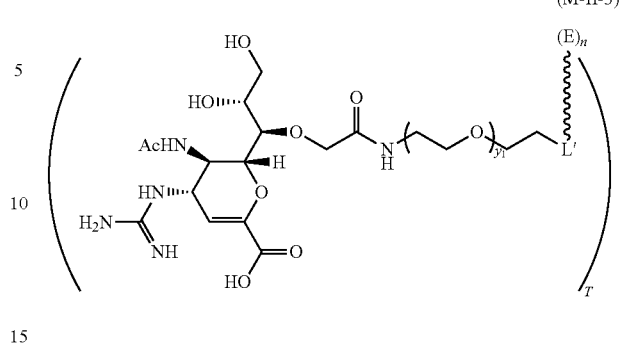

(M-II-3)

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-II-4):

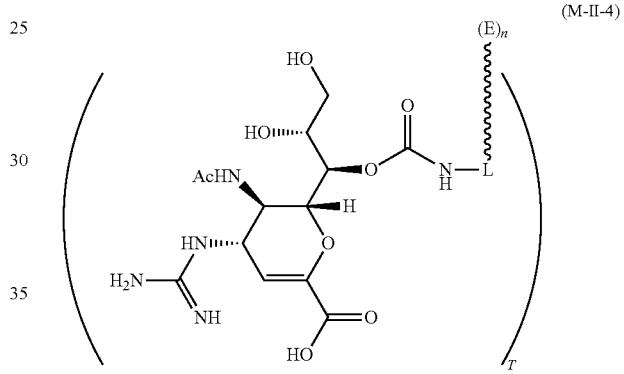

(M-II-4)

or a pharmaceutically acceptable salt thereof.

In some embodiments, the conjugate is described by formula (M-II-5):

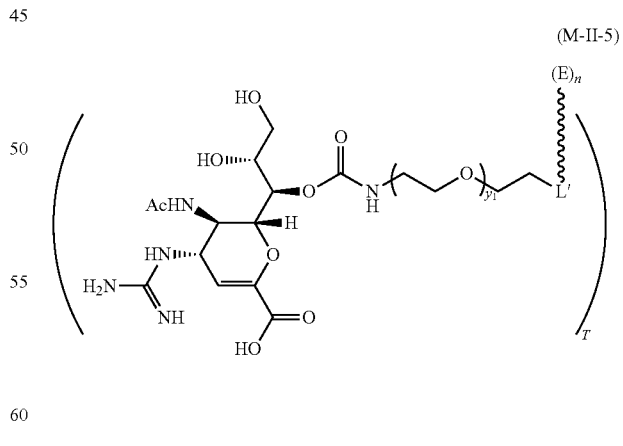

(M-II-5)

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate has the structure

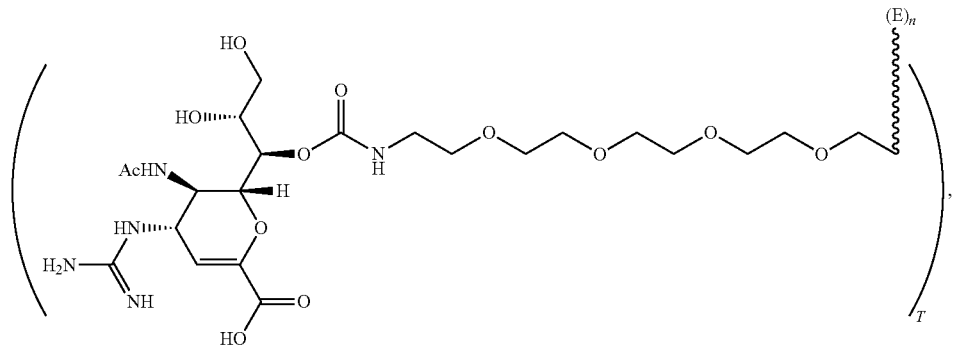

or a pharmaceutically acceptable salt thereof.

In some embodiments, the conjugate is described by formula (M-II-6):

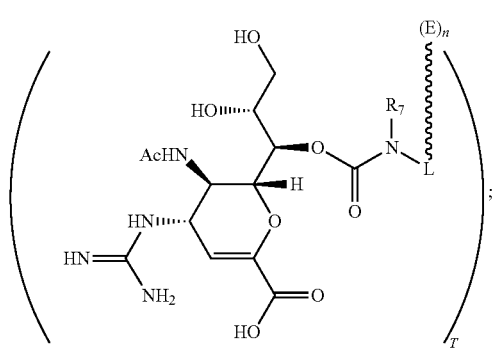

(M-II-6)

wherein $R_7$ is selected from H, C1-C20 alkyl, C3-C20 cycloalkyl, C3-C20 heterocycloalkyl; C5-C15 aryl, and C2-C15 heteroaryl; or a pharmaceutically acceptable salt thereof. In some embodiments, $R_7$ is selected from C1-C20 alkyl (e.g., methyl, ethyl, propyl, or butyl).

In some embodiments, the conjugate is described by formula (M-II-7):

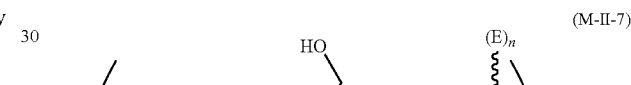

(M-II-7)

or a pharmaceutically acceptable salt thereof.

In some embodiments, the conjugate is described by formula (M-II-8):

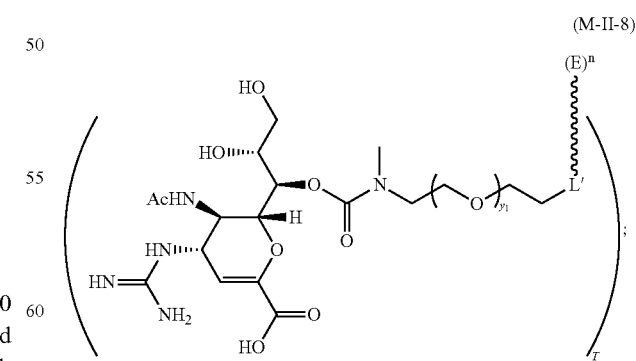

(M-II-8)

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate has the structure:

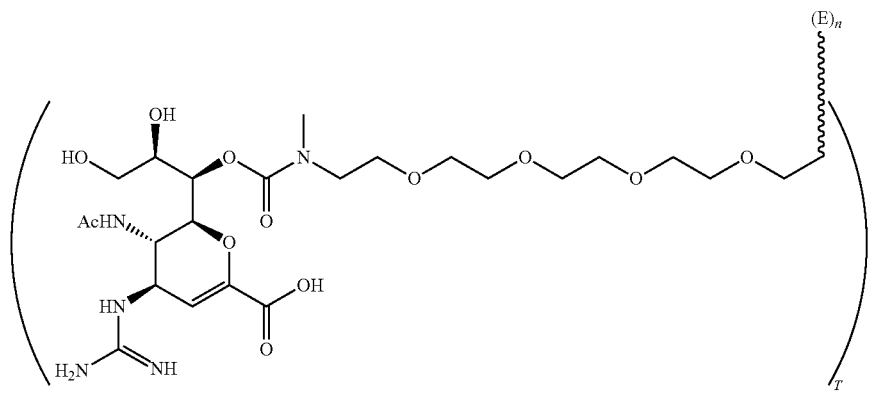

In some embodiments, the conjugate is described by formula (M-II-9):

(M-II-9)

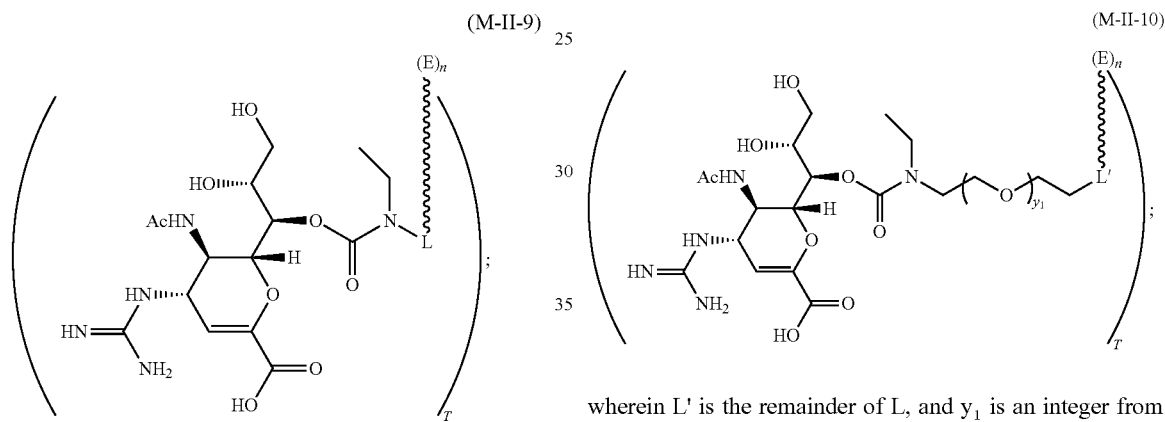

or a pharmaceutically acceptable salt thereof.

In some embodiments, the conjugate is described by formula (M-II-10):

(M-II-10)

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate has the structure

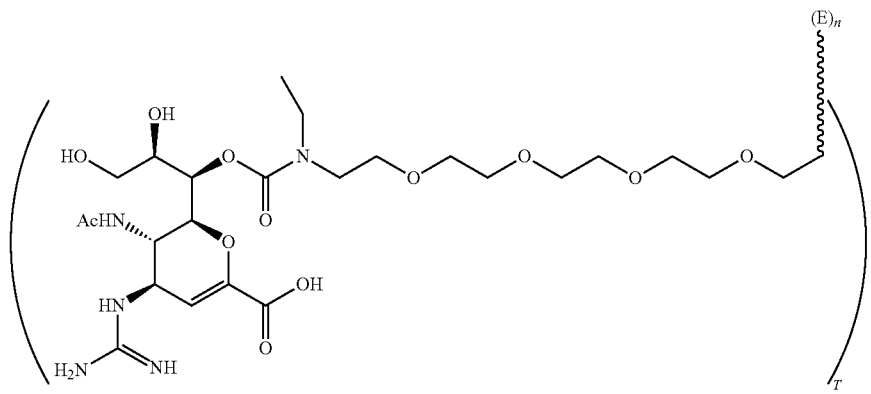

or a pharmaceutically acceptable salt thereof.

In some embodiments, the conjugate is described by formula (M-III):

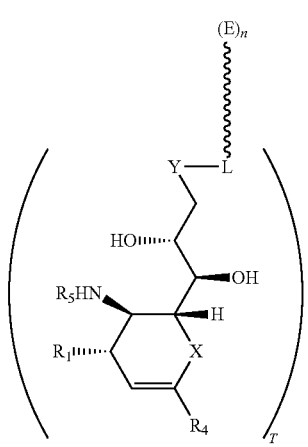
(M-III)

or a pharmaceutically acceptable salt thereof.

In some embodiments, the conjugate is described by formula (M-III-1):

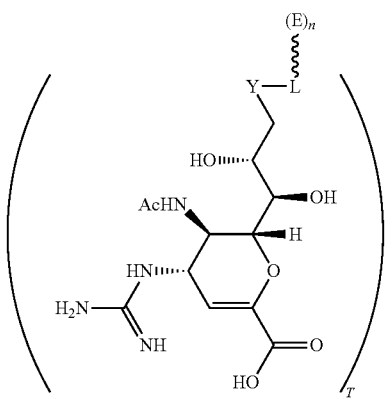
(M-III-1)

or a pharmaceutically acceptable salt thereof.

In some embodiments, the conjugate is described by formula (M-III-2):

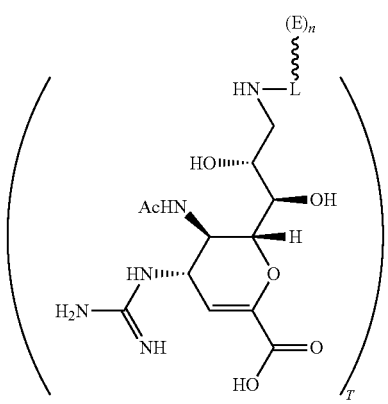
(M-III-2)

or a pharmaceutically acceptable salt thereof.

In some embodiments, the conjugate is described by formula (M-III-3):

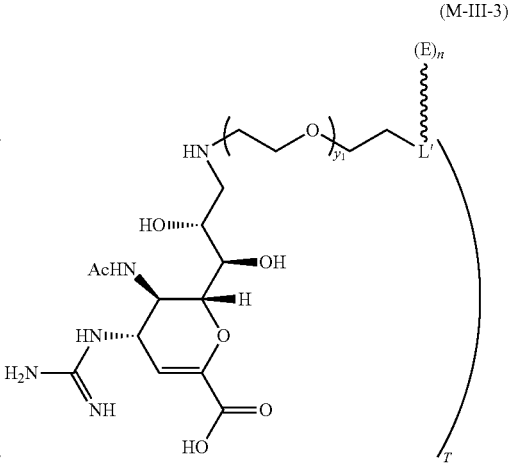
(M-III-3)

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-III-4):

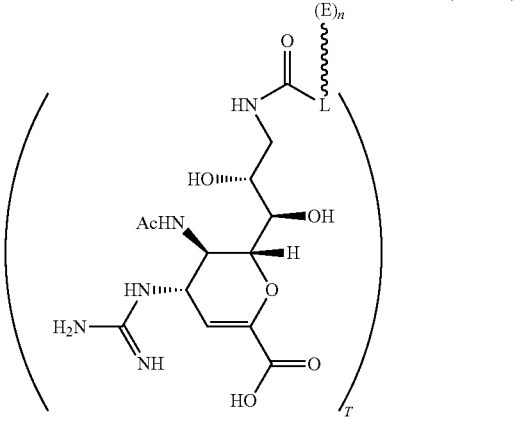
(M-III-4)

or a pharmaceutically acceptable salt thereof.

In some embodiments, the conjugate is described by formula (M-III-5):

(M-III-5)

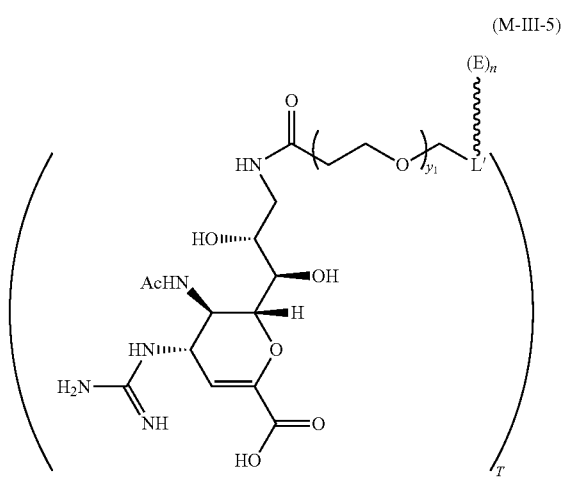

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-III-6):

(M-III-7)

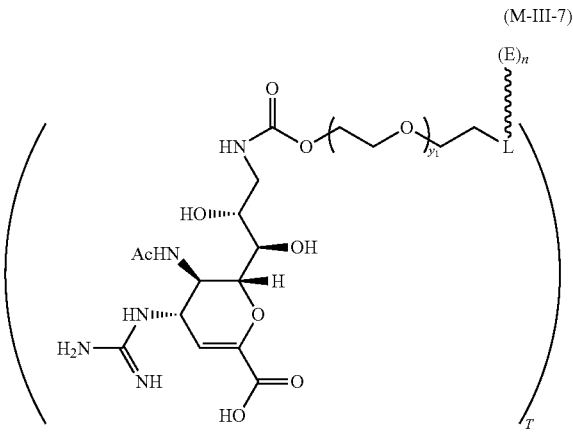

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-III-8):

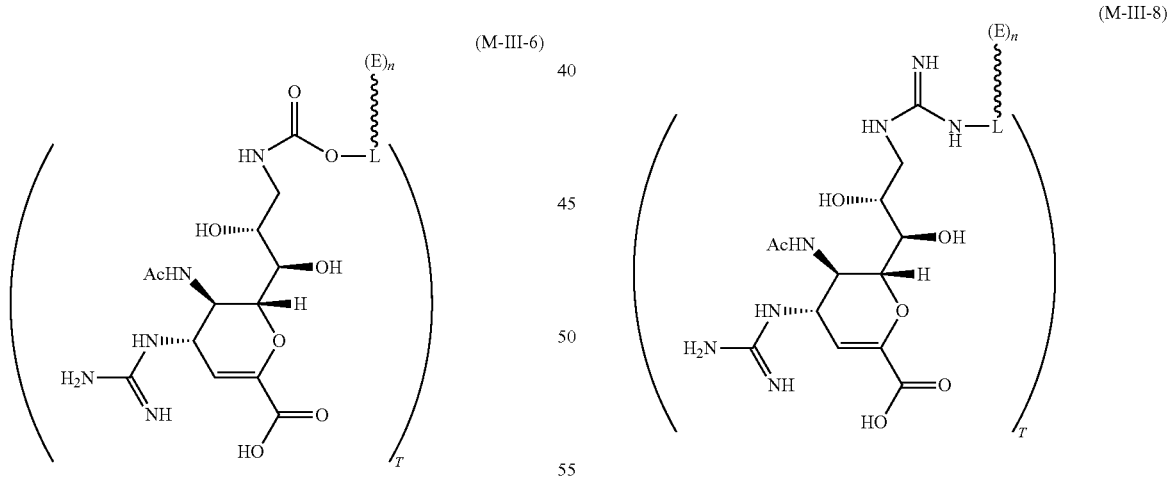

(M-III-6)

(M-III-8)

or a pharmaceutically acceptable salt thereof.

In some embodiments, the conjugate is described by formula (M-III-7):

or a pharmaceutically acceptable salt thereof.

In some embodiments, the conjugate is described by formula (M-III-9):

(M-III-9)

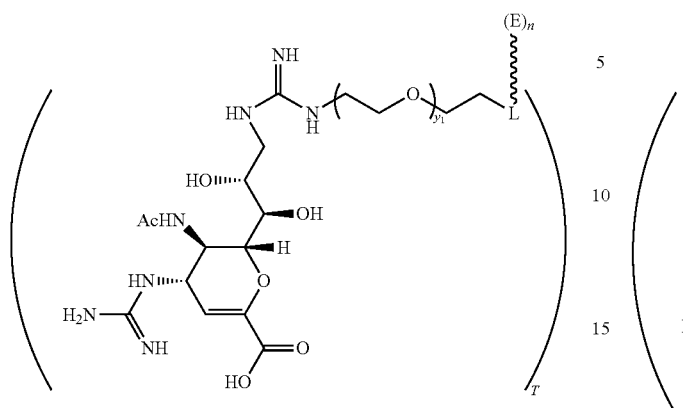

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-IV):

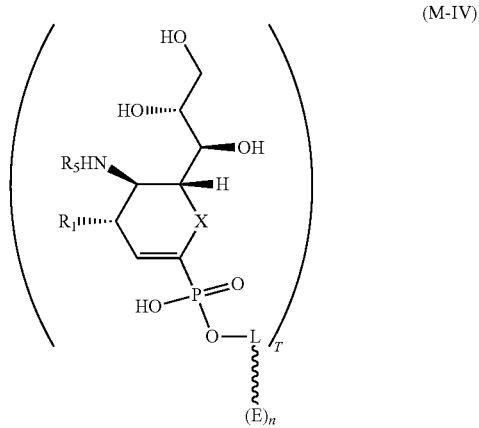

(M-IV)

or a pharmaceutically acceptable salt thereof.

In some embodiments, the conjugate is described by formula (M-IV-1):

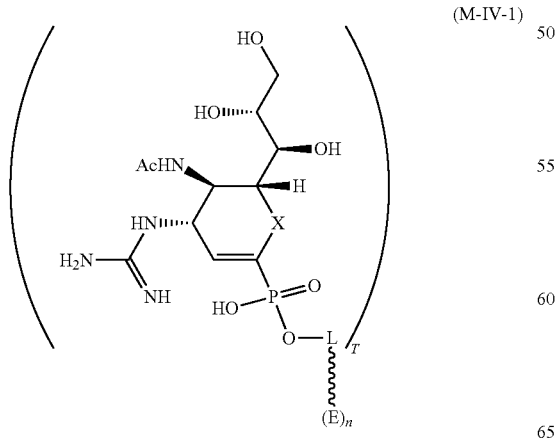

(M-IV-1)

or a pharmaceutically acceptable salt thereof.

In some embodiments, the conjugate is described by formula (M-IV-2):

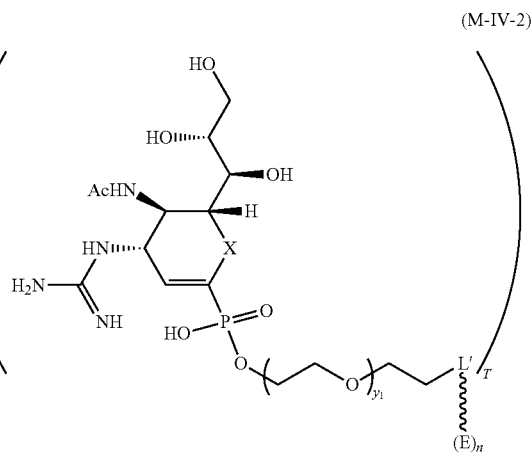

(M-IV-2)

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-V):

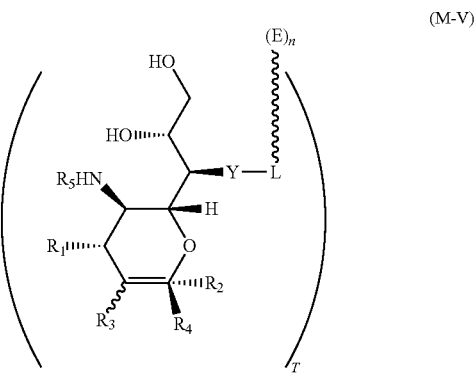

(M-V)

or a pharmaceutically acceptable salt thereof.

In some embodiments, the conjugate is described by formula (M-V-1):

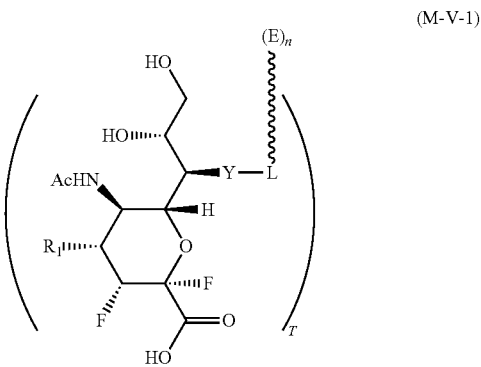

(M-V-1)

or a pharmaceutically acceptable salt thereof.

In some embodiments, the conjugate is described by formula (M-V-2):

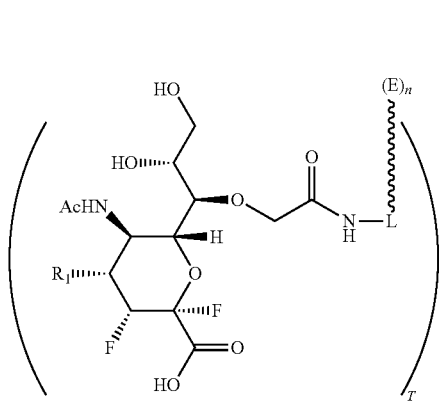

(M-V-2)

or a pharmaceutically acceptable salt thereof.

In some embodiments, the conjugate is described by formula (M-V-3):

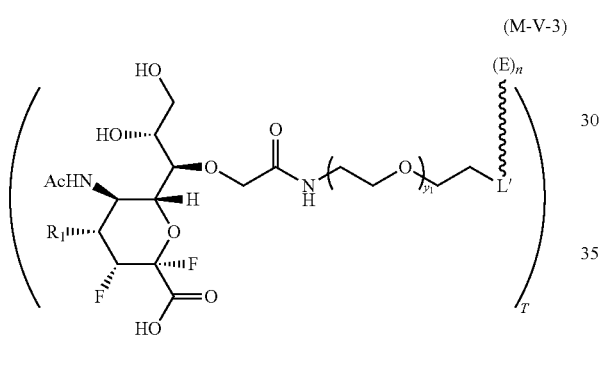

(M-V-3)

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-V-4):

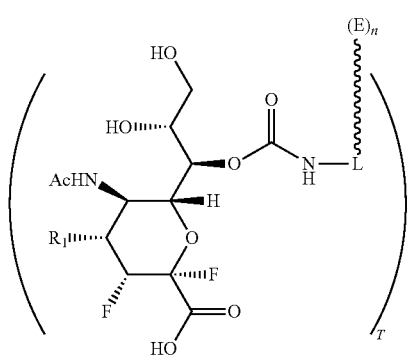

(M-V-4)

or a pharmaceutically acceptable salt thereof.

In some embodiments, the conjugate is described by formula (M-V-5):

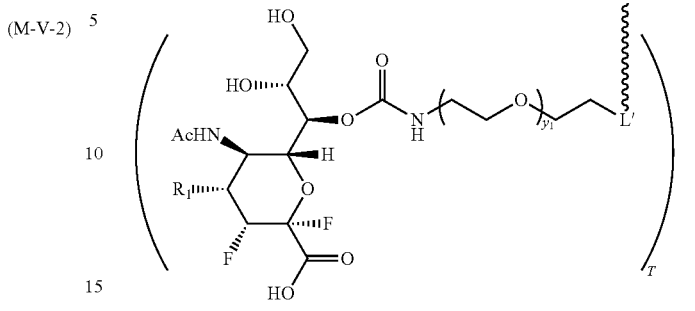

(M-V-5)

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-V-6):

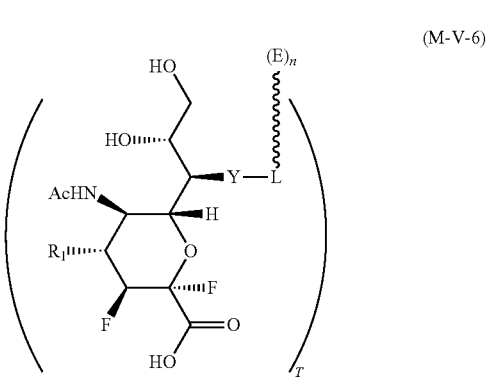

(M-V-6)

or a pharmaceutically acceptable salt thereof.

In some embodiments, the conjugate is described by formula (M-V-7):

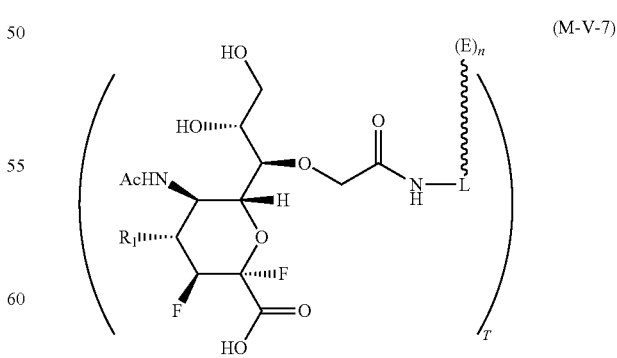

(M-V-7)

or a pharmaceutically acceptable salt thereof.

In some embodiments, the conjugate is described by formula (M-V-8):

(M-V-8)

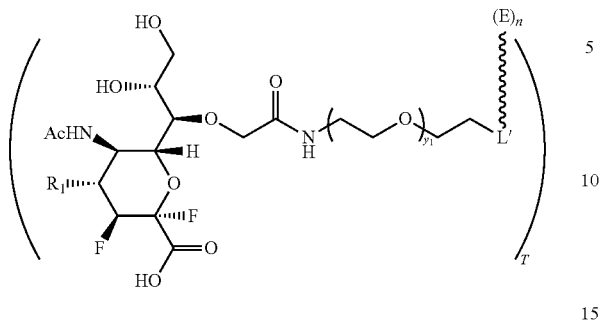

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-V-9):

(M-V-9)

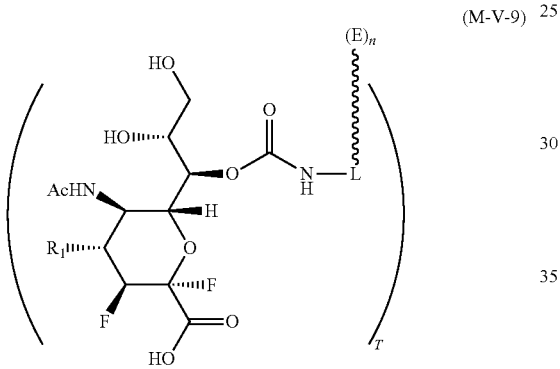

or a pharmaceutically acceptable salt thereof.

In some embodiments, the conjugate is described by formula (M-V-10):

(M-V-10)

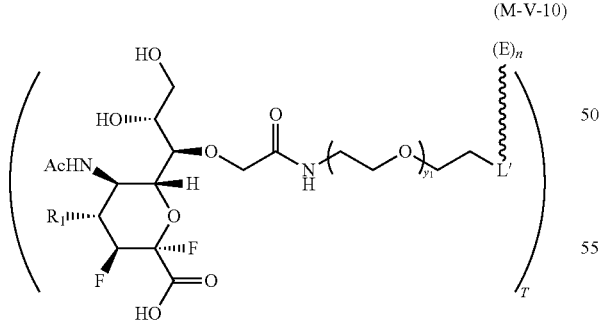

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-VI):

(M-VI)

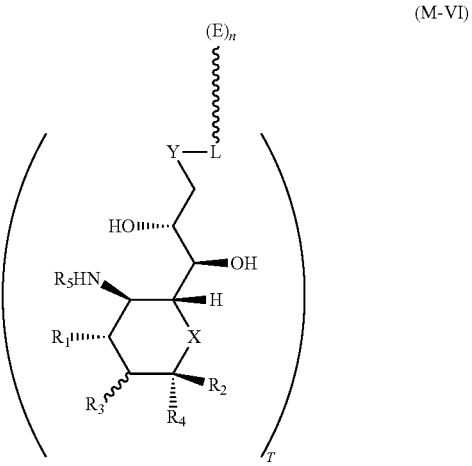

or a pharmaceutically acceptable salt thereof.

In some embodiments, the conjugate is described by formula (M-VI-1):

(M-VI-1)

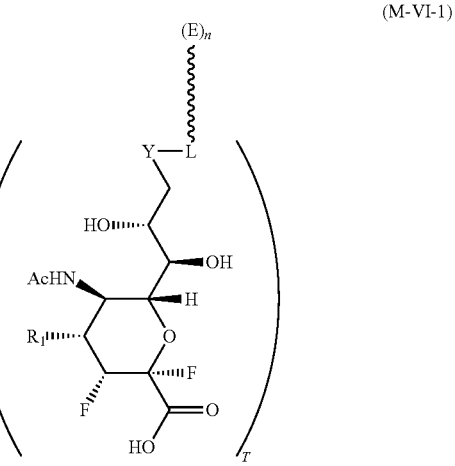

or a pharmaceutically acceptable salt thereof.

In some embodiments, the conjugate is described by formula (M-VI-2):

(M-VI-2)

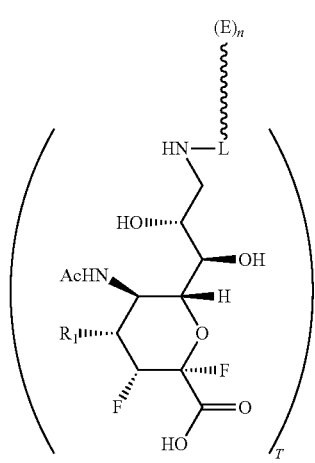

or a pharmaceutically acceptable salt thereof.

In some embodiments, the conjugate is described by formula (M-VI-3):

(M-VI-3)

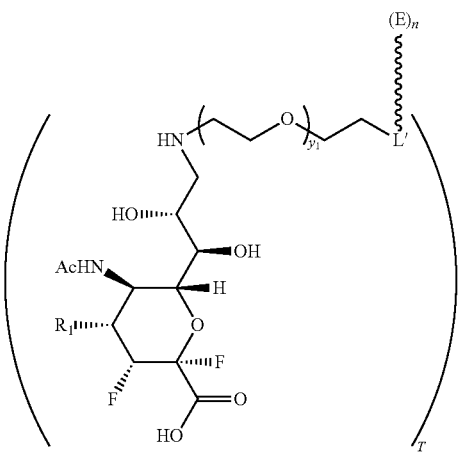

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-VI-4):

(M-VI-4)

or a pharmaceutically acceptable salt thereof.

In some embodiments, the conjugate is described by formula (M-VI-5):

(M-VI-5)

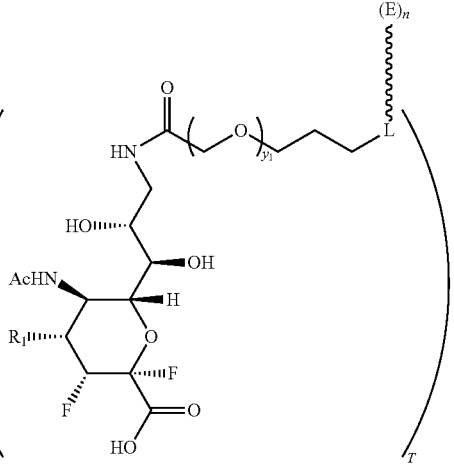

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-VI-6):

(M-VI-6)

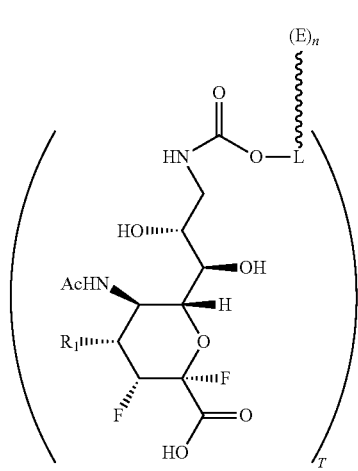

or a pharmaceutically acceptable salt thereof.

In some embodiments, the conjugate is described by formula (M-VI-7):

(M-VI-8)

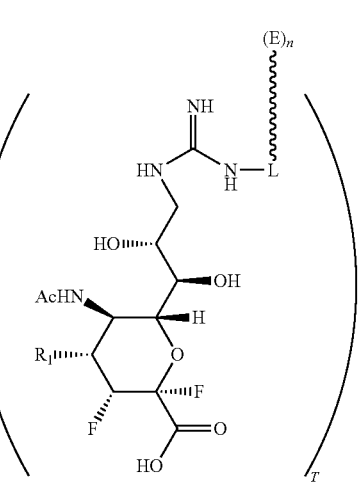

or a pharmaceutically acceptable salt thereof.

In some embodiments, the conjugate is described by formula (M-VI-9):

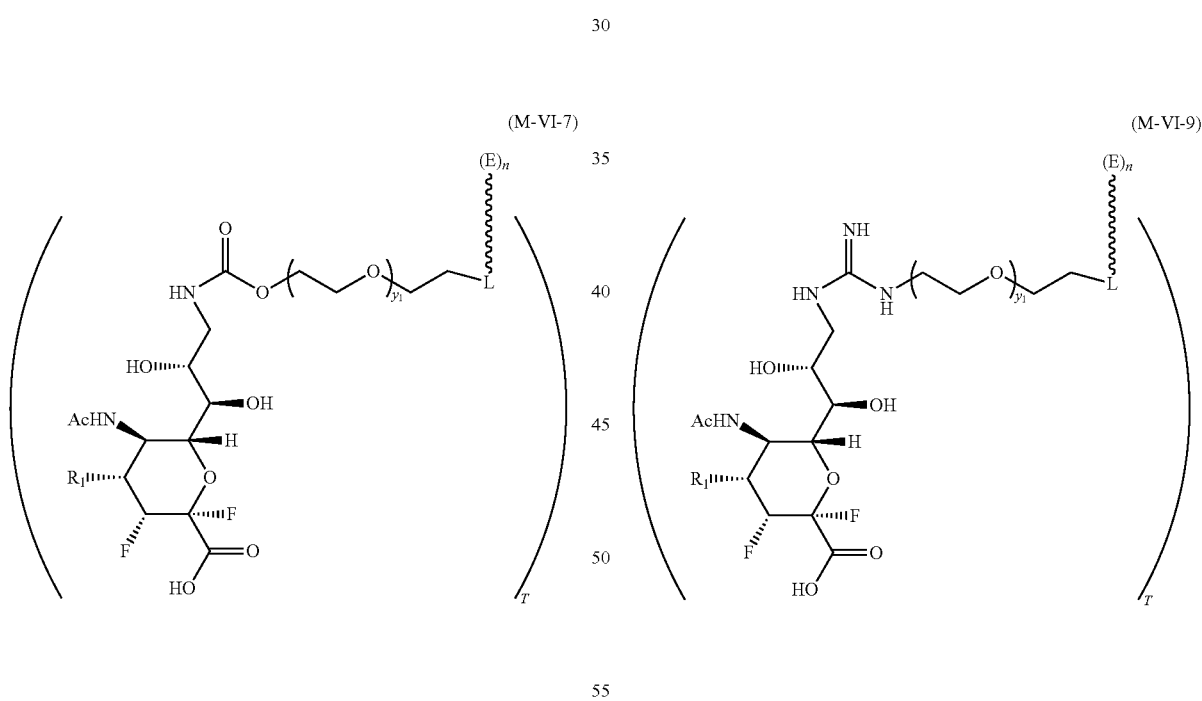

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-VI-8):

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-VII):

(M-VII)

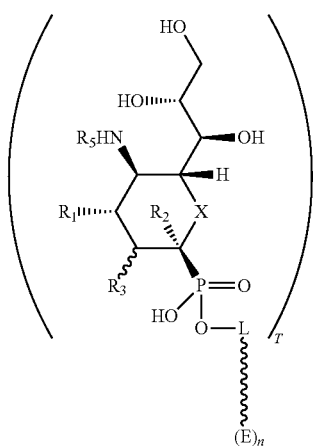

or a pharmaceutically acceptable salt thereof.

In some embodiments of any of the aspects described herein, $R_1$ is OH. In some embodiments of any of the aspects described herein, $R_1$ is $NH_2$. In some embodiments of any of the aspects described herein, $R_1$ is —NHC(=NH)NH$_2$.

In some embodiments, the conjugate is described by formula (M-VIII):

(M-VIII)

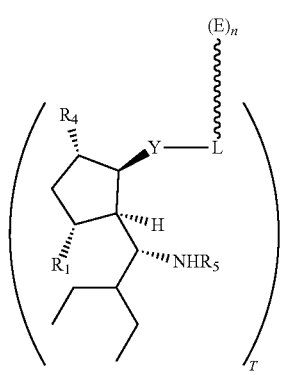

or a pharmaceutically acceptable salt thereof.

In some embodiments, the conjugate is described by formula (M-VIII-1):

(M-VIII-1)

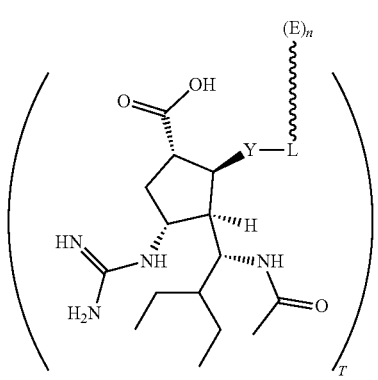

or a pharmaceutically acceptable salt thereof.

In some embodiments, the conjugate is described by (M-VIII-2):

(M-VIII-2)

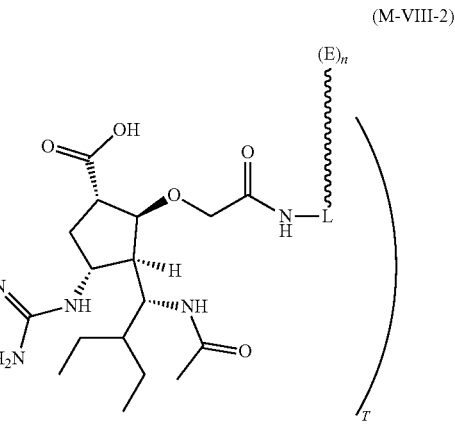

or a pharmaceutically acceptable salt thereof.

In some embodiments, the conjugate is described by formula (M-VIII-3):

(M-VIII-3)

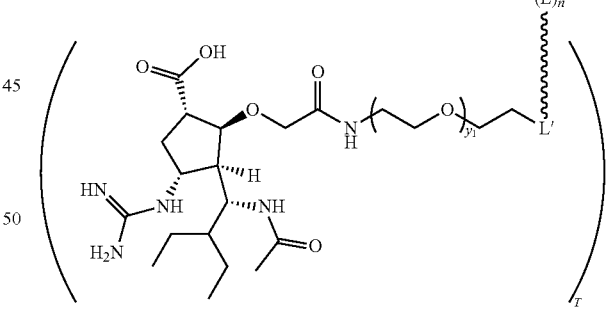

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-VIII-4):

(M-VIII-4)

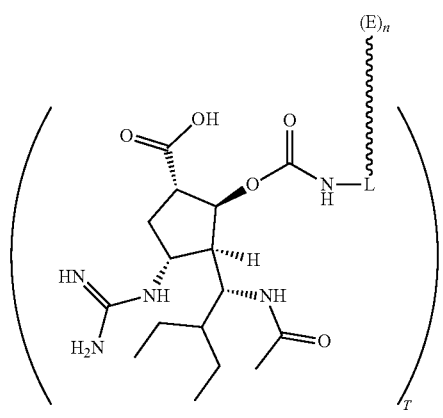

or a pharmaceutically acceptable salt thereof.

In some embodiments, the conjugate is described by formula (M-VIII-5):

(M-VIII-5)

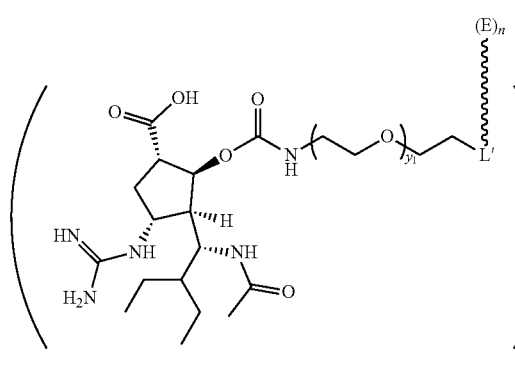

wherein L' is the remainder of L, and $y_1$ is an integer from 1-20, or a pharmaceutically acceptable salt thereof.

In some embodiments, the conjugate has the structure of

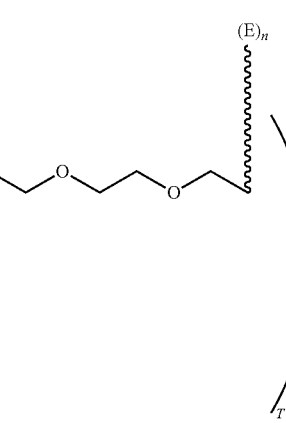

or a pharmaceutically acceptable salt thereof.

In some embodiments, the conjugate is described by formula (M-VIII-6):

(M-VIII-6)

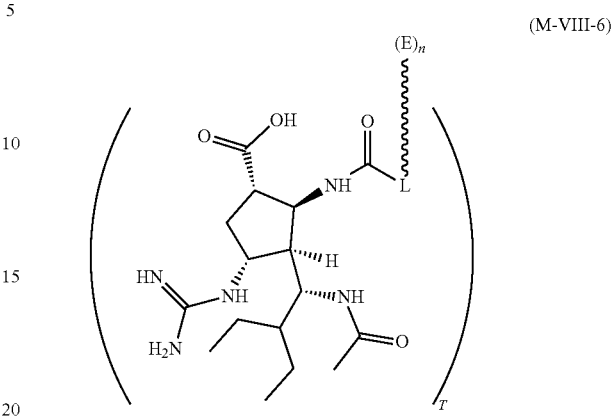

or a pharmaceutically acceptable salt thereof.

In some embodiments, the conjugate is described by formula (M-VIII-7):

(M-VIII-7)

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-VIII-8):

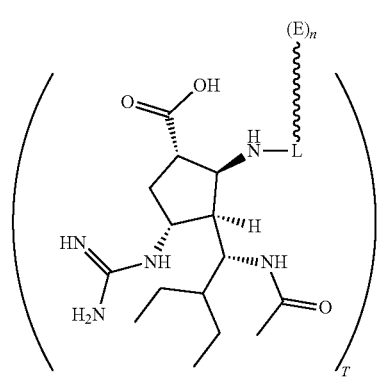

(M-VIII-8)

or a pharmaceutically acceptable salt thereof.

In some embodiments, the conjugate is described by formula (M-VIII-9):

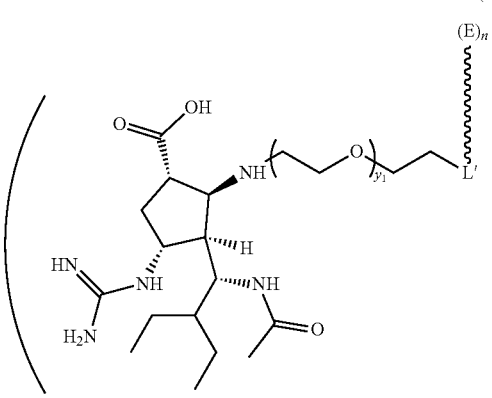

(M-VIII-9)

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-VIII-10):

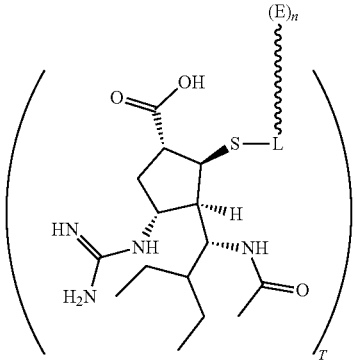

(M-VIII-10)

or a pharmaceutically acceptable salt thereof.

In some embodiments, the conjugate is described by formula (M-VIII-11):

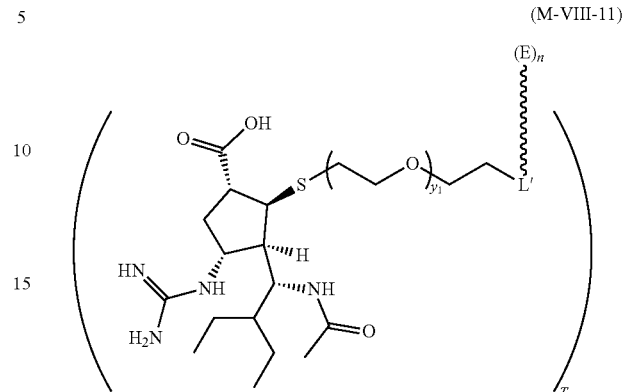

(M-VIII-11)

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-IX):

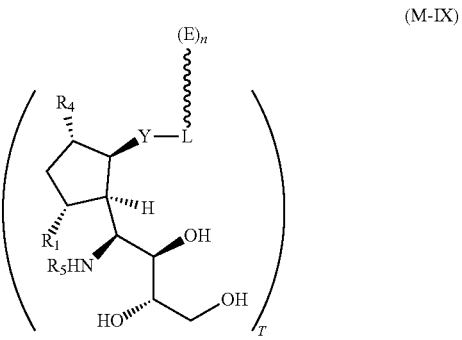

(M-IX)

or a pharmaceutically acceptable salt thereof.

In some embodiments, the conjugate is described by formula (M-IX-1):

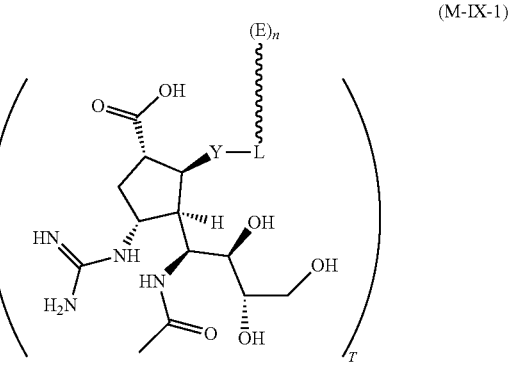

(M-IX-1)

or a pharmaceutically acceptable salt thereof.

In some embodiments, the conjugate is described by formula (M-IX-2):

(M-IX-2)

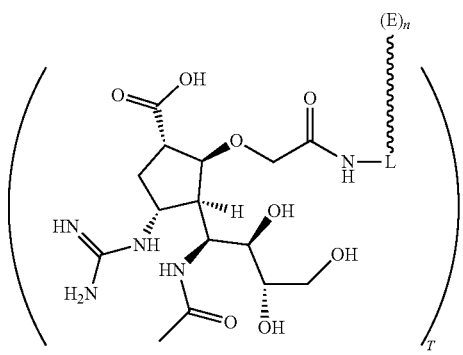

or a pharmaceutically acceptable salt thereof.

In some embodiments, the conjugate is described by formula (M-IX-3):

(M-IX-3)

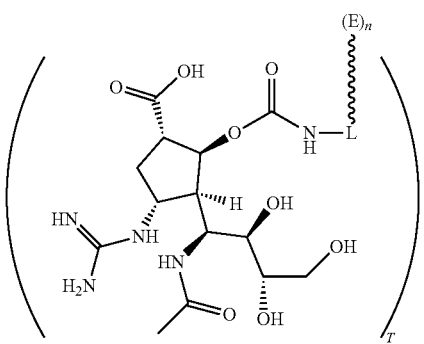

or a pharmaceutically acceptable salt thereof.

In some embodiments, the conjugate is described by formula (M-IX-4):

(M-IX-4)

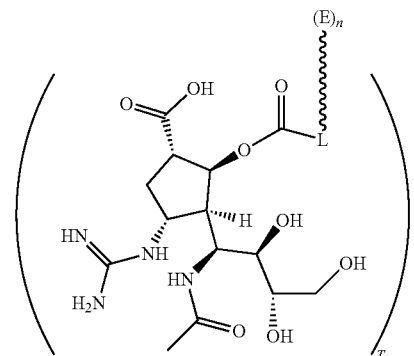

or a pharmaceutically acceptable salt thereof.

In some embodiments, the conjugate is described by formula (M-IX-5):

(M-IX-5)

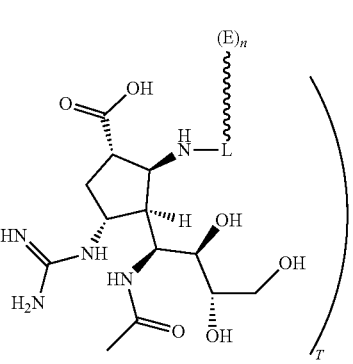

or a pharmaceutically acceptable salt thereof.

In some embodiments, the conjugate is described by formula (M-IX-6):

(M-IX-6)

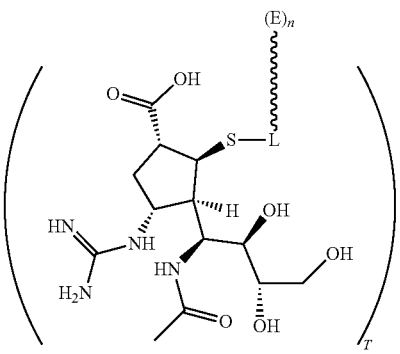

or a pharmaceutically acceptable salt thereof.

In some embodiments, the conjugate is described by formula (M-X):

(M-X)

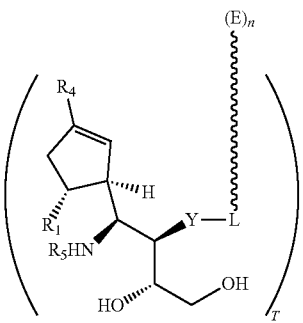

or a pharmaceutically acceptable salt thereof.

In some embodiments, the conjugate is described by formula (M-X-1):

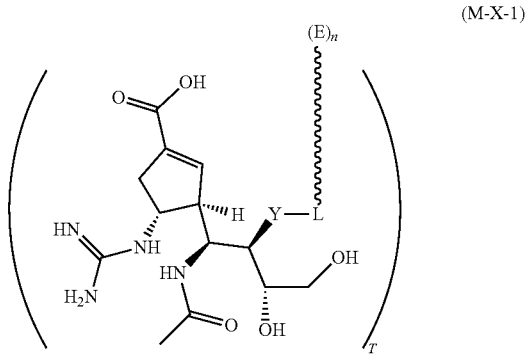

(M-X-1)

or a pharmaceutically acceptable salt thereof.

In some embodiments, the conjugate is described by formula (M-X-2):

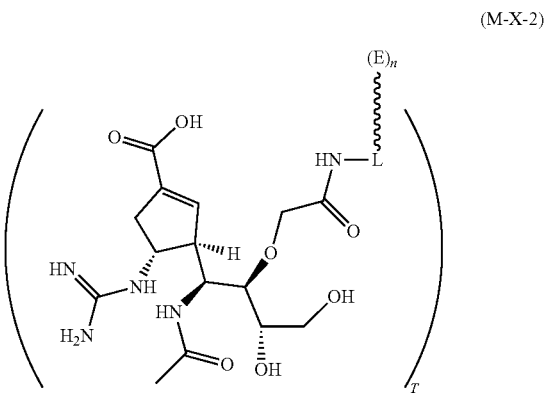

(M-X-2)

or a pharmaceutically acceptable salt thereof.

In some embodiments, the conjugate is described by formula (M-X-3):

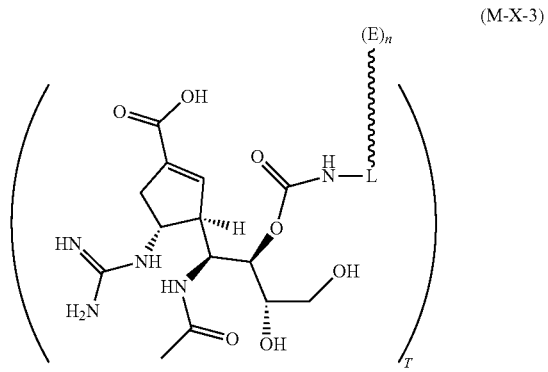

(M-X-3)

or a pharmaceutically acceptable salt thereof.

In some embodiments of any of the aspects described herein, L or L' comprises one or more optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, optionally substituted C2-C15 heteroarylene, O, S, $NR^i$, P, carbonyl, thiocarbonyl, sulfonyl, phosphate, phosphoryl, or imino, wherein $R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl.

In some embodiments of any of the aspects described herein, the backbone of L or L' consists of one or more optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, optionally substituted C2-C15 heteroarylene, O, S, $NR^i$, P, carbonyl, thiocarbonyl, sulfonyl, phosphate, phosphoryl, or imino, wherein $R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl.

In some embodiments of any of the aspects described herein, L or L' is oxo substituted. In some embodiments, the backbone of L or L' comprises no more than 250 atoms. In some embodiments, L or L' is capable of forming an amide, a carbamate, a sulfonyl, or a urea linkage. In some embodiments, L or L' is a bond. In some embodiments, L or L' is an atom. In some embodiments, L' is a nitrogen atom.

In some embodiments, each L is described by formula (M-L-I):

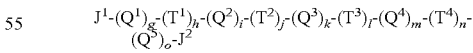

wherein: $J^1$ is a bond attached to $A_1$; $J^2$ is a bond attached to E or a functional group capable of reacting with a functional group conjugated to E (e.g., maleimide and cysteine, amine and activated carboxylic acid, thiol and maleimide, activated sulfonic acid and amine, isocyanate and amine, azide and alkyne, and alkene and tetrazine); each of $Q^1$, $Q^2$, $Q^3$, $Q^4$ and $Q^5$ is, independently, optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, or optionally substituted C2-C15 heteroarylene; each of $T^1$, $T^2$, $T^3$, $T^4$ is, independently, O, S, $NR^i$, P, carbonyl, thiocarbonyl, sulfonyl, phosphate, phosphoryl, or imino; $R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl; and each of g, h, i, j, k, l, m, n, and o is, independently, 0 or 1; or a pharmaceutically acceptable salt thereof.

In some embodiments, $J^2$ may have two points of attachment to the Fc domain, Fc-binding peptide, albumin protein, or albumin protein-binding peptide (e.g., two $J^2$).

In some embodiments, L is

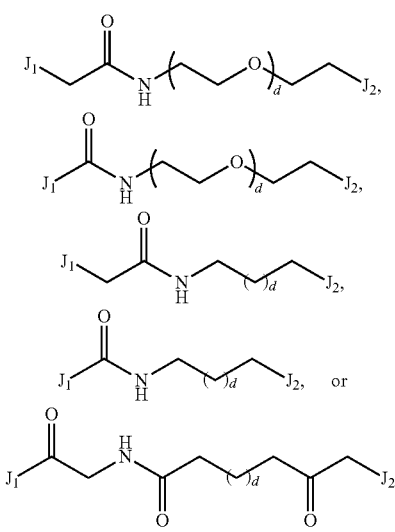

wherein d is an integer from 1 to 20 (e.g., d is 1, 2, 3, 4, 5, 6, 7, 8, 9, 10, 11, 12, 13, 14, 15, 16, 17, 18, 19, or 20).

In some embodiments, L is

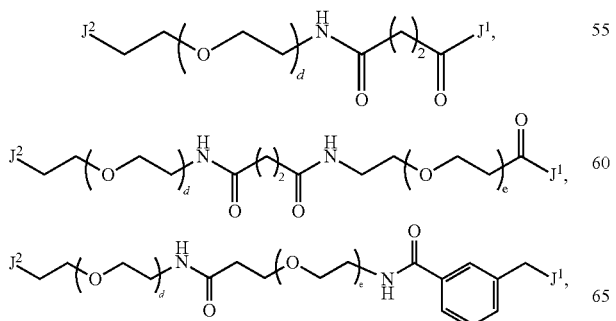

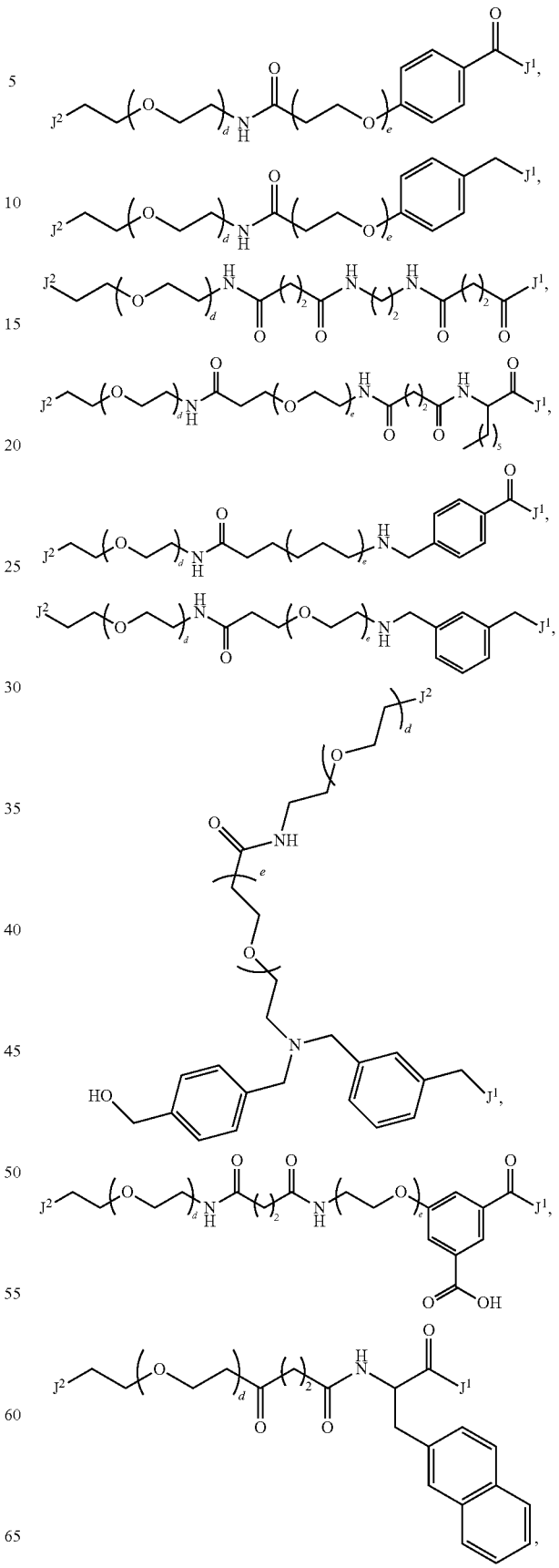

-continued

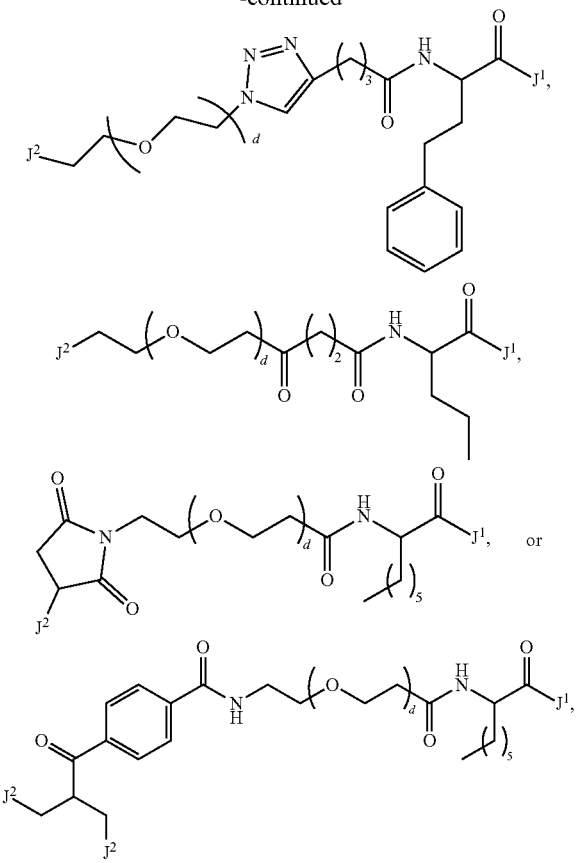
,

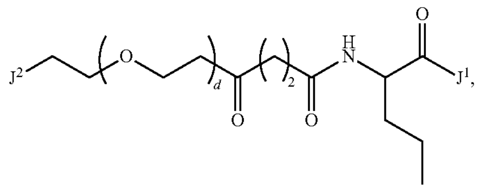

,

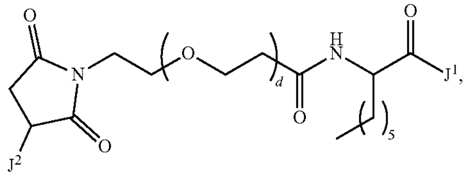

, or

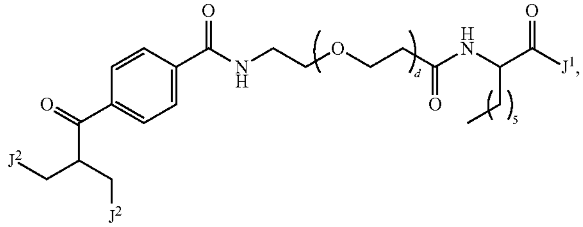

, wherein each of d and e is, independently, an integer from 1 to 26; or a pharmaceutically acceptable salt thereof.

In some embodiments of any of the aspects described herein, L includes a polyethylene glycol (PEG) linker. A PEG linker includes a linker having the repeating unit structure $(—CH_2CH_2O—)_n$, wherein n is an integer from 2 to 100. A polyethylene glycol linker may covalently join a neuraminidase inhibitor and E (e.g., in a conjugate of any one of formulas (M-I)-(M-XI)). A polyethylene glycol linker may covalently join a first neuraminidase inhibitor and a second neuraminidase inhibitor (e.g., in a conjugate of any one of formulas (D-I)-(D-XI)). A polyethylene glycol linker may covalently join a neuraminidase inhibitor dimer and E (e.g., in a conjugate of any one of formulas (D-I)-(D-XI)). A polyethylene glycol linker may be selected any one of $PEG_2$ to $PEG_{100}$ (e.g., $PEG_2$, $PEG_3$, $PEG_4$, $PEG_5$, $PEG_5$-$PEG_{10}$, $PEG_{10}$-$PEG_{20}$, $PEG_{20}$-$PEG_{30}$, $PEG_{30}$-$PEG_{40}$, $PEG_{50}$-$PEG_{60}$, $PEG_{60}$-$PEG_{70}$, $PEG_{70}$-$PEG_{80}$, $PEG_{80}$-$PEG_{90}$, $PEG_{90}$-$PEG_{100}$). In some embodiments, $L^c$ includes a PEG linker, where $L^c$ is covalently attached to each of Q and E.

In some embodiments of any of the aspects described herein, $R_1$ is $—NHC(=NH)NH_2$. In some embodiments of any of the aspects described herein, $R_2$ is —F. In some embodiments of any of the aspects described herein, $R_3$ is —F. In some embodiments of any of the aspects described herein, $R_4$ is $—CO_2H$. In some embodiments of any of the aspects described herein, $R_5$ is $—COCH_3$.

In some embodiments of any of the aspects described herein, L is covalently attached to the nitrogen atom of a surface exposed lysine of E or L is covalently attached to the sulfur atom of a surface exposed cysteine of E.

In some embodiments of any of the aspects described herein, E is an Fc domain monomer. In some embodiments, n is 2 and each E dimerizes to form an Fc domain.

In some embodiments, n is 2, each E is an Fc domain monomer, each E dimerizes to form an Fc domain, and the conjugate is described by formula (D-I-1):

(D-I-1)

wherein J is an Fc domain; and T is an integer from 1 to 20 (e.g., T is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate has the structure of

-continued

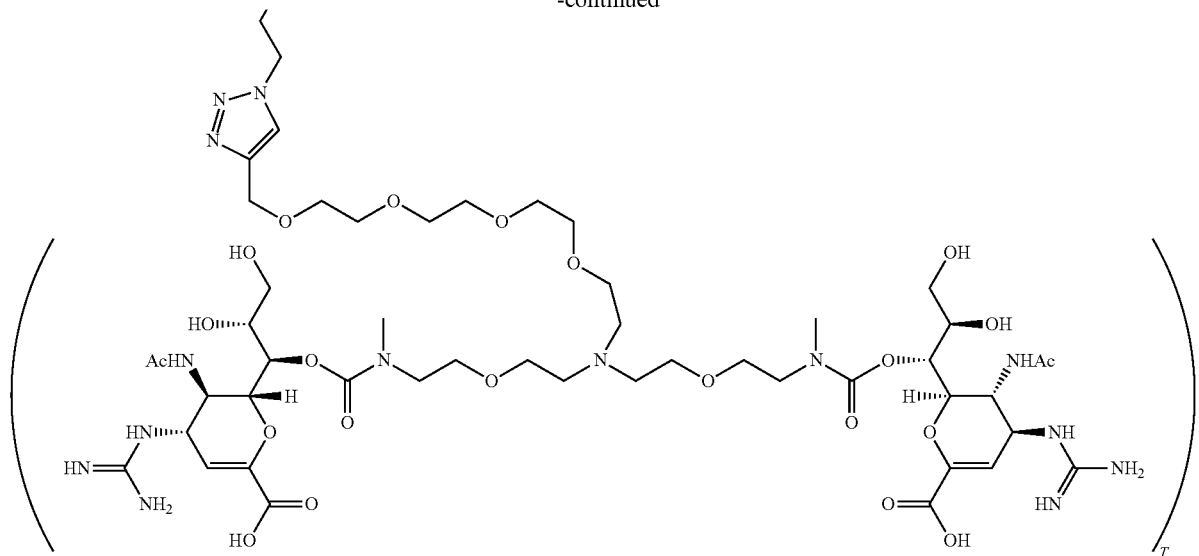

or a pharmaceutically acceptable salt thereof.

In some embodiments, n is 2, each E is an Fc domain monomer, each E dimerizes to form an Fc domain, and the conjugate is described by formula (M-I-1):

(M-I-1)

wherein J is an Fc domain; and T is an integer from 1 to 20 (e.g., T is 1, 2, 3, 4, 5, 6, 7, 8, 9, 10, 11, 12, 13, 14, 15, 16, 17, 18, 19, or 20), or a pharmaceutically acceptable salt thereof.

In some embodiments of any of the aspects described herein, E has the sequence of any one of SEQ ID NOs: 1-138.

In some embodiments of any of the aspects described herein, E is an albumin protein, an albumin protein-binding peptide, or an Fc-binding peptide. In some embodiments, where E is an albumin protein, an albumin protein-binding peptide, or an Fc-binding peptide, n is 1.

In some embodiments, n is 1, E is an albumin protein, an albumin protein-binding peptide, or an Fc-binding peptide and the conjugate is described by formula (D-I-2):

(D-I-2)

wherein E is an albumin protein, an albumin protein-binding peptide, or Fc-binding peptide; and T is an integer from 1 to 20, or a pharmaceutically acceptable salt thereof.

In some embodiments, n is 1, E is an albumin protein, an albumin protein-binding peptide, or an Fc-binding peptide, and the conjugate is described by formula (M-I-2):

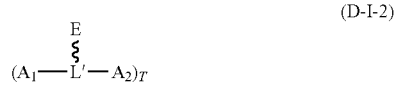

(M-I-2)

wherein E is an albumin protein, an albumin protein-binding peptide, or an Fc-binding peptide; and T is an integer from 1 to 20, or a pharmaceutically acceptable salt thereof.

In some embodiments of any of the aspects described herein, E is an albumin protein having the sequence of any one of SEQ ID NOs: 139-141.

In some embodiments of any of the aspects described herein, T is 1, 2, 3, 4, or 5.

In another aspect, the invention provides a population of conjugates having the structure of any of the conjugates described herein (e.g., a population of conjugates having the formula of any one of formulas (1)-(5), (D-I)-(D-XI), (D'-I), (M-I)-(M-XI), or (M'-I)), wherein the average value of T is 1 to 20 (e.g., the average value of T is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5). In some embodiments, the average value of T is about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20.

In some embodiments of any of the aspects described herein, when T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein). In some embodiments, E may be conjugated to 2, 3, 4, 5, 6, 7, 8, 9, 10, or more different $A_1$-L-$A_2$ moieties. In some embodiments, E is conjugated to a first $A_1$-L-$A_2$ moiety, and a second $A_1$-L-$A_2$ moiety. In some embodiments, $A_1$ and $A_2$ of the first $A_1$-L-$A_2$ moiety are independently selected from any one of formulas (A-III)-(A-V), and $A_1$ and $A_2$ of the second $A_1$-L-$A_2$ moiety are independently selected from any one of formulas (A-I), (A-II), (A-VI), (A-VII), (A-VIII), and (A-IX).

In some embodiments, each of the first $A_1$-L-$A_2$ moieties is conjugated specifically to a lysine residue of E (e.g., the nitrogen atom of a surface exposed lysine residue of E), and each of the second $A_1$-L-$A_2$ moieties is conjugated specifically to a cysteine residue of E (e.g., the sulfur atom of a surface exposed cysteine residue of E). In some embodiments, each of the first $A_1$-L-$A_2$ moieties is conjugated specifically to a cysteine residue of E (e.g., the sulfur atom of a surface exposed cysteine residue of E), and each of the second $A_1$-L-$A_2$ moieties is conjugated specifically to a lysine residue of E (e.g., the nitrogen atom of a surface exposed lysine residue of E).

In some embodiments, the number of first $A_1$-L-$A_2$ moieties conjugated to E is an integer from 1 to 10 (e.g., 1, 2, 3, 4, 5, 6, 7, 8, 9, or 10). In some embodiments, the number of second $A_1$-L-$A_2$ moieties conjugated to E is an integer from 1 to 10 (e.g. 1, 2, 3, 4, 5, 6, 7, 8, 9, 10).

In some embodiments of any of the aspects described herein, when T is greater than 1 (e.g., T is 2, 3, 4, 5, 6, 7, 8, 9, 10, 11, 12, 13, 14, 15, 16, 17, 18, 19, or 20), each $A_1$-L may be independently selected (e.g., independently selected from any of the $A_1$-L structures described herein). In some embodiments, E may be conjugated to 2, 3, 4, 5, 6, 7, 8, 9, 10, or more different $A_1$-L moieties. In some embodiments, E is conjugated to a first $A_1$-L moiety, and a second $A_1$-L, moiety. In some embodiments, $A_1$ of the first $A_1$-L moiety is selected from any one of formulas (A-III)-(A-V), and $A_1$ of the second $A_1$-L moiety is selected from any one of formulas (A-I), (A-II), (A-VI), (A-VII), (A-VIII), or (A-IX).

In some embodiments, each of the first $A_1$-L moieties is conjugated specifically to a lysine residue of E (e.g., the nitrogen atom of a surface exposed lysine residue of E), and each of the second $A_1$-L moieties is conjugated specifically to a cysteine residue of E (e.g., the sulfur atom of a surface exposed cysteine residue of E). In some embodiments, each of the first $A_1$-L moieties is conjugated specifically to a cysteine residue of E (e.g., the sulfur atom of a surface exposed cysteine residue of E), and each of the second $A_1$-L moieties is conjugated specifically to a lysine residue of E (e.g., the nitrogen atom of a surface exposed lysine residue of E).

In some embodiments, the number of first $A_1$-L moieties conjugated to E is an integer from 1 to 10 (e.g., 1, 2, 3, 4, 5, 6, 7, 8, 9, or 10). In some embodiments, the number of second $A_1$-L moieties conjugated to E is an integer from 1 to 10 (e.g. 1, 2, 3, 4, 5, 6, 7, 8, 9, 10).

In another aspect, the invention features a conjugate described by formula (D'-I):

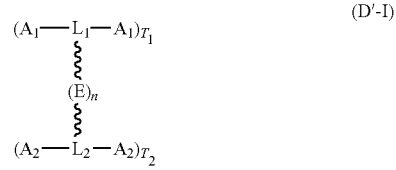

(D'-I)

wherein each $A_1$ is independently selected from any one of formulas (A-III)-(A-V); wherein each $A_2$ is independently selected from any one of formulas (A-I), (A-II), (A-VI), (A-VII), (A-VIII), and (A-IX); each E comprises an Fc domain monomer (e.g., an Fc domain monomer having the sequence of any one of SEQ ID NOs: 1-138), an albumin protein (e.g., an albumin protein having the sequence of any one of SEQ ID NOs: 139-141), an albumin protein-binding peptide, or an Fc-binding peptide; n is 1 or 2; Ti is an integer from 1 to 10 (e.g., $T_1$ is 1, 2, 3, 4, 5, 6, 7, 8, 9, 10); $L_1$ is a linker covalently conjugated to E and to each $A_1$; Ti is an integer from 1 to 10 (e.g., Ti is 1, 2, 3, 4, 5, 6, 7, 8, 9, 10); $L_2$ is a linker covalently conjugated to E and each $A_2$; $T_2$ is an integer from 1 to 10 (e.g., $T_2$ is 1, 2, 3, 4, 5, 6, 7, 8, 9, 10), or a pharmaceutically acceptable salt thereof.

In some embodiments, each $A_1$-L-$A_1$ is conjugated specifically to a lysine residue of E (e.g., the nitrogen atom of a surface exposed lysine residue of E), and each the $A_2$-L-$A_2$ is conjugated specifically to a cysteine residue of E (e.g., the sulfur atom of a surface exposed cysteine residue of E). In some embodiments, each $A_1$-L-$A_1$ moiety is conjugated specifically a cysteine residue of E (e.g., the sulfur atom of a surface exposed cysteine residue of E), and each $A_2$-L-$A_2$ moiety is conjugated specifically to a lysine residue of E (e.g., the nitrogen atom of a surface exposed lysine residue of E).

In another aspect, the invention features a conjugate described by formula (M'-I):

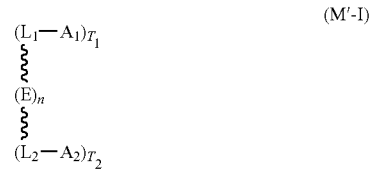

(M'-I)

wherein each $A_1$ is independently selected from any one (M-IX) of formulas (A-III)-(A-V); wherein each $A_2$ is independently selected from any one of formulas (A-I), (A-II), (A-VI), (A-VII), (A-VIII), and (A-IX); each E comprises an Fc domain monomer (e.g., an Fc domain monomer having the sequence of any one of SEQ ID NOs: 1-138), an albumin protein (e.g., an albumin protein having the sequence of any one of SEQ ID NOs: 139-141), an albumin protein-binding peptide, or an Fc-binding peptide; n is 1 or 2; $T_1$ is an integer from 1 to 10 (e.g., $T_1$ is 1, 2, 3, 4, 5, 6, 7, 8, 9, 10); $L_1$ is a linker covalently conjugated to E and $A_1$; $T_1$ is an integer from 1 to 10 (e.g., $T_1$ is 1, 2, 3, 4, 5, 6, 7, 8, 9, 10); $L_2$ is a linker covalently conjugated to E and $A_2$; $T_2$ is an integer from 1 to 10 (e.g., $T_2$ is 1, 2, 3, 4, 5, 6, 7, 8, 9, 10), or a pharmaceutically acceptable salt thereof.

In some embodiments, each $A_1$-L is conjugated specifically to a lysine residue of E (e.g., the nitrogen atom of a surface exposed lysine residue of E), and each the $A_2$-L is conjugated specifically to a cysteine residue of E (e.g., the sulfur atom of a surface exposed cysteine residue of E). In some embodiments, each $A_1$-L moiety is conjugated specifically a cysteine residue of E (e.g., the sulfur atom of a surface exposed cysteine residue of E), and each $A_2$-L moiety is conjugated specifically to a lysine residue of E (e.g., the nitrogen atom of a surface exposed lysine residue of E).

In another aspect, the invention provides a pharmaceutical composition comprising any of the conjugates described herein (e.g., a conjugate of any one of formulas (1)-(5), (D-I)-(D-XI), (D'-I), (M-I)-(M-XI), or (M'-I)), or a pharmaceutically acceptable salt thereof, and a pharmaceutically acceptable excipient.

In another aspect, the invention provides a method for the treatment of a subject having a viral infection or presumed to have a viral infection, the method comprising administering to the subject an effective amount of any of the conjugates or compositions described herein (e.g., a conjugate of any one of formulas (1)-(5), (D-I)-(D-XI), (D'-I), (M-I)-(M-XI), or (M'-I)).

In another aspect, the invention provides a method for the prophylactic treatment of a viral infection in a subject in need thereof, the method comprising administering to the subject an effective amount of any of the conjugates or compositions described herein (e.g., a conjugate of any one of formulas (1)-(5), (D-I)-(D-XI), (D'-I), (M-I)-(M-XI), or (M'-I)).

In some embodiments, the viral infection is caused by influenza virus or parainfluenza virus. In some embodiments, the viral infection is influenza virus A, B, or C, or parainfluenza virus.

In some embodiments, the subject is immunocompromised.

In some embodiments, the subject has been diagnosed with humoral immune deficiency, T cell deficiency, neutropenia, asplenia, or complement deficiency.

In some embodiments, the subject is being treated or is about to be treated with an immunosuppressive therapy.

In some embodiments, the subject has been diagnosed with a disease which causes immunosuppression. In some embodiments, the disease is cancer or acquired immunodeficiency syndrome. In some embodiments, the cancer is leukemia, lymphoma, or multiple myeloma.

In some embodiments, the subject has undergone or is about to undergo hematopoietic stem cell transplantation.

In some embodiments, the subject has undergone or is about to undergo an organ transplant.

In some embodiments, the subject has or is at risk of developing a secondary infection. In some embodiments, the secondary infection is a bacterial infection (e.g., methicillin-resistant *Staphylococcus aureus* (MRSA), *Streptococcus pneumoniae, Pseudomonas aeruginosa*, and/or *Haemophilus influenzae*), a viral infection, or a fungal infection. In particular embodiments, the secondary infection is MRSA. In certain embodiments, the secondary infection is *S. pneumoniae*. In some embodiments, the secondary infection is a respiratory infection (e.g., an infection of the respiratory tract). In some embodiments, the secondary infection is associated with (e.g., causes) pneumonia (e.g., bacterial or viral pneumonia). In some embodiments, the subject has or is at risk of developing pneumonia.

In another aspect, the disclosure features a method of preventing a secondary infection in a subject diagnosed with an influenza infection, wherein the method includes administering to the subject a conjugate or composition described herein. In some embodiments, the method includes administering to the subject conjugate 45 or a pharmaceutical composition including conjugate 45.

In some embodiments, administering a conjugate or composition of the present invention to a subject diagnosed with an influenza infection decreases the likelihood of developing a secondary infection, e.g., by 10%, 20%, 30%, 40%, 50%, 60%, 70%, 80%, 90%, 100%, 200%, 300%, 400%, 500% or more (e.g., as compared to a subject suffering from influenza not treated with the conjugate or composition). For example, administering a conjugate or composition of the present invention to a subject diagnosed with an influenza infection decreases the likelihood of developing a secondary bacterial infection (e.g., MRSA, *Streptococcus pneumoniae, Pseudomonas aeruginosa*, and/or *Haemophilus influenzae*), e.g., by 10%, 20%, 30%, 40%, 50%, 60%, 70%, 80%, 90%, 100%, 200%, 300%, 400%, 500% or more. In some embodiments, the conjugate or composition is administered intramuscularly, intravenously, intradermally, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctival, intravesicularlly, mucosally, intrapericardially, intraumbilically, intraocularally, orally, locally, by inhalation, by injection, or by infusion.

In some embodiments, the subject is treated with a second therapeutic agent. In some embodiments, the second therapeutic agent is an antiviral agent. In some embodiments, the antiviral agent is selected from pimovidir, oseltamivir, zanamivir, peramivir, laninamivir, amantadine, or rimantadine. In particular embodiments, the second therapeutic agent is pimovidir. In some embodiments, the second therapeutic agent is a viral vaccine. In some embodiments, the viral vaccine elicits an immune response in the subject against influenza virus A, B, or C, or parainfluenza virus.

In some embodiments, the conjugate is administered in combination with an antiviral agent, where the antiviral agent is baloxavir. In certain embodiments, the conjugate is described by formula (D-II-6). In other embodiments, the conjugate is described by formula (D-II-7). In certain embodiments, each E includes an Fc domain that has an amino acid sequence at least 95% identical to the sequence of any one of SEQ ID NOs: 63-138. In particular embodiments, each E includes an Fc domain that has an amino acid sequence at least 95% identical to the sequence of any one of SEQ ID NO: 63, SEQ ID NO: 64, SEQ ID NO: 67, SEQ ID NO: 68, SEQ ID NO: 72, SEQ ID NO: 73, SEQ ID NO: 76, SEQ ID NO: 77, SEQ ID NO: 81, SEQ ID NO: 82, SEQ ID NO: 85, or SEQ ID NO: 86. In particular embodiments, each E includes an Fc domain that has the amino acid sequence of any one of SEQ ID NO: 63, SEQ ID NO: 64, SEQ ID NO: 67, SEQ ID NO: 68, SEQ ID NO: 72, SEQ ID NO: 73, SEQ ID NO: 76, SEQ ID NO: 77, SEQ ID NO: 81, SEQ ID NO: 82, SEQ ID NO: 85, or SEQ ID NO: 86. In preferred embodiments, the conjugate is conjugate 45 (e.g., conjugate 45a or 45b) or conjugate 46.

In certain embodiments, the conjugate and baloxavir are administered sequentially. In other embodiments, the conjugate and baloxavir are administered simultaneously.

In one aspect, the disclosure provides a method for treating or preventing a viral infection in subject by administering to the subject: a) an effective amount of a conjugate or composition of any one of claims 1-215; and b) a second therapeutic agent. In certain embodiments, the conjugate is administered to the subject after the subject has a viral infection, is presumed to have a viral infection, or has been exposed to a virus. In some embodiments, the conjugate is administered to the subject prophylactically. In certain embodiments, the second therapeutic agent is administered to the subject after the subject has a viral infection, is presumed to have a viral infection, or has been exposed to the virus. In some embodiments, the second therapeutic agent is administered to the subject prophylactically. In some embodiments, the second therapeutic agent is administered within 30 days, within 14 days, within 7 days, within 2 days, or within 24 hours days of the conjugate. In particular embodiments, the second therapeutic agent is administered within 2 days of the conjugate. In certain embodiments, the second therapeutic agent is an antiviral agent (e.g., pimovidir, oseltamivir, zanamivir, peramivir, laninamivir, amantadine, baloxavir marboxil, baloxavir acid, rimantadine, or a pharmaceutically acceptable salt thereof). In particular embodiments, the antiviral agent is baloxavir marboxil, baloxavir acid, or a pharmaceutically acceptable salt thereof. In certain embodiments, the baloxavir marboxil is administered in an amount between 20 mg and 90 mg (e.g., between 25 mg and 50 mg, between 45 mg and 70 mg, or between 65 and 90 mg). In some embodiments, the baloxavir marboxil is administered orally. In certain embodiments, the baloxavir marboxil is administered as a single dose. In other embodiments, the baloxavir marboxil is administered as more than one dose. In particular embodiments, the baloxavir marboxil is administered in an amount between 20 mg and 40 mg. In other embodiments, the baloxavir marboxil is administered in an amount between 30 and 80 mg. In certain embodiments, conjugate is described by formula (D-II-6). In other embodiments, the conjugate is described by formula (D-II-7). In certain embodiments, each E has a sequence at least 95% identical to the sequence of any one of SEQ ID NOs: 63-138. In particular embodiments, each E includes an Fc domain that has an amino acid sequence at least 95% identical to the sequence of any one of SEQ ID NO: 63, SEQ ID NO: 64, SEQ ID NO: 67, SEQ ID NO: 68, SEQ ID NO: 72, SEQ ID NO: 73, SEQ ID NO: 76, SEQ ID NO: 77, SEQ ID NO: 81, SEQ ID NO: 82, SEQ ID NO: 85, or SEQ ID NO: 86. In particular embodiments, each E includes an Fc domain that has the amino acid sequence of any one of SEQ ID NO: 63, SEQ ID NO: 64, SEQ ID NO: 67, SEQ ID NO: 68, SEQ ID NO: 72, SEQ ID NO: 73, SEQ ID NO: 76, SEQ ID NO: 77, SEQ ID NO: 81, SEQ ID NO: 82, SEQ ID NO: 85, or SEQ ID NO: 86. In certain embodiments, the conjugate is conjugate 45 (e.g., conjugate 45a or conjugate 45b) or conjugate 46. In particular embodiments, the conjugate is administered intramuscularly, intravenously, intradermally, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctival, intravesicularlly, mucosally, intrapericardially, intraumbilically, intraocularally, orally, locally, by inhalation, by injection, or by infusion. In some embodiments, the conjugate is administered intravenously. In some embodiments, the conjugate is administered intramuscularly. In some embodiments, the viral infection is caused by an influenza virus or a parainfluenza virus. In certain embodiments, the virus is influenza virus A, B, or C, or parainfluenza virus.

In some embodiments, an Fc-domain-containing composition may be substituted for an Fc domain and an FC-domain-monomer-containing composition may be substituted for an Fc domain monomer in any one of formulas (1)-(5), (D-I)-(D-XI), (D'-I), (M-I)-(M-XI), or (M'-I) (e.g., any one of formulas (1), (2), (3), (4), (5), (D-I), (D-I-1), (D-II-2), (D-II-3), (D-II-4), (D-II-5), (D-II-6), (D-II-7), (D-II-8), (D-IV-9), (D-II-10), (D-III), (D-II-1), (D-II-2), (D-III-3), (D-III-4), (D-III-5), (D-I-6), (D-III-7), (D-II-8), (D-III-9), (D-IV), (D-IV-1), (D-IV-2), (D-V), (D-V-1), (D-V-2), (D-V-3), (D-V-4), (D-V-5), (D-V-6), (D-V-7), (D-V-8), (D-V-9), (D-V-10), (D-VI), (D-VI-1), (D-VI-2), (D-VI-3), (D-VI-4), (D-VI-5), (D-VI-6), (D-VI-7), (D-VI-8), (D-VI-9), (D-VII), (D-VIII), (D-VIII-1), (D-VIII-2), (D-VIII-3), (D-VIII-4), (D-VIII-5), (D-VIII-6), (D-VIII-7), (D-VIII-8), (D-VIII-9), (D-VIII-10), (D-VIII-11), (D-IX), (D-IX-1), (D-IX-2), (D-X-3), (D-IX-4), (D-IX-5), (D-IX-6), (D-X), (D-X-1), (D-X-2), (D-X-3), (D-XI), (D-XI-1), (D'-I), (M-I), (M-II), (M-II-1), (M-II-2), (M-II-3), (M-II-4), (M-II-5), (M-II-6), (M-II-7), (M-II-8), (M-II-9), (M-II-10), (M-III), (M-III-1), (M-III-2), (M-III-3), (M-III-4), (M-III-5), (M-III-6), (M-III-7), (M-III-8), (M-III-9), (M-IV), (M-IV-1), (M-IV-2), (M-V), (M-V-1), (M-V-2), (M-V-3), (M-V-4), (M-V-5), (M-V-6), (M-V-7), (M-V-8), (M-V-9), (M-V-10), (M-VI), (M-VI-1), (M-VI-2), (M-VI-3), (M-VI-4), (M-VI-5), (M-VI-6), (M-VI-7), (M-VI-8), (M-VI-9), (M-VII), (M-VIII), (M-VIII-1), (M-VIII-2), (M-VIII-3), (M-VIII-4), (M-VIII-5), (M-VIII-6), (M-VIII-7), (M-VIII-8), (M-VIII-9), (M-VIII-10), (M-VIII-11), (M-IX), (M-IX-1), (M-IX-2), (M-IX-3), (M-IX-4), (M-IX-5), (M-IX-6), (M-X), (M-X-1), (M-X-2), (M-X-3), (M-XI), (M-XI-1), or (M'-I)). In any of the formulas described herein (e.g., any one of formulas (1)-(5), (D-I)-(D-XI), (D'-I), (M-I)-(M-XI), or (M'-I)), when n is 1, E is an Fc-domain-monomer-containing composition. In any of the formulas described herein (e.g., any one of formulas (1)-(5), (D-I)-(D-XI), (D'-I), (M-I)-(M-XI), or (M'-I)), when n is 2, E is an Fc-domain-containing composition.

In certain embodiments, the Fc-domain-containing composition is an antibody or an antibody fragment. An antibody may include any form of immunoglobulin, heavy chain antibody, light chain antibody, LRR-based antibody, or other protein scaffold with antibody-like properties, as well as any other immunological binding moiety known in the art, including antibody fragments (e.g., a Fab, Fab', Fab'2, F(ab')2, Fd, Fv, Feb, scFv, or SMIP). The subunit structures and three-dimensional configurations of different classes of antibodies are known in the art. An antibody fragment may include a binding moiety that includes a portion derived from or having significant homology to an antibody, such as the antigen-determining region of an antibody. Exemplary antibody fragments include Fab, Fab', Fab'2, F(ab')2, Fd, Fv, Feb, scFv, and SMIP.

In particular embodiments, the antibody or antibody fragment is a human, mouse, camelid (e.g., llama, alpaca, or camel), goat, sheep, rabbit, chicken, guinea pig, hamster, horse, or rat antibody or antibody fragment. In specific embodiments, the antibody is an IgG, IgA, IgD, IgE, IgM, or intrabody. In certain embodiments, the antibody fragment includes an scFv, sdAb, dAb, Fab, Fab', Fab'2, F(ab)2, Fd, Fv, Feb, or SMIP.

In some embodiments, the Fc-domain-containing composition (e.g., an antibody or antibody fragment) confers binding specificity to a one or more targets (e.g., an antigen).

In some embodiments, the one or more targets (e.g., an antigen) bound by the Fc-domain-containing composition (e.g., an antibody or antibody fragment) is a viral (e.g., influenza) protein such as neuraminidase or hemagglutinin. In some embodiments, the antibody or antibody fragment recognizes a viral surface antigen. In some embodiments, the antibody or antibody fragment targets hemagglutinin. Hemagglutinin-targeting antibodies include monoclonal antibodies, such as CR6261, CR8020, MED18852, MHAA4549A, and VIS410. In some embodiments, the antibody or antibody fragment is a broadly neutralizing antibody or antibody fragment targeting influenza hemagglutinin (e.g., an antibody or antibody fragment described in Wu et al., J. Mol. Biol. 429:2694-2709 (2017)). In some embodiments the antibody or antibody fragment targets a viral matrix protein (e.g., matrix 2 protein). TCN032 is a matrix 2 protein targeting monoclonal antibody.

In some embodiments, the Fc-domain-containing composition (e.g., an antibody or antibody fragment) includes one or more single-domain antibodies (sdAbs). In some embodiments the Fc-domain-containing composition is an antibody or antibody fragment including a sdAb with influenza A reactivity, such as a sdAb that binds to hemagglutinin of influenza A (e.g., SD38 or SD38, described in Laursen et al. Science. 362:598-602 (2018)). In some embodiments the Fc-domain-containing composition is an antibody or antibody fragment including a sdAb with influenza B reactivity, such as a sdAb that binds to hemagglutinin of influenza B (e.g., SD83 or SD84, described in Laursen et al. Science. 362:598-802 (2018)).

In some embodiments the Fc-domain-containing composition is a multidomain antibody (MDAb) or multidomain antibody fragment including 2 or more (e.g., 2, 3, 4, 5, 6, 7, 8, 9 or 10 or more) sdAbs. In some embodiments, the MDAb or fragment thereof includes one or more sdABs that binds to hemagglutinin of influenza A, and one or more sdAbs that binds to hemagglutinin of influenza B. In some embodiments, the MDAb is JNJ-7445 (also known as MD3806), which is described in Laursen et al. Science. 362:598-802 (2018). In brief, JNJ-7445 is an MDAb that includes two sdAbs that bind to hemagglutinin of influenza A (SD36 and SD38) and two sdAbs that bind to hemagglutinin of influenza B (SD83 and SD84), which are linked to an Fc domain (IgG1). The sdAbs were produced by immunizing llamas with influenza vaccine and H7 and H2 recombinant hemagglutinin.

In another aspect, the invention includes a conjugate described by any one of formulas (1)-(5), (D-I)-(D-XI), (D'-I), (M-I)-(M-XI), or (M'-I) (e.g., any one of formulas (1), (2), (3), (4), (5), (D-I), (D-II), (D-II-1), (D-II-2), (D-II-3), (D-II-4), (D-II-5), (D-II-6), (D-II-7), (D-II-8), (D-II-9), (D-II-10), (D-III), (D-III-1), (D-III-2), (D-III-3), (D-III-4), (D-III-5), (D-III-6), (D-III-7), (D-III-8), (D-III-9), (D-IV), (D-IV-1), (D-IV-2), (D-V), (D-V-1), (D-V-2), (D-V-3), (D-V-4), (D-V-5), (D-V-6), (D-V-7), (D-V-8), (D-V-9), (D-V-10), (D-VI), (D-VI-1), (D-VI-2), (D-VI-3), (D-VI-4), (D-VI-5), (D-VI-6), (D-VI-7), (D-VI-8), (D-VI-9), (D-VII), (D-VIII), (D-VIII-1), (D-VIII-2), (D-VIII-3), (D-VIII-4), (D-VIII-5), (D-VIII-6), (D-VIII-7), (D-VIII-8), (D-VIII-9), (D-VIII-10), (D-VIII-11), (D-IX), (D-IX-1), (D-IX-2), (D-IX-3), (D-IX-4), (D-IX-5), (D-IX-6), (D-X), (D-X-1), (D-X-2), (D-X-3), (D-XI), (D-XI-1), (D'-1), (M-I), (M-V), (M-V-1), (M-II-2), (M-V-3), (M-V-4), (M-V-5), (M-V-6), (M-V-7), (M-V-8), (M-M-II-10), (M-III), (M-III-1), (M-III-2), (M-III-3), (M-III-4), (M-III-5), (M-III-6), (M-III-7), (M-III-8), (M-III-9), (M-IV), (M-IV-1), (M-IV-2), (M-V), (M-V-1), (M-V-2), (M-V-3), (M-V-4), (M-V-5), (M-V-6), (M-V-7), (M-V-8), (M-V-9), (M-V-10), (M-VI), (M-VI-1), (M-VI-2), (M-VI-3), (M-VI-4), (M-VI-5), (M-VI-6), (M-VI-7), (M-VI-8), (M-VI-9), (M-VII), (M-VIII), (M-VIII-1), (M-VIII-2), (M-VIII-3), (M-VIII-4), (M-VIII-5), (M-VIII-6), (M-VII-7), (M-VIII-8), (M-VIII-9), (M-VIII-10), (M-VIII-11), (M-IX), (M-IX-1), (M-IX-2), (M-IX-3), (M-IX-4), (M-IX-5), (M-IX-6), (M-X), (M-X-1), (M-X-2), (M-X-3), or (M'-I)), where E is an antibody or antibody fragment. In preferred embodiments, where E is an antibody or antibody fragment, n is 1. In some embodiments, the antibody or antibody fragment includes any antibody or antibody fragment described herein, such as a monoclonal antibody that binds to viral hemagglutinin (e.g., CR6261, CR8020, MED18852, MHAA4549A, or VIS410); a broadly neutralizing antibody or antibody fragment targeting viral hemagglutinin (e.g., antibodies or antibody fragments described in Wu et al., J. Mol. Biol. 429:2694-2709 (2017)); a sdAb targeting viral hemagglutinin (e.g., SD36, SD38, SD83, or SD84); or a MDAb or fragment thereof targeting viral hemagglutinin (e.g., JNJ-7445).

In some embodiments of any of the aspects described herein. E (e.g., each E) includes the amino acid sequence of SEQ ID NO: 1. In some embodiments, E includes an amino acid sequence that is at least 70%, 75%, 80%. 85%, 90%, 95%. 96%, 97%, 98%. 99%, or 100% identical to the amino acid sequence of SEQ ID NO: 1.

In some embodiments of any of the aspects described herein. E (e.g., each E) includes the amino acid sequence of SEQ ID NO: 2. In some embodiments, E includes an amino acid sequence that is at least 70%, 75%, 80%. 85%, 90%, 95%. 96%, 97%, 98%. 99%, or 100% identical to the amino acid sequence of SEQ ID NO: 2.

In some embodiments of any of the aspects described herein. E (e.g., each E) includes the amino acid sequence of SEQ ID NO: 3. In some embodiments, E includes an amino acid sequence that is at least 70%, 75%, 80%, 85%, 90%, 95%, 96%, 97%, 98%, 99%, or 100% identical to the amino acid sequence of SEQ ID NO: 3.

In some embodiments of any of the aspects described herein, E (e.g., each E) includes the amino acid sequence of SEQ ID NO: 4. In some embodiments, E includes an amino acid sequence that is at least 70%, 75%, 80%, 85%, 90%, 95%, 96%, 97%, 98%, 99%, or 100% identical to the amino acid sequence of SEQ ID NO: 4.

In some embodiments of any of the aspects described herein, E (e.g., each E) includes the amino acid sequence of SEQ ID NO: 5. In some embodiments, E includes an amino acid sequence that is at least 70%, 75%, 80%, 85%, 90%, 95%, 96%, 97%, 98%, 99%, or 100% identical to the amino acid sequence of SEQ ID NO: 5.

In some embodiments of any of the aspects described herein, E (e.g., each E) includes the amino acid sequence of SEQ ID NO: 6. In some embodiments, E includes an amino acid sequence that is at least 70%, 75%, 80%, 85%, 90%, 95%, 96%, 97%, 98%, 99%, or 100% identical to the amino acid sequence of SEQ ID NO: 6.

In some embodiments of any of the aspects described herein, E (e.g., each E) includes the amino acid sequence of SEQ ID NO: 7. In some embodiments, E includes an amino acid sequence that is at least 70%, 75%, 80%, 85%, 90%, 95%, 96%, 97%, 98%, 99%, or 100% identical to the amino acid sequence of SEQ ID NO: 7.

In some embodiments of any of the aspects described herein, E (e.g., each E) includes the amino acid sequence of SEQ ID NO: 8. In some embodiments, E includes an amino acid sequence that is at least 70%, 75%, 80%, 85%, 90%, 95%, 96%, 97%, 98%, 99%, or 100% identical to the amino acid sequence of SEQ ID NO: 8.

In some embodiments of any of the aspects described herein, E (e.g., each E) includes the amino acid sequence of SEQ ID NO: 9. In some embodiments, E includes an amino acid sequence that is at least 70%, 75%, 80%, 85%, 90%, 95%, 96%, 97%, 98%, 99%, or 100% identical to the amino acid sequence of SEQ ID NO: 9.

In some embodiments of any of the aspects described herein, E (e.g., each E) includes the amino acid sequence of SEQ ID NO: 10. In some embodiments, E includes an amino acid sequence that is at least 70%, 75%, 80%, 85%, 90%, 95%, 96%, 97%, 98%, 99%, or 100% identical to the amino acid sequence of SEQ ID NO: 10.

In some embodiments of any of the aspects described herein, E (e.g., each E) includes the amino acid sequence of SEQ ID NO: 11. In some embodiments, E includes an amino acid sequence that is at least 70%, 75%, 80%. 85%, 90%, 95%. 96%, 97%, 98%. 99%, or 100% identical to the amino acid sequence of SEQ ID NO: 11.

In some embodiments of any of the aspects described herein. E (e.g., each E) includes the amino acid sequence of SEQ ID NO: 12. In some embodiments, E includes an amino acid sequence that is at least 70%, 75%, 80%. 85%, 90%, 95%. 96%, 97%, 98%. 99%, or 100% identical to the amino acid sequence of SEQ ID NO: 12.

In some embodiments of any of the aspects described herein. E (e.g., each E) includes the amino acid sequence of SEQ ID NO: 13. In some embodiments, E includes an amino acid sequence that is at least 70%, 75%, 80%, 85%, 90%, 95%, 96%, 97%, 98%, 99%, or 100% identical to the amino acid sequence of SEQ ID NO: 13.

In some embodiments of any of the aspects described herein, E (e.g., each E) includes the amino acid sequence of SEQ ID NO: 14. In some embodiments, E includes an amino acid sequence that is at least 70%, 75%, 80%, 85%, 90%, 95%, 96%, 97%, 98%, 99%, or 100% identical to the amino acid sequence of SEQ ID NO: 14.

In some embodiments of any of the aspects described herein, E (e.g., each E) includes the amino acid sequence of SEQ ID NO: 15. In some embodiments. E includes an amino acid sequence that is at least 70%, 75%, 80%, 85%, 90%, 95%, 96%, 97%, 98%, 99%, or 100% identical to the amino acid sequence of SEQ ID NO: 15.

In some embodiments of any of the aspects described herein, E (e.g., each E) includes the amino acid sequence of SEQ ID NO: 16. In some embodiments, E includes an amino acid sequence that is at least 70%, 75%, 80%, 85%, 90%, 95%, 96%, 97%, 98%, 99%, or 100% identical to the amino acid sequence of SEQ ID NO: 16.

In some embodiments of any of the aspects described herein, E (e.g., each E) includes the amino acid sequence of SEQ ID NO: 17. In some embodiments, E includes an amino acid sequence that is at least 70%, 75%, 80%, 85%, 90%, 95%, 96%, 97%, 98%, 99%, or 100% identical to the amino acid sequence of SEQ ID NO: 17.

In some embodiments of any of the aspects described herein, E (e.g., each E) includes the amino acid sequence of SEQ ID NO: 18. In some embodiments, E includes an amino acid sequence that is at least 70%, 75%, 80%, 85%, 90%, 95%, 96%, 97%, 98%, 99%, or 100% identical to the amino acid sequence of SEQ ID NO: 18.

In some embodiments of any of the aspects described herein, E (e.g., each E) includes the amino acid sequence of SEQ ID NO: 19. In some embodiments, E includes an amino acid sequence that is at least 70%, 75%, 80%, 85%, 90%, 95%, 96%, 97%, 98%, 99%, or 100% identical to the amino acid sequence of SEQ ID NO: 19.

In some embodiments of any of the aspects described herein, E (e.g., each E) includes the amino acid sequence of SEQ ID NO: 20. In some embodiments, E includes an amino acid sequence that is at least 70%, 75%, 80%, 85%, 90%, 95%, 96%, 97%, 98%, 99%, or 100% identical to the amino acid sequence of SEQ ID NO: 20.

In some embodiments of any of the aspects described herein, E (e.g., each E) includes the amino acid sequence of SEQ ID NO: 21. In some embodiments, E includes an amino acid sequence that is at least 70%, 75%, 80%. 85%, 90%, 95%. 96%, 97%, 98%. 99%, or 100% identical to the amino acid sequence of SEQ ID NO: 21.

In some embodiments of any of the aspects described herein. E (e.g., each E) includes the amino acid sequence of SEQ ID NO: 22. In some embodiments, E includes an amino acid sequence that is at least 70%, 75%, 80%. 85%, 90%, 95%. 96%, 97%, 98%. 99%, or 100% identical to the amino acid sequence of SEQ ID NO: 22.

In some embodiments of any of the aspects described herein. E (e.g., each E) includes the amino acid sequence of SEQ ID NO: 23. In some embodiments, E includes an amino acid sequence that is at least 70%, 75%, 80%, 85%, 90%, 95%, 96%, 97%, 98%, 99%, or 100% identical to the amino acid sequence of SEQ ID NO: 23.

In some embodiments of any of the aspects described herein, E (e.g., each E) includes the amino acid sequence of SEQ ID NO: 24. In some embodiments, E includes an amino acid sequence that is at least 70%, 75%, 80%, 85%, 90%, 95%, 96%, 97%, 98%, 99%, or 100% identical to the amino acid sequence of SEQ ID NO: 24.

In some embodiments of any of the aspects described herein, E (e.g., each E) includes the amino acid sequence of SEQ ID NO: 25. In some embodiments. E includes an amino acid sequence that is at least 70%, 75%, 80%, 85%, 90%, 95%, 96%, 97%, 98%, 99%, or 100% identical to the amino acid sequence of SEQ ID NO: 25.

In some embodiments of any of the aspects described herein, E (e.g., each E) includes the amino acid sequence of SEQ ID NO: 26. In some embodiments, E includes an amino acid sequence that is at least 70%, 75%, 80%, 85%, 90%, 95%, 96%, 97%, 98%, 99%, or 100% identical to the amino acid sequence of SEQ ID NO: 26.

In some embodiments of any of the aspects described herein, E (e.g., each E) includes the amino acid sequence of SEQ ID NO: 27. In some embodiments, E includes an amino acid sequence that is at least 70%, 75%, 80%, 85%, 90%, 95%, 96%, 97%, 98%, 99%, or 100% identical to the amino acid sequence of SEQ ID NO: 27.

In some embodiments of any of the aspects described herein, E (e.g., each E) includes the amino acid sequence of SEQ ID NO: 28. In some embodiments, E includes an amino acid sequence that is at least 70%, 75%, 80%, 85%, 90%, 95%, 96%, 97%, 98%, 99%, or 100% identical to the amino acid sequence of SEQ ID NO: 28.

In some embodiments of any of the aspects described herein, E (e.g., each E) includes the amino acid sequence of SEQ ID NO: 29. In some embodiments, E includes an amino acid sequence that is at least 70%, 75%, 80%, 85%, 90%, 95%, 96%, 97%, 98%, 99%, or 100% identical to the amino acid sequence of SEQ ID NO: 29.

In some embodiments of any of the aspects described herein, E (e.g., each E) includes the amino acid sequence of SEQ ID NO: 30. In some embodiments, E includes an amino acid sequence that is at least 70%, 75%, 80%, 85%, 90%, 95%, 96%, 97%, 98%, 99%, or 100% identical to the amino acid sequence of SEQ ID NO: 30.

In some embodiments of any of the aspects described herein, E (e.g., each E) includes the amino acid sequence of SEQ ID NO: 31. In some embodiments, E includes an amino acid sequence that is at least 70%, 75%, 80%. 85%, 90%, 95%. 96%, 97%, 98%. 99%, or 100% identical to the amino acid sequence of SEQ ID NO: 31.

In some embodiments of any of the aspects described herein. E (e.g., each E) includes the amino acid sequence of SEQ ID NO: 32. In some embodiments, E includes an amino acid sequence that is at least 70%, 75%, 80%. 85%, 90%, 95%. 96%, 97%, 98%. 99%, or 100% identical to the amino acid sequence of SEQ ID NO: 32.

In some embodiments of any of the aspects described herein. E (e.g., each E) includes the amino acid sequence of SEQ ID NO: 33. In some embodiments, E includes an amino acid sequence that is at least 70%, 75%, 80%, 85%, 90%, 95%, 96%, 97%, 98%, 99%, or 100% identical to the amino acid sequence of SEQ ID NO: 33.

In some embodiments of any of the aspects described herein, E (e.g., each E) includes the amino acid sequence of SEQ ID NO: 34. In some embodiments, E includes an amino acid sequence that is at least 70%, 75%, 80%, 85%, 90%, 95%, 96%, 97%, 98%, 99%, or 100% identical to the amino acid sequence of SEQ ID NO: 34.

In some embodiments of any of the aspects described herein, E (e.g., each E) includes the amino acid sequence of SEQ ID NO: 35. In some embodiments. E includes an amino acid sequence that is at least 70%, 75%, 80%, 85%, 90%, 95%, 96%, 97%, 98%, 99%, or 100% identical to the amino acid sequence of SEQ ID NO: 35.

In some embodiments of any of the aspects described herein, E (e.g., each E) includes the amino acid sequence of SEQ ID NO: 36. In some embodiments, E includes an amino acid sequence that is at least 70%, 75%, 80%, 85%, 90%, 95%, 96%, 97%, 98%, 99%, or 100% identical to the amino acid sequence of SEQ ID NO: 36.

In some embodiments of any of the aspects described herein, E (e.g., each E) includes the amino acid sequence of SEQ ID NO: 37. In some embodiments, E includes an amino acid sequence that is at least 70%, 75%, 80%, 85%, 90%, 95%, 96%, 97%, 98%, 99%, or 100% identical to the amino acid sequence of SEQ ID NO: 37.

In some embodiments of any of the aspects described herein, E (e.g., each E) includes the amino acid sequence of SEQ ID NO: 38. In some embodiments, E includes an amino acid sequence that is at least 70%, 75%, 80%, 85%, 90%, 95%, 96%, 97%, 98%, 99%, or 100% identical to the amino acid sequence of SEQ ID NO: 38.

In some embodiments of any of the aspects described herein, E (e.g., each E) includes the amino acid sequence of SEQ ID NO: 39. In some embodiments, E includes an amino acid sequence that is at least 70%, 75%, 80%, 85%, 90%, 95%, 96%, 97%, 98%, 99%, or 100% identical to the amino acid sequence of SEQ ID NO: 39.

In some embodiments of any of the aspects described herein, E (e.g., each E) includes the amino acid sequence of SEQ ID NO: 40. In some embodiments, E includes an amino acid sequence that is at least 70%, 75%, 80%, 85%, 90%, 95%, 96%, 97%, 98%, 99%, or 100% identical to the amino acid sequence of SEQ ID NO: 40.

In some embodiments of any of the aspects described herein, E (e.g., each E) includes the amino acid sequence of SEQ ID NO: 41. In some embodiments, E includes an amino acid sequence that is at least 70%, 75%, 80%. 85%, 90%, 95%. 96%, 97%, 98%. 99%, or 100% identical to the amino acid sequence of SEQ ID NO: 41.

In some embodiments of any of the aspects described herein. E (e.g., each E) includes the amino acid sequence of SEQ ID NO: 42. In some embodiments, E includes an amino acid sequence that is at least 70%, 75%, 80%. 85%, 90%, 95%. 96%, 97%, 98%. 99%, or 100% identical to the amino acid sequence of SEQ ID NO: 42.

In some embodiments of any of the aspects described herein. E (e.g., each E) includes the amino acid sequence of SEQ ID NO: 43. In some embodiments, E includes an amino acid sequence that is at least 70%, 75%, 80%, 85%, 90%, 95%, 96%, 97%, 98%, 99%, or 100% identical to the amino acid sequence of SEQ ID NO: 43.

In some embodiments of any of the aspects described herein, E (e.g., each E) includes the amino acid sequence of SEQ ID NO: 44. In some embodiments, E includes an amino acid sequence that is at least 70%, 75%, 80%, 85%, 90%, 95%, 96%, 97%, 98%, 99%, or 100% identical to the amino acid sequence of SEQ ID NO: 45.

In some embodiments of any of the aspects described herein, E (e.g., each E) includes the amino acid sequence of SEQ ID NO: 46. In some embodiments. E includes an amino acid sequence that is at least 70%, 75%, 80%, 85%, 90%, 95%, 96%, 97%, 98%, 99%, or 100% identical to the amino acid sequence of SEQ ID NO: 46.

In some embodiments of any of the aspects described herein, E (e.g., each E) includes the amino acid sequence of SEQ ID NO: 47. In some embodiments, E includes an amino acid sequence that is at least 70%, 75%, 80%, 85%, 90%, 95%, 96%, 97%, 98%, 99%, or 100% identical to the amino acid sequence of SEQ ID NO: 47.

In some embodiments of any of the aspects described herein, E (e.g., each E) includes the amino acid sequence of SEQ ID NO: 48. In some embodiments, E includes an amino acid sequence that is at least 70%, 75%, 80%, 85%, 90%, 95%, 96%, 97%, 98%, 99%, or 100% identical to the amino acid sequence of SEQ ID NO: 48.

In some embodiments of any of the aspects described herein, E (e.g., each E) includes the amino acid sequence of SEQ ID NO: 49. In some embodiments, E includes an amino acid sequence that is at least 70%, 75%, 80%, 85%, 90%, 95%, 96%, 97%, 98%, 99%, or 100% identical to the amino acid sequence of SEQ ID NO: 49.

In some embodiments of any of the aspects described herein, E (e.g., each E) includes the amino acid sequence of SEQ ID NO: 50. In some embodiments, E includes an amino acid sequence that is at least 70%, 75%, 80%, 85%, 90%, 95%, 96%, 97%, 98%, 99%, or 100% identical to the amino acid sequence of SEQ ID NO: 50.

In some embodiments of any of the aspects described herein, E (e.g., each E) includes the amino acid sequence of SEQ ID NO: 51. In some embodiments, E includes an amino acid sequence that is at least 70%, 75%, 80%, 85%, 90%, 95%, 96%, 97%, 98%, 99%, or 100% identical to the amino acid sequence of SEQ ID NO: 51.

In some embodiments of any of the aspects described herein, E (e.g., each E) includes the amino acid sequence of SEQ ID NO: 52. In some embodiments, E includes an amino acid sequence that is at least 70%, 75%, 80%. 85%, 90%, 95%. 96%, 97%, 98%. 99%, or 100% identical to the amino acid sequence of SEQ ID NO: 52.

In some embodiments of any of the aspects described herein. E (e.g., each E) includes the amino acid sequence of SEQ ID NO: 53. In some embodiments, E includes an amino acid sequence that is at least 70%, 75%, 80%. 85%, 90%, 95%. 96%, 97%, 98%. 99%, or 100% identical to the amino acid sequence of SEQ ID NO: 53.

In some embodiments of any of the aspects described herein. E (e.g., each E) includes the amino acid sequence of SEQ ID NO: 54. In some embodiments, E includes an amino acid sequence that is at least 70%, 75%, 80%, 85%, 90%, 95%, 96%, 97%, 98%, 99%, or 100% identical to the amino acid sequence of SEQ ID NO: 54.

In some embodiments of any of the aspects described herein, E (e.g., each E) includes the amino acid sequence of SEQ ID NO: 55. In some embodiments, E includes an amino acid sequence that is at least 70%, 75%, 80%, 85%, 90%, 95%, 96%, 97%, 98%, 99%, or 100% identical to the amino acid sequence of SEQ ID NO: 55.

In some embodiments of any of the aspects described herein, E (e.g., each E) includes the amino acid sequence of SEQ ID NO: 56. In some embodiments. E includes an amino acid sequence that is at least 70%, 75%, 80%, 85%, 90%, 95%, 96%, 97%, 98%, 99%, or 100% identical to the amino acid sequence of SEQ ID NO: 56.

In some embodiments of any of the aspects described herein, E (e.g., each E) includes the amino acid sequence of SEQ ID NO: 57. In some embodiments, E includes an amino acid sequence that is at least 70%, 75%, 80%, 85%, 90%, 95%, 96%, 97%, 98%, 99%, or 100% identical to the amino acid sequence of SEQ ID NO: 57.

In some embodiments of any of the aspects described herein, E (e.g., each E) includes the amino acid sequence of SEQ ID NO: 58. In some embodiments, E includes an amino acid sequence that is at least 70%, 75%, 80%, 85%, 90%, 95%, 96%, 97%, 98%, 99%, or 100% identical to the amino acid sequence of SEQ ID NO: 58.

In some embodiments of any of the aspects described herein, E (e.g., each E) includes the amino acid sequence of SEQ ID NO: 59. In some embodiments, E includes an amino acid sequence that is at least 70%, 75%, 80%, 85%, 90%, 95%, 96%, 97%, 98%, 99%, or 100% identical to the amino acid sequence of SEQ ID NO: 59.

In some embodiments of any of the aspects described herein, E (e.g., each E) includes the amino acid sequence of SEQ ID NO: 60. In some embodiments, E includes an amino acid sequence that is at least 70%, 75%, 80%, 85%, 90%, 95%, 96%, 97%, 98%, 99%, or 100% identical to the amino acid sequence of SEQ ID NO: 60.

In some embodiments of any of the aspects described herein, E (e.g., each E) includes the amino acid sequence of SEQ ID NO: 61. In some embodiments, E includes an amino acid sequence that is at least 70%, 75%, 80%, 85%, 90%, 95%, 96%, 97%, 98%, 99%, or 100% identical to the amino acid sequence of SEQ ID NO: 61.

In some embodiments of any of the aspects described herein, E (e.g., each E) includes the amino acid sequence of SEQ ID NO: 62. In some embodiments, E includes an amino acid sequence that is at least 70%, 75%, 80%. 85%, 90%, 95%. 96%, 97%, 98%. 99%, or 100% identical to the amino acid sequence of SEQ ID NO: 62.

In some embodiments of any of the aspects described herein. E (e.g., each E) includes the amino acid sequence of SEQ ID NO: 63. In some embodiments, E includes an amino acid sequence that is at least 70%, 75%, 80%. 85%, 90%, 95%. 96%, 97%, 98%. 99%, or 100% identical to the amino acid sequence of SEQ ID NO: 63.

In some embodiments of any of the aspects described herein. E (e.g., each E) includes the amino acid sequence of SEQ ID NO: 64. In some embodiments, E includes an amino acid sequence that is at least 70%, 75%, 80%, 85%, 90%, 95%, 96%, 97%, 98%, 99%, or 100% identical to the amino acid sequence of SEQ ID NO: 64.

In some embodiments of any of the aspects described herein, E (e.g., each E) includes the amino acid sequence of SEQ ID NO: 65. In some embodiments, E includes an amino acid sequence that is at least 70%, 75%, 80%, 85%, 90%, 95%, 96%, 97%, 98%, 99%, or 100% identical to the amino acid sequence of SEQ ID NO: 65.

In some embodiments of any of the aspects described herein, E (e.g., each E) includes the amino acid sequence of SEQ ID NO: 66. In some embodiments. E includes an amino acid sequence that is at least 70%, 75%, 80%, 85%, 90%, 95%, 96%, 97%, 98%, 99%, or 100% identical to the amino acid sequence of SEQ ID NO: 66.

In some embodiments of any of the aspects described herein, E (e.g., each E) includes the amino acid sequence of SEQ ID NO: 67. In some embodiments, E includes an amino acid sequence that is at least 70%, 75%, 80%, 85%, 90%, 95%, 96%, 97%, 98%, 99%, or 100% identical to the amino acid sequence of SEQ ID NO: 67.

In some embodiments of any of the aspects described herein, E (e.g., each E) includes the amino acid sequence of SEQ ID NO: 68. In some embodiments, E includes an amino acid sequence that is at least 70%, 75%, 80%, 85%, 90%, 95%, 96%, 97%, 98%, 99%, or 100% identical to the amino acid sequence of SEQ ID NO: 68.

In some embodiments of any of the aspects described herein, E (e.g., each E) includes the amino acid sequence of SEQ ID NO: 69. In some embodiments, E includes an amino acid sequence that is at least 70%, 75%, 80%, 85%, 90%, 95%, 96%, 97%, 98%, 99%, or 100% identical to the amino acid sequence of SEQ ID NO: 69.

In some embodiments of any of the aspects described herein, E (e.g., each E) includes the amino acid sequence of SEQ ID NO: 70. In some embodiments, E includes an amino acid sequence that is at least 70%, 75%, 80%, 85%, 90%, 95%, 96%, 97%, 98%, 99%, or 100% identical to the amino acid sequence of SEQ ID NO: 70.

In some embodiments of any of the aspects described herein, E (e.g., each E) includes the amino acid sequence of SEQ ID NO: 71. In some embodiments, E includes an amino acid sequence that is at least 70%, 75%, 80%, 85%, 90%, 95%, 96%, 97%, 98%, 99%, or 100% identical to the amino acid sequence of SEQ ID NO: 71.

In some embodiments of any of the aspects described herein, E (e.g., each E) includes the amino acid sequence of SEQ ID NO: 72. In some embodiments, E includes an amino acid sequence that is at least 70%, 75%, 80%. 85%, 90%, 95%. 96%, 97%, 98%. 99%, or 100% identical to the amino acid sequence of SEQ ID NO: 72.

In some embodiments of any of the aspects described herein. E (e.g., each E) includes the amino acid sequence of SEQ ID NO: 73. In some embodiments, E includes an amino acid sequence that is at least 70%, 75%, 80%. 85%, 90%, 95%. 96%, 97%, 98%. 99%, or 100% identical to the amino acid sequence of SEQ ID NO: 73.

In some embodiments of any of the aspects described herein. E (e.g., each E) includes the amino acid sequence of SEQ ID NO: 74. In some embodiments, E includes an amino acid sequence that is at least 70%, 75%, 80%, 85%, 90%, 95%, 96%, 97%, 98%, 99%, or 100% identical to the amino acid sequence of SEQ ID NO: 74.

In some embodiments of any of the aspects described herein, E (e.g., each E) includes the amino acid sequence of SEQ ID NO: 75. In some embodiments, E includes an amino acid sequence that is at least 70%, 75%, 80%, 85%, 90%, 95%, 96%, 97%, 98%, 99%, or 100% identical to the amino acid sequence of SEQ ID NO: 75.

In some embodiments of any of the aspects described herein, E (e.g., each E) includes the amino acid sequence of SEQ ID NO: 76. In some embodiments. E includes an amino acid sequence that is at least 70%, 75%, 80%, 85%, 90%, 95%, 96%, 97%, 98%, 99%, or 100% identical to the amino acid sequence of SEQ ID NO: 76.

In some embodiments of any of the aspects described herein, E (e.g., each E) includes the amino acid sequence of SEQ ID NO: 77. In some embodiments, E includes an amino acid sequence that is at least 70%, 75%, 80%, 85%, 90%, 95%, 96%, 97%, 98%, 99%, or 100% identical to the amino acid sequence of SEQ ID NO: 77.

In some embodiments of any of the aspects described herein, E (e.g., each E) includes the amino acid sequence of SEQ ID NO: 78. In some embodiments, E includes an amino acid sequence that is at least 70%, 75%, 80%, 85%, 90%, 95%, 96%, 97%, 98%, 99%, or 100% identical to the amino acid sequence of SEQ ID NO: 78.

In some embodiments of any of the aspects described herein, E (e.g., each E) includes the amino acid sequence of SEQ ID NO: 79. In some embodiments, E includes an amino acid sequence that is at least 70%, 75%, 80%, 85%, 90%, 95%, 96%, 97%, 98%, 99%, or 100% identical to the amino acid sequence of SEQ ID NO: 79.

In some embodiments of any of the aspects described herein, E (e.g., each E) includes the amino acid sequence of SEQ ID NO: 80. In some embodiments, E includes an amino acid sequence that is at least 70%, 75%, 80%, 85%, 90%, 95%, 96%, 97%, 98%, 99%, or 100% identical to the amino acid sequence of SEQ ID NO: 80.

In some embodiments of any of the aspects described herein, E (e.g., each E) includes the amino acid sequence of SEQ ID NO: 81. In some embodiments, E includes an amino acid sequence that is at least 70%, 75%, 80%, 85%, 90%, 95%, 96%, 97%, 98%, 99%, or 100% identical to the amino acid sequence of SEQ ID NO: 81.

In some embodiments of any of the aspects described herein, E (e.g., each E) includes the amino acid sequence of SEQ ID NO: 82. In some embodiments, E includes an amino acid sequence that is at least 70%, 75%, 80%. 85%, 90%, 95%. 96%, 97%, 98%. 99%, or 100% identical to the amino acid sequence of SEQ ID NO: 82.

In some embodiments of any of the aspects described herein. E (e.g., each E) includes the amino acid sequence of SEQ ID NO: 83. In some embodiments, E includes an amino acid sequence that is at least 70%, 75%, 80%. 85%, 90%, 95%. 96%, 97%, 98%. 99%, or 100% identical to the amino acid sequence of SEQ ID NO: 83.

In some embodiments of any of the aspects described herein. E (e.g., each E) includes the amino acid sequence of SEQ ID NO: 84. In some embodiments, E includes an amino acid sequence that is at least 70%, 75%, 80%, 85%, 90%, 95%, 96%, 97%, 98%, 99%, or 100% identical to the amino acid sequence of SEQ ID NO: 84.

In some embodiments of any of the aspects described herein, E (e.g., each E) includes the amino acid sequence of SEQ ID NO: 85. In some embodiments, E includes an amino acid sequence that is at least 70%, 75%, 80%, 85%, 90%, 95%, 96%, 97%, 98%, 99%, or 100% identical to the amino acid sequence of SEQ ID NO: 85.

In some embodiments of any of the aspects described herein, E (e.g., each E) includes the amino acid sequence of SEQ ID NO: 86. In some embodiments. E includes an amino acid sequence that is at least 70%, 75%, 80%, 85%, 90%, 95%, 96%, 97%, 98%, 99%, or 100% identical to the amino acid sequence of SEQ ID NO: 86.

In some embodiments of any of the aspects described herein, E (e.g., each E) includes the amino acid sequence of SEQ ID NO: 87. In some embodiments, E includes an amino acid sequence that is at least 70%, 75%, 80%, 85%, 90%, 95%, 96%, 97%, 98%, 99%, or 100% identical to the amino acid sequence of SEQ ID NO: 87.

In some embodiments of any of the aspects described herein, E (e.g., each E) includes the amino acid sequence of SEQ ID NO: 88. In some embodiments, E includes an amino acid sequence that is at least 70%, 75%, 80%, 85%, 90%, 95%, 96%, 97%, 98%, 99%, or 100% identical to the amino acid sequence of SEQ ID NO: 88.

In some embodiments of any of the aspects described herein, E (e.g., each E) includes the amino acid sequence of SEQ ID NO: 89. In some embodiments, E includes an amino acid sequence that is at least 70%, 75%, 80%, 85%, 90%, 95%, 96%, 97%, 98%, 99%, or 100% identical to the amino acid sequence of SEQ ID NO: 89.

In some embodiments of any of the aspects described herein, E (e.g., each E) includes the amino acid sequence of SEQ ID NO: 90. In some embodiments, E includes an amino acid sequence that is at least 70%, 75%, 80%, 85%, 90%, 95%, 96%, 97%, 98%, 99%, or 100% identical to the amino acid sequence of SEQ ID NO: 90.

In some embodiments of any of the aspects described herein, E (e.g., each E) includes the amino acid sequence of SEQ ID NO: 91. In some embodiments, E includes an amino acid sequence that is at least 70%, 75%, 80%, 85%, 90%, 95%, 96%, 97%, 98%, 99%, or 100% identical to the amino acid sequence of SEQ ID NO: 91.

In some embodiments of any of the aspects described herein, E (e.g., each E) includes the amino acid sequence of SEQ ID NO: 92. In some embodiments, E includes an amino acid sequence that is at least 70%, 75%, 80%. 85%, 90%, 95%. 96%, 97%, 98%. 99%, or 100% identical to the amino acid sequence of SEQ ID NO: 92.

In some embodiments of any of the aspects described herein. E (e.g., each E) includes the amino acid sequence of SEQ ID NO: 93. In some embodiments, E includes an amino acid sequence that is at least 70%, 75%, 80%. 85%, 90%, 95%. 96%, 97%, 98%. 99%, or 100% identical to the amino acid sequence of SEQ ID NO: 93.

In some embodiments of any of the aspects described herein. E (e.g., each E) includes the amino acid sequence of SEQ ID NO: 94. In some embodiments, E includes an amino acid sequence that is at least 70%, 75%, 80%, 85%, 90%, 95%, 96%, 97%, 98%, 99%, or 100% identical to the amino acid sequence of SEQ ID NO: 94.

In some embodiments of any of the aspects described herein, E (e.g., each E) includes the amino acid sequence of SEQ ID NO: 95. In some embodiments, E includes an amino acid sequence that is at least 70%, 75%, 80%, 85%, 90%, 95%, 96%, 97%, 98%, 99%, or 100% identical to the amino acid sequence of SEQ ID NO: 95.

In some embodiments of any of the aspects described herein, E (e.g., each E) includes the amino acid sequence of SEQ ID NO: 96. In some embodiments. E includes an amino acid sequence that is at least 70%, 75%, 80%, 85%, 90%, 95%, 96%, 97%, 98%, 99%, or 100% identical to the amino acid sequence of SEQ ID NO: 96.

In some embodiments of any of the aspects described herein, E (e.g., each E) includes the amino acid sequence of SEQ ID NO: 97. In some embodiments, E includes an amino acid sequence that is at least 70%, 75%, 80%, 85%, 90%, 95%, 96%, 97%, 98%, 99%, or 100% identical to the amino acid sequence of SEQ ID NO: 97.

In some embodiments of any of the aspects described herein, E (e.g., each E) includes the amino acid sequence of SEQ ID NO: 98. In some embodiments, E includes an amino acid sequence that is at least 70%, 75%, 80%, 85%, 90%, 95%, 96%, 97%, 98%, 99%, or 100% identical to the amino acid sequence of SEQ ID NO: 98.

In some embodiments of any of the aspects described herein, E (e.g., each E) includes the amino acid sequence of SEQ ID NO: 99. In some embodiments, E includes an amino acid sequence that is at least 70%, 75%, 80%, 85%, 90%, 95%, 96%, 97%, 98%, 99%, or 100% identical to the amino acid sequence of SEQ ID NO: 99.

In some embodiments of any of the aspects described herein, E (e.g., each E) includes the amino acid sequence of SEQ ID NO: 100. In some embodiments, E includes an amino acid sequence that is at least 70%, 75%, 80%, 85%, 90%, 95%, 96%, 97%, 98%, 99%, or 100% identical to the amino acid sequence of SEQ ID NO: 100.

In some embodiments of any of the aspects described herein, E (e.g., each E) includes the amino acid sequence of SEQ ID NO: 101. In some embodiments, E includes an amino acid sequence that is at least 70%, 75%, 80%, 85%, 90%, 95%, 96%, 97%, 98%, 99%, or 100% identical to the amino acid sequence of SEQ ID NO: 101.

In some embodiments of any of the aspects described herein, E (e.g., each E) includes the amino acid sequence of SEQ ID NO: 102. In some embodiments, E includes an amino acid sequence that is at least 70%, 75%, 80%, 85%, 90%, 95%, 96%, 97%, 98%, 99%, or 100% identical to the amino acid sequence of SEQ ID NO: 102.

In some embodiments of any of the aspects described herein, E (e.g., each E) includes the amino acid sequence of SEQ ID NO: 103. In some embodiments, E includes an amino acid sequence that is at least 70%, 75%, 80%, 85%, 90%, 95%, 96%, 97%, 98%, 99%, or 100% identical to the amino acid sequence of SEQ ID NO: 103.

In some embodiments of any of the aspects described herein, E (e.g., each E) includes the amino acid sequence of SEQ ID NO: 104. In some embodiments, E includes an amino acid sequence that is at least 70%, 75%, 80%, 85%, 90%, 95%, 96%, 97%, 98%, 99%, or 100% identical to the amino acid sequence of SEQ ID NO: 104.

In some embodiments of any of the aspects described herein, E (e.g., each E) includes the amino acid sequence of SEQ ID NO: 105. In some embodiments, E includes an amino acid sequence that is at least 70%, 75%, 80%, 85%, 90%, 95%, 96%, 97%, 98%, 99%, or 100% identical to the amino acid sequence of SEQ ID NO: 105.

In some embodiments of any of the aspects described herein, E (e.g., each E) includes the amino acid sequence of SEQ ID NO: 106. In some embodiments, E includes an amino acid sequence that is at least 70%, 75%, 80%, 85%, 90%, 95%, 96%, 97%, 98%, 99%, or 100% identical to the amino acid sequence of SEQ ID NO: 106.

In some embodiments of any of the aspects described herein, E (e.g., each E) includes the amino acid sequence of SEQ ID NO: 107. In some embodiments, E includes an amino acid sequence that is at least 70%, 75%, 80%, 85%, 90%, 95%, 96%, 97%, 98%, 99%, or 100% identical to the amino acid sequence of SEQ ID NO: 107.

In some embodiments of any of the aspects described herein, E (e.g., each E) includes the amino acid sequence of SEQ ID NO: 108. In some embodiments, E includes an amino acid sequence that is at least 70%, 75%, 80%, 85%, 90%, 95%, 96%, 97%, 98%, 99%, or 100% identical to the amino acid sequence of SEQ ID NO: 108.

In some embodiments of any of the aspects described herein, E (e.g., each E) includes the amino acid sequence of SEQ ID NO: 109. In some embodiments, E includes an amino acid sequence that is at least 70%, 75%, 80%, 85%, 90%, 95%, 96%, 97%, 98%, 99%, or 100% identical to the amino acid sequence of SEQ ID NO: 109.

In some embodiments of any of the aspects described herein, E (e.g., each E) includes the amino acid sequence of SEQ ID NO: 110. In some embodiments, E includes an amino acid sequence that is at least 70%, 75%, 80%, 85%, 90%, 95%, 96%, 97%, 98%, 99%, or 100% identical to the amino acid sequence of SEQ ID NO: 110.

In some embodiments of any of the aspects described herein, E (e.g., each E) includes the amino acid sequence of SEQ ID NO: 111. In some embodiments, E includes an amino acid sequence that is at least 70%, 75%, 80%, 85%, 90%, 95%, 96%, 97%, 98%, 99%, or 100% identical to the amino acid sequence of SEQ ID NO: 111.

In some embodiments of any of the aspects described herein, E (e.g., each E) includes the amino acid sequence of SEQ ID NO: 112. In some embodiments, E includes an amino acid sequence that is at least 70%, 75%, 80%, 85%, 90%, 95%, 96%, 97%, 98%, 99%, or 100% identical to the amino acid sequence of SEQ ID NO: 112.

In some embodiments of any of the aspects described herein, E (e.g., each E) includes the amino acid sequence of SEQ ID NO: 113. In some embodiments, E includes an amino acid sequence that is at least 70%, 75%, 80%, 85%, 90%, 95%, 96%, 97%, 98%, 99%, or 100% identical to the amino acid sequence of SEQ ID NO: 113.

In some embodiments of any of the aspects described herein, E (e.g., each E) includes the amino acid sequence of SEQ ID NO: 114. In some embodiments, E includes an amino acid sequence that is at least 70%, 75%, 80%, 85%, 90%, 95%, 96%, 97%, 98%, 99%, or 100% identical to the amino acid sequence of SEQ ID NO: 114.

In some embodiments of any of the aspects described herein, E (e.g., each E) includes the amino acid sequence of SEQ ID NO: 115. In some embodiments, E includes an amino acid sequence that is at least 70%, 75%, 80%, 85%, 90%, 95%, 96%, 97%, 98%, 99%, or 100% identical to the amino acid sequence of SEQ ID NO: 115.

In some embodiments of any of the aspects described herein, E (e.g., each E) includes the amino acid sequence of SEQ ID NO: 116. In some embodiments, E includes an amino acid sequence that is at least 70%, 75%, 80%, 85%, 90%, 95%, 96%, 97%, 98%, 99%, or 100% identical to the amino acid sequence of SEQ ID NO: 116.

In some embodiments of any of the aspects described herein, E (e.g., each E) includes the amino acid sequence of SEQ ID NO: 117. In some embodiments, E includes an amino acid sequence that is at least 70%, 75%, 80%, 85%, 90%, 95%, 96%, 97%, 98%, 99%, or 100% identical to the amino acid sequence of SEQ ID NO: 117.

In some embodiments of any of the aspects described herein, E (e.g., each E) includes the amino acid sequence of SEQ ID NO: 118. In some embodiments, E includes an amino acid sequence that is at least 70%, 75%, 80%, 85%, 90%, 95%, 96%, 97%, 98%, 99%, or 100% identical to the amino acid sequence of SEQ ID NO: 118.

In some embodiments of any of the aspects described herein, E (e.g., each E) includes the amino acid sequence of SEQ ID NO: 119. In some embodiments, E includes an amino acid sequence that is at least 70%, 75%, 80%, 85%, 90%, 95%, 96%, 97%, 98%, 99%, or 100% identical to the amino acid sequence of SEQ ID NO: 119.

In some embodiments of any of the aspects described herein, E (e.g., each E) includes the amino acid sequence of SEQ ID NO: 120. In some embodiments, E includes an amino acid sequence that is at least 70%, 75%, 80%, 85%, 90%, 95%, 96%, 97%, 98%, 99%, or 100% identical to the amino acid sequence of SEQ ID NO: 120.

In some embodiments of any of the aspects described herein, E (e.g., each E) includes the amino acid sequence of SEQ ID NO: 121. In some embodiments, E includes an amino acid sequence that is at least 70%, 75%, 80%, 85%, 90%, 95%, 96%, 97%, 98%, 99%, or 100% identical to the amino acid sequence of SEQ ID NO: 121.

In some embodiments of any of the aspects described herein, E (e.g., each E) includes the amino acid sequence of SEQ ID NO: 122. In some embodiments, E includes an amino acid sequence that is at least 70%, 75%, 80%, 85%, 90%, 95%, 96%, 97%, 98%, 99%, or 100% identical to the amino acid sequence of SEQ ID NO: 122.

In some embodiments of any of the aspects described herein, E (e.g., each E) includes the amino acid sequence of SEQ ID NO: 123. In some embodiments, E includes an amino acid sequence that is at least 70%, 75%, 80%, 85%, 90%, 95%, 96%, 97%, 98%, 99%, or 100% identical to the amino acid sequence of SEQ ID NO: 123.

In some embodiments of any of the aspects described herein, E (e.g., each E) includes the amino acid sequence of SEQ ID NO: 124. In some embodiments, E includes an amino acid sequence that is at least 70%, 75%, 80%, 85%, 90%, 95%, 96%, 97%, 98%, 99%, or 100% identical to the amino acid sequence of SEQ ID NO: 124.

In some embodiments of any of the aspects described herein, E (e.g., each E) includes the amino acid sequence of SEQ ID NO: 125. In some embodiments, E includes an amino acid sequence that is at least 70%, 75%, 80%, 85%, 90%, 95%, 96%, 97%, 98%, 99%, or 100% identical to the amino acid sequence of SEQ ID NO: 125.

In some embodiments of any of the aspects described herein, E (e.g., each E) includes the amino acid sequence of SEQ ID NO: 126. In some embodiments, E includes an amino acid sequence that is at least 70%, 75%, 80%, 85%, 90%, 95%, 96%, 97%, 98%, 99%, or 100% identical to the amino acid sequence of SEQ ID NO: 126.

In some embodiments of any of the aspects described herein, E (e.g., each E) includes the amino acid sequence of SEQ ID NO: 127. In some embodiments, E includes an amino acid sequence that is at least 70%, 75%, 80%, 85%, 90%, 95%, 96%, 97%, 98%, 99%, or 100% identical to the amino acid sequence of SEQ ID NO: 127.

In some embodiments of any of the aspects described herein, E (e.g., each E) includes the amino acid sequence of SEQ ID NO: 128. In some embodiments, E includes an amino acid sequence that is at least 70%, 75%, 80%, 85%, 90%, 95%, 96%, 97%, 98%, 99%, or 100% identical to the amino acid sequence of SEQ ID NO: 128.

In some embodiments of any of the aspects described herein, E (e.g., each E) includes the amino acid sequence of SEQ ID NO: 129. In some embodiments, E includes an amino acid sequence that is at least 70%, 75%, 80%, 85%, 90%, 95%, 96%, 97%, 98%, 99%, or 100% identical to the amino acid sequence of SEQ ID NO: 129.

In some embodiments of any of the aspects described herein, E (e.g., each E) includes the amino acid sequence of SEQ ID NO: 130. In some embodiments, E includes an amino acid sequence that is at least 70%, 75%, 80%, 85%, 90%, 95%, 96%, 97%, 98%, 99%, or 100% identical to the amino acid sequence of SEQ ID NO: 130.

In some embodiments of any of the aspects described herein, E (e.g., each E) includes the amino acid sequence of SEQ ID NO: 131. In some embodiments, E includes an amino acid sequence that is at least 70%, 75%, 80%, 85%, 90%, 95%, 96%, 97%, 98%, 99%, or 100% identical to the amino acid sequence of SEQ ID NO: 131.

In some embodiments of any of the aspects described herein, E (e.g., each E) includes the amino acid sequence of SEQ ID NO: 132. In some embodiments, E includes an amino acid sequence that is at least 70%, 75%, 80%, 85%, 90%, 95%, 96%, 97%, 98%, 99%, or 100% identical to the amino acid sequence of SEQ ID NO: 132.

In some embodiments of any of the aspects described herein, E (e.g., each E) includes the amino acid sequence of SEQ ID NO: 133. In some embodiments, E includes an amino acid sequence that is at least 70%, 75%, 80%, 85%, 90%, 95%, 96%, 97%, 98%, 99%, or 100% identical to the amino acid sequence of SEQ ID NO: 133.

In some embodiments of any of the aspects described herein, E (e.g., each E) includes the amino acid sequence of SEQ ID NO: 134. In some embodiments, E includes an amino acid sequence that is at least 70%, 75%, 80%, 85%, 90%, 95%, 96%, 97%, 98%, 99%, or 100% identical to the amino acid sequence of SEQ ID NO: 134.

In some embodiments of any of the aspects described herein, E (e.g., each E) includes the amino acid sequence of SEQ ID NO: 135. In some embodiments, E includes an amino acid sequence that is at least 70%, 75%, 80%, 85%, 90%, 95%, 96%, 97%, 98%, 99%, or 100% identical to the amino acid sequence of SEQ ID NO: 135.

In some embodiments of any of the aspects described herein, E (e.g., each E) includes the amino acid sequence of SEQ ID NO: 136. In some embodiments, E includes an amino acid sequence that is at least 70%, 75%, 80%, 85%, 90%, 95%, 96%, 97%, 98%, 99%, or 100% identical to the amino acid sequence of SEQ ID NO: 136.

In some embodiments of any of the aspects described herein, E (e.g., each E) includes the amino acid sequence of SEQ ID NO: 137. In some embodiments, E includes an amino acid sequence that is at least 70%, 75%, 80%, 85%, 90%, 95%, 96%, 97%, 98%, 99%, or 100% identical to the amino acid sequence of SEQ ID NO: 137.

In some embodiments of any of the aspects described herein, E (e.g., each E) includes the amino acid sequence of SEQ ID NO: 138. In some embodiments, E includes an amino acid sequence that is at least 70%, 75%, 80%, 85%, 90%, 95%, 96%, 97%, 98%, 99%, or 100% identical to the amino acid sequence of SEQ ID NO: 138.

In some embodiments of any of the aspects described herein, E (e.g., each E) includes the amino acid sequence of SEQ ID NO: 139. In some embodiments, E includes an amino acid sequence that is at least 70%, 75%, 80%, 85%, 90%, 95%, 96%, 97%, 98%, 99%, or 100% identical to the amino acid sequence of SEQ ID NO: 139.

In some embodiments of any of the aspects described herein, E (e.g., each E) includes the amino acid sequence of SEQ ID NO: 140. In some embodiments, E includes an amino acid sequence that is at least 70%, 75%, 80%, 85%, 90%, 95%, 96%, 97%, 98%, 99%, or 100% identical to the amino acid sequence of SEQ ID NO: 140.

In some embodiments of any of the aspects described herein, E (e.g., each E) includes the amino acid sequence of SEQ ID NO: 145. In some embodiments, E includes an amino acid sequence that is at least 70%, 75%, 80%, 85%, 90%, 95%, 96%, 97%, 98%, 99%, or 100% identical to the amino acid sequence of SEQ ID NO: 141.

In some embodiments of any of the aspects described herein, wherein E includes an Fc domain monomer, the Fc domain monomer (e.g., the Fc domain monomer having the sequence of any one of SEQ ID NOs: 1-138) includes a triple mutation corresponding to M252Y/S254T/T256E (YTE). As used herein, an amino acid "corresponding to" a particular amino acid residue (e.g., of a particular SEQ ID NO.) should be understood to include any amino acid residue that one of skill in the art would understand to align to the particular residue (e.g., of the particular sequence). For example, any one of SEQ ID NOs: 1-138 may be mutated to include a YTE mutation.

In some embodiments of any of the aspects described herein, wherein E includes an Fc domain monomer, the Fc domain monomer (e.g., the Fc domain monomer having the sequence of any one of SEQ ID NOs: 1-138) includes a double mutant corresponding to M428L/N434S (LS). As used herein, an amino acid "corresponding to" a particular amino acid residue (e.g., of a particular SEQ ID NO.) should be understood to include any amino acid residue that one of skill in the art would understand to align to the particular residue (e.g., of the particular sequence). For example, any one of SEQ ID NOs: 1-138 may be mutated to include a LS mutation.

In some embodiments of any of the aspects described herein, wherein E includes an Fc domain monomer, the Fc domain monomer (e.g., the Fc domain monomer having the sequence of any one of SEQ ID NOs: 1-138) includes a mutant corresponding to N434H. As used herein, an amino acid "corresponding to" a particular amino acid residue (e.g., of a particular SEQ ID NO.) should be understood to include any amino acid residue that one of skill in the art would understand to align to the particular residue (e.g., of the particular sequence). For example, any one of SEQ ID NOs: 1-138 may be mutated to include an N434H mutation.

In some embodiments of any of the aspects described herein, wherein E includes an Fc domain monomer, the Fc domain monomer (e.g., the Fc domain monomer having the sequence of any one of SEQ ID NOs: 1-138) includes a mutant corresponding to C220S. As used herein, an amino acid "corresponding to" a particular amino acid residue (e.g., of a particular SEQ ID NO.) should be understood to include any amino acid residue that one of skill in the art would understand to align to the particular residue (e.g., of the particular sequence). For example, any one of SEQ ID NOs: 1-138 may be mutated to include a C220S mutation.

In some embodiments of any of the aspects described herein, the Fc domain monomer (e.g., the Fc domain monomer having the sequence of any one of SEQ ID NOs: 1-95) includes a triple mutation corresponding to V309D/Q311H/N434S (DHS). As used herein, an amino acid "corresponding to" a particular amino acid residue (e.g., of a particular SEQ ID NO.) should be understood to include any amino acid residue that one of skill in the art would understand to align to the particular residue (e.g., of the particular sequence). For example, any one of SEQ ID NOs: 1-95 may be mutated to include a DHS mutation.

In some embodiments of any of the aspects described herein, wherein E includes an Fc domain monomer, the Fc domain monomer (e.g., the Fc domain monomer having the sequence of any one of SEQ ID NOs: 1-138) is a fragment of the Fc domain monomer (e.g., a fragment of at least 25 (e.g., 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more), at least 50 (e.g., 51, 52, 53, 54, 55, 56, 57, 58, 59, 60, 61, 62, 63, 64, 65, 66, 67, 68, 69, 70, 71, 72, 73, 74, 75 or more), at least 75 (e.g., 75, 76, 77, 78, 79, 80, 81, 82, 83, 84, 85, 86, 87, 88, 89, 90, 91, 92, 93, 94, 95, 96, 97, 98, 99, 100 or more) consecutive amino acids in length from SEQ ID NOs: 1-138.

In some embodiments of any of the aspects described herein (e.g., a conjugate of any one of formulas (1)-(5), (D-I)-(D-XI), (D'-I), (M-I)-(M-XI), or (M'-II)), one or more nitrogen atoms of one or more surface exposed lysine residues of E or one or more sulfur atoms of one or more surface exposed cysteines in E is covalently conjugated to a linker (e.g., a PEG$_2$-PEG$_{20}$ linker). The linker conjugated to E may be functionalized such that it may reacts to form a covalent bond with the L of any A$_1$-L or any A$_2$-L-A$_1$ described herein. In preferred embodiments, E is conjugated to a linker functionalized with an azido group and the L of A$_1$-L or any A$_2$-L-A$_1$ is functionalized with an alkyne group. Conjugation (e.g., by click chemistry) of the linker-azido of E and linker-alkyne of A$_1$-L or A$_2$-L-A$_1$ forms a conjugate of the invention, for example a conjugate described by any one of formulas (1)-(5), (D-I)-(D-XI), (D'-I), (M-I)-(M-XI), or (M'-1). In yet other embodiments, E is conjugated to a linker functionalized with an alkyne group and L of any A$_1$-L or of any A$_2$-L-A$_1$ is functionalized with an azido group. Conjugation (e.g., by click chemistry, see, e.g., FIG. 103) of the linker-alkyne of E and linker-azido of A$_1$-L or A$_2$-L-A$_1$ forms a conjugate of the invention, for example a conjugate described by formula (1)-(5), (D-I)-(D-XI), (D'-I), (M-I)-(M-XI), or (M'-I).

In some embodiments of any of the aspects described herein, the squiggly line of any one of formulas (1)-(5), (D-I)-(D-XI), (D'-I), (M-I)-(M-XI), or (M'-I) may represent a covalent bond between E and the L of A$_1$-L or A$_2$-L-A$_1$.

In some embodiments of any of the aspects described herein, the squiggly line of any one of formulas (1)-(5), (D-I)-(D-XI), (D'-I), (M-I)-(M-XI), or (M'-I) may represent that one or more amino acid side chains of E (e.g., one or more nitrogen atoms of one or more surface exposed lysine residues of E or one or more sulfur atoms of one or more surface exposed cysteines in E) have been conjugated to a linker (e.g., a PEG$_2$-PEG$_{20}$ linker) wherein the linker has been functionalized with a reactive moiety, such that the reactive moiety forms a covalent bond with the L of any A$_1$-L or any A$_2$-L-A$_1$ described herein (e.g., by click chemistry between an azido functionalized linker and an alkyne functionalized linker, as described above; see, e.g., FIG. 103).

In some embodiments of any of the aspects described herein, A$_1$ and/or A$_2$ have the structure described by (A-I):

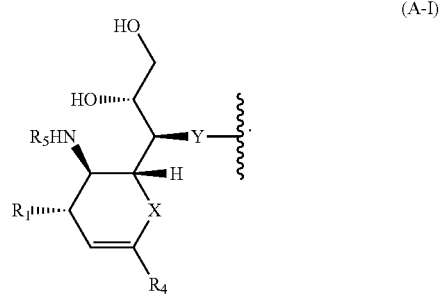

(A-I)

In preferred embodiments, wherein A$_1$ and/or A$_2$ have the structure described by (A-I): R$_1$ is —NHC(=NH)NH$_2$, R$_4$ is —CO$_2$H, R$_5$ is —COCH$_3$, and/or X is —O—. In preferred embodiments, A$_1$ and/or A$_2$ have the structure of zanamivir described by:

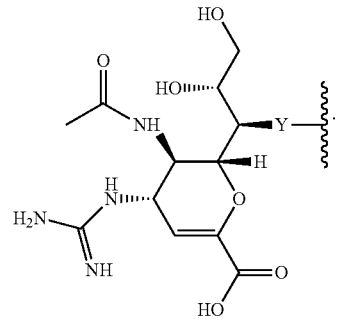

In some embodiments of any of the aspects described herein, A$_1$ and/or A$_2$ have the structure described by (A-II):

(A-II)

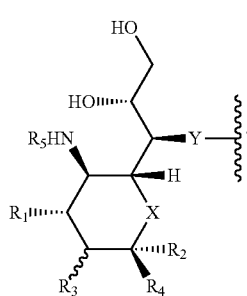

In preferred embodiments, wherein $A_1$ and/or $A_2$ have the structure described by (A-II): $R_1$ is —NHC(=NH)NH$_2$, $R_2$ is H or F, $R_3$ is H or F, $R_4$ is —CO$_2$H, $R_5$ is —COCH$_3$, and/or X is —O—. In preferred embodiments, $A_1$ and/or $A_2$ have the structure described by:

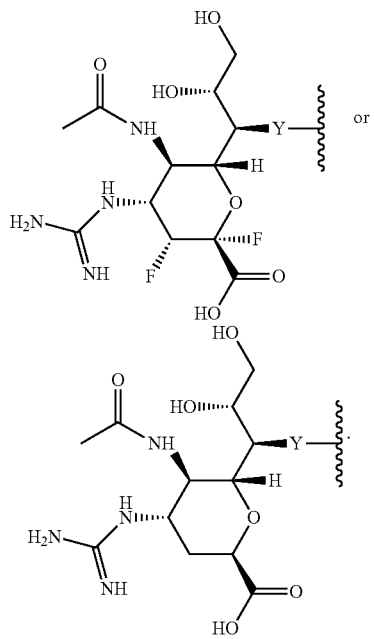

In some embodiments of any of the aspects described herein, $A_1$ and/or $A_2$ have the structure described by (A-III):

(A-III)

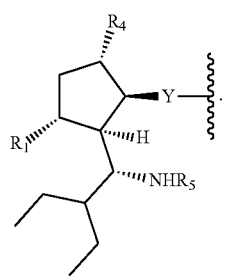

In preferred embodiments, wherein $A_1$ and/or $A_2$ have the structure described by (A-III): $R_1$ is —NHC(=NH)NH$_2$, $R_4$ is —CO$_2$H, and/or $R_5$ is —COCH$_3$. In preferred embodiments, $A_1$ and/or $A_2$ have the structure of peramivir described by:

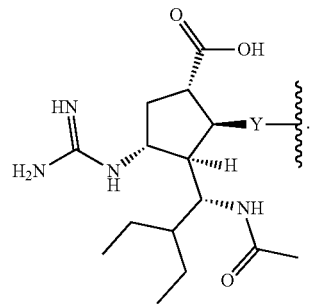

In some embodiments of any of the aspects described herein, $A_1$ and/or $A_2$ have the structure described by (A-IV):

(A-IV)

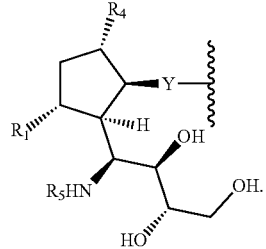

In preferred embodiments, wherein $A_1$ and/or $A_2$ have the structure described by (A-IV): $R_1$ is —NHC(=NH)NH$_2$, $R_4$ is —CO$_2$H, and/or $R_5$ is —COCH$_3$. In preferred embodiments, $A_1$ and/or $A_2$ have the structure described by:

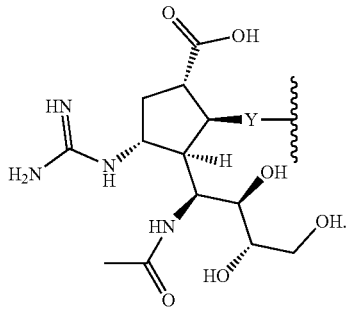

In some embodiments of any of the aspects described herein, $A_1$ and/or $A_2$ have the structure described by (A-V):

(A-V)

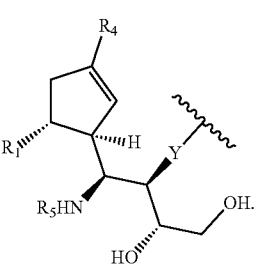

In preferred embodiments, wherein $A_1$ and/or $A_2$ have the structure described by (A-V): $R_1$ is —NHC(=NH)NH$_2$, $R_4$ is —CO$_2$H, and/or R$_5$ is —COCH$_3$. In preferred embodiments, A$_1$ and/or A$_2$ have the structure described by:

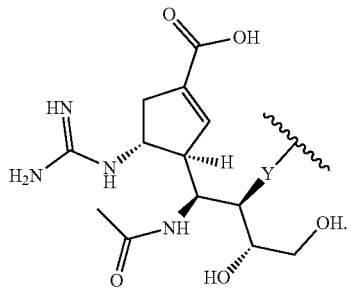

In some embodiments of any of the aspects described herein, A$_1$ and/or A$_2$ have the structure described by (A-VI):

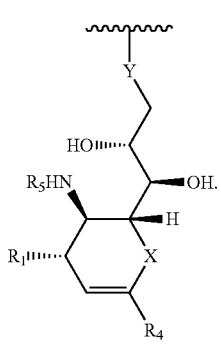

(A-VI)

In preferred embodiments, wherein A$_1$ and/or A$_2$ have the structure described by (A-VI): R$_1$ is —NHC(=NH)NH$_2$, R$_4$ is —CO$_2$H, R$_5$ is —COCH$_3$, and/or X is —O—. In preferred embodiments, A$_1$ and/or A$_2$ have the structure of zanamivir described by:

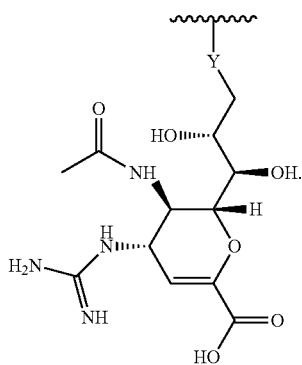

In some embodiments of any of the aspects described herein, A$_1$ and/or A$_2$ have the structure described by (A-VII):

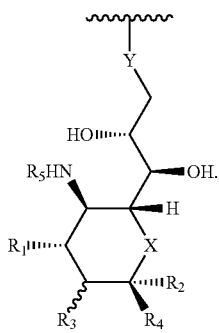

(A-VII)

In preferred embodiments, wherein A$_1$ and/or A$_2$ have the structure described by (A-VII): R$_1$ is —NHC(=NH)NH$_2$, R$_2$ is H or F, R$_3$ is H or F, R$_4$ is —CO$_2$H, R$_5$ is —COCH$_3$, and/or X is —O—. In preferred embodiments, A$_1$ and/or A$_2$ have the structure described by:

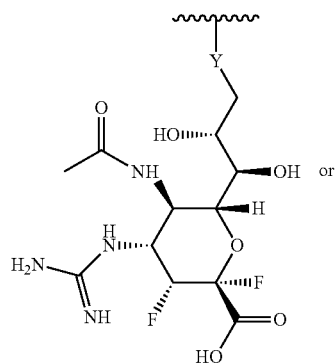

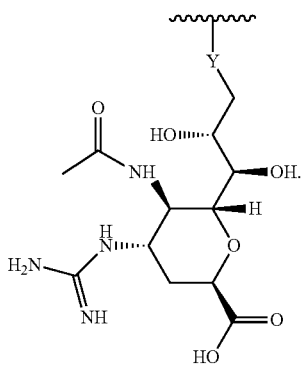

In some embodiments of any of the aspects described herein, A$_1$ and/or A$_2$ have the structure described by (A-VIII):

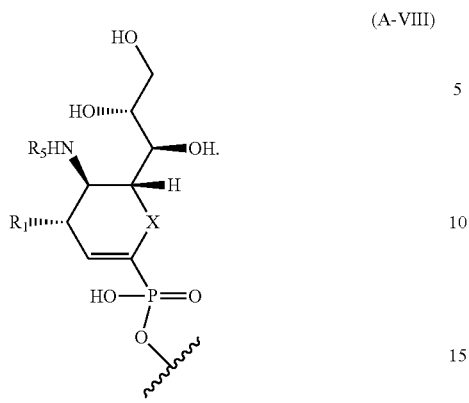

(A-VIII)

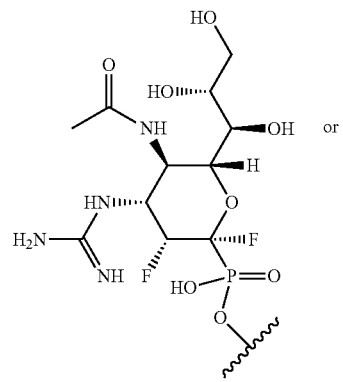

or

In preferred embodiments, wherein $A_1$ and/or $A_2$ have the structure described by (A-VIII): $R_1$ is —NHC(=NH)NH$_2$, $R_5$ is —COCH$_3$, and/or X is —O—. In preferred embodiments, $A_1$ and/or $A_2$ have the structure described by:

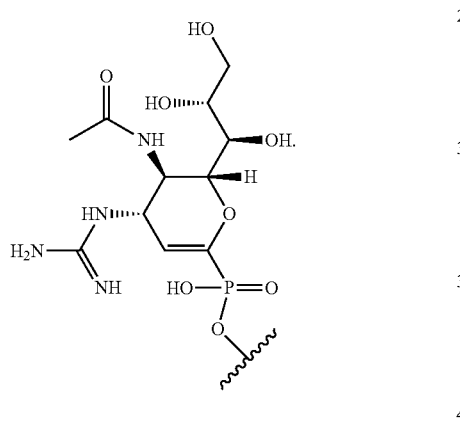

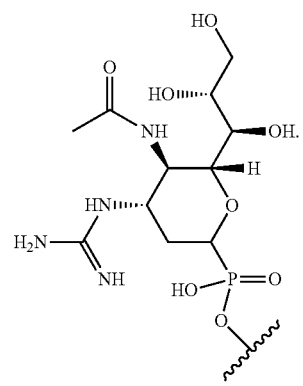 [SMILES: *OP(=O)(O)C1=C[C@H](NC(=N)N)[C@@H](NC(C)=O)[C@H]([C@H](O)[C@H](O)CO)O1]

In some embodiments of any of the aspects described herein, $A_1$ and/or $A_2$ have the structure described by (A-IX):

In some embodiments of any of the aspects described herein, $A_1$ and/or $A_2$ have the structure described by (A-X):

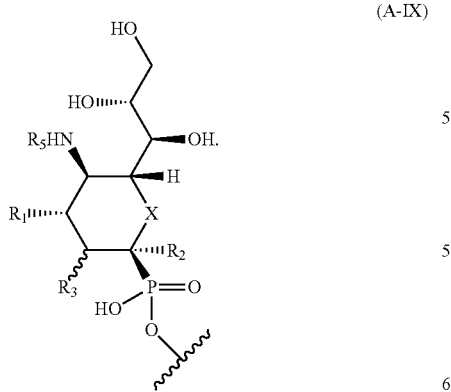

(A-IX)

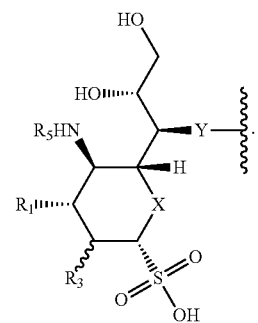

(A-X)

In preferred embodiments, wherein $A_1$ and/or $A_2$ have the structure described by (A-IX): $R_1$ is —NHC(=NH)NH$_2$, $R_2$ is H or F, $R_3$ is H or F, $R_5$ is —COCH$_3$, and/or X is —O—. In preferred embodiments, $A_1$ and/or $A_2$ have the structure described by:

In preferred embodiments, wherein $A_1$ and/or $A_2$ have the structure described by (A-X): $R_1$ is —NHC(=NH)NH$_2$, $R_3$ is H, $R_5$ is —COCH$_3$, and/or X is —O—. In preferred embodiments, $A_1$ and/or $A_2$ have the structure of sulfozanamivir described by:

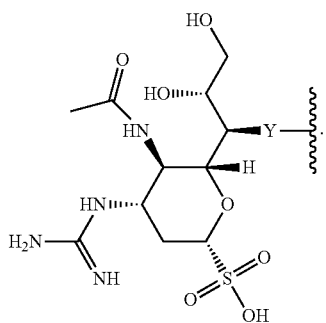

In some embodiments of any of the aspects described herein, $A_1$ and/or $A_2$ have the structure described by (A-XI):

(A-XI)

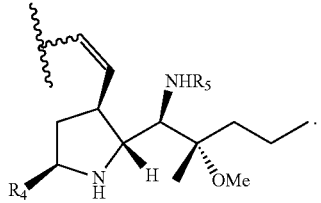

In preferred embodiments, wherein $A_1$ and/or $A_2$ have the structure described by (A-XI): $R_4$ is —$CO_2H$, and/or $R_5$ is —$COCH_3$. In preferred embodiments, the alkene is (E), (Z), or a racemic mixture of (E)/(Z). In preferred embodiments, $A_1$ and/or $A_2$ have the structure of A-315675 (Abbott) described by:

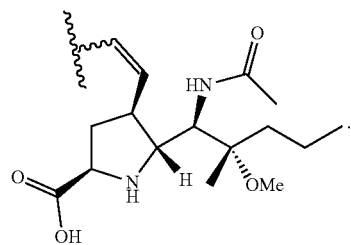

In some embodiments of any of the aspects described herein, $A_1$ and/or $A_2$ have the structure described by (A-XII):

(A-XII)

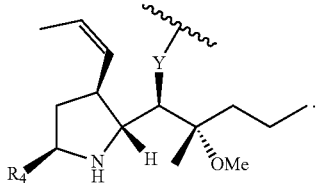

In preferred embodiments, wherein $A_1$ and/or $A_2$ have the structure described by (A-XII): $R_4$ is —$CO_2H$. In preferred embodiments, $A_1$ and/or $A_2$ have the structure of A-315675 (Abbott) described by:

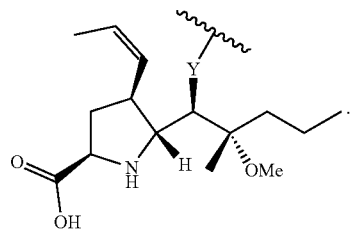

In some embodiments, the conjugate is conjugate 1, or any regioisomer thereof, and the drug-to-antibody ratio (DAR) (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 1, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 2, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 2, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 3, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 3, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 4, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 4, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 5, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 5, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 6, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 6, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 7, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 7, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 8, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 8, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 9, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 9, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 10, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 10, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 11, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 11, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 12, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 12, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 13, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 13, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 14, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 14, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 15, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 15, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 16, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 16, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 17, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 17, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 18, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 18, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 19, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 19, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 20, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 20, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 21, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 21, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 22, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 22, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 23, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 23, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 24, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 24, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 25, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 25, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 26, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 26, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 27, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 27, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 28, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 28, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 29, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 29, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 30, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 30, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 31, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 31, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 32, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 32, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 33, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 33 wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 34, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 34, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 35, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 35, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 36, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 36, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 37, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 37, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 38, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 38, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 39, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 39, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 40, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 40, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 41, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 41, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 42, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 42, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 43, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 43, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 44, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 44, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 45 (e.g., conjugate 45a or conjugate 45b), or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 45 (e.g., conjugate 45a or conjugate 45b), wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 46, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 46, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 47, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 47, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments, the conjugate is conjugate 48, or any regioisomer thereof, and the DAR (e.g., T) is between 0.5 and 10.0, e.g., about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0, between 6.0 and 8.0, or between 8.0 and 10.0. In another aspect the invention provides a population of conjugates, each conjugate having the structure of conjugate 48, wherein the average DAR (e.g., T) of the population of conjugates is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5.

In some embodiments of any of the aspects described herein, the invention features a conjugate described by any one of formulas (D-I), (M-I), (1), or (2): wherein each $A_1$ and each $A_2$ is independently selected from any one of formulas (A-XIII):

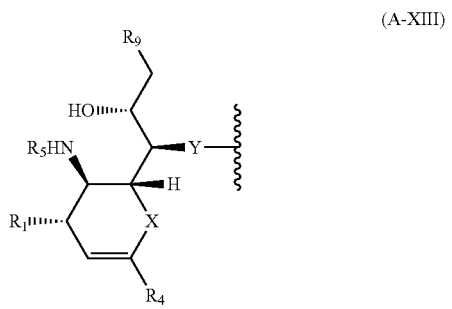

wherein $R_1$ is selected from —OH, —NH$_2$, —NHC(=NH)NH$_2$, and —NHC(=NH)NHR$_6$; $R_4$ is selected from —CO$_2$H, —P(=O)(OH)$_2$, —SO$_3$H; $R_5$ is selected from —COCH$_3$, —COCF$_3$, —SO$_2$CH$_3$; X is selected from —O— and —S—; Y is selected from

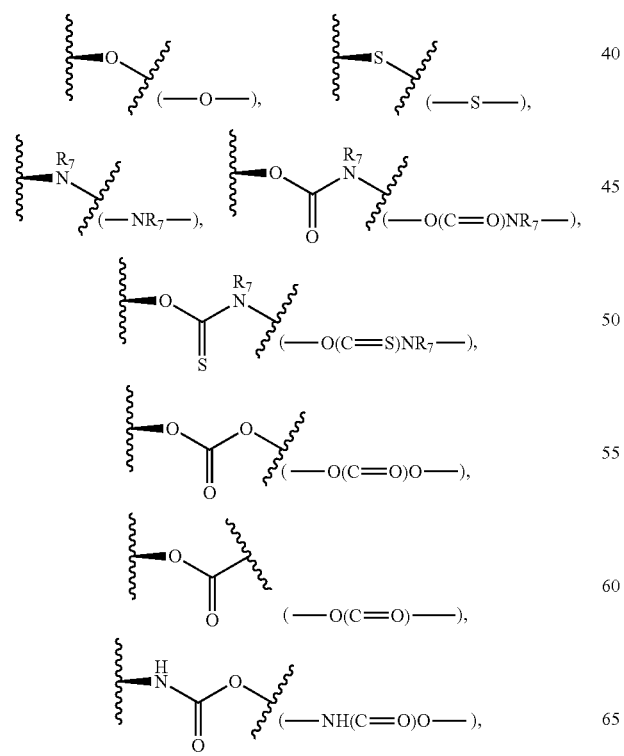

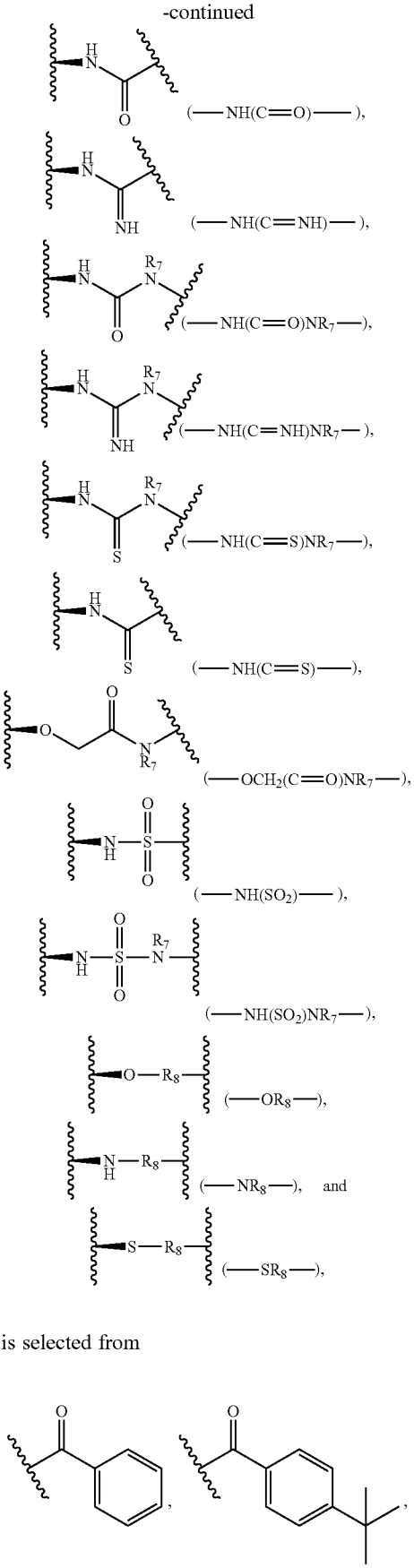

$R_6$ is selected from

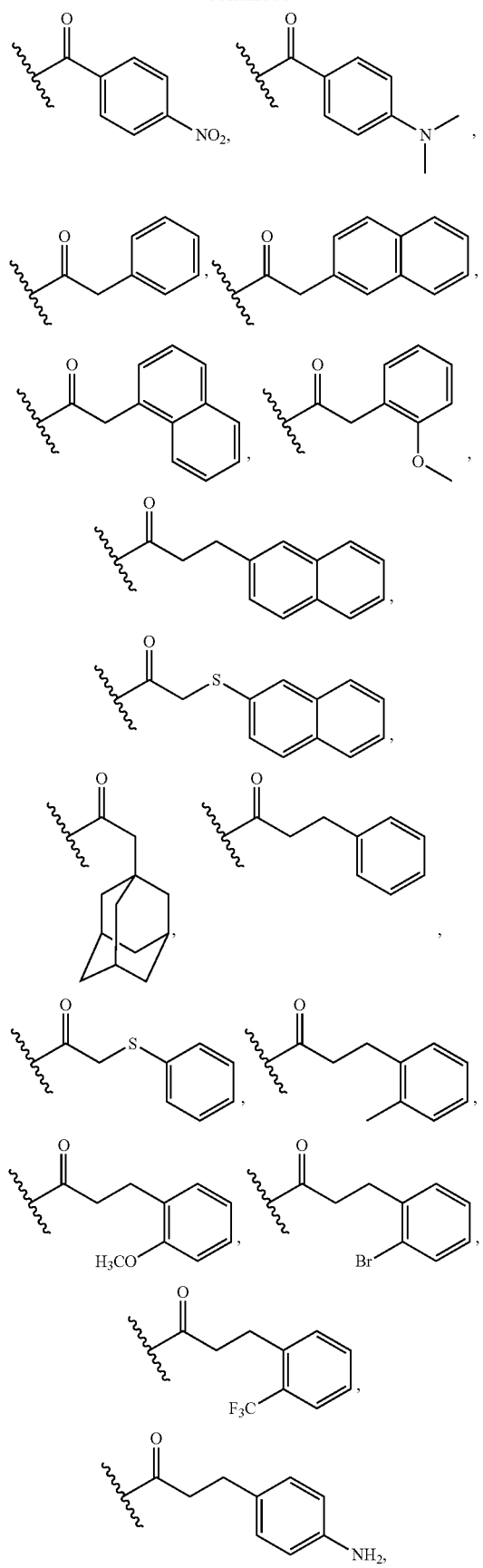
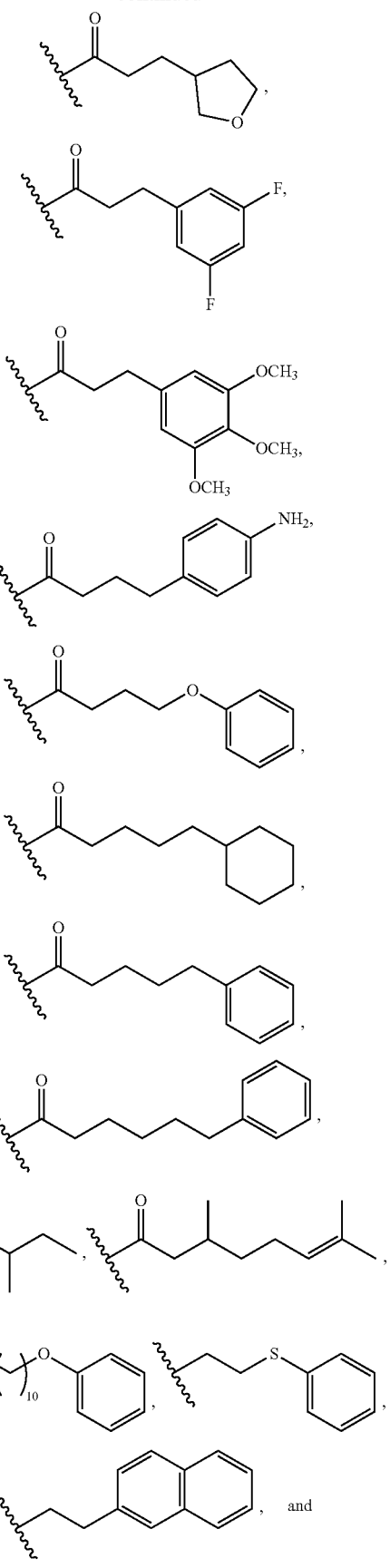

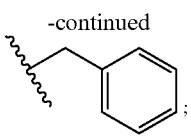

R$_7$ is selected from H, C1-C20 alkyl, C3-C20 cycloalkyl, C3-C20 heterocycloalkyl; C5-C15 aryl, and C2-C15 heteroaryl;

R$_8$ is selected from C3-C20 heterocycloalkyl, C5-C15 aryl, and C2-C15 heteroaryl;

R$_9$ is selected from —H, a halogen (e.g., Cl or F), —OR$_{10}$, —NHC(=O)R$_7$, optionally substituted C1-C20 alkyl, C3-C20 cycloalkyl, C3-C20 heterocycloalkyl; C5-C15 aryl, and C2-C15 heteroaryl;

R$_{10}$ is selected from C1-C20 alkyl, C3-C20 cycloalkyl, C3-C20 heterocycloalkyl; C5-C15 aryl, and C2-C15 heteroaryl;

n is 1 or 2;

each E comprises an Fc domain monomer, an albumin protein, an albumin protein-binding peptide, or an Fc-binding peptide;

L is a linker covalently attached to E and to each Y of each A$_1$ or each A$_1$ and A$_2$;

T is an integer from 1 to 20, and each squiggly line in formulas (D-I), (M-I), (1), or (2) indicates that L is covalently attached to each E;

or a pharmaceutically acceptable salt thereof.

In some embodiments, each A$_1$ and each A$_2$ is described by formula (A-XIII-1):

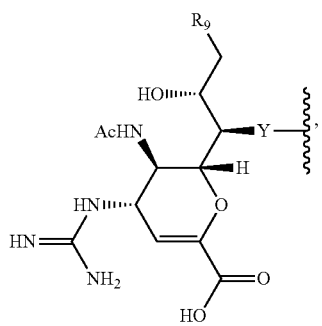

(A-XIII-1)

In some embodiments, each A$_1$ and each A$_2$ is independently selected from any one of formulas (A-XIII-1a)-(A-XIII-1d):

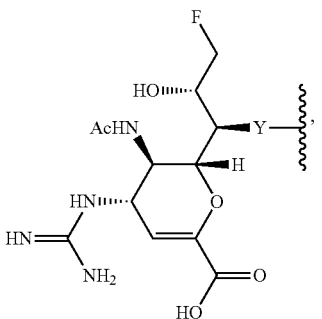

(A-XIII-1a)

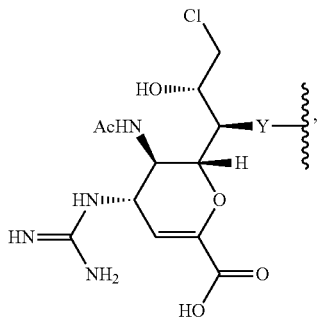

(A-XIII-1b)

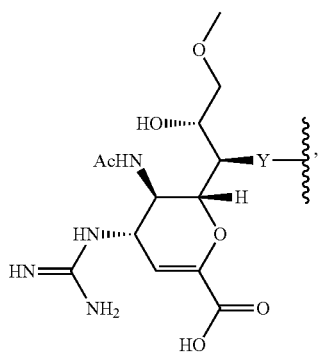

(A-XIII-1c)

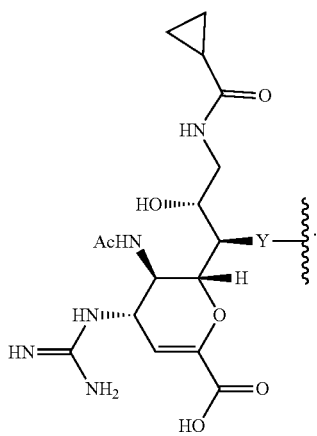

(A-XIII-1d)

In some embodiments, the conjugate is described by formula (D-XI):

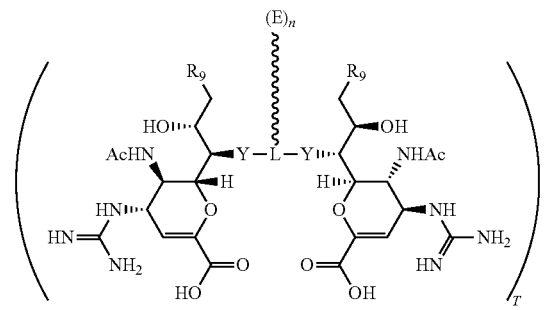

(D-XI)

or a pharmaceutically acceptable salt thereof.

In some embodiments, the conjugate is described by formula (D-XI-1):

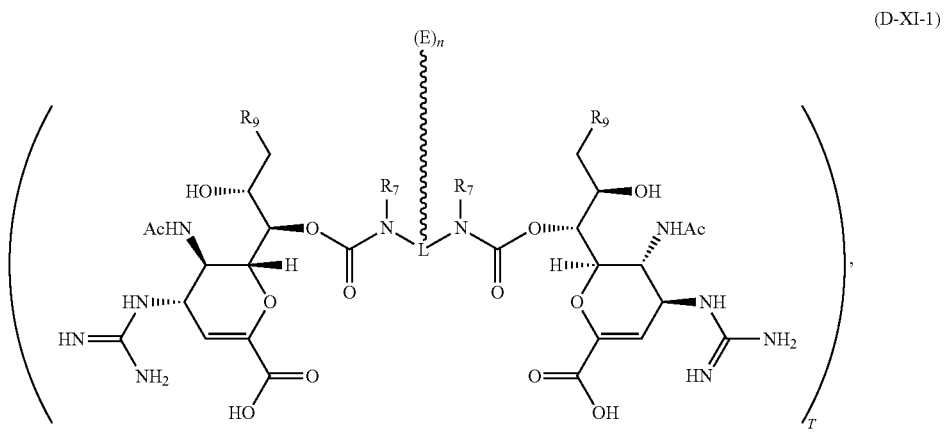

(D-XI-1)

wherein $R_7$ is selected from H, C1-C20 alkyl, C3-C20 cycloalkyl, C3-C20 heterocycloalkyl; C5-C15 aryl, and C2-C15 heteroaryl; or a pharmaceutically acceptable salt thereof.

In some embodiments, the conjugate is described by formula (M-XI):

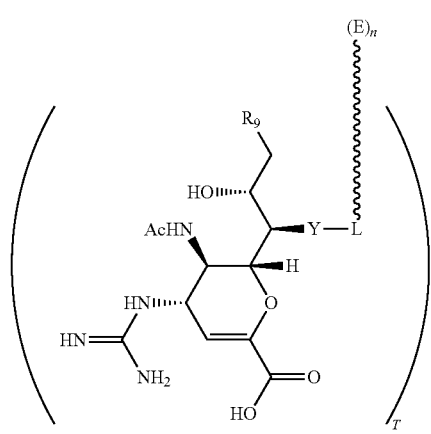

(M-XI)

or a pharmaceutically acceptable salt thereof.

In some embodiments, the conjugate is described by formula (M-XI-1):

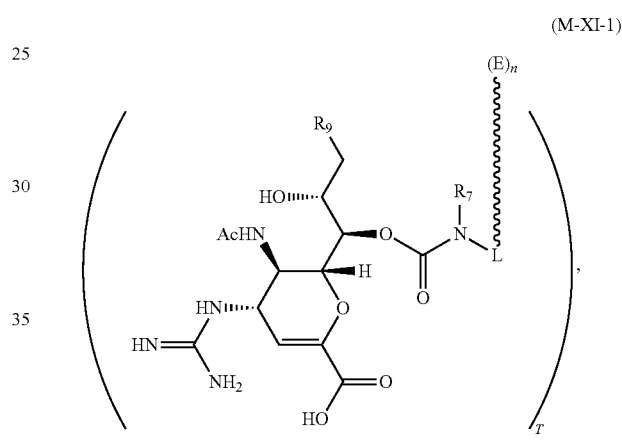

(M-XI-1)

wherein $R_7$ is selected from H, C1-C20 alkyl, C3-C20 cycloalkyl, C3-C20 heterocycloalkyl; C5-C15 aryl, and C2-C15 heteroaryl; or a pharmaceutically acceptable salt thereof.

Definitions

To facilitate the understanding of this invention, a number of terms are defined below. Terms defined herein have meanings as commonly understood by a person of ordinary skill in the areas relevant to the present invention. Terms such as "a", "an," and "the" are not intended to refer to only a singular entity, but include the general class of which a specific example may be used for illustration. The terminology herein is used to describe specific embodiments of the invention, but their usage does not delimit the invention, except as outlined in the claims.

The term "neuraminidase inhibitor" or ""viral neuraminidase inhibitor," as used herein, refers to compounds that decreases the activity of the enzyme influenza virus neuraminidase (e.g., from influenza virus A, B, or C). A neuraminidase inhibitor may be identified by methods known to those of skill in the art, for example, by reduction of viral replication in an influenza viral plaque reduction assay, e.g., at concentrations less than 20 μM (e.g., less than 10 μM, 5 μM, 2 μM, 1 μM, 500 nM or 100 nM). Viral neuraminidase inhibitors known to those of skill in the art include zanamivir, sulfozanamivir, peramivir, and A-315675

(Abbott) (see, for example, Hadházi et al. A sulfozanamivir analogue has potent anti-influenza virus activity. *ChemMedChem Comm.* 13:785-789 (2018) and In vitro characterization of A-315675, a highly potent inhibitor of A and B strain of influenza virus neuraminidases and influenza virus replication. *Antimicrobial Agents and Chemotherapy* 46(4): 1014-1021 (2002)). Viral neuraminidase inhibitors of the invention include zanamivir, sulfozanamivir, peramivir, A-315675 and analogs thereof, such as the viral neuraminidase inhibitors of formulas (A-I)-(A-XIII):

(A-I)

(A-II)

(A-III)

(A-IV)

(A-V)

-continued (A-VI)

(A-VII)

(A-VIII)

(A-IX)

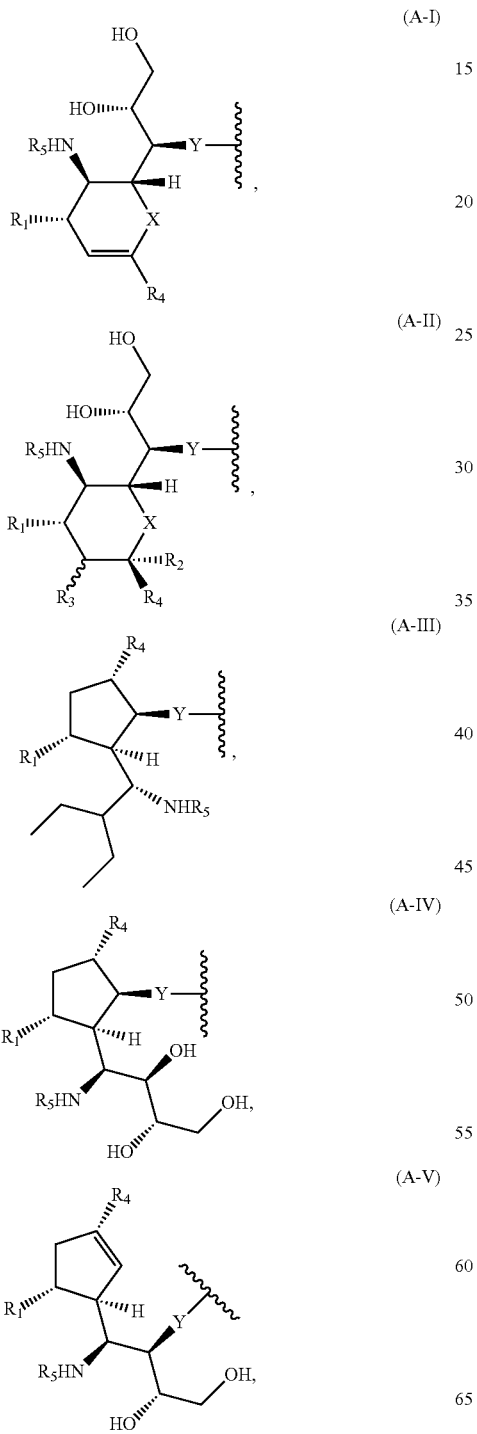

427

-continued (A-X)
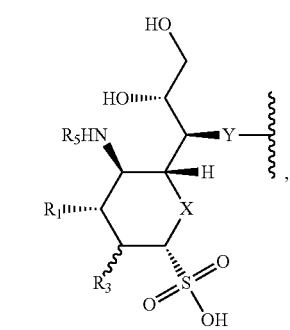

(A-XI)
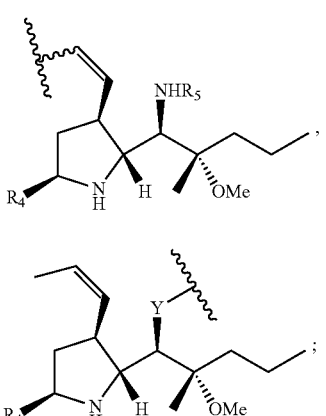

(A-XII)
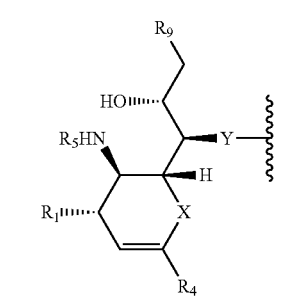

(A-XIII)
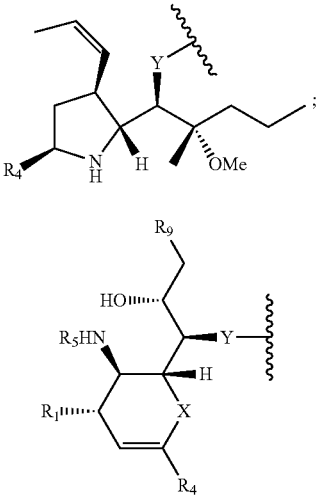

wherein $R_1$ is selected from —OH, —NH$_2$, —NHC(=NH)NH$_2$, and —NHC(=NH)NHR$_6$; $R_2$ and $R_3$ are each independently selected from —H, —OH, —F, —Cl, and —Br; $R_4$ is selected from —CO$_2$H, —P(=O)(OH)$_2$, —SO$_3$H; $R_5$ is selected from —COCH$_3$, —COCF$_3$, —SO$_2$CH$_3$; X is selected from —O— and —S—; Y is selected from

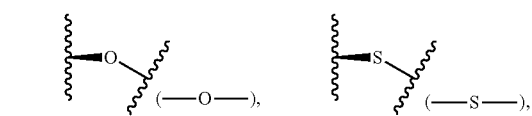

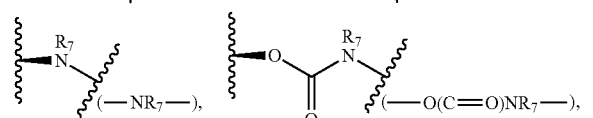

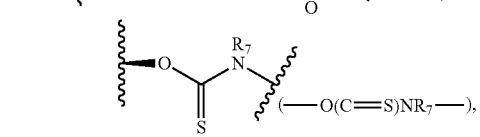

428

-continued

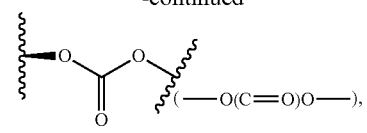(—O(C=O)O—),

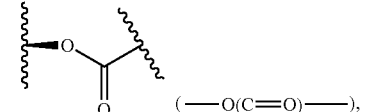(—O(C=O)—),

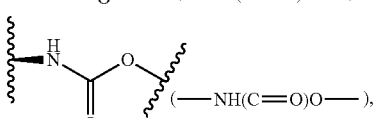(—NH(C=O)O—),

(—NH(C=O)—),

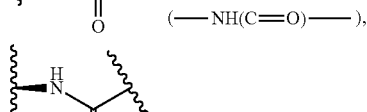(—NH(C=NH)—),

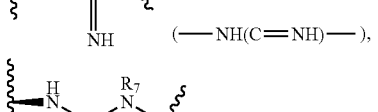(—NH(C=O)NR$_7$—),

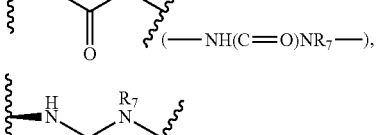(—NH(C=NH)NR$_7$—),

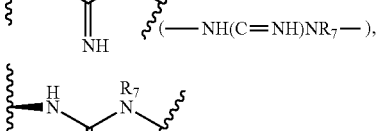(—NH(C=S)NR$_7$—),

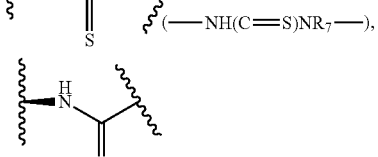(—NH(C=S)—),

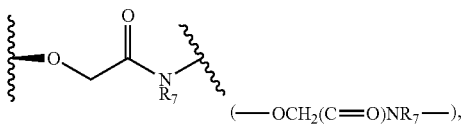(—OCH$_2$(C=O)NR$_7$—),

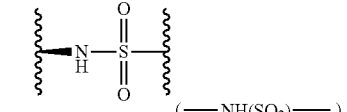(—NH(SO$_2$)—),

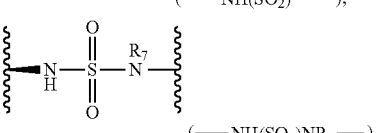(—NH(SO$_2$)NR$_7$—),

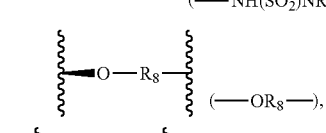(—OR$_8$—),

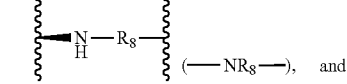(—NR$_8$—), and

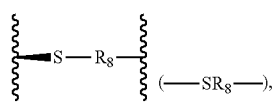
$R_6$ is selected from
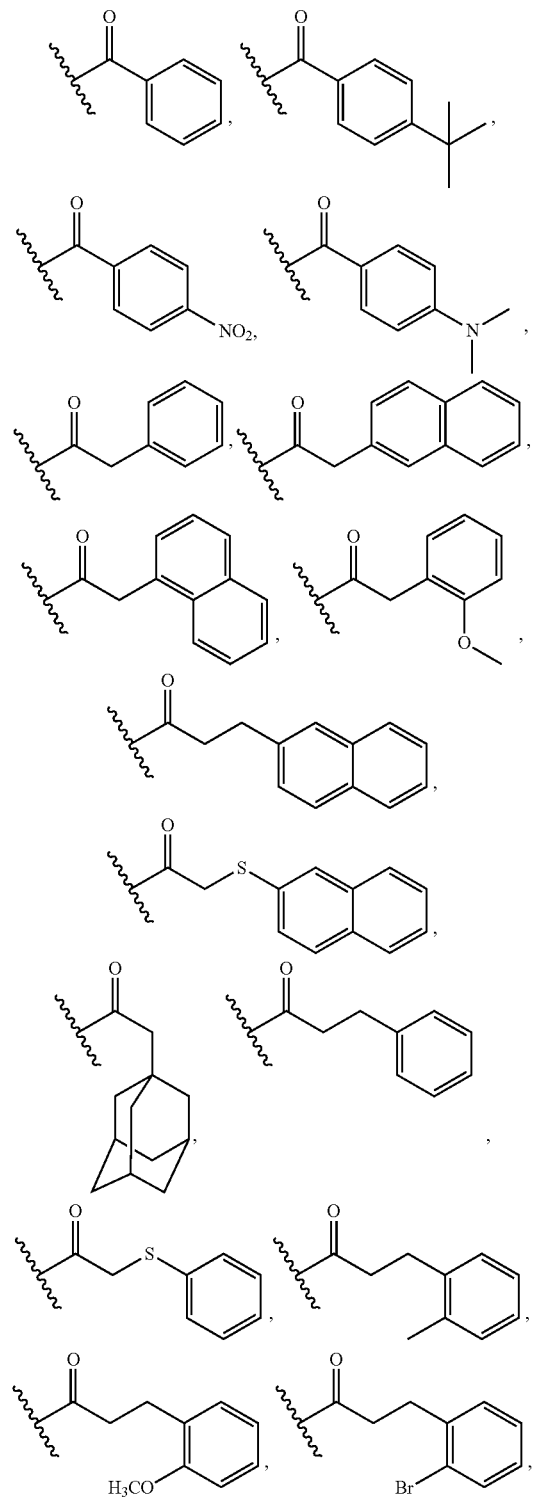
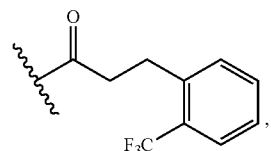
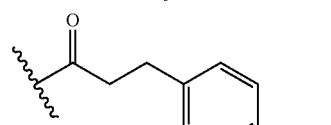
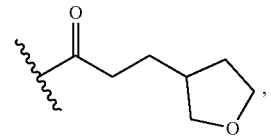
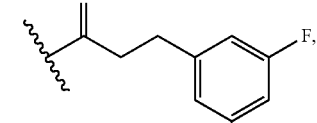
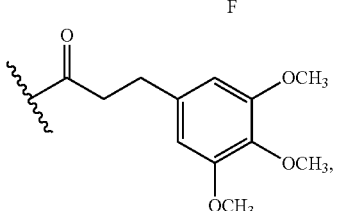
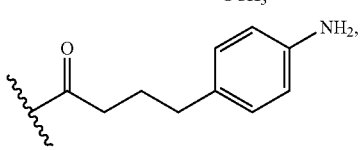
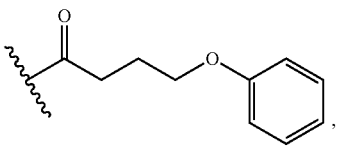
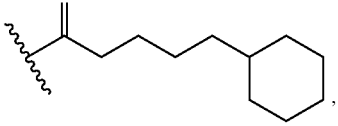
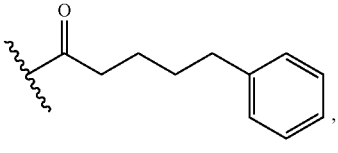
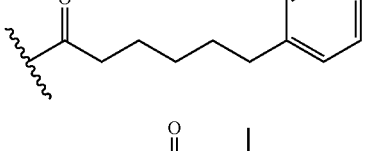
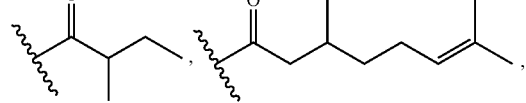

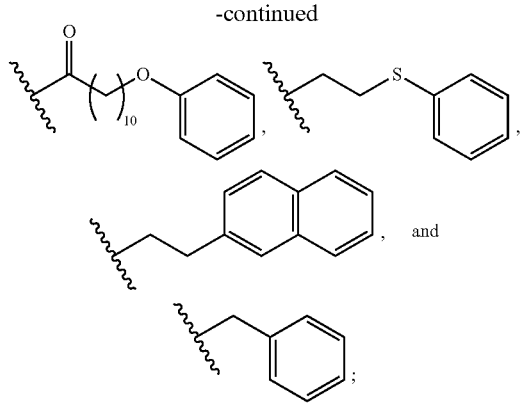

R$_7$ is selected from H, C1-C20 alkyl, C3-C20 cycloalkyl, C3-C20 heterocycloalkyl; C5-C15 aryl, and C2-C15 heteroaryl; and R$_8$ is selected from C3-C20 heterocycloalkyl, C5-C15 aryl, and C2-C15 heteroaryl; R$_9$ is selected from —H, a halogen (e.g., Cl, F, or Br), —OR$_{10}$, —NHC(=O)R$_7$, optionally substituted C1-C20 alkyl, C3-C20 cycloalkyl, C3-C20 heterocycloalkyl; C5-C15 aryl, and C2-C15 heteroaryl; and R$_{10}$ is selected from C1-C20 alkyl, C3-C20 cycloalkyl, C3-C20 heterocycloalkyl; C5-C15 aryl, and C2-C15 heteroaryl.

The term "inhibits neuraminidase activity," as used herein refers to an IC$_{50}$ of less than or equal to 1,000 nM, for example, as measured in accordance with the neuraminidase inhibition assay in Example 2 herein. Specifically, the IC$_{50}$ represents the concentration of the influenza virus neuraminidase inhibitor that is required for 50% inhibition in vitro. In some aspects, an IC$_{50}$ of less than or equal to 100 nM or less than or equal to 10 nM in accordance with neuraminidase inhibition assay is indicative of a compound inhibiting neuraminidase activity.

By "viral infection" is meant the pathogenic growth of a virus (e.g., the influenza virus) in a host organism (e.g., a human subject). A viral infection can be any situation in which the presence of a viral population(s) is damaging to a host body. Thus, a subject is "suffering" from a viral infection when an excessive amount of a viral population is present in or on the subject's body, or when the presence of a viral population(s) is damaging the cells or other tissue of the subject.

As used herein, the term "Fc domain monomer" refers to a polypeptide chain that includes at least a hinge domain and second and third antibody constant domains (C$_H$2 and C$_H$3) or functional fragments thereof (e.g., fragments that that capable of (i) dimerizing with another Fc domain monomer to form an Fc domain, and (ii) binding to an Fc receptor. The Fc domain monomer can be any immunoglobulin antibody isotype, including IgG, IgE, IgM, IgA, or IgD (e.g., IgG). Additionally, the Fc domain monomer can be an IgG subtype (e.g., IgG1, IgG2a, IgG2b, IgG3, or IgG4) (e.g., IgG1). An Fc domain monomer does not include any portion of an immunoglobulin that is capable of acting as an antigen-recognition region, e.g., a variable domain or a complementarity determining region (CDR). Fc domain monomers in the conjugates as described herein can contain one or more changes from a wild-type Fc domain monomer sequence (e.g., 1-10, 1-8, 1-6, 1-4 amino acid substitutions, additions, or deletions) that alter the interaction between an Fc domain and an Fc receptor. Examples of suitable changes are known in the art. In certain embodiments, a human Fc domain monomer (e.g., an IgG heavy chain, such as IgG1) comprises a region that extends from any of Asn208, Glu216, Asp221, Lys222, or Cys226 to the carboxyl-terminus of the heavy chain at Lys447. C-terminal Lys447 of the Fc region may or may not be present, without affecting the structure or stability of the Fc region. C-terminal Lys 447 may be proteolytically cleaved upon expression of the polypeptide. In some embodiments of any of the Fc domain monomers described herein, C-terminal Lys 447 is optionally present or absent. The disclosure specifically contemplates any of SEQ ID NOs: 1-4, 11, 16, 19, 20, 32-37, 48-53, and 60-68 that do not include the C-terminal Lys corresponding to Lys447. The N-terminal N (Asn) of the Fc region (e.g., of any one of SEQ ID NOs: 60-77) may or may not be present, without affecting the structure of stability of the Fc region. N-terminal Asn may be deamidated upon expression of the polypeptide. In some embodiments of any of the Fc domain monomers described herein, N-terminal Asn is optionally present or absent. The disclosure specifically contemplates any of SEQ ID NOs: 60-77 that do not include the N-terminal Asn. Unless otherwise specified herein, numbering of amino acid residues in the IgG or Fc domain monomer is according to the EU numbering system for antibodies, also called the Kabat EU index, as described, for example, in Kabat et al., Sequences of Proteins of Immunological Interest, 5th Ed. Public Health Service, National Institutes of Health, Bethesda, Md., 1991.

As used herein, the term "Fc domain" refers to a dimer of two Fc domain monomers that is capable of binding an Fc receptor. In the wild-type Fc domain, the two Fc domain monomers dimerize by the interaction between the two C$_H$3 antibody constant domains, in some embodiments, one or more disulfide bonds form between the hinge domains of the two dimerizing Fc domain monomers. The term "covalently attached" refers to two parts of a conjugate that are linked to each other by a covalent bond formed between two atoms in the two parts of the conjugate.

As used herein, the term "Fc-binding peptide" refers to refers to a polypeptide having an amino acid sequence of 5 to 50 (e.g., 5 to 40, 5 to 30, 5 to 20, 5 to 15, 5 to 10, 10 to 50, 10 to 30, or 10 to 20) amino acid residues that has affinity for and functions to bind an Fc domain, such as any of the Fc domain described herein. An Fc-binding peptide can be of different origins, e.g., synthetic, human, mouse, or rat. Fc-binding peptides of the invention include Fc-binding peptides which have been engineered to include one or more (e.g., two, three, four, or five) solvent-exposed cysteine or lysine residues, which may provide a site for conjugation to a compound of the invention (e.g., conjugation to a neuraminidase inhibitor monomer or dimer, including by way of a linker). Most preferably, the Fc-binding peptide will contain a single solvent-exposed cysteine or lysine, thus enabling site-specific conjugation of a compound of the invention. Fc-binding peptides may include only naturally occurring amino acid residues, or may include one or more non-naturally occurring amino acid residues. Where included, a non-naturally occurring amino acid residue (e.g., the side chain of a non-naturally occurring amino acid residue) may be used as the point of attachment for a compound of the invention (e.g., a neuraminidase inhibitor monomer or dimer, including by way of a linker). Fc-binding peptides of the invention may be linear or cyclic. Fc-binding peptides of the invention include any Fc-binding peptides known to one of skill in the art.

As used here, the term "albumin protein" refers to a polypeptide comprising an amino acid sequence corresponding to a naturally-occurring albumin protein (e.g., human serum albumin) or a variant thereof, such as an engineered variant of a naturally-occurring albumin protein. Variants of albumin proteins include polymorphisms, fragments such as domains and sub-domains, and fusion proteins (e.g., an albumin protein having a C-terminal or N-terminal fusion, such as a polypeptide linker). Preferably the albumin protein has the amino acid sequence of human serum albumin (HSA) or a variant or fragment thereof, most preferably a functional variant or fragment thereof. Albumin proteins of the invention include proteins having at least 70%, 75%, 80%, 85%, 90%, 91%, 92%, 93%, 94%, 95%, 96%, 97%, 98%, or 99% identity to any one of SEQ ID NOs: 139-141. Albumin proteins of the invention include albumin proteins which have been engineered to include one or more (e.g., two, three, four, or five) solvent-exposed cysteine or lysine residues, which may provide a site for conjugation to a compound of the invention (e.g., conjugation to a neuraminidase inhibitor monomer or dimer, including by way of a linker). Most preferably, the albumin protein will contain a single solvent-exposed cysteine or lysine, thus enabling site-specific conjugation of a compound of the invention. Albumin proteins may include only naturally occurring amino acid residues, or may include one or more non-naturally occurring amino acid residues. Where included, a non-naturally occurring amino acid residue (e.g., the side chain of a non-naturally occurring amino acid residue) may be used as the point of attachment for a compound of the invention (e.g., a neuraminidase inhibitor monomer or dimer, including by way of a linker).

As used herein, the term "albumin protein-binding peptide" refers to a polypeptide having an amino acid sequence of 5 to 50 (e.g., 5 to 40, 5 to 30, 5 to 20, 5 to 15, 5 to 10, 10 to 50, 10 to 30, or 10 to 20) amino acid residues that has affinity for and functions to bind an albumin protein, such as any of the albumin proteins described herein. Preferably, the albumin protein-binding peptide binds to a naturally-occurring serum albumin, most preferably human serum albumin. An albumin protein-binding peptide can be of different origins, e.g., synthetic, human, mouse, or rat. Albumin protein-binding peptides of the invention include albumin protein-binding peptides which have been engineered to include one or more (e.g., two, three, four, or five) solvent-exposed cysteine or lysine residues, which may provide a site for conjugation to a compound of the invention (e.g., conjugation to a neuraminidase inhibitor monomer or dimer, including by way of a linker). Most preferably, the albumin protein-binding peptide will contain a single solvent-exposed cysteine or lysine, thus enabling site-specific conjugation of a compound of the invention. Albumin protein-binding peptides may include only naturally occurring amino acid residues, or may include one or more non-naturally occurring amino acid residues. Where included, a non-naturally occurring amino acid residue (e.g., the side chain of a non-naturally occurring amino acid residue) may be used as the point of attachment for a compound of the invention (e.g., a neuraminidase inhibitor monomer or dimer, including by way of a linker). Albumin protein-binding peptides of the invention may be linear or cyclic. Albumin protein-binding peptide of the invention include any albumin protein-binding peptides known to one of skill in the art, examples of which, are provided herein. Further exemplary albumin protein-binding peptides are provided in U.S. Patent Application No. 2005/0287153, which is incorporated herein by reference in its entirety.

As used-herein, a "surface exposed amino acid" or "solvent-exposed amino acid," such as a surface exposed cysteine or a surface exposed lysine refers to an amino acid that is accessible to the solvent surrounding the protein. A surface exposed amino acid may be a naturally-occurring or an engineered variant (e.g., a substitution or insertion) of the protein. In some embodiments, a surface exposed amino acid is an amino acid that when substituted does not substantially change the three-dimensional structure of the protein.

The terms "linker," "L," and "L'," as used herein, refer to a covalent linkage or connection between two or more components in a conjugate (e.g., between two neuraminidase inhibitors in a conjugate described herein, between a neuraminidase inhibitor and an Fc domain or albumin protein in a conjugate described herein, and between a dimer of two neuraminidase inhibitors and an Fc domain or an albumin protein in a conjugate described herein). In some embodiments, a conjugate described herein may contain a linker that has a trivalent structure (e.g., a trivalent linker). A trivalent linker has three arms, in which each arm is covalently linked to a component of the conjugate (e.g., a first arm conjugated to a first neuraminidase inhibitor, a second arm conjugated to a second neuraminidase inhibitor, and a third arm conjugated to an Fc domain or an albumin protein).

Molecules that may be used as linkers include at least two functional groups, which may be the same or different, e.g., two carboxylic acid groups, two amine groups, two sulfonic acid groups, a carboxylic acid group and a maleimide group, a carboxylic acid group and an alkyne group, a carboxylic acid group and an amine group, a carboxylic acid group and a sulfonic acid group, an amine group and a maleimide group, an amine group and an alkyne group, or an amine group and a sulfonic acid group. The first functional group may form a covalent linkage with a first component in the conjugate and the second functional group may form a covalent linkage with the second component in the conjugate. In some embodiments of a trivalent linker, two arms of a linker may contain two dicarboxylic acids, in which the first carboxylic acid may form a covalent linkage with the first neuraminidase inhibitor in the conjugate and the second carboxylic acid may form a covalent linkage with the second neuraminidase inhibitor in the conjugate, and the third arm of the linker may for a covalent linkage with an Fc domain or albumin protein in the conjugate. Examples of dicarboxylic acids are described further herein. In some embodiments, a molecule containing one or more maleimide groups may be used as a linker, in which the maleimide group may form a carbon-sulfur linkage with a cysteine in a component (e.g., an Fc domain or an albumin protein) in the conjugate. In some embodiments, a molecule containing one or more alkyne groups may be used as a linker, in which the alkyne group may form a 1,2,3-triazole linkage with an azide in a component (e.g., an Fc domain or an albumin protein) in the conjugate. In some embodiments, a molecule containing one or more azide groups may be used as a linker, in which the azide group may form a 1,2,3-triazole linkage with an alkyne in a component (e.g., an Fc domain or an albumin protein) in the conjugate. In some embodiments, a molecule containing one or more bis-sulfone groups may be used as a linker, in which the bis-sulfone group may form a linkage with an amine group a component (e.g., an Fc domain or an albumin protein) in the conjugate. In some embodiments, a molecule containing one or more sulfonic acid groups may be used as a linker, in which the sulfonic acid group may form a sulfonamide linkage with a component in the conjugate. In some embodiments, a molecule containing one or more isocyanate groups may be used as a linker, in which the isocyanate group may form a urea linkage with a component in the conjugate. In some embodiments, a molecule containing one or more haloalkyl groups may be used as a linker, in which the haloalkyl group may form a covalent linkage, e.g., C—N and C—O linkages, with a component in the conjugate.

In some embodiments, a linker provides space, rigidity, and/or flexibility between the two or more components. In some embodiments, a linker may be a bond, e.g., a covalent bond. The term "bond" refers to a chemical bond, e.g., an amide bond, a disulfide bond, a C—O bond, a C—N bond, a N—N bond, a C—S bond, or any kind of bond created from a chemical reaction, e.g., chemical conjugation. In some embodiments, a linker includes no more than 250 atoms. In some embodiments, a linker includes no more than 250 non-hydrogen atoms. In some embodiments, the backbone of a linker includes no more than 250 atoms. The "backbone" of a linker refers to the atoms in the linker that together form the shortest path from one part of a conjugate to another part of the conjugate (e.g., the shortest path linking a first neuraminidase inhibitor and a second neuraminidase inhibitor). The atoms in the backbone of the linker are directly involved in linking one part of a conjugate to another part of the conjugate (e.g., linking a first neuraminidase inhibitor and a second neuraminidase inhibitor). For examples, hydrogen atoms attached to carbons in the backbone of the linker are not considered as directly involved in linking one part of the conjugate to another part of the conjugate.

In some embodiments, a linker may comprise a synthetic group derived from, e.g., a synthetic polymer (e.g., a polyethylene glycol (PEG) polymer). In some embodiments, a linker may comprise one or more amino acid residues, such as D- or L-amino acid residues. In some embodiments, a linker may be a residue of an amino acid sequence (e.g., a 1-25 amino acid, 1-10 amino acid, 1-9 amino acid, 1-8 amino acid, 1-7 amino acid, 1-6 amino acid, 1-5 amino acid, 1-4 amino acid, 1-3 amino acid, 1-2 amino acid, or 1 amino acid sequence). In some embodiments, a linker may comprise one or more, e.g., 1-100, 1-50, 1-25, 1-10, 1-5, or 1-3, optionally substituted alkylene, optionally substituted heteroalkylene (e.g., a PEG unit), optionally substituted alkenylene, optionally substituted heteroalkenylene, optionally substituted alkynylene, optionally substituted heteroalkynylene, optionally substituted cycloalkylene, optionally substituted heterocycloalkylene, optionally substituted cycloalkenylene, optionally substituted heterocycloalkenylene, optionally substituted cycloalkynylene, optionally substituted heterocycloalkynylene, optionally substituted arylene, optionally substituted heteroarylene (e.g., pyridine), O, S, $NR^i$ ($R^i$ is H, optionally substituted alkyl, optionally substituted heteroalkyl, optionally substituted alkenyl, optionally substituted heteroalkenyl, optionally substituted alkynyl, optionally substituted heteroalkynyl, optionally substituted cycloalkyl, optionally substituted heterocycloalkyl, optionally substituted cycloalkenyl, optionally substituted heterocycloalkenyl, optionally substituted cycloalkynyl, optionally substituted heterocycloalkynyl, optionally substituted aryl, or optionally substituted heteroaryl), P, carbonyl, thiocarbonyl, sulfonyl, phosphate, phosphoryl, or imino. For example, a linker may comprise one or more optionally substituted C1-C20 alkylene, optionally substituted C1-C20 heteroalkylene (e.g., a PEG unit), optionally substituted C2-C20 alkenylene (e.g., C2 alkenylene), optionally substituted C2-C20 heteroalkenylene, optionally substituted C2-C20 alkynylene, optionally substituted C2-C20 heteroalkynylene, optionally substituted C3-C20 cycloalkylene (e.g., cyclopropylene, cyclobutylene), optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene (e.g., C6 arylene), optionally substituted C2-C15 heteroarylene (e.g., imidazole, pyridine), O, S, $NR^i$ ($R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl), P, carbonyl, thiocarbonyl, sulfonyl, phosphate, phosphoryl, or imino.

The terms "alkyl," "alkenyl," and "alkynyl," as used herein, include straight-chain and branched-chain monovalent substituents, as well as combinations of these, containing only C and H when unsubstituted. When the alkyl group includes at least one carbon-carbon double bond or carbon-carbon triple bond, the alkyl group can be referred to as an "alkenyl" or "alkynyl" group respectively. The monovalency of an alkyl, alkenyl, or alkynyl group does not include the optional substituents on the alkyl, alkenyl, or alkynyl group. For example, if an alkyl, alkenyl, or alkynyl group is attached to a compound, monovalency of the alkyl, alkenyl, or alkynyl group refers to its attachment to the compound and does not include any additional substituents that may be present on the alkyl, alkenyl, or alkynyl group. In some embodiments, the alkyl or heteroalkyl group may contain, e.g., 1-20. 1-18, 1-16, 1-14, 1-12, 1-10, 1-8, 1-6, 1-4, or 1-2 carbon atoms (e.g., C1-C20, C1-C18, C1-C16, C1-C14, C1-C12, C1-C10, C1-C8, C1-C6, C1-C4, or C1-C2). In some embodiments, the alkenyl, heteroalkenyl, alkynyl, or heteroalkynyl group may contain, e.g., 2-20, 2-18, 2-16, 2-14, 2-12, 2-10, 2-8, 2-6, or 2-4 carbon atoms (e.g., C2-C20, C2-C18, C2-C16, C2-C14, C2-C12, C2-C10, C2-C8, C2-C6, or C2-C4). Examples include, but are not limited to, methyl, ethyl, isobutyl, sec-butyl, tert-butyl, 2-propenyl, and 3-butynyl.

The term "cycloalkyl," as used herein, represents a monovalent saturated or unsaturated non-aromatic cyclic alkyl group. A cycloalkyl may have, e.g., three to twenty carbons (e.g., a C3-C7, C3-C8, C3-C9, C3-C10, C3-C11, C3-C12, C3-C14, C3-C16, C3-C18, or C3-C20 cycloalkyl). Examples of cycloalkyls include, but are not limited to, cyclopropyl, cyclobutyl, cyclopentyl, cyclohexyl, and cycloheptyl. When the cycloalkyl group includes at least one carbon-carbon double bond, the cycloalkyl group can be referred to as a "cycloalkenyl" group. A cycloalkenyl may have, e.g., four to twenty carbons (e.g., a C4-C7, C4-C8, C4-C9, C4-C10, C4-C11, C4-C12, C4-C14, C4-C16, C4-C18, or C4-C20 cycloalkenyl). Exemplary cycloalkenyl groups include, but are not limited to, cyclopentenyl, cyclohexenyl, and cycloheptenyl. When the cycloalkyl group includes at least one carbon-carbon triple bond, the cycloalkyl group can be referred to as a "cycloalkynyl" group. A cycloalkynyl may have, e.g., eight to twenty carbons (e.g., a C8-C9, C8-C10, C8-C11, C8-C12, C8-C14, C8-C16, C8-C18, or C8-C20 cycloalkynyl). The term "cycloalkyl" also includes a cyclic compound having a bridged multicyclic structure in which one or more carbons bridges two non-adjacent members of a monocyclic ring, e.g., bicyclo [2.2.1.]heptyl and adamantane. The term "cycloalkyl" also includes bicyclic, tricyclic, and tetracyclic fused ring structures, e.g., decalin and spiro cyclic compounds.

The term "aryl," as used herein, refers to any monocyclic or fused ring bicyclic or tricyclic system which has the characteristics of aromaticity in terms of electron distribution throughout the ring system, e.g., phenyl, naphthyl, or phenanthrene. In some embodiments, a ring system contains 5-15 ring member atoms or 5-10 ring member atoms. An aryl group may have, e.g., five to fifteen carbons (e.g., a C5-C6, C5-C7, C5-C8, C5-C9, C5-C10, C5-C11, C5-C12, C5-C13, C5-C14, or C5-C15 aryl). The term "heteroaryl" also refers to such monocyclic or fused bicyclic ring systems containing one or more, e.g., 1-4, 1-3, 1, 2, 3, or 4, heteroatoms selected from O, S and N. A heteroaryl group may have, e.g., two to fifteen carbons (e.g., a C2-C3, C2-C4, C2-C5, C2-C6, C2-C7, C2-C8, C2-C9. C2-C10, C2-C11, C2-C12, C2-C13, C2-C14, or C2-C15 heteroaryl). The inclusion of a heteroatom permits inclusion of 5-membered rings to be considered aromatic as well as 6-membered rings. Thus, typical heteroaryl systems include, e.g., pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, isoxazolyl, benzoxazolyl, benzoisoxazolyl, and imidazolyl. Because tautomers are possible, a group such as phthalimido is also considered heteroaryl. In some embodiments, the aryl or heteroaryl group is a 5- or 6-membered aromatic rings system optionally containing 1-2 nitrogen atoms. In some embodiments, the aryl or heteroaryl group is an optionally substituted phenyl, pyridyl, indolyl, pyrimidyl, pyridazinyl, benzothiazolyl, benzimidazolyl, pyrazolyl, imidazolyl, isoxazolyl, thiazolyl, or imidazopyridinyl. In some embodiments, the aryl group is phenyl. In some embodiments, an aryl group may be optionally substituted with a substituent such an aryl substituent, e.g., biphenyl.

The term "alkaryl," refers to an aryl group that is connected to an alkylene, alkenylene, or alkynylene group. In general, if a compound is attached to an alkaryl group, the alkylene, alkenylene, or alkynylene portion of the alkaryl is attached to the compound. In some embodiments, an alkaryl is C6-C35 alkaryl (e.g., C6-C16, C6-C14, C6-C12, C6-C10, C6-C9, C6-C8, C7, or C6 alkaryl), in which the number of carbons indicates the total number of carbons in both the aryl portion and the alkylene, alkenylene, or alkynylene portion of the alkaryl. Examples of alkaryls include, but are not limited to, (C1-C8)alkylene(C6-C12)aryl, (C2-C8)alkenylene(C6-C12)aryl, or (C2-C8)alkynylene(C6-C12)aryl. In some embodiments, an alkaryl is benzyl or phenethyl. In a heteroalkaryl, one or more heteroatoms selected from N, O, and S may be present in the alkylene, alkenylene, or alkynylene portion of the alkaryl group and/or may be present in the aryl portion of the alkaryl group. In an optionally substituted alkaryl, the substituent may be present on the alkylene, alkenylene, or alkynylene portion of the alkaryl group and/or may be present on the aryl portion of the alkaryl group.

The term "amino," as used herein, represents —N($R^x$)$_2$ or —N$^+$($R^x$)$_3$, where each $R^x$ is, independently, H, alkyl, alkenyl, alkynyl, aryl, alkaryl, cycloalkyl, or two $R^x$ combine to form a heterocycloalkyl. In some embodiment, the amino group is —NH$_2$.

The term "alkamino," as used herein, refers to an amino group, described herein, that is attached to an alkylene (e.g., C1-C5 alkylene), alkenylene (e.g., C2-C5 alkenylene), or alkynylene group (e.g., C2-C5 alkenylene). In general, if a compound is attached to an alkamino group, the alkylene, alkenylene, or alkynylene portion of the alkamino is attached to the compound. The amino portion of an alkamino refers to —N($R^x$)$_2$ or —N$^+$($R^x$)$_3$, where each $R^x$ is, independently, H, alkyl, alkenyl, alkynyl, aryl, alkaryl, cycloalkyl, or two $R^x$ combine to form a heterocycloalkyl. In some embodiment, the amino portion of an alkamino is —NH$_2$. An example of an alkamino group is C1-C5 alkamino, e.g., C2 alkamino (e.g., CH$_2$CH$_2$NH$_2$ or CH$_2$CH$_2$N(CH$_3$)$_2$). In a heteroalkamino group, one or more, e.g., 1-4, 1-3, 1, 2, 3, or 4, heteroatoms selected from N, O, and S may be present in the alkylene, alkenylene, or alkynylene portion of the heteroalkamino group. In some embodiments, an alkamino group may be optionally substituted. In a substituted alkamino group, the substituent may be present on the alkylene, alkenylene, or alkynylene portion of the alkamino group and/or may be present on the amino portion of the alkamino group. The term "alkamide," as used herein, refers to an amide group that is attached to an alkylene (e.g., C1-C5 alkylene), alkenylene (e.g., C2-C5 alkenylene), or alkynylene (e.g., C2-C5 alkenylene) group. In general, if a compound is attached to an alkamide group, the alkylene, alkenylene, or alkynylene portion of the alkamide is attached to the compound. The amide portion of an alkamide refers to —C(O)—N($R^x$)$_2$, where each $R^x$ is, independently, H, alkyl, alkenyl, alkynyl, aryl, alkaryl, cycloalkyl, or two $R^x$ combine to form a heterocycloalkyl. In some embodiment, the amide portion of an alkamide is —C(O)NH$_2$. An alkamide group may be —(CH$_2$)$_2$—C(O)NH$_2$ or —CH$_2$—C(O)NH$_2$. In a heteroalkamide group, one or more, e.g., 1-4, 1-3, 1, 2, 3, or 4, heteroatoms selected from N, O, and S may be present in the alkylene, alkenylene, or alkynylene portion of the heteroalkamide group. In some embodiments, an alkamide group may be optionally substituted. In a substituted alkamide group, the substituent may be present on the alkylene, alkenylene, or alkynylene portion of the alkamide group and/or may be present on the amide portion of the alkamide group.

The terms "alkylene," "alkenylene," and "alkynylene," as used herein, refer to divalent groups having a specified size. In some embodiments, an alkylene may contain, e.g., 1-20, 1-18, 1-16, 1-14, 1-12, 1-10, 1-8, 1-6, 1-4, or 1-2 carbon atoms (e.g., C1-C20, C1-C18, C1-C16, C1-C14, C1-C12, C1-C10, C1-C8, C1-C6, C1-C4, or C1-C2). In some embodiments, an alkenylene or alkynylene may contain, e.g., 2-20, 2-18, 2-16, 2-14, 2-12, 2-10, 2-8, 2-6, or 2-4 carbon atoms (e.g., C2-C20, C2-C18, C2-C16, C2-C14, C2-C12, C2-C10, C2-C8, C2-C6, or C2-C4). Alkylene, alkenylene, and/or alkynylene includes straight-chain and branched-chain forms, as well as combinations of these. The divalency of an alkylene, alkenylene, or alkynylene group does not include the optional substituents on the alkylene, alkenylene, or alkynylene group. For example, two neuraminidase inhibitors may be attached to each other by way of a linker that includes alkylene, alkenylene, and/or alkynylene, or combinations thereof. Each of the alkylene, alkenylene, and/or alkynylene groups in the linker is considered divalent with respect to the two attachments on either end of alkylene, alkenylene, and/or alkynylene group. For example, if a linker includes -(optionally substituted alkylene)-(optionally substituted alkenylene)-(optionally substituted alkylene)-, the alkenylene is considered divalent with respect to its attachments to the two alkylenes at the ends of the linker. The optional substituents on the alkenylene are not included in the divalency of the alkenylene. The divalent nature of an alkylene, alkenylene, or alkynylene group (e.g., an alkylene, alkenylene, or alkynylene group in a linker) refers to both of the ends of the group and does not include optional substituents that may be present in an alkylene, alkenylene, or alkynylene group. Because they are divalent, they can link together multiple (e.g., two) parts of a conjugate, e.g., a first neuraminidase inhibitor and a second neuraminidase inhibitor. Alkylene, alkenylene, and/or alkynylene groups can be substituted by the groups typically suitable as substituents for alkyl, alkenyl and alkynyl groups as set forth herein. For example, C=O is a C1 alkylene that is substituted by an oxo (=O). For example, —HCR—C=C— may be considered as an optionally substituted alkynylene and is considered a divalent group even though it has an optional substituent, R. Heteroalkylene, heteroalkenylene, and/or heteroalkynylene groups refer to alkylene, alkenylene, and/or alkynylene groups including one or more, e.g., 1-4, 1-3, 1, 2, 3, or 4, heteroatoms, e.g., N, O, and S. For example, a polyethylene glycol (PEG) polymer or a PEG unit —(CH$_2$)$_2$—O— in a PEG polymer is considered a heteroalkylene containing one or more oxygen atoms.

As used herein, a "combination therapy" or "administered in combination" means that a conjugate described herein (e.g., a conjugate of any one of formulas (1)-(5), (D-I)-(D-XI), (D'-I), (M-I)-(M-XI), or (M'-I)) and one (or more) different agents or treatments are administered to a subject as part of a defined treatment regimen for a viral infection. The treatment regimen defines the doses and periodicity of administration of each agent such that the effects of the separate agents on the subject overlap. In some embodiments, the delivery of the conjugate and the one or more agents is simultaneous or concurrent and the conjugate and the one or more agents may be co-formulated. In some embodiments, the conjugate and the one or more agents are not co-formulated and are administered in a sequential manner as part of a prescribed regimen. In some embodiments, administration of the conjugate and the one or more agents or treatments in combination is such that the reduction in a symptom, or other parameter related to the viral infection, is greater than what would be observed with one agent or treatment delivered alone or in the absence of the other. The effect of the conjugate and the one or more agents can be partially additive, wholly additive, or greater than additive (e.g., synergistic). Sequential or substantially simultaneous administration of each therapeutic agent can be by any appropriate route including, but not limited to, oral routes, intravenous routes, intramuscular routes, and direct absorption through mucous membrane tissues. The therapeutic agents can be administered by the same route or by different routes. For example, a conjugate described herein may be administered by intravenous injection while a second therapeutic agent of the combination may be administered orally.

The term "cycloalkylene," as used herein, refers to a divalent cyclic group linking together two parts of a compound. For example, one carbon within the cycloalkylene group may be linked to one part of the compound, while another carbon within the cycloalkylene group may be linked to another part of the compound. A cycloalkylene group may include saturated or unsaturated non-aromatic cyclic groups. A cycloalkylene may have, e.g., three to twenty carbons in the cyclic portion of the cycloalkylene (e.g., a C3-C7, C3-C8, C3-C9, C3-C10, C3-C11, C3-C12, C3-C14, C3-C16, C3-C18, or C3-C20 cycloalkylene). When the cycloalkylene group includes at least one carbon-carbon double bond, the cycloalkylene group can be referred to as a "cycloalkenylene" group. A cycloalkenylene may have, e.g., four to twenty carbons in the cyclic portion of the cycloalkenylene (e.g., a C4-C7, C4-C8, C4-C9. C4-C10, C4-C11, C4-C12, C4-C14, C4-C16, C4-C18, or C4-C20 cycloalkenylene). When the cycloalkenylene group includes at least one carbon-carbon triple bond, the cycloalkylene group can be referred to as a "cycloalkynylene" group. A cycloalkynylene may have, e.g., four to twenty carbons in the cyclic portion of the cycloalkynylene (e.g., a C4-C7, C4-C8, C4-C9. C4-C10, C4-C11, C4-C12, C4-C14, C4-C16, C4-C18, or C8-C20 cycloalkynylene). A cycloalkylene group can be substituted by the groups typically suitable as substituents for alkyl, alkenyl and alkynyl groups as set forth herein. Heterocycloalkylene refers to a cycloalkylene group including one or more, e.g., 1-4, 1-3, 1, 2, 3, or 4, heteroatoms, e.g., N, O, and S. Examples of cycloalkylenes include, but are not limited to, cyclopropylene and cyclobutylene. A tetrahydrofuran may be considered as a heterocycloalkylene.

The term "arylene," as used herein, refers to a multivalent (e.g., divalent or trivalent) aryl group linking together multiple (e.g., two or three) parts of a compound. For example, one carbon within the arylene group may be linked to one part of the compound, while another carbon within the arylene group may be linked to another part of the compound. An arylene may have, e.g., five to fifteen carbons in the aryl portion of the arylene (e.g., a C5-C6, C5-C7, C5-C8, C5-C9. C5-C10, C5-C11, C5-C12, C5-C13, C5-C14, or C5-C15 arylene). An arylene group can be substituted by the groups typically suitable as substituents for alkyl, alkenyl and alkynyl groups as set forth herein. Heteroarylene refers to an aromatic group including one or more, e.g., 1-4, 1-3, 1, 2, 3, or 4, heteroatoms, e.g., N, O, and S. A heteroarylene group may have, e.g., two to fifteen carbons (e.g., a C2-C3, C2-C4, C2-C5, C2-C6, C2-C7, C2-C8, C2-C9. C2-C10, C2-C11, C2-C12, C2-C13, C2-C14, or C2-C15 heteroarylene).

The term "optionally substituted," as used herein, refers to having 0, 1, or more substituents, such as 0-25, 0-20, 0-10 or 0-5 substituents. Substituents include, but are not limited to, alkyl, alkenyl, alkynyl, aryl, alkaryl, acyl, heteroaryl, heteroalkyl, heteroalkenyl, heteroalkynyl, heteroalkaryl, halogen, oxo, cyano, nitro, amino, alkamino, hydroxy, alkoxy, alkanoyl, carbonyl, carbamoyl, guanidinyl, ureido, amidinyl, any of the groups or moieties described above, and hetero versions of any of the groups or moieties described above. Substituents include, but are not limited to, F, Cl, methyl, phenyl, benzyl, OR, NR$_2$, SR, SOR, SO$_2$R, OCOR, NRCOR, NRCONR$_2$, NRCOOR, OCONR$_2$, RCO, COOR, alkyl-OOCR, SO$_3$R, CONR$_2$, SO$_2$NR$_2$, NRSO$_2$NR$_2$, CN, CF$_3$, OCF$_3$, SiR$_3$, and NO$_2$, wherein each R is, independently, H, alkyl, alkenyl, aryl, heteroalkyl, heteroalkenyl, or heteroaryl, and wherein two of the optional substituents on the same or adjacent atoms can be joined to form a fused, optionally substituted aromatic or nonaromatic, saturated or unsaturated ring which contains 3-8 members, or two of the optional substituents on the same atom can be joined to form an optionally substituted aromatic or nonaromatic, saturated or unsaturated ring which contains 3-8 members.

An optionally substituted group or moiety refers to a group or moiety (e.g., any one of the groups or moieties described above) in which one of the atoms (e.g., a hydrogen atom) is optionally replaced with another substituent. For example, an optionally substituted alkyl may be an optionally substituted methyl, in which a hydrogen atom of the methyl group is replaced by, e.g., OH. As another example, a substituent on a heteroalkyl or its divalent counterpart, heteroalkylene, may replace a hydrogen on a carbon or a hydrogen on a heteroatom such as N. For example, the hydrogen atom in the group —R—NH—R— may be substituted with an alkamide substituent, e.g., —R—N[(CH$_2$C (O)N(CH$_3$)$_2$]—R. Generally, an optional substituent is a noninterfering substituent. A "noninterfering substituent" refers to a substituent that leaves the ability of the conjugates described herein (e.g., conjugates of any one of formulas (1)-(5), (D-I)-(D-XI), (D'-I), (M-I)-(M-XI), or (M'-I)) to either bind to viral neuraminidase or to inhibit the proliferation of influenza virus. Thus, in some embodiments, the substituent may alter the degree of such activity. However, as long as the conjugate retains the ability to bind to viral neuraminidase or to inhibitor viral proliferation, the substituent will be classified as "noninterfering." For example, the noninterfering substituent would leave the ability of the compound to provide antiviral efficacy based on an IC50 value of 10 µM or less in a viral plaque reduction assay, such as in Example 2 based on an IC50 value against influenza virus neuraminidase of less than 500 nM. Thus, the substituent may alter the degree of inhibition based on plaque reduction or influenza virus neuraminidase inhibition. However, as long as the compounds herein such as compounds of formulas (A-I), (A-II), (A-III), (A-IV), (A-V), (A-VI), (A-VII), (A-VIII), (A-IX), (A-X), (A-XI), (A-XII), and (A-XIII) retain the ability to inhibit influenza virus neuraminidase activity, the substituent will be classified as "noninterfering." A number of assays for determining viral plaque reduction or the ability of any compound to inhibit influenza virus neuraminidase are available in the art, and some are exemplified in the Examples below.

The term "hetero," when used to describe a chemical group or moiety, refers to having at least one heteroatom that is not a carbon or a hydrogen, e.g., N, O, and S. Any one of the groups or moieties described above may be referred to as hetero if it contains at least one heteroatom. For example, a heterocycloalkyl, heterocycloalkenyl, or heterocycloalkynyl group refers to a cycloalkyl, cycloalkenyl, or cycloalkynyl group that has one or more heteroatoms independently selected from, e.g., N, O, and S. An example of a heterocycloalkenyl group is a maleimido. For example, a heteroaryl group refers to an aromatic group that has one or more heteroatoms independently selected from, e.g., N, O, and S. One or more heteroatoms may also be included in a substituent that replaced a hydrogen atom in a group or moiety as described herein. For example, in an optionally substituted heteroaryl group, if one of the hydrogen atoms in the heteroaryl group is replaced with a substituent (e.g., methyl), the substituent may also contain one or more heteroatoms (e.g., methanol).

The term "acyl," as used herein, refers to a group having the structure:

wherein R$^z$ is an optionally substituted alkyl, alkenyl, alkynyl, cycloalkyl, cycloalkenyl, cycloalkynyl, aryl, alkaryl, alkamino, heteroalkyl, heteroalkenyl, heteroalkynyl, heterocycloalkyl, heterocycloalkenyl, heterocycloalkynyl, heteroaryl, heteroalkaryl, or heteroalkamino.

The term "halo" or "halogen," as used herein, refers to any halogen atom, e.g., F, Cl, Br, or I. Any one of the groups or moieties described herein may be referred to as a "halo moiety" if it contains at least one halogen atom, such as haloalkyl.

The term "hydroxyl," as used herein, represents an —OH group.

The term "oxo," as used herein, refers to a substituent having the structure =O, where there is a double bond between an atom and an oxygen atom.

The term "carbonyl," as used herein, refers to a group having the structure:

The term "thiocarbonyl," as used herein, refers to a group having the structure:

The term "phosphate," as used herein, represents the group having the structure:

The term "phosphoryl," as used herein, represents the group having the structure:

or

The term "sulfonyl," as used herein, represents the group having the structure:

The term "imino," as used herein, represents the group having the structure:

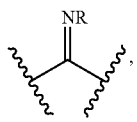

wherein R is an optional substituent.

The term "N-protecting group," as used herein, represents those groups intended to protect an amino group against undesirable reactions during synthetic procedures. Commonly used N-protecting groups are disclosed in Greene, "Protective Groups in Organic Synthesis," 5th Edition (John Wiley & Sons, New York, 2014), which is incorporated herein by reference. N-protecting groups include, e.g., acyl, aryloyl, and carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, carboxybenzyl (CBz), 4-chlorobenzoyl, 4-bromobenzoyl, 4-nitrobenzoyl, and chiral auxiliaries such as protected or unprotected D, L or D, L-amino acid residues such as alanine, leucine, phenylalanine; sulfonyl-containing groups such as benzenesulfonyl and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl (BOC), diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl (Fmoc), cyclopentyloxycarbonyl, adamantyloxycarbonyl, cyclohexyloxycarbonyl, and phenylthiocarbonyl; alkaryl groups such as benzyl, triphenylmethyl, and benzyloxymethyl; and silyl groups such as trimethylsilyl.

The term "amino acid," as used herein, means naturally occurring amino acids and non-naturally occurring amino acids.

The term "naturally occurring amino acids," as used herein, means amino acids including Ala, Arg, Asn, Asp, Cys, Gln, Glu, Gly, His, lie, Leu, Lys, Met, Phe, Pro, Ser, Thr, Trp, Tyr, and Val.

The term "non-naturally occurring amino acid," as used herein, means an alpha amino acid that is not naturally produced or found in a mammal. Examples of non-naturally occurring amino acids include D-amino acids; an amino acid having an acetylaminomethyl group attached to a sulfur atom of a cysteine; a pegylated amino acid; the omega amino acids of the formula $NH_2(CH_2)_nCOOH$ where n is 2-6, neutral nonpolar amino acids, such as sarcosine, t-butyl alanine, t-butyl glycine, N-methyl isoleucine, and norleucine; oxymethionine; phenylglycine; citrulline; methionine sulfoxide; cysteic acid; ornithine; diaminobutyric acid; 3-aminoalanine; 3-hydroxy-D-proline; 2,4-diaminobutyric acid; 2-aminopentanoic acid; 2-aminooctanoic acid, 2-carboxy piperazine; piperazine-2-carboxylic acid, 2-amino-4-phenylbutanoic acid; 3-(2-naphthyl)alanine, and hydroxyproline. Other amino acids are α-aminobutyric acid, α-amino-α-methylbutyrate, aminocyclopropane-carboxylate, aminoisobutyric acid, aminonorbornyl-carboxylate, L-cyclohexylalanine, cyclopentylalanine, L-N-methylleucine, L-N-methylmethionine, L-N-methylnorvaline, L-N-methylphenylalanine, L-N-methylproline, L-N-methylserine, L-N-methyltryptophan, D-ornithine, L-N-methylethylglycine, L-norleucine, α-methyl-aminoisobutyrate, α-methylcyclohexylalanine, D-α-methylalanine, D-α-methylarginine, D-α-methylasparagine, D-α-methylaspartate, D-α-methylcysteine, D-α-methylglutamine, D-α-methylhistidine, D-α-methylisoleucine, D-α-methylleucine, D-α-methyllysine, D-α-methylmethionine, D-α-methylornithine, D-α-methylphenylalanine, D-α-methylproline, D-α-methylserine, D-N-methylserine, D-α-methylthreonine, D-α-methyltryptophan, D-α-methyltyrosine, D-α-methylvaline, D-N-methylalanine, D-N-methylarginine, D-N-methylasparagine, D-N-methylaspartate, D-N-methylcysteine, D-N-methylglutamine, D-N-methylglutamate, D-N-methylhistidine, D-N-methylisoleucine, D-N-methylleucine, D-N-methyllysine, N-methylcyclohexylalanine, D-N-methylornithine, N-methylglycine, N-methyl-aminoisobutyrate, N-(1-methylpropyl)glycine, N-(2-methylpropyl)glycine, D-N-methyltryptophan, D-N-methyltyrosine, D-N-methylvaline, γ-aminobutyric acid, L-t-butylglycine, L-ethylglycine, L-homophenylalanine, L-α-methylarginine, L-α-methylaspartate, L-α-methylcysteine, L-α-methylglutamine, L-α-methylhistidine, L-α-methylisoleucine, L-α-methylleucine, L-α-methylmethionine, L-α-methylnorvaline, L-α-methylphenylalanine, L-α-methylserine, L-α-methyltryptophan, L-α-methylvaline, N-(N-(2,2-diphenylethyl) carbamylmethylglycine, 1-carboxy-1-(2,2-diphenyl-ethylamino) cyclopropane, 4-hydroxyproline, ornithine, 2-aminobenzoyl (anthraniloyl), D-cyclohexylalanine, 4-phenyl-phenylalanine, L-citrulline, α-cyclohexylglycine, L-1,2,3,4-tetrahydroisoquinoline-3-carboxylic acid, L-thiazolidine-4-carboxylic acid, L-homotyrosine, L-2-furylalanine, L-histidine (3-methyl), N-(3-guanidinopropyl)glycine, O-methyl-L-tyrosine, O-glycan-serine, meta-tyrosine, nor-tyrosine, L-N,N',N"-trimethyllysine, homolysine, norlysine, N-glycan asparagine, 7-hydroxy-1,2,3,4-tetrahydro-4-fluorophenylalanine, 4-methylphenylalanine, bis-(2-picolyl)amine, pentafluorophenylalanine, indoline-2-carboxylic acid, 2-aminobenzoic acid, 3-amino-2-naphthoic acid, asymmetric dimethylarginine, L-tetrahydroisoquinoline-1-carboxylic acid, D-tetrahydroisoquinoline-1-carboxylic acid, 1-amino-cyclohexane acetic acid, D/L-allylglycine, 4-aminobenzoic acid, 1-amino-cyclobutane carboxylic acid, 2 or 3 or 4-aminocyclohexane carboxylic acid, 1-amino-1-cyclopentane carboxylic acid, 1-aminoindane-1-carboxylic acid, 4-amino-pyrrolidine-2-carboxylic acid, 2-aminotetraline-2-carboxylic acid, azetidine-3-carboxylic acid, 4-benzyl-pyrolidine-2-carboxylic acid, tert-butylglycine, b-(benzothiazolyl-2-yl)-alanine, b-cyclopropyl alanine, 5,5-dimethyl-1,3-thiazolidine-4-carboxylic acid, (2R,4S)4-hydroxypiperidine-2-carboxylic acid, (2S,4S) and (2S,4R)-4-(2-naphthylmethoxy)-pyrolidine-2-carboxylic acid, (2S,4S) and (2S,4R)4-phenoxy-pyrrolidine-2-carboxylic acid, (2R, 5S) and (2S,5R)-5-phenyl-pyrrolidine-2-carboxylic acid, (2S,4S)-4-amino-1-benzoyl-pyrrolidine-2-carboxylic acid, t-butylalanine, (2S,5R)-5-phenyl-pyrrolidine-2-carboxylic acid, 1-aminomethyl-cyclohexane-acetic acid, 3,5-bis-(2-amino)ethoxy-benzoic acid, 3,5-diamino-benzoic acid, 2-methylamino-benzoic acid, N-methylanthranylic acid, L-N-methylalanine, L-N-methylarginine, L-N-methylasparagine, L-N-methylaspartic acid, L-N-methylcysteine, L-N-methylglutamine, L-N-methylglutamic acid, L-N-methylhistidine, L-N-methylisoleucine, L-N-methyllysine, L-N-methylnorleucine, L-N-methylornithine, L-N-methylthreonine, L-N-methyltyrosine, L-N-methylvaline, L-N-methyl-t-butylglycine, L-norvaline, α-methyl-γ-aminobutyrate, 4,4'-biphenylalanine, α-methylcylcopentylalanine, α-methyl-α-napthylalanine, α-methylpenicillamine, N-(4-aminobutyl)glycine, N-(2-aminoethyl)glycine, N-(3-aminopropyl)glycine, N-amino-α-methylbutyrate, α-napthylalanine, N-benzylglycine, N-(2-carbamylethyl)glycine, N-(carbamylmethyl)glycine, N-(2-carboxyethyl)glycine, N-(carboxymethyl)glycine, N-cyclobutylglycine, N-cyclodecylglycine, N-cycloheptylglycine, N-cyclohexylglycine, N-cyclodecylglycine, N-cylcododecylglycine, N-cyclooctylglycine, N-cyclopropylglycine, N-cycloundecylglycine, N-(2,2-diphenylethyl)glycine, N-(3,3-diphenylpropyl)glycine, N-(3-guanidinopropyl)glycine, N-(1-hydroxyethyl)glycine, N-(hydroxyethyl))glycine, N-(imidazolylethyl))glycine, N-(3-indolylyethyl)glycine, N-methyl-γ-aminobutyrate, D-N-methylmethionine, N-methylcyclopentylalanine, D-N-methylphenylalanine, D-N-methylproline, D-N-methylthreonine, N-(1-methylethyl)glycine, N-methyl-napthylalanine, N-methylpenicillamine, N-(p-hydroxyphenyl)glycine, N-(thiomethyl)glycine, penicillamine, L-α-methylalanine, L-α-methylasparagine, L-α-methyl-t-butylglycine, L-methylethylglycine, L-α-methylglutamate, L-α-methylhomophenylalanine, N-(2-methylthioethyl)glycine, L-α-methyllysine, L-α-methylnorleucine, L-α-methylornithine, L-α-methylproline, L-α-methylthreonine, L-α-methyltyrosine, L-N-methyl-homophenylalanine, N-(N-(3,3-diphenylpropyl) carbamylmethylglycine, L-pyroglutamic acid, D-pyroglutamic acid, O-methyl-L-serine, O-methyl-L-homoserine, 5-hydroxylysine, α-carboxyglutamate, phenylglycine, L-pipecolic acid (homoproline), L-homoleucine, L-lysine (dimethyl), L-2-naphthylalanine, L-dimethyldopa or L-dimethoxy-phenylalanine, L-3-pyridylalanine, L-histidine (benzoyloxymethyl), N-cycloheptylglycine, L-diphenylalanine, O-methyl-L-homotyrosine, L-β-homolysine, O-glycan-threoine, Ortho-tyrosine, L-N,N'-dimethyllysine, L-homoarginine, neotryptophan, 3-benzothienylalanine, isoquinoline-3-carboxylic acid, diaminopropionic acid, homocysteine, 3,4-dimethoxyphenylalanine, 4-chlorophenylalanine, L-1,2,3,4-tetrahydronorharman-3-carboxylic acid, adamantylalanine, symmetrical dimethylarginine, 3-carboxythiomorpholine, D-1,2,3,4-tetrahydronorharman-3-carboxylic acid, 3-aminobenzoic acid, 3-amino-1-carboxymethyl-pyridin-2-one, 1-amino-1-cyclohexane carboxylic acid, 2-aminocyclopentane carboxylic acid, 1-amino-1-cyclopropane carboxylic acid, 2-aminoindane-2-carboxylic acid, 4-amino-tetrahydrothiopyran-4-carboxylic acid, azetidine-2-carboxylic acid, b-(benzothiazol-2-yl)-alanine, neopentylglycine, 2-carboxymethyl piperidine, b-cyclobutyl alanine, allylglycine, diaminopropionic acid, homo-cyclohexyl alanine, (2S,4R)-4-hydroxypiperidine-2-carboxylic acid, octahydroindole-2-carboxylic acid, (2S,4R) and (2S,4R)-4-(2-naphthyl), pyrrolidine-2-carboxylic acid, nipecotic acid, (2S,4R) and (2S,4S)-4-(4-phenylbenzyl) pyrrolidine-2-carboxylic acid, (3S)-1-pyrrolidine-3-carboxylic acid, (2S,4S)-4-tritylmercapto-pyrrolidine-2-carboxylic acid, (2S,4S)-4-mercaptoproline, t-butylglycine, N,N-bis(3-aminopropyl)glycine, 1-amino-cyclohexane-1-carboxylic acid, N-mercaptoethylglycine, and selenocysteine. In some embodiments, amino acid residues may be charged or polar. Charged amino acids include alanine, lysine, aspartic acid, or glutamic acid, or non-naturally occurring analogs thereof. Polar amino acids include glutamine, asparagine, histidine, serine, threonine, tyrosine, methionine, or tryptophan, or non-naturally occurring analogs thereof. It is specifically contemplated that in some embodiments, a terminal amino group in the amino acid may be an amido group or a carbamate group.

As used herein, the term "percent (%) identity" refers to the percentage of amino acid residues of a candidate sequence, e.g., an Fc-IgG, or fragment thereof, that are identical to the amino acid residues of a reference sequence after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared. In some embodiments, the percent amino acid sequence identity of a given candidate sequence to, with, or against a given reference sequence (which can alternatively be phrased as a given candidate sequence that has or includes a certain percent amino acid sequence identity to, with, or against a given reference sequence) is calculated as follows:

$$100 \times (\text{fraction of } A/B)$$

where A is the number of amino acid residues scored as identical in the alignment of the candidate sequence and the reference sequence, and where B is the total number of amino acid residues in the reference sequence. In some embodiments where the length of the candidate sequence does not equal to the length of the reference sequence, the percent amino acid sequence identity of the candidate sequence to the reference sequence would not equal to the percent amino acid sequence identity of the reference sequence to the candidate sequence.

Two polynucleotide or polypeptide sequences are said to be "identical" if the sequence of nucleotides or amino acids in the two sequences is the same when aligned for maximum correspondence as described above. Comparisons between two sequences are typically performed by comparing the sequences over a comparison window to identify and compare local regions of sequence similarity. A "comparison window" as used herein, refers to a segment of at least about 15 contiguous positions, about 20 contiguous positions, about 25 contiguous positions, or more (e.g., about 30 to about 75 contiguous positions, or about 40 to about 50 contiguous positions), in which a sequence may be compared to a reference sequence of the same number of contiguous positions after the two sequences are optimally aligned.

The term "treating" or "to treat," as used herein, refers to a therapeutic treatment of a viral infection (e.g., a viral infection such as and influenza infection) in a subject. In some embodiments, a therapeutic treatment may slow the progression of the viral infection, improve the subject's outcome, and/or eliminate the infection. In some embodiments, a therapeutic treatment of a viral infection in a subject may alleviate or ameliorate of one or more symptoms or conditions associated with the viral infection, diminish the extent of the viral, stabilize (i.e., not worsening) the state of the viral infection, prevent the spread of the viral infection, and/or delay or slow the progress of the viral infection, as compare the state and/or the condition of the viral infection in the absence of the therapeutic treatment.

The term "average value of T," as used herein, refers to the mean number of monomers of neuraminidase inhibitor or dimers of neuraminidase inhibitors conjugated to an Fc domain or an albumin protein within a population of conjugates. In some embodiments, within a population of conjugates, the average number of monomers of neuraminidase inhibitor or dimers of neuraminidase inhibitors conjugated to an Fc domain monomer may be from 1 to 20 (e.g., the average value of T is 1 to 2, 1 to 3, 1 to 4, 1 to 5, 5 to 10, 10 to 15, 15 to 20, 1.5 to 3.5, 2.5 to 4.5, 3.5 to 5.5, 4.5 to 6.5, 5.5 to 7.5, 6.5 to 8.5, 7.5 to 9.5, or 8.5 to 10.5). In some embodiments, the average value of T is 1, 2, 3, 4, 5, 6, 7, 8, 9, 10, 11, 12, 13, 14, 15, 16, 17, 18, 19, or 20.

The term "subject," as used herein, can be a human, non-human primate, or other mammal, such as but not limited to dog, cat, horse, cow, pig, turkey, goat, fish, monkey, chicken, rat, mouse, and sheep. The term "therapeutically effective amount," as used herein, refers to an amount, e.g., pharmaceutical dose, effective in inducing a desired effect in a subject or in treating a subject having a condition or disorder described herein (e.g., a viral infection, such as an influenza infection). It is also to be understood herein that a "therapeutically effective amount" may be interpreted as an amount giving a desired therapeutic and/or preventative effect, taken in one or more doses or in any dosage or route, and/or taken alone or in combination with other therapeutic agents (e.g., an antiviral agent described herein). For example, in the context of administering a conjugate described herein (e.g., a conjugate of any one of formulas (1)-(5), (D-I)-(D-XI), (D'-I), (M-I)-(M-XI), or (M'-I)) that is used for the treatment of a viral infection, an effective amount of a conjugate is, for example, an amount sufficient to prevent, slow down, or reverse the progression of the viral infection as compared to the response obtained without administration of the conjugate.

As used herein, the term "pharmaceutical composition" refers to a medicinal or pharmaceutical formulation that contains at least one active ingredient (e.g., a conjugate of any one of formulas (1)-(5), (D-I)-(D-XI), (D'-I), (M-I)-(M-XI), or (M'-I)) as well as one or more excipients and diluents to enable the active ingredient suitable for the method of administration. The pharmaceutical composition of the present disclosure includes pharmaceutically acceptable components that are compatible with a conjugate described herein (e.g., a conjugate of any one of formulas (1)-(5), (D-I)-(D-XI), (D'-I), (M-I)-(M-XI), or (M'-I)).

As used herein, the term "pharmaceutically acceptable carrier" refers to an excipient or diluent in a pharmaceutical composition. For example, a pharmaceutically acceptable carrier may be a vehicle capable of suspending or dissolving the active conjugate (e.g., a conjugate of any one of formulas (1)-(5), (D-I)-(D-XI), or (M-I)-(M-VI)). The pharmaceutically acceptable carrier must be compatible with the other ingredients of the formulation and not deleterious to the recipient. In the present disclosure, the pharmaceutically acceptable carrier must provide adequate pharmaceutical stability to a conjugate described herein. The nature of the carrier differs with the mode of administration. For example, for oral administration, a solid carrier is preferred; for intravenous administration, an aqueous solution carrier (e.g., WFI, and/or a buffered solution) is generally used.

The term "pharmaceutically acceptable salt," as used herein, represents salts of the conjugates described herein (e.g., conjugates of any one of formulas (1)-(5), (D-I)-(D-XI), (D'-I), (M-I)-(M-XI), or (M'-I)) that are, within the scope of sound medical judgment, suitable for use in methods described herein without undue toxicity, irritation, and/or allergic response. Pharmaceutically acceptable salts are well known in the art. For example, pharmaceutically acceptable salts are described in: *Pharmaceutical Salts: Properties, Selection, and Use* (Eds. P. H. Stahl and C. G. Wermuth), Wiley-VCH, 2008. The salts can be prepared in situ during the final isolation and purification of the conjugates described herein or separately by reacting the free base group with a suitable organic acid.

The term "drug-to-antibody ratio" or "DAR" refers to the average number of small molecule drug moieties (e.g., the average number of small molecule drug monomers or dimers) conjugated to an antibody, Fc domain, or albumin protein described herein. In some embodiments described herein, the DAR is represented by "T" (e.g., in formulas (1)-(5), (D-I)-(D-XI), (D'-I), (M-I)-(M-XI), or (M'-I)). As used herein, each monomer moiety (e.g., each zanamivir or peramivir monomer) or each dimer moiety (e.g., each zanamivir dimer or peramivir dimer) conjugated to the Fc domain, antibody, or albumin protein corresponds to a DAR value of 1.0 (e.g., a "T" value of 1.0). For example, an Fc domain conjugated to 4 zanamivir monomers would have a DAR of 4.0 (e.g., a "T" of 4.0). An Fc domain conjugated to 4 zanamivir dimers (e.g., 8 total zanamivir molecules) would also have a DAR of 4.0 (e.g., a "T" of 4.0). DAR may also be computed as the average DAR for a population of molecules, such as a population of Fc domains, antibodies, or albumin proteins. DAR values may affect the efficacy, potency, pharmacokinetics, or toxicity of the drug.

The term "secondary infection," as used herein, refers to an infection that occurs in a subject during or after another (referred to as primary) infection in that subject (e.g., during or after a primary influenza infection). A secondary infections may be caused by the primary infection or may be caused by treatment of the primary infection. In some cases, primary infections alter the immune system making the subject more susceptible to a secondary infection. In some cases, treatment of the primary infection makes the subject more susceptible to a secondary infection. For example, the influenza virus has been associated with secondary infections (e.g., increased risk of developing a secondary infection), such as bacterial secondary infections, for example of the respiratory tract. Secondary infections associated with influenza infection increase the morbidity and mortality of influenza. Secondary infections include co-infections. The terms "secondary infection" and "co-infection" are used interchangeably herein.

The term "about," as used herein, indicates a deviation of up to ±5%. For example, about 10% refers to from 9.5% to 10.5%.

Any values provided in a range of values include both the upper and lower bounds, and any values contained within the upper and lower bounds.

The term "(1)-(5), (D-I)-(D-XI), (D'-I), (M-I)-(M-XI), or (M'-)", as used herein, represents the formulas of any one of (1), (2), (3), (4), (5), (D-I), (D-II), (D-II-1), (D-II-2), (D-I1-3), (D-I1-4), (D-I1-5), (D-II-6), (D-I1-7), (D-II-8), (D-II-9), (D-II-10), (D-III), (D-III-1), (D-III-2), (D-III-3), (D-III-4), (D-III-5), (D-III-6), (D-II-7), (D-III-8), (D-III-9), (D-IV), (D-IV-1), (D-IV-2), (D-V), (D-V-1), (D-V-2), (D-V-3), (D-V-4), (D-V-5), (D-V-6), (D-V-7), (D-V-8), (D-V-9), (D-V-10), (D-VI), (D-VI-1), (D-VI-2), (D-VI-3), (D-VI-4), (D-VI-5), (D-VI-6), (D-VI-7), (D-VI-8), (D-VI-9), (D-VII), (D-VIII), (D-VIII-1), (D-VIII-2), (D-VIII-3), (D-VIII-4), (D-VIII-5), (D-VIII-6), (D-VIII-7), (D-VIII-8), (D-VIII-9), (D-VIII-10), (D-VIII-11), (D-IX), (D-IX-1), (D-IX-2), (D-IX-3), (D-IX-4), (D-IX-5), (D-IX-6), (D-X), (D-X-1), (D-X-2), (D-X-3), (D-XI), (D-XI-1), (D'-I), (M-I), (M-II), (M-II-1), (M-II-2), (M-II-3), (M-II-4), (M-II-5), (M-II-6), (M-II-7), (M-II-8), (M-II-9), (M-I1-10), (M-III), (M-III-1), (M-III-2), (M-III-3), (M-III-4), (M-III-5), (M-III-6), (M-III-7), (M-III-8), (M-III-9), (M-IV), (M-IV-1), (M-IV-2), (M-V), (M-V-1), (M-V-2), (M-V-3), (M-V-4), (M-V-5), (M-V-6), (M-V-7), (M-V-8), (M-V-9), (M-V-10), (M-VI), (M-VI-1), (M-VI-2), (M-VI-3), (M-V1-4), (M-VI-5), (M-VI-6), (M-VI-7), (M-VI-8), (M-VI-9), (M-VI-10), (M-VIII-2), (M-VIII-1), (M-VIII-2), (M-VIII-3), (M-VIII-4), (M-VIII-5), (M-VIII-6), (M-VIII-7), (M-VIII-8), (M-VIII-9), (M-VIII-10), (M-VIII-11), (M-IX), (M-IX-1), (M-IX-2), (M-IX-3), (M-IX-4), (M-IX-5), (M-IX-6), (M-X), (M-X-1), (M-X-2), (M-X-3), (M-XI), (M-XI-1), or (M'-I)).

Other features and advantages of the conjugates described herein will be apparent from the following Detailed Description and the claims.

DESCRIPTION OF THE DRAWINGS

FIG. 16 is a graph showing the IC50 values from an H1N1 neuraminidase inhibition assay for Conjugates 1-6.

FIG. 17 is a graph showing the IC50 values from an H3N2 neuraminidase inhibition assay for Conjugates 1-6.

FIGS. 19A-19E are a series of graphs showing the ability of Conjugate 3 to inhibit the growth of pathogenic influenza viral strains A/WSN/33 H1N1 (FIG. 19A), A/Wyoming/3/03 H3N2 (FIG. 19B), A/California/04/09 H1N1 pdm (FIG. 19C), A/Vietnam/1203/04 H5N1 HALo (FIG. 19D), or B/Lee/40 Victoria (FIG. 19E) in human epithelial cells.

FIGS. 20A-20E are a series of graphs showing the ability of Conjugate 4 to inhibit the growth of pathogenic influenza viral strains A/WSN/33 H1N1 (FIG. 20A), A/Wyoming/3/03 H3N2 (FIG. 20B), A/California/04/09 H1N1 pdm (FIG. 20C), A/Vietnam/1203/04 H5N1 HALo (FIG. 20D), or B/Lee/40 Victoria (FIG. 20E) in human epithelial cells.

FIGS. 21A-21E are a series of graphs showing the ability of Conjugate 6 to inhibit the growth of pathogenic influenza viral strains A/WSN/33 H1N1 (FIG. 21A), A/Wyoming/3/03 H3N2 (FIG. 21B), A/California/04/09 H1N1 pdm (FIG. 21C), A/Vietnam/1203/04 H5N1 HALo (FIG. 21D), or B/Lee/40 Victoria (FIG. 21E) in human epithelial cells.

FIGS. 22A-22E are a series of graphs showing the ability of Conjugate 6 to inhibit the growth of pathogenic influenza viral strains A/WSN/33 H1N1 (FIG. 22A), A/Wyoming/3/03 H3N2 (FIG. 22B), A/California/04/09 H1N1 pdm (FIG. 22C), B/Lee/40 Victoria (FIG. 22D), or A/Vietnam/1203/04 (FIG. 22E) in human epithelial cells, compared to Oseltamivir.

FIG. 23 is a graph showing the relative mouse serum concentration of Conjugate 6 compared to Fc (hIgG1) alone.

FIG. 24 is a graph showing the effect of Conjugate 6 on mouse weight in a lethal mouse influenza model. The study was performed as described in Example 29.

FIG. 25 is a graph showing the effect of Conjugate 6 on survival in a lethal mouse influenza model. The study was performed as described in Example 29.

FIG. 26 is a graph showing the effect of Conjugate 6 on mouse weight in a lethal mouse influenza model. The study was performed as described in Example 30.

Figure 31A:
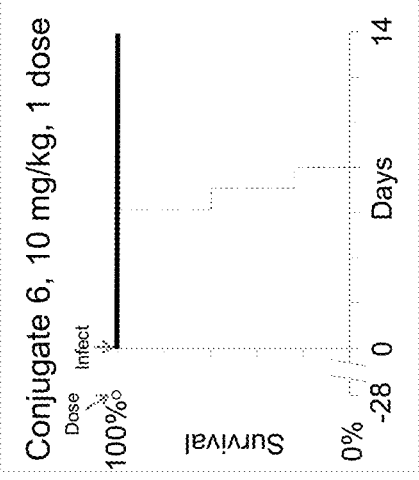
FIGS. 31A-31F are a series of graphs showing the survival of mice treated with Conjugate 6 in a lethal mouse influenza model. Mice were treated with either Oseltamivir (Tamiflu™) control, 20 mg/kg, 2× daily, starting 8 hours post-infection (FIG. 31A); Conjugate 6, 50 mg/kg, 1 dose 28 days prior to infection (FIG. 31B); Conjugate 6, 10 mg/kg, 1 dose 28 days prior to infection (FIG. 31C); Conjugate 6, 5 mg/kg, 1 dose 28 days prior to infection (FIG. 31D)
Figure 31B:
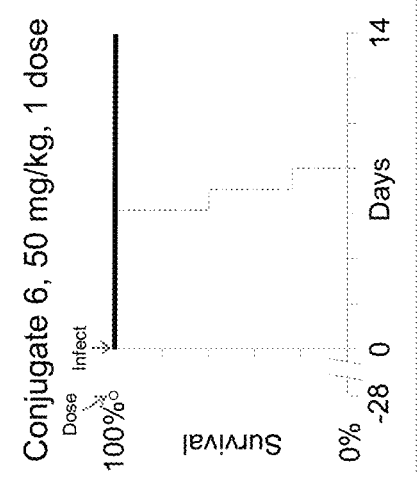
Figure 31C:
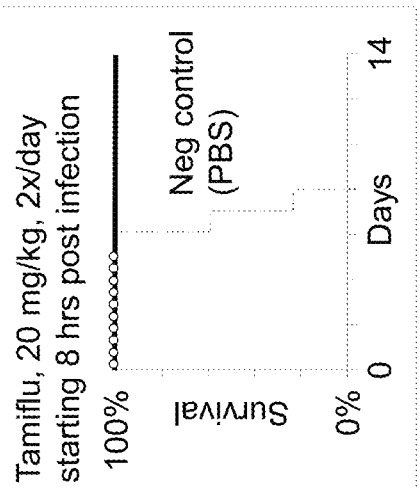
Figure 31D:
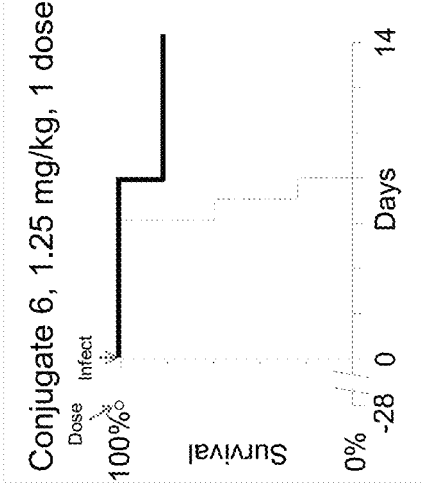
Figure 31E:
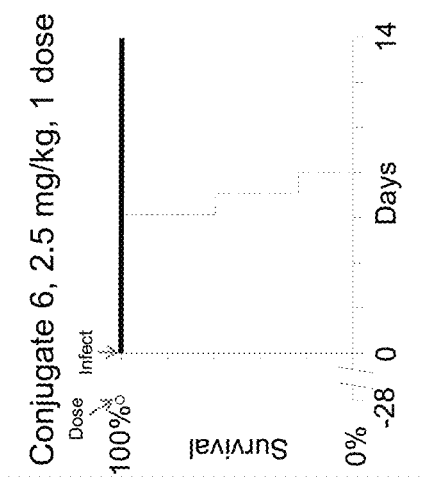
Figure 31F:
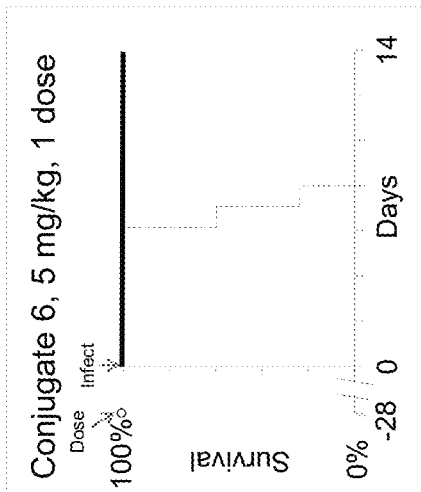

Conjugate 6, 2.5 mg/kg, 1 dose 28 days prior to infection (FIG. 31E); or Conjugate 6, 1.25 mg/kg, 1 dose 28 days prior to infection (FIG. 31F). This study was performed as described in Example 33.

Figure 32C:
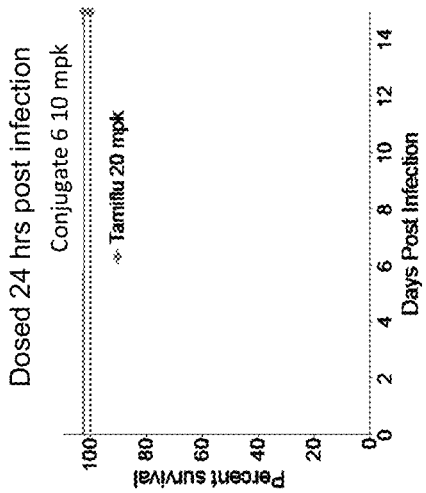
Figure 32F:
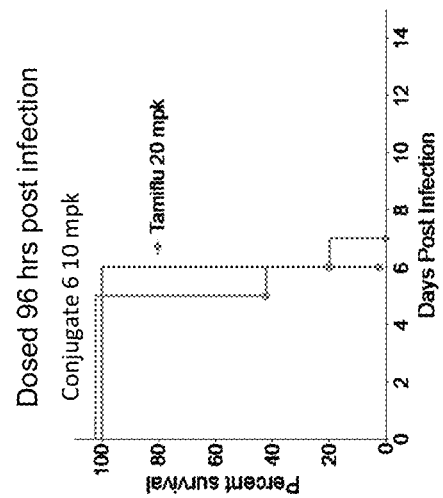
Figure 32B:
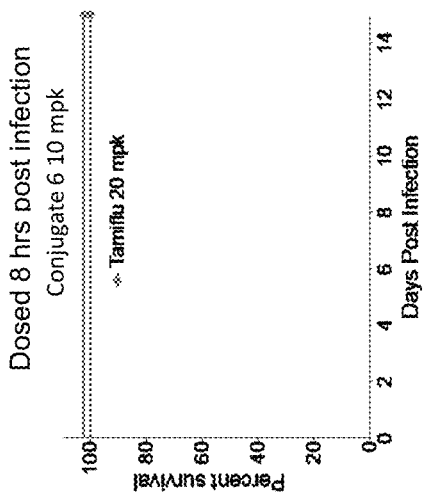
Figure 32E:
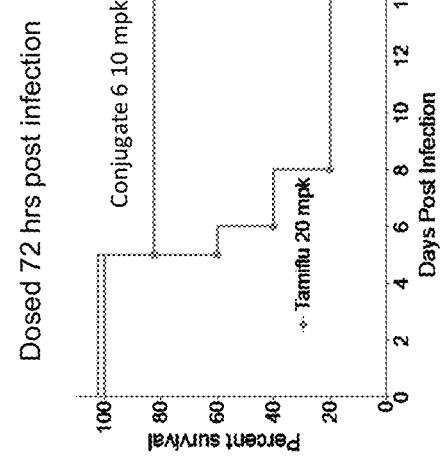
Figure 32A:
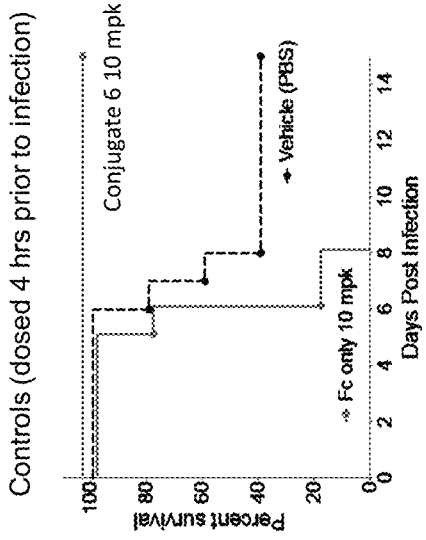
Figure 32D:
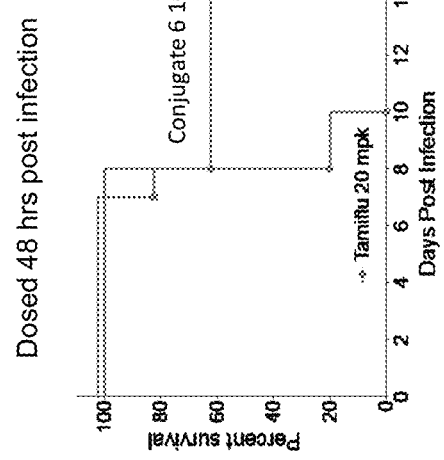

FIGS. 32A-32F is a series of graphs showing that Conjugate 6 extends treatment window as compared to Oseltamivir (Tamiflu™) as determined by survival in a lethal mouse influenza model. Mice were treated with either vehicle (PBS), Fc only 10 mpk, or Conjugate 6, 4 hours prior to infection (FIG. 32A); Conjugate 6 or Oseltamivir (Tamiflu™), 8 hours post-infection (FIG. 32B); Conjugate 6 or Oseltamivir (Tamiflu™), 24 hours post-infection (FIG. 32C); Conjugate 6 or Oseltamivir (Tamiflu™), 48 hours post-infection (FIG. 32D); Conjugate 6 or Oseltamivir (Tamiflu™), 72 hours post-infection (FIG. 32E); or Conjugate 6 or Oseltamivir (Tamiflu™), 96 hours post-infection (FIG. 32F). The study was performed as described in Example 34.

Figure 33:
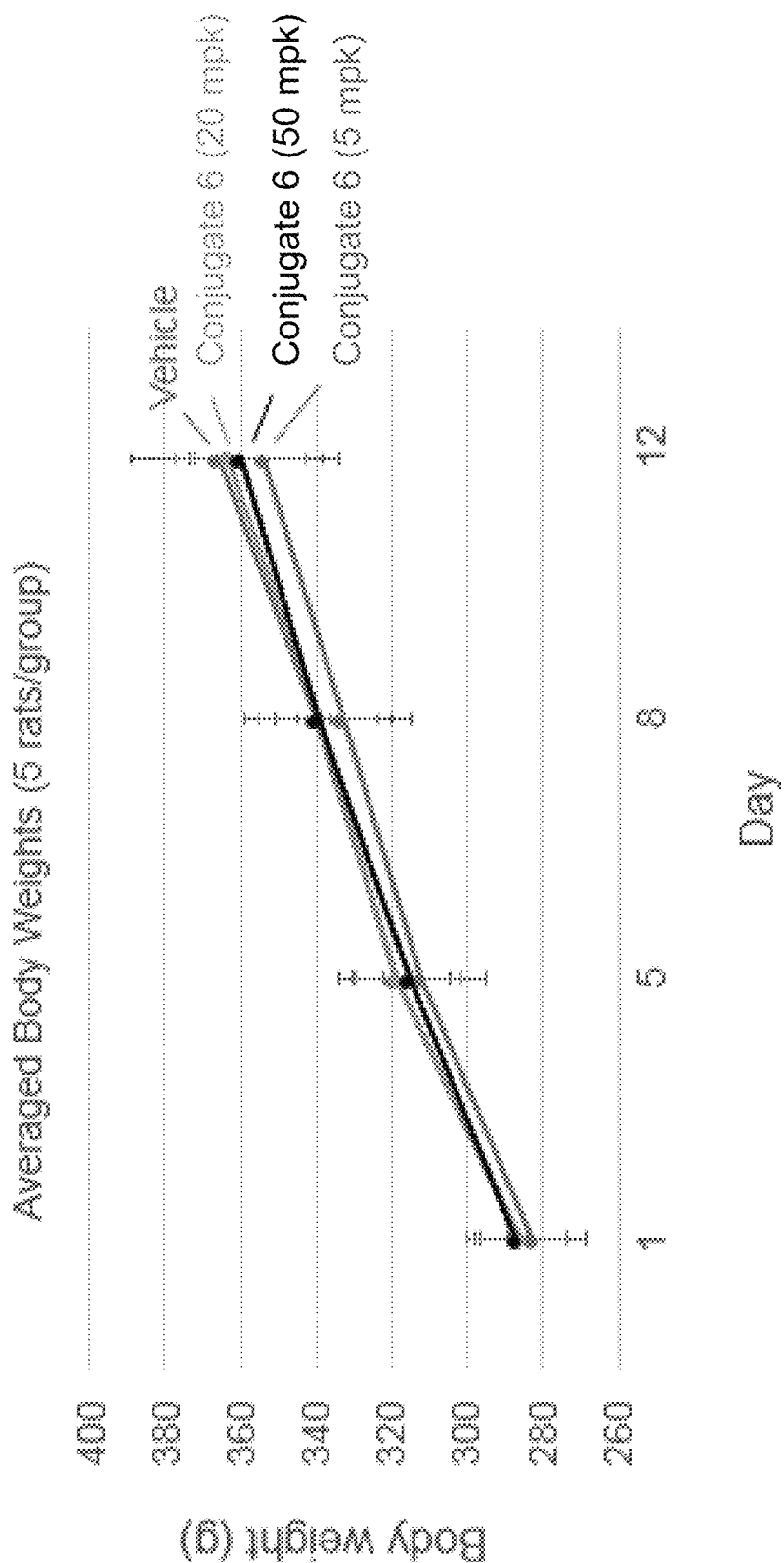

FIG. 33 is a graph showing no significant effect of body weight gain were observed following administration of Conjugate 6 in a 14 day rat dose-range finder toxicity study. The study was performed as described in Example 35.

FIGS. 34A-34D is a series of graphs showing that Conjugate 6 extends treatment window as compared to Oseltamivir (Tamiflu™) as determined by survival in a lethal mouse influenza model. Mice were treated with either Oseltamivir (Tamiflu™) control, 20 mg/kg, 2× daily, starting 8 hours post-infection (FIG. 34A); Conjugate 6, 10 mg/kg, 1 dose 4 hours prior to infection (FIG. 34B); Conjugate 6, 2 mg/kg, 1 dose 4 hours prior to infection (FIG. 34C); or Conjugate 6, 0.4 mg/kg, 1 dose 4 days prior to infection (FIG. 34D). The study was performed as described in Example 37.

Figure 35:
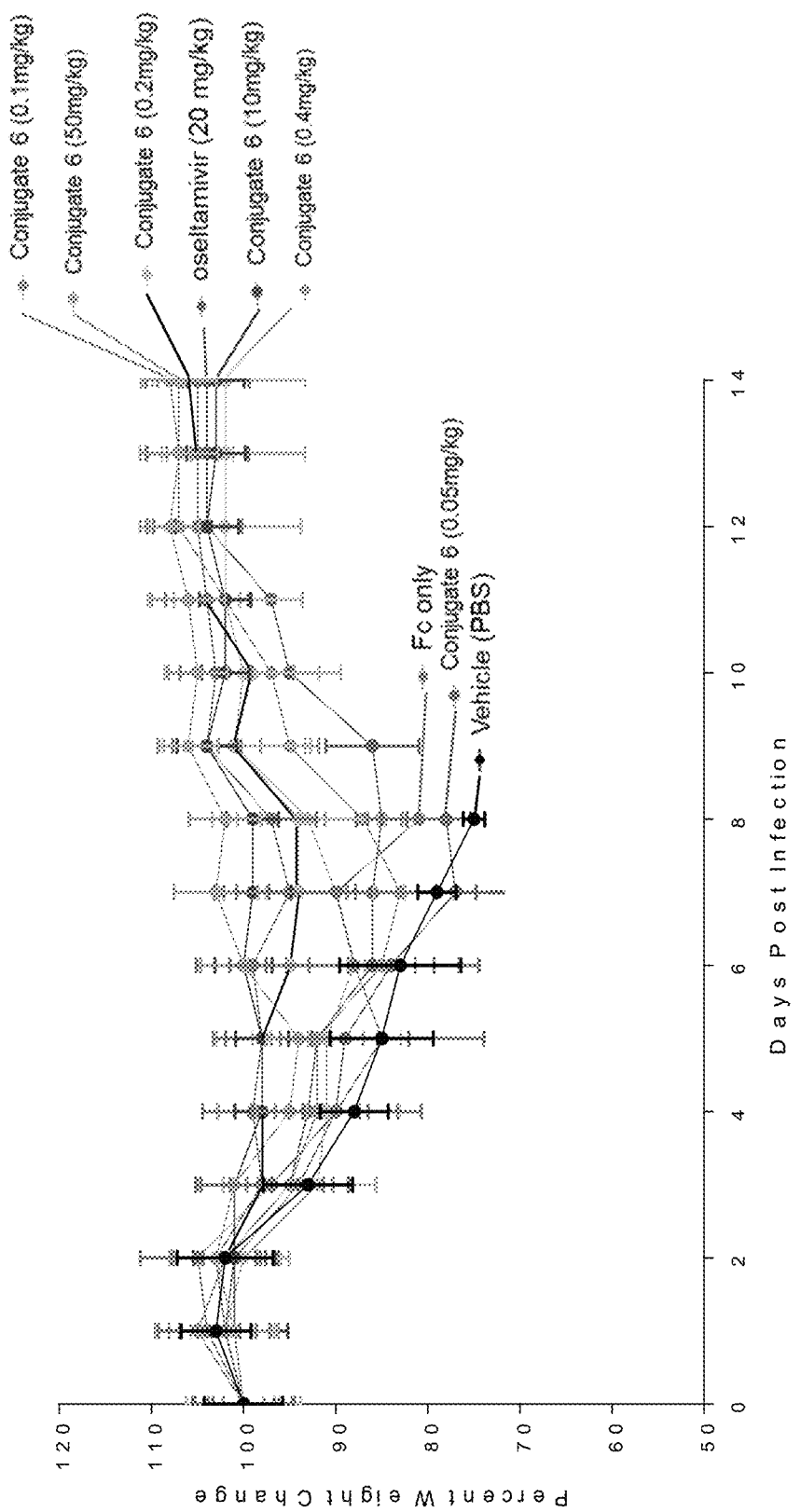

FIG. 35 is a graph showing the effect of Conjugate 6 on mouse weight in a lethal mouse influenza model. The study was performed as described in Example 37.

Figure 36:
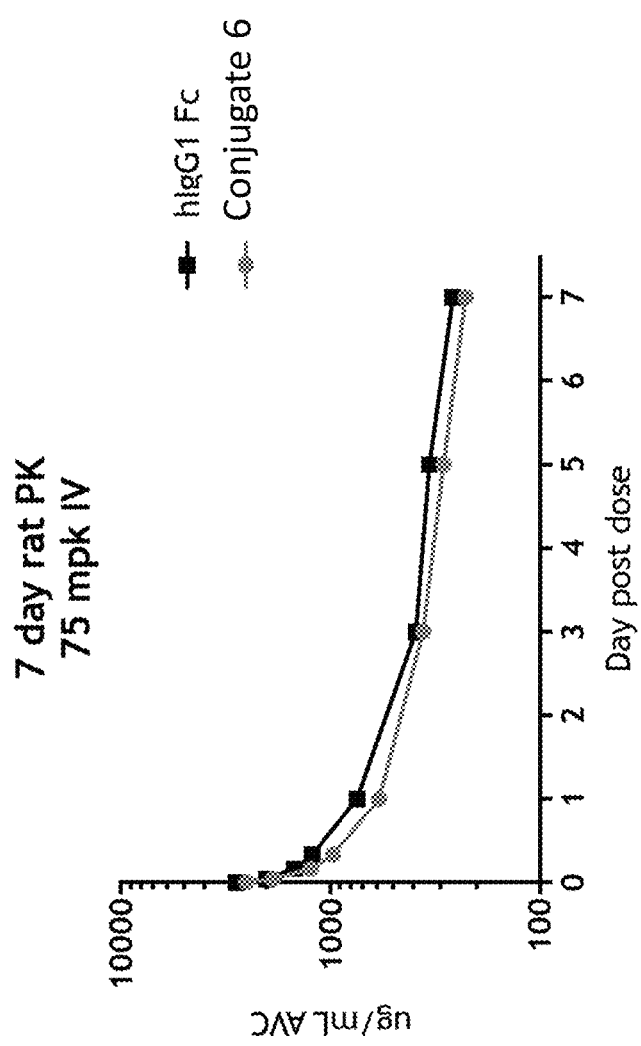

FIG. 36 is a graph showing a 7-day rat pharmacokinetic study following IV administration of Conjugate 6. The study was performed as described in Example 38.

Figure 37:
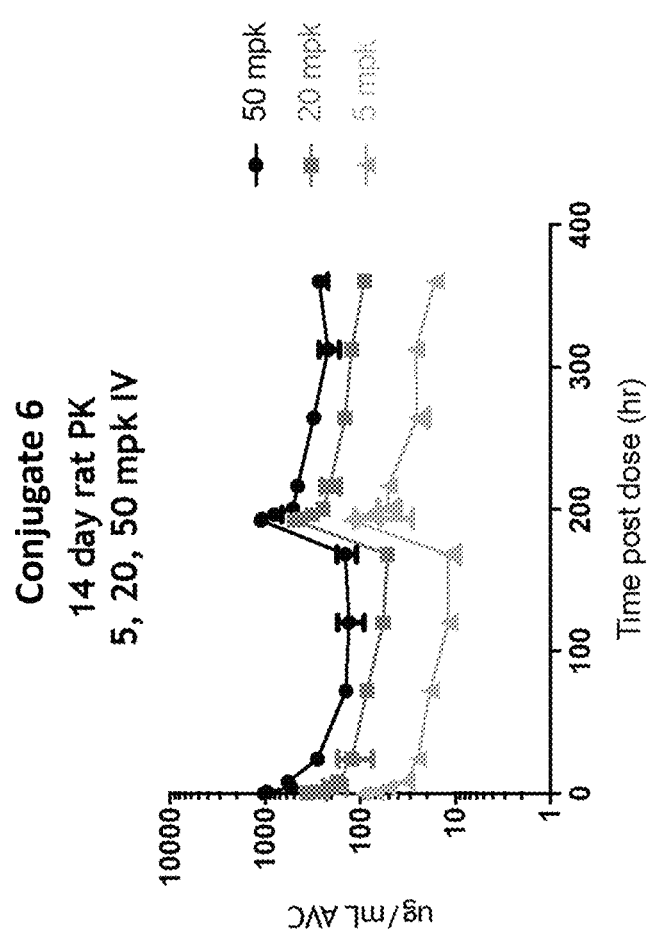

FIG. 37 is a graph showing a 14-day rat pharmacokinetic study following IV administration of Conjugate 6. The study was performed as described in Example 39.

Figure 38:
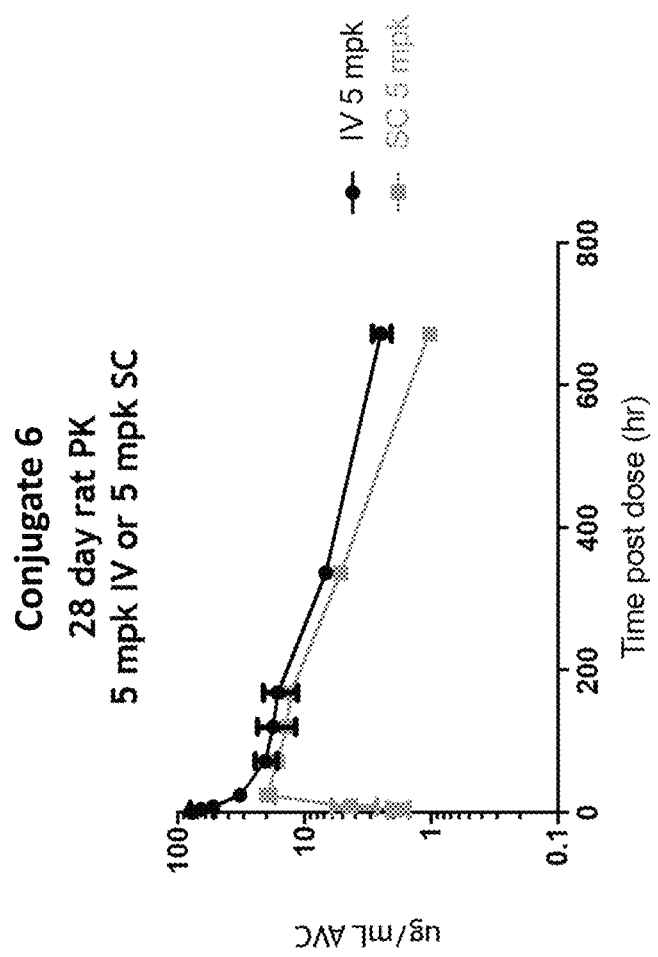

FIG. 38 is a graph showing a 28-day rat pharmacokinetic study comparing IV and SC administration of Conjugate 6. The study was performed as described in Example 40.

Figure 39:
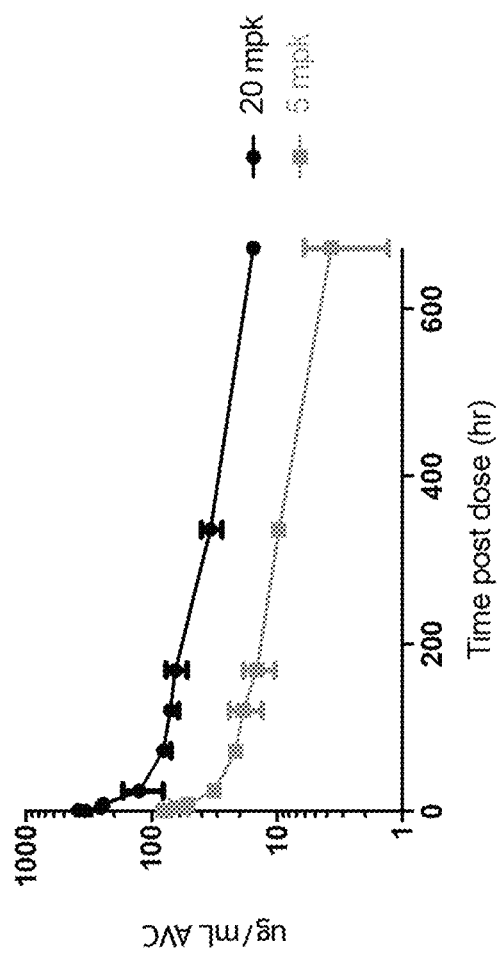

FIG. 39 is a graph showing a 28-day non-human primate pharmacokinetic study following IV administration of Conjugate 6. The study was performed as described in Example 41.

Figure 40:
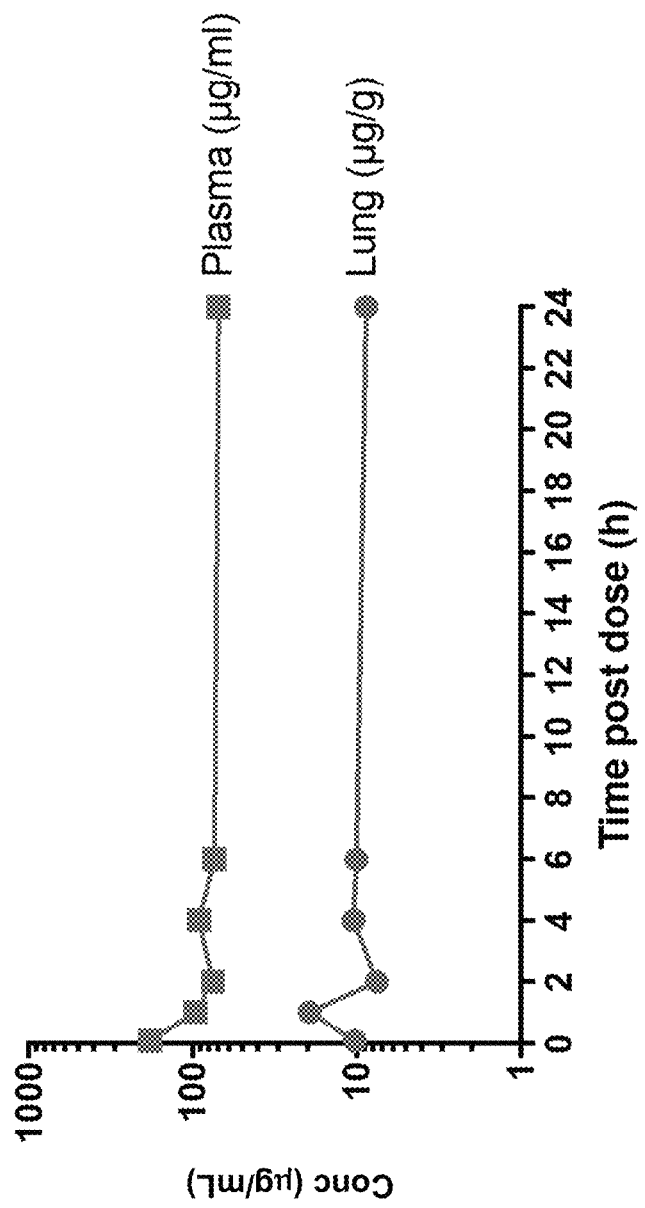

FIG. 40 is a graph showing a mouse lung distribution pharmacokinetic study following IV administration of Conjugate 6. The study was performed as described in Example 42.

Figure 41:
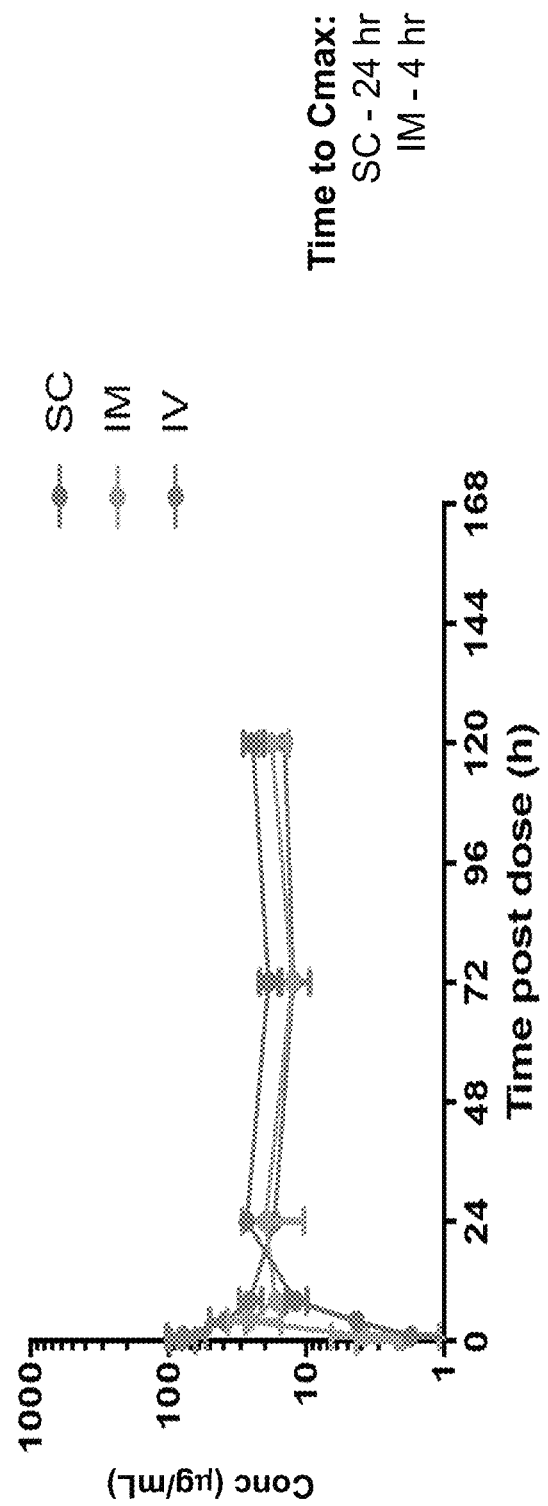

FIG. 41 is a graph showing a 5-day mouse pharmacokinetic study comparing IV, SC and IM administration of Conjugate 6. The study was performed as described in Example 43.

Figure 42:
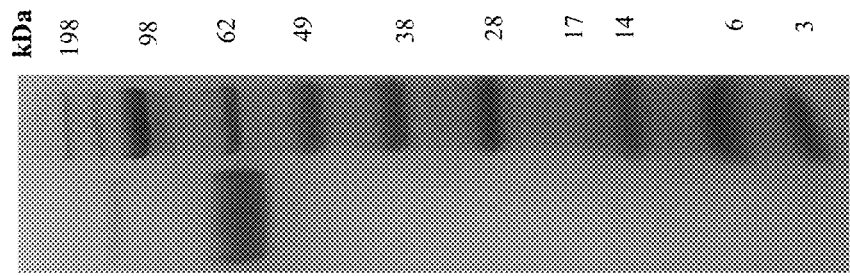

FIG. 42 shows a non-reducing SDS-PAGE of Conjugate 8.

Figure 43:
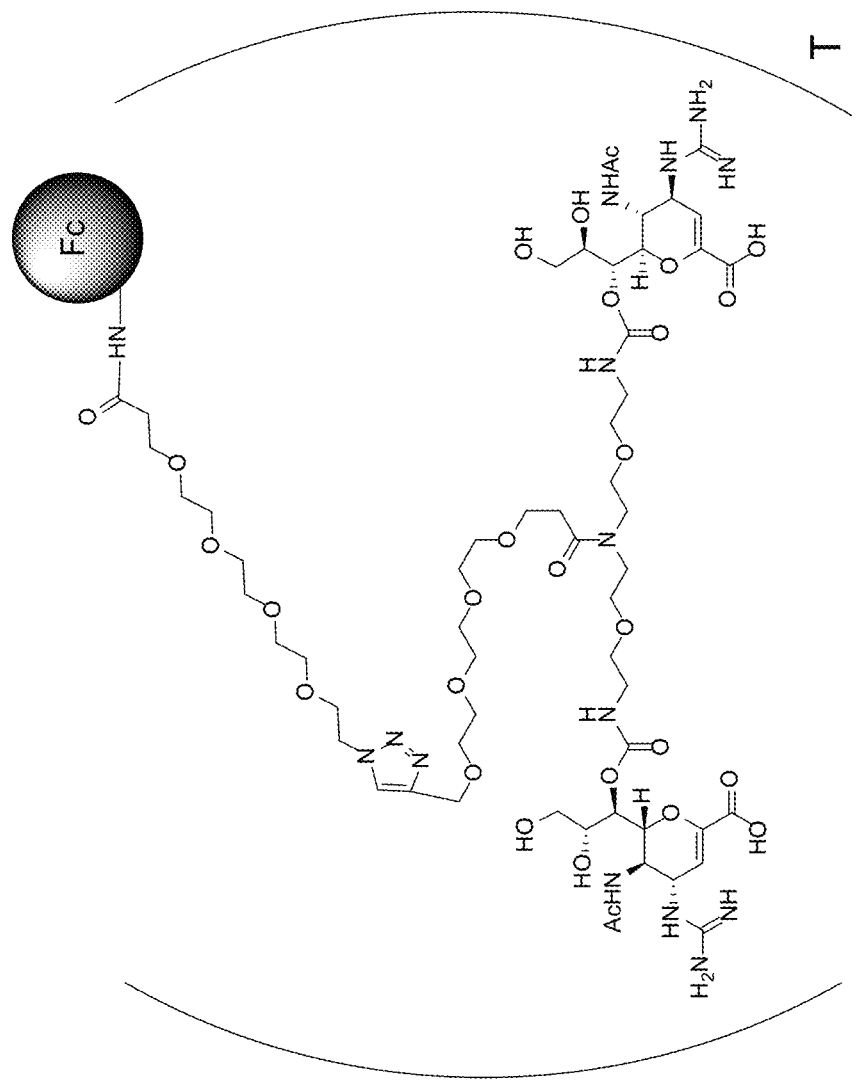

FIG. 43 shows the structure of Conjugate 6.

Figure 44:
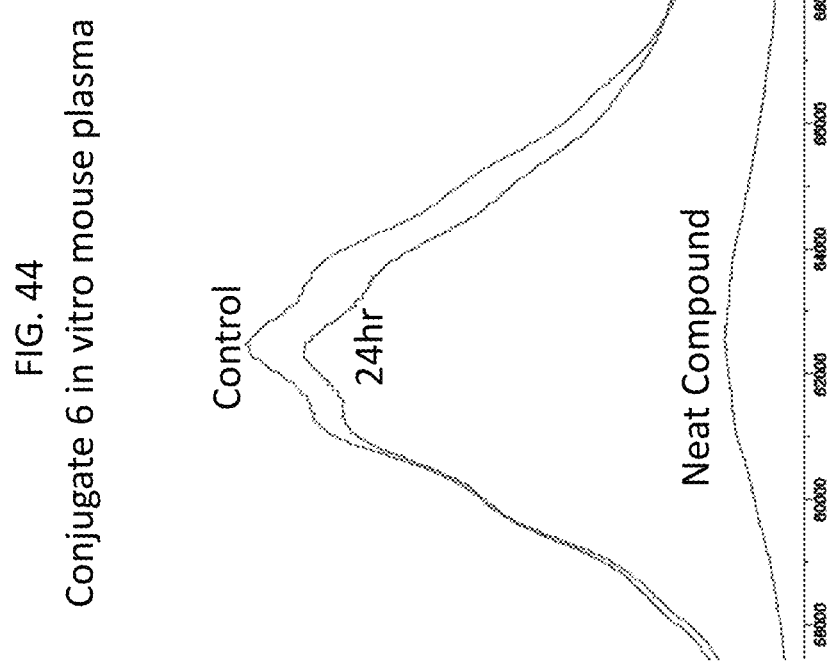

FIG. 44 is a graph showing a 24 hour in vitro mouse plasma stability study comparing Conjugate 6 incubated at 37° C. for 24 hr compared to a control and neat compound.

Figure 45:
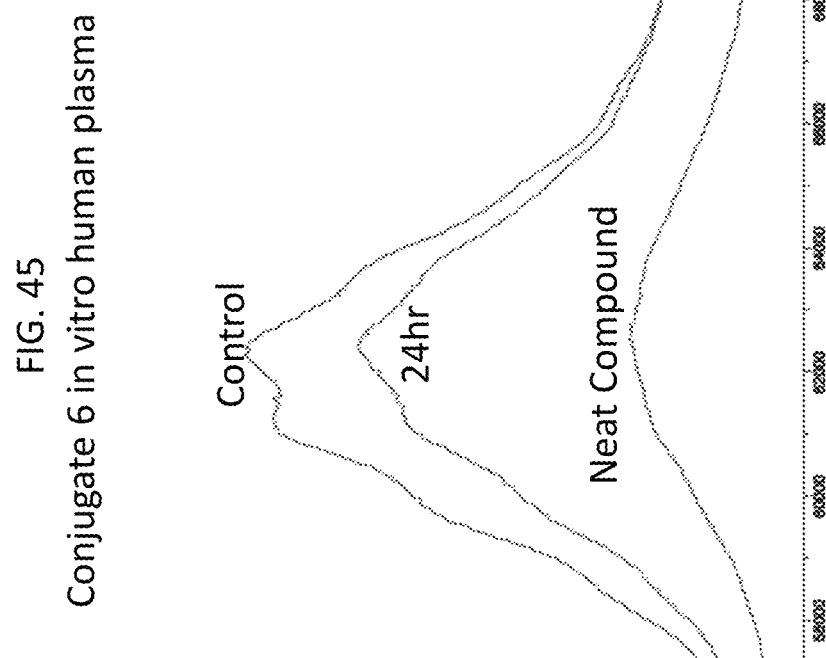

FIG. 45 is a graph showing a 24 hour in vitro human plasma stability study comparing Conjugate 6 incubated at 37° C. for 24 hr compared to a control and neat compound.

Figure 46:
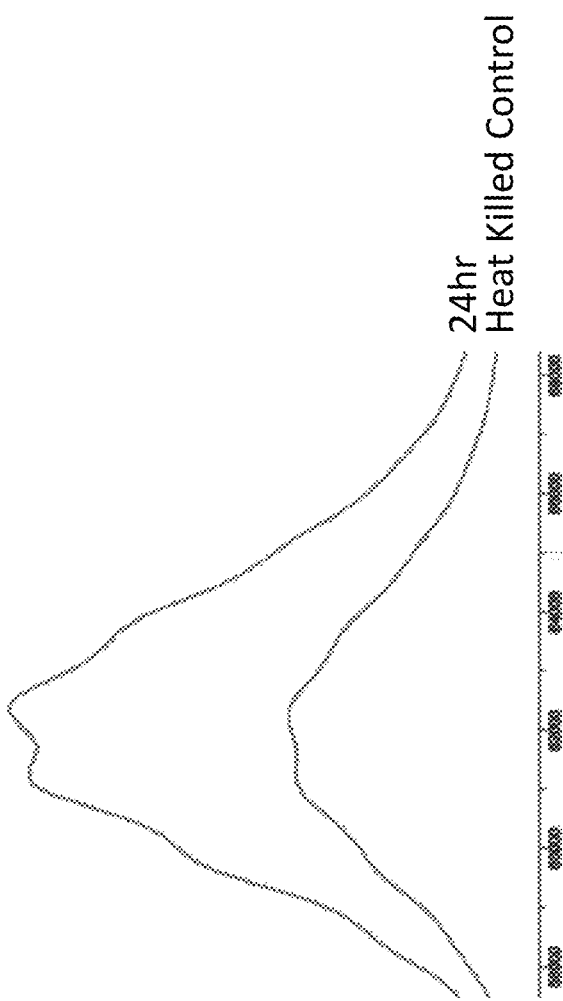

FIG. 46 is a graph showing a 24 hour mouse liver microsomal stability study comparing Conjugate 6 incubated at 37° C. for 24 hr in mouse liver microsomal cells and heat killed mouse liver microsomal cells as a control.

Figure 47:
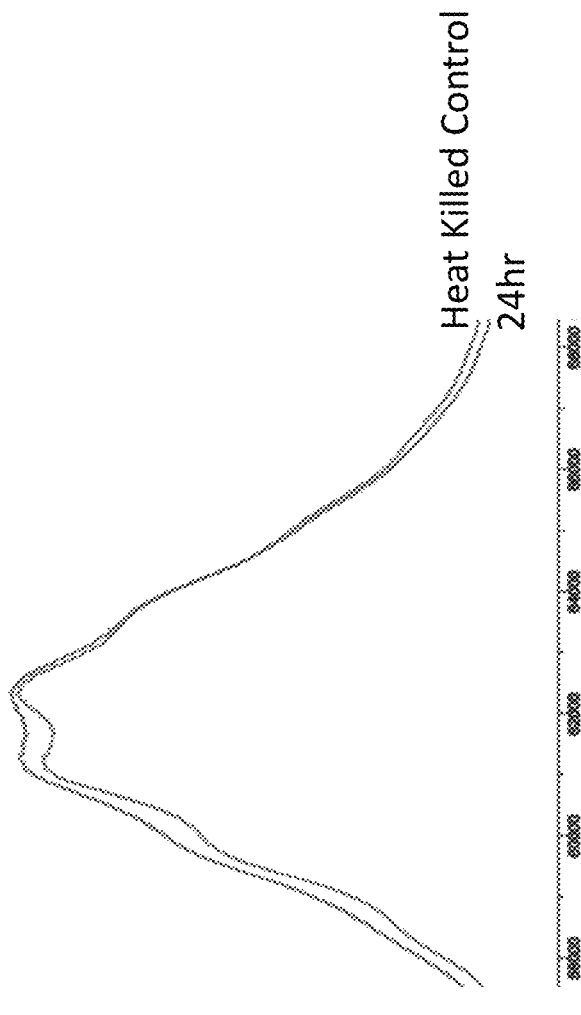

FIG. 47 is a graph showing a 24 hour human liver microsomal stability study comparing Conjugate 6 incubated at 37° C. for 24 hr in human liver microsomal cells and heat killed mouse liver microsomal cells as a control.

Figure 48:
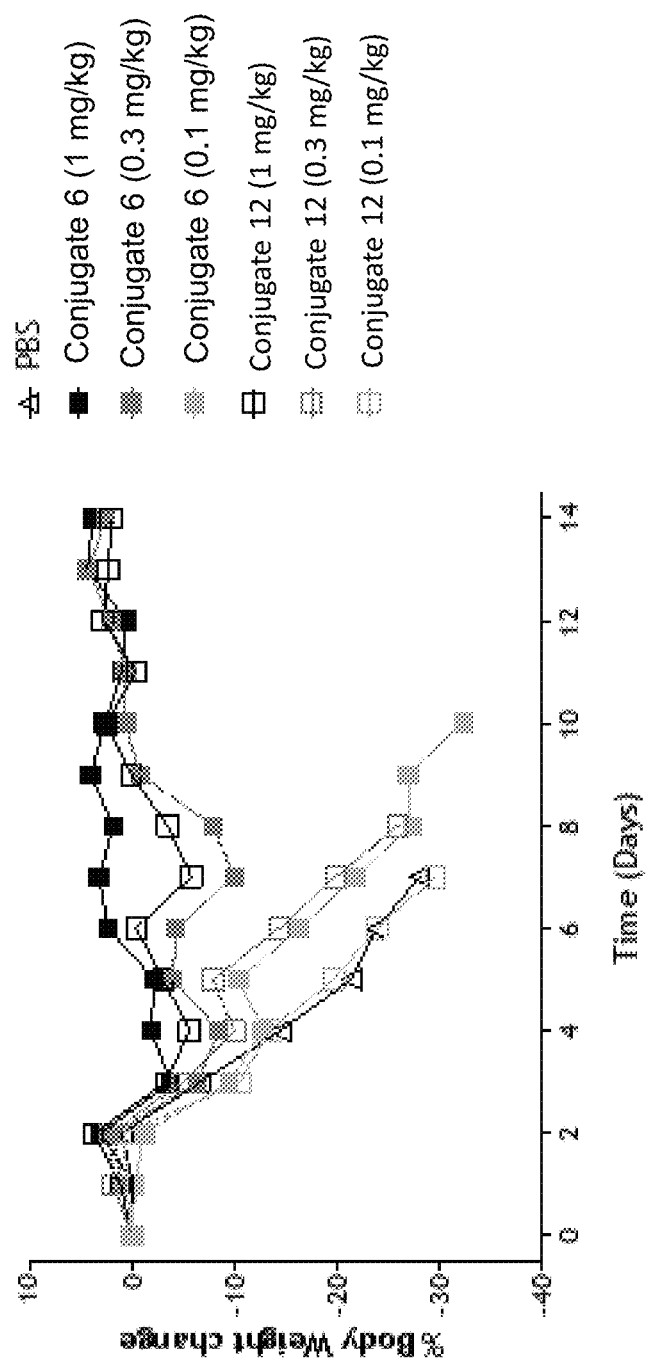

FIG. 48 is a graph showing the % body weight change in mice over 15 days post viral challenge. The study was performed as described in Example 66.

Figure 49:
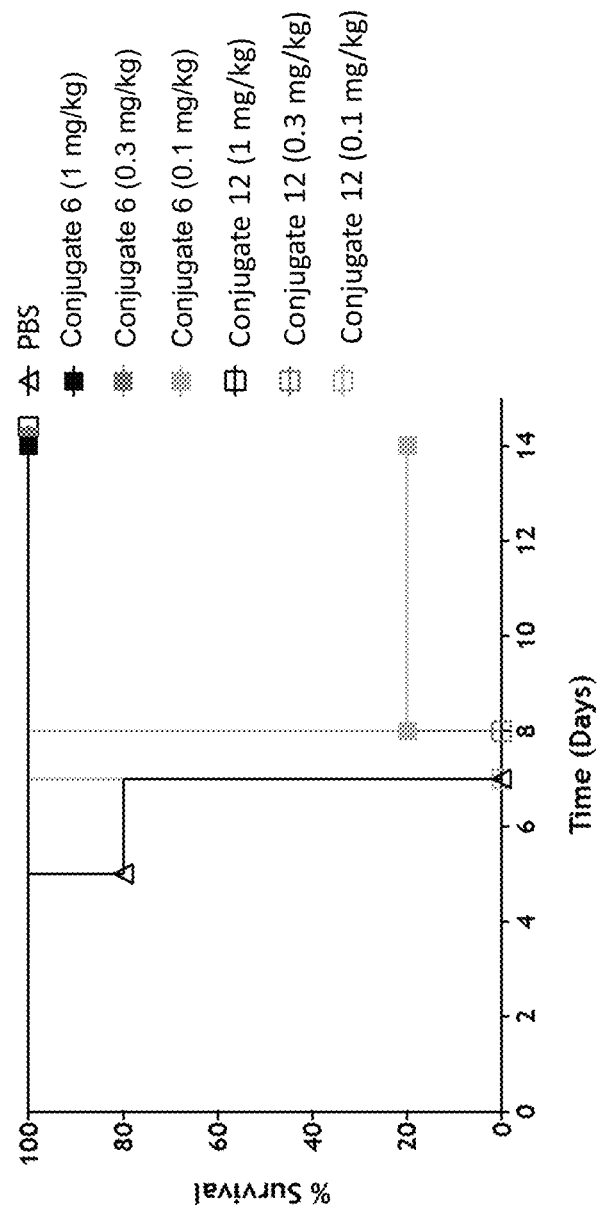

FIG. 49 is a graph showing the % survival in mice over 15 days post viral challenge. The study was performed as described in Example 66.

Figure 50:
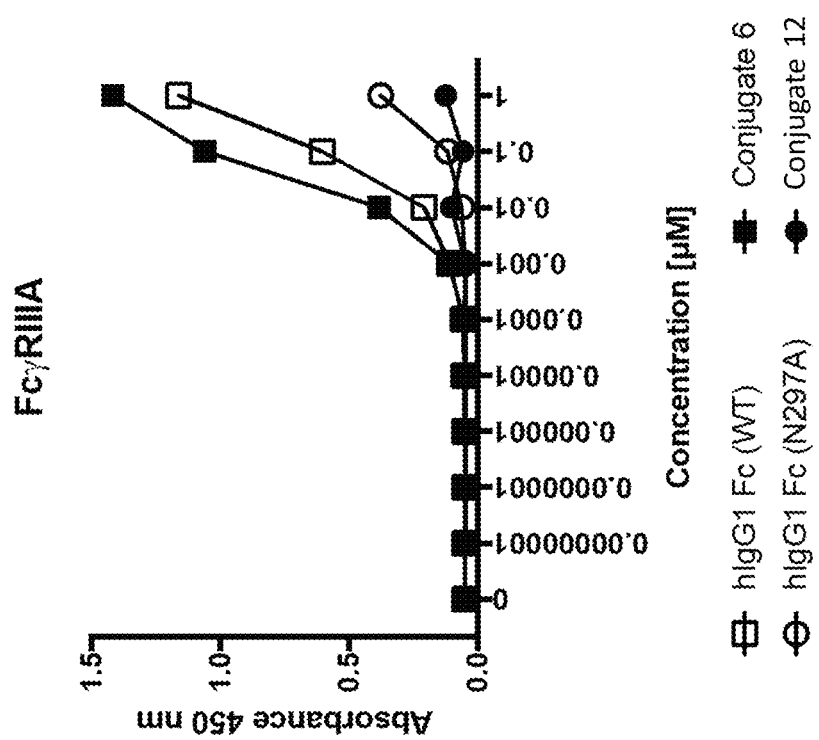

FIG. 50 is a graph showing the binding of Conjugate 6 and Conjugate 12 compared to hIgG1 Fc (WT) and hIgG1 Fc (N297A) to Fcγ receptor IIIA. The study was performed as described in Example 67.

Figure 51:
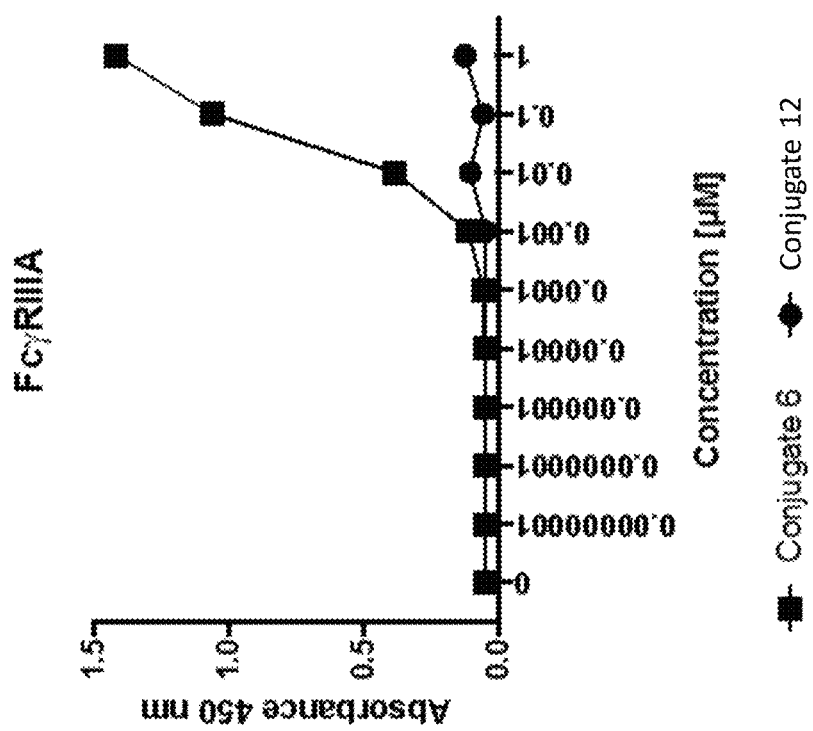

FIG. 51 is a graph showing the binding of Conjugate 6 and Conjugate to Fcγ receptor IIIA. The study was performed as described in Example 67.

Figure 52:
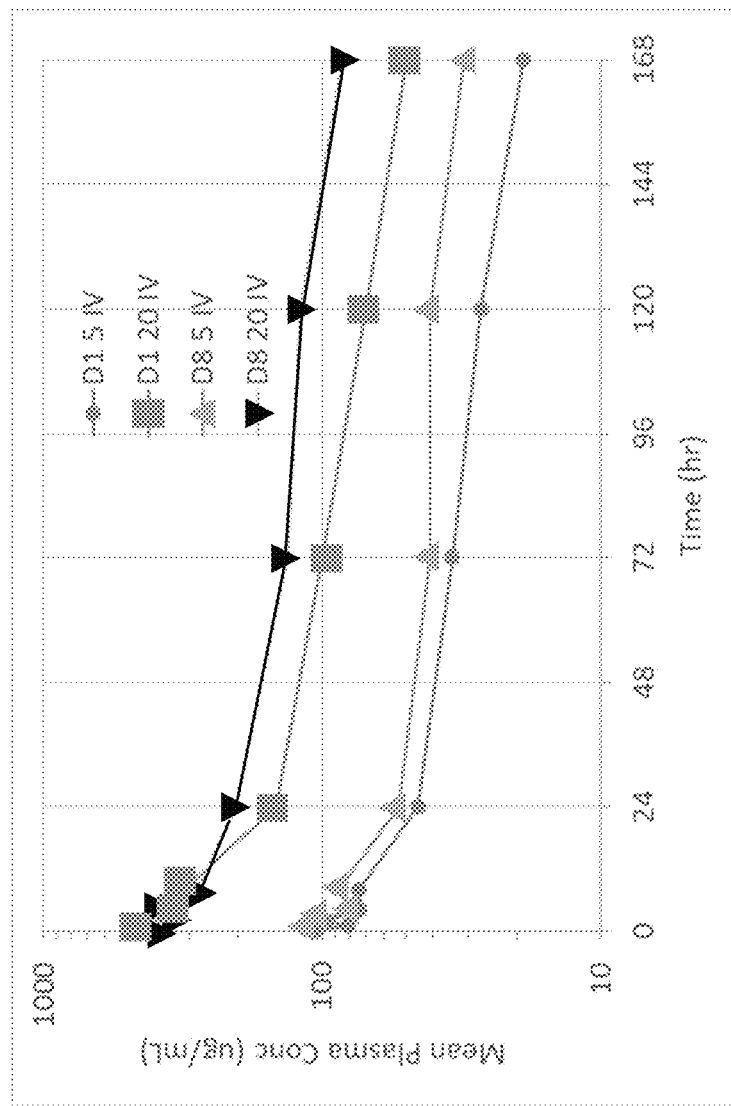

FIG. 52 is a graph showing a 7-day non-human primate toxicokinetic study following IV administration of Conjugate 6. The study was performed as described in Example 68.

Figure 53:
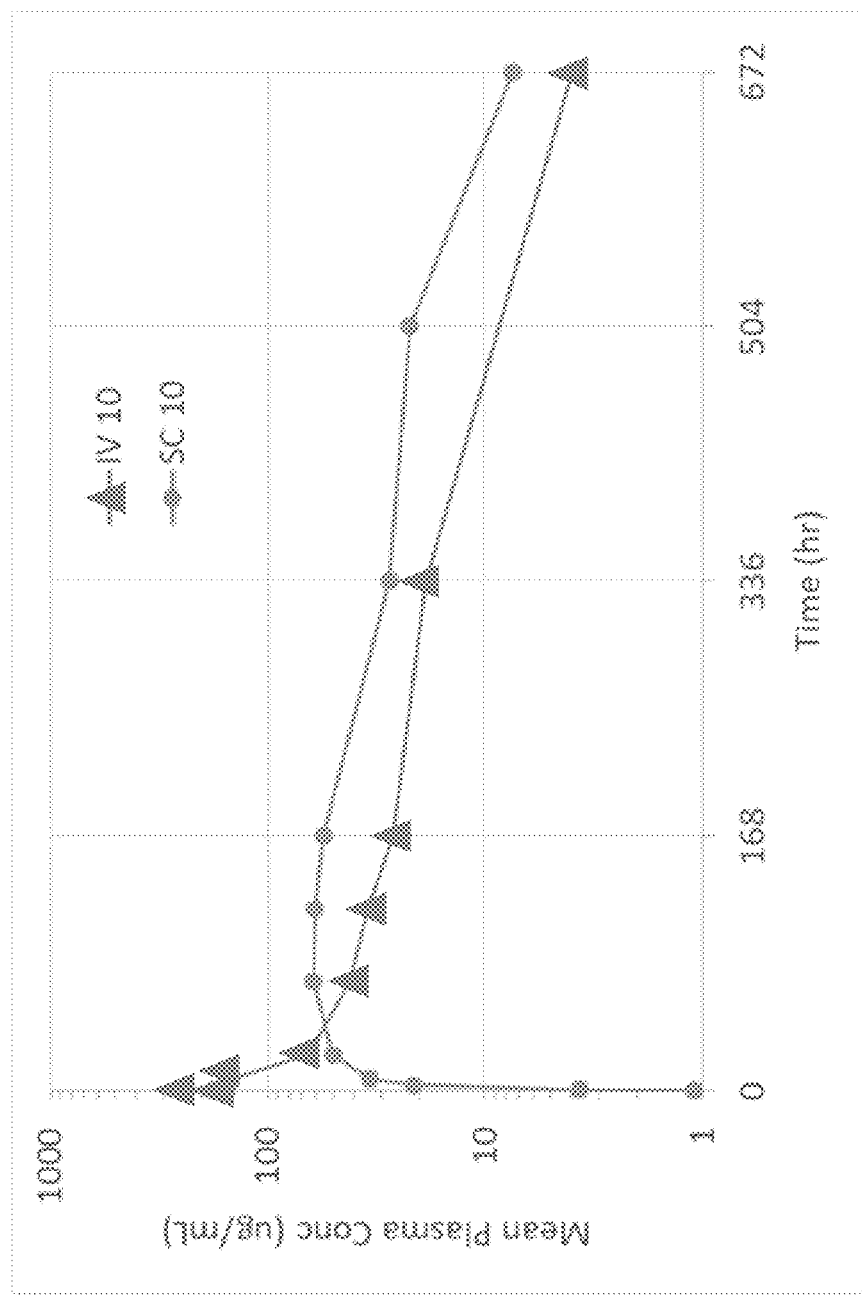

FIG. 53 is a graph showing a 28-day non-human primate pharmacokinetic study comparing IV and SC administration of Conjugate 6. The study was performed as described in Example 68.

Figure 54:
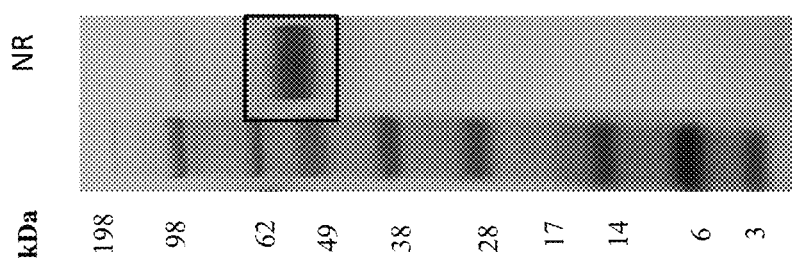

FIG. 54 shows a non-reducing SDS-PAGE of Conjugate 12.

Figure 55:
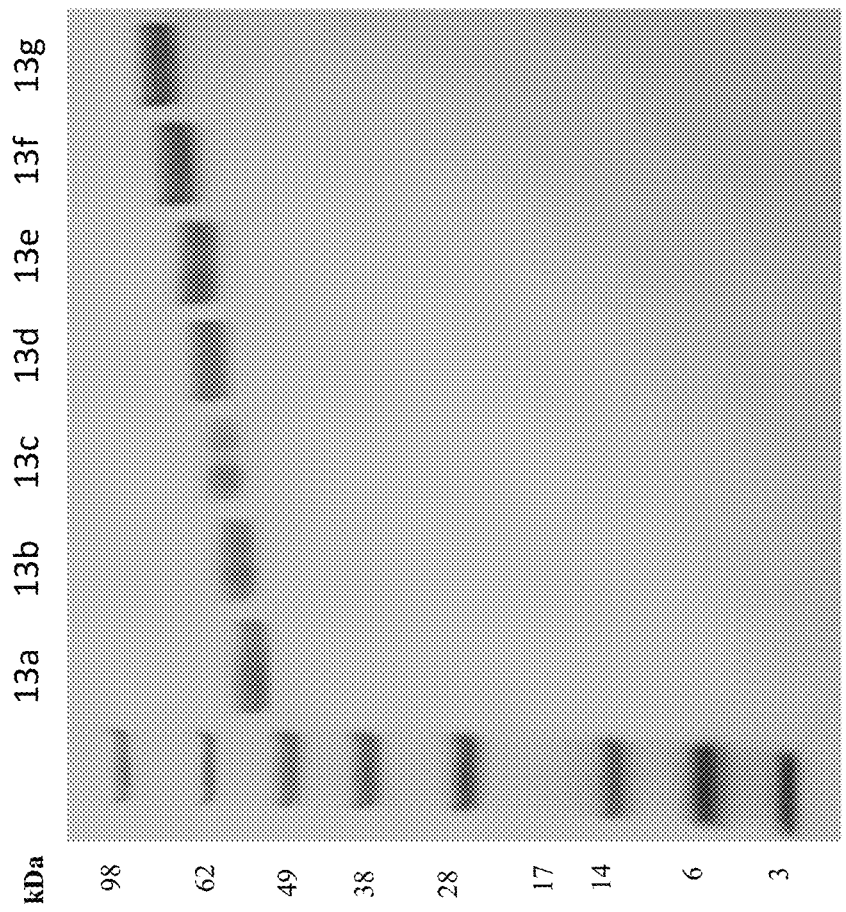

FIG. 55 shows a non-reducing SDS-PAGE of Conjugate 13 having different drug-to-antibody (DAR) ratio values (Conjugate 13a, Conjugate 13b, Conjugate 13c, Conjugate 13d, Conjugate 13e, Conjugate 13f, and Conjugate 13g).

Figure 56:
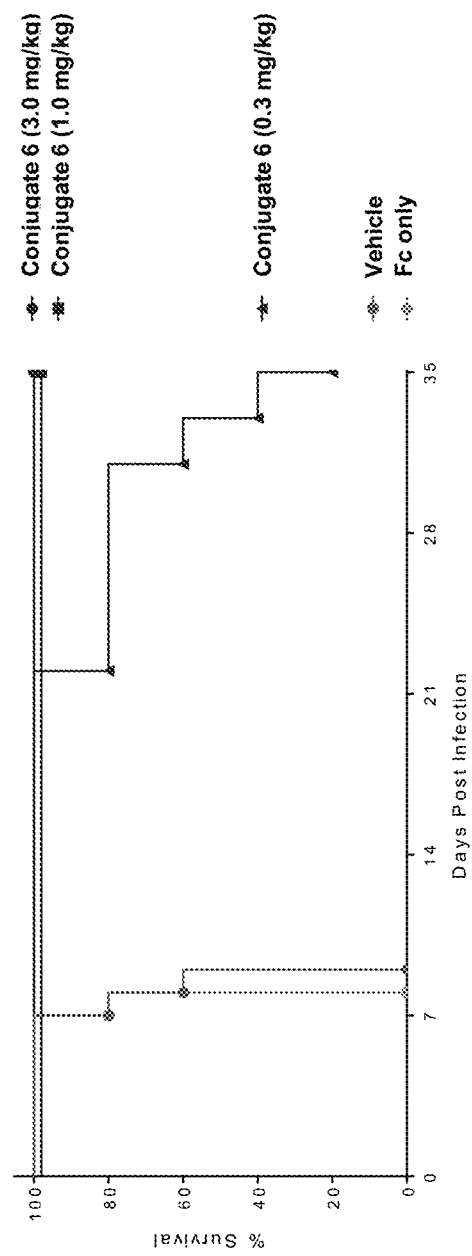
Figure 57:
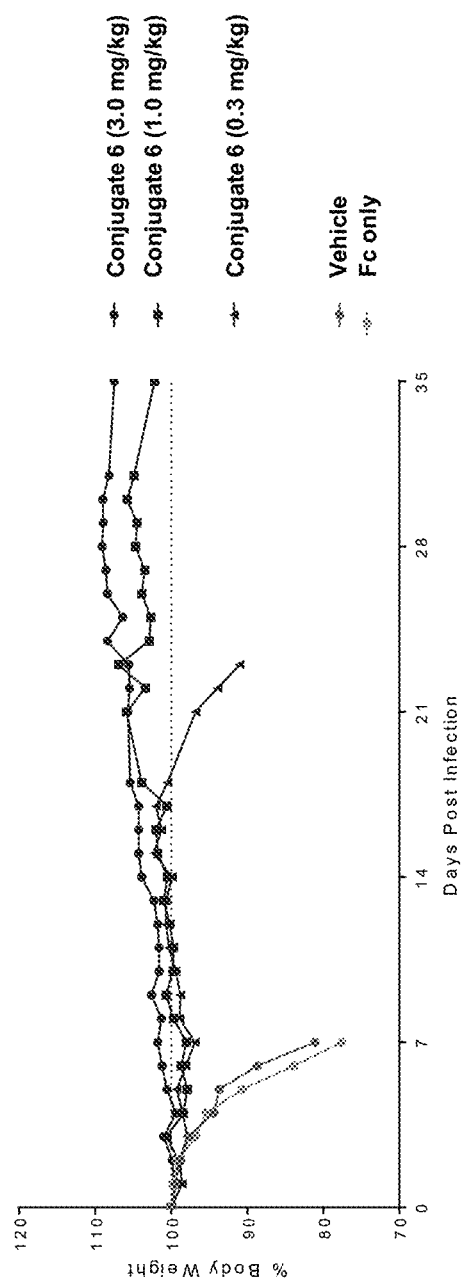

FIG. 56 is a graph showing the % survival in immune compromised mice over 35 days post viral challenge. The 0.3 mg/kg conjugate 6 treatment group remained at 100% survival but is slightly offset in the graph for clarity. The study was performed as described in Example 95 FIG. 57 is a graph showing the % body weight change in immune compromised mice over 35 days post viral challenge. The study was performed as described in Example 95.

Figure 58:
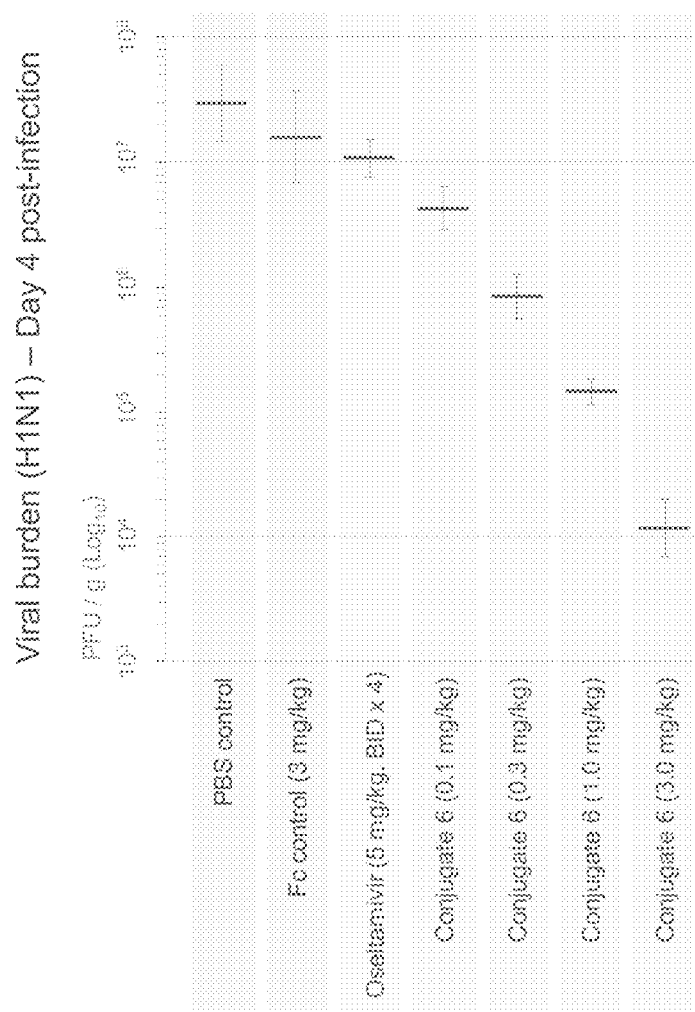

FIG. 58 is a graph showing administration of conjugate 6 results in dose-dependent viral clearance in the lungs of a mouse model infected with Influenza A (H1N1) and that this viral clearance is greater than PBS control, Fc-only control, or Oseltamivir control. This study was performed as described in Example 96.

Figure 59:
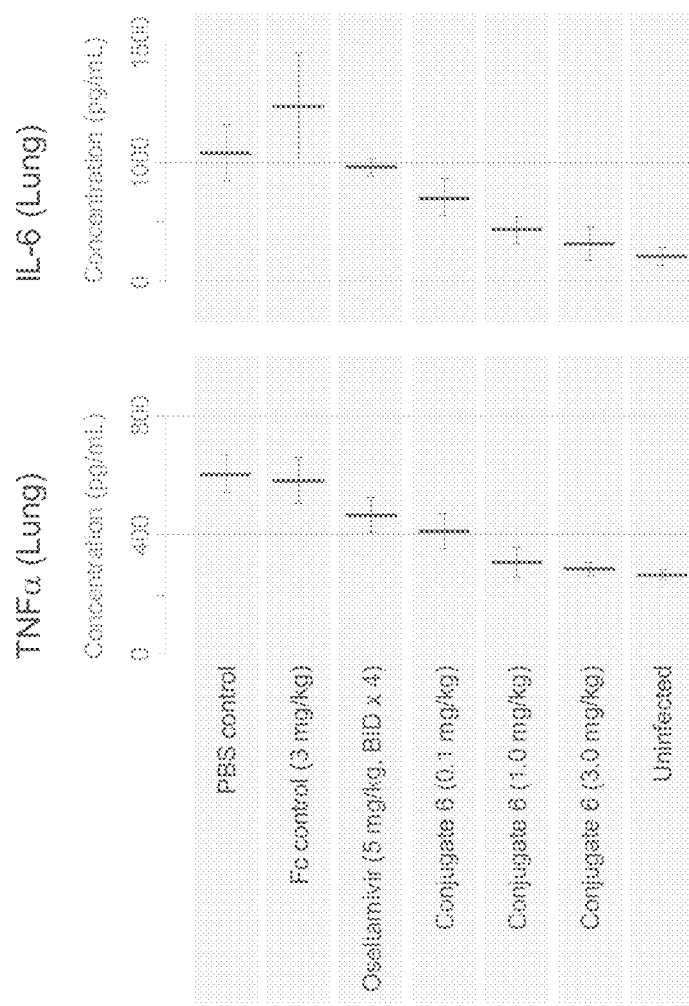

FIG. 59 is a graph showing that administration of conjugate 6 results in a dose-dependent reduction in inflammatory cytokines in the lungs in a mouse model infected with Influenza A (H1N1). This study was performed as described in Example 97.

Figure 60:
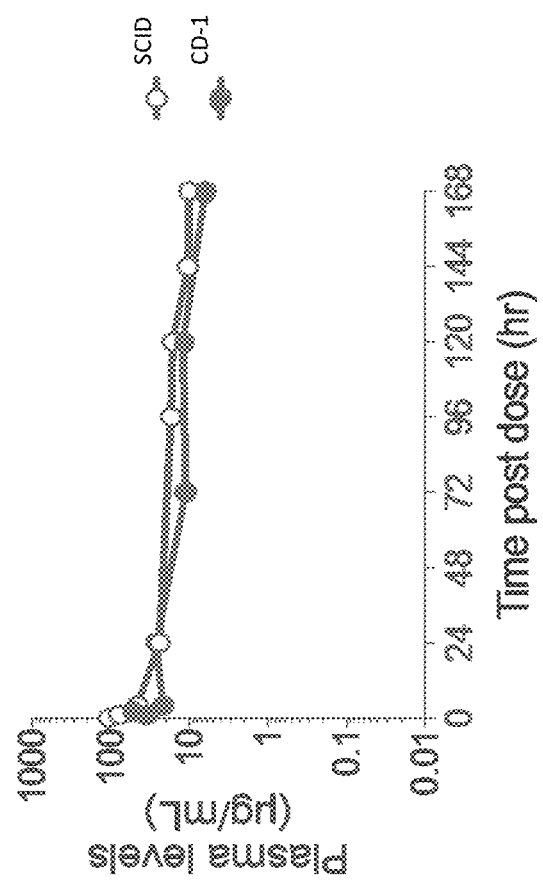

FIG. 60 is a graph showing the pharmacokinetics of conjugate 6 in BALB/c SCID (immunocompromised) mice and CD-1 mice (immunocompetent). This study was performed as described in Example 98.

Figure 61:
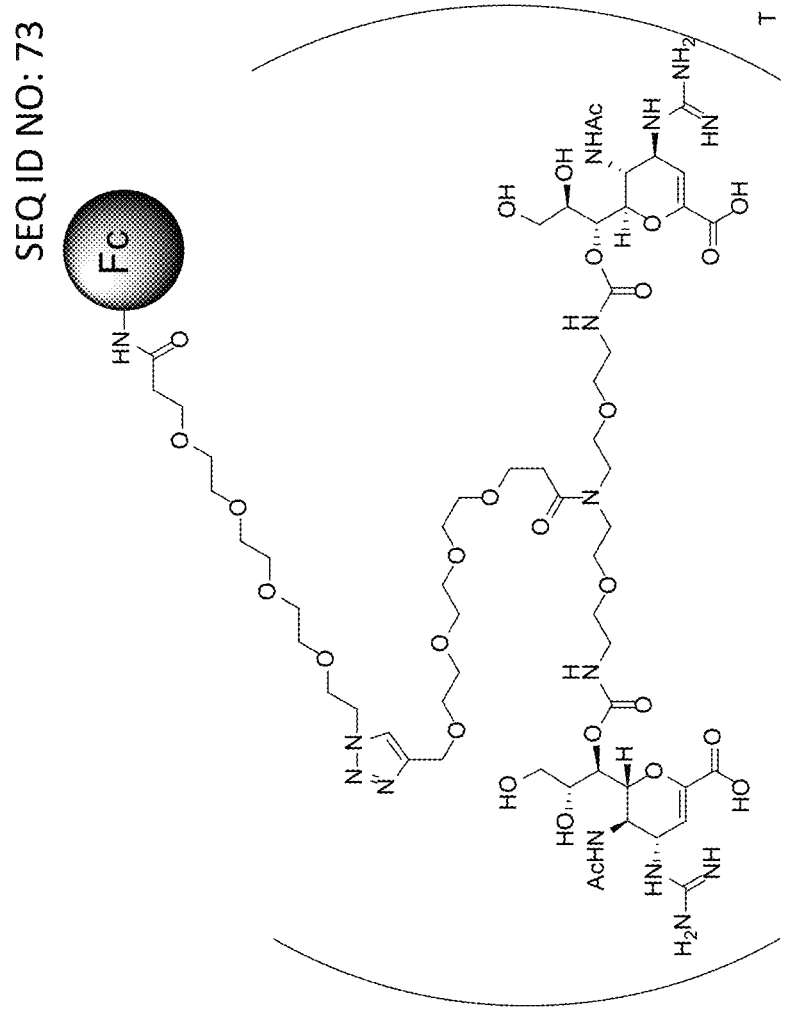

FIG. 61 is an image depicting conjugate 33.

Figure 62A:
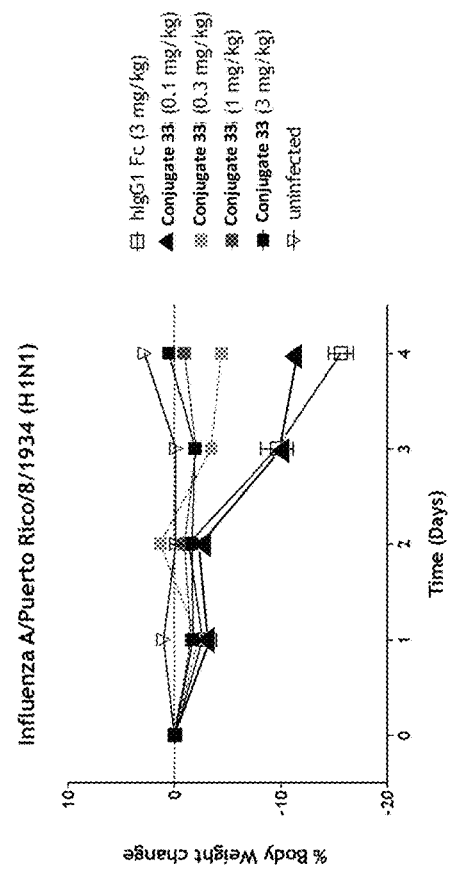
Figure 62B:
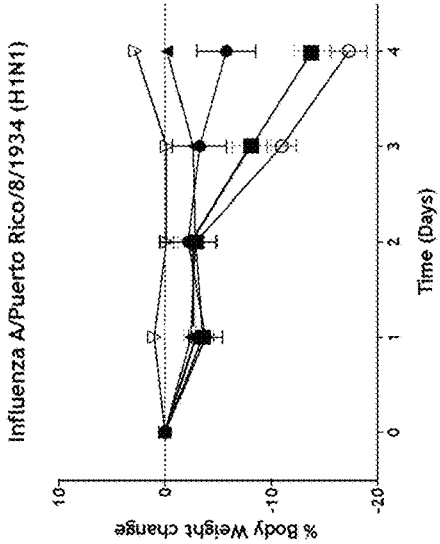

FIGS. 62A-62B are graphs showing the body weight change (%) in BALB/c mice challenged intranasally with 3× the $LD_{95}$ of mouse adapted influenza A.PR/8/1934 (H1N1). This study was performed as described in Example 133.

Figure 63B:
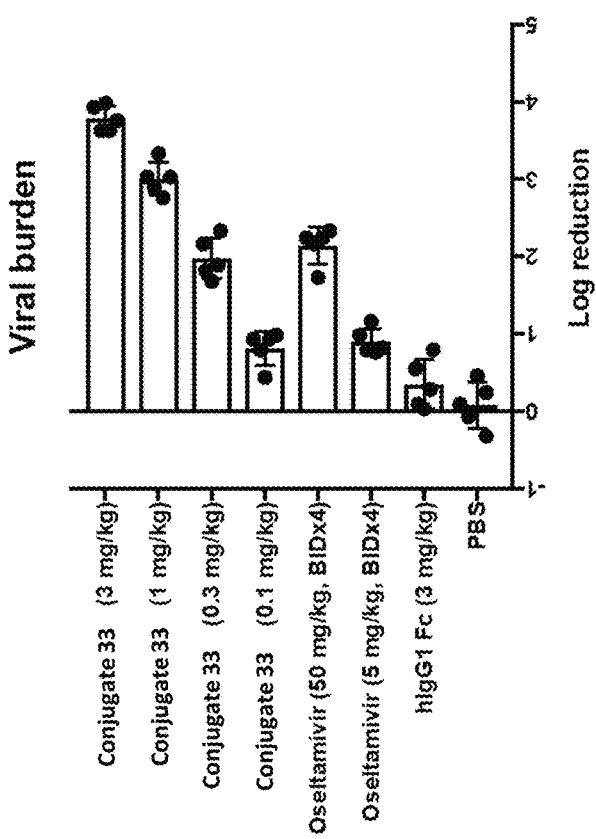
Figure 63A:
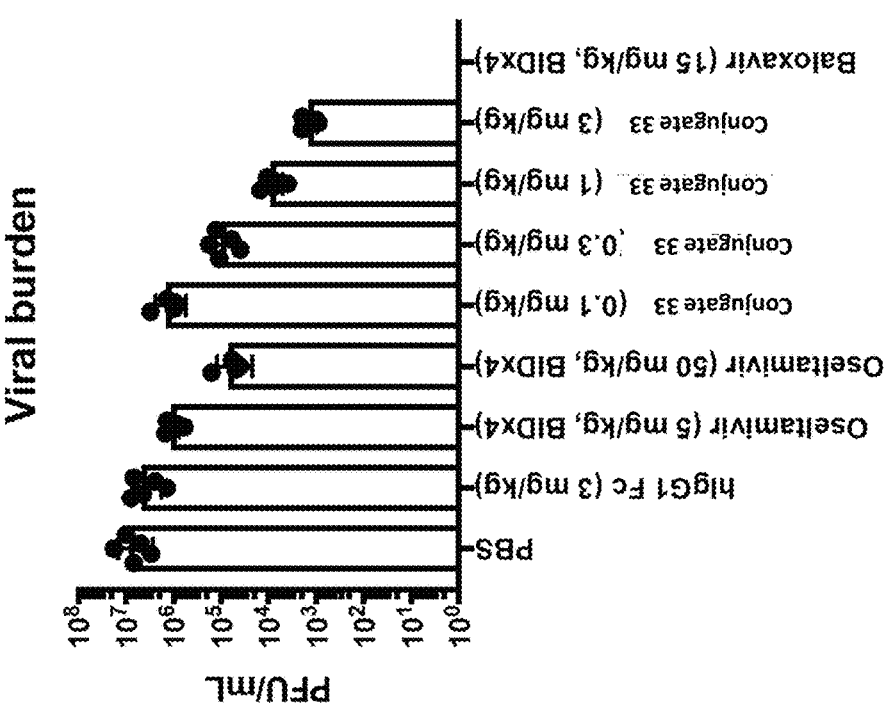

FIG. 63A is a graph showing the viral burden on day 4 post infection. This study was performed as described in Example 133.

FIG. 63B is a graph showing the log reduction in viral burden on day 4 post infection. This study was performed as described in Example 133.

Figure 64B:
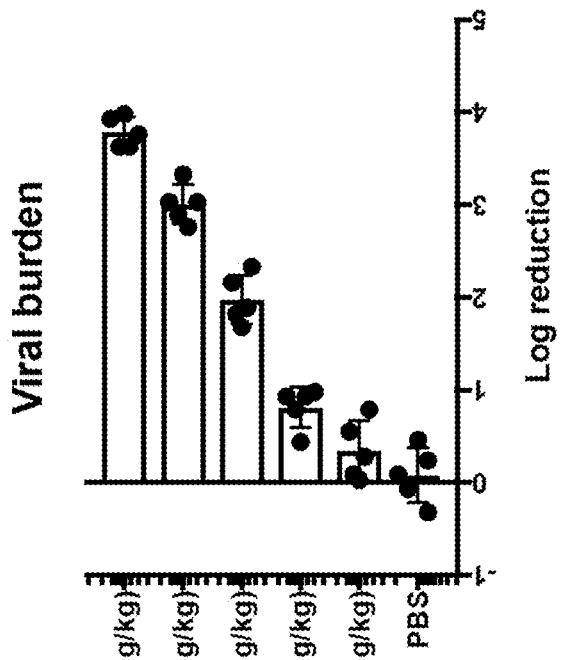
Figure 64A:
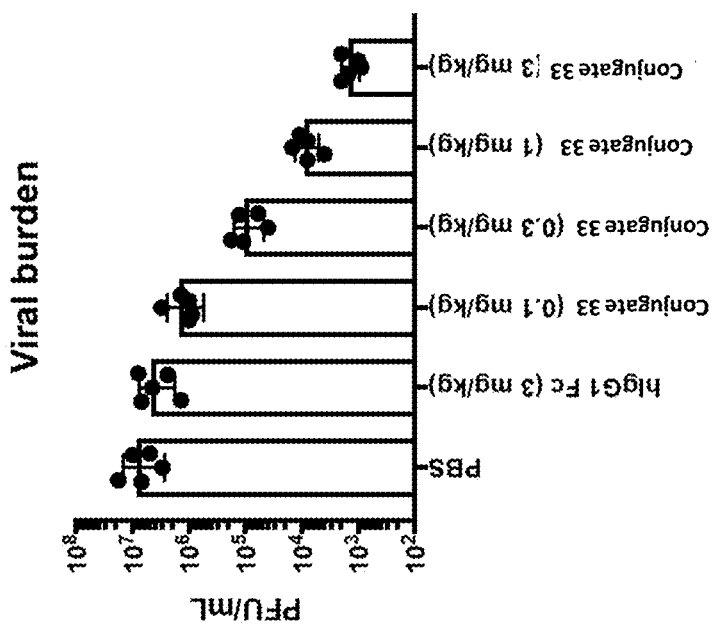

FIG. 64A is a graph showing administration of conjugate 33 results in dose-dependent reduction of viral burden in a mouse model infected with Influenza A (H1N1) compared with PBS control or Fc-only control. This study was performed as described in Example 133.

FIG. 64B is a graph showing the log reduction in viral burden on day 4 post infection. This study was performed as described in Example 133.

Figure 65A:
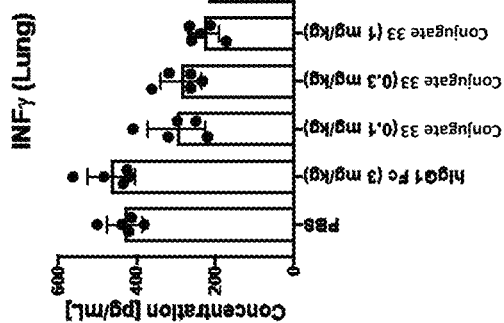
Figure 65B:
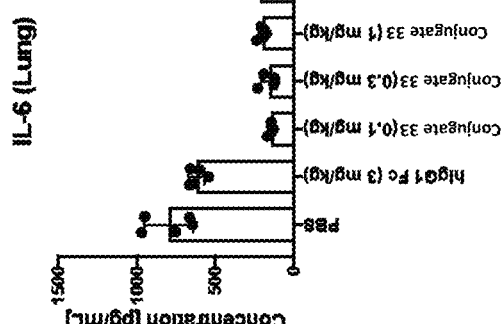
Figure 65C:
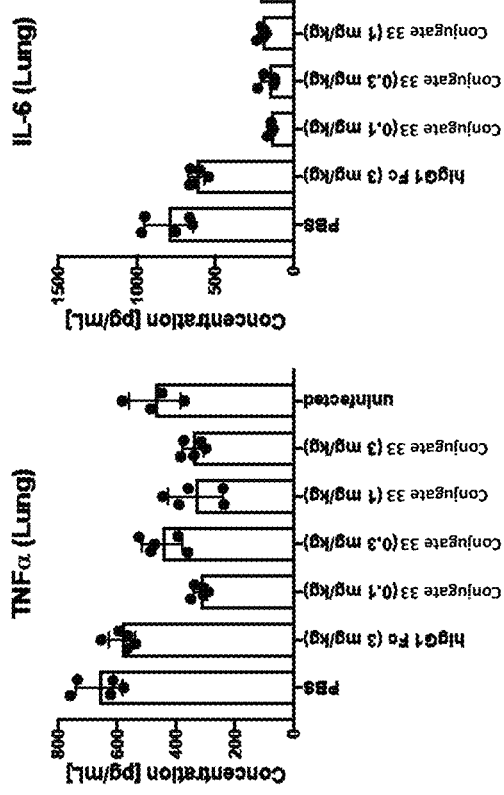
Figure 65D:
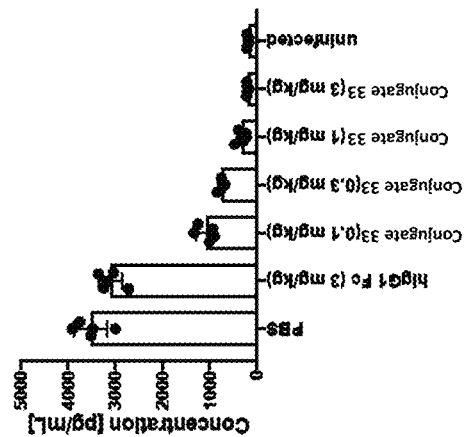
Figure 65E:
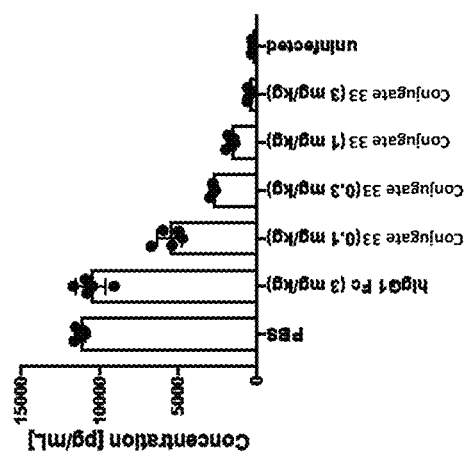

FIGS. 65A-65E are a series bar graphs showing administration of conjugate 33 results in dose-dependent fold-reduction in cytokine levels for TNF-α (FIG. 65A), IL-6 (FIG. 65B), INF-γ (FIG. 65C), MCP-1 (FIG. 65D), and MIP-1α (FIG. 65E). This study was performed as described in Example 133.

Figure 66:
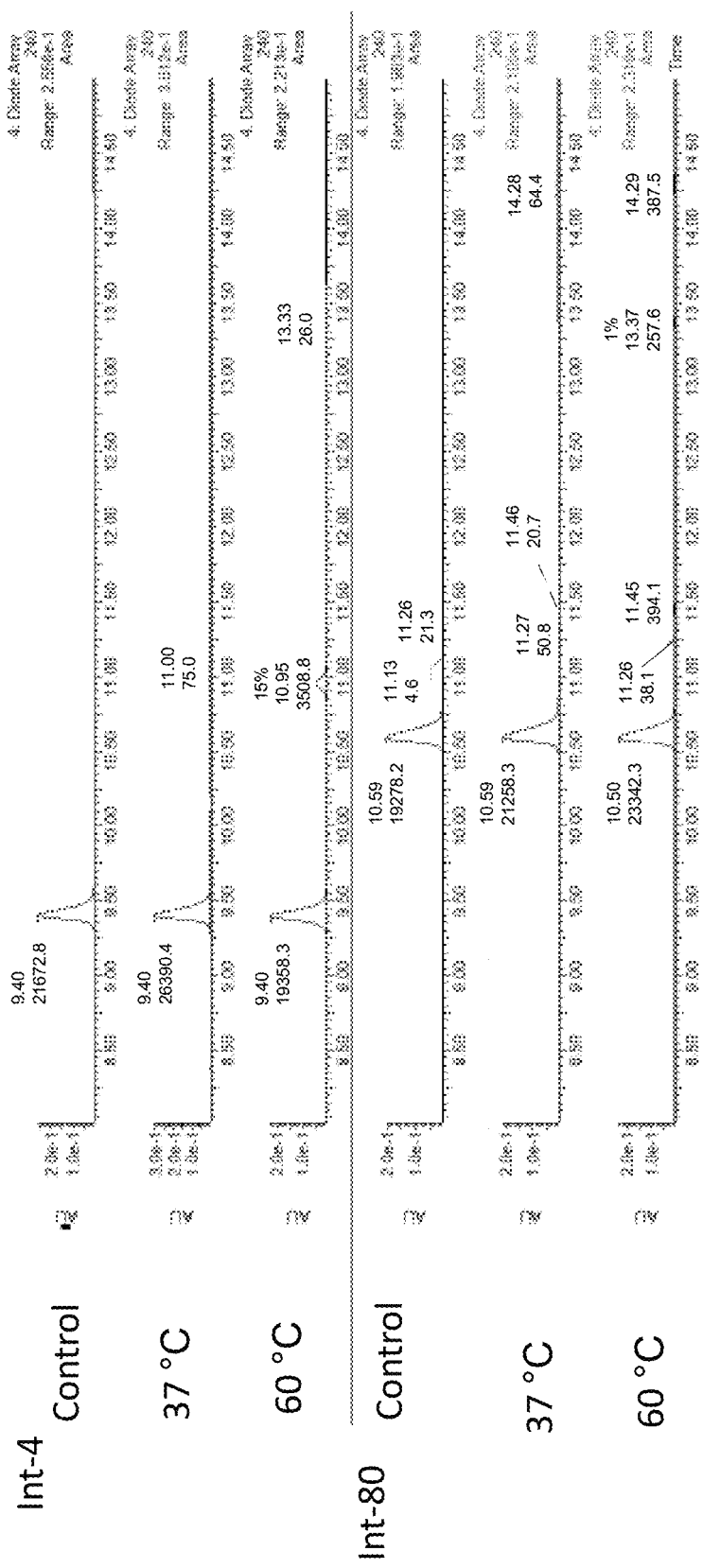

FIG. 66 is a chromatograph showing the stability of Int-80 compared to Int-4 on day 7 of incubating at 37° C. and 60° C. This study was performed as describe in Example 142.

Figure 67:
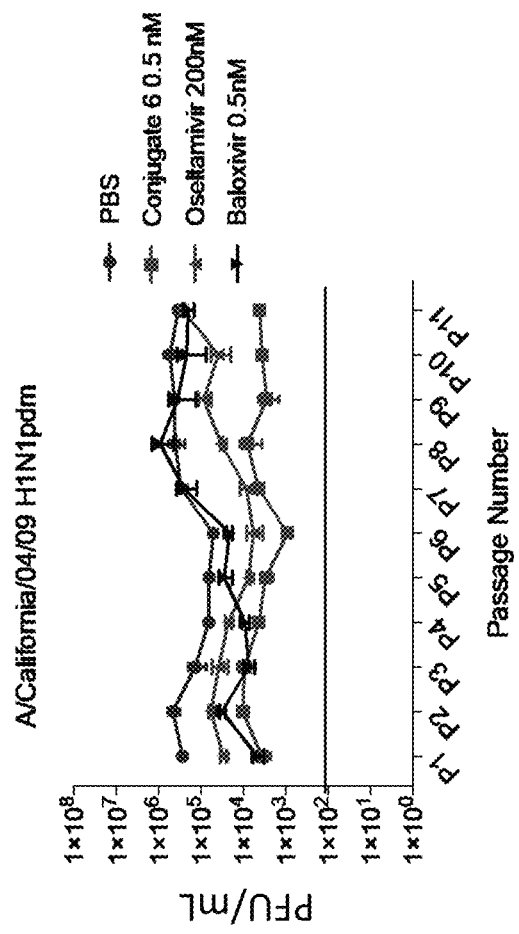

FIG. 67 is a graph showing serial passage of A/CA/09 pdm in the presence of Conjugate 6, oseltamivir, baloxavir or PBS control in A549 cells to evaluate the potential for development of drug resistant mutant viral strains under selective pressure with viral inhibitors. This study was performed as described in Example 147.

Figure 68:
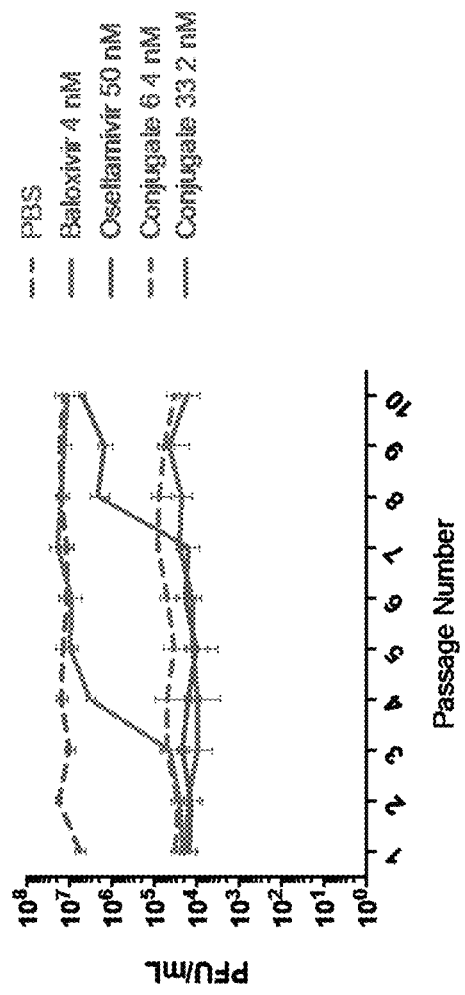

FIG. 68 is a graph showing serial passage of A/WSN/1933 in the presence of Conjugate 6, Conjugate 33, oseltamivir, baloxavir or PBS control in MDCK cells to evaluate the potential for development of drug resistant mutant viral strains under selective pressure with viral inhibitors. This study was performed as described in Example 147.

Figure 69:
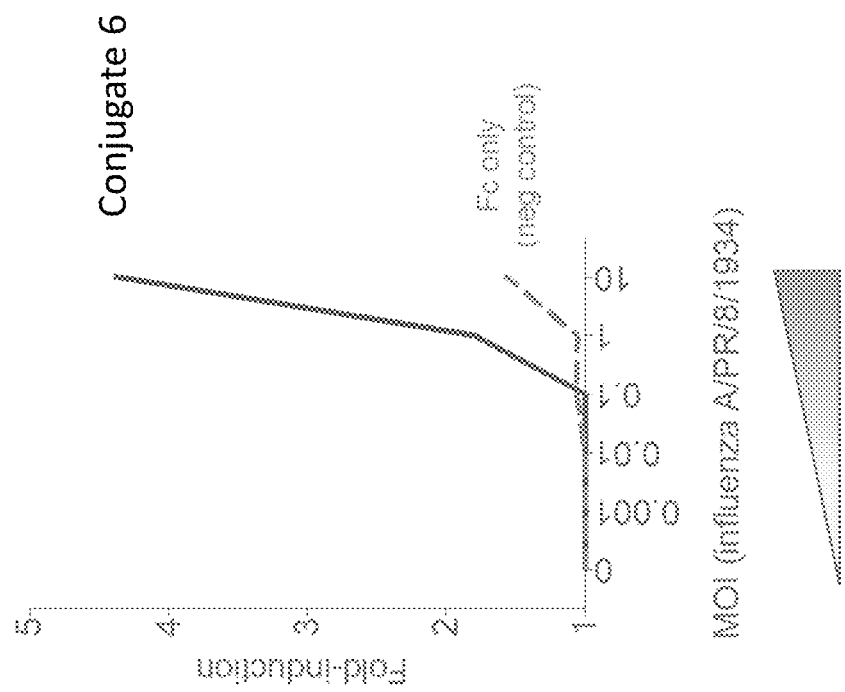

FIG. 69 is a graph showing an MOI-dependent increase in ADCC by conjugate 6 against influenza A H1N1. This study was performed as described in Example 152.

Figure 70:
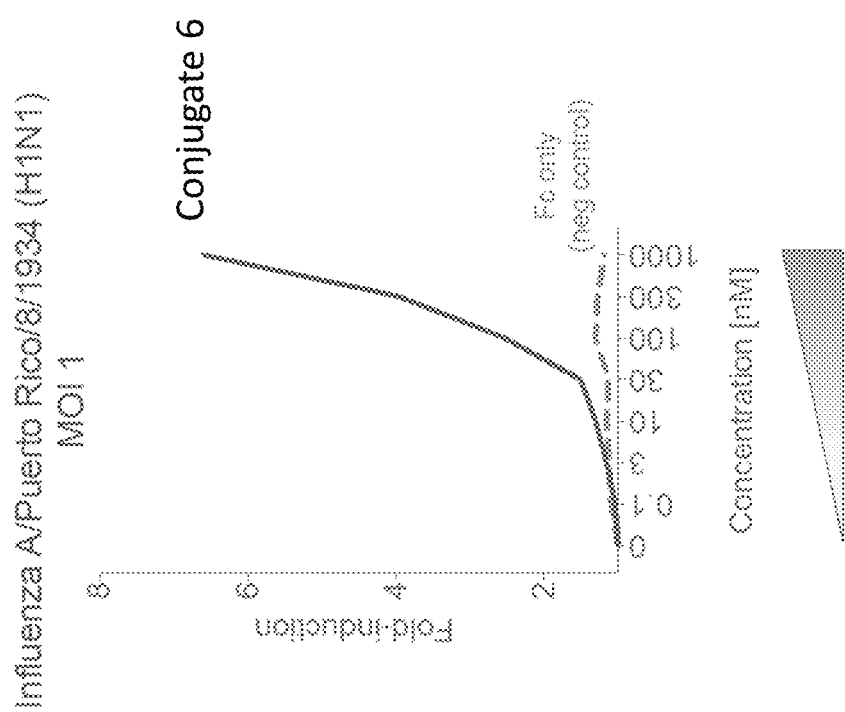

FIG. 70 is a graph showing a dose-dependent increase in ADCC by conjugate 6 against influenza A/PR/8/1934 (H1N1) at an MOI of 1. This study was performed as described in Example 152.

Figure 71A:
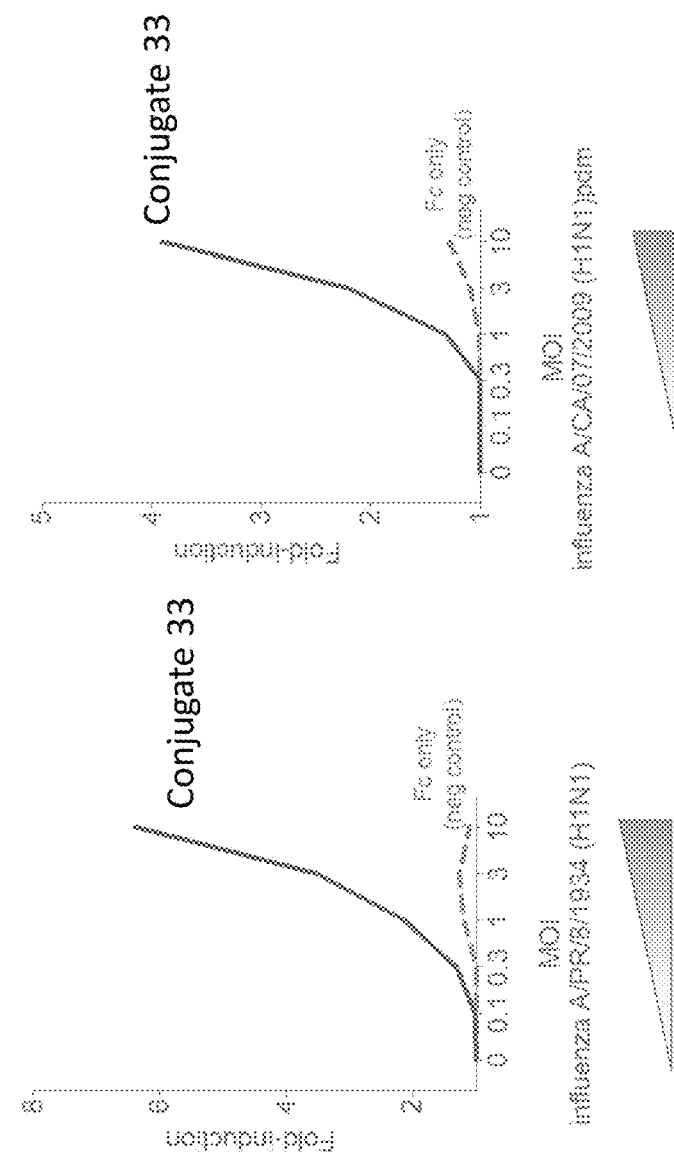
Figure 71B:
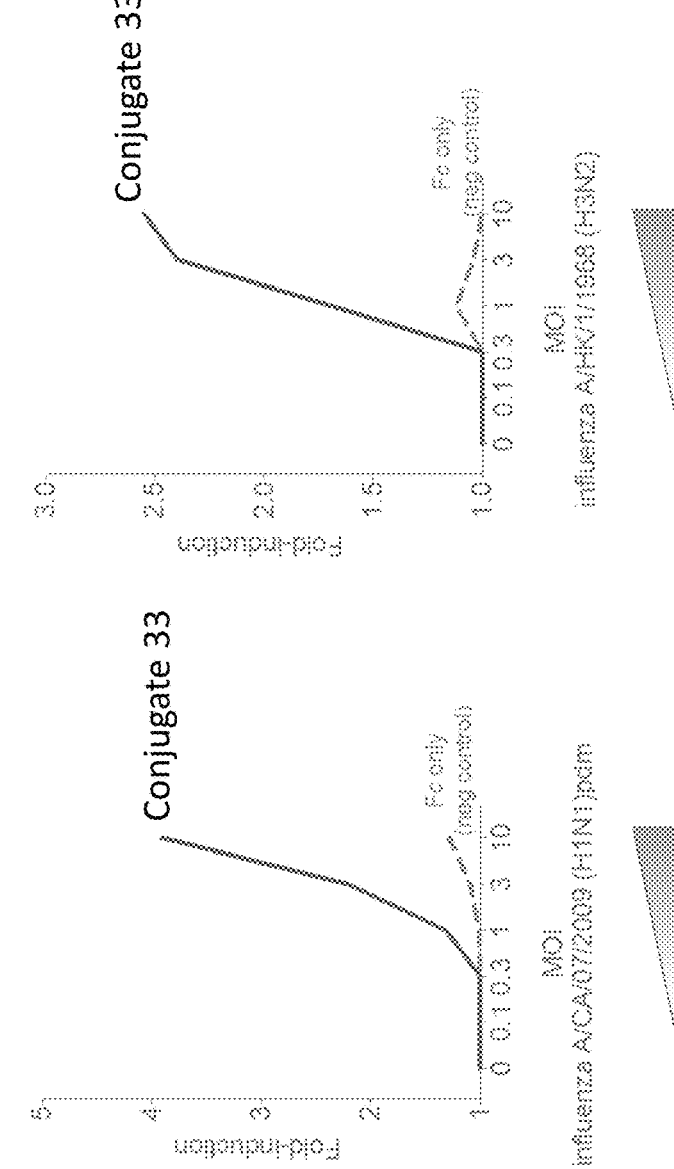
Figure 71C:
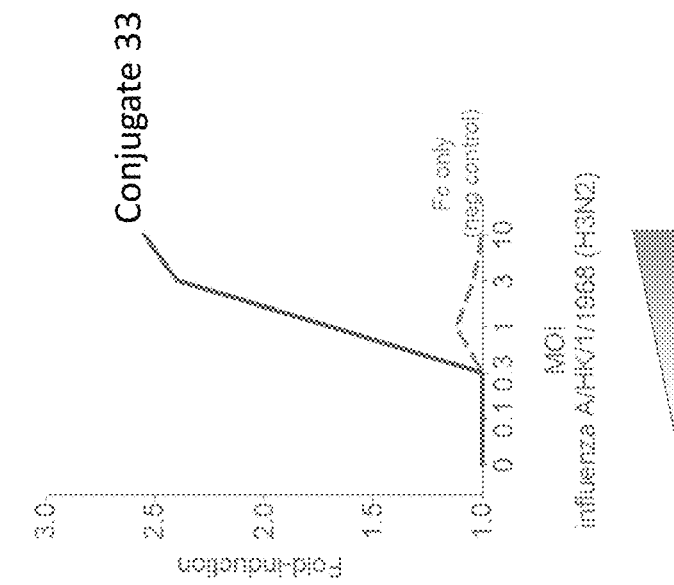

FIGS. 71A-71C are graphs showing an MOI-dependent increase in conjugate 33 against influenza A/PR/8/1934 (H1N1, FIG. 71A), influenza A/CA/07/2009 (H1N1)pdm (FIG. 71B) and influenza A/HK/1/1968 (H3N2, FIG. 71C). This study was performed as described in Example 152.

Figure 72:
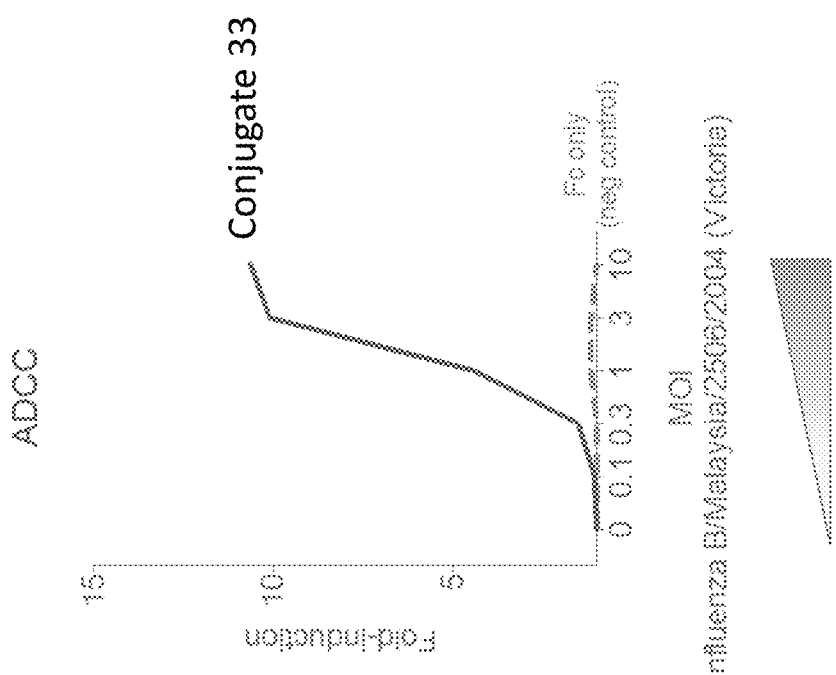

FIG. 72 is a graph showing an MOI-dependent increase in ADCC by conjugate 33 against influenza B/Malaysia/2506/2004 (Victoria). This study was performed as described in Example 152.

Figure 73A:
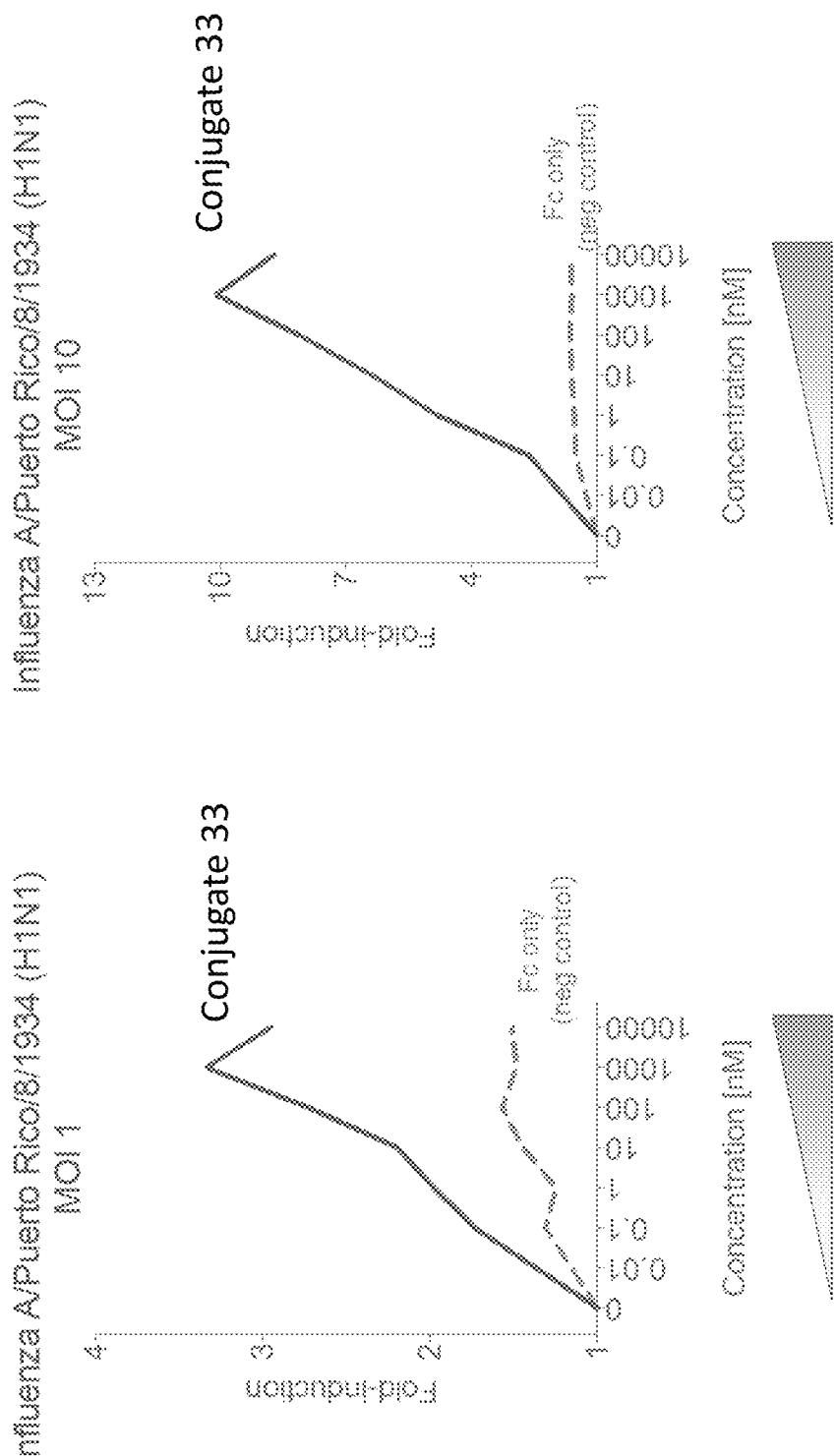
Figure 73B:
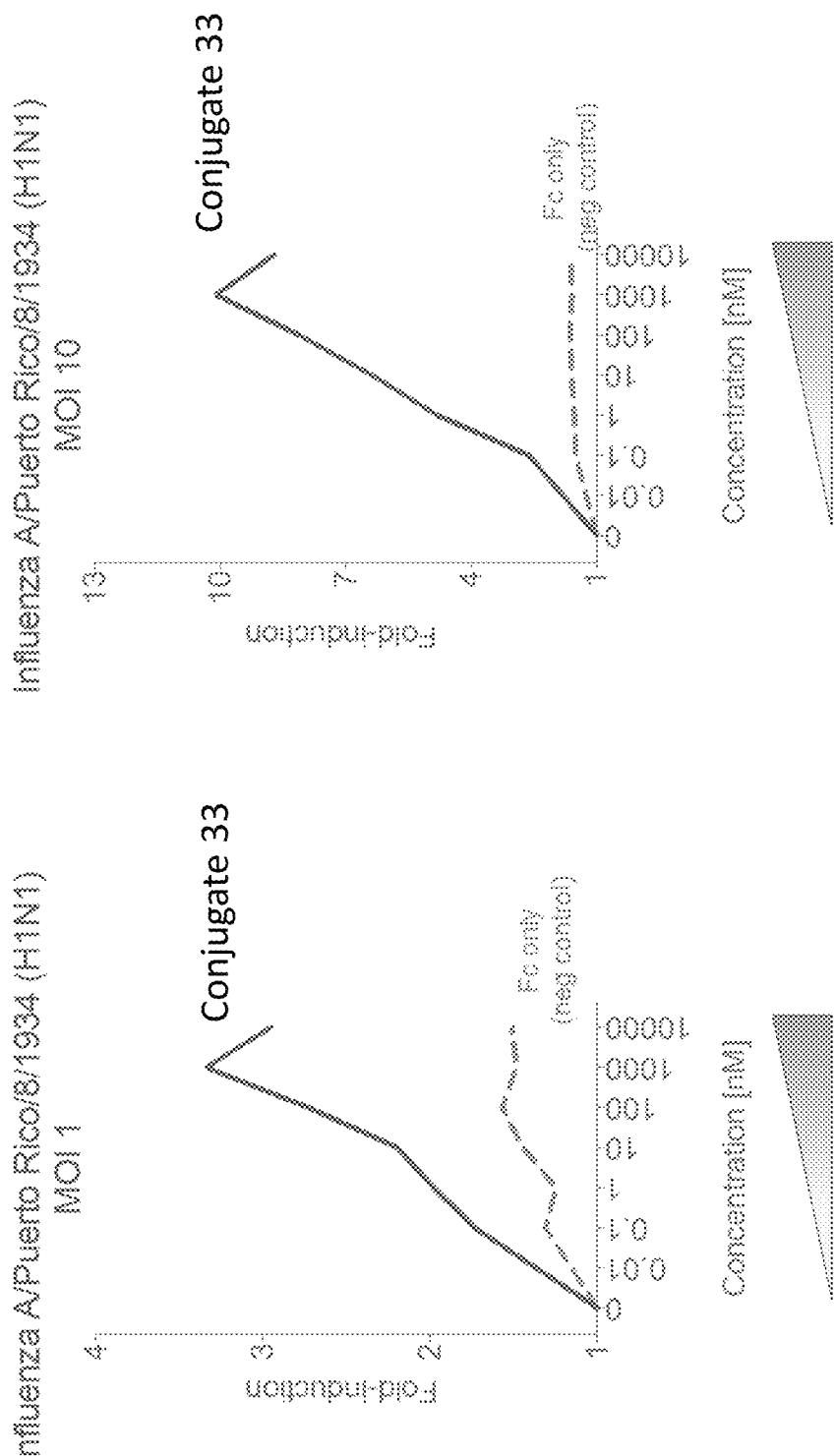

FIGS. 73A-73B are graphs showing a dose-dependent increase in ADCC by conjugate 33 against influenza A/PR/8/1934 at an MOI of 1 (FIG. 73A) and an MOI of 10 (FIG. 73B). This study was performed as described in Example 152.

Figure 74:
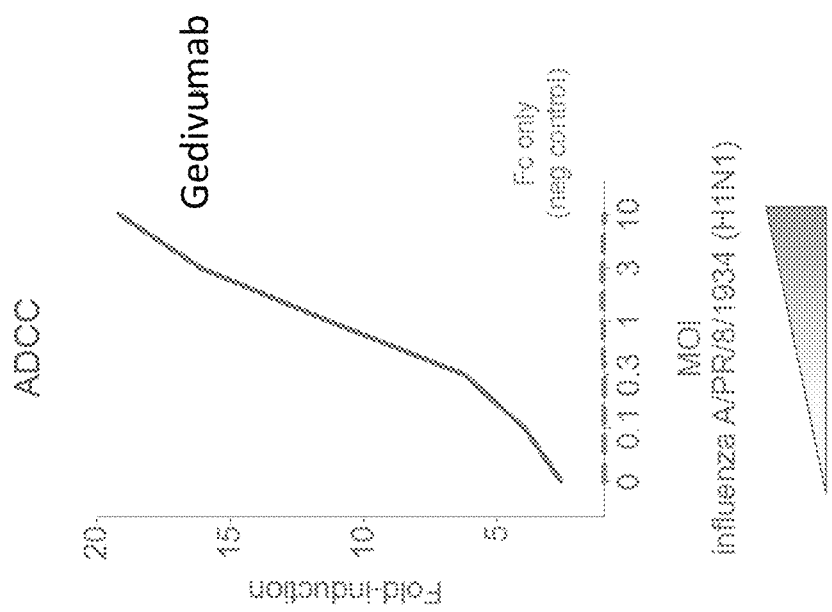

FIG. 74 is a graph showing an MOI-dependent increase in ADCC by a control full-length monoclonal antibody, Gedivumab (Genentech), against influenza A/PR/8/1934 (H1N1). This study was performed as described in Example 152.

Figure 75B:
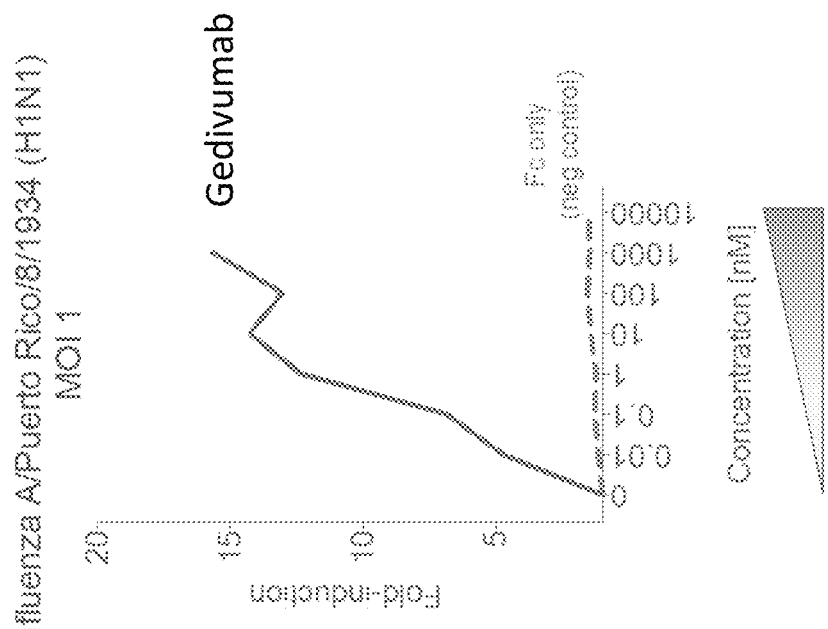
Figure 75A:
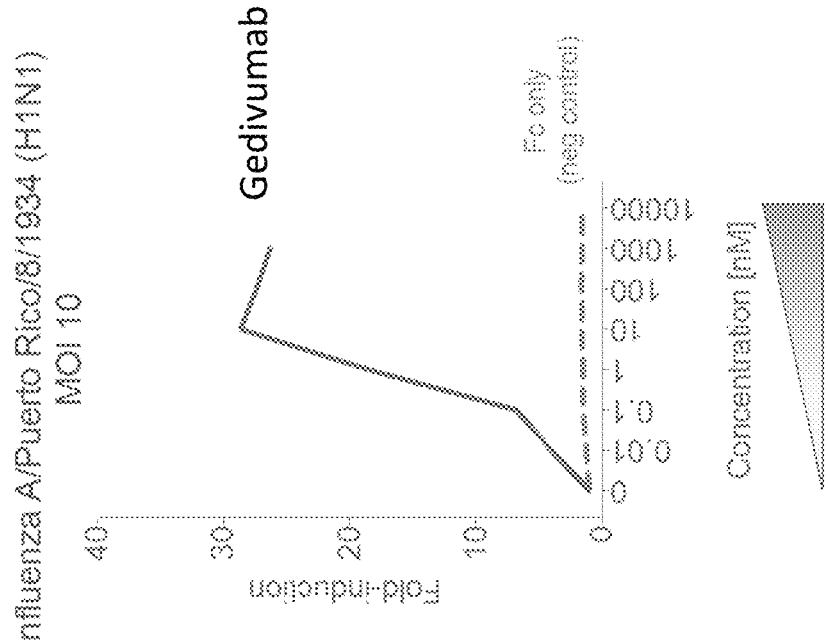

FIGS. 75A-75B are graphs showing a dose-dependent increase in ADCC by a control full-length monoclonal antibody, Gedivumab (Genentech), against influenza A/PR/8/1934 at an MOI of 1 (FIG. 75A) and an MOI of 10 (FIG. 75B). This study was performed as described in Example 152.

Figure 76:
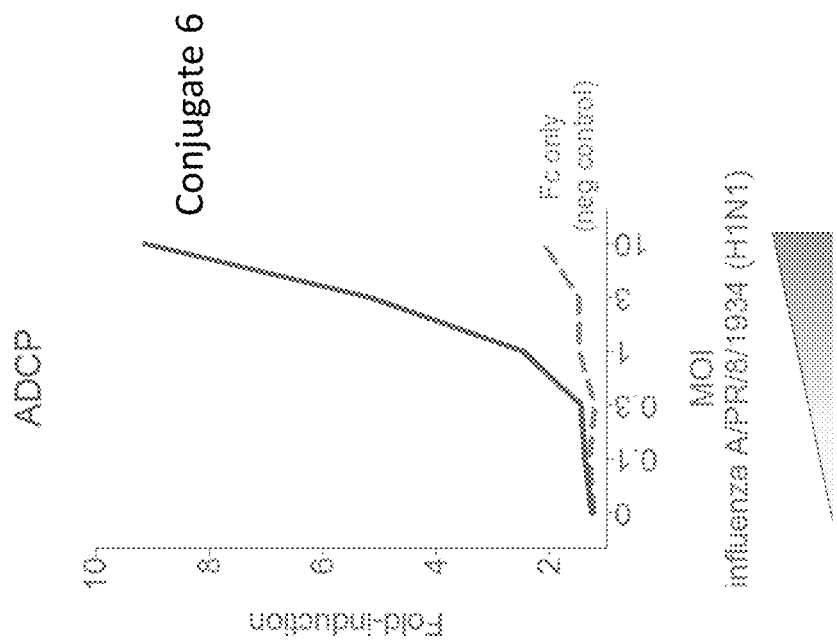

FIG. 76 is a graph showing an MOI-dependent increase in ADCP by conjugate 6 against influenza A H1N1. This study was performed as described in Example 153.

Figure 77B:
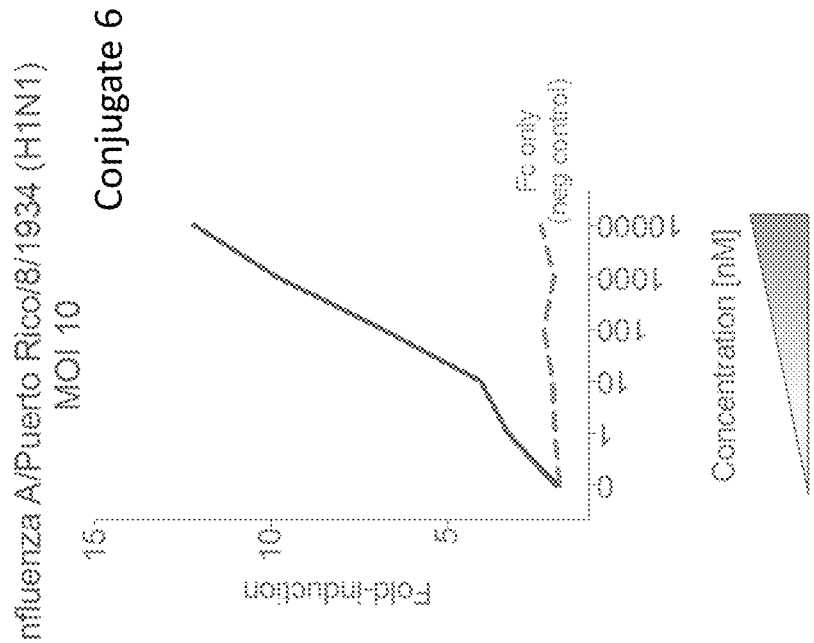
Figure 77A:
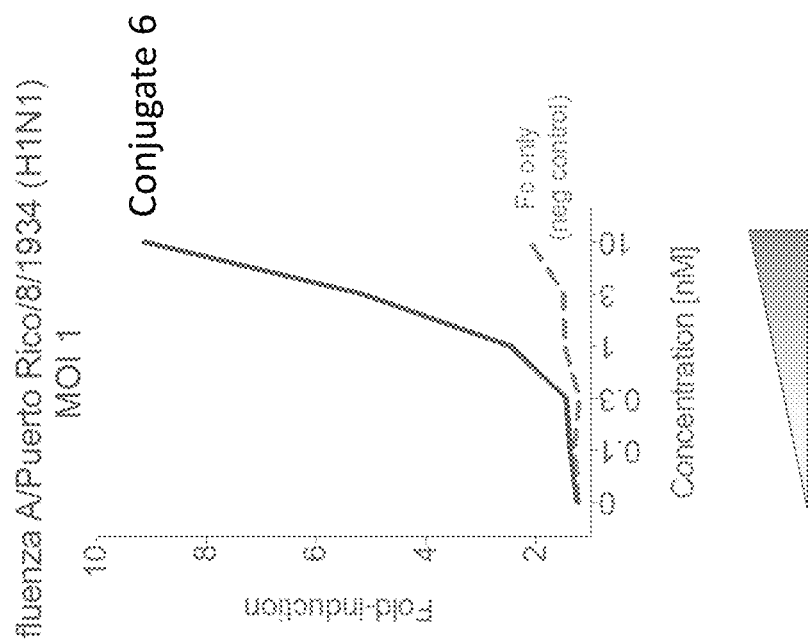

FIGS. 77A-77B are graphs showing a dose-dependent increase in ADCP by conjugate 6 against influenza A/PR/8/1934 (H1N1) at an MOI of 1 (FIG. 77A) and an MOI of 10 (FIG. 77B). This study was performed as described in Example 153.

FIGS. 78A-78C are graphs showing an MOI-dependent increase in conjugate 33 against influenza A/PR/8/1934 (H1N1, FIG. 78A), influenza A/CA/07/2009 (H1N1)pdm (FIG. 78B) and influenza A/HK/1/1968 (H3N2, FIG. 78C). This study was performed as described in Example 153.

FIG. 79 is a graph showing an MOI-dependent increase in ADCP by conjugate 33 against influenza B/Malaysia/2506/2004 (Victoria). This study was performed as described in Example 153.

Figure 80B:
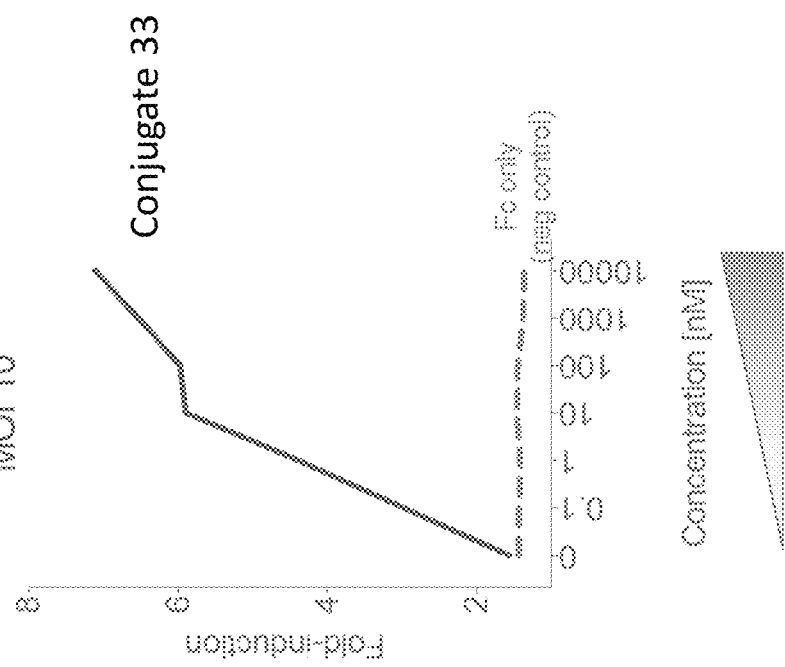
Figure 80A:
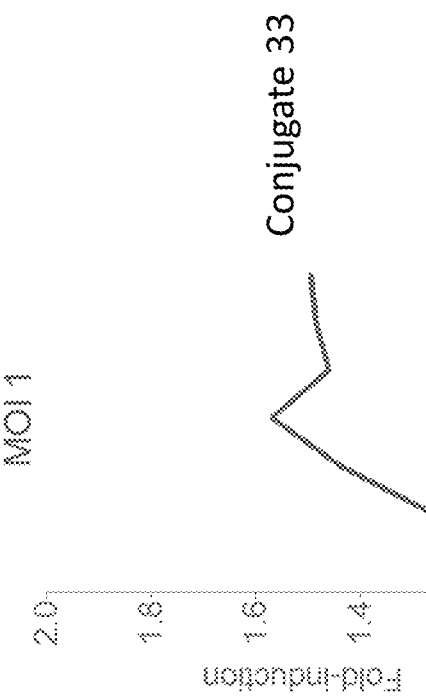

FIGS. 80A-80B are graphs showing a dose-dependent increase in ADCP by conjugate 33 against influenza A/PR/8/1934 at an MOI of 1 (FIG. 80A) and an MOI of 10 (FIG. 80B). This study was performed as described in Example 153.

FIG. 81 is a graph showing an MOI-dependent increase in ADCP by a control full-length monoclonal antibody, Gedivumab (Genentech), against influenza A/PR/8/1934 (H1N1). This study was performed as described in Example 153.

Figure 82B:
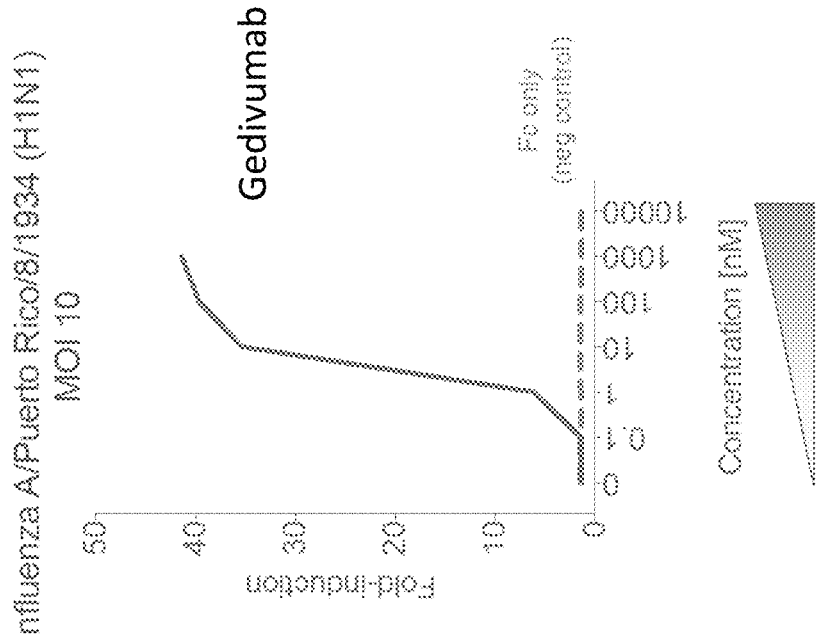
Figure 82A:
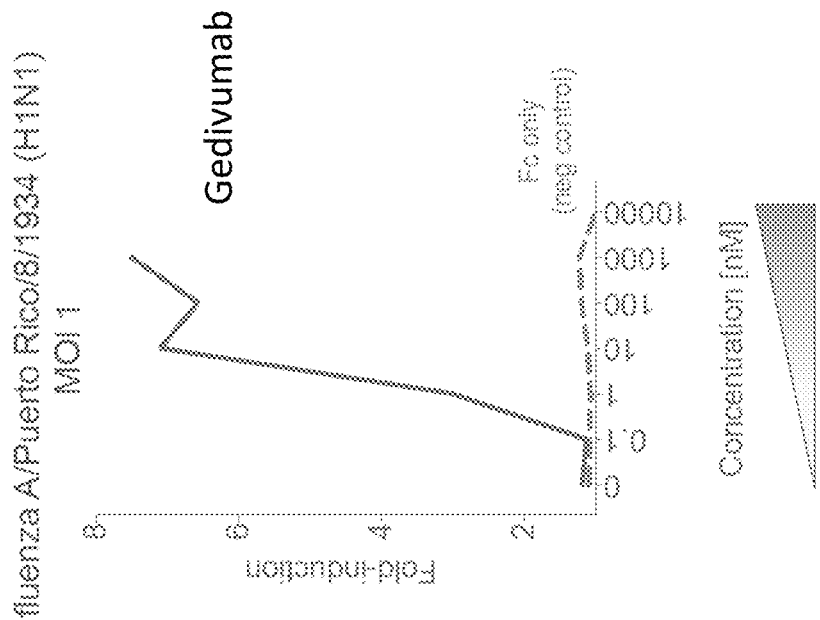

FIGS. 82A-82B are graphs showing a dose-dependent increase in ADCP by a control full-length monoclonal antibody, Gedivumab (Genentech), against influenza A/PR/8/1934 at an MOI of 1 (FIG. 82A) and an MOI of 10 (FIG. 82B). This study was performed as described in Example 153.

Figure 83:
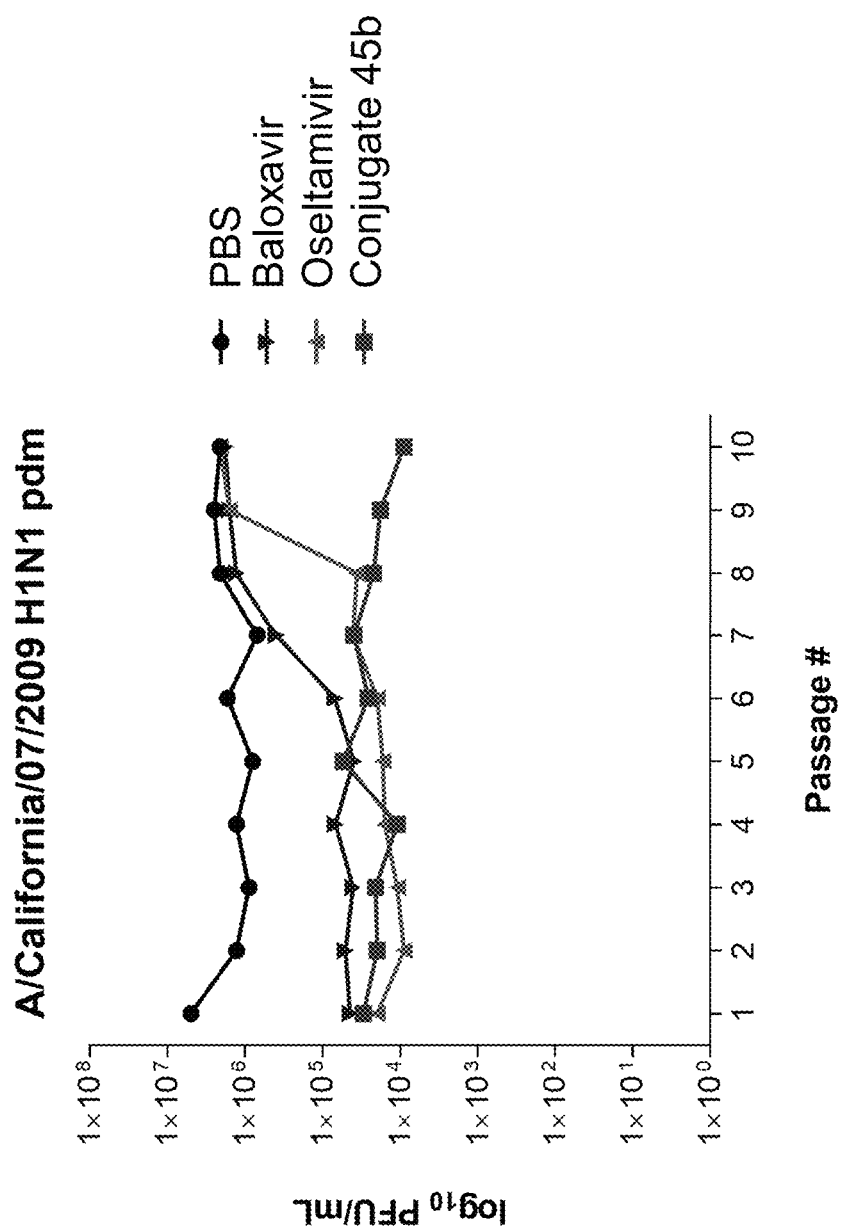

FIG. 83 is a graph showing serial passage of A/Ca/07/2009 (H1N1)pdm in the presence of Conjugate 45b, oseltamivir, baloxavir, or PBS control in MDCK cells to evaluate the potential for development of drug resistant mutant viral strains under selective pressure with viral inhibitors. This study was performed as described in Example 165.

Figure 84:
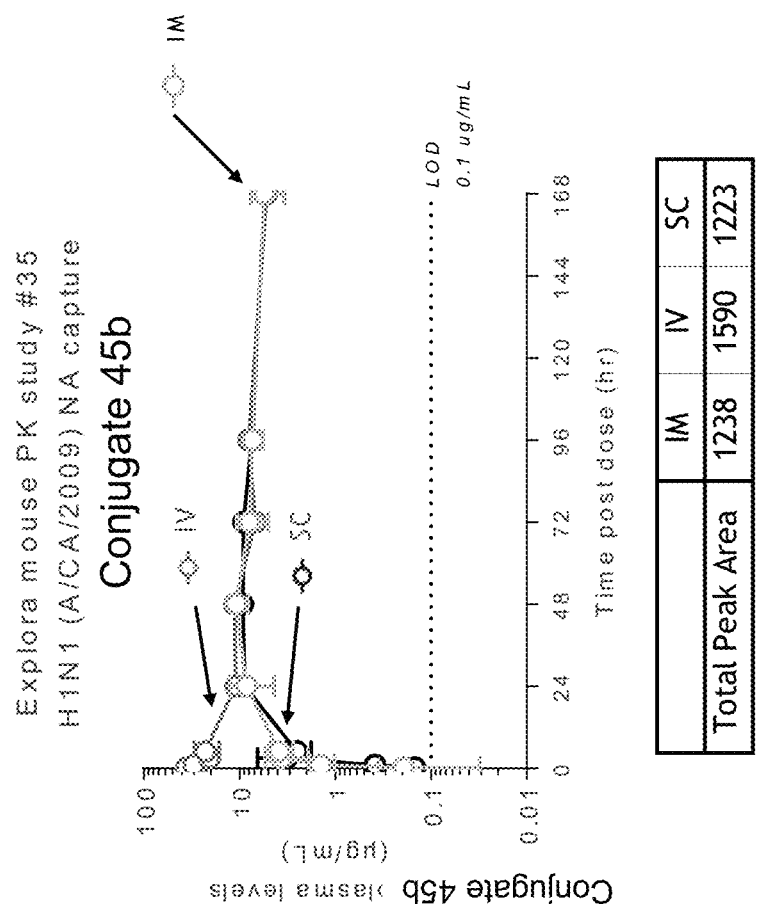

FIG. 84 is a graph showing plasma levels of conjugate 45b in a mouse PK study comparing IV, SC, and IM administration. Plasma concentration levels were determined by NA capture. This study was performed as described in Example 173.

Figure 85:
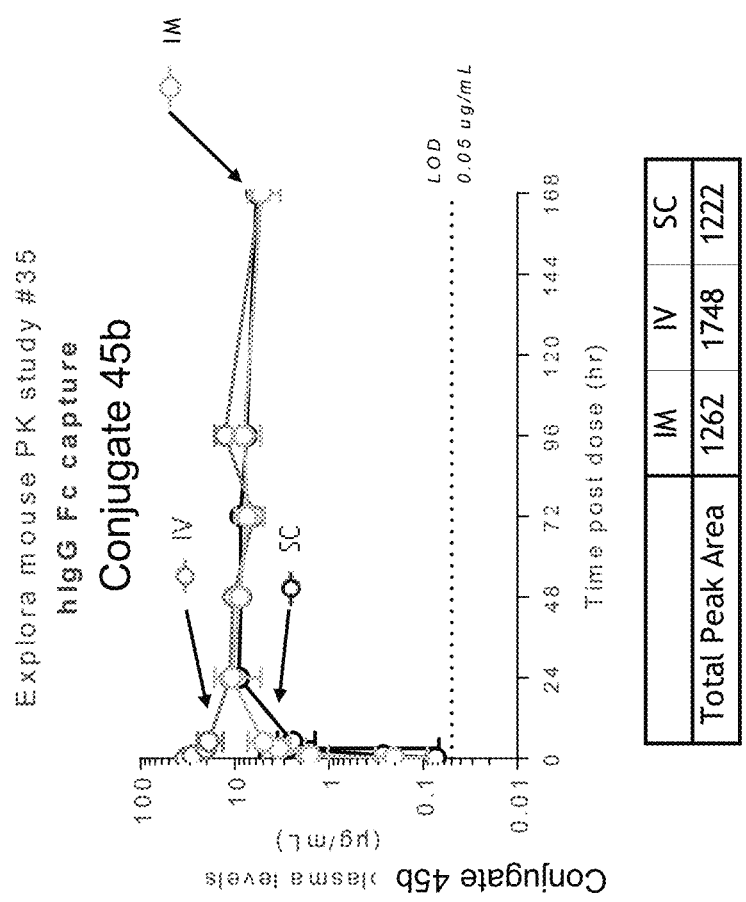

FIG. 85 is a graph showing plasma levels of conjugate 45b in a mouse PK study comparing IV, SV, and IM administration. Plasma concentration levels were determined by hIgG Fc capture. This study was performed as described in Example 173.

Figure 86:
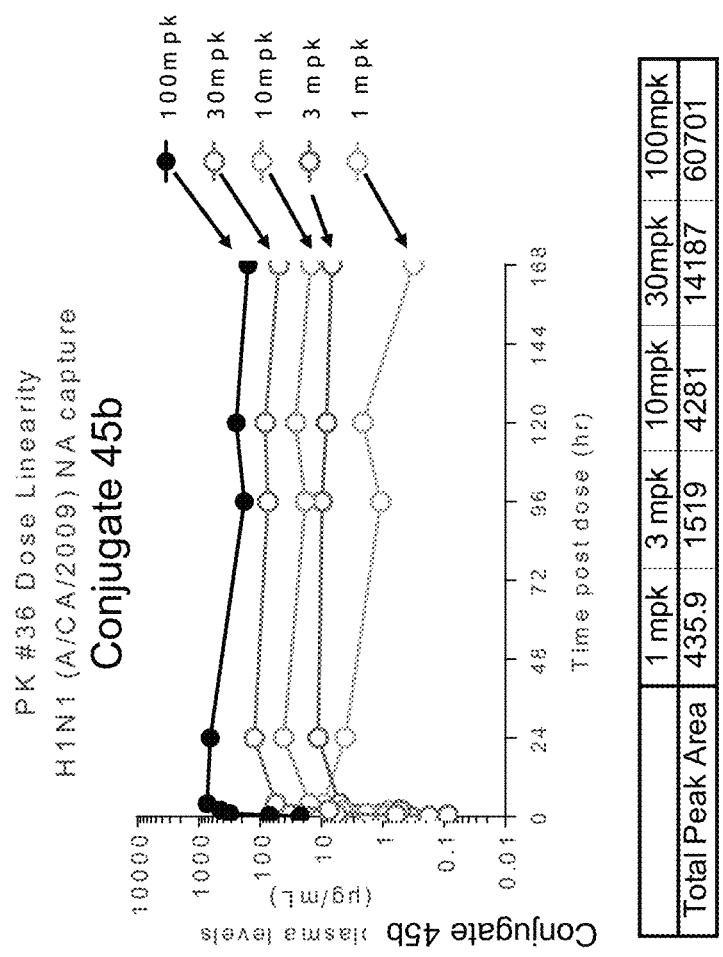

FIG. 86 is a graph showing dose linearity in plasma levels of conjugate 45b by NA capture. This study was performed as described in Example 174.

Figure 87:
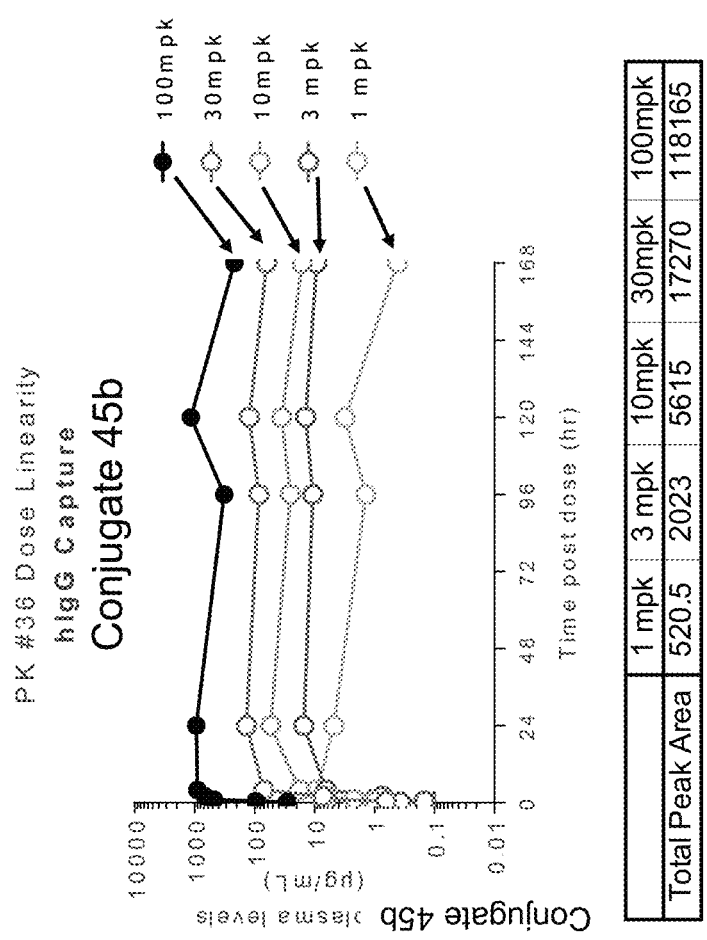

FIG. 87 is a graph showing dose linearity in plasma levels of conjugate 45b by hIgG capture. This study was performed as described in Example 174.

Figure 88:
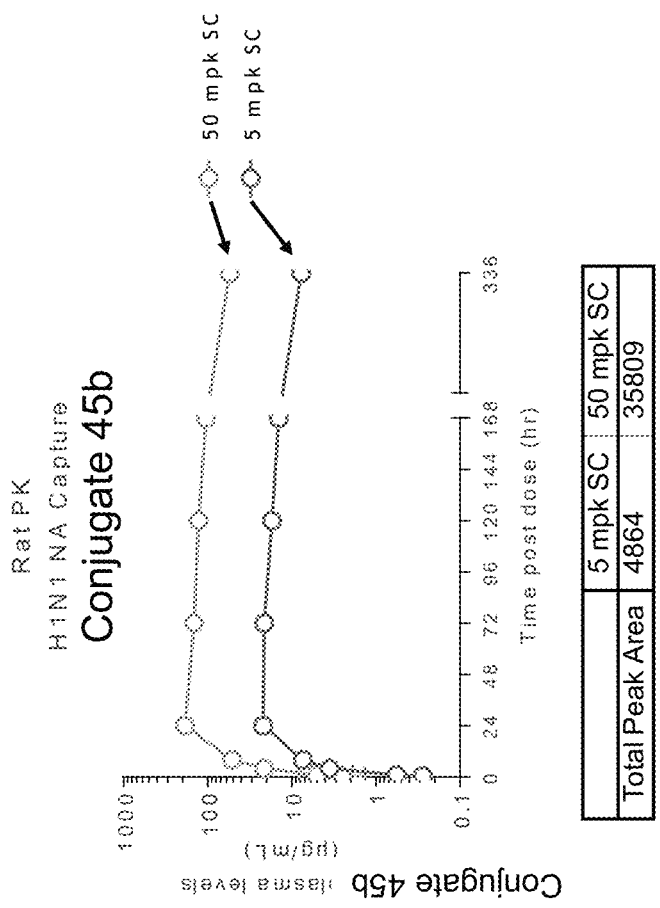

FIG. 88 is a graph showing the plasma concentration of conjugate 45b at 50 mg/kg and 5 mg/kg SC dosing in a rat PK study. Plasma concentrations were determined by ELISA using a neuraminidase coated plate. This study was performed as described in Example 175.

Figure 89:
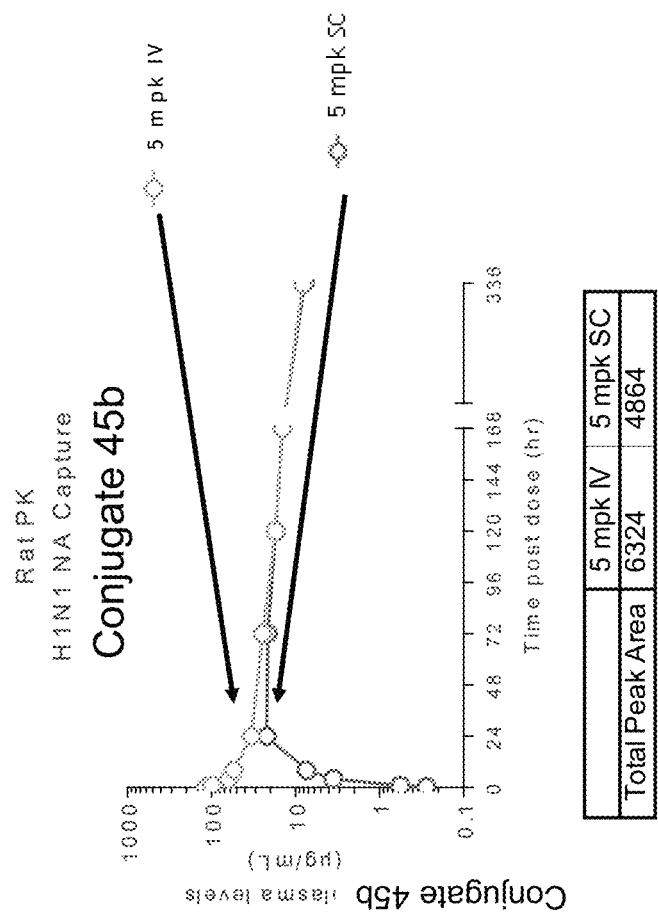

FIG. 89 is a graph showing the plasma concentrations of conjugate 45b comparing IV and SV administration of conjugate 45b at 5 mg/kg. Plasma concentrations were determined by ELISA using a neuraminidase coated place. This study was performed as described in Example 175.

Figure 90:
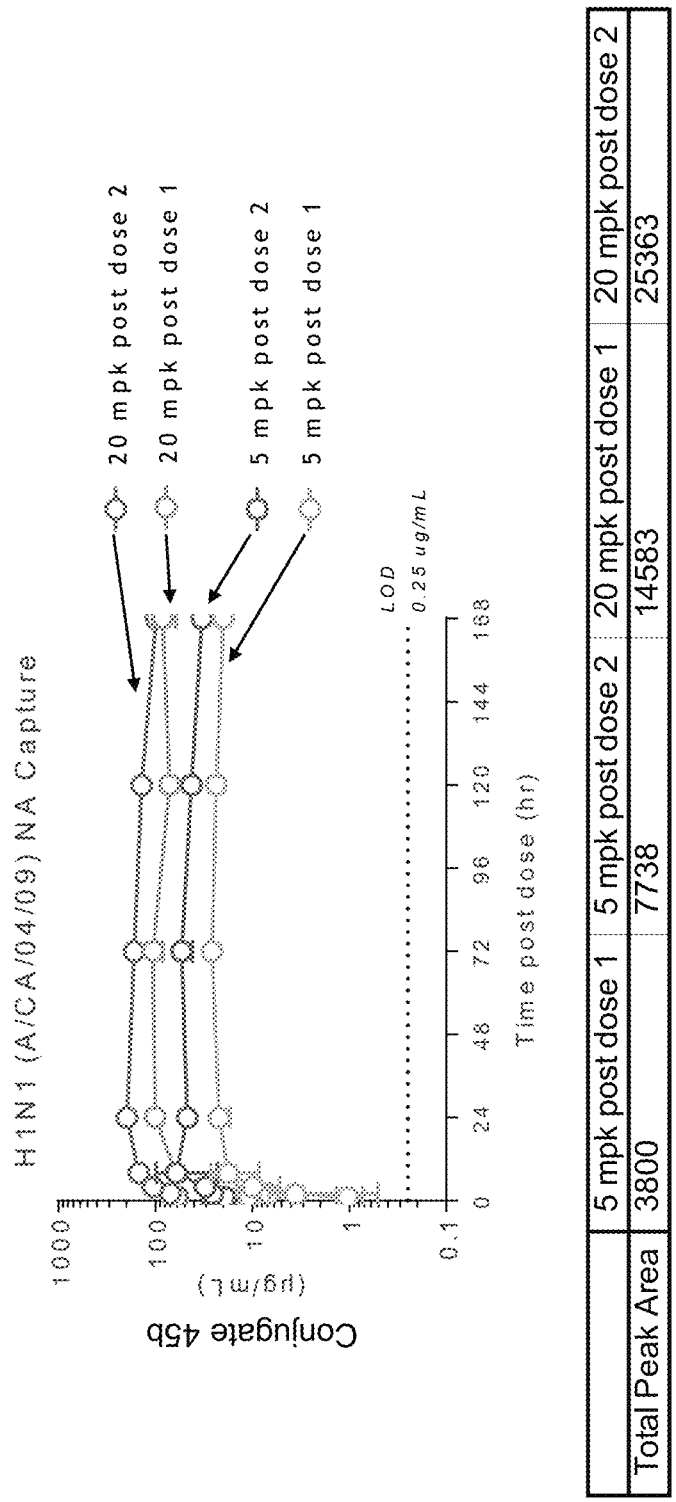

FIG. 90 is a graph showing the plasma concentrations of conjugate 45b in a non-human primate, cynomolgus monkeys. Plasma concentrations were determined by ELISA using a neuraminidase coated plate. This study was performed as described in Example 176.

Figure 91:
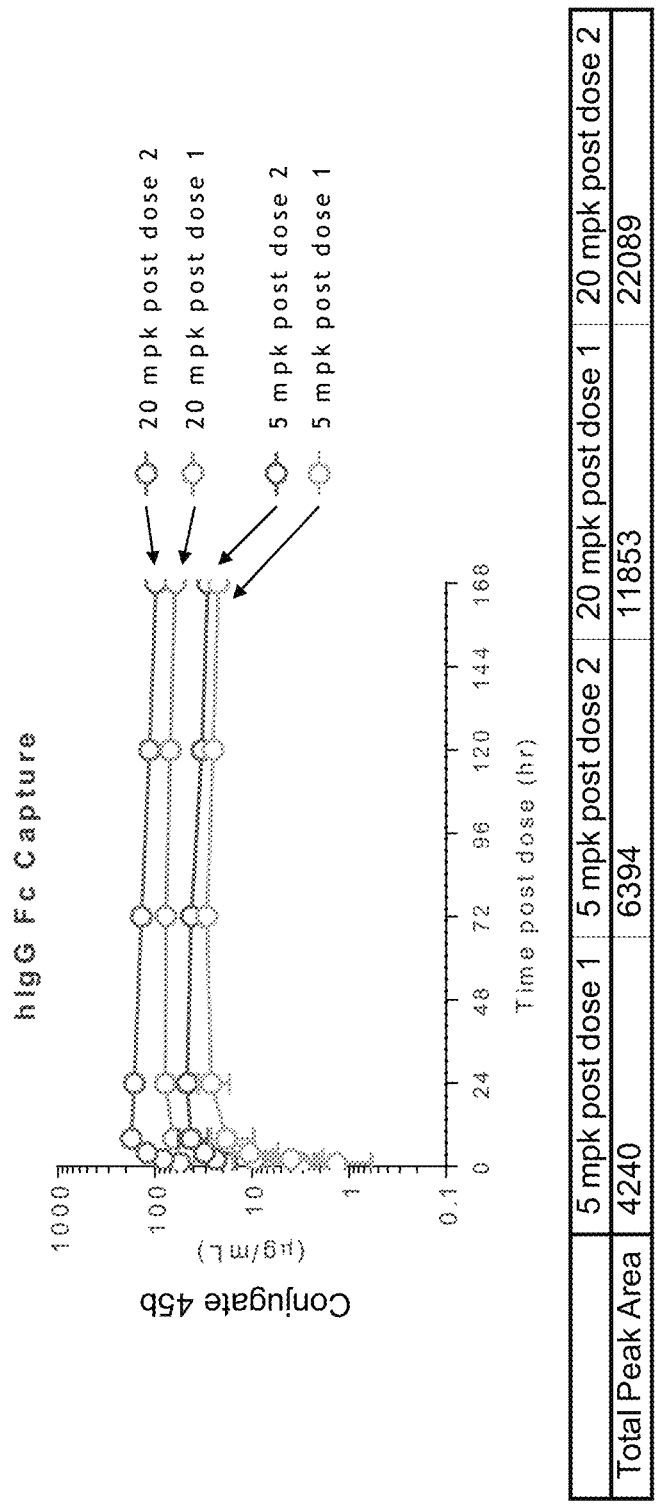

FIG. 91 is a graph showing the plasma concentrations of conjugate 45b in non-human primate, cynomolgus monkeys. Plasma concentrations were determined by hIgG Fc capture. This study was performed as described in Example 176.

Figure 92:
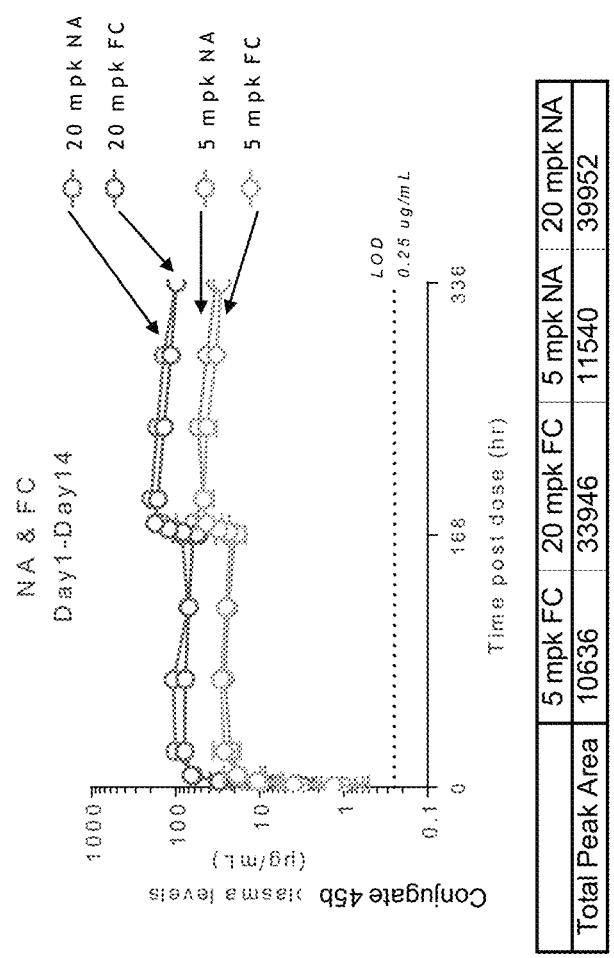

FIG. 92 is a graph showing the plasma concentrations of conjugate 45b from day 1 to day 14 in non-human primate, cynomolgus monkeys. Plasma concentrations were determined by neuraminidase (NA) capture and Fc capture. This study was performed as described in Example 176.

Figure 93:
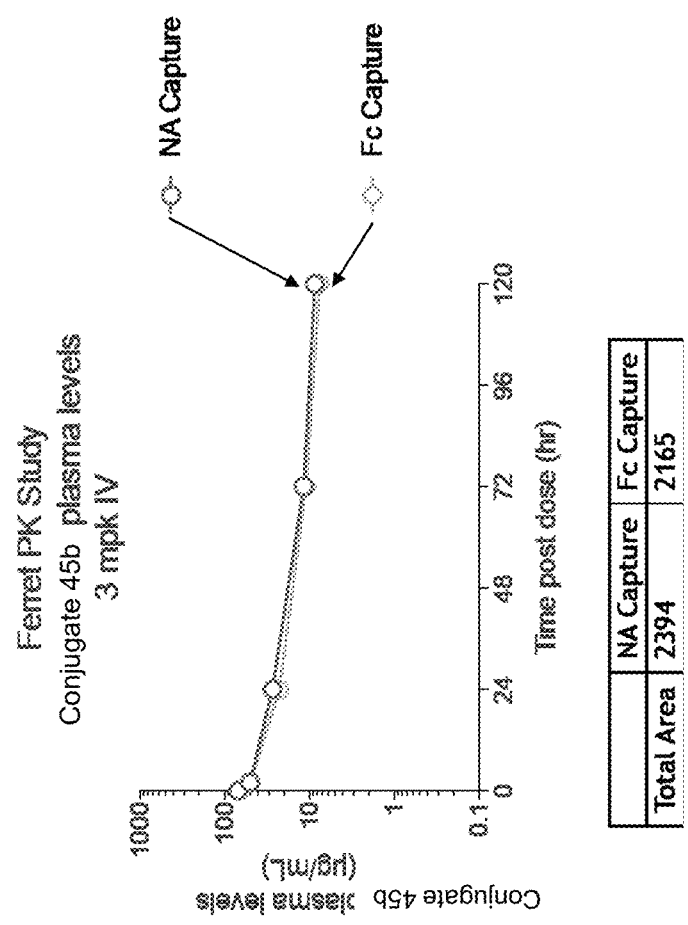

FIG. 93 is a graph showing the plasma levels of conjugate 45b (3 mpk IV) in ferret PK studies determined by neuraminidase (NA) capture and Fc capture. This study was performed as described in Example 183.

Figure 94:
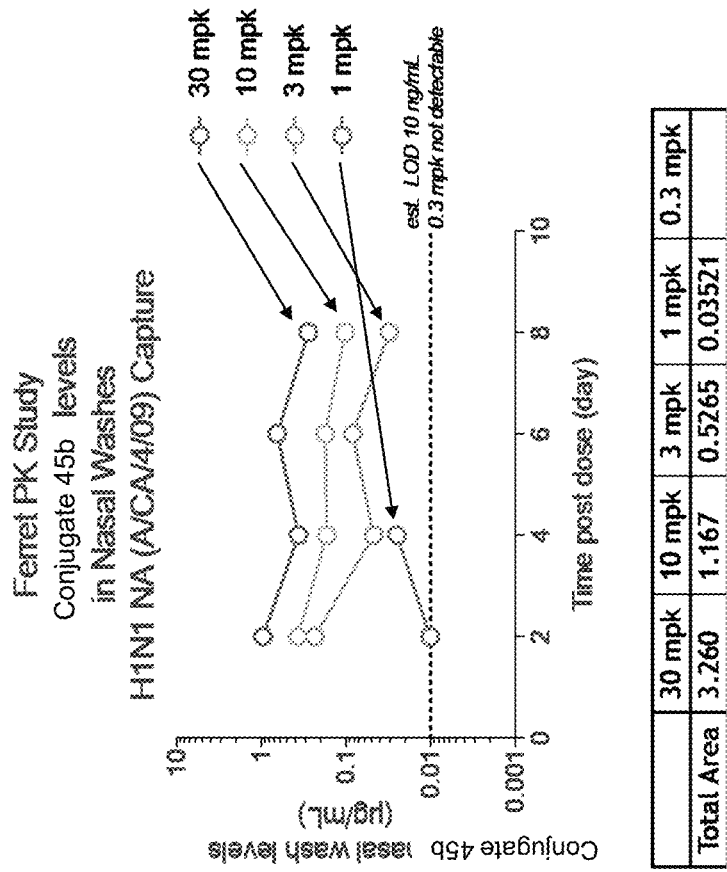

FIG. 94 is a graph showing nasal wash levels of conjugate 45b in ferret PK studies determined by H1N1 neuraminidase (NA) capture. This study was performed as described in Example 186.

Figure 95:
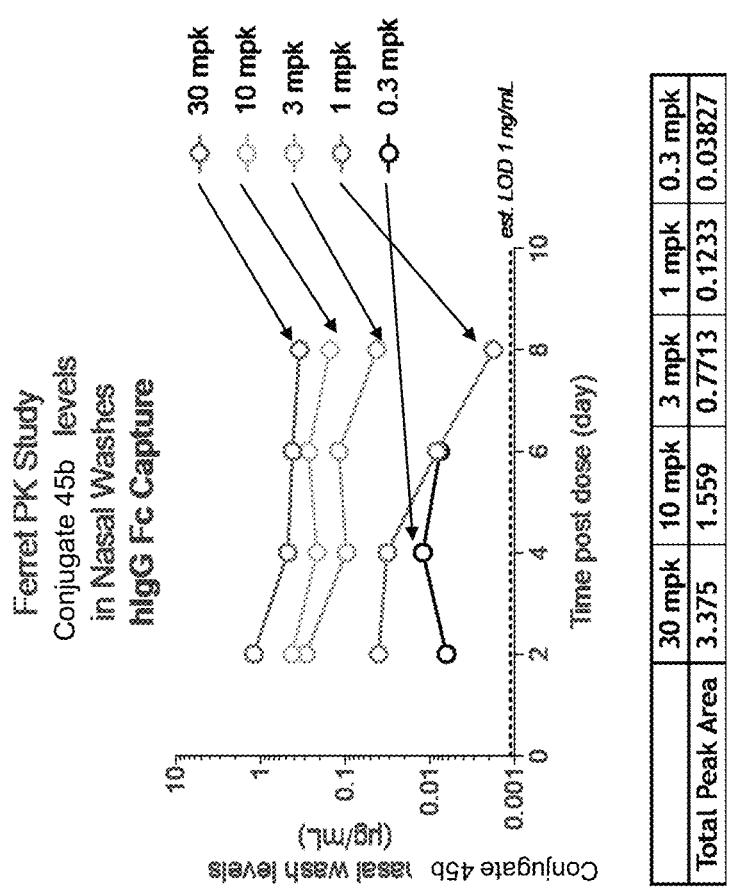

FIG. 95 is a graph showing nasal wash levels of conjugate 45b in ferret PK studies determined by hIgG Fc capture. This study was performed as described in Example 186.

Figure 96:
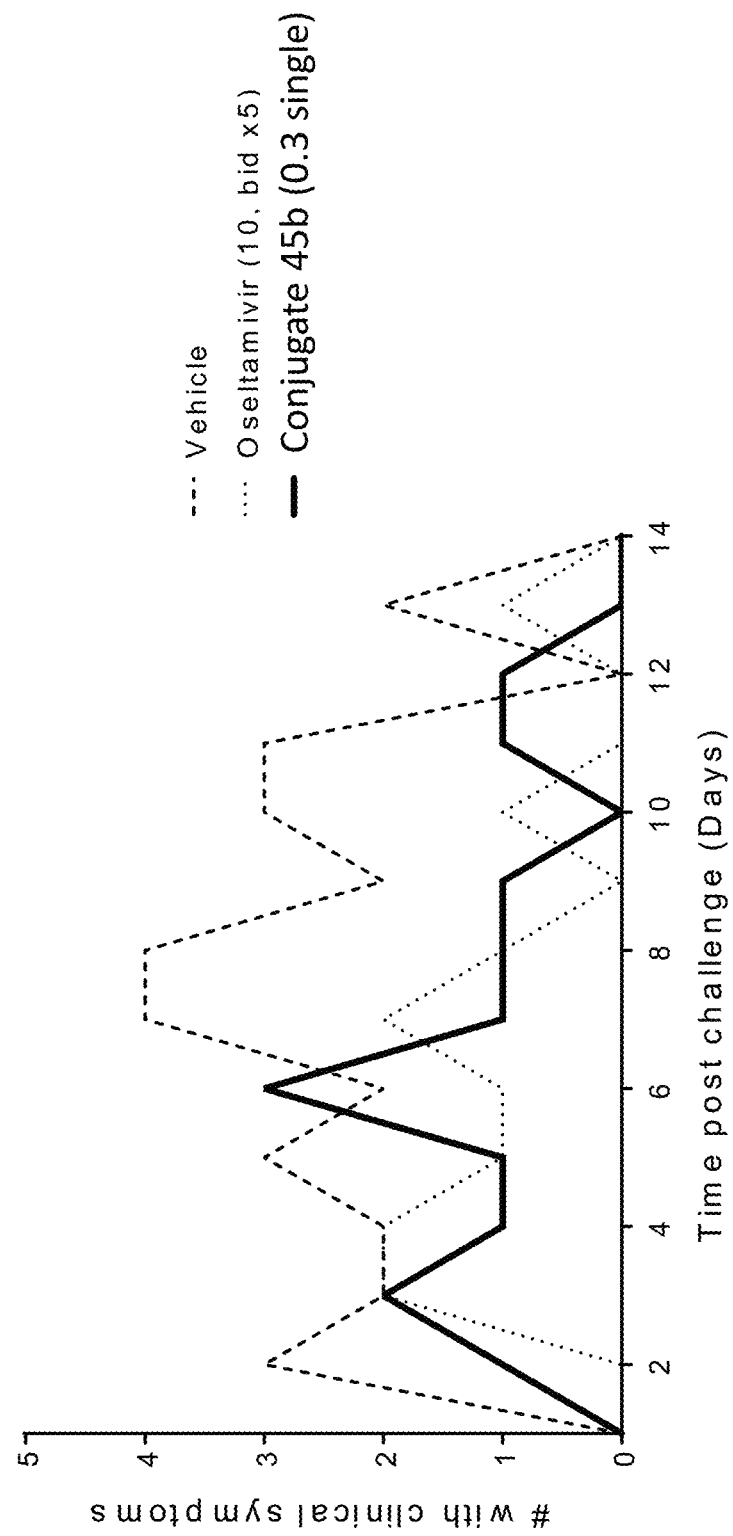

FIG. 96 is a graph showing the comparison of clinical observations following administration of conjugate 45b (0.3 mg/kg, single) as compared to oseltamivir (10 mg/kg, bid×5) or vehicle. This study was performed as described in Example 182.

Figure 97:
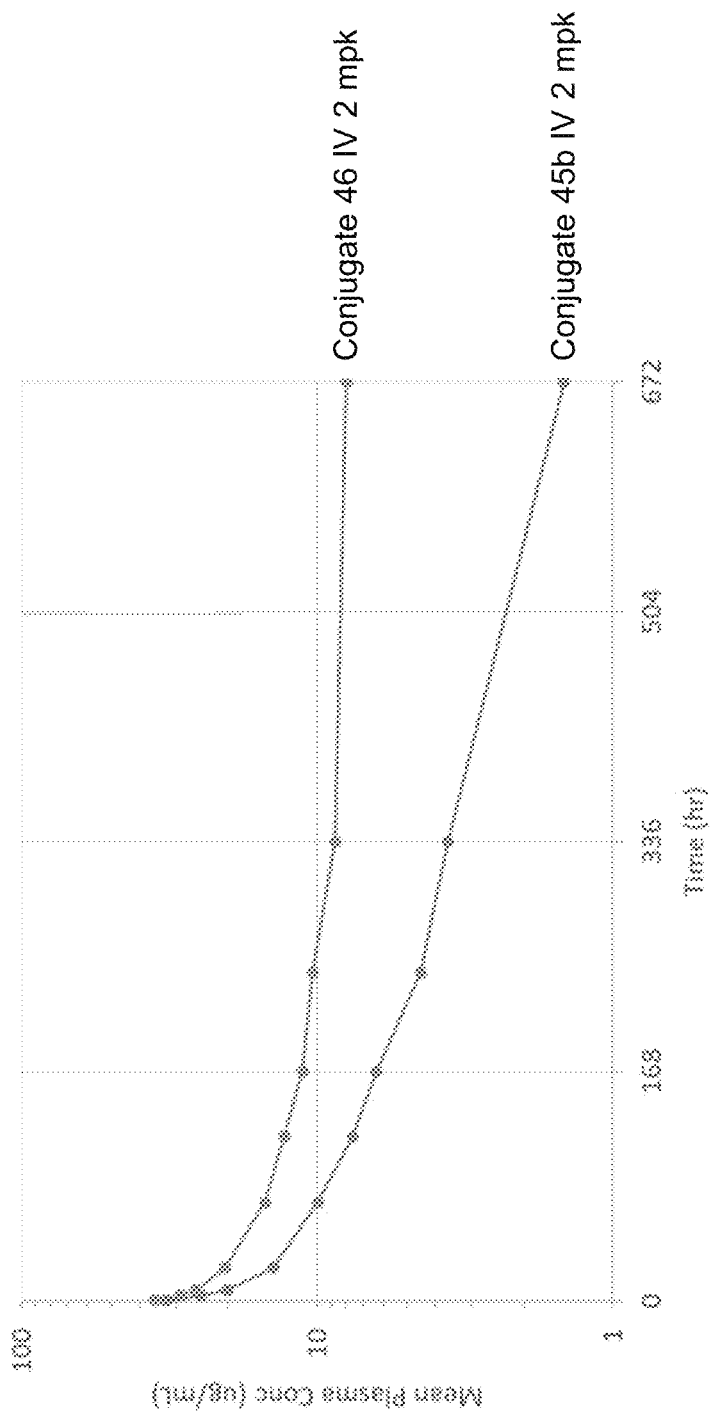

FIG. 97 is a graph showing plasma levels of conjugate 45b (2 mpk IV) compared to conjugate 46 (2 mpk IV) in non-human primate PK studies determined by Fc capture. This study was performed as described in Example 189.

Figure 98:
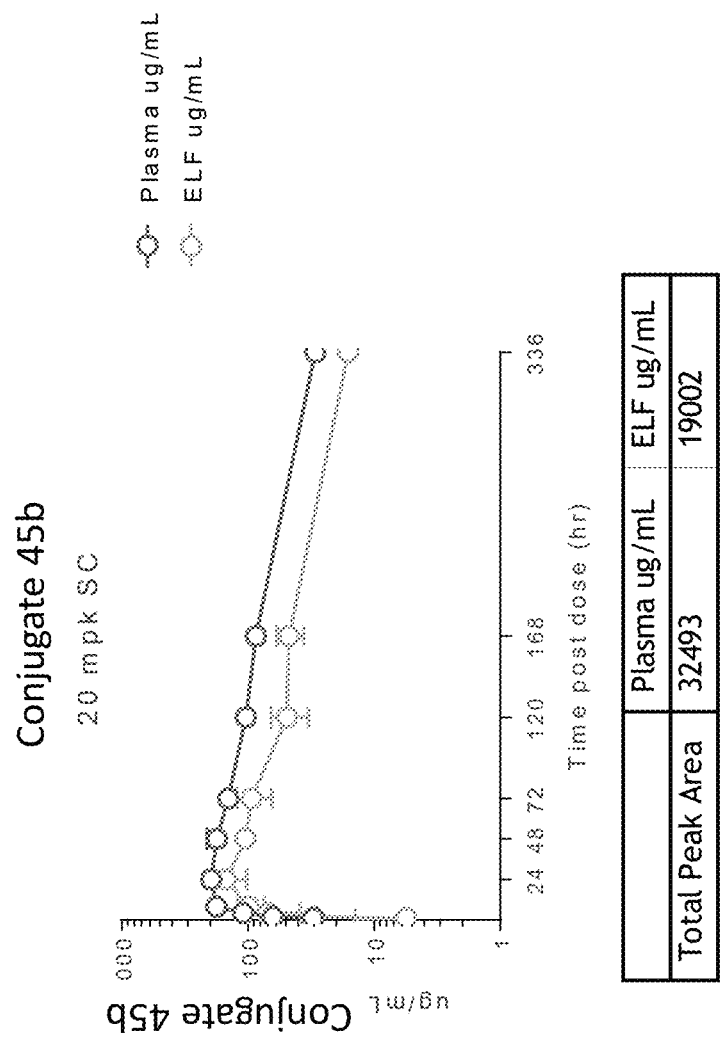

FIG. 98 is a graph showing plasma concentration levels of conjugate 45b compared to epithelial lining fluid (ELF) levels of conjugate 45b in mice. This study was performed as described in Example 191.

Figure 99:
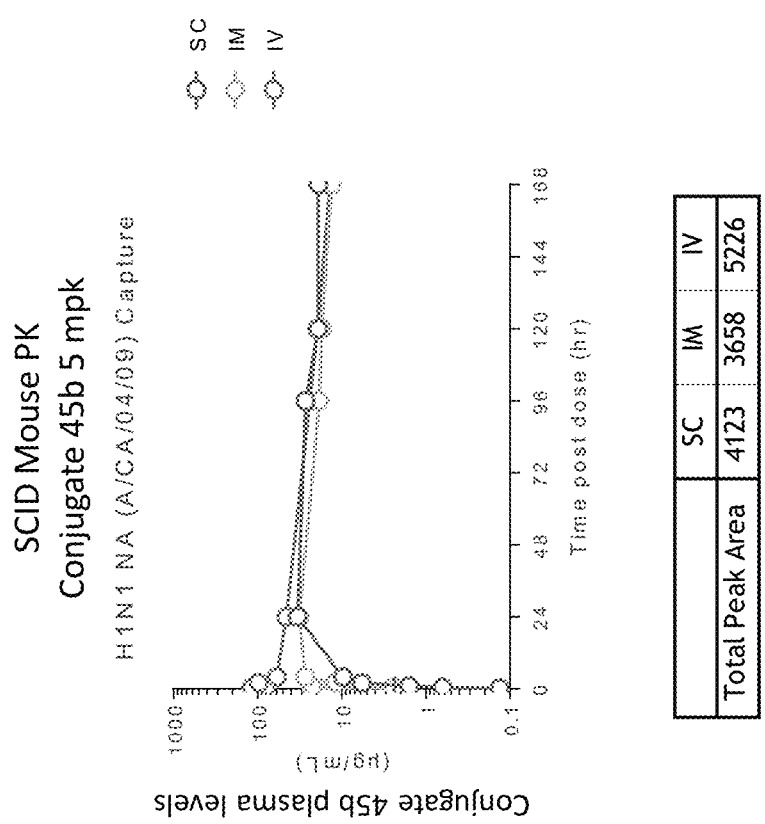

FIG. 99 is a graph showing the plasma levels of conjugate 45b in SCID mouse PK studies determined by H1N1 Fc capture. This study was performed as described in Example 192.

Figure 100:
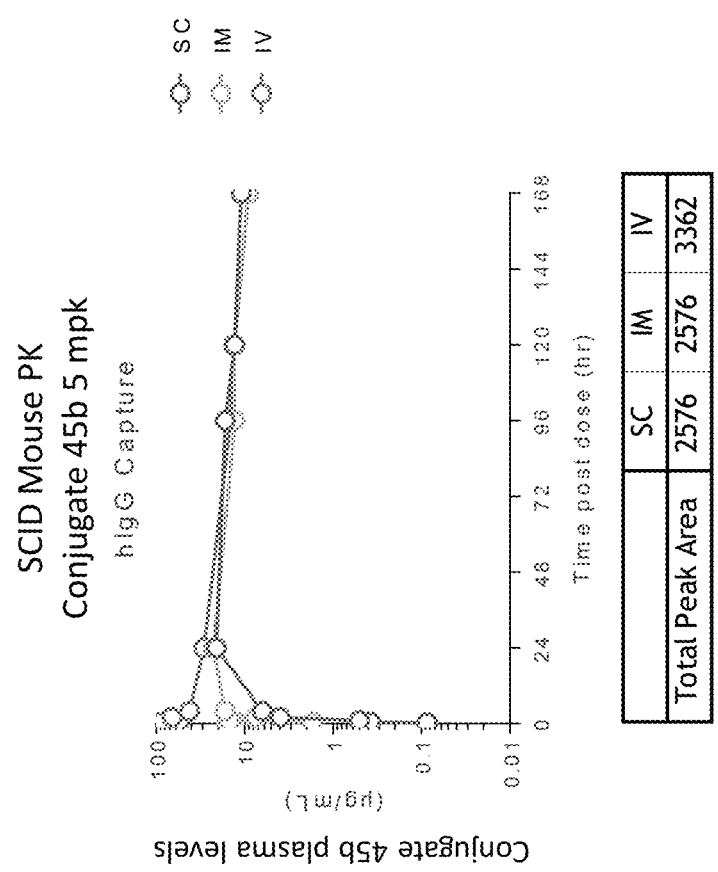

FIG. 100 is a graph showing plasma levels of conjugate 45b in SCID mouse PK studies determined by neuraminidase (NA) capture. This study was performed as described in Example 192.

Figure 101:
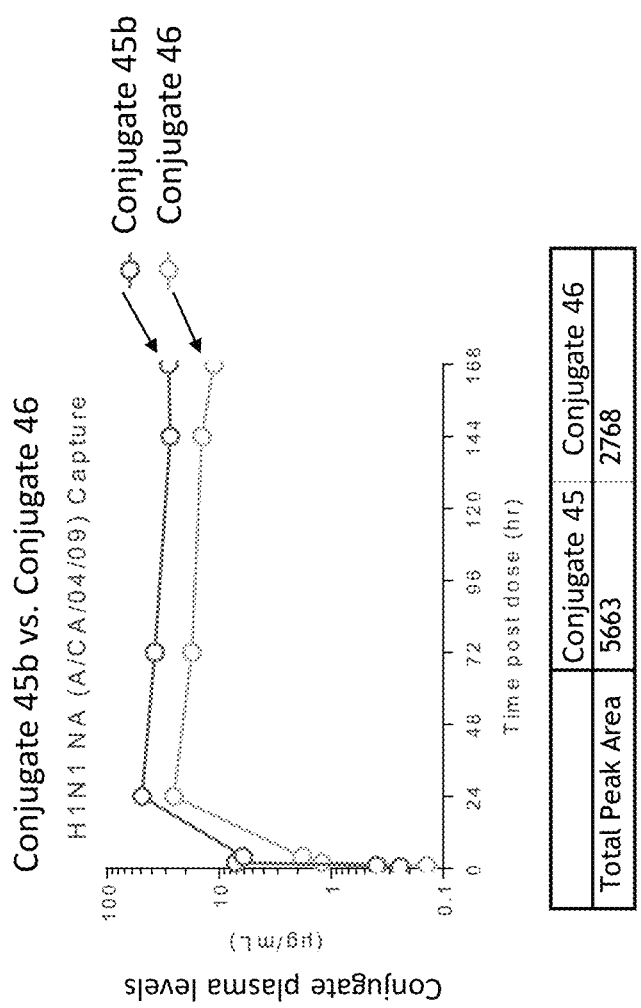

FIG. 101 is a graph showing the plasma levels of conjugate 45b compared to conjugate 46 in mouse PK studies determined by neuraminidase (NA) capture. This study was performed as described in Example 193.

Figure 102:
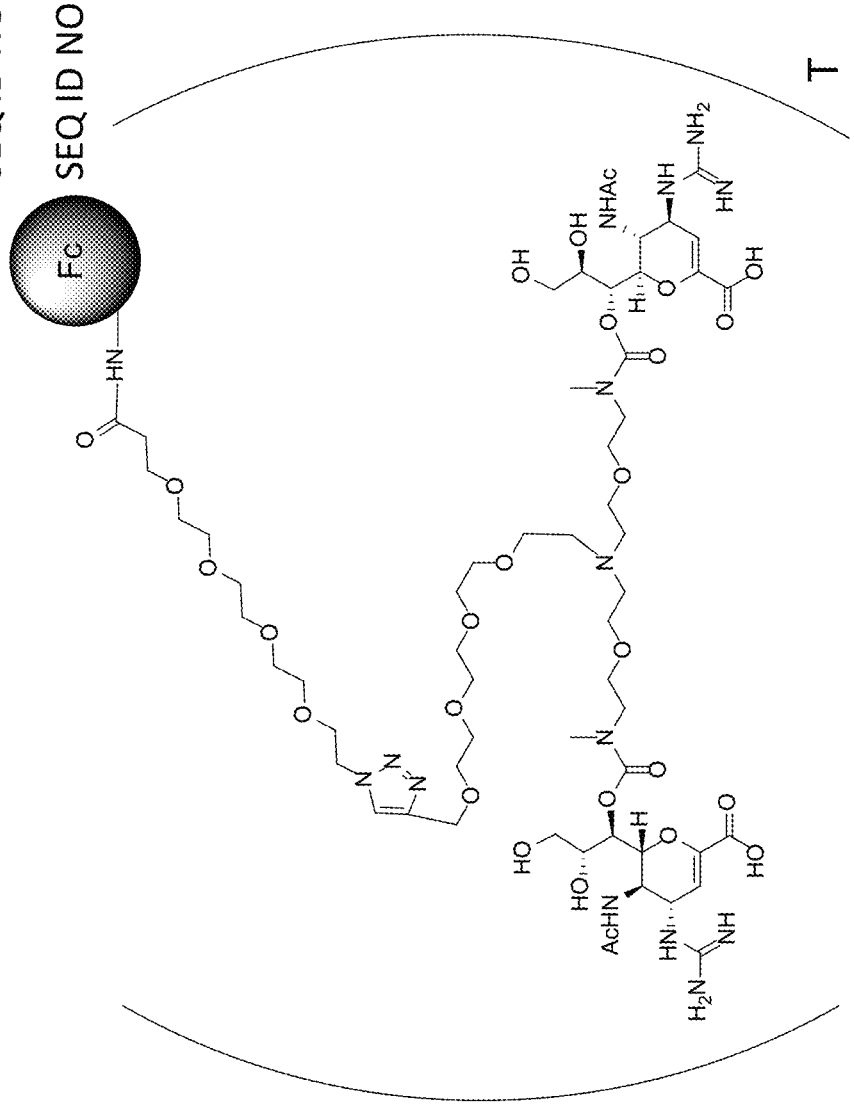

FIG. 102 is an image depicting conjugate 45 and conjugate 46.

Figure 103:
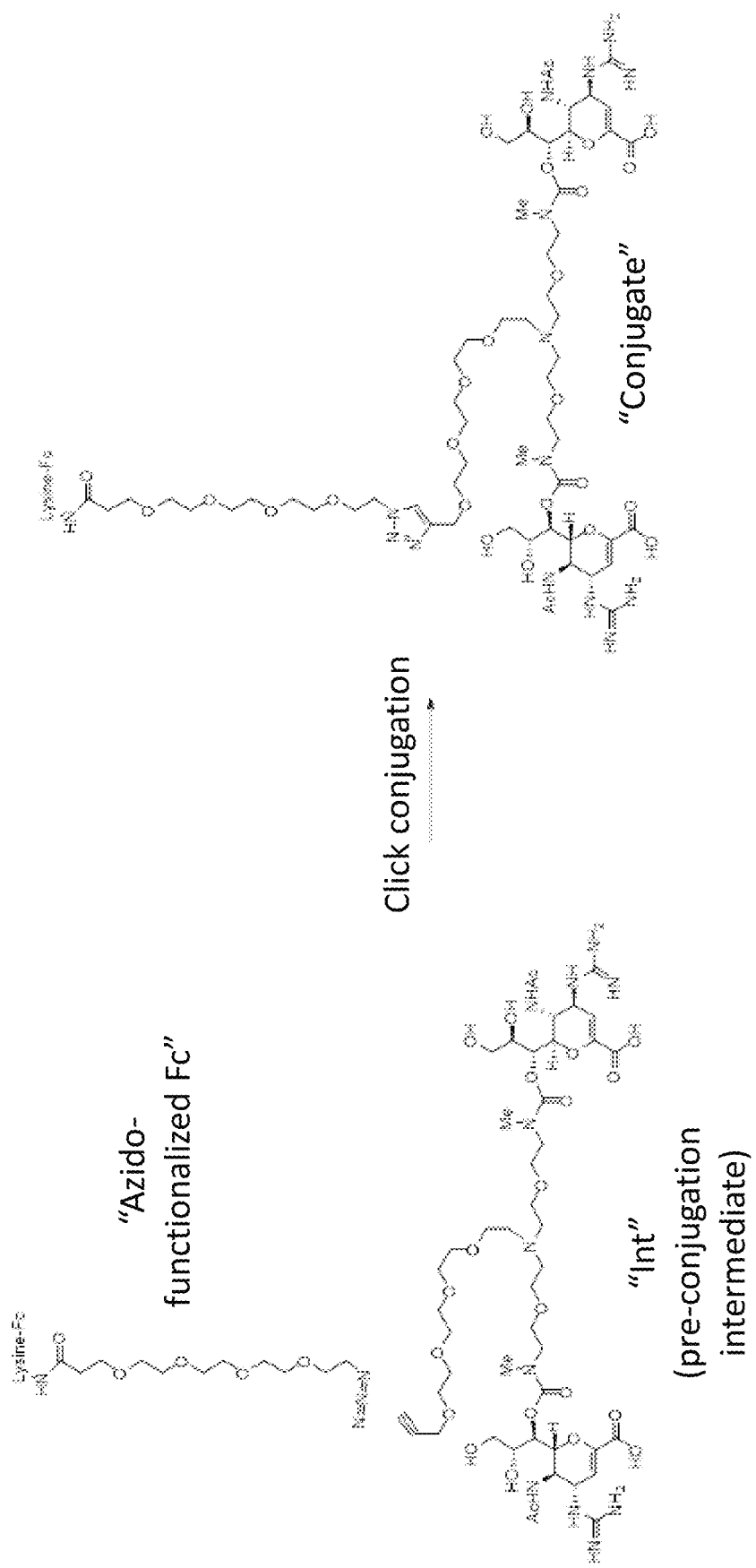

FIG. 103 is an image depicting an exemplary click chemistry conjugation of an azido-functionalized Fc domain monomer or Fc domain with a pre-conjugation intermediate (Int).

Figure 104:
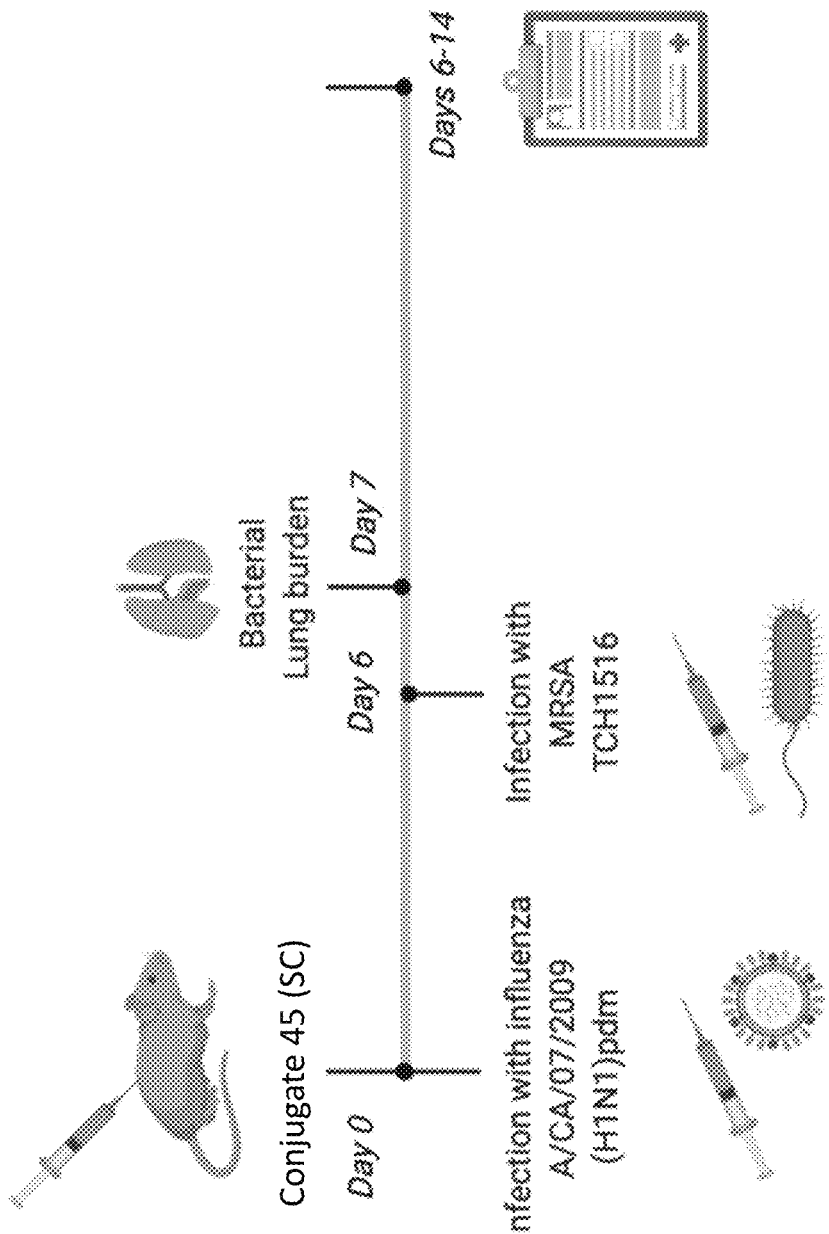

FIG. 104 is an image depicting the experimental procedure for secondary bacterial infection model with methicillin-resistant *Staphylococcus aureus* (MRSA) as described in Example 200.

Figure 105B:
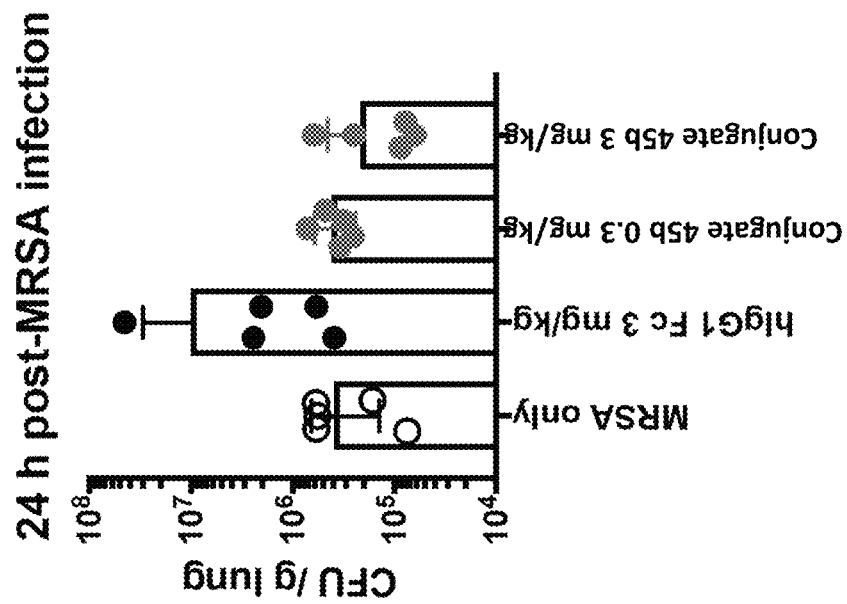
Figure 105A:
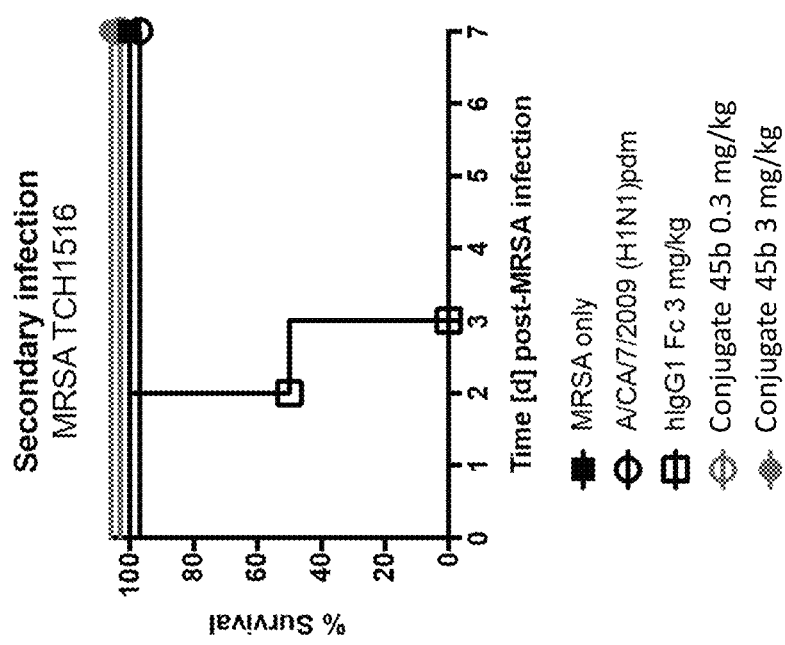

FIGS. 105A-105B are graphs showing the percent survival (FIG. 105A) and the CFU/g lung (FIG. 105B) of secondary infection mouse model after treatment with conjugate 45b. This study was performed as described in Example 200.

Figure 106:
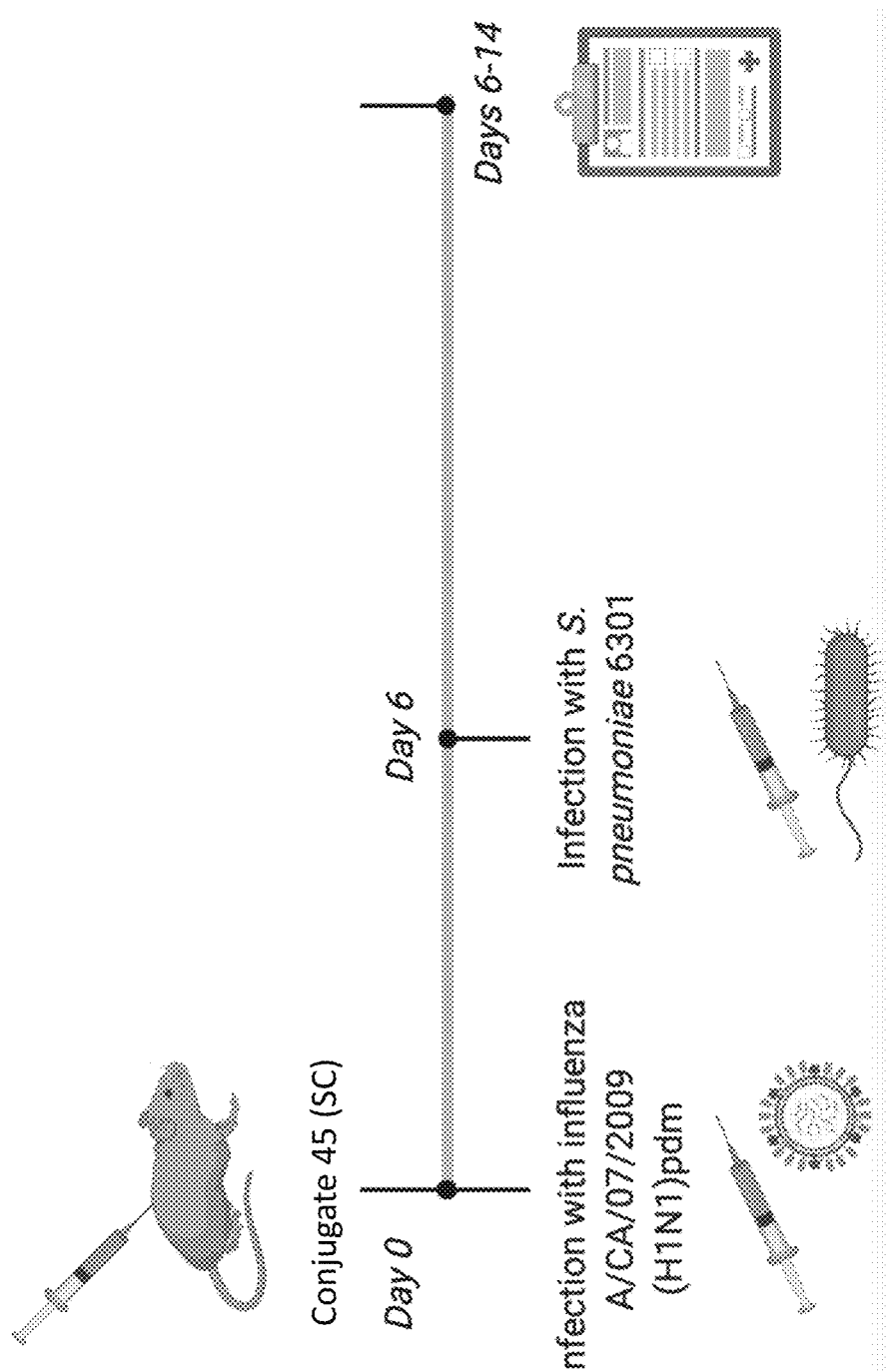

FIG. 106 is an image depicting the experimental procedure for secondary bacterial infection model with *Streptococcus pneumoniae* as described in Example 200.

Figure 107:
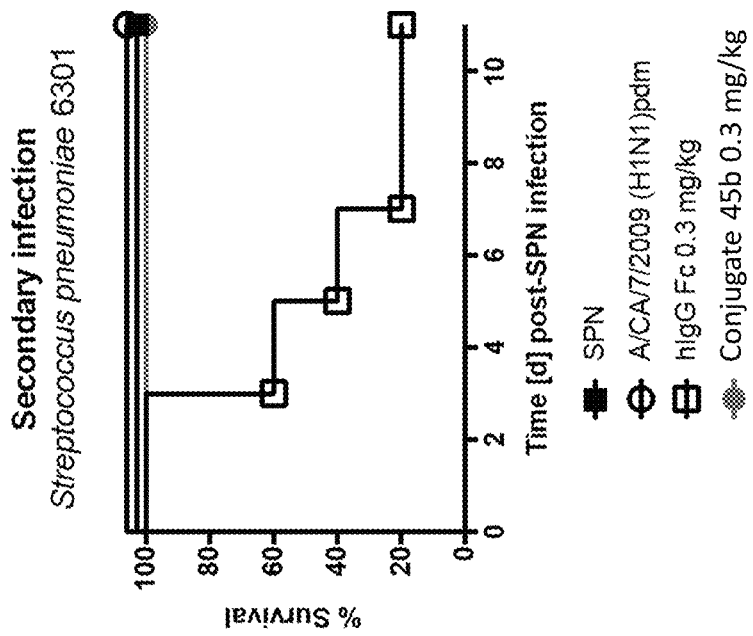

FIG. 107 is a graph depicting the percent survival of mice in a secondary infection model of *S. pneumoniae* after treatment with conjugate 45b. This study was performed as described in Example 200.

Figure 108B:
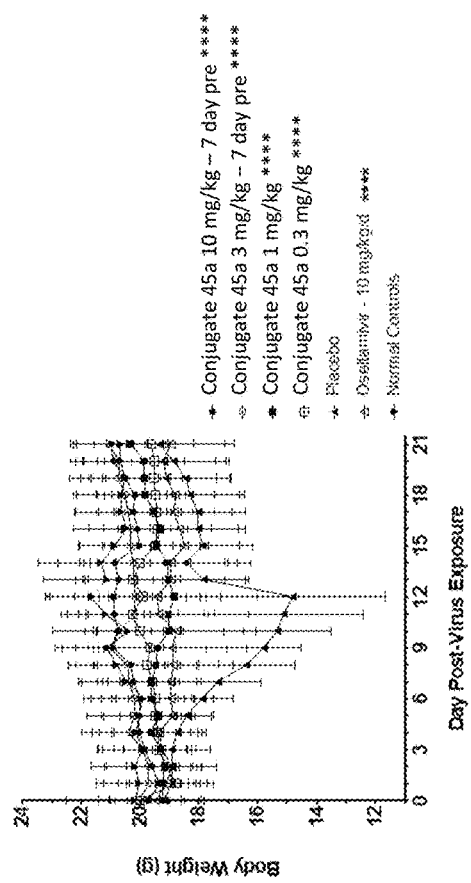
Figure 108A:
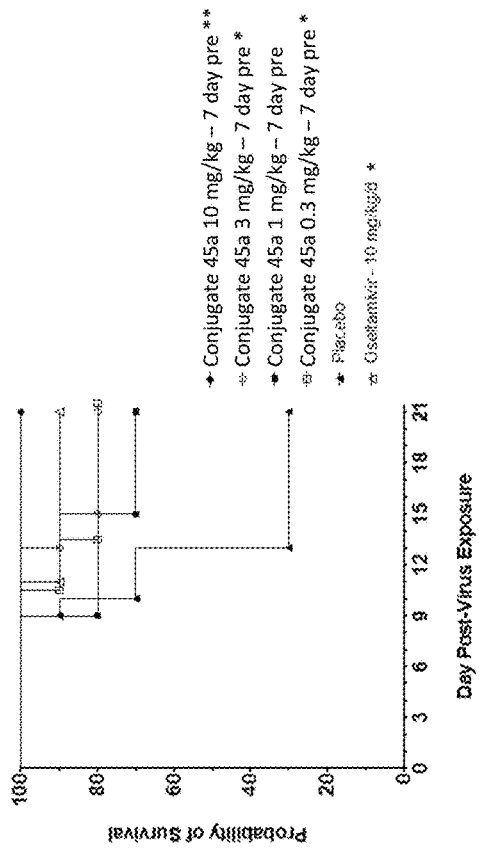

FIG. 108A-108B are graphs showing the survival of mice (FIG. 108A) and mean body weight (FIG. 108B) following treatment with conjugate 45a on a single occasion, 7 days before virus challenge, with influenza A/Vietnam/1203/2004 (H5N1). Following challenge infection and treatment with conjugate 45a, 100% protection was observed for the 10 mg/kg dose, 80% protection for the 0.3 and 3.0 mg/kg doses, and 70% protection for the 1 mg/kg dose (FIG. 108A). 30% survival in the placebo group is unusual, so the 1 mg/kg dose did not provide significant protection. In addition, all doses provided significant protection from weight loss (FIG. 108B), (*$P<0.05$, $P<0.01$, **$P<0.0001$). This study was performed as described in Example 201.

Figure 109B:
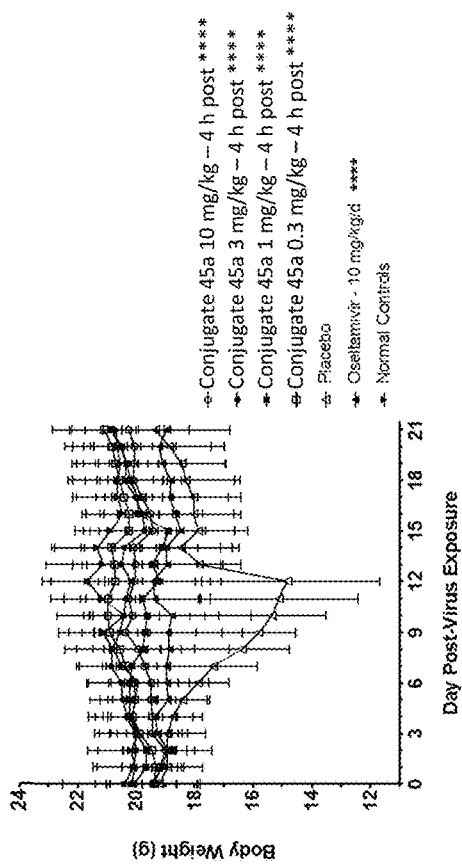
Figure 109A:
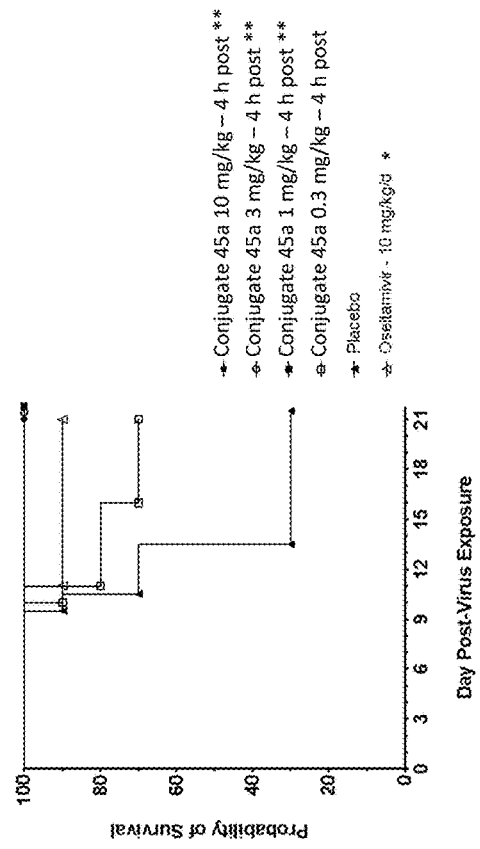

FIG. 109A-109B are graphs showing the survival of mice (FIG. 109A) and mean body weight (FIG. 109B) following treatment with conjugate 45a on a single occasion, 4 hours post-virus challenge with influenza A/Vietnam/1203/2004 (H5N1). Following challenge infection and treatment with Conjugate 45a, 100% protection was observed for the 1, 3, and 10 mg/kg doses, and 70% protection for the 0.3 mg/kg dose (FIG. 109A). 30% survival in the placebo group is unusual, so the 0.3 mg/kg dose did not provide significant protection. In addition, all doses provided significant protection from weight loss (FIG. 109B), (*$P<0.05$, $P<0.01$, **$P<0.0001$). This study was performed as described in Example 201.

Figure 110B:
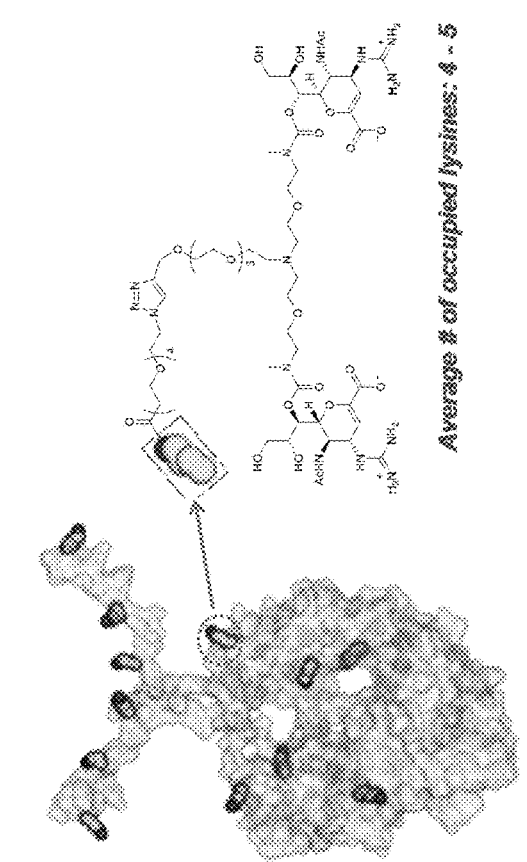
Figure 110A:
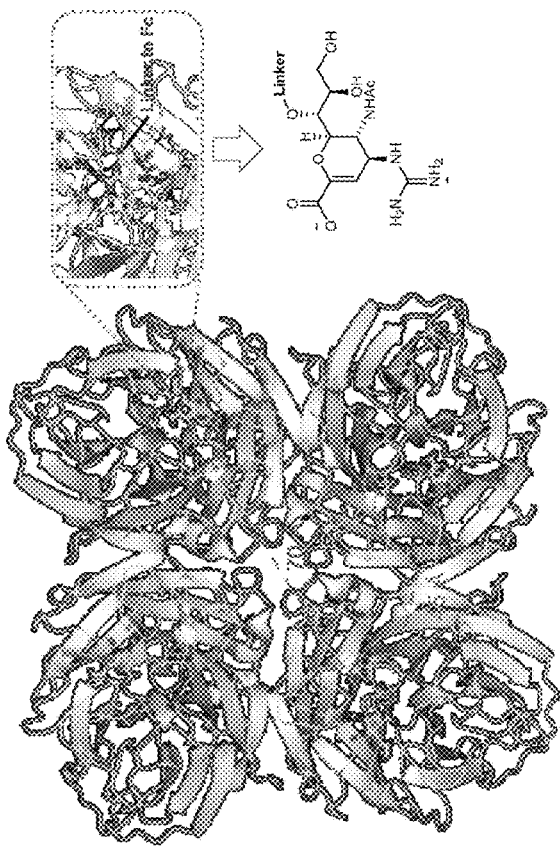

FIG. 110A is an image depicting a crystal structure presentation of tetrameric zanamivir (shown in ball and stick model) complexed to A/California/04/2009 H1N1 neuraminidase (NA) (PDB code 3T15). The linear distance between adjacent NA active sites within the tetramer are shown. The C7 position on zanamivir that was chosen for attachment to the Fc carrier (via an NHS ester) is highlighted. C7 on zanamivir is solvent exposed and unencumbered sterically, allowing for conjugation to C7 with minimal impact on binding affinity. This study was performed as described in Example 203.

FIG. 110B is an image of a semi-transparent molecular surface representation of the structure of full length hIgG1 (PDB code 1 HZH) redacted to show the only the Fc construct boundaries used in conjugate 45b. Positions of lysines that were preferentially conjugated in conjugate 45b are shown in green. Conjugate 45b is a multivalent conjugate of zanamivir dimers (Int-83, structure shown on right) stably conjugated to lysine on the N-terminal extended hIgG1 Fc with an average drug-antibody ratio (DAR) of 4.5:1. The spatial disposition of conjugated lysine of the Fc domain surface and the length and flexibility of the PEG linkers result in Int.83 dimer constellations on conjugate 45b where sufficient separation (>90 A) exists between zanamivir dimers to allow simultaneous engagement of multiple active-sites within an NA tetramer, between neighboring NA tetramers on the same virus particle, or between NA tetramers on different virus particles by a single conjugate 45b molecule. This study was performed as described in Example 203.

Figure 111E:
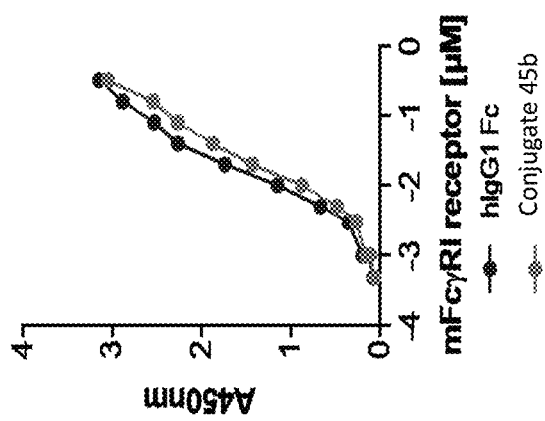
Figure 111D:
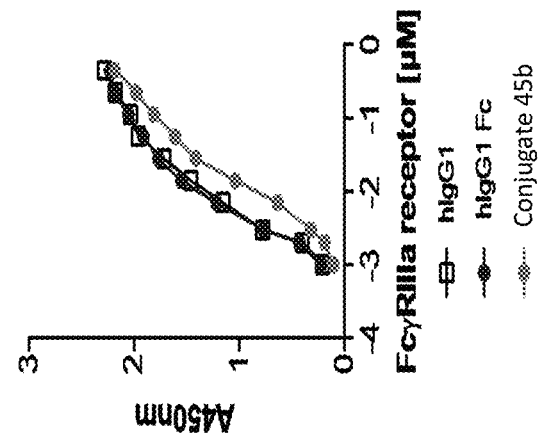
Figure 111J:
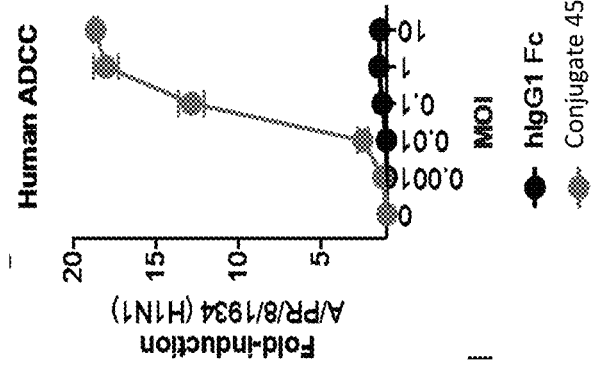
Figure 111I:
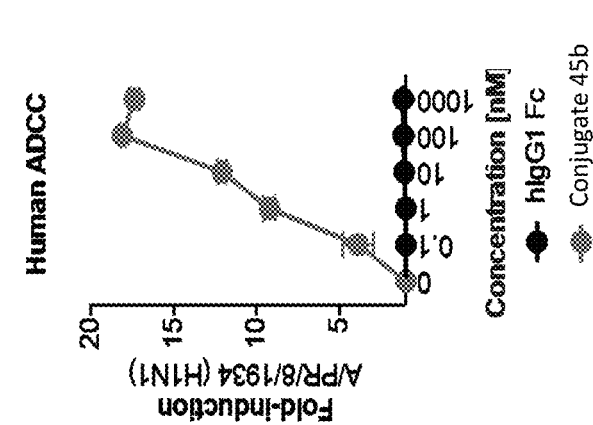

FIGS. 111A-111J are graphs showing conjugate 45b binding to Fcγ receptors and triggering ADCC. FIGS. 111A-111D show conjugate 45b binds to human Fcγ RI (FIG. 111A), RIIa (FIG. 111B), RIIb (FIG. 111C), and RIIIa (FIG. 111D), as determined by ELISA. FIGS. 111E-111H show conjugate 45b binds to murine Fcγ RI (FIG. 111E), RIII (FIG. 111F), RIIb (FIG. 111G), and RIV (FIG. 111H), as determined by ELISA. FIGS. 111I-111J show conjugate 45b induces antibody-dependent cellular toxicity in dose—(FIG.

111I) and MOI—(FIG. 111J) dependency, using reporter cells. This study was performed as described in Example 203.

Figure 112A:
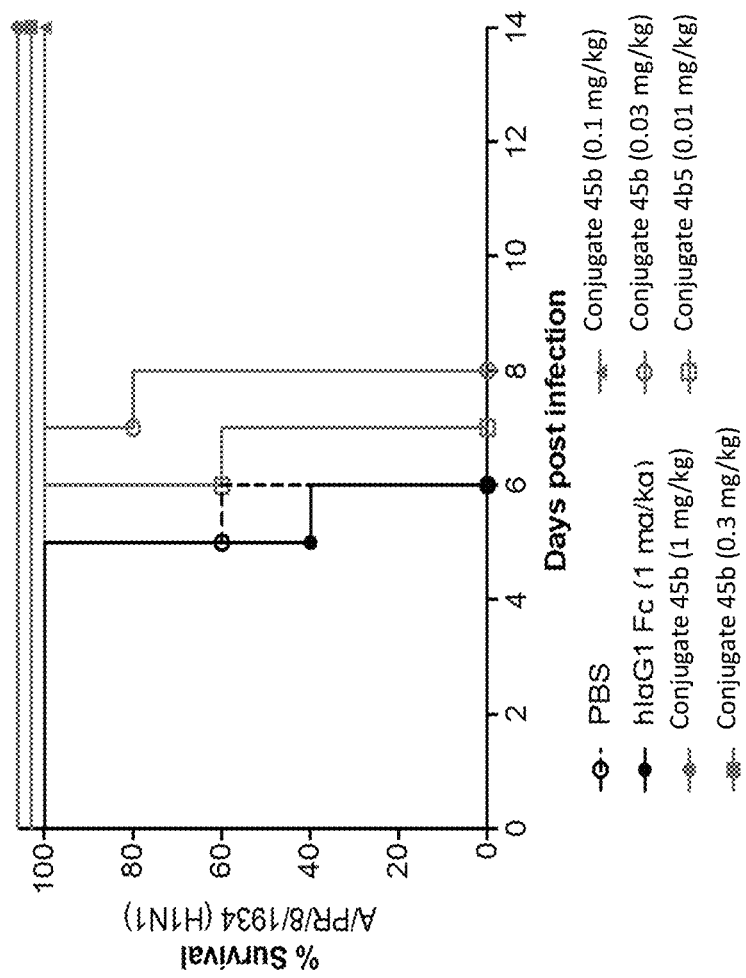
Figure 112B:
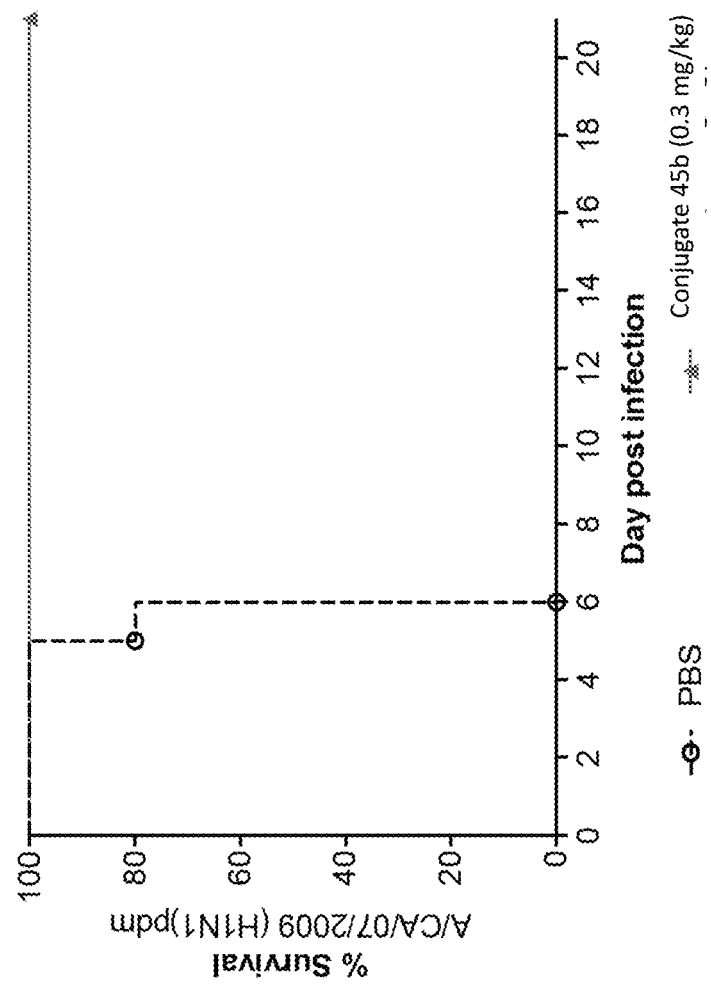
Figure 112C:
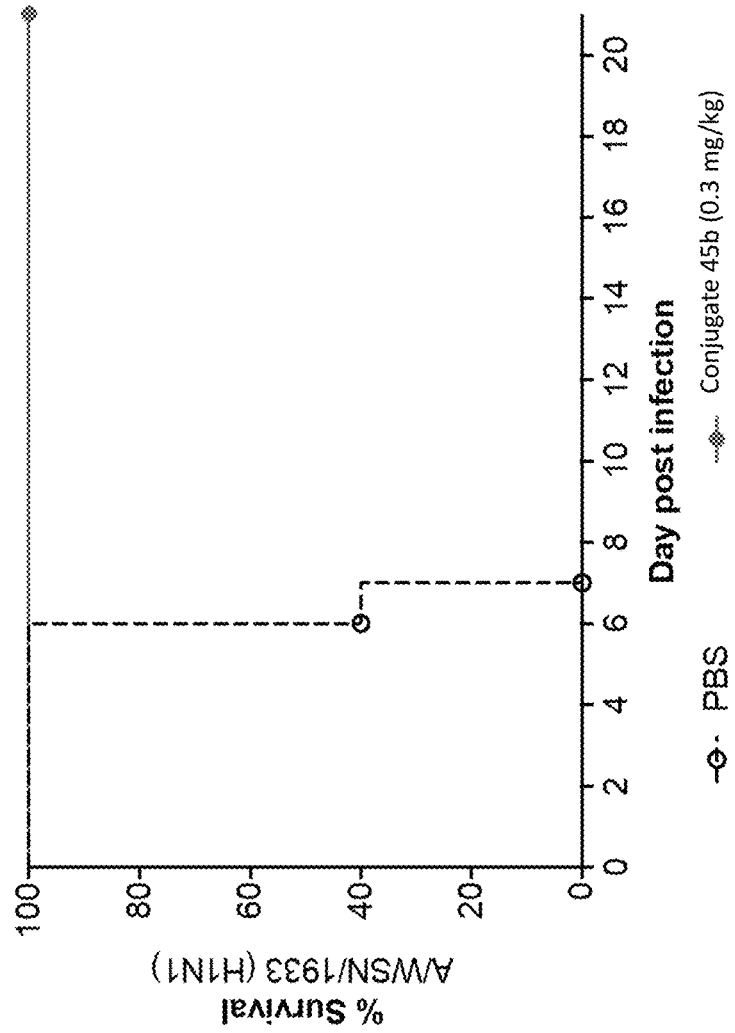
Figure 112D:
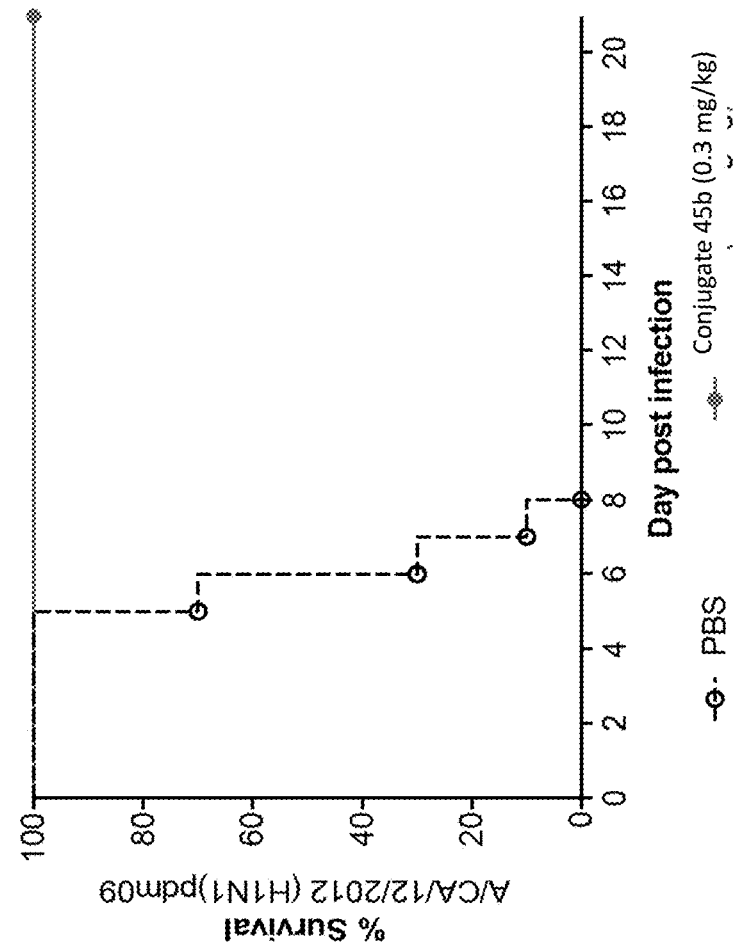
Figure 112E:
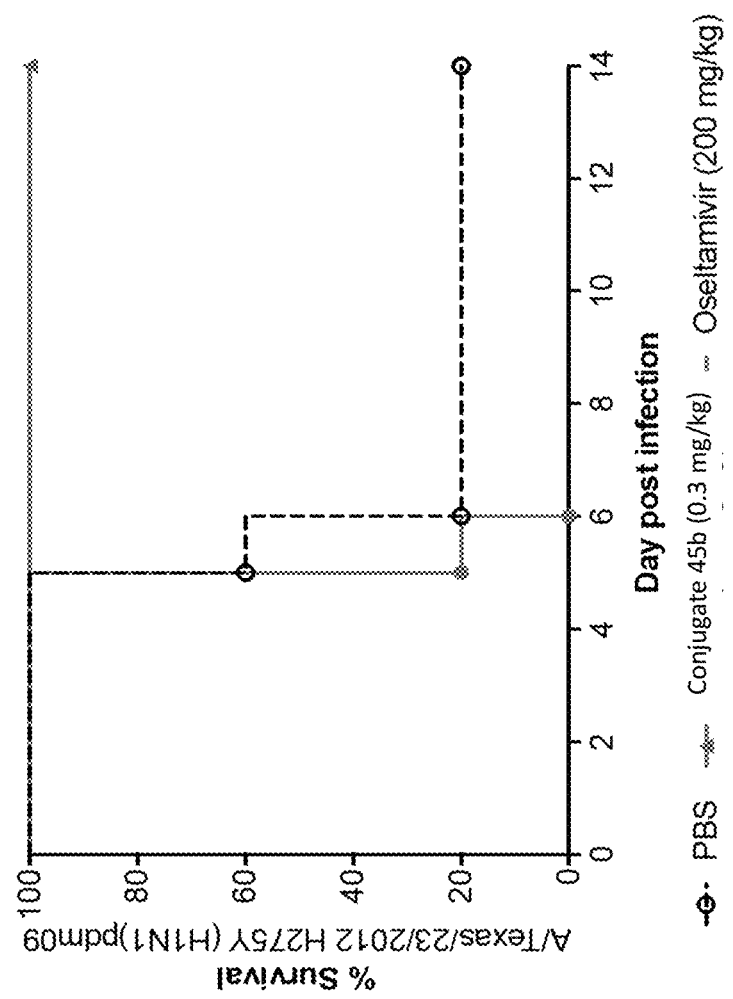
Figure 112G:
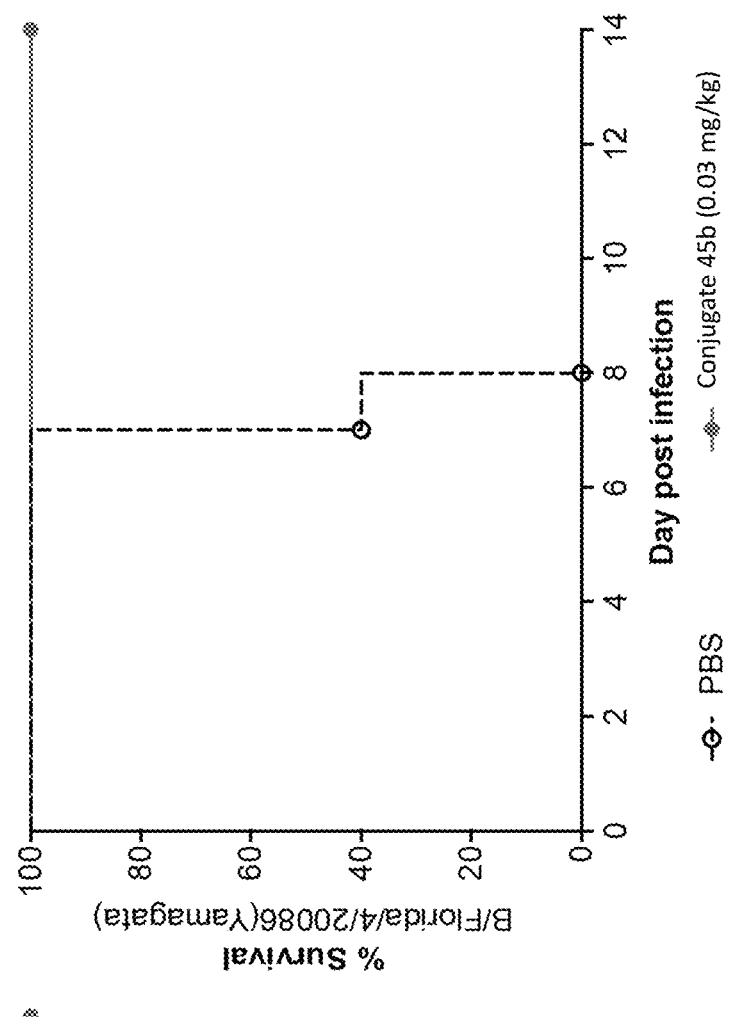
Figure 112H:
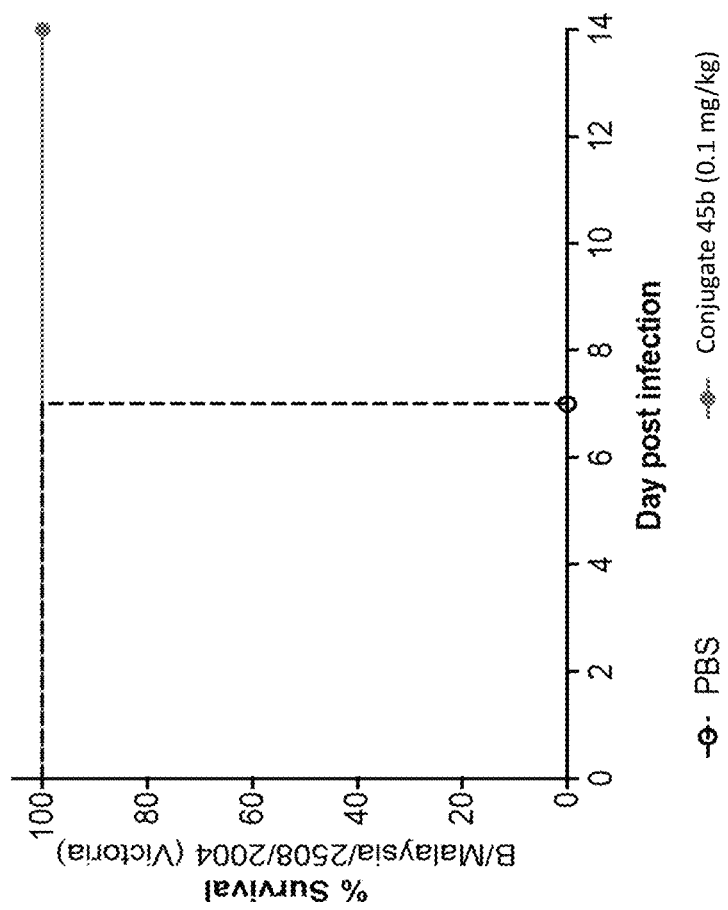
Figure 112I:
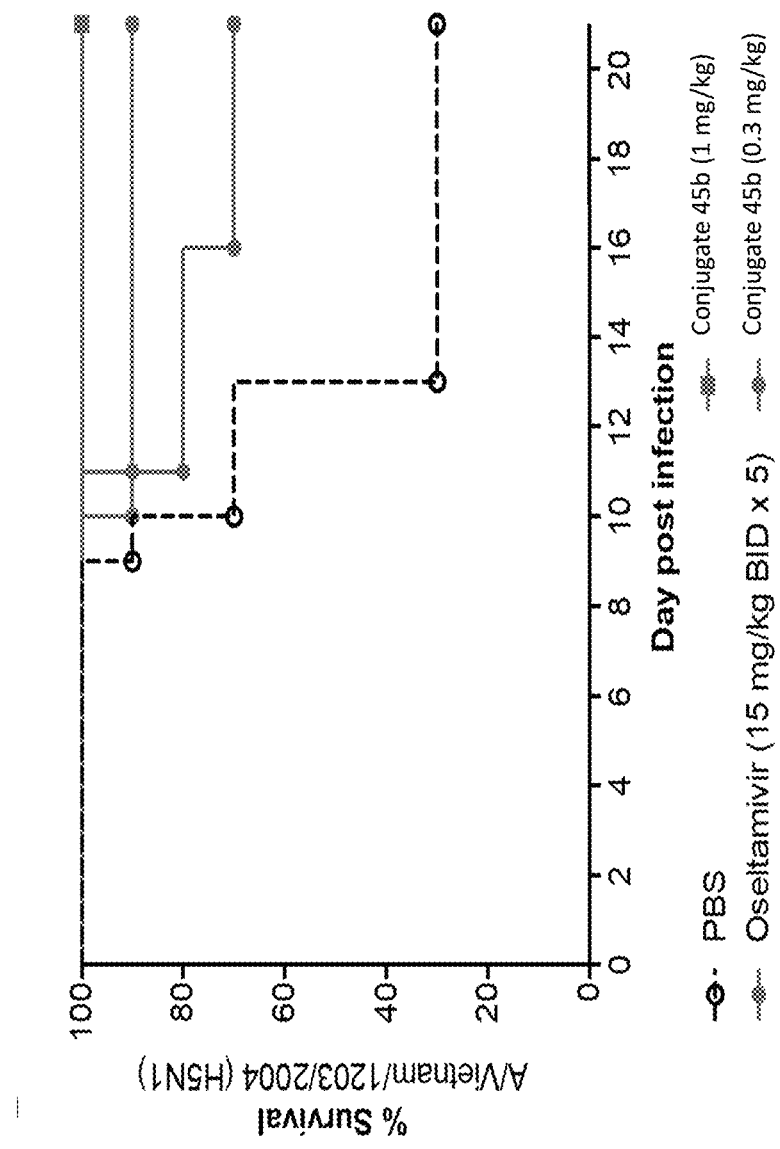
Figure 112K:
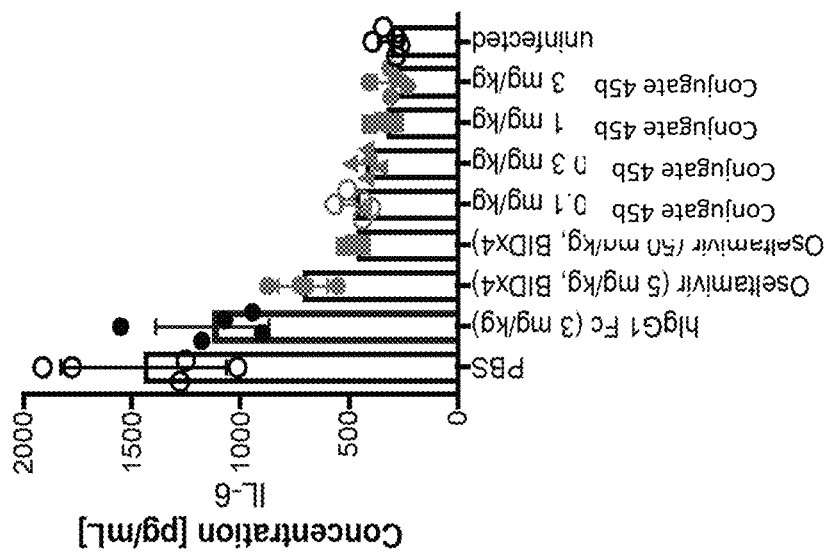
Figure 112J:
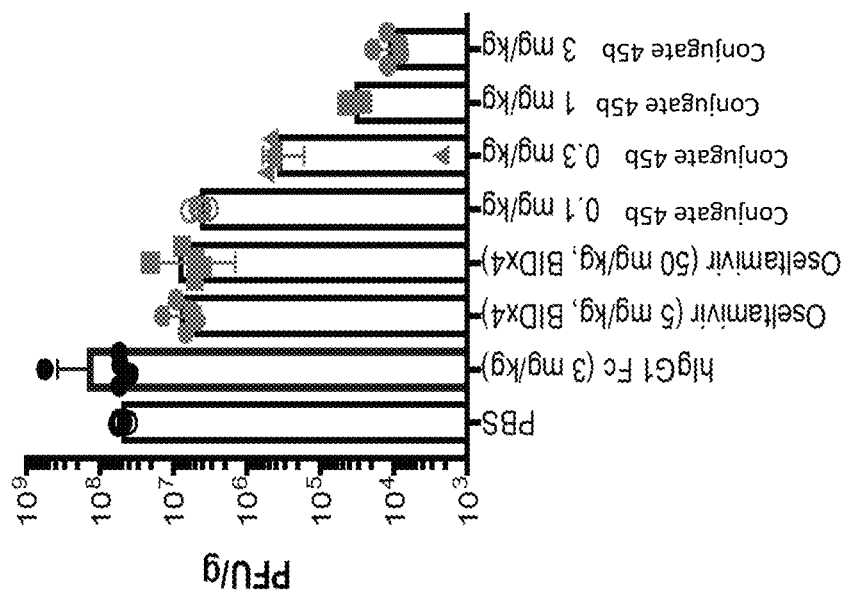
Figure 112M:
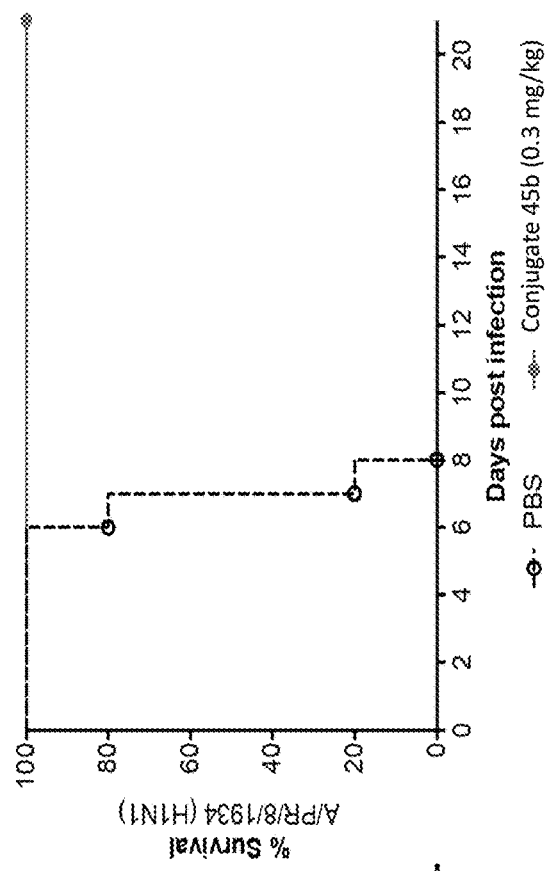
Figure 112L:
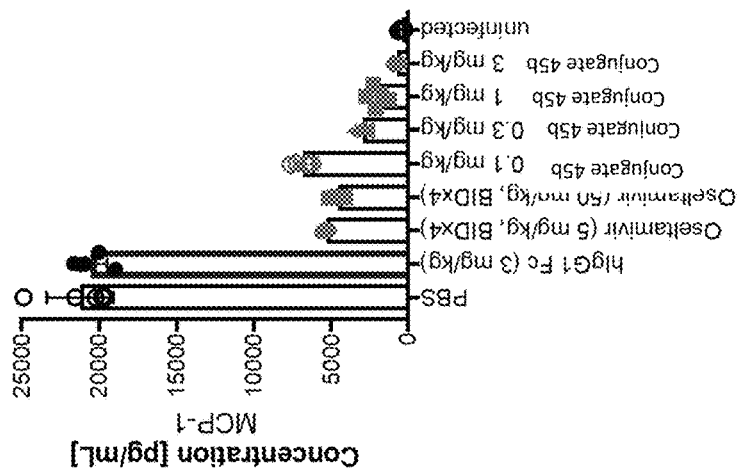

FIGS. 112A-112M are graphs showing the efficacy of conjugate 45b against lethal challenge with influenza in Balb/C mice. FIG. 112A is a graph showing dose-response of conjugate 45b ranging from 0.01-1 mg/kg dosed SC at 2 h post-infection against lethal challenge with influenza A/PR/8/1934 (H1N1) in survival. FIGS. 112B-112H are graphs showing the efficacy of minimal protective dose of conjugate 45b administered SC against influenza A/CA/07/2009 (H1N1)pdm (FIG. 112B), A/WSN/1933 (H1N1) (FIG. 112C), A/CA/12/2012 (H1N1)pdm09 (FIG. 112D), A/Texas/23/2012 (H1N1)pdm09 H275Y (FIG. 112E), A/Hong Kong/1/1968 (H3N2) (FIG. 112F), B/Florida/4/2006 (Yamagata) (FIG. 112G), and B/Malaysia/2506/2004 (Victoria) (FIG. 112H). FIG. 112I is a graph showing the efficacy of conjugate 45 against BSL-3 strain A/Vietnam/1203/2005 (H5N1). FIG. 112J is a bar graph showing viral burden in the lung on day 4 post-infection. FIGS. 112K-112L are graphs depicting the lung cytokine levels of IL-6 (FIG. 112K) and MCP-1 (FIG. 112L). FIG. 112M is a graph showing the minimal protective dose of conjugate 45b administered SC against influenza A/PR/8/1934 (H1N1). This study was performed as described in Example 203.

Figure 113B:
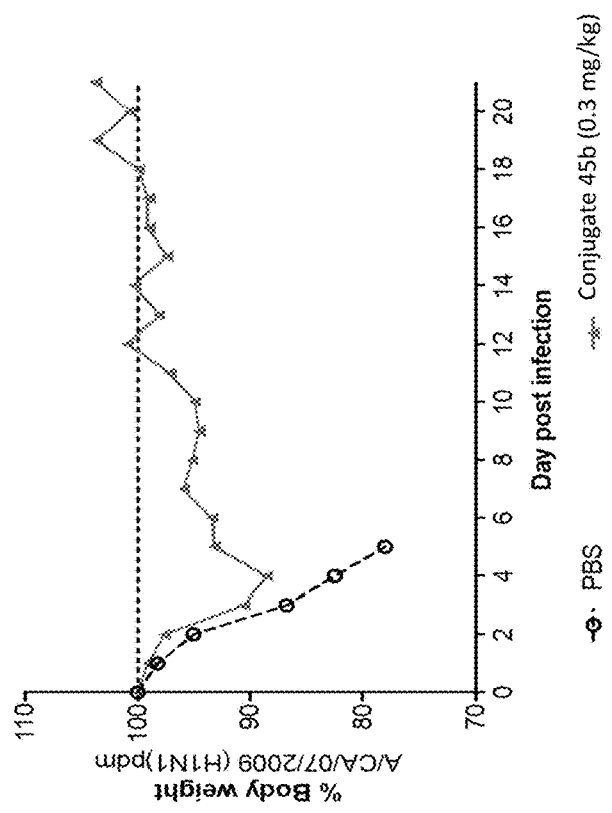
Figure 113A:
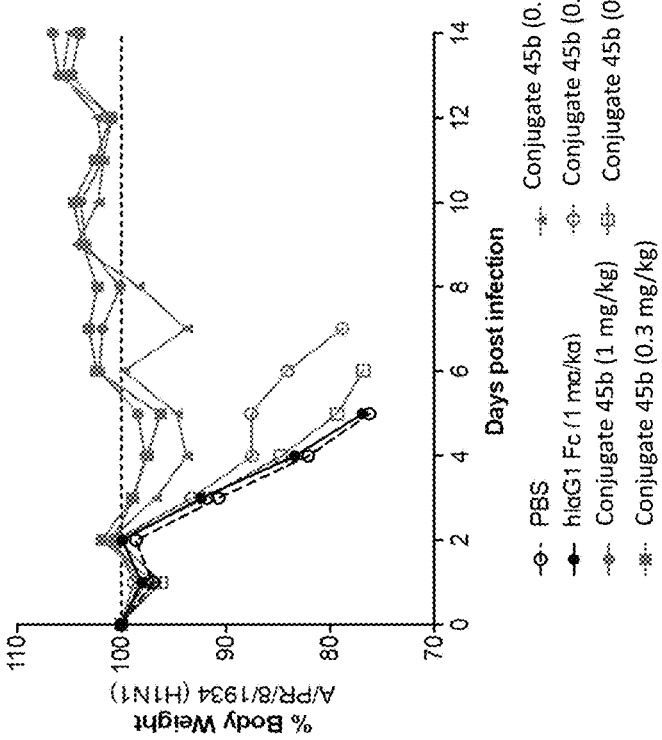
Figure 113C:
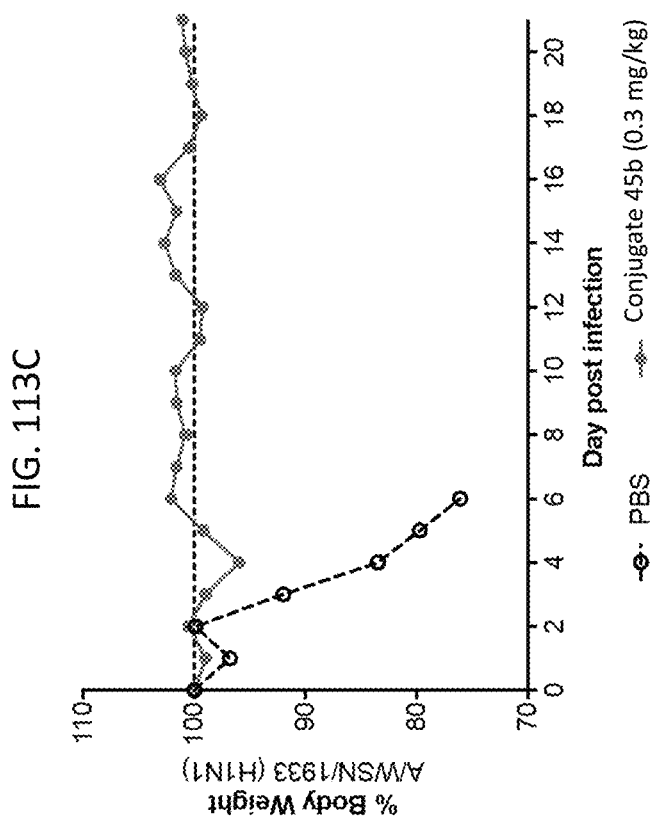
Figure 113E:
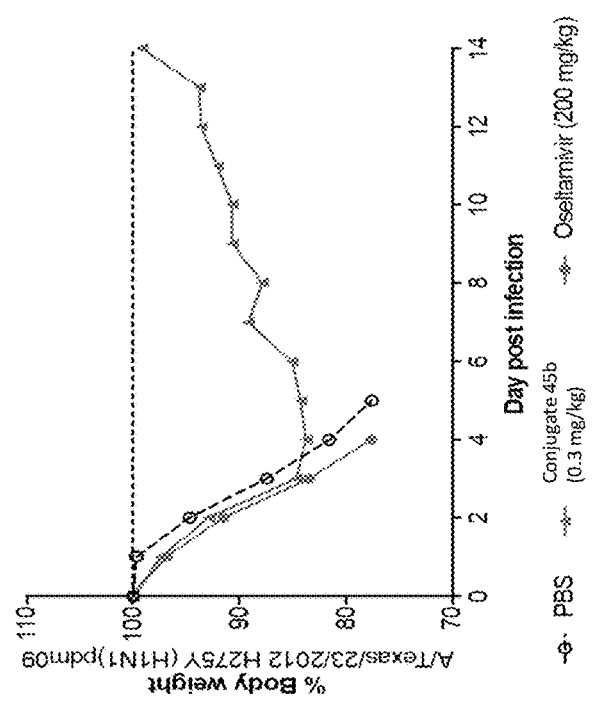
Figure 113D:
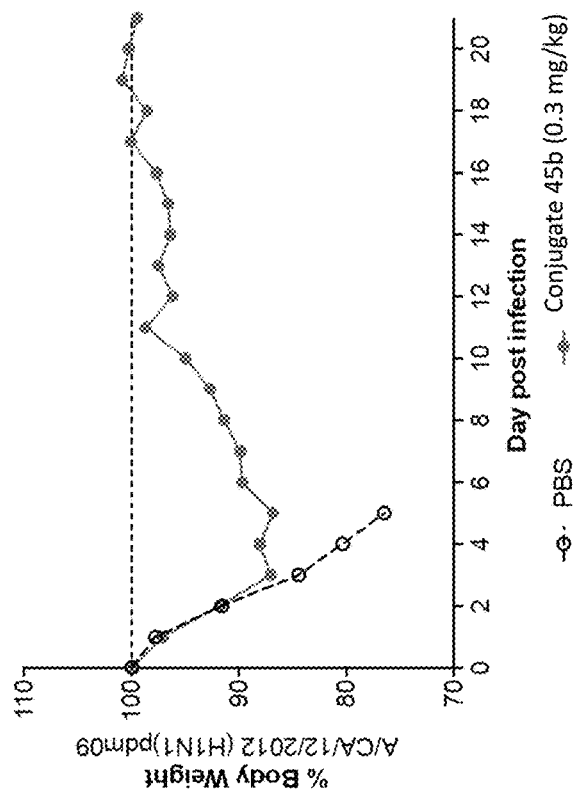
Figure 113G:
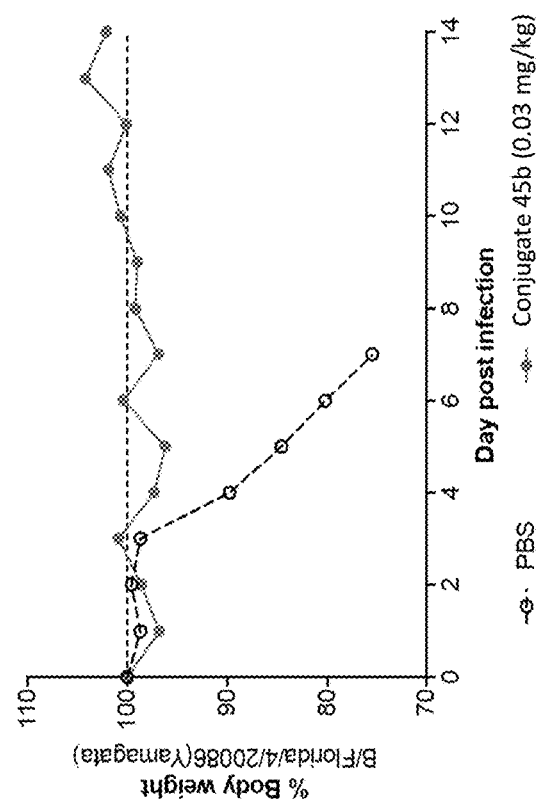
Figure 113F:
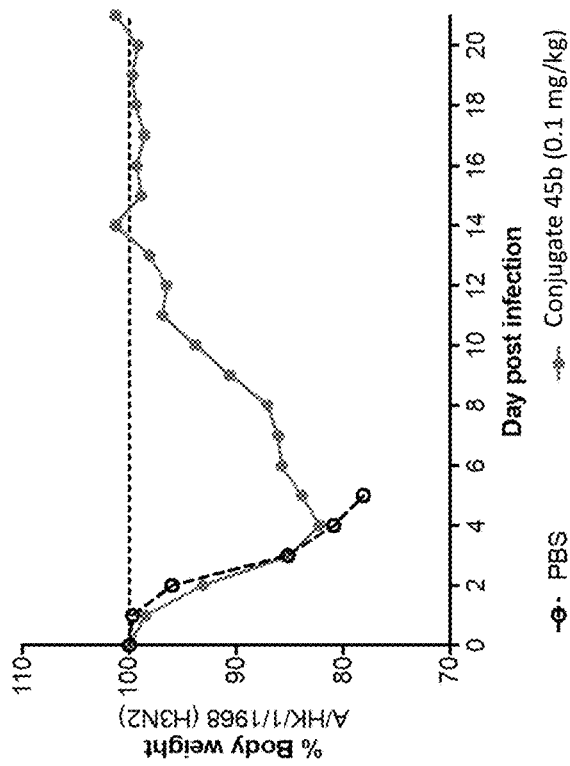
Figure 113H:
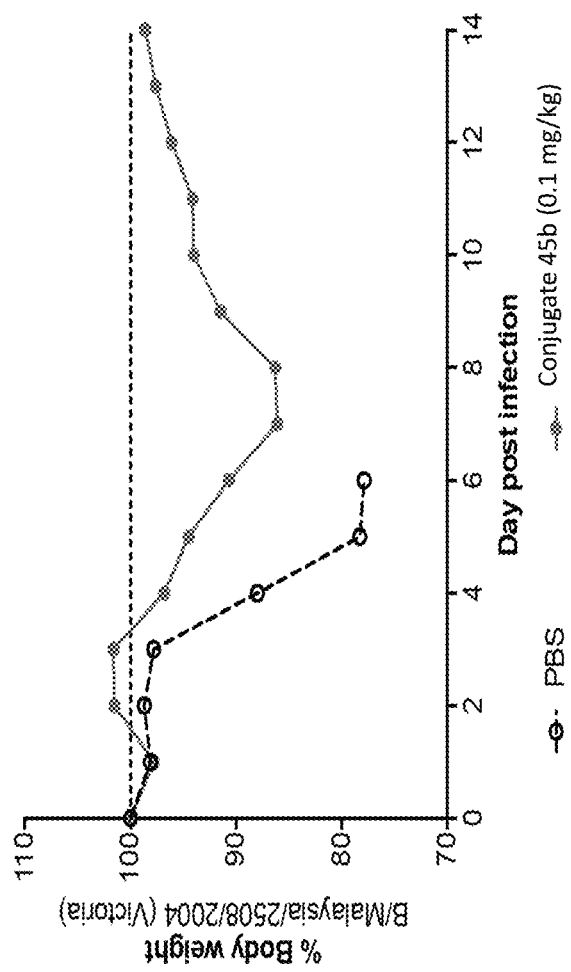

FIGS. 113A-113J are graphs showing the efficacy of conjugate 45b against lethal challenge with influenza in Balb/C mice by percent body weight change. FIG. 113A is a graph showing dose-response of conjugate 45b ranging from 0.01-1 mg/kg dosed SC at 2 h post-infection against lethal challenge with influenza A/PR/8/1934 (H1N1). FIGS. 113B-113H show percent body weight change following minimal protective dose of conjugate 45b administered SC against influenza A/CA/07/2009 (H1N1)pdm (FIG. 113B), A/WSN/1933 (H1N1) (FIG. 113C), A/CA/12/2012 (H1N1)pdm09 (FIG. 113D), A/Texas/23/2012 (H1N1)pdm09 H275Y (FIG. 113E), A/Hong Kong/1/1968 (H3N2) (FIG. 113F), B/Florida/4/2006 (Yamagata) (FIG. 113G), and B/Malaysia/2506/2004 (Victoria) (FIG. 113H).

Figures 113I, 113J:
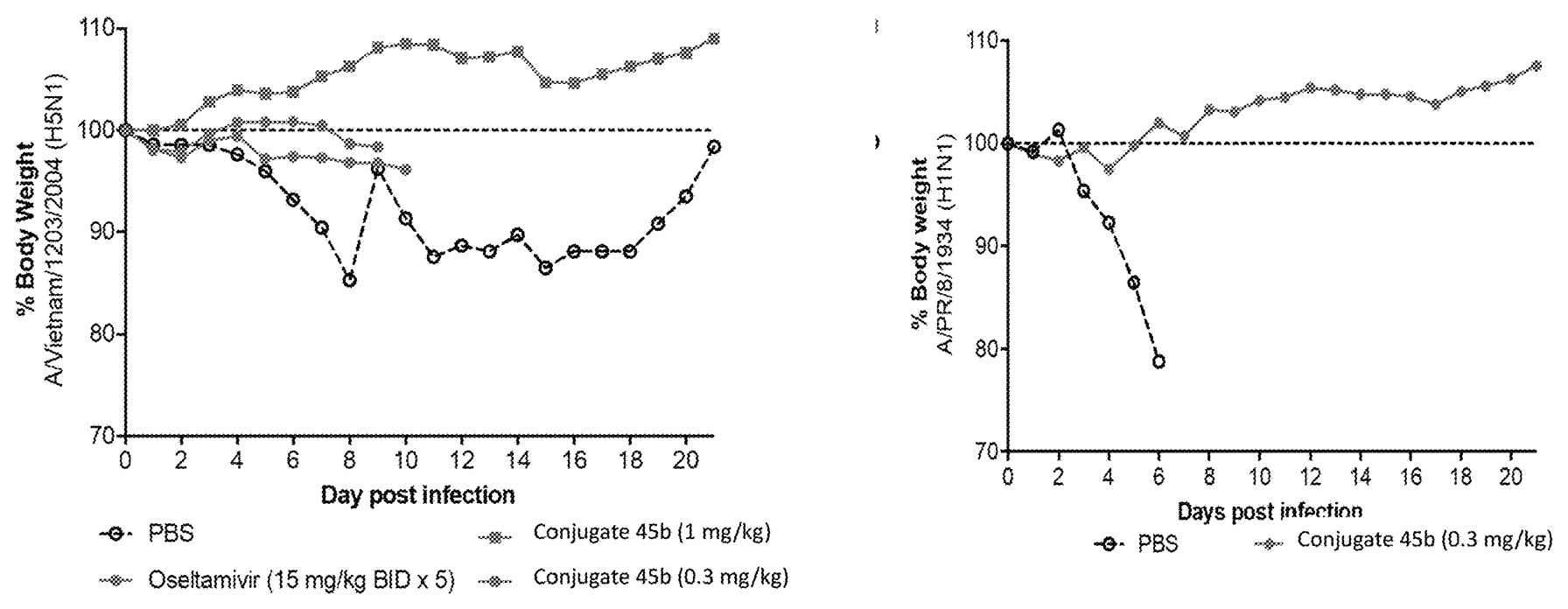

FIG. 113I is a graph showing the efficacy of conjugate 45b against BSL-3 strain A/Vietnam/1203/2005 (H5N1). FIG. 113J is a graph showing the body weight change when the minimal protective dose of conjugate 45b is administered SC against influenza A/PR/8/1934 (H1N1). This study was performed as described in Example 203.

Figure 114B:
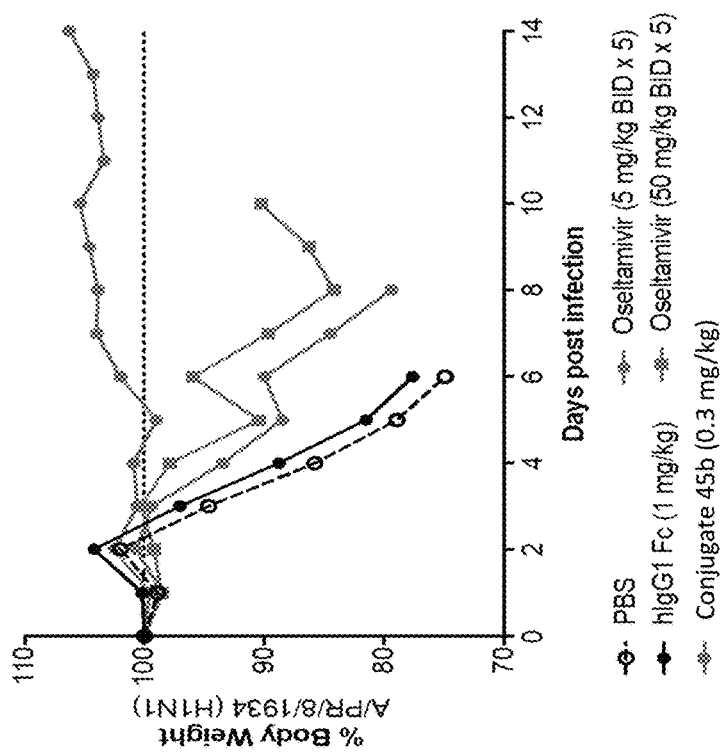
Figure 114A:
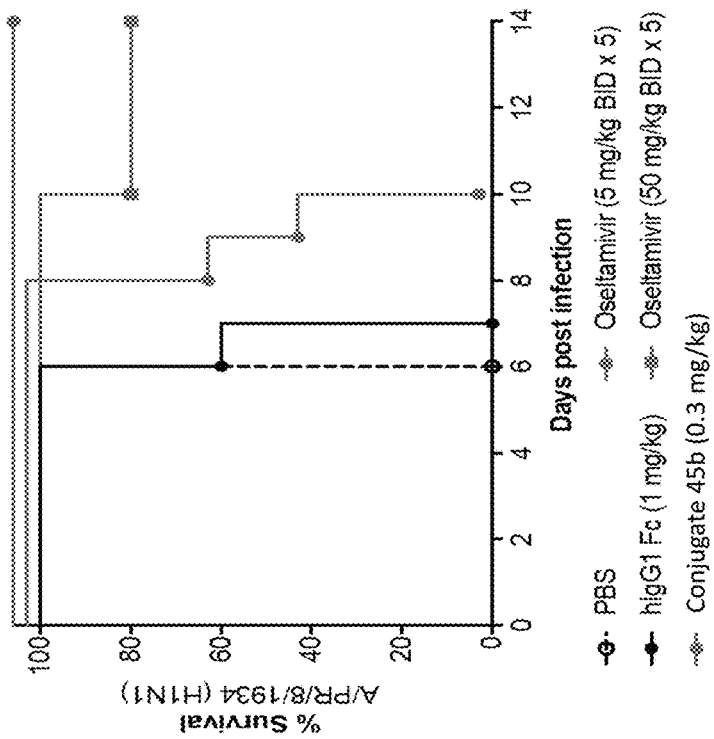

FIGS. 114A-114B is a pair of graphs showing the efficacy of oseltamivir at a human equivalent dose at 5 mg/kg (BID x 5 days) or 10× human equivalent dose at 50 mg/kg (BID x 5 days) in lethal mouse model of A/PR/8/1934 (H1N1) in survival (FIG. 114A) and body weight change (FIG. 114B).

Figure 115C:
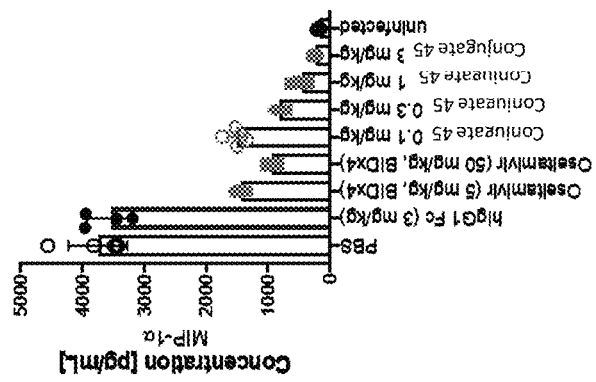
Figure 115B:
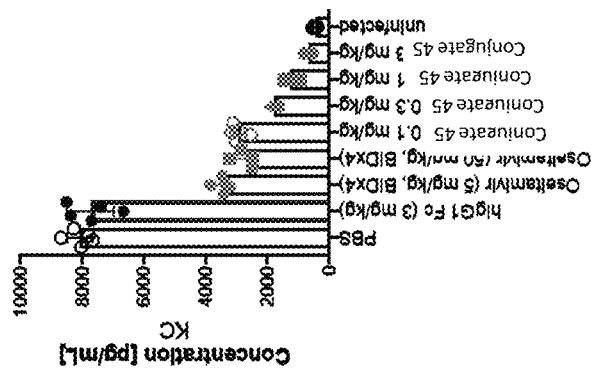
Figure 115A:
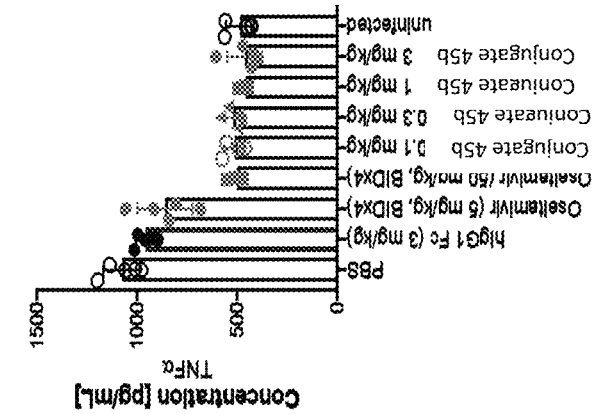

FIGS. 115A-115C are bar graphs showing lung cytokine levels for NF-α (FIG. 115A), KC (FIG. 115B), MIP-1α (FIG. 115C) on day 4 post-infection with lethal challenge of A/PR/8/1934 (H1N1).

Figure 116B:
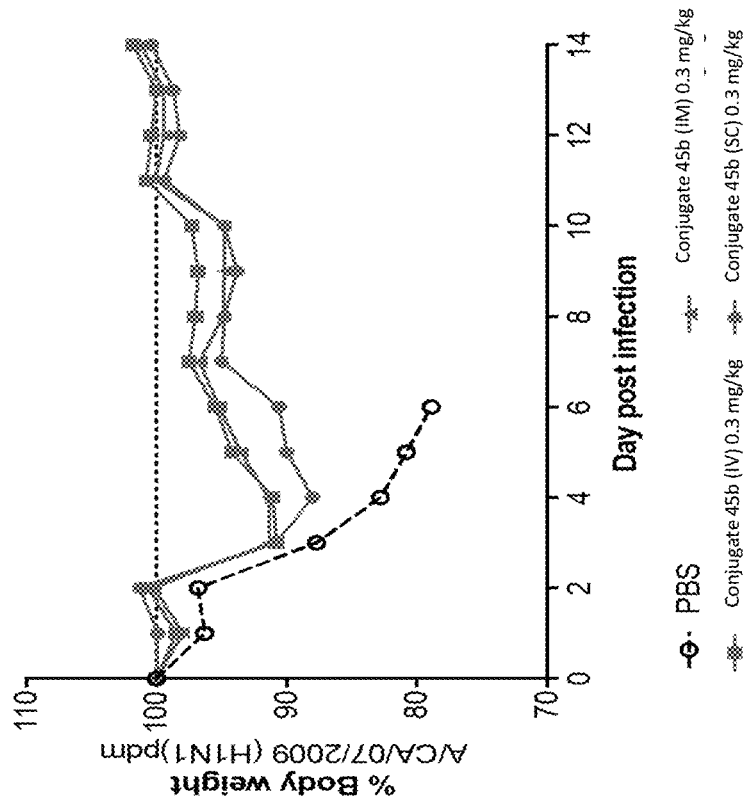
Figure 116A:
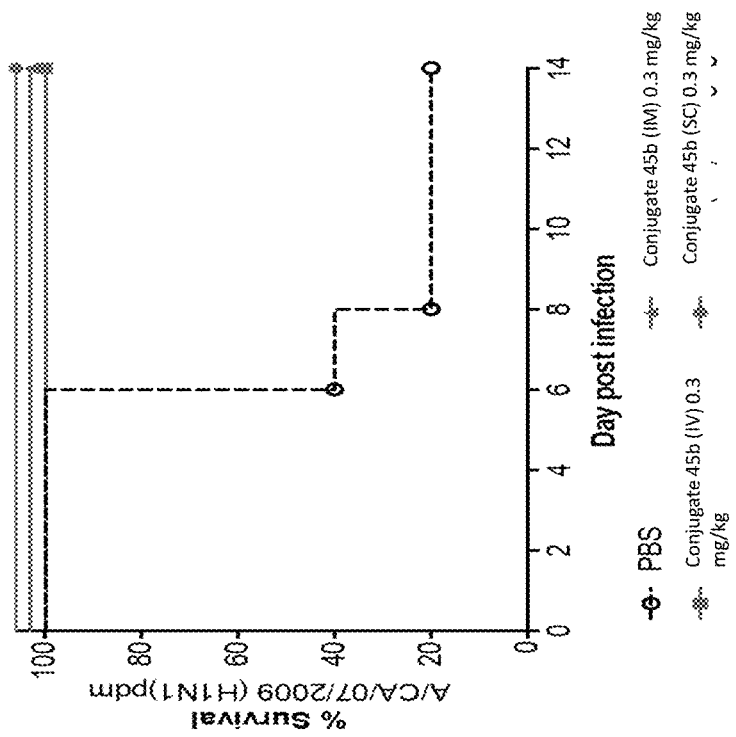

FIGS. 116A-116B are graphs depicting the efficacy of conjugate 45b following a single dose administered SC, IM, or IV against influenza A/CA/07/2009 (H1N1)pdm in percent survival (FIG. 111A) and percent body weight change (FIG. 116B).

Figure 116D:
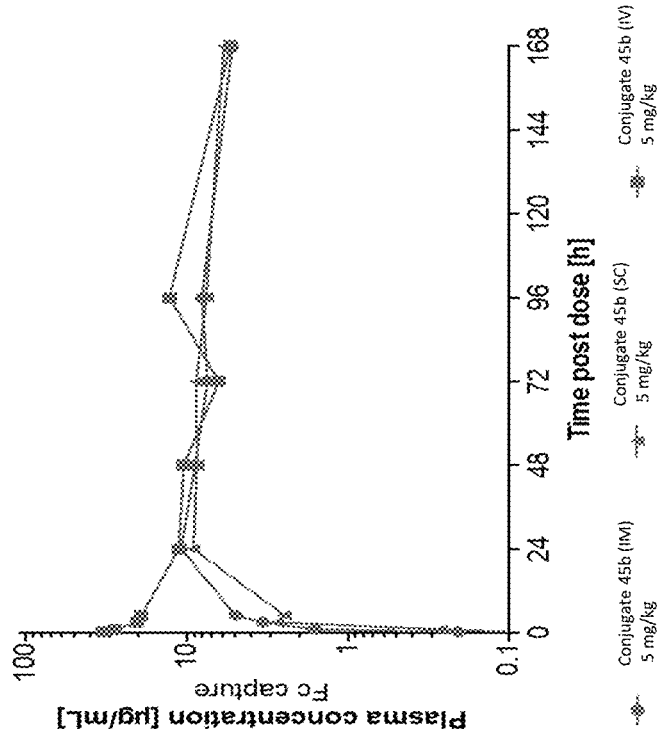
Figure 116C:
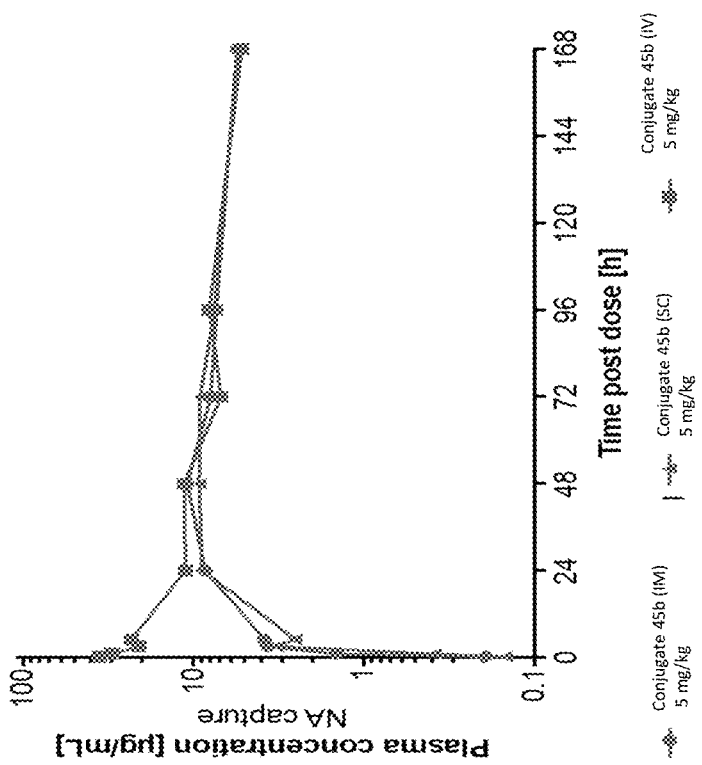

FIGS. 116C-116D are graphs depicting the plasma level of conjugate 45b following a single dose administered SC, IM, or IV in mice over 168 h determined by NA capture (FIG. 116C) or Fc capture (FIG. 116D).

Figure 117A:
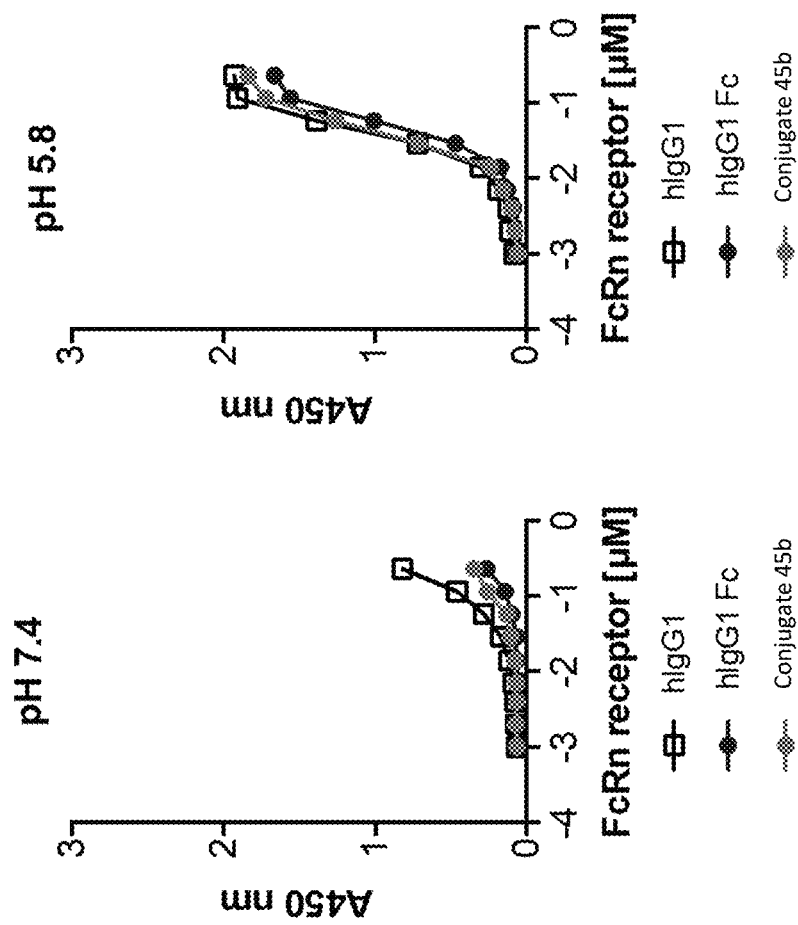
Figure 117B:
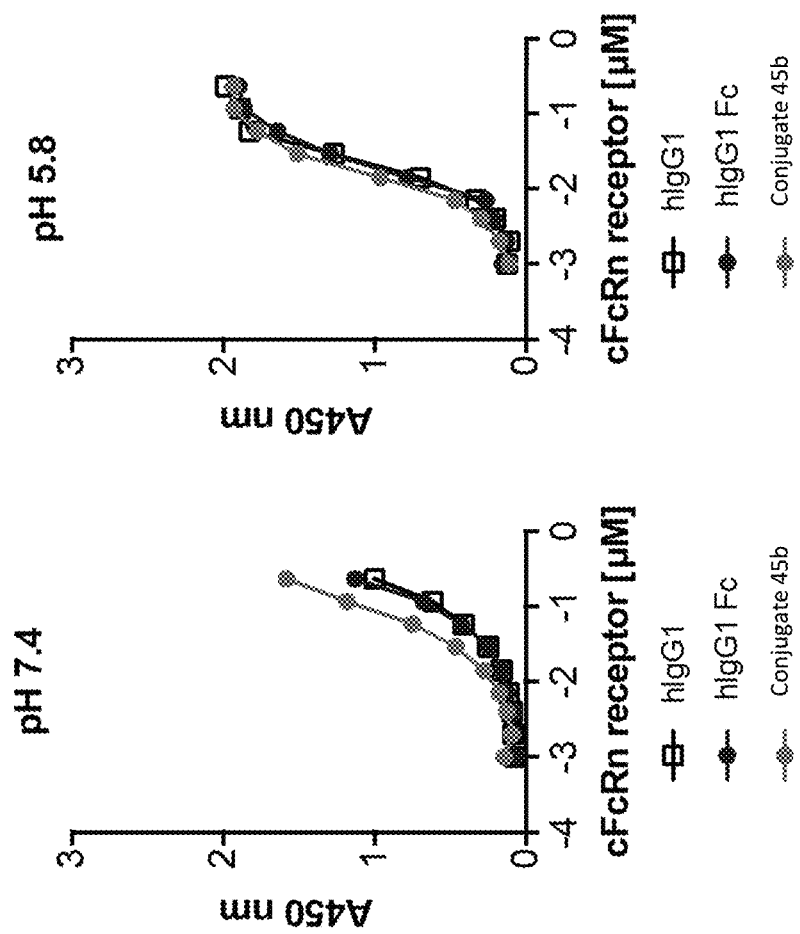
Figure 117C:
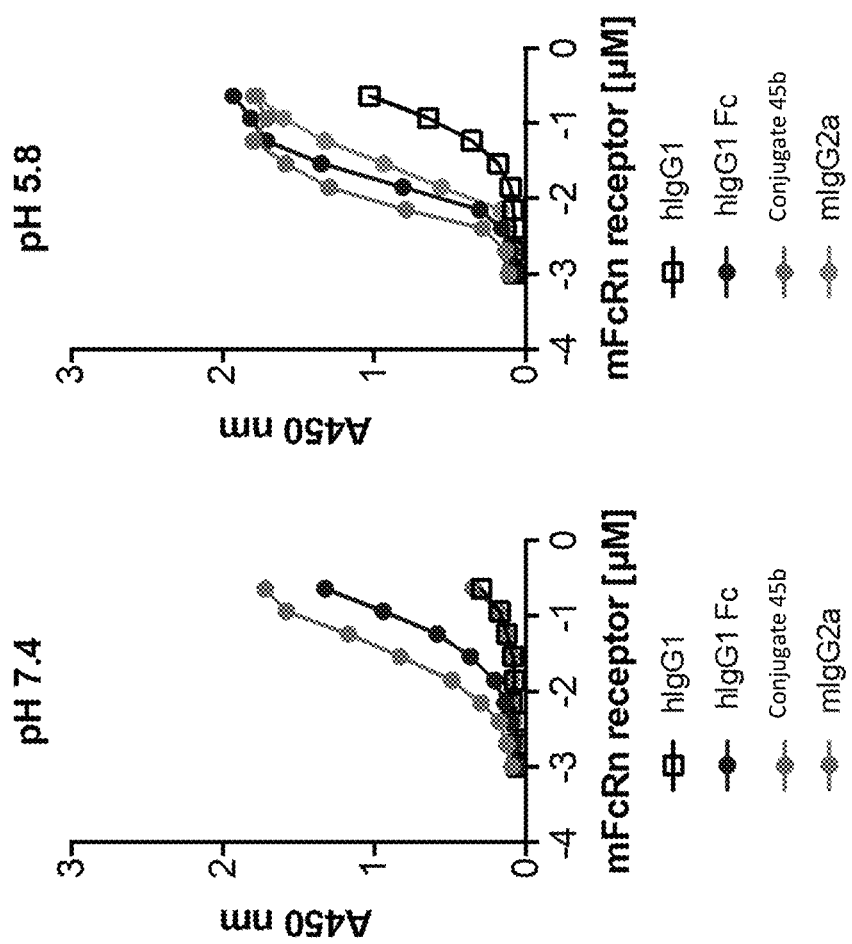

FIGS. 117A-117C are graphs showing comparable FcRn binding pattern as hIgG1 Fc or full-length IgG1 isotype control to human (FIG. 117A), cynomolgus monkey (FIG. 117B), and mouse (FIG. 117C) with stronger binding at pH 5.8 and reduced binding at pH 7.4.

Figure 118B:
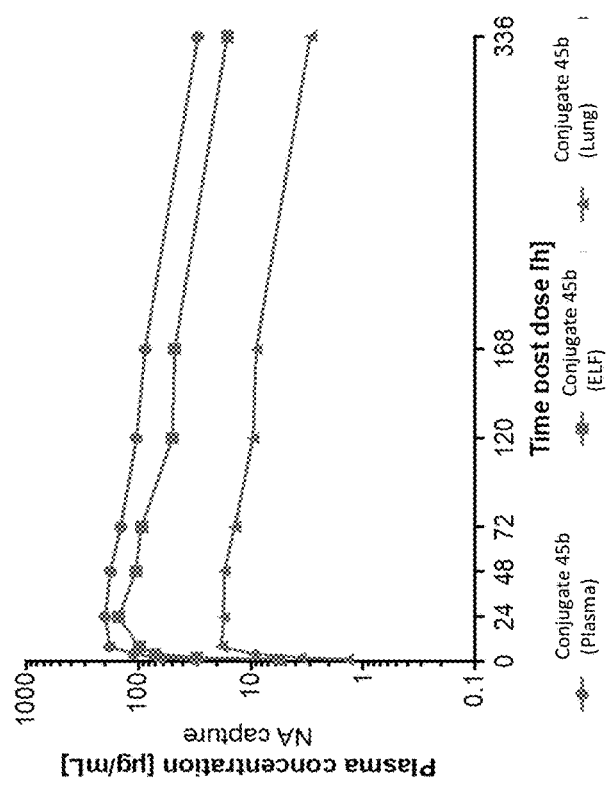
Figure 118A:
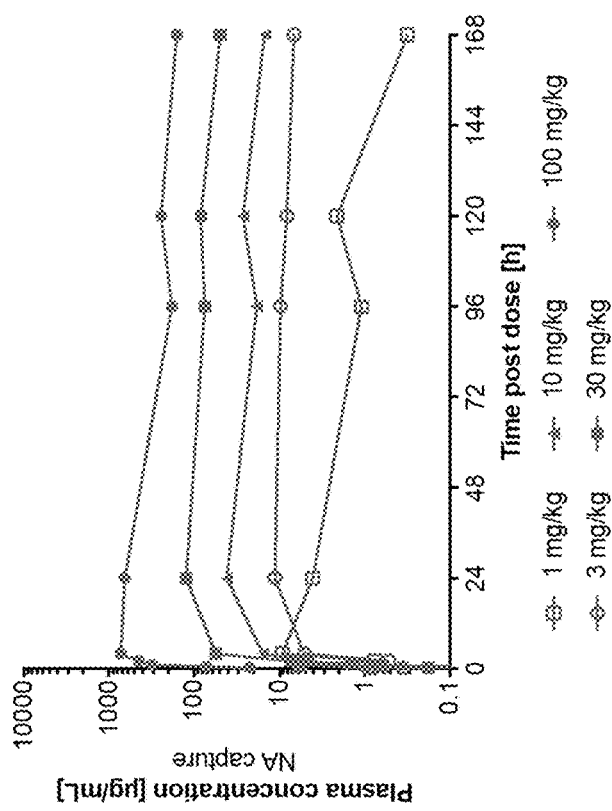
Figure 118D:
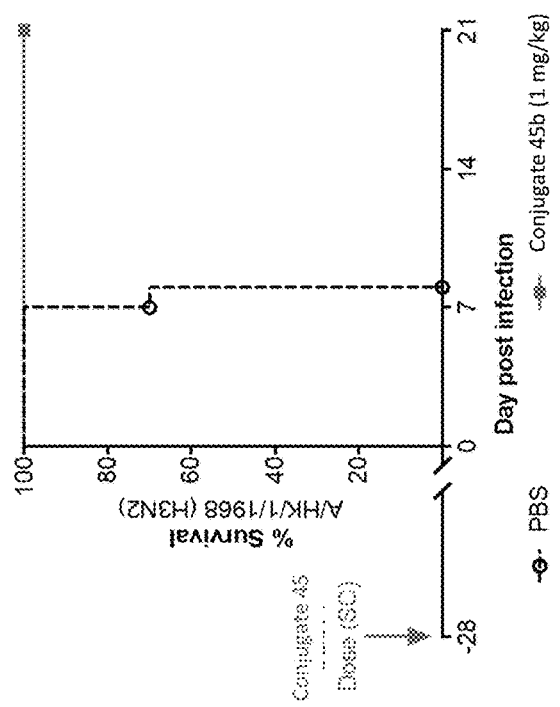
Figure 118C:
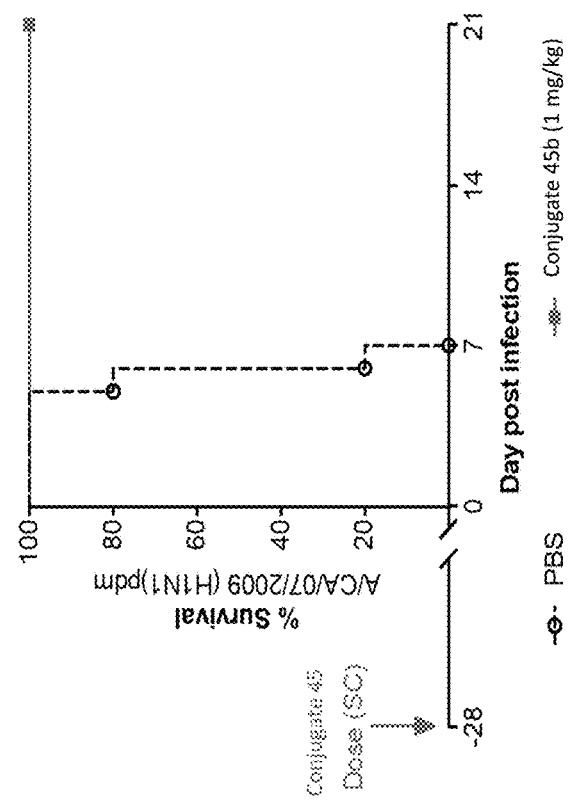
Figure 118F:
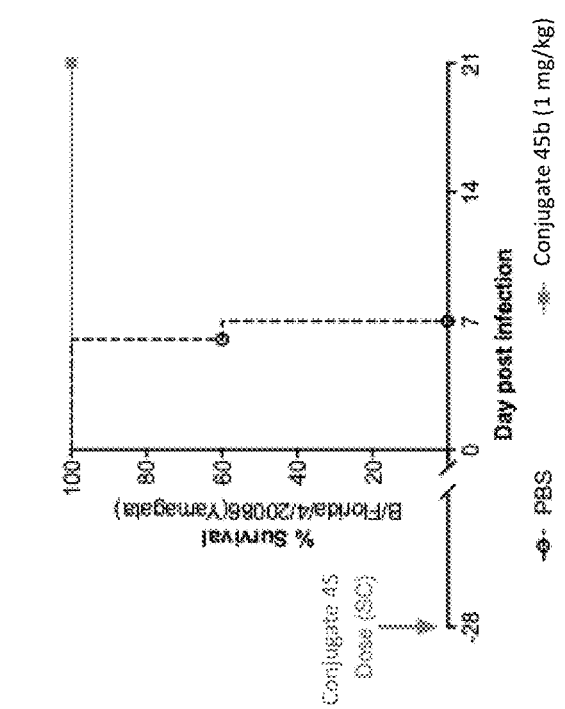
Figure 118E:
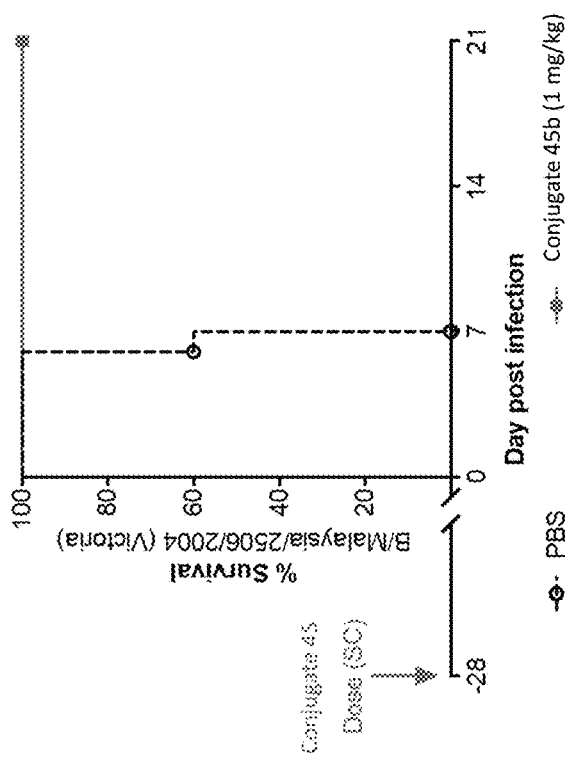

FIGS. 118A-118F are graphs depicting the long duration of action of conjugate 45b. FIG. 118A is a graph showing the plasma levels of conjugate 45b dose response from 1-100 mg/kg after SC administration in mice. FIG. 118B is a graph depicting the levels of conjugate 45b after SC dosing in plasma, ELF, and lung of mice. FIGS. 118C-F show the protection provided by conjugate 45b dosed 28 days priorto lethal challenge against influenza A/CA/07/2009 (H1N1) pdm (FIG. 118C), A/HK/1/1968 (H3N2) (FIG. 118D), B/Malaysia/2506/2004 (Victoria) (FIG. 118E), and B/Florida/4/2006 (Yamagata) (FIG. 118F) in percent survival.

FIG. 119 is a graph depicting survival curve of lower conjugate 45a dose groups. This study was performed as described in Example 209.

Figure 120:
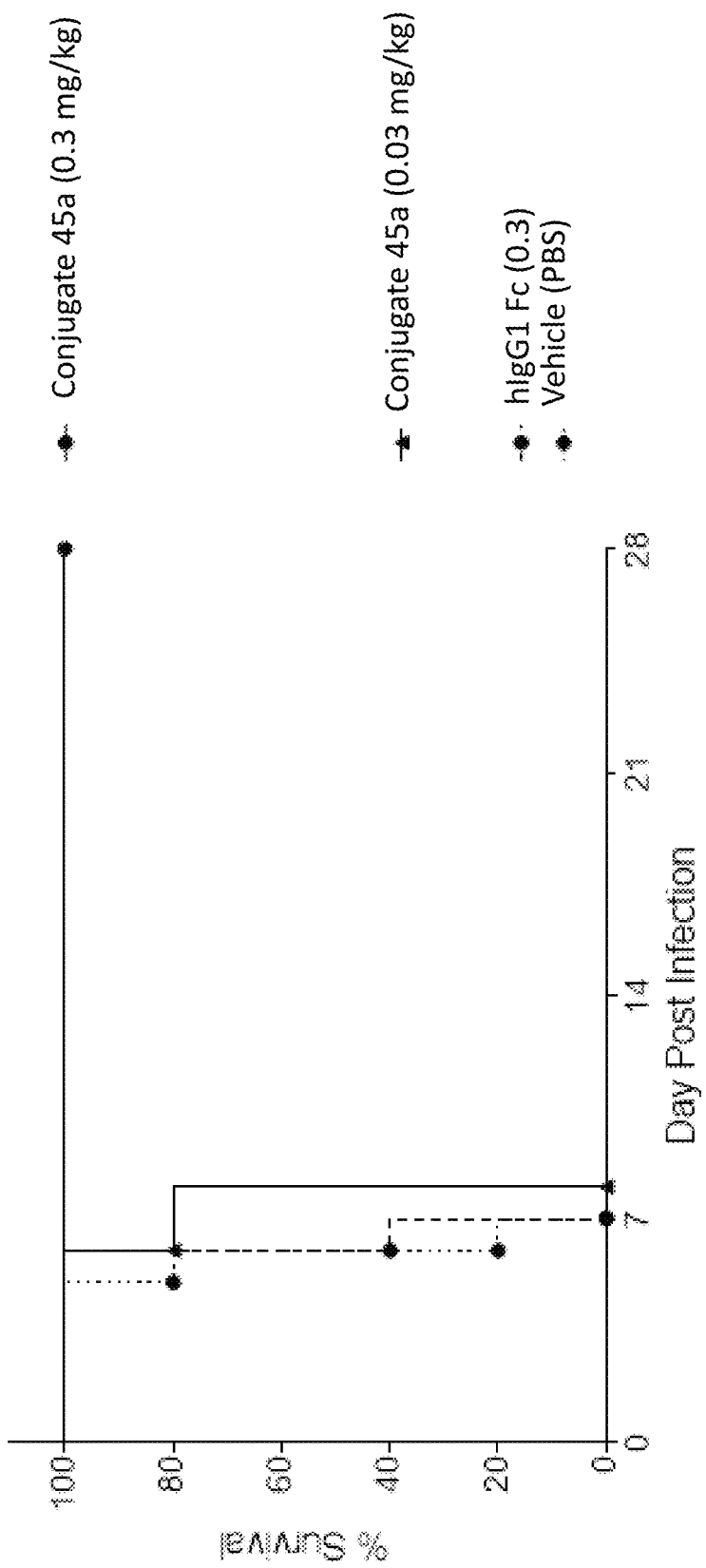

FIG. 120 is a graph depicting Kaplan-Meier survival curve of controls and conjugate 45a at 0.3 and 0.03 mg/kg. This study was performed as described in Example 210.

Figure 121:
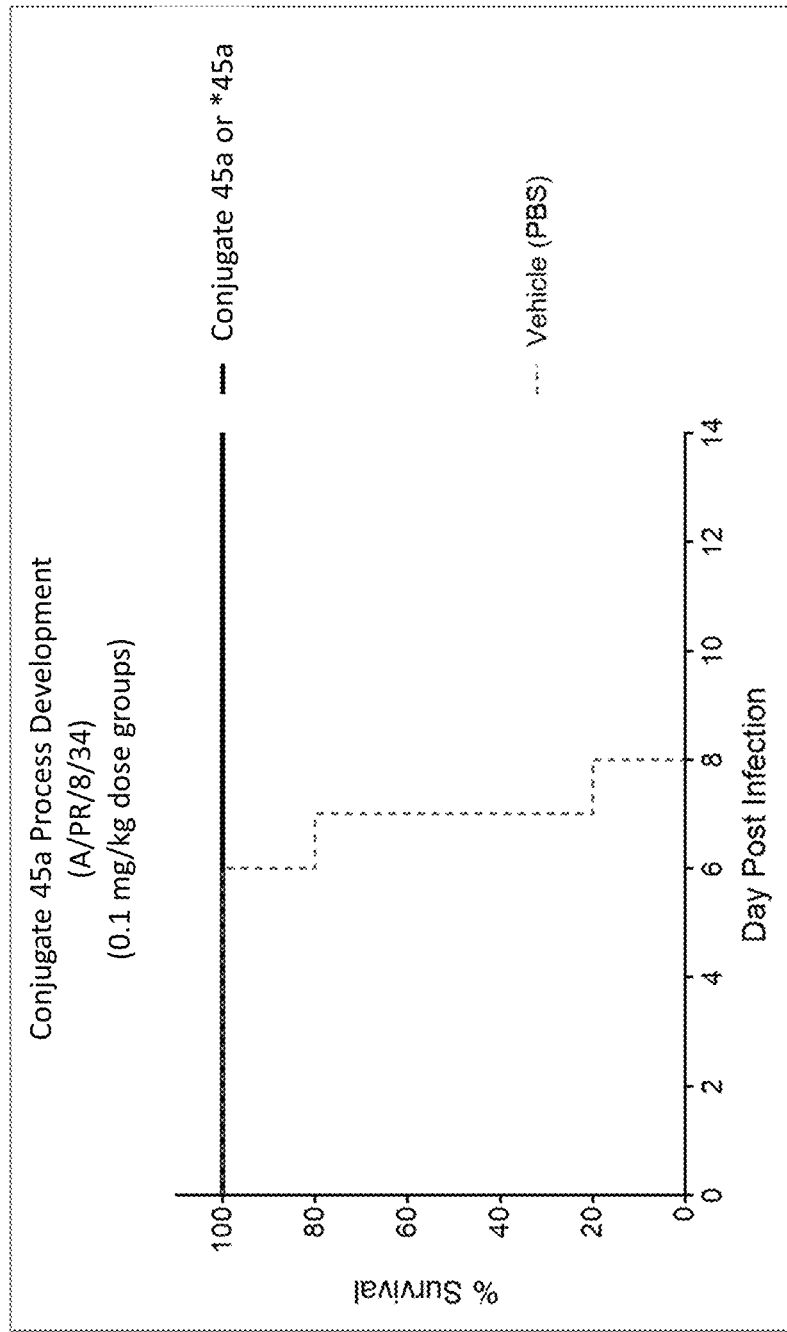

FIG. 121 is a graph depicting Kaplan-Meier survival curve of controls and conjugate 45a (protein A column purified) and *conjugate 45a (protein A column flow-through) at 0.1 mg/kg. This study was performed as described in Example 215.

Figure 122:
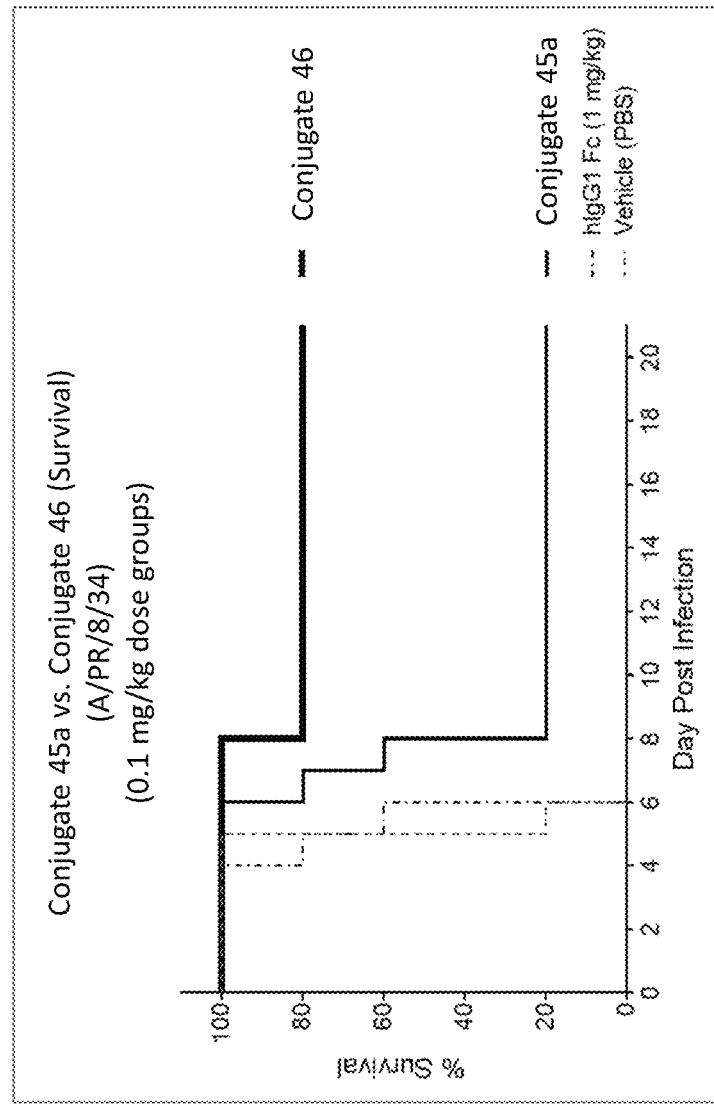

FIG. 122 is a graph depicting Kaplan-Meier survival curve of controls and conjugates 45a and 46 at 0.1 mg/kg. This study was performed as described in Example 216.

DETAILED DESCRIPTION

The disclosure features conjugates, compositions, and methods for the treatment of viral infections (e.g., influenza viral infections). The conjugates disclosed herein include monomers or dimers of viral neuraminidase inhibitors (e.g., zanamivir, peramivir, or analogs thereof) conjugated to Fc monomers, Fc domains, Fc-binding peptides, albumin proteins, or albumin protein-binding peptides. The neuraminidase inhibitor (e.g., zanamivir, peramivir, or analogs thereof) in the conjugates targets neuraminidase on the surface of the viral particle. The Fc monomers or Fc domains in the conjugates bind to FcγRs (e.g., FcRn, FcγRI, FcγRIIa, FcγRIIc, FcγRIIIa, and FcγRIIIb) on immune cells, e.g., neutrophils, to activate phagocytosis and effector functions, such as antibody-dependent cell-mediated cytotoxicity (ADCC), thus leading to the engulfment and destruction of viral particles by immune cells and further enhancing the antiviral activity of the conjugates. The albumin or albumin-binding peptide may extend the half-life of the conjugate, for example, by binding of albumin to the recycling neonatal Fc receptor. Such compositions are useful in methods for the inhibition of viral growth and in methods for the treatment of viral infections, such as those caused by an influenza virus A, influenza virus B and influenza virus C.

I. Viral Infections

The compounds and pharmaceutical compositions described herein (e.g., a conjugate of any one of formulas (1)-(5), (D-I)-(D-XI), (D'-I), (M-I)-(M-XI), or (M'-I)) can be used to treat a viral infection (e.g., an influenza viral infection, such as influenza A, B, C, or parainfluenza).

Viral infection refers to the pathogenic growth of a virus (e.g., the influenza virus) in a host organism (e.g., a human subject). A viral infection can be any situation in which the presence of a viral population(s) is damaging to a host body. Thus, a subject is suffering from a viral infection when an excessive amount of a viral population is present in or on the subject's body, or when the presence of a viral population(s) is damaging the cells or other tissue of the subject.

Influenza, commonly known as "the flu", is an infectious disease caused by an influenza virus. Symptoms can be mild to severe. The most common symptoms include: a high fever, runny nose, sore throat, muscle pains, headache, coughing, and feeling tired. These symptoms typically begin two days after exposure to the virus and most last less than a week. The cough, however, may last for more than two weeks. In children, there may be nausea and vomiting, but these are less common in adults. Complications of influenza may include viral pneumonia, secondary bacterial pneumonia, sinus infections, and worsening of previous health problems such as asthma or heart failure. Severe complications may occur in subjects having weakened immune systems, such as the young, the old, those with illnesses that weaken the immune system, and those undergoing therapy treatment resulting in a weakening of the immune system.

Subjects infected with influenza are also at increased risk of developing secondary infections (e.g., secondary bacterial, viral, or fungal infections), in particular, bacterial infections such as methicillin-resistant *Staphylococcus aureus* (MRSA), *Streptococcus pneumoniae, Pseudomonas aeruginosa*, and/or *Haemophilus influenzae*. Bacterial secondary infections further increase morbidity and mortality of influenza infection.

Three types of influenza viruses affect human subjects, namely Type A, Type B, and Type C. Usually, the virus is spread through the air from coughs or sneezes. This is believed to occur mostly over relatively short distances. It can also be spread by touching surfaces contaminated by the virus and then touching the mouth or eyes. A person may be infectious to others both before and during the time they are showing symptoms. The infection may be confirmed by testing the throat, sputum, or nose for the virus. A number of rapid tests are available; however, people may still have the infection if the results are negative. A type of polymerase chain reaction that detects the virus's RNA may be used to diagnose influenza infection.

II. Conjugates of the Disclosure

Provided herein are synthetic conjugates useful in the treatment of viral infections (e.g., influenza infections). The conjugates disclosed herein include an Fc domain or an albumin protein conjugated to one or more monomers neuraminidase inhibitors or one or more dimers of two neuraminidase inhibitors (e.g., neuraminidase inhibitors selected from zanamivir, sulfozanamivir, peramivir, A-315675, or analogs thereof). The dimers of two neuraminidase inhibitors include a neuraminidase inhibitor (e.g., a first neuraminidase inhibitor of formula (A-I), (A-II), (A-III), (A-IV), (A-V), (A-VI), (A-VII), (A-VIII), (A-IX), (A-X), (A-XI), (A-XII), or (A-XIII)) and a second neuraminidase inhibitor (e.g., a second neuraminidase inhibitor of formula (A-I), (A-II), (A-III), (A-IV), (A-V), (A-VI), (A-VII), (A-VIII), (A-IX), (A-X), (A-XI), (A-XII), or (A-XIII)). The first and second neuraminidase inhibitors are linked to each other by way of a linker. Without being bound by theory, in some aspects, conjugates described herein bind to the surface of a viral particle (e.g., bind to viral neuraminidase enzyme on the surface on an influenza viral particle) through the interactions between the neuraminidase inhibitor moieties in the conjugates and proteins on the surface of the viral particle. The neuraminidase inhibitor disrupts neuraminidase, an envelope glycoprotein that cleaves sialic acids, i.e., terminal neuraminic acid residues, from glycan structures on the surface of infected host cells, releasing progeny viruses and allowing the spread of the virus from the host cell to uninfected surrounding cells.

Conjugates of the invention include neuraminidase inhibitor monomers and dimers conjugated to an Fc domain, Fc monomer, or Fc-binding peptide. The Fc domain in the conjugates described herein binds to the FcγRs (e.g., FcRn, FcγRI, FcγRIIa, FcγRIIc, FcγRIIIa, and FcγRIIIb) on immune cells. The binding of the Fc domain in the conjugates described herein to the FcγRs on immune cells activates phagocytosis and effector functions, such as antibody-dependent cell-mediated cytotoxicity (ADCC), thus leading to the engulfment and destruction of viral particles by immune cells and further enhancing the antiviral activity of the conjugates.

Conjugates of the invention include neuraminidase inhibitor monomers and dimers conjugated to an albumin protein or an albumin protein-binding peptide. The albumin protein or albumin protein-binding peptide may extend the half-life of the conjugate, for example, by binding of albumin to the recycling neonatal Fc receptor.

Conjugates provided herein are described by any one of formulas (1)-(5), (D-I)-(D-XI), (D'-I), (M-I)-(M-XI), or (M'-I). In some embodiments, the conjugates described herein include one or more monomers of neuraminidase inhibitors conjugated to an Fc domain or an albumin protein. In some embodiments, the conjugates described herein include one or more dimers of neuraminidase inhibitors conjugated to an Fc domain or an albumin protein. In some embodiments, when n is 2, E (an Fc domain monomer) dimerizes to form an Fc domain.

Conjugates described herein may be synthesized using available chemical synthesis techniques in the art. In cases where a functional group is not available for conjugation, a molecule may be derivatized using conventional chemical synthesis techniques that are well known in the art. In some embodiments, the conjugates described herein contain one or more chiral centers. The conjugates include each of the isolated stereoisomeric forms as well as mixtures of stereoisomers in varying degrees of chiral purity, including racemic mixtures. It also encompasses the various diastereomers, enantiomers, and tautomers that can be formed.

Neuraminidase inhibitors

A component of the conjugates described herein is an influenza virus neuraminidase inhibitor moiety. An influenza virus neuraminidase inhibitor disrupts neuraminidase, an envelope glycoprotein that cleaves sialic acids, i.e., terminal neuraminic acid residues, from glycan structures on the surface of infected host cells, releasing progeny viruses and allowing the spread of the virus from the host cell to uninfected surrounding cells. Examples of an influenza virus neuraminidase inhibitor include zanamivir (Relenza), sulfozanamivir, A-315675 and peramivir. In addition, derivatives of zanamivir, sulfozanamivir, A-315675 and peramivir, such as those found in the literature, have neuraminidase inhibitor activity and are useful as neuraminidase inhibitor moieties of the compounds herein (see, for example, Hadházi et al. A sulfozanamivir analogue has potent anti-influenza virus activity. *ChemMedChem Comm*. 13:785-789 (2018) and In vitro characterization of A-315675, a highly potent inhibitor of A and B strain of influenza virus neuraminidases and influenza virus replication. *Antimicrobial Agents and Chemotherapy* 46(4):1014-1021 (2002)).

Conjugates described herein are separated into two types: (1) one or more dimers of neuraminidase inhibitors conjugated to an Fc domain or an albumin protein and (2) one or more monomers of neuraminidase inhibitors conjugated to an Fc domain or an albumin protein. The dimers of neuraminidase inhibitors are linked to each other by way of a linker, such as the linkers described herein.

Viral neuraminidase inhibitors of the invention include zanamivir, sulfozanamivir, A-315675, peramivir, and analogs thereof, such as the viral neuraminidase inhibitors of formulas (A-I)-(A-XIII):

(A-I)

(A-II)

(A-III)

(A-IV)

(A-V)

-continued (A-VI)

(A-VII)

(A-VIII)

(A-IX)

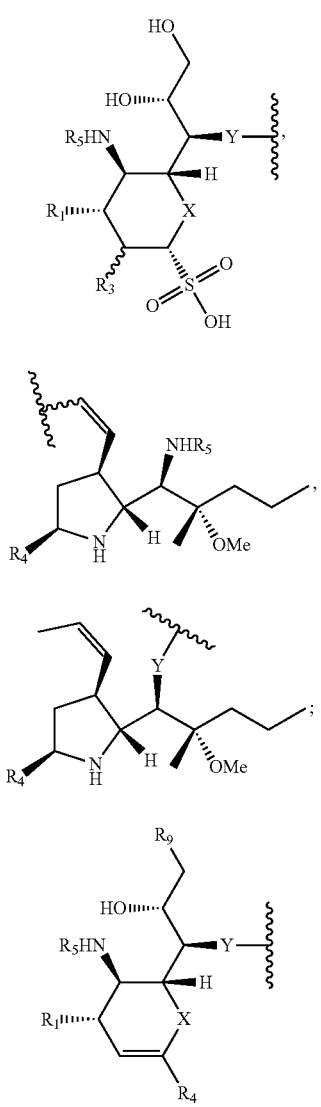
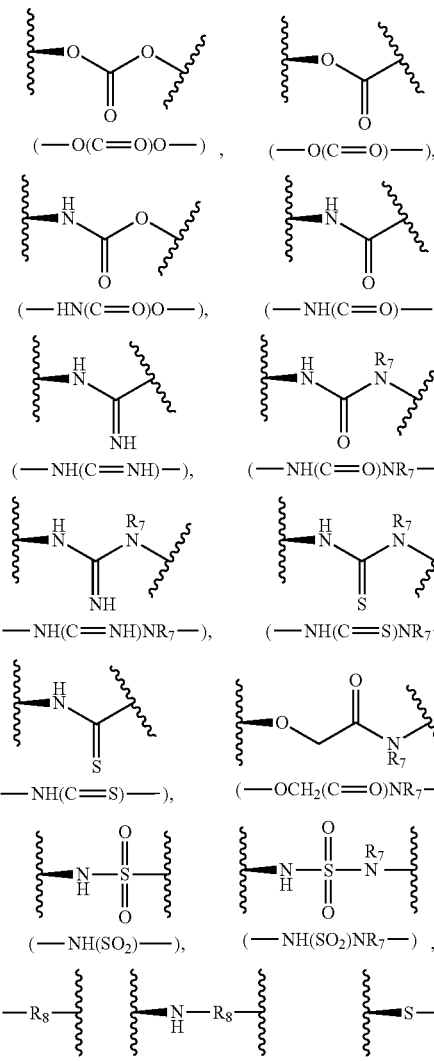
wherein $R_1$ is selected from —OH, —NH$_2$, —NHC(=NH)NH$_2$, and —NHC(=NH)NHR$_6$; $R_2$ and $R_3$ are each independently selected from —H, —OH, —F, —Cl, and —Br; $R_4$ is selected from —CO$_2$H, —P(=O)(OH)$_2$, —SO$_3$H; Rs is selected from —COCH$_3$, —COCF$_3$, —SO$_2$CH$_3$; X is selected from —O— and —S—; Y is selected from
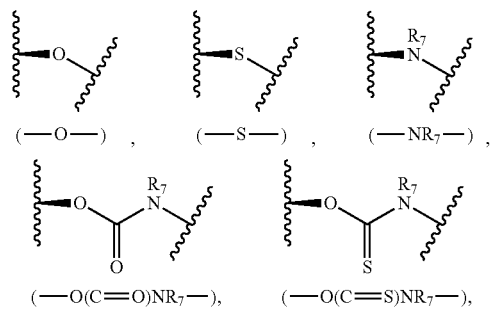
$R_6$ is selected from
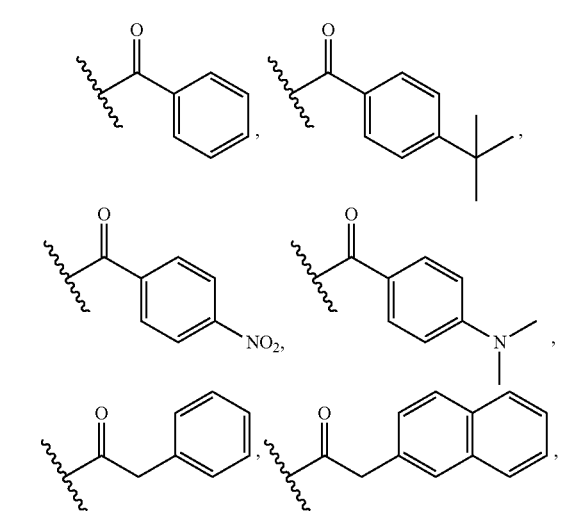

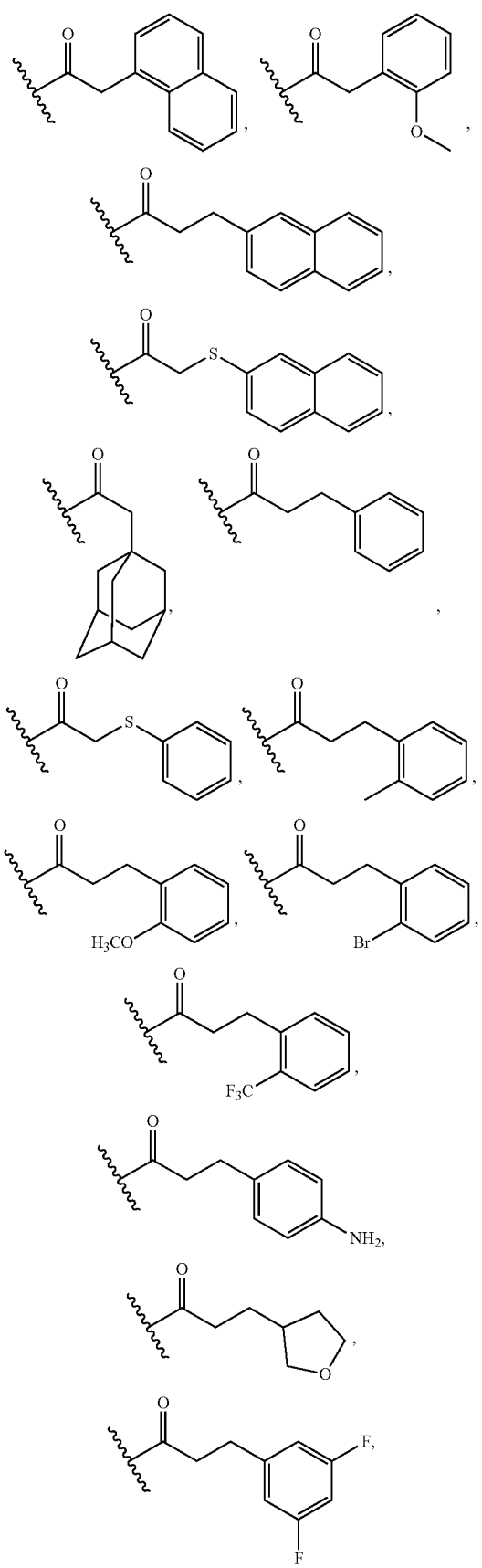
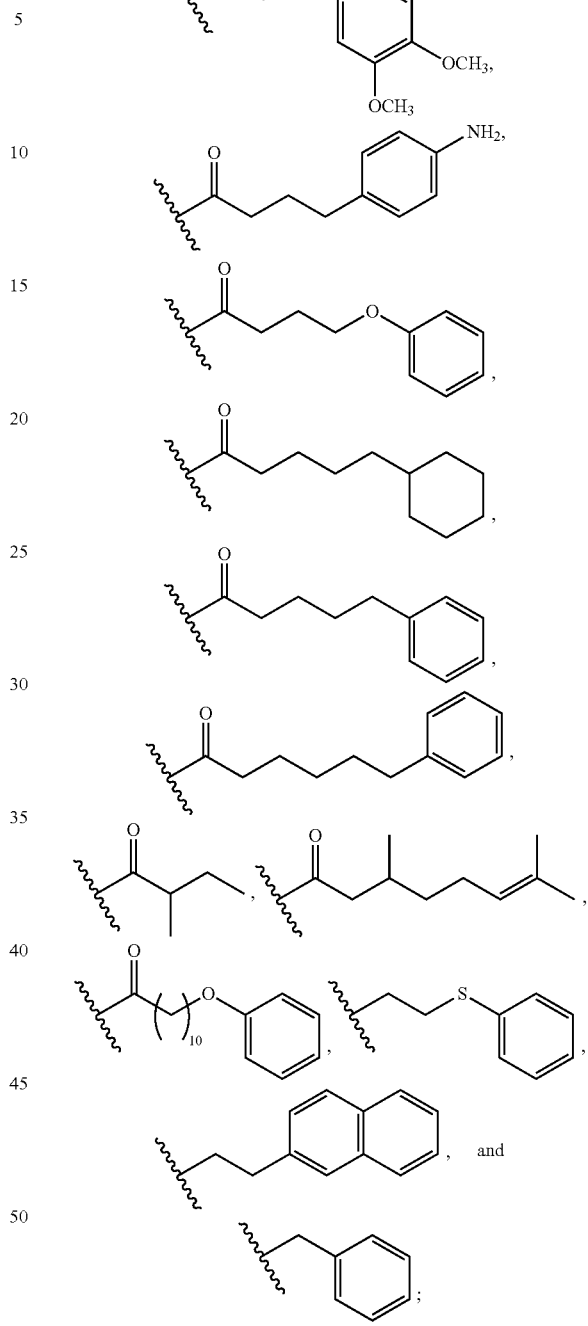

R₇ is selected from H, C1-C20 alkyl, C3-C20 cycloalkyl, C3-C20 heterocycloalkyl; C5-C15 aryl, and C2-C15 heteroaryl; R₈ is selected from C3-C20 heterocycloalkyl, C5-C15 aryl, and C2-C15 heteroaryl; R₉ is selected from —H, a halogen (e.g., Cl, F, or Br), —OR₁₀, —NHC(=O) R₇, optionally substituted C1-C20 alkyl, C3-C20 cycloalkyl, C3-C20 heterocycloalkyl; C5-C15 aryl, and C2-C15 heteroaryl; and R₁₀ is selected from C1-C20 alkyl, C3-C20 cycloalkyl, C3-C20 heterocycloalkyl; C5-C15 aryl, and C2-C15 heteroaryl. Most preferably the viral neuraminidase inhibitor of formula (A-I), (A-II), (A-III), (A-IV), (A-V), (A-VI), (A-VII), (A-VIII), (A-IX), (A-X), (A-XI), (A-XII), or (A-XIII) is covalently attached to the conjugate through Y.

Preferably the viral neuraminidase inhibitor is selected from zanamivir, sulfozanamivir, peramivir, or A-315675:

Zanamivir

Sulfozanamivir

Peramivir

A-315675

Conjugates of Dimers of Neuraminidase Inhibitors Linked to an Fc Domain or an Albumin Protein The conjugates described herein include an Fc domain, and Fc monomer, an Fc-binding peptide, and albumin protein, or an albumin protein-binding peptide covalently linked to one or more dimers of neuraminidase inhibitors. The dimers of two neuraminidase inhibitors include a first neuraminidase inhibitor (e.g., a first viral neuraminidase inhibitor of formulas (A-I)-(A-XIII)) and a second neuraminidase inhibitor (e.g., a second viral neuraminidase inhibitor of formulas (A-I)-(A-XIII)). The first and second neuraminidase inhibitors are linked to each other by way of a linker, such as a linker described herein. In some embodiments of the dimers of neuraminidase inhibitors, the first and second neuraminidase inhibitors are the same. In some embodiments, the first and second neuraminidase inhibitors are different.

Dimers of neuraminidase inhibitors include homo-dimers of zanamivir or analogs thereof (e.g., (A-I), (A-II), (A-VI), (A-VII), (A-VIII), (A-IX), (A-X), or (A-XIII). For example, neuraminidase inhibitor dimers of the invention include dimers having the structure $A_1$-L-$A_2$, wherein each $A_1$ and each $A_2$ is selected from (A-I), (A-II), (A-VI), (A-VII), (A-VIII), (A-IX), (A-X), and (A-XIII).

Dimers of neuraminidase inhibitors include homo-dimers of peramivir or analogs thereof (e.g., (A-III), (A-IV), or (A-V)). For example, neuraminidase inhibitor dimers of the invention include dimers having the structure $A_1$-L-$A_2$, wherein each $A_1$ and each $A_2$ is selected from (A-III), (A-IV), and (A-V).

Dimers of neuraminidase inhibitors include hetero-dimers including zanamivir or analogs thereof and peramivir of analogs thereof (e.g., (A-I)-(A-XIII)). For example, neuraminidase inhibitor dimers of the invention include dimers having the structure $A_1$-L-$A_2$, wherein each $A_1$ is selected from (A-I), (A-II), (A-VI), (A-VII), (A-VIII), (A-IX), (A-X), and (A-XIII), and each $A_2$ is selected from (A-III), (A-IV), and (A-V).

In some embodiments, when T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein). In some embodiments, E may be conjugated to 2, 3, 4, 5, 6, 7, 8, 9, 10, or more different $A_1$-L-$A_2$ moieties. In some embodiments, E is conjugated to a first $A_1$-L-$A_2$ moiety, and a second $A_1$-L-$A_2$, moiety. In some embodiments, $A_1$ and $A_2$ of the first $A_1$-L-$A_2$ moiety are independently selected from any one of formulas (A-III)-(A-V):

(A-III)

(A-IV)

-continued
(A-V)
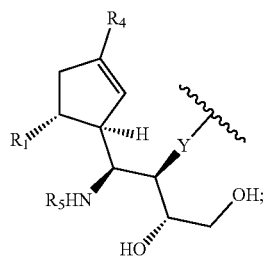
and A₁ and A₂ of the second A₁-L-A₂ moiety are independently selected from any one of formulas (A-I), (A-II), (A-VI), (A-VII), (A-VIII), (A-IX), (A-X), or (A-XIII):
(A-I)
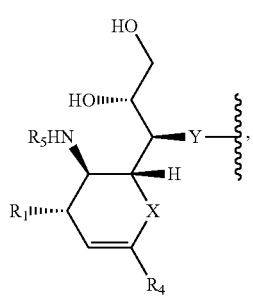
(A-II)
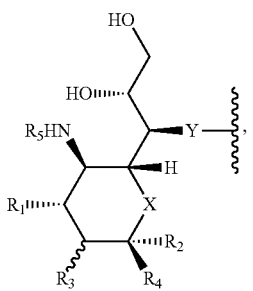
(A-VI)
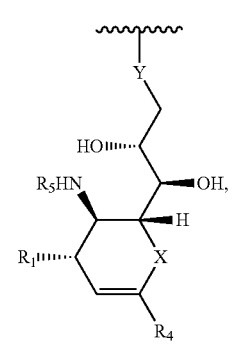
(A-VII)
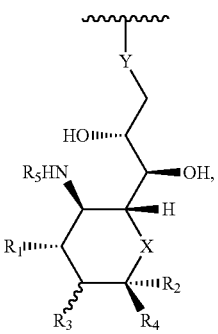
(A-VIII)
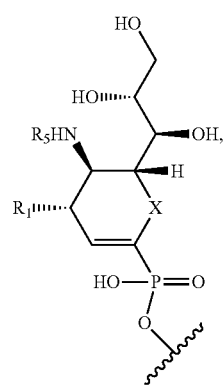
(A-IX)
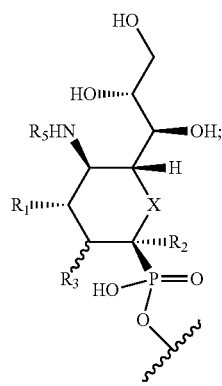
(A-X)
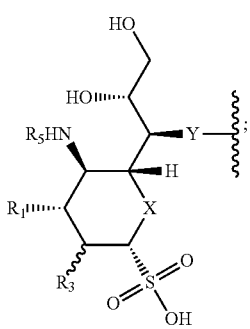

-continued (A-XIII)
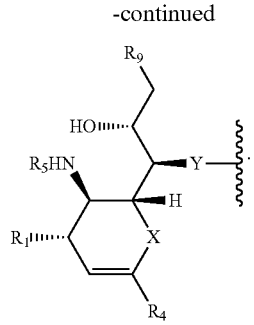

In some embodiments, the first $A_1$-L-$A_2$ moiety is conjugated specifically to lysine residues of E (e.g., the nitrogen atoms of surface exposed lysine residues of E), and the second $A_1$-L-$A_2$ moiety is conjugated specifically to cysteine residues of E (e.g., the sulfur atoms of surface exposed cysteine residues of E). In some embodiments, the first $A_1$-L-$A_2$ moiety is conjugated specifically to cysteine residues of E (e.g., the sulfur atoms of surface exposed cysteine residues of E), and the second $A_1$-L-$A_2$ moiety is conjugated specifically to lysine residues of E (e.g., the nitrogen atoms of surface exposed lysine residues of E).

In some embodiments, the disclosure provides a conjugate, or a pharmaceutically acceptable salt thereof, described by the formulae below:

(1)
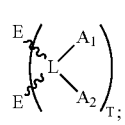

(D-I)
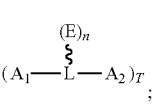

(D-II)
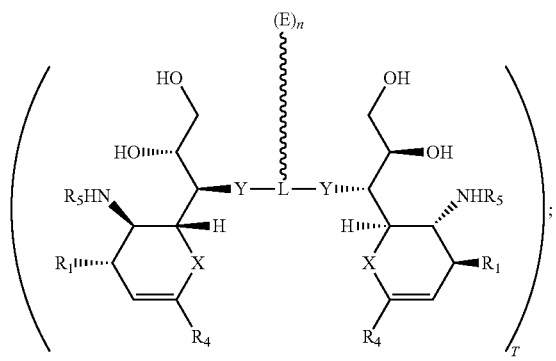

(DII-1)
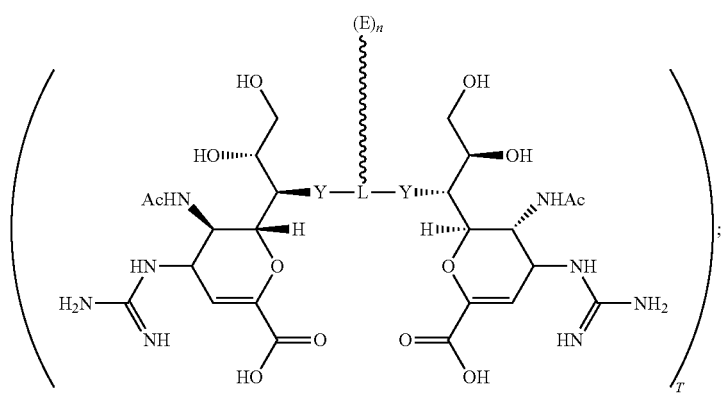

(D-II-2)
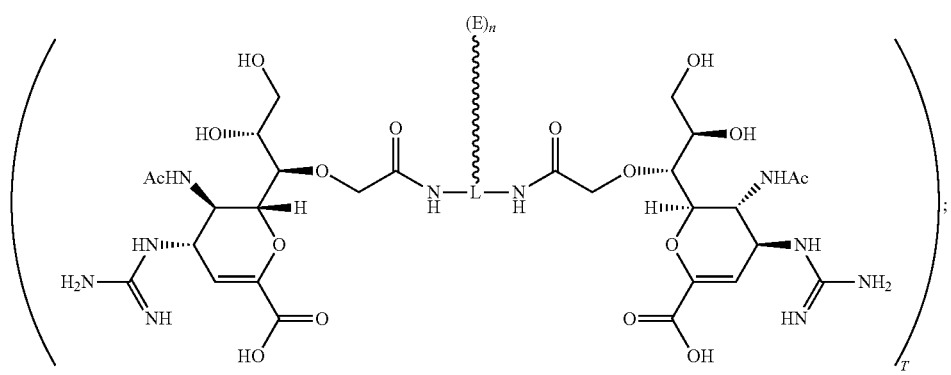

-continued

(D-II-3)

(D-II-4)
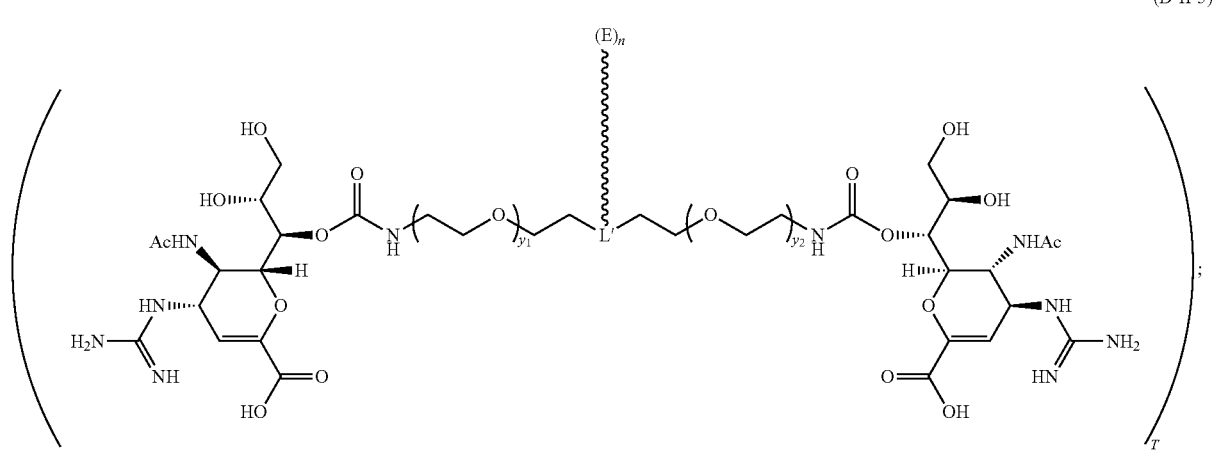
(D-II-5)
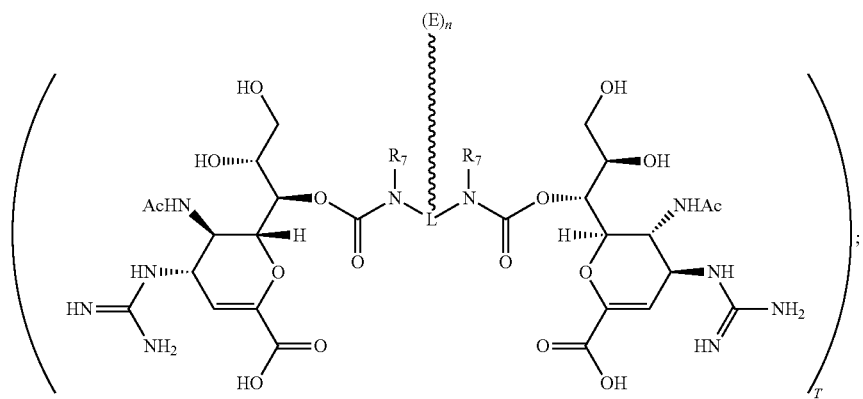
(D-II-6)

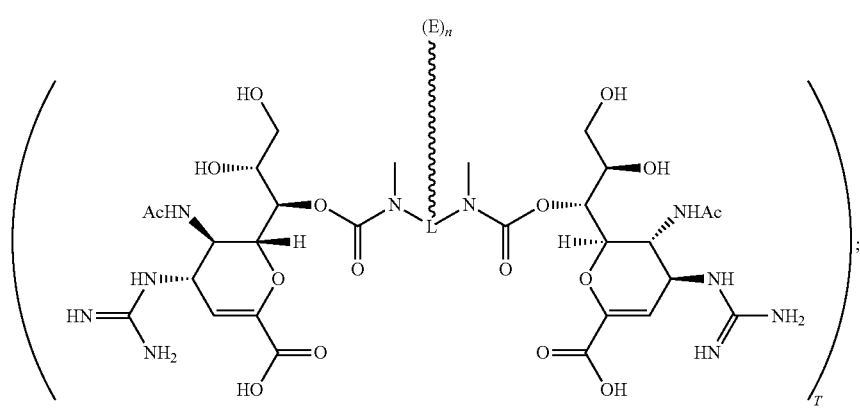
(D-II-7)
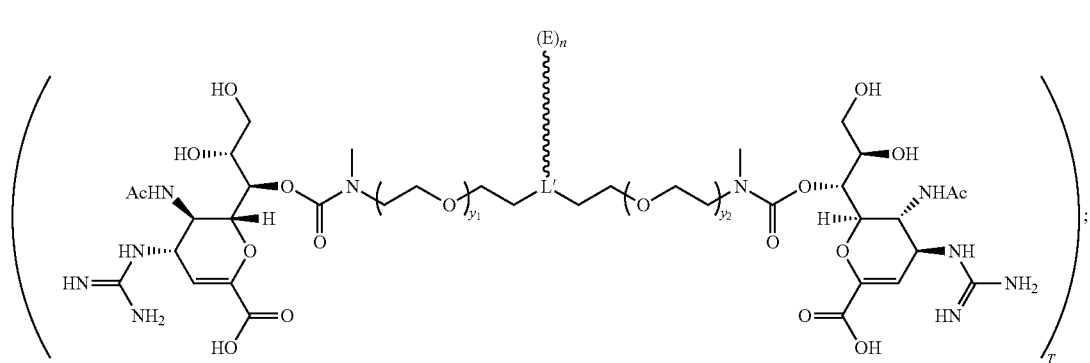
(D-II-8)
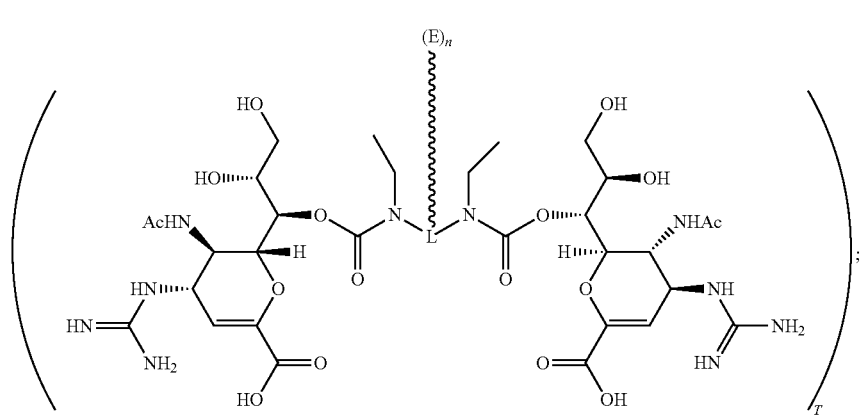
(D-II-9)
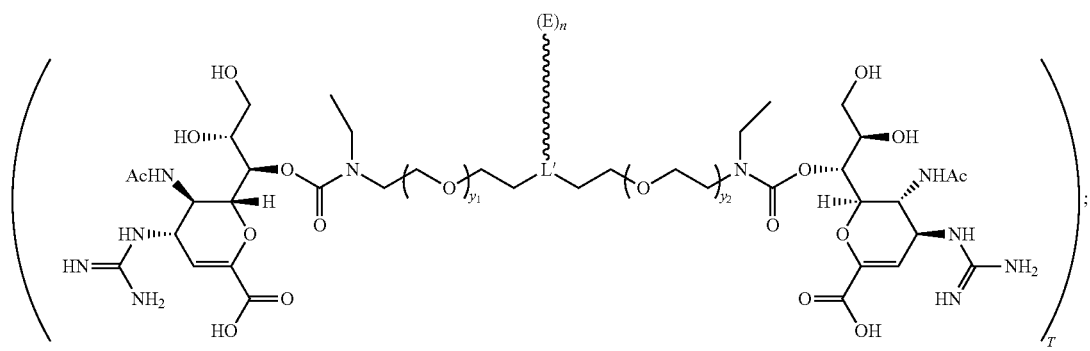
(D-II-10)

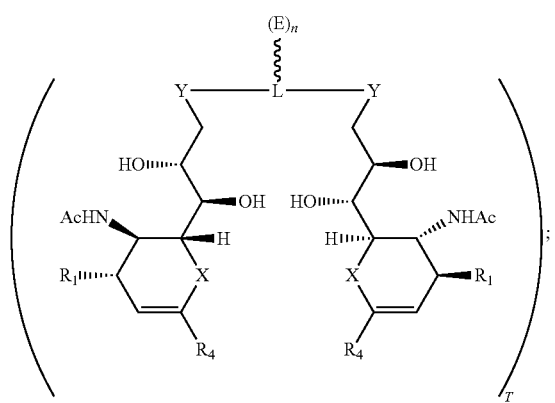
(D-III)
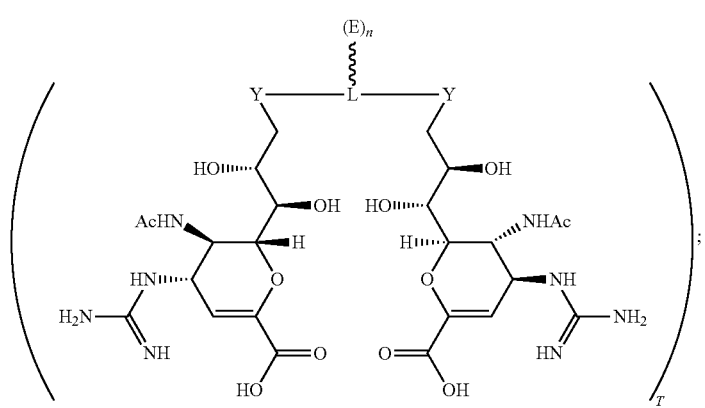
(D-III-1)
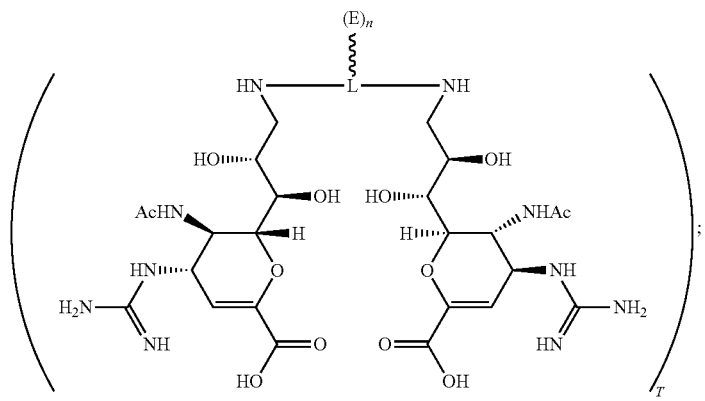
(D-III-2)
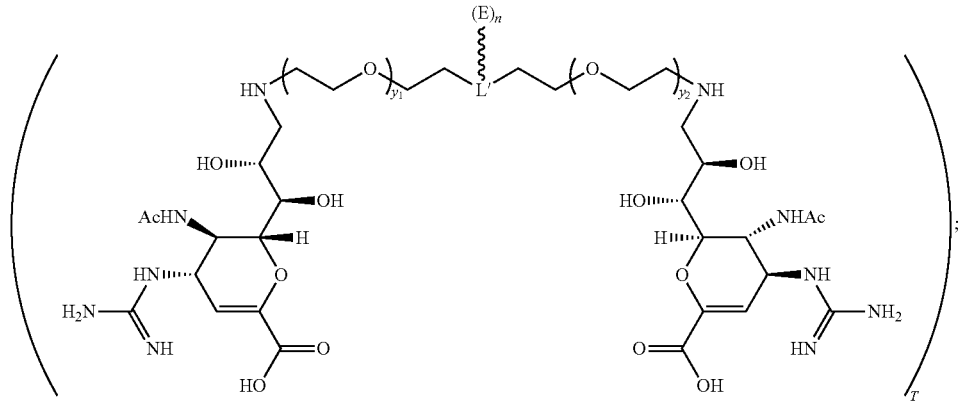
(D-III-3)

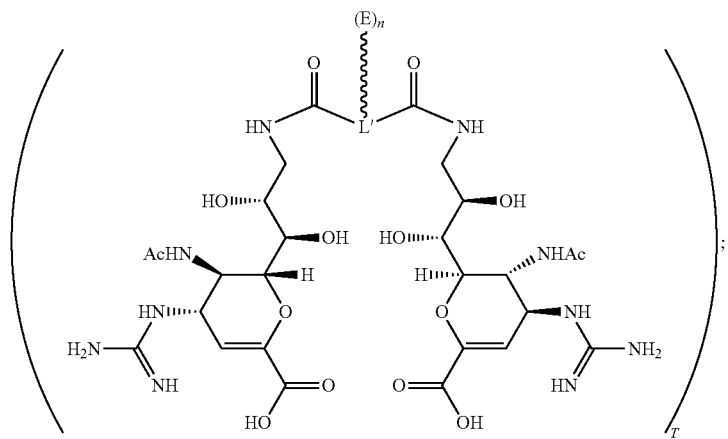
(D-III-4)
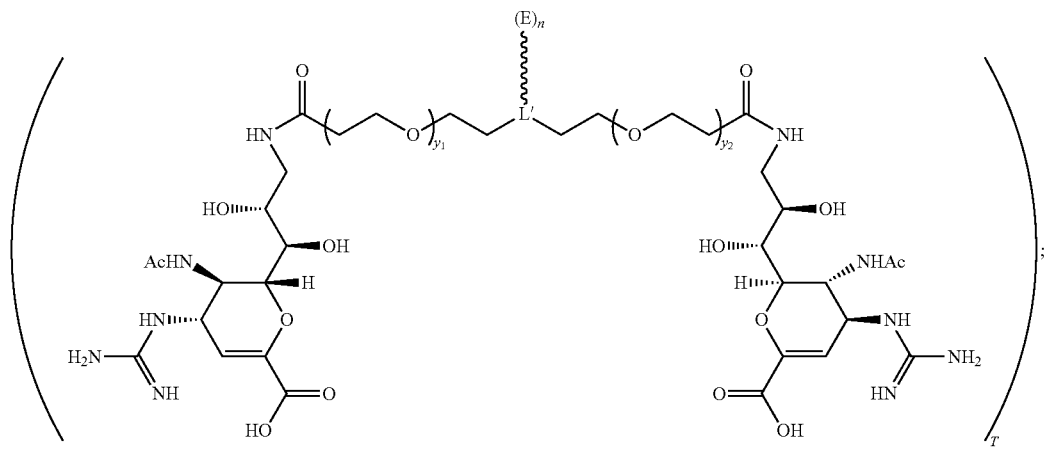
(D-III-5)
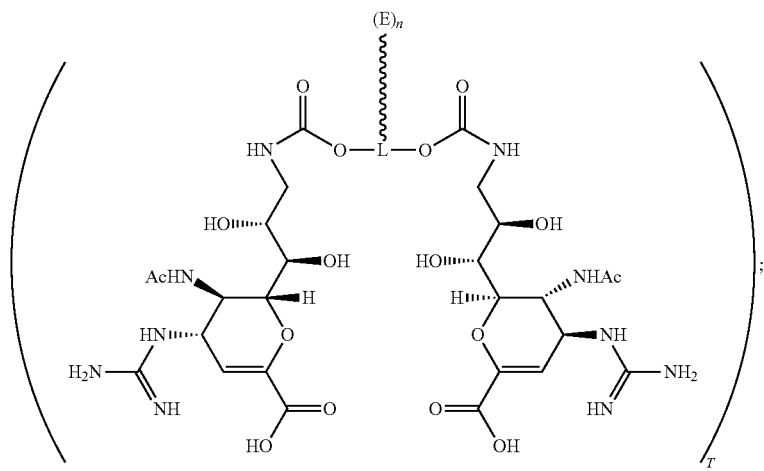
(D-III-6)

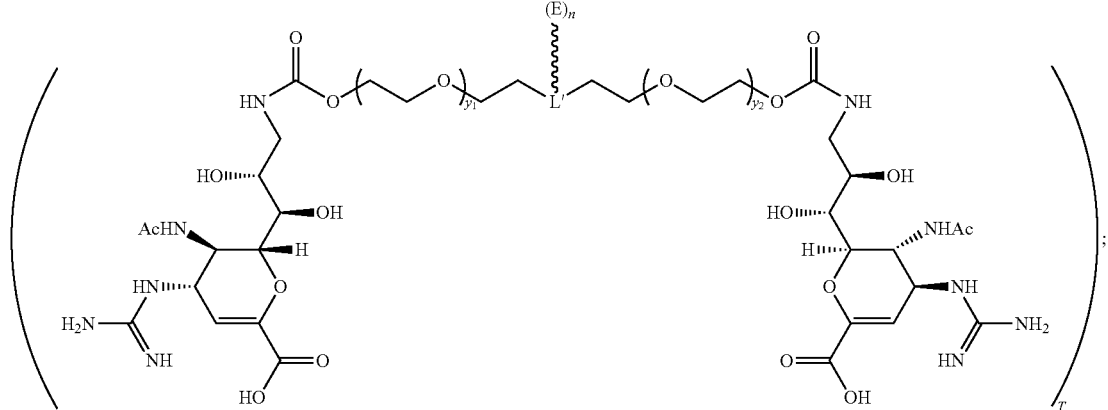
(D-III-7)
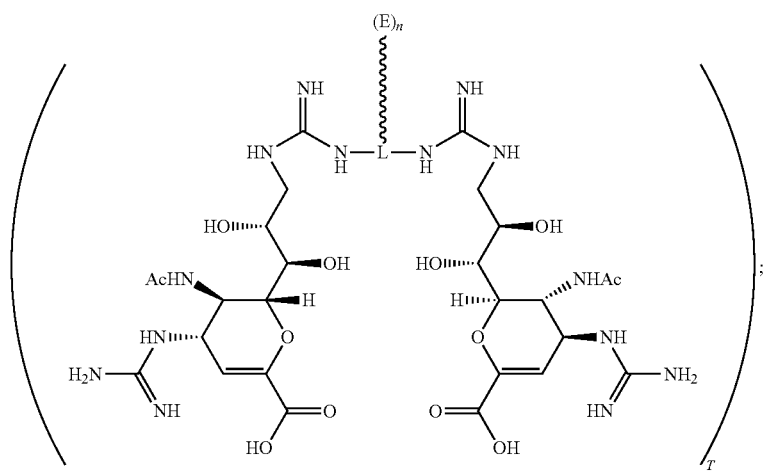
(D-III-8)
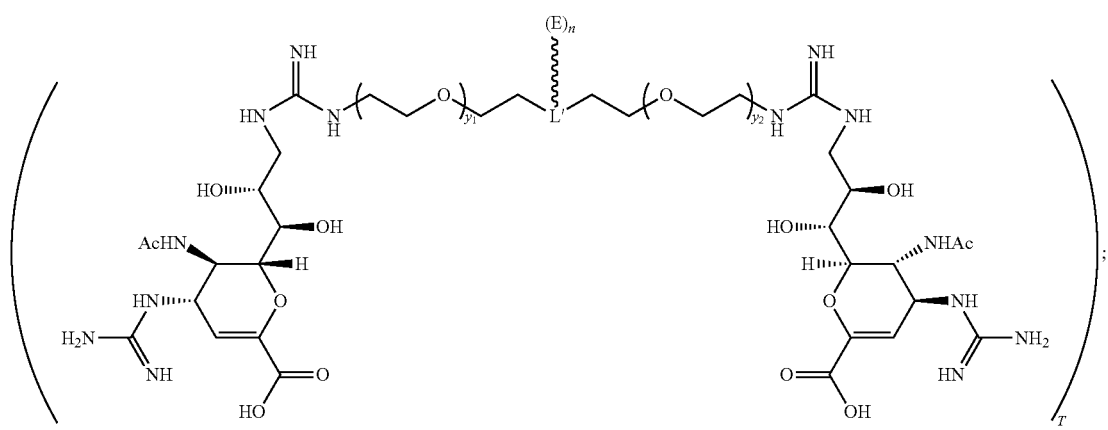
(D-III-9)

-continued
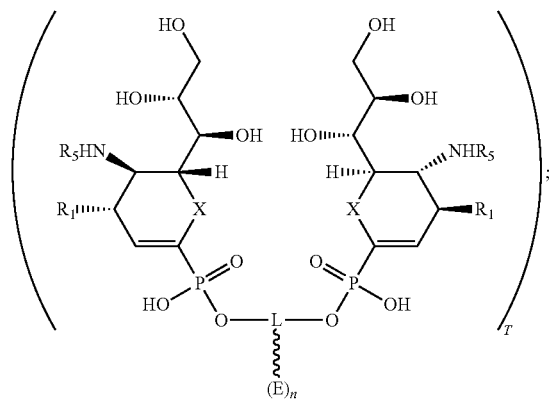
(D-IV)
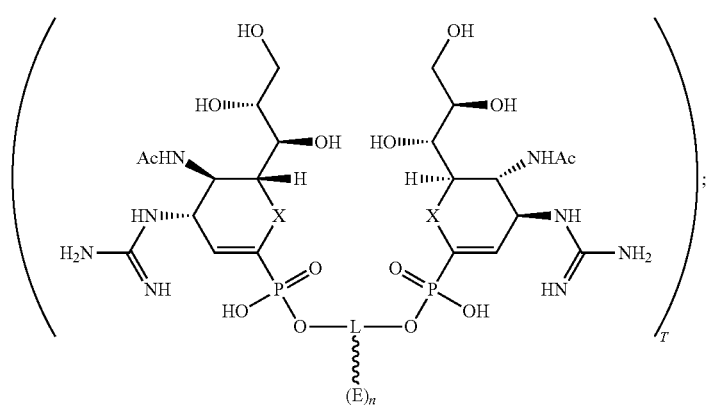
(D-IV-1)
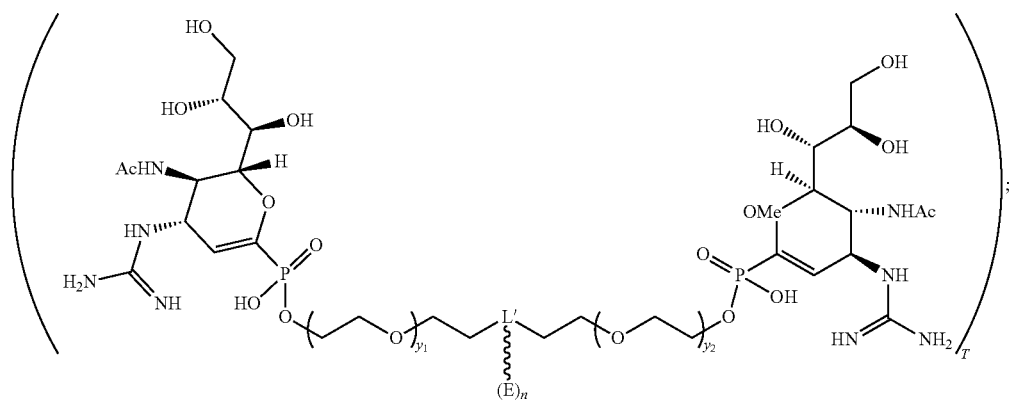
(D-IV-2)
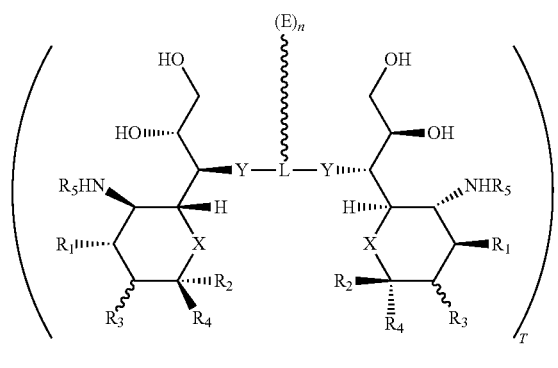
(D-V)
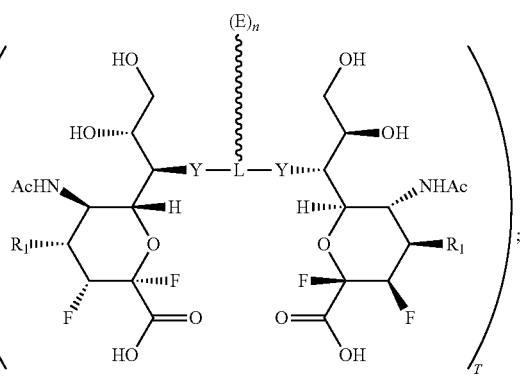
(D-V-1)

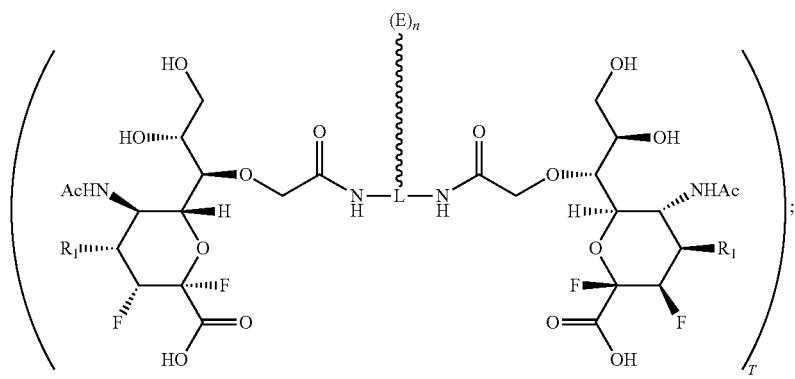
(D-V-2);
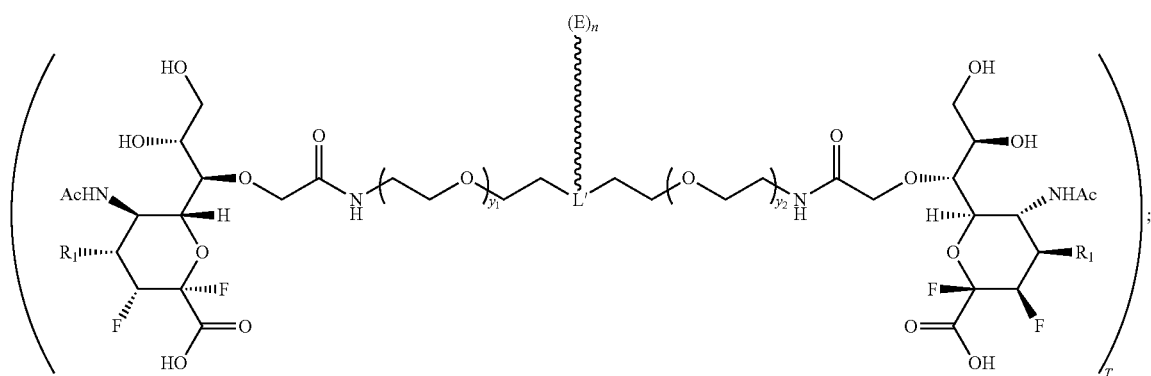
(D-V-3);
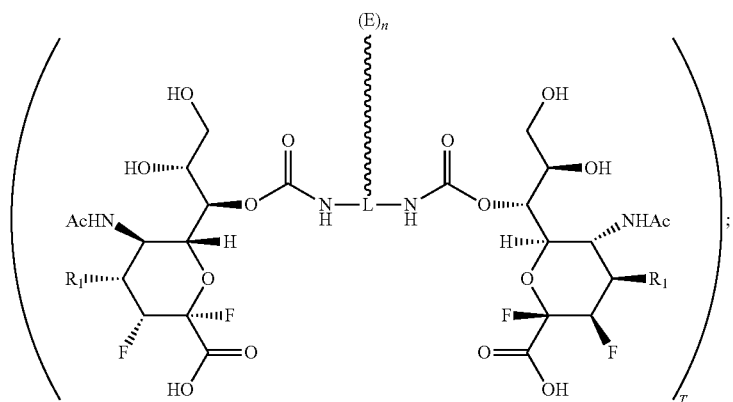
(D-V-4);
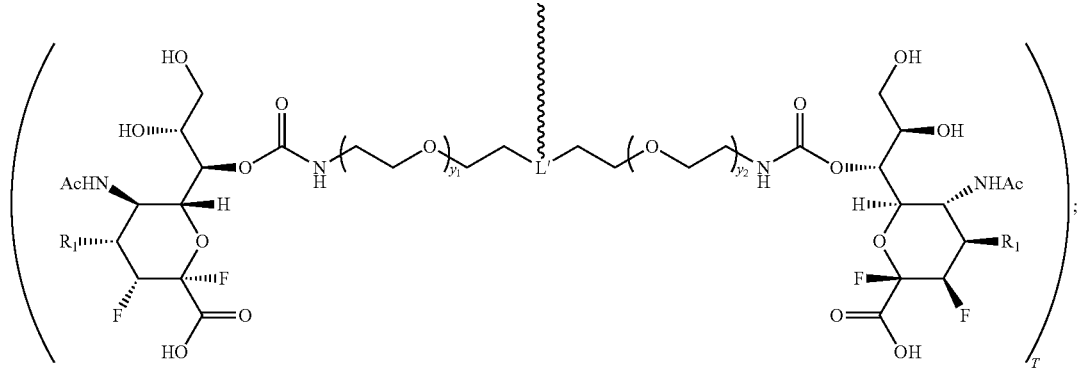
(D-V-5);

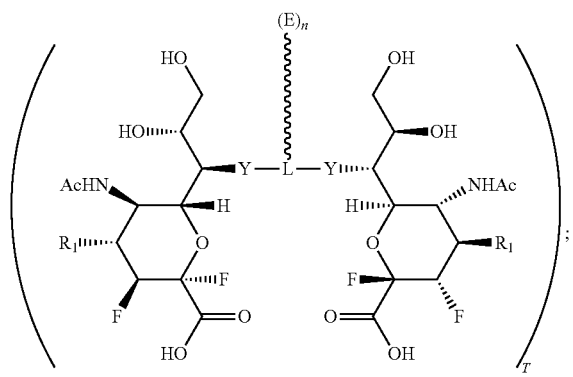
(D-V-6)
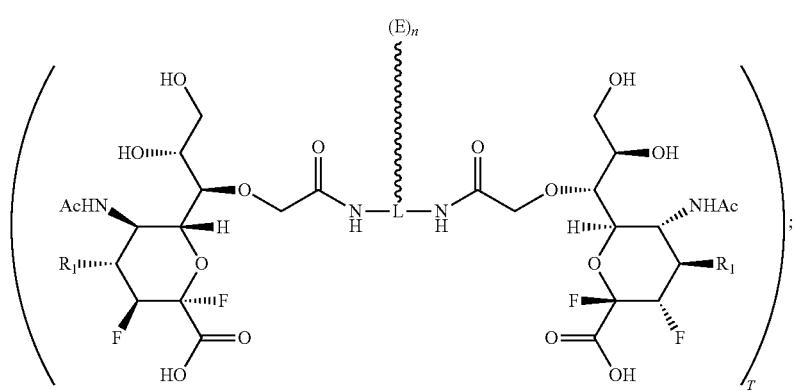
(D-V-7)
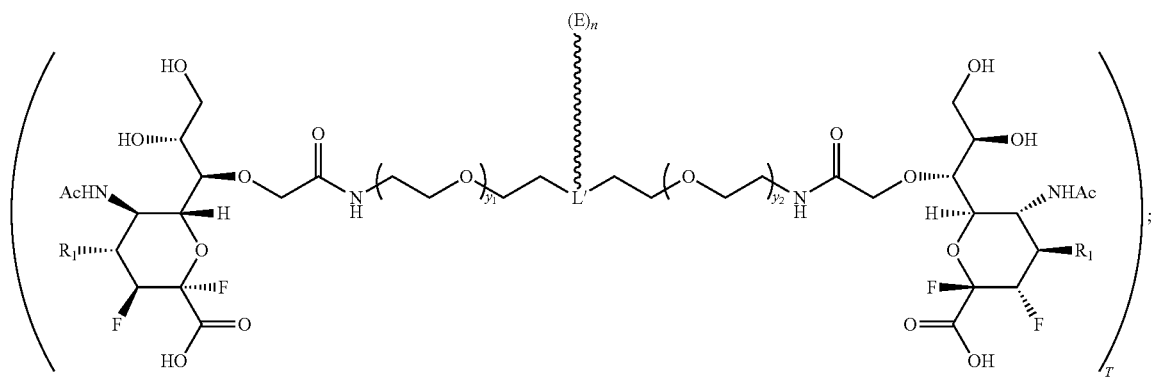
(D-V-8)
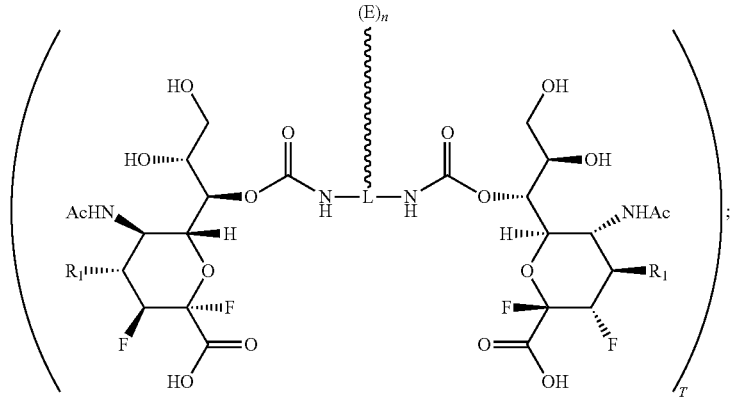
(D-V-9)

-continued
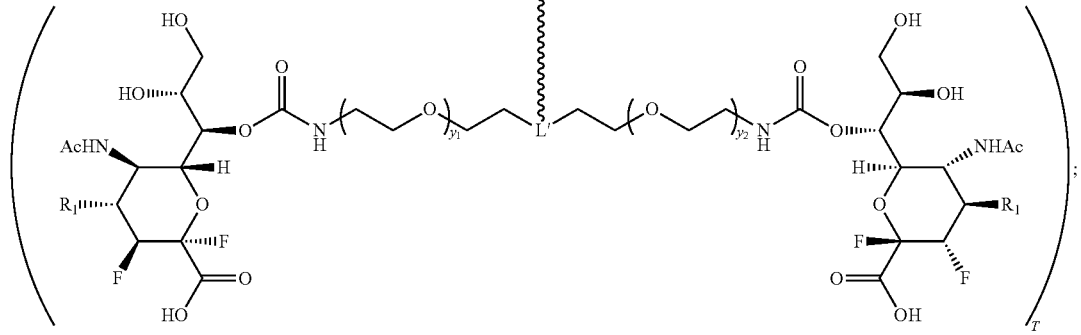
(D-V-10)
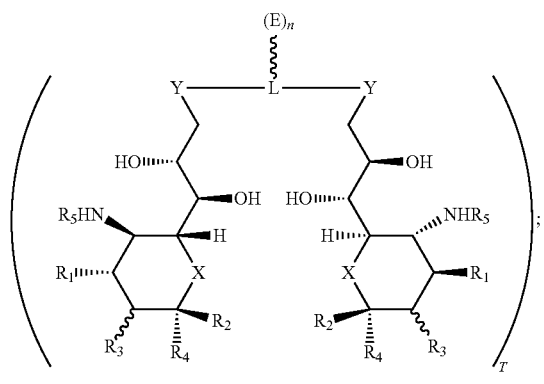
(D-VI)
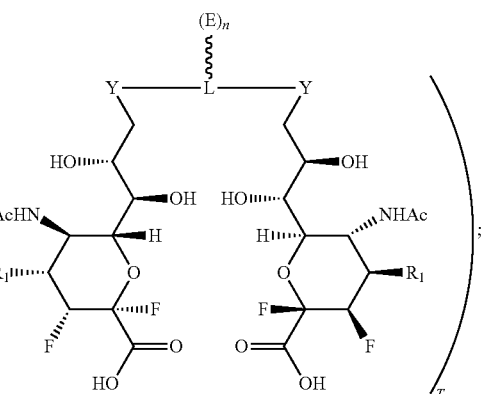
(D-VI-1)
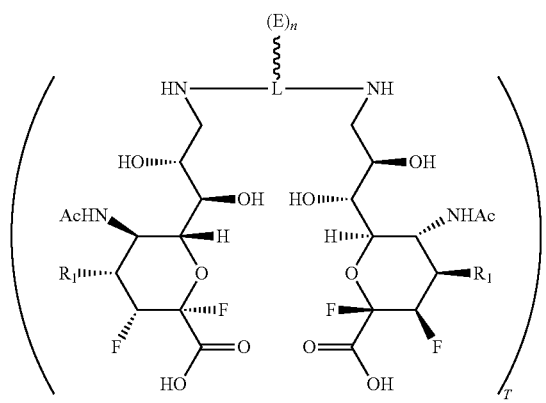
(D-VI-2)
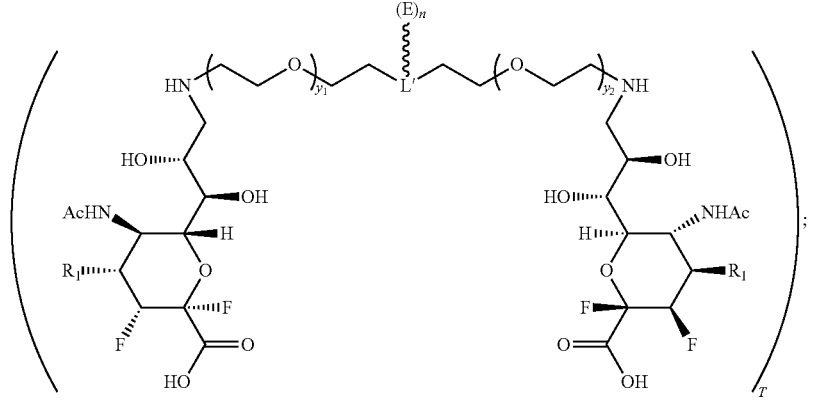
(D-VI-3)

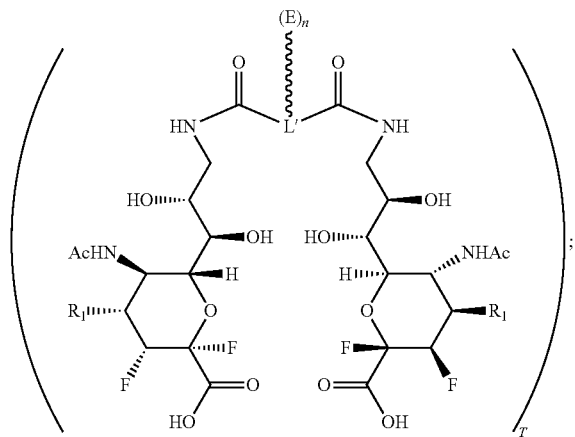
(D-VI-4)
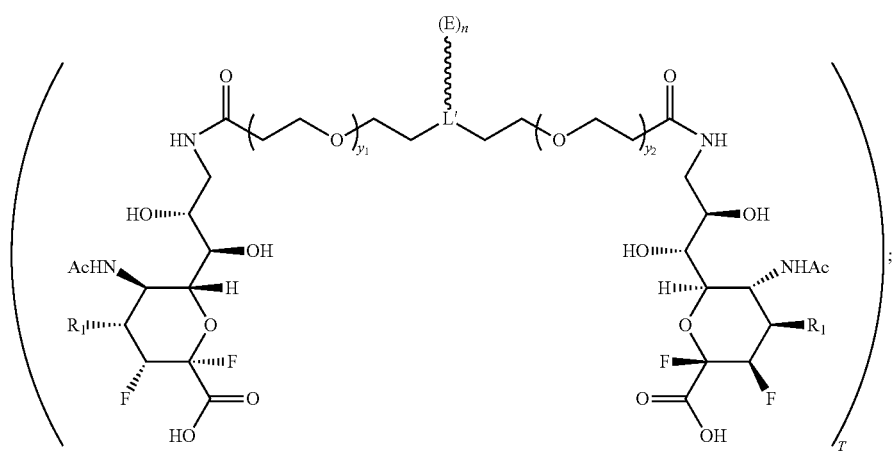
(D-VI-5)
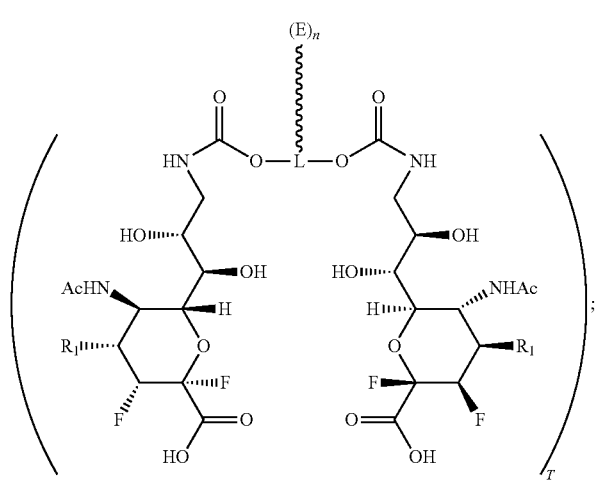
(D-VI-6)

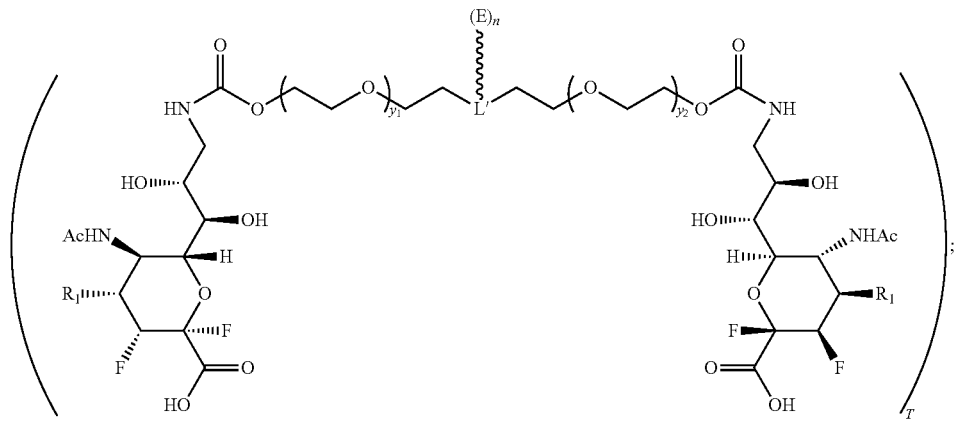
(D-VI-7)
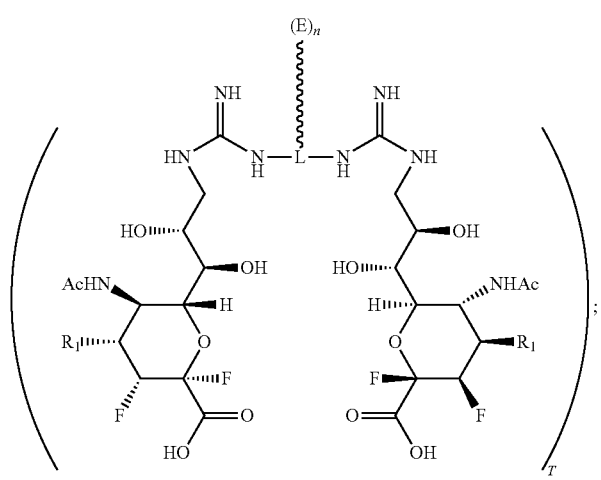
(D-VI-8)
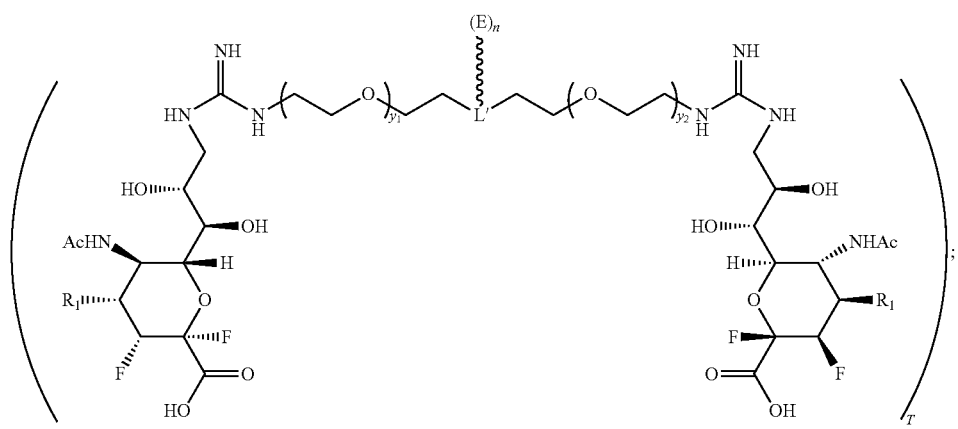
(D-VI-9)

(D-VII)
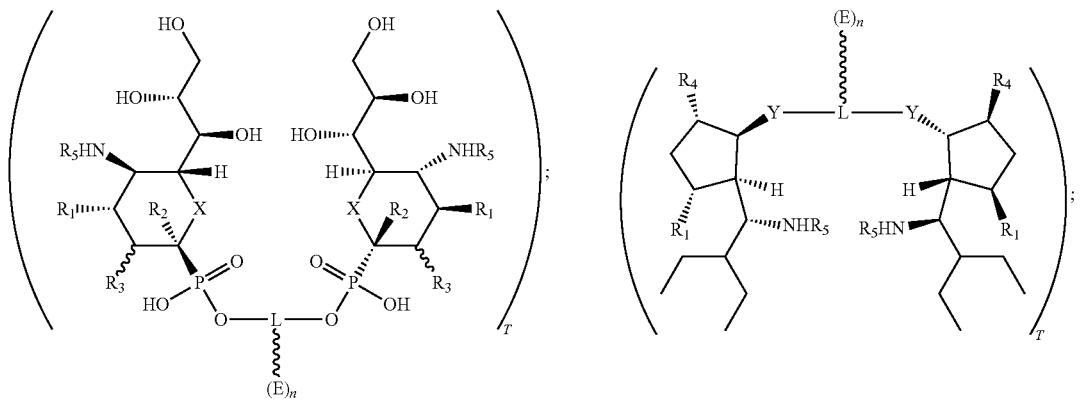
(D-VIII)
(D-VIII-1)
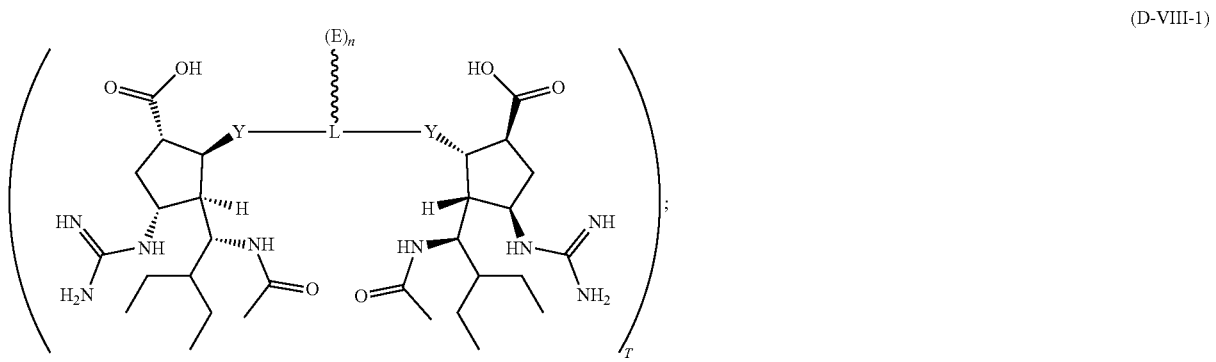
(D-VIII-2)
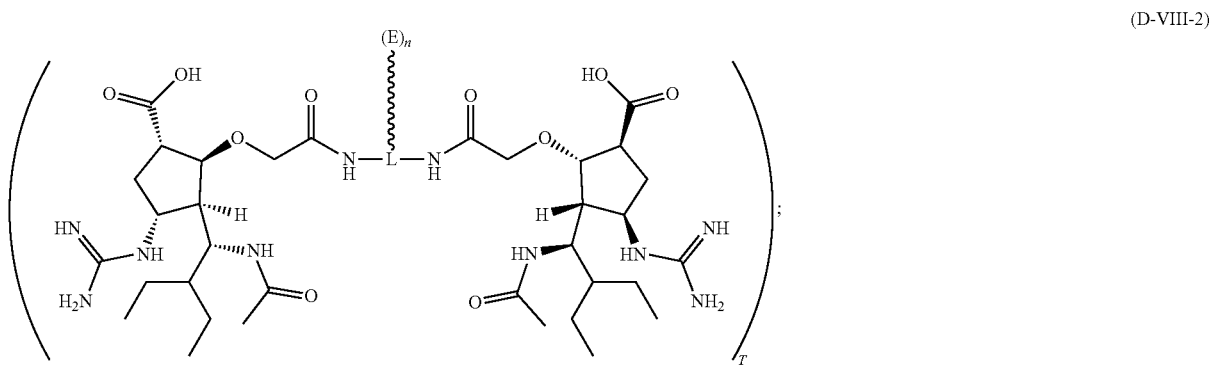
(D-VIII-3)
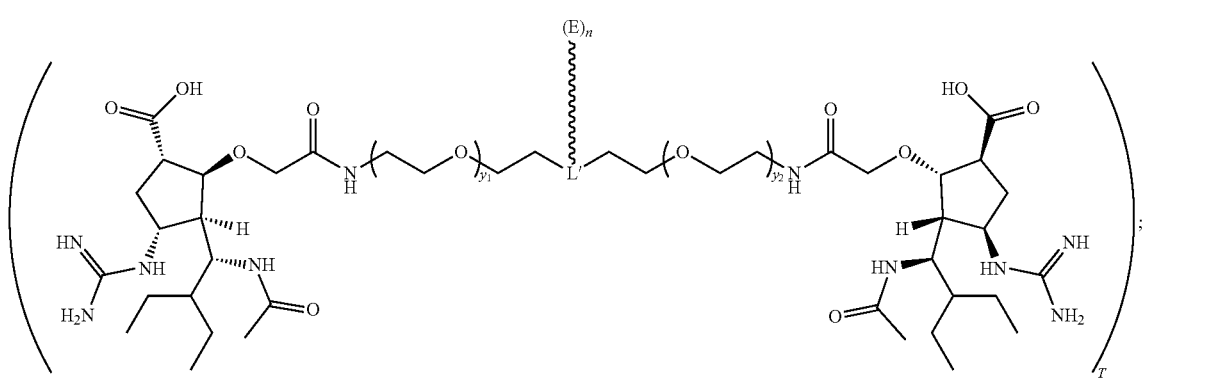

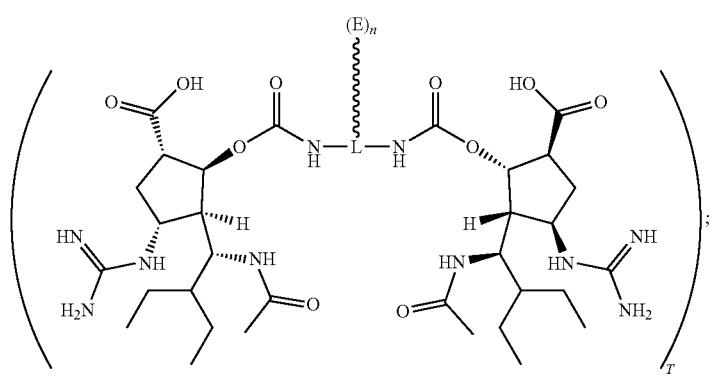
(D-VIII-4)
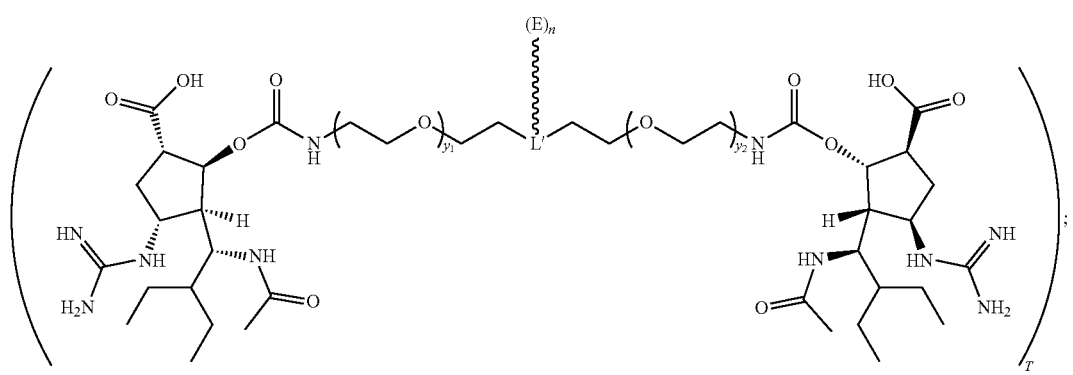
(D-VIII-5)
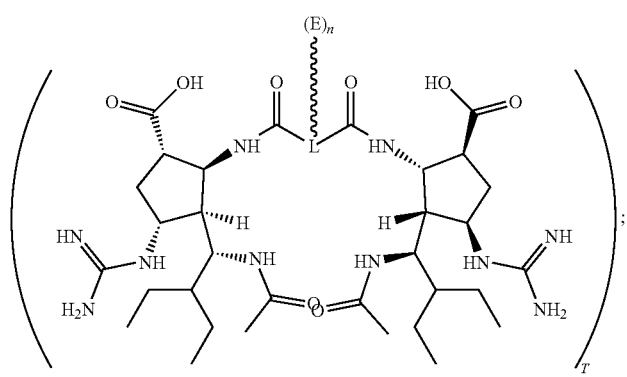
(D-VIII-6)
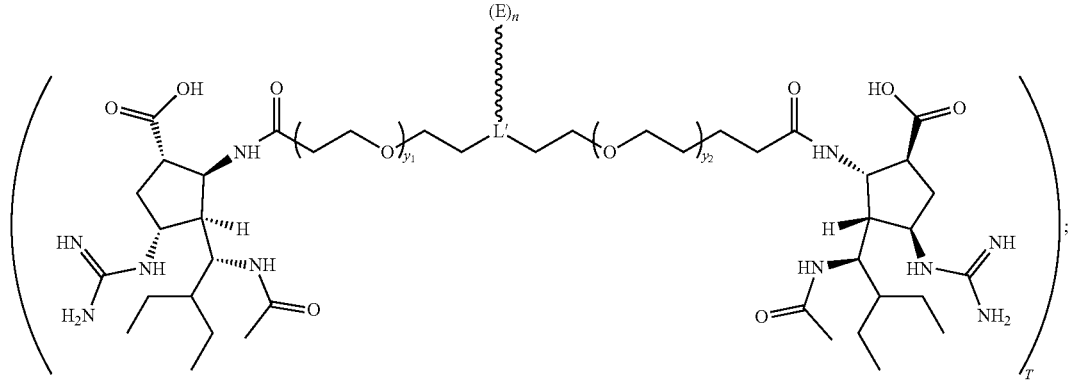
(D-VIII-7)

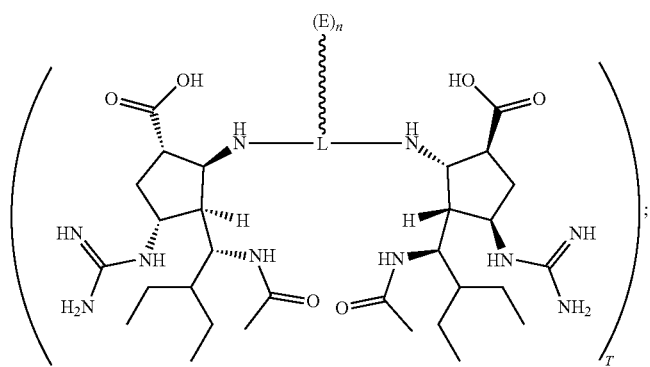
(D-VIII-8)
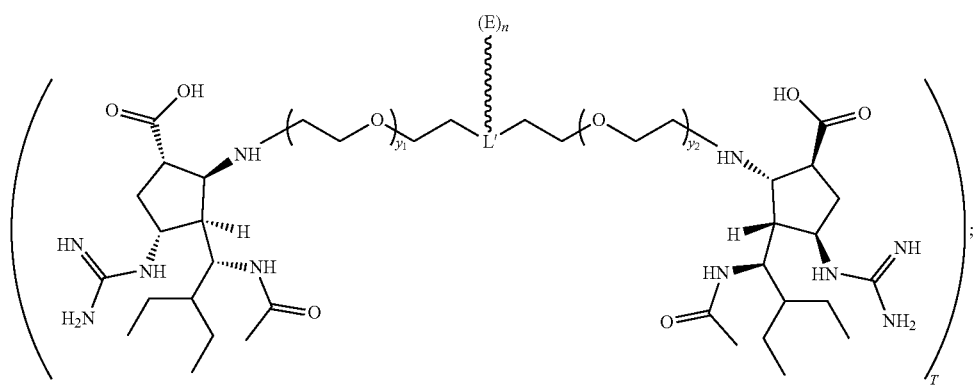
(D-VIII-9)
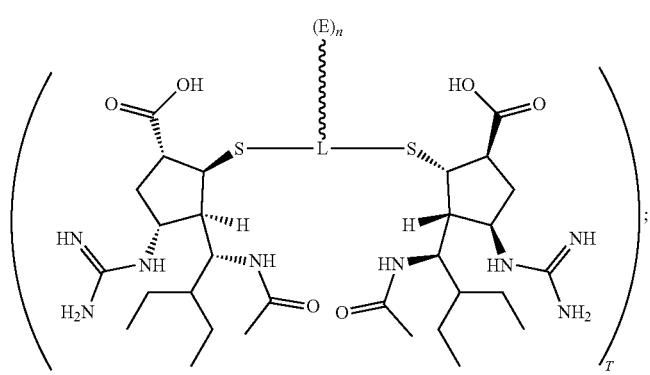
(D-VIII-10)
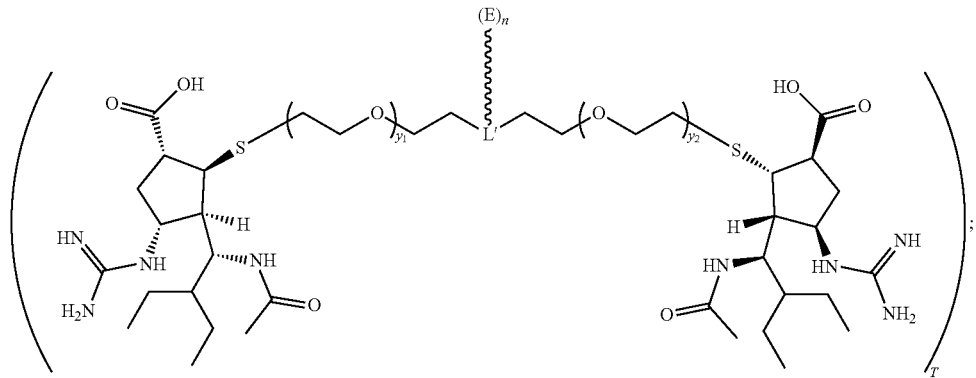
(D-VIII-11)

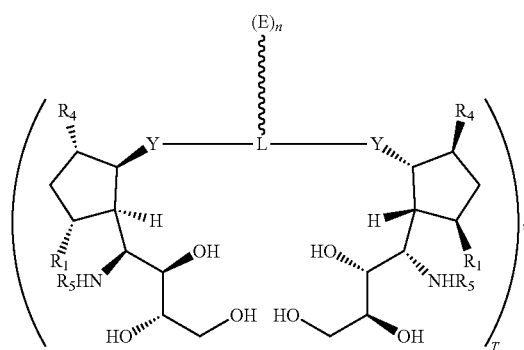
(D-IX)
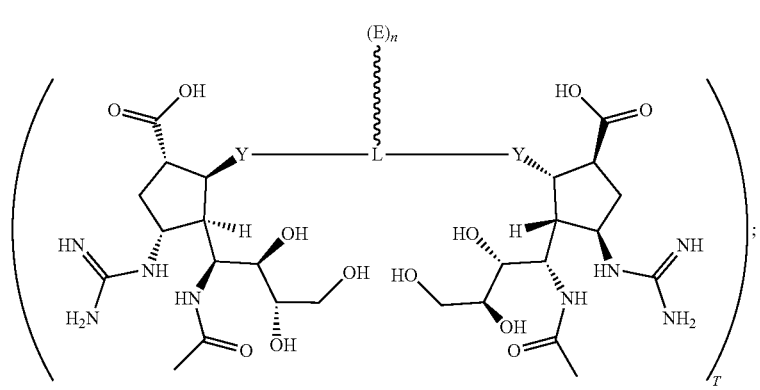
(D-IX-1)
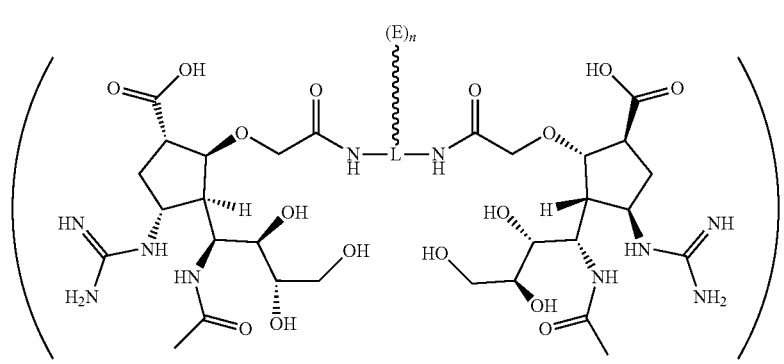
(D-IX-2)
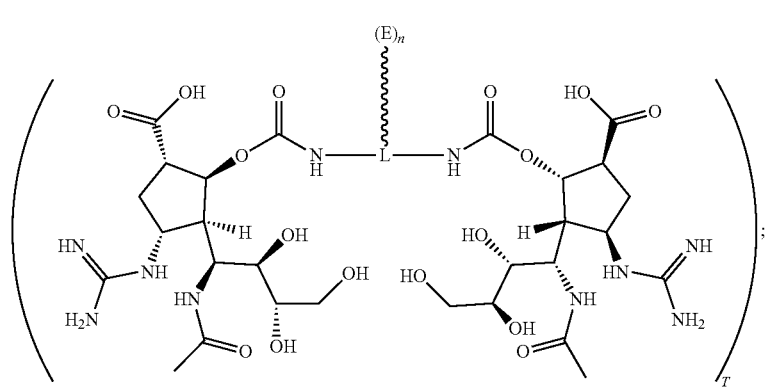
(D-IX-3)

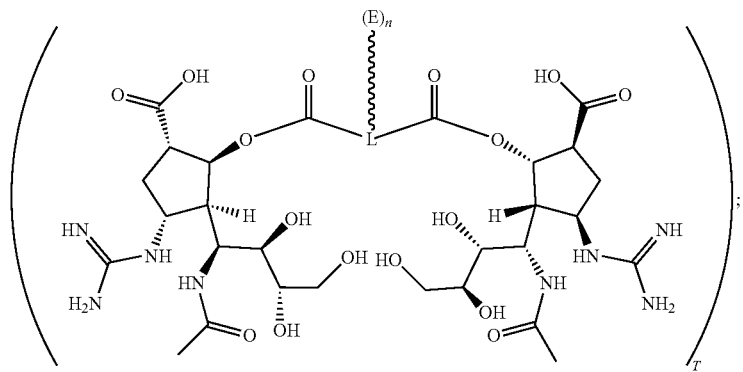
(D-IX-4)
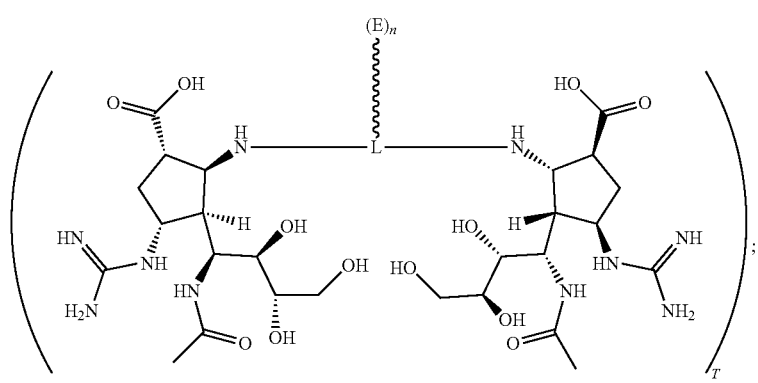
(D-IX-5)
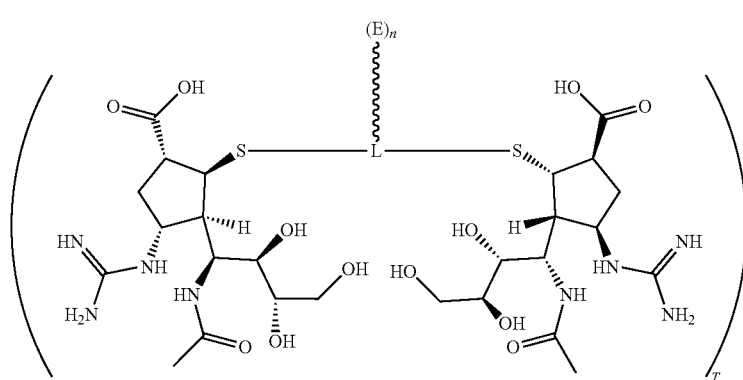
(D-IX-6)
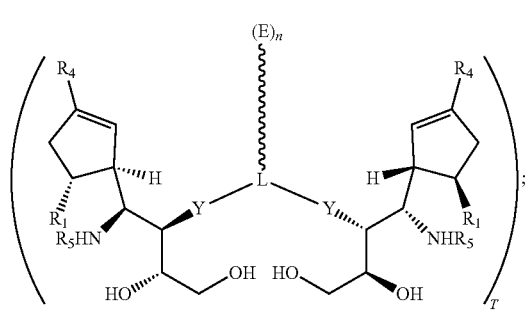
(D-X)

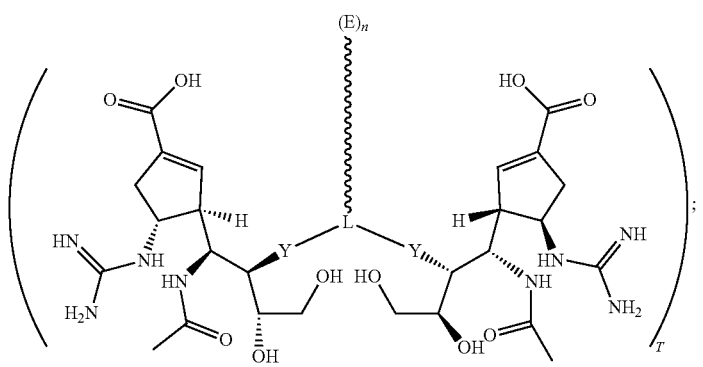
(D-X-1)
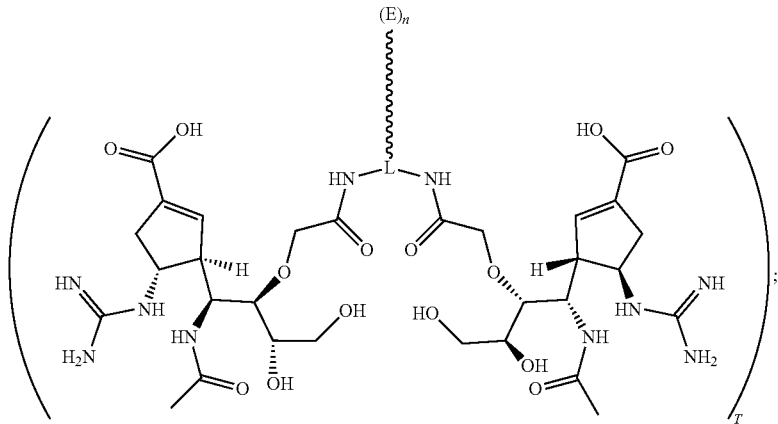
(D-X-2)
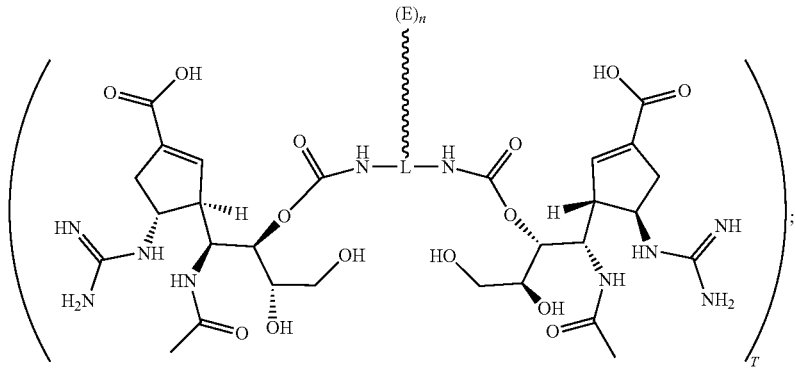
(D-X-3)
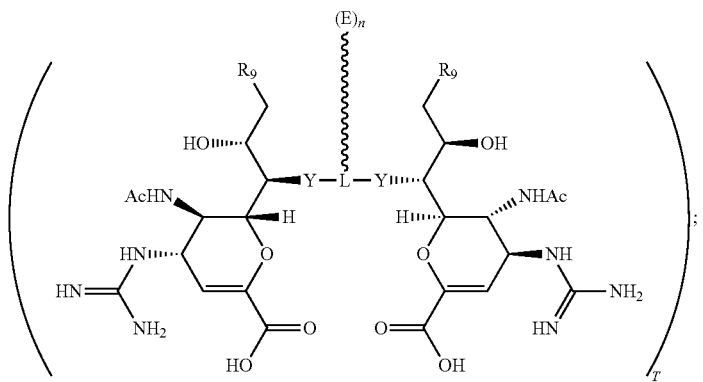
(D-XI)

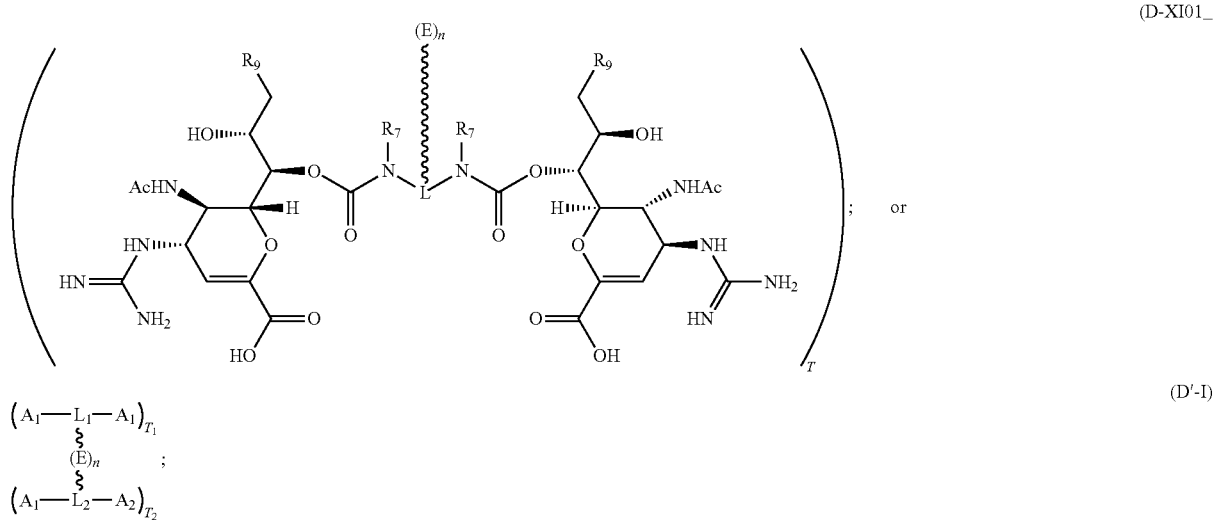

(D-XI01_

(D'-I)

or a pharmaceutically acceptable salt thereof.

In the conjugates described herein, the squiggly line connected to E indicates that one or more (e.g., 1, 2, 3, 4, 5, 6, 7, 8, 9, 10, 11, 12, 13, 14, 15, 16, 17, 18, 19, or 20) dimers of neuraminidase inhibitors may be attached to an Fc domain monomer, Fc domain, Fc-binding peptide, albumin protein, or albumin protein-binding peptide. In some embodiments, when n is 1, one or more (e.g., 1, 2, 3, 4, 5, 6, 7, 8, 9, or 10) dimers of neuraminidase inhibitors may be attached to an Fc domain monomer, Fc domain, Fc-binding peptide, albumin protein, or albumin protein-binding peptide. In some embodiments, when n is 2, one or more (e.g., 1, 2, 3, 4, 5, 6, 7, 8, 9, 10, 11, 12, 13, 14, 15, 16, 17, 18, 19, or 20) dimers of neuraminidase inhibitors may be attached to an Fc domain. The squiggly line in the conjugates described herein is not to be construed as a single bond between one or more dimers of neuraminidase inhibitors and an atom in the Fc domain or albumin protein. In some embodiments, when T is 1, one dimer of neuraminidase inhibitors may be attached to an atom in the Fc domain monomer, Fc domain, Fc-binding peptide, albumin protein, or albumin protein-binding peptide. In some embodiments, when T is 2, two dimers of neuraminidase inhibitors may be attached to an atom in the Fc domain monomer, Fc domain, Fc-binding peptide, albumin protein, or albumin protein-binding peptide.

As described further herein, a linker in a conjugate described herein (e.g., L or L') may be a branched structure. As described further herein, a linker in a conjugate described herein (e.g., L or L') may be a multivalent structure, e.g., a divalent or trivalent structure having two or three arms, respectively. In some embodiments when the linker has three arms, two of the arms may be attached to the first and second neuraminidase inhibitors and the third arm may be attached to the Fc domain monomer, Fc domain, Fc-binding peptide, albumin protein, or albumin protein-binding peptide.

In conjugates having an Fc domain covalently linked to one or more dimers of neuraminidase inhibitors, as represented by the formulae above, when n is 2, two Fc domain monomers (each Fc domain monomer is represented by E) dimerize to form an Fc domain.

Conjugates of Monomers of Neuraminidase Inhibitors Linked to an Fc Domain or an Albumin Protein In some embodiments, the conjugates described herein include an Fc domain monomer, Fc domain, Fc-binding peptide, albumin protein, or albumin protein-binding peptide covalently linked to one or more monomers of neuraminidase inhibitors. Conjugates of an Fc domain monomer or albumin protein and one or more monomers of neuraminidase inhibitors may be formed by linking the Fc domain or albumin protein to each of the monomers of neuraminidase inhibitors through a linker, such as any of the linkers described herein.

In the conjugates having an Fc domain or albumin protein covalently linked to one or more monomers of neuraminidase inhibitors described herein, the squiggly line connected to E indicates that one or more (e.g., 1, 2, 3, 4, 5, 6, 7, 8, 9, 10, 11, 12, 13, 14, 15, 16, 17, 18, 19, or 20) monomers of neuraminidase inhibitors may be attached to an Fc domain monomer, Fc domain, Fc-binding peptide, albumin protein, or albumin protein-binding peptide. In some embodiments, when n is 1, one or more (e.g., 1, 2, 3, 4, 5, 6, 7, 8, 9, or 10) monomers of neuraminidase inhibitors may be attached to an Fc domain monomer or an albumin protein. In some embodiments, when n is 2, one or more (e.g., 1, 2, 3, 4, 5, 6, 7, 8, 9, 10, 11, 12, 13, 14, 15, 16, 17, 18, 19, or 20) monomers of neuraminidase inhibitors may be attached to an Fc domain. The squiggly line in the conjugates described herein is not to be construed as a single bond between one or more monomers of neuraminidase inhibitors and an atom in the Fc domain monomer, Fc domain, Fc-binding peptide, albumin protein, or albumin protein-binding peptide. In some embodiments, when T is 1, one monomer of neuraminidase inhibitor may be attached to an atom in the Fc domain monomer, Fc domain, Fc-binding peptide, albumin protein, or albumin protein-binding peptide. In some embodiments, when T is 2, two monomers of neuraminidase inhibitors may be attached to an atom in the Fc domain monomer, Fc domain, Fc-binding peptide, albumin protein, or albumin protein-binding peptide.

In some embodiments, when T is greater than 1 (e.g., T is 2, 3, 4, 5, 6, 7, 8, 9, 10, 11, 12, 13, 14, 15, 16, 17, 18, 19, or 20), each $A_1$-L may be independently selected (e.g., independently selected from any of the $A_1$-L structures described herein). In some embodiments, E may be conjugated to 2, 3, 4, 5, 6, 7, 8, 9, 10, or more different $A_1$-L moieties. In some embodiments, E is conjugated to a first $A_1$-L moiety, and a second $A_1$-L, moiety. In some embodiments, $A_1$ of the first $A_1$-L moiety is selected from any one of formulas (A-III)-(A-V):
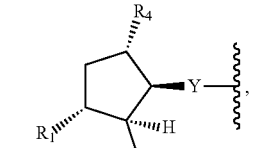
(A-III)
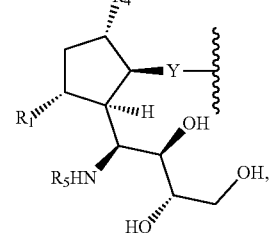
(A-IV)
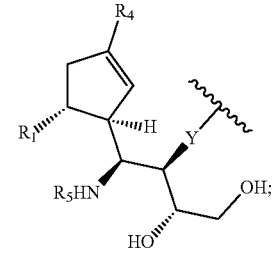
(A-V)
and $A_1$ of the second $A_1$-L moiety is selected from any one of formulas (A-I), (A-II), (A-VI), (A-VII), (A-VIII), (A-IX), (A-X), or (A-XIII):
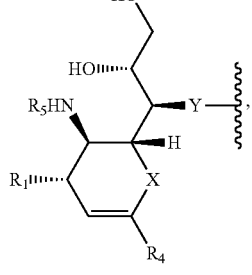
(A-I)
-continued
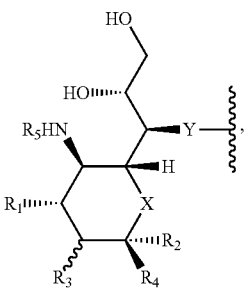
(A-II)
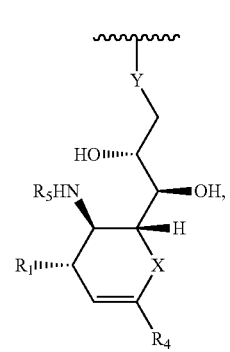
(A-VI)
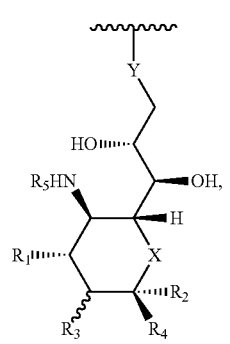
(A-VII)
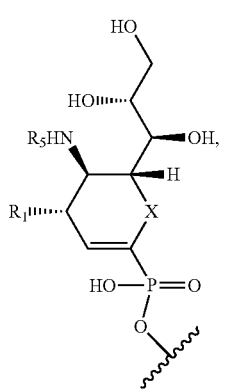
(A-VIII)

-continued

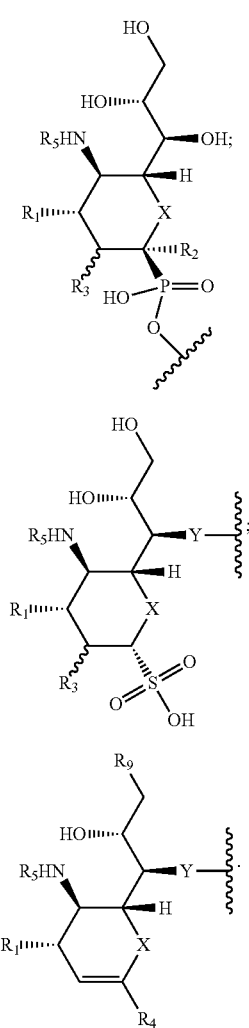

(A-IX)

(A-X)

(A-XIII)

In some embodiments, the first $A_1$-L moiety is conjugated specifically to lysine residues of E (e.g., the nitrogen atoms of surface exposed lysine residues of E), and the second $A_1$-L moiety is conjugated specifically to cysteine residues of E (e.g., the sulfur atoms of surface exposed cysteine residues of E). In some embodiments, the first $A_1$-L moiety is conjugated specifically to cysteine residues of E (e.g., the sulfur atoms of surface exposed cysteine residues of E), and the second $A_1$-L moiety is conjugated specifically to lysine residues of E (e.g., the nitrogen atoms of surface exposed lysine residues of E).

As described further herein, a linker in a conjugate having an Fc domain monomer, Fc domain, Fc-binding peptide, albumin protein, or albumin protein-binding peptide covalently linked to one or more monomers of neuraminidase in (M-II-3)
(M-II-4)
(M-II-5)
(M-II-6)
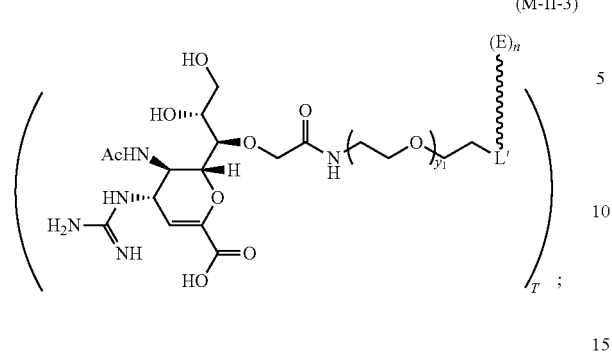
(M-II-7)
(M-II-8)
(M-II-9)
(M-II-10)
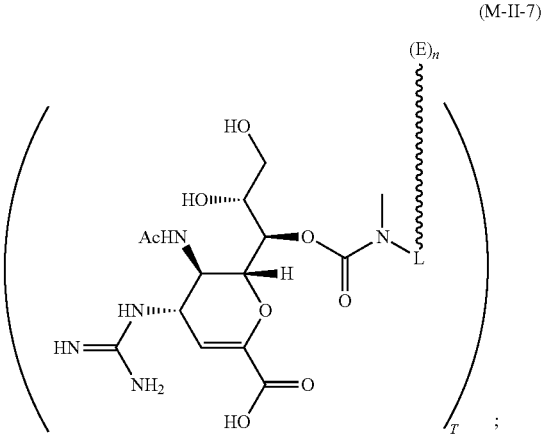
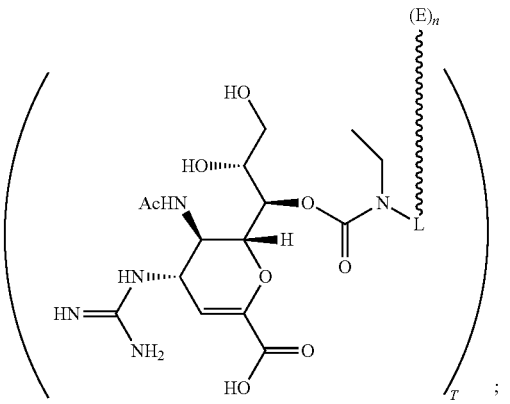
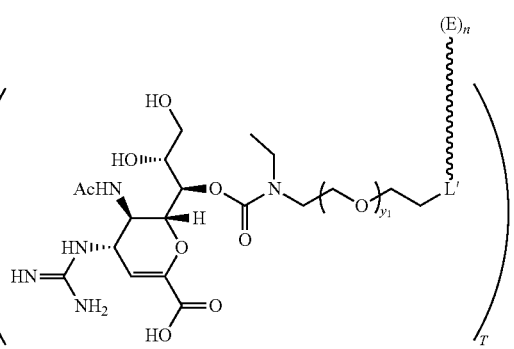

(M-III)
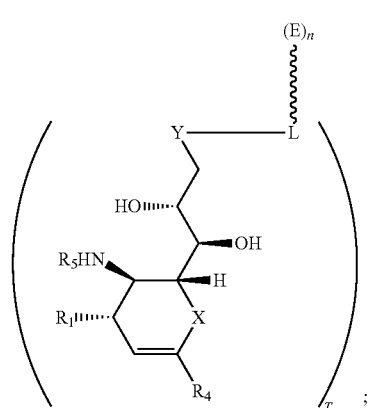
(M-III-3)
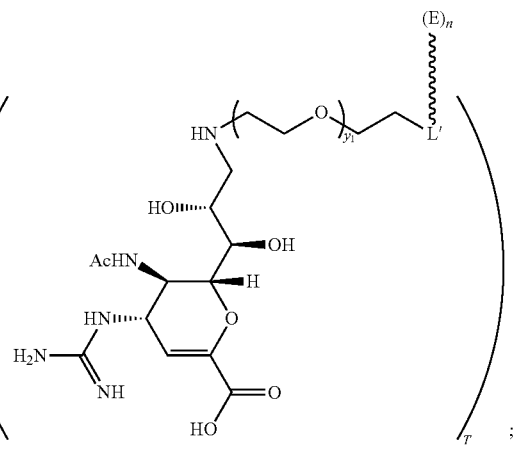
(M-III-1)
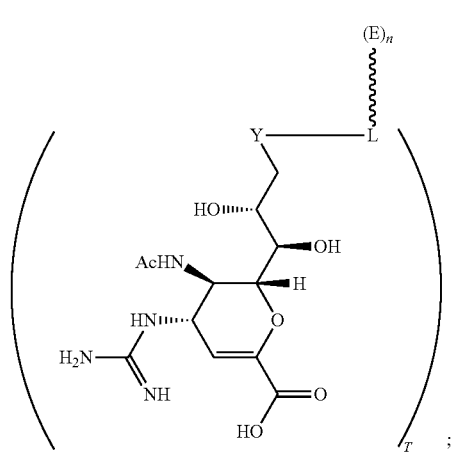
(M-III-4)
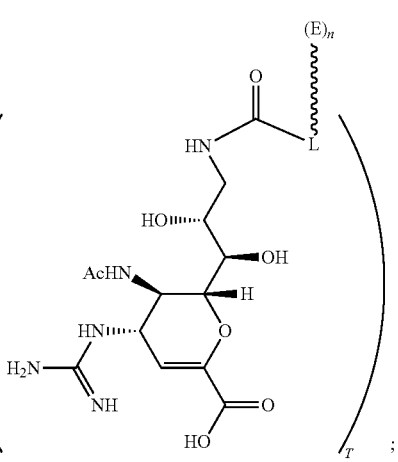
(M-III-2)
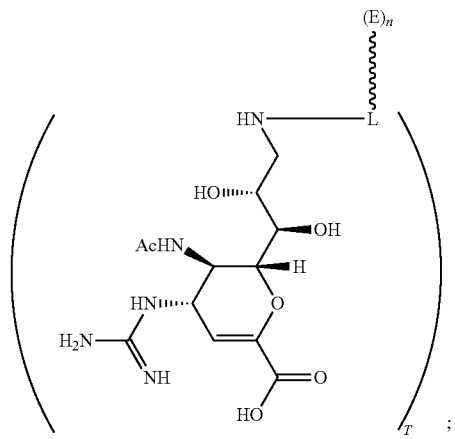
(M-III-5)
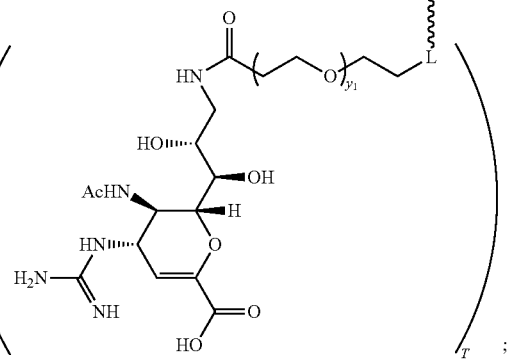

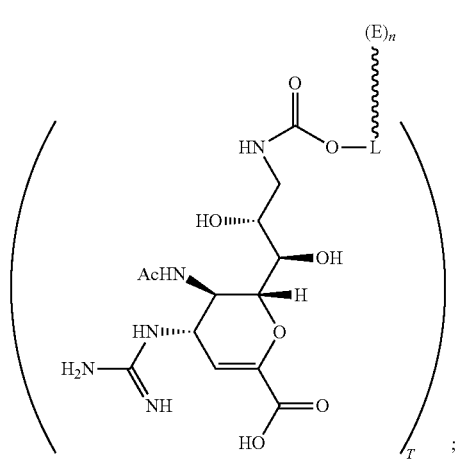
(M-III-6)
(M-III-7)
(M-III-8)
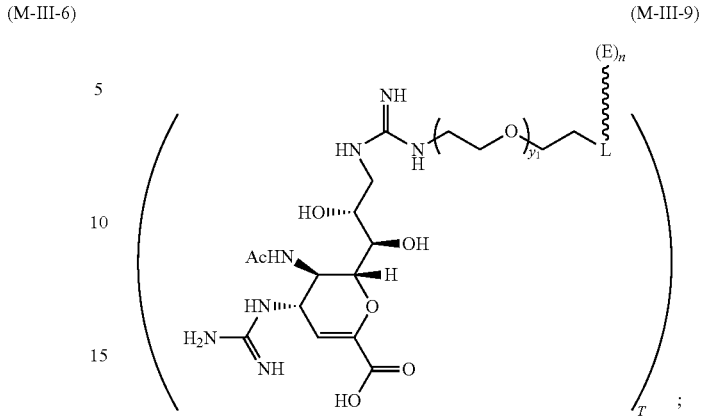
(M-III-9)
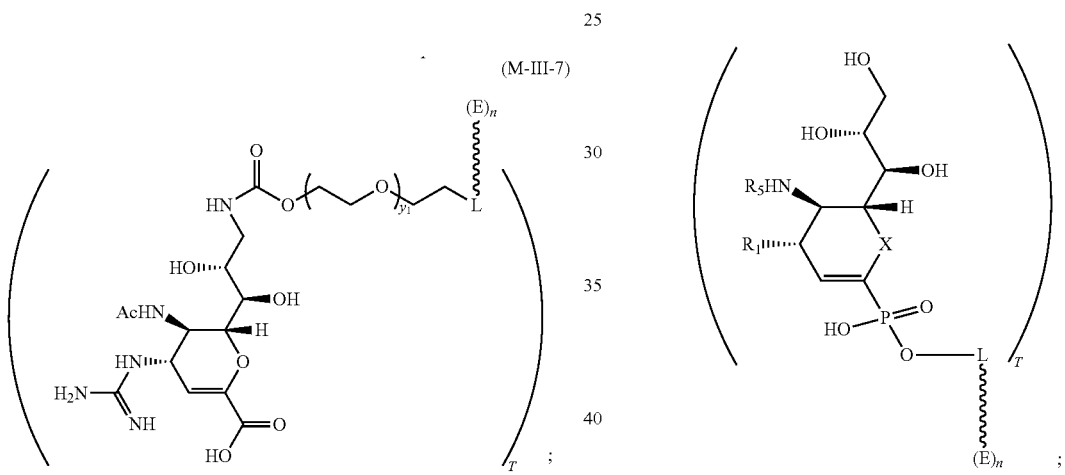
(M-IV)
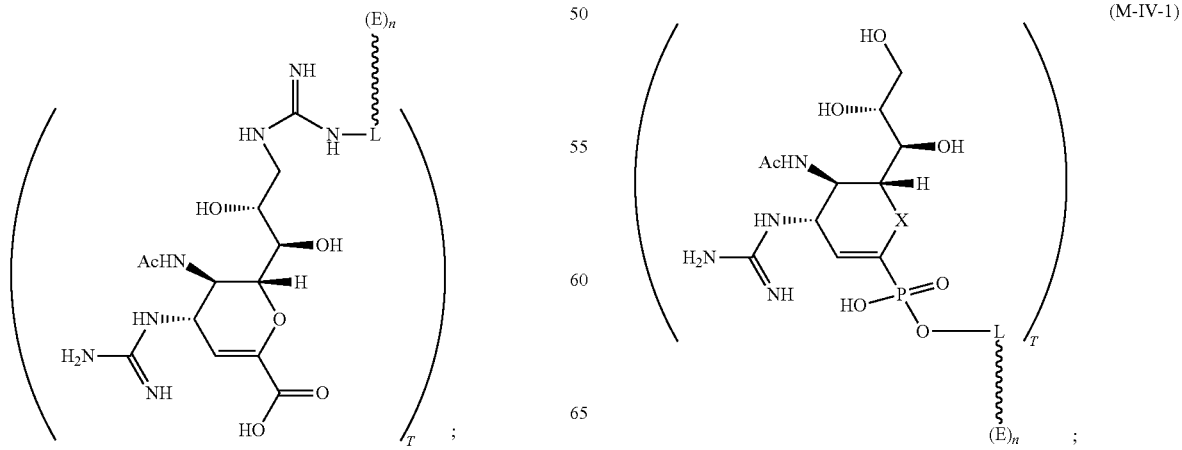
(M-IV-1)

(M-IV-2)
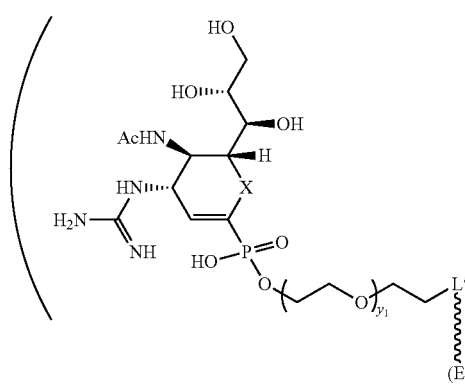
(M-V)
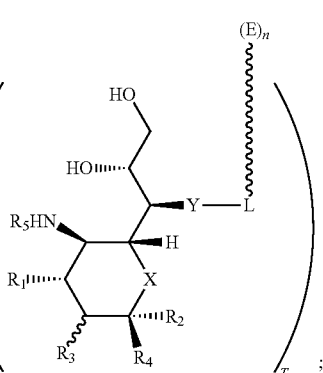
(M-V-1)
(M-V-2)
(M-V-3)
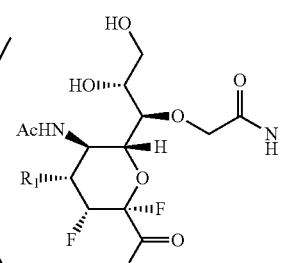
(M-V-4)
(M-V-5)
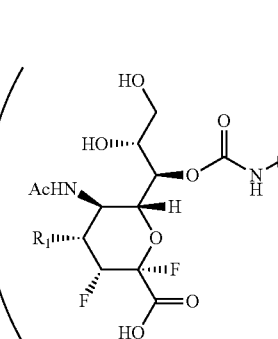
(M-V-6)
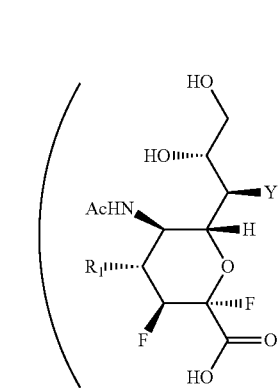

(M-V-7)
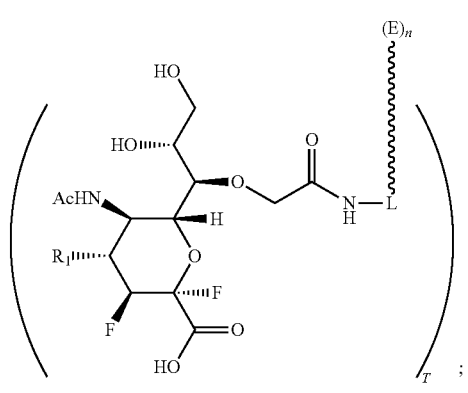
(M-V-8)
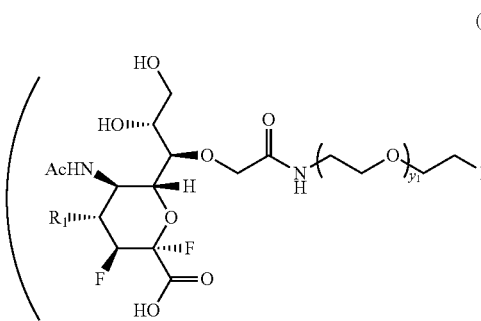
(M-V-9)
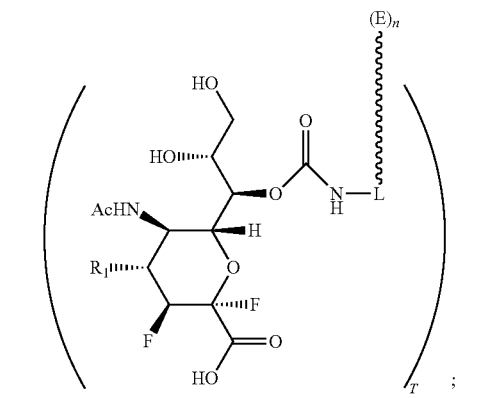
(M-V-10)
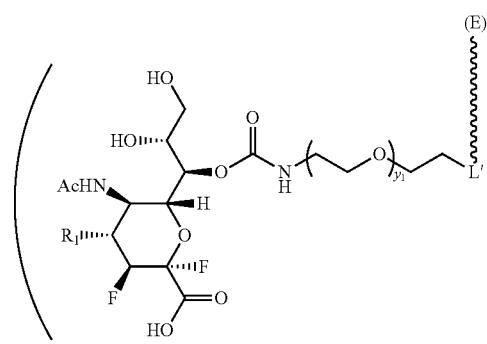
(M-VI)
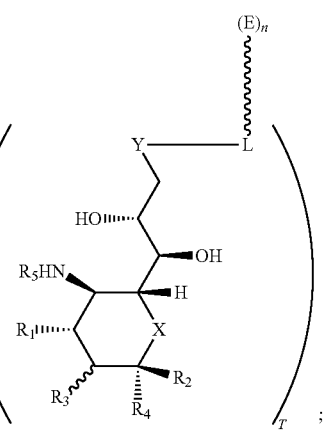
(M-VI-1)
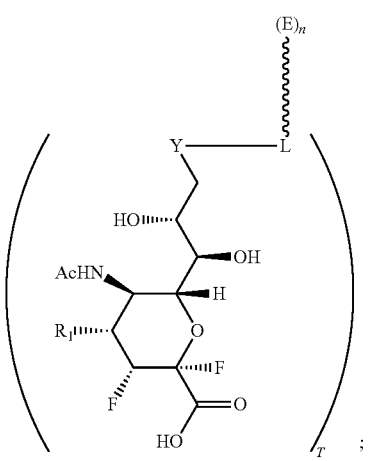
(M-VI-2)
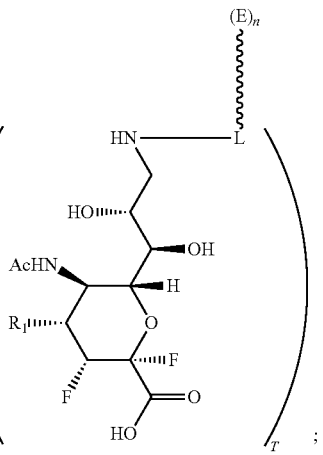

(M-VI-3)
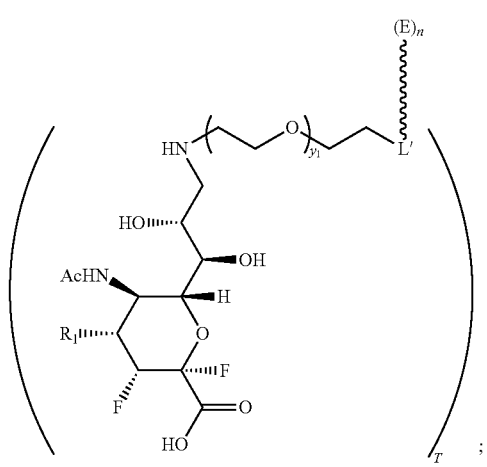
(M-VI-6)
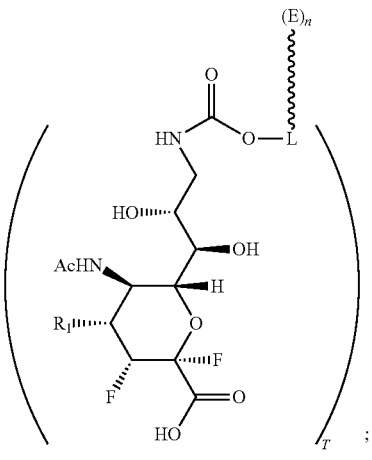
(M-VI-4)
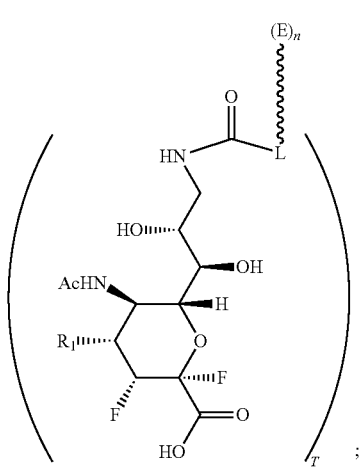
(M-VI-7)
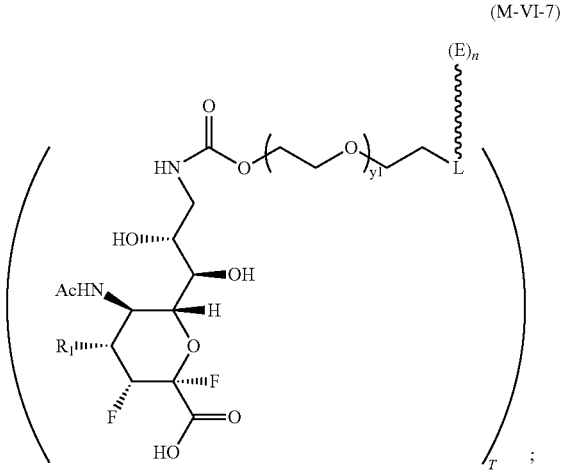
(M-VI-5)
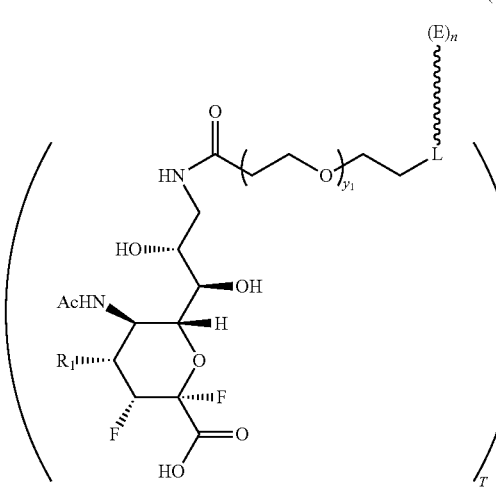
(M-VI-8)
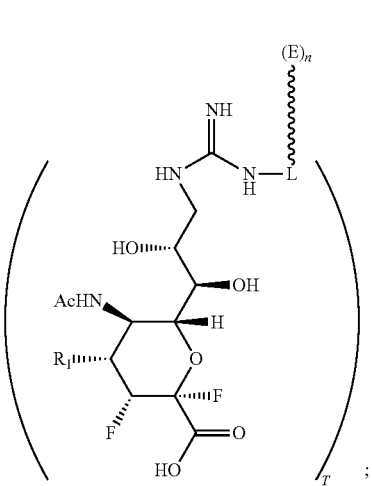

525
-continued
(M-VI-9)
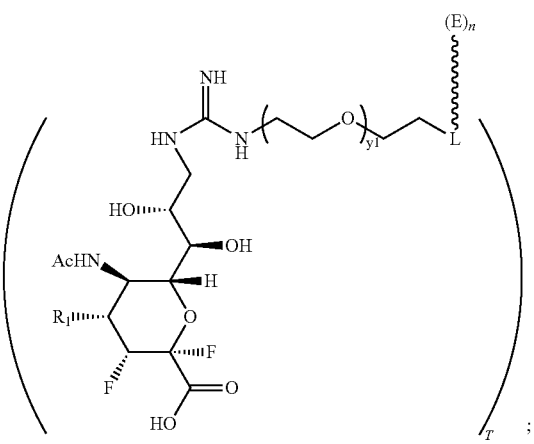
(M-VII)
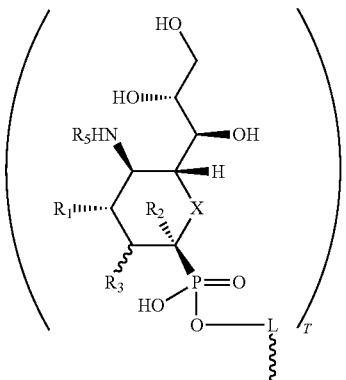
(M-VIII)
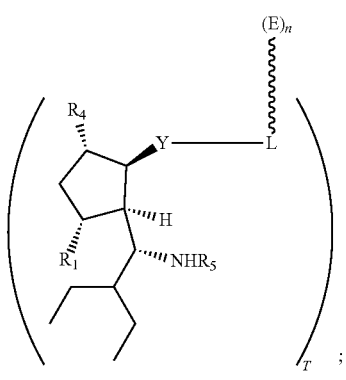
(M-VIII-1)
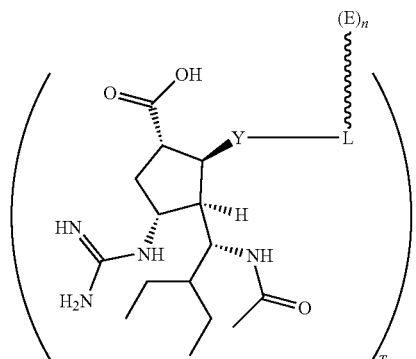
526
-continued
(M-VIII-2)
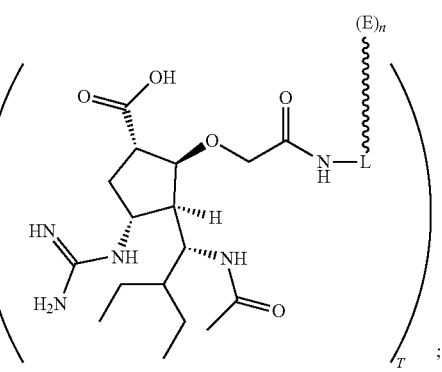
(M-VIII-3)
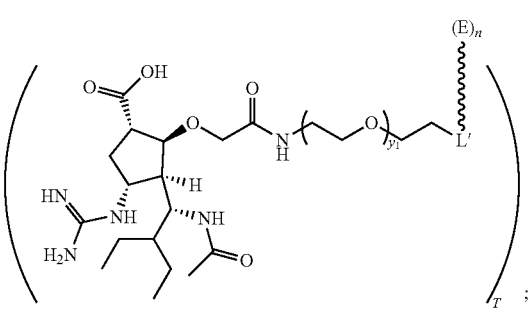
(M-VIII-4)
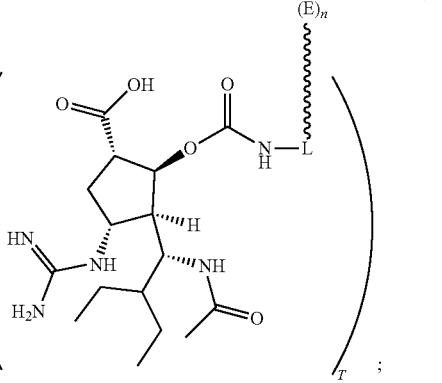
(M-VIII-5)
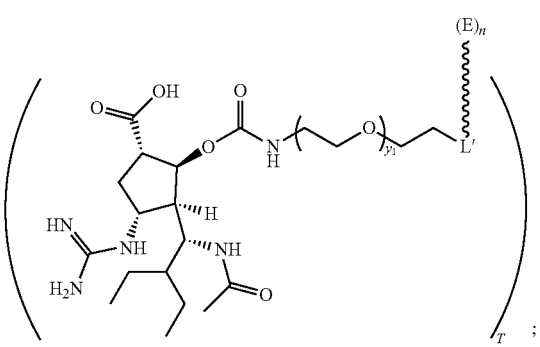

(M-VIII-6)
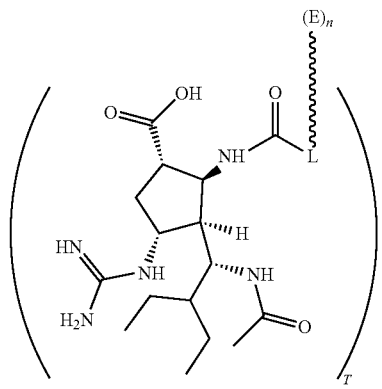
(M-VIII-10)
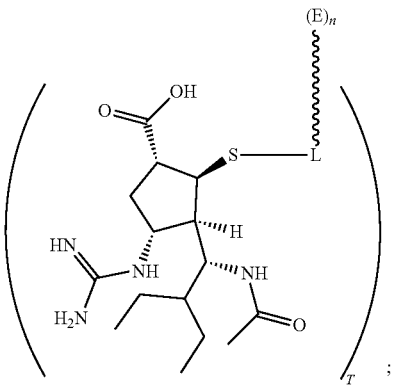
(M-VIII-7)
(M-VIII-11)
(M-VIII-8)
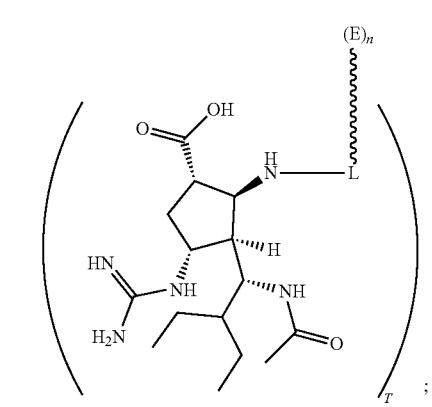
(M-IX)
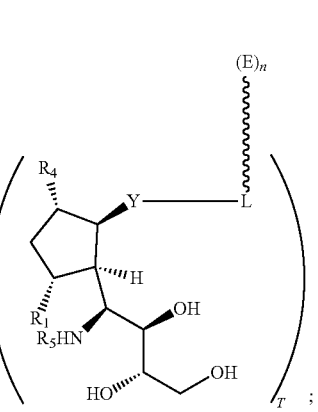
(M-VIII-9)
(M-IX-1)
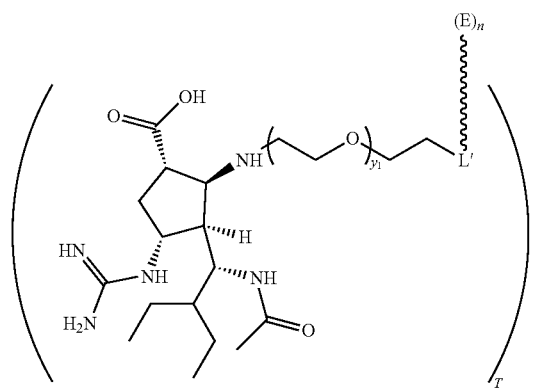
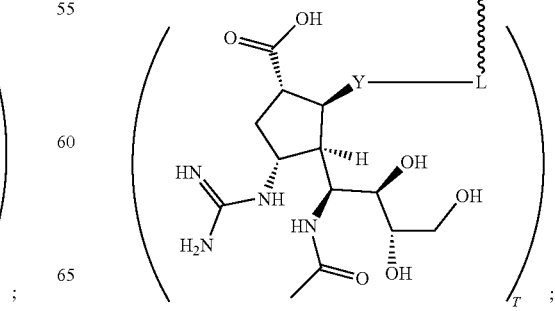

(M-IX-2)
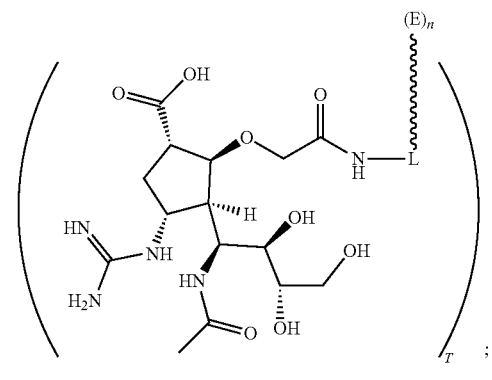
(M-IX-3)
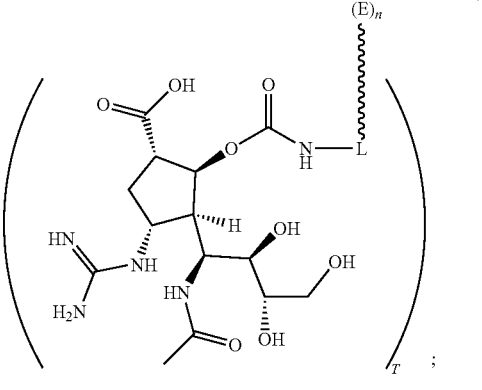
(M-IX-4)
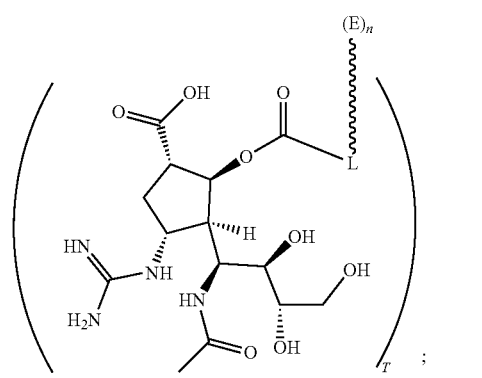
(M-IX-5)
(M-IX-6)
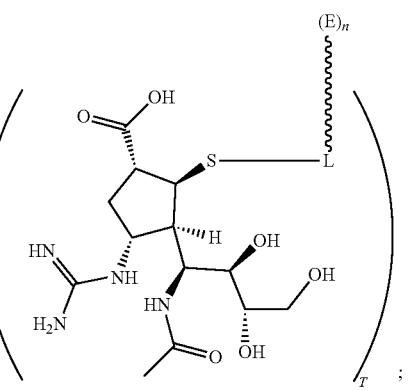
(M-X)
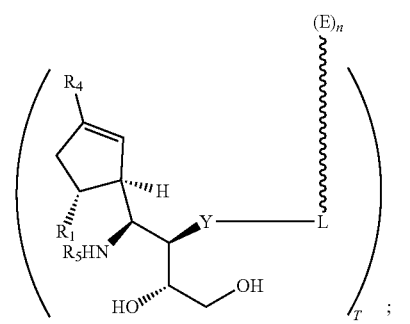
(M-X-1)
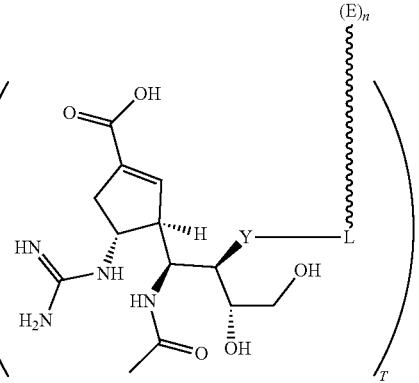
(M-X-2)
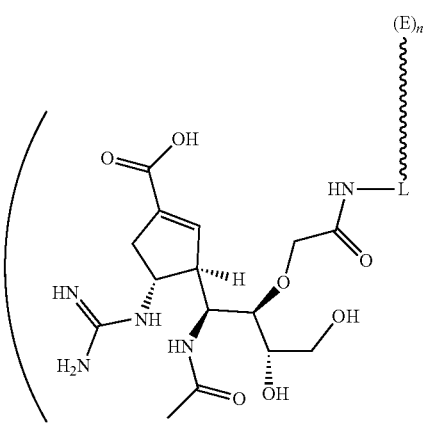

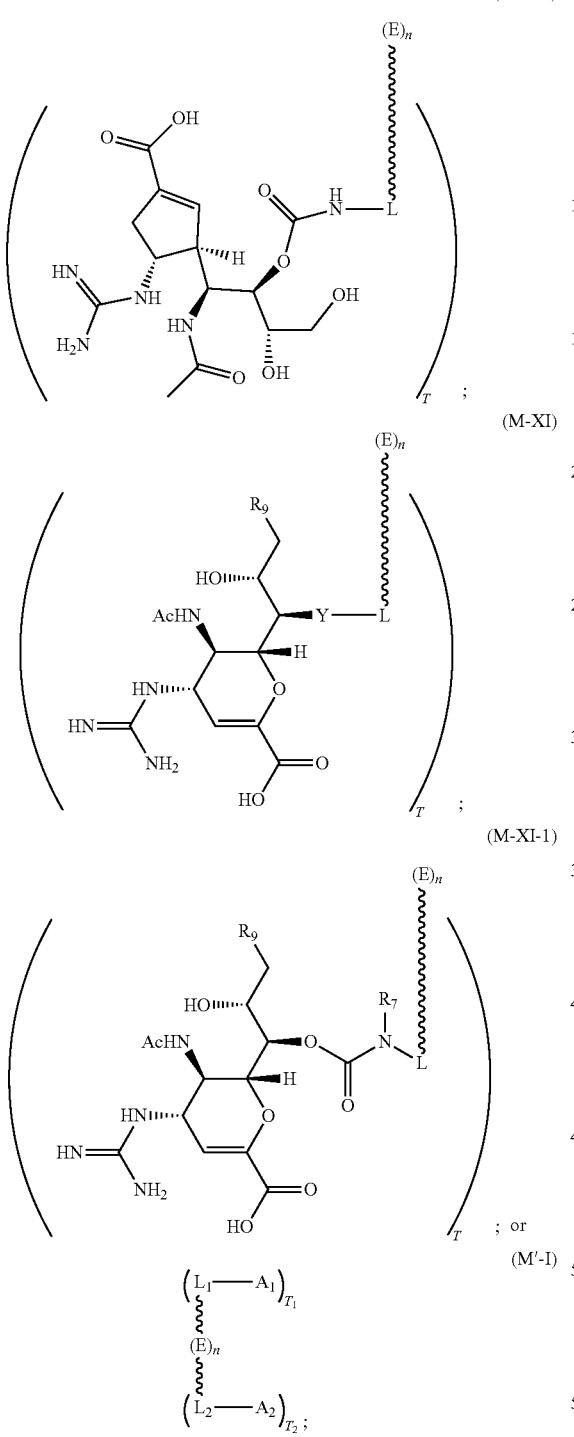

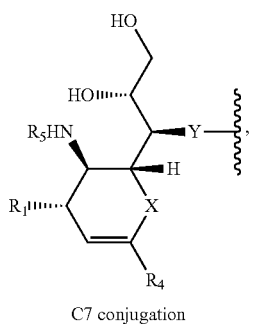

(A-I)

C7 conjugation


(A-II)

C7 conjugation

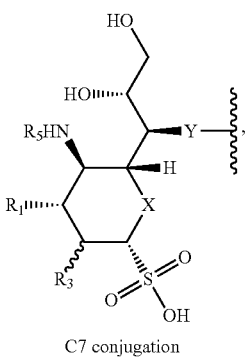

(A-X)

C7 conjugation regioisomers. A particular regioisomer or mixture of regioisomers may be preferred for reasons such as ease of synthesis, thermostability, oxidative stability, pharmacokinetics (e.g., metabolic stability or bioavailability), effector binding, or therapeutic efficacy.

In some embodiments, a conjugate of the invention includes zanamivir or an analog thereof (e.g., any of (A-I), (A-II), (A-VI), (A-VII), (A-VIII), (A-IX), (A-X), or (A-XIII)). Zanamivir or an analog thereof may be conjugated to an Fc domain or an albumin protein (e.g., by way of a linker) through, for example, the C7 position (see, e.g., (A-I), (A-II), (A-X), or (A-XIII)) or through the C9 position (see, e.g., (A-VI) or (A-VII)):

or a pharmaceutically acceptable salt thereof.

In conjugates having an Fc domain covalently linked to one or more monomers of neuraminidase inhibitors, as

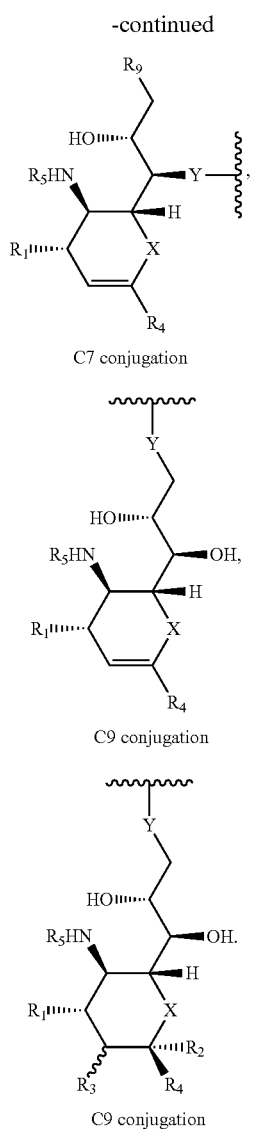

(A-XIII)

C7 conjugation (A-VI)

C9 conjugation (A-VII)

C9 conjugation

The present disclosure includes a population of monomeric conjugates (e.g., a population of conjugates of formula (M-I)) wherein the population of conjugates includes any of the monomeric conjugates described herein and one or more of its corresponding regioisomers. For example, a population of conjugates may include (1) zanamivir or an analog thereof conjugated (e.g., by way of a linker) at the C7 position to an Fc domain or an albumin protein, and (2) zanamivir or an analog thereof conjugated (e.g., by way of a linker) at the C9 position to an Fc domain or an albumin protein. The population of monomeric conjugates may have a specified ratio of C7-linked conjugate to C9-linked conjugate. For example, the population of conjugates may have substantially 100% C-7 linked conjugate and substantially 0% C-9 linked conjugate. The population of conjugates may have about 95% C-7 linked conjugate and about 5% C-9 linked conjugate. The population of conjugates may have about 90% C-7 linked conjugate and about 10% C-9 linked conjugate. The population of conjugates may have about 85% C-7 linked conjugate and about 15% C-9 linked conjugate. The population of conjugates may have about 80% C-7 linked conjugate and about 20% C-9 linked conjugate. The population of conjugates may have about 75% C-7 linked conjugate and about 25% C-9 linked conjugate. The population of conjugates may have about 70% C-7 linked conjugate and about 30% C-9 linked conjugate. The population of conjugates may have about 65% C-7 linked conjugate and about 35% C-9 linked conjugate. The population of conjugates may have about 60% C-7 linked conjugate and about 40% C-9 linked conjugate. The population of conjugates may have about 55% C-7 linked conjugate and about 45% C-9 linked conjugate. The population of conjugates may have about 50% C-7 linked conjugate and about 50% C-9 linked conjugate. The population of conjugates may have about 45% C-7 linked conjugate and about 55% C-9 linked conjugate. The population of conjugates may have about 40% C-7 linked conjugate and about 60% C-9 linked conjugate. The population of conjugates may have about 35% C-7 linked conjugate and about 65% C-9 linked conjugate. The population of conjugates may have about 30% C-7 linked conjugate and about 70% C-9 linked conjugate. The population of conjugates may have about 25% C-7 linked conjugate and about 75% C-9 linked conjugate. The population of conjugates may have about 20% C-7 linked conjugate and about 80% C-9 linked conjugate. The population of conjugates may have about 15% C-7 linked conjugate and about 85% C-9 linked conjugate. The population of conjugates may have about 10% C-7 linked conjugate and about 90% C-9 linked conjugate. The population of conjugates may have substantially 0% C-7 linked conjugate and substantially 100% C-9 linked conjugate. The population of conjugates may have greater than 99%, 98%, 97%, 96%, 95%, 90%, 85%, 80%, 75%, 70%, 60%, 65%, 60%, 55%, or 50% C7-linked conjugate. The population of conjugates may have less than 50%, 40%, 30%, 25%, 20%, 15%, 10%, 5%, 4%, 3%, 2%, or 1% C9-linked conjugate.

The present disclosure also includes a population of dimeric conjugates (e.g., a population of conjugates of formula (D-I)) wherein the population of conjugates includes any of the dimeric conjugates described herein and one or more of its corresponding regioisomers. For example, a population of conjugates may include a (1) a C7-C7 dimer (e.g., both zanamivir or analog thereof moieties of the dimer are conjugated (e.g., by way of a linker) at their respective C7 positions to an Fc domain or an albumin protein), (2) a C9-C9 dimer (e.g., both zanamivir or analog thereof moieties of the dimer are conjugated (e.g., by way of a linker) at their respective C9 positions to an Fc domain or an albumin protein), and/or (3) a C7-C7 dimer (e.g., one zanamivir or analog thereof moiety is conjugated (e.g., by way of a linker) to and Fc domain or an albumin protein through its C7 position and the other zanamivir or analog thereof moiety is conjugated (e.g., by way of a linker) to an Fc domain or an albumin protein through its C9 position).

The population of dimeric conjugates may have a specified ratio of C7-C7 linked conjugate to C7-C9 linked conjugate to C9-C9 linked conjugate. For example, the population of conjugates may have substantially 100% C7-C7 linked conjugate, and substantially 0% C7-C9 or C9-C9 linked conjugate. The population of conjugates may have substantially 100% C9-C9 linked conjugate, and substantially 0% C7-C7 or C7-C9 linked conjugate. The population of conjugates may have substantially 100% C7-C9 linked conjugate, and substantially 0% C7-C7 or C9-C9 linked conjugate.

The population of conjugates may have greater than 99%, 98%, 97%, 96%, 95%, 90%, 85%, 80%, 75%, 70%, 60%, 65%, 60%, 55%, or 50% C7-C7 linked conjugate.

The population of conjugates may have less than 50%, 40%, 30%, 25%, 20%, 15%, 10%, 5%, 4%, 3%, 2%, or 1% C9-C9 linked conjugate.

The population of conjugates may have less than 50%, 40%, 30%, 25%, 20%, 15%, 10%, 5%, 4%, 3%, 2%, or 1% C7-C9 linked conjugate.

For any of the above-described populations of regioisomers, $A_1$ and/or $A_2$ (e.g., of (M-I) or (D-I)) may be selected from zanamivir or any of the zanamivir analogs described herein (e.g., any of (A-I), (A-II), (A-VI), (A-VII), (A-VIII), (A-IX), (A-X), or (A-XIII)). In particular, the C7-linked zanamivir or analogs thereof is described by (A-I), (A-II), (A-X), and (A-XIII), and C9-linked zanamivir or analogs thereof is described by (A-VI) or (A-VII). Exemplary methods for preparing regioisomers, e.g., C7, C9, C7-C7, C7-C9, and C9-C9 linked regioisomers, are described in Examples 100-103, 123 and 124. In some instances, it may be preferable to have 95% or more, 96% or more, 97% or more, 98% or more, 99% or more, or substantially 100% C7-linked monomer conjugates or C7-C7 linked dimer conjugates. In these instances, it may be preferable to prepare the intermediate with a method that forms substantially C7 linked monomer or C7-C7 linked dimer intermediates, such as the methods described, for example, in Examples 103 and 123. The method of Example 103 is exemplary of methods used to achieve primarily the C7 or C7-C7 linked intermediate and may be used to prepare any intermediate described herein. Zanamivir analogs having a modification (e.g., a substituent other than OH) at position C9 (e.g., zanamivir analogs described by (A-XIII)) may increase the ratio of C7-linked zanamivir to C9-linked zanamivir by preventing the migration from C7-linked zanamivir to C9-linked zanamivir. Exemplary C9-modified zanamivir analogs are described herein (see, e.g., conjugates described by D-XI or M-XI, for example Conjugate 47 (Int-91) or Conjugate 48 (Int-92).

In preferred embodiments, the conjugate is a conjugate of any one of formulas (D-I)-(D-XI), (D'-I), (M-I)-(M-XI), or (M'-I), wherein $A_1$ and/or $A_2$ are described by formula (A-I), (A-II), (A-X), or (A-XIII) and Y is $$(-O(C=O)NR_7-),$$

wherein $R_7$ is selected from H, C1-C20 alkyl, C3-C20 cycloalkyl, C3-C20 heterocycloalkyl; C5-C15 aryl, and C2-C15 heteroaryl. In preferred embodiments, $A_1$ and/or $A_2$ are described by formula (A-I) (e.g., zanamivir). In preferred embodiments, $R_7$ is C1-C20 alkyl (e.g., —CH$_3$, —CH$_2$CH$_3$, —CH$_2$CH$_2$CH$_3$). Such conjugates have been shown to exhibit increased stability of the C7-linkage, resulting in less C7 to C9 migration (see, e.g., conjugates described by D-II-6 or D-II-7, such as Conjugate 45 (Int-83) or Conjugate 46 (Int-83)). The resulting product is therefore expected to be more homogenous and exhibit increased efficacy. The preferred conjugate is more homogenous, has an increased proportion (e.g., substantially pure, such as greater than 95%, 96%, 97%, 98%, or 99% pure) C7-linked zanamivir, and retains efficacy against influenza.

III. Fc Domain Monomers and Fc Domains

An Fc domain monomer includes a hinge domain, a $C_H2$ antibody constant domain, and a $C_H3$ antibody constant domain. The Fc domain monomer can be of immunoglobulin antibody isotype IgG, IgE, IgM, IgA, or IgD. The Fc domain monomer can also be of any immunoglobulin antibody isotype (e.g., IgG1, IgG2a, IgG2b, IgG3, or IgG4). The Fc domain monomer can be of any immunoglobulin antibody allotype (e.g., IGHG1*01 (i.e., G1m(za)), IGHG1*07 (i.e., G1m(zax)), IGHG1*04 (i.e., G1m(zav)), IGHG1*03 (G1m(f)), IGHG1*08 (i.e., G1m(fa)), IGHG2*01, IGHG2*06, IGHG2*02, IGHG3*01, IGHG3*05, IGHG3*10, IGHG3*04, IGHG3*09, IGHG3*11, IGHG3*12, IGHG3*06, IGHG3*07, IGHG3*08, IGHG3*13, IGHG3*03, IGHG3*14, IGHG3*15, IGHG3*16, IGHG3*17, IGHG3*18, IGHG3*19, IGHG2*04, IGHG4*01, IGHG4*03, or IGHG4*02) (as described in, for example, in Vidarsson et al. IgG subclasses and allotypes: from structure to effector function. Frontiers in Immunology. 5(520):1-17 (2014)). The Fc domain monomer can also be of any species, e.g., human, murine, or mouse. A dimer of Fc domain monomers is an Fc domain that can bind to an Fc receptor, which is a receptor located on the surface of leukocytes.

In some embodiments, an Fc domain monomer in the conjugates described herein may contain one or more amino acid substitutions, additions, and/or deletion relative to an Fc domain monomer having a sequence of any one of SEQ ID NOs: 1-138. In some embodiments, an Asn in an Fc domain monomer in the conjugates as described herein may be replaced by Ala in order to prevent N-linked glycosylation (see, e.g., SEQ ID NOs: 12-15, where Asn to Ala substitution is labeled with *). In some embodiments, an Fc domain monomer in the conjugates described herein may also containing additional Cys additions (see, e.g., SEQ ID NOs: 9, 10, and 11, where Cys additions are labeled with *).

In some embodiments, an Fc domain monomer in the conjugates as described herein includes an additional moiety, e.g., an albumin-binding peptide, a purification peptide (e.g., a hexa-histidine peptide (HHHHHH (SEQ ID NO: 146)), or a signal sequence (e.g., IL2 signal sequence MYRMQLLSCIALSLALVTNS (SEQ ID NO: 147)) attached to the N- or C-terminus of the Fc domain monomer. In some embodiments, an Fc domain monomer in the conjugate does not contain any type of antibody variable region, e.g., $V_H$, $V_L$, a complementarity determining region (CDR), or a hypervariable region (HVR).

In some embodiments, an Fc domain monomer in the conjugates as described herein may have a sequence that is at least 95% identical (e.g., 97%, 99%, or 99.5% identical) to the sequence of any one of SEQ ID NOs: 1-138 shown below. In some embodiments, an Fc domain monomer in the conjugates as described herein may have a sequence of any one of SEQ ID NOs: 1-138 shown below.

```
SEQ ID NO: 1: murine Fc-IgG2a with IL2 signal sequence at the N-terminus (bold)
MYRMQLLSCIALSLALVTNSPRGPTIKPCPPCKCPAPNLLGGPSVFIFPPKIKDVLMISLSPIVTCVVVDVS

EDDPDVQISWFVNNVEVHTAQTQTHREDYNSTLRVVSALPIQHQDWMSGKEFKCKVNNKDLPAPIERTIS

KPKGSVRAPQVYVLPPPEEEMTKKQVTLTCMVTDFMPEDIYVEWTNNGKTELNYKNTEPVLDSDGSYFM

YSKLRVEKKNWVERNSYSCSVVHEGLHNHHTTKSFSRTPGK
```

-continued

SEQ ID NO: 2: mature murine Fc-IgG2a
PRGPTIKPCPPCKCPAPNLLGGPSVFIFPPKIKDVLMISLSPIVTCVVVDVSEDDPDVQISWFVNNVEVHTA

QTQTHREDYNSTLRVVSALPIQHQDWMSGKEFKCKVNNKDLPAPIERTISKPKGSVRAPQVYVLPPPEEE

MTKKQVTLTCMVTDFMPEDIYVEWTNNGKTELNYKNTEPVLDSDGSYFMYSKLRVEKKNWVERNSYSC

SVVHEGLHNHHTTKSFSRTPGK

SEQ ID NO: 3: human Fc-IgG1 with IL2 signal sequence at the N-terminus (bold) and N-terminal MVRS
amino acid residues added (underlined)
MYRMQLLSCIALSLALVTNSMVRSDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPIEKT

ISKAKGQPREPQVYTLPPSREEMTKNQVSLTCLVKGFYPSDIAVEWESNGQPENNYKTTPPVLDSDGSF

FLYSKLTVDKSRWQQGNVFSCSVMHEALHNHYTQKSLSLSPGK

SEQ ID NO: 4: mature human Fc-IgG1 with N-terminal MVRS amino acid residues added (underlined)
MVRSDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFLYSKLTVDKSRWQQGNVFS

CSVMHEALHNHYTQKSLSLSPGK

SEQ ID NO: 5: murine Fc-IgG2a with IL2 signal sequence (bold) at the N-terminus and hexa-histidine
peptide (italicized) at the C-terminus
MYRMQLLSCIALSLALVTNSPRGPTIKPCPPCKCPAPNLLGGPSVFIFPPKIKDVLMISLSPIVTCVVVDVS

EDDPDVQISWFVNNVEVHTAQTQTHREDYNSTLRVVSALPIQHQDWMSGKEFKCKVNNKDLPAPIERTIS

KPKGSVRAPQVYVLPPPEEEMTKKQVTLTCMVTDFMPEDIYVEWTNNGKTELNYKNTEPVLDSDGSYFM

YSKLRVEKKNWVERNSYSCSVVHEGLHNHHTTKSFSRTPGK*HHHHHH*

SEQ ID NO: 6: mature murine Fc-IgG2a with hexa-histidine peptide (italicized) at the C-terminus

PRGPTIKPCPPCKCPAPNLLGGPSVFIFPPKIKDVLMISLSPIVTCVVVDVSEDDPDVQISWFVNNVEVHTA

QTQTHREDYNSTLRVVSALPIQHQDWMSGKEFKCKVNNKDLPAPIERTISKPKGSVRAPQVYVLPPPEEE

MTKKQVTLTCMVTDFMPEDIYVEWTNNGKTELNYKNTEPVLDSDGSYFMYSKLRVEKKNWVERNSYSC

SVVHEGLHNHHTTKSFSRTPGK*HHHHHH*

SEQ ID NO: 7: human Fc-IgG1 with IL2 signal sequence (bold) at the N-terminus, N-terminal MVRS
amino acid residues added (underlined), and hexa-histidine peptide (italicized) at the C-terminus
MYRMQLLSCIALSLALVTNSMVRSDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPIEKT

ISKAKGQPREPQVYTLPPSREEMTKNQVSLTCLVKGFYPSDIAVEWESNGQPENNYKTTPPVLDSDGSF

FLYSKLTVDKSRWQQGNVFSCSVMHEALHNHYTQKSLSLSPGK*HHHHHH*

SEQ ID NO: 8: mature human Fc-IgG1 with hexa-histidine peptide (italicized) at the C-terminus and
N-terminal MVRS amino acid residues added (underlined)
MVRSDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFLYSKLTVDKSRWQQGNVFS

CSVMHEALHNHYTQKSLSLSPGK*HHHHHH*

SEQ ID NO: 9: human Fc-IgG1 with IL2 signal sequence (bold) at the N-terminus, N-terminal MVRS
amino acid residues added (underlined), two additional cysteines in the hinge region (*), and hexa-
histidine peptide (italicized) at the C-terminus
MYRMQLLSCIALSLALVTNSMVRSDKTHTCPPCPPC*KC*PAPELLGGPSVFLFPPKPKDTLMISRTPEVT

CVVVDVSHEDPEVKFNWYVDGVEVHNAKTKPREEQYNSTYRVVSVLTVLHQDWLNGKEYKCKVSNKAL

PAPIEKTISKAKGQPREPQVYTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK*HHHHHH*

-continued

SEQ ID NO: 10: mature human Fc-IgG1 with N-terminal MVRS amino acid residues added (underlined), two additional cysteines in the hinge region (*), and hexa-histidine peptide (italicized) at the C-terminus
MVRSDKTHTCPPCPPC*KC*PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVLDSDGSFFLYSKLTVDKSRW

QQGNVFSCSVMHEALHNHYTQKSLSLSPGK*HHHHHH*

SEQ ID NO: 11: mature human Fc-IgG1 with N-terminal MVRS amino acid residues added (underlined) and two additional cysteines in the hinge region (*)
MVRSDKTHTCPPCPPC*KC*PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVLDSDGSFFLYSKLTVDKSRW

QQGNVFSCSVMHEALHNHYTQKSLSLSPGK

SEQ ID NO: 12: murine Fc-IgG2a with IL2 signal sequence (bold) at the N-terminus, Asn to Ala substitution (*), and hexa-histidine peptide (italicized) at the C-terminus
MYRMQLLSCIALSLALVTNSPRGPTIKPCPPCKCPAPNLLGGPSVFIFPPKIKDVLMISLSPIVTCVVVDVS

EDDPDVQISWFVNNVEVHTAQTQTHREDYA*STLRVVSALPIQHQDWMSGKEFKCKVNNKDLPAPIERTI

SKPKGSVRAPQVYVLPPPEEEMTKKQVTLTCMVTDFMPEDIYVEWTNNGKTELNYKNTEPVLDSDGSYF

MYSKLRVEKKNWVERNSYSCSVVHEGLHNHHTTKSFSRTPGK*HHHHHH*

SEQ ID NO: 13: mature murine Fc-IgG2a with Asn to Ala substitution (*) and hexa-histidine peptide (italicized) at the C-terminus
PRGPTIKPCPPCKCPAPNLLGGPSVFIFPPKIKDVLMISLSPIVTCVVVDVSEDDPDVQISWFVNNVEVHTA

QTQTHREDYA*STLRVVSALPIQHQDWMSGKEFKCKVNNKDLPAPIERTISKPKGSVRAPQVYVLPPPEE

EMTKKQVTLTCMVTDFMPEDIYVEWTNNGKTELNYKNTEPVLDSDGSYFMYSKLRVEKKNWVERNSYS

CSVVHEGLHNHHTTKSFSRTPGK*HHHHHH*

SEQ ID NO: 14: human Fc-IgG1 with IL2 signal sequence (bold) at the N-terminus, N-terminal MVRS amino acid residues added (underlined), Asn to Ala substitution (*), and hexa-histidine peptide (italicized) at the C-terminus
MYRMQLLSCIALSLALVTNSMVRSDKTHTCPPCPAPELLGGPSVFLFPPKPKDTLMISRTPEVTCVVVDV

SHEDPEVKFNWYVDGVEVHNAKTKPREEQYA*STYRVVSVLTVLHQDWLNGKEYKCKVSNKALPAPIEK

TISKAKGQPREPQVYTLPPSREEMTKNQVSLTCLVKGFYPSDIAVEWESNGQPENNYKTTPPVLDSDGS

FFLYSKLTVDKSRWQQGNVFSCSVMHEALHNHYTQKSLSLSPGK*HHHHHH*

SEQ ID NO: 15: mature human Fc-IgG1 with Asn to Ala substitution (*), N-terminal MVRS amino acid residues added (underlined), and hexa-histidine peptide (italicized) at the C-terminus
MVRSDKTHTCPPCPAPELLGGPSVFLFPPKPKDTLMISRTPEVTCVVVDVSHEDPEVKFNWYVDGVEVH

NAKTKPREEQYA*STYRVVSVLTVLHQDWLNGKEYKCKVSNKALPAPIEKTISKAKGQPREPQVYTLPPS

REEMTKNQVSLTCLVKGFYPSDIAVEWESNGQPENNYKTTPPVLDSDGSFFLYSKLTVDKSRWQQGNV

FSCSVMHEALHNHYTQKSLSLSPGK*HHHHHH*

SEQ ID NO: 16: human IgG1 Fc with Human Serum Albumin Signal Sequence (bold) at the N-terminus and N-terminal ISAMVRS amino acid residues added (underlined)
MKWVTFISLLFLFSSAYSISAMVRSDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPIEKT

ISKAKGQPREPQVYTLPPSREEMTKNQVSLTCLVKGFYPSDIAVEWESNGQPENNYKTTPPVLDSDGSF

FLYSKLTVDKSRWQQGNVFSCSVMHEALHNHYTQKSLSLSPGK

SEQ ID NO: 17: human IgG1 Fc with Human Serum Albumin Signal Sequence (bold) at the N-terminus, N-terminal ISAMVRS amino acid residues added (underlined), C-terminal G45 linker (italicized), and C-terminal c-Myc tag (underlined, italicized)
MKWVTFISLLFLFSSAYSISAMVRSDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPIEKT

ISKAKGQPREPQVYTLPPSREEMTKNQVSLTCLVKGFYPSDIAVEWESNGQPENNYKTTPPVLDSDGSF

FLYSKLTVDKSRWQQGNVFSCSVMHEALHNHYTQKSLSLSPG*GGGGS*<u>*EQKLISEEDL*</u>

SEQ ID NO: 18: mature human IgG1 Fc with N-terminal ISAMVRS amino acid residues added (underlined), C-terminal G4S linker (italicized), and C-terminal c-Myc tag (underlined, italicized)
<u>ISAMVRS</u>DKTHTCPPCPAPELLGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPIEKTISKAKGQPREPQVYTLPP

SREEMTKNQVSLTCLVKGFYPSDIAVEWESNGQPENNYKTTPPVLDSDGSFFLYSKLTVDKSRWQQGN

VFSCSVMHEALHNHYTQKSLSLSPG*GGGGS*<u>*EQKLISEEDL*</u>

SEQ ID NO: 19: human IgG1 Fc with Human Serum Albumin Signal Sequence (bold), N-terminal ISAMVRS amino acid residues added (underlined), and lysine to serine modification (*) to prevent lysine conjugation at this site
MKWVTFISLLFLFSSAYS<u>ISAMVRS</u>DKTHTCPPCPAPELLGGPSVFLFPPKPS*DTLMISRTPEVTCVVVD

VSHEDPEVKFNWYVDGVEVHNAKTKPREEQYNSTYRVVSVLTVLHQDWLNGKEYKCKVSNKALPAPIEK

TISKAKGQPREPQVYTLPPSREEMTKNQVSLTCLVKGFYPSDIAVEWESNGQPENNYKTTPPVLDSDGS

FFLYSKLTVDKSRWQQGNVFSCSVMHEALHNHYTQKSLSLSPGK

SEQ ID NO: 20: mature human IgG1 Fc with N-terminal ISAMVRS amino acid residues added (underlined) and lysine to serine modification (*) to prevent lysine conjugation at this site
<u>ISAMVRS</u>DKTHTCPPCPAPELLGGPSVFLFPPKPS*DTLMISRTPEVTCVVVDVSHEDPEVKFNWYVDGV

EVHNAKTKPREEQYNSTYRVVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGSFFLYSKLTVDKSRWQQG

NVFSCSVMHEALHNHYTQKSLSLSPGK

SEQ ID NO: 21: human IgG1 Fc with Human Serum Albumin Signal Sequence (bold) at the N-terminus, N-terminal ISAMVRS amino acid residues added (underlined), lysine to serine modification (*) to prevent lysine conjugation at this site, C-terminal G4S linker (italicized), and C-terminal C-Myc tag (underlined, italicized)
MKWVTFISLLFLFSSAYS<u>ISAMVRS</u>DKTHTCPPCPAPELLGGPSVFLFPPKPS(*)DTLMISRTPEVTCVVV

DVSHEDPEVKFNWYVDGVEVHNAKTKPREEQYNSTYRVVSVLTVLHQDWLNGKEYKCKVSNKALPAPI

EKTISKAKGQPREPQVYTLPPSREEMTKNQVSLTCLVKGFYPSDIAVEWESNGQPENNYKTTPPVLSD

GSFFLYSKLTVDKSRWQQGNVFSCSVMHEALHNHYTQKSLSLSPG*GGGGS*<u>*EQKLISEEDL*</u>

SEQ ID NO: 22: mature human IgG1 Fc with N-terminal ISAMVRS amino acid residues added (underlined), lysine to serine modification (*) to prevent lysine conjugation at this site, C-terminal G4S linker (italicized), and C-terminal C-Myc tag (underlined, italicized)
<u>ISAMVRS</u>DKTHTCPPCPAPELLGGPSVFLFPPKPS(*)DTLMISRTPEVTCVVVDVSHEDPEVKFNWYVDG

VEVHNAKTKPREEQYNSTYRVVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSDGSFFLYSKLTVDKSRWQQ

GNVFSCSVMHEALHNHYTQKSLSLSPG*GGGGS*<u>*EQKLISEEDL*</u>

SEQ ID NO: 23: human IgG1 Fc with Human Serum Albumin Signal Sequence (bold) at the N-terminus, N-terminal ISAMVRS amino acid residues added (underlined), Asn to Ala substitution (*), C-terminal G4S linker (italicized), and C-myc tag (underlined, italicized)
MKWVTFISLLFLFSSAYS<u>ISAMVRS</u>DKTHTCPPCPAPELLGGPSVFLFPPKPKDTLMISRTPEVTCVVVDV

SHEDPEVKFNWYVDGVEVHNAKTKPREEQYA(*)STYRVVSVLTVLHQDWLNGKEYKCKVSNKALPAPIE

KTISKAKGQPREPQVYTLPPSREEMTKNQVSLTCLVKGFYPSDIAVEWESNGQPENNYKTTPPVLDSDG

SFFLYSKLTVDKSRWQQGNVFSCSVMHEALHNHYTQKSLSLSPG*GGGGS*<u>*EQKLISEEDL*</u>

SEQ ID NO: 24: mature human IgG1 Fc with N-terminal ISAMVRS amino acid residues added (underlined), Asn to Ala substitution (*), C-terminal G4S linker (italicized), and C-myc tag (underlined, italicized)
<u>ISAMVRS</u>DKTHTCPPCPAPELLGGPSVFLFPPKPKDTLMISRTPEVTCVVVDVSHEDPEVKFNWYVDGVE

VHNAKTKPREEQYA(*)STYRVVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSDGSFFLYSKLTVDKSRWQQ

GNVFSCSVMHEALHNHYTQKSLSLSPG*GGGGS*<u>*EQKLISEEDL*</u>

SEQ ID NO: 25: human IgG1 Fc with Human Serum Albumin Signal Sequence (bold) at the N-terminus, N-terminal ISAMVRS amino acid residues added (underlined), H310A (*) and H435A (*) mutations to impede FcRn binding, C-terminal G4S (italicized), and C-terminal C-myc tag (underlined, italicized)
MKWVTFISLLFLFSSAYSISAMVRSDKTHTCPPCPAPELLGGPSVFLFPPKPKDTLMISRTPEVTCVVVDV

SHEDPEVKFNWYVDGVEVHNAKTKPREEQYNSTYRVVSVLTVLA(*)QDWLNGKEYKCKVSNKALPAPIE

KTISKA(*)KGQPREPQVYTLPPSREEMTKNQVSLTCLVKGFYPSDIAVEWESNGQPENNYKTTPPVLDSD

GSFFLYSKLTVDKSRWQQGNVFSCSVMHEALHNAYTQKSLSLSPG*GGGGS*<u>*EQKLISEEDL*</u>

SEQ ID NO: 26: mature human IgG1 Fc with Human Serum Albumin Signal Sequence (bold) at the N-terminus, N-terminal ISAMVRS amino acid residues added (underlined), with H310A (*) and H435A (*) mutations to impede FcRn binding, C-terminal G4S (italicized), and C-terminal C-myc tag (underlined, italicized)
ISAMVRSDKTHTCPPCPAPELLGGPSVFLFPPKPKDTLMISRTPEVTCVVVDVSHEDPEVKFNWYVDGVE

VHNAKTKPREEQYNSTYRVVSVLTVLA(*)QDWLNGKEYKCKVSNKALPAPIEKTISKA(*)KGQPREPQVY

TLPPSREEMTKNQVSLTCLVKGFYPSDIAVEWESNGQPENNYKTTPPVLDSDGSFFLYSKLTVDKSRWQ

QGNVFSCSVMHEALHNAYTQKSLSLSPG*GGGGS*<u>*EQKLISEEDL*</u>

SEQ ID NO: 27: human IgG1 Fc with Human Serum Albumin Signal Sequence (bold) at the N-terminus, N-terminal ISAMVRS amino acid residues added (underlined), C-terminal G4S linker (italicized), and C-terminal mutated (lysine to phenylalanine, bold) C-myc tag (underlined, italicized)
MKWVTFISLLFLFSSAYSISAMVRSDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPIEKT

ISKAKGQPREPQVYTLPPSREEMTKNQVSLTCLVKGFYPSDIAVEWESNGQPENNYKTTPPVLDSDGSF

FLYSKLTVDKSRWQQGNVFSCSVMHEALHNHYTQKSLSLSPG*GGGGS*<u>*EQFLISEEDL*</u>

SEQ ID NO: 28: mature human IgG1 Fc with N-terminal ISAMVRS amino acid residues added (underlined), C-terminal G4S linker (italicized), and C-terminal mutated (lysine to phenylalanine, bold) C-myc tag (underlined, italicized)
ISAMVRSDKTHTCPPCPAPELLGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPIEKTISKAKGQPREPQVYTLPP

SREEMTKNQVSLTCLVKGFYPSDIAVEWESNGQPENNYKTTPPVLDSDGSFFLYSKLTVDKSRWQQGN

VFSCSVMHEALHNHYTQKSLSLSPG*GGGGS*<u>*EQFLISEEDL*</u>

SEQ ID NO: 29: human IgG1 Fc with Human Serum Albumin Signal Sequence (bold) at the N-terminus, N-terminal ISAMVRS amino acid residues added (underlined), Asn to Ala substitution (*), C-terminal G4S linker (italicized), and C-terminal mutated (lysine to phenylalanine, bold) C-myc tag (underlined, italicized)
MKWVTFISLLFLFSSAYSISAMVRSDKTHTCPPCPAPELLGGPSVFLFPPKPKDTLMISRTPEVTCVVVDV

SHEDPEVKFNWYVDGVEVHNAKTKPREEQYA(*)STYRVVSVLTVLHQDWLNGKEYKCKVSNKALPAPIE

KTISKAKGQPREPQVYTLPPSREEMTKNQVSLTCLVKGFYPSDIAVEWESNGQPENNYKTTPPVLDSDG

SFFLYSKLTVDKSRWQQGNVFSCSVMHEALHNHYTQKSLSLSPG*GGGGS*<u>*EQFLISEEDL*</u>

SEQ ID NO: 30: mature human IgG1 Fc with N-terminal MVRS amino acid residues added (underlined), Asn to Ala substitution (*), C-terminal G4S linker (italicized), and C-terminal mutated (lysine to phenylalanine, bold) C-myc tag (underlined, italicized)
ISAMVRSDKTHTCPPCPAPELLGGPSVFLFPPKPKDTLMISRTPEVTCVVVDVSHEDPEVKFNWYVDGVE

VHNAKTKPREEQYA(*)STYRVVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSDGSFFLYSKLTVDKSRWQQ

GNVFSCSVMHEALHNHYTQKSLSLSPG*GGGGS*<u>*EQFLISEEDL*</u>

SEQ ID NO: 31: human IgG1 Fc with Human Serum Albumin Signal Sequence (bold) at the N-terminus, allotype G1m(fa) (bold italics), C-terminal G4S linker (italicized), and C-terminal mutated (lysine to phenylalanine, bold) C-myc tag (underlined)
MKWVTFISLLFLFSSAYSDKTHTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCKVSNKALPAPIEKTISKAKG

QPREPQVYTLPPSR*DEL***TKNQVSLTCLVKGFYPSDIAVEWESNGQPENNYKTTPPVLDSDGSFFLYSKLT

VDKSRWQQGNVFSCSVMHEALHNHYTQKSLSLSPG*GGGGS*<u>EQFLISEEDL</u>

SEQ ID NO: 32: human IgG1 Fc with Human Serum Albumin Signal Sequence (bold) at the N-terminus, allotype G1m(fa) (bold italics)
MKWVTFISLLFLFSSAYSDKTHTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCKVSNKALPAPIEKTISKAKG

QPREPQVYTLPPSR*DE**L*TKNQVSLTCLVKGFYPSDIAVEWESNGQPENNYKTTPPVLDSDGSFFLYSKLT

VDKSRWQQGNVFSCSVMHEALHNHYTQKSLSLSPGK

SEQ ID NO: 33: mature human IgG1 Fc with a YTE triple mutation (bold and underlined) with N-terminal MVRS amino acid residues added (underlined)
<u>MVRS</u>DKTHTCPPCPAPELLGGPSVFLFPPKPKDTL<u>YITRE</u>PEVTCVVVDVSHEDPEVKFNWYVDGVEVH

NAKTKPREEQYNSTYRVVSVLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFLYSKLTVDKSRWQQGNVFS

CSVMHEALHNHYTQKSLSLSPGK

SEQ ID NO: 34: human IgG1 Fc with Human Serum Albumin Signal Sequence (bold) at the N-terminus, contains residues EPKSS comprising the full hinge region on the N-terminus of mature human IgG1 Fc (underlined), Cys to Ser substitution (#), allotype G1m(fa) (bold italics)
MKWVTFISLLFLFSSAYS<u>EPKSS</u>(#)DKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPIEKT

ISKAKGQPREPQVYTLPPSR*DE**L*TKNQVSLTCLVKGFYPSDIAVEWESNGQPENNYKTTPPVLDSDGSFF

LYSKLTVDKSRWQQGNVFSCSVMHEALHNHYTQKSLSLSPGK

SEQ ID NO: 35: human IgG1 Fc with murine IgG signal sequence (bold) at the N-terminus, with removal of EPKSSD hinge residues from the N-terminus of the mature human IgG1 Fc, allotype G1m(fa) (bold italics)
MGWSCIILFLVATATGVHSKTHTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCKVSNKALPAPIEKTISKAKG

QPREPQVYTLPPSR*DE**L*TKNQVSLTCLVKGFYPSDIAVEWESNGQPENNYKTTPPVLDSDGSFFLYSKLT

VDKSRWQQGNVFSCSVMHEALHNHYTQKSLSLSPGK

SEQ ID NO: 36: mature human IgG1 Fc with a YTE triple mutation (bold and underlined), with removal of EPKSSD hinge residues from the N-terminus of the mature human IgG1 Fc, allotype G1m(fa) (bold italics)
KTHTCPPCPAPELLGGPSVFLFPPKPKDTL<u>YITRE</u>PEVTCVVVDVSHEDPEVKFNWYVDGVEVHNAKTKP

REEQYNSTYRVVSVLTVLHQDWLNGKEYKCKVSNKALPAPIEKTISKAKGQPREPQVYTLPPSR*DE*

*L*TKNQVSLTCLVKGFYPSDIAVEWESNGQPENNYKTTPPVLDSDGSFFLYSKLTVDKSRWQQGNVFSCS

VMHEALHNHYTQKSLSLSPGK

SEQ ID NO: 37: mature human IgG1 Fc with an LS double mutation (bold and underlined), with removal of EPKSSD hinge residues from the N-terminus of the mature human IgG1 Fc, allotype G1m(fa) (bold italics)
KTHTCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAKGQPREPQVYTLPPSR*DE*

*L*TKNQVSLTCLVKGFYPSDIAVEWESNGQPENNYKTTPPVLDSDGSFFLYSKLTVDKSRWQQGNVFSCS

V<u>L</u>HEALH<u>S</u>HYTQKSLSLSPGK

SEQ ID NO: 38: mature human IgG1 Fc with Human Serum Albumin Signal Sequence (bold) at the N-terminus, a YTE triple mutation (bold and underlined), allotype G1m(fa) (bold italics), C-terminal G4S linker (italicized), and C-terminal C-myc tag (underlined)
MKWVTFISLLFLFSSAYSDKTHTCPPCPAPELLGGPSVFLFPPKPKDTL<u>YITRE</u>PEVTCVVVDVSHEDPEV

KFNWYVDGVEVHNAKTKPREEQYNSTYRVVSVLTVLHQDWLNGKEYKCKVSNKALPAPIEKTISKAKGQ

PREPQVYTLPPSR*DE**L*TKNQVSLTCLVKGFYPSDIAVEWESNGQPENNYKTTPPVLDSDGSFFLYSKLTV

DKSRWQQGNVFSCSVMHEALHNHYTQKSLSLSPG*GGGGS*<u>EQKLISEEDL</u>

-continued

SEQ ID NO: 39: mature human Fc IgG1, wherein $X_1$ is Met or Tyr, $X_2$ is Ser or Thr, $X_3$ is Thr or Glu, $X_4$ is Asp or Glu, and $X_5$ is Leu or Met, $X_6$ is Met or Leu, and $X_7$ is Asn or Ser
DKTHTCPPCPAPELLGGPSVFLFPPKPKDTL$X_1$I$X_2$R$X_3$PEVTCVVVDVSHEDPEVKFNWYVDGVEVHNAK

TKPREEQYNSTYRVVSVLTVLHQDWLNGKEYKCKVSNKALPAPIEKTISKAKGQPREPQVYTLPPSR$X_4$E $X_5$TKNQVSLTCLVKGFYPSDIAVEWESNGQPENNYKTTPPVLDSDGSFFLYSKLTVDKSRWQQGNVFSC

SV$X_6$HEALH$X_7$HYTQKSLSLSPG

SEQ ID NO: 40: mature human Fc IgG1 wherein $X_4$ is Asp or Glu, and $X_5$ is Leu or Met
DKTHTCPPCPAPELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREPQVYTLPPSR$X_4$E$X_5$

TKNQVSLTCLVKGFYPSDIAVEWESNGQPENNYKTTPPVLDSDGSFFLYSKLTVDKSRWQQGNVFSCSV

MHEALHNHYTQKSLSLSPG

SEQ ID NO: 41: mature human Fc IgG1 with a YTE triple mutation (bold and underlined), and wherein $X_4$ is Asp or Glu, and $X_5$ is Leu or Met
DKTHTCPPCPAPELLGGPSVFLFPPKPKDTLYITREPEVTCVVVDVSHEDPEVKFNWYVDGVEVHNAKTK

PREEQYNSTYRVVSVLTVLHQDWLNGKEYKCKVSNKALPAPIEKTISKAKGQPREPQVYTLPPSR$X_4$E$X_5$T

KNQVSLTCLVKGFYPSDIAVEWESNGQPENNYKTTPPVLDSDGSFFLYSKLTVDKSRWQQGNVFSCSV

MHEALHNHYTQKSLSLSPG

SEQ ID NO: 42: mature human Fc IgG1 with a YTE triple mutation (bold and underlined), allotype G1m(fa) (bold italics)
DKTHTCPPCPAPELLGGPSVFLFPPKPKDTLYITREPEVTCVVVDVSHEDPEVKFNWYVDGVEVHNAKTK

PREEQYNSTYRVVSVLTVLHQDWLNGKEYKCKVSNKALPAPIEKTISKAKGQPREPQVYTLPPSR*DEL*TK

NQVSLTCLVKGFYPSDIAVEWESNGQPENNYKTTPPVLDSDGSFFLYSKLTVDKSRWQQGNVFSCSVM

HEALHNHYTQKSLSLSPG

SEQ ID NO: 43: mature human Fc IgG1 with a YTE triple mutation (bold and underlined), allotype G1m(f) (bold italics)
DKTHTCPPCPAPELLGGPSVFLFPPKPKDTLYITREPEVTCVVVDVSHEDPEVKFNWYVDGVEVHNAKTK

PREEQYNSTYRVVSVLTVLHQDWLNGKEYKCKVSNKALPAPIEKTISKAKGQPREPQVYTLPPSR*EEM*TK

NQVSLTCLVKGFYPSDIAVEWESNGQPENNYKTTPPVLDSDGSFFLYSKLTVDKSRWQQGNVFSCSVM

HEALHNHYTQKSLSLSPG

SEQ ID NO: 44: mature human Fc IgG1 with a LS double mutation (bold and underlined), and wherein $X_4$ is Asp or Glu, and $X_5$ is Leu or Met
DKTHTCPPCPAPELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREPQVYTLPPSR$X_4$E$X_5$

TKNQVSLTCLVKGFYPSDIAVEWESNGQPENNYKTTPPVLDSDGSFFLYSKLTVDKSRWQQGNVFSCSV

LHEALHSHYTQKSLSLSPG

SEQ ID NO: 45: mature human Fc IgG1 with a LS double mutation (bold and underlined), allotype G1m(fa) (bold italics)
DKTHTCPPCPAPELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREPQVYTLPPSR*DEL*T

KNQVSLTCLVKGFYPSDIAVEWESNGQPENNYKTTPPVLDSDGSFFLYSKLTVDKSRWQQGNVFSCSVL

HEALHSHYTQKSLSLSPG

SEQ ID NO: 46: mature human Fc IgG1 with a LS double mutation (bold and underlined), allotype G1m(f) (bold italics)
DKTHTCPPCPAPELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREPQVYTLPPSR*EEM*T

KNQVSLTCLVKGFYPSDIAVEWESNGQPENNYKTTPPVLDSDGSFFLYSKLTVDKSRWQQGNVFSCSVL

HEALHSHYTQKSLSLSPG

-continued

SEQ ID NO: 47: mature human Fc IgG1 with mouse heavy chain MIgG Vh signal sequence (bold), Cys to Ser substitution (#), and wherein $X_1$ is Met or Tyr, $X_2$ is Ser or Thr, $X_3$ is Thr or Glu, $X_4$ is Asp or Glu, and $X_5$ is Leu or Met, $X_6$ is Met or Leu, and $X_7$ is Asn or Ser
MGWSCIILFLVATATGVHSNVNHKPSNTKVDKKVEPKSS(#)DKTHTCPPCPAPELLGGPSVFLFPPKPKD

TL$X_1$I$X_2$R$X_3$PEVTCVVVDVSHEDPEVKFNWYVDGVEVHNAKTKPREEQYNSTYRVVSVLTVLHQDWLNG

KEYKCKVSNKALPAPIEKTISKAKGQPREPQVYTLPPSR$X_4$E$X_5$TKNQVSLTCLVKGFYPSDIAVEWESNG

QPENNYKTTPPVLDSDGSFFLYSKLTVDKSRWQQGNVFSCSV$X_6$HEALH$X_7$HYTQKSLSLSPG

SEQ ID NO: 48: mature human IgG1 Fc with mouse heavy chain MIgG Vh signal sequence (bold), Cys to Ser substitution (#), allotype G1m(fa) (bold italics)
MGWSCIILFLVATATGVHSNVNHKPSNTKVDKKVEPKSS(#)DKTHTCPPCPAPELLGGPSVFLFPPKPKD

TLMISRTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSR*DEL*TKNQVSLTCLVKGFYPSDIAVEWESNGQPE

NNYKTTPPVLDSDGSFFLYSKLTVDKSRWQQGNVFSCSVMHEALHNHYTQKSLSLSPGK

SEQ ID NO: 49: mature human IgG1 Fc with mouse heavy chain MIgG Vh signal sequence (bold), Cys to Ser substitution (#), allotype G1m(f) (bold italics)
MGWSCIILFLVATATGVHSNVNHKPSNTKVDKKVEPKSS(#)DKTHTCPPCPAPELLGGPSVFLFPPKPKD

TLMISRTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSR*EEM*TKNQVSLTCLVKGFYPSDIAVEWESNGQPE

NNYKTTPPVLDSDGSFFLYSKLTVDKSRWQQGNVFSCSVMHEALHNHYTQKSLSLSPGK

SEQ ID NO: 50: mature human IgG1 Fc with mouse heavy chain MIgG Vh signal sequence (bold), Cys to Ser substitution (#), M428L, N434S mutations (Bold/Underlined), allotype G1m(fa) (bold italics)
MGWSCIILFLVATATGVHSNVNHKPSNTKVDKKVEPKSS(#)DKTHTCPPCPAPELLGGPSVFLFPPKPKD

TLMISRTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSR*DEL*TKNQVSLTCLVKGFYPSDIAVEWESNGQPE

NNYKTTPPVLDSDGSFFLYSKLTVDKSRWQQGNVFSCSV<u>L</u>HEALH<u>S</u>HYTQKSLSLSPGK

SEQ ID NO: 51: mature human IgG1 Fc with mouse heavy chain MIgG Vh signal sequence (bold), Cys to Ser substitution (#), M428L, N434S mutations (Bold/Underlined), allotype G1m(f) (bold italics)
MGWSCIILFLVATATGVHSNVNHKPSNTKVDKKVEPKSS(#)DKTHTCPPCPAPELLGGPSVFLFPPKPKD

TLMISRTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSR*EEM*TKNQVSLTCLVKGFYPSDIAVEWESNGQPE

NNYKTTPPVLDSDGSFFLYSKLTVDKSRWQQGNVFSCSV<u>L</u>HEALH<u>S</u>HYTQKSLSLSPGK

SEQ ID NO: 52: mature human IgG1 Fc with mouse heavy chain MIgG Vh signal sequence (bold), Cys to Ser substitution (#), YTE triple mutation (bold and underlined), allotype G1m(fa) (bold italics)
MGWSCIILFLVATATGVHSNVNHKPSNTKVDKKVEPKSS(#)DKTHTCPPCPAPELLGGPSVFLFPPKPKD TL<u>YITRE</u>PEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSR*DEL*TKNQVSLTCLVKGFYPSDIAVEWESNGQPE

NNYKTTPPVLDSDGSFFLYSKLTVDKSRWQQGNVFSCSVMHEALHNHYTQKSLSLSPGK

SEQ ID NO: 53: mature human IgG1 Fc with mouse heavy chain MIgG Vh signal sequence (bold), Cys to Ser substitution (#), YTE triple mutation (bold and underlined), allotype G1m(f) (bold italics)
MGWSCIILFLVATATGVHSNVNHKPSNTKVDKKVEPKSS(#)DKTHTCPPCPAPELLGGPSVFLFPPKPKD TL<u>YITRE</u>PEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSR*EEM*TKNQVSLTCLVKGFYPSDIAVEWESNGQPE

NNYKTTPPVLDSDGSFFLYSKLTVDKSRWQQGNVFSCSVMHEALHNHYTQKSLSLSPGK

SEQ ID NO: 54: mature human IgG1 Fc with mouse heavy chain MIgG Vh signal sequence (bold), N-terminal ISAMVRS amino acid residues added (italicized), M428L, N434S mutations (bold/underlined), G4S linker (italicized), and C-terminal C-myc-tag (underlined), allotype G1m(f) (bold italics)
MGWSCIILFLVATATGVHS_ISAMVRS_DKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAPIEK

TISKAKGQPREPQVYTLPPSR_EEM_TKNQVSLTCLVKGFYPSDIAVEWESNGQPENNYKTTPPVLDSDGS

FFLYSKLTVDKSRWQQGNVFSCSVLHEALHSHYTQKSLSLSPG_GGGGS_EQKLISEEDL

SEQ ID NO: 55: mature human IgG1 Fc with mouse heavy chain MIgG Vh signal sequence (bold), N-terminal ISAMVRS amino acid residues added (italicized), M428L, N434S mutations (bold/underlined), G4S linker (italicized), C-terminal C-myc-tag (underlined), allotype G1m(fa) (bold italics)
MGWSCIILFLVATATGVHS_ISAMVRS_DKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAPIEK

TISKAKGQPREPQVYTLPPSR_DEL_TKNQVSLTCLVKGFYPSDIAVEWESNGQPENNYKTTPPVLDSDGSF

FLYSKLTVDKSRWQQGNVFSCSVLHEALHSHYTQKSLSLSPG_GGGGS_EQKLISEEDL

SEQ ID NO: 56: mature human IgG1 Fc with mouse heavy chain MIgG Vh signal sequence (bold), N-terminal ISAMVRS amino acid residues added (italicized), YTE triple mutant (bold/underlined), G4S linker (italicized), and C-terminal C-myc-tag (underlined), allotype G1m(f) (bold italics)
MGWSCIILFLVATATGVHS_ISAMVRS_DKTHTCPPCPAPELLGGPSVFLFPPKPKDTLYITREPEVTCVVVD

VSHEDPEVKFNWYVDGVEVHNAKTKPREEQYNSTYRVVSVLTVLHQDWLNGKEYKCKVSNKALPAPIEK

TISKAKGQPREPQVYTLPPSR_EEM_TKNQVSLTCLVKGFYPSDIAVEWESNGQPENNYKTTPPVLDSDGS

FFLYSKLTVDKSRWQQGNVFSCSVMHEALHNHYTQKSLSLSPG_GGGGS_EQKLISEEDL

SEQ ID NO: 57: mature human IgG1 Fc with mouse heavy chain MIgG Vh signal sequence (bold), N-terminal ISAMVRS amino acid residues added (italicized), YTE triple mutant (bold/underlined), G4S linker (italicized), C-terminal C-myc-tag (underlined), allotype G1m(fa) (bold italics)
MGWSCIILFLVATATGVHS_ISAMVRS_DKTHTCPPCPAPELLGGPSVFLFPPKPKDTLYITREPEVTCVVVD

VSHEDPEVKFNWYVDGVEVHNAKTKPREEQYNSTYRVVSVLTVLHQDWLNGKEYKCKVSNKALPAPIEK

TISKAKGQPREPQVYTLPPSR_DEL_TKNQVSLTCLVKGFYPSDIAVEWESNGQPENNYKTTPPVLDSDGSF

FLYSKLTVDKSRWQQGNVFSCSVMHEALHNHYTQKSLSLSPG_GGGGS_EQKLISEEDL

SEQ ID NO: 58: mature human IgG1 with mouse heavy chain MIgG1 signal sequence (bold), Cys to Ser substitution (#), C-terminal G4S (italics), and C-terminal IgA peptide (underline), allotype G1m(fa) (bold italics)
MGWSCIILFLVATATGVHSEPKSS(#)DKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAPIEK

TISKAKGQPREPQVYTLPPSR_DEL_TKNQVSLTCLVKGFYPSDIAVEWESNGQPENNYKTTPPVLDSDGSF

FLYSKLTVDKSRWQQGNVFSCSVMHEALHNHYTQKSLSLSPG_GGGGS_QRNPRLRLIRRHPTLRIPPI

SEQ ID NO: 59: mature human IgG1 with mouse heavy chain MIgG1 signal sequence (bold), Cys to Ser substitution (#), M428L, N4345 mutations (bold/underlined), C-terminal G4S (italics), and C-terminal IgA peptide (underline), allotype G1m(fa) (bold italics)
MGWSCIILFLVATATGVHSEPKSS(#)DKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAPIEK

TISKAKGQPREPQVYTLPPSR_DEL_TKNQVSLTCLVKGFYPSDIAVEWESNGQPENNYKTTPPVLDSDGSF

FLYSKLTVDKSRWQQGNVFSCSVLHEALHSHYTQKSLSLSPG_GGGGS_QRNPRLRLIRRHPTLRIPPI

SEQ ID NO: 60: mature human Fc IgG1, $Z_1$ is Cys or Ser, and wherein $X_1$ is Met or Tyr, $X_2$ is Ser or Thr, $X_3$ is Thr or Glu, $X_4$ is Asp or Glu, and $X_5$ is Leu or Met, $X_6$ is Met or Leu, and $X_7$ is Asn or Ser
NVNHKPSNTKVDKKVEPKS$Z_1$DKTHTCPPCPAPELLGGPSVFLFPPKPKDTL$X_1$I$X_2$R$X_3$PEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR$X_4$E$X_5$TKNQVSLTCLVKGFYPSDIAVEWESNGQPENNYKTTPPVLDSDGSFF

LYSKLTVDKSRWQQGNVFSCSV$X_6$HEALH$X_7$HYTQKSLSLSPGK

-continued

SEQ ID NO: 61: mature human Fc IgG1, Cys to Ser substitution (#), and wherein $X_1$ is Met or Tyr, $X_2$ is Ser or Thr, $X_3$ is Thr or Glu, $X_4$ is Asp or Glu, and $X_5$ is Leu or Met, $X_6$ is Met or Leu, and $X_7$ is Asn or Ser
NVNHKPSNTKVDKKVEPKSS(#)DKTHTCPPCPAPELLGGPSVFLFPPKPKDTL$X_1$I$X_2$R$X_3$PEVTCVVVDVS

HEDPEVKFNWYVDGVEVHNAKTKPREEQYNSTYRVVSVLTVLHQDWLNGKEYKCKVSNKALPAPIEKTI

SKAKGQPREPQVYTLPPSR$X_4$E$X_5$TKNQVSLTCLVKGFYPSDIAVEWESNGQPENNYKTTPPVLDSDGSF

FLYSKLTVDKSRWQQGNVFSCSV$X_6$HEALH$X_7$HYTQKSLSLSPGK

SEQ ID NO: 62: mature human IgG1 Fc, Cys to Ser substitution (#), $X_4$ is Asp or Glu, and $X_5$ is Leu or Met
NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR$X_4$E$X_5$TKNQVSLTCLVKGFYPSDIAVEWESNGQPENNYKTTPPVLDSDGSFF

LYSKLTVDKSRWQQGNVFSCSVMHEALHNHYTQKSLSLSPGK

SEQ ID NO: 63: mature human IgG1 Fc, Cys to Ser substitution (#), allotype G1m(f) (bold italics)
NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR*EEM*TKNQVSLTCLVKGFYPSDIAVEWESNGQPENNYKTTPPVLDSDGSFFL

YSKLTVDKSRWQQGNVFSCSVMHEALHNHYTQKSLSLSPGK

SEQ ID NO: 64: mature human IgG1 Fc, Cys to Ser substitution (#), allotype G1m(fa) (bold italics)
NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR*DEL*TKNQVSLTCLVKGFYPSDIAVEWESNGQPENNYKTTPPVLDSDGSFFL

YSKLTVDKSRWQQGNVFSCSVMHEALHNHYTQKSLSLSPGK

SEQ ID NO: 65: mature human IgG1 Fc, Cys to Ser substitution (#), M428L, N434S mutations (Bold/Underlined), allotype G1m(fa) (bold italics)
NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR*DEL*TKNQVSLTCLVKGFYPSDIAVEWESNGQPENNYKTTPPVLDSDGSFFL

YSKLTVDKSRWQQGNVFSCSVLHEAL<u>H</u><u>S</u>HYTQKSLSLSPGK

SEQ ID NO: 66: mature human IgG1 Fc, Cys to Ser substitution (#), M428L, N434S mutations (Bold/Underlined), allotype G1m(f) (bold italics)
NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR*EEM*TKNQVSLTCLVKGFYPSDIAVEWESNGQPENNYKTTPPVLDSDGSFFL

YSKLTVDKSRWQQGNVFSCSV<u>L</u>HEALH<u>S</u>HYTQKSLSLSPGK

SEQ ID NO: 67: mature human IgG1 Fc, Cys to Ser substitution (#), YTE triple mutation (bold and underlined), allotype G1m(fa) (bold italics)
NVNHKPSNTKVDKKVEPKSS(#)DKTHTCPPCPAPELLGGPSVFLFPPKPKDTL<u>YITRE</u>PEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR*DEL*TKNQVSLTCLVKGFYPSDIAVEWESNGQPENNYKTTPPVLDSDGSFFL

YSKLTVDKSRWQQGNVFSCSVMHEALHNHYTQKSLSLSPGK

SEQ ID NO: 68: mature human IgG1 Fc, Cys to Ser substitution (#), YTE triple mutation (bold and underlined), allotype G1m(f) (bold italics)
NVNHKPSNTKVDKKVEPKSS(#)DKTHTCPPCPAPELLGGPSVFLFPPKPKDTL<u>YITRE</u>PEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR*EEM*TKNQVSLTCLVKGFYPSDIAVEWESNGQPENNYKTTPPVLDSDGSFFL

YSKLTVDKSRWQQGNVFSCSVMHEALHNHYTQKSLSLSPGK

SEQ ID NO: 69: mature human Fc IgG1, $Z_1$ is Cys or Ser, and wherein $X_1$ is Met or Tyr, $X_2$ is Ser or Thr, $X_3$ is Thr or Glu, $X_4$ is Asp or Glu, and $X_5$ is Leu or Met, $X_6$ is Met or Leu, and $X_7$ is Asn or Ser
NVNHKPSNTKVDKKVEPKS$Z_1$DKTHTCPPCPAPELLGGPSVFLFPPKPKDTL$X_1$I$X_2$R$X_3$PEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR$X_4$E$X_5$TKNQVSLTCLVKGFYPSDIAVEWESNGQPENNYKTTPPVLDSDGSFF

LYSKLTVDKSRWQQGNVFSCSV$X_6$HEALH$X_7$HYTQKSLSLSPG

SEQ ID NO: 70: mature human Fc IgG1, Cys to Ser substitution (#), and wherein $X_1$ is Met or Tyr, $X_2$ is Ser or Thr, $X_3$ is Thr or Glu, $X_4$ is Asp or Glu, and $X_5$ is Leu or Met, $X_6$ is Met or Leu, and $X_7$ is Asn or Ser
NVNHKPSNTKVDKKVEPKSS(#)DKTHTCPPCPAPELLGGPSVFLFPPKPKDTL$X_1$I$X_2$R$X_3$PEVTCVVVDVS

HEDPEVKFNWYVDGVEVHNAKTKPREEQYNSTYRVVSVLTVLHQDWLNGKEYKCKVSNKALPAPIEKTI

SKAKGQPREPQVYTLPPSR$X_4$E$X_5$TKNQVSLTCLVKGFYPSDIAVEWESNGQPENNYKTTPPVLDSDGSF

FLYSKLTVDKSRWQQGNVFSCSV$X_6$HEALH$X_7$HYTQKSLSLSPG

SEQ ID NO: 71: mature human IgG1 Fc, Cys to Ser substitution (#), $X_4$ is Asp or Glu, and $X_5$ is Leu or Met
NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR$X_4$E$X_5$TKNQVSLTCLVKGFYPSDIAVEWESNGQPENNYKTTPPVLDSDGSFF

LYSKLTVDKSRWQQGNVFSCSVMHEALHNHYTQKSLSLSPG

SEQ ID NO: 72: mature human IgG1 Fc, Cys to Ser substitution (#), allotype G1m(f) (bold italics)
NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR*EEM*TKNQVSLTCLVKGFYPSDIAVEWESNGQPENNYKTTPPVLDSDGSFFL

YSKLTVDKSRWQQGNVFSCSVMHEALHNHYTQKSLSLSPG

SEQ ID NO: 73: mature human IgG1 Fc, Cys to Ser substitution (#), allotype G1m(fa) (bold italics)
NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR*DEL*TKNQVSLTCLVKGFYPSDIAVEWESNGQPENNYKTTPPVLDSDGSFFL

YSKLTVDKSRWQQGNVFSCSVMHEALHNHYTQKSLSLSPG

SEQ ID NO: 74: mature human IgG1 Fc, Cys to Ser substitution (#), M428L, N434S mutations (Bold/Underlined), allotype G1m(fa) (bold italics)
NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR*DEL*TKNQVSLTCLVKGFYPSDIAVEWESNGQPENNYKTTPPVLDSDGSFFL

YSKLTVDKSRWQQGNVFSCSVLHEALHSHYTQKSLSLSPG

SEQ ID NO: 75: mature human IgG1 Fc, Cys to Ser substitution (#), M428L, N434S mutations (Bold/Underlined), allotype G1m(f) (bold italics)
NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR*EEM*TKNQVSLTCLVKGFYPSDIAVEWESNGQPENNYKTTPPVLDSDGSFFL

YSKLTVDKSRWQQGNVFSCSVLHEALHSHYTQKSLSLSPG

SEQ ID NO: 76: mature human IgG1 Fc, Cys to Ser substitution (#), YTE triple mutation (bold and underlined), allotype G1m(fa) (bold italics)
NVNHKPSNTKVDKKVEPKSS(#)DKTHTCPPCPAPELLGGPSVFLFPPKPKDTLYITREPEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR*DEL*TKNQVSLTCLVKGFYPSDIAVEWESNGQPENNYKTTPPVLDSDGSFFL

YSKLTVDKSRWQQGNVFSCSVMHEALHNHYTQKSLSLSPG

-continued

SEQ ID NO: 77: mature human IgG1 Fc, Cys to Ser substitution (#), YTE triple mutation (bold and underlined), allotype G1m(f) (bold italics)
NVNHKPSNTKVDKKVEPKSS(#)DKTHTCPPCPAPELLGGPSVFLFPPKPKDTLYITREPEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR*EEM*TKNQVSLTCLVKGFYPSDIAVEWESNGQPENNYKTTPPVLDSDGSFFL

YSKLTVDKSRWQQGNVFSCSVMHEALHNHYTQKSLSLSPG

SEQ ID NO: 78: mature human Fc IgG1, $Z_1$ is Cys or Ser, and wherein $X_1$ is Met or Tyr, $X_2$ is Ser or Thr, $X_3$ is Thr or Glu, $X_4$ is Asp or Glu, and $X_5$ is Leu or Met, $X_6$ is Met or Leu, and $X_7$ is Asn or Ser
VNHKPSNTKVDKKVEPKS$Z_1$DKTHTCPPCPAPELLGGPSVFLFPPKPKDTL$X_1$I$X_2$R$X_3$PEVTCVVVDVSHE

DPEVKFNWYVDGVEVHNAKTKPREEQYNSTYRVVSVLTVLHQDWLNGKEYKCKVSNKALPAPIEKTISK

AKGQPREPQVYTLPPSR$X_4$E$X_5$TKNQVSLTCLVKGFYPSDIAVEWESNGQPENNYKTTPPVLDSDGSFFL

YSKLTVDKSRWQQGNVFSCSV$X_6$HEALH$X_7$HYTQKSLSLSPGK

SEQ ID NO: 79: mature human Fc IgG1, Cys to Ser substitution (#), and wherein $X_1$ is Met or Tyr, $X_2$ is Ser or Thr, $X_3$ is Thr or Glu, $X_4$ is Asp or Glu, and $X_5$ is Leu or Met, $X_6$ is Met or Leu, and $X_7$ is Asn or Ser
VNHKPSNTKVDKKVEPKSS(#)DKTHTCPPCPAPELLGGPSVFLFPPKPKDTL$X_1$I$X_2$R$X_3$PEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR$X_4$E$X_5$TKNQVSLTCLVKGFYPSDIAVEWESNGQPENNYKTTPPVLDSDGSFF

LYSKLTVDKSRWQQGNVFSCSV$X_6$HEALH$X_7$HYTQKSLSLSPGK

SEQ ID NO: 80: mature human IgG1 Fc, Cys to Ser substitution (#), $X_4$ is Asp or Glu, and $X_5$ is Leu or Met
VNHKPSNTKVDKKVEPKSS(#)DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEYKCKVSNKALPAPIEKTISK

AKGQPREPQVYTLPPSR$X_4$E$X_5$TKNQVSLTCLVKGFYPSDIAVEWESNGQPENNYKTTPPVLDSDGSFFL

YSKLTVDKSRWQQGNVFSCSVMHEALHNHYTQKSLSLSPGK

SEQ ID NO: 81: mature human IgG1 Fc, Cys to Ser substitution (#), allotype G1m(f) (bold italics)
VNHKPSNTKVDKKVEPKSS(#)DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEYKCKVSNKALPAPIEKTISK

AKGQPREPQVYTLPPSR*EEM*TKNQVSLTCLVKGFYPSDIAVEWESNGQPENNYKTTPPVLDSDGSFFLY

SKLTVDKSRWQQGNVFSCSVMHEALHNHYTQKSLSLSPGK

SEQ ID NO: 82: mature human IgG1 Fc, Cys to Ser substitution (#), allotype G1m(fa) (bold italics)
VNHKPSNTKVDKKVEPKSS(#)DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEYKCKVSNKALPAPIEKTISK

AKGQPREPQVYTLPPSR*DEL*TKNQVSLTCLVKGFYPSDIAVEWESNGQPENNYKTTPPVLDSDGSFFLY

SKLTVDKSRWQQGNVFSCSVMHEALHNHYTQKSLSLSPGK

SEQ ID NO: 83: mature human IgG1 Fc, Cys to Ser substitution (#), M428L, N434S mutations (Bold/Underlined), allotype G1m(fa) (bold italics)
VNHKPSNTKVDKKVEPKSS(#)DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEYKCKVSNKALPAPIEKTISK

AKGQPREPQVYTLPPSR*DEL*TKNQVSLTCLVKGFYPSDIAVEWESNGQPENNYKTTPPVLDSDGSFFLY

SKLTVDKSRWQQGNVFSCSVLHEALHSHYTQKSLSLSPGK

SEQ ID NO: 84: mature human IgG1 Fc, Cys to Ser substitution (#), M428L, N434S mutations (Bold/Underlined), allotype G1m(f) (bold italics)
VNHKPSNTKVDKKVEPKSS(#)DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEYKCKVSNKALPAPIEKTISK

AKGQPREPQVYTLPPSR*EEM*TKNQVSLTCLVKGFYPSDIAVEWESNGQPENNYKTTPPVLDSDGSFFLY

SKLTVDKSRWQQGNVFSCSVLHEALHSHYTQKSLSLSPGK

SEQ ID NO: 85: mature human IgG1 Fc, Cys to Ser substitution (#), YTE triple mutation (bold and underlined), allotype G1m(fa) (bold italics)
VNHKPSNTKVDKKVEPKSS(#)DKTHTCPPCPAPELLGGPSVFLFPPKPKDTLYITREPEVTCVVVDVSHE

DPEVKFNWYVDGVEVHNAKTKPREEQYNSTYRVVSVLTVLHQDWLNGKEYKCKVSNKALPAPIEKTISK

AKGQPREPQVYTLPPSR*DEL*TKNQVSLTCLVKGFYPSDIAVEWESNGQPENNYKTTPPVLDSDGSFFLY

SKLTVDKSRWQQGNVFSCSVMHEALHNHYTQKSLSLSPGK

SEQ ID NO: 86: mature human IgG1 Fc, Cys to Ser substitution (#), YTE triple mutation (bold and underlined), allotype G1m(f) (bold italics)
VNHKPSNTKVDKKVEPKSS(#)DKTHTCPPCPAPELLGGPSVFLFPPKPKDTLYITREPEVTCVVVDVSHE

DPEVKFNWYVDGVEVHNAKTKPREEQYNSTYRVVSVLTVLHQDWLNGKEYKCKVSNKALPAPIEKTISK

AKGQPREPQVYTLPPSR*EEM*TKNQVSLTCLVKGFYPSDIAVEWESNGQPENNYKTTPPVLDSDGSFFLY

SKLTVDKSRWQQGNVFSCSVMHEALHNHYTQKSLSLSPGK

SEQ ID NO: 87: mature human Fc IgG1, $Z_1$ is Cys or Ser, and wherein $X_1$ is Met or Tyr, $X_2$ is Ser or Thr, $X_3$ is Thr or Glu, $X_4$ is Asp or Glu, and $X_5$ is Leu or Met, $X_6$ is Met or Leu, and $X_7$ is Asn or Ser
VNHKPSNTKVDKKVEPKS$Z_1$DKTHTCPPCPAPELLGGPSVFLFPPKPKDTL$X_1$I$X_2$R$X_3$PEVTCVVVDVSHE

DPEVKFNWYVDGVEVHNAKTKPREEQYNSTYRVVSVLTVLHQDWLNGKEYKCKVSNKALPAPIEKTISK

AKGQPREPQVYTLPPSR$X_4$E$X_5$TKNQVSLTCLVKGFYPSDIAVEWESNGQPENNYKTTPPVLDSDGSFFL

YSKLTVDKSRWQQGNVFSCSV$X_6$HEALH$X_7$HYTQKSLSLSPG

SEQ ID NO: 88: mature human Fc IgG1, Cys to Ser substitution (#), and wherein $X_1$ is Met or Tyr, $X_2$ is Ser or Thr, $X_3$ is Thr or Glu, $X_4$ is Asp or Glu, and $X_5$ is Leu or Met, $X_6$ is Met or Leu, and $X_7$ is Asn or Ser
VNHKPSNTKVDKKVEPKSS(#)DKTHTCPPCPAPELLGGPSVFLFPPKPKDTL$X_1$I$X_2$R$X_3$PEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR$X_4$E$X_5$TKNQVSLTCLVKGFYPSDIAVEWESNGQPENNYKTTPPVLDSDGSFF

LYSKLTVDKSRWQQGNVFSCSV$X_6$HEALH$X_7$HYTQKSLSLSPG

SEQ ID NO: 89: mature human IgG1 Fc, Cys to Ser substitution (#), $X_4$ is Asp or Glu, and $X_5$ is Leu or Met
VNHKPSNTKVDKKVEPKSS(#)DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEYKCKVSNKALPAPIEKTISK

AKGQPREPQVYTLPPSR$X_4$E$X_5$TKNQVSLTCLVKGFYPSDIAVEWESNGQPENNYKTTPPVLDSDGSFFL

YSKLTVDKSRWQQGNVFSCSVMHEALHNHYTQKSLSLSPG

SEQ ID NO: 90: mature human IgG1 Fc, Cys to Ser substitution (#), allotype G1m(f) (bold italics)
VNHKPSNTKVDKKVEPKSS(#)DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEYKCKVSNKALPAPIEKTISK

AKGQPREPQVYTLPPSR*EEM*TKNQVSLTCLVKGFYPSDIAVEWESNGQPENNYKTTPPVLDSDGSFFLY

SKLTVDKSRWQQGNVFSCSVMHEALHNHYTQKSLSLSPG

SEQ ID NO: 91: mature human IgG1 Fc, Cys to Ser substitution (#), allotype G1m(fa) (bold italics)
VNHKPSNTKVDKKVEPKSS(#)DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEYKCKVSNKALPAPIEKTISK

AKGQPREPQVYTLPPSR*DEL*TKNQVSLTCLVKGFYPSDIAVEWESNGQPENNYKTTPPVLDSDGSFFLY

SKLTVDKSRWQQGNVFSCSVMHEALHNHYTQKSLSLSPG

SEQ ID NO: 92: mature human IgG1 Fc, Cys to Ser substitution (#), M428L, N434S mutations (Bold/Underlined), allotype G1m(fa) (bold italics)
VNHKPSNTKVDKKVEPKSS(#)DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEYKCKVSNKALPAPIEKTISK

AKGQPREPQVYTLPPSR*DEL*TKNQVSLTCLVKGFYPSDIAVEWESNGQPENNYKTTPPVLDSDGSFFLY

SKLTVDKSRWQQGNVFSCSVLHEALHSHYTQKSLSLSPG

SEQ ID NO: 93: mature human IgG1 Fc, Cys to Ser substitution (#), M428L, N434S mutations (Bold/Underlined), allotype G1m(f) (bold italics)
VNHKPSNTKVDKKVEPKSS(#)DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEYKCKVSNKALPAPIEKTISK

AKGQPREPQVYTLPPSR*EEM*TKNQVSLTCLVKGFYPSDIAVEWESNGQPENNYKTTPPVLDSDGSFFLY

SKLTVDKSRWQQGNVFSCSVLHEALHSHYTQKSLSLSPG

SEQ ID NO: 94: mature human IgG1 Fc, Cys to Ser substitution (#), YTE triple mutation (bold and underlined), allotype G1m(fa) (bold italics)
VNHKPSNTKVDKKVEPKSS(#)DKTHTCPPCPAPELLGGPSVFLFPPKPKDTLYITREPEVTCVVVDVSHE

DPEVKFNWYVDGVEVHNAKTKPREEQYNSTYRVVSVLTVLHQDWLNGKEYKCKVSNKALPAPIEKTISK

AKGQPREPQVYTLPPSR*DEL*TKNQVSLTCLVKGFYPSDIAVEWESNGQPENNYKTTPPVLDSDGSFFLY

SKLTVDKSRWQQGNVFSCSVMHEALHNHYTQKSLSLSPG

SEQ ID NO: 95: mature human IgG1 Fc, Cys to Ser substitution (#), YTE triple mutation (bold and underlined), allotype G1m(f) (bold italics)
VNHKPSNTKVDKKVEPKSS(#)DKTHTCPPCPAPELLGGPSVFLFPPKPKDTLYITREPEVTCVVVDVSHE

DPEVKFNWYVDGVEVHNAKTKPREEQYNSTYRVVSVLTVLHQDWLNGKEYKCKVSNKALPAPIEKTISK

AKGQPREPQVYTLPPSR*EEM*TKNQVSLTCLVKGFYPSDIAVEWESNGQPENNYKTTPPVLDSDGSFFLY

SKLTVDKSRWQQGNVFSCSVMHEALHNHYTQKSLSLSPG

SEQ ID NO: 96: mature human Fc IgG1, $J_1$ is Asn or absent, $J_2$ is Lys or absent, $Z_1$ is Cys or Ser, and wherein $X_1$ is Met or Tyr, $X_2$ is Ser or Thr, $X_3$ is Thr or Glu, $X_4$ is Asn or Ala, $X_5$ is Leu or Asp, $X_6$ is Gln or His, $X_7$ is Asp or Glu, and $X_8$ is Leu or Met, $X_9$ is Met or Leu, and $X_{10}$ is Asn or Ser
J$_1$VNHKPSNTKVDKKVEPKSZ$_1$DKTHTCPPCPAPELLGGPSVFLFPPKPKDTLX$_1$IX$_2$RX$_3$PEVTCVVVDVSH EDPEVKFNWYVDGVEVHNAKTKPREEQYX$_4$STYRVVSVLTVX$_5$HX$_6$DWLNGKEYKCKVSNKALPAPIEKTI SKAKGQPREPQVYTLPPSRX$_7$EX$_8$TKNQVSLTCLVKGFYPSDIAVEWESNGQPENNYKTTPPVLDSDGSF

FLYSKLTVDKSRWQQGNVFSCSVX$_9$HEALHX$_{10}$HYTQKSLSLSPGJ$_2$

SEQ ID NO: 97: mature human Fc IgG1, Cys to Ser substitution (#), $J_1$ is Asn or absent, $J_2$ is Lys or absent, and wherein $X_4$ is Asn or Ala, $X_5$ is Leu or Asp, $X_6$ is Gln or His, $X_7$ is Asp or Glu, and $X_8$ is Leu or Met, and $X_{10}$ is Asn or Ser
J$_1$VNHKPSNTKVDKKVEPKSS(#)DKTHTCPPCPAPELLGGPSVFLFPPKPKDTLMISRTPEVTCVVVDVSH EDPEVKFNWYVDGVEVHNAKTKPREEQYX$_4$STYRVVSVLTVX$_5$HX$_6$DWLNGKEYKCKVSNKALPAPIEKTI SKAKGQPREPQVYTLPPSRX$_7$EX$_8$TKNQVSLTCLVKGFYPSDIAVEWESNGQPENNYKTTPPVLDSDGSF

FLYSKLTVDKSRWQQGNVFSCSVMHEALHX$_{10}$HYTQKSLSLSPGJ$_2$

SEQ ID NO: 98: mature human Fc IgG1, Cys to Ser substitution (#), DHS triple mutation (bold and underlined), $J_1$ is Asn or absent, $J_2$ is Lys or absent, wherein $X_4$ is Asn or Ala, $X_7$ is Asp or Glu, and $X_8$ is Leu or Met
J$_1$VNHKPSNTKVDKKVEPKSS(#)DKTHTCPPCPAPELLGGPSVFLFPPKPKDTLMISRTPEVTCVVVDVSH EDPEVKFNWYVDGVEVHNAKTKPREEQYX$_4$STYRVVSVLTVDHHDWLNGKEYKCKVSNKALPAPIEKTIS KAKGQPREPQVYTLPPSRX$_7$EX$_8$TKNQVSLTCLVKGFYPSDIAVEWESNGQPENNYKTTPPVLDSDGSFF

LYSKLTVDKSRWQQGNVFSCSVMHEALHSHYTQKSLSLSPGJ$_2$

SEQ ID NO: 99: mature human Fc IgG1, Cys to Ser substitution (#), DHS triple mutation (bold and underlined), wherein $X_4$ is Asn or Ala, $X_7$ is Asp or Glu, and $X_8$ is Leu or Met
NVNHKPSNTKVDKKVEPKSS(#)DKTHTCPPCPAPELLGGPSVFLFPPKPKDTLMISRTPEVTCVVVDVSH EDPEVKFNWYVDGVEVHNAKTKPREEQYX$_4$STYRVVSVLTVDHHDWLNGKEYKCKVSNKALPAPIEKTIS KAKGQPREPQVYTLPPSRX$_7$EX$_8$TKNQVSLTCLVKGFYPSDIAVEWESNGQPENNYKTTPPVLDSDGSFF

LYSKLTVDKSRWQQGNVFSCSVMHEALHSHYTQKSLSLSPGK

SEQ ID NO: 100: mature human Fc IgG1, Cys to Ser substitution (#), DHS triple mutation (bold and underlined), wherein X$_7$ is Asp or Glu and X$_8$ is Leu or Met
NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYNSTYRVVSVLTVDHHDWLNGKEYKCKVSNKALPAPIEKTIS

KAKGQPREPQVYTLPPSRX$_7$EX$_8$TKNQVSLTCLVKGFYPSDIAVEWESNGQPENNYKTTPPVLDSDGSFF

LYSKLTVDKSRWQQGNVFSCSVMHEALHSHYTQKSLSLSPGK

SEQ ID NO: 101: mature human Fc IgG1, Cys to Ser substitution (#), DHS triple mutation (bold and underlined), allotype G1m(fa) (bold italics)
NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYNSTYRVVSVLTVDHHDWLNGKEYKCKVSNKALPAPIEKTIS

KAKGQPREPQVYTLPPSR*DEL*TKNQVSLTCLVKGFYPSDIAVEWESNGQPENNYKTTPPVLDSDGSFFL

YSKLTVDKSRWQQGNVFSCSVMHEALHSHYTQKSLSLSPGK

SEQ ID NO: 102: mature human Fc IgG1, Cys to Ser substitution (#), DHS triple mutation (bold and underlined), allotype G1m(f) (bold italics)
NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYNSTYRVVSVLTVDHHDWLNGKEYKCKVSNKALPAPIEKTIS

KAKGQPREPQVYTLPPSR*EEM*TKNQVSLTCLVKGFYPSDIAVEWESNGQPENNYKTTPPVLDSDGSFFL

YSKLTVDKSRWQQGNVFSCSVMHEALHSHYTQKSLSLSPGK

SEQ ID NO: 103: mature human Fc IgG1, Cys to Ser substitution (#), DHS triple mutation (bold and underlined), allotype G1m(fa) (bold italics)
VNHKPSNTKVDKKVEPKSS(#)DKTHTCPPCPAPELLGGPSVFLFPPKPKDTLMISRTPEVTCVVVDVSHE

DPEVKFNWYVDGVEVHNAKTKPREEQYNSTYRVVSVLTVDHHDWLNGKEYKCKVSNKALPAPIEKTISK

AKGQPREPQVYTLPPSR*DEL*TKNQVSLTCLVKGFYPSDIAVEWESNGQPENNYKTTPPVLDSDGSFFLY

SKLTVDKSRWQQGNVFSCSVMHEALHSHYTQKSLSLSPGK

SEQ ID NO: 104: mature human Fc IgG1, Cys to Ser substitution (#), DHS triple mutation (bold and underlined), allotype G1m(f) (bold italics)
VNHKPSNTKVDKKVEPKSS(#)DKTHTCPPCPAPELLGGPSVFLFPPKPKDTLMISRTPEVTCVVVDVSHE

DPEVKFNWYVDGVEVHNAKTKPREEQYNSTYRVVSVLTVDHHDWLNGKEYKCKVSNKALPAPIEKTISK

AKGQPREPQVYTLPPSR*EEM*TKNQVSLTCLVKGFYPSDIAVEWESNGQPENNYKTTPPVLDSDGSFFLY

SKLTVDKSRWQQGNVFSCSVMHEALHSHYTQKSLSLSPGK

SEQ ID NO: 105: mature human Fc IgG1, Cys to Ser substitution (#), DHS triple mutation (bold and underlined), allotype G1m(fa) (bold italics)
NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYNSTYRVVSVLTVDHHDWLNGKEYKCKVSNKALPAPIEKTIS

KAKGQPREPQVYTLPPSR*DEL*TKNQVSLTCLVKGFYPSDIAVEWESNGQPENNYKTTPPVLDSDGSFFL

YSKLTVDKSRWQQGNVFSCSVMHEALHSHYTQKSLSLSPGK

SEQ ID NO: 106: mature human Fc IgG1, Cys to Ser substitution (#), DHS triple mutation (bold and underlined), allotype G1m(f) (bold italics)
NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYNSTYRVVSVLTVDHHDWLNGKEYKCKVSNKALPAPIEKTIS

KAKGQPREPQVYTLPPSR*EEM*TKNQVSLTCLVKGFYPSDIAVEWESNGQPENNYKTTPPVLDSDGSFFL

YSKLTVDKSRWQQGNVFSCSVMHEALHSHYTQKSLSLSPGK

SEQ ID NO: 107: mature human Fc IgG1, Cys to Ser substitution (#), DHS triple mutation (bold and underlined), allotype G1m(fa) (bold italics)
VNHKPSNTKVDKKVEPKSS(#)DKTHTCPPCPAPELLGGPSVFLFPPKPKDTLMISRTPEVTCVVVDVSHE

DPEVKFNWYVDGVEVHNAKTKPREEQYNSTYRVVSVLTVDHHDWLNGKEYKCKVSNKALPAPIEKTISK

AKGQPREPQVYTLPPSR*DEL*TKNQVSLTCLVKGFYPSDIAVEWESNGQPENNYKTTPPVLDSDGSFFLY

SKLTVDKSRWQQGNVFSCSVMHEALHSHYTQKSLSLSPG

-continued

SEQ ID NO: 108: mature human Fc IgG1, Cys to Ser substitution (#), DHS triple mutation (bold and underlined), allotype G1m(f) (bold italics)
VNHKPSNTKVDKKVEPKSS(#)DKTHTCPPCPAPELLGGPSVFLFPPKPKDTLMISRTPEVTCVVVDVSHE

DPEVKFNWYVDGVEVHNAKTKPREEQYNSTYRVVSVLTVDHHDWLNGKEYKCKVSNKALPAPIEKTISK

AKGQPREPQVYTLPPSR*EEM*TKNQVSLTCLVKGFYPSDIAVEWESNGQPENNYKTTPPVLDSDGSFFLY

SKLTVDKSRWQQGNVFSCSVMHEALHSHYTQKSLSLSPG

SEQ ID NO: 109: mature human Fc IgG1, Cys to Ser substitution (#), Asn to Ala substitution (*), DHS triple mutation (bold and underlined), wherein X$_7$ is Asp or Glu and X$_8$ is Leu or Met
NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYA(*)STYRVVSVLTVDHHDWLNGKEYKCKVSNKALPAPIEKTI

SKAKGQPREPQVYTLPPSRX$_7$EX$_8$TKNQVSLTCLVKGFYPSDIAVEWESNGQPENNYKTTPPVLDSDGSF

FLYSKLTVDKSRWQQGNVFSCSVMHEALHSHYTQKSLSLSPGK

SEQ ID NO: 110: mature human Fc IgG1, Cys to Ser substitution (#), Asn to Ala substitution (*), DHS triple mutation (bold and underlined), allotype G1m(fa) (bold italics)
NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYA(*)STYRVVSVLTVDHHDWLNGKEYKCKVSNKALPAPIEKTI

SKAKGQPREPQVYTLPPSR*DEL*TKNQVSLTCLVKGFYPSDIAVEWESNGQPENNYKTTPPVLDSDGSFF

LYSKLTVDKSRWQQGNVFSCSVMHEALHSHYTQKSLSLSPGK

SEQ ID NO: 111: mature human Fc IgG1, Cys to Ser substitution (#), Asn to Ala substitution (*), DHS triple mutation (bold and underlined), allotype G1m(f) (bold italics)
NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYA(*)STYRVVSVLTVDHHDWLNGKEYKCKVSNKALPAPIEKTI

SKAKGQPREPQVYTLPPSR*EEM*TKNQVSLTCLVKGFYPSDIAVEWESNGQPENNYKTTPPVLDSDGSFF

LYSKLTVDKSRWQQGNVFSCSVMHEALHSHYTQKSLSLSPGK

SEQ ID NO: 112: mature human Fc IgG1, Cys to Ser substitution (#), Asn to Ala substitution (*), DHS triple mutation (bold and underlined), allotype G1m(fa) (bold italics)
VNHKPSNTKVDKKVEPKSS(#)DKTHTCPPCPAPELLGGPSVFLFPPKPKDTLMISRTPEVTCVVVDVSHE

DPEVKFNWYVDGVEVHNAKTKPREEQYA(*)STYRVVSVLTVDHHDWLNGKEYKCKVSNKALPAPIEKTIS

KAKGQPREPQVYTLPPSR*DEL*TKNQVSLTCLVKGFYPSDIAVEWESNGQPENNYKTTPPVLDSDGSFFL

YSKLTVDKSRWQQGNVFSCSVMHEALHSHYTQKSLSLSPGK

SEQ ID NO: 113: mature human Fc IgG1, Cys to Ser substitution (#), Asn to Ala substitution (*), DHS triple mutation (bold and underlined), allotype G1m(f) (bold italics)
VNHKPSNTKVDKKVEPKSS(#)DKTHTCPPCPAPELLGGPSVFLFPPKPKDTLMISRTPEVTCVVVDVSHE

DPEVKFNWYVDGVEVHNAKTKPREEQYA(*)STYRVVSVLTVDHHDWLNGKEYKCKVSNKALPAPIEKTIS

KAKGQPREPQVYTLPPSR*EEM*TKNQVSLTCLVKGFYPSDIAVEWESNGQPENNYKTTPPVLDSDGSFFL

YSKLTVDKSRWQQGNVFSCSVMHEALHSHYTQKSLSLSPGK

SEQ ID NO: 114: mature human Fc IgG1, Cys to Ser substitution (#), Asn to Ala substitution (*), DHS triple mutation (bold and underlined), allotype G1m(fa) (bold italics)
NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYA(*)STYRVVSVLTVDHHDWLNGKEYKCKVSNKALPAPIEKTI

SKAKGQPREPQVYTLPPSR*DEL*TKNQVSLTCLVKGFYPSDIAVEWESNGQPENNYKTTPPVLDSDGSFF

LYSKLTVDKSRWQQGNVFSCSVMHEALHSHYTQKSLSLSPGK

SEQ ID NO: 115: mature human Fc IgG1, Cys to Ser substitution (#), Asn to Ala substitution (*), DHS triple mutation (bold and underlined), allotype G1m(f) (bold italics)
NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYA(*)STYRVVSVLTVDHHDWLNGKEYKCKVSNKALPAPIEKTI

SKAKGQPREPQVYTLPPSR*EEM*TKNQVSLTCLVKGFYPSDIAVEWESNGQPENNYKTTPPVLDSDGSFF

LYSKLTVDKSRWQQGNVFSCSVMHEALHSHYTQKSLSLSPGK

-continued

SEQ ID NO: 116: mature human Fc IgG1, Cys to Ser substitution (#), Asn to Ala substitution (*),
DHS triple mutation (bold and underlined), allotype G1m(fa) (bold italics)
VNHKPSNTKVDKKVEPKSS(#)DKTHTCPPCPAPELLGGPSVFLFPPKPKDTLMISRTPEVTCVVVDVSHE

DPEVKFNWYVDGVEVHNAKTKPREEQYA(*)STYRVVSVLTVDHHDWLNGKEYKCKVSNKALPAPIEKTIS

KAKGQPREPQVYTLPPSR*DEL*TKNQVSLTCLVKGFYPSDIAVEWESNGQPENNYKTTPPVLDSDGSFFL

YSKLTVDKSRWQQGNVFSCSVMHEALHSHYTQKSLSLSPG

SEQ ID NO: 117: mature human Fc IgG1, Cys to Ser substitution (#), Asn to Ala substitution (*),
DHS triple mutation (bold and underlined), allotype G1m(f) (bold italics)
VNHKPSNTKVDKKVEPKSS(#)DKTHTCPPCPAPELLGGPSVFLFPPKPKDTLMISRTPEVTCVVVDVSHE

DPEVKFNWYVDGVEVHNAKTKPREEQYA(*)STYRVVSVLTVDHHDWLNGKEYKCKVSNKALPAPIEKTIS

KAKGQPREPQVYTLPPSR*EEM*TKNQVSLTCLVKGFYPSDIAVEWESNGQPENNYKTTPPVLDSDGSFFL

YSKLTVDKSRWQQGNVFSCSVMHEALHSHYTQKSLSLSPG

SEQ ID NO: 118: mature human Fc IgG1, J$_1$ is Asn or absent, J$_2$ is Lys or absent, and wherein X$_4$ is
Asn or Ala, X$_5$ is Leu or Asp, X$_6$ is Gln or His, X$_7$ is Asp or Glu, and X$_8$ is Leu or Met, and X$_{10}$ is
Asn or Ser
J$_1$VNHKPSNTKVDKKVEPKSCDKTHTCPPCPAPELLGGPSVFLFPPKPKDTLMISRTPEVTCVVVDVSHE DPEVKFNWYVDGVEVHNAKTKPREEQYX$_4$STYRVVSVLTVX$_5$HX$_6$DWLNGKEYKCKVSNKALPAPIEKTIS KAKGQPREPQVYTLPPSRX$_7$EX$_8$TKNQVSLTCLVKGFYPSDIAVEWESNGQPENNYKTTPPVLDSDGSFF

LYSKLTVDKSRWQQGNVFSCSVMHEALHX$_{10}$HYTQKSLSLSPGJ$_2$

SEQ ID NO: 119: mature human Fc IgG1, DHS triple mutation (bold and underlined), J$_1$ is Asn or
absent, J$_2$ is Lys or absent, and wherein X$_4$ is Asn or Ala, X$_7$ is Asp or Glu, and X$_8$ is Leu or Met
J$_1$VNHKPSNTKVDKKVEPKSCDKTHTCPPCPAPELLGGPSVFLFPPKPKDTLMISRTPEVTCVVVDVSHE DPEVKFNWYVDGVEVHNAKTKPREEQYX$_4$STYRVVSVLTVDHHDWLNGKEYKCKVSNKALPAPIEKTISK AKGQPREPQVYTLPPSRX$_7$EX$_8$TKNQVSLTCLVKGFYPSDIAVEWESNGQPENNYKTTPPVLDSDGSFFL

YSKLTVDKSRWQQGNVFSCSVMHEALHSHYTQKSLSLSPGJ$_2$

SEQ ID NO: 120: mature human Fc IgG1, DHS triple mutation (bold and underlined), wherein X$_4$ is Asn
or Ala, and X$_7$ is Asp or Glu, and X$_8$ is Leu or Met
NVNHKPSNTKVDKKVEPKSCDKTHTCPPCPAPELLGGPSVFLFPPKPKDTLMISRTPEVTCVVVDVSHED PEVKFNWYVDGVEVHNAKTKPREEQYX$_4$STYRVVSVLTVDHHDWLNGKEYKCKVSNKALPAPIEKTISKA KGQPREPQVYTLPPSRX$_7$EX$_8$TKNQVSLTCLVKGFYPSDIAVEWESNGQPENNYKTTPPVLDSDGSFFLY

SKLTVDKSRWQQGNVFSCSVMHEALHSHYTQKSLSLSPGK

SEQ ID NO: 121: mature human Fc IgG1, DHS triple mutation (bold and underlined), wherein X$_7$ is Asp
or Glu and X$_8$ is Leu or Met
NVNHKPSNTKVDKKVEPKSCDKTHTCPPCPAPELLGGPSVFLFPPKPKDTLMISRTPEVTCVVVDVSHED

PEVKFNWYVDGVEVHNAKTKPREEQYNSTYRVVSVLTVDHHDWLNGKEYKCKVSNKALPAPIEKTISKA

KGQPREPQVYTLPPSRX$_7$EX$_8$TKNQVSLTCLVKGFYPSDIAVEWESNGQPENNYKTTPPVLDSDGSFFLY

SKLTVDKSRWQQGNVFSCSVMHEALHSHYTQKSLSLSPGK

SEQ ID NO: 122: mature human Fc IgG1, DHS triple mutation (bold and underlined), allotype G1m(fa)
(bold italics)
NVNHKPSNTKVDKKVEPKSCDKTHTCPPCPAPELLGGPSVFLFPPKPKDTLMISRTPEVTCVVVDVSHED

PEVKFNWYVDGVEVHNAKTKPREEQYNSTYRVVSVLTVDHHDWLNGKEYKCKVSNKALPAPIEKTISKA

KGQPREPQVYTLPPSR*DEL*TKNQVSLTCLVKGFYPSDIAVEWESNGQPENNYKTTPPVLDSDGSFFLYS

KLTVDKSRWQQGNVFSCSVMHEALHSHYTQKSLSLSPGK

SEQ ID NO: 123: mature human Fc IgG1, DHS triple mutation (bold and underlined), allotype G1m(f) (bold italics)
NVNHKPSNTKVDKKVEPKSCDKTHTCPPCPAPELLGGPSVFLFPPKPKDTLMISRTPEVTCVVVDVSHED

PEVKFNWYVDGVEVHNAKTKPREEQYNSTYRVVSVLTVDHHDWLNGKEYKCKVSNKALPAPIEKTISKA

KGQPREPQVYTLPPSR*EEM*TKNQVSLTCLVKGFYPSDIAVEWESNGQPENNYKTTPPVLDSDGSFFLYS

KLTVDKSRWQQGNVFSCSVMHEALHSHYTQKSLSLSPGK

SEQ ID NO: 124: mature human Fc IgG1, DHS triple mutation (bold and underlined), allotype G1m(fa) (bold italics)
VNHKPSNTKVDKKVEPKSCDKTHTCPPCPAPELLGGPSVFLFPPKPKDTLMISRTPEVTCVVVDVSHEDP

EVKFNWYVDGVEVHNAKTKPREEQYNSTYRVVSVLTVDHHDWLNGKEYKCKVSNKALPAPIEKTISKAK

GQPREPQVYTLPPSR*DEL*TKNQVSLTCLVKGFYPSDIAVEWESNGQPENNYKTTPPVLDSDGSFFLYSK

LTVDKSRWQQGNVFSCSVMHEALHSHYTQKSLSLSPGK

SEQ ID NO: 125: mature human Fc IgG1, DHS triple mutation (bold and underlined), allotype G1m(f) (bold italics)
VNHKPSNTKVDKKVEPKSCDKTHTCPPCPAPELLGGPSVFLFPPKPKDTLMISRTPEVTCVVVDVSHEDP

EVKFNWYVDGVEVHNAKTKPREEQYNSTYRVVSVLTVDHHDWLNGKEYKCKVSNKALPAPIEKTISKAK

GQPREPQVYTLPPSR*EEM*TKNQVSLTCLVKGFYPSDIAVEWESNGQPENNYKTTPPVLDSDGSFFLYSK

LTVDKSRWQQGNVFSCSVMHEALHSHYTQKSLSLSPGK

SEQ ID NO: 126: mature human Fc IgG1, DHS triple mutation (bold and underlined), allotype G1m(fa) (bold italics)
NVNHKPSNTKVDKKVEPKSCDKTHTCPPCPAPELLGGPSVFLFPPKPKDTLMISRTPEVTCVVVDVSHED

PEVKFNWYVDGVEVHNAKTKPREEQYNSTYRVVSVLTVDHHDWLNGKEYKCKVSNKALPAPIEKTISKA

KGQPREPQVYTLPPSR*DEL*TKNQVSLTCLVKGFYPSDIAVEWESNGQPENNYKTTPPVLDSDGSFFLYS

KLTVDKSRWQQGNVFSCSVMHEALHSHYTQKSLSLSPGK

SEQ ID NO: 127: mature human Fc IgG1, DHS triple mutation (bold and underlined), allotype G1m(f) (bold italics)
NVNHKPSNTKVDKKVEPKSCDKTHTCPPCPAPELLGGPSVFLFPPKPKDTLMISRTPEVTCVVVDVSHED

PEVKFNWYVDGVEVHNAKTKPREEQYNSTYRVVSVLTVDHHDWLNGKEYKCKVSNKALPAPIEKTISKA

KGQPREPQVYTLPPSR*EEM*TKNQVSLTCLVKGFYPSDIAVEWESNGQPENNYKTTPPVLDSDGSFFLYS

KLTVDKSRWQQGNVFSCSVMHEALHSHYTQKSLSLSPGK

SEQ ID NO: 128: mature human Fc IgG1, DHS triple mutation (bold and underlined), allotype G1m(fa) (bold italics)
VNHKPSNTKVDKKVEPKSCDKTHTCPPCPAPELLGGPSVFLFPPKPKDTLMISRTPEVTCVVVDVSHEDP

EVKFNWYVDGVEVHNAKTKPREEQYNSTYRVVSVLTVDHHDWLNGKEYKCKVSNKALPAPIEKTISKAK

GQPREPQVYTLPPSR*DEL*TKNQVSLTCLVKGFYPSDIAVEWESNGQPENNYKTTPPVLDSDGSFFLYSK

LTVDKSRWQQGNVFSCSVMHEALHSHYTQKSLSLSPG

SEQ ID NO: 129: mature human Fc IgG1, DHS triple mutation (bold and underlined), allotype G1m(f) (bold italics)
VNHKPSNTKVDKKVEPKSCDKTHTCPPCPAPELLGGPSVFLFPPKPKDTLMISRTPEVTCVVVDVSHEDP

EVKFNWYVDGVEVHNAKTKPREEQYNSTYRVVSVLTVDHHDWLNGKEYKCKVSNKALPAPIEKTISKAK

GQPREPQVYTLPPSR*EEM*TKNQVSLTCLVKGFYPSDIAVEWESNGQPENNYKTTPPVLDSDGSFFLYSK

LTVDKSRWQQGNVFSCSVMHEALHSHYTQKSLSLSPG

SEQ ID NO: 130: mature human Fc IgG1, Asn to Ala substitution (*), DHS triple mutation (bold and underlined), wherein $X_7$ is Asp or Glu and $X_8$ is Leu or Met
NVNHKPSNTKVDKKVEPKSCDKTHTCPPCPAPELLGGPSVFLFPPKPKDTLMISRTPEVTCVVVDVSHED

PEVKFNWYVDGVEVHNAKTKPREEQYA(*)STYRVVSVLTVDHHDWLNGKEYKCKVSNKALPAPIEKTISK

AKGQPREPQVYTLPPSR$X_7$E$X_8$TKNQVSLTCLVKGFYPSDIAVEWESNGQPENNYKTTPPVLDSDGSFFL

YSKLTVDKSRWQQGNVFSCSVMHEALHSHYTQKSLSLSPGK

-continued

SEQ ID NO: 131: mature human Fc IgG1, Asn to Ala substitution (*), DHS triple mutation (bold and underlined), allotype G1m(fa) (bold italics)
NVNHKPSNTKVDKKVEPKSCDKTHTCPPCPAPELLGGPSVFLFPPKPKDTLMISRTPEVTCVVVDVSHED

PEVKFNWYVDGVEVHNAKTKPREEQYA(*)STYRVVSVLTVDHHDWLNGKEYKCKVSNKALPAPIEKTISK

AKGQPREPQVYTLPPSR*DEL*TKNQVSLTCLVKGFYPSDIAVEWESNGQPENNYKTTPPVLDSDGSFFLY

SKLTVDKSRWQQGNVFSCSVMHEALHSHYTQKSLSLSPGK

SEQ ID NO: 132: mature human Fc IgG1, Asn to Ala substitution (*), DHS triple mutation (bold and underlined), allotype G1m(f) (bold italics)
NVNHKPSNTKVDKKVEPKSCDKTHTCPPCPAPELLGGPSVFLFPPKPKDTLMISRTPEVTCVVVDVSHED

PEVKFNWYVDGVEVHNAKTKPREEQYA(*)STYRVVSVLTVDHHDWLNGKEYKCKVSNKALPAPIEKTISK

AKGQPREPQVYTLPPSR*EEM*TKNQVSLTCLVKGFYPSDIAVEWESNGQPENNYKTTPPVLDSDGSFFLY

SKLTVDKSRWQQGNVFSCSVMHEALHSHYTQKSLSLSPGK

SEQ ID NO: 133: mature human Fc IgG1, Asn to Ala substitution (*), DHS triple mutation (bold and underlined), allotype G1m(fa) (bold italics)
VNHKPSNTKVDKKVEPKSCDKTHTCPPCPAPELLGGPSVFLFPPKPKDTLMISRTPEVTCVVVDVSHEDP

EVKFNWYVDGVEVHNAKTKPREEQYA(*)STYRVVSVLTVDHHDWLNGKEYKCKVSNKALPAPIEKTISKA

KGQPREPQVYTLPPSR*DEL*TKNQVSLTCLVKGFYPSDIAVEWESNGQPENNYKTTPPVLDSDGSFFLYS

KLTVDKSRWQQGNVFSCSVMHEALHSHYTQKSLSLSPGK

SEQ ID NO: 134: mature human Fc IgG1, Asn to Ala substitution (*), DHS triple mutation (bold and underlined), allotype G1m(f) (bold italics)
VNHKPSNTKVDKKVEPKSCDKTHTCPPCPAPELLGGPSVFLFPPKPKDTLMISRTPEVTCVVVDVSHEDP

EVKFNWYVDGVEVHNAKTKPREEQYA(*)STYRVVSVLTVDHHDWLNGKEYKCKVSNKALPAPIEKTISKA

KGQPREPQVYTLPPSR*EEM*TKNQVSLTCLVKGFYPSDIAVEWESNGQPENNYKTTPPVLDSDGSFFLYS

KLTVDKSRWQQGNVFSCSVMHEALHSHYTQKSLSLSPGK

SEQ ID NO: 135: mature human Fc IgG1, Asn to Ala substitution (*), DHS triple mutation (bold and underlined), allotype G1m(fa) (bold italics)
NVNHKPSNTKVDKKVEPKSCDKTHTCPPCPAPELLGGPSVFLFPPKPKDTLMISRTPEVTCVVVDVSHED

PEVKFNWYVDGVEVHNAKTKPREEQYA(*)STYRVVSVLTVDHHDWLNGKEYKCKVSNKALPAPIEKTISK

AKGQPREPQVYTLPPSR*DEL*TKNQVSLTCLVKGFYPSDIAVEWESNGQPENNYKTTPPVLDSDGSFFLY

SKLTVDKSRWQQGNVFSCSVMHEALHSHYTQKSLSLSPGK

SEQ ID NO: 136: mature human Fc IgG1, Asn to Ala substitution (*), DHS triple mutation (bold and underlined), allotype G1m(f) (bold italics)
NVNHKPSNTKVDKKVEPKSCDKTHTCPPCPAPELLGGPSVFLFPPKPKDTLMISRTPEVTCVVVDVSHED

PEVKFNWYVDGVEVHNAKTKPREEQYA(*)STYRVVSVLTVDHHDWLNGKEYKCKVSNKALPAPIEKTISK

AKGQPREPQVYTLPPSR*EEM*TKNQVSLTCLVKGFYPSDIAVEWESNGQPENNYKTTPPVLDSDGSFFLY

SKLTVDKSRWQQGNVFSCSVMHEALHSHYTQKSLSLSPGK

SEQ ID NO: 137: mature human Fc IgG1, Asn to Ala substitution (*), DHS triple mutation (bold and underlined), allotype G1m(fa) (bold italics)
VNHKPSNTKVDKKVEPKSCDKTHTCPPCPAPELLGGPSVFLFPPKPKDTLMISRTPEVTCVVVDVSHEDP

EVKFNWYVDGVEVHNAKTKPREEQYA(*)STYRVVSVLTVDHHDWLNGKEYKCKVSNKALPAPIEKTISKA

KGQPREPQVYTLPPSR*DEL*TKNQVSLTCLVKGFYPSDIAVEWESNGQPENNYKTTPPVLDSDGSFFLYS

KLTVDKSRWQQGNVFSCSVMHEALHSHYTQKSLSLSPG

SEQ ID NO: 138: mature human Fc IgG1, Asn to Ala substitution (*), DHS triple mutation (bold and underlined), allotype G1m(f) (bold italics)
VNHKPSNTKVDKKVEPKSCDKTHTCPPCPAPELLGGPSVFLFPPKPKDTLMISRTPEVTCVVVDVSHEDP

EVKFNWYVDGVEVHNAKTKPREEQYA(*)STYRVVSVLTVDHHDWLNGKEYKCKVSNKALPAPIEKTISKA

KGQPREPQVYTLPPSR*EEM*TKNQVSLTCLVKGFYPSDIAVEWESNGQPENNYKTTPPVLDSDGSFFLYS

KLTVDKSRWQQGNVFSCSVMHEALHSHYTQKSLSLSPG

As defined herein, an Fc domain includes two Fc domain monomers that are dimerized by the interaction between the $C_H3$ antibody constant domains, as well as one or more disulfide bonds that form between the hinge domains of the two dimerizing Fc domain monomers. An Fc domain forms the minimum structure that binds to an Fc receptor, e.g., Fc-gamma receptors (i.e., Fcγ receptors (FcγR)), Fc-alpha receptors (i.e., Fcα receptors (FcαR)), Fc-epsilon receptors (i.e., Fcε receptors (FcεR)), and/or the neonatal Fc receptor (FcRn). In some embodiments, an Fc domain of the present invention binds to an Fcγ receptor (e.g., FcRn, FcγRI (CD64), FcγRIIa (CD32), FcγRIIb (CD32), FcγRIIIa (CD16a), FcγRIIIb (CD16b)), and/or FcγRIV and/or the neonatal Fc receptor (FcRn).

In some embodiments, the Fc domain monomer or Fc domain of the invention is an aglycosylated Fc domain monomer or Fc domain (e.g., an Fc domain monomer or and Fc domain that maintains engagement to an Fc receptor (e.g., FcRn). For example, the Fc domain is an aglycosylated IgG1 variants that maintains engagement to an Fc receptor (e.g., an IgG1 having an amino acid substitution at N297 and/or T299 of the glycosylation motif). Exemplary aglycosylated Fc domains and methods for making aglycosylated Fc domains are known in the art, for example, as described in Sazinsky S. L. et al., Aglycosylated immunoglobulin G1 variants productively engage activating Fc receptors, PNAS, 2008, 105(51):20167-20172, which is incorporated herein in its entirety.

In some embodiments, the Fc domain or Fc domain monomer of the invention is engineered to enhance binding to the neonatal Fc receptor (FcRn). For example, the Fc domain may include the triple mutation corresponding to M252Y/S254T/T256E (YTE) (e.g., an IgG1, such as a human or humanized IgG1 having a YTE mutation, for example SEQ ID NO: 33, SEQ ID NO: 36, SEQ ID NO: 38, SEQ ID NO: 39, SEQ ID NO: 41, SEQ ID NO: 42, SEQ ID NO: 43, SEQ ID NO: 52, SEQ ID NO: 53, SEQ ID NO: 56, or SEQ ID NO: 57). The Fc domain may include the double mutant corresponding to M428L/N434S (LS) (e.g., an IgG1, such as a human or humanized IgG1 having an LS mutation, such as SEQ ID NO: 37, SEQ ID NO: 39, SEQ ID NO: 44, SEQ ID NO: 45, SEQ ID NO: 46, SEQ ID NO: 50, SEQ ID NO: 51, SEQ ID NO: 54, SEQ ID NO: 55, or SEQ ID NO: 59). The Fc domain may include the single mutant corresponding to N434H (e.g., an IgG1, such as a human or humanized IgG1 having an N434H mutation). The Fc domain may include the single mutant corresponding to C220S (e.g., an IgG1, such as a human or humanized IgG1 having a C220S mutation, such as SEQ ID NO: 34, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 58, SEQ ID NO: 59, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, and SEQ ID NO: 95). The Fc domain may include a quadruple mutant corresponding to C220S/L309D/Q311 H/N434S (CDHS) (e.g., an IgG1, such as a human or humanized IgG1 having a DHS mutation, such as SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, and SEQ ID NO: 117). The Fc domain may include a triple mutant corresponding to L309D/Q311 H/N434S (DHS) (e.g., an IgG1, such as a human or humanized IgG1 having a DHS mutation, such as SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, and SEQ ID NO: 138). The Fc domain may include a combination of one or more of the above-described mutations that enhance binding to the FcRn. Enhanced binding to the FcRn may increase the half-life Fc domain-containing conjugate. For example, incorporation of one or more amino acid mutations that increase binding to the FcRn (e.g., a YTE mutation, an LS mutation, or an N434H mutation) may increase the half-life of the conjugate by 5%, 10%, 15%, 20%, 30%, 40%, 50%, 60%, 70%, 80%, 90%. 100%, 200%, 300%, 400%, 500% or more relative to a conjugate having the corresponding Fc domain without the mutation that enhances FcRn binding. Exemplary Fc domains with enhanced binding to the FcRN and methods for making Fc domains having enhanced binding to the FcRN are known in the art, for example, as described in Maeda, A. et al., Identification of human IgG1 variant with enhanced FcRn binding and without increased binding to rheumatoid factor autoantibody, MABS, 2017, 9(5):844-853, which is incorporated herein in its entirety.

As used herein, an amino acid "corresponding to" a particular amino acid residue (e.g., of a particular SEQ ID NO.) should be understood to include any amino acid residue that one of skill in the art would understand to align to the particular residue (e.g., of the particular sequence). For example, any one of SEQ ID NOs: 1-138 may be mutated to include a YTE mutation, an LS mutation, and/or an N434H mutation by mutating the "corresponding residues" of the amino acid sequence.

As used herein, a sulfur atom "corresponding to" a particular cysteine residue of a particular SEQ ID NO. should be understood to include the sulfur atom of any cysteine residue that one of skill in the art would understand to align to the particular cysteine of the particular sequence. The protein sequence alignment of human IgG1 (UniProtKB: P01857; SEQ ID NO: 142), human IgG2 (UniProtKB: P01859; SEQ ID NO: 143), human IgG3 (UniProtKB: P01860; SEQ ID NO: 144), and human IgG4 (UniProtKB: P01861; SEQ ID NO: 145) is provided below (aligned with Clustal Omega Multiple Pairwise Alignment). The alignment indicates cysteine residues (e.g., sulfur atoms of cysteine residues) that "correspond to" one another (in boxes and indicated by the · symbol). One of skill in the art would readily be able to perform such an alignment with any IgG variant of the invention to determine the sulfur atom of a cysteine that corresponds to any sulfur atom of a particular cysteine of a particular SEQ ID NO. described herein (e.g., any one of SEQ ID NOs: 1-138). For example, one of skill in the art would readily be able to determine that Cys10 of SEQ ID NO: 10 (the first cysteine of the conserved CPPC motif of the hinge region of the Fc domain) corresponds to, for example, Cys109 of IgG1, Cys106 of IgG2, Cys156 of IgG3, Cys29 of SEQ ID NO: 1, Cys9 of SEQ ID NO: 2, Cys30 of SEQ ID NO: 3, or Cys10 of SEQ ID NO: 10. In some embodiments, the Fc domain or Fc domain monomer of the invention has the sequence of any one of SEQ ID NOs: 39-138 may further include additional amino acids at the N-terminus (Xaa)x and/or additional amino acids at the C-terminus (Xaa)z, wherein Xaa is any amino acid and x and z are a whole number greater than or equal to zero, generally less than 100, preferably less than 10 and more preferably 0, 1, 2, 3, 4, or 5. In some embodiments, the additional amino acids are least 70% (e.g., 70%, 75%, 80%, 85%, 90%, 95%, 96%, 97%, 98%, 99%, or 100%) identical to one or more consecutive amino acids of SEQ ID NO: 81. For example, the additional amino acids may be a single amino acid on the C-terminus corresponding to Lys330 of IgG1 (SEQ ID NO: 119).

As used herein, a nitrogen atom "corresponding to" a particular lysine residue of a particular SEQ ID NO. should be understood to include the nitrogen atom of any lysine residue that one of skill in the art would understand to align to the particular lysine of the particular sequence. The protein sequence alignment of human IgG1 (UniProtKB: P01857; SEQ ID NO: 142), human IgG2 (UniProtKB: P01859; SEQ ID NO: 143), human IgG3 (UniProtKB: P01860; SEQ ID NO: 144), and human IgG4 (UniProtKB: P01861; SEQ ID NO: 145) is provided below (aligned with Clustal Omega Multiple Pairwise Alignment). The alignment indicates lysine residues (e.g., nitrogen atoms of lysine residues) that "correspond to" one another (in boxes and indicated by the * symbol). One of skill in the art would readily be able to perform such an alignment with any IgG variant of the invention to determine the nitrogen atom of a lysine that corresponds to any nitrogen atom of a particular lysine of a particular SEQ ID NO. described herein (e.g., any one of SEQ ID NOs: 1-138). For example, one of skill in the art would readily be able to determine that Lys35 of SEQ ID NO: 10 corresponds to, for example, Lys129 of IgG1, Lys126 of IgG2, Lys176 of IgG3, Lys51 of SEQ ID NO: 1, Lys31 of SEQ ID NO: 2, Lys50 of SEQ ID NO: 3, or Lys30 of SEQ ID NO: 10.

Protein sequence alignment of IgG1 (SEQ ID NO: 142), IgG2 (SEQ ID NO: 143), IgG3 (SEQ ID NO:

```
human_IgG1    ASTKGPSVFPLAPSSKSTSGGTAALGCLVKDYFPEPVTVSWNSGALTSGVHTFPAVLQSS
human_IgG2    ASTKGPSVFPLAPCSRSTSESTAALGCLVKDYFPEPVTVSWNSGALTSGVHTFPAVLQSS
human_IgG3    ASTKGPSVFPLAPCSRSTSGGTAALGCLVKDYFPEPVTVSWNSGALTSGVHTFPAVLQSS
human_IgG4    ASTKGPSVFPLAPSSKSTSESTAALGCLVRDYFPEPVTVSWNSGALTSGVHTFPAVLQSS
                 *           *              * * human_IgG1    GLYSLSSVVTVPSSSLGTQTYICNVNHKPSNTKVDKKVE--------------------
human_IgG2    GLYSLSSVVTVPSSNFGTQTYICNVDHKPSNTKVDKTVERKC-----------------
human_IgG3    GLYSLSSVVTVPSSSLGTQTYICNVNHKPSNTKVDKRVELKTPLGDTTHTCPRCPEPKSC
humaN_IgG4    GLYSLSSVVTVPSSSLGTKTYTCNVDHKPSNTKVDKRVESK-----------------
                                  *       *       *  * human_IgG1    -----------------------PKSCDKTHTCPPCPAPELLGGPSVFLFPPKPKDT
human_IgG2    ------------------------C---VECPPCPAPP-VAGPSVFLFPPKPKDT
human_IgG3    DIPPPCPRCPEPKSCDIPPPCPRCPEPKSCDIPPPCPRCPAPELLGGPSVFLFPPKPKDT
human_IgG4    -----------------------YGPPCPSCPAPEFLGGPSVFLFPPKPKDT
                                       *  *    *  *                * * human_IgG1    LMISRTPEVTCVVVDVSHEDPEVKFNWYVDGVEVHNAKTKPREEQYNSTYRVVSVLTVLH
human_IgG2    LMISRTPEVTCVVVDVSHEDPEVQFNWYVDGVEVHNAKTKPREEQFNSTFRVVSVLTVLH
human_IgG3    LMISRTPEVTCVVVDVSHEDPEVQFKWYVDGVEVHNAKTKPREEQYNSTFRVVSVLTVLH
humaN_IgG4    LMISRTPEVTCVVVDVSQEDPEVQFNWYVDGVEVHNAKTKPREEQFNSTYRVVSVLTVLH
                       *                              * * human_IgG1    QDWLNGKEYKCKVSNKALPAPIEKTISKAKGQPREPQVYILPPSRDELTKNQVSLTCLVK
human_IgG2    QDWLNGKEYKCKVSNKGLPAPIEKTISKTKGQPREPQVYILPPSREEMTKNQVSLTCLVK
human_IgG3    QDWLNGKEYKCKVSNKALPAPIEKTISKTKGQPREPQVYILPPSREEMTKNQVSLTCLVK
human_IgG4    QDWLNGKEYKCKVSNKGLPSSIEKTISKAKGQPREPQVYILPPSQEEMTKNQVSLTCLVK
                   *  * ***      *    * *                   *    *     * human_IgG1    GFYPSDIAVEWESNGQPENNYKTTPPVLDSDGSFFLYSKLTVDKSRWQQGNVFSCSVMHE
human_IgG2    GFYPSDISVEWESNGQPENNYKTTPPMLDSDGSFFLYSKLTVDKSRWQQGNVFSCSVMHE
human_IgG3    GFYPSDIAVEWESSGQPENNYKTTPPMLDSDGSFFLYSKLTVDKSRWQQGNIFSCSVMHE
human_IgG4    GFYPSDIAVEWESNGQPENNYKITPPVLDSDGSFFLYSKLTVDKSRWQQGNVFSCSVMHE
                                  *                     *          * human_IgG1    ALHNHYTQKSLSLSPGK
human_IgG2    ALHNHYTQKSLSLSPGK
human_IgG3    ALHNRFTQKSLSLSPGK
human_IgG4    ALHNHYTQKSLSLSPGK
                     *        *
```

Activation of Immune Cells

Fc-gamma receptors (FcγRs) bind the Fc portion of immunoglobulin G (IgG) and play important roles in immune activation and regulation. For example, the IgG Fc domains in immune complexes (ICs) engage FcγRs with high avidity, thus triggering signaling cascades that regulate immune cell activation. The human FcγR family contains several activating receptors (FcγRI, FcγRIIa, FcγRIIc, FcγRIIIa, and FcγRIIIb) and one inhibitory receptor (FcγRIIb). FcγR signaling is mediated by intracellular domains that contain immune tyrosine activating motifs (ITAMs) for activating FcγRs and immune tyrosine inhibitory motifs (ITIM) for inhibitory receptor FcγRIIb. In some embodiments, FcγR binding by Fc domains results in ITAM phosphorylation by Src family kinases; this activates Syk family kinases and induces downstream signaling networks, which include PI3K and Ras pathways.

In the conjugates described herein, the portion of the conjugates including monomers or dimers of neuraminidase inhibitors bind to and inhibits viral neuraminidase leading to inhibition of viral replication, while the Fc domain portion of the conjugates bind to FcγRs (e.g., FcRn, FcγRI, FcγRIIa, FcγRIIc, FcγRIIIa, and FcγRIIIb) on immune cells and activate phagocytosis and effector functions, such as antibody-dependent cell-mediated cytotoxicity (ADCC), thus leading to the engulfment and destruction of viral particles by immune cells and further enhancing the antiviral activity of the conjugates. Examples of immune cells that may be activated by the conjugates described herein include, but are not limited to, macrophages, neutrophils, eosinophils, basophils, lymphocytes, follicular dendritic cells, natural killer cells, and mast cells.

Tissue Distribution

After a therapeutic enters the systemic circulation, it is distributed to the body's tissues. Distribution is generally uneven because of different in blood perfusion, tissue binding, regional pH, and permeability of cell membranes. The entry rate of a drug into a tissue depends on the rate of blood flow to the tissue, tissue mass, and partition characteristics between blood and tissue. Distribution equilibrium (when the entry and exit rates are the same) between blood and tissue is reached more rapidly in richly vascularized areas, unless diffusion across cell membranes is the rate-limiting step. The size, shape, charge, target binding, FcRn and target binding mechanisms, route of administration, and formulation affect tissue distribution.

In some instances, the conjugates described herein may be optimized to distribute to lung tissue. In some instances, the conjugates have a concentration ratio of distribution in epithelial lining fluid of at least 30% the concentration of the conjugates in plasma within 2 hours after administration. In certain embodiments, ratio of the concentration is at least 45% within 2 hours after administration. In some embodiments, the ratio of concentration is at least 55% within 2 hours after administration. In particular, the ratio of concentration is at least 60% within 2 hours after administration. As shown in Example 190 and FIG. 98, by 2 hours post injection, a conjugate having an Fc domain (SEQ ID NO: 73) ELF levels are surprisingly ~60% of plasma exposure levels as measured by AUC across the rest of the time course indicating nearly immediate partitioning of the conjugate from plasma to the ELF in the lung. This demonstrates that an Fc containing conjugate rapidly distributes to lung, and maintains high concentrations in lung relative to levels in plasma.

IV. Albumin Proteins and Albumin Protein-Binding Peptides

Albumin Proteins

An albumin protein of the invention may be a naturally-occurring albumin or a variant thereof, such as an engineered variant of a naturally-occurring albumin protein. Variants include polymorphisms, fragments such as domains and sub-domains, and fusion proteins. An albumin protein may include the sequence of an albumin protein obtained from any source. Preferably the source is mammalian, such as human or bovine. Most preferably, the albumin protein is human serum albumin (HSA), or a variant thereof. Human serum albumins include any albumin protein having an amino acid sequence naturally occurring in humans, and variants thereof. An albumin protein coding sequence is obtainable by methods know to those of skill in the art for isolating and sequencing cDNA corresponding to human genes. An albumin protein of the invention may include the amino acid sequence of human serum albumin (HSA), provided in SEQ ID NO: 139 or SEQ ID NO: 140, or the amino acid sequence of mouse serum albumin (MSA), provided in SEQ ID NO: 141, or a variant or fragment thereof, preferably a functional variant or fragment thereof. A fragment or variant may or may not be functional, or may retain the function of albumin to some degree. For example, a fragment or variant may retain the ability to bind to an albumin receptor, such as HSA or MSA, by at least 10%, 20%, 30%, 40%, 50%, 60%, 70%, 80%, 90%, 100%, or 105% of the ability of the parent albumin (e.g., the parent albumin from which the fragment or variant is derived). Relative binding ability may be determined by methods known in the art, such as by surface plasmon resonance.

The albumin protein may be a naturally-occurring polymorphic variant of an albumin protein, such as human serum albumin. Generally, variants or fragments of human serum albumin will have at least 5%, 10%, 15%, 20%, 30%, 40%, 50%, 60%, or 70%, and preferably 80%, 90%, 95%, 100%, or 105% or more of human serum albumin or mouse serum albumin's ligand binding activity.

The albumin protein may include the amino acid sequence of bovine serum albumin. Bovine serum albumin proteins include any albumin having an amino acid sequence naturally occurring in cows, for example, as described by Swissprot accession number P02769, and variants thereof as defined herein. Bovine serum albumin proteins also include fragments of full-length bovine serum albumin or variants thereof, as defined herein.

The albumin protein may comprise the sequence of an albumin derived from one of serum albumin from dog (e.g., Swissprot accession number P49822-1), pig (e.g., Swissprot accession number P08835-1), goat (e.g., Sigma product no. A2514 or A4164), cat (e.g., Swissprot accession number P49064-1), chicken (e.g., Swissprot accession number P19121-1), ovalbumin (e.g., chicken ovalbumin) (e.g., Swissprot accession number P01012-1), turkey ovalbumin (e.g., Swissprot accession number O73860-1), donkey (e.g., Swissprot accession number Q5XLE4-1), guinea pig (e.g., Swissprot accession number Q6WDN9-1), hamster (e.g., as described in DeMarco et al. International Journal for Parasitology 37(11): 1201-1208 (2007)), horse (e.g., Swissprot accession number P35747-1), rhesus monkey (e.g., Swissprot accession number Q28522-1), mouse (e.g., Swissprot accession number P07724-1), pigeon (e.g., as defined by Khan et al. Int. J. Biol. Macromol. 30(3-4), 171-8 (2002)), rabbit (e.g., Swissprot accession number P49065-1), rat (e.g., Swissprot accession number P02770-1) or sheep (e.g., Swissprot accession number P14639-1), and includes variants and fragments thereof as defined herein. Many naturally-occurring mutant forms of albumin are known to those skilled in the art. Naturally-occurring mutant forms of albumin are described in, for example, Peters, et al. *All About Albumin: Biochemistry, Genetics and Medical Applications*, Academic Press, Inc., San Diego, Calif., p. 170-181 (1996).

Albumin proteins of the invention include variants of naturally-occurring albumin proteins. A variant albumin refers to an albumin protein having at least one amino acid mutation, such as an amino acid mutation generated by an insertion, deletion, or substitution, either conservative or non-conservative, provided that such changes result in an albumin protein for which at least one basic property has not been significantly altered (e.g., has not been altered by more than 5%, 10%, 15%, 20%, 25%, 30%, 35%, or 40%). Exemplary properties which may define the activity of an albumin protein include binding activity (e.g., including binding specificity or affinity to bilirubin, or a fatty acid such as a long-chain fatty acid), osmolarity, or behavior in a certain pH-range.

Typically an albumin protein variant will have at least 40%, at least 50%, at least 60%, and preferably at least 70%, at least 80%, at least 90%, at least 95%, at least 96%, at least 97%, at least 98%, or at least 99% amino acid sequence identity with a naturally-occurring albumin protein, such as the albumin protein of any one of SEQ ID NOs: 139-141.

Methods for the production and purification of recombinant human albumins are well-established (Sleep et al. Biotechnology, 8(1):42-6 (1990)), and include the production of recombinant human albumin for pharmaceutical applications (Bosse et al. J Clin Pharmacol 45(1):57-67 (2005)). The three-dimensional structure of HSA has been elucidated by X-ray crystallography (Carter et al. Science. 244(4909): 1195-8(1998)); Sugio et al. Protein Eng. 12(6): 439-46 (1999)). The HSA polypeptide chain has 35 cysteine residues, which form 17 disulfide bonds, and one unpaired (e.g., free) cysteine at position 34 of the mature protein. Cys-34 of HSA has been used for conjugation of molecules to albumin (Leger et al. Bioorg Med Chem Lett 14(17): 4395-8 (2004); Thibaudeau et al. Bioconjug Chem 16(4): 1000-8 (2005)), and provides a site for site-specific conjugation.

SEQ ID NO: 139 (Human serum albumin (HSA), variant 1) DAHKSEVAHRFKDLGEENFKALVLIAFAQYLQQC-PFEDHVKLVNEVTEFAKTCVADESAENCDKSLHTLF GDKLCTVATLRETYGEMADCCAKQEPERNECFLQ-HKDDNPNLPRLVRPEVDVMCTAFHDNEETFLKKYL YEIARRHPYFYAPELLFFAKRYKAAFTECCQAAD-KAACLLPKLDELRDEGKASSAKQRLKCASLQKFGER AFKAWAVARLSQRFPKAEFAEVSKLVTDLTKVHTEC-CHGDLLECADDRADLAKYICENQDSISSKLKECC EKPLLEKSHCLAEVENDEMPADLPSLAADFVES-KDVCKNYAEAKDVFLGMFLYEYARRHPDYSVV-LLLRL AKTYETTLEKCCAAADPHECYAKVFDEF-KPLVEEPQNLIKQNCELFEQLGEYKFQNALLVRYT-KKVPQVS TPTLVEVSRNLGKVGSKCCKHPEAKRMP-CAEDYLSVVLNQLCVLHEKTPVSDRVTKCCTES-LVNRRPCF SALEVDETYVPKEFNAETFTFHADICT-LSEKERQIKKQTALVELVKHKPKATKEQLKAVMDD-FAAFVEKCC KADDKETCFAEEGKKLVAASQAALGL SEQ ID NO: 140 (Human serum albumin (HSA), variant 2) RGVFRRDAHKSEVAHRFKDLGEENFKALVLIA-FAQYLQQCPFEDHVKLVNEVTEFAKTCVADESAE-NCD KSLHTLFGDKLCTVATLRETYGEMADCCAKQ-EPERNECFLQHKDDNPNLPRLVRPEVDVMCTAFHD-NEE TFLKKYLYEIARRHPYFYAPELLFFAKRYKAAF-TECCQAADKAACLLPKLDELRDEGKASSAKQRLK-CASL QKFGERAFKAWAVARLSQRFPKAEFAEVSK-LVTDLTKVHTECCHGDLLECADDRADLAKYICENQ-DSISS KLKECCEKPLLEKSHCLAEVENDEMPADLPS-LAADFVESKDVCKNYAEAKDVFLGMFLYEYAR-RHPDYSV VLLLRLAKTYETTLEKCCAAADPHECYA-KVFDEFKPLVEEPQNLIKQNCELFEQLGEYKFQNALL-VRYTKK VPQVSTPTLVEVSRNLGKVGSKCCKHPEA-KRMPCAEDYLSVVLNQLCVLHEKTPVSDRVTKC-CTESLVN RRPCFSALEVDETYVPKEFNAETFTFHAD-ICTLSEKERQIKKQTALVELVKHKPKATKEQLK-AVMDDFAAF VEKCCKADDKETCFAEEGKKLVA-ASQAALGL SEQ ID NO: 141 (Mouse serum albumin (MSA)) RGVFR-REAHKSEIAHRYNDLGEQHFKGLVLIAFSQYLQKC-SYDEHAKLVQEVTDFAKTCVADESAANCDK SLHTLFGDKLCAIPNLRENYGELADCCTKQEPER-NECFLQHKDDNPSLPPFERPEAEAMCTSFKENPTTF MGHYLHEVARRHPYFYAPELLYYAEQYNEILTQC-CAEADKESCLTPKLDGVKEKALVSSVRQRMKCSSM QKFGERAFKAWAVARLSQTFPNADFAEITKLAT-DLTKVNKECCHGDLLECADDRAELAKYMCE-NQATISS KLQTCCDKPLLKKAHCLSEVEHDTMPADL-PAIAADFVEDQEVCKNYAEAKDVFLGTFLYEYSR-RHPDYSV SLLLRLAKKYEATLEKCCAEANPPA-CYGTVLAEFQPLVEEPKNLVKTNCDLYEKLGEYGF-QNAILVRYTQK APQVSTPTLVEAARNLGRVGT-KCCTLPEDQRLPCVEDYLSAILNRVCLLHEKTPVS-EHVTKCCSGSLVER RPCFSALTVDETYVPKEF-KAETFTFHSDICTLPEKEKQIKKQTALAELVKHKPKA-TAEQLKTVMDDFAQFL DTCCKAADKDTCFSTE-GPNLVTRCKDALA Conjugation of Albumin Proteins An albumin protein of the invention may be conjugated to (e.g., by way of a covalent bond) to any compound of the invention (e.g., by way of the linker portion of a neuraminidase inhibitor monomer or dimer). The albumin protein may be conjugated to any compound of the invention by any method well-known to those of skill in the art for producing small-molecule-protein conjugates. This may include covalent conjugation to a solvent-exposed amino acid, such as a solvent exposed cysteine or lysine. For example, human serum albumin may be conjugated to a compound of the invention by covalent linkage to the sulfur atom corresponding to Cys34 of SEQ ID NO: 139 or Cys40 of SEQ ID NO: 140.

An albumin protein of the invention may be conjugated to any compound of the invention by way of an amino acid located within 10 amino acid residues of the C-terminal or N-terminal end of the albumin protein. An albumin protein may include a C-terminal or N-terminal polypeptide fusion of 1, 2, 3, 4, 5, 6, 7, 8, 9, 10, 15, or 20 or more amino acid. The C-terminal or N-terminal polypeptide fusion may include one or more solvent-exposed cysteine or lysine residues, which may be used for covalent conjugation of a compound of the invention (e.g., conjugation to a neuraminidase inhibitor monomer or dimer, including by way of a linker).

Albumin proteins of the invention include any albumin protein which has been engineered to include one or more solvent-exposed cysteine or lysine residues, which may provide a site for conjugation to a compound of the invention (e.g., conjugation to a neuraminidase inhibitor monomer or dimer, including by way of a linker). Most preferably, the albumin protein will contain a single solvent-exposed cysteine or lysine, thus enabling site-specific conjugation of a compound of the invention. Exemplary methods for the production of engineered variants of albumin proteins that include one or more conjugation-competent cysteine residues are provided in U.S. Patent Application No. 2017/0081389, which is incorporated herein by reference in its entirety. Briefly, preferred albumin protein variants are those comprising a single, solvent-exposed, unpaired (e.g., free) cysteine residue, thus enabling site-specific conjugation of a linker to the cysteine residue.

Albumin proteins which have been engineered to enable chemical conjugation to a solvent-exposed, unpaired cysteine residue include the following albumin protein variants:

(a) an albumin protein having a substitution of a non-cysteine amino acid residue with a cysteine at an amino acid residue corresponding to any of L585, D1, A2, D562, A364, A504, E505, T79, E86, D129, D549, A581, D121, E82, S270, Q397, and A578 of SEQ ID NO: 139;

(b) an albumin protein having an insertion of a cysteine at a position adjacent the N- or C-terminal side of an amino acid residue corresponding to any of L585, D1, A2, D562, A364, A504, E505, T79, E86, D129, D549, A581, D121, E82, S270, Q397, and A578 of SEQ ID NO: 139;

(c) an albumin protein engineered to have an unpaired cysteine having a free thiol group at a residue corresponding to any of C369, C361, C91, C177, C567, C316, C75, C169, C124, or C558 of SEQ ID NO: 96, and which may or may not be generated by deletion or substitution of a residue corresponding to C360, C316, C75, C168, C558, C361, C91, C124, C169, or C567 of SEQ ID NO: 139; and/or (d) addition of a cysteine to the N- or C-terminus of an albumin protein.

In some embodiments of the invention, the net result of the substitution, deletion, addition, or insertion events of (a), (b), (c) and/or (d) is that the number of conjugation competent cysteine residues of the polypeptide sequence is increased relative to the parent albumin sequence. In some embodiments of the invention, the net result of the substitution, deletion, addition, or insertion events of (a), (b), (c) and/or (d) is that the number of conjugation competent cysteine residues of the polypeptide sequence is one, thus enabling site-specific conjugation.

Preferred albumin protein variants also include albumin proteins having a single solvent-exposed lysine residue, thus enabling site-specific conjugation of a linker to the lysine residue. Such variants may be generated by engineering an albumin protein, including any of the methods previously described (e.g., insertion, deletion, substitution, or C-terminal or N-terminal fusion).

Albumin Protein-Binding Peptides

Conjugation of a biologically-active compound to an albumin protein-binding peptide can alter the pharmacodynamics of the biologically-active compound, including the alteration of tissue uptake, penetration, and diffusion. In a preferred embodiment, conjugation of an albumin protein-binding peptide to a compound of the invention (e.g., a neuraminidase inhibitor monomer or dimer, by way of a linker) increases the efficacy or decreases the toxicity of the compound, as compared to the compound alone.

Albumin protein-binding peptides of the invention include any polypeptide having an amino acid sequence of 5 to 50 (e.g., 5 to 40, 5 to 30, 5 to 20, 5 to 15, 5 to 10, 10 to 50, 10 to 30, or 10 to 20) amino acid residues that has affinity for and functions to bind an albumin protein, such as any of the albumin proteins described herein. Preferably, the albumin protein-binding peptide binds to a naturally occurring serum albumin, most preferably human serum albumin.

An albumin protein-binding peptide can be of different origins, e.g., synthetic, human, mouse, or rat. Albumin protein-binding peptides of the invention include albumin protein-binding peptides which have been engineered to include one or more (e.g., two, three, four, or five) solvent-exposed cysteine or lysine residues, which may provide a site for conjugation to a compound of the invention (e.g., conjugation to a neuraminidase inhibitor monomer or dimer, including by way of a linker). Most preferably, the albumin protein-binding peptide will contain a single solvent-exposed cysteine or lysine, thus enabling site-specific conjugation of a compound of the invention. Albumin protein-binding peptides may include only naturally occurring amino acid residues, or may include one or more non-naturally occurring amino acid residues. Where included, a non-naturally occurring amino acid residue (e.g., the side chain of a non-naturally occurring amino acid residue) may be used as the point of attachment for a compound of the invention (e.g., a neuraminidase inhibitor monomer or dimer, including by way of a linker). Albumin protein-binding peptides of the invention may be linear or cyclic. Albumin protein-binding peptides of the invention include any albumin protein-binding peptides known to one of skill in the art, examples of which, are provided herein.

Albumin protein-binding peptide, and conjugates including an albumin protein-binding peptide, preferably bind an albumin protein (e.g., human serum albumin) with an affinity characterized by a dissociation constant, Kd, that is less than about 100 μM, preferably less than about 100 nM, and most preferably do not substantially bind other plasma proteins. Specific examples of such compounds are linear or cyclic peptides, preferably between about 10 and 20 amino acid residues in length, optionally modified at the N-terminus or C-terminus or both.

Albumin protein-binding peptides include linear and cyclic peptides comprising the following general formulae, wherein Xaa is any amino acid:

| | |
|---|---|
| Xaa-Xaa-Cys-Xaa-Xaa-Xaa-Xaa-Xaa-Cys-Xaa-Xaa-Phe-Cys-Xaa-Asp-Trp-Pro-Xaa-Xaa-Xaa-Ser-Cys | SEQ ID NO: 148 |
| Val-Cys-Tyr-Xaa-Xaa-Xaa-Ile-Cys-Phe | SEQ ID NO: 149 |
| Cys-Tyr-Xaa-Pro-Gly-Xaa-Cys | SEQ ID NO: 150 |
| Asp-Xaa-Cys-Leu-Pro-Xaa-Trp-Gly-Cys-Leu-Trp | SEQ ID NO: 151 |
| Trp-Cys-Asp-Xaa-Xaa-Leu-Xaa-Ala-Xaa-Asp-Leu-Cys | SEQ ID NO: 152 |
| Asp-Leu-Val-Xaa-Leu-Gly-Leu-Glu-Cys-Trp | SEQ ID NO: 153 |

Albumin protein-binding peptides of the invention further include any of the following peptide sequences, which may be linear or cyclic:

| | |
|---|---|
| DLCLRDWGCLW | SEQ ID NO: 154 |
| DICLPRWGCLW | SEQ ID NO: 155 |
| MEDICLPRWGCLWGD | SEQ ID NO: 156 |
| QRLMEDICLPRWGCLWEDDE | SEQ ID NO: 157 |
| QGLIGDICLPRWGCLWGRSV | SEQ ID NO: 158 |
| QGLIGDICLPRWGCLWGRSVK | SEQ ID NO: 159 |
| EDICLPRWGCLWEDD | SEQ ID NO: 160 |

| | |
|---|---|
| RLMEDICLPRWGCLWEDD | SEQ ID NO: 161 |
| MEDICLPRWGCLWEDD | SEQ ID NO: 162 |
| MEDICLPRWGCLWED | SEQ ID NO: 163 |
| RLMEDICLARWGCLWEDD | SEQ ID NO: 164 |
| EVRSFCTRWPAEKSCKPLRG | SEQ ID NO: 165 |
| RAPESFVCYWETICFERSEQ | SEQ ID NO: 166 |
| EMCYFPGICWM | SEQ ID NO: 167 |

Albumin protein-binding peptides of SEQ ID NOs: 154-167 may further include additional amino acids at the N-terminus (Xaa)x and/or additional amino acids at the C-terminus (Xaa)z, wherein Xaa is any amino acid and x and z are a whole number greater or equal to zero, generally less than 100, preferably less than 10 and more preferably 0, 1, 2, 3, 4 or 5.

Further exemplary albumin protein-binding peptides are provided in U.S. Patent Application No. 2005/0287153, which is incorporated herein by reference in its entirety.

Conjugation of Albumin Protein-Binding Peptides

An albumin protein-binding peptide of the invention may be conjugated to (e.g., by way of a covalent bond) to any compound of the invention (e.g., by way of the linker portion of a neuraminidase inhibitor monomer or dimer). The albumin protein-binding peptide may be conjugated to any compound of the invention by any method known to those of skill in the art for producing peptide-small molecule conjugates. This may include covalent conjugation to the side chain group of an amino acid residue, such as a cysteine, a lysine, or a non-natural amino acid. Alternately, covalent conjugation may occur at the C-terminus (e.g., to the C-terminal carboxylic acid, or to the side chain group of the C-terminal residue) or at the N-terminus (e.g., to the N-terminal amino group, or to the side chain group of the N-terminal amino acid).

V. Linkers

A linker refers to a linkage or connection between two or more components in a conjugate described herein (e.g., between two neuraminidase inhibitors in a conjugate described herein, between a neuraminidase inhibitor and an Fc domain or an albumin protein in a conjugate described herein, and between a dimer of two neuraminidase inhibitors and an Fc domain or an albumin protein in a conjugate described herein).

Linkers in Conjugates Having an Fc Domain or an Albumin Protein Covalently Linked to Dimers of Neuraminidase Inhibitors In a conjugate containing an Fc domain monomer, an Fc domain, an Fc-binding peptide, an albumin protein, or an albumin protein-binding peptide covalently linked to one or more dimers of neuraminidase inhibitors as described herein, a linker in the conjugate (e.g., L or L') may be a branched structure. As described further herein, a linker in a conjugate described herein (e.g., L or L) may be a multivalent structure, e.g., a divalent or trivalent structure having two or three arms, respectively. In some embodiments when the linker has three arms, two of the arms may be attached to the first and second neuraminidase inhibitors and the third arm may be attached to the Fc domain monomer, and Fc domain, an Fc-binding peptide, an albumin protein, or an albumin protein-binding peptide. In some embodiments when the linker has two arms, one arm may be attached to an Fc domain or an albumin protein and the other arm may be attached to one of the two neuraminidase inhibitors. In other embodiments, a linker with two arms may be used to attach the two neuraminidase inhibitors on a conjugate containing an Fc domain or albumin protein covalently linked to one or more dimers of neuraminidase inhibitors.

In some embodiments, a linker in a conjugate having an Fc domain or an albumin protein covalently linked to one or more dimers of neuraminidase inhibitors is described by formula (D-L-I):

$$L^B - Q{\overset{L^C}{|}} - L^A \qquad \text{(L-I)}$$

wherein $L^A$ is described by formula $G^{A1}$-$(Z^{A1})_{g1}$—$(Y^{A1})_{h1}$—$(Z^{A2})_{i1}$—$(Y^{A2})_{j1}$—$(Z^{A3})_{k1}$—$(Y^{A3})_{l1}$—$(Z^{A4})_{m1}$—$(Y^{A4})_{n1}$—$(Z^{A5})_{o1}$-$G^{A2}$; $L^B$ is described by formula $G^{B1}$-$(Z^{B1})_{g2}$—$(Y^{B1})_{h2}$—$(Z^{B2})_{i2}$—$(Y^{B2})_{j2}$—$(Z^{B3})_{k2}$—$(Y^{B3})_{l2}$—$(Z^{B4})_{m2}$—$(Y^{B4})_{n2}$—$(Z^{B5})_{o2}$-$G^{B2}$; $L^C$ is described by formula $G^{C1}$-$(Z^{C1})_{g3}$—$(Y^{C1})_{h3}$—$(Z^{C2})_{i3}$—$(Y^{C2})_{j3}$—$(Z^{C3})_{k3}$—$(Y^{C3})_{l3}$—$(Z^{C4})_{m3}$—$(Y^{C4})_{n3}$—$(Z^{C5})_{o3}$-$G^{C2}$; $G^{A1}$ is a bond attached to Q; $G^{A2}$ is a bond attached to $A_1$; $G^{B1}$ is a bond attached to Q); $G^{B2}$ is a bond attached to $A_2$; $G^{C1}$ is a bond attached to Q; $G^{C2}$ is a bond attached to E or a functional group capable of reacting with a functional group conjugated to E (e.g., maleimide and cysteine, amine and activated carboxylic acid, thiol and maleimide, activated sulfonic acid and amine, isocyanate and amine, azide and alkyne, and alkene and tetrazine); each of $Z^{A1}$, $Z^{A2}$, $Z^{A3}$, $Z^{A4}$, $Z^{A5}$, $Z^{B1}$, $Z^{B2}$, $Z^{B3}$, $Z^{B4}$, $Z^{B5}$, $Z^{C1}$, $Z^{C2}$, $Z^{C3}$, $Z^{C4}$ and $Z^{C5}$ is, independently, optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, or optionally substituted C2-C15 heteroarylene; each of $Y^{A1}$, $Y^{A2}$, $Y^{A3}$, $Y^{A4}$, $Y^{B1}$, $Y^{B2}$, $Y^{B3}$, $Y^{B4}$, $Y^{C1}$, $Y^{C2}$, $Y^{C3}$ and $Y^{C4}$ is, independently, O, S, $NR^i$, P, carbonyl, thiocarbonyl, sulfonyl, phosphate, phosphoryl, or imino; $R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl; each of g1, h1, i1, j1, k1, l1, m1, n1, o1, g2, h2, i2, j2, k2, l2, m2, n2, o2, g3, h3, i3, j3, k3, l3, m3, n3, and o3 is, independently, 0 or 1; Q is a nitrogen atom, optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, or optionally substituted C2-C15 heteroarylene.

In some embodiments, $L^c$ may have two points of attachment to the Fc domain (e.g., two $G^{C2}$) In some embodiments, L includes a polyethylene glycol (PEG) linker. A PEG linker includes a linker having the repeating unit structure $(—CH_2CH_2O—)_n$, where n is an integer from 2 to 100. A polyethylene glycol linker may covalently join a neuraminidase inhibitor and E (e.g., in a conjugate of any one of formulas (M-I)-(M-XI)). A polyethylene glycol linker may covalently join a first neuraminidase inhibitor and a second neuraminidase inhibitor (e.g., in a conjugate of any one of formulas (D-I)-(D-XI)). A polyethylene glycol linker may covalently join a neuraminidase inhibitor dimer and E (e.g., in a conjugate of any one of formulas (D-I)-(D-XI)). A polyethylene glycol linker may be selected any one of $PEG_2$ to $PEG_{100}$ (e.g., $PEG_2$, $PEG_3$, $PEG_4$, $PEG_5$, $PEG_5$-$PEG_{10}$, $PEG_{10}$-$PEG_{20}$, $PEG_{20}$-$PEG_{30}$, $PEG_{30}$-$PEG_{40}$, $PEG_{50}$-$PEG_{60}$, $PEG_{60}$-$PEG_{70}$, $PEG_{70}$-$PEG_{80}$, $PEG_{80}$-$PEG_{90}$, $PEG_{90}$-$PEG_{100}$). In some embodiments, $L^c$ includes a PEG linker, where $L^c$ is covalently attached to each of Q and E.

Linkers of formula (D-L-I) that may be used in conjugates described herein include, but are not limited to

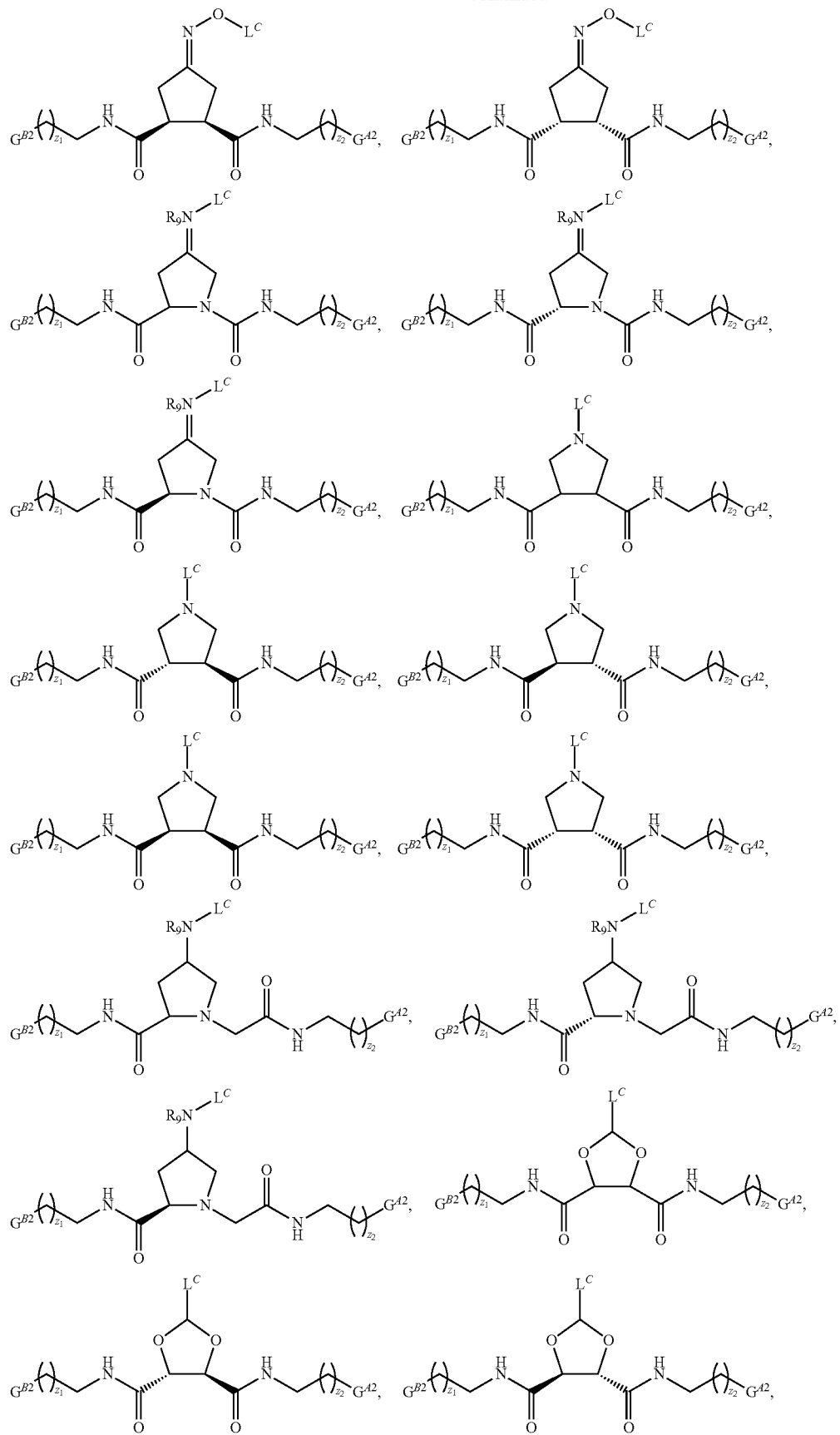

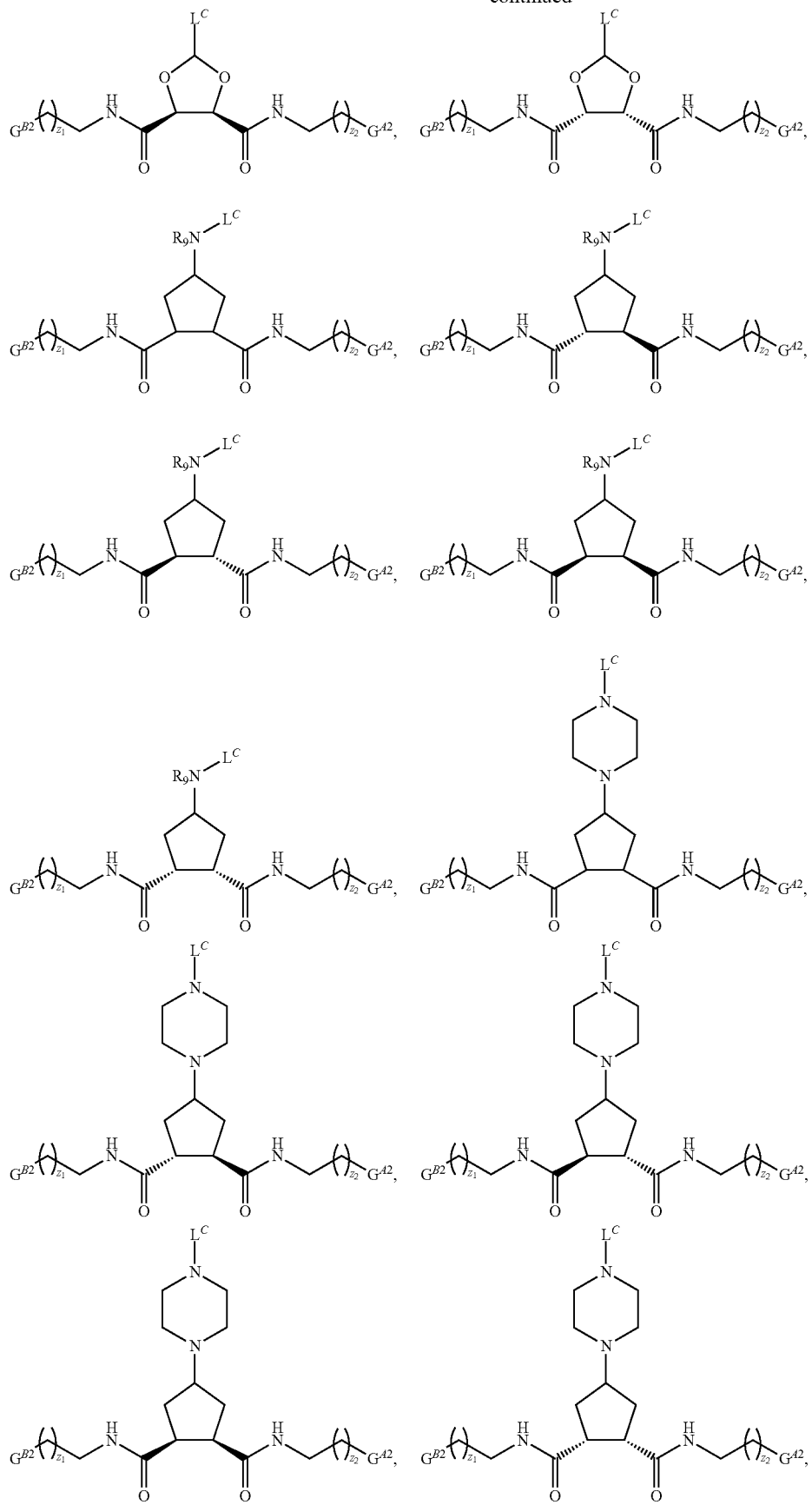

591
592
-continued
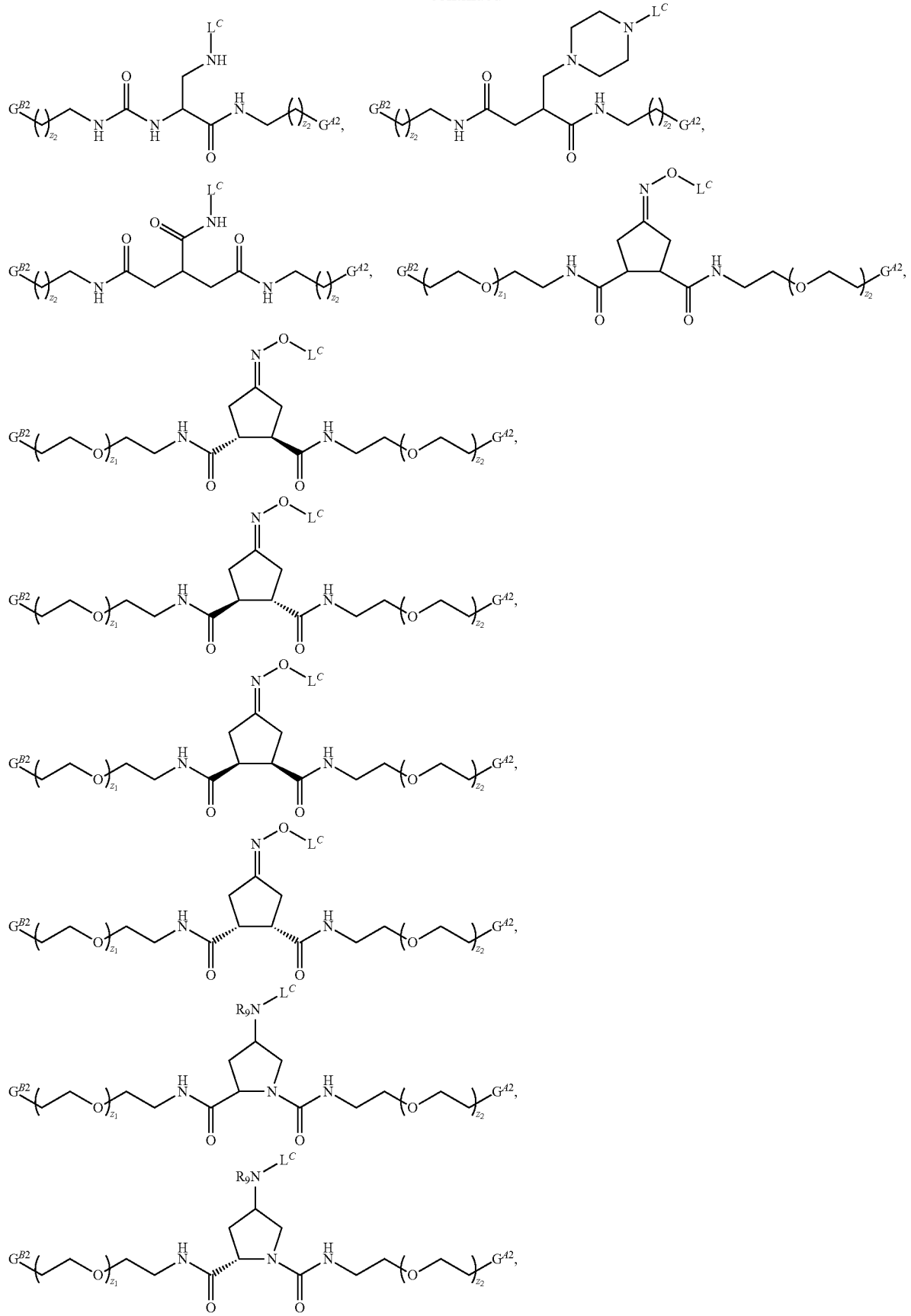

-continued
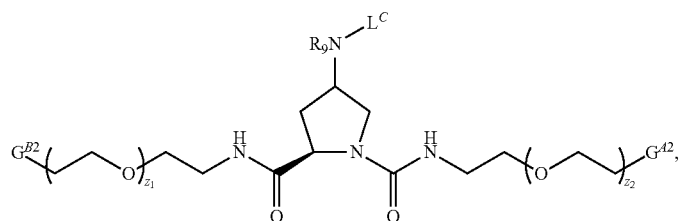
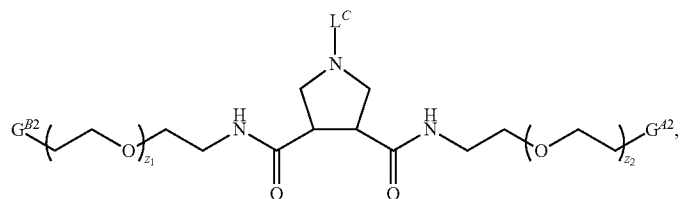
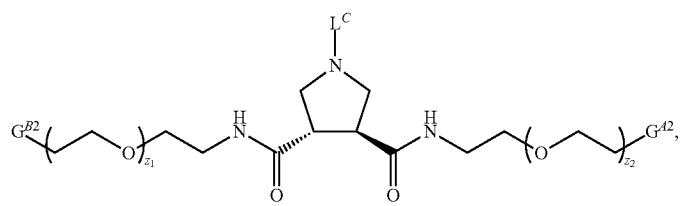
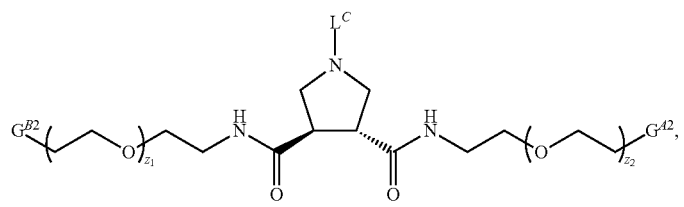
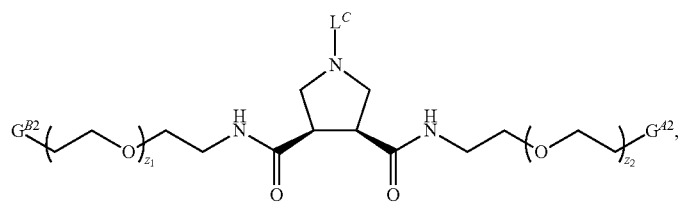
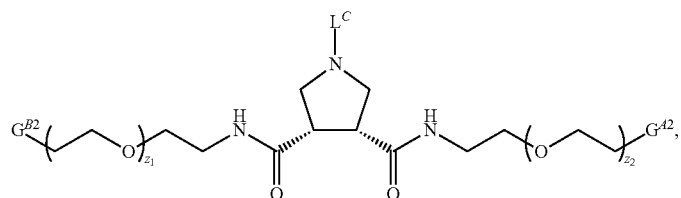
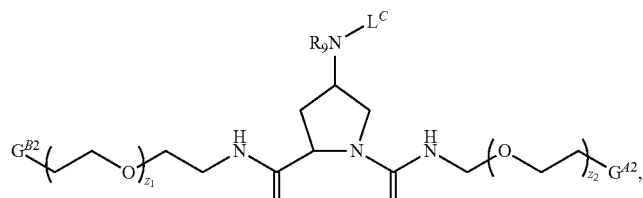
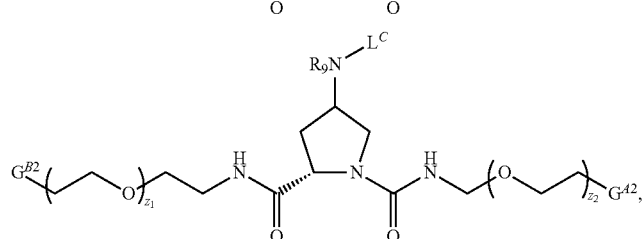

-continued
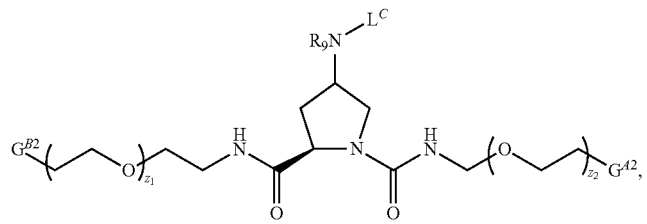
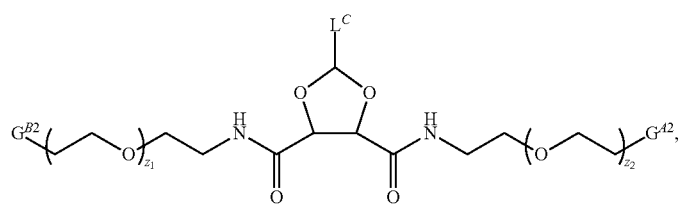
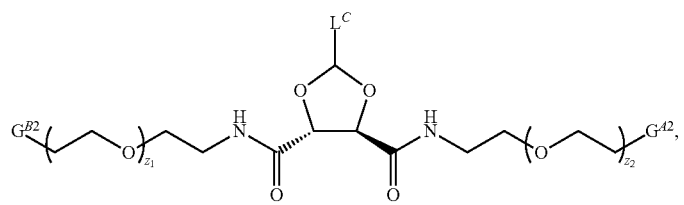
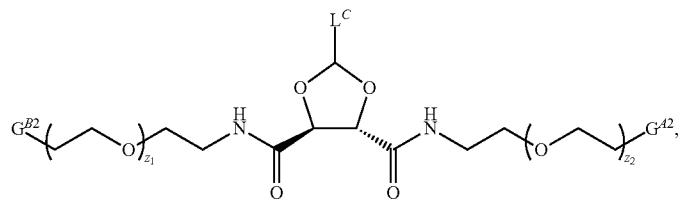
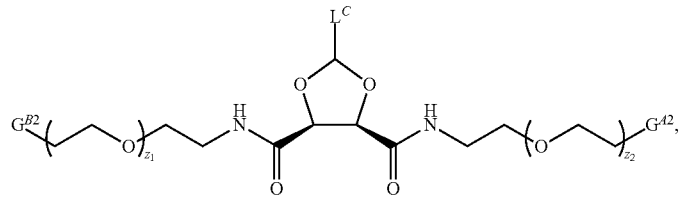
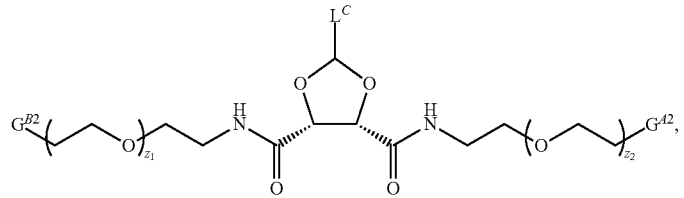
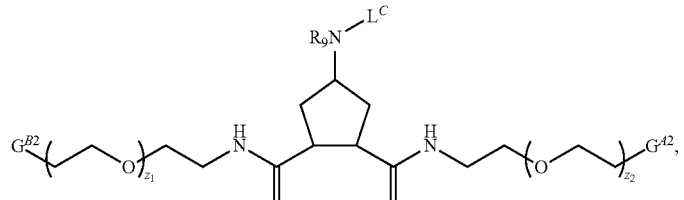
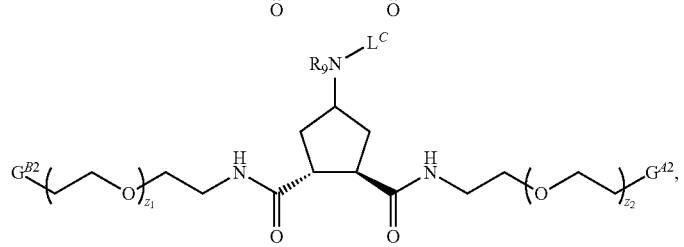

-continued
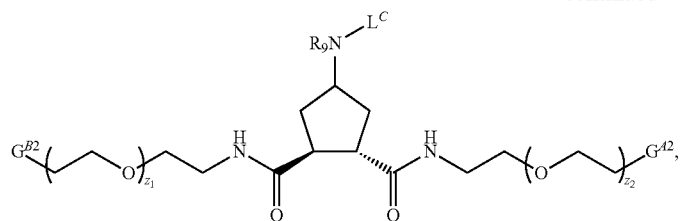
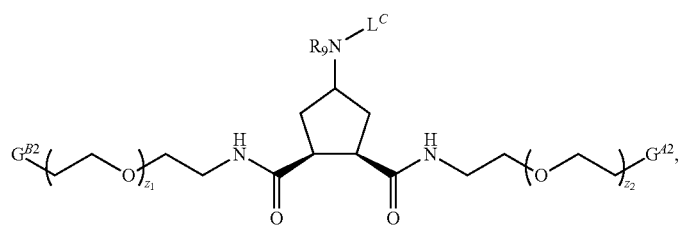
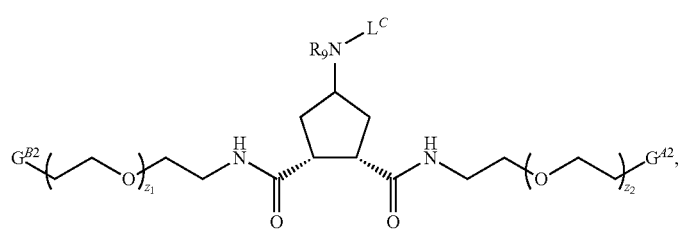
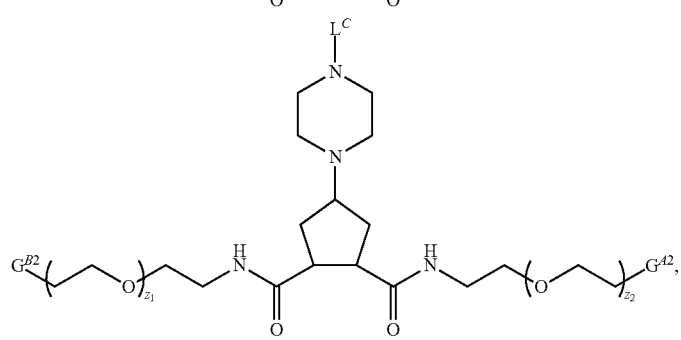
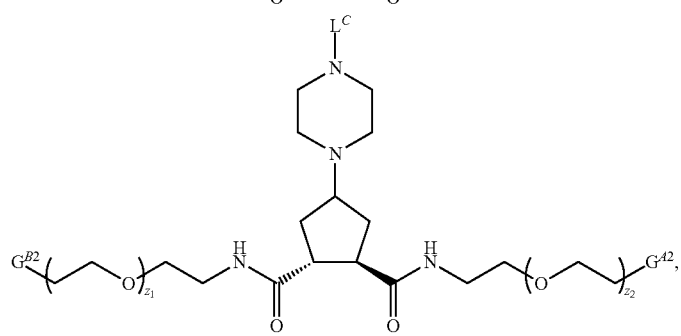
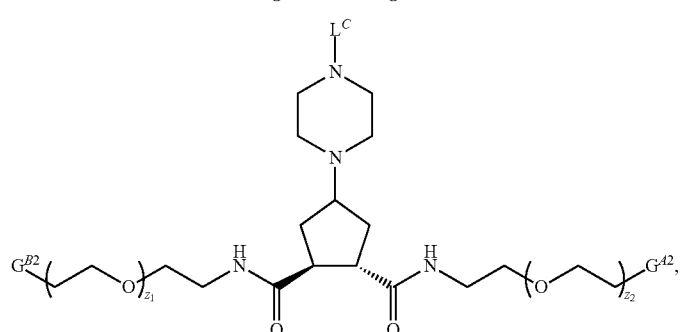

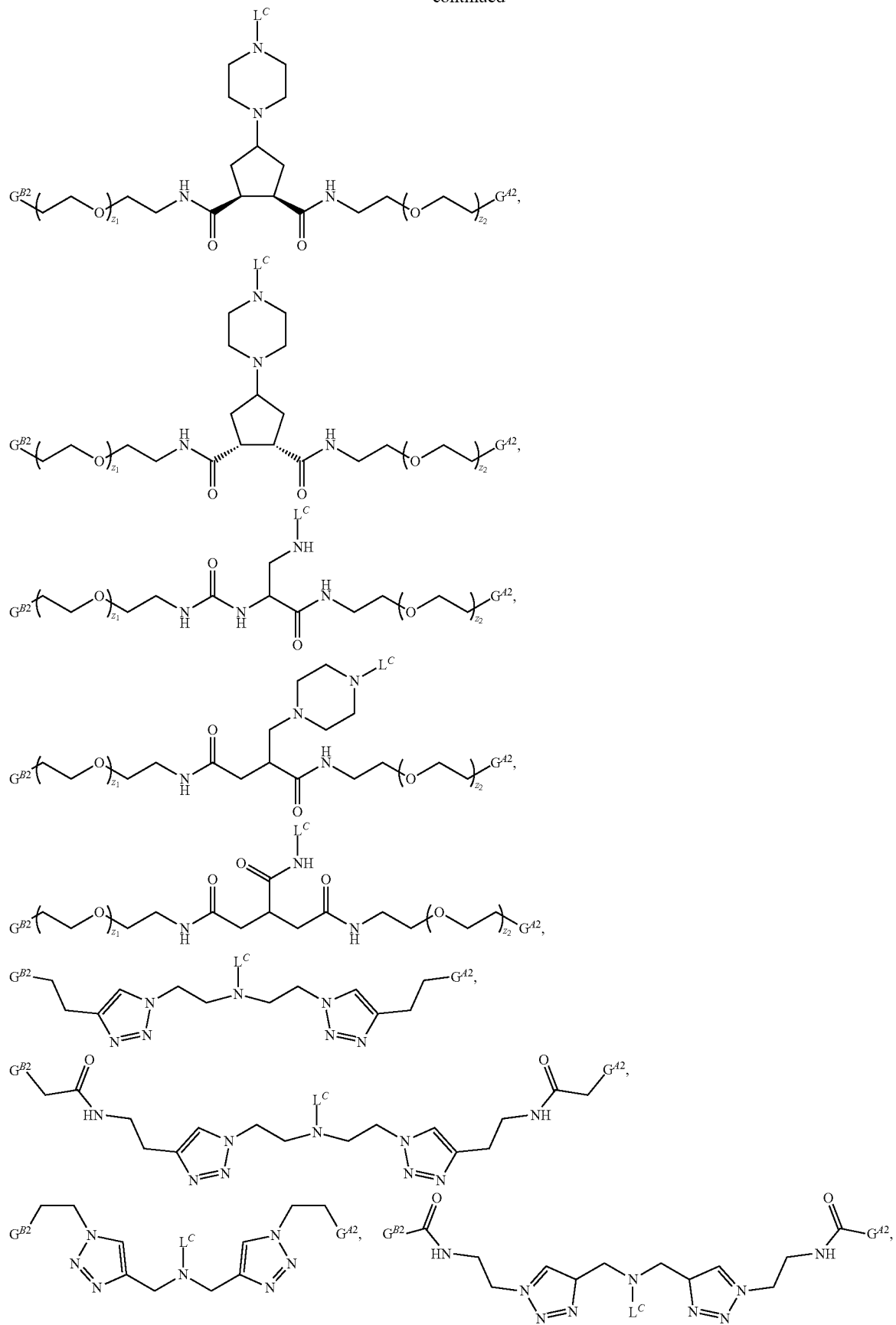

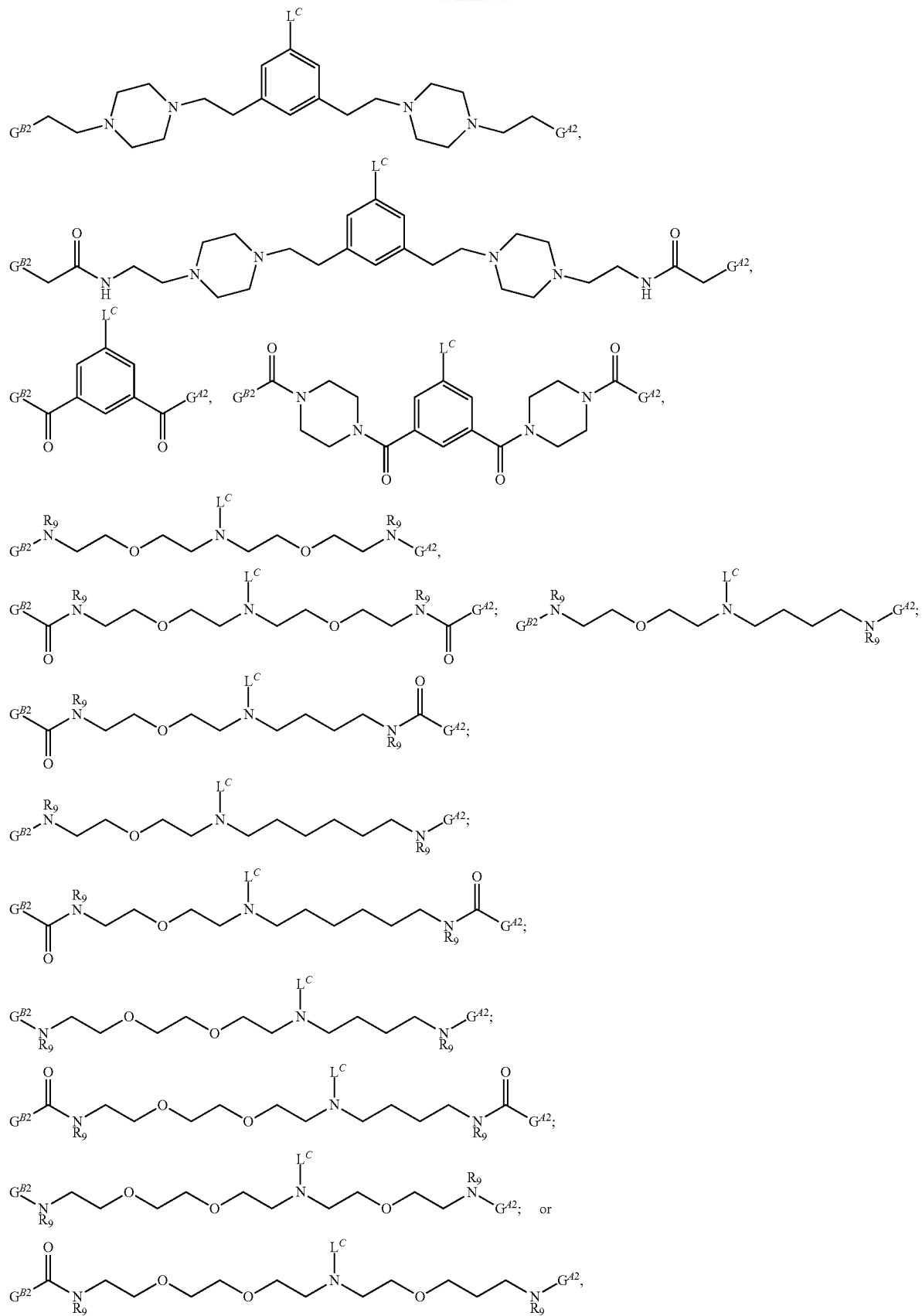

wherein $z_1$ and $z_2$ are each, independently, and integer from 1 to 20; and $R_9$ is selected from H, C1-C20 alkyl, C3-C20 cycloalkyl, C3-C20 heterocycloalkyl; C5-C15 aryl, and C2-C15 heteroaryl.
Linkers of the formula (D-L-I) may also include any of
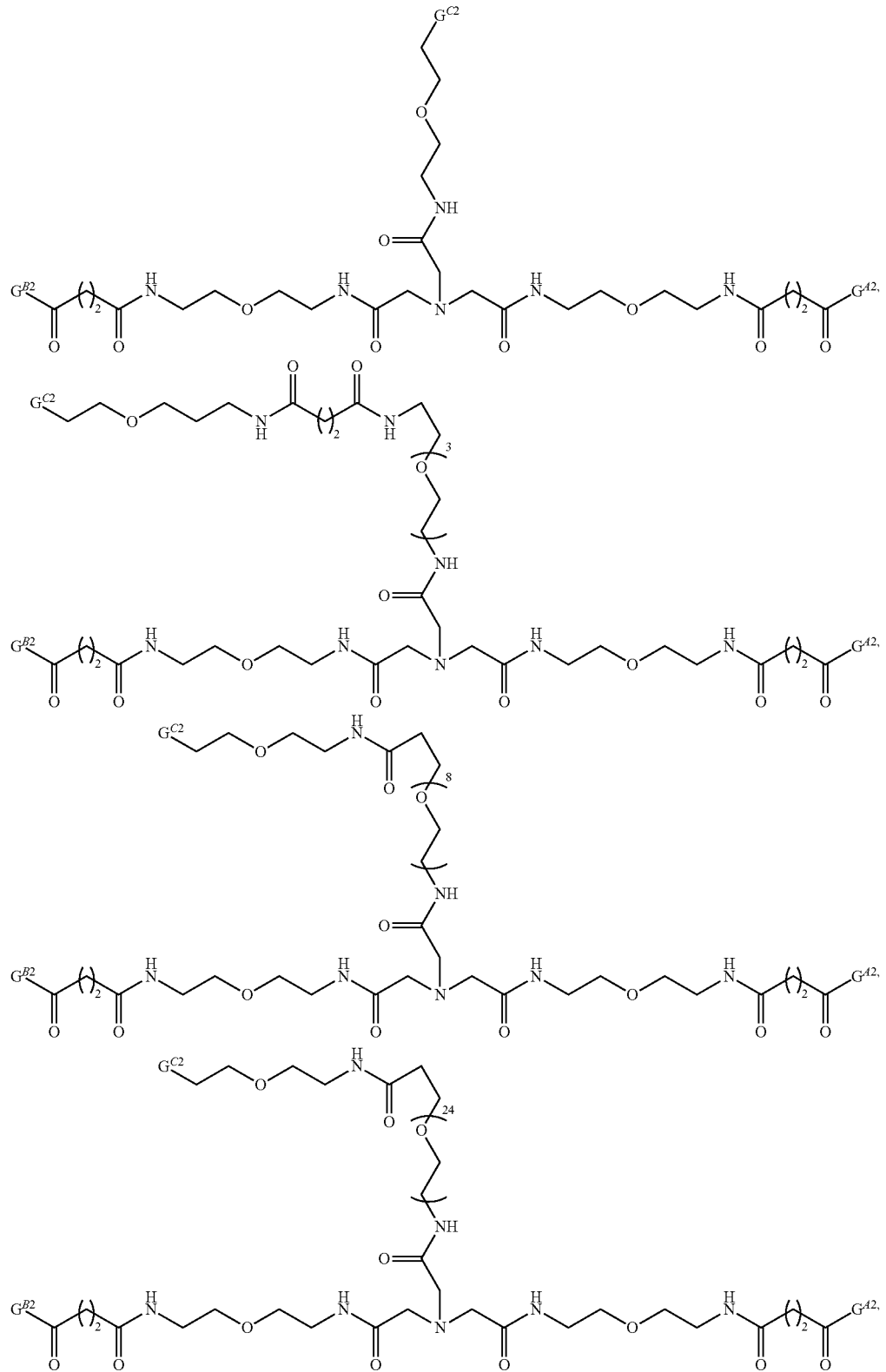

-continued
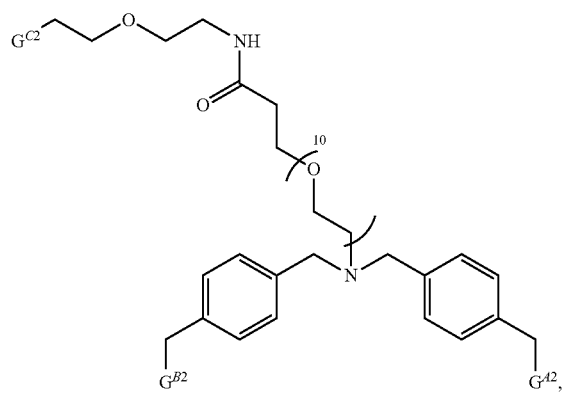
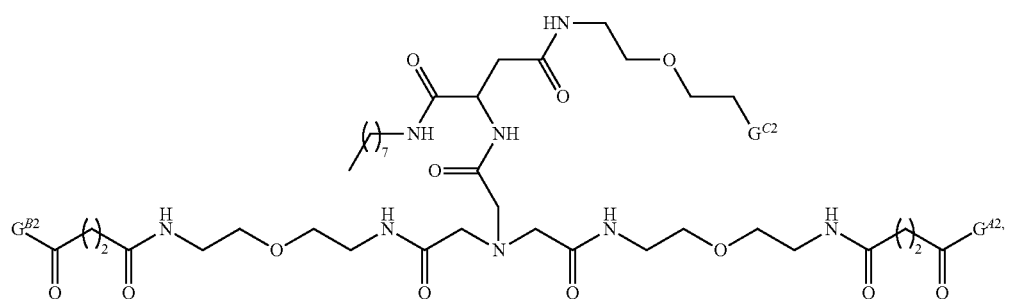
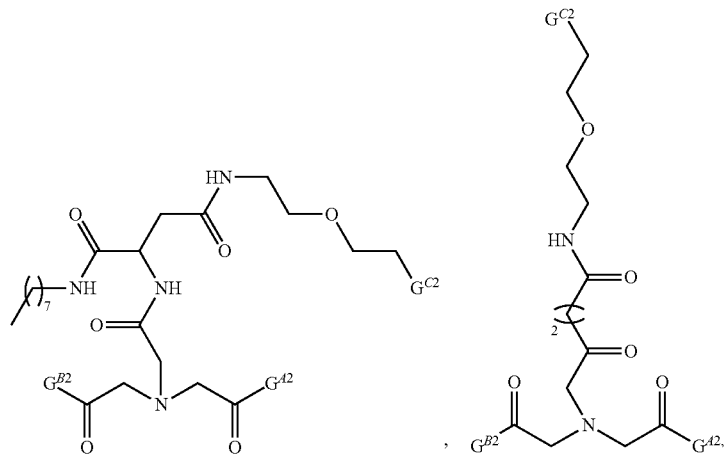
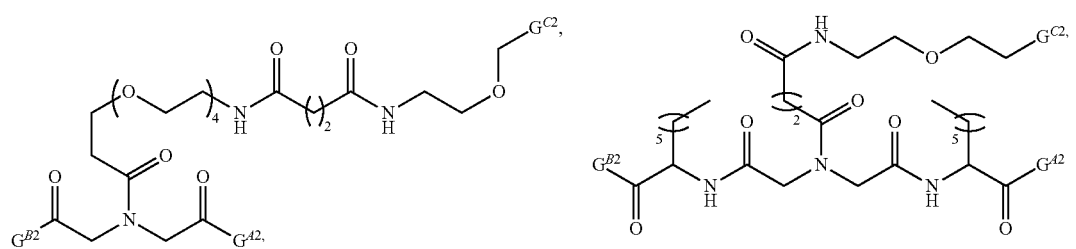

-continued
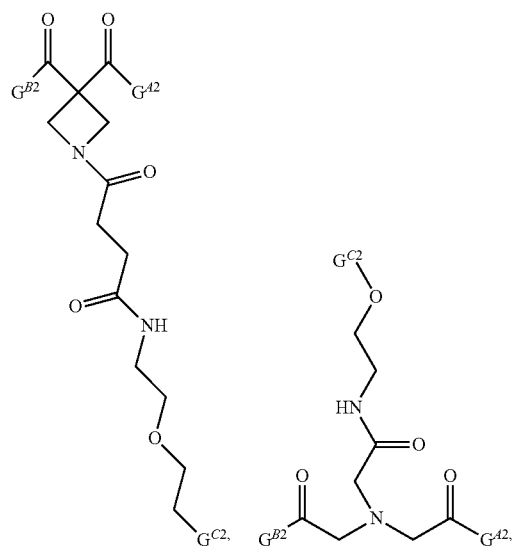
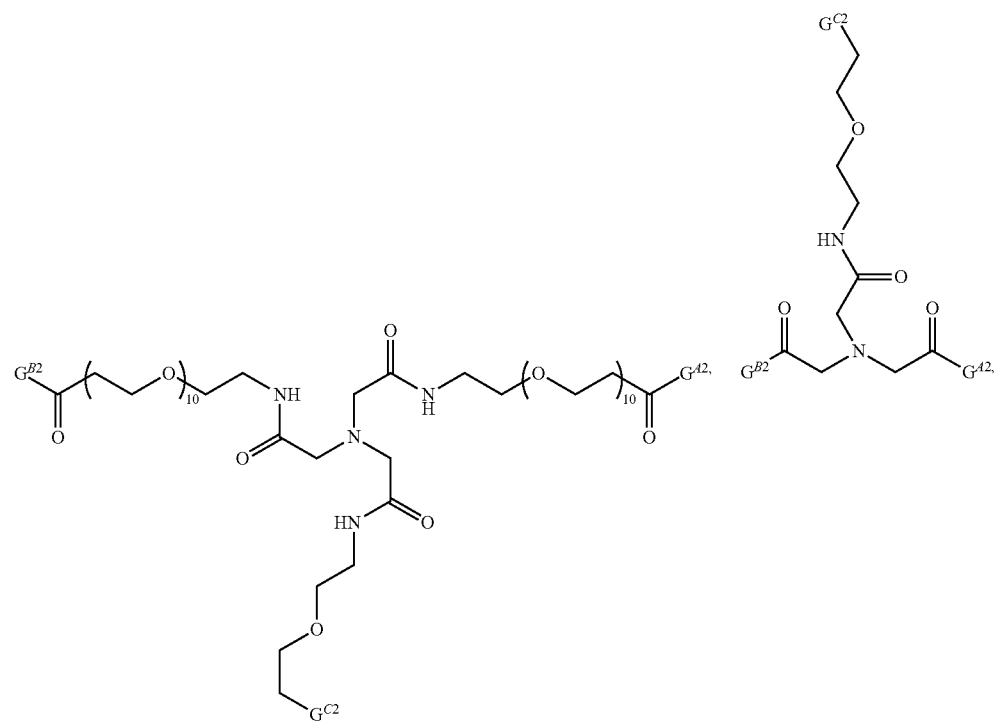

-continued
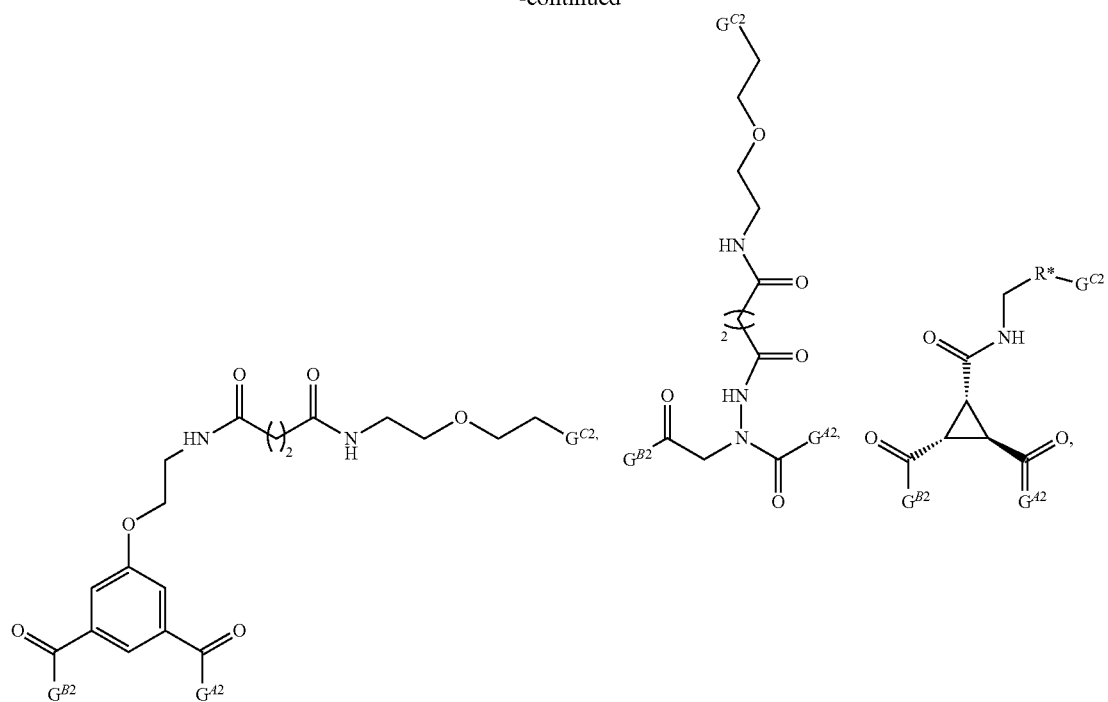
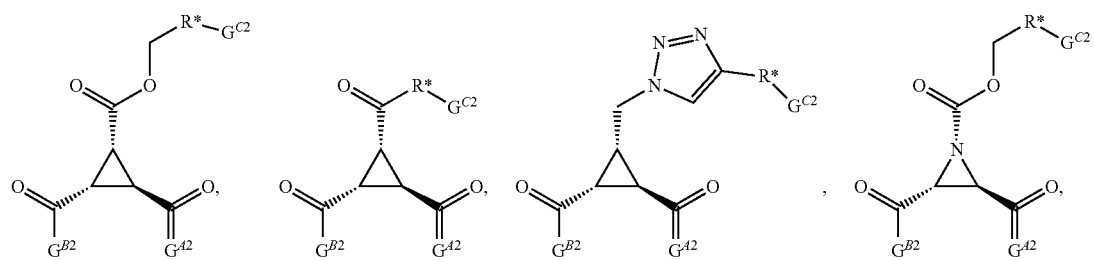
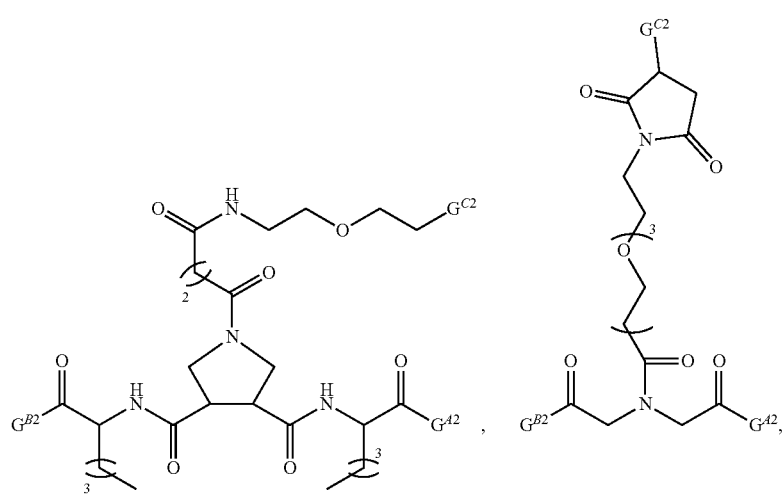

-continued
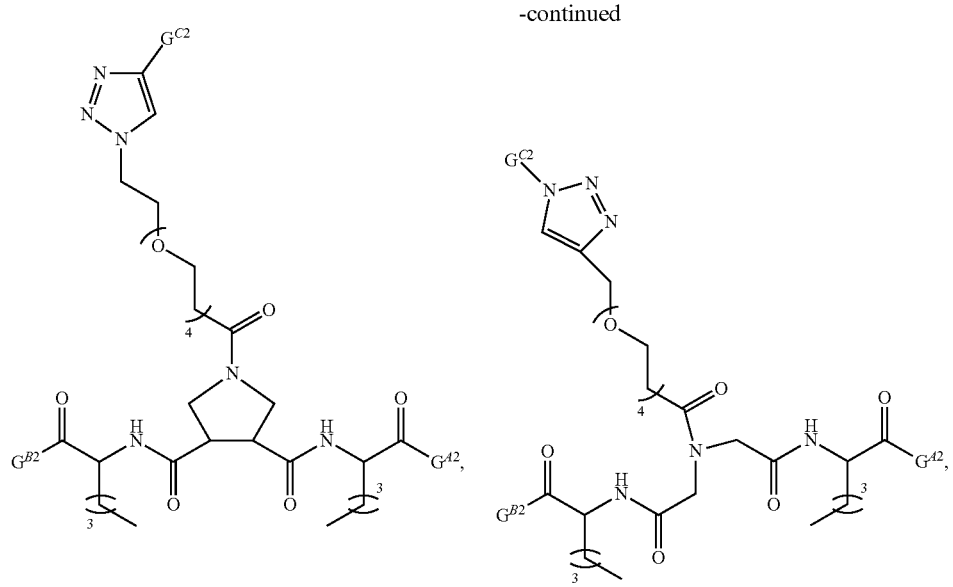
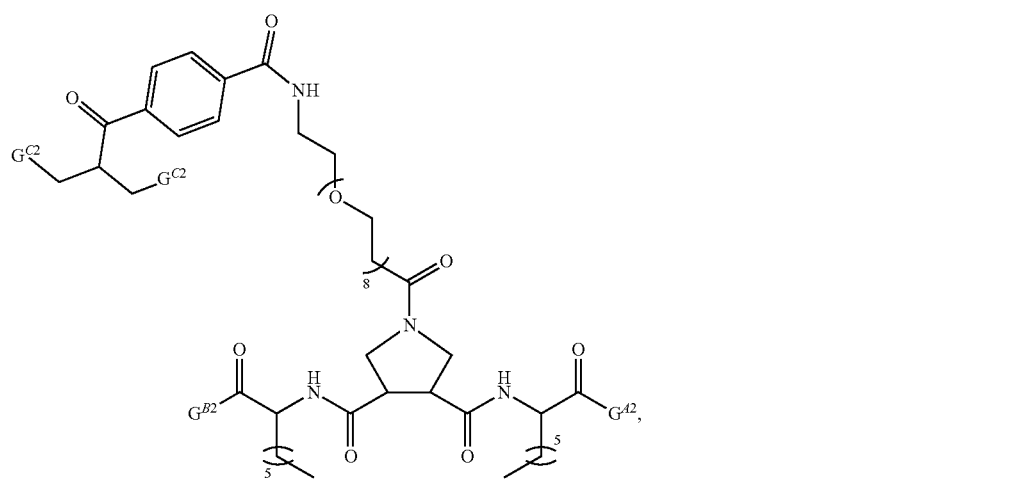
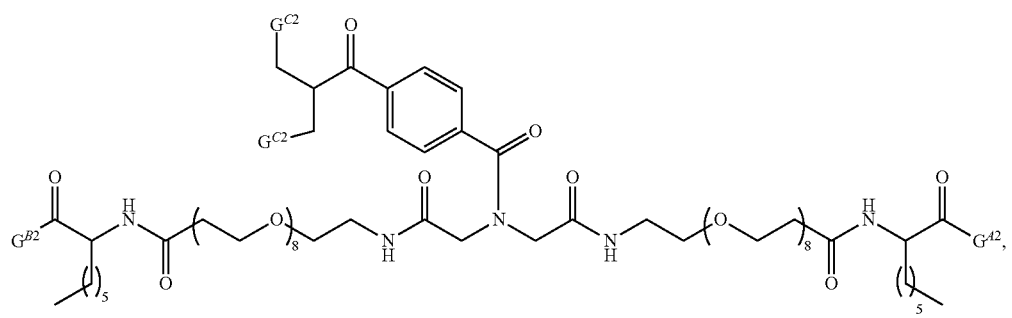
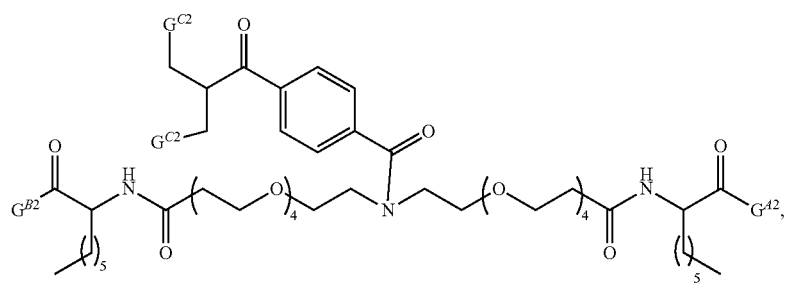

-continued
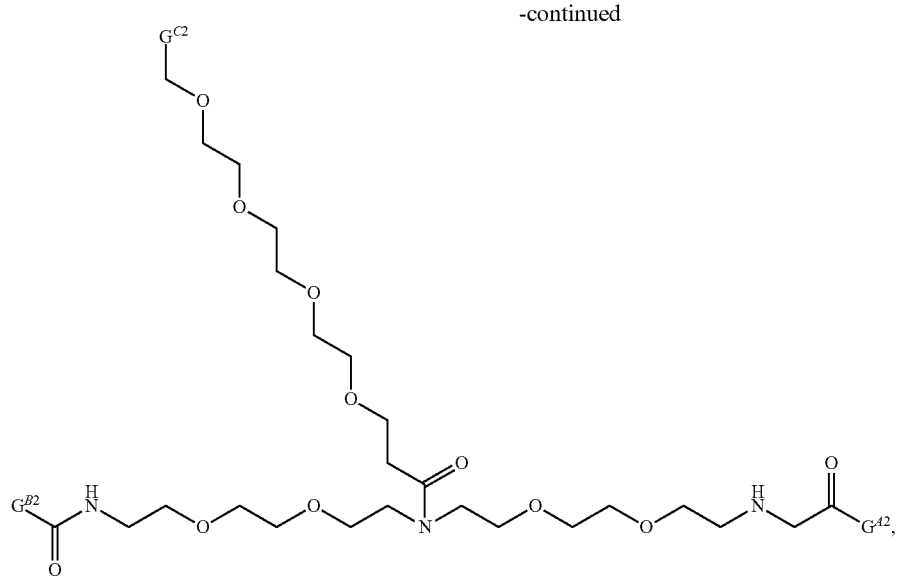
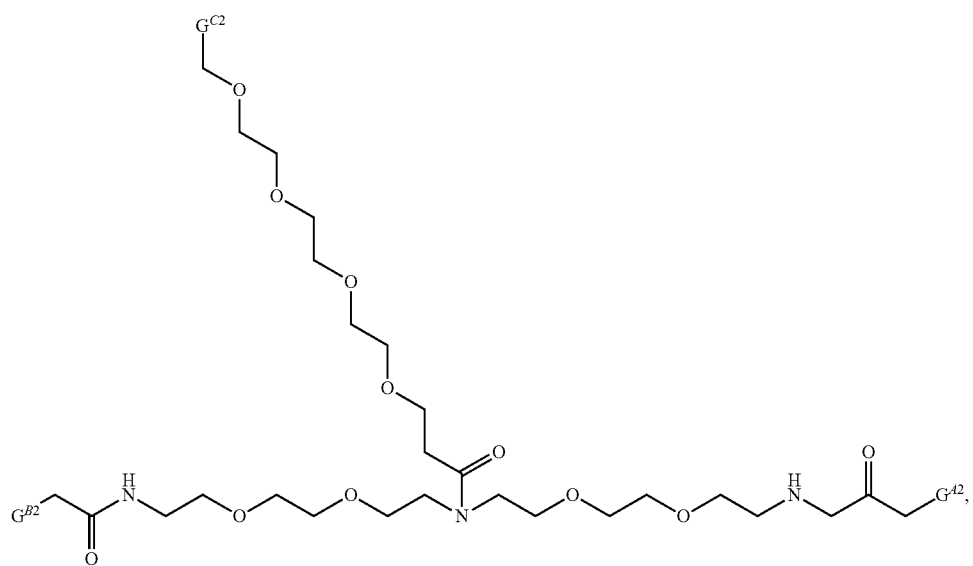
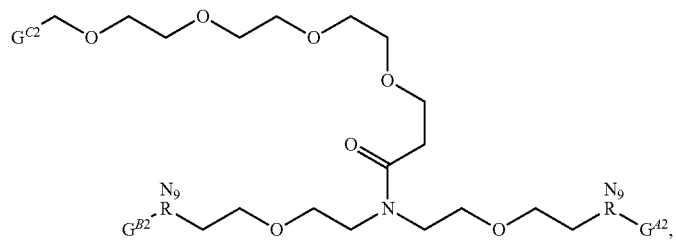
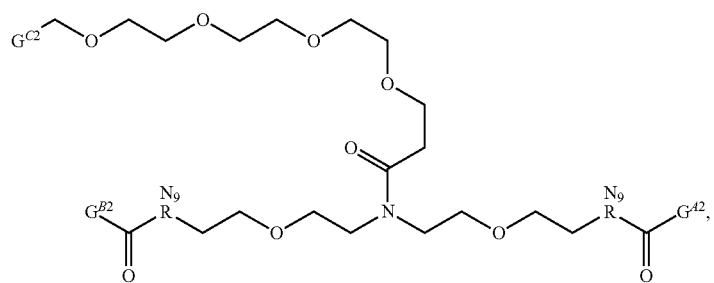

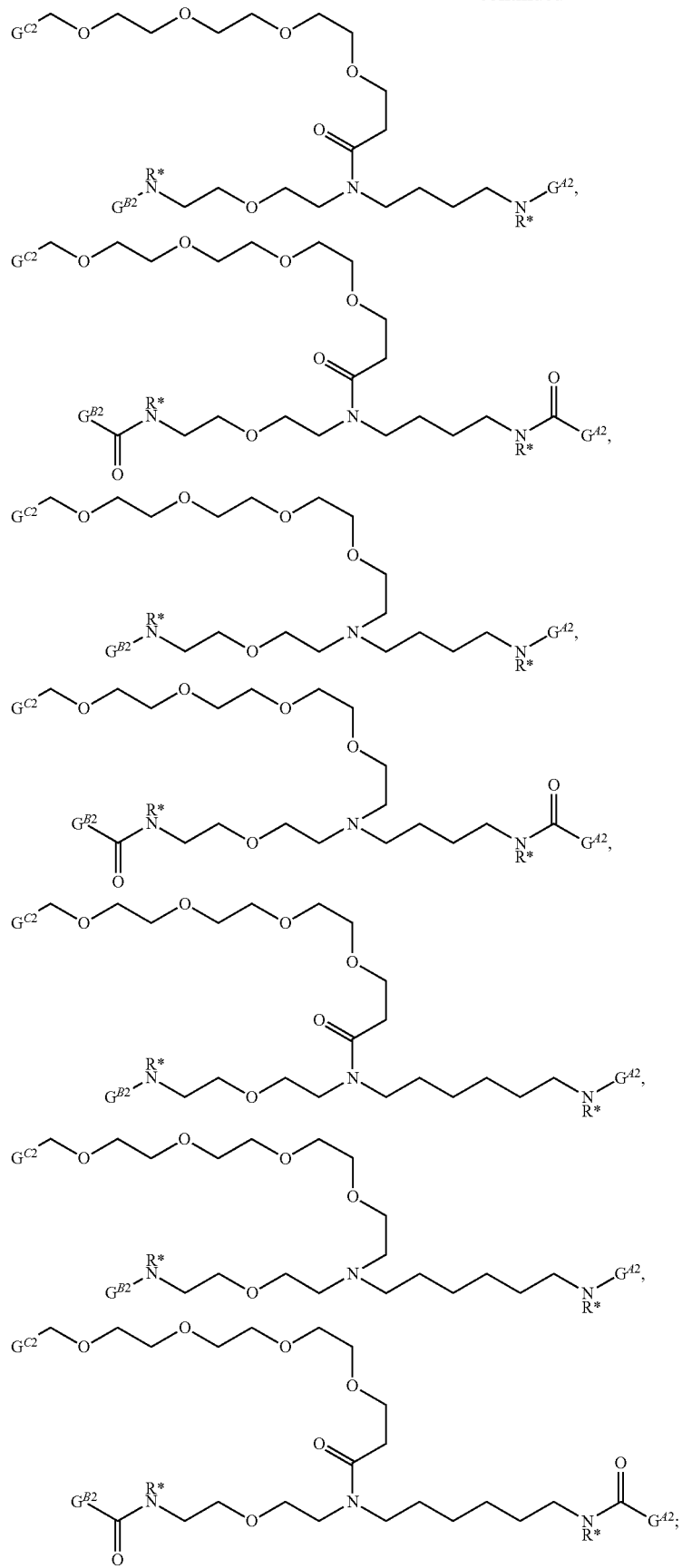

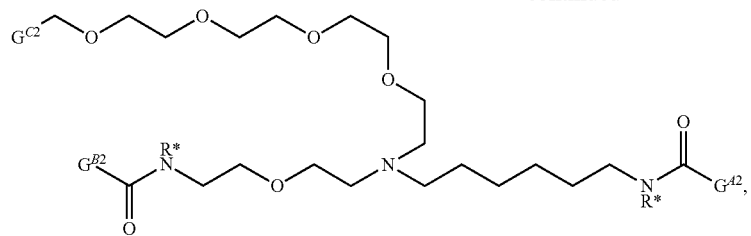
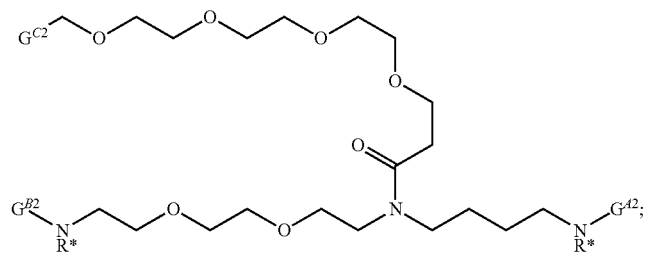
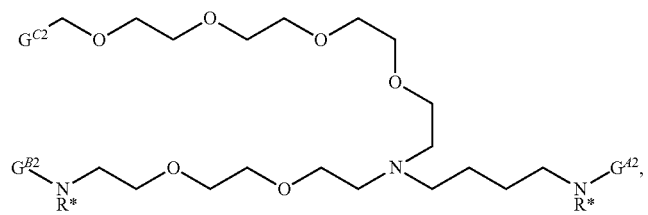
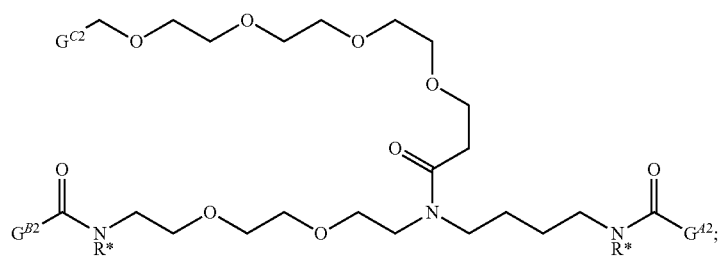
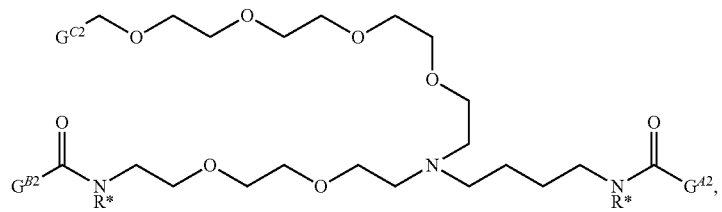
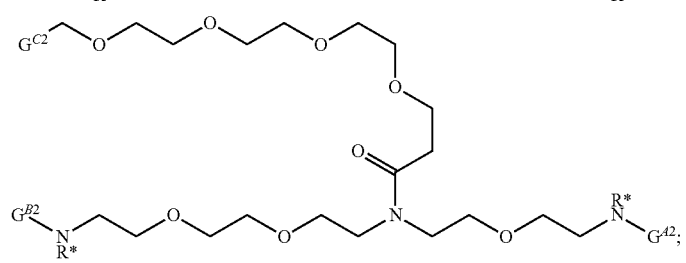
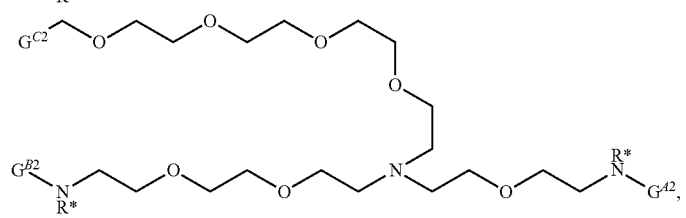

Linkers in Conjugates Having an Fc Domain or an Albumin Protein Covalently Linked to Monomers of Neuraminidase Inhibitors In a conjugate containing an Fc domain monomer, an Fc domain, an Fc-binding peptide, an albumin protein, or an albumin protein-binding peptide covalently linked to one or more monomers of neuraminidase inhibitors as described herein, a linker in the conjugate (e.g., L, or L') may be a divalent structure having two arms. One arm in a divalent linker may be attached to the monomer of neuraminidase inhibitor and the other arm may be attached to the Fc domain monomer, and Fc domain, an Fc-binding peptide, an albumin protein, or an albumin protein-binding peptide. In some embodiments, the one or more monomers of neuraminidase inhibitors in the conjugates described herein may each be, independently, connected to an atom in the Fc domain monomer, and Fc domain, an Fc-binding peptide, an albumin protein, or an albumin protein-binding peptide.

In some embodiments, a linker is described by formula (M-L-I):

$$J^1-(Q^1)_g-(T^1)_h-(Q^2)_i-(T^2)_j-(Q^3)_k-(T^3)_l-(Q^4)_m-(T^4)_n-(Q^5)_o-J^2$$

wherein $J^1$ is a bond attached to a neuraminidase inhibitor; $J^2$ is a bond attached to an Fc domain monomer, an Fc domain, an Fc-binding peptide, an albumin protein, or an albumin protein-binding peptide, or a functional group capable of reacting with a functional group conjugated to an Fc domain monomer, an Fc domain, an Fc-binding peptide, an albumin protein, or an albumin protein-binding peptide (e.g., maleimide and cysteine, amine and activated carboxylic acid, thiol and maleimide, activated sulfonic acid and amine, isocyanate and amine, azide and alkyne, and alkene and tetrazine); each of $Q^1$, $Q^2$, $Q^3$, $Q^4$ and $Q^5$ is, independently, optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, or optionally substituted C2-C15 heteroarylene; each of $T^1$, $T^2$, $T^3$, $T^4$ is, independently, O, S, $NR^i$, P, carbonyl, thiocarbonyl, sulfonyl, phosphate, phosphoryl, or imino; $R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl; and each of g, h, i, j, k, l, m, n, and o is, independently, 0 or 1.

In some embodiments, $J_2$ may have two points of attachment to the Fc domain monomer, and Fc domain, an Fc-binding peptide, an albumin protein, or an albumin protein-binding peptide (e.g., two $J^2$).

Linkers of formula (M-L-I) that may be used in conjugates described herein include, but are not limited to,

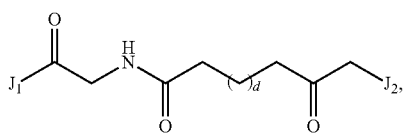
wherein d is an integer from 1 to 20 (e.g., d is 1, 2, 3, 4, 5, 6, 7, 8, 9, 10, 11, 12, 13, 14, 15, 16, 17, 18, 19, or 20).
Linkers of formula (M-L-I) that may be used in conjugates described herein include, but are not limited to,
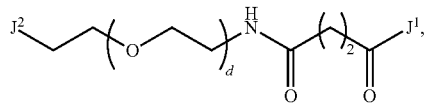
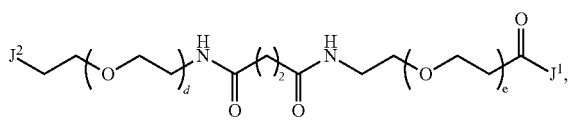
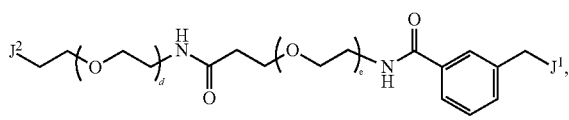
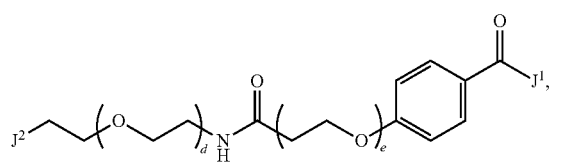
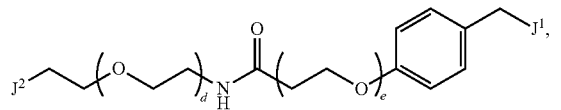
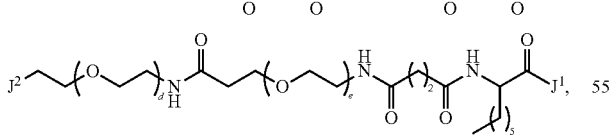
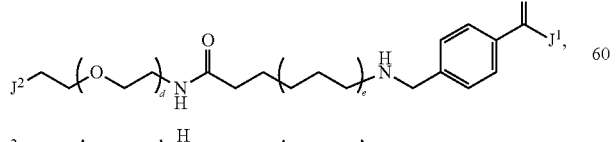
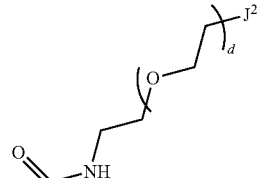
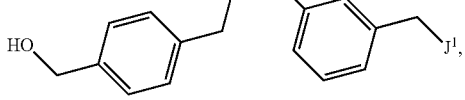
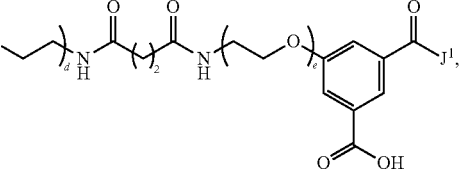
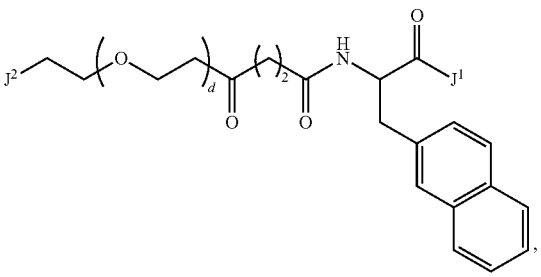
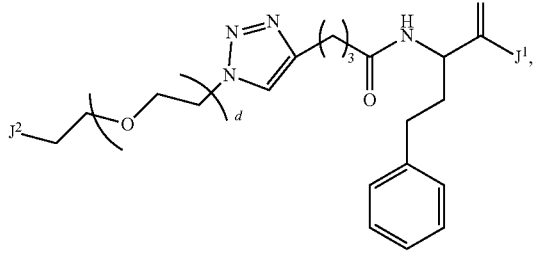
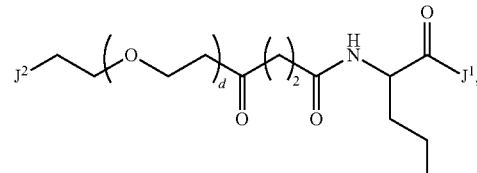
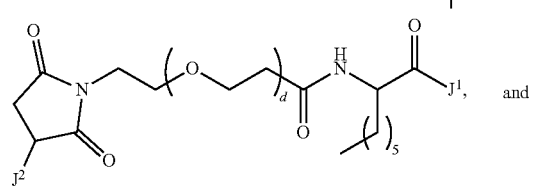
and -continued wherein each of d and e is, independently, an integer from 1 to 26.

Linking Groups

In some embodiments, a linker provides space, rigidity, and/or flexibility between the neuraminidase inhibitors and the Fc domain monomer, and Fc domain, an Fc-binding peptide, an albumin protein, or an albumin protein-binding peptide in the conjugates described here or between two neuraminidase inhibitors in the conjugates described herein. In some embodiments, a linker may be a bond, e.g., a covalent bond, e.g., an amide bond, a disulfide bond, a C—O bond, a C—N bond, a N—N bond, a C—S bond, or any kind of bond created from a chemical reaction, e.g., chemical conjugation. In some embodiments, a linker (L or L' as shown in any one of formulas (1)-(5), (D-I)-(D-XI), (D'-I), (M-I)-(M-XI), or (M'-I)) includes no more than 250 atoms (e.g., 1-2, 1-4, 1-6, 1-8, 1-10, 1-12, 1-14, 1-16, 1-18, 1-20, 1-25, 1-30, 1-35, 1-40, 1-45, 1-50, 1-55, 1-60, 1-65, 1-70, 1-75, 1-80, 1-85, 1-90, 1-95, 1-100, 1-110, 1-120, 1-130, 1-140, 1-150, 1-160, 1-170, 1-180, 1-190, 1-200, 1-210, 1-220, 1-230, 1-240, or 1-250 atom(s); 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 28, 26, 24, 22, 20, 18, 16, 14, 12, 10, 9, 8, 7, 6, 5, 4, 3, 2, or 1 atom(s)). In some embodiments, a linker (L or L) includes no more than 250 non-hydrogen atoms (e.g., 1-2, 1-4, 1-6, 1-8, 1-10, 1-12, 1-14, 1-16, 1-18, 1-20, 1-25, 1-30, 1-35, 1-40, 1-45, 1-50, 1-55, 1-60, 1-65, 1-70, 1-75, 1-80, 1-85, 1-90, 1-95, 1-100, 1-110, 1-120, 1-130, 1-140, 1-150, 1-160, 1-170, 1-180, 1-190, 1-200, 1-210, 1-220, 1-230, 1-240, or 1-250 non-hydrogen atom(s); 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 28, 26, 24, 22, 20, 18, 16, 14, 12, 10, 9, 8, 7, 6, 5, 4, 3, 2, or 1 non-hydrogen atom(s)). In some embodiments, the backbone of a linker (L or L) includes no more than 250 atoms (e.g., 1-2, 1-4, 1-6, 1-8, 1-10, 1-12, 1-14, 1-16, 1-18, 1-20, 1-25, 1-30, 1-35, 1-40, 1-45, 1-50, 1-55, 1-60, 1-65, 1-70, 1-75, 1-80, 1-85, 1-90, 1-95, 1-100, 1-110, 1-120, 1-130, 1-140, 1-150, 1-160, 1-170, 1-180, 1-190, 1-200, 1-210, 1-220, 1-230, 1-240, or 1-250 atom(s); 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 28, 26, 24, 22, 20, 18, 16, 14, 12, 10, 9, 8, 7, 6, 5, 4, 3, 2, or 1 atom(s)). The "backbone" of a linker refers to the atoms in the linker that together form the shortest path from one part of the conjugate to another part of the conjugate. The atoms in the backbone of the linker are directly involved in linking one part of the conjugate to another part of the conjugate. For examples, hydrogen atoms attached to carbons in the backbone of the linker are not considered as directly involved in linking one part of the conjugate to another part of the conjugate.

Molecules that may be used to make linkers (L or L') include at least two functional groups, e.g., two carboxylic acid groups. In some embodiments of a trivalent linker, two arms of a linker may contain two dicarboxylic acids, in which the first carboxylic acid may form a covalent linkage with the first neuraminidase inhibitor in the conjugate and the second carboxylic acid may form a covalent linkage with the second neuraminidase inhibitor in the conjugate, and the third arm of the linker may for a covalent linkage (e.g., a C—O bond) with an Fc domain monomer, an Fc domain, an Fc-binding peptide, an albumin protein, or an albumin protein-binding peptide in the conjugate. In some embodiments of a divalent linker, the divalent linker may contain two carboxylic acids, in which the first carboxylic acid may form a covalent linkage with one component (e.g., a neuraminidase inhibitor) in the conjugate and the second carboxylic acid may form a covalent linkage (e.g., a C—S bond or a C—N bond) with another component (e.g., an Fc domain monomer, an Fc domain, an Fc-binding peptide, an albumin protein, or an albumin protein-binding peptide) in the conjugate.

In some embodiments, dicarboxylic acid molecules may be used as linkers (e.g., a dicarboxylic acid linker). For example, in a conjugate containing an Fc domain monomer, an Fc domain, an Fc-binding peptide, an albumin protein, or an albumin protein-binding peptide covalently linked to one or more dimers of neuraminidase inhibitors, the first carboxylic acid in a dicarboxylic acid molecule may form a covalent linkage with a hydroxyl or amine group of the first neuraminidase inhibitor and the second carboxylic acid may form a covalent linkage with a hydroxyl or amine group of the second neuraminidase inhibitor.

Examples of dicarboxylic acids molecules that may be used to form linkers include, but are not limited to, 625
-continued
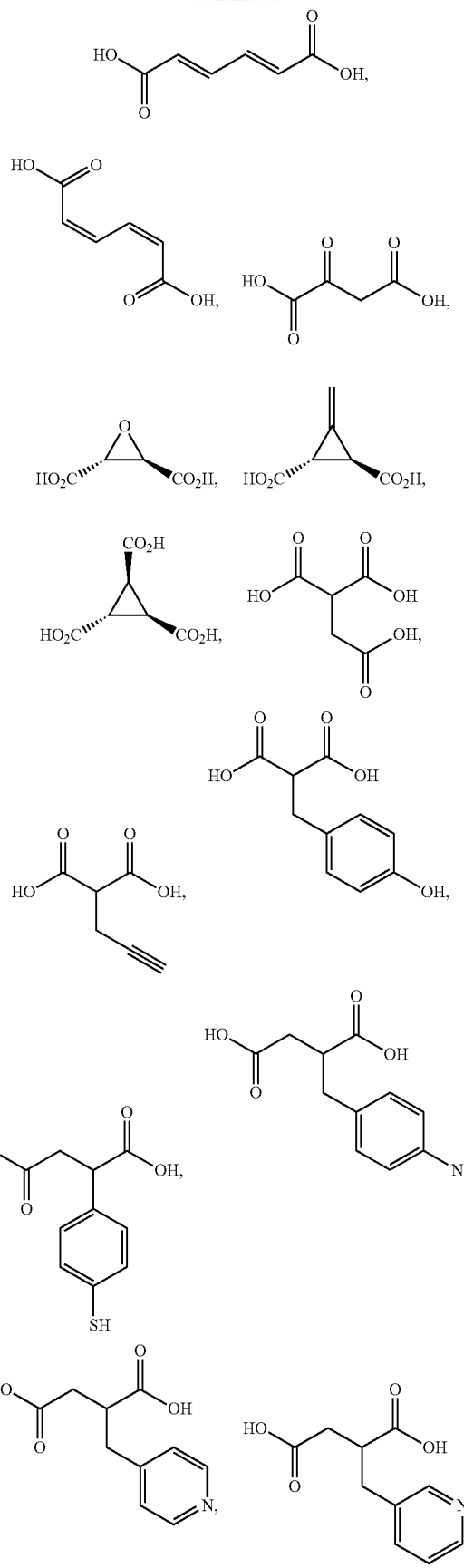
626
-continued
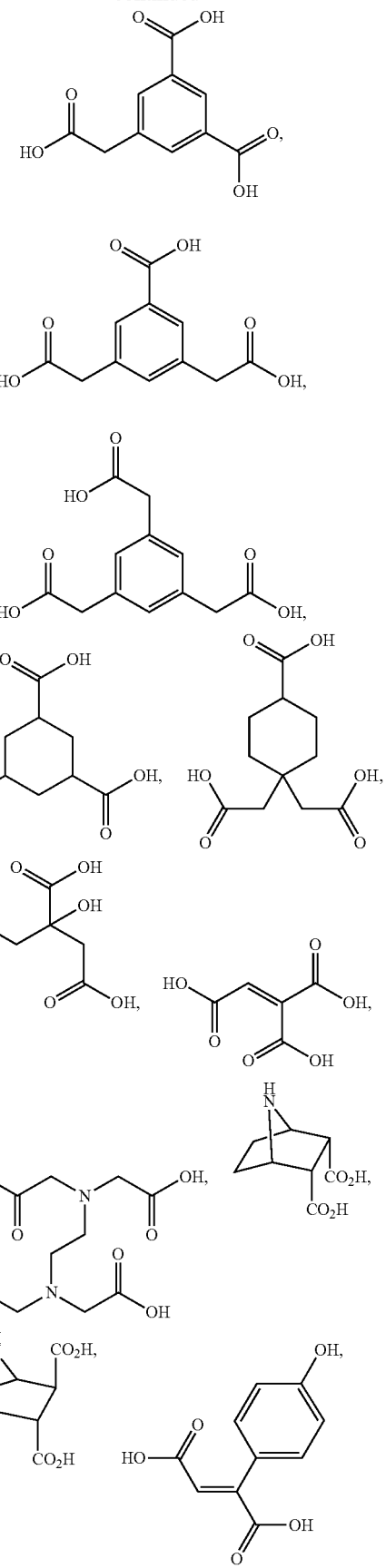

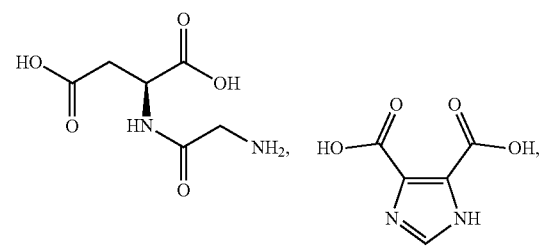
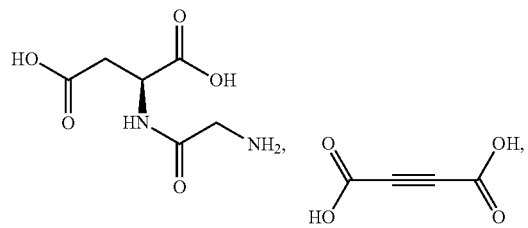
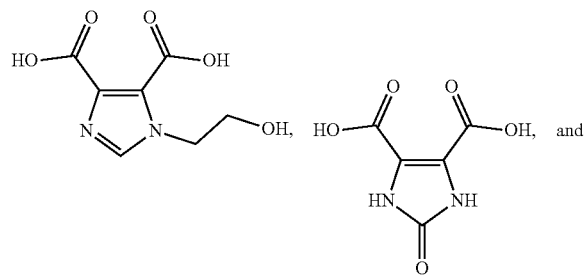
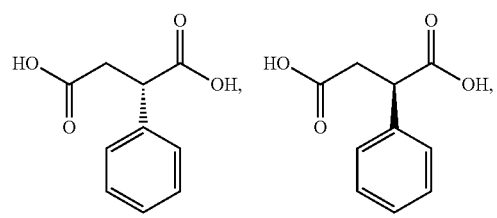
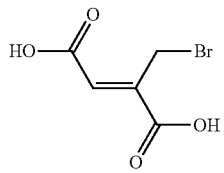
and
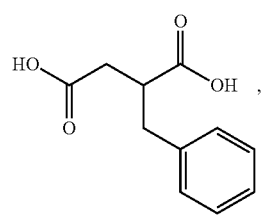
wherein n is an integer from 1 to 20 (e.g., n is 1, 2, 3, 4, 5, 6, 7, 8, 9, 10, 11, 12, 13, 14, 15, 16, 17, 18, 19, or 20).
Other examples of dicarboxylic acids molecules that may be used to form linkers include, but are not limited to,
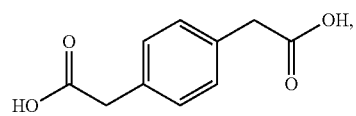
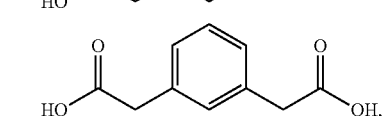
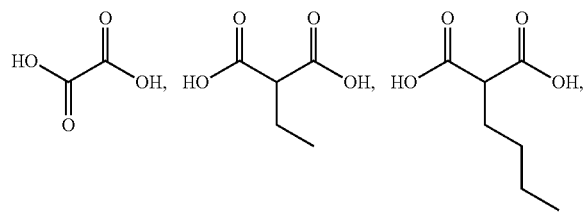
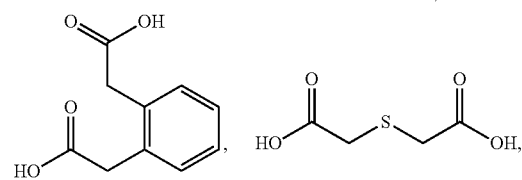
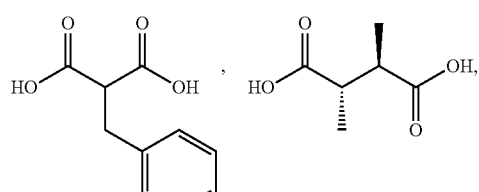
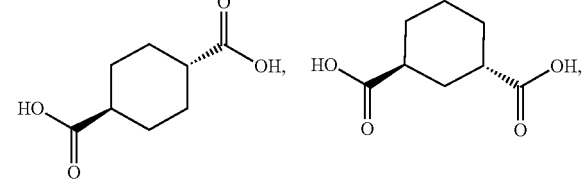
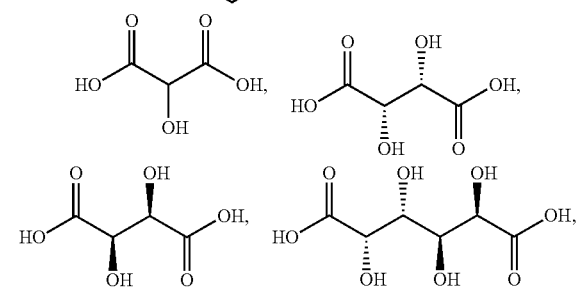
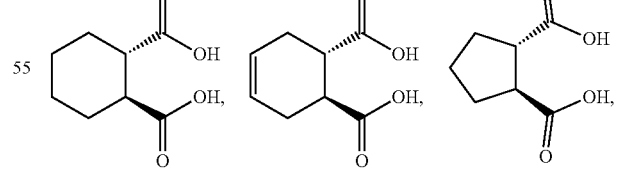
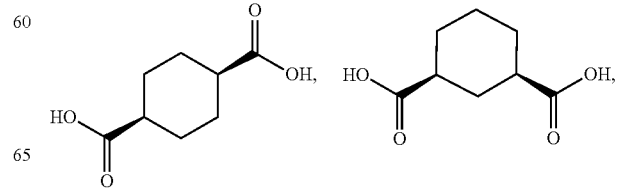

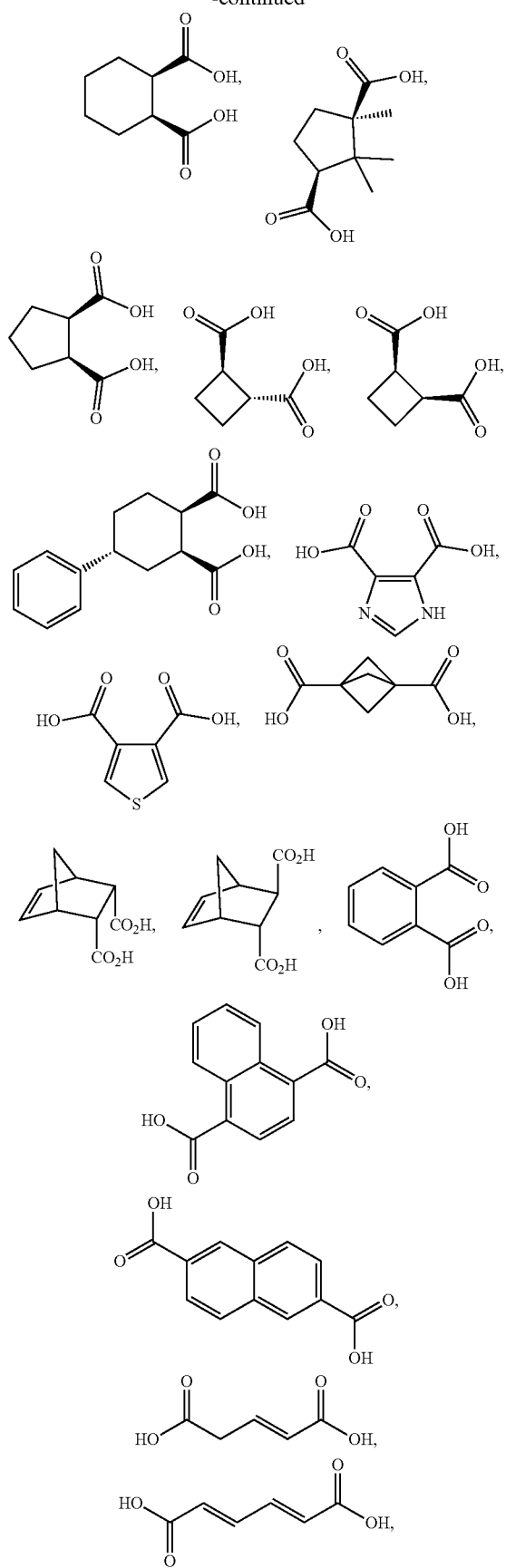

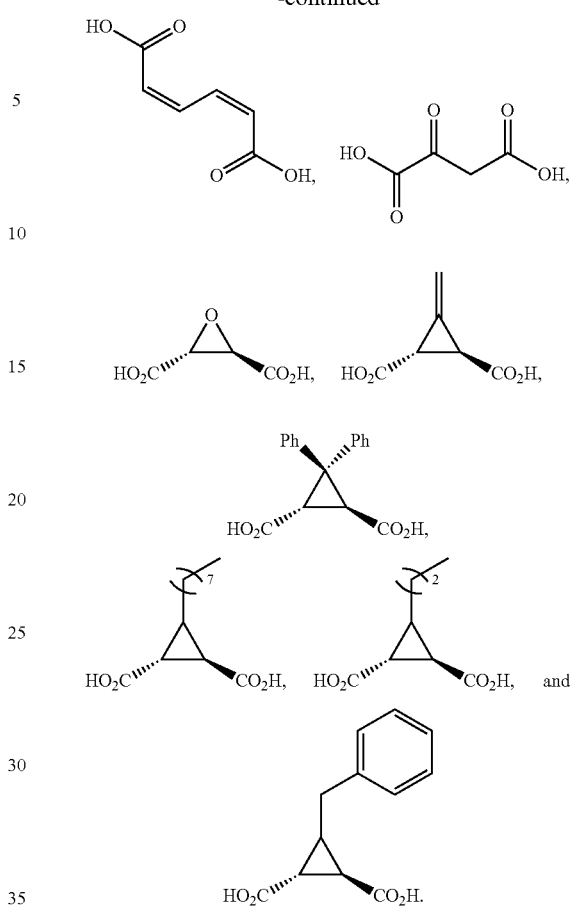

In some embodiments, dicarboxylic acid molecules, such as the ones described herein, may be further functionalized to contain one or more additional functional groups. Dicarboxylic acids may be further functionalized, for example, to provide an attachment point to an Fc domain monomer, an Fc domain, an Fc-binding peptide, an albumin protein, or an albumin protein-binding peptide (e.g., by way of a linker, such as a PEG linker).

In some embodiments, when the neuraminidase inhibitor is attached to Fc domain monomer, an Fc domain, an Fc-binding peptide, an albumin protein, or an albumin protein-binding peptide, the linking group may comprise a moiety comprising a carboxylic acid moiety and an amino moiety that are spaced by from 1 to 25 atoms. Examples of such linking groups include, but are not limited to,

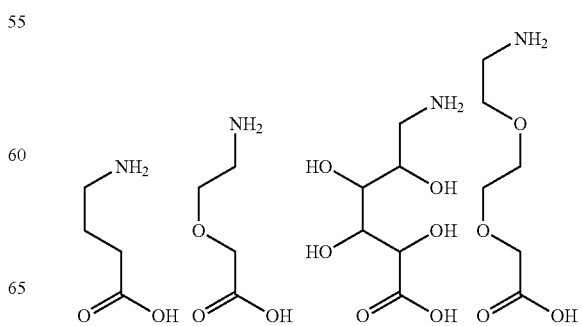

631
-continued

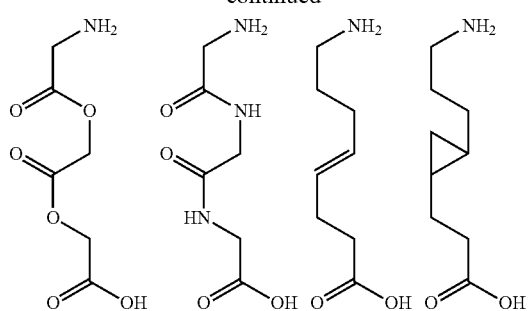

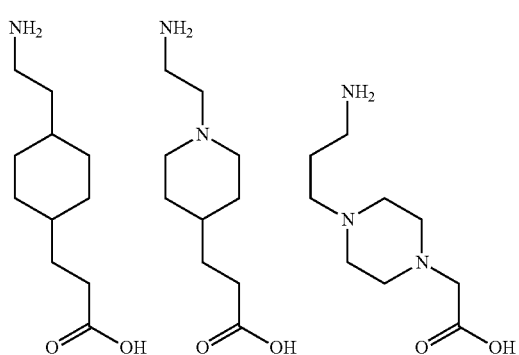

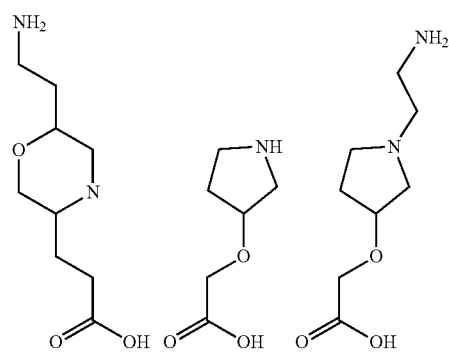

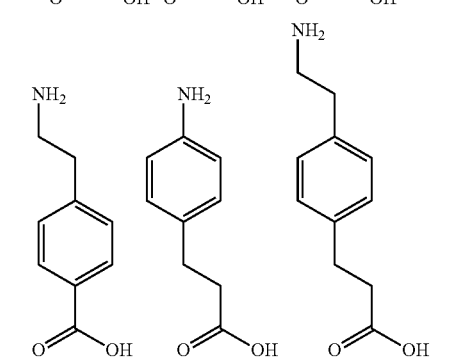

632
-continued

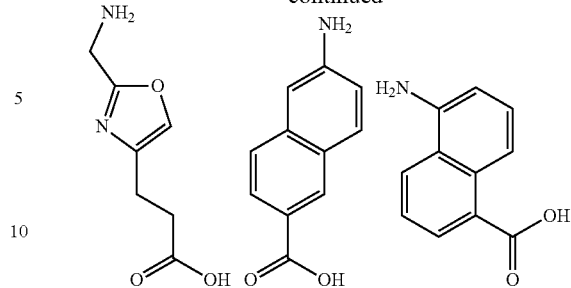

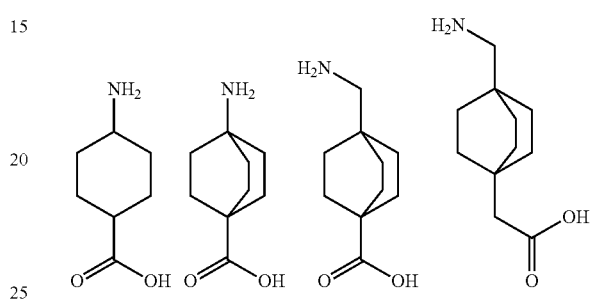

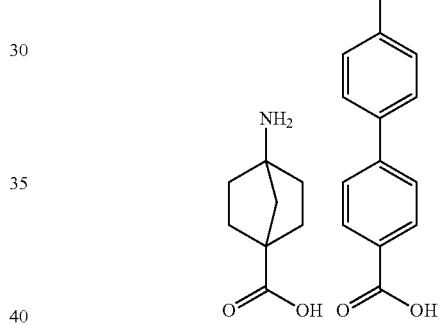

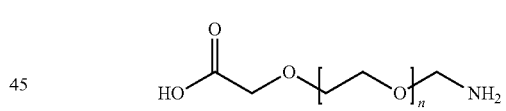

wherein n is an integer from 1 to 20 (e.g., n is 1, 2, 3, 4, 5, 6, 7, 8, 9, 10, 11, 12, 13, 14, 15, 16, 17, 18, 19, or 20).

In some embodiments, a linking group may include a moiety including a carboxylic acid moiety and an amino moiety, such as the ones described herein, may be further functionalized to contain one or more additional functional groups. Such linking groups may be further functionalized, for example, to provide an attachment point to an Fc domain monomer, an Fc domain, an Fc-binding peptide, an albumin protein, or an albumin protein-binding peptide (e.g., by way of a linker, such as a PEG linker).

In some embodiments, when the neuraminidase inhibitor is attached to Fc domain monomer, an Fc domain, an Fc-binding peptide, an albumin protein, or an albumin protein-binding peptide, the linking group may comprise a moiety comprising two or amino moieties (e.g., a diamino moiety) that are spaced by from 1 to 25 atoms. Examples of such linking groups include, but are not limited to,

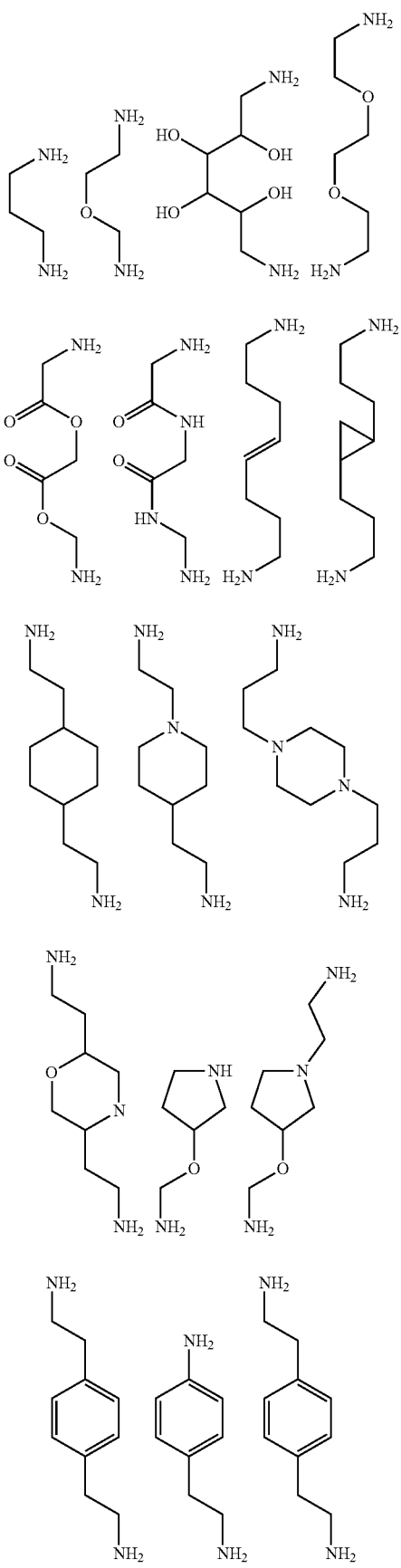
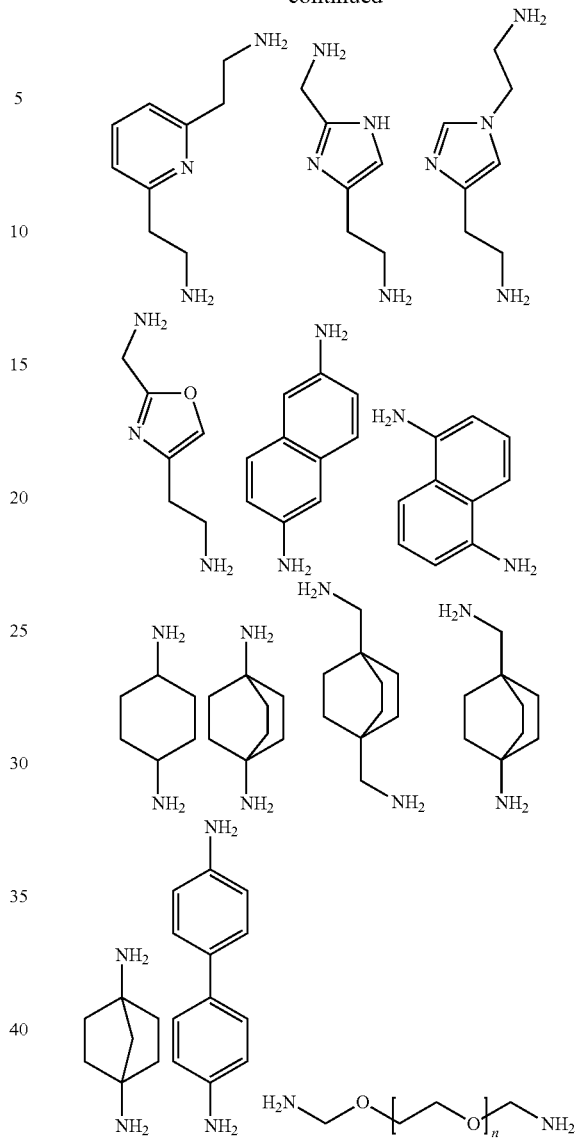

wherein n is an integer from 1 to 20 (e.g., n is 1, 2, 3, 4, 5, 6, 7, 8, 9, 10, 11, 12, 13, 14, 15, 16, 17, 18, 19, or 20).

In some embodiments, a linking group may include a diamino moiety, such as the ones described herein, may be further functionalized to contain one or more additional functional groups. Such diamino linking groups may be further functionalized, for example, to provide an attachment point to an Fc domain monomer, an Fc domain, an Fc-binding peptide, an albumin protein, or an albumin protein-binding peptide (e.g., by way of a linker, such as a PEG linker).

In some embodiments, a molecule containing an azide group may be used to form a linker, in which the azide group may undergo cycloaddition with an alkyne to form a 1,2,3-triazole linkage. In some embodiments, a molecule containing an alkyne group may be used to form a linker, in which the alkyne group may undergo cycloaddition with an azide to form a 1,2,3-triazole linkage. In some embodiments, a molecule containing a maleimide group may be used to form a linker, in which the maleimide group may react with a cysteine to form a C—S linkage. In some embodiments, a molecule containing one or more sulfonic acid groups may be used to form a linker, in which the sulfonic acid group may form a sulfonamide linkage with the linking nitrogen in a neuraminidase inhibitor. In some embodiments, a molecule containing one or more isocyanate groups may be used to form a linker, in which the isocyanate group may form a urea linkage with the linking nitrogen in a neuraminidase inhibitor. In some embodiments, a molecule containing one or more haloalkyl groups may be used to form a linker, in which the haloalkyl group may form a covalent linkage, e.g., C—N and C—O linkages, with a neuraminidase inhibitor.

In some embodiments, a linker (L or L') may comprise a synthetic group derived from, e.g., a synthetic polymer (e.g., a polyethylene glycol (PEG) polymer). In some embodiments, a linker may comprise one or more amino acid residues. In some embodiments, a linker may be an amino acid sequence (e.g., a 1-25 amino acid, 1-10 amino acid, 1-9 amino acid, 1-8 amino acid, 1-7 amino acid, 1-6 amino acid, 1-5 amino acid, 1-4 amino acid, 1-3 amino acid, 1-2 amino acid, or 1 amino acid sequence). In some embodiments, a linker (L or L') may include one or more optionally substituted C1-C20 alkylene, optionally substituted C1-C20 heteroalkylene (e.g., a PEG unit), optionally substituted C2-C20 alkenylene (e.g., C2 alkenylene), optionally substituted C2-C20 heteroalkenylene, optionally substituted C2-C20 alkynylene, optionally substituted C2-C20 heteroalkynylene, optionally substituted C3-C20 cycloalkylene (e.g., cyclopropylene, cyclobutylene), optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene (e.g., C6 arylene), optionally substituted C2-C15 heteroarylene (e.g., imidazole, pyridine), O, S, $NR^i$ ($R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl), P, carbonyl, thiocarbonyl, sulfonyl, phosphate, phosphoryl, or imino.

Conjugation Chemistries

Neuraminidase inhibitor monomer or dimers (e.g., in a conjugate of any one of formulas (1)-(5), (D-I)-(D-XI), (D'-I), (M-I)-(M-XI), or (M'-I)) may be conjugated to an Fc domain monomer, an Fc domain, an Fc-binding peptide, an albumin protein, or an albumin protein-binding peptide, e.g., by way of a linker, by any standard conjugation chemistries known to those of skill in the art. The following conjugation chemistries are specifically contemplated, e.g., for conjugation of a PEG linker (e.g., a functionalized PEG linker) to an Fc domain monomer, an Fc domain, an Fc-binding peptide, an albumin protein, or an albumin protein-binding peptide.

Covalent conjugation of two or more components in a conjugate using a linker may be accomplished using well-known organic chemical synthesis techniques and methods. Complementary functional groups on two components may react with each other to form a covalent bond. Examples of complementary reactive functional groups include, but are not limited to, e.g., maleimide and cysteine, amine and activated carboxylic acid, thiol and maleimide, activated sulfonic acid and amine, isocyanate and amine, azide and alkyne, and alkene and tetrazine. Site-specific conjugation to a polypeptide (e.g., an Fc domain monomer, an Fc domain, an Fc-binding peptide, an albumin protein, or an albumin protein-binding peptide) may be accomplished using techniques known in the art. Exemplary techniques for site-specific conjugation of a small molecule to an Fc domain are provided in Agarwall. P., et al. Bioconjugate Chem. 26:176-192 (2015).

Other examples of functional groups capable of reacting with amino groups include, e.g., alkylating and acylating agents. Representative alkylating agents include: (i) an α-haloacetyl group, e.g., $XCH_2CO$— (where X═Br, Cl, or I); (ii) a N-maleimide group, which may react with amino groups either through a Michael type reaction or through acylation by addition to the ring carbonyl group; (iii) an aryl halide, e.g., a nitrohaloaromatic group; (iv) an alkyl halide; (v) an aldehyde or ketone capable of Schiff's base formation with amino groups; (vi) an epoxide, e.g., an epichlorohydrin and a bisoxirane, which may react with amino, sulfhydryl, or phenolic hydroxyl groups; (vii) a chlorine-containing of s-triazine, which is reactive towards nucleophiles such as amino, sufhydryl, and hydroxyl groups; (viii) an aziridine, which is reactive towards nucleophiles such as amino groups by ring opening; (ix) a squaric acid diethyl ester; and (x) an α-haloalkyl ether.

Examples of amino-reactive acylating groups include, e.g., (i) an isocyanate and an isothiocyanate; (ii) a sulfonyl chloride; (iii) an acid halide; (iv) an active ester, e.g., a nitrophenylester or N-hydroxysuccinimidyl ester, or derivatives thereof (e.g., azido-$PEG_2$-$PEG_{40}$-NHS ester); (v) an acid anhydride, e.g., a mixed, symmetrical, or N-carboxyanhydride; (vi) an acylazide; and (vii) an imidoester. Aldehydes and ketones may be reacted with amines to form Schiff's bases, which may be stabilized through reductive amination.

It will be appreciated that certain functional groups may be converted to other functional groups prior to reaction, for example, to confer additional reactivity or selectivity. Examples of methods useful for this purpose include conversion of amines to carboxyls using reagents such as dicarboxylic anhydrides; conversion of amines to thiols using reagents such as N-acetylhomocysteine thiolactone, S-acetylmercaptosuccinic anhydride, 2-iminothiolane, or thiol-containing succinimidyl derivatives; conversion of thiols to carboxyls using reagents such as a -haloacetates; conversion of thiols to amines using reagents such as ethylenimine or 2-bromoethylamine; conversion of carboxyls to amines using reagents such as carbodiimides followed by diamines; and conversion of alcohols to thiols using reagents such as tosyl chloride followed by transesterification with thioacetate and hydrolysis to the thiol with sodium acetate.

In some embodiments, a linker of the invention (e.g., L or L', such as $L^c$ of D-L-I), is conjugated (e.g., by any of the methods described herein) to E (e.g., an Fc domain or albumin protein). In preferred embodiments of the invention, the linker is conjugated by way of: (a) a thiourea linkage (i.e., —NH(C═S)NH—) to a lysine of E; (b) a carbamate linkage (i.e., —NH(C═O)—O) to a lysine of E; (c) an amine linkage by reductive amination (i.e., —$NHCH_2$) between a lysine and E; (d) an amide (i.e., —NH—(C═O)$CH_2$) to a lysine of E; (e) a cysteine-maleimide conjugate between a maleimide of the linker to a cysteine of E; (f) an amine linkage by reductive amination (i.e., —$NHCH_2$) between the linker and a carbohydrate of E (e.g., a glycosyl group of an Fc domain monomer or an Fc domain); (g) a rebridged cysteine conjugate, wherein the linker is conjugated to two cysteines of E; (h) an oxime linkage between the linker and a carbohydrate of E (e.g., a glycosyl group of an Fc domain monomer or an Fc domain); (i) an oxime linkage between the linker and an amino acid residue of E; (j) an azido linkage between the linker and E; (k) direct acylation of a linker to E; or (l) a thioether linkage between the linker and E.

In some embodiments, a linker is conjugated to E, wherein the linkage includes the structure —NH(C=NH)X—, wherein X is O, HN, or a bond. In some embodiments, a linker is conjugated to E, wherein the linkage between the remainder of the linker and E includes the structure —NH(C=O)NH—. In some embodiments, a linker (e.g., an active ester, e.g., a nitrophenylester or N-hydroxysuccinimidyl ester, or derivatives thereof (e.g., a functionalized PEG linker (e.g., azido-$PEG_2$-$PEG_{40}$-NHS ester), is conjugated to E, with a T of (e.g., DAR) of between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In these instances, the E-($PEG_2$-$PEG_{40}$)-azide can react with an Int having a terminal alkyne linker (e.g., L, or L', such as $L^c$ of D-L-I) through click conjugation. During click conjugation, the copper-catalyzed reaction of the an azide (e.g., the Fc-($PEG_2$-$PEG_{40}$)-azide) with the alkyne (e.g., the Int having a terminal alkyne linker (e.g., L or L', such as $L^c$ of D-L-I) forming a 5-membered heteroatom ring. In some embodiments, the linker conjugated to E is a terminal alkyne and is conjugated to an Int having a terminal azide. Exemplary preparations of preparations of E-($PEG_2$-$PEG_{40}$)-azide are described in Examples 7, 8, 61, 84, 88, and 124. Exemplary conjugates prepared through click conjugation are depicted in FIGS. 43, 61, and 102. The click chemistry conjugation procedure is depicted in FIG. 103. One of skill in the art would readily understand the final product from a click chemistry conjugation.

Exemplary linking strategies (e.g., methods for linking a monomer or a dimer of a neuraminidase inhibitor to E, such as, by way of a linker) are further depicted in FIGS. 1, 28, 29, 30, 43, and 61.

VI. Combination Therapies

Antiviral Agents

In some embodiments, one or more antiviral agents may be administered in combination (e.g., administered substantially simultaneously (e.g., in the same pharmaceutical composition or in separate pharmaceutical compositions) or administered separately at different times) with a conjugate described herein (e.g., a conjugate of any one of formulas (1)-(5), (D-I)-(D-XI), (D'-I), (M-I)-(M-XI), or (M'-I)). The antiviral agent may be administered substantially simultaneously (e.g., in the same pharmaceutical composition or in separate pharmaceutical compositions) as the conjugates, or may be administered prior to or following the conjugates (e.g., within a period of 1 day, 2, days, 5, days, 1 week, 2 weeks, 3 weeks, 1 month, 2 months, 6 months, or 12 months, or more). In some embodiments, the conjugate is administered by injection (e.g., intramuscularly, intradermally, intranasally, or subcutaneously), and the antiviral agent is administered orally. Most preferably, the conjugate is administered intravenously, and the antiviral agent is administered orally.

In some embodiments, the conjugate is administered prophylactically (e.g., prior to the subject coming into contact with the virus) and the antiviral agent is administered after the subject has a viral infection, is presumed to have a viral infection, or has been exposed to the virus. In some embodiments, the conjugate and the antiviral agent are both administered after the subject has a viral infection, is presumed to have a viral infection, or has been exposed to the virus. In some embodiments, the conjugate and the antiviral agent are both administered prophylactically.

The conjugate and the antiviral agent may be formulated in the same pharmaceutical composition or in separate pharmaceutical compositions. In preferred embodiments, the conjugate and the antiviral agent is formulated in separate pharmaceutical compositions (e.g., formulated for different routes of administration). In some embodiments, the conjugate and the antiviral agent are administered simultaneously (e.g., at substantially the same time, such as within 5 minutes, 30 minutes, 1-6 hours, 1-12 hours, or 1 day) or sequentially (e.g., at different times, such as more than 1 day apart). Provided the antiviral agent and the conjugate are administered sequentially, the antiviral agent is administered 1-50 (e.g., 1-15, 10-25, 20-35, 30-45, or 35-50) times after the administration of the conjugate (e.g., administrations 1 day, 2, days, 5, days, 1 week, 2 weeks, 3 weeks, 1 month, 2 months, 6 months, or 12 months, or more after the conjugate).

In some instances, an antiviral agent is administered to a subject in need thereof one or more times (e.g., 1-10 times or more; 1, 2, 3, 4, 5, 6, 7, 8, 9, or 10 times) daily, weekly, monthly, biannually, annually, or as medically necessary after the administration of a conjugate described herein (e.g., a conjugate of any one of formulas (1)-(5), (D-I)-(D-XI), (D'-I), (M-I)-(M-XI), or (M'-I)).

In some embodiments, the antiviral agent is an antiviral agent for the treatment of influenza virus. For example, the antiviral agent may be an M2 ion channel blocker, a neuraminidase inhibitor (e.g., a long-acting neuraminidase inhibitor), a polymerase inhibitor, a hemagglutinin inhibitor, a fusion protein inhibitor, a COX-2 inhibitor, or a PPAR agonist. The antiviral agent may target either the virus or the host subject. The antiviral agent for the treatment of influenza virus used in combination with a conjugate described herein (e.g., a conjugate of any one of formulas (1)-(5), (D-I)-(D-XI), (D'-I), (M-I)-(M-XI), or (M'-I)) may be selected from pimovidir, oseltamivir, zanamivir, peramivir, Ianinamivir, CS-8958, amantadine, rimantadine, cyanovirin-N, a cap-dependent endonuclease inhibitor (e.g., baloxavir marboxil), a polymerase inhibitor (e.g., T-705), a PB2 inhibitor (e.g., JNJ-63623872), a conjugated sialidase (e.g., DAS181), a thiazolide (e.g., nitazoxanide), a COX inhibitor, a PPAR agonist, a hemagglutinin-targeting antibody (e.g., a monoclonal antibody such as CR6261, CR8020, MED18852, MHAA4549A, or VIS410), or an siRNA targeting a host or viral gene, or prodrugs thereof, or pharmaceutically acceptable salts thereof.

Preferably, the antiviral agent is directed to a different therapeutic target than the conjugate, for example an M2 ion channel blocker, a polymerase inhibitor, a hemagglutinin inhibitor, a viral replication inhibitor (e.g., a cap-dependent endonuclease inhibitor), a fusion protein inhibitor, a COX-2 inhibitor, or a PPAR agonist. Most preferably, the antiviral agent is a cap-dependent endonuclease inhibitor (e.g., baloxavir marboxil). In some embodiments, the antiviral agent is administered in combination with a conjugate described by formula (D-II-6). In some embodiments, the antiviral agent is administered in combination with a conjugate described by formula (D-II-7). In preferred embodiments, an antiviral agent (e.g., baloxavir marboxil) is administered in combination with a conjugate described by formula (D-II-6). Most preferably, an antiviral agent (e.g., baloxavir marboxil) is administered in combination with a conjugate described formula (D-II-7). More preferably, the conjugate is conjugate 45 or conjugate 46.

Baloxavir

In some embodiments, Baloxavir marboxil (BXM, prodrug form) or baloxavir acid (BXA, active form) or any salt thereof (Omoto et al. *Scientific Reports.* 8:9633, 2018; Japic CTI-153090; Japic CTI-163417; each of which are incorporated herein by reference in their entirety) may be administered in combination (e.g., administered substantially simultaneously (e.g., in the same pharmaceutical composition or in separate pharmaceutical compositions) or administered separately at different times) with a conjugate described herein (e.g., a conjugate of any one of formulas (1)-(5), (D-I)-(D-XI), (D'-I), (M-I)-(M-XI), or (M'-I)).

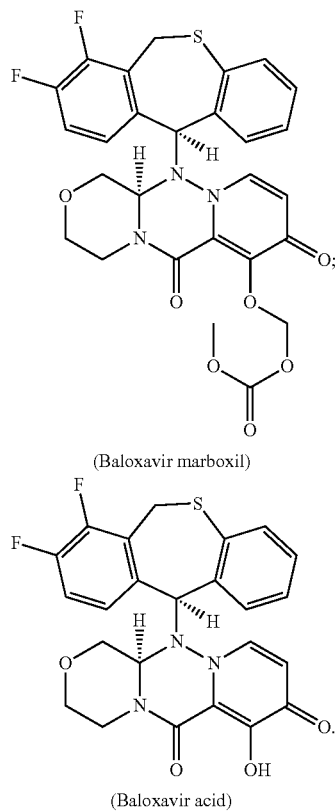

(Baloxavir marboxil)

(Baloxavir acid)

In some embodiments, Baloxavir marboxil, Baloxavir acid, or salt thereof is administered in a dosage ranging from about 0.1 mg to about 3000 mg, preferably about 0.1 mg to about 1000 mg, most preferable about 10 mg to about 100 mg (e.g., about 10 mg, about 20 mg, about 30 mg, about 40 mg, about 50 mg, about 60 mg, about 70 mg, about 80 mg, about 90 mg, or about 100 mg) per adult a day, if necessary, by division. In some embodiments, the Baloxavir marboxil, Baloxavir acid, or salt thereof is administered at a decreased dose or frequency compared to standard of care when administered in combination with the conjugate. The conjugate may be administered at a dose described herein.

In some embodiments, Baloxavir marboxil, Baloxavir acid, or a salt thereof is administered more frequently than the conjugate. For example, the conjugate may be administered once every 12 months, 6 months, 3 months, 2 months, 1 month, every 3 weeks, every 2 weeks, or weekly. The Baloxavir marboxil, Baloxavir acid, or salt thereof may be administered three times daily, twice daily, once daily, once every 2-6 days, once weekly, or once every two weeks. In some embodiments, Baloxavir marboxil, Baloxavir acid, or salts thereof, are administered one or more times (e.g., 1-10 times or more; 1, 2, 3, 4, 5, 6, 7, 8, 9, 10 times or more) after (e.g., within 6 months, 3 months, 2 months, 1 month, 3 weeks, 2 weeks, or 1 week) the administration of a conjugate described herein.

In some embodiments, Baloxavir marboxil, Baloxavir acid, or a salt thereof is administered orally.

In some embodiments, Baloxavir marboxil, Baloxavir acid, or a salt thereof is administered, e.g., orally, in a dosage ranging from about 0.01 mg to about 1000 mg, preferably about 0.05 mg to about 500 mg, per day. Dosage forms and strengths for Baloxavir marboxil (XOFLUZA™) are well known, with a single 40 mg oral dose for adults 40 to <80 kg and a single 80 mg oral dose for adults ≥80 kg. Dosage forms and strengths for Baloxavir marboxil (XOFLUZA™) for pediatric subjects (e.g., subjects ≥12 years old and ≥40 kg) is well known, with a single 40 mg oral dose for pediatric subjects 40 to <80 kg and a single 80 mg oral dose for pediatric subjects >80 kg.

When administered in combination with a conjugate of the present invention, the efficacy of baloxavir (e.g., baloxavir marboxil, baloxavir acid, or a salt thereof) may be enhanced, e.g., by a synergistic interaction of the baloxavir and the conjugate. This may permit the administration of baloxavir at a reduced dose (e.g., relative to the present clinical standard of care) without any loss of efficacy. This has the advantage of decreasding adverse events associate with administration of baloxavir. In some embodiments, Baloxavir marboxil, Baloxavir acid, or a salt thereof is administered in a reduced or subclinical dose (e.g., administered at a dose lower than without a conjugate described herein and/or lower than the present clinical standard of care (e.g., a dose lower than 40 mg oral dose (e.g., a dose ranging from 0.01 mg to 40 mg (e.g., 0.5 mg, 1.0 mg, 1.5 mg, 2.0 mg, 2.5 mg, 5.0 mg, 7.5 mg, 10 mg, 15 mg, 18 mg, 20 mg, 23 mg, 25 mg, 30 mg, 35 mg, or 38 mg oral dose))). Baloxavir marboxil (XOFLUZA™) may be provided in any amount sufficient to treat an influenza viral infection in a subject having previously been administered any conjugate described herein.

Antiviral Vaccines

In some embodiments, any one of conjugates described herein (e.g., a conjugate of any one of formulas (1)-(5), (D-I)-(D-XI), (D'-I), (M-I)-(M-XI), or (M'-I)) is administered in combination with an antiviral vaccine (e.g., a composition that elicits an immune response in a subject directed against a virus). The antiviral vaccine may be administered substantially simultaneously (e.g., in the same pharmaceutical composition or in separate pharmaceutical compositions) as the conjugates, or may be administered prior to or following the conjugates (e.g., within a period of 1 day, 2, days, 5, days, 1 week, 2 weeks, 3 weeks, 1 month, 2 months, 6 months, or 12 months, or more).

In some embodiments the viral vaccine comprises an immunogen that elicits an immune response in the subject against influenza virus A, B, C, or parainfluenza virus. In some embodiments the immunogen is an inactivated virus (e.g., the vaccine is a trivalent influenza vaccine that contains purified and inactivated material influenza virus A, B, C, or parainfluenza virus or any combination thereof). In some embodiments the vaccine is given as an intramuscular injection. In some embodiments, the vaccine is a live virus vaccine that contains live viruses that have been attenuated (weakened). In some embodiments the vaccine is administered as a nasal spray.

VII. Methods

Methods described herein include, e.g., methods of protecting against or treating a viral infection (e.g., an influenza viral infection) in a subject and methods of preventing, stabilizing, or inhibiting the growth of viral particles. A method of treating a viral infection (e.g., an influenza viral infection) in a subject includes administering to the subject a conjugate described herein (e.g., a conjugate of any one of formulas (1)-(5), (D-I)-(D-XI), (D'-I), (M-I)-(M-XI), or (M'-I)) or a pharmaceutical composition thereof. In some embodiments, the viral infection is cause by the influenza virus (e.g., influenza virus A, B, C, or parainfluenza virus). In some embodiments, the viral infection is caused by a resistant strain of virus. A method of preventing, stabilizing, or inhibiting the growth of viral particles or preventing the replication and spread of the virus includes contacting the virus or a site susceptible to viral growth with a conjugate described herein (e.g., a conjugate of any one of formulas (1)-(5), (D-I)-(D-XI), (D'-I), (M-I)-(M-XI), or (M'-I)) or a pharmaceutical composition thereof.

The disclosure also provides a method of protecting against or treating a viral infection (e.g., an influenza viral infection) in a subject having or at risk of developing a secondary infection (e.g., a secondary bacterial infection, a secondary viral infection, or a secondary fungal infection), wherein the method includes administering to the subject a conjugate or composition described herein. The disclosure further provides a method of preventing a secondary infection in a subject diagnosed with an influenza infection, wherein the method includes administering to the subject a conjugate or composition described herein. In some embodiments, the secondary infection is a bacterial infection (e.g., methicillin-resistant *Staphylococcus aureus* (MRSA), *Streptococcus pneumoniae, Pseudomonas aeruginosa*, and/or *Haemophilus influenzae*), a viral infection, or a fungal infection. In particular embodiments, the secondary infection is MRSA. In certain embodiments, the secondary infection is *S. pneumoniae*. In some embodiments, the secondary infection is a respiratory infection (e.g., an infection of the respiratory tract). In some embodiments, the secondary infection is associated with (e.g., causes) pneumonia (e.g., bacterial or viral pneumonia). In some embodiments, the subject has or is at risk of developing pneumonia.

Moreover, methods described herein also include methods of protecting against or treating viral infection in a subject by administering to the subject a conjugate described herein (e.g., a conjugate of any one of formulas (1)-(5), (D-I)-(D-XI), (D'-I), (M-I)-(M-XI), or (M'-I)). In some embodiments, the method further includes administering to the subject an antiviral agent or an antiviral vaccine.

Methods described herein also include methods of protecting against or treating a viral infection in a subject by administering to said subject (1) a conjugate described herein (e.g., a conjugate of any one of formulas (1)-(5), (D-I)-(D-XI), (D'-I), (M-I)-(M-XI), or (M'-I)) and (2) an antiviral agent or an antiviral vaccine. Methods described herein also include methods of preventing, stabilizing, or inhibiting the growth of viral particles or preventing the replication or spread of a virus, by contacting the virus or a site susceptible to viral growth with (1) a conjugate described herein (e.g., a conjugate of any one of formulas (1)-(5), (D-I)-(D-XI), (D'-I), (M-I)-(M-XI), or (M'-I)) and (2) an antiviral agent or an antiviral vaccine.

In some embodiments, the conjugate described herein (e.g., a conjugate of any one of formulas (1)-(5), (D-I)-(D-XI), (D'-I), (M-I)-(M-XI), or (M'-I)) is administered first, followed by administering of the antiviral agent or antiviral vaccine alone. In some embodiments, the antiviral agent or antiviral vaccine is administered first, followed by administering of the conjugate described herein alone. In some embodiments, the conjugate described herein and the antiviral agent or antiviral vaccine are administered substantially simultaneously (e.g., in the same pharmaceutical composition or in separate pharmaceutical compositions). In some embodiments, the conjugate described herein or the antiviral agent or antiviral vaccine is administered first, followed by administering of the conjugate described herein and the antiviral agent or antiviral vaccine substantially simultaneously (e.g., in the same pharmaceutical composition or in separate pharmaceutical compositions). In some embodiments, the conjugate described herein and the antiviral agent or antiviral vaccine are administered first substantially simultaneously (e.g., in the same pharmaceutical composition or in separate pharmaceutical compositions), followed by administering of the conjugate described herein or the antiviral agent or antiviral vaccine alone. In some embodiments, when a conjugate described herein (e.g., a conjugate of any one of formulas (1)-(5), (D-I)-(D-XI), (D'-I), (M-I)-(M-XI), or (M'-I)) and an antiviral agent or antiviral vaccine are administered together (e.g., substantially simultaneously in the same or separate pharmaceutical compositions, or separately in the same treatment regimen), inhibition of viral replication of each of the conjugate and the antiviral agent or antiviral vaccine may be greater (e.g., occur at a lower concentration) than inhibition of viral replication of each of the conjugate and the antiviral agent or antiviral vaccine when each is used alone in a treatment regimen.

VII. Pharmaceutical Compositions and Preparations

A conjugate described herein may be formulated in a pharmaceutical composition for use in the methods described herein. In some embodiments, a conjugate described herein may be formulated in a pharmaceutical composition alone. In some embodiments, a conjugate described herein may be formulated in combination with an antiviral agent or antiviral vaccine in a pharmaceutical composition. In some embodiments, the pharmaceutical composition includes a conjugate described herein (e.g., a conjugate described by any one of formulas (1)-(5), (D-I)-(D-XI), (D'-I), (M-I)-(M-XI), or (M'-I)) and pharmaceutically acceptable carriers and excipients.

Acceptable carriers and excipients in the pharmaceutical compositions are nontoxic to recipients at the dosages and concentrations employed. Acceptable carriers and excipients may include buffers such as phosphate, citrate, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acid residues such as glycine, glutamine, histidine, and lysine, and carbohydrates such as glucose, mannose, sucrose, and sorbitol.

Examples of other excipients include, but are not limited to, antiadherents, binders, coatings, compression aids, disintegrants, dyes, emollients, emulsifiers, fillers (diluents), film formers or coatings, flavors, fragrances, glidants (flow enhancers), lubricants, sorbents, suspending or dispersing agents, or sweeteners. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The conjugates herein may have ionizable groups so as to be capable of preparation as pharmaceutically acceptable salts. These salts may be acid addition salts involving inorganic or organic acids or the salts may, in the case of acidic forms of the conjugates herein be prepared from inorganic or organic bases. Frequently, the conjugates are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art.

Representative acid addition salts include, but are not limited to, acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include, but are not limited to, sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

Depending on the route of administration and the dosage, a conjugate herein or a pharmaceutical composition thereof used in the methods described herein will be formulated into suitable pharmaceutical compositions to permit facile delivery. A conjugate (e.g., a conjugate of any one of formulas (1)-(5), (D-I)-(D-XI), (D'-I), (M-I)-(M-XI), or (M'-I)) or a pharmaceutical composition thereof may be formulated to be administered intramuscularly, intravenously (e.g., as a sterile solution and in a solvent system suitable for intravenous use), intradermally, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctival, intravesicularlly, mucosally, intrapericardially, intraumbilically, intraocularally, orally (e.g., a tablet, capsule, caplet, gelcap, or syrup), topically (e.g., as a cream, gel, lotion, or ointment), locally, by inhalation, by injection, or by infusion (e.g., continuous infusion, localized perfusion bathing target cells directly, catheter, lavage, in cremes, or lipid compositions). Depending on the route of administration, a conjugate herein or a pharmaceutical composition thereof may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, preparations suitable for iontophoretic delivery, or aerosols. The compositions may be formulated according to conventional pharmaceutical practice.

A conjugate described herein may be formulated in a variety of ways that are known in the art. For use as treatment of human and animal subjects, a conjugate described herein can be formulated as pharmaceutical or veterinary compositions. Depending on the subject (e.g., a human) to be treated, the mode of administration, and the type of treatment desired, e.g., prophylaxis or therapy, a conjugate described herein is formulated in ways consonant with these parameters. A summary of such techniques is found in Remington: The Science and Practice of Pharmacy, 22nd Edition, Lippincott Williams & Wilkins (2012); and Encyclopedia of Pharmaceutical Technology, 4th Edition, J. Swarbrick and J. C. Boylan, Marcel Dekker, New York (2013), each of which is incorporated herein by reference.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, and preservatives. The conjugates can be administered also in liposomal compositions or as microemulsions. Systemic administration may also include relatively noninvasive methods such as the use of suppositories, transdermal patches, transmucosal delivery and intranasal administration. Oral administration is also suitable for conjugates herein. Suitable forms include syrups, capsules, and tablets, as is understood in the art.

The pharmaceutical compositions can be administered parenterally in the form of an injectable formulation. Pharmaceutical compositions for injection can be formulated using a sterile solution or any pharmaceutically acceptable liquid as a vehicle. Formulations may be prepared as solid forms suitable for solution or suspension in liquid prior to injection or as emulsions. Pharmaceutically acceptable vehicles include, but are not limited to, sterile water, physiological saline, and cell culture media (e.g., Dulbecco's Modified Eagle Medium (DMEM), α-Modified Eagles Medium (α-MEM), F-12 medium). Such injectable compositions may also contain amounts of nontoxic auxiliary substances such as wetting or emulsifying agents, pH buffering agents, such as sodium acetate and sorbitan monolaurate. Formulation methods are known in the art, see e.g., Pharmaceutical Preformulation and Formulation, 2nd Edition, M. Gibson, Taylor & Francis Group, CRC Press (2009).

The pharmaceutical compositions can be prepared in the form of an oral formulation. Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Other pharmaceutically acceptable excipients for oral formulations include, but are not limited to, colorants, flavoring agents, plasticizers, humectants, and buffering agents. Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion controlled release of a conjugate described herein (e.g., a conjugate of any one of formulas (1)-(5), (D-I)-(D-XI), (D'-I), (M-I)-(M-XI), or (M'-I)) or a pharmaceutical composition thereof can be achieved by appropriate coating of a tablet, capsule, pellet, or granulate formulation of the conjugate, or by incorporating the conjugate into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The pharmaceutical composition may be formed in a unit dose form as needed. The amount of active component, e.g., a conjugate described herein (e.g., a conjugate of any one of formulas (1)-(5), (D-I)-(D-XI), (D'-I), (M-I)-(M-XI), or (M'-I)), included in the pharmaceutical compositions are such that a suitable dose within the designated range is provided (e.g., a dose within the range of 0.01-100 mg/kg of body weight).

IX. Routes of Administration and Dosages

In any of the methods described herein, conjugates herein may be administered by any appropriate route for treating or protecting against a viral infection (e.g., an influenza infection), or for preventing, stabilizing, or inhibiting the proliferation or spread of a virus (e.g., an influenza virus). Conjugates described herein may be administered to humans, domestic pets, livestock, or other animals with a pharmaceutically acceptable diluent, carrier, or excipient. In some embodiments, administering comprises administration of any of the conjugates described herein (e.g., conjugates of any one of formulas (1)-(5), (D-I)-(D-XI), (D'-I), (M-I)-(M-XI), or (M'-I)) or compositions intramuscularly, intravenously (e.g., as a sterile solution and in a solvent system suitable for intravenous use), intradermally, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctival, intravesicularlly, mucosally, intrapericardially, intraumbilically, intraocularally, orally (e.g., a tablet, capsule, caplet, gelcap, or syrup), topically (e.g., as a cream, gel, lotion, or ointment), locally, by inhalation, by injection, or by infusion (e.g., continuous infusion, localized perfusion bathing target cells directly, catheter, lavage, in cremes, or lipid compositions). In some embodiments, if an antiviral agent is also administered in addition to a conjugate described herein, the antiviral agent or a pharmaceutical composition thereof may also be administered in any of the routes of administration described herein.

The dosage of a conjugate described herein (e.g., a conjugate of any one of formulas (1)-(5), (D-I)-(D-XI), (D'-I), (M-I)-(M-XI), or (M'-I)) or pharmaceutical compositions thereof depends on factors including the route of administration, the disease to be treated (e.g., the extent and/or condition of the viral infection), and physical characteristics, e.g., age, weight, general health, of the subject. Typically, the amount of the conjugate or the pharmaceutical composition thereof contained within a single dose may be an amount that effectively prevents, delays, or treats the viral infection without inducing significant toxicity. A pharmaceutical composition may include a dosage of a conjugate described herein ranging from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg) and, in a more specific embodiment, about 0.1 to about 30 mg/kg and, in a more specific embodiment, about 1 to about 30 mg/kg. In some embodiments, when a conjugate described herein (e.g., a conjugate of any one of formulas (1)-(5), (D-I)-(D-XI), (D'-I), (M-I)-(M-XI), or (M'-I)) and an antiviral agent or antiviral vaccine are administered in combination (e.g., substantially simultaneously in the same or separate pharmaceutical compositions, or separately in the same treatment regimen), the dosage needed of the conjugate described herein may be lower than the dosage needed of the conjugate if the conjugate was used alone in a treatment regimen.

A conjugate described herein (e.g., a conjugate of any one of formulas (1)-(5), (D-I)-(D-XI), (D'-I), (M-I)-(M-XI), or (M'-I)) or a pharmaceutical composition thereof may be administered to a subject in need thereof, for example, one or more times (e.g., 1-10 times or more; 1, 2, 3, 4, 5, 6, 7, 8, 9, or 10 times) daily, weekly, monthly, biannually, annually, or as medically necessary. Dosages may be provided in either a single or multiple dosage regimens. The timing between administrations may decrease as the medical condition improves or increase as the health of the patient declines. The dosage and frequency of administration may be adapted by the physician in accordance with conventional factors such as the extent of the infection and different parameters of the subject.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1: Preparation of Fc Constructs

Reverse translations of the amino acids comprising the protein constructs (SEQ ID NOs: 1, 3, 5, 7, 9, 12, and 14) were synthesized by solid-phase synthesis. The oligonucleotide templates were cloned into pcDNA3.1 (Life Technologies, Carlsbad, Calif., USA) at the cloning sites BamHI and XhoI (New England Biolabs, Ipswich, Mass., USA) and included signal sequences derived from the human Interleukin-2 or human albumin. The pcDNA3.1 plasmids were transformed into Top10 *E. coli* cells (LifeTech). DNA was amplified, extracted, and purified using the PURELINK® HiPure Plasmid Filter Maxiprep Kit (LifeTech). The plasmid DNA is delivered, using the ExpiFectamine™ 293 Transfection Kit (LifeTech), into HEK-293 cells per the manufacturer's protocol. Cells were centrifuged, filtered, and the supernatants were purified using MabSelect Sure Resin (GE Healthcare, Chicago, Ill., USA). Purified molecules were analyzed using 4-12% Bis Tris SDS PAGE gels by loading 1-2 µg of each molecule into the gel, and staining using instant Blue staining. Each gel included a molecular weight ladder with the indicated molecular weight standards (FIGS. 2-8). Reduced and non-reduced lanes are denoted by "R" and "NR". FIGS. 2-8 show non-reducing and reducing SDS-PAGE of an Fc domain formed from Fc domain monomers having the sequences of SEQ ID NOs: 1, 3, 5, 7, 9, 12, and 14, respectively.

Example 2. Synthesis of Zanamivir Intermediate

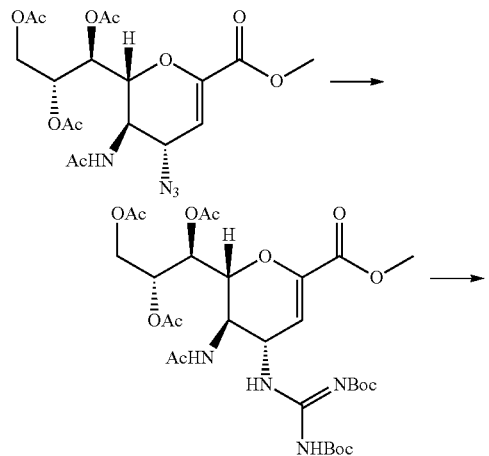

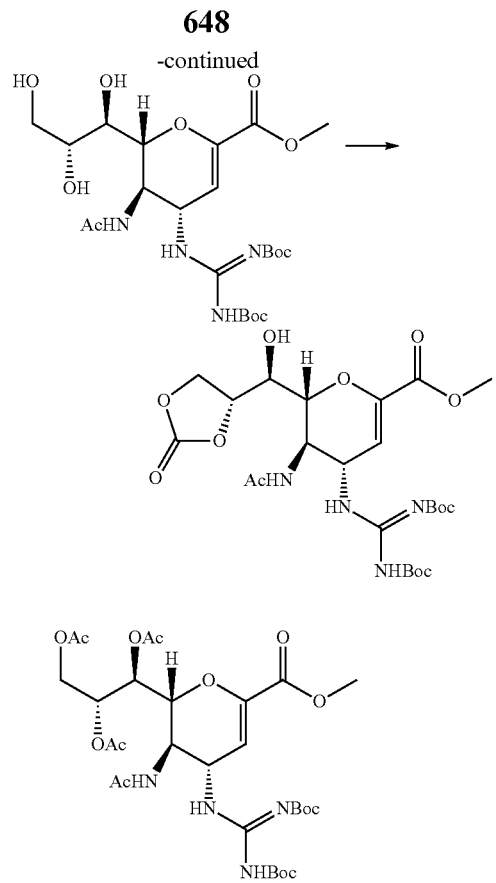

Step a.

Methyl 5-acetamido-7,8,9-O-triacetyl-2,6-anhydro-4-azido-3,4,5-trideoxy-D-glycero-D-galacto-non-2-enonate (4.56 g, 10.0 mmol) was dissolved in anhydrous THF (15 mL), and the solution was cooled to approximately 13° C. Triphenylphosphine (2.89 g, 11 mmol) was added in portions over 20 minutes. The resulting mixture was stirred at approximately 13° C. to room temperature for 2 hours, then a solution of LiOH (24 mg, 1 mmol) in water (1.5 mL) was added dropwise. After stirring for 28 hours, the reaction mixture was added with N,N'-bis-boc-1-guanylpyrazole (3.26 g, 10.5 mmol) and 4-dimethylaminopyridine (244.4 mg, 2 mmol). The reaction was stirred for 1.5 days. It was then diluted with a 1:1 mixture of ethyl acetate: hexanes (100 mL) and extracted with water (30 mL). The aqueous layer was back-extracted with ethyl acetate (30 mL). The combined organic layers were concentrated by rotary evaporation. The residue was purified through C18 reversed phase column chromatography (150 g, 25 to 70% acetonitrile and water). The collected fractions were concentrated by rotary evaporation at room temperature. A cloudy aqueous solution resulted and the majority of the product deposited on the flask as a gel. The solution was then extracted with ethyl acetate (150 mL). The organic layer was used to re-dissolve the gel material. It was then dried over $Na_2SO_4$, concentrated by rotary evaporation, and further dried under high vacuum to afford the title compound as a white foam. Yield 6.24 g, 92.8%. Ion found by LCMS: $[M+H]^+=673.2$.

Step b.

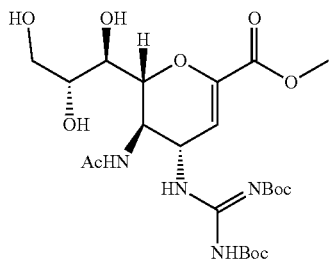

Step c.

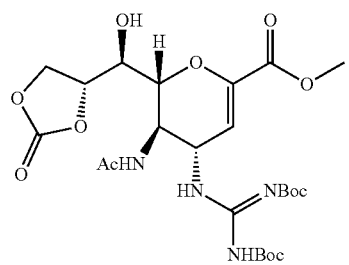

A solution of the product from step-a (6.24 g, 9.28 mmol) in anhydrous MeOH (20 mL) was cooled in an ice-water bath and a 0.5 M solution of sodium methoxide in MeOH (26 mL, 13 mmol) was slowly added. The reaction was stirred for 1 hour, then its pH was carefully adjusted to 7 to 7.5 by dropwise addition of a 4 N solution of HCl in dioxane (3 mL). The solvent was removed by rotary evaporation at a temperature not greater than room temperature. The residue was diluted with a 2:1 mixture of ethyl acetate and hexanes (150 mL), and the resulting solution was extracted with water (20 mL). The aqueous layer was back-extracted with ethyl acetate (30 mL). The combined organic layers were dried over $Na_2SO_4$, concentrated by rotary evaporation, and further dried under high vacuum. The product was carried to the subsequent step without further purification. Yield 5.03 g, 99.2%. Ion found by LCMS: $[M+H]^+=547.2$.

The step-b product (713 mg, 1.3 mmol) in anhydrous DCM (6 mL) was cooled in an ice-water bath and 4-dimethylaminopyridine (159.8 mg, 1.3 mmol) and DIPEA (520 mg, 4 mmol) were added. The mixture was then dropwise added with a solution of 4-nitrophenyl chloroformate (356.6 mg, 2.2 mmol) in anhydrous DCM (2 mL). The ice-water bath was then removed, and the reaction mixture was stirred for 3 hours and monitored by LCMS (additional 4-nitrophenyl chloroformate may be added if needed). After the reaction was complete, it was quenched with water (10 mL), and the organic layer was extracted and concentrated by rotary evaporation. The residue was purified by C18 reversed phase column chromatography (100 g, 20 to 70% acetonitrile and water). Acetonitrile in the collected fractions was removed by rotary evaporation at room temperature. The aqueous layer was then extracted with a 1:1 mixture of ethyl acetate and hexane (120 mL). The aqueous layer was back-extracted with ethyl acetate (30 mL). The combined organic layers were dried over $Na_2SO_4$, concentrated by rotary evaporation, and further dried under high vacuum to afford the title compound as a white solid. Yield 520 mg, 70%. Ion found by LCMS: $[M+H]^+=573.2$.

Example 3. Synthesis of Linker-1

Step a.

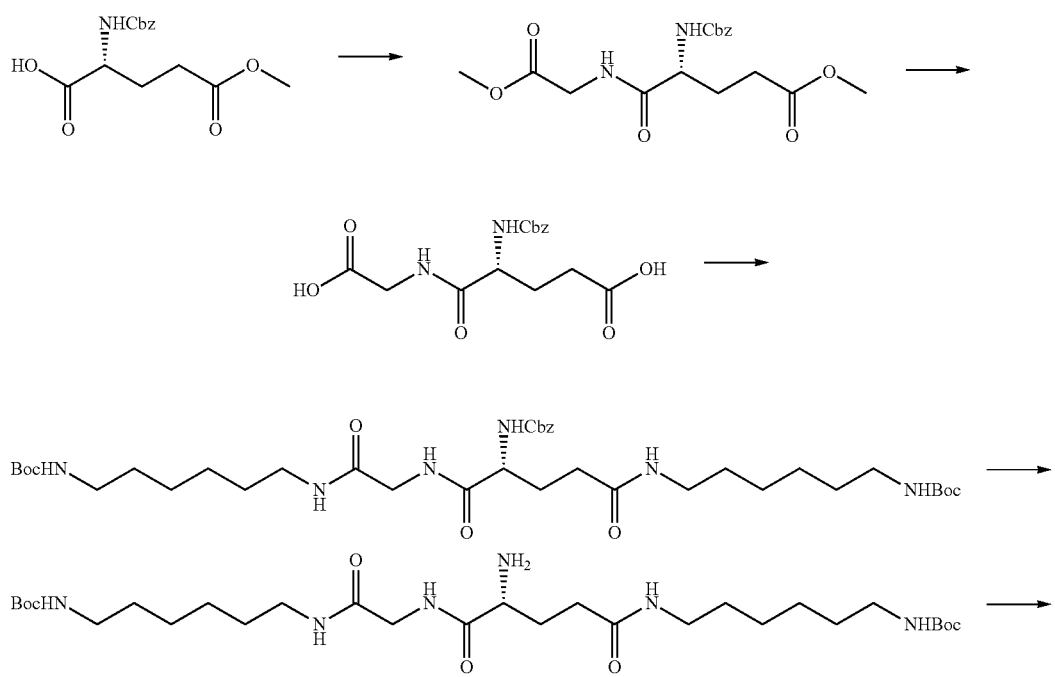

-continued

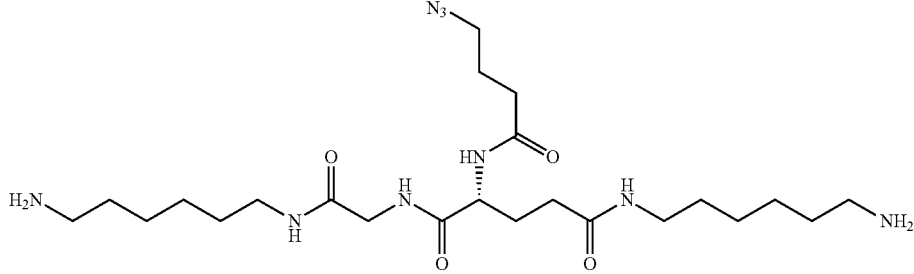

Step a.

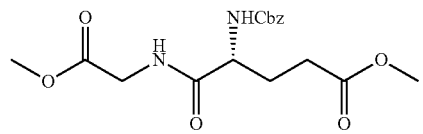

To a mixture of Z-D-glutamic γ-methyl ester (2.0 g, 6.77 mmol) and glycine methyl ester HCl (1.282 g, 10.2 mmol) in anhydrous DMF (7 mL) was added DIPEA (2.02 g, 15.57 mmol) followed by HATU (2.66 g, 7.0 mmol) in portions over 25 minutes. After HATU was dissolved, an additional amount of DIPEA (1.15 g, 8.8 mmol) was added. The reaction mixture was stirred for 1.5 hours, then extracted with 5% aqueous HCl (100 mL) and EtOAc (100 mL×2). The organic layer was concentrated by rotary evaporation. The residue was re-extracted with water (100 mL) and EtOAc/hexanes (2:1, 150 mL). The organic layer was dried over $Na_2SO_4$, concentrated by rotary evaporation and further dried under high vacuum to a white solid. The crude product was carried on to the subsequent step without further purification. Yield 2.3 g, 93%. Ion found by LCMS: $[M+H]^+=367$.

Step b.

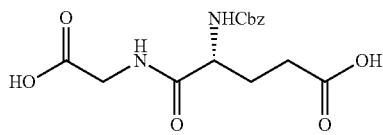 [SMILES: O=C(O)CC[C@@H](NC(=O)OCc1ccccc1)C(=O)NCC(=O)O]

The step-a product (2.3 g, 6.29 mmol) was dissolved in a 1:1 mixture of MeOH and THF (10 mL).

After the solution was cooled in an ice-water bath, a LiOH monohydrate (630 mg, 15 mmol) solution in water (9 mL) was added in portions over 1.5 hours. After stirring for 2 additional hours, the reaction mixture was neutralized with 4N HCl in dioxane (3.7 mL). The organic solvent was partially removed by rotary evaporation at room temperature. The remaining material was directly purified by RPLC (150 g, 0 to 39% acetonitrile and water). Yield 2.03 g, 88.7% over two steps. Ion found by LCMS: $[M+H]^+=339.2$.

Step c.

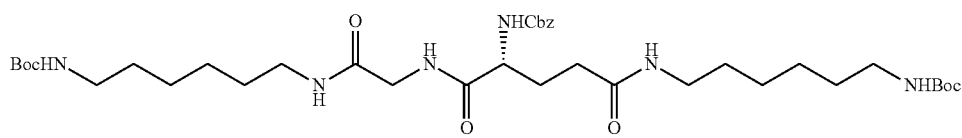 [SMILES: CC(C)(C)OC(=O)NCCCCCCNC(=O)CC[C@@H](NC(=O)OCc1ccccc1)C(=O)NCC(=O)NCCCCCCNC(=O)OC(C)(C)C]

To a mixture of the step-b product (1.41 g, 4.17 mmol) and N-Boc-1,6-diaminohexane (1.99 g, 9.2 mmol) in anhydrous DMF (6 mL) and DIPEA (1.3 g, 10 mmol), a solution of HATU (3.5 g, 9.2 mmol) in DMF (10 mL) was added by way of syringe pump at a rate of 11 mL/hr. Upon complete addition of the HATU, the reaction was stirred for 30 more minutes and directly purified by RPLC (150 g, 10 to 50% acetonitrile and water, using 0.1% TFA as modifier). Yield 1.3 g, 42.4%. Ion found by LCMS: $[M+H]^+=735$, $[M-Boc+H]+=635.4$.

Step d.

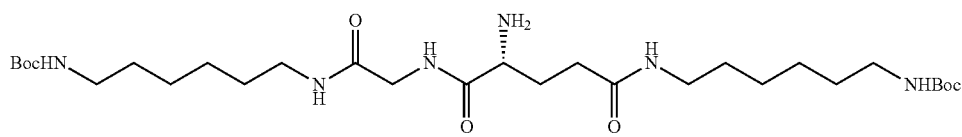 [SMILES: CC(C)(C)OC(=O)NCCCCCCNC(=O)CC[C@@H](N)C(=O)NCC(=O)NCCCCCCNC(=O)OC(C)(C)C]

The step-c product (1.3 g, 1.77 mmol) was dissolved in MeOH (20 mL), and Pd/C was added to the solution. The mixture was stirred under hydrogen for 4 hours. Pd/C was filtered off, and the filtrate was concentrated by rotary evaporation and further dried under high vacuum. Yield 1.03 g, 96.9%. Ion found by LCMS: [M+H]⁺=601.

Step e.

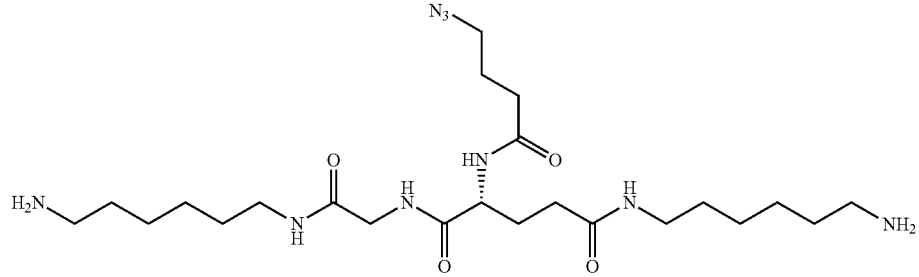 [SMILES: [N-]=[N+]=NCCCC(=O)N[C@H](CCC(=O)NCCCCCCN)C(=O)NCC(=O)NCCCCCCN]

A flamed-dried reaction flask was flushed with nitrogen and charged with 4-azidobutyric acid (77 mg, 0.6 mmol), N-hydroxy succinimide (92 mg, 0.8 mmol) and anhydrous DMF (0.5 mL). The mixture was stirred to dissolve the solids, and then DCC (125.5 mg, 0.608 mmol) was added. After stirring for one hour, the step-d product (300 mg, 0.5 mmol) was added to the reaction mixture. The reaction was stirred for 6 hours and directly purified using RPLC (150 g, 10 to 70% acetonitrile and water, using 01.% TFA as modifier). The collected fractions were lyophilized to a white solid (LCMS: [M+H]⁺=712, [M-Boc+H]⁺=612). The material was re-dissolved in DCM (~2 mL) and TFA (~1 mL) and stirred for 15 minutes. It was then concentrated by rotary evaporation, and the residue was purified by RPLC (50 g, 0 to 40% acetonitrile and water). Yield 255 mg, 68.9%. Ions found by LCMS: [M+H]⁺=512, [(M+2H)/2]⁺=256.

Example 4. Synthesis of Int-1

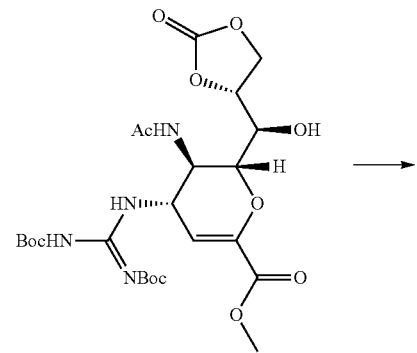

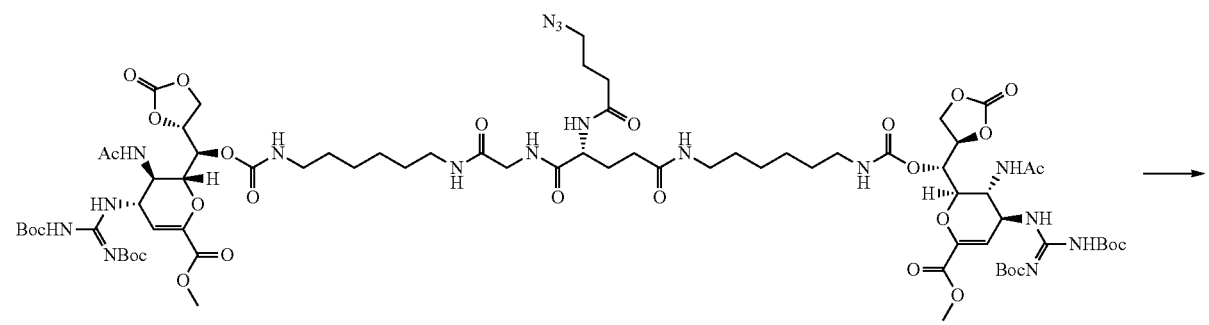

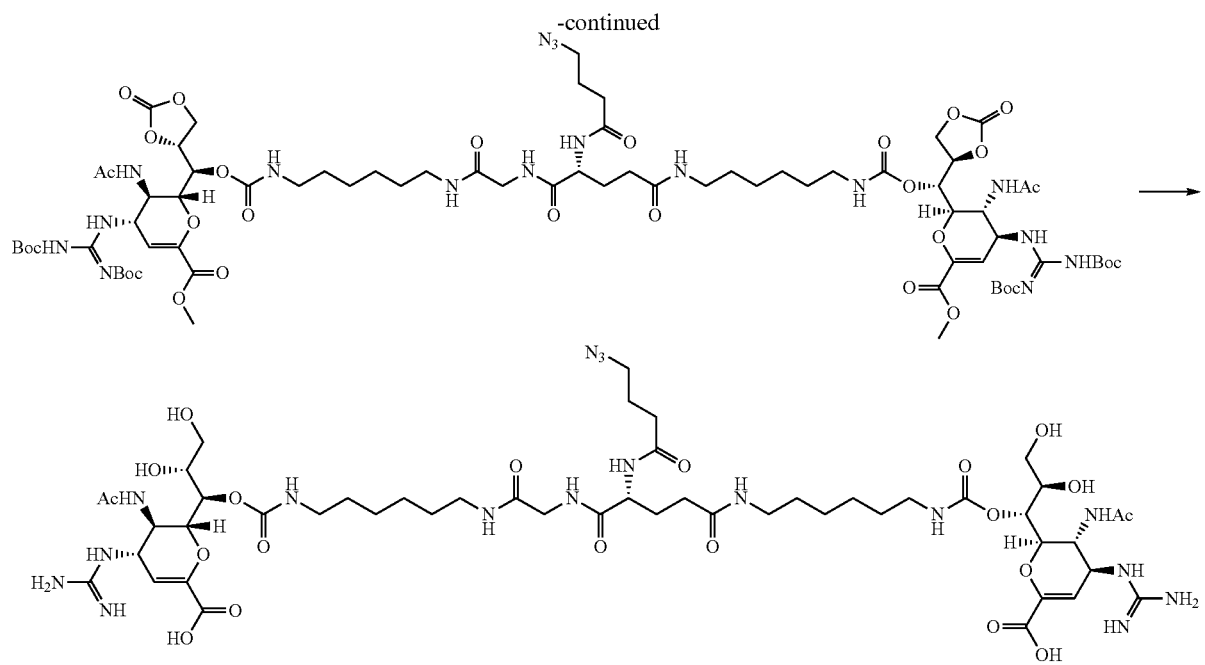

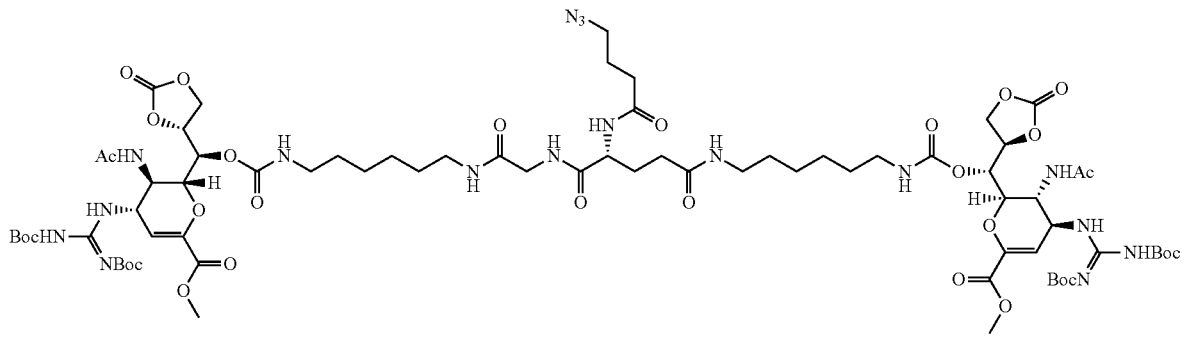

Step a.

To a solution of the Zanamivir intermediate (Example 2) (532.5 mg, 0.93 mmol) in anhydrous THF (2 mL) was added DMAP (490 mg, 4 mmol), followed by bis(pentafluorophenyl)carbonate (385 mg, 0.911 mmol). After stirring overnight, a solution of Linker-1 (Example 3) (245.6 mg, 0.332 mmol) in anhydrous DMF (1 mL) and DIPEA (91 mg, 0.3 mmol) was added to the reaction mixture. The reaction was continued for 2 hours, then purified by RPLC (100 g, 5 to 67% acetonitrile and water). Yield 135 mg, 23.8%. Ion found by LCMS: $[(M+2H)/2]^+=845.9$.

Step b.

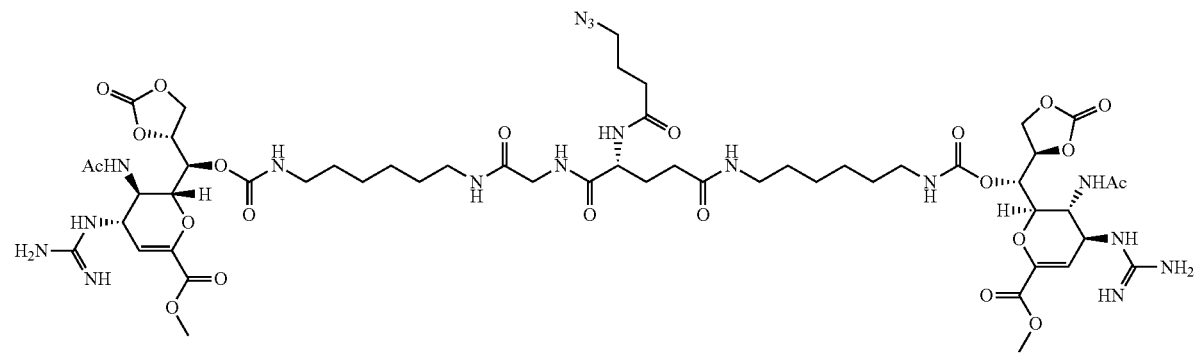 [SMILES: COC(=O)C1=C[C@H](NC(=N)N)[C@@H](NC(C)=O)[C@H]([C@H](OC(=O)NCCCCCCNC(=O)CC[C@@H](NC(=O)CCCN=[N+]=[N-])C(=O)NCC(=O)NCCCCCCNC(=O)O[C@@H]([C@@H]2OC(C(=O)OC)=C[C@H](NC(=N)N)[C@H]2NC(C)=O)[C@H]2COC(=O)O2)[C@H]2COC(=O)O2)O1]

The step-a product (135 mg, 0.079 mmol) was dissolved in TFA (0.5 mL), and the solution was stirred at room temperature for 20 minutes. It was then directly purified by RPLC (50 g, 5 to 32% acetonitrile and water). Yield 88 mg, 85.1%. Ion found by LCMS: $[(M+2H)/2]^+=654.8$.

Step c.

A solution of the step-b product (88 mg, 0.0673 mmol) in MeOH (1.5 mL) was cooled in an ice-water bath and LiOH (5 mg, 0.2 mmol) in water (0.5 mL) was added. After the mixture was stirred for 5 hours, it was acidified with 4N HCl solution in dioxane (0.1 mL) and purified by HPLC (5 to 20% acetonitrile and water, using 0.1% TFA as modifier). Yield 76.4 mg, 78%. Ion found by LCM: $[(M+2H)/2]^+=614.8$.

Example 5. Synthesis of Linker-2

Step a.

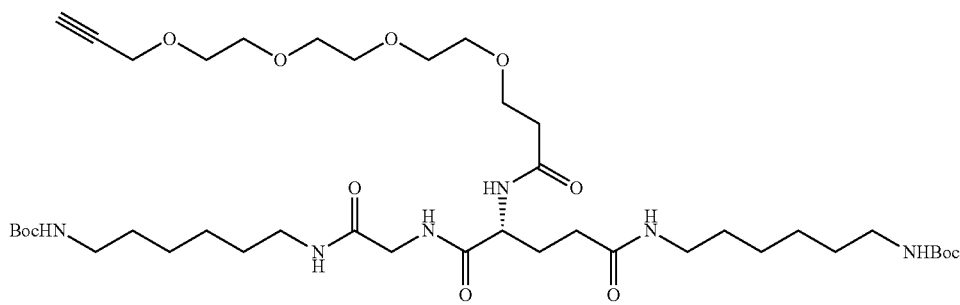 [SMILES: C#CCOCCOCCOCCOCCC(=O)N[C@H](CCC(=O)NCCCCCCNC(=O)OC(C)(C)C)C(=O)NCC(=O)NCCCCCCNC(=O)OC(C)(C)C]

To a solution of propargyl-PEG4-acid (364.4 mg, 1.4 mmol) in anhydrous DMF (2 mL) was added HATU (558.9 mg, 1.47 mmol). After stirring to dissolve all the coupling reagent, DIPEA (390 mg, 3 mmol) was added and stirred for 10 minutes. A solution of the Linker-1 step-d product (Example 3, step d) (701.1 mg, 1.167 mmol) in anhydrous DMF (1 mL) was added. The resulting mixture was stirred for 30 minutes and directly purified by RPLC (100 g, 5 to 60% acetonitrile and water). Yield 830 mg, 84.4%. Ion found by LCMS: $[M+H]^+=843$.

Step b.

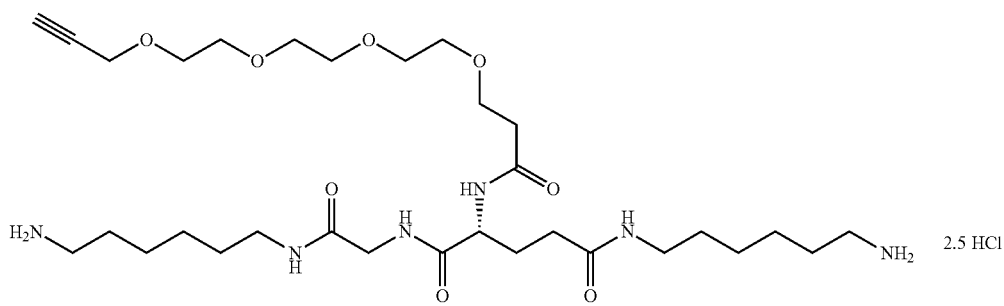 [SMILES: C#CCOCCOCCOCCOCCC(=O)N[C@H](CCC(=O)NCCCCCCN)C(=O)NCC(=O)NCCCCCCN ; "2.5 HCl"]

The step-a product was dissolved in THF (5 mL) and treated with 4N HCl solution in dioxane (2.5 mL). After stirring at room temperature overnight, the reaction mixture was concentrated by rotary evaporation. The residue was re-dissolved in acetonitrile/water (1:1, 16 mL), and the solution was lyophilized. The crude product was carried on to the subsequent step without further purification. Yield 761.8 mg, 100%. Ion found by LCMS: $[M+H]^+=643.8$.

Example 6. Synthesis of Int-2

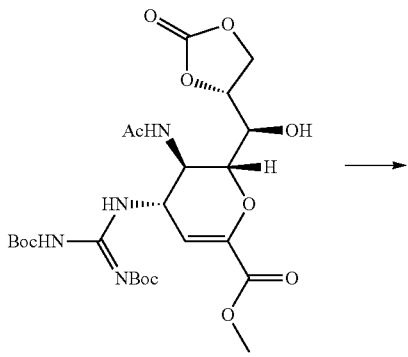

-continued

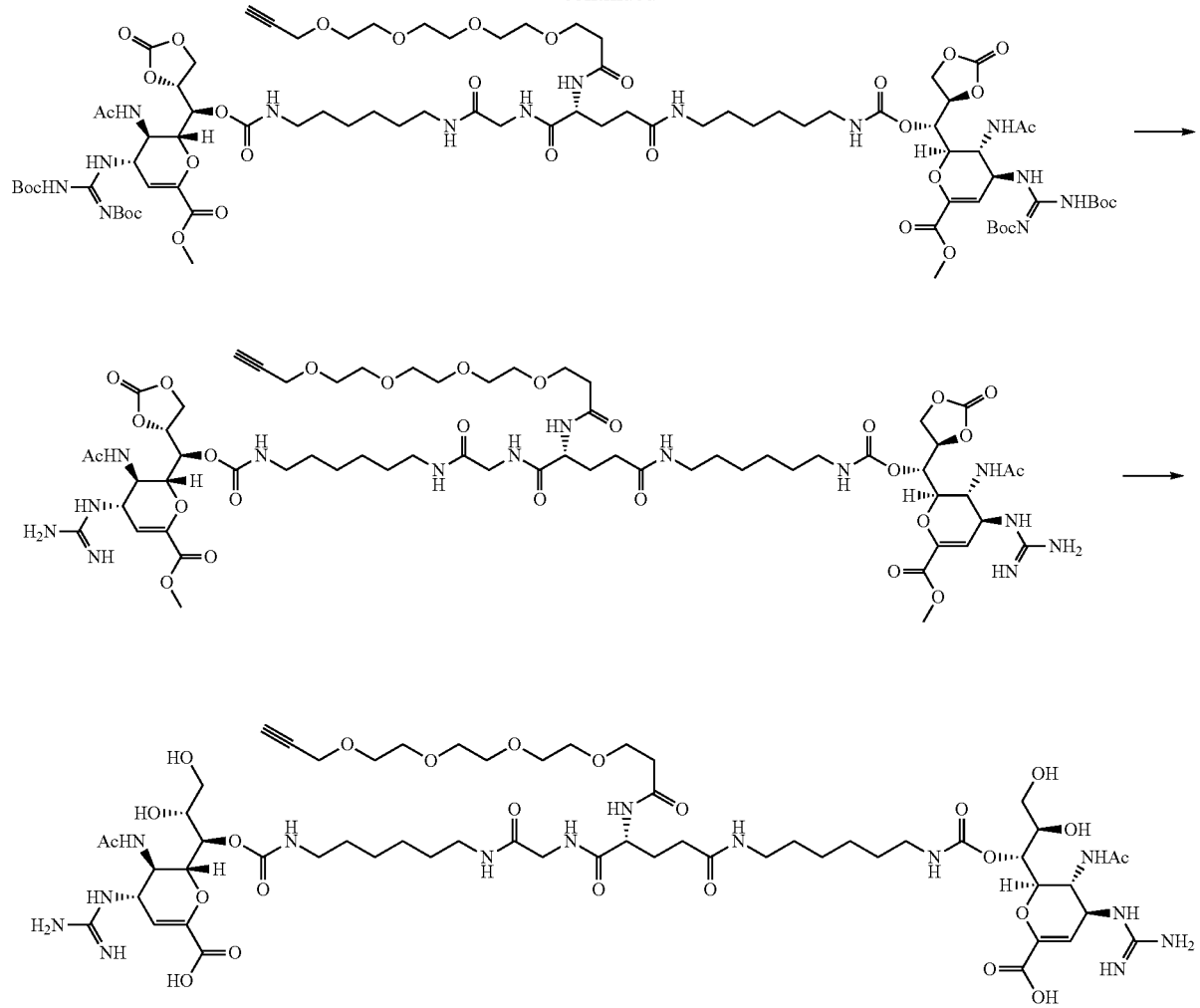

Step a.

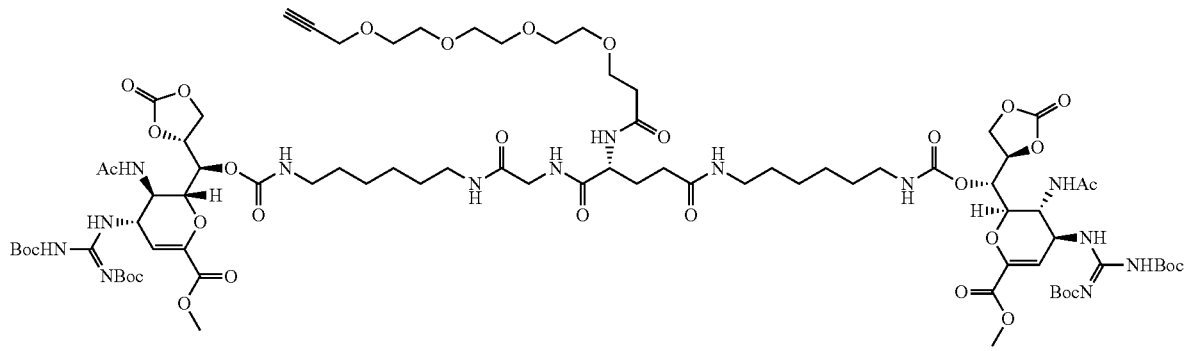

A flame-dried reaction flask was flushed with nitrogen and charged with Zanamivir intermediate (Example 2) (533.6 mg, 0.812 mmol), DMAP (99.8 mg, 0.81 mmol), and anhydrous DCM (1 mL). After stirring to dissolve the starting material, the solution was cooled in an ice-water bath and 4-nitrophenyl chloroformate (242 mg, 1 0.2 mmol) was added. The resulting mixture was stirred for 5 hours, then added into a solution of the Linker-2 (Example 5) (228.4 mg, 0.319 mmol) in anhydrous DMF (1 mL) and DIPEA (130 mg, 1 mmol). The reaction was stirred overnight and purified by RPLC (150 g, 20 to 65% acetonitrile and water, using 0.1% TEA as modifier). The collected fractions were lyophilized. Yield 178.3 mg, 30.4%. Ion found by LCMS: $[(M+2H)/2]^+=920.5$, $[(M+3H)/3]^+=614.2$.

Step b.

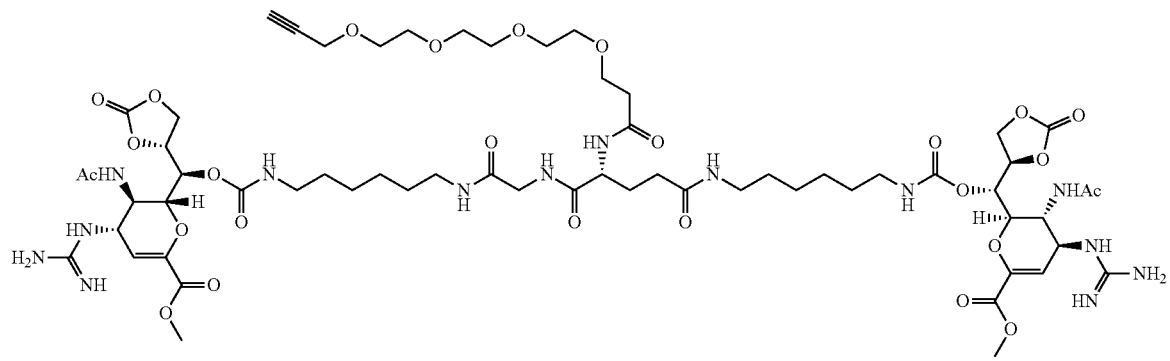 [SMILES: C#CCOCCOCCOCCOCCC(=O)N[C@H](CCC(=O)NCCCCCCNC(=O)O[C@@H]([C@@H]1OC(C(=O)OC)=C[C@H](NC(=N)N)[C@H]1NC(C)=O)[C@H]1COC(=O)O1)C(=O)NCC(=O)NCCCCCCNC(=O)O[C@@H]([C@@H]1OC(C(=O)OC)=C[C@H](NC(=N)N)[C@H]1NC(C)=O)[C@H]1COC(=O)O1]

The step-a product (178.3 mg, 0.0969 mmol) was dissolved in TFA (0.5 mL). The solution was stirred for 20 minutes, then directly purified by HPLC (0 to 25% acetonitrile and water, using 0.1% TFA as modifier). Yield 91.8 mg, 56.8%. Ions found by LCMS: $[(M+2H)/2]^+=720.4$, $[(M+3H)/3]^+=480.6$.

Step c.

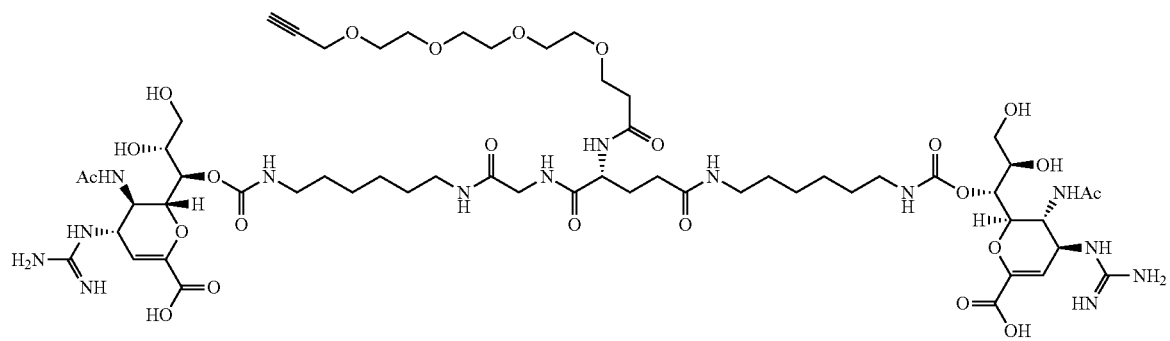 [SMILES: C#CCOCCOCCOCCOCCC(=O)N[C@H](CCC(=O)NCCCCCCNC(=O)O[C@@H]([C@@H]1OC(C(=O)O)=C[C@H](NC(=N)N)[C@H]1NC(C)=O)[C@H](O)CO)C(=O)NCC(=O)NCCCCCCNC(=O)O[C@@H]([C@@H]1OC(C(=O)O)=C[C@H](NC(=N)N)[C@H]1NC(C)=O)[C@H](O)CO]

The step-b product (91.8 mg, 0.055 mmol) was dissolved in MeOH (1 mL), and the solution was cooled in an ice-water bath. LiOH monohydrate (21 mg, 0.5 mmol) in water (1 mL) was added in portions over 1 hour. After stirring for 2 more hours, the reaction mixture was acidified with a 4N HCl solution in dioxane (0.3 mL) and purified by HPLC (0 to 20% acetonitrile and water, using 0.1% TFA as modifier). Yield 36.2 mg, 59.4%.%. Ions found by LCMS: $[(M+2H)/2]^+=680.3$, $[(M+3H)/3]^+=454.0$.

Example 7. Synthesis of h-IgG1 Fc-PEG$_4$-azide

PEG4-azidoNHS ester (98%, 180 µmol, 9.5 equivalents, 71.4 mg in 0.5 mL of DMF and diluted to 3.60 mL with pH 7.4 PBS 1× buffer solution) was added to a solution of h-IgG1 Fc (SEQ ID NO: 4) (1103 mg in 70.0 mL of pH 7.4 PBS, MW-58,000 Da, 19.0 µmol) and the mixture was shaken gently for 12 hours at ambient temperature. The solution was concentrated using a centrifugal concentrator (30,000 MWCO) to a volume of ~1.5 mL. The crude mixture was diluted 1:10 in PBS pH 7.4, and concentrated again. This wash procedure was repeated for total of three times. The small molecule reagent was removed with this wash procedure. The concentrated Fc-PEG4-azide was diluted to 70.0 mL with pH 7.4 PBS 1× buffer and ready for Click conjugation. The purified material was quantified using a Nanodrop™ UV visible spectrophotometer (using a calculated extinction coefficient based on the amino acid sequence of h-IgG1). Yield is quantitative after purification. DAR=4.3 determined by MALDI. The DAR value can be adjusted by altering the equivalents of PEG4-azido NHS ester in near linear relation. For example, when 7.0 equivalents of PEG4-azide NHS ester is used the DAR value will be at 3.0.

The nucleic acid construct encoding the Fc for any conjugate described herein may include a nucleic acid sequence encoding for an Fc including the amino acid Lys447 (e.g., a C-terminal lysine residue). Upon expression, the C-terminal lysine of the Fc is proteolytically cleaved, resulting in an Fc having the sequence lacking Lys447 (e.g., lacking a C-terminal lysine residue). The presence or absence of a C-terminal lysine does not alter the properties of the Fc or the corresponding conjugate.

Example 8. Synthesis of Recombinant Mouse Serum Albumin (MSA)-PEG4-Azide

PEG4-azidoNHS ester (98%, 81.7 µmol, 4.5 equivalents, 32.4 mg in 0.3 mL of DMF and diluted to 1.63 mL with pH 7.4 PBS 1× buffer solution) was added to a solution of recombinant mouse serum albumin (SEQ ID NO: 80) (1200 mg in 75.0 mL of pH 7.4 PBS, MW-66,000 Da, 18.2 µmol) and the mixture was shaken gently for 12 hours at ambient temperature. The solution was concentrated using a centrifugal concentrator (30,000 MWCO) to a volume of ~1.5 mL. The crude mixture was diluted 1:10 in PBS pH 7.4, and concentrated again. This wash procedure was repeated for total of three times. The small molecule reagent was removed with this wash procedure. The concentrated MSA- PEG4-azide was diluted to 75.0 mL with pH 7.4 PBS 1× buffer and ready for Click conjugation. The purified material was quantified using a Nanodrop™ UV visible spectrophotometer (using a calculated extinction coefficient based on the amino acid sequence of h-IgG1). Yield is quantitative after purification. DAR=3.5 determined by MALDI. The DAR value can be adjusted by altering the equivalents of PEG4-azido NHS ester similar to h-IgG1 Fc (Example 7).

Example 9. Synthesis of Conjugate 1

Figure 1:
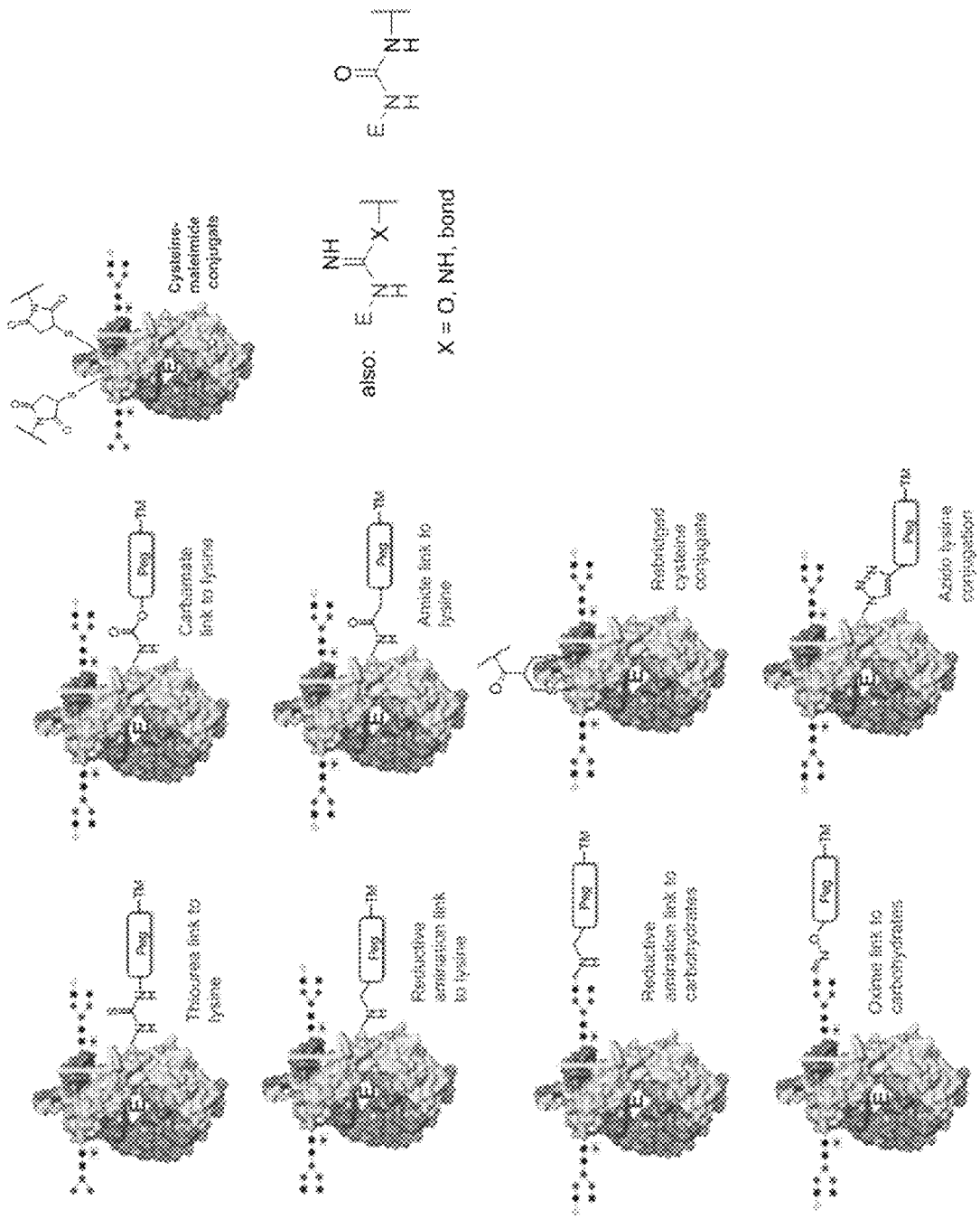
FIG. 1 is an image depicting exemplary methods of conjugating a neuraminidase inhibitor monomer or dimer, e.g., by way of a linker, to an Fc domain monomer, an Fc domain, an Fc-binding peptide, an albumin protein, or an albumin protein-binding peptide.
Figure 2:
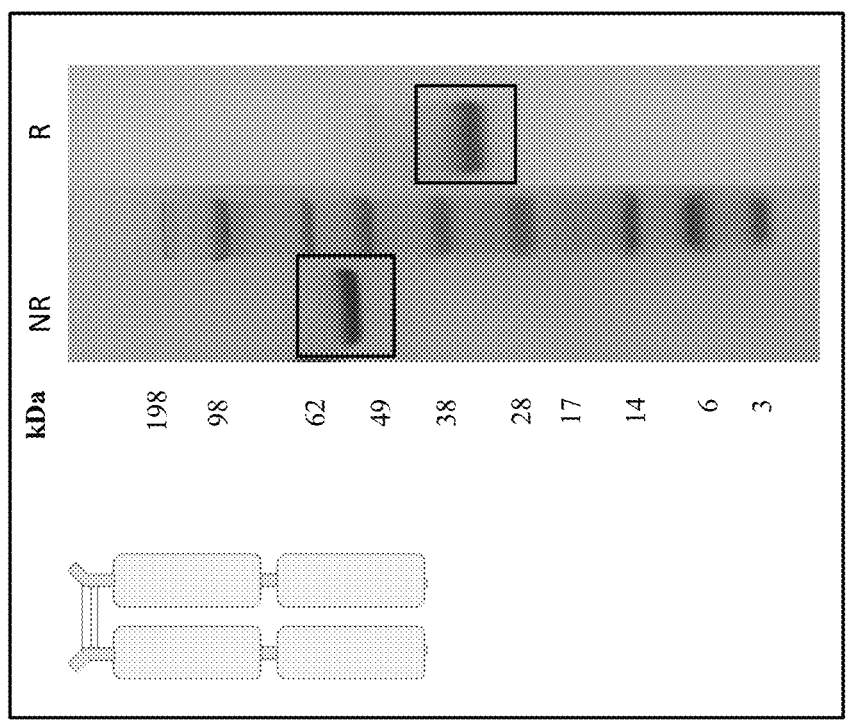
FIG. 2 shows non-reducing and reducing SDS-PAGE and a schematic illustration of an Fc domain formed from Fc domain monomers having the sequence of SEQ ID NO: 1.
Figure 3:
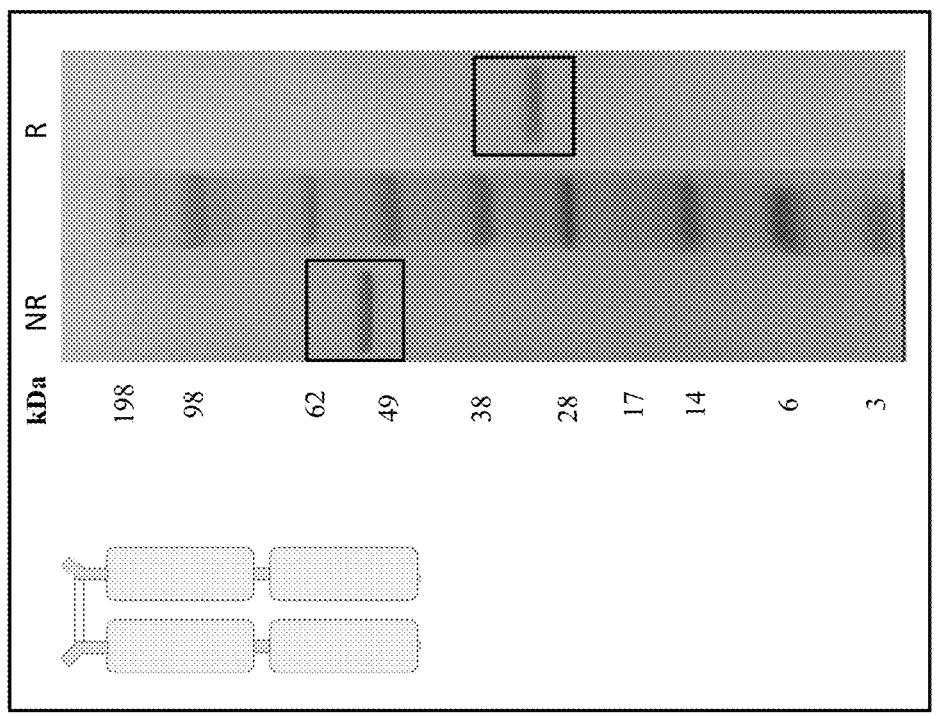
FIG. 3 shows non-reducing and reducing SDS-PAGE and a schematic illustration of an Fc domain formed from Fc domain monomers having the sequence of SEQ ID NO: 3.
Figure 4:
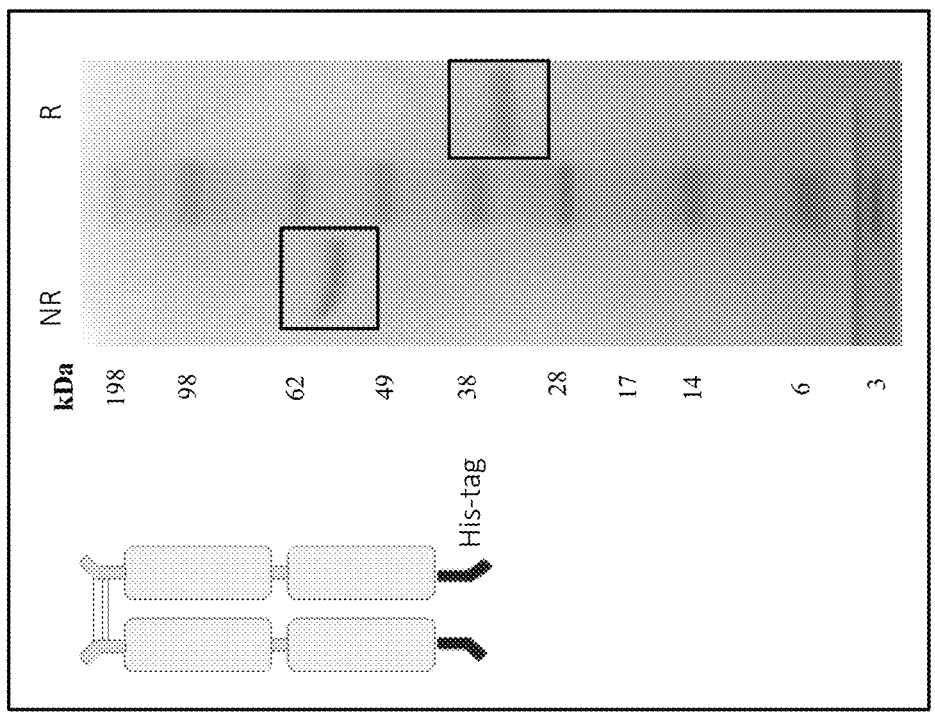
FIG. 4 shows non-reducing and reducing SDS-PAGE and a schematic illustration of an Fc domain formed from Fc domain monomers having the sequence of SEQ ID NO: 5.
Figure 5:
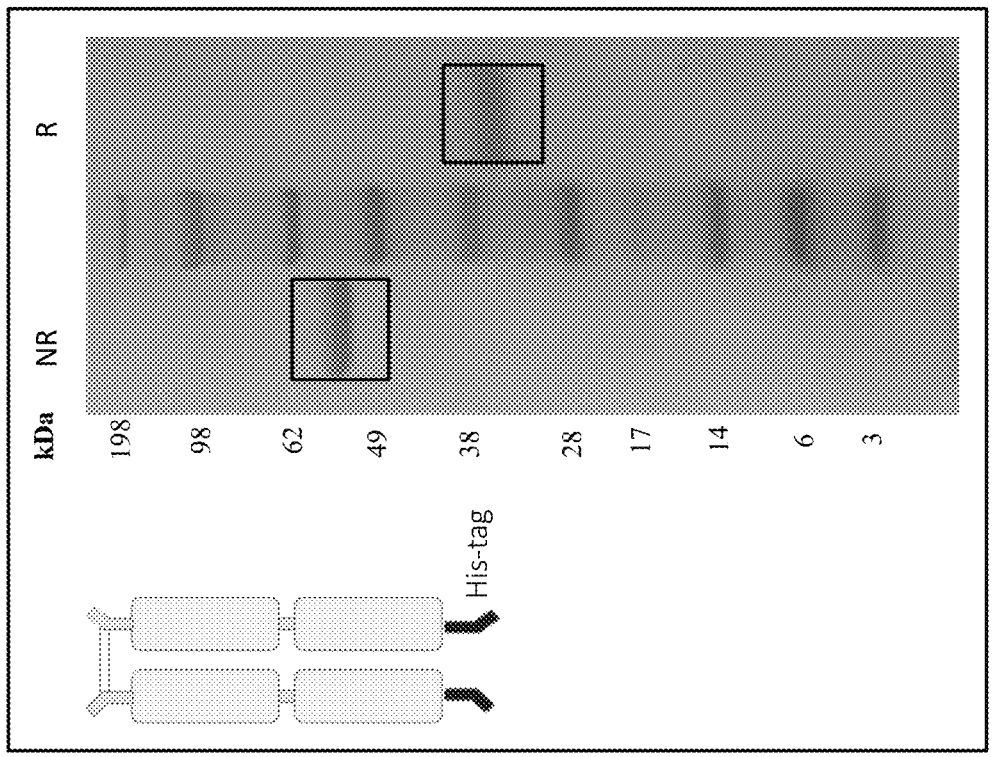
FIG. 5 shows non-reducing and reducing SDS-PAGE and a schematic illustration of an Fc domain formed from Fc domain monomers having the sequence of SEQ ID NO: 7.
Figure 6:
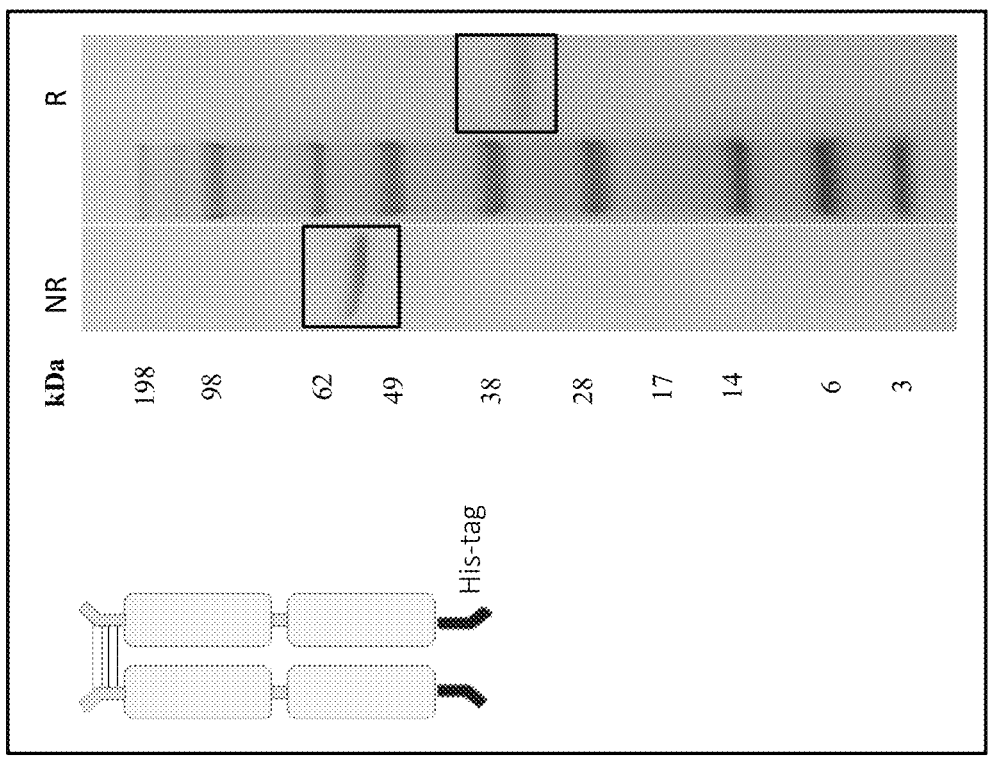
FIG. 6 shows non-reducing and reducing SDS-PAGE and a schematic illustration of an Fc domain formed from Fc domain monomers having the sequence of SEQ ID NO: 9.
Figure 7:
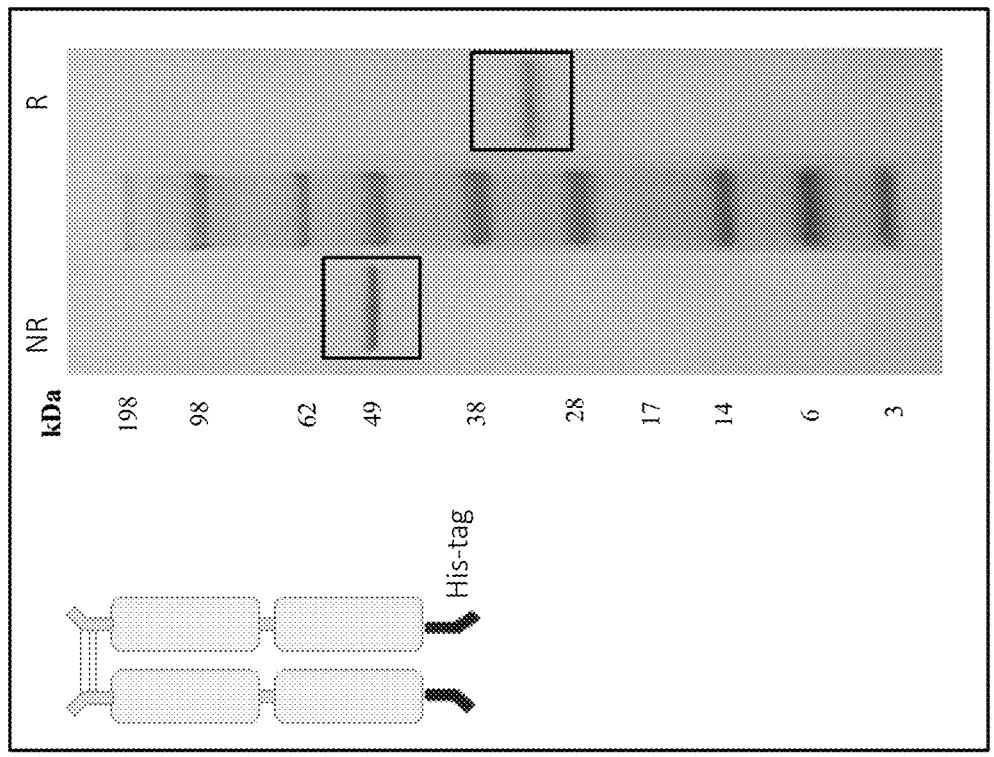
FIG. 7 shows non-reducing and reducing SDS-PAGE and a schematic illustration of an Fc domain formed from Fc domain monomers having the sequence of SEQ ID NO: 12.
Figure 8:
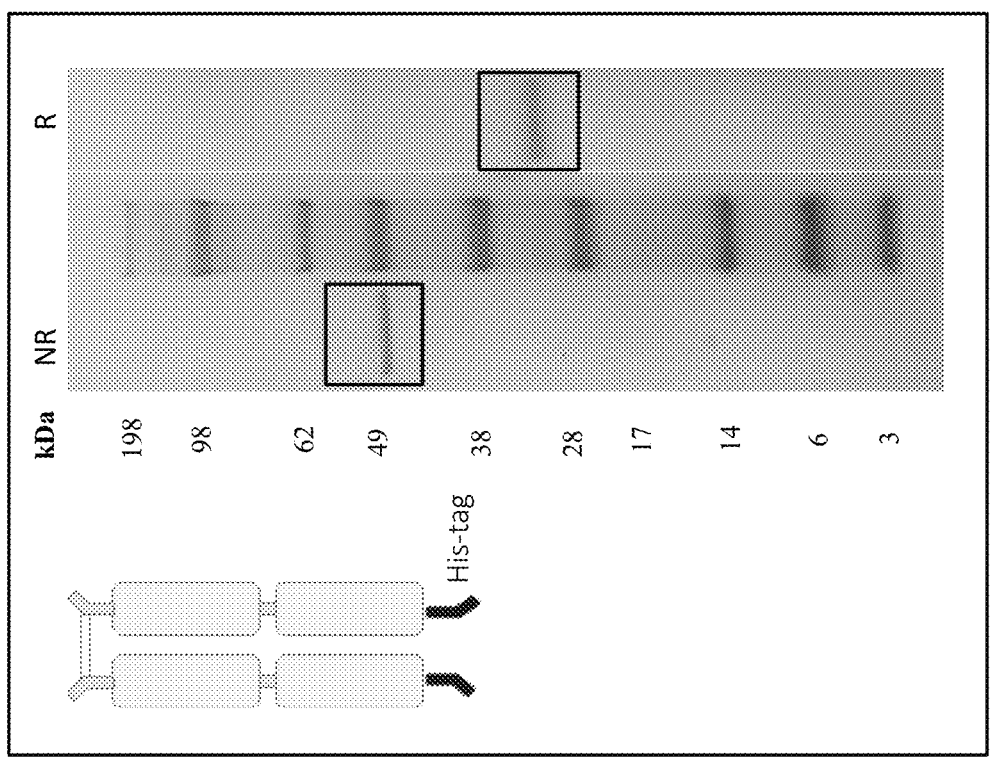
FIG. 8 shows non-reducing and reducing SDS-PAGE and a schematic illustration of an Fc domain formed from Fc domain monomers having the sequence of SEQ ID NO: 14.
Figure 9:
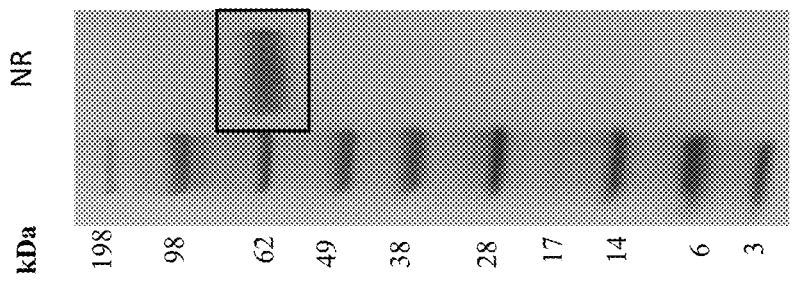
FIG. 9 shows a non-reducing SDS-PAGE of Conjugate 1.

A PBS solution of h-IgG1 Fc-PEG4-azide (Example 7) (50 mg, 2.815 mL, 0.8591 µmol) was added into a 15 mL centrifuge tube containing Int-2 (Example 6) (35.2 mg, 0.02217 mmol). After the mixture was gently shaken to dissolve all Int-2, 344 µl of a solution of L-ascorbic acid sodium (59.4 mg, 0.3 mmol), copper (II) sulfate (10 mg, 0.05 mmol), and THPTA (23 mg, 0.05 mmol) in PBS 7.4 buffer (1 mL) was added. The resulting mixture was gently shaken overnight. It was purified by affinity chromatography over a protein A column, followed by size exclusion chromatography as described in Example 8. Maldi TOF analysis of the purified final product gave an average mass of 63797 Da (DAR=3.4). Yield 27.39 mg, 55% yield. FIG. 9 shows a non-reducing SDS-PAGE of Conjugate 1.

Example 10. Purification of Conjugates Crude mixture was diluted 1:10 in PBS pH 7.4, and purified using MabSelect Sure Resin (GE Healthcare, Chicago, Ill., USA), followed by size exclusion chromatography. (HiLoad 26/600 Superdex200 pg, GE Healthcare, Chicago, Ill., USA). Fractions containing purified conjugate were pooled and concentrated to approximately 20 mg/mL using a centrifugal concentrator (30,000 MWCO). Purified material was quantified using a Nanodrop™ UV visible spectrophotometer using a calculated extinction coefficient based on the amino acid sequence of hIgG1 Fc(myc). Purified molecules were analyzed using 4-12% Bis Tris SDS PAGE gels by loading 1 µg of each molecule into the gel, and staining using Instant Blue (Expedeon, San Diego, Calif., USA). Each gel included a molecular weight ladder with the indicated molecular weight standards. Yields were calculated and purity determined by Agilent Analytical HPLC. Product peak and MW were found by Maldi MS and a final DAR calculated.

Example 11. Synthesis of Int-3

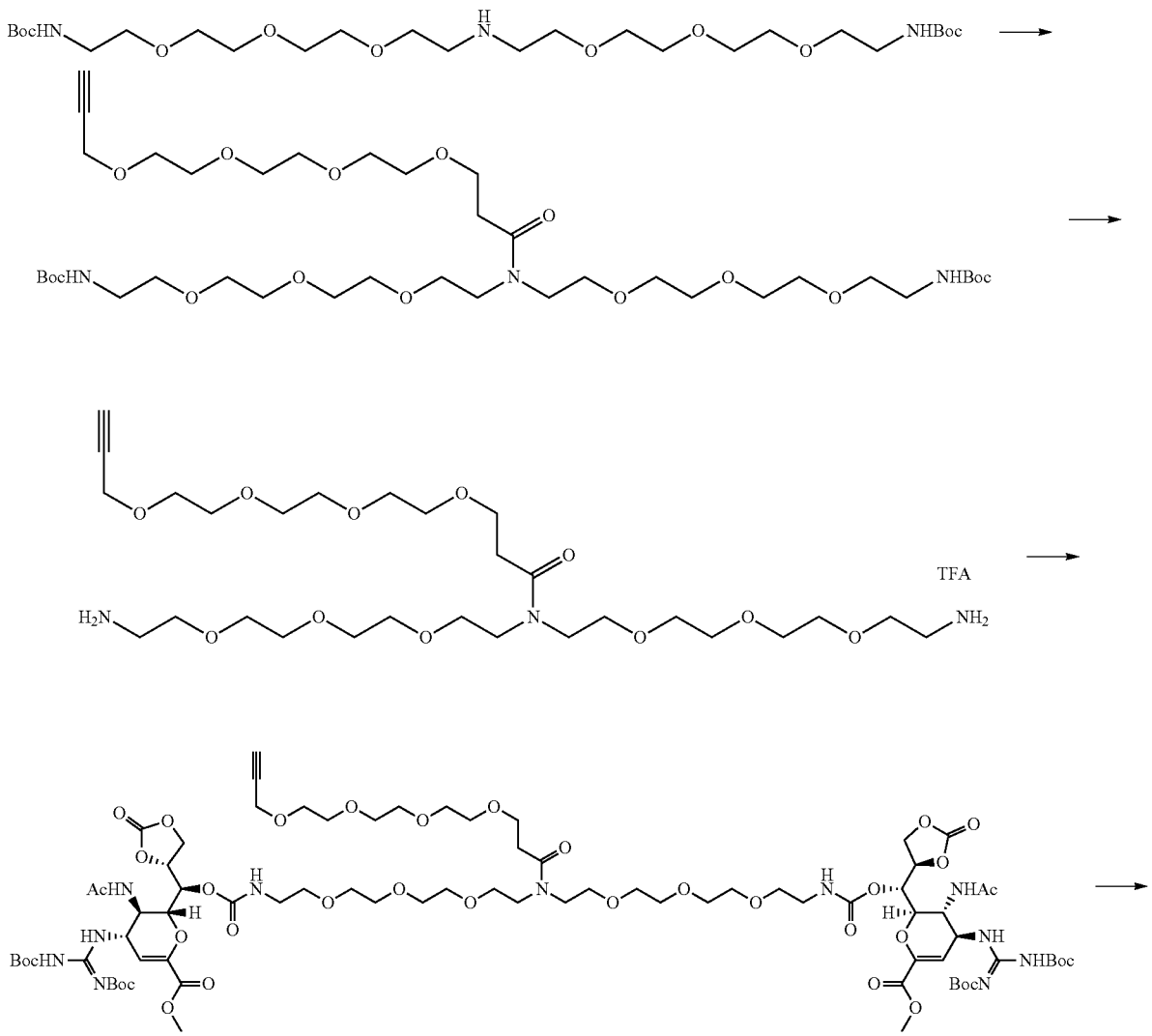

-continued

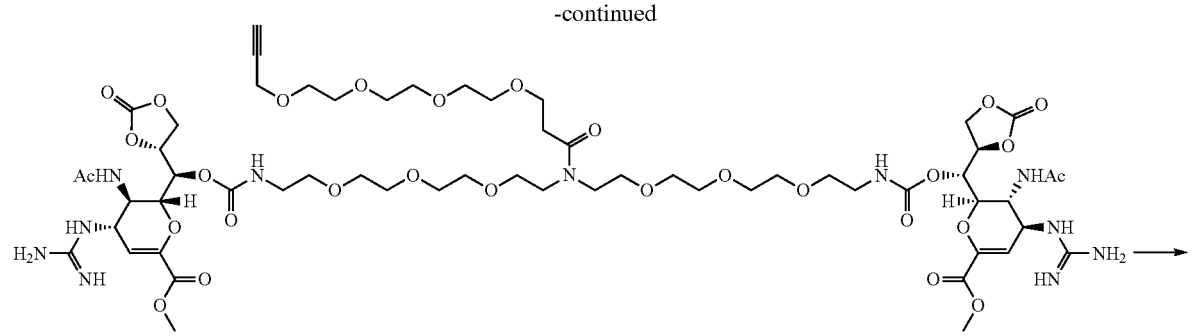

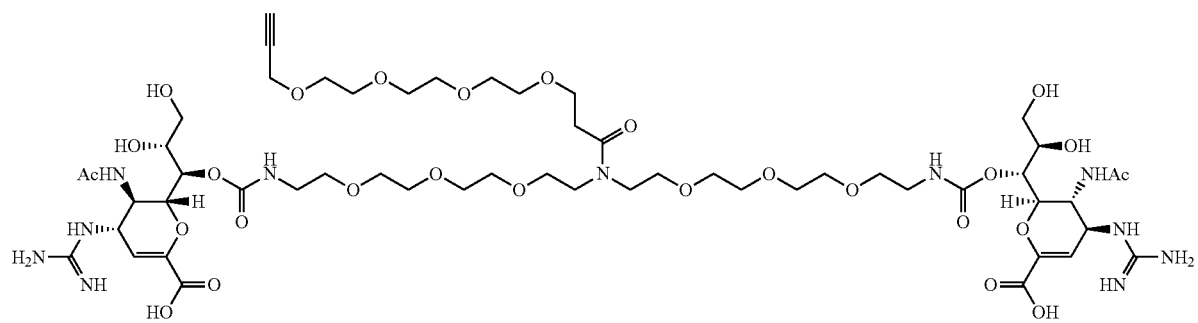

Step a.

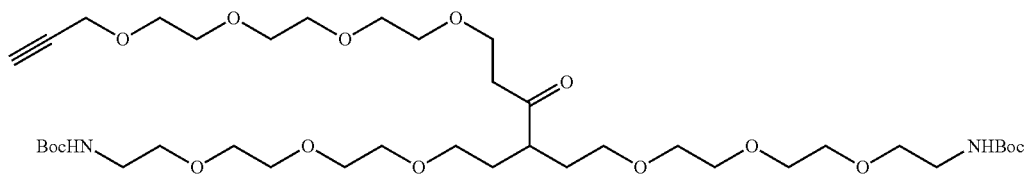

To a solution of propargyl-PEG4-acid (260 mg, 1 mmol) and HATU (380.2 mg, 1 mmol) in anhydrous DMF (1 mL) was added DIPEA (130 mg). After stirring 5 minutes, NH-bis(PEG3-Boc) (500 mg, 0.881 mmol) was added and stirring was continued at room temperature overnight. It was then directly purified by RPLC 9100 g, 5 to 50% acetonitrile and water, using 0.1% TFA as modifier). Yield 683 mg, 95.8%. Ions found by LCMS: $[M+H]^+=810.4$, $[M-Boc+H]^+=710.4$, $[(M-2Boc+2H)/2]^+=305.8$.

Step b.

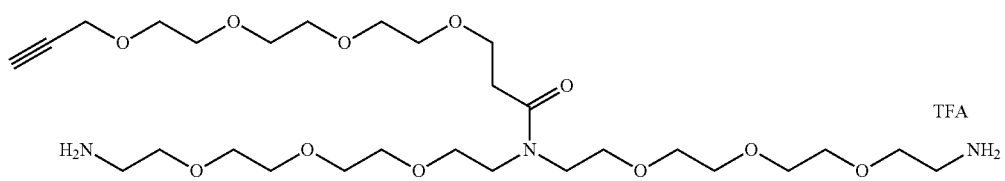 [SMILES: C#CCOCCOCCOCCOCCC(=O)N(CCOCCOCCOCCN)CCOCCOCCOCCN ; "TFA"]

The step-a product was dissolved in TFA (1 mL). The solution was stirred for 2 hours and then directly purified through RPLC (100 g, 0 to 30% acetonitrile and water). Yield 589 mg, 98.7%. Ion found by LCMS: $[(M+2H)/2]^+=305.8$.

Step c.

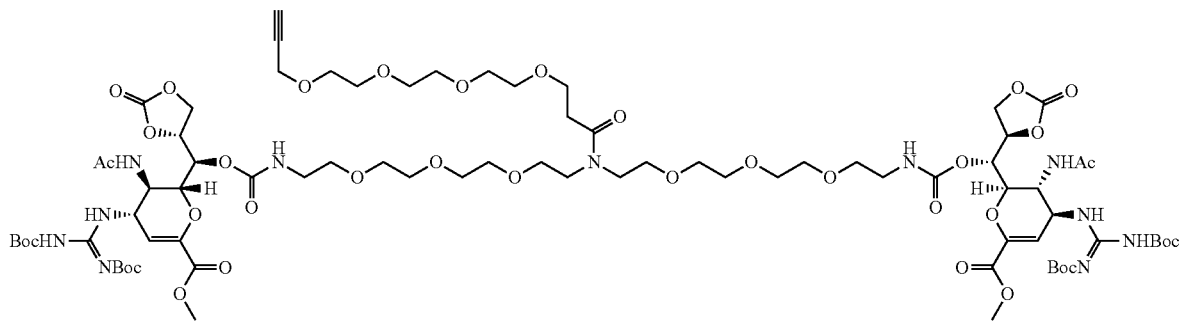

A flame-dried reaction flask was flushed with nitrogen and charged with Zanamivir intermediate (Example 2) (572 mg, 1 mmol) and anhydrous DCM (1 mL). After stirring to dissolve the starting material, the solution was cooled in an ice-water bath and 4-nitrophenyl chloroformate (302.4 mg, 1.5 mmol) was added followed by DMAP (22.4 mg, 0.2 mmol). The resulting mixture was stirred for 5 hours, then quenched water (0.2 mL) was added. After stirring for 10 minutes, the step-b product (256.7 mg, 0.355 mmol) in anhydrous DMF (1 mL) and DIPEA (163.8 mg, 1.26 mmol) was added. Stirring was continued for 2 hours and then the reaction was directly purified by RPLC (150 g, 20 to 65% acetonitrile and water, using 0.1% TFA as modifier). The collected fractions were lyophilized. Yield 422.8 mg of the desired product, which was contaminated with some impurities, <69% yield. The material was carried on to the subsequent step without further purification. Ion found by LCMS: $[(M+2H)/2]^+=903.9$, $[(M+3H)/3]^+=603.2$.

Step d.

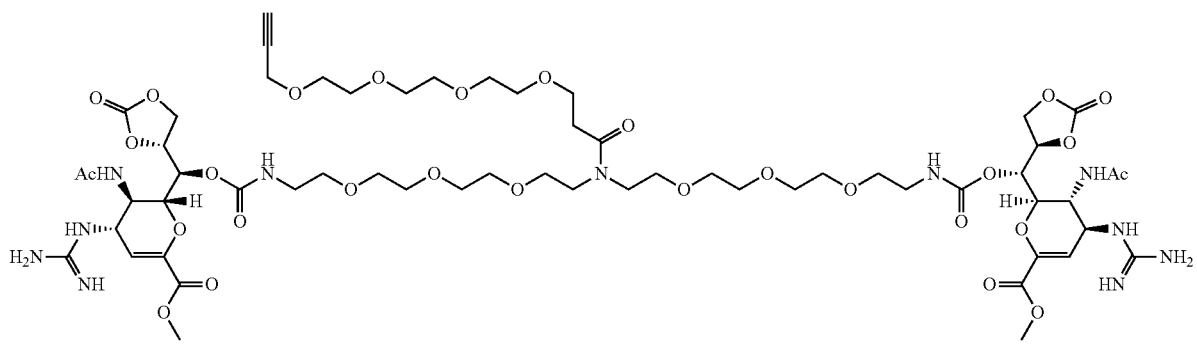 [SMILES: C#CCOCCOCCOCCOCCC(=O)N(CCOCCOCCOCCNC(=O)O[C@@H]([C@@H]1OC(C(=O)OC)=C[C@H](NC(=N)N)[C@H]1NC(C)=O)[C@H]1COC(=O)O1)CCOCCOCCOCCNC(=O)O[C@@H]([C@@H]1OC(C(=O)OC)=C[C@H](NC(=N)N)[C@H]1NC(C)=O)[C@H]1COC(=O)O1]

The step-c product (422.8 mg, <0.245 mmol) was dissolved in TFA (1 mL). The solution was stirred for 20 minutes, then directly purified by HPLC (5 to 25% acetonitrile and water, using 0.1% TFA as modifier). Yield 169.7 mg, 29.2% over two steps. Ions found by LCMS: $[(M+2H)/2]^+=704.0$, $[(M+3H)/3]^+=469.6$.

Step e.

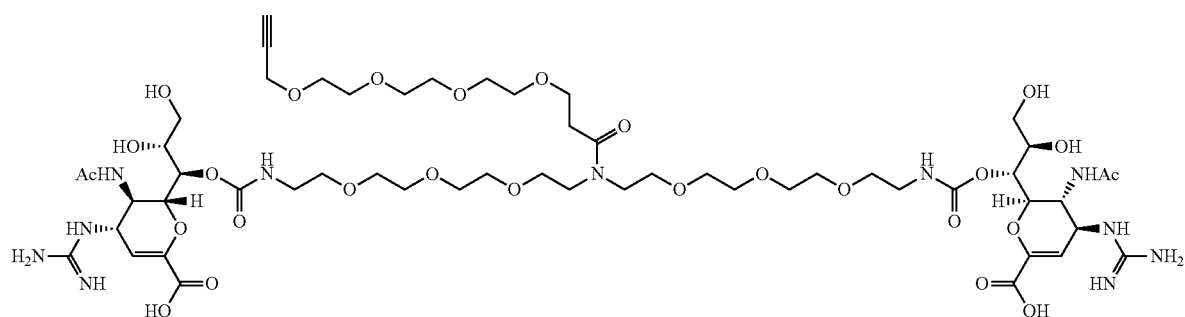 [SMILES: C#CCOCCOCCOCCOCCC(=O)N(CCOCCOCCOCCNC(=O)O[C@@H]([C@@H]1OC(C(=O)O)=C[C@H](NC(=N)N)[C@H]1NC(C)=O)[C@H](O)CO)CCOCCOCCOCCNC(=O)O[C@@H]([C@@H]1OC(C(=O)O)=C[C@H](NC(=N)N)[C@H]1NC(C)=O)[C@H](O)CO]

The step-d product (169.7 mg, 0.0923 mmol) was dissolved in MeOH (1.5 mL), and the solution was cooled in an ice-water bath. LiOH monohydrate (21 mg, 0.5 mmol) in water (1 mL) was added in portions over 1 hour. After stirring overnight, the reaction mixture was acidified with Dowex 50W×8 hydrogen form and purified through RPLC (0 to 30% acetonitrile and water, using 0.1% TFA as modifier). Yield 107.9 mg, 66.9%. Ions found by LCMS: $[(M+2H)/2]^+=663.8$, $[(M+3H)/3]^+=442.9$.

Example 12. Synthesis of Conjugate 2

Figure 10:
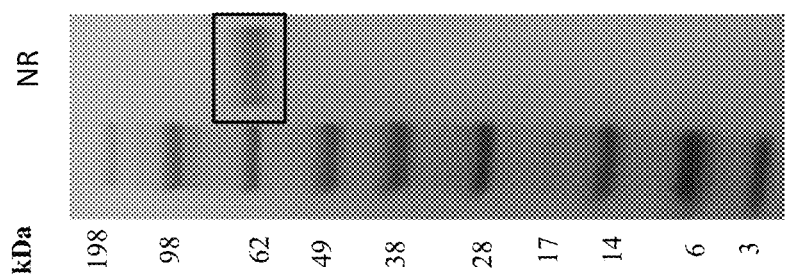
FIG. 10 shows a non-reducing SDS-PAGE of Conjugate 2.

The title conjugate was prepared analogously to Conjugate 1 (Example 9) using Int-3 (Example 11). Maldi TOF analysis of the purified final product gave an average mass of 63561 Da (DAR=3.3). Yield 43.4 mg, 43% yield. FIG. 10 shows a non-reducing SDS-PAGE of Conjugate 2.

Example 13. Synthesis of Int-4

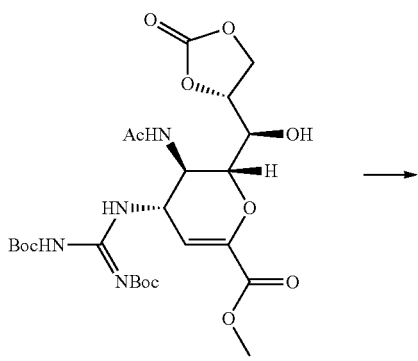

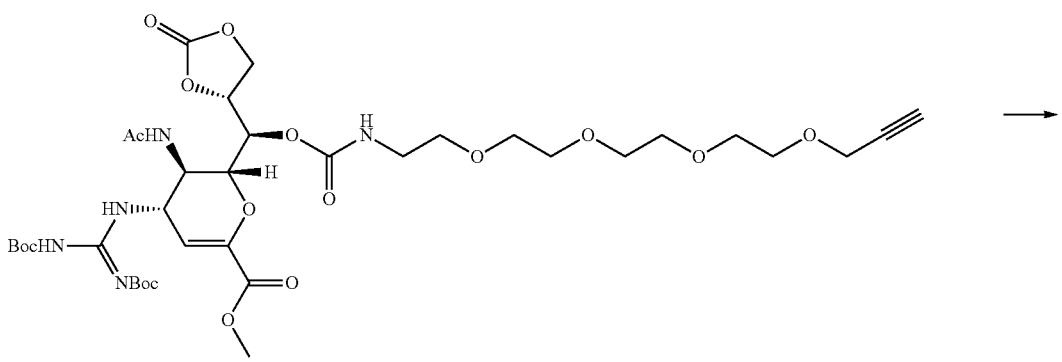

-continued

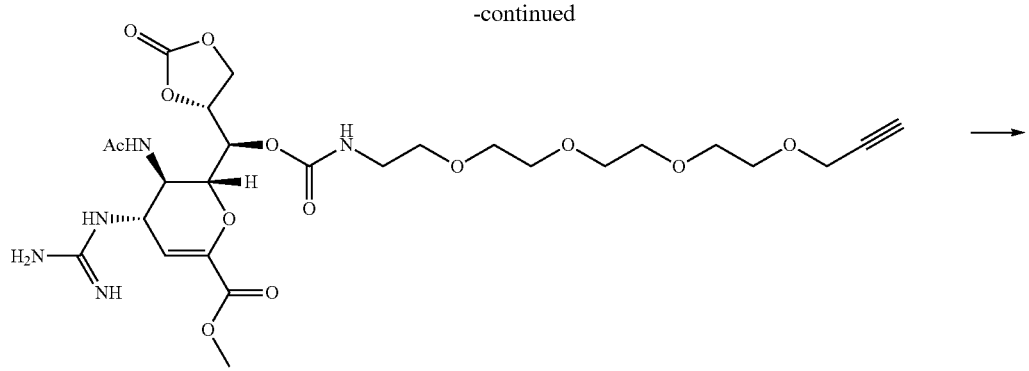

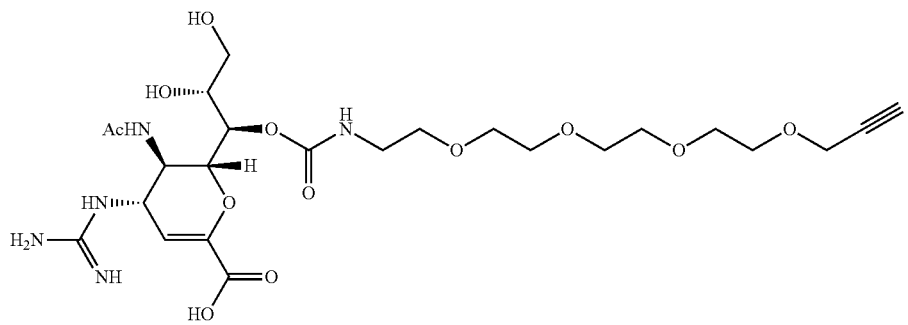

40

Step a.

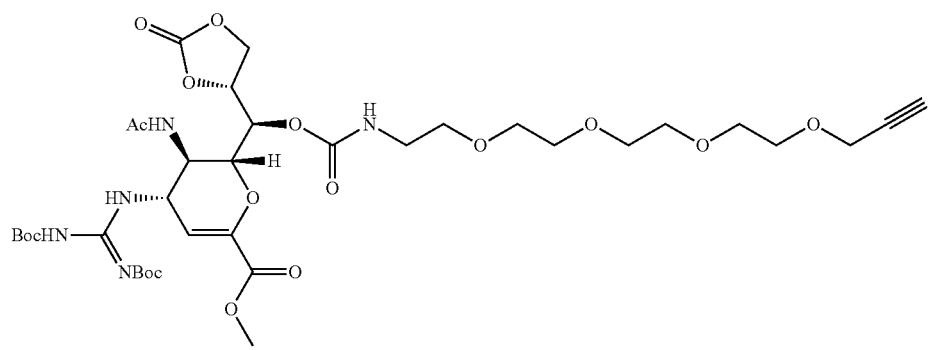

A flame-dried reaction flask was flushed with nitrogen and charged with Zanamivir Intermediate (Example 2) (343.2 mg, 0.6 mmol) and anhydrous DCM (1.5 mL). The solution was cooled in an ice-water bath and added with DIPEA (234 mg, 1.8 mmol) followed by 4-nitrophenyl chloroformate (121 mg, 0.6 mmol) and DMAP (67.4 mg, 0.6 mmol). The resulting mixture was stirred for 15 minutes, then added with an additional amount of 4-nitrophenyl chloroformate (121 mg, 0.6 mmol). After stirring for 2 hours, water (0.2 mL) was added to quench unreacted chloroformate. After stirred for 10 minutes, the reaction mixture was added with a solution of propargyl-PEG4-amine (185 mg, 0.8 mmol) in anhydrous DMF (0.5 mL). The reaction was continued for 1 hour and then directly purified through RPLC (100 g, 5 to 60% acetonitrile and water, using 0.1% TFA as modifier). The collected fractions were lyophilized. Yield 355 mg, 71.3%. Ion found by LCMS: $[M+H]^+$=830.2.

Step b.

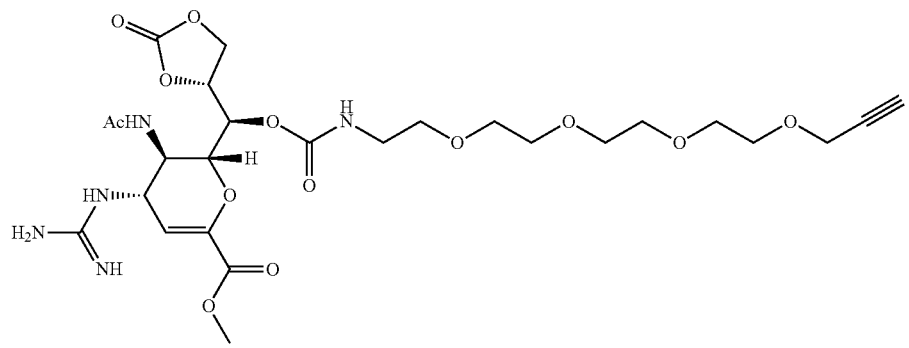 [SMILES: C#CCOCCOCCOCCOCCNC(=O)O[C@@H]([C@@H]1OC(C(=O)OC)=C[C@H](NC(=N)N)[C@H]1NC(C)=O)[C@H]1COC(=O)O1]

The step-a product (355 mg, 0.428 mmol) was dissolved in TFA (1 mL). The solution was stirred overnight, then directly purified by RPLC (5 to 25% acetonitrile and water, using 0.1% TFA as modifier). Yield 260.2 mg, 70.9% over two steps. Ion found by LCMS: $[M+H]^+=630.2$.

Step c.

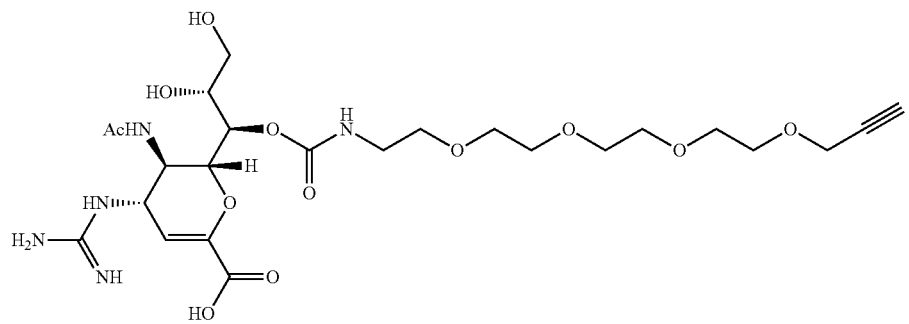 [SMILES: C#CCOCCOCCOCCOCCNC(=O)O[C@@H]([C@@H]1OC(C(=O)O)=C[C@H](NC(=N)N)[C@H]1NC(C)=O)[C@H](O)CO]

The step-b product (260.2 mg, 0.303 mmol) was dissolved in MeOH (1.5 mL). After the solution was cooled in an ice-water bath, a solution of LiOH monohydrate (42 mg, 1 mmol) in water (1 mL) was added in portions over 1 hour. The reaction was stirred overnight, then acidified with Dowex 50W×8 hydrogen form and purified by RPLC (0 to 50% acetonitrile and water, using 0.1% TFA as modifier). Yield 78.1 mg, 99%. Ions found by LCMS: $[M+H]^+=590.2$.

Example 14. Synthesis of Conjugate 3

Figure 11:
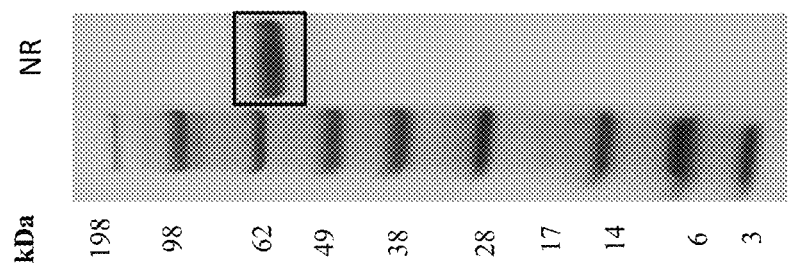
FIG. 11 shows a non-reducing SDS-PAGE of Conjugate 3.

The title conjugate was prepared analogously to Conjugate 1 (Example 9) using Int-4 (Example 13). Maldi TOF analysis of the purified final product gave an average mass of 61182 Da (DAR=3.4). Yield 50.89 mg, 51% yield. FIG. 11 shows a non-reducing SDS-PAGE of Conjugate 3.

Example 15. Synthesis of Int-5

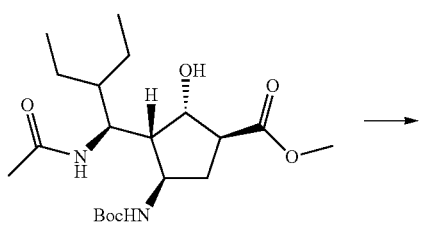

677
-continued
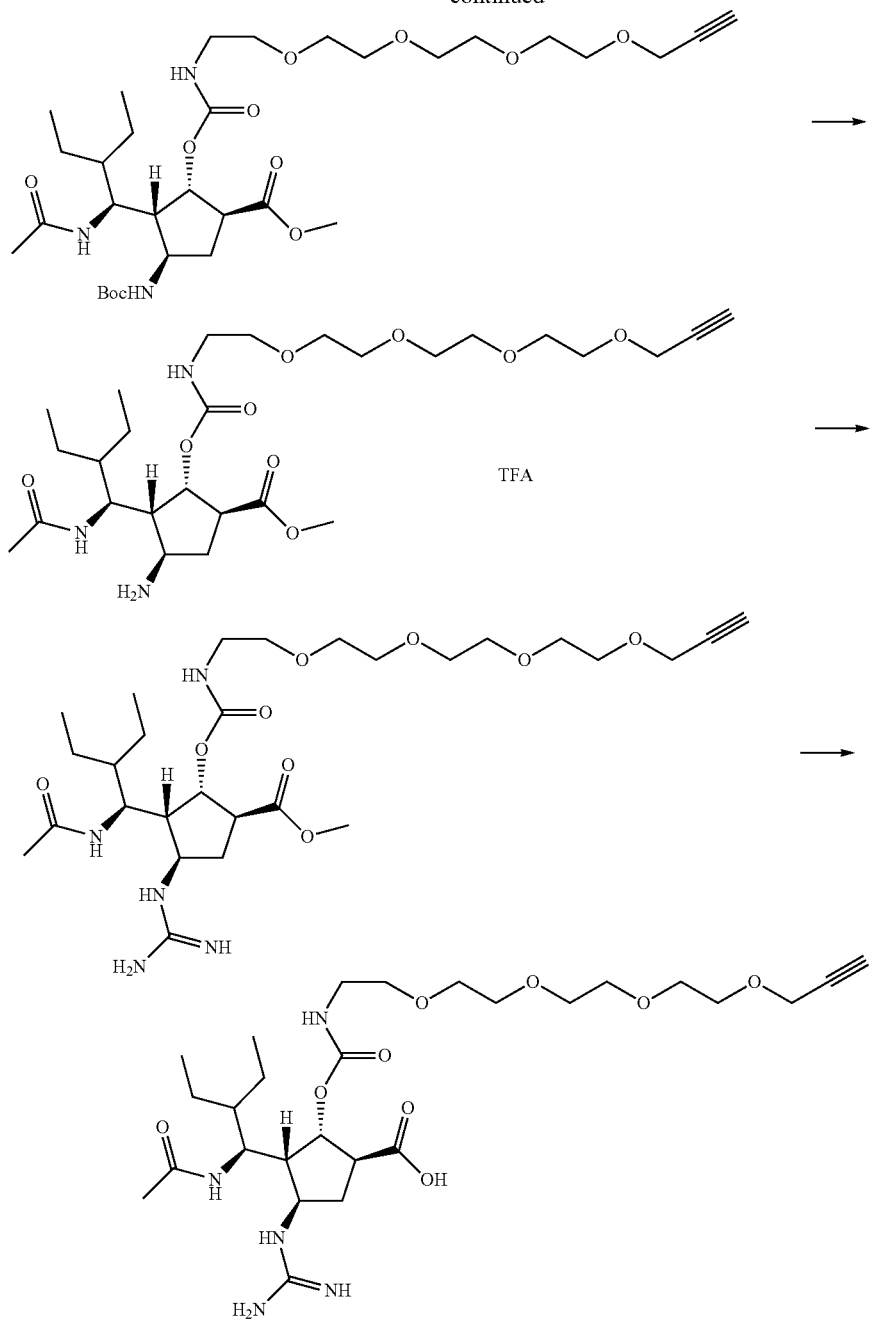
Step a.
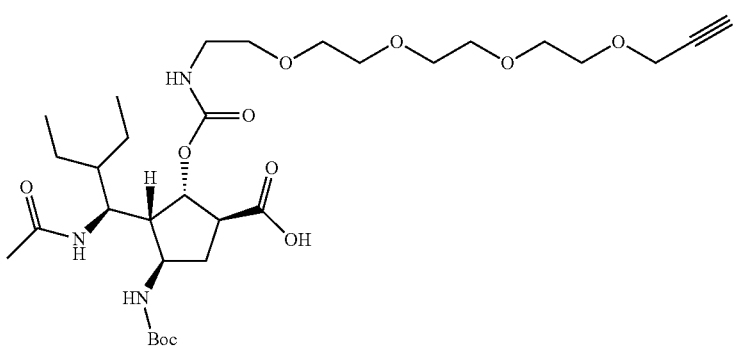
678

A flame-dried reaction flask was flushed with nitrogen and charged with (1S, 2S, 3R, 4R)-methyl 3-((S)-1-acetamido-2-ethylbutyl)-4-(tert-butoxycarbonylamino)-2-hydroxycyclopentanecarboxylate (320.4 mg, 0.8 mmol) and anhydrous DCM (2 mL). The solution was cooled in an ice-water bath and DIPEA (312 mg, 2.4 mmol) was added followed by 4-nitrophenyl chloroformate (161.3 mg, 0.8 mmol) and DMAP (98 mg, 0.8 mmol). The resulting mixture was stirred for 15 minutes, then an additional amount of 4-nitrophenyl chloroformate (161.3 mg, 0.8 mmol) was added. The reaction was stirred for 2 hours, then water (0.2 mL) was added to quench unreacted chloroformate. After stirring for 10 minutes, a solution of propargyl-PEG4-amine (259 mg, 1.12 mmol) in anhydrous DMF (0.5 mL) was added. The reaction was stirred for 1 hour and then purified directly by RPLC (100 g, 5 to 60% acetonitrile and water, using 0.1% TFA as modifier). The collected fractions were lyophilized. Yield 391.2 mg, 74.4%. Ion found by LCMS: [M+H]$^+$=658.3, [M-Boc+H]$^+$=558.3.

Step b.

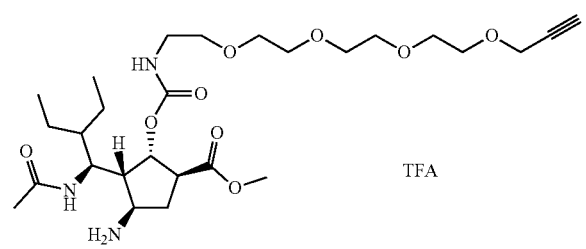 [SMILES: C#CCOCCOCCOCCOCCNC(=O)O[C@H]1[C@@H]([C@@H](NC(C)=O)C(CC)CC)[C@H](N)C[C@@H]1C(=O)OC]

The step-a product (391.2 mg, 0.595 mmol) was dissolved in TFA (0.8 mL), and the solution was stirred at room temperature for 20 minutes. It was then directly purified by RPLC (100 g, 5 to 60% acetonitrile and water). Yield 323.2 mg, 81%. Ion found by LCMS: [M+H]$^+$=558.3.

Step c.

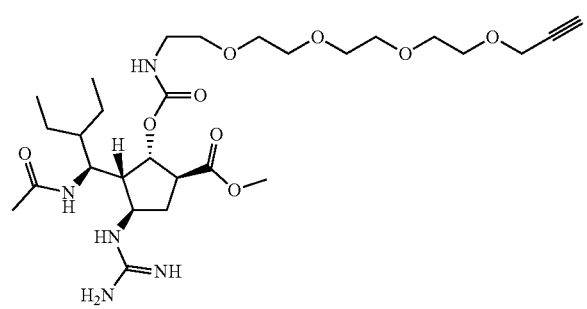 [SMILES: C#CCOCCOCCOCCOCCNC(=O)O[C@H]1[C@@H]([C@@H](NC(C)=O)C(CC)CC)[C@H](NC(=N)N)C[C@@H]1C(=O)OC]

To a solution of the step-b product (323.2 mg, 0.482 mmol) in THE (2 mL) was added N,N'-Bis-Boc-1-guanylpyrazole (224.4 mg, 0.723 mmol) and PIPEA (260 mg, 2 mmol). The reaction mixture was stirred for 1 day and then extracted with water (3 mL) and EtOAc/hexanes (1:1, 8 mL). The organic layer was dried over Na$_2$SO$_4$ and concentrated by rotary evaporation. The residue was re-dissolved in TFA (~1 mL), and the solution was stirred overnight. It was then directly purified by RPLC (100 g, 0 to 30% acetonitrile and water, using 0.1% TFA as modifier). The collected fractions were lyophilized. Yield 254.2 mg, 83.2%. Ions found by LCMS: [M+H]$^+$=600.3, [M-Boc+H]$^+$=300.6.

Step d.

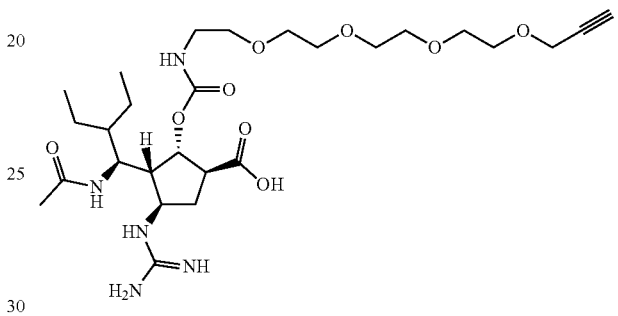

The step-c product (254.2 mg, 0.356 mmol) was dissolved in THE (1.5 mL), and the solution was cooled in an ice-water bath. CaCl$_2$ dihydrate (419 mg, 2.85 mmol) was added, then 1.8 mL of KOH (112 mg, 2 mmol) in water (2 mL) was added in portions over 1 hour. After stirred for 3 more hours, the reaction mixture was acidified by Dowex 50W×8 hydrogen form and purified by RPLC (0 to 30% acetonitrile and water, using 0.1% TFA as modifier). Yield 102 mg, 49.8%. Ions found by LCMS: [M+H]$^+$=586.4, [(M+2H)/2]$^+$=293.8.

Example 16. Synthesis of Conjugate 4

Figure 12:
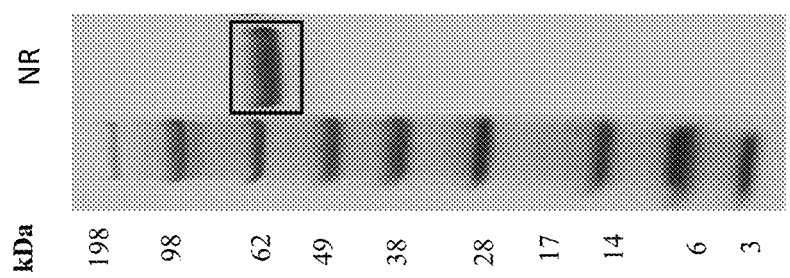
FIG. 12 shows a non-reducing SDS-PAGE of Conjugate 4.

The title conjugate was prepared analogously to Conjugate 1 (Example 9) using Int-5 (Example 15). Maldi TOF analysis of the purified final product gave an average mass of 63002 Da (DAR=3.4). Yield 49.315 mg, 49% yield. FIG. 12 shows a non-reducing SDS-PAGE of Conjugate 4.

Example 17. Synthesis of Int-6

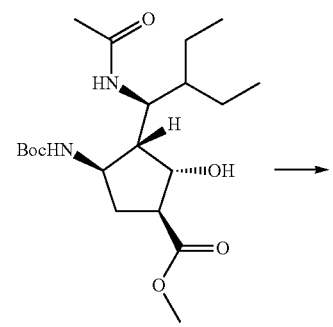

681                                                          682
-continued
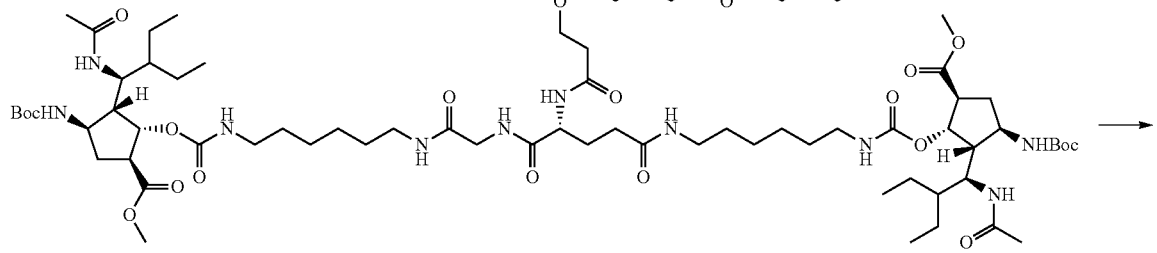
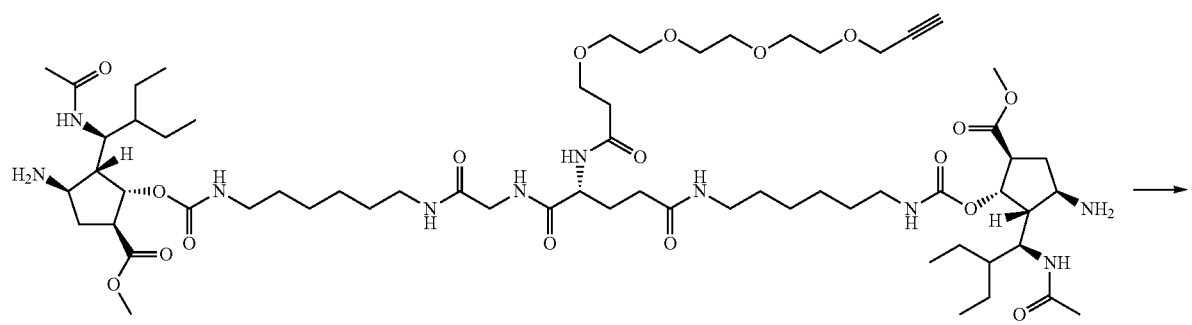
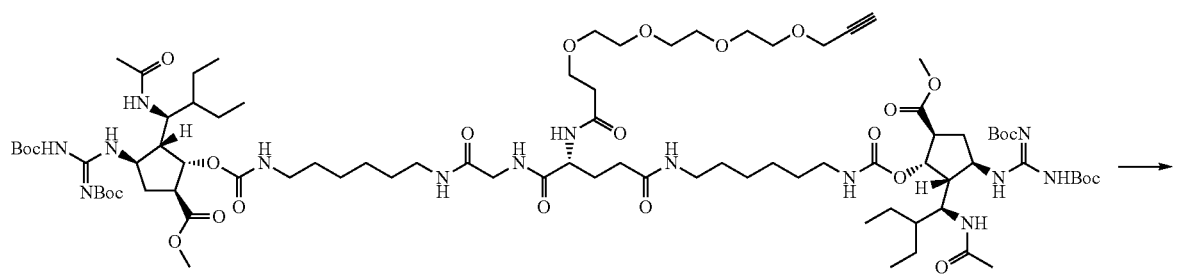
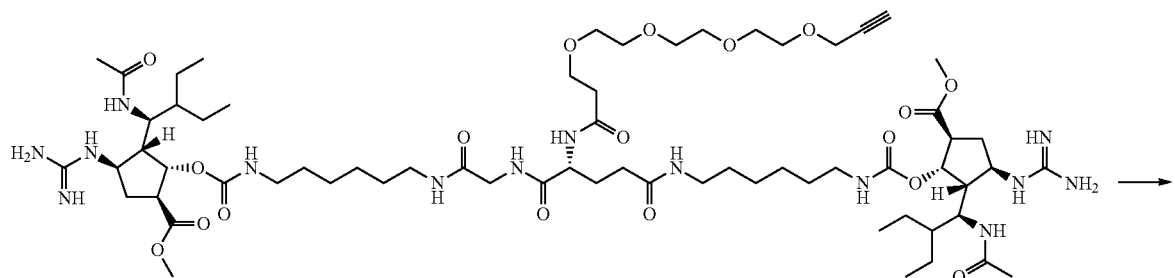
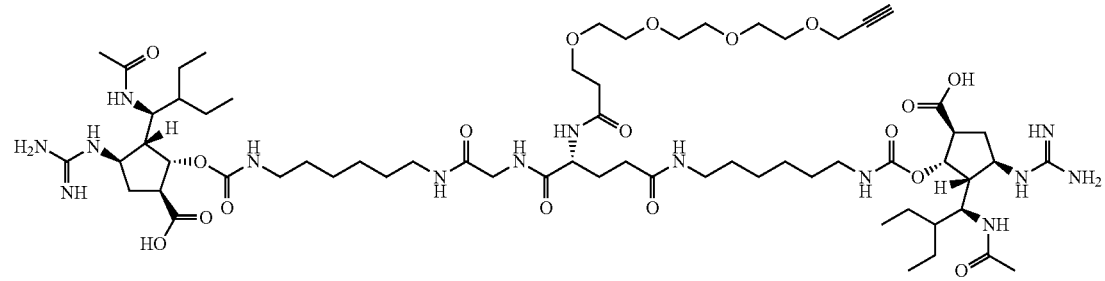

Step a.

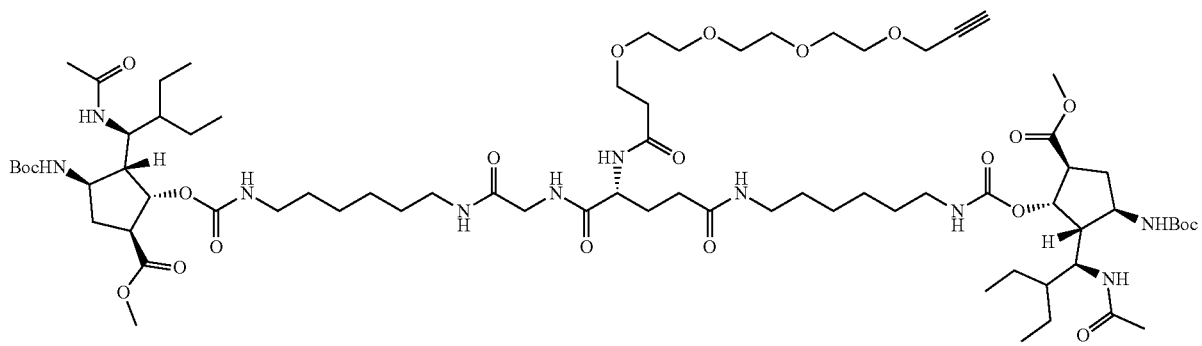 [SMILES: C#CCOCCOCCOCCOCCC(=O)N[C@H](CCC(=O)NCCCCCCNC(=O)O[C@H]1[C@@H]([C@@H](NC(C)=O)C(CC)CC)[C@H](NC(=O)OC(C)(C)C)C[C@@H]1C(=O)OC)C(=O)NCC(=O)NCCCCCCNC(=O)O[C@H]1[C@@H]([C@@H](NC(C)=O)C(CC)CC)[C@H](NC(=O)OC(C)(C)C)C[C@@H]1C(=O)OC]

A flame-dried reaction flask was flushed with nitrogen and charged with (1S, 2S, 3R, 4R)-methyl 3-((S)-1-acetamido-2-ethylbutyl)-4-(tert-butoxycarbonylamino)-2-hydroxy cyclopentanecarboxylate (280.4 mg, 0.7 mmol) and anhydrous DCM (1 mL). After stirring to dissolve the starting material, DMAP (85.7 mg, 0.7 mmol) was added to the solution, followed by bis(pentafluorophenyl)carbonate (295.6 mg, 0.75 mmol). The resulting mixture was stirred for 1 hour, then added into a solution of Linker-2 (Example 5) (157.5 mg, 0.22 mmol) in anhydrous DMF (1 mL) and DIPEA (130 mg, 1 mmol). The reaction was stirred overnight and purified by RPLC (50 g, 5 to 90% acetonitrile and water). The collected fractions were lyophilized. Yield 134.1 mg, 40.7%. Ion found by LCMS: $[(M+2H)/2]^+=748.6$.

Step b.

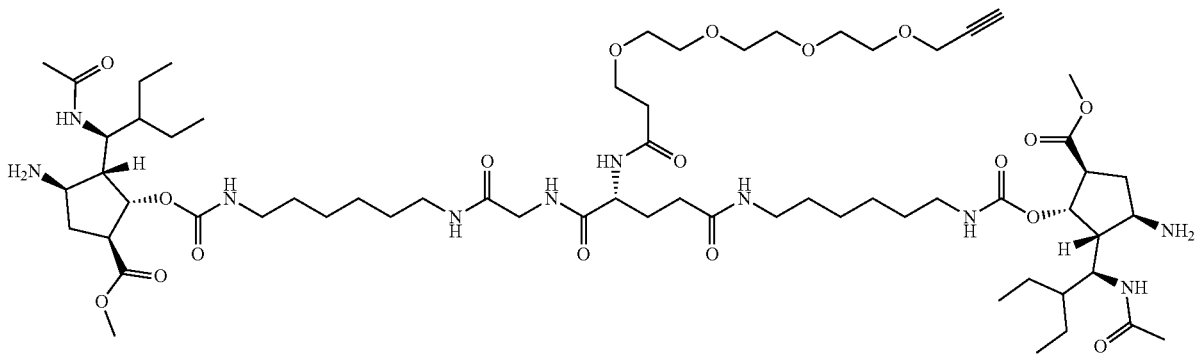 [SMILES: C#CCOCCOCCOCCOCCC(=O)N[C@H](CCC(=O)NCCCCCCNC(=O)O[C@H]1[C@@H]([C@@H](NC(C)=O)C(CC)CC)[C@H](N)C[C@@H]1C(=O)OC)C(=O)NCC(=O)NCCCCCCNC(=O)O[C@H]1[C@@H]([C@@H](NC(C)=O)C(CC)CC)[C@H](N)C[C@@H]1C(=O)OC]

The step-a product (134.1 mg, 0.0896 mmol) was dissolved in TFA (0.5 mL). The solution was stirred for 20 minutes, then directly purified by RPLC (50 g, 5 to 60% acetonitrile and water). Yield 108.4 mg, 93.4%. Ions found by LCMS: $[(M+2H)/2]^+=648.3$, $[(M+3H)/3]^+=432.8$.

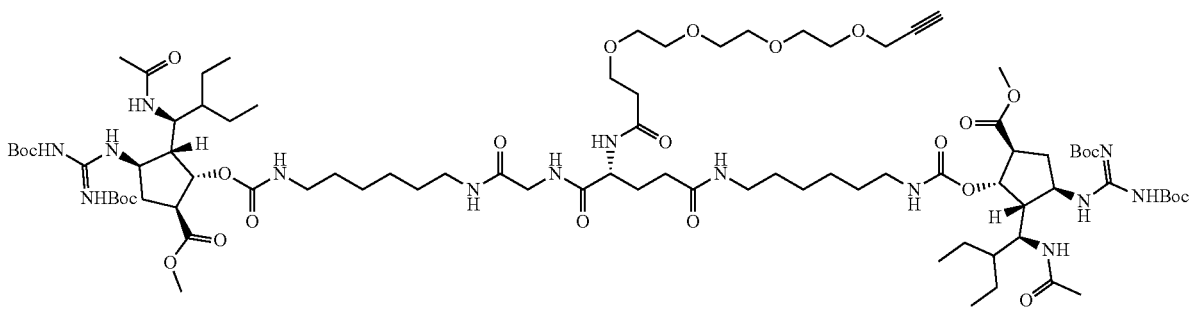

Step c.

To a solution of the step-b product (108.4 mg, 0.0837 mmol) in anhydrous THF (1 mL) was added N,N'-bis-boc-1-guanylpyrazole (81.3 mg, 0.285 mmol) and DIEPA (65 mg, 0.5 mmol). The reaction was stirred at room temperature for 2.5 days, then directly purified by RPLC (100 g, 40 to 75% acetonitrile and water). Yield 73.6 mg, 49.4%. Ion found by LCMS: $[(M+3H)/3]^+=594.2$.

Step d.

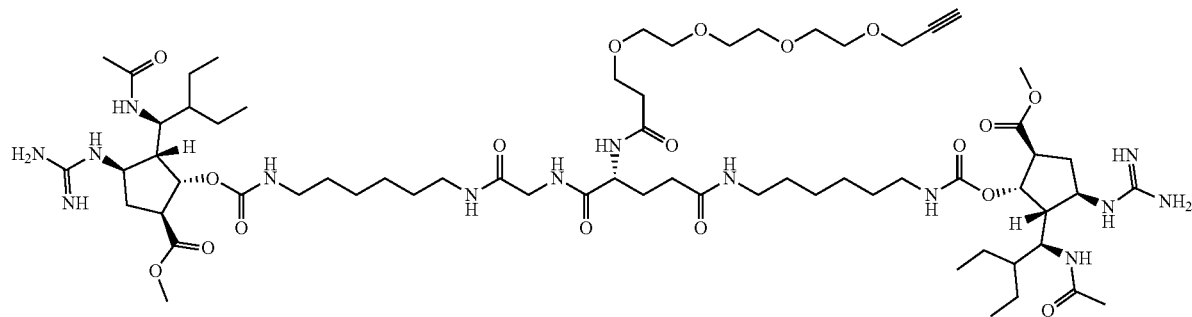 [SMILES: C#CCOCCOCCOCCOCCC(=O)N[C@H](CCC(=O)NCCCCCCNC(=O)O[C@H]1[C@@H]([C@@H](NC(C)=O)C(CC)CC)[C@H](NC(=N)N)C[C@@H]1C(=O)OC)C(=O)NCC(=O)NCCCCCCNC(=O)O[C@H]1[C@@H]([C@@H](NC(C)=O)C(CC)CC)[C@H](NC(=N)N)C[C@@H]1C(=O)OC]

The step-c product (73.6 mg, 0.041 mmol) was dissolved in TFA (0.5 mL). The solution was stirred for 20 minutes, then directly purified by RPLC (50 g, 5 to 60% acetonitrile and water). Yield 62.1 mg, 94.1%. Ions found by LCMS: $[(M+2H)/2]^+=690.4$, $[(M+3H)/3]^+=460.8$.

Step e.

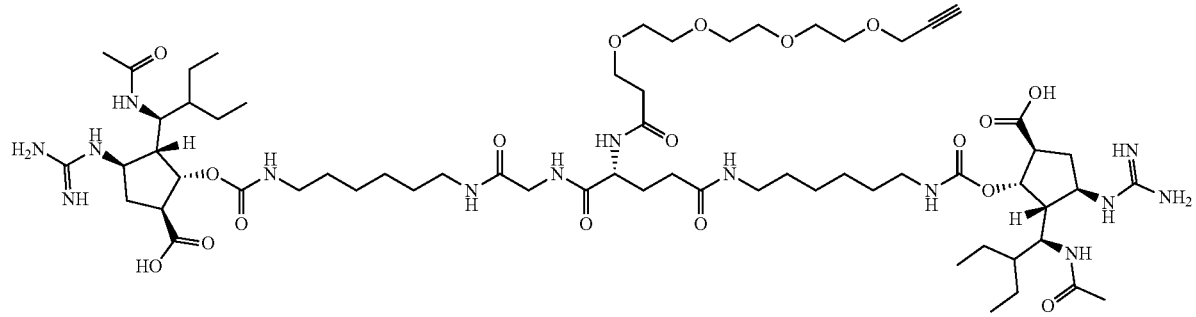 [SMILES: C#CCOCCOCCOCCOCCC(=O)N[C@H](CCC(=O)NCCCCCCNC(=O)O[C@H]1[C@@H]([C@@H](NC(C)=O)C(CC)CC)[C@H](NC(=N)N)C[C@@H]1C(=O)O)C(=O)NCC(=O)NCCCCCCNC(=O)O[C@H]1[C@@H]([C@@H](NC(C)=O)C(CC)CC)[C@H](NC(=N)N)C[C@@H]1C(=O)O]

The step-d product (62.1 mg, 0.0386 mmol) in THF (3 mL) was cooled in an ice-water bath and a 45% w/w solution of KOH (0.2 mL) was added in portions over 1 hour. The reaction was stirred for 2 more hours, then acidified with 4N HCl solution in dioxane (0.8 mL) and extracted with hexanes (10 mL) and water (1.5 mL). The aqueous layer was purified by HPLC (0 to 20% acetonitrile and water, using 0.1% TFA as modifier). Yield 36.2 mg, 59.4%. Ions found by LCMS: $[(M+2H)/2]^+=676.5$, $[(M+3H)/3]^+=451.4$.

Example 18. Synthesis of Conjugate 5

Figure 13:
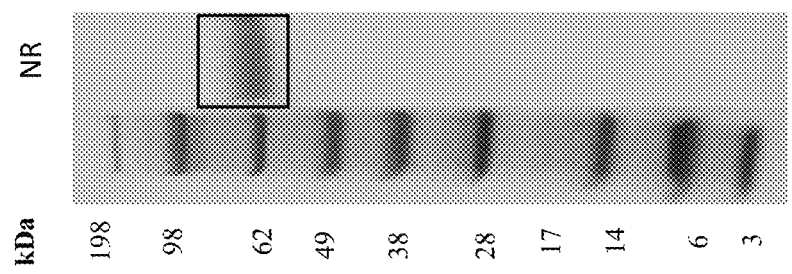
FIG. 13 shows a non-reducing SDS-PAGE of Conjugate 5.

The title conjugate was prepared analogously to Conjugate 1 (Example 9) using Int-6 (Example 17). Maldi TOF analysis of the purified final product gave an average mass of 63561 Da (DAR=3.3). Yield 43.4 mg, 43% yield. FIG. 13 shows a non-reducing SDS-PAGE of Conjugate 5.

Example 19. Synthesis of Int-7

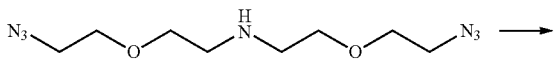

687 -continued 688
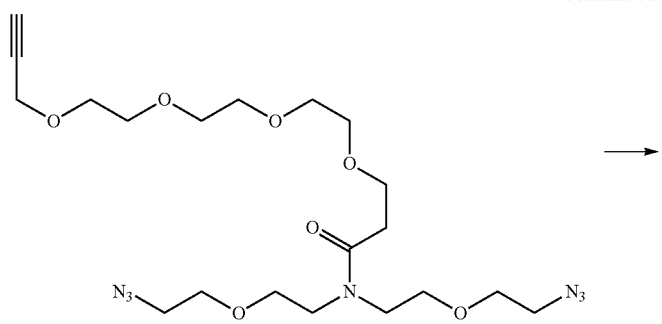
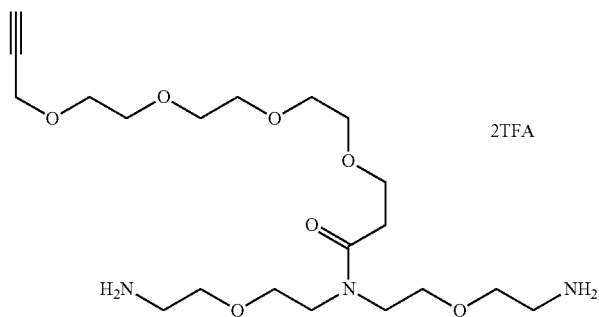
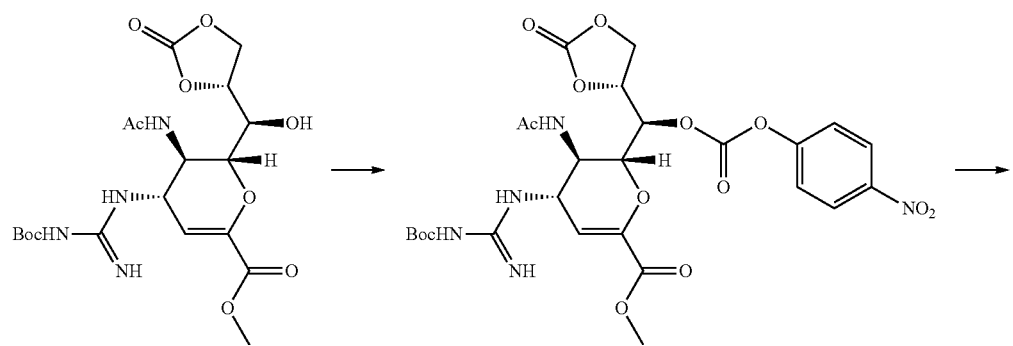
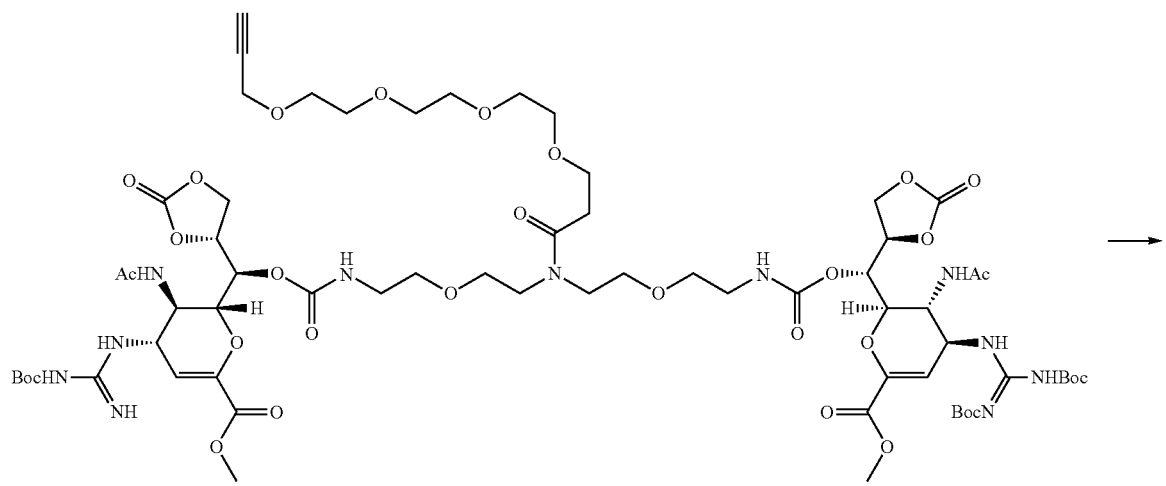

-continued

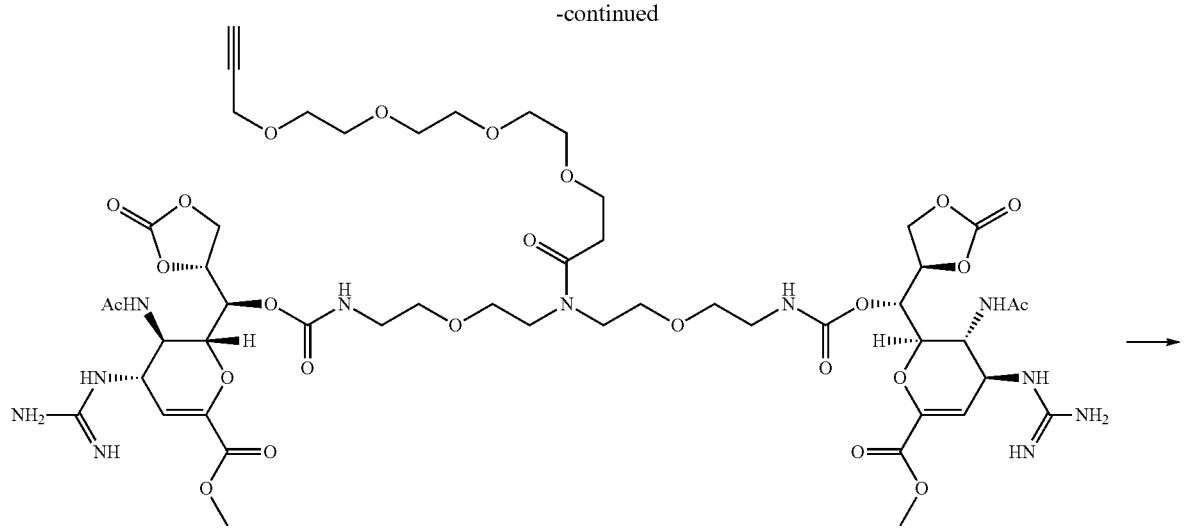

Step a.

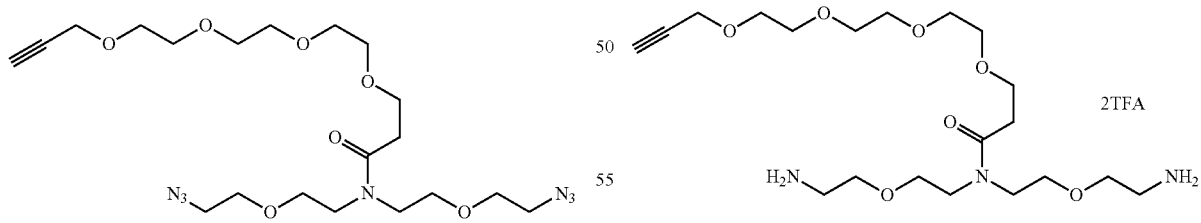

To a solution of propargyl-PEG4-acid (609 mg, 2.34 mmol) and NH-bis(PEG1-azide) (500 mg, 2.055 mmol) in anhydrous DMF (2 mL) was added HATU (889.7 mg, 2.34 mmol) in portions over 5 minutes. After stirring to dissolve all the coupling reagent, DIPEA (390 mg, 3 mmol) was added and stirring continued for 1 hour. It was then purified directly by RPLC (100 g, 5 to 40% acetonitrile and water). Yield 918 mg, 92%. Ion found by LCMS: [M+H]$^+$=486.2.

Step b.

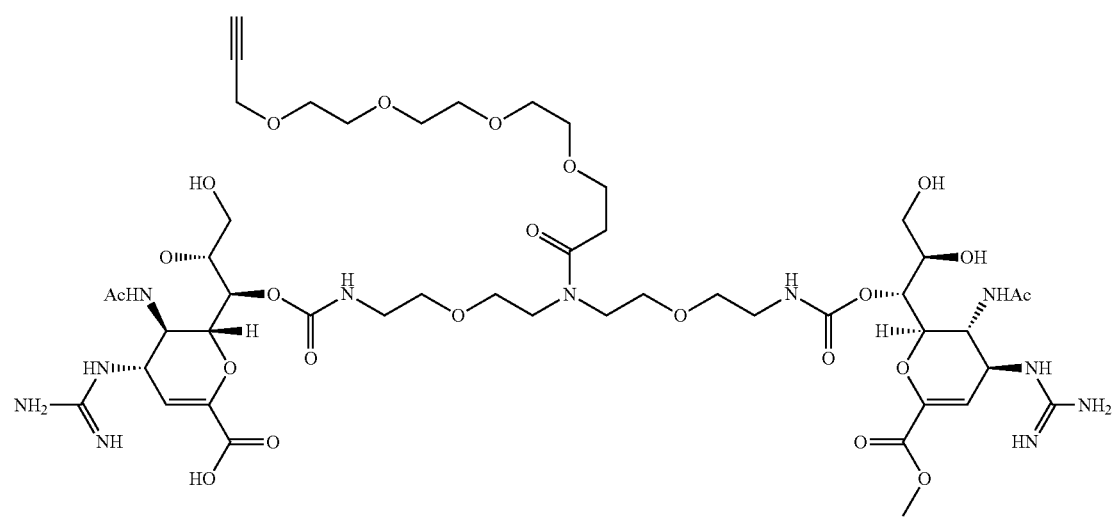

The step-a product (918 mg, 1.89 mmol) was dissolved in THF, and the solution was cooled to 13° C. Triphenylphosphine (1.141 g, 4.35 mmol) was added in portions over 10 minutes. The resulting mixture was stirred at ~ 13° C. to room temperature for 2 hours. A solution of LiOH monohydrate (42 mg, 1 mmol) in water (2 mL) and MeOH (1 mL) was added. After stirring was continued for 20 hours, the reaction was purified by RPLC (100 g, 0 to 30% acetonitrile and water, using 0.1% TFA as modifier). Yield 825 mg, 65.9%. Ion found by LCMS: [M+H]$^+$=434.4.

Step c.

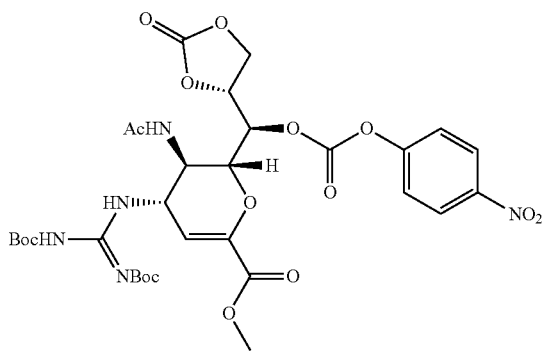

A flame-dried reaction flask was flushed with nitrogen and charged with Zanamivir intermediate (Example 2) (865 mg, 1.51 mmol) and anhydrous DCM (5 mL). After stirring to dissolve the starting material, the solution was cooled in an ice-water bath and 4-nitrophenyl chloroformate (365.3 mg, 1.81 mmol) was added followed by DMAP (152.2 mg, 0.755 mmol). The ice-water bath was removed, and the mixture was stirred for 3 hours. An additional amount of 4-nitrophenyl chloroformate (304.4 mg, 1.51 mmol) was added, and stirring was continued for 1 hour. The reaction was then quenched with water (1 mL). After vigorously stirred for 1 hour, the reaction mixture was extracted with water (20 mL×2) and DCM (20 mL). The organic layer was stirred overnight, dried over $Na_2SO_4$, and concentrated by rotary evaporation. The material was carried on to the subsequent step without further purification. Ion found by LCMS: $[M+H]^+=738.2$.

Step d.

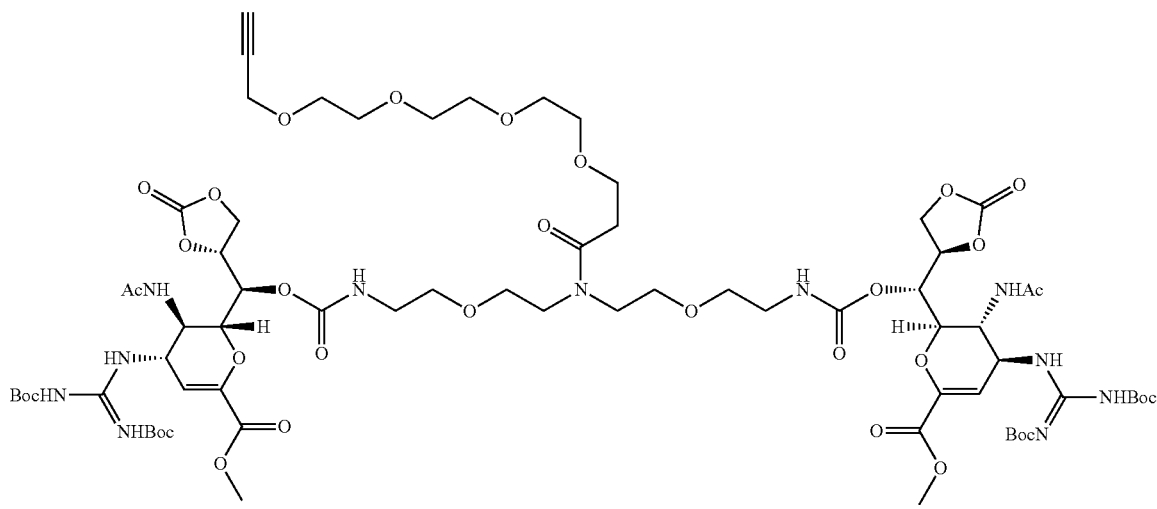

A solution of a mixture of the step-b product (429.7 mg, 0.65 mmol) and DIPEA (260 mg, 2 mmol) in anhydrous THF (1 mL) was added dropwise to the step-c product. The resulting mixture was stirred for 2 hours, then directly purified by RPLC (100 g, 10 to 65% acetonitrile and water). Acetonitrile in the collected fractions was removed by rotary evaporation at room temperature. The heterogeneous aqueous layer was extracted with EtOAc (200 mL), then back-extracted with EtOAc (50 mL). The combined organic layers were dried over $Na_2SO_4$ and concentrated by rotary evaporation to dryness. Yield 442 mg, 41.7%. Ions found by LCMS: $[(M+2H)/2]^+=815.8$, $[(M-Boc+2H)/2]^+=765.8$, $[(M-2Boc+2H)/2]^+=716$.

Step e.

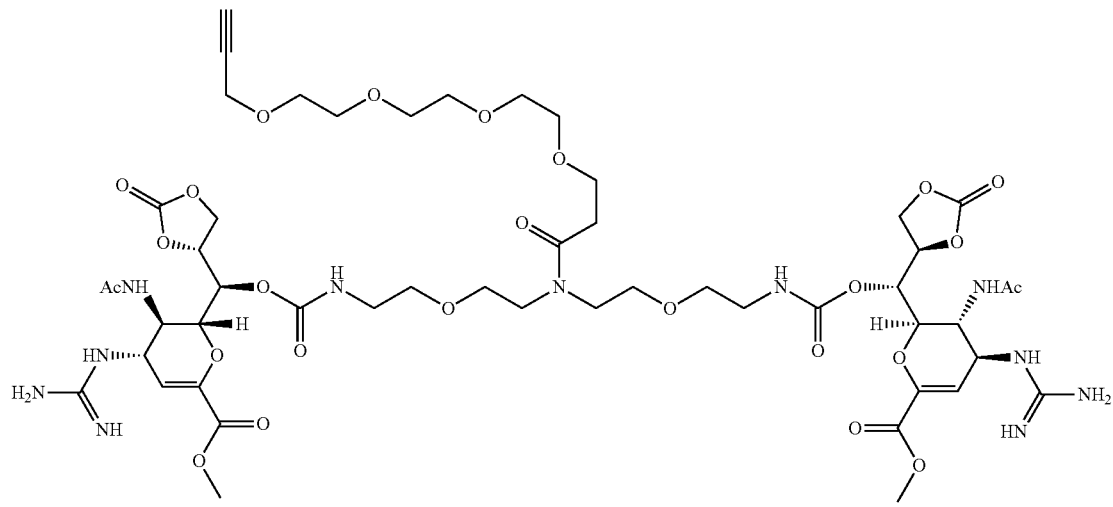

The step-d product (441 mg, 0.271 mmol) was dissolved in TFA (1 mL). The solution was stirred for 20 minutes, then directly purified by HPLC (5 to 20% acetonitrile and water, using 0.1% TFA as modifier). Yield 308 mg, 77.9%. Ions found by LCMS: $[(M+2H)/2]^+=615.8$, $[(M+3H)/3]^+=411$.

Step f.

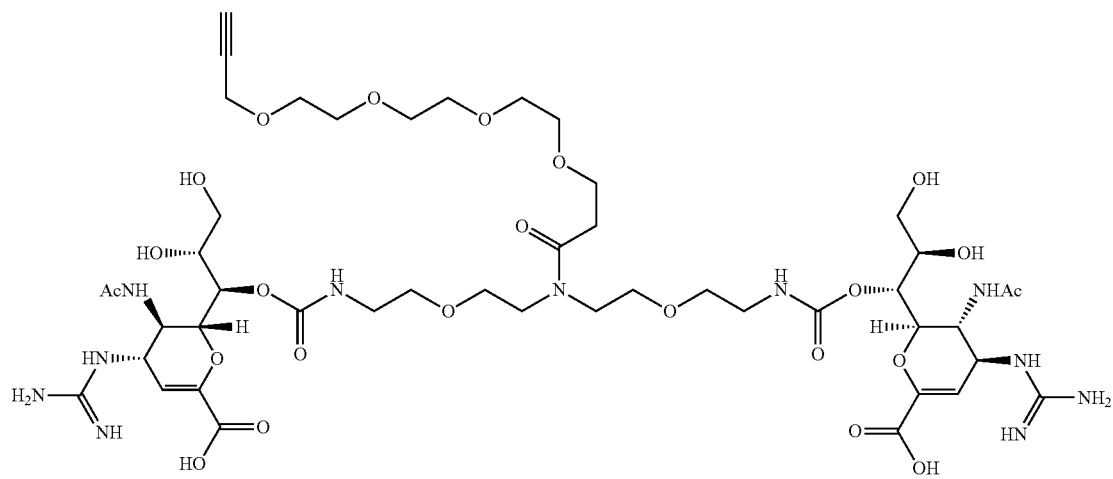

The step-e product (308 mg, 0.211 mmol) was dissolved in MeOH (1 mL) and water (0.5 mL), and the solution was cooled in an ice-water bath. A solution of LiOH monohydrate (42 mg, 1 mmol) in water (1 mL) was added in portions over 1 hour. The reaction was stirred overnight, acidified by 4 N HCl solution in dioxane (0.25 mL), and purified by RPLC (0 to 20% acetonitrile and water, using 0.1% TFA as modifier). Yield 198 mg, 64%. Ions found by LCMS: $[(M+2H)/2]^+=575.8$, $[(M+3H)/3]^+=384.2$.

Example 20. Synthesis of Conjugate 6

Figure 14:
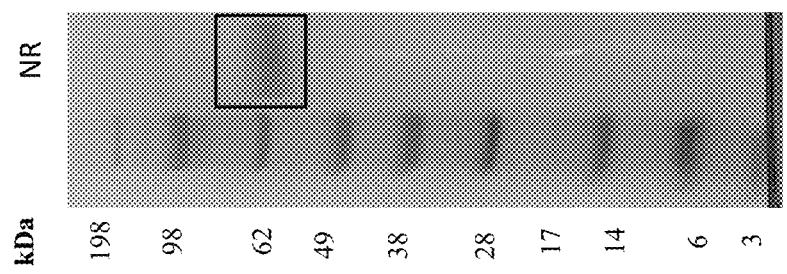
FIG. 14 shows a non-reducing SDS-PAGE of Conjugate 6.

The title conjugate is prepared analogously to Conjugate 1 (Example 9) using Int-7 (Example 19) (SEQ ID NO: 18). Maldi TOF analysis of the purified final product gave an average mass of 62854. Da (DAR=3.1). Yield 175.4 mg, 50% yield. FIG. 14 shows a non-reducing SDS-PAGE of Conjugate 6. The resulting conjugate is depicted in FIG. 43.

Example 21. Synthesis of Int-1
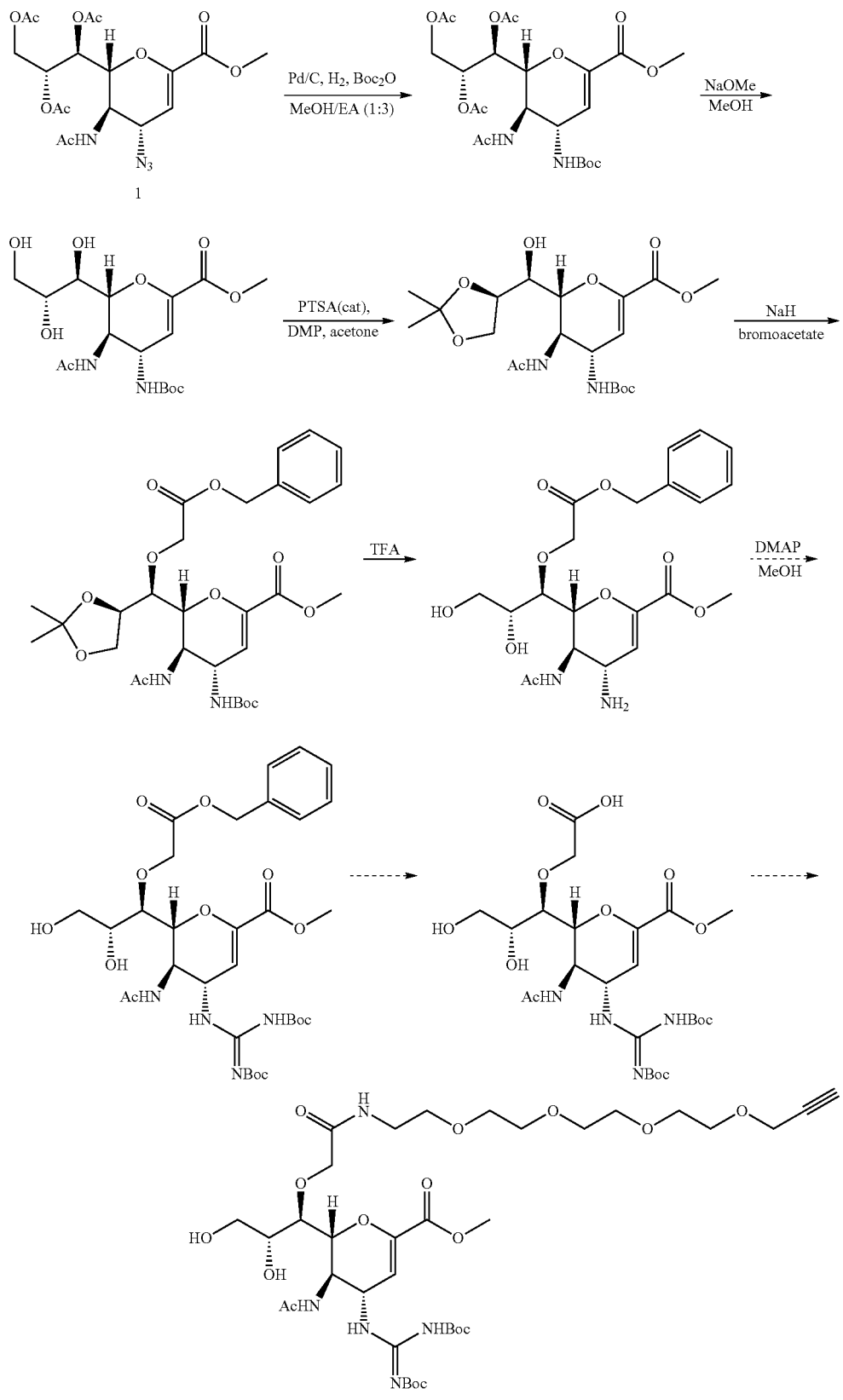

Step a.

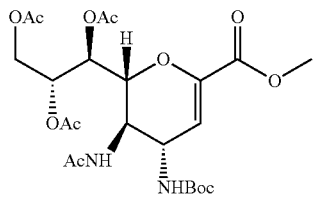

Methyl 5-acetoamido-7,8,9-O-triacetyl-2,6-anhydro-4-azido-3,4,5-trideoxy-D-glycero-D-galacto-non-2-enonate (1.8 g, 4.0 mmol) was dissolved into 40 mL methanol and then treated with 400 mg of 5% Pd/C and 1.1 g Boc anhydride (5.0 mmol), then the reaction mixture was stirred at room temperature under a hydrogen atmosphere for 1 hour. The palladium-charcoal was removed by filtration. The filtrate was concentrated and used in next step without purification.

Step b.

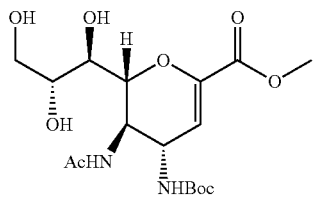 [SMILES: COC(=O)C1=C[C@H](NC(=O)OC(C)(C)C)[C@@H](NC(C)=O)[C@H]([C@H](O)[C@H](O)CO)O1]

The product from the previous step was dissolved into 20 mL dry methanol and then treated with 2 mL sodium methoxide in methanol (0.5 M) dropwise with cooling in an ice-water bath. After 2 hours, the progress of reaction was determined by LCMS. The reaction was quenched with 1 N HCl to pH 5-6. The resulting solution was concentrated and purified by reversed phase liquid chromatography (RPLC) using an Isco COMBIFLASH® liquid chromatograph eluted with 5% to 100% acetonitrile and water, using 0.1% TFA as the modifier. Ion(s) found by LCMS: $(M+H)^+=405$ Step c.

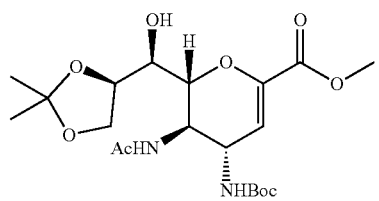

Methyl 5-acetamido-2,6-anhydro-4-[(tert-butoxycarbonyl)amino]-3,4,5-trideoxy-D-erythro-non-2-enonate (0.4 g, 1 mmol) was dissolved in 10 mL of acetone, 4 mL of 2,2-dimethoxypropane and 20 mg of p-toluenesulfonic acid hydrate (0.1 mmol). The resulting solution was stirred at room temperature overnight, then quenched with 1 mL saturated NaHCO₃. The mixture was concentrated and purified by reversed phase liquid chromatography (RPLC) using an Isco COMBIFLASH® liquid chromatograph eluted with 5% to 100% acetonitrile and water without modifier. Ion(s) found by LCMS: $(M+H)^+=445$.

Step d.

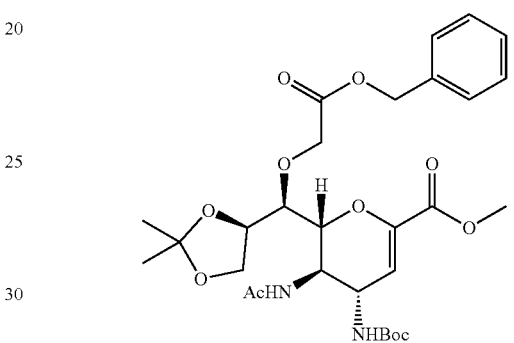

Sodium hydride (40 mg, 60% in oil, 1.0 mmol) was added into methyl 5-acetamido-2,6-anhydro-4-[(tert-butoxycarbonyl)amino]-3,4,5-trideoxy-8,9-O-(1-methylethylidene)-D-erythro-non-2-enonate (0.25 g, 0.50 mmol) in 5 mL dry THF with cooling from an ice-water bath. The resulting solution was stirred for 0.5 hour, then benzyl bromoacetate (0.23 g, 1.0 mmol) was added. The resulting solution was stirred for 2 hours and quenched with 5 mL 10% ammonium chloride in water. Then the solution was diluted with 50 mL ethyl acetate. The organic layer was separated and dried with sodium sulfate. The dried organic solution was concentrated and purified by reversed phase liquid chromatography (RPLC) using an Isco COMBIFLASH® liquid chromatograph eluted with 5% to 100% acetonitrile and water without modifier. Ion(s) found by LCMS: $(M+H)^+=593$.

Example 22. Synthesis of Int-9

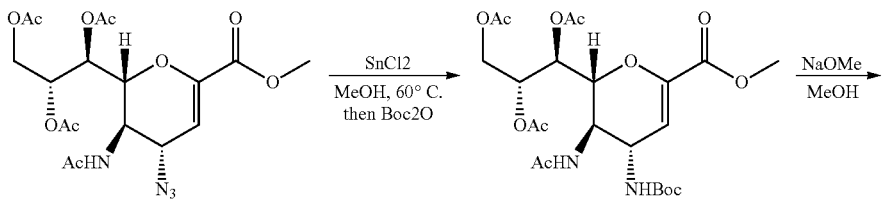

699 700
-continued
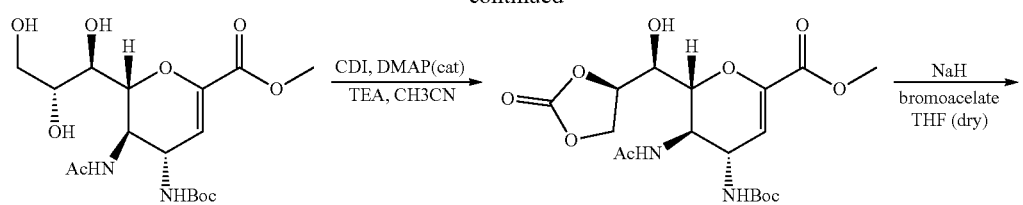
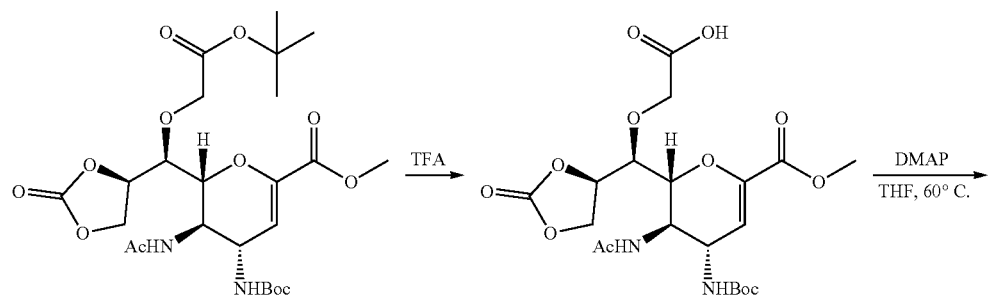
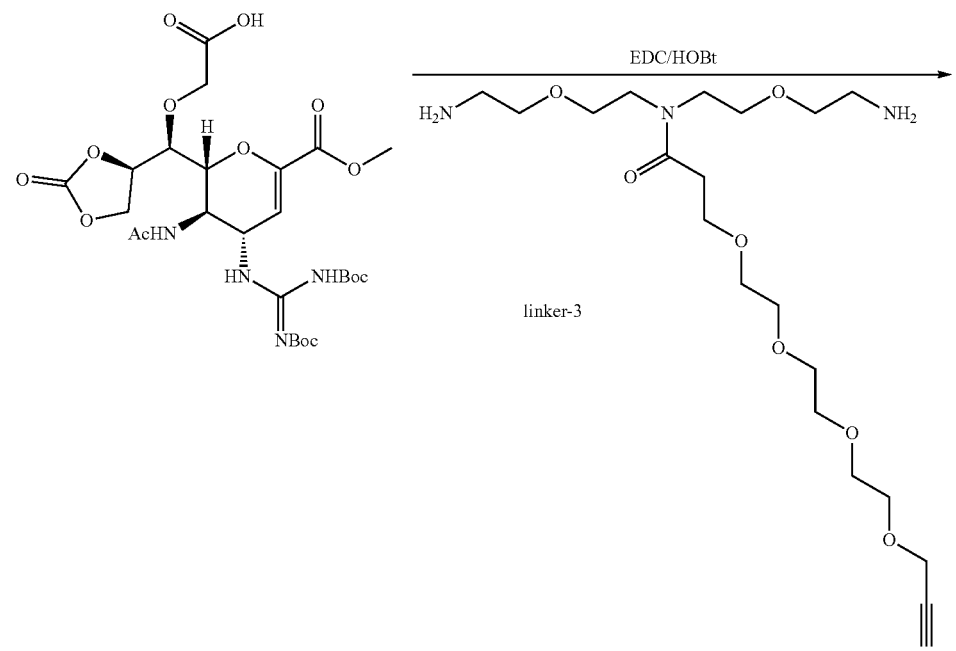
linker-3

701
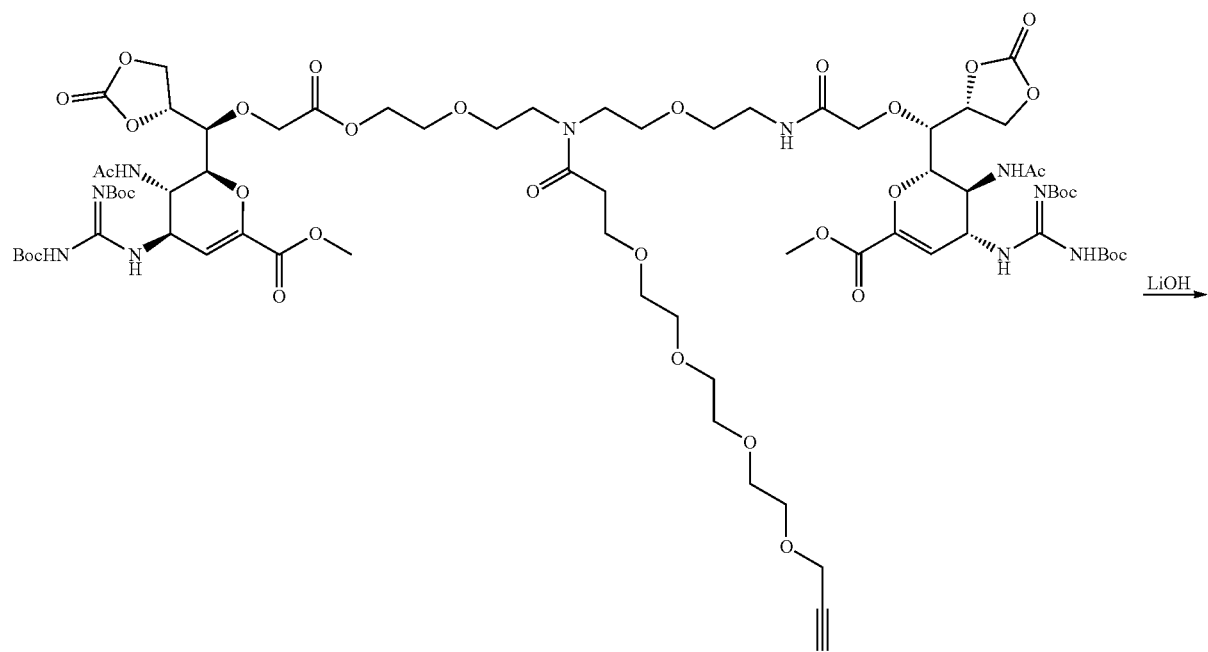
LiOH →
702
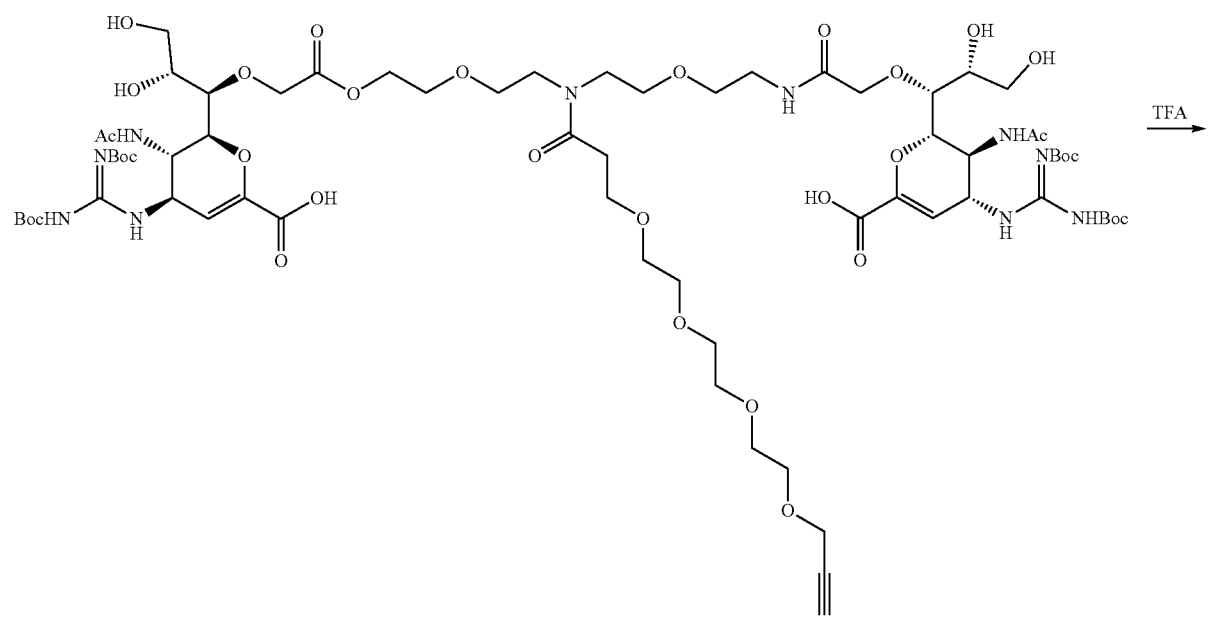
TFA →

703

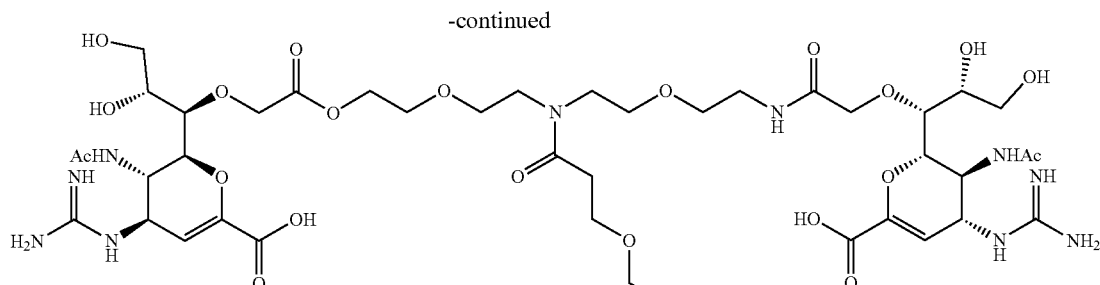

704

-continued

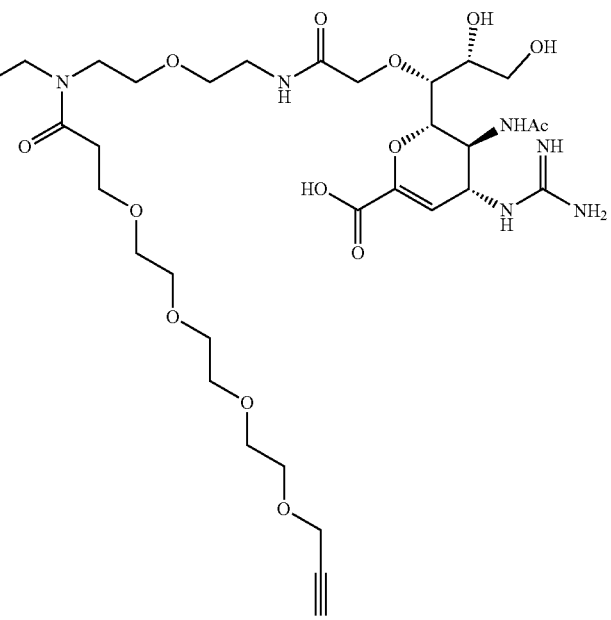

Int-9

Step a.

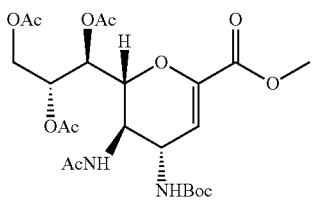

Methyl 5-acetoamido-7,8,9-O-triacetyl-2,6-anhydro-4-azido-3,4,5-trideoxy-D-glycero-D-galacto-non-2-enonate (10 g, 22 mmol) was dissolved into 100 ml methanol and then heated to 60° C. with an oil bath, the SnCl₂ (5.7 g, 20 mmol) was added to the solution in 3 portions (caution, gas evolves). The reaction mixture was stirred for 10 min, at which time the reaction was complete by HPLC. The reaction solution was slowly added to a solution of 50 ml Sat NaHCO₃ and 50 g celite with vigorous stirring. The resulting slurry was filtered. The filtrate was treated with Boc₂O (6.6 g, 30 mmol, 1.5 equiv). After 2 hour at room temperature, the solution was concentrated to remove most of the methanol, dissolved in 200 ml DCM, and extracted twice with 100 ml DCM. The combined extracts were dried with sodium sulfate, filtered and used for next step without further purification. Crude yield 12 g, 100%. Ion(s) found by LCMS: M+H=531.

Step b.

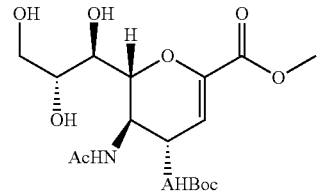

The material from the previous step was dissolved into 60 ml dry methanol, then treated with 10 ml sodium methoxide in methanol (0.5 M) while cooling with an ice-water bath. Progress of reaction was monitored by LCMS which was complete after 2 h. The reaction was quenched with 1 N HCl to a pH of 5-6. The resulting solution was concentrated and purified by reverse phase liquid chromatography (RPLC) using an Isco COMBIFLASH® liquid chromatograph eluted with 0% to 30% acetonitrile and water, using 0.1% TFA as the modifier. Yield of the products 7.2 g, 80%. Ion(s) found by LCMS: M+H=405.

Step c.

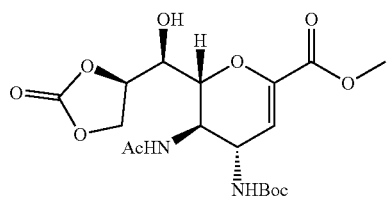 [SMILES: COC(=O)C1=C[C@H](NC(=O)OC(C)(C)C)[C@@H](NC(C)=O)[C@H]([C@H](O)[C@H]2COC(=O)O2)O1]

A solution of the product from the previous step (3.5 g, 8.5 mmol), CDI (2.8 g, 2 equiv), trimethylamine (4.2 ml, 30 mmol) and DMAP (240 mg, 2 mmol) were heated in acetonitrile (50 ml) overnight, then concentrated and purified by reverse phase liquid chromatography (RPLC) using an Isco COMBIFLASH® liquid chromatograph eluted with 0% to 30% acetonitrile and water without modifier. Yield of desired product 2.3 g, 60%. Ion(s) found by LCMS: M+H=431.

Step d.

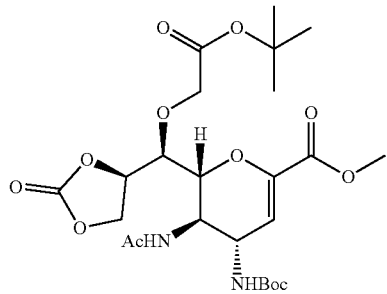 [SMILES: COC(=O)C1=C[C@H](NC(=O)OC(C)(C)C)[C@@H](NC(C)=O)[C@H]([C@H](OCC(=O)OC(C)(C)C)[C@H]2COC(=O)O2)O1]

Sodium hydride (400 mg, 60% in oil, 10 mmol) was added to the product from the previous step (1.45 g, 3.3 mmol) in 50 ml dry THF (moisture-sensitive reaction) under the ice-water bath. The resulted solution was stirred for 0.5 hour, then tertbutyl bromo-acetate (2 g, 10 mmol) was added to the above solution, the resulted solution was heated up to 60° C. for overnight and quenched with acetic acid. The resulting solution was concentrated and purified by reverse phase liquid chromatography (RPLC) using an Isco COMBIFLASH® liquid chromatograph eluted with 0% to 50% acetonitrile and water with TFA as modifier. Yield of 1 g, 57%. Ion(s) found by LCMS: M+H=593.

Step e.

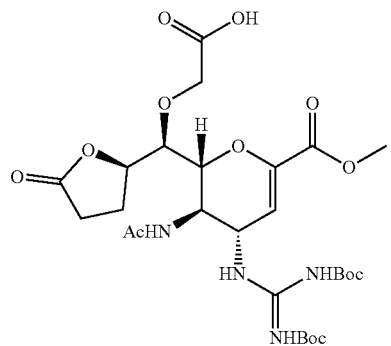

The product from the previous step (1.2 g, 2.2 mmol) was stirred with 10 ml TFA at room temperature for overnight, and the progress of deprotection was monitored by LCMS. The resulted solution was concentrated and used for next step without purification. The residue was re-dissolved into 20 ml THF, then N,N'-bis-boc-1-guanylpyrazole (1 g, 3.3 mmol), 4-dimethylaminopyridine (120 mg, 1 mmol) and triethylamine (0.7 ml, 5 mmol) were added to the solution, and the resulting solution was heated to 60° C. for 2 hours. The resulting solution was concentrated and purified by reverse phase liquid chromatography (RPLC) using an Isco COMBIFLASH® liquid chromatograph eluted with 0% to 50% acetonitrile and water with no modifier. Yield of 700 mg, 84%. Ion(s) found by LCMS: M+H=631.

Step f.

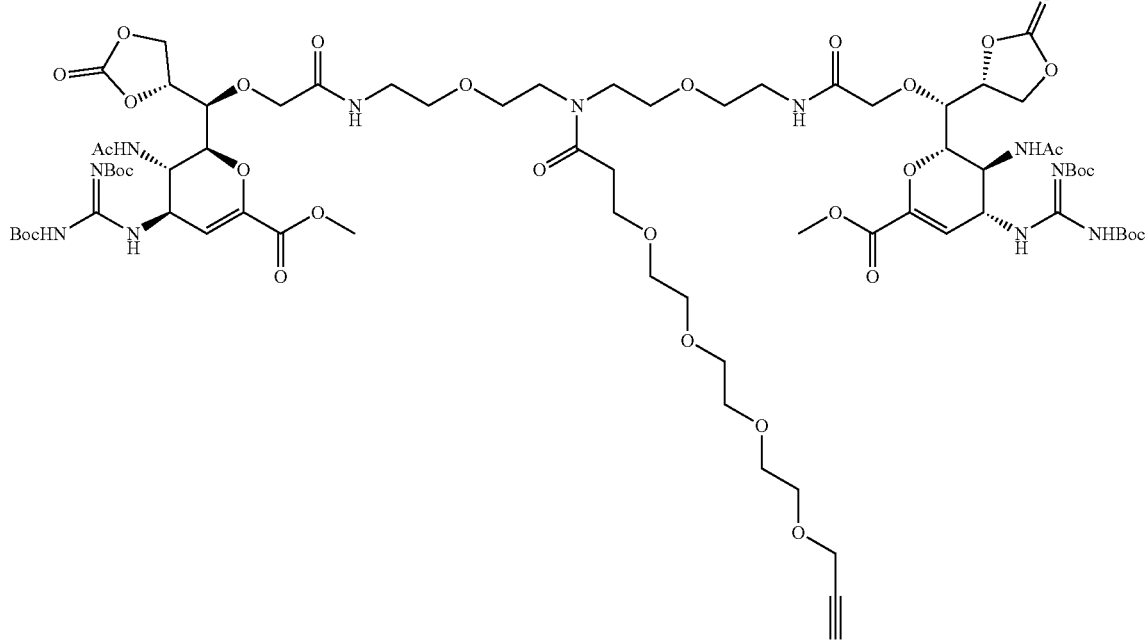

To a solution of linker-3 (prepared as described in Example 19) (73 mg, 0.14 mmol) and the product of the previous step (200 mg, 0.32 mmol, 2.2 equi) in DMF (30 ml) was added EDC (100 mg, 0.5 mmol), HOAt (65 mg, 3 mmol), and DIEA (0.14 ml, 1 mmol) at room temperature. The solution was stirred overnight. The resulting solution was concentrated and purified by and purified by reverse phase liquid chromatography (RPLC) using an Isco COMBIFLASH® liquid chromatograph eluted with 0% to 50% acetonitrile and water with no modifier. Yield of 120 mg, 52%. Ion(s) found by LCMS: M/2+H=830.

Step g.

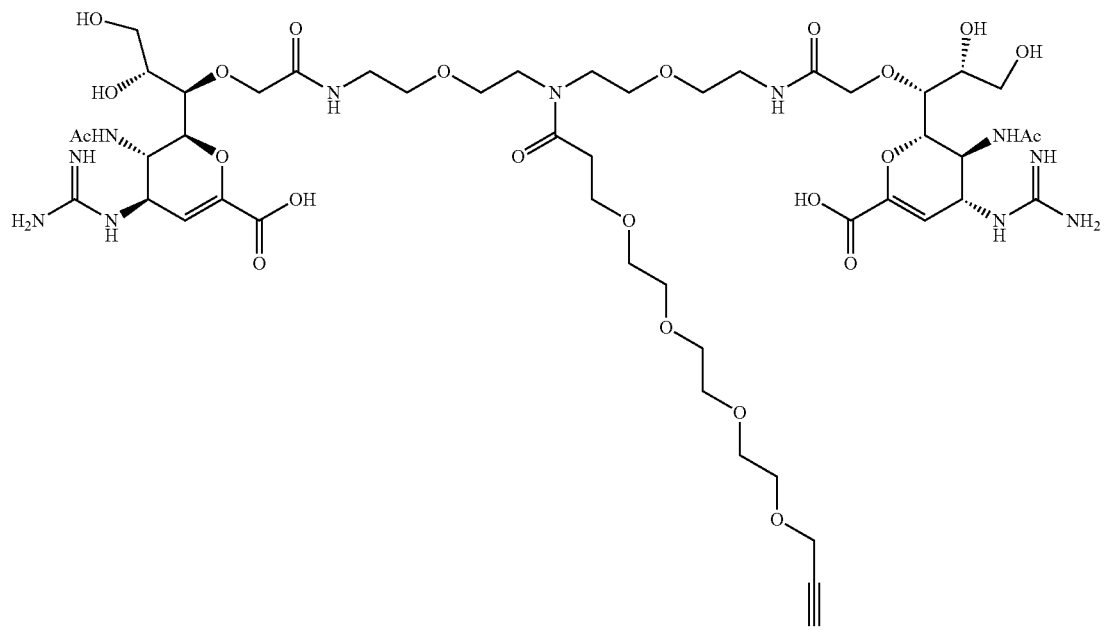 [SMILES: C#CCOCCOCCOCCOCCC(=O)N(CCOCCNC(=O)CO[C@@H]([C@H]1OC(C(=O)O)=C[C@@H](NC(=N)N)[C@@H]1NC(C)=O)[C@H](O)CO)CCOCCNC(=O)CO[C@@H]([C@H]1OC(C(=O)O)=C[C@@H](NC(=N)N)[C@@H]1NC(C)=O)[C@H](O)CO]

Lithium hydroxide (24 mg, 1 mmol) in 2 ml H2O was added into the solution of the product from the previous step (120 mg, 0.07 mmol) in 2 ml THF and 1 ml MeOH, LCMS monitored the progress of the reaction. After the completion, the solution was added AMBERLITE® IRN-77, ion exchange resin to adjust to pH1, then the resulting solution was filtered and the filtrate was concentrated and used for next step without purification. The resulting compound was treated with 2 ml TFA at room temperature, the solution was stirred for overnight at 40° C., then concentrated and purified by HPLC eluted with 0% to 20% acetonitrile and water, using TFA as the modifier. Yield 60 mg, 74% yield. Ion(s) found by LCMS: [M/2]+1=589.8.

Example 23. Neuraminidase Inhibition Assay

Figure 15:
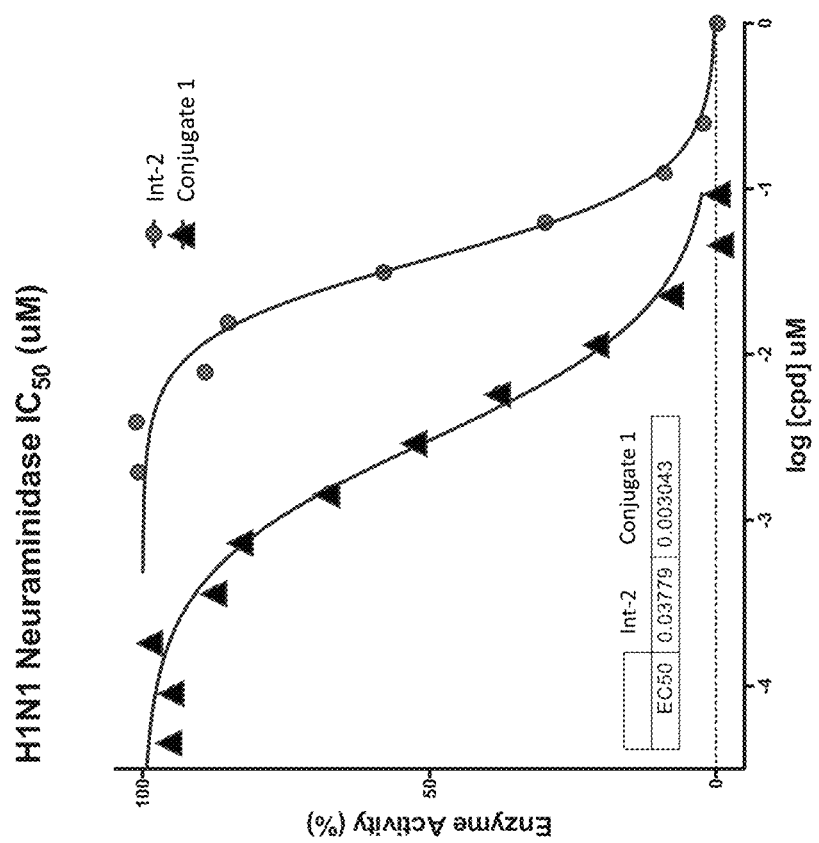
FIG. 15 is a graph showing the IC50 values from an H1N1 neuraminidase inhibition assay for Int-2 and Conjugate 1.
Figure 18A:
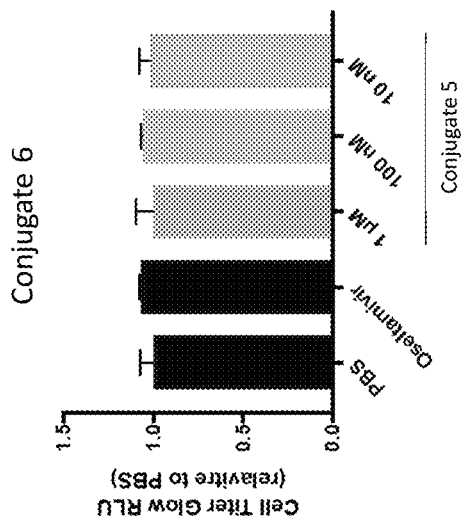
FIGS. 18A-18C are a series of graphs showing the cell by viability of A549 cells treated with Conjugate 3 (FIG. 18A), Conjugate 4 (FIG. 18B), or Conjugate 6 (FIG. 18C).
Figure 18B:
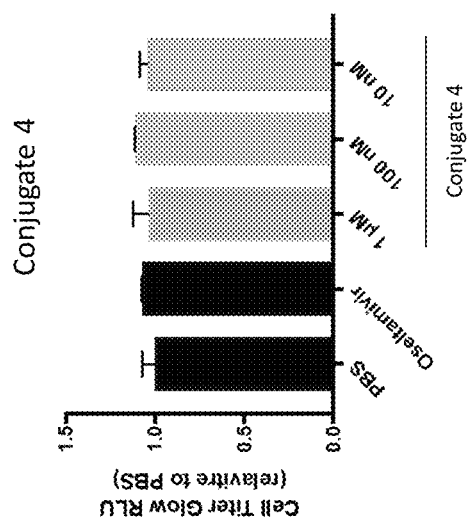
Figure 18C:
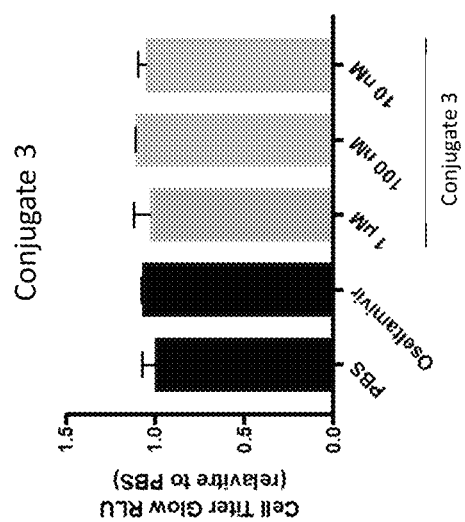
Figure 19B:
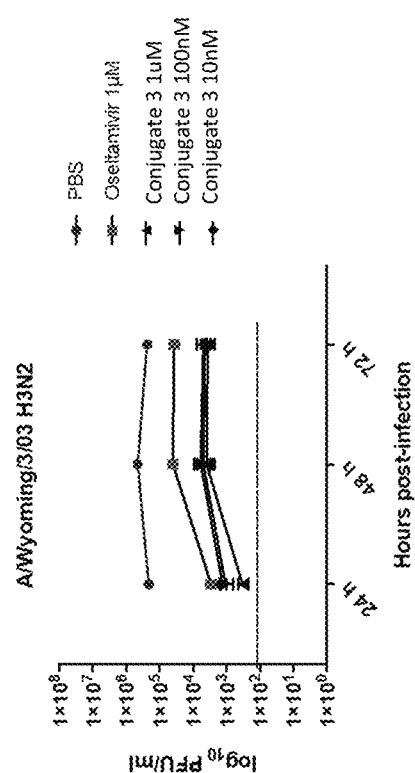
Figure 19A:
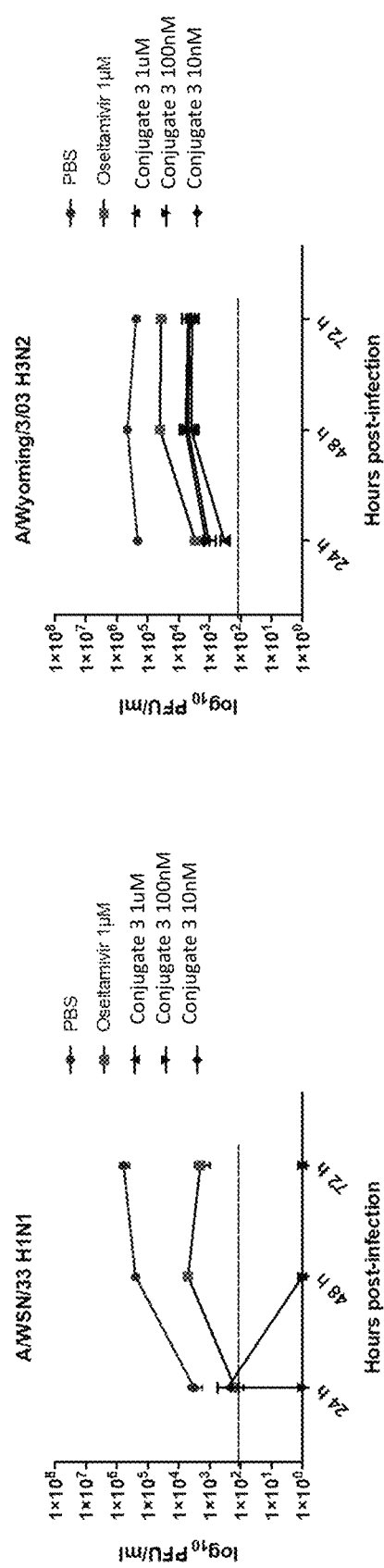
Figure 20B:
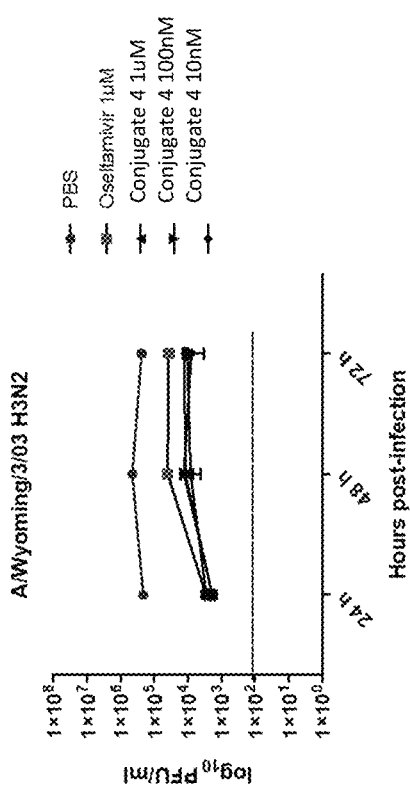
Figure 20A:
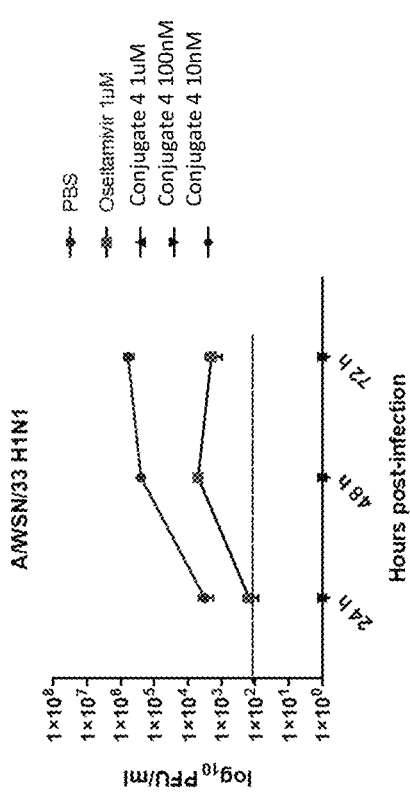
Figure 22E:
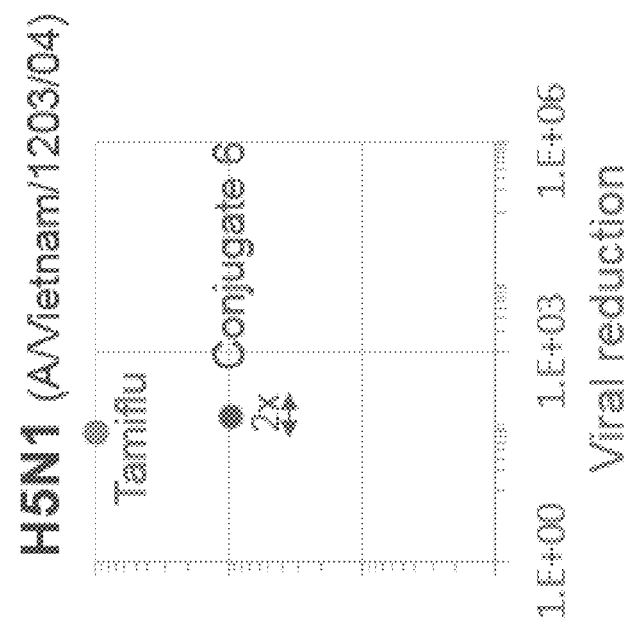
Figure 22D:
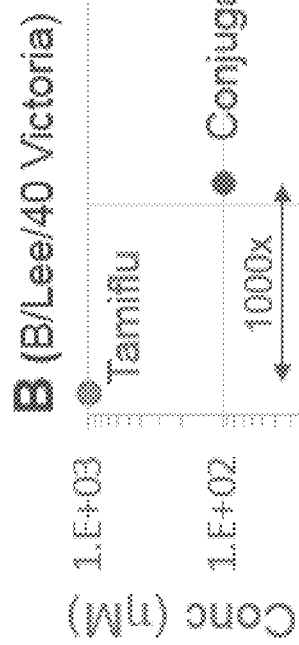

A neuraminidase inhibition assay using 2'-(4-Methylumbelliferyl)-alpha-D-N-aceylneuraminic acid (MUNANA) substrate was performed as described below. Briefly, 50 μL of purified, recombinant influenza virus neuraminidase (0.1 ng/μL, 50 mM Tris, 5 mM $CaCl_2$, 200 mM NaCl, pH 7.5) was mixed with 50 μL of inhibitor and incubated for 30 min at room temperature. At least 5 concentrations of each inhibitor at an appropriate range were used for each repeat. Following incubation, 50 μL of 400 μM MUNANA in 50 mM Tris, 5 mM $CaCl_2$, 200 mM NaCl, (pH 7.5) was added to the solution to start the reaction using a 12-tip pipette (Eppendorf). A positive and a negative control were included in each 12-well lane. After starting the reaction for each lane on the plate, the reaction mixture was immediately loaded on a SpectraMax M5 (Molecular Devices) where fluorescence was quantified over the course of 25 min at an excitation wavelength of 365 nm and an emission wavelength of 445 nm. Single time points were chosen where the positive control produced a fluorescence signal of approximately 1,000. All assays were done in triplicates and IC50 values for each inhibitor were calculated with sigmoidal fitting of the log[inhibitor] vs. inhibition percentage using GraphPad Prism. FIG. 15 shows the plot of the kinetic data as RFU/min over a linear range for Conjugate 1 and Int-2 showing the greater efficacy of Conjugate 1 as a neuraminidase inhibitor. FIG. 16 and FIG. 17 show the assay results for Conjugates 1-6 against rH1N1 Neuraminidase and rH3N2 Neuraminidase, respectively (Table 2).

TABLE 2

IC50 values for conjugates against H1N1 and H3N2 Neuraminidase

| Conjugate Number | H1N1 IC50 (nM) | H3N2 IC50 (nM) |
|---|---|---|
| Conjugate 1 | 3.9 | 32.5 |
| Conjugate 2 | 3.7 | 17.6 |
| Conjugate 3 | 3.6 | 38 |
| Conjugate 4 | 1.9 | 17.2 |
| Conjugate 5 | 1.1 | 14.3 |
| Conjugate 6 | 4.1 | 29.8 |

Example 24: Cytotoxicity Assay

Conjugates 1, 2, 3, and 6 were tested for cytotoxicity. Ten two-fold serial dilutions of each conjugate starting at 10 μM were prepared in triplicate for inoculation with MDCK cells in 96-well culture plates. The cell viability was determined four days post treatment using CellTiter-GLO kit. 50% of cytotoxicity concentration ($CC_{50}$) was calculated using XLfit dose response model (Table 3). For all compounds tested, cytotoxicity was not observed up to the 10 μM, with the exception of conjugate 3. In the case of Conjugate 3, The $EC_{50}$ in the cytopathic effect (CPE) assay (see Example 23) is 725-fold below the $CC_{50}$ in this assay.

TABLE 3

Cytotoxicity test

| Conjugate Number | CC50 (µM) |
|---|---|
| Conjugate 1 | >10 |
| Conjugate 2 | >10 |
| Conjugate 3 | 7.98 |
| Conjugate 6 | >10 |
| PBS | >10 |
| Zanamivir | >10 |

Example 25. Cytopathic Effect Assay

CPE-Based Microneutralization Assay #1

To measure the ability of neuraminidase conjugates to protect mammalian cells from infection and destruction by influenza virus, cytopathic effect (CPE)-based microneutralization assays were conducted. Briefly, twenty two-fold serial dilutions of each conjugate starting at 0.25 μM were prepared in duplicate for one-hour inoculation with MDCK cells seeded in 96-well plates. INFV CA/09 virus was added to cells at a multiplicity of infection (MOI) 0.001 for one-hour incubation. On day four post incubation, cells were stained with crystal violet and optical density was read for calculation of 50 percent effective concentration (EC50) of each TA using XLfit dose response model. Zanamivir was used as a comparator and positive control. human Fc was included as a negative control. Conjugates 1, 2, 3, and 6 all demonstrated superior performance to the zanamivir control, demonstrating EC50s 42- to 227-fold lower than zanamivir (Table 4).

TABLE 4

| CPE-based microneutralization assay #1 | |
|---|---|
| Conjugate Number | EC50 (nM) |
| 1 | 2.0574 |
| 2 | 4.1487 |
| 3 | 11.007 |
| 6 | 5.2167 |
| PBS | N/C |
| Human Fc | N/C |
| Zanamivir† | 468.7 |

N/C: Not calculatable

†Starting concentration 10000 nM

CPE-Based Microneutralization Assay #2

An additional CPE-based microneutralization assay was run to further evaluate the in vitro activity of Conjugate 6 and Conjugate 7. Briefly, test articles were prepared at a starting concentration of 160 nM, and a total of ten, 2-fold dilutions were made. The test article dilutions were then pre-mixed with Influenza A virus (INFV CA/09) at a multiplicity of infection of 0.001 relative to the monolayer. After one hour the test article+viral mix was added to Madin-Darby Canine Kidney (MDCK) cells grown to 70-80% confluence under standard conditions in a 96-well plate. The zanamivir control was treated the same, except the starting concentration was 9600 nM since it was expected to be less potent than the Conjugates being tested. After four days of incubation the monolayer was stained with crystal violet and optical density (reflective of monolayer health) was determined to calculate the 50% effective concentration (EC50) using the XLfit dose response model (idbs; https://www.idbs.com). As shown in Table 5, zanamivir at a concentration of 496 nM reduced the virus mediated cytopathic effects by half. In contrast, conjugate 6 was approximately 100× more active with an EC50 of only 4.64 nM. Conjugate 7, further improved activity by approximately 15-fold, reducing the EC50 to the sub-nM level.

TABLE 5

| CPE-based microneutralization assay #2 | |
|---|---|
| Conjugate Number | EC50 (nM) |
| 6 | 4.64 |
| 7 | 0.31 |
| Zanamivir | 496 |

Example 26. Cell Viability Assay

A549 cells were seeded in 96-well plates one day prior to compound treatment. Cells were treated with either Conjugate 3 (FIG. 18A), Conjugate 4 (FIG. 18B), or Conjugate 6 (FIG. 18C) at concentrations 1 μM-10 nM for 24 hours. Cell viability was then measured using Cell Titer Glow (Promega). Results represent average and SD of three biological replicates. No effects were observed on cell viability for any of the conjugates at any concentrations at any of the concentrations used in the viral growth assay (Example 27).

Example 27. Viral Growth Assay

To measure the ability of neuraminidase conjugates to inhibit the growth of pathogenic influenza viral strains of interest in human epithelial cells, viral plaque reduction assays were conducted. Briefly, A549 cells were seeded in 24-well plates one day prior to compound treatment. Cells were treated with compounds at concentrations 1 μM-10 nM for 2 hours and infected with indicated viral strains at MOI 0.01 for one-hour incubation. Virus was removed, cells were washed and compounds were re-applied at concentrations 1 μM-10 nM. Supernatants were collected at indicated time points and titrated using plaque assay method in MDCK cells. Results represent average and SD of three biological replicates. Oseltamivir was used as a comparator and a positive control. Conjugate 3 (FIGS. 19A-19E), Conjugate 4 (FIGS. 20A-E), or Conjugate 6 (FIGS. 21A-21E and FIGS. 22A-22E) all demonstrated superior performance to the oseltamivir control, showing similar or (usually) superior plaque reduction to oseltamivir at 100-fold lower concentrations. The effects of the compounds (to evaluate test articles for potential cytotoxicity) on the A549 cells was evaluated for each test article using a cell viability assay (Example 26). Briefly, A549 cells were seeded in 96-well plates one day prior to compound treatment. Cells were treated with compounds at concentrations 1 μM-10 nM for 24 hours. Cell viability was then measured using Cell Titer Glow (Promega). Results represent average and SD of three biological replicates.

Example 28. Mouse Serum Half-Life

Pharmacokinetic (PK) studies used female CD-1 mice (Charles River Laboratories) between 20 and 22 grams. Mice were injected IV by way of the tail vein, with 50 mg/kg of test article (10 m1/kg dose volume). Animals were housed under standard IACUC approved housing conditions. At appropriate times animals were non-terminally bled (retro-orbital, cheek, or by tail vein) with blood collected in EDTA tubes to prevent coagulation. Collected blood was centrifuged (2,000×g, for 10 minutes) and plasma withdrawn for analysis of test article concentrations over time.

The plasma concentrations for Conjugate 6 or hIgG1 Fc at each time point were measured by sandwich ELISA as follows: Conjugate 6 molecules were captured either on Neuraminidase coated plates or anti-hIgG1 antibody coated plates and then detected using an HRP-conjugated anti-human IgG-Fc antibody. hIgG1 was captured using anti-hIgG1 Fc antibody. Protein concentration was calculated in GraphPad Prism using 4PL non-linear regression of Conjugate 6 (or hIgG1 Fc) standard curves. A more detailed method description is provided below.

Qiagen Ni-NTA HisSorb plates (Cat No. 35061, Qiagen) were coated with either Neuraminidase from A/California/04/2009 (H1N1) (11058-VNAHC, Sino Bio) or anti-IgG1 Fc antibody in 1×KPL coating buffer (5150-0041, SeraCare). In the cases where the anti-IgG1 Fc antibody was used to capture test article, capture and detection anti-IgG1 Fc antibodies were selected that bind different epitopes. Plates were incubated at room temperature for 1 hour. Serial dilutions of the plasma samples were plated and incubated at room temperature for 2 hrs (sample diluent: 0.5% nonfat dry milk+3% Goat serum in PBS 0.05% Tween20; naïve mouse plasma final concentration of 1:900). Conjugate 6 or hIgG1 Fc standard curves ranging from 500-0.230 ng/mL, in duplicate were run on each plate.

Following the 2 hr incubation, plates were washed 5× in 300 uL PBS with 0.05% Tween20. Conjugate 6 bound to neuraminidase on the plates (or anti-hIgG1 Fc antibody) was then probed with an HRP conjugated anti-human IgG Fc F(ab')2 (Jackson 709-036-098) diluted 1:2000 in sample diluent for 1 hour at room temp. Plates were then washed 8× in 300 uL PBS with 0.05% Tween20 and developed with TMB substrate for 7 minutes. The reaction was stopped with 1 N H2SO4. Absorbance was read at 450 nm. A similar protocol was used for hIgG1 Fc, where only anti-hIgG1 Fc antibody was used for capture. The quantities of Conjugate 6 measured at different timepoints using either neuraminidase or anti-hIgG1 Fc antibody capture were similar within experimental error, suggesting that the intact conjugate is stable in vivo.

Total Conjugate 6 (or hIgG1 Fc) in test samples was interpolated using in GraphPad Prism Version 6 following nonlinear regression analysis (Sigmoidal, 4PL analysis) of the Conjugate 6 (or hIgG1 Fc) standard curves. PK parameters were calculated using WinNonlin software. The curves comparing Conjugate 6 and hIgG1 Fc are shown in FIG. 23 and a summary of key PK parameters is provided in Table 6. Unexpectedly, plasma exposures and terminal half-life are significantly better for Conjugate 6 than for wild-type hIgG1 Fc. The AUCs over 8-days are 3× higher for Conjugate 6 than for hIgG1 Fc, and the terminal half-life for Conjugate 6 is 214 hours, versus 52 hours for human IgG1 Fc.

TABLE 6

Mouse PK of Conjugate 6 compared to hIgG1 Fc

| | Half-life (hrs) | AUClast (hr*mg/mL) |
|---|---|---|
| Conjugate 6 | 214 | 33100 |
| hIgG1 | 51.8 | 10600 |

Example 29. Efficacy of Conjugate 6 in a Lethal Mouse Influenza Model: Study #1

Conjugate 6 was evaluated against a lethal INFV A H1N1 influenza infection in female BALB/c mice. The experiment comprised 7 groups of 5 mice. At day 0, all mice were challenged with 1×LD90 H1N1 A/Texas/36/91. Groups 1-6 received treatment IV, 4 hours before challenge (Table 7). Human IgG1 (Fc alone) was included as an additional negative control. Group 7 received Oseltamivir phosphate by way of oral delivery, starting 8 hours post infection twice daily for 5 days. All mice were monitored for weight loss (FIG. 24, Table 8) and survival (FIG. 25, Table 9) for 15 days after challenge.

Mice treated with Conjugate 6 showed 100% survival with single doses in all the concentrations tested, compared with 20% and 0% survival in the vehicle control and hIgG1 control groups, respectively. The results were statistically significant when compared to the vehicle group (p=0.0135) despite the small group size (n=5). When compared to the Oseltamivir phosphate group, conjugate 6 demonstrated similar efficacy at a 500× lower cumulative dose (in mg/kg). Mice at all Conjugate 6 doses maintained their weight through the entire course of the experiment, superior to the Oseltamivir control group.

TABLE 7

Study design

| Group n = 5 | Challenge Day 0 | Compound | Dose (mg/kg) | Treatment Route/Schedule |
|---|---|---|---|---|
| 1 | Influenza A virus, H1N1 strain A/Texas/36/91 by way of IN route. | Vehicle (PBS) | N/A | IV, q.d. 4 hours pre-challenge |
| 2 | | Fc alone | 50 | |
| 3 | | Conjugate 6 | 50 | |
| 4 | | Conjugate 6 | 10 | |
| 5 | | Conjugate 6 | 2 | |
| 6 | | Conjugate 6 | 0.4 | |
| 7 | | Oseltamivir (Tamiflu ™) | 20 | PO, b.i.d. 8 hours after challenge for 5 days |

TABLE 8

Daily Weight Average

Daily average weight (The mice number is added only for Group 1 & 2)

| Days post infection | Vehicle (PBS) | Fc alone 50 mg/kg | Conjugate 6 50 mg/kg | Conjugate 6 10 mg/kg | Conjugate 6 2 mg/kg | Conjugate 6 0.4 mg/kg | Oseltamivir phosphate 20 mg/kg |
|---|---|---|---|---|---|---|---|
| 0 | 17.9 (5) | 17.9 (5) | 18.7 | 19.3 | 18.5 | 18.8 | 18.8 |
| 1 | 18.0 (5) | 18.0 (5) | 18.8 | 19.36 | 18.6 | 18.8 | 18.9 |
| 2 | 18.5 (5) | 18.8 (5) | 19.2 | 19.6 | 19.4 | 18.8 | 19.2 |
| 3 | 17.7 (5) | 17.7 (5) | 18.9 | 19.5 | 19.1 | 18.9 | 19.1 |
| 4 | 17.2 (5) | 17.0 (5) | 19.5 | 19.9 | 19.3 | 18.9 | 18.9 |
| 5 | 16.3 (5) | 15.8 (5) | 19.2 | 19.8 | 19.5 | 18.7 | 18.8 |

TABLE 8-continued

Daily Weight Average

Daily average weight (The mice number is added only for Group 1 & 2)

| Days post infection | Vehicle (PBS) | Fc alone 50 mg/kg | Conjugate 6 | | | | Oseltamivir phosphate 20 mg/kg |
|---|---|---|---|---|---|---|---|
| | | | 50 mg/kg | 10 mg/kg | 2 mg/kg | 0.4 mg/kg | |
| 6 | 15.6 (4) | 15.0 (5) | 19.1 | 19.9 | 19.5 | 18.7 | 18.4 |
| 7 | 15.5 (2) | 14.0 (2) | 18.8 | 19.6 | 19.2 | 18.9 | 17.3 |
| 8 | 17.2 (1) | | 19.1 | 20.0 | 19.7 | 19.2 | 17.1 |
| 9 | 20.1 (1) | | 18.7 | 19.3 | 19.1 | 18.8 | 17.8 |
| 10 | 20.0 (1) | | 19.1 | 20.1 | 19.5 | 19.3 | 18.9 |
| 11 | 20.4 (1) | | 19.0 | 19.8 | 19.2 | 19.2 | 18.7 |
| 12 | 20.6 (1) | | 19.6 | 20.3 | 19.8 | 19.3 | 19.2 |
| 13 | 20.3 (1) | | 19.2 | 20.4 | 19.7 | 19.7 | 19.3 |
| 14 | 20.7 (1) | | 19.5 | 20.6 | 19.9 | 19.8 | 19.6 |

TABLE 9

Mouse survival

| Compound | Dosage | Mean Survival | % Survival | Significance to vehicle (p) |
|---|---|---|---|---|
| Vehicle (PBS) | N/A | 7 | 20 | N/A |
| Fc alone | 50 mg/kg | 7 | 0 | 0.8335 |
| Conjugate 6 | 50 mg/kg | 15 | 100 | 0.0135 |
| Conjugate 6 | 10 mg/kg | 15 | 100 | 0.0135 |
| Conjugate 6 | 2 mg/kg | 15 | 100 | 0.0135 |
| Conjugate 6 | 0.4 mg/kg | 15 | 100 | 0.0135 |
| Oseltamivir phosphate | 20 mg/kg B.I.D | 15 | 100 | 0.0135 |

Example 30. Efficacy of Conjugate 6 in a Lethal Mouse Influenza Model: Study #2

Figure 27:
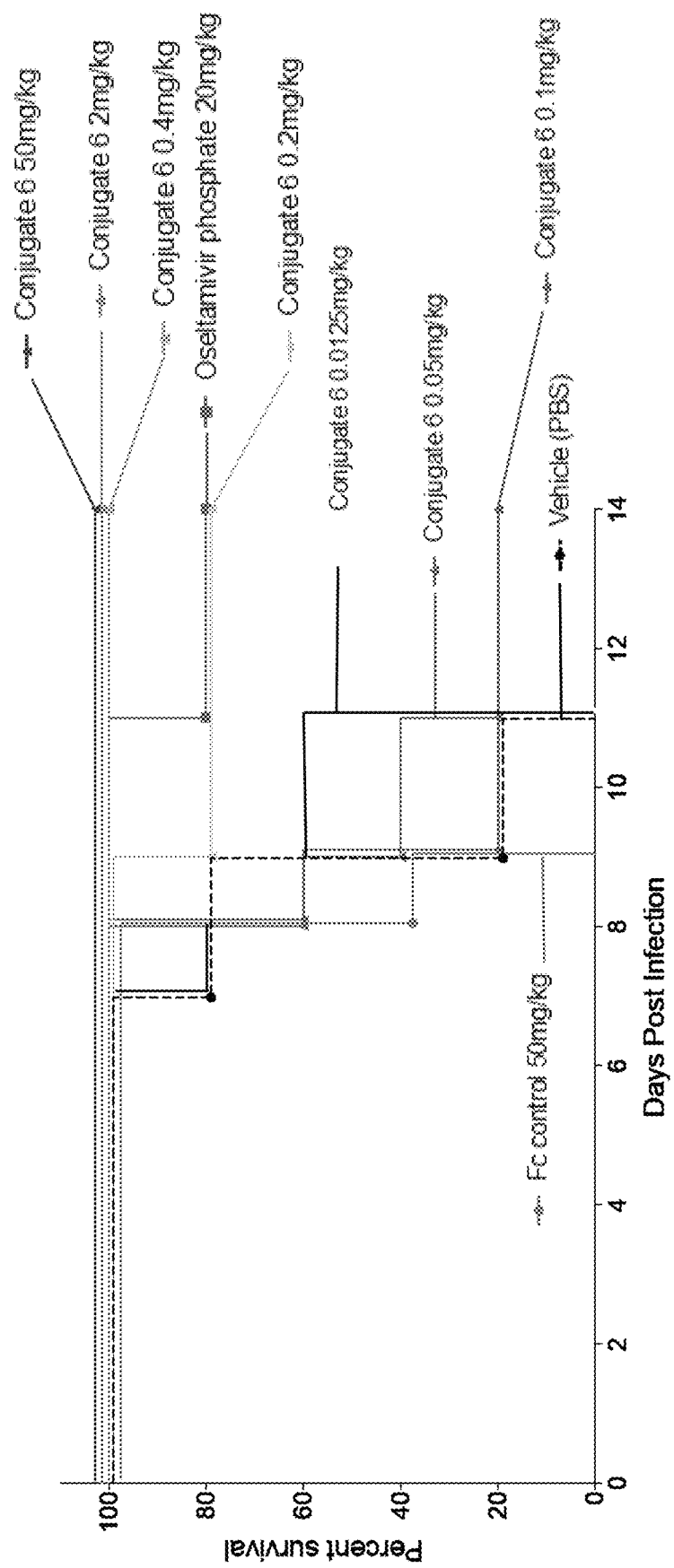
FIG. 27 is a graph showing the effect of Conjugate 6 on survival in a lethal mouse influenza model. The study was performed as described in Example 30.
Figure 28:
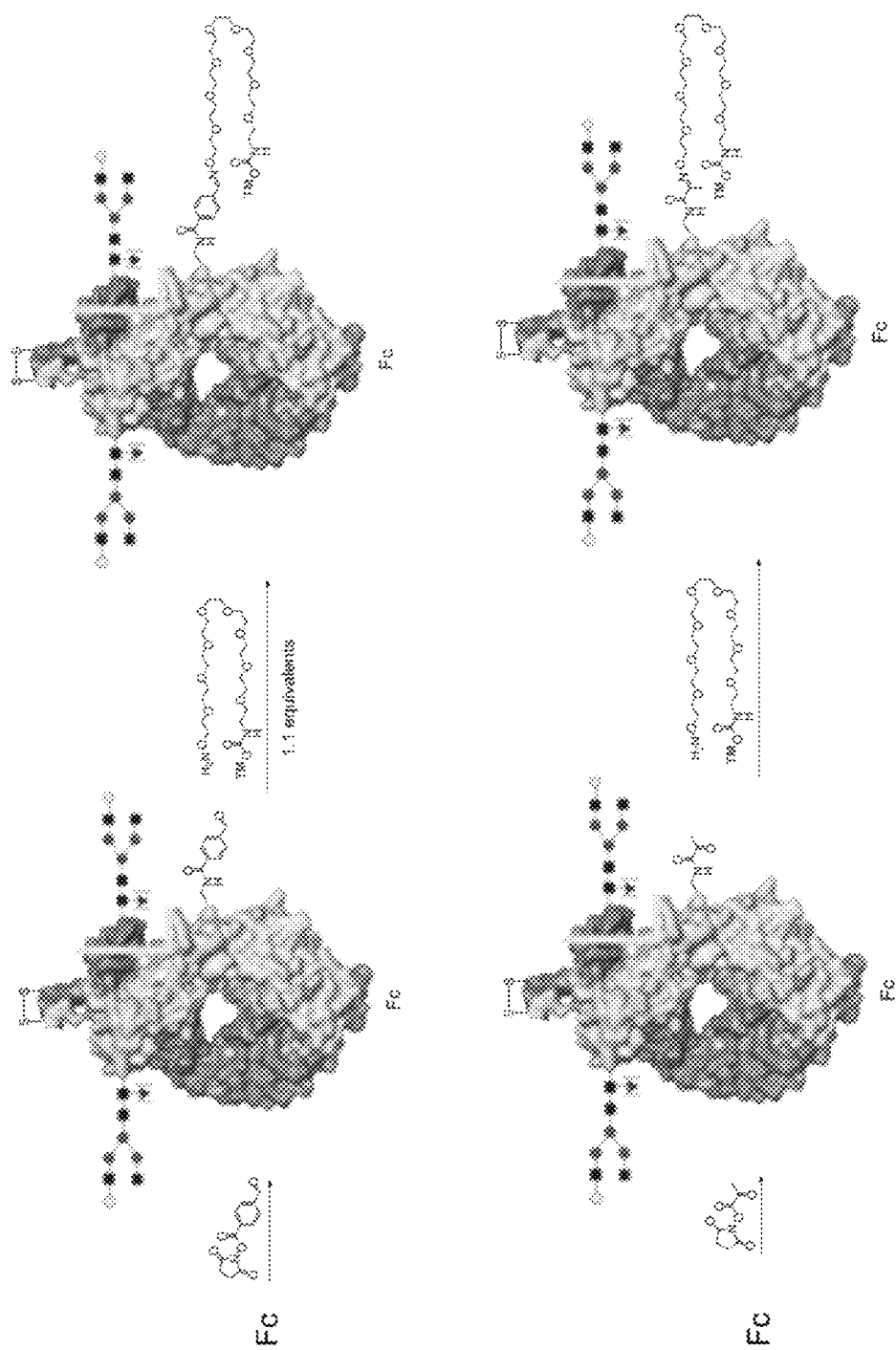
FIG. 28 is an image depicting a method of conjugating a neuraminidase inhibitor monomer or dimer, e.g., by way of a linker, to an Fc domain monomer, an Fc domain, an Fc-binding peptide, an albumin protein, or an albumin protein-binding peptide by oxime conjugation to an amino acid residue, e.g., a nitrogen atom of a surface exposed lysine.
Figure 29:
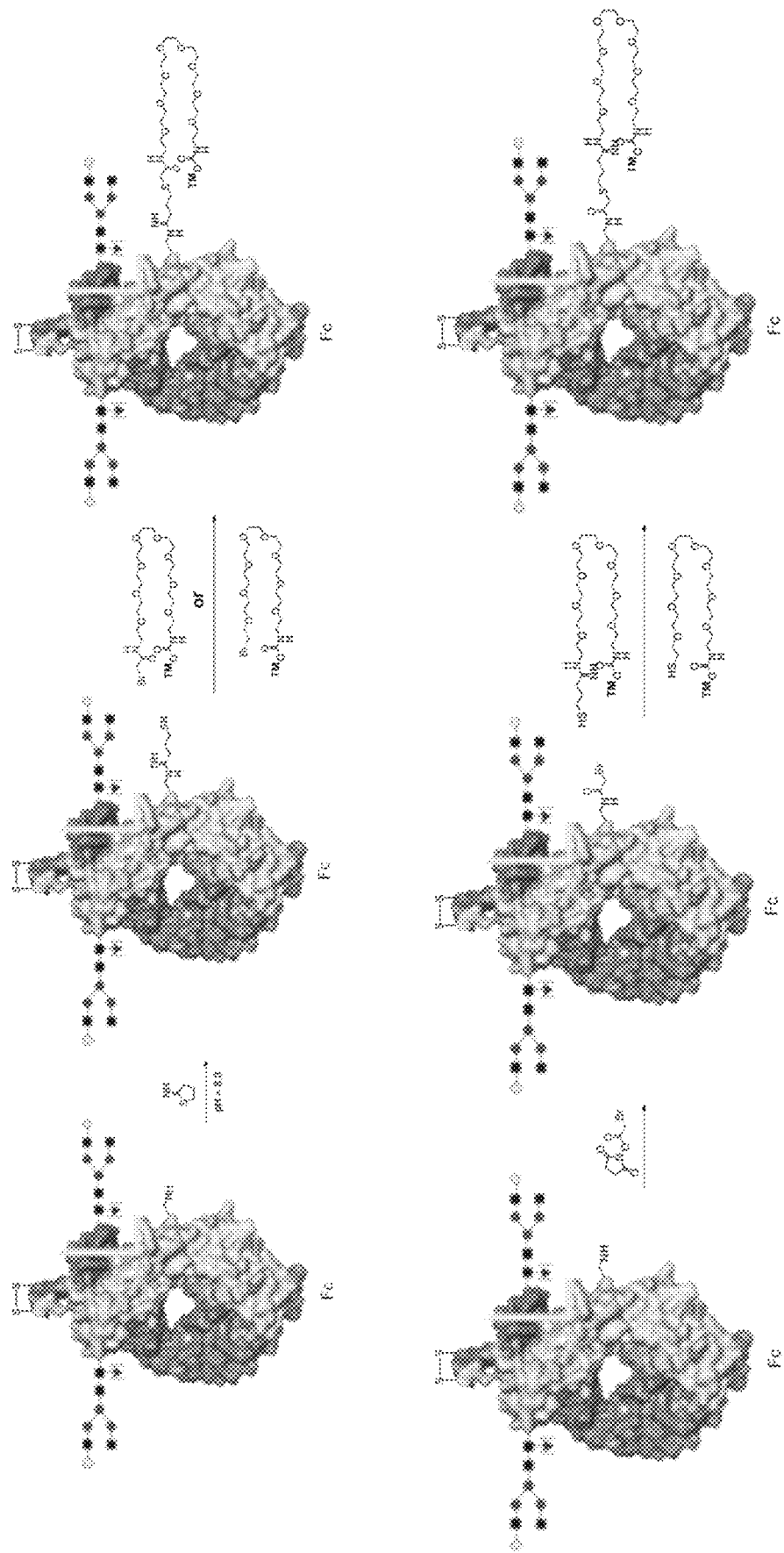
FIG. 29 is an image depicting a method of conjugating a neuraminidase inhibitor monomer or dimer, e.g., by way of a linker, to an Fc domain monomer, an Fc domain, an Fc-binding peptide, an albumin protein, or an albumin protein-binding peptide by thioether conjugation to an amino acid residue, e.g., a nitrogen atom of a surface exposed lysine.
Figure 30:
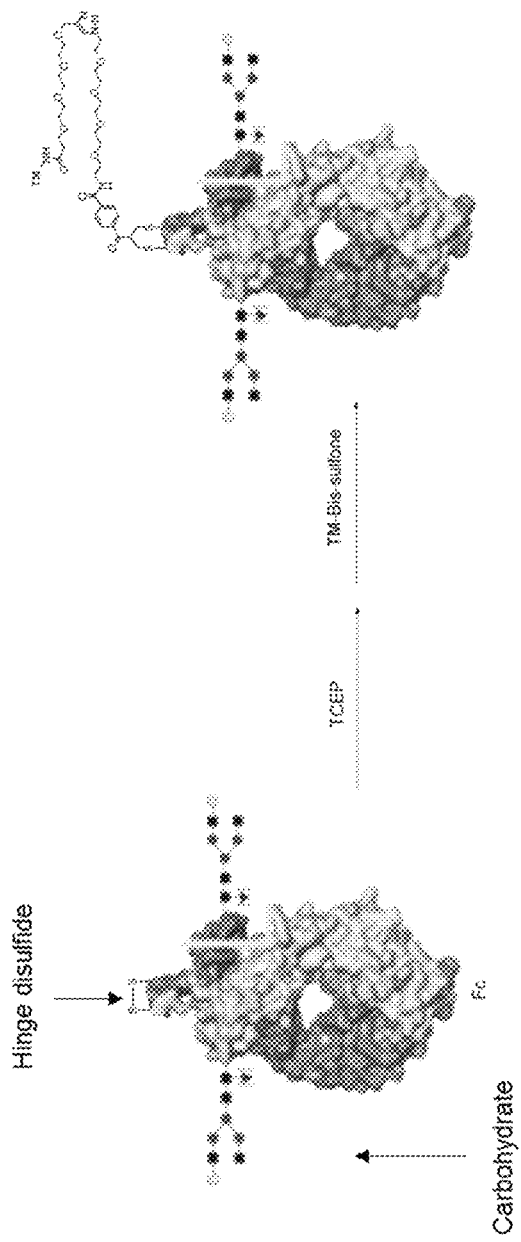
FIG. 30 is an image depicting a method of conjugating a neuraminidase inhibitor monomer or dimer, e.g., by way of a linker, to an Fc domain monomer, an Fc domain, an Fc-binding peptide, an albumin protein, or an albumin protein-binding peptide by rebridged cysteine conjugation, e.g., rebridged cysteine conjugation to a pair of sulfur atoms of two hinge cysteines in an Fc domain monomer or Fc domain.

Conjugate 6 was evaluated against a lethal INFV A H3N2 influenza infection in female BALB/c mice. The experiment comprised 11 groups of 5 mice. At day 0, all mice were challenged with 1×LD90 H3N2 A/Hong Kong/1/68. Groups 1-10 received treatment IV, 4 hours before challenge (Table 10). Human IgG1 (Fc alone) was included as an additional negative control. Group 11 received Oseltamivir phosphate by way of oral delivery, starting 8 hours post infection twice daily for 5 days. All mice were monitored for weight loss (FIG. 26) and survival (FIG. 27, Table 11) for 15 days after challenge.

Mice treated with Conjugate 6 showed 100% survival with single doses in down to 0.4 mg/kg, and 80% survival with a single dose of 0.2 mg/kg compared with 0% survival in the vehicle control and hIgG1 control groups, respectively. 80% of the mice survived in the oseltamivir control group. The results were statistically significant when compared to the vehicle group (p=0.0128) despite the small group size (n=5). When compared to the Oseltamivir phosphate group, conjugate 6 demonstrated similar efficacy at a 1000× lower cumulative dose (in mg/kg). Mice at all Conjugate 6 doses maintained down to 0.4 mg/kg their weight within 5%, superior to the Oseltamivir control group.

TABLE 10

Study design

| Group n = 5 | Challenge Day 0 | Test Article | Dose (mg/kg) | Treatment Route/ Schedule | Readout/ Endpoint |
|---|---|---|---|---|---|
| 1 | H3N2 A/Hong Kong/1/68 by way of IN route | Vehicle (PBS) | N/A | IV, q.d. 4 hours pre-challenge | Daily weight and health score monitoring for 15 days after challenge % Survival |
| 2 | | Fc alone | 50 | | |
| 3 | | Conjugate 6 | 50 | | |
| 4 | | | 2 | | |
| 5 | | | 0.4 | | |
| 6 | | | 0.2 | | |
| 7 | | | 0.1 | | |
| 8 | | | 0.05 | | |
| 9 | | | 0.025 | | |
| 10 | | | 0.0125 | | |
| 11 | | Oseltamivir (Tamiflu ™) | 20 | PO, b.i.d. 8 hours after challenge for 5 days | |

TABLE 11

Mouse survival

| Compound | Dosage | Mean Survival (days) | % Survival | Significance to vehicle (p-value) |
|---|---|---|---|---|
| Vehicle (PBS) | N/A | 9 | 0 | N/A |
| Fc control | 50 mg/kg | 8 | 0 | 0.2498 |
| Conjugate 6 | 50 mg/kg | 15 | 100 | 0.002 |
| | 2 mg/kg | 15 | 100 | 0.002 |
| | 0.4 mg/kg | 15 | 100 | 0.002 |
| | 0.2 mg/kg | 15 | 80 | 0.0128 |
| | 0.1 mg/kg | 9 | 20 | 0.8264 |
| | 0.05 mg/kg | 9 | 20 | 0.5769 |
| | 0.025 mg/kg | 8 | 20 | >0.9999 |
| | 0.0125 mg/kg | 11 | 0 | 0.4703 |
| Oseltamivir phosphate (B.I.D for 5 days) | 20 mg/kg | 15 | 80 | 0.0052 |

Example 31. Synthesis of Int-10
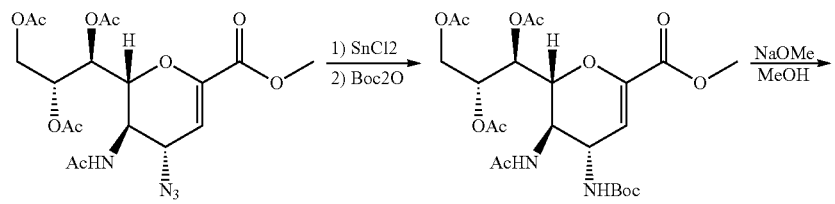
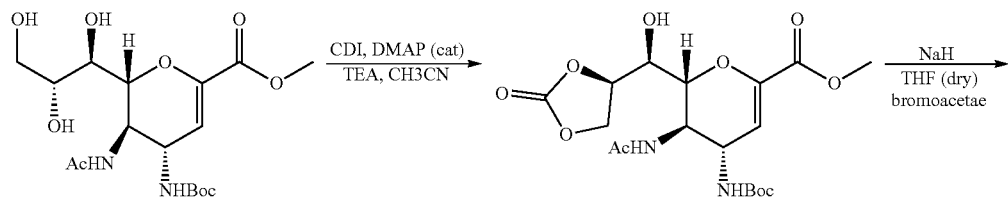
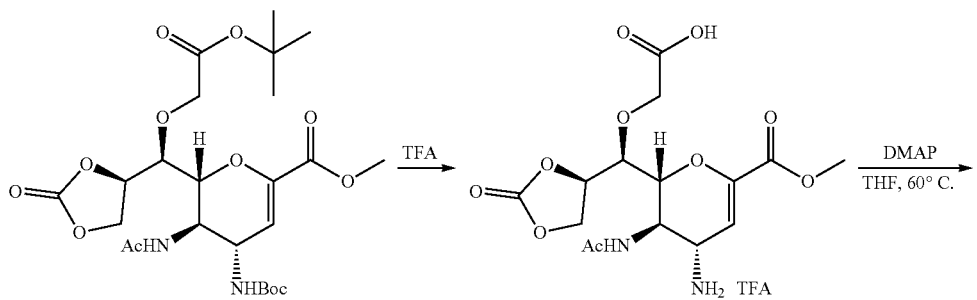
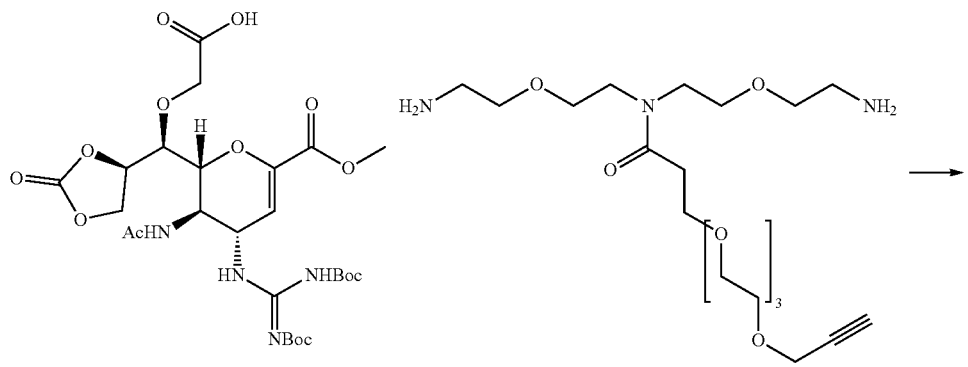
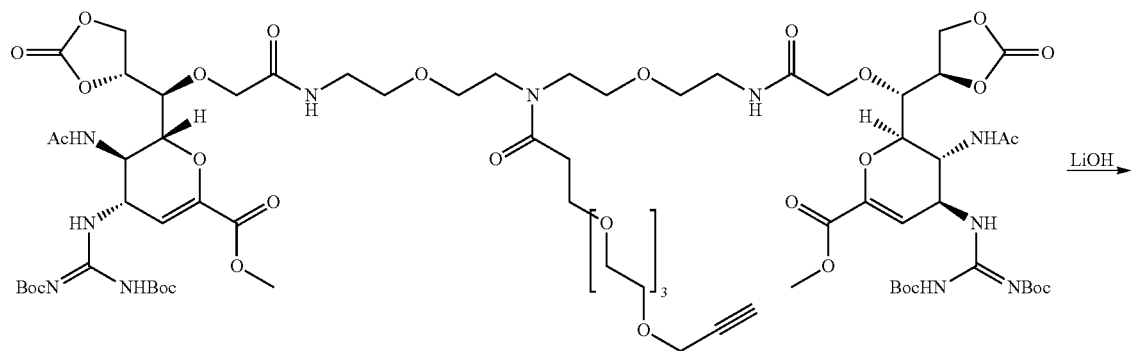

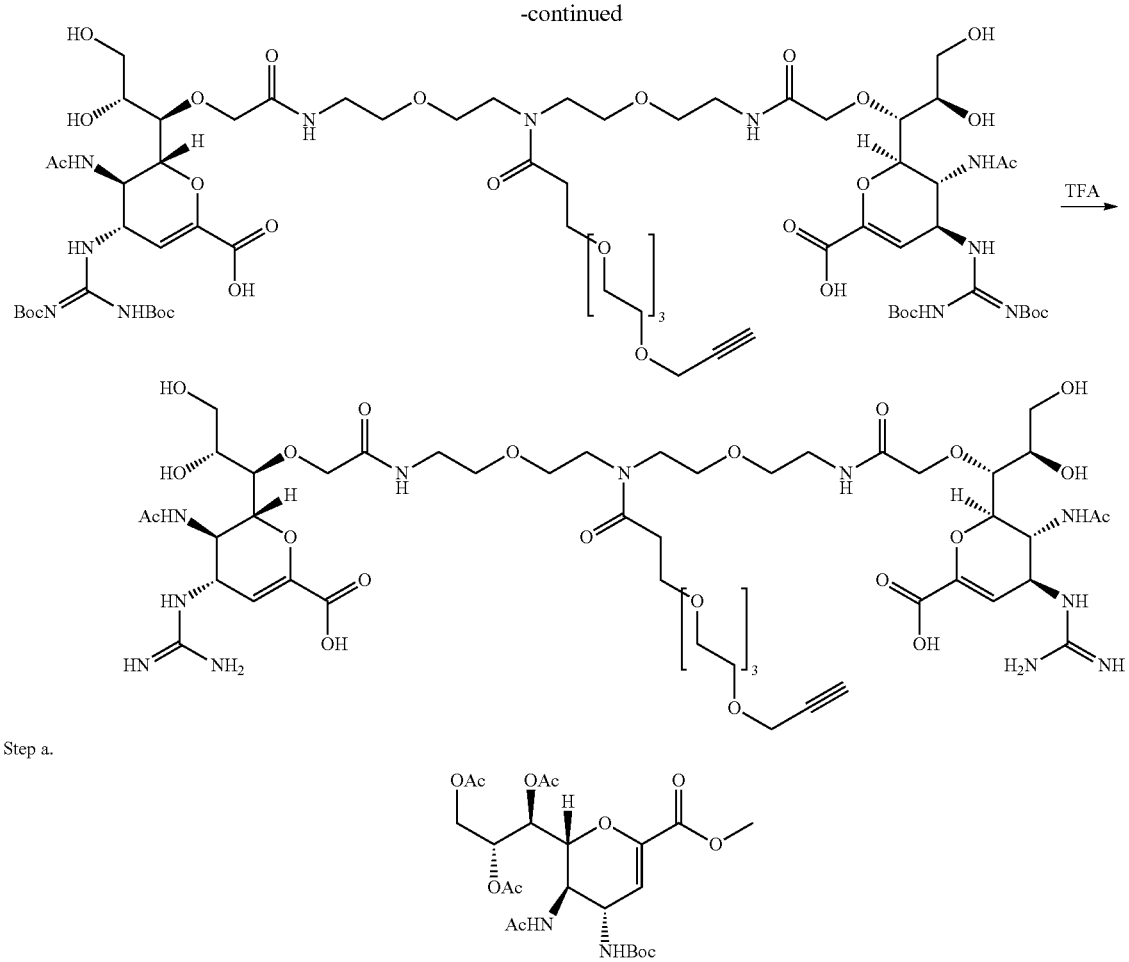

Step a.

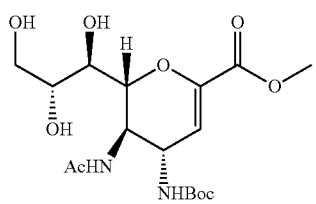 [SMILES: COC(=O)C1=C[C@H](NC(=O)OC(C)(C)C)[C@@H](NC(C)=O)[C@H]([C@H](O)[C@H](O)CO)O1]

Methyl 5-acetamido-7,8,9-O-triacetyl-2,6-anhydro-4-azido-3,4,5-trideoxy-D-glycero-D-galacto-non-2-enonate (SM-1, 10 g, 22 mmol) was dissolved into 100 ml methanol and then heated to 60° C. with an oil bath, the SnCl₂ (5.7 g, 20 mmol) was added to the solution in 3 portions (caution, gas evolves). The reaction mixture was stirred for 10 min, at which time the reaction was complete by HPLC. The reaction solution was slowly added to a solution of 50 ml Sat NaHCO₃ and 50 g celite with vigorous stirring. The resulting slurry was filtered. The filtrate was treated with Boc₂O (6.6 g, 30 mmol, 1.5 equiv). After 2 hour at room temperature, the solution was concentrated to remove most of the methanol, dissolved in 200 ml DCM, and extracted twice with 100 ml DCM. The combined extracts were dried with sodium sulfate, filtered and used for next step without further purification. Crude yield 12 g, 100%. Ion(s) found by LCMS: M+H=531.

Step b.

The material from the previous step was dissolved into 60 ml dry methanol, then treated with 10 ml sodium methoxide in methanol (0.5 M) while cooling with an ice-water bath. Progress of reaction was monitored by LCMS which was complete after 2 h. The reaction was quenched with 1 N HCl to a pH of 5-6. The resulting solution was concentrated and purified by reverse phase liquid chromatography (RPLC) using an Isco COMBIFLASH® liquid chromatograph eluted with 0% to 30% acetonitrile and water, using 0.1% TFA as the modifier. Yield of the products 7.2 g, 80%. Ion(s) found by LCMS: M+H=405.

Step c.

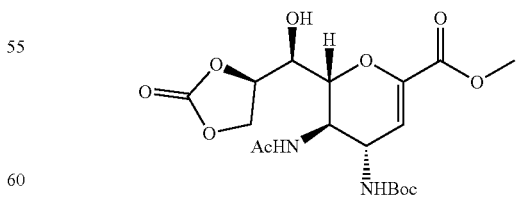

A solution of intermediate from the previous step (3.5 g, 8.5 mmol), CDI (2.8 g, 2 equiv), trimethylamine (4.2 ml, 30 mmol) and DMAP (240 mg, 2 mmol) were heated at 60° C. in DMF (50 ml) overnight, then concentrated and purified by reverse phase liquid chromatography (RPLC) using an Isco COMBIFLASH® liquid chromatograph eluted with 0% to 30% acetonitrile and resulting without modifier. Yield of desired product 2.3 g, 60%. Ion(s) found by LCMS: M+H=431.

Step d.

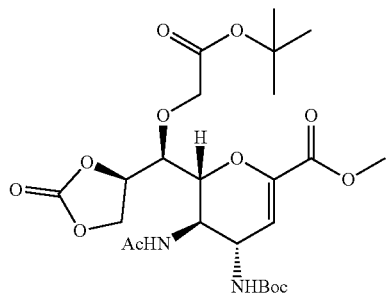 [SMILES: COC(=O)C1=C[C@H](NC(=O)OC(C)(C)C)[C@@H](NC(C)=O)[C@H]([C@H](OCC(=O)OC(C)(C)C)[C@H]2COC(=O)O2)O1]

Sodium hydride (400 mg, 60% in oil, 10 mmol) was added to Int-4 (1.45 g, 3.3 mmol) in 50 ml dry THE (moisture-sensitive reaction) under the ice-water bath. The resulting solution was stirred for 0.5 hour, then tert-butyl bromo acetate (2 g, 10 mmol) was added to the above solution. The resulting solution was heated to 60° C. overnight and quenched with acetic acid, concentrated and purified by reverse phase liquid chromatography (RPLC) using an Isco COMBIFLASH® liquid chromatograph eluted with 0% to 50% acetonitrile and water with TFA as modifier. Yield of 1 g, 57%. Ion(s) found by LCMS: M+H=593. (The reaction is pretty clean by HPLC, but low isolated yield)

Step f.

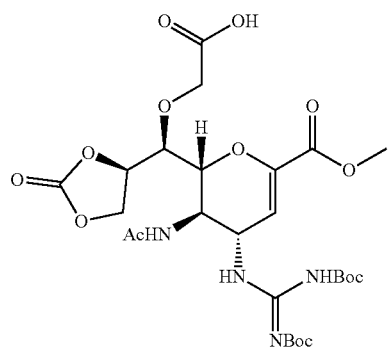

Intermediate from the previous step (1.2 g, 2.2 mmol) was stirred with 10 ml TFA at room temperature overnight. The progress of deprotection was monitored by LCMS. The resulting solution was concentrated and used in the next step without purification.

The residue from the previous reaction was dissolved into 20 ml THF, then N,N'-bis-boc-1-guanylpyrazole (1 g, 3.3 mmol), 4-dimethylaminopyridine (120 mg, 1 mmol) and triethyl amine(0.7 ml, 5 mmol) were added to the solution, and the resulting solution was heated to 60° C. for 2 hours. The resulting solution was concentrated and purified by reverse phase liquid chromatography (RPLC) using an Isco COMBIFLASH® liquid chromatograph eluted with 0% to 50% acetonitrile and water with no modifier. Yield of 700 mg, 84%. Ion(s) found by LCMS: M+H=631.

Step g.

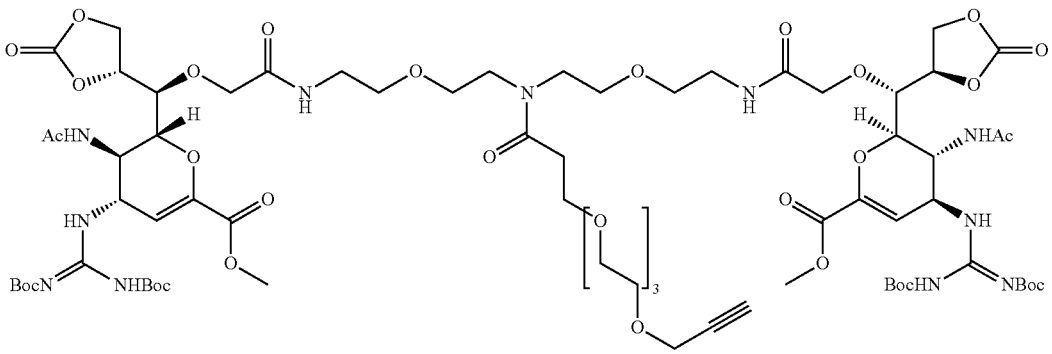

To a solution of linker-3 (prepared as described in Example 19) (73 mg, 0.14 mmol) and intermediate from the previous step. (200 mg, 0.32 mmol, 2.2 equi) in DMF (30 ml) was added EDC (100 mg, 0.5 mmol), HOAt (65 mg, 3 mmol), and DIEA (0.14 ml, 1 mmol) at room temperature. The solution was stirred overnight. The resulting solution was concentrated and purified by and purified by reverse phase liquid chromatography (RPLC) using an Isco COMBIFLASH® liquid chromatograph eluted with 0% to 50% acetonitrile and water with no modifier. Yield of 120 mg, 52%. Ion(s) found by LCMS: M/2+H=830.

Step h.

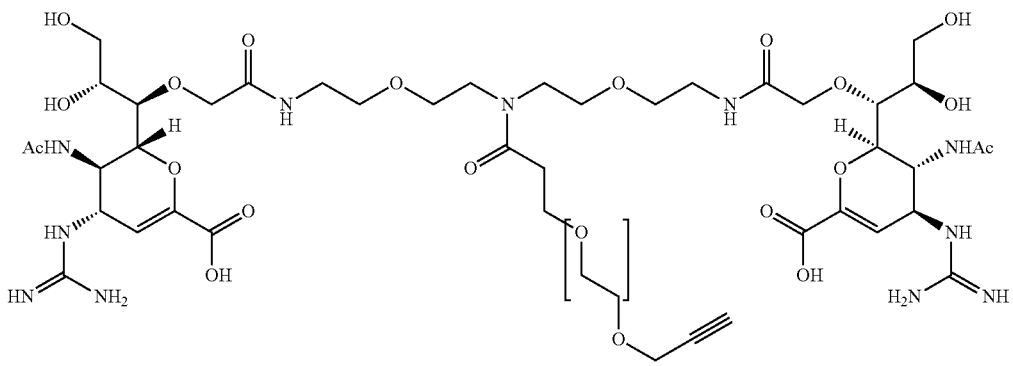

Lithium hydroxide (24 mg, 1 mmol) in 2 ml water was added to a solution of intermediate from the previous step (120 mg, 0.07 mmol) in 2 ml THF and 1 ml MeOH. After the reaction is complete by LCMS, the solution was quenched with AMBERLITE® IRN-77, ion exchange resin to adjust to pH=1, then the solution was filtered and the filtrate was concentrated and in the next step without further purification. Intermediate from the previous step was treated in 2 ml TFA at room temperature overnight at 40° C. The crude reaction was concentrated and purified by HPLC with 0% to 20% acetonitrile and water, using TFA as the modifier. Yield 60 mg, 74% yield. Ion(s) found by LCMS: [M/2]+1=589.8.

Example 32. Synthesis of Conjugate 7

A solution of Fc-PEG4-azide (each Fc domain monomer having the sequence of SEQ ID NO: 38) in PBS×1 buffer solution (100 mg, 1.28 µmol, 6.1 mL, MW=57260 Da, DAR=3.6) were added to Int-10 (prepared as described in Example 31) (TFA salt, 44 mg, 0.031 mmol) and freshly prepared pH 7.4 PBS solutions of $CuSO_4$ (0.7 mL of 50.0 mM, 20 eq), tris(3-hydroxypropyltriazolylmethyl)-amine (THPTA, 0.7 mL of 50.0 mM, 20 eq), and sodium ascorbate (1.05 mL of 50.0 mM, 30 eq). The resulting homogeneous solution was agitated by rocker table for 12 h. The crude solutions were diluted with pH 7.4 PBS to a final concentration of 1 mg/mL, and ultra-filtered (10,000 MWCO) to a volume of 1 mL, two times. The crude mixtures were then diluted 1:10 in PBS pH 7.4, and purified using MabSelect Sure Resin (GE Healthcare, Chicago, Ill., USA), followed by size exclusion chromatography. Purified material was quantified using a NANODROP™ UV visible spectrophotometer (using a calculated extinction coefficient based on the amino acid sequence of the Fc used in the conjugation, and concentrated to approximately 10 mg/mL using a centrifugal concentrator (10,000 MWCO). Purified molecules were analyzed using 4-12% Bis Tris SDS PAGE gels by loading 1-2 µg of each molecule into the gel, and staining using instant Blue staining. Each gel included a molecular weight ladder with the indicated molecular weight standards. Yields are typically 40-60%. MALDI MS analysis showed a range of masses (60000-90000) with an average of mass of 63633. Average DAR=4.5.

Example 33. Efficacy of Conjugate 6 in a Lethal Mouse Influenza Model: Study #3

Conjugate 6 was evaluated against a lethal INFV A H1N1 influenza infection in female BALB/c mice. The experiment comprised 7 groups of 5 mice. At day 0, all mice were challenged with 1×LD90 H1N1 A/Texas/36/91. Groups 1-6 received treatment IV, 28 days before challenge (Table 12). Vehicle (PBS) was included as an additional negative control. Group 7 received Oseltamivir phosphate by way of oral delivery, starting 8 hours post infection twice daily for 5 days. All mice were monitored for survival (FIGS. 31A-31F) for 15 days after challenge.

Mice treated with Conjugate 6 showed 100% survival with single doses in all the concentrations down to 2.5 mg/kg, and 80% survival at 1.25 mg/kg, compared with 0% survival in the vehicle control group. All mice in the Oseltamivir phosphate control group survived. When compared to the Oseltamivir phosphate group, conjugate 6 demonstrated similar efficacy to Oseltamivir at a 20× lower cumulative dose (in mg/kg), despite the fact that all Conjugate 6 groups were dosed once, 28 days prior to infection.

TABLE 12

| Study design | | | | |
|---|---|---|---|---|
| Group n = 5 | Challenge Day 0 | Compound | Dose (mg/kg) | Treatment Route/Schedule |
| 1 | Influenza A virus, H1N1 strain A/Texas/36/91 by way of IN route. | Vehicle (PBS) | N/A | IV, q.d. 28 days pre-challenge |
| 2 | | Conjugate 6 | 50 | |
| 3 | | Conjugate 6 | 10 | |
| 4 | | Conjugate 6 | 5 | |
| 5 | | Conjugate 6 | 2.5 | |
| 6 | | Conjugate 6 | 1.25 | |
| 7 | | Oseltamivir (Tamiflu ™) | 20 | PO, b.i.d. 8 hours after challenge for 5 days |

Example 34. Efficacy of Conjugate 6 in a Lethal Mouse Influenza Model: Study #4

Conjugate 6 was evaluated against a lethal INFV A H1N1 influenza infection in female BALB/c mice. The experiment comprised 13 groups of 5 mice. At day 0, all mice were challenged with 1×LD90 H1N1 A/Texas/36/91. All Conjugate 6 groups (8-13) received single 10 mg/kg IV doses at different times, pre- and post-infection, as outlined in Table 13. Vehicle (PBS) and Fc only were included as negative controls. Groups 3-7 received Oseltamivir phosphate (20 mg/kg) by way of oral delivery, starting at different time points post-infection twice daily for 5 days, as outlined in Table 13. All mice were monitored for survival (FIGS. 32A-32F) for 15 days after challenge.

Mice treated with Conjugate 6 showed 100% survival with single 10 mg/kg doses when treated out to 24 hrs post-infection, and 60 and 80% survival at 48 and 72 hrs post-infection, respectively. In the Oseltamivir phosphate group, survival dropped sharply to 0% and 20%, respectively, in the groups where treatment was initiated at 48 and 72 hrs post-infection. These results suggest that Conjugate 6 potentially possesses a superior treatment window versus Oseltamivir for treating influenza A infections.

TABLE 13

Study design

| Group (N = 5) | Influenza A strain | Test Article | Route, Schedule | Dose (mg/kg) | Dose timing (hours) |
|---|---|---|---|---|---|
| 1 | A/Texas/36/91 (H1N1) by way of IN | Vehicle (PBS) | IV, single | — | T − 4 |
| 2 | | Fc only | IV, single | 10 | T − 4 |
| 3 | | Oseltamivir | PO, bid × 5 days | 20 | T + 8 |
| 4 | | Oseltamivir | PO, bid × 5 days | 20 | T + 24 |
| 5 | | Oseltamivir | PO, bid × 5 days | 20 | T + 48 |
| 6 | | Oseltamivir | PO, bid × 5 days | 20 | T + 72 |
| 7 | | Oseltamivir | PO, bid × 5 days | 20 | T + 96 |
| 8 | | Conjugate 6 | IV, single | 10 | T − 4 |
| 9 | | Conjugate 6 | IV, single | 10 | T + 8 |
| 10 | | Conjugate 6 | IV, single | 10 | T + 24 |
| 11 | | Conjugate 6 | IV, single | 10 | T + 48 |
| 12 | | Conjugate 6 | IV, single | 10 | T + 72 |
| 13 | | Conjugate 6 | IV, single | 10 | T + 96 |

Example 35. Conjugate 6 Toxicity Study

The safety of Conjugate 6 was evaluated in a 14 day rat dose-range finder toxicity study. Rats were administered either 5 mpk, 20 mpk, or 50 mpk of Conjugate 6 by intravenous administration on days 0 and 7 of the study. Compared with vehicle controls, no significant effects on body weight gain (FIG. 33), organ weights, food consumption were observed at any dose tested. Plasma exposures (measured by AUC) increased proportionally with dose. These preclinical safety results are consistent with a high therapeutic index. A summary of observations is provided in Table 14.

TABLE 14

Summary of 14-day rat dose-range finder toxicity study

| Parameter | Findings at highest dose (50 mpk), compared to vehicle |
|---|---|
| Clinical observations | No findings |
| Hematology | No change from vehicle |
| Clinical Chemistry | No change from vehicle |
| Coagulation | No change from vehicle |
| Urinalysis | No change from vehicle |
| Histopathology | No observations |

Example 36. Efficacy of Conjugate 6 Against in a Lethal Mouse Influenza Model Dose by Three Different Routes: Study #5

Conjugate 6 was evaluated against a lethal IAV H1N1 influenza infection in female BALB/c mice (Charles River Laboratories, 6-8 weeks). The challenge virus (A/Texas/36/91) is a mouse-adapted isolate capable of causing lethal infections in mice. The experiment comprised 15 groups of 5 mice. At day 0, all mice were challenged with virus at 1× the LD90 by intranasal inoculation in a volume of 50 μl, after being lightly anesthetized with isoflurane. Groups 1-14 received a single treatment, 4 hours before challenge (Table 15). In order to determine the potency of Conjugate 6 by different dose routes matching concentrations of Conjugate (10, 2, 0.4, and 0.1 mg/kg) were dosed either IV, IM, or SC. In addition to the vehicle (PBS) only group, Human IgG1 (Fc alone) was included as an additional negative control (group 2). Group 15 received Oseltamivir phosphate by way of oral delivery, starting 8 hours post infection twice daily for 5 days. All mice were monitored for survival (Table 15) for 14 days.

Mice treated with Conjugate 6 showed 100% survival at day 14 against challenge by influenza (H1N1) with single doses of 10, 2, or 0.4 mg/kg, regardless of dose route. Only at the lowest test article concentration were single mouse differences seen between IV, IM, and SC dosing (Table 16; 60, 80, and 100% survival, respectively). These results strongly suggest that protective lung concentrations of Conjugate 6 is achievable by multiple dose routes.

TABLE 15

Study design

| Group n = 5 | Challenge Day 0 | Compound | Dose (mg/kg) | Dose route | Treatment Route/Schedule |
|---|---|---|---|---|---|
| 1 | Influenza A virus (H1N1) A/Texas/36/91 by way of IN | Vehicle (PBS) | N/A | | Single dose, 4 hours before viral challenge |
| 2 | | Fc alone | 50 | IV | |
| 3 | | Conjugate 6 | 10 | IV | |
| 4 | | Conjugate 6 | 2 | | |
| 5 | | Conjugate 6 | 0.4 | | |
| 6 | | Conjugate 6 | 0.1 | | |
| 7 | | Conjugate 6 | 10 | IM | |
| 8 | | Conjugate 6 | 2 | | |
| 9 | | Conjugate 6 | 0.4 | | |
| 10 | | Conjugate 6 | 0.1 | | |
| 11 | | Conjugate 6 | 10 | SC | |
| 12 | | Conjugate 6 | 2 | | |
| 13 | | Conjugate 6 | 0.4 | | |
| 14 | | Conjugate 6 | 0.1 | | |
| 15 | | Oseltamivir (Tamiflu ™) | 20 | PO | b.i.d. 8 hours after challenge for 5 days |

TABLE 16

Mouse survival

| Test article | mg/kg | Dose route | % Survival (Day 14) |
|---|---|---|---|
| Vehicle (PBS) | na | IV | 0 |
| hIgG1 (Fc only) | 10 | IV | 0 |
| Conjugate 6 | 10 | IV | 100 |
| | 2 | | 100 |
| | 0.4 | | 100 |
| | 0.1 | | 60 |
| Conjugate 6 | 10 | IM | 100 |
| | 2 | | 100 |
| | 0.4 | | 100 |
| | 0.1 | | 80 |
| Conjugate 6 | 10 | SC | 100 |
| | 2 | | 100 |
| | 0.4 | | 100 |
| | 0.1 | | 100 |
| oseltamivir | 20 | PO | 100 |

Example 37. Efficacy of Conjugate 6 Against an Oseltamivir-Resistant Isolate in a Lethal Mouse Influenza Model: Study #6

Conjugate 6 was evaluated against a lethal IAV H1N1 influenza infection in female BALB/c mice (Charles River Laboratories, 6-8 weeks). The challenge virus (A/Perth/261/2009) is a mouse-adapted isolate that carries the H275Y mutation resulting in resistance to the neuraminidase inhibitor oseltamivir. The experiment comprised 10 groups of 5 mice. At day 0, all mice were challenged with A/Perth/261/2009 (H1N1) at 1× the LD90 by intranasal inoculation in a volume of 50 µl, to mice lightly anesthetized with isoflurane. Groups 1-9 received a single treatment by IV, 4 hours before challenge (Table 17). In addition to the vehicle (PBS) only group, Human IgG1 (Fc alone) was included as an additional negative control. Group 10 received Oseltamivir phosphate by way of oral delivery, starting 8 hours post infection twice daily for 5 days. All mice were monitored for survival (FIGS. 34A-34D, Table 18) and weight loss (FIG. 35, Table 19) for 15 days after challenge.

Mice treated with Conjugate 6 showed 100% survival against challenge by influenza (A/Perth/261/2009) with single doses at 50, 10, and 2 mg/kg. Furthermore, despite the small group size (n=5) these results were statistically significant relative to the vehicle control (Table 18).

At Conjugate 6 concentrations of 0.4, 0.2, or 0.1 mg/kg survival was 60%, while no mice survived to the end of the study if dosed with vehicle (PBS) or hIgG1 (Fc only) only. The oseltamivir group only had a single animal surviving (20% efficacy) despite treatment with a dose shown to be protective against oseltamivir sensitive isolates previously (20 mg/kg, bid×5 days). These results confirm that the challenge virus is resistant to oseltamivir, and sensitive to Conjugate 6.

The potency of Conjugate 6 against mutants containing the H275Y mutation was further supported by body weight data (FIG. 35, Table 19). Groups receiving a single dose of Conjugate 6 at concentrations of 2 mg/kg or more demonstrated 5%, or less, transient weight loss.

TABLE 17

Study design

| Group n = 5 | Challenge Day 0 | Compound | Dose (mg/kg) | Treatment Route/Schedule |
|---|---|---|---|---|
| 1 | Influenza A virus (H1N1) A/Perth/261/2009 by way of IN route. | Vehicle (PBS) | N/A | IV, q.d. 4 hours pre-challenge |
| 2 | | Fc alone | 50 | |
| 3 | | Conjugate 6 | 50 | |
| 4 | | Conjugate 6 | 10 | |
| 5 | | Conjugate 6 | 2 | |
| 6 | | Conjugate 6 | 0.4 | |
| 7 | | Conjugate 6 | 0.2 | |
| 8 | | Conjugate 6 | 0.1 | |
| 9 | | Conjugate 6 | 0.05 | |
| 10 | | Oseltamivir (Tamiflu ™) | 20 | PO, b.i.d. 8 hours after challenge for 5 days |

TABLE 18

Mouse survival

| Compound | Dosage | Median Survival | % Survival | Significance to vehicle (p) |
|---|---|---|---|---|
| Vehicle (PBS) | N/A | 7 | 0 | N/A |
| Fc alone | 50 mg/kg | 6 | 0 | ns |
| Conjugate 6 | 50 mg/kg | Undef | 100 | 0.0027 |
| Conjugate 6 | 10 mg/kg | Undef | 100 | 0.0027 |
| Conjugate 6 | 2 mg/kg | Undef | 100 | 0.0027 |
| Conjugate 6 | 0.4 mg/kg | Undef | 60 | 0.1167 |
| Conjugate 6 | 0.2 mg/kg | Undef | 60 | 0.0185 |
| Conjugate 6 | 0.1 mg/kg | Undef | 60 | 0.1047 |
| Conjugate 6 | 0.05 mg/kg | 7 | 0 | 0.9241 |
| Oseltamivir phosphate | 20 mg/kg B.I.D | 7 | 20 | 0.3470 |

TABLE 19

Daily Weight Average

Daily average weight (# of mice shown in parenthesis if less than 5)

| Days post infection | Vehicle (PBS) | Fc alone 50 mg/kg | Conjugate 6 50 mg/kg | Conjugate 6 10 mg/kg | Conjugate 6 2 mg/kg | Conjugate 6 0.4 mg/kg | Conjugate 6 0.2 mg/kg | Conjugate 6 0.1 mg/kg | Conjugate 6 0.05 mg/kg | Oseltamivir phosphate 20 mg/kg |
|---|---|---|---|---|---|---|---|---|---|---|
| 0 | 100 (5) | 100 (5) | 100 | 100 | 100 | 100 | 100 | 100 | 100 | 100 |
| 1 | 103 (5) | 104 (5) | 101 | 101 | 102 | 102 | 103 | 105 | 102 | 105 |
| 2 | 102 (5) | 105 (5) | 103 | 101 | 103 | 100 | 102 | 102 | 101 | 102 |
| 3 | 93 (5) | 97 (5) | 101 | 101 | 98 | 92 | 98 | 95 | 94 | 95 |
| 4 | 88 (5) | 90 (5) | 95 | 98 | 99 | 91 | 98 | 92 | 90 | 93 |
| 5 | 85 (5) | 85 (5) | 94 | 98 | 98 | 91 | 98 | 92 | 89 | 92 |
| 6 | 83 (4) | 88 (3) | 100 | 100 | 99 | 88 | 95 | 85 | 84 (4) | 86 |
| 7 | 79 (3) | 90 (2) | 103 | 99 | 95 | 90 (3) | 94 | 83 (4) | 77 (1) | 86 (3) |
| 8 | 75 (2) | 81 (1) | 102 | 99 | 97 | 93 (3) | 94 (4) | 87 (3) | 78 (1) | 85 (2) |
| 9 | | | 106 | 104 | 104 | 101 (3) | 101 (4) | 95 (3) | | 86 (2) |
| 10 | | | 105 | 102 | 103 | 100 (3) | 99 (4) | 97 (3) | | 95 (1) |
| 11 | | | 106 | 102 | 104 | 102 (3) | 104 (4) | 102 (3) | | 97 (1) |
| 12 | | | 108 | 104 | 105 | 102 (3) | 105 (3) | 107 (3) | | 104 (1) |
| 13 | | | 107 | 103 | 105 | 102 (3) | 105 (3) | 107 (3) | | 104 (1) |
| 14 | | | 107 | 103 | 105 | 102 (3) | 106 (3) | 108 (3) | | 104 (1) |
| 15 | | | 100 | 100 | 100 | 100 (3) | 100 (3) | 100 (3) | | 100 (1) |

Example 38. 7-Day Rat PK Study Following IV Administration of Test Article

Rat pharmacokinetic (PK) studies were performed by Seventh Wave Laboratories (Maryland Heights, Mo.) using male Sprague Dawley Rats 46-49 days of age. Rats were injected IV by way of the tail vein with 75 mg/kg of test article (5 ml/kg dose volume). Animals were housed under standard IACUC approved housing conditions. At appropriate times animals were non-terminally bled (retro-orbital, cheek, or by tail vein) with blood collected in K2EDTA tubes to prevent coagulation. Collected blood was centrifuged (2,000×g, for 10 minutes) and plasma withdrawn for analysis of test article concentrations over time.

The plasma concentrations for Conjugate 6 or hIgG1 Fc at each time point were measured by sandwich ELISA as follows: Conjugate 6 molecules were captured either on neuraminidase coated plates or anti-hIgG1 antibody coated plates and then detected using an HRP-conjugated anti-human IgG-Fc antibody. hIgG1 was captured using anti-hIgG1 Fc antibody. Protein concentration was calculated in GraphPad Prism using 4PL non-linear regression of Conjugate 6 (or hIgG1 Fc) standard curves. A more detailed method description is provided below.

Nunc Maxisorp 96-well plates (Cat No. 12-565-136, ThermoFisher) were coated with either neuraminidase from A/California/04/2009 (H1N1) (11058-VNAHC, Sino Biological) or anti-IgG1 Fc antibody in 1×KPL coating buffer (5150-0041, SeraCare). In the cases where the anti-IgG1 Fc antibody was used to capture test article, capture and detection anti-IgG1 Fc antibodies were selected that bind different epitopes. Plates were incubated at room temperature for 1 hr on an orbital plate shaker (500 rpm). Serial dilutions of the plasma samples were plated and incubated at room temperature for 2 hrs (sample diluent: 1% BSA in PBS 0.05% Tween 20+naïve rat plasma final concentration of 1:900). Conjugate 6 or hIgG1 Fc standard curves ranging from 500-0.230 ng/mL, in duplicate were run on each plate.

Following the 2 hr incubation, plates were washed 5× in 300 µL PBS with 0.05% Tween 20. Conjugate 6 bound to neuraminidase on the plates (or anti-hIgG1 Fc antibody) was then probed with an HRP conjugated anti-human IgG Fc F(ab')2 (709-036-098, Jackson) diluted 1:1,000 in sample diluent for 1 hr at room temp. Plates were then washed 8× in 300 µL PBS with 0.05% Tween 20 and developed with TMB substrate for 7-8 minutes. The reaction was stopped with 1 N $H_2SO_4$. Absorbance was read at 450 nm. A similar protocol was used for hIgG1 Fc, where only anti-hIgG1 Fc antibody was used for capture. The quantities of Conjugate 6 measured at different time points using either neuraminidase or anti-hIgG1 Fc antibody capture were similar within experimental error, suggesting that the intact conjugate is stable in vivo.

Total Conjugate 6 (or hIgG1 Fc) in test samples was interpolated using in GraphPad Prism Version 6 following nonlinear regression analysis (Sigmoidal, 4PL analysis) of the Conjugate 6 (or hIgG1 Fc) standard curves. The curves comparing Conjugate 6 and hIgG1 Fc are shown in FIG. 36. The quantities of Conjugate 6 measured at different time points using either neuraminidase or anti-hIgG1 Fc antibody capture were similar within experimental error, suggesting that the intact conjugate is stable in vivo.

Example 39. 14-Day Rat PK Study Following IV Administration of Test Article

Rat PK studies were performed by Seventh Wave Laboratories (Maryland Heights, Mo.) using male Sprague Dawley Rats 46-49 days of age. Rats were injected IV by way of the tail vein with 5, 20, or 50 mg/kg of test article (5 ml/kg dose volume) at days 1 and 8. Animals were housed under standard IACUC approved housing conditions. At appropriate times animals were non-terminally bled (retro-orbital, cheek, or by tail vein) with blood collected in K2EDTA tubes to prevent coagulation. Collected blood was centrifuged (2,000×g, for 10 minutes) and plasma withdrawn for analysis of test article concentrations over time.

The plasma concentrations for Conjugate 6 at each time point were measured by sandwich ELISA as follows: Conjugate 6 molecules were captured either on neuraminidase coated plates and then detected using an HRP-conjugated anti-human IgG-Fc antibody. hIgG1 was captured using anti-hIgG1 Fc antibody. Protein concentration was calculated in GraphPad Prism using 4PL non-linear regression of Conjugate 6 standard curves. A more detailed method description is provided below.

Nunc Maxisorp 96-well plates (Cat No. 12-565-136, ThermoFisher) were coated with either neuraminidase from A/California/04/2009 (H1N1) (11058-VNAHC, Sino Biological) in 1×KPL coating buffer (5150-0041, SeraCare). Plates were incubated at room temperature for 1 hr on an orbital plate shaker (500 rpm). Serial dilutions of the plasma samples were plated and incubated at room temperature for 2 hrs (sample diluent: 1% BSA in PBS 0.05% Tween 20+naïve rat plasma final concentration of 1:900). Conjugate 6 standard curves ranging from 500-0.230 ng/mL, in duplicate were run on each plate.

Following the 2 hr incubation, plates were washed 5× in 300 µL PBS with 0.05% Tween 20. Conjugate 6 bound to neuraminidase on the plates was then probed with an HRP conjugated anti-human IgG Fc F(ab')2 (709-036-098, Jackson) diluted 1:1,000 in sample diluent for 1 hr at room temp. Plates were then washed 8× in 300 µL PBS with 0.05% Tween 20 and developed with TMB substrate for 7-8 minutes. The reaction was stopped with 1 N $H_2SO_4$. Absorbance was read at 450 nm. Total Conjugate 6 (or hIgG1 Fc) in test samples was interpolated using in GraphPad Prism Version 6 following nonlinear regression analysis (Sigmoidal, 4PL analysis) of the Conjugate 6 standard curves. The curves comparing Conjugate 6 shown in FIG. 37 demonstrate linear dose proportionality.

Example 40. 28-Day Rat PK Study Comparing IV and SC Administration of Test Article Rat PK studies were performed by Seventh Wave Laboratories (Maryland Heights, Mo.) using male Sprague Dawley Rats 46-49 days of age. Rats were injected IV or SC with 5 mg/kg of test article (5 ml/kg dose volume). Animals were housed under standard IACUC approved housing conditions. At appropriate times animals were non-terminally bled (retro-orbital, cheek, or by tail vein) with blood collected in K2EDTA tubes to prevent coagulation. Collected blood was centrifuged (2,000×g, for 10 minutes) and plasma withdrawn for analysis of test article concentrations overtime.

The plasma concentrations for Conjugate 6 or hIgG1 Fc at each time point were measured by sandwich ELISA as follows: Conjugate 6 molecules were captured on neuraminidase coated plates and then detected using an HRP-conjugated anti-human IgG-Fc antibody. Protein concentration was calculated in GraphPad Prism using 4PL non-linear regression of Conjugate 6 standard curves. A more detailed method description is provided below.

Nunc Maxisorp 96-well plates (Cat No. 12-565-136, ThermoFisher) were coated with either neuraminidase from A/California/04/2009 (H1N1) (11058-VNAHC, Sino Biological) in 1×KPL coating buffer (5150-0041, SeraCare). Plates were incubated at room temperature for 1 hr on an orbital plate shaker (500 rpm). Serial dilutions of the plasma samples were plated and incubated at room temperature for 2 hrs (sample diluent: 1% BSA in PBS 0.05% Tween 20+naïve rat plasma final concentration of 1:900). Conjugate 6 standard curves ranging from 500-0.230 ng/mL, in duplicate were run on each plate.

Following the 2 hr incubation, plates were washed 5× in 300 μL PBS with 0.05% Tween 20. Conjugate 6 bound to neuraminidase on the plates was then probed with an HRP conjugated anti-human IgG Fc F(ab')2 (709-036-098, Jackson) diluted 1:1,000 in sample diluent for 1 hr at room temp. Plates were then washed 8× in 300 μL PBS with 0.05% Tween 20 and developed with TMB substrate for 7-8 minutes. The reaction was stopped with 1 N $H_2SO_4$. Absorbance was read at 450 nm.

Total Conjugate 6 (or hIgG1 Fc) in test samples was interpolated using in GraphPad Prism Version 6 following nonlinear regression analysis (Sigmoidal, 4PL analysis) of the Conjugate 6 standard curves. The curves comparing Conjugate 6 in FIG. 38 show that SC and IV plasma levels converged at 24 h and were similar within experimental error out to 336 h.

Example 41. 28-Day Non-Human Primate PK Study Following IV Administration of Test Article Non-human primate (NHP) PK studies were performed by BTS Research (San Diego, Calif.) using male and female Cynomolgus monkeys 4.5-8 years old with body weights ranging from 2.5-6.5 kg. NHPs were injected IV by way of the saphenous or cephalic vein with 5 or 20 mg/kg of test article (5 ml/kg dose volume). Animals were housed under standard IACUC approved housing conditions. At appropriate times animals were non-terminally bled (by way of femoral or cephalic veins) with blood collected in K2EDTA tubes to prevent coagulation. Collected blood was centrifuged (2,000×g, for 10 minutes) and plasma withdrawn for analysis of test article concentrations overtime.

The plasma concentrations for Conjugate 6 at each time point were measured by sandwich ELISA as follows: Conjugate 6 molecules were captured on neuraminidase coated plates and then detected using an HRP-conjugated anti-human IgG-Fc antibody. Protein concentration was calculated in GraphPad Prism using 4PL non-linear regression of Conjugate 6 standard curves. A more detailed method description is provided below.

Nunc Maxisorp 96-well plates (Cat No. 12-565-136, ThermoFisher) were coated with neuraminidase from A/California/04/2009 (H1N1) (11058-VNAHC, Sino Biological) in 1×KPL coating buffer (5150-0041, SeraCare). Plates were incubated at room temperature for 1 hr on an orbital plate shaker (500 rpm). Serial dilutions of the plasma samples were plated and incubated at room temperature for 2 hrs (sample diluent: 1% BSA in PBS 0.05% Tween 20+naïve cynomolgus monkey plasma final concentration of 1:2,500). Conjugate 6 standard curves ranging from 500-0.230 ng/mL, in duplicate were run on each plate.

Following the 2 hr incubation, plates were washed 5× in 300 μL PBS with 0.05% Tween 20. Conjugate 6 bound to neuraminidase on the plates was then probed with an HRP conjugated anti-human IgG Fc F(ab')2 (709-036-098, Jackson) diluted 1:1,000 in sample diluent for 1 hr at room temp. Plates were then washed 8× in 300 μL PBS with 0.05% Tween 20 and developed with TMB substrate for 7-8 minutes. The reaction was stopped with 1 N $H_2SO_4$. Absorbance was read at 450 nm.

Total Conjugate 6 in test samples was interpolated using in GraphPad Prism Version 6 following nonlinear regression analysis (Sigmoidal, 4PL analysis) of the Conjugate 6 (or hIgG1 Fc) standard curves. PK parameters were calculated using WinNonlin software. The curves comparing Conjugate 6 are shown in FIG. 39 and a summary of key PK parameters is provided in Table 20. The dose response is linear between 5 and 20 mg/kg IV, resulting in a half-life of approximately 9 days across both doses (comparable to mouse/rat).

TABLE 20

| Cynomolgus monkey PK of Conjugate 6 | | |
|---|---|---|
| Conjugate 6 | Half-life (hrs) | AUClast (hr * mg/mL) |
| 5 mg/kg IV | 230 | 6240 |
| 20 mg/kg IV | 197 | 25400 |

Example 42. Mouse Lung Distribution PK Study Following IV Administration of Test Article Mouse PK studies were performed using male CD-1 mice 6 weeks of age. Mice were injected IV by way of the tail vein with 10 mg/kg of test article (5 ml/kg dose volume). Animals were housed under standard IACUC approved housing conditions. At the indicated time points, the animals were euthanized to harvest blood (by way of cardiac puncture) in K2EDTA tubes and lungs. Blood was centrifuged (2,000×g, for 10 minutes) to obtain plasma. The lungs were weighed and homogenized in 1.5 ml tubes with a sterile disposable pestle (Z359947, Sigma) in 100 μL of homogenization buffer comprised of 11.64 mL tissue protein extraction reagent (78510, Thermo Scientific), 0.24 ml of protease inhibitor cocktail (78410, Thermo Scientific), and 0.12 ml of EDTA. After 1-2 min homogenization, the volume was adjusted to 1 mL with homogenization buffer and the samples incubated on ice for 20 min with periodic mixing by gentle vortexing. The homogenates were centrifuged at 8,000×g for 10 min and the supernatant retained for analysis of test article concentrations over time.

The plasma and lung concentrations for Conjugate 6 at each time point were measured by sandwich ELISA as follows: Conjugate 6 molecules were captured on neuraminidase coated plates and detected using an HRP-conjugated anti-human IgG-Fc antibody. Protein concentration was calculated in GraphPad Prism using 4PL non-linear regression of Conjugate 6 standard curves. A more detailed method description is provided below.

Nunc Maxisorp 96-well plates (Cat No. 12-565-136, ThermoFisher) were coated with neuraminidase from A/California/04/2009 (H1N1) (11058-VNAHC, Sino Biological) in 1×KPL coating buffer (5150-0041, SeraCare). Plates were incubated at room temperature for 1 hr on an orbital plate shaker (500 rpm). Serial dilutions of the plasma samples were plated and incubated at room temperature for 2 hrs (sample diluent: 1% BSA in PBS 0.05% Tween 20+naïve mouse plasma final concentration of 1:100). Conjugate 6 standard curves ranging from 500-0.230 ng/mL, in duplicate were run on each plate.

Following the 2 hr incubation, plates were washed 5× in 300 μL PBS with 0.05% Tween 20. Conjugate 6 bound to neuraminidase on the plates was then probed with an HRP conjugated anti-human IgG Fc F(ab')2 (709-036-098, Jackson) diluted 1:1,000 in sample diluent for 1 hr at room temp. Plates were then washed 8× in 300 μL PBS with 0.05% Tween 20 and developed with TMB substrate for 7-8 minutes. The reaction was stopped with 1 N $H_2SO_4$. Absorbance was read at 450 nm.

Total Conjugate 6 in test samples was interpolated using in GraphPad Prism Version 6 following nonlinear regression analysis (Sigmoidal, 4PL analysis) of the Conjugate 6 standard curves. The curves comparing Conjugate 6 plasma and lung concentrations are shown in FIG. 40. Unexpectedly, lung $C_{max}$ was reached at t=1 h (19.5 μg/g lung tissue, ~310 nM). There was approximately 10% lung exposure of Conjugate 6, relative to plasma Example 43. 5-Day Mouse PK Study Comparing IV, SC and IM Administration of Test Article Mouse PK studies were performed using male CD-1 mice 6 weeks of age. Mice were injected IV by way of the tail vein with 5 mg/kg of test article (5 ml/kg dose volume). Animals were housed under standard IACUC approved housing conditions. At appropriate times animals were non-terminally bled (retro-orbital, cheek, or by tail vein) with blood collected in $K_2$EDTA tubes to prevent coagulation. Collected blood was centrifuged (2,000×g, for 10 minutes) and plasma withdrawn for analysis of test article concentrations over time.

The plasma concentrations for Conjugate 6 at each time point were measured by sandwich ELISA as follows: Conjugate 6 molecules were captured on neuraminidase coated plates and then detected using an HRP-conjugated anti-human IgG-Fc antibody. Protein concentration was calculated in GraphPad Prism using 4PL non-linear regression of Conjugate 6 (or hIgG1 Fc) standard curves. A more detailed method description is provided below.

Nunc Maxisorp 96-well plates (Cat No. 12-565-136, ThermoFisher) were coated with neuraminidase from A/California/04/2009 (H1N1) (11058-VNAHC, Sino Biological) in 1×KPL coating buffer (5150-0041, SeraCare). Plates were incubated at room temperature for 1 hr on an orbital plate shaker (500 rpm). Serial dilutions of the plasma samples were plated and incubated at room temperature for 2 hrs (sample diluent: 1% BSA in PBS 0.05% Tween 20+naïve mouse plasma final concentration of 1:100). Conjugate 6 standard curves ranging from 500-0.230 ng/mL, in duplicate were run on each plate.

Following the 2 hr incubation, plates were washed 5× in 300 μL PBS with 0.05% Tween 20. Conjugate 6 bound to neuraminidase on the plates was then probed with an HRP conjugated anti-human IgG Fc F(ab')2 (709-036-098, Jackson) diluted 1:1,000 in sample diluent for 1 hr at room temp. Plates were then washed 8× in 300 μL PBS with 0.05% Tween 20 and developed with TMB substrate for 7-8 minutes. The reaction was stopped with 1 N $H_2SO_4$. Absorbance was read at 450 nm.

Total Conjugate 6 in test samples was interpolated using in GraphPad Prism Version 6 following nonlinear regression analysis (Sigmoidal, 4PL analysis) of the Conjugate 6 standard curves. The curves comparing Conjugate 6 are shown in FIG. 41. The exposure levels for IV, IM and SC were similar with AUCs of 2082, 1944 and 2500, respectively.

Example 44. Mouse Efficacy and Multi-Species PK Supports Infrequent Prophylactic Dosing in Human Subjects Allometric scaling of mouse efficacy dosing based on mouse, rat, and primate PK studies was used to predict dosing and PK parameters in human subjects. Allometric scaling was based on the Area Under the Curve (AUC) at a 2.5 mg/kg efficacious dose in a 28-day mouse prevention study (see Example 33).

For cynomolgus monkey-only allometric scaling, human clearance (CL) was calculated based on cynomolgus monkey PK data (Example 41) only using a simple allometric equation: CL(human)=CL(monkey)·[BW(human)/BW(monkey)]$^w$, where BW=bodyweight and w is the scaling exponent fixed at 0.85. The results of cynomolgus monkey-only scaling are provided in Table 21.

For Mouse-rat-cynomolgus allometric scaling, human clearance (CL) from animal species was plotted against the animal body weight (BW) on a log-log scale according to the following allometric equation: CL=a·BW$^x$, where a is the coefficient and x is the exponent of the allometric equation. The coefficient a and exponent x were calculated from the intercept and slope of the linear regression line, respectively. The results of mouse-rat-cyno scaling are provided in Table 22.

Human clearance values calculated by respective algorithms above were then used to calculate the corresponding human dose needed to achieve the Efficacy AUC target of 3700 ug-hr/mL (from mouse 2.5 mg/kg dose, Example 33) using the following equation: Dose=CL·AUC.

TABLE 21

| Cynomolgus monkey-only allometric scaling (β = 0.85) | |
|---|---|
| Efficacy Area Under the Curve (AUC) | 3700 μg-hr/mL |
| Human Clearance (CL) | 0.43 mL/min |
| Human Dose | 95.46 mg, |
|  | 1.4 mg/kg |

TABLE 22

| Mouse-rat-cyno allometric scaling (β = 0.97) | |
|---|---|
| Efficacy Area Under the Curve (AUC) | 3700 μg-hr/mL |
| Human Clearance (CL) | 0.59 mL/min |
| Human Dose | 130.98 mg, |
|  | 1.9 mg/kg |

Example 45. Synthesis of Int-11

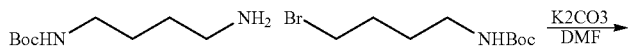

733
734
-continued
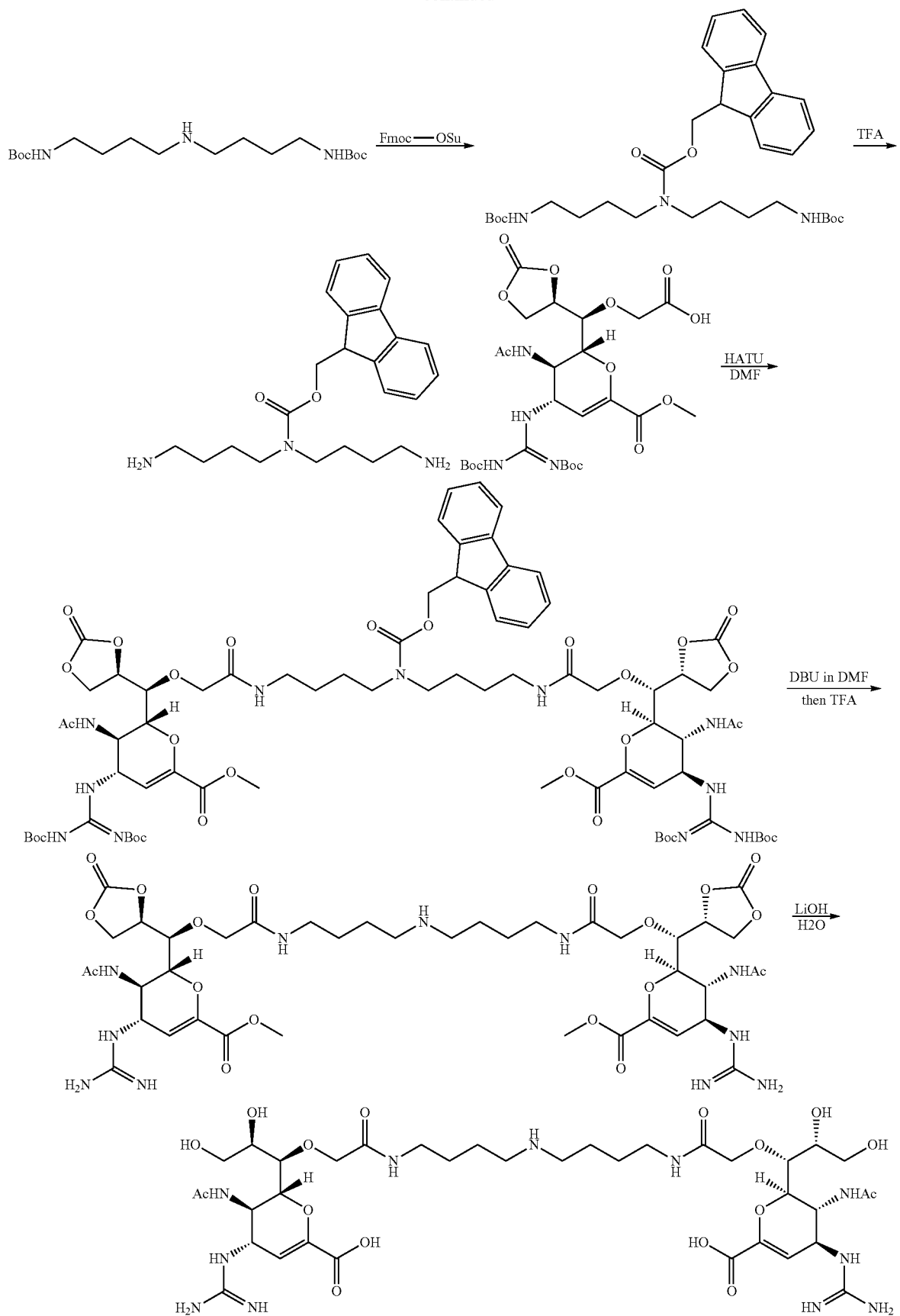

Step a.

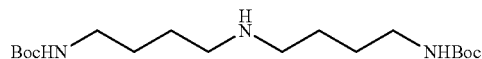

A solution of the tert-butyl (4-bromobutyl)carbamate (11.2 g, 60 mmol) and tert-butyl (4-aminobutyl)carbamate (10 g, 40 mmol) dissolved in DMF (150 mL) was treated with potassium carbonate (16.4 g, 120 mmol), then stirred at 80° C. for 6 hrs. The reaction mixture was partitioned between DCM (500 ml) and brine (100 ml). The organic layer was separated and washed with brine then dried with sodium sulfate. The solution was filtered, concentrated, and purified by reverse phase liquid chromatography (RPLC) using an Isco COMBIFLASH® liquid chromatograph eluted with 10% to 100% acetonitrile and water with 0.1% TFA as modifier. Yield of the product 11.0 g, 77%. Ion(s) found by LCMS: M+H=360.4

Step b.

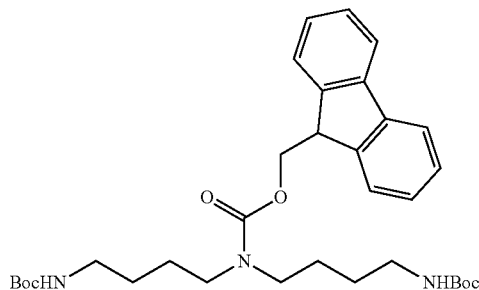 [SMILES: CC(C)(C)OC(=O)NCCCCN(CCCCNC(=O)OC(C)(C)C)C(=O)OCC1c2ccccc2-c2ccccc21]

Yield of the products 450 mg, 69%. Ion(s) found by LCMS: M/2+H=582.4.

Step c.

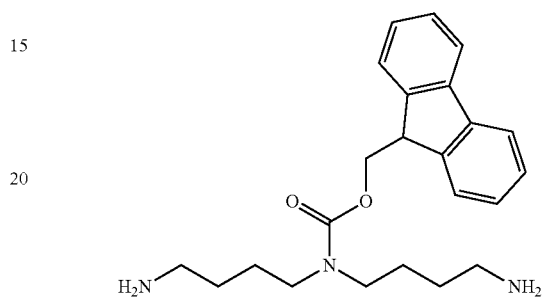

Product from the previous step (0.4 g, 0.7 mmol) was treated with TFA (5 mL) at room temperature for 0.5 hour, then concentrated to dryness and used for next step without further purification. Yield was quantitative for this step. Ion(s) found by LCMS: M/2+H=382.3.

Step d.

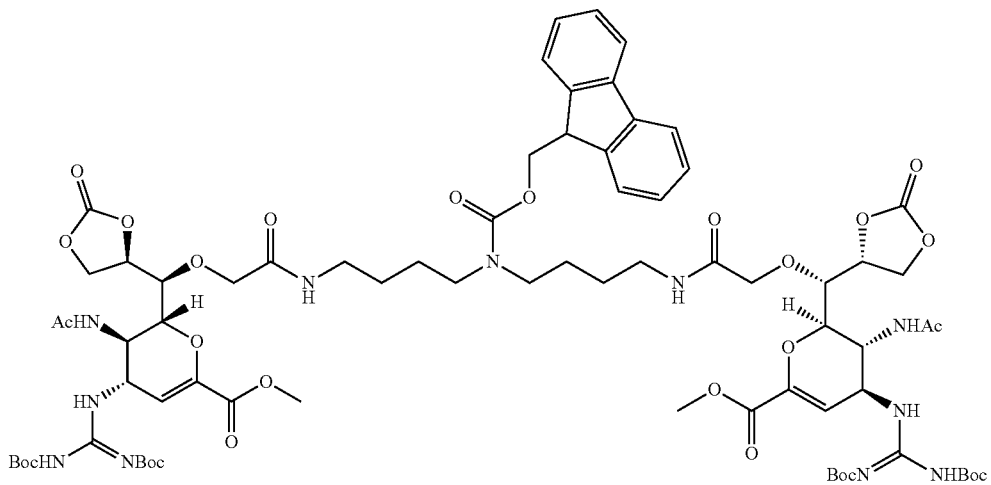

Product from the previous step (0.4 g, 1.11 mmol) and Fmoc-OSu (0.45 mg, 1.3 mmol) were dissolved in DCM (10 mL), then treated with N-methylmorpholine (0.22 ml, 2 mmol), and stirred for 1 hr at room temperature. The reaction was concentrated and purified by and purified by reverse phase liquid chromatography (RPLC) using an Isco COMBIFLASH® liquid chromatograph eluted with 10% to 100% acetonitrile and water with no 0.1% TFA as modifier.

Fmoc diamine (24 mg, 0.063 mmol) from the previous step was added to a solution of carboxylic acid (80 mg, 0.126 mmol, described in the synthesis Int-10, step f) in DMF (5 mL), then treated with HATU (50 mg, 0.13 mmol), followed N-methylmorpholine (0.06 ml, 0.50 mmol). After stirring for 1 h the resulting solution was concentrated and purified by reverse phase liquid chromatography (RPLC) using an Isco COMBIFLASH® liquid chromatograph eluted with 10% to 100% acetonitrile and water without TFA as a modifier. Yield of the products 80 mg, 79%. Ion(s) found by LCMS: M/2+H=803.9.

Step e.

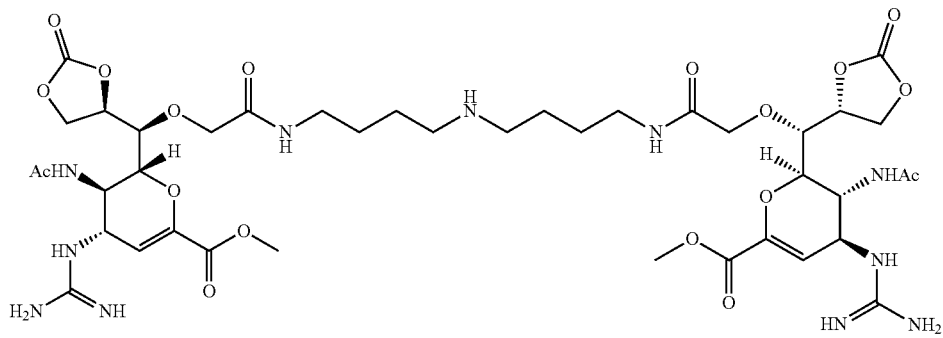 [SMILES: COC(=O)C1=C[C@H](NC(=N)N)[C@@H](NC(C)=O)[C@H]([C@H](OCC(=O)NCCCCNCCCCNC(=O)CO[C@@H]([C@@H]2OC(C(=O)OC)=C[C@H](NC(=N)N)[C@H]2NC(C)=O)[C@H]2COC(=O)O2)[C@H]2COC(=O)O2)O1]

Product from the previous step (80 mg, 0.050 mmol) was treated with 1% DBU (1,8-diazabicyclo[5.4.0]undec-7-ene) in DMF (2 mL) and stirred at room temperature. When the reaction was complete by LCMS (15 min), it was concentrated, then treated with TFA (2 mL) and stirred for 30 min at room temperature. The reaction solution was concentrated and purified by reverse phase liquid chromatography (RPLC) using an Isco COMBIFLASH® liquid chromatograph eluted with 10% to 100% acetonitrile and water, using 0.1% TFA as the modifier. Yield of product was 52 mg as TFA salt. Ion(s) found by LCMS: M/2+H=492.7.

Step f.

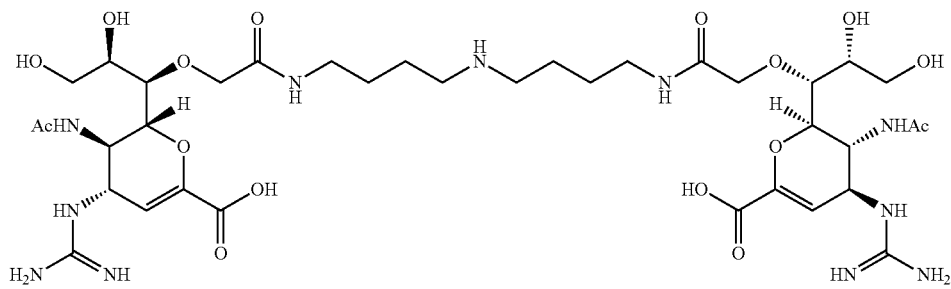 [SMILES: CC(=O)N[C@H]1[C@H]([C@H](OCC(=O)NCCCCNCCCCNC(=O)CO[C@@H]([C@@H]2OC(C(=O)O)=C[C@H](NC(=N)N)[C@H]2NC(C)=O)[C@H](O)CO)[C@H](O)CO)OC(C(=O)O)=C[C@@H]1NC(=N)N]

Product from the previous step was dissolved into water (2 mL), then treated with a lithium hydroxide (12 mg, 0.50 mmol, in 1 mL water) solution. The resulting reaction was monitored by LCMS. After stirring for 10 min the reaction was quenched with 0.1 ml acetic acid. The resulting solution was concentrated and purified by reverse phase liquid chromatography (RPLC) using an Isco COMBIFLASH® liquid chromatograph eluted with 0% to 30% acetonitrile and water, using 0.1% TFA as the modifier. Yield of the product: 30 mg as TFA salt, 66%. Ion(s) found by LCMS: M/2+H=452.7. M/3+H=302.1.

Example 46. Synthesis of Int-12

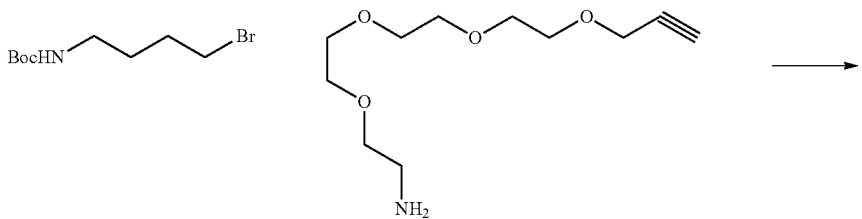

739
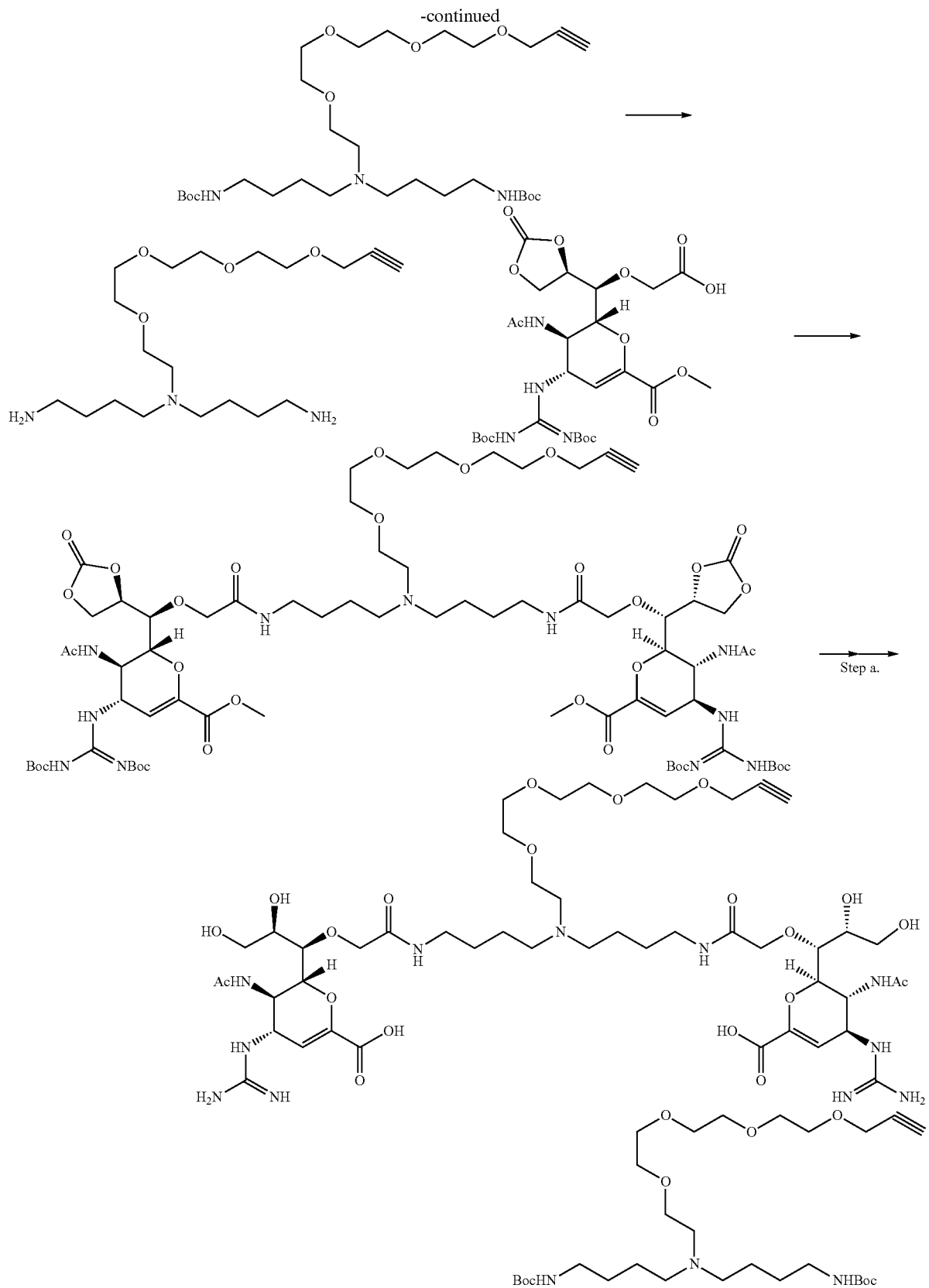
740
To a solution of tert-butyl (4-bromobutyl)carbamate (4.8 g, 19 mmol) and propargyl-PEG4 amine (2 g, 8.6 mmol) in DMF (50 mL) was added potassium carbonate (3.6 g, 26 mmol). The solution was stirred at 80° C. for 6 hrs, then partitioned between DCM (200 ml) and brine (50 ml). The organic layer was separated, washed with brine, dried with sodium sulfate, filtered, and concentrated, then purified by reverse phase liquid chromatography (RPLC) using an Isco COMBIFLASH® liquid chromatograph eluted with 10% to 100% acetonitrile and water with 0.1% TFA as modifier. Yield of product 3.5 g, 70%. Ion(s) found by LCMS: M/2+H=574.4.

Step b.

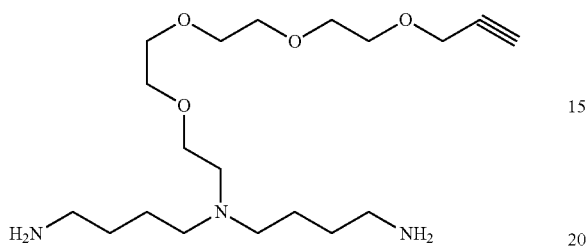

Product from the previous step (3.5 g, 8.6 mmol) was treated with TFA (20 ml) at room temperature for 0.5 hour, then concentrated to dryness, dissolved in water, frozen, lyophilized, and used in the next step without further purification. The yield was quantitative for this step. Ion(s) found by LCMS: M/2+H=374.3.

Step c.

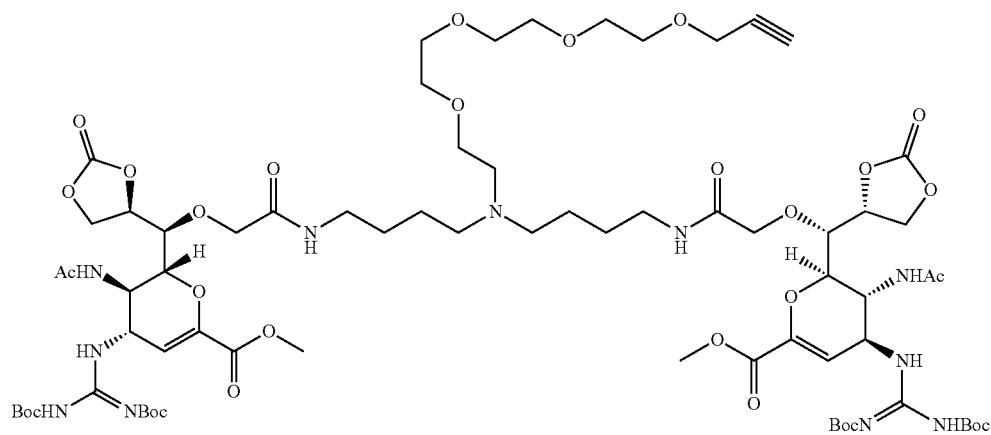

Diamine TFA salt from the previous step (37 mg, 0.1 mmol) was added to a solution of the carboxylic acid (130 mg, 0.2 mmol, described in the synthesis Int-10, step f) in 10 ml DMF, then treated with HATU (80 mg, 0.2 mmol), and N-methylmorpholine (0.25 ml, 2 mmol). The resulting solution was stirred for 1 hr, then concentrated and purified by reverse phase liquid chromatography (RPLC) using an Isco COMBIFLASH® liquid chromatograph eluted with 10% to 100% acetonitrile and water with no 0.1% TFA as modifier. Yield of the product 120 mg, 75%. Ion(s) found by LCMS: M/2+H=799.9.

Step d.

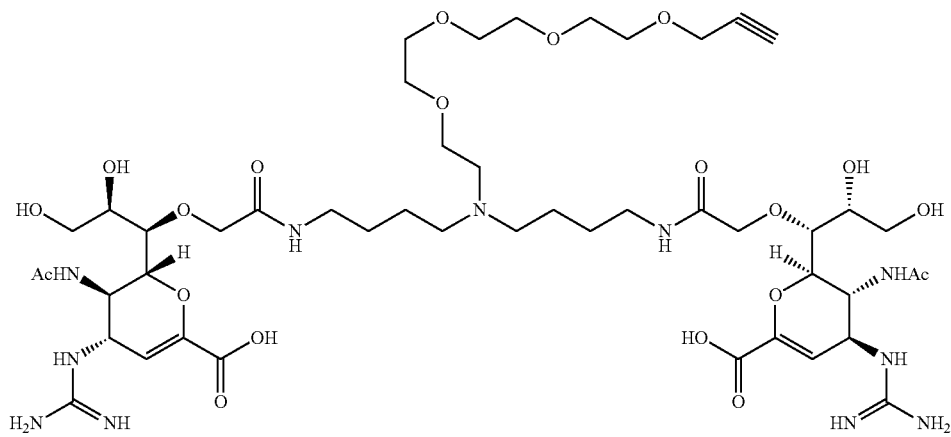 [SMILES: C#CCOCCOCCOCCOCCN(CCCCNC(=O)CO[C@@H]([C@@H]1OC(C(=O)O)=C[C@H](NC(=N)N)[C@H]1NC(C)=O)[C@H](O)CO)CCCCNC(=O)CO[C@@H]([C@@H]1OC(C(=O)O)=C[C@H](NC(=N)N)[C@H]1NC(C)=O)[C@H](O)CO]

Product from the previous step (120 mg, 0.075 mmol) was treated with 2 ml trifluoroacetic acid and stirred for 30 min at room temperature. The resulting solution was concentrated, dissolved into water (2 mL), then treated with a solution of lithium hydroxide (12 mg, 0.5 mmol) dissolved in water (1 mL). The resulting solution was stirred 10 min, then made slightly acidic with 0.1 ml acetic acid, concentrated and purified by reverse phase liquid chromatography (RPLC) using an Isco COMBIFLASH® liquid chromatograph eluted with 0% to 30% acetonitrile and water, using 0.1% TFA as the modifier. Yield of the products 48 mg as TFA salt, 57%. Ion(s) found by LCMS: M/2+H=559.757. M/3+H=373.5.

Example 47. Synthesis of Conjugate 8

A solution of h-IgG1 Fc-PEG4-azide in PBS×1 buffer solution (100 mg, 1.71 μmol, 7.011 mL, MW=58200 Da, DAR=3.7) were added alkyne derivatized small molecule (Int-12 TFA salt, 45 mg, 0.031 mmol) and freshly prepared pH 7.4 PBS solutions of CuSO4 (0.7 mL of 50.0 mM, 20 eq), tris(3-hydroxypropyltriazolylmethyl)-amine (THPTA, 0.7 mL of 50.0 mM, 20 eq), and sodium ascorbate (1.05 mL of 50.0 mM, 30 eq). The resulting homogeneous solution was agitated by rocker table for 12 h. The crude solutions were diluted with pH 7.4 PBS to a final concentration of 1 mg/mL, and ultra filtered (10,000 MWCO) to a volume of 1 mL, two times. The crude mixtures were then diluted 1:10 in PBS pH 7.4, and purified using MabSelect Sure Resin (GE Healthcare, Chicago, Ill., USA), followed by size exclusion chromatography. Purified material was quantified using a NANODROP™ UV visible spectrophotometer (using a calculated extinction coefficient based on the amino acid sequence of the Fc used in the conjugation, and concentrated to approximately 10 mg/mL using a centrifugal concentrator (10,000 MWCO). Purified molecules were analyzed using 4-12% Bis Tris SDS PAGE gels by loading 1-2 μg of each molecule into the gel, and staining using instant Blue staining. Each gel included a molecular weight ladder with the indicated molecular weight standards (FIG. 42). Yields are typically 40-60%. MALDI MS analysis showed a range of masses (60000-90000) with an average of mass of 62358. Average DAR=3.

Example 48. Comparison of In Vitro and In Vivo Potency of Selected Inhibitors with their Fc-Conjugates in CPE Assays and in a Lethal Mouse Influenza Model To demonstrate that conjugation of neuraminidase inhibitors described herein to Fc enhances their activities in viral replication assays and in in vivo efficacy models, we compared the activities of selected unconjugated inhibitors to their Fc conjugates in Cytopathic Effect (CPE) assays, and in a lethal mouse influenza infection model. For the CPE microneutralization assay, ten two-fold serial dilutions of each test article (TA), starting at 160 nM or 400 nM (9600 nM for zanamivir and oseltamivir controls), were prepared in duplicate for one-hour inoculation with INFV A (A/CA/09 H1N1) at a multiplicity of infection (MOI) 0.001 and INFV B at a MOI of 0.01 for one-hour incubation. The TA-virus mix was then added to MDCK cells seeded in 96-well plates, and incubated for one hour. On day 3 post infection for INFV A and 5 for INFV B (B/Brisbane), Cells were fixed and stained with crystal violet and optical density was read for calculation of 50 percent effective concentration ($EC_{50}$) of each TA using XLfit dose response model. The intrinsic cytotoxicity of each TA was also evaluated using ten two-fold serial dilutions of each TA starting at 160 nM or 400 nM were prepared in duplicate for inoculation with MDCK cells in 96-well culture plates. The cell viability was determined 3 and 5 days post treatment using CellTiter-Glo kit. 50% of cytotoxicity concentration ($CC_{50}$) was calculated using XLfit dose response model. No cytotoxicity was observed for any of the TAs to the highest concentrations tested. A summary of the CPE-based microneutralization assay is shown in Table 23.

TABLE 23

CPE-based microneutralization assay

| | $EC_{50}$ vs INFV A (nM) | $EC_{50}$ vs INFV B (nM) |
|---|---|---|
| Oseltamivir | 390.0 | 1065.0 |
| Zanamivir | 264.8 | 382.6 |
| Int -7 (Targeting Moiety corresponding to Conjugate 6) | 665.7 | 106.6 |
| Int-12 (Targeting Moiety corresponding to Conjugate 8) | 15.4 | 0.6 |
| Conjugate 6 | 4.0 | 52.1 |
| Conjugate 8 | 0.6 | 0.3 |

The data summarized in Table 23 demonstrate that the Fc-conjugated forms of the neuraminidase dimers possess superior activity in CPE microneutralization assay to their unconjugated counterpart. Enhancements of 166-fold and 2-fold, versus INFV A and INFV B, respectively, were observed when comparing Conjugate 6 to Int-7. Enhancements of 26-fold and 2-fold, versus INFV A and INFV B, respectively, were observed when comparing Conjugate 8 to Int-12.

Conjugate 6 was compared to a the most potent neuraminidase inhibitor dimer from the study summarized in Table 23 (Int-11, dimer-only corresponding to Int-12 without the trimeric linker allowing for conjugation to an Fc) in a lethal IAV H1N1 influenza infection model using female BALB/c mice (Charles River Laboratories, 6-8 weeks). The challenge virus (A/Puerto Rico/08/1934, aka PR8) is a mouse-adapted isolate with a $LD_{90}$ of approximately 30 plaque-forming units (pfu) per mouse.

The experiment comprised 8 groups of 5 mice. At day 0, all mice were challenged with PR8 at 10× the $LD_{90}$ by intranasal inoculation in a volume of 50 μl, to mice anesthetized with a mixture of ketamine/xylazine (150 and 10 mg/kg respectively). Groups received a single treatment of vehicle, hIgG1 Fc only, conjugate 6, or Int-11 by IV, 2 hours after challenge (Table 24; groups 1-6). Group 7 received Int-11 (15 mg/kg) twice daily (bid) for 5 days, also by IV. Group 8 received oseltamivir (15 mg/kg) orally (PO), bid, for 5 days. All mice were monitored for survival (Table 25) and weight loss (data not shown) for 10 days after viral challenge.

As expected, mice treated with vehicle or hIgG1 Fc only succumbed to the infection by day 7 (Table 25). Mice treated with 10 doses (150 mg/mouse in total) of oseltamivir demonstrated a statistically significant delay in death but only a single animal survived until day 10. All mice receiving a single dose of conjugate 6 at 0.3 or 3 mg/kg survived to the end of the study and showed a net weight gain over the course of the experiment. Importantly, all mice receiving the Int-11 at 0.3 or 3 mg/kg died over the course of the study, with only a minimal (2 days or less) delay in death relative to the vehicle and hIgG1 Fc only controls. As the hIgG1 Fc has no inherent antiviral activity (group 2) this suggests the greatly improved activity of conjugate 6 is the result of the improved avidity resulting from the multivalent display on an Fc, as suggested by the results summarized in Table 23, as well as improved pharmacokinetics and contribution from Fc mediated immune engagement. The difference in activity between the inhibitor dimer alone and conjugate 6 was statistically significant at both dose concentrations (compare groups 3 and 6, and groups 4 and 5; Table 25). On a mass basis, a 500× greater cumulative dose of Int-11 was required to observe equivalent efficacy to conjugate 6.

TABLE 24

Study design

| Group n = 5 | Challenge Day 0 | Compound | Dose (mg/kg) | Treatment Route/ Schedule |
|---|---|---|---|---|
| 1 | Influenza A virus | Vehicle (PBS) | N/A | IV, Singe dose starting |
| 2 | (H1N1) A/Puerto | hIgG1 Fc only | 3 | 2 hours post infection |
| 3 | Rico/08/1934 | Conjugate 6 | 3 | |
| 4 | by way | Conjugate 6 | 0.3 | |
| 5 | of IN route. | Int-11 | 0.3 | |
| 6 | | Int-11 | 3 | |
| 7 | | Int-11 | 15 | IV, bid for 5 days starting 2 hours post infection |
| 8 | | Oseltamivir (TAMIFLU ™) | 20 | PO, bid for 5 days starting 2 hours post infection |

TABLE 25

Mouse survival

| Group | Test article | Dose (mg/ kg) | Dosing schedule | % Survival | Significance to vehicle | Significance to Int-11 0.3 mg/kg* or 3 mg/kg^ |
|---|---|---|---|---|---|---|
| 1 | Vehicle (PBS) | | IV, Single | 0 | | |
| 2 | hIgG1 Fc only | 3 | IV, Single | 0 | NS | |
| 3 | Conjugate 6 | 3 | IV, Single | 100 | 0.0027 | 0.0035 |
| 4 | Conjugate 6 | 0.3 | IV, Single | 100 | 0.0027 | 0.0027* |
| 5 | Int-11 | 0.3 | IV, Single | 0 | 0.0027 | |
| 6 | Int-11 | 3 | IV, Single | 0 | 0.0027 | |
| 7 | Int-11 | 15 | IV, bid × 5 days | 100 | 0.0027 | |
| 8 | Oselta-mivir | 15 | PO, bid × 5 days | 20 | 0.0027 | |

Example 49. Synthesis of Int-13 ((5R)-((1R)-Acetylamino-(2S)-methoxy-(2S)-methylpentyl)-(4S)-E/Z-[3-(propargyl-PEG4)-propenyl]-pyrrolidine-(2R)-carboxylic acid)
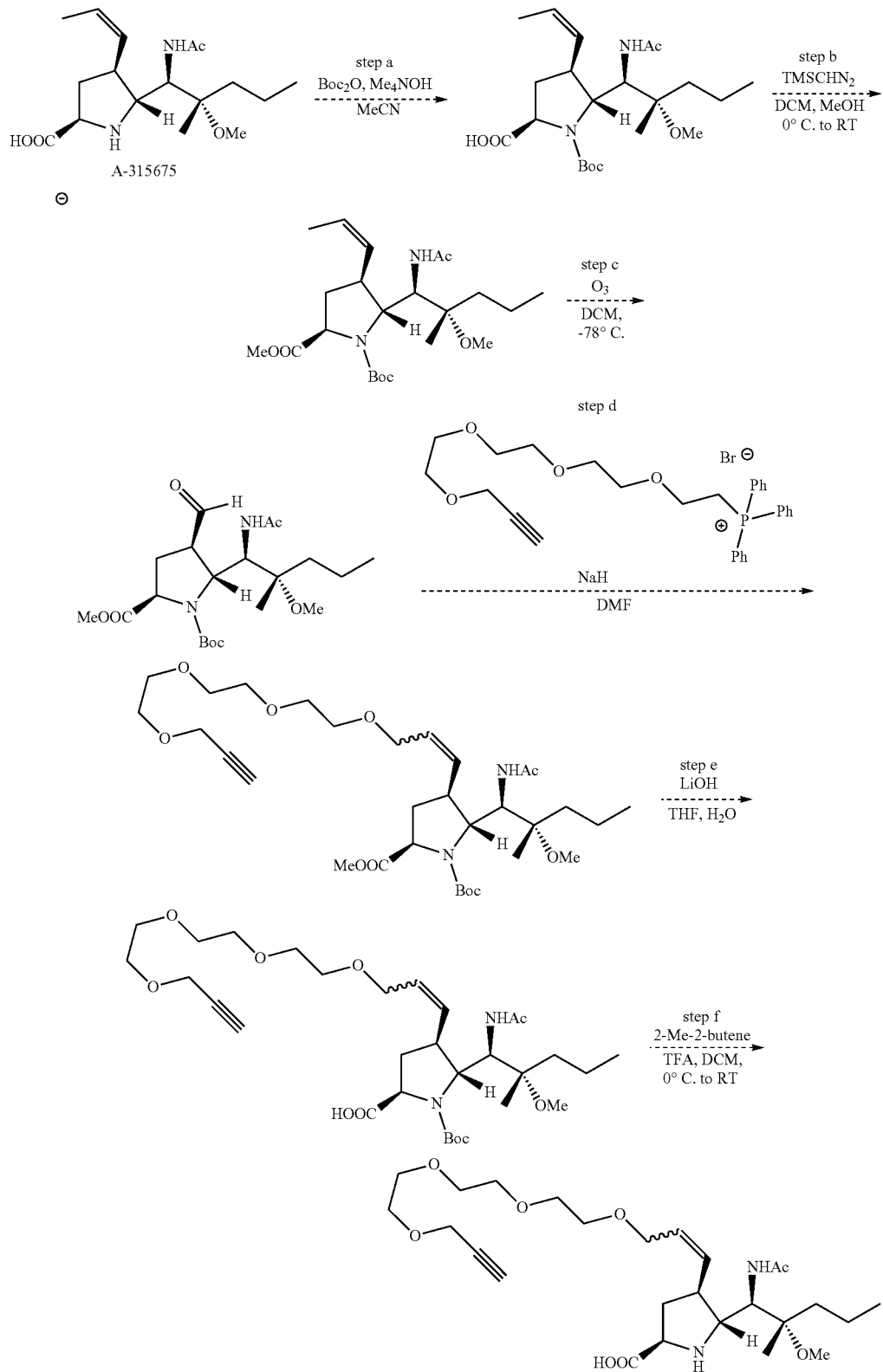

Step a. (2R)-((1R)-Acetylamino-(2S)-methoxy-(2S)-methylpentyl)-(5R)-carboxy-(3S)-Z-propenylpyrrolidine-1-carboxylic acid tert-butyl ester.

To a stirring mixture of (5R)-((1R)-acetylamino-(2S)-methoxy-(2S)-methylpentyl)-(4S)-Z-propenylpyrrolidine-(2R)-carboxylic acid, HCl salt (prepared accordingly to reference JACS, 2002, 124, 4716-4721; 1.0 mmol) in acetonitrile (10 mL) it is added trimethylammonium hydroxide (1.5 mmol). After stirring for 3 h at room temperature the di-tert-butyldicarbonate (4 eqmol) is added. Upon reaction completion, all the volatiles are evaporated per vacuum techniques. The residue is diluted with water (10 ml). Ethyl acetate (10 ml) is added, and 1 M sulfuric acid aqueous solution is added until the water layer reaches pH ~3. The water layer is washed with two additional aliquots of ethyl acetate (10 mL). The combined organics are dried over sodium sulfate, filtered and concentrated. The residue is purified by chromatographic techniques to afford the desired product.

Step b. (2R)-((1R)-Acetylamino-(2S)-methoxy-(2S)-methylpentyl)-(5R)-carboxymethyl-(3S)-Z-propenylpyrrolidine-1-carboxylic acid tert-butyl ester.

To a 0° C. stirring mixture of (2R)-((1R)-acetylamino-(2S)-methoxy-(2S)-methylpentyl)-(5R)-carboxy-(3S)-Z-propenylpyrrolidine-1-carboxylic acid tert-butyl ester (1.0 mmol) in dichloromethane (5.0 mL) and methanol (1.0 mL) it is slowly added (trimethylsilyl)diazomethane (1.1 mmol). The mixture is stirred until completion, while temperature is gently allowed to reach ambient. All the volatiles are evaporated per vacuum techniques. If necessary, the residue is purified by chromatographic techniques to afford the desired product.

Step c. (2R)-((1R)-Acetylamino-(2S)-methoxy-(2S)-methylpentyl)-(5R)-carboxymethyl-(3S)-formylpyrrolidine-1-carboxylic acid tert-butyl ester.

A room temperature mixture of (2R)-((1R)-acetylamino-(2S)-methoxy-(2S)-methylpentyl)-(5R)-carboxymethyl-(3S)-Z-propenylpyrrolidine-1-carboxylic acid tert-butyl ester (1 mmol) in dichloromethane (15 mL) is cooled to −78° C. Ozone is bubbled through the solution until a faint blue color of dissolved ozone persists. Nitrogen is bubbled through the solution until blue color disappears, then dimethyl sulfide (4.0 mmol) is added, the flask transferred into a freezer (−20° C.) and let sit for 1 hour. The solution is concentrated and the residue is purified by chromatographic techniques to afford the desired product.

Step d. (2R)-((1R)-Acetylamino-(2S)-methoxy-(2S)-methylpentyl)-(5R)-carboxymethyl-(3S)-E/Z-[3-(propargyl-PEG4)-propenyl]pyrrolidine-1-carboxylic acid tert-butyl ester.

To a 0° C. stirring mixture of propargyl-PEG4-phosphonium bromide (1.0 mmol) in DMF (5.0 mL) it is added sodium hydride (1.1 mmol), and after 10 minutes temperature is raised to ambient. Stirring is continued for 1 h, then (2R)-((1R)-Acetylamino-(2S)-methoxy-(2S)-methylpentyl)-(5R)-carboxymethyl-(3S)-formylpyrrolidine-1-carboxylic acid tert-butyl ester (1.0 mmol) is added in DMF (1.0 mL). Upon completion, the reaction is quenched by saturated ammonium chloride solution. The aqueous solution is extracted several times with ethyl acetate, and the combined organic phases are washed with brine, dried, and evaporated. The residue is purified by chromatographic techniques to afford the desired product.

Step e. (2R)-((1R)-Acetylamino-(2S)-methoxy-(2S)-methylpentyl)-(5R)-carboxy-(3S) E/Z-[3-(propargyl-PEG4)-propenyl]pyrrolidine-1-carboxylic acid tert-butyl ester.

To a 0° C. stirring mixture of (2R)-((1R)-Acetylamino-(2S)-methoxy-(2S)-methylpentyl)-(5R)-carboxymethyl-(3S)-E/Z-[3-(propargyl-PEG4)-propenyl]pyrrolidine-1-carboxylic acid tert-butyl ester (1.0 mmol) in tetrahydrofuran (12.0 mL) and water (3.0 mL) it is added lithium hydroxide (1.1 mmol). Stirring is continued and the temperature is raised to ambient after 15 minutes. Upon completion, the solution is brought to acidic pH by the means of the excess addition of AMBERLITE® IRN-77 resin. The mixture is filtered and the filtrate is concentrated per vacuum techniques, yielding to the title compound. If necessary, the residue is purified by chromatographic techniques to afford the desired product.

Step f. (5R)-((1R)-Acetylamino-(2S)-methoxy-(2S)-methylpentyl)-(4S)-E/Z-[3-(propargyl-PEG4)-propenyl]-pyrrolidine-(2R)-carboxylic acid.

To a 0° C. stirring mixture of (2R)-((1R)-Acetylamino-(2S)-methoxy-(2S)-methylpentyl)-(5R)-carboxy-(3S) E/Z-[3-(propargyl-PEG4)-propenyl]pyrrolidine-1-carboxylic acid tert-butyl ester (1.0 mmol) and 2-methyl-2-butene (0.5 mL) in dichloromethane (8.0 mL), it is added trifluoroacetic acid (4.0 mL).

After 10 minutes, the temperature is raised to ambient. Upon completion, all the volatiles are evaporated per vacuum techniques. The residue is purified by chromatographic techniques to afford the desired product.

Example 50. Synthesis of Conjugate 9

A solution of hIgG1 Fc-PEG4-azide in pH 7.4 PBS×1 buffer solution (100 mg, 1.71 µmol, 7.011 mL, MW=58,200 Da, DAR=3.7) is added to a pH 7.4 PBS×1 buffer solution (2.45 mL) of Int-13 ((5R)-((1R)-Acetylamino-(2S)-methoxy-(2S)-methylpentyl)-(4S)-E/Z-[3-(propargyl-PEG4)-propenyl]-pyrrolidine-(2R)-carboxylic acid) (0.031 mmol), cupric sulfate (0.62 mmol), tris(3-hydroxypropyltriazolylmethyl)-amine (0.62 mmol), and sodium ascorbate (0.93 mmol). The resulting homogeneous solution is gently shaken with a rocker table for 12 h. The crude solution is diluted with pH 7.4 PBS to a final concentration of 1 mg/mL, and ultra-filtered (10,000 MWCO) to a volume of 1 mL, for two times. The crude mixture is then diluted 1:10 in PBS pH 7.4, and purified using MabSelect Sure Resin (GE Healthcare, Chicago, Ill., USA), followed by size exclusion chromatography. Purified material is quantified using a NANODROP™ UV visible spectrophotometer (using a calculated extinction coefficient based on the amino acid sequence of the Fc used in the conjugation, and concentrated to approximately 10 mg/mL using a centrifugal concentrator (10,000 MWCO). Purified molecules are analyzed using 4-12% Bis Tris SDS PAGE gels by loading 1-2 ug of each molecule into the gel, and staining using instant Blue staining. Each gel includes a molecular weight ladder with the indicated molecular weight standards. MALDI MS analysis is used to determine the average DAR.

Example 51. Synthesis of propargyl-PEG4-phosphonium bromide

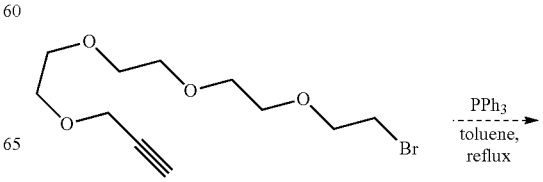

751
-continued

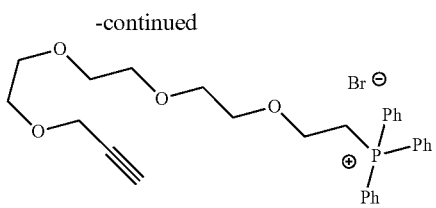

A mixture of propargyl-PEG4-bromide (1.0 mmol) and triphenylphosphine (1.2 mmol) in toluene (10 mL) are refluxed. Upon completion, the mixture is cooled to ambient. The solids are filtered and used in the next step without any additional purification.

Example 52. Synthesis of Int-14 ((5R)-[(1R)-(propargyl-PEG4-carboxyamide)-(2S)-methoxy-(2S)-methylpentyl]-(4S)-Z-propenylpyrrolidine-(2R)-carboxylic acid, HCl salt)

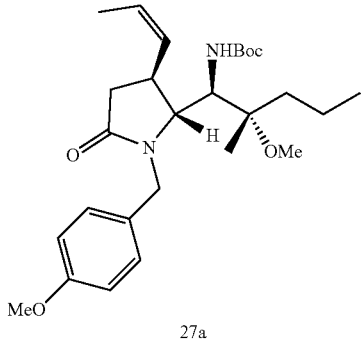

27a step a
1. TFA, DCM, 0° C. to RT
2. Propargyle-PEG4-acid, DIPEA, HATU DMF, 0° C. to RT

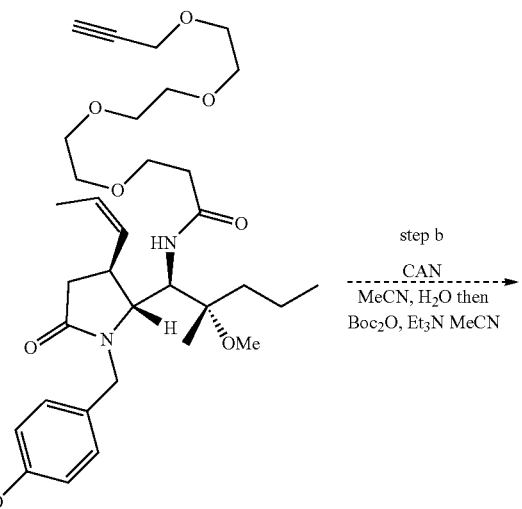

step b
CAN
MeCN, H₂O then
Boc₂O, Et₃N MeCN

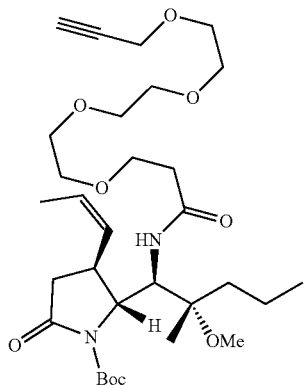

step c
Super-H
THF, -78° C.
then
pTsOH
MeOH

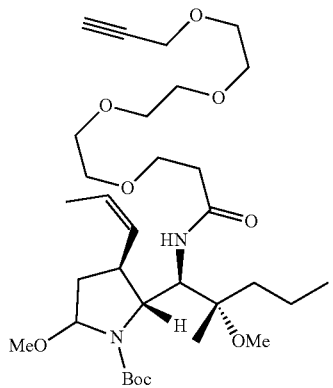

step d
TMSCN, Et₂O BF₃
DCM, -78° C.
to -50° C.

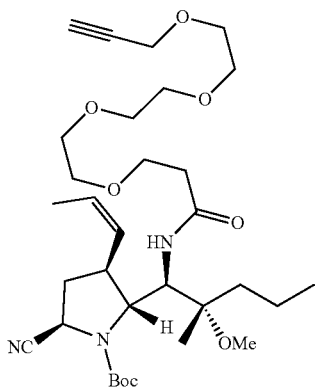

step e
HCl
AcOH

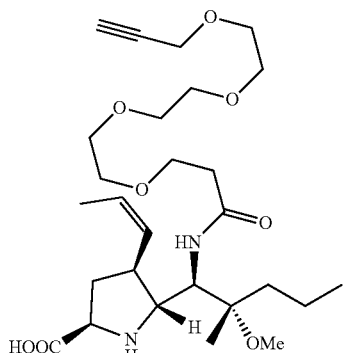

Step a. N-{(2.S)-methoxy-((1R)-[1-(4-methoxybenzyl)-5-oxo-(3S)-Z-propenylpyrrolidin-(2R)-yl]-(2S)-methylpentyl}-(propargyl-PEG4)-carboxyamide.

To 0° C. a stirring mixture of {(2S)-Methoxy-(1R)-[1-(4-methoxybenzyl)-5-oxo-(3S)-Z-propenylpyrrolidin-(2R)-yl]-(2S)-methylpentyl}-carbamic acid tert-butyl ester (it is prepared accordingly to reference *JACS,* 2002, 124, 4716-4721; 1.0 mmol) in dry dichloromethane (5 mL) is added trifluoroacetic acid (10 mmol), and the temperature is raised to ambient. Upon completion, the solvent is removed under reduced pressure. The resulting residue is dissolved in dichloromethane (20 mL) and extracted with a saturated aqueous solution of sodium bicarbonate. The organic layer is separated, dried (sodium sulfate), filtered and evaporated. The crude amine is dissolved in DMF (5 mL) and treated at 0° C. under stirring with propargyl-PEG4-acid (1.1 mmol), diisopropylethylamine (3.0 mmol) and HATU (1.1 mmol). Upon reaction completion, all the volatiles are evaporated per vacuum techniques. The residue is taken up in ethyl acetate (15 ml), and washed with saturated aqueous solution of sodium bicarbonate (10 mL), then 1 M sulfuric acid aqueous solution (10 mL). The combined organics are dried over sodium sulfate, filtered and concentrated. The residue is purified by chromatographic techniques to afford the desired product.

Step b. (2R)-((1R)-(propargyl-PEG4-carboxyamide)-(2S)-methoxy-(2S)-methylpentyl)-(5R)-oxo-(3S)-Z-propenylpyrrolidine-1-carboxylic acid tert-butyl ester.

To a stirring solution of N-{(2.S)-methoxy-(1R)-[1-(4-methoxybenzyl)-5-oxo-(3S)-Z-propenylpyrrolidin-(2R)-yl]-(2S)-methylpentyl}-(propargyl-PEG4)-carboxyamide (1.0 mmol) in a mixture of acetonitrile and water (10:1, 5 mL) is added ceric ammonium nitrate (2.0 mmol) in small portions at 45° C. during 1 h, and stirring is continued until completion. The reaction is quenched with a saturated aqueous solution of sodium bicarbonate (5 mL). The aqueous layer is extracted with EtOAc (3×10 mL), the combined organic layers are dried (sodium sulfate) and evaporated to give a crude which is used for the next step without further purification. The material is dissolved in acetonitrile (5 mL), di-tert-butylcarbonate is added (1.5 mmol) followed by triethylamine (2.0 mmol) and DMAP (catalytic). Upon completion, the reaction is quenched with a saturated solution of ammonium chloride (5 mL). The aqueous layer is extracted with EtOAc (3×10 mL), and the combined organic layers are dried (sodium sulfate). All the volatiles are removed per vacuum techniques. If necessary, the residue is purified by chromatographic techniques to afford the desired product.

Step c. (2R)-((1R)-(propargyl-PEG4-carboxyamide)-(2S)-methoxy-(2S)-methylpentyl)-(5R/S)-methoxy-(3S)-Z-propenylpyrrolidine-1-carboxylic acid tert-butyl ester.

To a –78° C. stirring solution of (2R)-((1R)-(propargyl-PEG4-carboxyamide)-(2S)-methoxy-(2S)-methylpentyl)-(5R)-oxo-(3S)-Z-propenylpyrrolidine-1-carboxylic acid tert-butyl ester (1.0 mmol) in THF (8 mL) is added SUPER-HYDRIDE® (1 M in THF, 2.2 mmol). After 30 min the reaction mixture is quenched with a saturated aqueous solution of sodium bicarbonate (4 mL) and 30% hydrogen peroxyde (5 drops). The mixture is warmed up to rt and stirred for another 30 min and the aqueous layer is extracted with EtOAc (3×10 mL). The combined organic layers are dried (sodium sulfate) and the solvent is evaporated to give the hemiaminal, which is used without further purification. To a solution of the above product in methanol (16 mL) is added p-toluenesulfonic acid hydrate (0.1 mmol) at rt. The reaction mixture is stirred overnight and is quenched with a saturated aqueous solution of sodium bicarbonate (10 mL). Methanol is removed under reduced pressure, water (10 mL) is added to the resulting residue and extracted with EtOAc (3×10 mL). The organics are separated and dried with brine and sodium sulfate, filtered and concentrated. If necessary, the residue is purified by chromatographic techniques to afford the desired product.

Step d. (2R)-((1R)-(propargyl-PEG4-carboxyamide)-(2S)-methoxy-(2S)-methylpentyl)-(5R)-cyano-(3S)-Z-propenylpyrrolidine-1-carboxylic acid tert-butyl ester.

To a –78° C. stirring solution of (2R)-((1R)-(propargyl-PEG4-carboxyamide)-(2S)-methoxy-(2S)-methylpentyl)-(5R/S)-methoxy-(3S)-Z-propenylpyrrolidine-1-carboxylic acid tert-butyl ester (1.0 mmol) in dichloromethane (20 mL) it is added trimethylsilyl cyanide (2.0 mmol) followed by boron trifluoride diethyl etherate (1.2 mmol). The reaction mixture is stirred from –78° C. to –50° C. over a period of 3 h. A saturated aqueous solution of sodium bicarbonate (40 mL) is added and the aqueous layer is extracted with EtOAc (3×15 mL). The combined organic layers are dried (sodium sulfate), filtered and concentrated under reduced pressure. The resulting residue consisting of a mixture of epimeric cyano derivatives is purified by chromatographic techniques to afford the desired product.

Step e. (5R)-[(1R)-(propargyl-PEG4-carboxyamide)-(2S)-methoxy-(2S)-methylpentyl]-(4S)-Z-propenylpyrrolidine-(2R)-carboxylic acid, HCl salt.

To a solution of (2R)-((1R)-(propargyl-PEG4-carboxyamide)-(2S)-methoxy-(2S)-methylpentyl)-(5R)-cyano-(3S)-Z-propenylpyrrolidine-1-carboxylic acid tert-butyl ester (1.0 mmol) in AcOH (10 mL), 12N HCl (10 mL) is added at rt. The solution is stirred at rt until completion, the solvent is evaporated under reduced pressure. If necessary, the residue is purified by chromatographic techniques to afford the desired product.

Example 53. Synthesis of Conjugate 10

A solution of hIgG1 Fc-PEG4-azide in pH 7.4 PBS×1 buffer solution (100 mg, 1.71 µmol, 7.011 mL, MW=58,200 Da, DAR=3.7) is added to a pH 7.4 PBS×1 buffer solution (2.45 mL) of Int-14 ((5R)-[(1R)-(propargyl-PEG4-carboxyamide)-(2S)-methoxy-(2S)-methylpentyl]-(4S)-Z-propenylpyrrolidine-(2R)-carboxylic acid, HCl salt) (0.031 mmol), cupric sulfate (0.62 mmol), tris(3-hydroxypropyltriazolylmethyl)-amine (0.62 mmol), and sodium ascorbate (0.93 mmol). The resulting homogeneous solution is gently shaken with a rocker table for 12 h. The crude solution is diluted with pH 7.4 PBS to a final concentration of 1 mg/mL, and ultra-filtered (10,000 MWCO) to a volume of 1 mL, for two times. The crude mixture is then diluted 1:10 in PBS pH 7.4, and purified using MabSelect Sure Resin (GE Healthcare, Chicago, Ill., USA), followed by size exclusion chromatography. Purified material is quantified using a NANODROP™ UV visible spectrophotometer (using a calculated extinction coefficient based on the amino acid sequence of the Fc used in the conjugation, and concentrated to approximately 10 mg/mL using a centrifugal concentrator (10,000 MWCO). Purified molecules are analyzed using 4-12% Bis Tris SDS PAGE gels by loading 1-2 µg of each molecule into the gel, and staining using instant Blue staining. Each gel includes a molecular weight ladder with the indicated molecular weight standards. MALDI MS analysis is used to determine the average DAR.

Example 54. Synthesis of Int-15, HCl salt
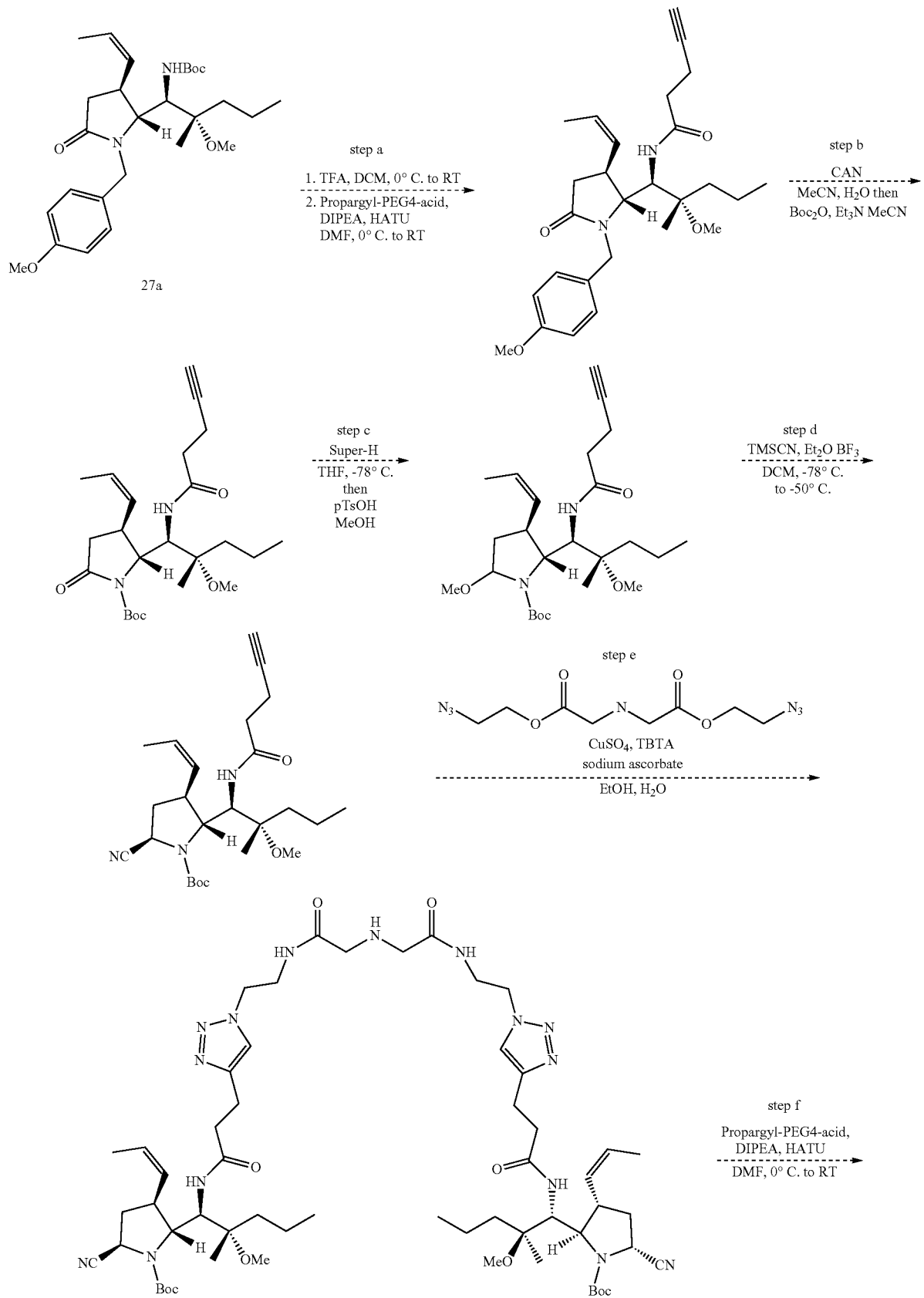

-continued

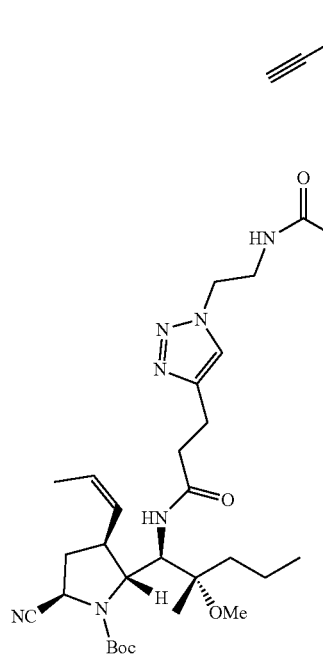

step g
HCl
―――→
AcOH

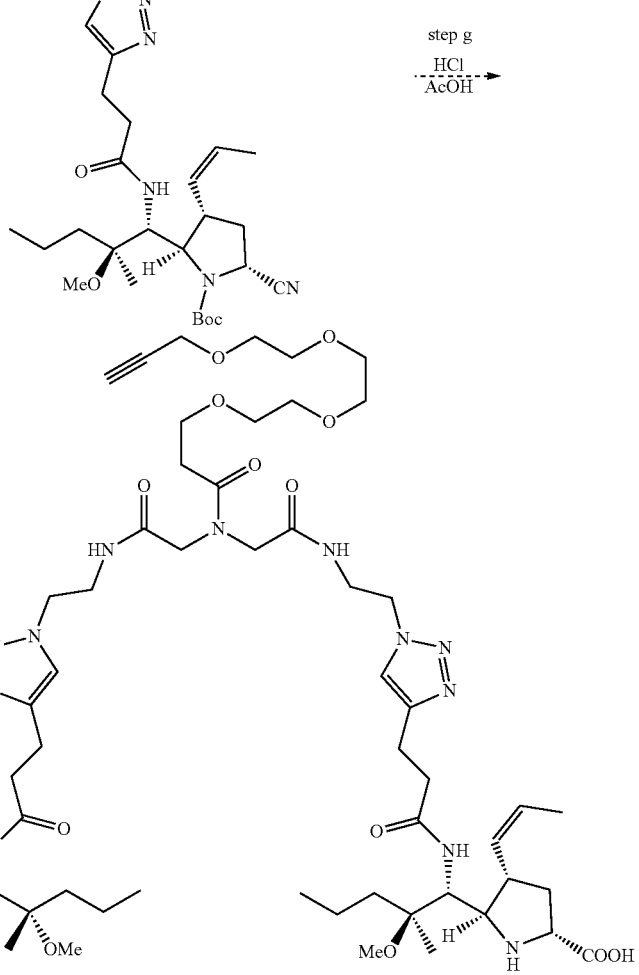

Step a. N-{(2.S)-methoxy-((1R)-[1-(4-methoxybenzyl)-5-oxo-(3S)-Z-propenylpyrrolidin-(2R)-yl]-(2S)-methylpentyl}-(3-butynyl)-carboxyamide.

To 0° C. a stirring mixture of {(2S)-Methoxy-(1R)-[1-(4-methoxybenzyl)-5-oxo-(3S)-Z-propenylpyrrolidin-(2R)-yl]-(2S)-methylpentyl}-carbamic acid tert-butyl ester (it is prepared accordingly to reference *JACS,* 2002, 124, 4716-4721; 1.0 mmol) in dry dichloromethane (5 mL) is added trifluoroacetic acid (10 mmol), and the temperature is raised to ambient. Upon completion, the solvent is removed under reduced pressure. The resulting residue is dissolved in dichloromethane (20 mL) and extracted with a saturated aqueous solution of sodium bicarbonate. The organic layer is separated, dried (sodium sulfate), filtered and evaporated. The crude amine is dissolved in DMF (5 mL) and treated at 0° C. under stirring with 4-pentynoic acid (1.1 mmol), diisopropylethylamine (3.0 mmol) and HATU (1.1 mmol). Upon reaction completion, all the volatiles are evaporated per vacuum techniques. The residue is taken up in ethyl acetate (15 ml), and washed with saturated aqueous solution of sodium bicarbonate (10 mL), then 1 M sulfuric acid aqueous solution (10 mL). The combined organics are dried over sodium sulfate, filtered and concentrated. The residue is purified by chromatographic techniques to afford the desired product.

Step b. (2R)-((1R)-(4-pentynoyl)-(2S)-methoxy-(2S)-methylpentyl)-(5R)-oxo-(3S)-Z-propenylpyrrolidine-1-carboxylic acid tert-butyl ester.

To a stirring solution of N-{(2.S)-methoxy-((1R)-[1-(4-methoxybenzyl)-5-oxo-(3S)-Z-propenylpyrrolidin-(2R)-yl]-

(2S)-methylpentyl}-(3-butynyl)-carboxyamide (1.0 mmol) in a mixture of acetonitrile and water (10:1, 5 mL) is added ceric ammonium nitrate (2.0 mmol) in small portions at 45° C. during 1 h, and stirring is continued until completion. The reaction is quenched with a saturated aqueous solution of sodium bicarbonate (5 mL). The aqueous layer is extracted with EtOAc (3×10 mL), the combined organic layers are dried (sodium sulfate) and evaporated to give a crude which is used for the next step without further purification. The material is dissolved in acetonitrile (5 mL), di-tert-butylcarbonate is added (1.5 mmol) followed by triethylamine (2.0 mmol) and DMAP (catalytic). Upon completion, the reaction is quenched with a saturated solution of ammonium chloride (5 mL). The aqueous layer is extracted with EtOAc (3×10 mL), and the combined organic layers are dried (sodium sulfate). All the volatiles are removed per vacuum techniques. If necessary, the residue is purified by chromatographic techniques to afford the desired product.

Step c. (2R)-((1R)-(4-pentynoyl)-(2S)-methoxy-(2S)-methylpentyl)-(5R/S)-methoxy-(3S)-Z-propenylpyrrolidine-1-carboxylic acid tert-butyl ester.

To a −78° C. stirring solution of (2R)-((1R)-(2R)-((1R)-(4-pentynoyl)-(2S)-methoxy-(2S)-methylpentyl)-(5R)-oxo-(3S)-Z-propenylpyrrolidine-1-carboxylic acid tert-butyl ester (1.0 mmol) in THF (8 mL) is added SUPER-HYDRIDE® (1 M in THF, 2.2 mmol). After 30 min the reaction mixture is quenched with a saturated aqueous solution of sodium bicarbonate (4 mL) and 30% hydrogen peroxide (5 drops). The mixture is warmed up to rt and stirred for another 30 min and the aqueous layer is extracted with EtOAc (3×10 mL). The combined organic layers are dried (sodium sulfate) and the solvent is evaporated to give the hemiaminal, which is used without further purification. To a solution of the above product in methanol (16 mL) is added p-toluenesulfonic acid hydrate (0.1 mmol) at rt. The reaction mixture is stirred overnight and is quenched with a saturated aqueous solution of sodium bicarbonate (10 mL). Methanol is removed under reduced pressure, water (10 mL) is added to the resulting residue and extracted with EtOAc (3×10 mL). The organics are separated and dried with brine and sodium sulfate, filtered and concentrated. If necessary, the residue is purified by chromatographic techniques to afford the desired product.

Step d. (2R)-((1R)-(4-pentynoyl)-(2S)-methoxy-(2S)-methylpentyl)-(5R)-cyano-(3S)-Z-propenylpyrrolidine-1-carboxylic acid tert-butyl ester.

To a −78° C. stirring solution of (2R)-((1R)-(4-pentynoyl)-(2S)-methoxy-(2S)-methylpentyl)-(5R/S)-methoxy-(3S)-Z-propenylpyrrolidine-1-carboxylic acid tert-butyl ester (1.0 mmol) in dichloromethane (20 mL) it is added trimethylsilyl cyanide (2.0 mmol) followed by boron trifluoride diethyl etherate (1.2 mmol). The reaction mixture is stirred from −78° C. to −50° C. over a period of 3 h. A saturated aqueous solution of sodium bicarbonate (40 mL) is added and the aqueous layer is extracted with EtOAc (3×15 mL). The combined organic layers are dried (sodium sulfate), filtered and concentrated under reduced pressure. The resulting residue consisting of a mixture of epimeric cyano derivatives is purified by chromatographic techniques to afford the desired product.

Step e.

To a stirring mixture of N-{(2.S)-methoxy-((1R)-[1-(4-methoxybenzyl)-5-oxo-(3S)-Z-propenylpyrrolidin-(2R)-yl]-(2S)-methylpentyl}-(3-butynyl)-carboxyamide (1.0 mmol), bis-[N'-(2-azidoethyl)]-iminodiacetic amide (0.5 mmol), 1H-1,2,3-Triazole-4-methanamine, 1-(phenylmethyl)-N,N-bis[1-(phenylmethyl)-1 H-1,2,3-triazol-4-yl]methyl]-(0.1 mmol) and sodium ascorbate (1.0 mmol) in ethanol (5 mL) and water (5 mL), it is added copper sulfate (0.1 mmol). Upon completion, the reaction is treated with SiliaMetS TAAcONa (0.3 mmol) for 30 minutes. The reaction is filtered and all the volatiles are evaporated per vacuum techniques. The residue is purified by chromatographic techniques to afford the desired product.

Step f.

To 0° C. a stirring solution of the intermediate from step e. (1.0 mmol), propargyl-PEG4-acid (1.05 mmol), and DIPEA (3.0 mmol) in DMF (10 mL) it is added HATU (2.0 mmol). All the volatiles are evaporated per vacuum techniques and the residue is purified by chromatographic techniques to afford the desired product.

Step g. Int-15, HCl salt

To a solution of the intermediate from step f. (1.0 mmol) in AcOH (10 mL), 12N HCl (10 mL) is added at rt. The solution is stirred at rt until completion, the solvent is evaporated under reduced pressure. If necessary, the residue is purified by chromatographic techniques to afford the desired product.

Example 55. Synthesis of Conjugate 11

A solution of hIgG1 Fc-PEG4-azide in pH 7.4 PBS×1 buffer solution (100 mg, 1.71 μmol, 7.011 mL, MW=58,200 Da, DAR=3.7) is added to a pH 7.4 PBS×1 buffer solution (2.45 mL) of Int-15 HCl salt (0.031 mmol), cupric sulfate (0.62 mmol), tris(3-hydroxypropyltriazolylmethyl)-amine (0.62 mmol), and sodium ascorbate (0.93 mmol). The resulting homogeneous solution is gently shaken with a rocker table for 12 h. The crude solution is diluted with pH 7.4 PBS to a final concentration of 1 mg/mL, and ultra-filtered (10,000 MWCO) to a volume of 1 mL, for two times. The crude mixture is then diluted 1:10 in PBS pH 7.4, and purified using MabSelect Sure Resin (GE Healthcare, Chicago, Ill., USA), followed by size exclusion chromatography. Purified material is quantified using a NANODROP™ UV visible spectrophotometer (using a calculated extinction coefficient based on the amino acid sequence of the Fc used in the conjugation, and concentrated to approximately 10 mg/mL using a centrifugal concentrator (10,000 MWCO). Purified molecules are analyzed using 4-12% Bis Tris SDS PAGE gels by loading 1-2 μg of each molecule into the gel, and staining using instant Blue staining. Each gel includes a molecular weight ladder with the indicated molecular weight standards. MALDI MS analysis is used to determine the average DAR.

Example 56. Synthesis of bis-[N'-(2-azidoethyl)]-iminodiacetic amide

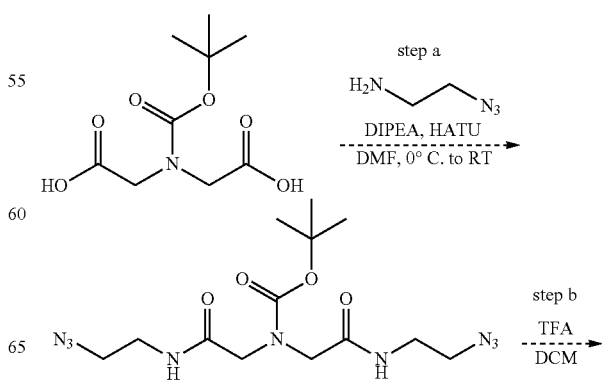

-continued

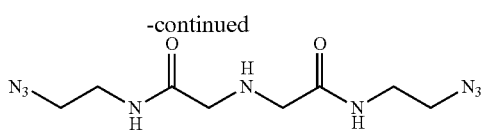

Step a. Bis-[N'-(2-azidoethyl)]-N-Boc-iminodiacetic amide.

To 0° C. a stirring solution of N-Boc-iminodiacetic acid (1.0 mmol), 2-azidoethan-1-amine hydrochloride (2.0 mmol), and DIPEA (6.0 mmol) in DMF (10 mL) it is added HATU (2.0 mmol). All the volatiles are evaporated per vacuum techniques and the residue is purified by chromatographic techniques to afford the desired product.

Step b. Bis-[N'-(2-azidoethyl)]-iminodiacetic amide.

To a 0° C. stirring mixture of Bis-[N'-(2-azidoethyl)]-N-Boc-iminodiacetic amide (1.0 mmol) and 2-methyl-2-butene (0.5 mL) in dichloromethane (8.0 mL), it is added trifluoroacetic acid (4.0 mL). After 10 minutes, the temperature is raised to ambient. Upon completion, all the volatiles are evaporated per vacuum techniques. The residue is purified by chromatographic techniques to afford the desired product.

Example 57. Synthesis of Int-16

A monomer of sulfozanamivir conjugated to a PEG4-alkyne linker and which may be further conjugated to an Fc domain or an albumin protein is produced according to the following synthetic scheme. Sulfozanamivir starting material is produced according to Hadházi et al. A sulfozanamivir analogue has potent anti-influenza virus activity. *ChemMedChem Comm.* 13:785-789 (2018).

Example 58. Synthesis of Int-17

A dimer of sulfozanamivir conjugated to a PEG4-alkyne linker and which may be further conjugated to an Fc domain or an albumin protein is produced according to the following synthetic scheme. Sulfozanamivir starting material is produced according to Hadházi et al. A sulfozanamivir analogue has potent anti-influenza virus activity. *ChemMedChem Comm.* 13:785-789 (2018).

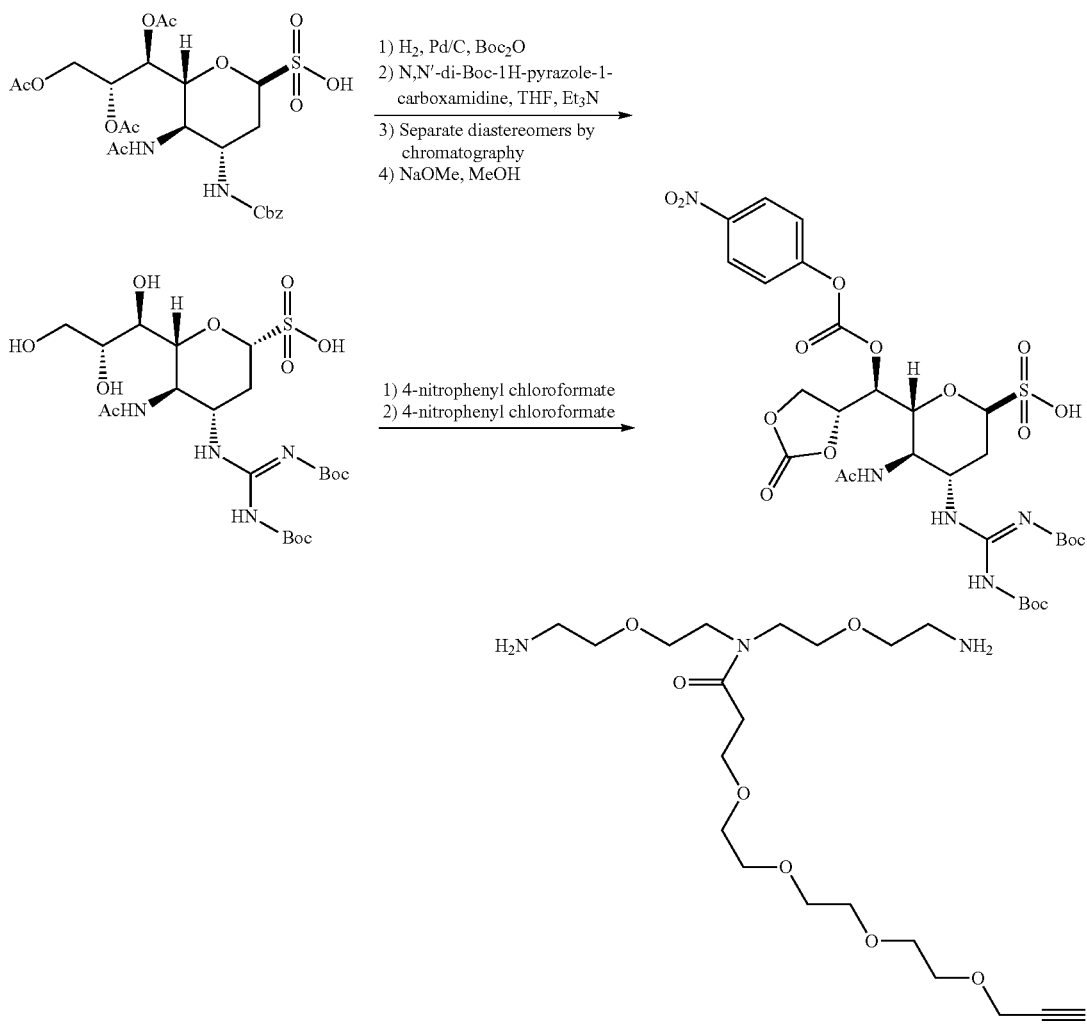

Example 59. Synthesis of Conjugate 12

A solution of azido functionalized aglycosylated Fc (70 mg, 4.7 mL, 1.3709 μmol) was added to a 15 mL centrifuge tube containing alkyne derivatized small molecule (29.8 mg, 0.0216 mmol, Int-7). After gently shaking to dissolve all solids, the mixture was added with 206 μl of a mixture solution of L-ascorbic acid sodium (59.4 mg, 0.3 mmol), copper (II) sulfate (15.9 mg, 0.1 mmol), and THPTA (43.5 mg, 0.1 mmol) in PBS 7.4 buffer (1 ml). The resulting mixture was gently shaken overnight. It was purified by affinity chromatography over a protein A column, followed by size exclusion chromatography as described in Example 8. Maldi TOF analysis of the purified final product gave an average mass of 56,177 Da (DAR=3.6). Yield 10.1 mg, 14% yield. A non-reducing SDS-PAGE of Conjugate 12 is provided in FIG. 54.

Example 60. Synthesis of Int-18

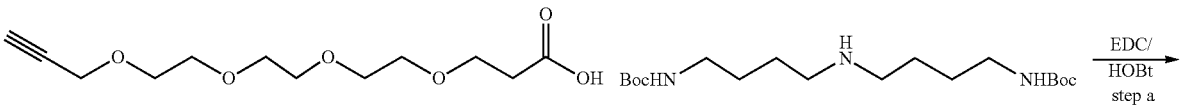

765  766
-continued
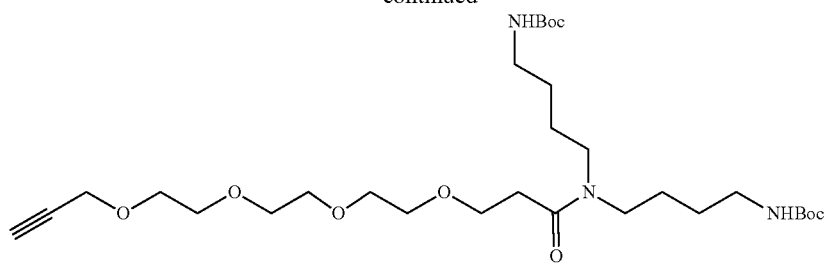
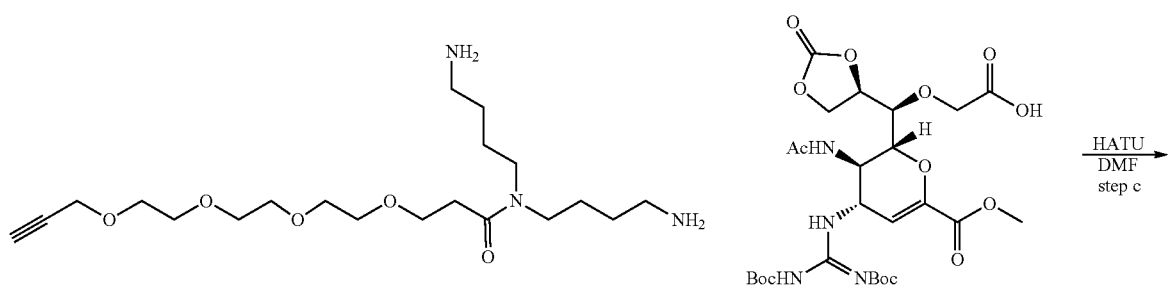
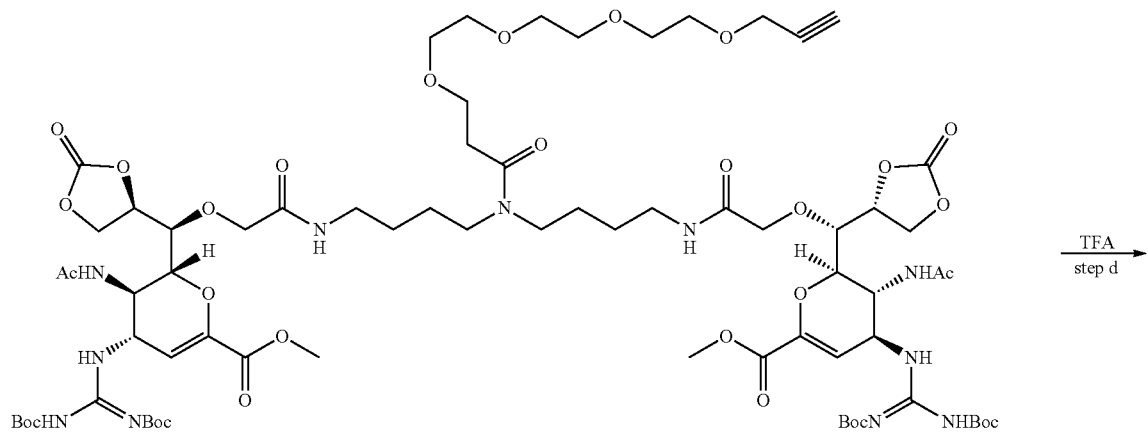
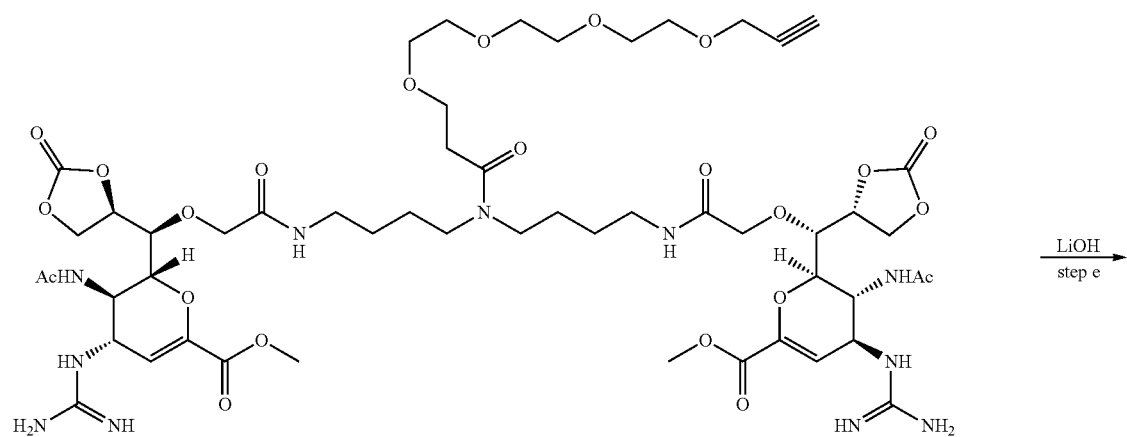

-continued

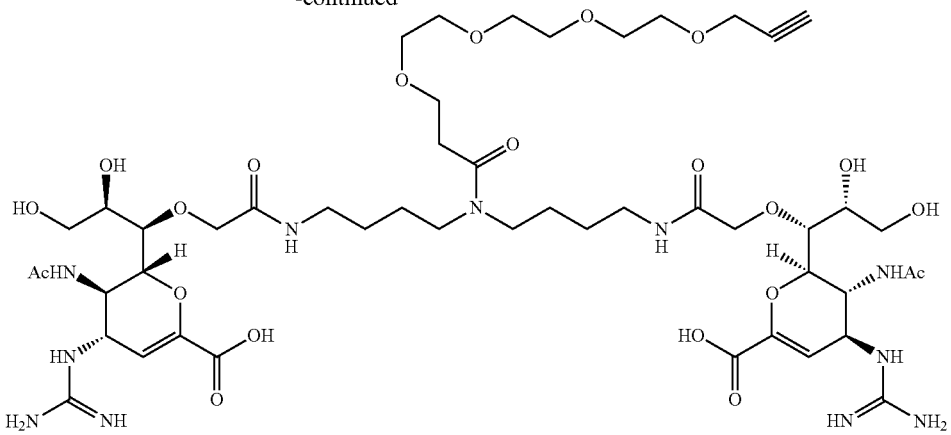

Step a. Synthesis of tert-butyl (17-{4-[(tert-butoxycarbonyl)amino]butyl}-16-oxo-4,7,10,13-tetraoxa-17-azahenicos-1-yn-21-yl)carbamate

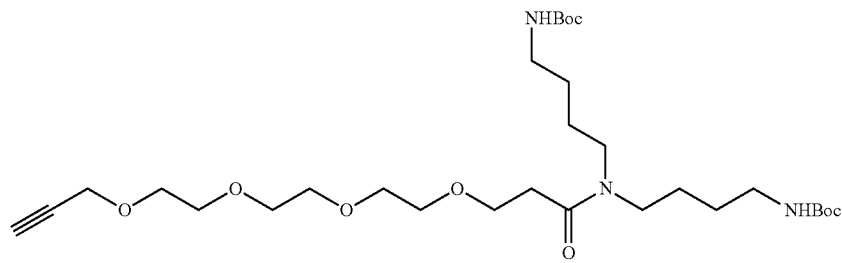 [SMILES: C#CCOCCOCCOCCOCCC(=O)N(CCCCNC(=O)OC(C)(C)C)CCCCNC(=O)OC(C)(C)C]

To the solution of di-tert-butyl [azanediyldi(butane-4,1-diyl)]biscarbamate (1.5 g, 4.17 mmol from Example 45, step a) and propargyl-PEG4-acid (1.08 g, 4.17 mmol) in DCM (40 mL) was added EDC (1.0 g, 5 mmol), HOBt (650 mg, 5 mmol), and DIEA (1.4 ml, 10 mmol) at room temperature, then stirred overnight at room temperature. The resulting solution was concentrated and purified by and purified by reverse phase liquid chromatography (RPLC) using an Isco COMBIFLASH® liquid chromatograph eluted with 10% to 100% acetonitrile and water with no modifier. Yield of 1.9 g, 76%. Ion(s) found by LCMS: M+H=602.4.

Step b. Synthesis of N,N-bis(4-aminobutyl)-4,7,10,13-tetraoxahexadec-15-yn-1-amide $NH_2$

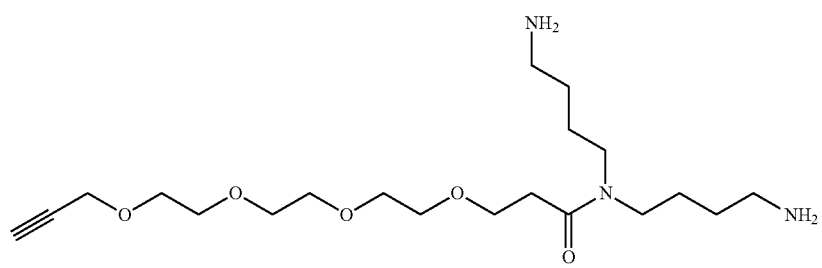 [SMILES: C#CCOCCOCCOCCOCCC(=O)N(CCCCN)CCCCN]

Tert-butyl (17-{4-[(tert-butoxycarbonyl)amino]butyl}-16-oxo-4,7,10,13-tetraoxa-17-azahenicos-1-yn-21-yl)carbamate (1.90, 3.1 mmol) was treated with 20 ml TFA at room temperature for 0.5 hour, then concentrated to dryness and used in the next step without further purification. Yield is quantitative for this step. Ion(s) found by LCMS: M/2+H=402.3.

Step c. Synthesis of fully protected Int-18

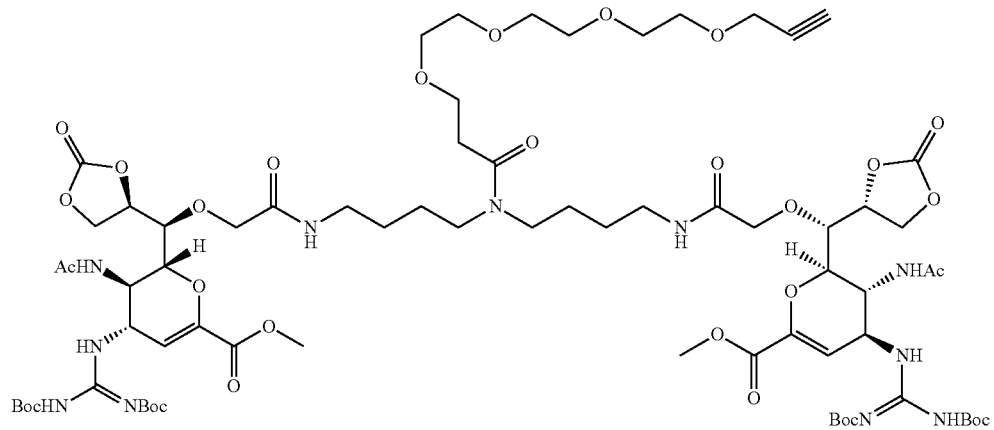

N,N-bis(4-aminobutyl)-4,7,10,13-tetraoxahexadec-15-yn-1-amide (0.150 g, 0.32 mmol) was added to a solution of the ether linked of zanamivir acid (0.400 g, 0.63 mmol, described in Example 31, step f) in DCM (10 mL), then treated with EDC (0.200 g, 1.0 mmol), HOBt (0.135 g, 1.00 mmol), and DIEA (0.14 ml, 1.00 mmol) at room temperature for overnight. The resulting solution was concentrated and purified by and purified by reverse phase liquid chromatography (RPLC) using an Isco COMBIFLASH® liquid chromatograph eluted with 10% to 100% acetonitrile and water with no 0.1% TFA as modifier. Yield of the products 310 mg, 60.3%. Ion(s) found by LCMS: M/2+H=813.9.

Step d. Synthesis of Int-18

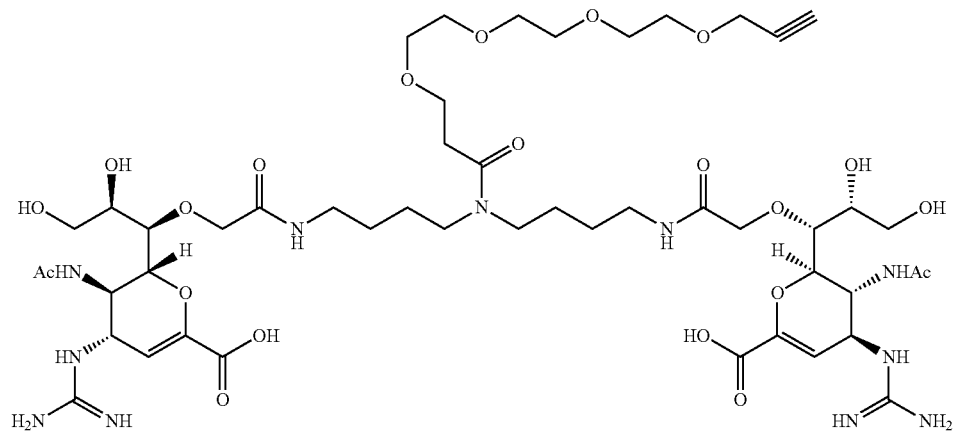 [SMILES: C#CCOCCOCCOCCOCCC(=O)N(CCCCNC(=O)CO[C@@H]([C@@H]1OC(C(=O)O)=C[C@H](NC(=N)N)[C@H]1NC(C)=O)[C@H](O)CO)CCCCNC(=O)CO[C@@H]([C@@H]1OC(C(=O)O)=C[C@H](NC(=N)N)[C@H]1NC(C)=O)[C@H](O)CO]

Product from the previous step (300 mg, 0.18 mmol) was treated with trifluoroacetic acid (2 mL) acid and stirred for 30 min at room temperature. The resulting solution was concentrated, re-dissolved in water (2 mL), then treated with a solution of lithium hydroxide (24 mg, 1 mmol) dissolved in water (1 mL). The reaction was stirred 10 min then quenched with 0.1 ml acetic acid, concentrated and purified by reverse phase liquid chromatography (RPLC) using an Isco COMBIFLASH® liquid chromatograph eluted with 0% to 50% acetonitrile and water, using 0.1% TFA as the modifier. Yield of the products 140 mg, 52%. Ion(s) found by LCMS: M/2+H=573.8, M/3+H=382.9.

Example 61. Synthesis of PEG4-azido Fc for Conjugate 13a

Preparation of 0.05M PEG4-azidoNHS Ester Solution in DMF/PBS

PEG4-azido NHS ester (80.5 mg) was dissolved in DMF (0.50 mL) at 0° C. and diluted to 4.063 mL by adding 3.50 mL of PBS 1× buffer at 0° C. This solution was used for preparing other PEG4-azido Fc with variety of drug-antibody ratio (DAR) values by adjusting the equivalents of this PEG4-azido NHS ester PBS×1 solution.

Preparation of PEG4-Azido Fc 0.05M PEG4-azidoNHS ester PBS×1 buffer solution (0.0984 mL, 4.92 μmol, 2.5 equivalents) was added to a solution of h-IgG1 Fc (105 mg in 5.031 mL of pH 7.4 PBS, MW-53,360 Da, 1.968 μmol) and the mixture was shaken gently for 12 hours at ambient temperature. The solution was concentrated using a centrifugal concentrator (30,000 MWCO) to a volume of—1.5 mL. The crude mixture was diluted 1:10 in PBS pH 7.4, and concentrated again. This wash procedure was repeated for total of three times. The unreacted azido reagent was removed with this procedure. The concentrated Fc-PEG4-azide was diluted to 5.03 mL with pH 7.4 PBS 1× buffer and ready for click conjugation. The purified material was quantified using a NANO-DROP™ UV visible spectrophotometer (using a calculated extinction coefficient based on the amino acid sequence of h-IgG1). The yield was quantitative after buffer exchange/purification.

The nucleic acid construct encoding the Fc for any conjugate described herein may include a nucleic acid sequence encoding the amino acid sequence of an Fc including Lys447 (e.g., a C-terminal lysine residue) and/or an N-terminal murine IgG signal sequence. Upon expression, the C-terminal lysine and, when present, the N-terminal murine IgG signal sequence of the Fc are proteolytically cleaved, resulting in an Fc having the amino acid sequence lacking Lys447 (e.g., lacking a C-terminal lysine residue) and, when present in the expression construct, the N-terminal murine IgG signal sequence. The presence or absence of a C-terminal lysine does not alter the properties of the Fc or the corresponding conjugate.

Example 62. Synthesis of Conjugate 13a

Preparation of click reagent solution: 0.0050M $CuSO_4$ in PBS buffer solution: 20.0 mg $CuSO_4$ was dissolved in 25.0 mL PBS×1, than took 22.0 mL above $CuSO_4$ solution and added 189.4 mg BTTAA and 1090 mg Na Ascorbate to give a clear solution (0.0050M $CuSO_4$, 0.020M BTTAA and 0.25M Sodium Ascorbate).

A solution of azido functionalized Fc (100 mg, 4.79 mL, 1.87 μmol, SEQ ID NO: 35) was added to a 15 mL centrifuge tube containing alkyne derivatized small molecule, Int-18 (11.2 mg, 0.00750 mmol, prepared in Example 60). After gently shaking to dissolve all solids, the solution was treated with 3.00 mL of above click reagent solution. The resulting colorless homogeneous solution was gently shaken overnight. It was purified by affinity chromatography over a protein A column, followed by size exclusion chromatography (see general conjugate purification protocol in Example 10). Maldi TOF analysis of the purified final product gave an average mass of 55,913 Da (DAR=1.7). Yield 54.0 mg, 54% yield.

The nucleic acid construct encoding the Fc for conjugate 13a included a nucleic acid encoding the amino acid sequence of SEQ ID NO: 35, which includes a C-terminal lysine residue and N-terminal murine IgG signal sequence. Upon expression, the C-terminal lysine and the N-terminal murine IgG signal sequence of the Fc of conjugate 13a are proteolytically cleaved, resulting in an Fc having the sequence lacking Lys447 (e.g., lacking a C-terminal lysine residue) and the N-terminal murine IgG signal sequence. The presence or absence of a C-terminal lysine does not alter the properties of the Fc or the corresponding conjugate.

Example 63. Syntheses of Conjugate 13b, Conjugate 13c, Conjugate 13d, Conjugate 13e, Conjugate 13f, and Conjugate 13g The PEG4-azido Fcs for Conjugate 13b, Conjugate 13c, Conjugate 13d, Conjugate 13e, Conjugate 13f, and Conjugate 13g were prepared analogously to the PEG4-azido Fc of Conjugate 13a (Example 61) adjusting the number of equivalents of PEG4-azido NHS ester as described in the table below. Conjugate 13b, Conjugate 13c, Conjugate 13d, Conjugate 13e, Conjugate 13f, and Conjugate 13g were prepared analogously to Conjugate 13a in Example 62 where the number of equivalents of targeting moiety (Int-18) was adjusted based on the desired DAR value (Table 26), and the volume of click reagent solution used was the same volume as employed in the procedure for Example 62. The DAR values, molecular weights and yields are listed in the table below. Product conjugates were purified by affinity chromatography over a protein A column, followed by size exclusion chromatography as described in Example 8. A non-reducing SDS-PAGE of Conjugates 13a-13g is provided in FIG. 55.

TABLE 26

Yields of Conjugates 13a-13g

| Sample Name | Equivalents of PEG4-azido NHS ester | DAR (Average) | MALDI mass Da (Average) | Targeting moiety (TM) | Equivalents of TM | Protein Type | Yield (%) |
| --- | --- | --- | --- | --- | --- | --- | --- |
| Conjugate 13a | 2.5 | 1.7 | 55913 | Int-18 | 4 | hIgG1 Fc | 54% |
| Conjugate 13b | 4.5 | 2.7 | 57278 | Int-18 | 6 | hIgG1 Fc | 50% |
| Conjugate 13c | 6.5 | 3.8 | 58908 | Int-18 | 8 | hIgG1 Fc | 60% |
| Conjugate 13d | 8.5 | 4.7 | 60149 | Int-18 | 10 | hIgG1 Fc | 54% |
| Conjugate 13e | 11 | 5.8 | 61726 | Int-18 | 12 | hIgG1 Fc | 55% |
| Conjugate 13f | 18 | 8.2 | 65146 | Int-18 | 16 | hIgG1 Fc | 53% |
| Conjugate 13g | 25 | 10.3 | 68153 | Int-18 | 20 | hIgG1 Fc | 45% |

Example 64. In vitro stability of Conjugate 6

To demonstrate the in vitro stability of Conjugate 6 using both mouse and human fresh K2EDTA treated plasma and liver microsomes. The in vitro mouse and human plasma stability were determined by comparing the Drug to Antibody Ratio (DAR) envelope after a 24 hr incubation in plasma at 37° C. by MALDI-TOF mass spectrometric detection. Liver microsomal stability using mouse and human microsomes was also performed after incubation for 24 hr at 37° C. with MALDI-TOF mass spectrometric detection. This was to identify potential metabolically labile sites on the Fc protein, linker, or target moiety.

64.1 Plasma Stability Sample Preparation

First, 60 μL of Conjugate 6 at 3 mg/ml was mixed with 120 μL plasma. Each plasma type was aliquoted into 2 tubes. One aliquot was immediately frozen from each plasma type. The remaining aliquot was placed in a water bath (37° C.) for 24 hours. MAGNE® Protein A beads (Promega) were equilibrated by gently vortexing the beads into suspension. In duplicate for both plasma types, 50 μL of bead slutty was added to a 1.5 mL microcentrifuge tube and placed on the magnetic stand for 10 seconds. After 10 seconds, the storage buffer was removed and discarded. 500 μL of bind/wash buffer (0.1% BSA in 1×PBS pH 7.4) was added to the 1.5 mL microcentrifuge tube containing the beads. The beads were mixed (vortexing) and placed on a magnetic stand for 10 seconds. After 10 seconds, the bind/wash buffer was removed and discarded. 50 μL of buffer (1×PBS, pH 7.4) was added to the microcentrifuge tube containing the beads.

50 μL of the plasma mixture was added to the beads and gently vortexed to mix. Using a tube shaker, the sample was mixed at room temperature for 60 minutes, ensuring the beads remained in suspension. After mixing, the tube was placed on a magnetic stand for seconds and the supernatant was removed. 500 μL of buffer (1×PBS, pH 7.4) was added and gently vortexed to mix. After mixing, the tube was placed on a magnetic stand for 10 seconds, followed by removal and discarding of wash buffer. The wash step was repeated for a total of 2 washes. Following 2 washes with 500 μL of buffer (1×PBS, pH 7.4), 3 washes with 500 μL, 200 μL, and 100 μL, respectively, of water were performed. The appropriate volume of water was added to the tube and gently vortexed to mix well and then placed on a magnetic stand for 10 seconds prior to removal and discarding of the water. After the third wash with water, 30 μL of elution buffer (90:10:0.4 Water:Acetonitrile:TFA) was added to the beads. Using a tube shaker, the elution buffer and sample were mixed for 30 minutes at room temperature. After mixing, the tube was placed on a magnetic stand for 10 seconds, the elution buffer, containing the sample, was removed and kept. 2 μL of sample were mixed with 2 μL of MALDI matrix (20 mg/mL Sinapic Acid in 70:30:0.1 water:acetonitrile:TFA) and spotted onto a MALDI target plate using a dual layer technique. The sample was then analyzed by MALDI-TOF mass spectrometry.

64.2 Liver Microsomal Sample Preparation

A 10× buffer was made with 500 mM Tris-HCl at pH 7.5 and 50 mM magnesium chloride hexahydrate. ACV-006 was diluted to 50 μM in 1×PBS, pH 7.4. Liver microsomes were thawed and vortexed. An aliquot of each species of liver microsomes (human and mouse) were heat killed at 70° C. for 15 minutes for use as a control. Reaction mixtures were prepared for both species according to Table 27. Tubes were incubated in a water bath (37° C.) for 24 hours. Samples were extracted for analysis using MAGNE® Protein A beads (Promega) following the protocol from 59.1.

TABLE 27

0.5 mg/mL final microsomes concentration with 5 μM Conjugate 6

|  | Heat Killed | Live |
| --- | --- | --- |
| Total | 400 μL | 400 μL |
| Water | 286 μL | 286 μL |
| 10x Buffer | 40 μL | 40 μL |
| Microsomes (20 mg/mL) | 10 μL | 10 μL |
| Compound (50 μM) | 40 μL | 40 μL |
| NADPH Regenerating Solution A | 20 μL | 20 μL |
| NADPH Regenerating Solution B | 4 μL | 4 μL |

64.3 Sample and Data Analysis

Samples were acquired using Bruker Compass Flex Control version 3.4 to obtain full scan MALDI-TOF mass spectra (Table 28). BSA was used as an internal calibrant for the acquisition mass range. Data was further analyzed with Bruker Compass Flex Analysis version 3.4 software. In addition, the DAR pattern of the control is compared to the DAR pattern of the test sample.

TABLE 28

Mass Spectrometer (MS) Parameters

| Mass Spectrometer | Bruker Microflex LT |
| --- | --- |
| Detection | |
| Mass Range | 17-141 kDa |
| Sample Rate and Digitizer Settings | 0.5 |
| Detector Gain | 2.05x |
| Baseline Offset Adjustment | 0% |
| Analog Offset | 0.5 mV |
| Laser Frequency | 60 Hz |
| Spectrometer | |
| Ion Source 1 (IS1) | 20.03 kV |
| Ion Source 2 (IS2) | 18.12 kV (90.5% IS1) |
| Lens | 7.17 kV (35.8% IS1) |
| Pulsed Ion Extraction | 1010 ns |
| Sample Carrier | |
| Random Walk | Partial Sample |
| Laser Shots | 100/section |
| Total Laser Shots | 500 |
| Shots at Raster | 20 |
| Raster Shot Diameter Limit | 2000 μm |
| Setup | |
| Laser Global Attenuator Offset | 0% |
| Laser Attenuator Offset | 20% |
| Laser Attenuator Range | 30% |
| Digitizer Sensitivity (Full Scale) | 100 mV |
| Digitizer Analog Offset Linear | 0.5 mV |
| Digitizer Digital Offset Linear | 0 cnt |
| Detector Gain Voltage—Linear Base | 2500 V |
| Detector Gain Voltage—Linear Boost | 0 V |
| Calibration | |
| Bovine Serum Albumin | [M + 2H], [M + H], [2M + H] |

64.4 Results

The test compound, conjugate 6 (FIG. 43), was tested for in vitro stability in both mouse and human fresh $K_2$EDTA treated plasma and liver microsomes.

Conjugate 6 was spiked into fresh K2EDTA mouse and human plasma at a final concentration of 1 mg/mL. The plasma was split into 2 aliquots, one being frozen immediately, and the other incubated in a water bath at 37° C. for 24 hours. At the end of the incubation, samples were extracted from the plasma matrix by MAGNE® Protein A magnetic beads. Following plasma incubations, samples were analyzed by MALDI-TOF mass spectrometry for changes in DAR. Conjugate 6 in either mouse (FIG. 44) or human (FIG. 45) plasma incubations were not found to generate any changes in DAR.

Conjugate 6 liver microsomal stability was tested at a final concentration of 5 μM into a 50 mM, pH 7.5 Tris-HCl buffer solution that contained either active or heat killed liver microsomes at a final concentration of 0.5 mg/mL and MgCl$_2$ at a final concentration of 5 mM. All samples were incubated at a constant temperature of 37° C., and nicotinamide adenine dinucleotide phosphate (NADPH) regenerating solution was utilized to provide continuous cofactor availability during the incubation. Incubations were carried out for 24 hours. At the end of the incubation, samples were extracted from the microsomal matrix by Protein A magnetic beads. Following liver microsomal incubations, samples were analyzed by MALDI-TOF mass spectrometry for changes in DAR. Conjugate 6 in either mouse (FIG. 46) or human (FIG. 47) liver microsomal incubations were not found to generate any changes in DAR.

The in vitro plasma stability after incubation at 37° C. for 24 hr, suggests a lack of degradation of the Conjugate 6 Fc, linker, or targeting moiety in either mouse or human. Similarly a lack of degradation was observed after incubation in both mouse and human liver microsomes, suggesting the absence of metabolites. The results of these in vitro stability studies support that this is a stable compound with degradants that could have biological liabilities.

Example 65. Efficacy of Conjugate 13 at Different Drug-to-Antibody Ratios (DARs) Against Influenza a (H1N1) in a Lethal Mouse Model Conjugate 13 was evaluated against a lethal IAV H1N1 influenza infection in female BALB/c mice (Charles River Laboratories, 6-8 weeks). The challenge virus (A/Puerto Rico/8/1934) is a mouse-adapted isolate capable of causing lethal infections in mice. The experiment comprised 13 groups of 5 mice. At day 0, all mice were challenged with virus at 3× the LD95 by intranasal inoculation in a volume of 30 μl, after being anesthetized with a mixture of ketamine/xylazine (150 and 10 mg/kg respectively). Groups 1-13 received a single IV treatment, 2 hours post viral challenge of test article or vehicle (PBS). The study evaluated 4 different OAR constructs of Conjugate 13 corresponding to Conjugate 13a, Conjugate 13c, Conjugate 13d, and Conjugate 13g (DARs of 1.7, 3.8, 5.8, and 10.3, respectively). The synthesis of Conjugate 13a, Conjugate 13c, Conjugate 13d, and Conjugate 13g is described in Example 61-Example 63. Each construct was evaluated at 0.03, 0.1, and 0.3 mg/kg. The general study design for each conjugate is summarized in Table 29.

TABLE 29

General study design of DAR scan

| Group | Conjugate | DAR | Route/Schedule | Dose (mg/kg) | Dose volume (ml/kg) |
|---|---|---|---|---|---|
| 1 | Conjugate 13a | 1.7 | IV, T + 2 hours | 0.3 | 5 |
| 2 | Conjugate 13a | 1.7 | IV, T + 2 hours | 0.1 | 5 |
| 3 | Conjugate 13a | 1.7 | IV, T + 2 hours | 0.03 | 5 |
| 4 | Conjugate 13c | 3.8 | IV, T + 2 hours | 0.3 | 5 |
| 5 | Conjugate 13c | 3.8 | IV, T + 2 hours | 0.1 | 5 |
| 6 | Conjugate 13c | 3.8 | IV, T + 2 hours | 0.03 | 5 |
| 7 | Conjugate 13d | 5.8 | IV, T + 2 hours | 0.3 | 5 |
| 8 | Conjugate 13d | 5.8 | IV, T + 2 hours | 0.1 | 5 |
| 9 | Conjugate 13d | 5.8 | IV, T + 2 hours | 0.03 | 5 |
| 10 | Conjugate 13g | 10.3 | IV, T + 2 hours | 0.3 | 5 |
| 11 | Conjugate 13g | 10.3 | IV, T + 2 hours | 0.1 | 5 |
| 12 | Conjugate 13g | 10.3 | IV, T + 2 hours | 0.03 | 5 |
| 13 | Vehicle (PBS) | Na | IV, T + 2 hours | na | 5 |

All constructs were fully protective at 0.3 mg/kg, in contrast, no construct was active at 0.03 mg/kg (0% survival for all groups) indicating the low dose was below the threshold efficacious dose. However, groups receiving 0.1 mg/kg of conjugates could be discriminated (Table 30). At this dose level conjugates with DARs of 1.7, 3.8, and 5.8 were significantly more protective than vehicle only treated mice (p=0.0027). The high OAR construct (10.3) however was not significantly more protective than vehicle only treated mice (p=0.091). The underlying mechanism by which the high OAR construct loses activity is currently unknown but could be caused by several factors, including interference with antibody recycling, resulting in shorter half-life.

TABLE 30

DAR Range Study (0.1 mg/kg dose groups)

| Conjugate | DAR | % Survival | Significance* |
|---|---|---|---|
| Conjugate 13a | 1.7 | 60 | p = 0.0027 |
| Conjugate 13c | 3.8 | 40 | p = 0.0027 |
| Conjugate 13d | 5.8 | 80 | p = 0.0027 |
| Conjugate 13g | 10.3 | 0 | p = 0.091** |

* = Significance relative to vehicle (PBS) only treated mice by the Log-rank (Mantel-Cox) test.
** = Not significant

Example 66. In vivo Efficacy of Conjugate 6 and Conjugate 12

Conjugate 6 and Conjugate 12, analog with Fc mutation at N297A, was evaluated against a lethal IAV H1N1 influenza infection in female BALB/c mice (Charles River Laboratories, 6-8 weeks). The challenge virus (A/Puerto Rico/8/34) is a mouse-adapted isolate. The experiment comprised 5 mice per group. Mice were anesthetized with ketamine/Xylazine (150/10 mg/kg) and were challenged with influenza virus at 3-5× the $LD_{95}$ by intranasal inoculation in a volume of 30 μL. A single 1 dose of treatment was administered by IV, 2 h post-infection. PBS was given as negative control. All mice were monitored for % body weight loss (FIG. 48) and for survival (FIG. 49) for 15 days after challenge.

Example 67. In Vitro Fcγ Receptor IIA Binding of Conjugate 6 and Conjugate 12

Binding of Conjugate 6 and Conjugate 12, analog with Fc mutation at N297A, was evaluated against FcγRIIIA by ELISA. The plate was coated with 1 μg/mL recombinant human FcγRIIIA overnight. The next day, the plate was blocked with 1% BSA solution for 1 h. Conjugates were added to plate in dose-response ranging from 0.01-1000 nM and incubated for 2 h. Binding was detected by incubation with peroxidase-conjugated anti-human Fc for 1 h and subsequent incubation with TMB substrate reagent for 10-15 min.

Binding was determined by reading absorbance at 450 nm (FIG. 50 and FIG. 51).

Example 68. In Vivo Conjugate 6 Plasma Sample Analysis

Conjugate 6 in plasma samples were quantified by a neuraminidase capture detection ELISA. Briefly, molecules were captured on neuraminidase coated plates and then detected using a HRP-conjugated anti-human IgG-Fc antibody. Protein concentration was calculated in GraphPad Prism using 4PL non-linear regression of Conjugate 6 standard curves. A more detailed method description is provided below.

Nunc Maxisorp 96-well plates (Cat No. 12-565-136, ThermoFisher) were coated with 0.1 U/well neuraminidase from A/California/04/2009 (H1N1) (11058-VNAHC, Sino Biological) in 1×KPL coating buffer (5150-0041, SeraCare). Plates were incubated at room temperature for 1 hr on an orbital plate shaker (500 rpm). Serial dilutions of the plasma samples were plated and incubated at room temperature for 2 hours (sample diluent: 0.5% BSA in PBS 0.025% Tween 20+naïve cynomolgus monkey plasma final concentration of 1:2,500). Conjugate 6 standard curves ranging from 0.230 to 500 ng/mL, in duplicate were run on each plate. Following the 2 hr incubation, plates were washed 5× in 300 μL PBS with 0.05% Tween 20. Conjugate bound to neuraminidase on the plates was then probed with an HRP conjugated anti-human IgG Fc F(ab')2 (709-036-098, Jackson) diluted 1:1,000 in sample diluent for 1 hr at room temp. Plates were then washed 8× in 300 μL PBS with 0.05% Tween 20 and developed with TMB substrate for 7-8 minutes. The reaction was stopped with 1 N $H_2SO_4$. Absorbance was read at 450 nm. Conjugate 6 in plasma samples was interpolated using GraphPad Prism Version 6 following nonlinear regression analysis (Sigmoidal, 4PL analysis) of the standard curves.

The resulting mean plasma concentrations were then used to calculate pharmacokinetic parameters by non-compartmental analysis using Phoenix WinNonlin 7.0.

Toxicokinetics (TK), Groups 2 (IV, 5 mg/kg) and 3 (IV, 20 mg/kg)

Concentrations were comparable between male and female animals within the same dose group on day 1 (Table 31) and day 8 (Table 32) after administration. Mean plasma exposures appeared to increase approximately dose-proportionally across both days. After the 2nd dose administration, a slight accumulation of about 30% was noted across the different dose groups. A plot of days 1 and 8 mean plasma concentrations across the different dose groups is shown in FIG. 52.

Table 31: Toxicokinetics Day 1

TABLE 31

Toxicokinetics Day 1

| Dose (mg/kg) | Route | Sex | Conc (μg/mL) at Time (hr) | | | | | | | | | Tmax (hr) | Cmax (μg/mL) | AUC0-t (μg·hr/mL) |
|---|---|---|---|---|---|---|---|---|---|---|---|---|---|---|
| | | | 0.083 | 1 | 2 | 4 | 8 | 24 | 72 | 120 | 168 | | | |
| 5 | IV | F | 112 | 78.8 | 85.8 | 71.0 | 75.1 | 52.5 | 38.6 | 18.5 | 22.3 | 0.083 | 112 | 6190 |
| | IV | M | 101 | 84.6 | 107 | 75.3 | 72.5 | 38.1 | 29.8 | 35.3 | 15.8 | 2 | 107 | 5970 |
| | | Mean | 107 | 81.7 | 96.5 | 73.2 | 73.8 | 45.3 | 34.2 | 26.9 | 19.0 | 1.04 | 110 | 6080 |
| 20 | IV | F | 449 | 510 | 353 | 331 | 303 | 134 | 105 | 63.6 | 46.6 | 1 | 510 | 18800 |
| | IV | M | 448 | 422 | 485 | 373 | 329 | 160 | 96.0 | 76.2 | 53.4 | 2 | 485 | 20500 |
| | | Mean | 449 | 466 | 419 | 352 | 316 | 147 | 100 | 69.9 | 50.0 | 1.50 | 497 | 19600 |

TABLE 32

Toxicokinetics Day 8

| Dose (mg/kg) | Route | Sex | Conc (μg/mL) at Time (hr) | | | | | | | | | Tmax (hr) | Cmax (μg/mL) | AUC0-t (μg·hr/mL) |
|---|---|---|---|---|---|---|---|---|---|---|---|---|---|---|
| | | | 0.083 | 1 | 2 | 4 | 8 | 24 | 72 | 120 | 168 | | | |
| 5 | IV | F | 111 | 111 | 99.3 | 82.3 | 100 | 52.2 | 46.7 | 35.0 | 33.9 | 1 | 111 | 7970 |
| | IV | M | 113 | 114 | 113 | 78.4 | 74.4 | 54.7 | 35.2 | 47.1 | 28.2 | 1 | 114 | 7700 |
| | | Mean | 112 | 112 | 106 | 80.4 | 87.3 | 53.5 | 41.0 | 41.1 | 31.0 | 1 | 112 | 7830 |
| 20 | IV | F | 398 | 359 | 319 | 315 | 298 | 190 | 126 | 99.3 | 85.5 | 0.083 | 398 | 23900 |
| | IV | M | 391 | 443 | 354 | 435 | 263 | 219 | 143 | 142 | 83.8 | 1 | 443 | 27800 |
| | | Mean | 394 | 401 | 337 | 375 | 280 | 205 | 134 | 120 | 84.7 | 0.542 | 420 | 25800 |

Pharmacokinetics (PK), Groups 4 (IV, 10 mg/kg) and 5 (SC, 10 mg/kg)

Following IV administration, plasma concentrations from the male and female animals were comparable. Very low clearance, resulting in a long terminal half-life was observed following IV administration (Table 33A and Table 33B).

TABLE 33A

Plasma concentrations for male and female animals

| Dose (mg/kg) | Route | Sex | Conc (μg/mL) at Time (hr) | | | | | | | | | | |
|---|---|---|---|---|---|---|---|---|---|---|---|---|---|
| | | | 0.083 | 1 | 2 | 4 | 8 | 24 | 72 | 120 | 168 | 336 | 504 | 672 |
| 5 | IV | F | 166 | 174 | 220 | 153 | 144 | 58.6 | 40.6 | 21.2 | 20.7 | 14.7 | n/a | 2.7 |
| 5 | IV | M | 191 | 135 | 258 | 161 | 154 | 71 | 43.7 | 47.6 | 32 | 22.9 | n/a | 5.3 |

TABLE 33B

| | | | PK parameters for male and female animals | | | | | |
|---|---|---|---|---|---|---|---|---|
| Tmax (hr) | C0 (μg/mL) | Cmax (μg/mL) | AUClast (hr*μg/mL) | AUCINF_obs (hr*μg/mL) | Half-life (hr) | Cl_obs (mL/min/kg) | Vss_obs (mL/kg) | Vz_obs (mL/kg) |
| 1 | 166 | 220 | 13700 | 14400 | 170 | 0.00579 | 68.9 | 85.1 |
| 1 | 204 | 258 | 19400 | 20800 | 183 | 0.004 | 56.6 | 63.2 |

Following SC administration, the time to reach maximum concentrations was reached 72 hours after dosing but concentrations were measurable through 672 hours post-dose (Table 34A and Table 34B). Bioavailability after SC dosing was high at approximately 139%. A comparison of the plasma concentration over time between 10 mg/kg IV and SC administration is shown in FIG. 53.

TABLE 34A

| | | | Plasma concentrations for male and female animals | | | | | | | | |
|---|---|---|---|---|---|---|---|---|---|---|---|
| | Dose | | | | | Conc (μg/mL) at Time (hr) | | | | | |
| Route | (mg/kg) | Sex | 0.083 | 0.5 | 1 | 4 | 8 | 24 | 72 | 120 | 168 | 336 | 504 | 672 |
| SC | 10 | F | n/a | 1.9 | 5.3 | 23.1 | 39.5 | 54 | 58.6 | 66.9 | 54 | 28.4 | 18.9 | 6.4 |
| SC | 10 | M | n/a | 0.3 | 2.1 | 19.9 | 28.1 | 46.8 | 64.9 | 54.7 | 57.2 | 26.8 | 25.5 | 8.6 |

TABLE 34B

| PK parameters for male and female animals | | | |
|---|---|---|---|
| $T_{max}$ (hr) | $C_{max}$ (μg/mL) | $AUC_{0-t}$ (μg × hr/mL) | F (%) |
| 120 | 66.9 | 22600 | 137% |
| 72 | 64.9 | 23300 | 141% |

Example 69. Efficacy of Conjugate 6 Against Influenza A/Puerto Rico/8/1934 (H1N1) in a Lethal Mouse Model Conjugate 6 was evaluated against a lethal IAV H1N1 influenza infection in female BALB/c mice (Charles River Laboratories, 6-8 weeks). The challenge virus (A/Puerto Rico/8/1934) is a mouse-adapted isolate capable of causing lethal infections in mice. The experiment comprised 7 groups of 5 mice. At day 0, all mice were challenged with virus at 3× the LD95 by intranasal inoculation in a volume of 30 μl, after being anesthetized with a mixture of ketamine/xylazine (150 and 10 mg/kg respectively). Mortality and body weights were recorded daily and any animal with a 20% loss of body weight was scored as a death. Test groups received a single IV treatment, 2 hours post viral challenge of conjugate 6, hIgG1 Fc control, or vehicle (PBS). Animals receiving oseltamivir were dosed orally, twice daily, for 5 days, starting 2 hours after viral challenge. The study design is summarized in Table 35.

TABLE 35

| Study design for Influenza A/PR/8/34 (h1N4) study | | | | | |
|---|---|---|---|---|---|
| Group | Test article | Route/Schedule | Dose (mq/kq) | Dose volume (ml/kq) | # of mice |
| 1 | Vehicle | IV, T + 2 hrs. | na | 5 | 5 |
| 2 | hIgG1 Fc | IV, T + 2 hrs. | 10 | 5 | 5 |

TABLE 35-continued

| Study design for Influenza A/PR/8/34 (h1N4) study | | | | | |
|---|---|---|---|---|---|
| Group | Test article | Route/Schedule | Dose (mq/kq) | Dose volume (ml/kq) | # of mice |
| 3 | Oseltamivir | PO, bid × 5, T + 2 hrs. | 20 | 5 | 5 |
| 4 | Oseltamivir | PO, bid × 5, T + 2 hrs. | 5 | 5 | 5 |
| 5 | Conjugate 6 | IV, T + 2 hrs. | 10 | 5 | 5 |
| 6 | Conjugate 6 | IV, T + 2 hrs. | 2 | 5 | 5 |
| 7 | Conjugate 6 | IV, T + 2 hrs. | 0.4 | 5 | 5 |

As expected, mice receiving vehicle or the hIgG Fc only succumbed to the infection by day 6. Similarly, mice treated with oseltamivir at the low dose (5 mg/kg; bid for 5 days) reached mortality by day 8 (Table 36). However, mice receiving 20 mg/kg of oseltamivir with the same dosing schedule were fully protected (p=0.0027). In contrast to that seen with oseltamivir, mice treated with conjugate 6 were fully protected at all dose levels (i0, 2, and 0.4 mg/kg) from a single IV dose (p=0.0027).

TABLE 36

| Survival for Influenza A/PR/8/34 (H1N1) study (Day 14) | | | |
|---|---|---|---|
| Test article | Dose | % Survival | Significance* |
| hIgG1 Fc | 10 | 0 | p = 0.85** |
| Oseltamivir | 20 | 100 | p = 0.0027 |
| Oseltamivir | 5 | 0 | p = 0.091** |
| Conjugate 6 | 10 | 100 | p = 0.0027 |
| Conjugate 6 | 2 | 100 | p = 0.0027 |
| Conjugate 6 | 0.4 | 100 | p = 0.0027 |

\* = Significance relative to vehicle (PBS) only treated mice by the Log-rank (Mantel-Cox) test.
\*\* = Not significant The potency of conjugate 6 was further supported by daily body weight measurements. As expected, mice treated with vehicle or hIgG1 Fc demonstrated a steady drop in body weight until it exceeded 20%, at which time they were scored as a death (Table 37). The group treated with oseltamivir at 5 mg/kg also displayed a consistent loss of weight until reaching mortality at day 8. Mice treated with oseltamivir at the high dose (20 mg/kg) showed a steady, but reduced loss of body weight, which reached i4% at day 8, before recovering.

In contrast to control and oseltamivir treated mice, those groups receiving conjugate 6 maintained healthy body weights throughout the study even at the lowest dose concentration (0.4 mg/kg) (Table 37). The largest transient loss of weight among conjugate 6 treated mice was only 2% at day 14 in the 2 mg/kg dose group. By both survival and body weight measurements conjugate 6 demonstrated robust protection from Influenza A/Puerto Rico/8/1934 with a single IV dose as low as 0.4 mg/kg.

TABLE 37

Mouse body weight data (% BW relative to day 0). Average of 5 mice; *data not included once the first animal reaches mortality within a group

| Day post challenge | Vehicle (PBS) | hIgG1 Fc (mg/kg) 10 | Oseltamivir (mg/kg) 20 | Oseltamivir (mg/kg) 5 | Conjugate 6 (mg/kg) 10 | Conjugate 6 (mg/kg) 2 | Conjugate 6 (mg/kg) 0.4 |
|---|---|---|---|---|---|---|---|
| 0 | 100 | 100 | 100 | 100 | 100 | 100 | 100 |
| 1 | 99 | 99 | 102 | 99 | 103 | 102 | 101 |
| 2 | 102 | 102 | 103 | 96 | 104 | 102 | 103 |
| 3 | 96 | 96 | 102 | 95 | 102 | 102 | 100 |
| 4 | 89 | 88 | 100 | 90 | 103 | 100 | 100 |
| 5 | 82 | 81 | 95 | 89 | 102 | 99 | 99 |
| 6 | 77 | 77 | 98 | 90 | 102 | 100 | 101 |
| 7 | | | 90 | 84 | 103 | 101 | 102 |
| 8 | | | 86 | 78 | 105 | 101 | 102 |
| 9 | | | 91 | | 101 | 102 | 102 |
| 10 | | | 95 | | 102 | 101 | 103 |
| 11 | | | 97 | | 102 | 101 | 102 |
| 12 | | | 97 | | 101 | 99 | 102 |
| 13 | | | 97 | | 103 | 100 | 102 |
| 14 | | | 96 | | 104 | 98 | 101 |

Example 70. Synthesis of Conjugate 14

The title conjugate was prepared analogously to Conjugate 13a (Example 62) using PEG-azido-Fc (SEQ ID NO:35) and Int-7 (Example 19). Maldi TOE analysis of the purified final product gave an average mass of 56,502. Da (DAR=2.1). Yield 43.4 mg, 43.4%.

Example 71. Synthesis of Conjugate 15

This conjugate was prepared analogously to Example 62 (Conjugate 13a) by PEG4-azido-Fc (SEQ ID NO: 35, Example 61) and Int-12 (Example 46). Maldi TOE analysis of the purified final product gave an average mass of 56,528. Da (OAR=2.2). Yield 40.0 mg, 40.0%.

Example 72. Synthesis of Conjugate 16

This conjugate was prepared analogously to Example 62 (Conjugate 13a) by PEG4-azido-Fc (SEQ ID NO: 35, Example 61) and Int-10 (Example 31). Maldi TOF analysis of the purified final product gave an average mass of 56,507. Da (DAR=2.1). Yield 41.7 mg, 42%.

Example 73. Synthesis of Int-19

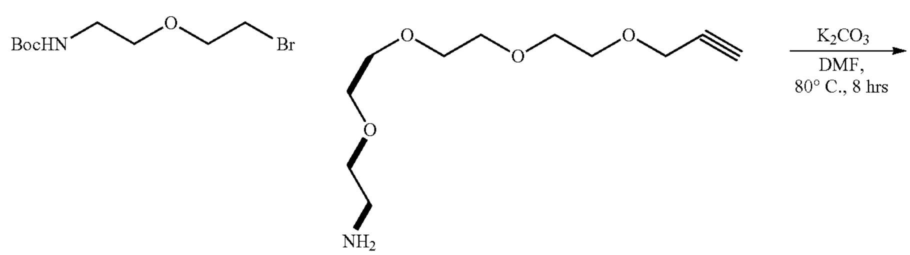

783 784
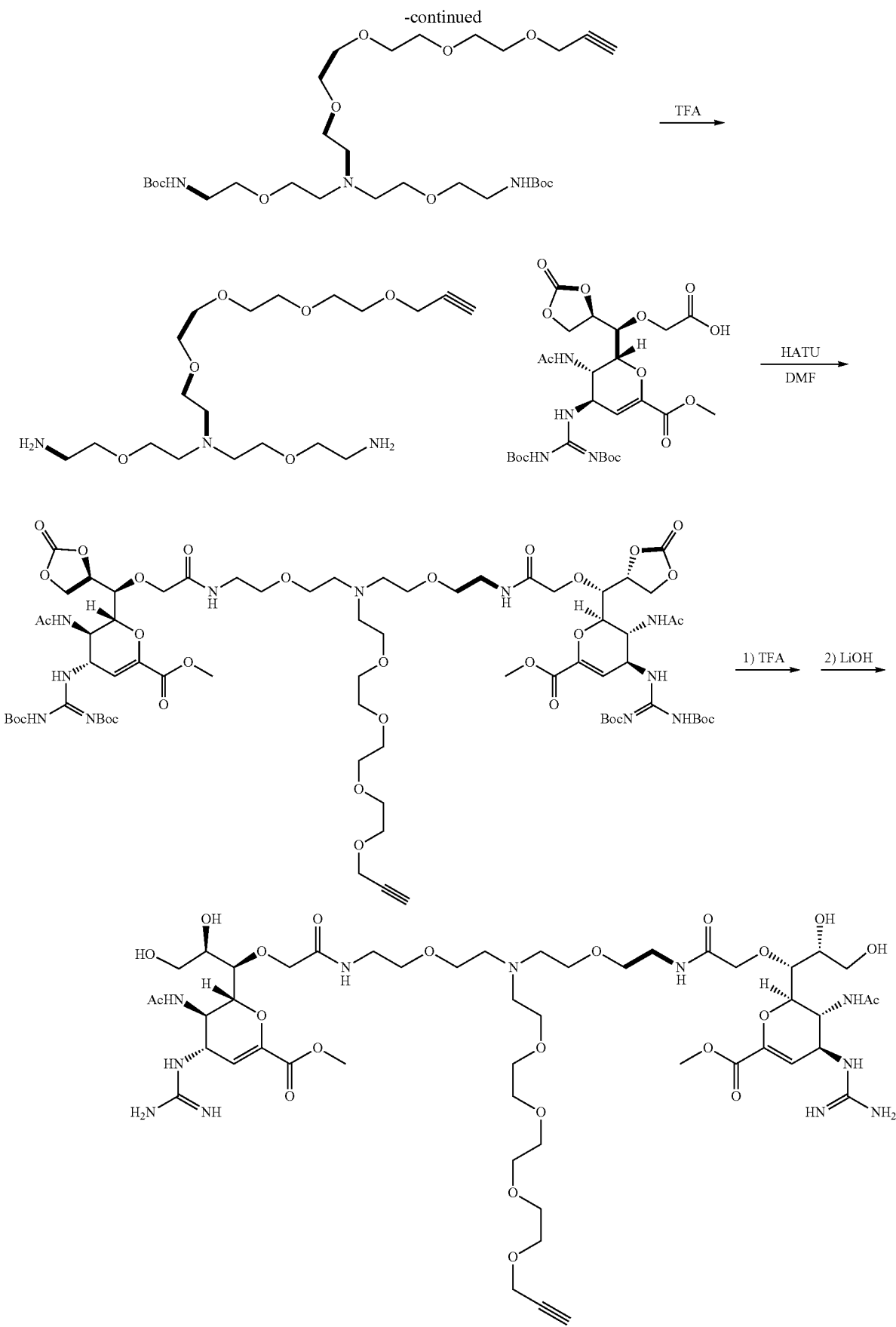

Step a.

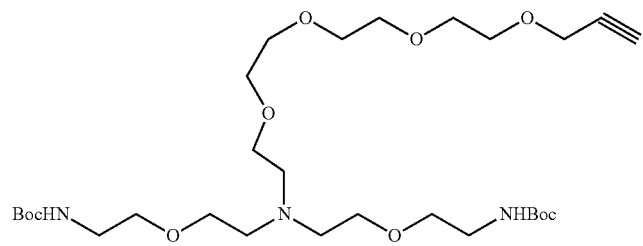

To a solution of tert-butyl [2-(2-bromoethoxy)ethyl]carbamate (1.8 g, 6.6 mmol) and propargyl-PEG4 amine (0.7 g, 3.0 mmol) in 30 ml DMF was added potassium carbonate (1.2 g, 9 mmol). The reaction was stirred at 80° C. for 6 hrs, and then partitioned between DCM (200 mL) and brine (50 mL). The organic layer was separated and washed with brine and dried with anhydrous sodium sulfate. Upon filtration, the resulting filtrate was concentrated and purified by reverse phase liquid chromatography (RPLC) using an Isco COMBIFLASH® liquid chromatograph eluted with 10% to 100% acetonitrile and water with 0.1% TFA as modifier. Yield of the products 1.0 g, 65%. Ion(s) found by LCMS: M/2+H=606.4.

Step b.

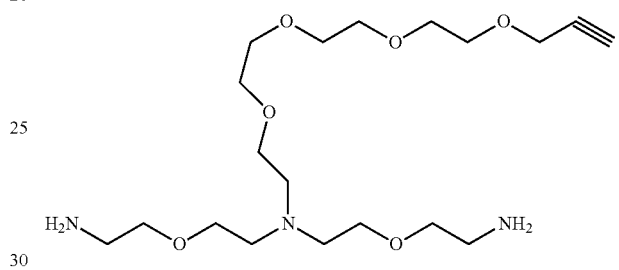

Product from the previous step (1.0 g, 1.6 mmol) was treated with TFA (10 mL) at room temperature for 0.5 hour, then concentrated to dryness and used in next step without further purification. Yield was quantitative for this step. Ion(s) found by LCMS: M/2+H=406.3.

Step c.

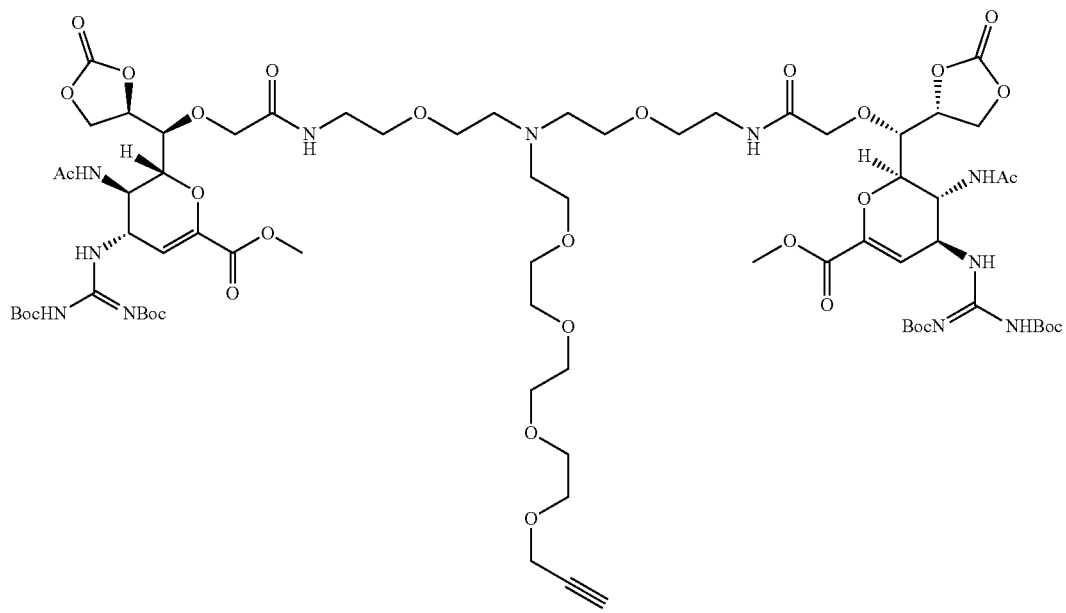

Product from the previous step (120 mg, 0.17 mmol) was treated with a solution of ether zanamivir acid (230 mg, 0.38 mmol, Example 31) in 10 ml DMF. To this solution was added EDC (100 mg, 0.5 mmol), HOBt (65 mg, 0.5 mmol), and DIEA (0.14 ml, 1 mmol). The resulting solution was stirred at room temperature overnight, then purified by and purified by reverse phase liquid chromatography (RPLC) using an Isco COMBIFLASH® liquid chromatograph eluted with 10% to 100% acetonitrile and water with no TFA as modifier. Yield of the products 180 mg, 60.2%. Ion(s) found by LCMS: M/2+H=816.9.

Step d.

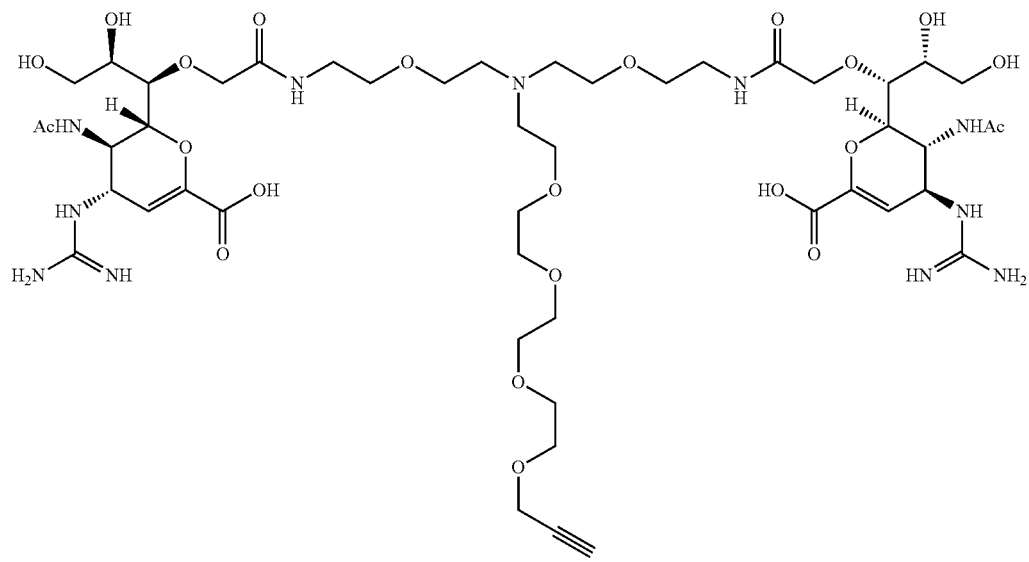 [SMILES: C#CCOCCOCCOCCOCCN(CCOCCNC(=O)CO[C@@H]([C@@H]1OC(C(=O)O)=C[C@H](NC(=N)N)[C@H]1NC(C)=O)[C@H](O)CO)CCOCCNC(=O)CO[C@@H]([C@@H]1OC(C(=O)O)=C[C@H](NC(=N)N)[C@H]1NC(C)=O)[C@H](O)CO]

Product from the previous step (180 mg, 0.11 mmol) was treated with trifluoroacetic acid (2 mL) for 30 min at room temperature. The resulting solution was concentrated and was dissolved into water (2 mL), then treated with a solution of lithium hydroxide (24 mg, 1 mmol) dissolved in $H_2O$ (1 mL). The resulting reaction was stirred 10 min then quenched with 0.1 ml acetic acid. The solution was concentrated and purified by reverse phase liquid chromatography (RPLC) using an Isco COMBIFLASH® liquid chromatograph eluted with 0% to 50% acetonitrile and water, using 0.1% TFA as the modifier. Yield of product 140 mg, 52%. Ion(s) found by LCMS: M/2+H=575.8, M/3+H=384.2.

Example 74. Synthesis of Conjugate 17

This conjugate was prepared analogously to Example 62 (Conjugate 13a) by PEG4-azido-Fc (SEQ ID NO: 35, Example 61) and Int-19 (Example 73). Maldi TOF analysis of the purified final product gave an average mass of 56,672. Da (DAR=2.2). Yield 36.7 mg, 36.7%.

Example 75. Synthesis of Int-20

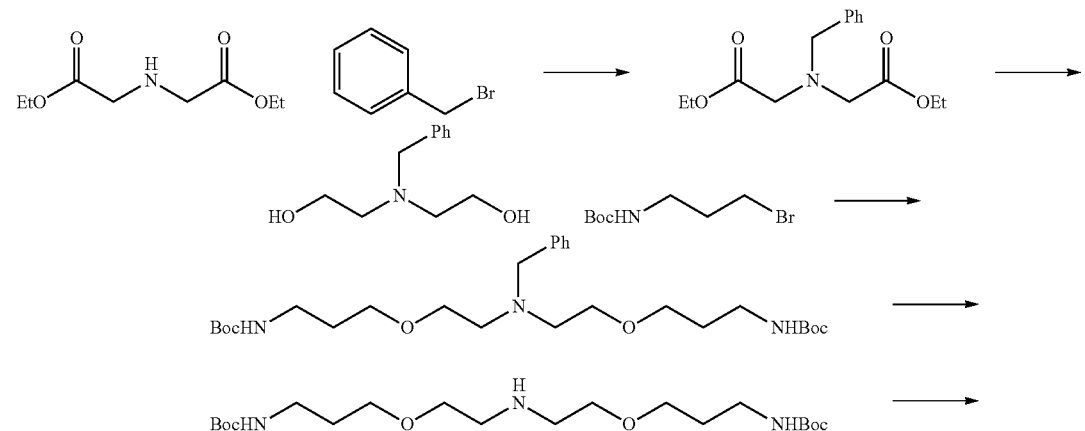

789   -continued   790
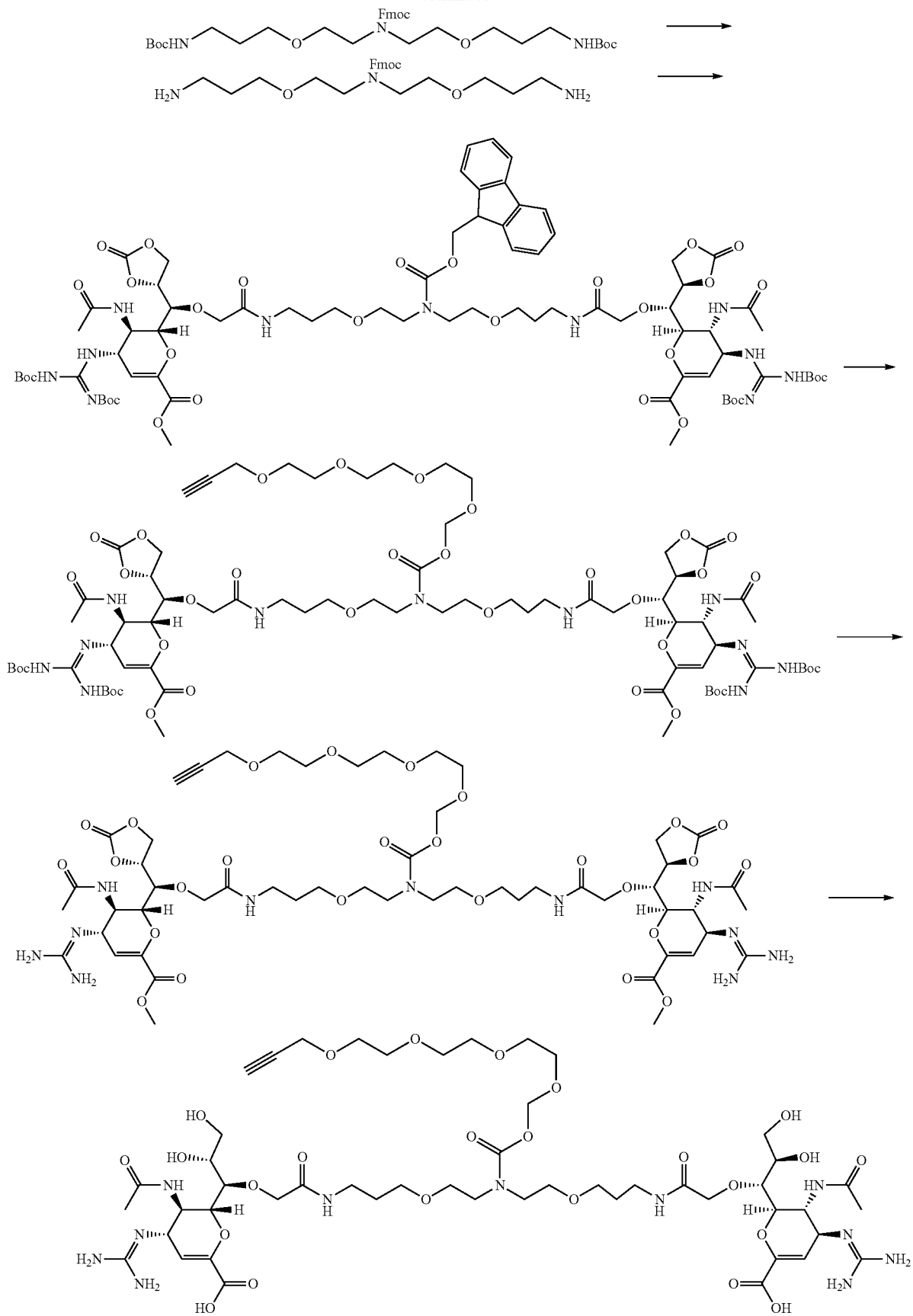

Step a.

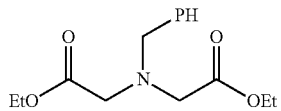

To a solution of diethyl iminodiacetate (3.1 g, 16.06 mmol) in anhydrous DMF (36 mL) was added benzyl bromide (2.38 mL, 19.64 mmol) and potassium carbonate (6.44 g, 46.46 mmol). The resulting mixture was heated at 70° C. for 16 hours. After cooling to room temperature, the reaction mixture was diluted water and extracted with tertiarybutylmethylether (3×100 mL). The organic layers were washed with brine, dried over $Na_2SO_4$ and filtered then concentrated. The residue was purified by normal phase silica gel chromatography (Isco, 0 to 10% ethyl acetate and hexane). Yield 3.13 g, 69.8%. Ion found by LCMS: $[M+H]^+=$ 280.2.

Step b.

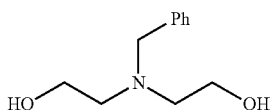

A solution of di-ethyl ester from step-a (3.2 g, 11.2 mmol) in anhydrous THE (5 mL) was added slowly to a round bottom flask containing $LiALH_4$ (425 mg, 14.2 mmol) in THE (2 mL) under nitrogen gas at 0° C. The syringe was rinsed with THE (2×5 mL). The resulting mixture was slowly warmed up to room temperature overnight. Methanol (2 mL) was added slowly to quench the reaction following by addition of NaOH aqueous (1 mL). The resulting mixture was stirred for 1 hour then filtered under vacuum. The filtrate was concentrated and used in the next step without purification. Yield 2.4 g, 109%. Ion found by LCMS: $[M+H]^+=$ 196.2.

Step c.

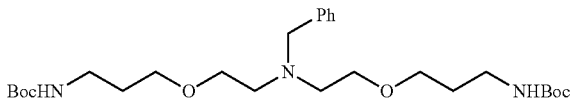 [SMILES: CC(C)(C)OC(=O)NCCCOCCN(CCOCCCNC(=O)OC(C)(C)C)Cc1ccccc1]

Product from the previous step (1.02 g, 5.24 mmol) in anhydrous THE (4 mL) was added slowly into a flask containing NaH (60% purity, 2.09 g, 52.4 mmol) and THE (5 mL) at 0° C. under nitrogen gas. The resulting mixture was stirred for 1 hour followed by dropwise addition of 3-(Boc-amino)propylbromide (3.8 g, 15.7 mmol) in THE (20 mL). The reaction mixture was slowly warmed to room temperature and stirred for 3 days. The reaction was cooled down to 0° C. then quenched with water (6 mL) and stirred for 1 hour. It was extracted with ethyl acetate (2×100 mL). The combined organic layers were washed with 1 N HCl aqueous and brine. It was dried over $Na_2SO_4$, filtered and concentrated. The residue was purified by normal phase chromatography (Isco, 0 to 5% methanol and dichloromethane). Yield 984 mg, 37%. Ion found by LCMS $[M+H]^+=$ 510.0.

Step d.

Palladium hydroxide (543 mg, 0.77 mmol) was added into a flask containing the step-c product (985.3 mg, 1.93 mmol) in anhydrous methanol (19.5 mL), under an H2 atmosphere. The resulting mixture was stirred at room temperature for 16 hours. It was then filtered through a pad of celite and washed with methanol, and concentrated. The residue was carried on to the next step without purification. Yield 828.6 mg, 102%. Ion found by LCMS $[M+H]^+=420.0$.

Step e.

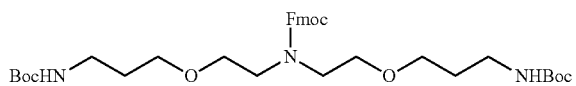

The step-d product (829 mg, 1.97 mmol) in $H_2O$:THF (1:1, 16 mL) was cooled down to 0° C. To this solution was added $Na_2CO_3$ (314 mg, 2.96 mmol) following by addition of Fmoc N-hydroxysuccinimide ester (826 mg, 2.37 mmol). The resulting mixture was warmed up to room temperature and stirred until complete by LCMS, then extracted with ethyl acetate. The organic layer was washed with brine and dried over $Na_2SO_4$, filtered and concentrated. The residue was purified by normal phase chromatography (Isco, 0 to 60% ethyl acetate and hexane). Yield 784 mg, 62%. Ion found by LCMS $[M+H-Boc]^+=542.0$.

Step f.

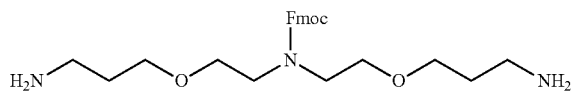

The step-e product (1.01 g, 1.57 mmol) was stirred in TFA (5 mL) and $CH_2Cl_2$ (9 ml) at room temperature for 1 hour then concentrated under reduced pressure. The residue was purified by RPLP (Isco, 5 to 100% methanol and water without modifier). Yield 903 mg, 86%. Ion found by LCMS $[M+H]^+=442.2$.

Step g.

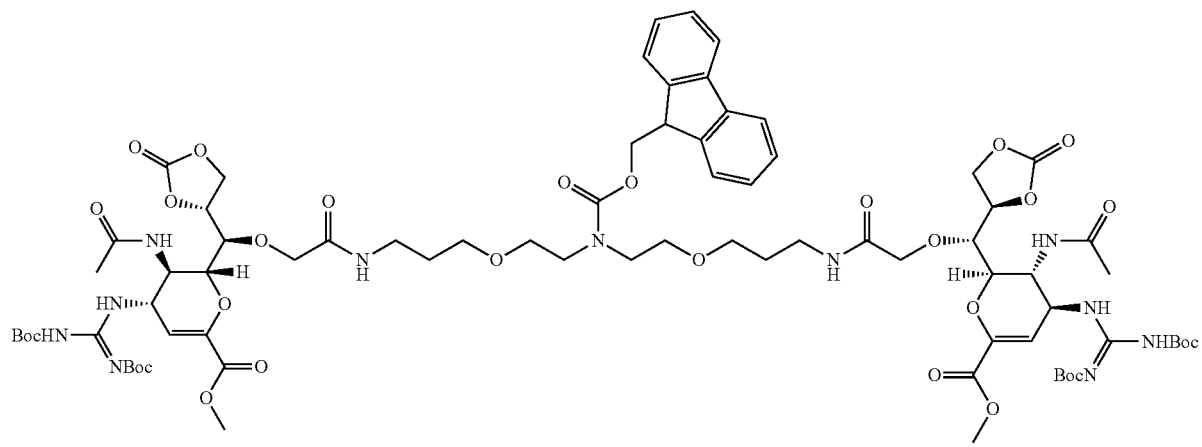

To a mixture of ether zanamivir acid (340 mg, 0.49 mmol), step-f product (111 mg, 0.25 mmol, Example 31) and HATU (206 mg, 0.53 mmol) in anhydrous DMF (3 mL) was added DIEA (162 mg, 1.23 mmol). The resulting mixture was stirred at room temperature for 1 hour, then directly purified by RPLC (Isco, 30 to 100% methanol and water without modifier). Yield 249 mg, 61%. Ion found by LCMS $[(M+2H)/2]^+=833.8$.

Step h.

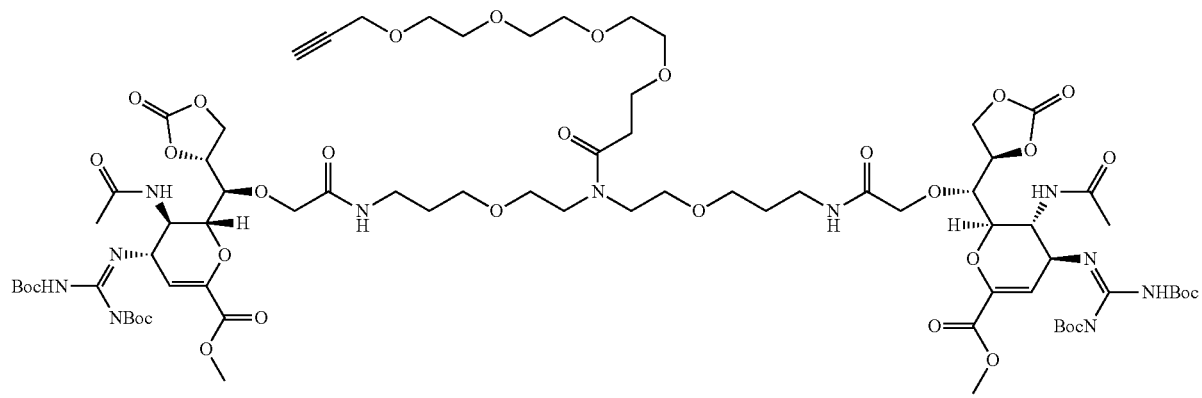

To a solution of the step-g product (249 mg, 0.15 mmol) in anhydrous DMF (0.5 mL) was added SilaMetS Thiol (1.2 g, 1.47 mmol) and 1,8-diazabicyclo[5.4.0]undec-7-ene (12 mg, 0.07 mmol). The resulting mixture was stirred for 1.5 hours, then filtered directly into a vial containing HATU (69 mg, 0.18 mmol), propargyl PEG-4 acid (43 mg, 0.16 mmol) and DIEA (43 mg, 0.33 mmol). The reaction mixture was stirred for 1 hour, then directly purified by RPLC (Isco, 30 to 100% methanol and water without modifier). Yield 298 mg, 118%. Ion found by LCMS $[(M+2H-Boc)/2]^+=843.9$.

Step i.

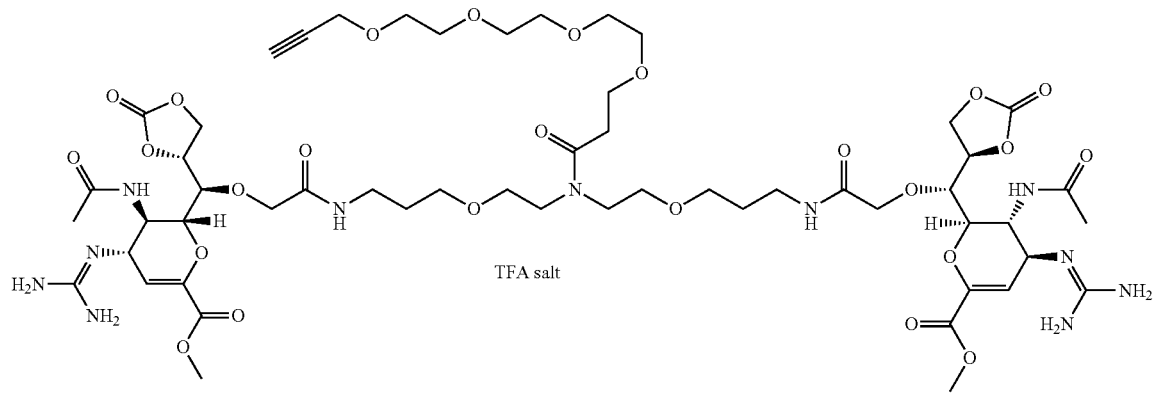 [SMILES: C#CCOCCOCCOCCOCCC(=O)N(CCOCCCNC(=O)CO[C@@H]([C@@H]1OC(C(=O)OC)=C[C@H](N=C(N)N)[C@H]1NC(C)=O)[C@H]1COC(=O)O1)CCOCCCNC(=O)CO[C@@H]([C@@H]1OC(C(=O)OC)=C[C@H](N=C(N)N)[C@H]1NC(C)=O)[C@H]1COC(=O)O1]

The step-h product (298 mg, 0.18 mmol) was dissolved in TFA (3 mL) and CH$_2$Cl2 (3 mL), and the solution was stirred at room temperature for 16 hours. It was then concentrated under reduced pressure and purified by HPLC (ACCQ Isco, 0 to 25% acetonitrile and water, using 0.1% TFA as a modifier). Yield 112 mg, 44%. Ions found by LCMS [(M+2H)/2]$^+$=643.8 and [(M+3H)/3]$^+$=429.6.

Step j.

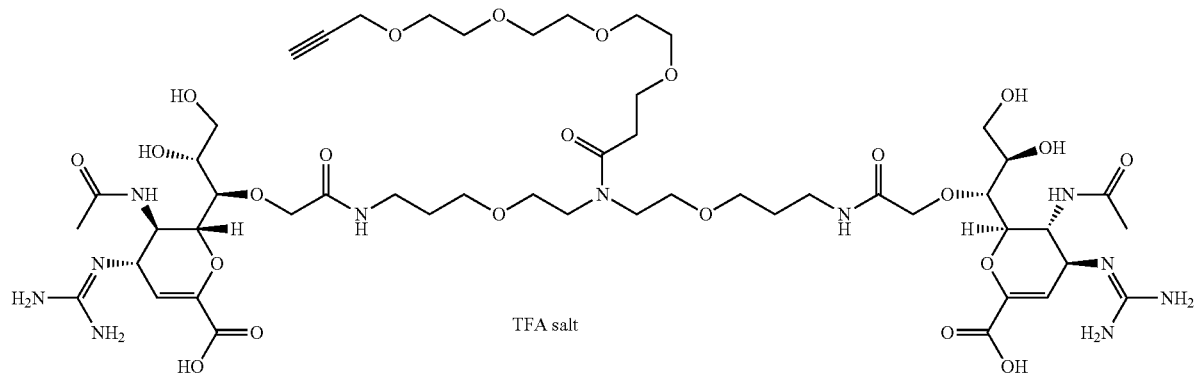 [SMILES: C#CCOCCOCCOCCOCCC(=O)N(CCOCCCNC(=O)CO[C@@H]([C@@H]1OC(C(=O)O)=C[C@H](N=C(N)N)[C@H]1NC(C)=O)[C@H](O)CO)CCOCCCNC(=O)CO[C@@H]([C@@H]1OC(C(=O)O)=C[C@H](N=C(N)N)[C@H]1NC(C)=O)[C@H](O)CO]

To a solution of the step-i product (112 mg, 0.072 mmol) in MeOH (4 mL) and water (2 mL) was added LiOH (10.6 mg, 0.43 mmol). The resulting solution was stirred at room temperature for 1 hour, then acidified with TFA and concentrated under reduced pressure. The residue was purified by HPLC (ACCQ Isco, 0 to 25% acetonitrile and water, using 0.1% TFA as modifier). Yield 37 mg, 36%. Ions found by LCMS [(M+2H)/2]$^+$=603.8, [(M+3H)/3]$^+$=402.9.

Example 76. Synthesis of Conjugate 18

A solution of azido functionalized aglycosylated Fc (100 mg, 5.4 mL, 1.87 µmol, SEQ ID NO: 35) was added to a 15 mL centrifuge tube containing alkyne derivatized small molecule (16.1 mg, 0.011 mmol, Int-20). After gently shaking to dissolve all solids, the mixture was added to 3 mL premixed solution of L-ascorbic acid sodium (149 mg, 0.75 mmol, 0.25 M), copper (II) sulfate (2.4 mg, 0.015 mmol, 0.005 M) and BTTAA (25.8 mg, 0.6 mmol, 0.02 M) in PBS 7.4 buffer. The resulting solution was gently shaken overnight. It was purified by affinity chromatography over a protein A column, followed by size exclusion chromatography (see general conjugate purification protocol in Example 10). Maldi TOF analysis of the purified final product gave an average mass of 56826 Da (DAR 2.2). Yield 36.64 mg, 37%.

The nucleic acid construct encoding the Fc for conjugate 18 included a nucleic acid encoding the amino acid sequence of SEQ ID NO: 35, which includes a C-terminal lysine residue and N-terminal murine IgG signal sequence. Upon expression, the C-terminal lysine and the N-terminal murine IgG signal sequence of the Fc of conjugate 18 are proteolytically cleaved, resulting in an Fc having the sequence lacking Lys447 (e.g., lacking a C-terminal lysine residue) and the N-terminal murine IgG signal sequence. The presence or absence of a C-terminal lysine does not alter the properties of the Fc or the corresponding conjugate.

Example 77. Synthesis of Int-21
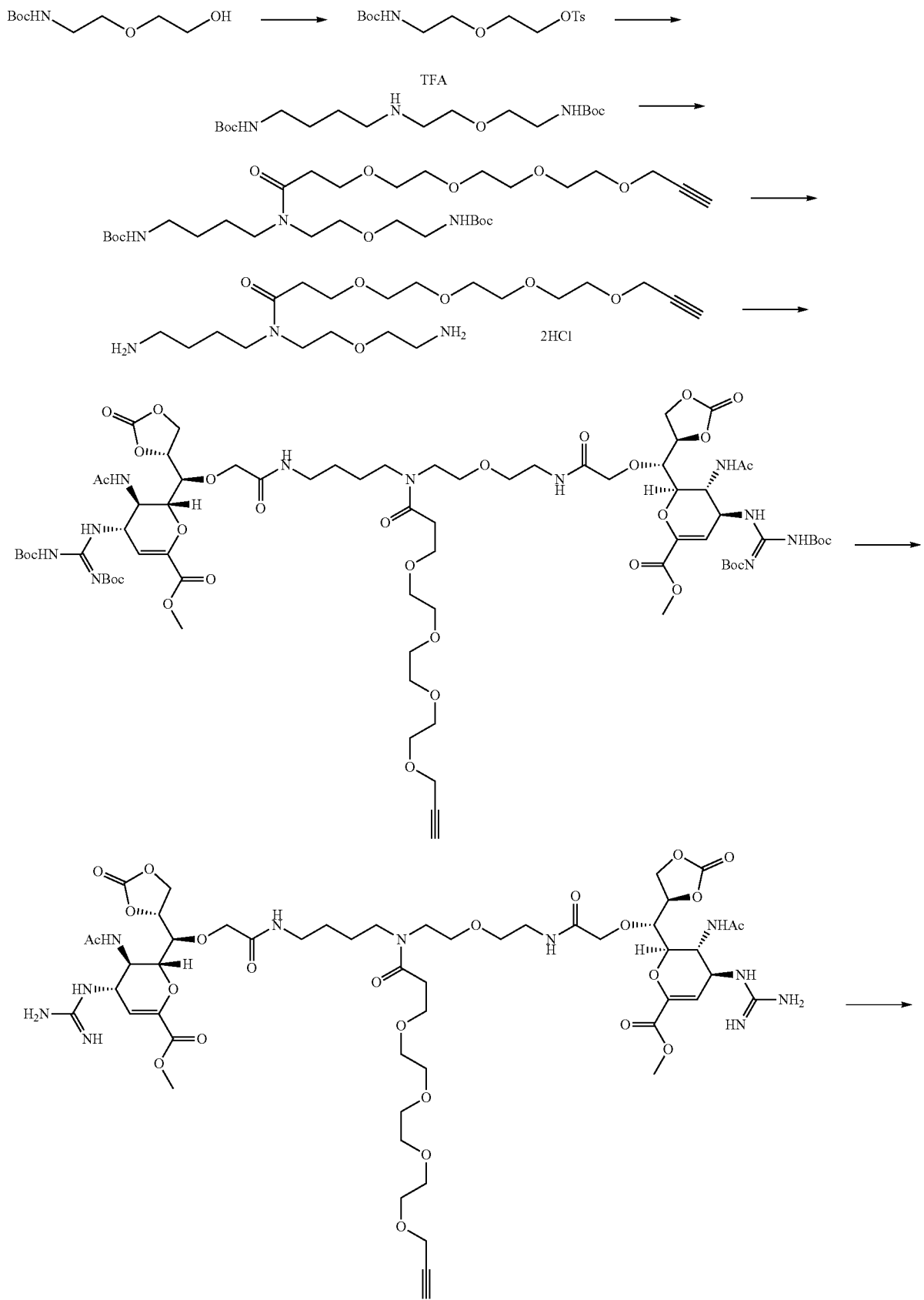

-continued

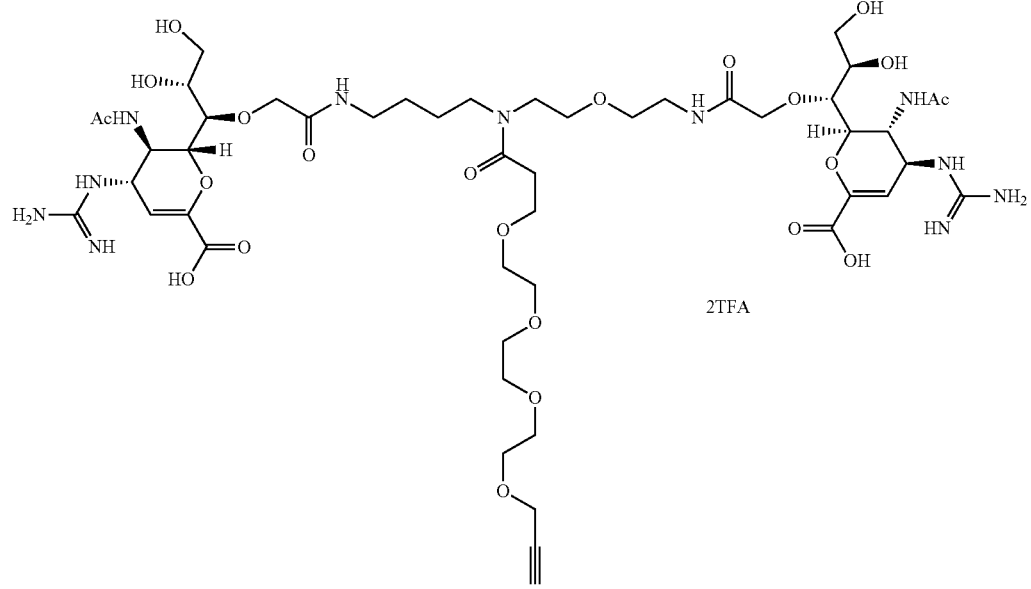

2TFA

Step a.

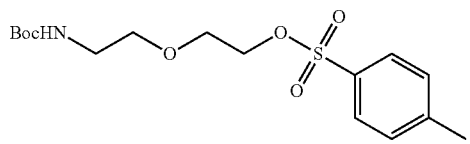

To a solution of 2-(2-Boc-aminoethoxy) ethanol (6.15 g, 30 mmol) in anhydrous DCM (60 ml) was added DIPEA (7.8 g, 60 mmol) and DMAP (366.6 mg, 3 mmol). P-toluenesulfonyl chloride (6.86 g, 36 mmol) was then added in portions over 30 minutes. After the resulting mixture was stirred for 3 days, it was concentrated by rotary evaporation and purified by RPLC (20% to 70% acetonitrile/water with no modifier). Yield 3.71 g, 34.4%. Ion found by LCMS: [M-Boc+H]$^+$=260.

Step b.

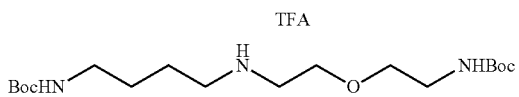 [SMILES: CC(C)(C)OC(=O)NCCCCNCCOCCNC(=O)OC(C)(C)C]

To a solution of the step-a product (2.1 g, 5.83 mmol) in anhydrous THF (10 ml) was added sodium carbonate (1.24 g, 11.7 mmol) and mono-N-Boc-1,4-diaminobutane (1.32 g, 7 mmol). The resulting mixture was heated at 60° C. for 1 day. The salt was then filtered off, and the filtrate was concentrated by rotary evaporation. The residue was purified through RPLC (100 g, 5 to 50% acetonitrile and water, using 0.1% TFA as modifier). Yield 1.94 g, 88.6%. Ion found by LCMS: [M+H]$^+$=376.0.

Step c.

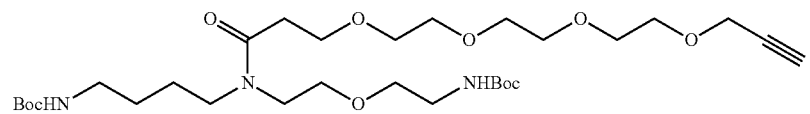 [SMILES: C#CCOCCOCCOCCOCCC(=O)N(CCCCNC(=O)OC(C)(C)C)CCOCCNC(=O)OC(C)(C)C]

To a solution of propargyl PEG-4 acid (781 mg, 3 mmol) and HATU (1.14 g, 3 mmol) in anhydrous DMF (3ml) was added DIPEA (390 mg, 3 mmol), followed by the addition of the solution step-b product (940 mg, 2.5 mmol) and DIPEA (390 mg, 3 mmol) in anhydrous DMF (3 ml). The reaction mixture was stirred for 30 minutes, then directly purified through RPLC (100 g, 5 to 80% acetonitrile and water, using 0.1% TFA as modifier). Yield 960 mg, 65.3%. Ion found by LCMS: $[M+H]^+=618.3$. $[M-Boc+H]^+=518.3$.

Step d.

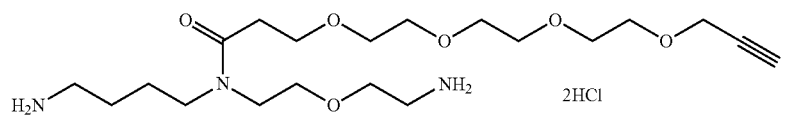

The step-c product (960.2 mg, 1.63 mmol) was dissolved in anhydrous THF (6 ml). 4N HCl solution in dioxane (4 ml) was added, and the reaction mixture was stirred overnight. It was then concentrated by rotary evaporation. The residue was extracted with water (3 ml×3) and ethyl acetate (10 ml). The combined aqueous layers were lyophilized. Yield 760 mg, 95.1%. Ion found by LCMS: $[M+H]^+=418.0$.

Step e.

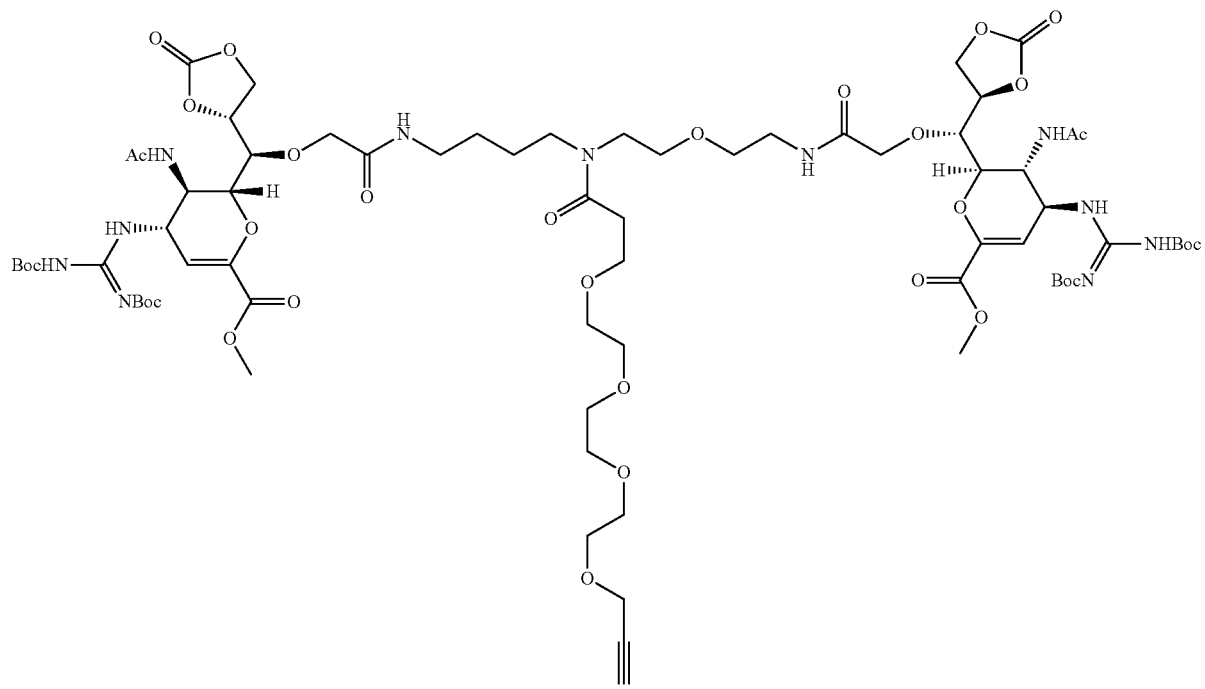

To a mixture of ether zanamivir acid (315 mg, 0.5 mmol) and HATU (190 mg, 0.5 mmol) in anhydrous DMF (1 ml) was added in portions a solution of the step-d diamine product (148 mg, 0.3 mmol) and DIPEA (165 mg, 1.5 mmol) in anhydrous DMF (1 ml) over 20 minutes. After the addition, the reaction was stirred for 30 more minutes and directly purified by RPLC (50 g, 30 to 90% acetonitrile and water, using 0.1% TFA as modifier). Yield 233 mg, 56.7%. Ion found by LCMS: $[(M+2H)/2]^+=821.3$.

Step f.

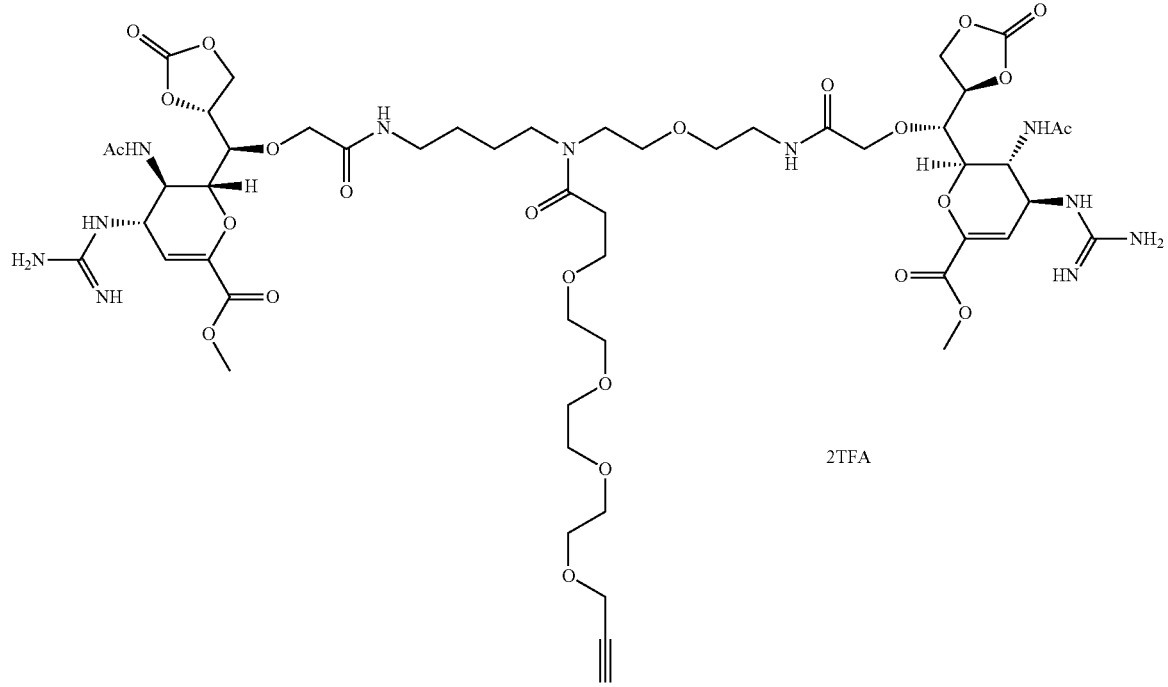 [SMILES: C#CCOCCOCCOCCOCCC(=O)N(CCCCNC(=O)CO[C@@H]([C@@H]1OC(C(=O)OC)=C[C@H](NC(=N)N)[C@H]1NC(C)=O)[C@H]1COC(=O)O1)CCOCCNC(=O)CO[C@@H]([C@@H]1OC(C(=O)OC)=C[C@H](NC(=N)N)[C@H]1NC(C)=O)[C@H]1COC(=O)O1]

The step-e product (233 mg, 0.142 mmol) was dissolved in TFA (1.5 ml), and the solution was heated at 30° C. for 30 minutes. It was then concentrated and directly purified by RPLC (0% to 30% acetonitrile and water, using 0.1% TFA as modifier). Yield 120 mg, 57.4%. Ions found by LCMS: $[(M+2H)/2]^+=621.4$, $[(M+3H)/3]^+=414.7$.

Step g.

To a solution of the step-f product (120 mg, 0.0816 mmol) in MeOH (2 ml) was added LiOH monohydrate (63 mg, 1.5 mmol) solution in water (2 ml). The resulting mixture was stirred for 1.5 hours and then concentrated by rotary evaporation. The residue was acidified by 4N HCl solution in dioxane (0.5 ml) and was purified by HPLC (0 to 15% acetonitrile and water, using 0.1% TFA as modifier). Yield

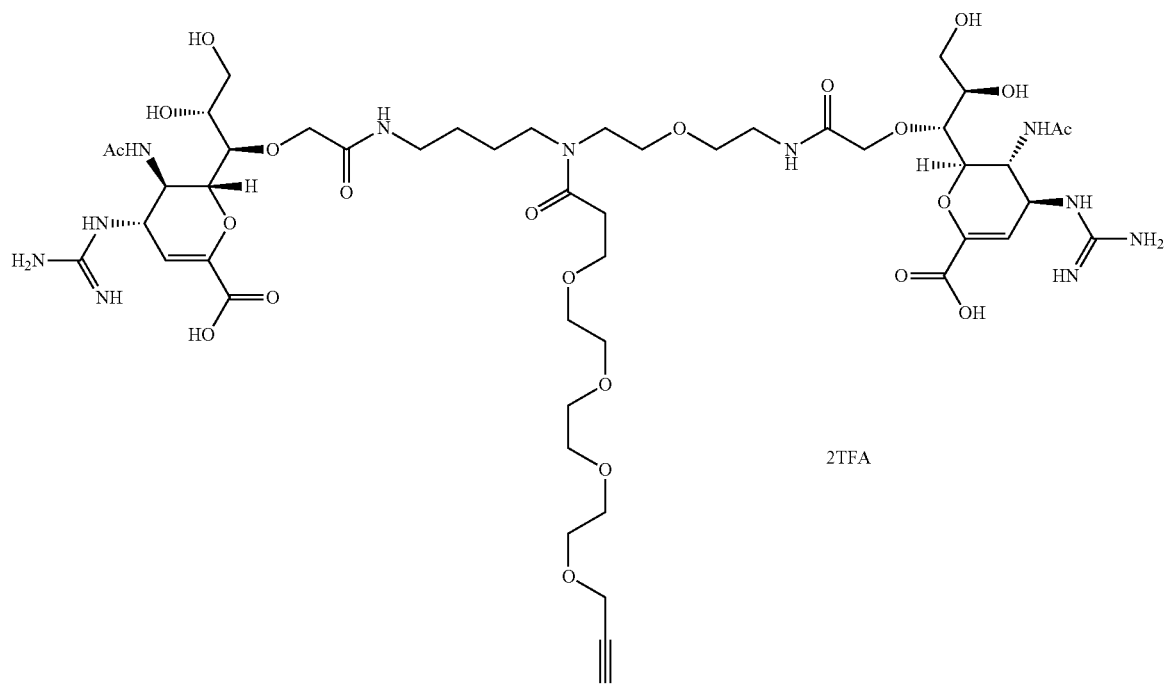 [SMILES: C#CCOCCOCCOCCOCCC(=O)N(CCCCNC(=O)CO[C@@H]([C@@H]1OC(C(=O)O)=C[C@H](NC(=N)N)[C@H]1NC(C)=O)[C@H](O)CO)CCOCCNC(=O)CO[C@@H]([C@@H]1OC(C(=O)O)=C[C@H](NC(=N)N)[C@H]1NC(C)=O)[C@H](O)CO]

805
98.2 mg, 86.6%. Ions found by LCMS: [(M+2H)/2]$^+$=581.8, [(M+3H)/3]$^+$=388.2.
Example 78. Synthesis of Conjugate 19
This conjugate was prepared analogously to Example 62 (Conjugate 13a) by PEG4-azido-Fc (SEQ ID NO: 35, Example 61) and Int-21 (Example 78). Maldi TOF analysis of the purified final product gave an average mass of 56,548. Da (DAR=2.1). Yield 39.7 mg, 39.7%.
Example 79. Synthesis of Int-22
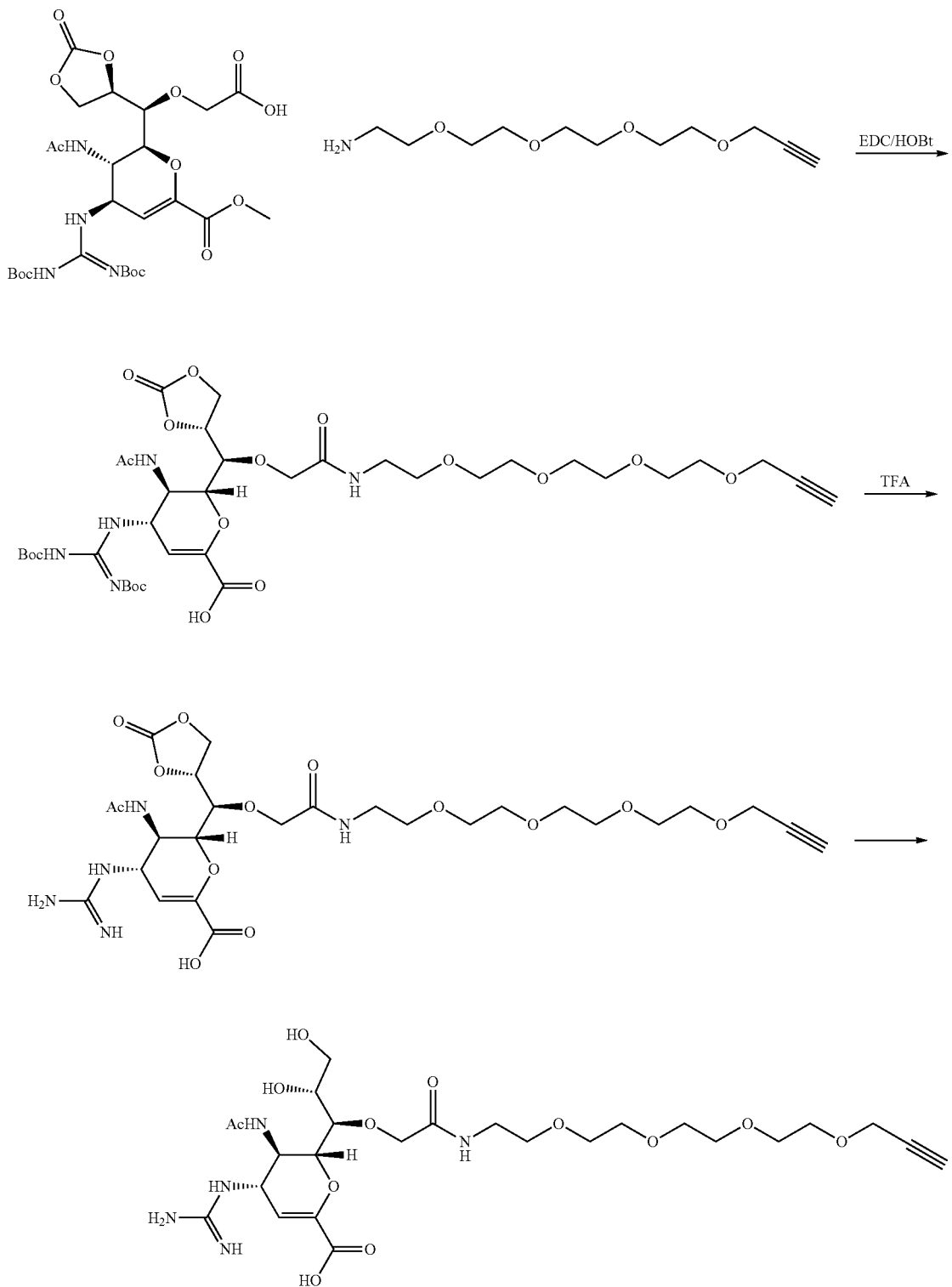

Step a.

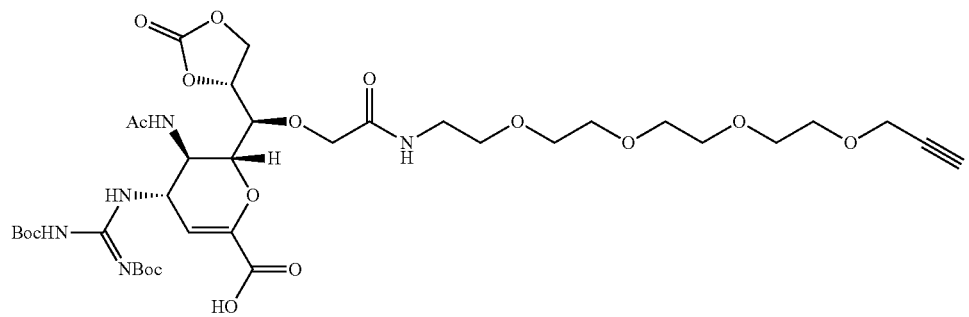

To a mixture of ether zanamivir acid (1.8 g, 2.8 mmol Example 31) and propargyl-PEG4-amine (0.82 g, 3.5 mmol. 1.2 eq.) in dichloromethane (50 mL), was added EDC (1.0 g, 5 mmol), HOBt (0.65 g, 5 mmol), and DIEA (1.4 ml, 10 mmol). The resulting solution was stirred at room temperature overnight, concentrated, and purified by reverse phase liquid chromatography (RPLC) using an Isco COMBI-FLASH® liquid chromatograph eluted with 10% to 100% acetonitrile and water with no 0.1% TFA as modifier. Yield of products 1.35 g, 50.2%. Ion(s) found by LCMS: M+H=830.4.

Step b.

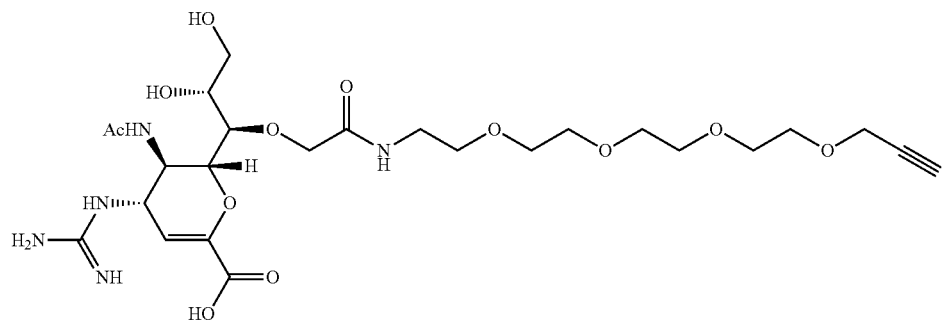 [SMILES: C#CCOCCOCCOCCOCCNC(=O)CO[C@@H]([C@@H]1OC(C(=O)O)=C[C@H](NC(=N)N)[C@H]1NC(C)=O)[C@H](O)CO]

Product from the previous step (1.35 g, 1.6 mmol) was treated with trifluoacetic acid (20 mL) for 30 min at room temperature. The resulting solution was concentrated, dissolved in water (10 mL) and MeOH (10 mL), then treated with a lithium hydroxide (120 mg, 5 mmol) solution in water (10 mL). The reaction solution was stirred 10 min then quenched with 0.5 ml acetic acid. The reaction was concentrated and purified by reverse phase liquid chromatography (RPLC) using an Isco COMBIFLASH® liquid chromatograph eluted with 0% to 50% acetonitrile and water, using 0.1% TFA as the modifier. Yield of the products 510 mg, 52.8%. Ion(s) found by LCMS: M+H=604.3.

Example 80. Synthesis of Conjugate 20

This conjugate was prepared analogously to Example 62 (Conjugate 13a) by PEG4-azido-Fc (SEQ ID NO: 35, Example 61) and Int-22 (Example 79). Maldi TOF analysis of the purified final product gave an average mass of 55,508. Da (DAR=2.3). Yield 37.0 mg, 37.0%.

Example 81. Synthesis of Int-23

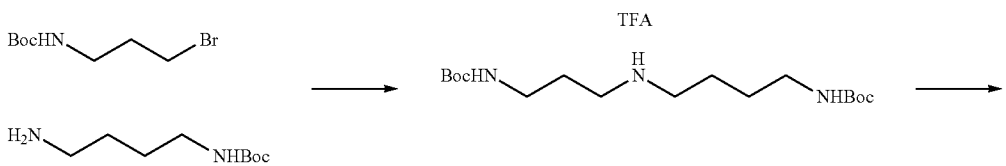

809 -continued 810
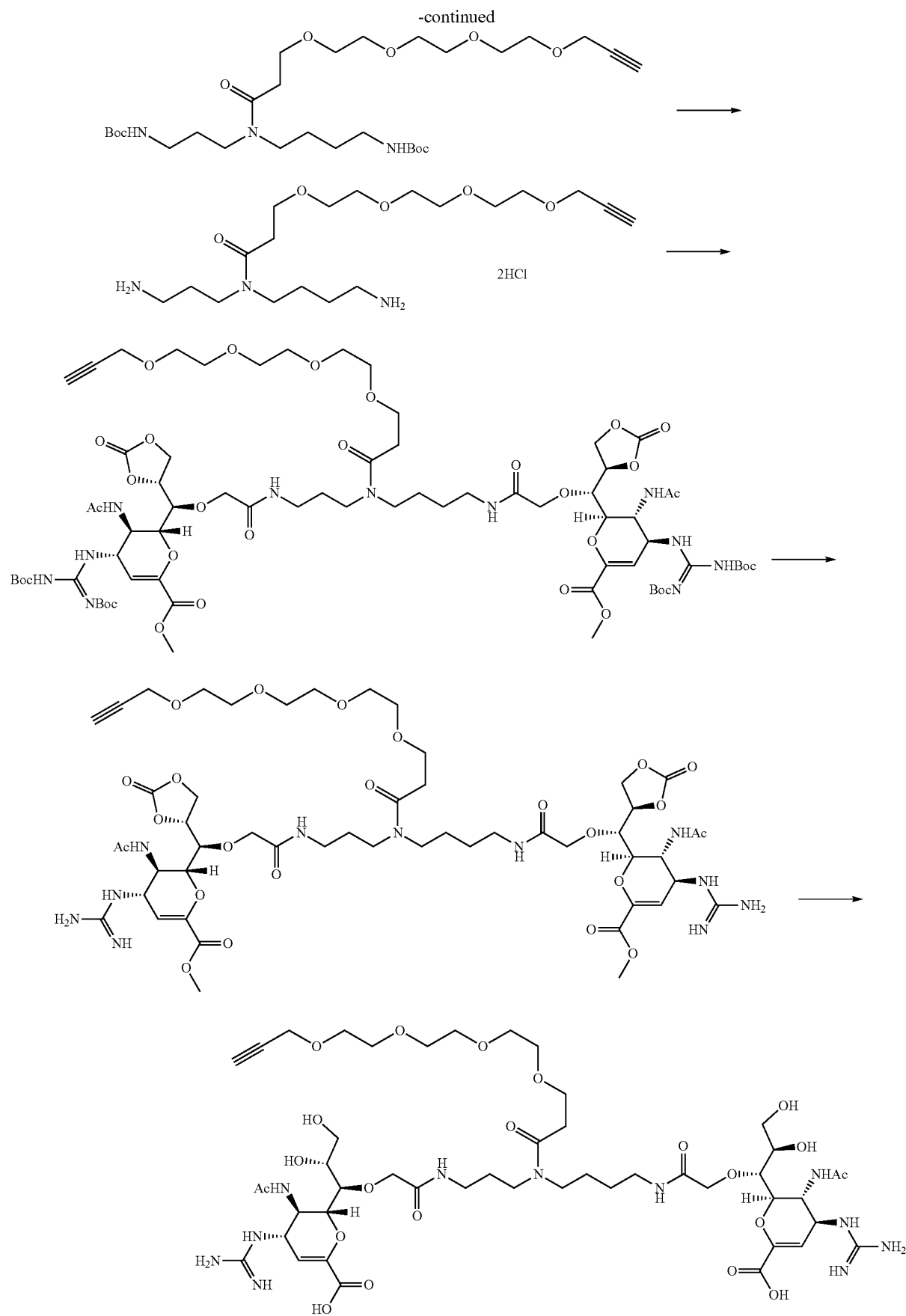

Step a.

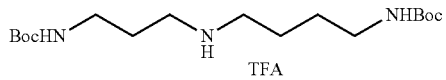

To a solution of N-Boc-1.4-diaminobutane (941.5 mg, 5 mmol) in anhydrous THF (10 ml) was added sodium carbonate (1.06 g, 10 mmol) and 3-(Boc-amino)propylbromide (1.43 g, 6 mmol). The resulting mixture was heated at 50° C. for 1 day. The salt was then filtered, and concentrated by rotary evaporation. The residue was purified by RPLC (100 g, 5 to 50% acetonitrile and water, using 0.1% TFA as modifier). Yield 1.35 g, 58.8%. Ion found by LCMS: $[M+H]^+=346.0$.

Step b.

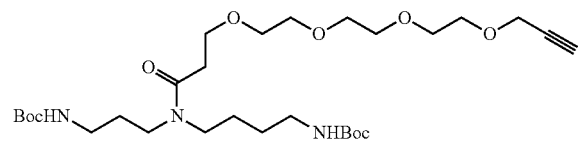 [SMILES: C#CCOCCOCCOCCOCCC(=O)N(CCCCNC(=O)OC(C)(C)C)CCCNC(=O)OC(C)(C)C]

Step c.

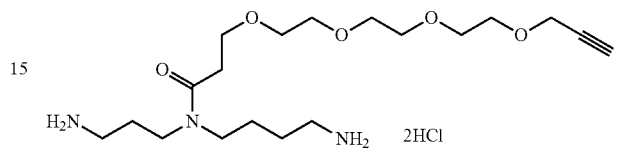

The step-b product (1.19 g, 2.02 mmol) was dissolved in anhydrous THF (6 ml). 4N HCl solution in dioxane (4.5 ml) was added, and the reaction mixture was stirred for 1 day. It was then concentrated by rotary evaporation. The residue was extracted with water (3 ml×3) and ethyl acetate (15 ml). The combined aqueous layers were lyophilized. Yield 940 mg, quantitative yield. Ion found by LCMS: $[M+H]^+=388.3$.

Step d.

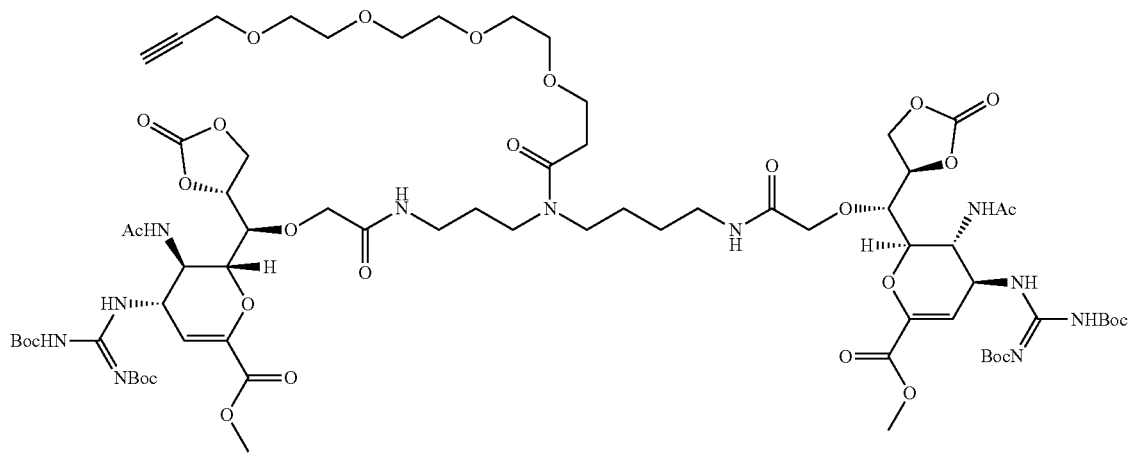

To a solution of propargyl PEG-4 acid (781 mg, 3 mmol) and HATU (1.14 g, 3 mmol) in anhydrous DMF (3 ml) was added DIPEA (390 mg, 3 mmol), followed by the addition of the solution step-a product (863.8 mg, 2.5 mmol) and DIPEA (390 mg, 3 mmol) in anhydrous DMF (3 ml). The reaction mixture was stirred for 30 minutes, then directly purified by RPLC (100 g, 5 to 80% acetonitrile and water, using 0.1% TFA as modifier). Yield 1.19 g, 81%. Ion found by LCMS: $[M+H]^+=588.3$.

To a mixture of ether zanamivir acid (315 mg, 0.5 mmol, Example 31) and HATU (209.1 mg, 0.55 mmol) in anhydrous DMF (1 ml) was added DIPEA (65 mg, 0.5 mmol). After 5 minutes, a solution of the step-c product (170 mg, 0.439 mmol) and DIPEA (130 mg, 1 mmol) in anhydrous DMF (1 ml) was added in portions over 20 minutes. The reaction was stirred for an additional 30 minutes, then directly purified by RPLC (50 g, 30 to 90% acetonitrile and water, using 0.1% TFA as modifier). Yield 208 mg, 51.6%. Ion found by LCMS: $[(M+2H)/2]^+=806.7$.

Step e.

The step-d product (208 mg, 0.129 mmol) was dissolved in TFA (1.5 ml), and the solution was heated at 30° C. for 30 minutes. It was then directly purified by RPLC (100 g, 0 to 30% acetonitrile and water, using 0.1% TFA as modifier). Yield 134 mg, 72%. Ions found by LCMS: $[(M+2H)/2]^+$=606.8, $[(M+3H)/3]^+$=405.0.

Step f.

To a solution of the step-e product (134 mg, 0.093 mmol) in MeOH (2 ml) was added a solution of LiOH monohydrate (63 mg, 1.5 mmol) in water (2 ml). The resulting mixture was stirred for 1.5 hours and then concentrated by rotary evaporation. The residue was acidified by 4N HCl solution in dioxane (0.5 ml) and was purified by HPLC (0 to 15% acetonitrile and water, using 0.1% TFA as modifier). Yield 78.4 mg, 62%. Ions found by LCMS: $[(M+2H)/2]^+$=566.4, $[(M+3H)/3]^+$=378.4.

Example 82. Synthesis of Conjugate 21

This conjugate was prepared analogously to Example 62 (Conjugate 13a) by PEG4-azido-Fc (SEQ ID NO: 35, Example 61) and Int-23 (Example 81). Maldi TOF analysis of the purified final product gave an average mass of 56,503. Da (DAR=2.2). Yield 34.4 mg, 34%.

Example 83. Activity of Conjugates 13 to 21 Against High Path H7N9 Influenza A, and Two Influenza B Isolates in a Cytopathic Effects (CPE) Assay A total of 9 conjugates (Table 38) were run at concentrations of 100, 10, 1, and 0.1 nM and compared to ribavirin in a CPE assay. The CPE assay followed standard methodology, but briefly, utilized 80-100% confluent monolayers of MDCK cells in a 96-well plate. To these, test articles were added in triplicate and allowed to incubate at 37° C. (+5% $CO_2$) until CPE effects were visually apparent. Once CPE was noted, cell layers were stained with 0.011% neutral red for approximately 2 hours. Afterwards, a 50:50 mix of Sorensen citrate buffer/ethanol was added and allowed to incubate for 30 m, then the $A_{540}$ was read on a spectrophotometer and $EC_{50}/CC_{50}$ values calculated by regression analysis. All conjugates had significant activity against the Influenza B/Florida/4/2006 isolate, with an $EC_{50}$ values ranging from 3.05 to 33.5 nm (Table 39). On average, conjugates demonstrated a 275-fold potency advantage over ribavirin ($EC_{50}$ of 3,250 nM). Activity of conjugates against Influenza B/Brisbane/60/2008 was very similar to that seen against B/Florida with the exception of conjugate 14, which had an $EC_{50}$ of greater than 100 nM Importantly, all conjugates were highly active against the high path Influenza A/Anhui/1/2013 (H7N9) isolate as well.

The average EC$_{50}$ for all conjugates was 21.2 nM against this isolate (ranging from 12 to 28.5 nM), compared to 14,000 nM for ribavirin. Lastly, no direct cytotoxic effects of the conjugates on MOCK monolayers were detected at the concentrations tested.

TABLE 38

Conjugates and properties

| Conjugate | Int | Fc domain | DAR | Linker | Notes |
|---|---|---|---|---|---|
| 13 | 18 | SEQ ID NO: 35 | 2.2 | 15 atom | ether, dimer |
| 14 | 7 | SEQ ID NO: 35 | 2.1 | 15 atom | carbamate, dimer |
| 15 | 12 | SEQ ID NO: 35 | 2.2 | 15 atom | ether, dimer |
| 16 | 9 | SEQ ID NO: 35 | 2.1 | 17 atom | ether, dimer |
| 17 | 19 | SEQ ID NO: 35 | 2.2 | 17 atom | ether, dimer |
| 18 | 20 | SEQ ID NO: 35 | 2.2 | 19 atom | ether, dimer |
| 19 | 21 | SEQ ID NO: 35 | 2.1 | 16 atom | ether, dimer |
| 20 | 22 | SEQ ID NO: 35 | 2.3 | na | ether, monomer |
| 21 | 23 | SEQ ID NO: 35 | 2.2 | 14 atom | ether, dimer |

TABLE 39

Activity of conjugates in a CPE assay against Influenza subtypes

| | EC50 (nM)* | | |
|---|---|---|---|
| Conjugate | A/Anhui/1/2013 (H7N9) (zoonotic avian) | B/Brisbane/60/2008 (Victoria lineage) | B/Florida/4/2006 (Yamagata lineage) |
| Ribavirin | 14000 | 3300 | 3250 |
| 13 | 24 | 21 | 33.5 |
| 14 | 12 | >100 | 18.5 |
| 15 | 21.5 | 5.95 | 4.6 |
| 16 | 28.5 | 14.5 | 11 |
| 17 | 28** | 11 | 13 |
| 18 | 31 | 4.35 | 3.05 |
| 19 | 14.5 | 6.8 | 4.55 |
| 20 | 20.5 | 12.5 | 14.5 |
| 21 | 17.5 | 4.05 | 3.05 |

*Average of 2 values (VIS + NR)
**EC50 of 28 by VIS, >100 by NR

Example 84. Syntheses of Conjugate 22

Step a. Synthesis of PEG4-Azido IVIG

Preparation of 0.05M PEG4-azidoNHS ester solution in DMF/PBS: 6.05 mg of PEG4-azido NHS ester was dissolved in 0.050 mL of DMF at 0° C. and diluted to 0.305 mL by adding 0.250 mL of PBS 1× buffer at 0° C. This solution was used for preparing other PEG4-azido IVIG with variety of DAR values by adjusting the equivalents of this PEG4-azido NHS ester PBS solution.

Preparation of PEG4-azido IVIG: 0.05M PEG4-azidoNHS ester PBS buffer solution (0.301 mL, 15.0 µmol, 5.5 equivalents) was added to a solution of IVIG (Intravenous Immune Globulin, Baxter)) (407 mg in 9.25 mL of pH 7.4 PBS, MW-148863 Da, 1.968 µmol) and the mixture was shaken gently for 12 hours at ambient temperature. The solution was concentrated using a centrifugal concentrator (100,000 MWCO) to a volume of ~1.5 mL. The crude mixture was diluted 1:10 in PBS pH 7.4, and concentrated again. This wash procedure was repeated for total of three times. The small molecule reagent was removed with this wash procedure. The concentrated IVIG-PEG4-azide was diluted to 9.25 mL with pH 7.4 PBS 1× buffer and ready for Click conjugation. The purified material was quantified using a NANODROP™ UV visible spectrophotometer (using a calculated extinction coefficient based on the amino acid sequence of IVIG). Yield is quantitative after purification.

Step b. Synthesis of Conjugates

Prepared the Click reagent solution: 0.0050M CuSO$_4$ in PBS buffer solution: 10.0 mg CuSO$_4$ was dissolved in 12.53 mL PBS×1, than took 6.00 mL 0.0050M CuSO$_4$ solution and added 57.7 mg BTTAA (CAS number 1334179-85-9) and 297.6 mg Na Ascorbate to give the Click reagent solution (0.0050M CuSO$_4$, 0.020M BTTAA and 0.25M Sodium Ascorbate).

A solution of azido functionalized IVIG (140 mg, 3.17 mL, 0.936 µmol, IVIG-Linker-1-Azide) was added to a 15 mL centrifuge tube containing alkyne derivatized small molecule (8.4 mg, 0.00618 mmol, 6.6 eq, described in Example 60). After gently shaking to dissolve all solids, 1.50 mL of above click reagent solution of (L-ascorbic acid sodium, 0.25 M, 74.2 mg, 0.374 mmol, copper (II) sulfate 0.0050M, 1.2 mg, 0.0075 mmol, and BTTAA 0.020M, 12.9 mg, 0.0300 mmol). The resulting mixture was gently shaken overnight. It was purified by affinity chromatography over a Protein A column, followed by size exclusion chromatography (see conjugate purification protocol in Example 10). Maldi TOF analysis of the purified final product gave an average mass of 151873 Da (DAR=2.7). Yield 51.0 mg, 36% yield.

Example 85. Syntheses of Conjugate 23

Conjugate 23 was prepared analogously to Conjugate 22, substituting the appropriate alkyne functionalized small molecule (Int-23 described in Example 81) in the click conjugation step.

Example 86. Syntheses of Conjugate 24

Conjugate 24 was prepared analogously to Conjugate 22, substituting the appropriate alkyne functionalized small molecule (described in Example 19) in the click conjugation step.

Example 87. Efficacy of Conjugates 13, 14, and 21 against Influenza B in a lethal mouse model Conjugates were evaluated against a lethal Influenza B influenza infection in female BALB/c mice (Charles River Laboratories, 6-8 weeks). The challenge virus (B/Malaysia/2506/04) is a mouse-adapted isolate capable of causing lethal infections in mice. The experiment comprised 11 groups of 5 mice. At day 0, all mice were challenged with virus at 3× the LD95 by intranasal inoculation in a volume of 30 µl (approx. 1 E4 per mouse), after being anesthetized with a mixture of ketamine/xylazine (150 and 10 mg/kg respectively).

All groups received a single IV treatment, 2 hours post viral challenge of test article, vehicle (PBS), or Fc only control (hIgG1 Fc). The study evaluated Int-18, Int-7, and Int-23 conjugated to identical Fc monomers (conjugates 13, 14, and 21, respectively), tested at 3.0, 1.0, and 0.3 mg/kg. Mice were monitored for 2 weeks and animals exceeding 20% body weight loss, or were found moribund, were scored as a mortality.

All mice treated with vehicle or the Fc only control, reached mortality by day 7. In contrast, mice receiving conjugates 13, 14, and 21 were fully protected after receiving a single IV dose at 0.3 mg/kg (Table 40). As expected, groups receiving the conjugates at 1.0 or 3.0 mg/kg were fully protected as well.

The potency of all conjugates against Influenza B was further supported by the daily body measurements (Table 41), which show a less than 5% transient drop across the entire study for any conjugate treated group. The activity of conjugates 13, 14, and 21 is comparable by dose to the activity of conjugate 6 against Influenza A H1N1 and H3N2 subtypes. Since conjugates, 6 and 14 have identical targeting moieties (corresponding to Int-7), a single conjugate may be active against the dominant seasonal influenza types (Influenza A (H1N1), Influenza A (H3N2), and Influenza B).

TABLE 40

Mortality data at study end (day 14).

| Compound | Dosage (mg/kg) | % Survival | Significance to vehicle (p-value) |
|---|---|---|---|
| Vehicle (PBS) | na | 0 | na |
| Fc alone | 3.0 | 0 | p = 1 |
| Conjugate 13 | 0.3 | 100 | (0.0027) |
| | 1.0 | 100 | (0.0027) |
| | 3.0 | 100 | (0.0027) |
| Conjugate 14 | 0.3 | 100 | p = 0.0027 |
| | 1.0 | 100 | p = 0.0027 |
| | 3.0 | 100 | p = 0.0027 |
| Conjugate 21 | 0.3 | 100 | (0.0027) |
| | 1.0 | 100 | (0.0027) |
| | 3.0 | 100 | (0.0027) |

Average of 5 mice;
p-values calculated by Log-rank (Mantel-Cox) test

TABLE 41

Mouse body weight data (% BW relative to day 0).

| Day post challenge | Vehicle (PBS) | Fc alone 3.0 | Conjugate 14 (mg/kg) 0.3 | 1.0 | 3.0 |
|---|---|---|---|---|---|
| 0 | 100.0 | 100.0 | 100.0 | 100.0 | 100.0 |
| 1 | 98.1 | 98.1 | 99.3 | 99.1 | 96.5 |
| 2 | 99.6 | 96.7 | 98.6 | 98.6 | 98.3 |
| 3 | 96.4 | 94.9 | 96.8 | 97.0 | 98.7 |
| 4 | 89.8 | 87.8 | 98.4 | 97.5 | 97.8 |
| 5 | 83.6 | 80.8 | 97.4 | 97.8 | 98.0 |
| 6 | 79.0 | 76.1 | 96.9 | 98.3 | 99.7 |
| 7 | * | * | 99.2 | 100.5 | 100.6 |
| 8 | * | * | 100.3 | 101.9 | 101.1 |
| 9 | * | * | 102.5 | 100.4 | 100.6 |
| 10 | * | * | 100.6 | 102.0 | 101.2 |
| 11 | * | * | 100.9 | 100.9 | 100.9 |
| 12 | * | * | 101.8 | 101.7 | 101.8 |
| 13 | * | * | 101.4 | 101.7 | 101.4 |
| 14 | * | * | 102.2 | 102.6 | 102.2 |

Average of 5 mice;
*data not included once the first animal reaches mortality within a group

Example 88. Synthesis of PEG4-azido Fc for Conjugate 25, Conjugate 26, Conjugate 27, and Conjugate 28

Preparation of 0.05M PEG4-azidoNHS ester solution in DMF/PBS×1:27.40 mg of PEG4-azido NHS ester was dissolved in 0.155 mL of DMF at 0° C. and diluted to by adding 1.200 mL of PBS 1× buffer at 0° C. This solution was used for preparing other PEG4-azido Fc with variety of OAR values by adjusting the equivalents of this PEG4-azido NHS ester PBS×1 solution.

Preparation of PEG4-azido Fc (SEQ ID NO: 48): 0.05M PEG4-azidoNHS ester PBS×1 buffer solution (0.0984 mL, 4.92 μmol, 2.5 equivalents) was added to a solution of h-IgG1 Fc (SEQ ID NO: 48) (234 mg in 13.605 mL of pH 7.4 PBS, MW-57,976 Da, 4.036 μmol) and the mixture was shaken gently for 2 hours at ambient temperature. The solution was concentrated using a centrifugal concentrator (30,000 MWCO) to a volume of ~2 mL. The crude mixture was diluted 1:7 in PBS pH 7.4, and concentrated again. This wash procedure was repeated for total of three times. The small molecule reagent was removed with this wash procedure. The concentrated Fc (SEQ ID NO: 48)-PEG4-azide was diluted to 13.60 mL with pH 7.4 PBS 1× buffer and ready for Click conjugation. The purified material was quantified using a NANODROP™ UV visible spectrophotometer (using a calculated extinction coefficient based on the amino acid sequence of h-IgG1).

Preparation of PEG4-azido Fc (SEQ ID NO: 50) was analogous to above PEG4-azido Fc (SEQ ID NO: 48).

Example 89. Synthesis of Conjugate 25

Preparation of the Click reagent solution: 0.0050M $CuSO_4$ in PBS×1 buffer solution: 10.0 mg $CuSO_4$ was dissolved in 12.53 mL PBS×1, than took 10.00 mL this $CuSO_4$ solution and added 86.1 mg BTTAA and 495.3 mg Na Ascorbate to give the Click reagent solution (0.0050M $CuSO_4$, 0.020M BTTAA and 0.25M Sodium Ascorbate). This Click reagent solution will be used for Conjugate 25 and Conjugate 26.

A solution of azido functionalized Fc (78.0 mg, 4.535 mL, 1.35 μmol, SEQ ID NO: 48-PEG4-Azide) was added to a 15 mL centrifuge tube containing alkyne derivatized small molecule (13.2 mg, 8.88 μmol, Int-23). After gently shaking to dissolve all solids, the mixture was added with 2.153 mL of above Click reagent solution of (L-ascorbic acid sodium, 0.25 M, 106.6 mg, 0.538 mmol, copper (II) sulfate 0.0050M, 1.72 mg, 0.0107 mmol, and BTTAA 0.020M, 18.5 mg, 0.0431 mmol). The resulting mixture was gently shaken for 6 hours at ambient temperature. It was purified by affinity chromatography over a protein A column, followed by size exclusion chromatography (see conjugate purification protocol in Example 10). Maldi TOF analysis of the purified final product gave an average mass of 60973 Da (DAR=2.1). Yield 50.3 mg, 64% yield.

The nucleic acid construct encoding the Fc for conjugate 25 included a nucleic acid encoding the amino acid sequence of SEQ ID NO: 48, which includes a C-terminal lysine residue and N-terminal murine IgG signal sequence. Upon expression, the C-terminal lysine and the N-terminal murine IgG signal sequence of the Fc of conjugate 25 are proteolytically cleaved, resulting in an Fc having the sequence lacking Lys447 (e.g., lacking a C-terminal lysine residue) and the N-terminal murine IgG signal sequence. The presence or absence of a C-terminal lysine does not alter the properties of the Fc or the corresponding conjugate.

Example 90. Synthesis of Conjugate 26

Preparation of Conjugate 26 was analogous to Conjugate 25 by using the same batch of PEG4-azido Fc(SEQ ID NO: 48) and an alkyne-derivatized small molecule (Int-7). Maldi TOF analysis of the purified final product gave an average mass of 61068 Da (DAR=2.2). Yield 49.5 mg, 63% yield.

Example 91. Synthesis of Conjugate 27

Preparation of the Click reagent solution: 0.0050M $CuSO_4$ in PBS×1 buffer solution: 10.0 mg $CuSO_4$ was dissolved in 12.53 mL PBS×1, than took 12.00 mL this CuSO$_4$ solution and added 103.3 mg BTTAA and 594.3 mg Na Ascorbate to give the Click reagent solution (0.0050M CuSO$_4$, 0.020M BTTAA and 0.25M Sodium Ascorbate). This Click reagent solution will be used for Conjugate 28.

A solution of azido functionalized Fc (80.0 mg, 4.535 mL, 1.38 μmol, SEQ ID NO: 50-PEG4-Azide) was added to a 15 mL centrifuge tube containing alkyne derivatized small molecule (13.5 mg, 9.10 μmol, Int-23). After gently shaking to dissolve all solids, the mixture was added with 2.21 mL of above Click reagent solution of (L-ascorbic acid sodium, 0.25 M, 109.3. mg, 0.552 mmol, copper (II) sulfate 0.0050M, 1.76 mg, 0.0110 mmol, and BTTAA 0.020M, 19.0 mg, 0.0441 mmol). The resulting mixture was gently shaken for 6 hours at ambient temperature. It was purified by affinity chromatography over a protein A column, followed by size exclusion chromatography (see conjugate purification protocol in Example 10). Maldi TOF analysis of the purified final product gave an average mass of 61447 Da (DAR=2.5). Yield 37.1 mg, 46% yield.

The nucleic acid construct encoding the Fc for conjugate 27 included a nucleic acid encoding the amino acid sequence of SEQ ID NO: 50, which includes a C-terminal lysine residue and N-terminal murine IgG signal sequence. Upon expression, the C-terminal lysine and the N-terminal murine IgG signal sequence of the Fc of conjugate 27 are proteolytically cleaved, resulting in an Fc having the sequence lacking Lys447 (e.g., lacking a C-terminal lysine residue) and the N-terminal murine IgG signal sequence. The presence or absence of a C-terminal lysine does not alter the properties of the Fc or the corresponding conjugate.

Example 92. Synthesis of Conjugate 28

Preparation of Conjugate 28 was analogous to Conjugate 27 by using the same batch of PEG4-azido Fc(SEQ ID NO: 50) and an alkyne-derivatized small molecule (Int-7). Maldi TOF analysis of the purified final product gave an average mass of 61388 Da (DAR=2.4). Yield 44.6 mg, 56% yield.

Example 93. Activity of Conjugate 6 and Conjugate 21 Against High Path Influenza A (H5N1, H7N9) in a Cytopathic Effects (CPE) Assay An in vitro assay to determine the potency of conjugates of the invention was conducted against BSL-3 (high path) influenza A, and generally followed standard procedures. Briefly, different concentrations of conjugates were mixed with virus (approximately 250 TC$_{ID50}$) and allowed to incubate at 35° C. for one hour. After incubation, the mixture was added to an 80-90% confluent monolayer of MDCK cells. After a 90 minute incubation cells were washed and conjugates re-applied. The monolayer was subsequently overlayed with carboxymethylcellulose to minimize viral spreading and allowed to incubate for two days. After two days of culture cells were washed with PBS and fixed with 10% formalin. After fixation the MDCK monolayer was permeabilized with Triton X-100 and immunostained with a mouse mAb against influenza nucleoprotein. Monolayers were read, and the stained area per well was calculated to determine EC$_{50/100}$ values.

The results of the study are summarized in Table 42 and demonstrate the potency of Conjugate 6 and Conjugate 21 against highly pathogenic strains with pandemic potential. Importantly, both conjugates generated EC$_{100}$ values at, or below, 15 nM against four H5N1 and one H7N9 isolate. In contrast, oseltamivir had an EC$_{100}$ of approximately 15 nM only against one isolate (A/Vietnam/i194/2004) and values ranging from 125 to >1000 nM against the other high path strains. These results suggest that the potential of Conjugate 6 and Conjugate 21 to treat pandemics caused by highly-virulent influenza to be superior to that of oseltamivir.

TABLE 42

In vitro activity of Conjugate 6 and Conjugate 12 against high path influenza isolates

| High Path Influenza | EC100 (nM) (CPE in MDCK cells) | | | |
|---|---|---|---|---|
| | Vehicle | Conjugate 6 | Conjugate 21 | Oseltamivir |
| H5N1 | | | | |
| A/Indonesia/5/2005 (clade 2.1) | N/A | ~15 | <15 | ~200-500 |
| A/Vietnam/1194/2004 (clade 1) | N/A | ~15 | <15 | ~15 |
| A/turkey/Turkey/1/2005 (clade 2.2) | N/A | <15 | <15 | ~125-250 |
| A/Hong Kong/156/1997 (clade 0) | N/A | ~15 | <15 | >1000 |
| H7N9 | | | | |
| A/Anhui/01/2013 H1N1 (positive control) | N/A | <15 | <15 | ~500-1000 |
| A/Netherlands/602/2009 | N/A | <15 | <15 | ~1000 |

Example 94. Activity of Conjugate 6 and Conjugate 21 Against Influenza A (HI NI) at Different Multiplicities of Infection (MOI) in a Cytopathic Effects (CPE) Assay MOCK cells were seeded at 4×10$^4$ cells/well in MEM media in 96 well plate (TC-treated) and incubated at 37° C., 5% C02 for 18-24 h. Test articles (Zanamivir, Oseltamivir, Baloxavir, Conjugate 6, and Conjugate 21) at dose-range between 1.93-10000 nM were incubated with influenza AMWSN/1933 at an multiplicity of infection (MOI) of virus:cell between 0.001-1 for 1 h at room temperature (RT). After 1 h, pre-incubated virus and test article were added to 90-100% confluent monolayer of MOCK cells and incubated for 1 h at RT.

After 1 h, MEM media supplemented with L-glutamine and penicillin/streptomycin was added to wells. Infected cells were incubated at 37° C., 5% CO$_2$ for 72 h. CPE was determined after fixing and staining cells with crystal violet. EC50 was calculated with non-linear regression analysis using GraphPad Prism 6 software. The results of the CPE assay provided in Table 43 indicate that Conjugate 6 and Conjugate 21 outperform standard of care agents in vitro, particularly at high MOIs.

TABLE 43

In vitro activity of Conjugate 6 and Conjugate 12 against influenza A (H1N1) at differentmultiplicities of infection EC$_{50}$ (nM) H1N1 A/WSN/1933 (CPE in MDCK cells)

| | MOI 0.001 | MOI 0.01 | MOI 0.1 | MOI 1 |
|---|---|---|---|---|
| Zanamivir | 137 | 938 | >10000 | >10000 |
| Oseltamivir | 525 | 1896 | >10000 | >10000 |
| Baloxavir | 5 | 4 | 79 | >100 |

TABLE 43-continued

In vitro activity of Conjugate 6 and Conjugate 12 against influenza A (H1N1) at different multiplicities of infection
$EC_{50}$ (nM) H1N1 A/WSN/1933 (CPE in MDCK cells)

|  | MOI 0.001 | MOI 0.01 | MOI 0.1 | MOI 1 |
|---|---|---|---|---|
| Conjugate 6 | 9 | 15 | >100 | >100 |
| Conjugate 12 | 0.6 | 2 | 7 | 10 |

Example 95. Efficacy of Conjugate 6 Against Influenza A (H1N1) in a Lethal Severe Combined Immunodeficiency Mouse Model Conjugates were evaluated against a lethal Influenza A infection in male BALB/c Severe Combined Immunodeficiency (SCID) mice (Stock #001803; Jackson Laboratories, 6-8 weeks old). The challenge virus (A/Puerto Rico/08/1934) is a mouse-adapted isolate capable of causing lethal infections in mice. The experiment comprised 5 groups of 5 mice each. At day 0, all mice were challenged with virus at 3× the LD95 by intranasal inoculation in a volume of 30 µl (approx. 1 E3 per mouse), after being anesthetized with a mixture of ketamine and xylazine (150 and 10 mg/kg, respectively). All groups received a single IV treatment of conjugate 6, 2 hours post viral challenge of test article, vehicle (PBS), or Fc only control (hIgG1 Fc). The study evaluated 3 different dose concentrations of conjugate 6 (0.3, 1.0, or 3.0 mg/kg). Mice were monitored for 5 weeks and animals exceeding 20% body weight loss, or who were found moribund, were scored as a mortality. Body weights were also recorded to monitor the general health of the animals.

All mice treated with vehicle, or the Fc only control, reached mortality by week 2. In contrast, mice receiving conjugate 6 were fully protected after receiving single IV doses of 1 or 3 mg/kg for the duration of the study (FIG. 56, Table 44). When dose of conjugate 6 was lowered to 0.3 mg/kg survival dropped to 20% by study end. The 0.3 mg/kg dose was fully protected for 3 weeks. The potency of conjugate 6 in this model of severe immunodeficiency was further supported by body weight data (FIG. 57, Table 45). Groups receiving conjugate 6 at the 1 or 3 mg/kg dose concentrations demonstrated no more than a transient body weight loss of less than 3% over the entire course of the study. Furthermore, at study end both dose groups showed a net gain in weight (7.5 and 2.2%, respectively). The group dosed with the lowest concentration of conjugate 6 (0.3 mg/kg) had less than a 4% transient loss of body weight over the first 3 weeks of the study before showing signs of infection in week 4, which ultimately resulted in death for four of five animals.

Collectively these data demonstrate the potency of conjugate 6 by protecting lethally challenged mice with single IV doses of conjugate as low as 1 mg/kg. Additionally, this protection was long lasting, extending over the 5 week duration of the study. This was accomplished in an extreme model of immunodeficiency in mice completely lacking T & B immune cells, which are essential in clearing influenza infections. This data supports the use of conjugate 6 to treat both immune competent and deficient patient populations.

TABLE 44

Mortality of study dose groups per week

| | % Survival (Day post viral challenge) | | | | |
|---|---|---|---|---|---|
| Test article | 7 | 14 | 21 | 28 | 35 |
| Vehicle | 80 | 0 | 0 | 0 | 0 |
| Fc only | 80 | 0 | 0 | 0 | 0 |
| Conjugate 6 (3 mg/kg) | 100 | 100 | 100 | 100 | 100 |
| Conjugate 6 (1 mg/kg) | 100 | 100 | 100 | 100 | 100 |
| Conjugate 6 (0.3 mg/kg) | 100 | 100 | 100 | 80 | 20 |

TABLE 45

Average group body weight for study animals over 35 days or until first death within a group

| | | | Conjugate 6 dose | | |
|---|---|---|---|---|---|
| Day | Vehicle | Fc only | 3 mg/kg | 1 mg/kg | 0.3 mg/kg |
| 0 | 100 | 100 | 100 | 100 | 100 |
| 1 | 99.5 | 99.8 | 99.6 | 99.4 | 98.6 |
| 2 | 98.8 | 99.2 | 99.9 | 99.1 | 98.9 |
| 3 | 97.7 | 96.8 | 101 | 100.6 | 97.9 |
| 4 | 94.4 | 95.4 | 99.4 | 98.4 | 98.5 |
| 5 | 93.7 | 90.7 | 100.6 | 97.9 | 99.3 |
| 6 | 88.7 | 83.9 | 101.2 | 98.7 | 98.1 |
| 7 | 81.1 | 77.6 | 101.8 | 98 | 96.9 |
| 8 | | | 101.3 | 99.7 | 98.9 |
| 9 | | | 102.6 | 100.7 | 98.8 |
| 10 | | | 101.6 | 99.8 | 99.4 |
| 11 | | | 101.6 | 99.7 | 100.3 |
| 12 | | | 101.8 | 100.2 | 100.7 |
| 13 | | | 102.3 | 101 | 100.7 |
| 14 | | | 103.9 | 100.5 | 99.9 |
| 15 | | | 104.3 | 101.8 | 102.3 |
| 16 | | | 104.3 | 102 | 101.3 |
| 17 | | | 104.3 | 100.6 | 102 |
| 18 | | | 105.4 | 103.9 | 100.5 |
| 21 | | | 105.7 | 105.9 | 96.8 |
| 22 | | | 105.5 | 103.4 | 93.9 |
| 23 | | | 105.6 | 106.9 | 91 |
| 24 | | | 108.4 | 102.9 | |
| 25 | | | 106.4 | 102.7 | |
| 26 | | | 108.4 | 103.9 | |
| 27 | | | 108.6 | 103.5 | |
| 28 | | | 109.1 | 104.7 | |
| 29 | | | 108.96 | 104.5 | |
| 30 | | | 109 | 105.8 | |
| 31 | | | 108.2 | 104.9 | |
| 35 | | | 107.5 | 102.2 | |

Example 96. Conjugate 6 Dose-Dependent Viral Clearance in Lungs

Efficacy studies were conducted in 6-8 weeks female BALB/c mice (Charles River) challenged intranasally with $3 \times 10^2$ PFU/mouse (3× the LD( ) of mouse-adapted influenza A/Puerto Rico/8/934 (Hi N1). Conjugate 6 or human IgG1 Fc control was administered as a single intravenous (IV) dose 2 h post-challenge at 0.1-3 mg/kg. Oseltamivir was dosed orally, twice daily for 4 days starting 2 h post-infection at 5 or 15 mg/kg. Body weights (BW) were recorded for 4 days. At 4 days post-infection, mice were sacrificed by C02 and both lung lobes were harvested. Lungs were homogenized with 1 mm silica beads in 1 mL PBS using a MagNA Lyser (Roche). Homogenization was carried out at 6,000 rpm for 60 s and chilled on ice for 5 min in-between runs. After lung homogenization tubes were centrifuged for 10 min at 600×g and supernatant was transferred into new tube.

To determine the viral burden in lungs (measured as Plaque Forming Units (PFUs)), supernatants of lung homogenate were diluted in infection buffer ranging from 10-i to 10-6. 100 μL of virus dilutions were added to confluent monolayer of MOCK cells in 24 well plates and incubated for 1 h at room temperature with rocking every 15 min. After removing the virus, liquid overlay media containing Avicel was added to MOCK cells. Cells were incubation at 37° C., 5% C02 for 40 h. After incubation, the media was removed and cells were stained with crystal violet to enumerate plaques. PFUs were calculated relative to weight of the lung (PFU/g lung).

The results of this study demonstrate that low doses of conjugate 6 rapidly lower the viral burden orders of magnitude better than Oseltamivir (TAMIFLUO) (FIG. 58, Table 46). This observation has clinical significance since severe influenza infections are caused by the virus moving from an initial upper respiratory tract infection to the lungs.

TABLE 46

Viral burden on day 4 post-infection

| Test article [mg/kg] | Log reduction (PFU/mL) | Log reduction (PFU/g) |
| --- | --- | --- |
| PBS [0] | 0.00 | 0.00 |
| hIgG1 Fc [3] | −0.04 | 0.26 |
| Oseltamivir [5] | 0.24 | 0.43 |
| Oseltamivir [15] | 0.52 | 0.75 |
| Conjugate 6 [0.1] | 0.60 | 0.79 |
| Conjugate 6 [0.3] | 1.33 | 1.55 |
| Conjugate 6 [1] | 2.25 | 2.34 |
| Conjugate 6 [3] | 3.20 | 3.40 |

Example 97. Conjugate 6 Dose-Dependent Reduction in Inflammatory Cytokines in Lungs Efficacy studies were conducted in 6-8 weeks female BALB/c mice (Charles River) challenged intranasally with $3 \times 10^2$ PFU/mouse (3× the $LD_{95}$) of mouse-adapted influenza A/Puerto Rico/8/1934 (H1N1). Conjugate 6 or human IgG1 Fc control was administered as a single intravenous (IV) dose 2 h post-challenge at 0.1-3 mg/kg. Oseltamivir was dosed orally, twice daily for 4 days starting 2 h post-infection at 5 or 15 mg/kg. Body weights (BW) were recorded for 4 days. At 4 days post-infection, mice were sacrificed by C02 and both lung lobes were harvested. Lungs were homogenized with 1 mm silica beads in 1 mL PBS using a MagNA Lyser (Roche). Homogenization was carried out at 6,000 rpm for 60 s and chilled on ice for 5 mi in-between runs. After lung homogenization tubes were centrifuged for 10 m at 600×g and supernatant was transferred into new tube.

For cytokine analysis, supernatants of lung homogenate were serially diluted 2-fold in 96 well plate. Cytokine levels for INF-γ, TNF-α, IL-6, MIP-1α and MCP-1 were determined by ELISA according to manufacturer's instructions (R&D Systems).

Morbidity and mortality from severe influenza is ultimately caused by virally induced influx of pro-inflammatory cytokines in the lungs. One potential concern of using an Fc-conjugate to treat influenza is whether the Fc fragment would exacerbate cytokine induced inflammation. The results of the H1N1 lethal infection model show just the opposite: a conjugate 6 dose-dependent decrease in pro-inflammatory cytokines (e.g., TNFα and IL-6) in infected lung tissues (FIG. 59, Table 47).

TABLE 47

Cytokine response on day 4 post-infection

| | Fold-shift compared to uninfected control | | | | |
| --- | --- | --- | --- | --- | --- |
| Test article [mg/kg] | INFy | TNFa | IL-6 | MCP-1 | MIP-1a |
| PBS [0] | 0.4 | 2.2 | 4.6 | 16.3 | 16.4 |
| hIgG1 Fc [3] | 0.5 | 2.2 | 6.2 | 20.2 | 16.8 |
| Oseltamivir [5] | 0.2 | 1.7 | 4.0 | 11.7 | 7.5 |
| Oseltamivir [15] | 0.2 | 1.8 | 3.5 | 10.5 | 6.1 |
| Conjugate 6 [0.1] | 0.3 | 1.5 | 3.0 | 10.8 | 7.9 |
| Conjugate 6 [0.3] | 0.2 | 1.2 | 1.9 | 6.7 | 7.4 |
| Conjugate 6 [1] | 0.2 | 1.1 | 1.9 | 6.1 | 3.6 |
| Conjugate 6 [3] | 0.8 | 1.1 | 1.4 | 2.8 | 2.6 |
| Uninfected | 1.0 | 1.0 | 1.0 | 1.0 | 1.0 |

Example 98. In Vivo Conjugate 6 Plasma Sample Analysis. Comparison of PK in CD-1 and BALB/c Severe Combined Immune Deficient Mice Conjugate 6 in plasma samples were quantified by a neuraminidase capture detection ELISA. Briefly, molecules were captured on neuraminidase coated plates and then detected using a HRP-conjugated anti-human IgG-Fc antibody. Protein concentration was calculated in GraphPad Prism using 4PL non-linear regression of Conjugate 6 standard curves. A more detailed method description is provided below.

Nunc Maxisorp 96-well plates (Cat No. 12-565-136, ThermoFisher) were coated with 0.1 U/well neuraminidase from A/California/04/2009 (H1N1) (11058-VNAHC, Sino Biological) in 1×KPL coating buffer (5150-0041, SeraCare). Plates were incubated at room temperature for 1 hr on an orbital plate shaker (500 rpm). Serial dilutions of the plasma samples were plated and incubated at room temperature for 2 hours (sample diluent: 0.5% BSA in PBS 0.025% Tween 20+naïve mouse plasma final concentration of 1:2,500). Conjugate 6 standard curves ranging from 0.230 to 500 ng/mL, in duplicate were run on each plate. Following the 2 hr incubation, plates were washed 5× in 300 μL PBS with 0.05% Tween 20. Conjugate bound to neuraminidase on the plates was then probed with an HRP conjugated anti-human IgG Fc F(ab')2 (709-036-098, Jackson) diluted 1:1,000 in sample diluent for 1 hr at room temp. Plates were then washed 8× in 300 μL PBS with 0.05% Tween 20 and developed with TMB substrate for 7-8 minutes. The reaction was stopped with 1 N $H_2SO_4$. Absorbance was read at 450 nm. Conjugate 6 in plasma samples was interpolated using GraphPad Prism Version 6 following nonlinear regression analysis (Sigmoidal, 4PL analysis) of the standard curves.

PK Profiles, CD-1 vs BALB/c SCID Mouse

Conjugate 6 administered intravenously to SCID and CD-1 (immune competent) mice at 5 mg/kg demonstrated similar PK profiles (FIG. 60). Concentrations were comparable at the sampled time points. The two-phase PK profiles comprise 24-hour distribution phases followed by a shallow elimination phase. Conjugate 6 plasma levels remained high (~10 μg/ml) relative to $C_{max}$ levels over the one-week course of the study.

Example 99. Synthesis of the Propargyl Diamine Central Linker

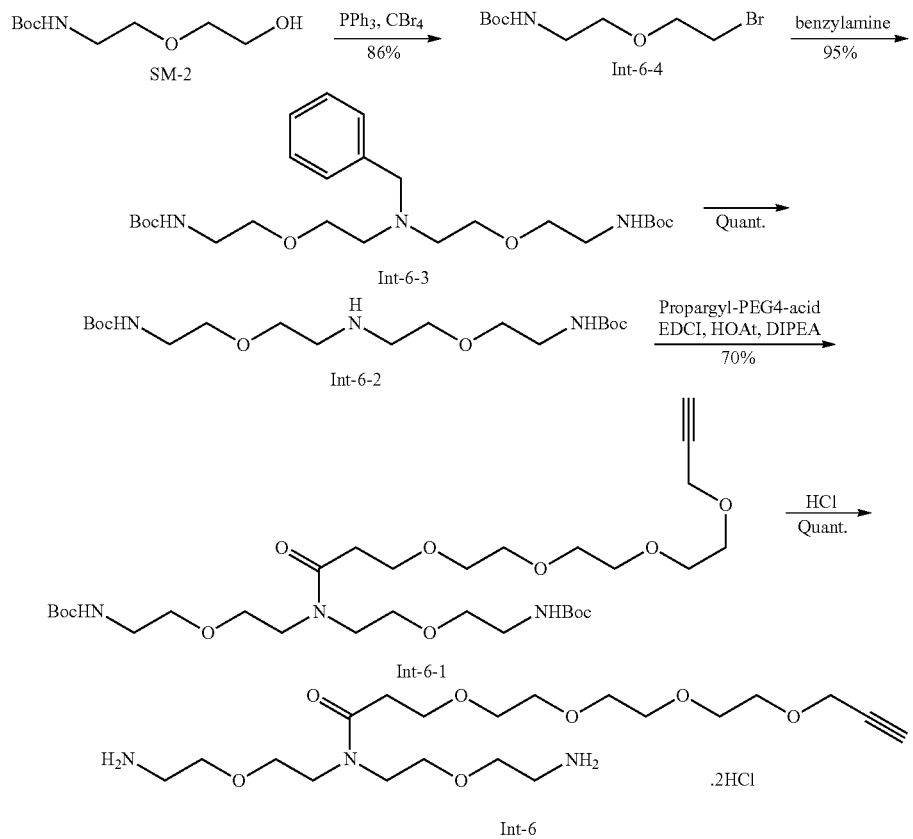

Step a.

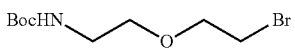

A solution of 2-(2-Boc-Aminoethoxy)ethanol (16.0 g, 78.0 mmol) and CBr$_4$ (31.0 g, 93.5 mmol) in DCM (100 mL) at 0° C. was treated with PPh$_3$ (24.5 g, 93.5 mmol) slowly over 15 minutes (exothermic). During the course of the addition the internal temperature was kept below 30° C. After addition of PPh$_3$ the reaction was stirred overnight at room temperature. The crude reaction was concentrated to an oil then purified by normal phase chromatography, eluting with 10% ethyl acetate/hexanes to 80% ethyl acetate/hexanes. Fractions containing oil droplets on the inside of the collection tubes were combined and concentrated to a colorless oil. Yield 18.1 g, 86%.

Step b.

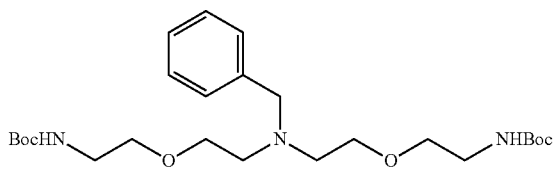 [SMILES: CC(C)(C)OC(=O)NCCOCCN(CCOCCNC(=O)OC(C)(C)C)Cc1ccccc1]

A solution of the step-a product (10 g, 37.3 mmol), benzylamine (1.60 g, 14.9 mmol), and K$_2$CO$_3$ (6.19 g, 44.8 mmol) in DMF (20 mL) were heated in an oil bath at 75° C. for 8 h. The mixture was filtered, concentrated and purified by RPLC (5% ACN/water to 100% ACN). Yield 6.8 g, 95%.

Step c.

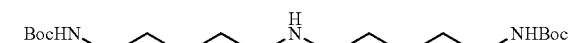

To a solution of the step-b product (5.35 g, 8.98 mmol) in CHCl$_3$/EtOH (1:20, 100 mL) was added 20% Pd(OH)$_2$/C (1.26 g, 1/80 mmol). The reaction was stirred overnight under hydrogen balloon at ambient temperature. The reaction mixture was filtered through a Celite pad. The solvents were removed and carried to the subsequent step without purification.

Step d.

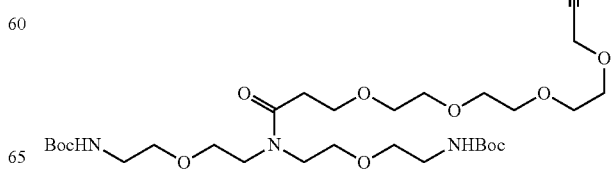

The step-c product was re-dissolved in 20 mL of DMF/dichloromethane (1:5). To this free amine solution propargyl PEG4 acid (2.36 g, 8.98 mmol), EDCl (2.57 g, 13.5 mmol), HOAt (1.83 g, 13.5 mmol) and Hunig's base (3.13 mL, 18.0 mmol) were added. The reaction mixture was stirred for four hours, then concentrated and purified by RPLC (10% ACN/water to 60% ACN/water. Yield 4.00 g, 70% over two steps. Ions found by LCMS: [M-Boc+H]$^+$=534.2, [M+H]$^+$=634.2.

Step e.

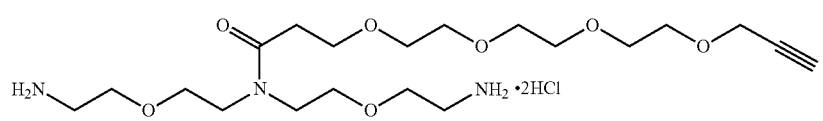 [SMILES: C#CCOCCOCCOCCOCCC(=O)N(CCOCCN)CCOCCN]

The step-d product (4.00 g, 6.31 mmol) was treated with 4N HCl in dioxane (30 mL) for 2 hours. Extra HCl and dioxane were removed by rotary evaporation, and the remaining was further dried under high vacuum to give Int-10 as 2HCL salt. Yield 3.15 g, 99%. Ion found by LCMS: [M+H]$^+$=434.2.

Example 100. Synthesis of Int-7a (C7-C7 isomer)

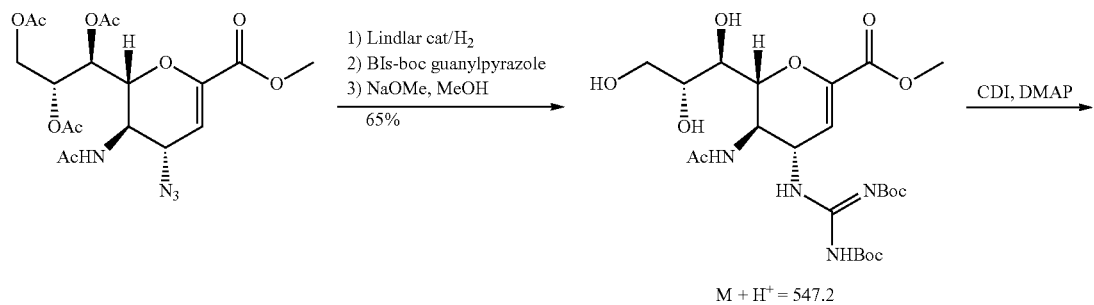

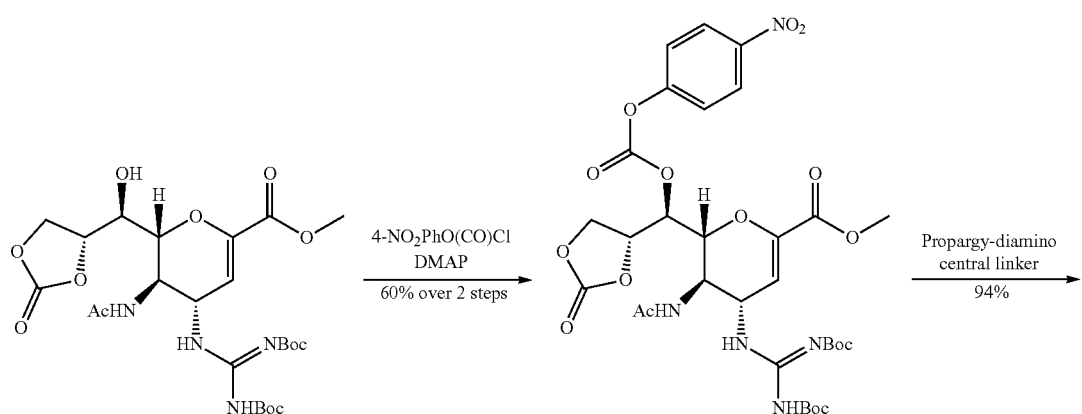

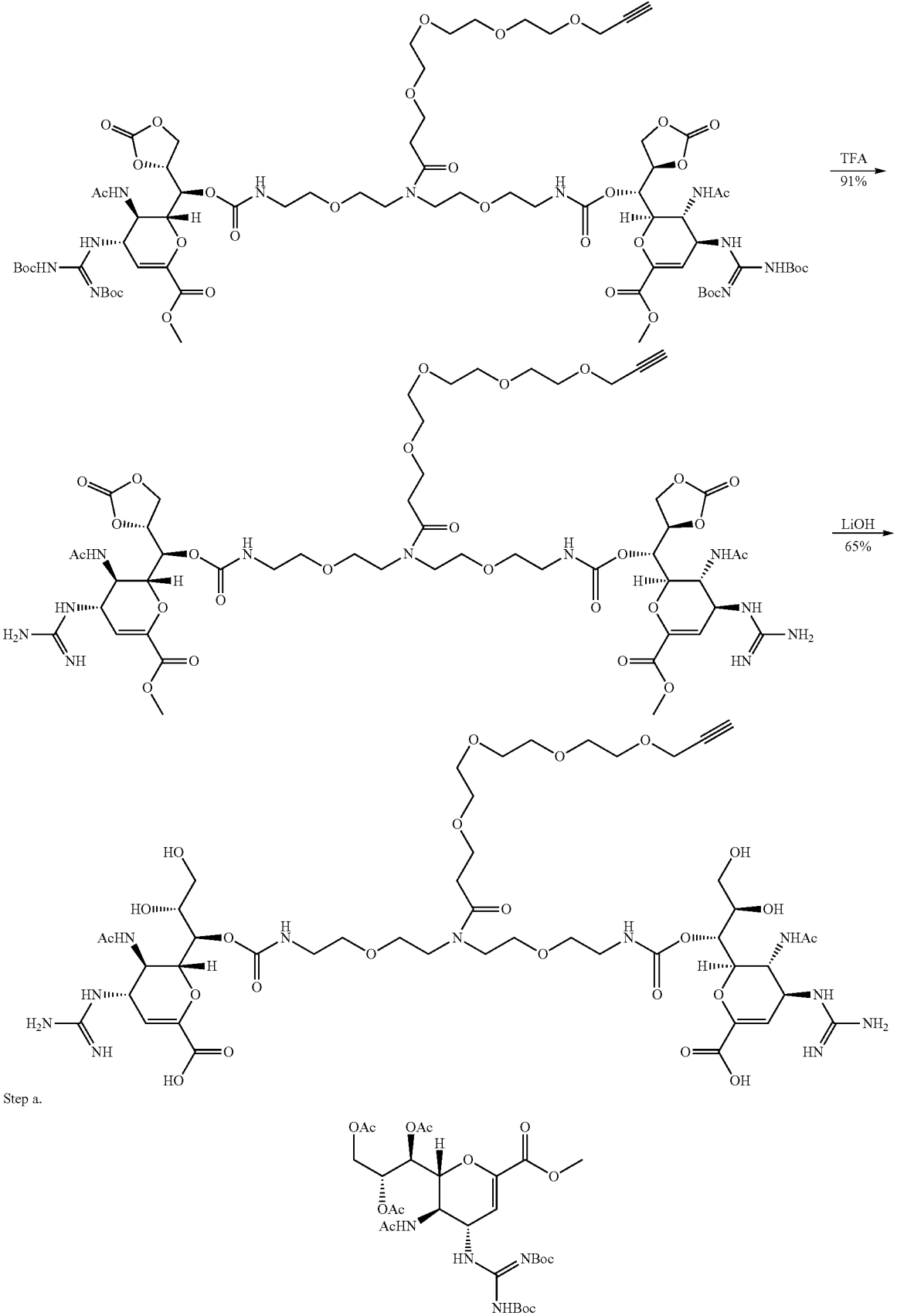
Step a.

831

Methyl 5-acetamido-7,8,9-O-triacetyl-2,6-anhydro-4-azido-3,4,5-trideoxy-D-glycero-D-galacto-non-2-enonate (30 g, 65.7 mmol) was dissolved into methanol (100 mL) and combined with Lindlar catalyst (15 g). The resulting mixture was flushed with hydrogen and stirred for 5 hours, flushing hydrogen through the headspace with hydrogen every 30 minutes. After complete reaction as determined by HPLC, the catalyst is filtered through celite. The filtrate was used in the next step.

Crude amine from the previous step (18.9 g, 43.8 mmol) was treated with N,N'-bis-boc-1-guanylpyrazole (14.3 g, 46.0 mmol), and DIEA (9.9 ml, 57.0 mmol) in methanol (100 mL). The resulting solution was stirred at room temperature until all starting material was consumed as determined by LCMS (~30 min). The solution was concentrated to a foam and stored under high vacuum overnight then used without further purification in the next step. Crude triacetate from the previous step (43.8 mmol) was dissolved in 100 ml dry methanol, then treated with sodium methoxide in methanol (1.9 mL, 25% solution in methanol, 8.76 mmol) at room temperature. Progress of reaction was monitored by LCMS which was complete after 10 minutes. The reaction was quenched with 1 N HCl to a pH of ~7. The resulting solution was concentrated and purified by reverse phase liquid chromatography (RPLC) using an Isco COMBI-FLASH® liquid chromatograph eluted with 10% to 100% acetonitrile and water. No TFA modifier was used for this purification. Yield of product 15.6 g, 65%.

Step b.

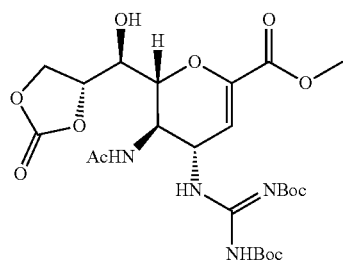

A mixture of the step-a product (5.47 g, 10 mmol) and DMAP (1.222 g, 10 mmol) was dissolved in anhydrous THF

832

(30 ml). After cooling in an ice-water bath, the solution was slowly treated with 1,1'-carbonyldiimidazole (2.6 g, 16 mmol), then stirred for 30 minutes at 0° C., followed by heating at 60° C. for 2 hours. It was then cooled to room temperature and extracted with water (50 ml) and EtOAc/hexane (1:1, 100 ml). The organic layer was washed with water (50 ml×3), dried over Na$_2$SO$_4$ and concentrated by rotary evaporation. The white foam product was further dried under high vacuum and carried to the subsequent step without further purification. Ion found by LCMS: [M+H]$^+$= 573.2.

Step c.

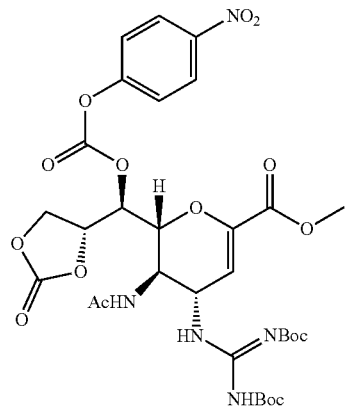

A reaction flask containing the step-b product was vacuum flushed with nitrogen and dissolved in anhydrous DCM (50 ml), then cooled in an ice-water bath. To the cooled solution was added DMAP (4.89 g, 40 mmol), followed by 4-nitrophenylchloroformate (6.05 g, 30 mmol) was added in portions over 20 minutes. The solution was stirred at 0° C. then warmed to room temperature for 1 hour. LCMS shows starting material 1 hr so additional DMAP (1.22 g, 10 mmol) and 4-nitrophenylchloroformate (1 g, 5 mmol) were added. The reaction was continued for 4 hours, then purified with two silica gel columns (220 g, pre-wet by 20% EtOAc and hexane) and eluted with 20% to 80% EtOAc and hexane. Yield 4.42 g, 59.9% for two steps. Ion found by LCMS: [M+H]$^+$=738.2.

Step d.

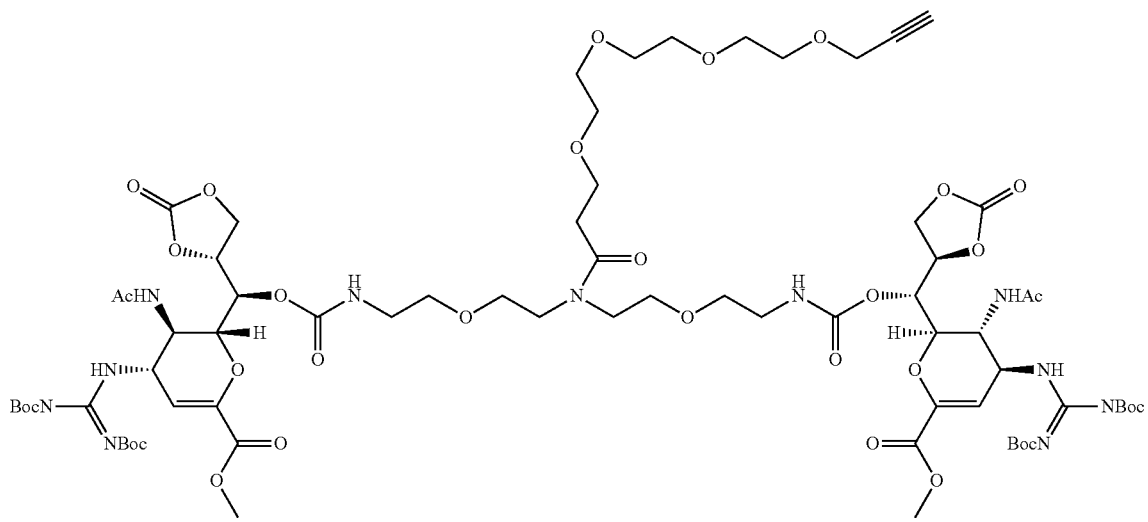

833

To a solution of the step-c product (3.2 g. 4.34 mmol) in anhydrous DCM (3 ml) was added in-portions over 30 minutes a mixture of propargyl diamine central linker (1.26 g, 2.5 mmol, described in Example 99) and DIPEA (1.68 g, 13 mmol) in anhydrous DMF (5 ml). The reaction was stirred at room temperature for 2 hours. It was then concentrated and purified by RPLC (30% to 90% acetonitrile and water, no TFA modifier). Ions found by LCMS: [(M+2H)/2]$^+$=815.8, [(M-Boc+2H)/2]$^+$=765.8, [(M-2Boc+2H)/2]$^+$=716. Yield 3.33 g, 94.2%.

Step e.

834

The step-e product (61.5 mg, 0.05 mmol) was dissolved in MeOH/water (1:1, 0.6 ml). After the solution was cooled to −6° C. (salt/ice bath), 1.0 M LiOH (0.3 ml, 0.3 mmol) was added drop-wise and the reaction was stirred for 30 minutes. It was then quenched to pH ~7.0 with 4N HCl in dioxane solution (75 μl) and directly purified by prep HPLC (Isco ACCQ prep, Luna 5 μm C18(2) 100 Å LC column 100 mm×30 mm; Gradient: 0% acetonitrile/water for 2 min, then 0% to 15% acetonitrile/water over 12 min, then isocratic at

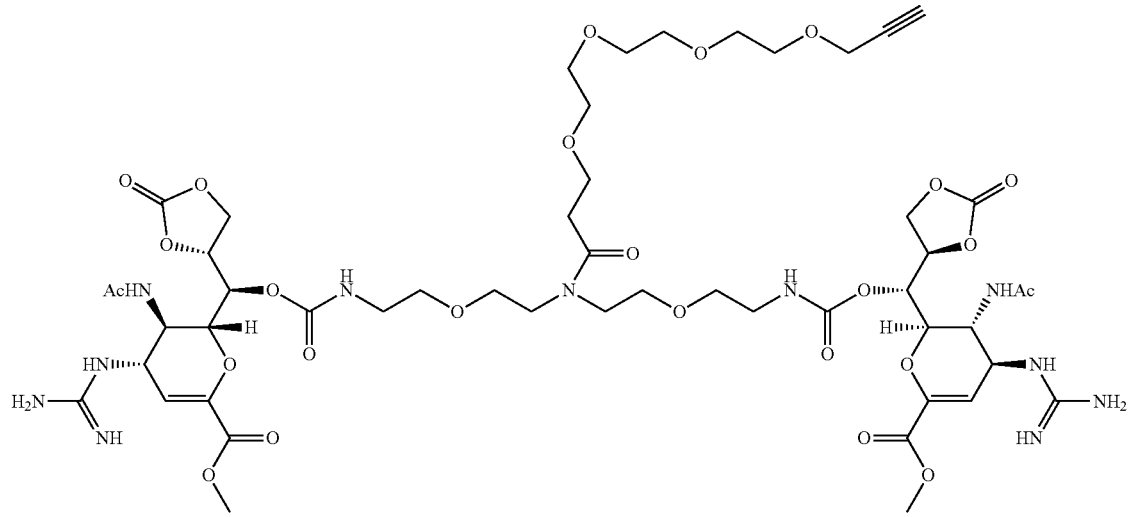 [SMILES: C#CCOCCOCCOCCOCCC(=O)N(CCOCCNC(=O)O[C@@H]([C@@H]1OC(C(=O)OC)=C[C@H](NC(=N)N)[C@H]1NC(C)=O)[C@H]1COC(=O)O1)CCOCCNC(=O)O[C@@H]([C@@H]1OC(C(=O)OC)=C[C@H](NC(=N)N)[C@H]1NC(C)=O)[C@H]1COC(=O)O1]

The step-d product (3.33 g, 2.04 mmol) was dissolved in DCM (5 ml) and TFA (5 ml) then stirred at 35° C. for ~6 hours. The reaction was monitored by LCMS. When complete the solution was concentrated and purified by RPLC (5 to 30% acetonitrile and water, no TFA). Ions found by LCMS: [(M+2H)/2]$^+$=615.8, [(M+3H)/3]$^+$=411. Yield 2.29 g, 91.3%.

Step f.

15% acetonitrile for 10 min, using 0.1% TFA). Yield 45 mg, 65.3%. Ions found by LCMS: [(M+2H)/2]$^+$=575.8, [(M+3H)/3]$^+$=384.2. Analytical retention time: 6.013 min. Conditions: Phenomenex Gemini HPLC column, 3 μm WX-C18 110 Å, 100 mm×3 mm, eluted over 25 minutes with 5-95% acetonitrile and water gradient, using 0.1% TFA.

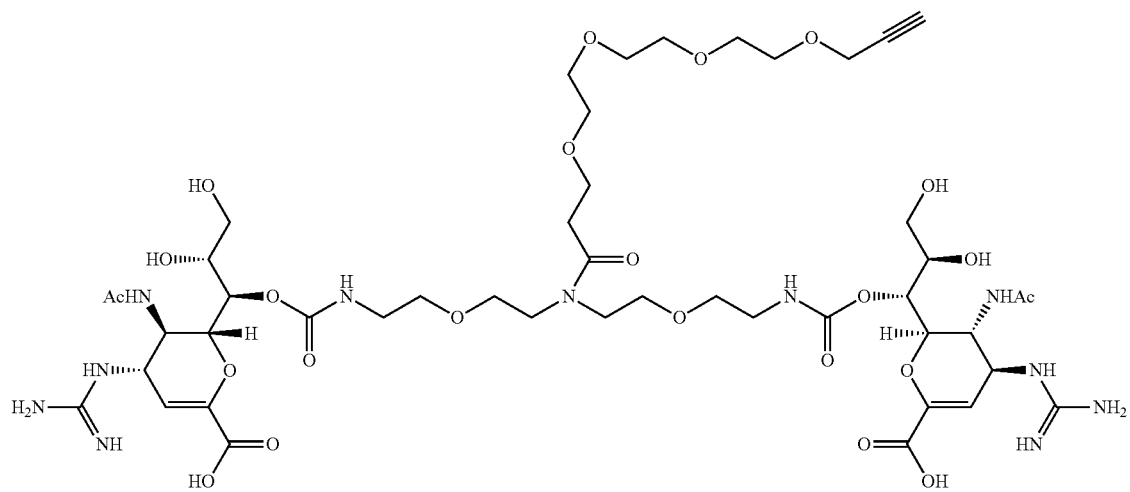 [SMILES: C#CCOCCOCCOCCOCCC(=O)N(CCOCCNC(=O)O[C@@H]([C@@H]1OC(C(=O)O)=C[C@H](NC(=N)N)[C@H]1NC(C)=O)[C@H](O)CO)CCOCCNC(=O)O[C@@H]([C@@H]1OC(C(=O)O)=C[C@H](NC(=N)N)[C@H]1NC(C)=O)[C@H](O)CO]

Example 101. Synthesis of Int-7b (C7-C9 isomer)

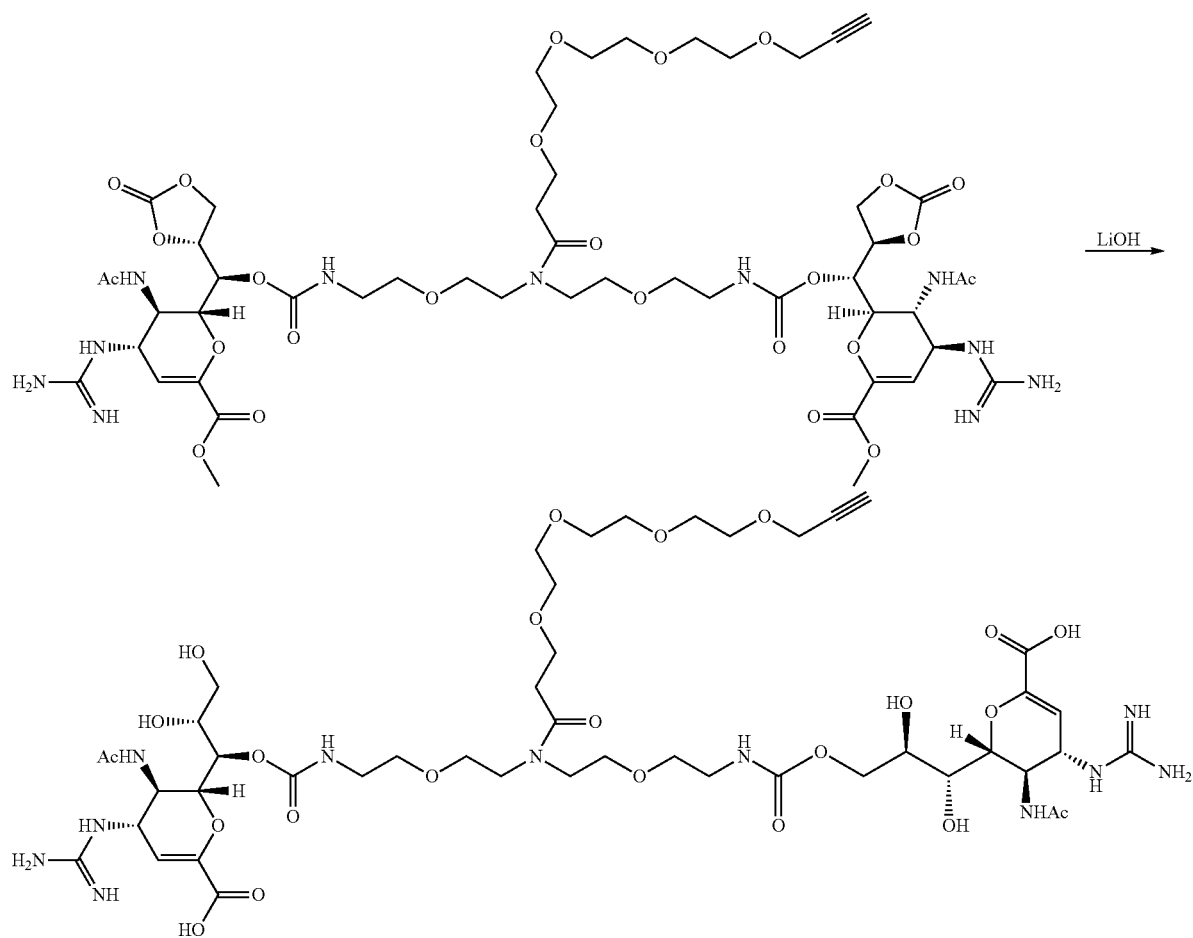

The C7-C9 heterodimer (Int-7b) was prepared analogously to Int-7a (C7-C7 isomer, Example 100), with the exception that the reaction is conducted at 0° C. and is monitored by HPLC (retention time: 6.112 min. Conditions: see Example 100, synthesis of Int-7a and stopped when the C7-C9 isomer predominates (~3 h). This isomer is isolated using the same conditions that were used to isolate Int-7a. Ions found by LCMS: $[(M+2H)/2]^+=575.8$, $[(M+3H)/3]^+=384.2$.

Example 102. Synthesis of Int-7c (C9-C9 isomer)

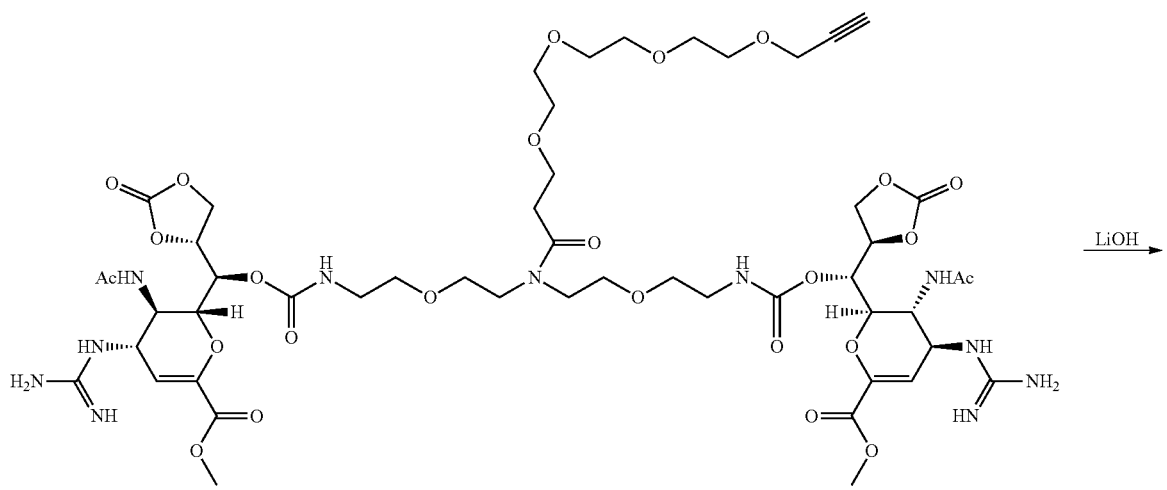

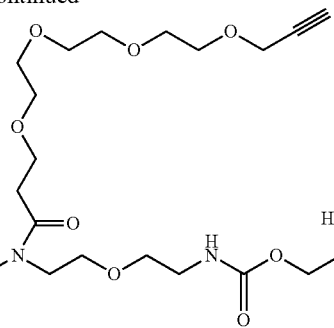

Int-7c (C9-C9 isomer) was prepared analogously to Int-7a (C7-C7 isomer, Example 100), with the exception that the reaction conducted at 0° C. and is monitored by HPLC (retention time: 6.232 min. Conditions: see Example 100, synthesis of Int-7a and stopped when the C9-C9 isomer predominates (~6 h). This isomer is isolated using the same conditions that were used to isolate Int-7a. Ions found by LCMS: $[(M+2H)/2]^+ = 575.8$, $[(M+3H)/3]^+ = 384.2$.

Example 103. Synthesis of Int-7 (acetonide route)

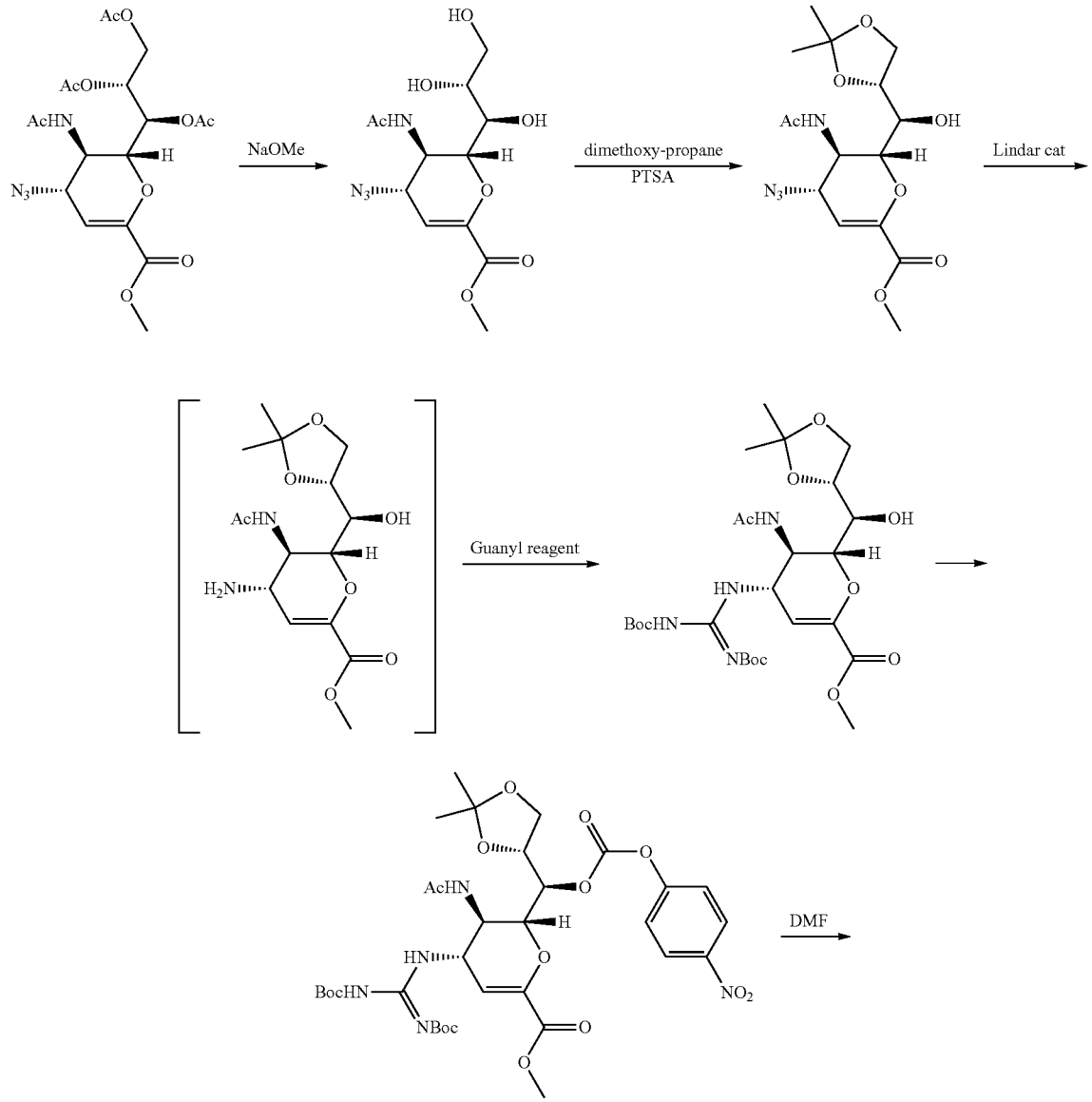

839 840
-continued
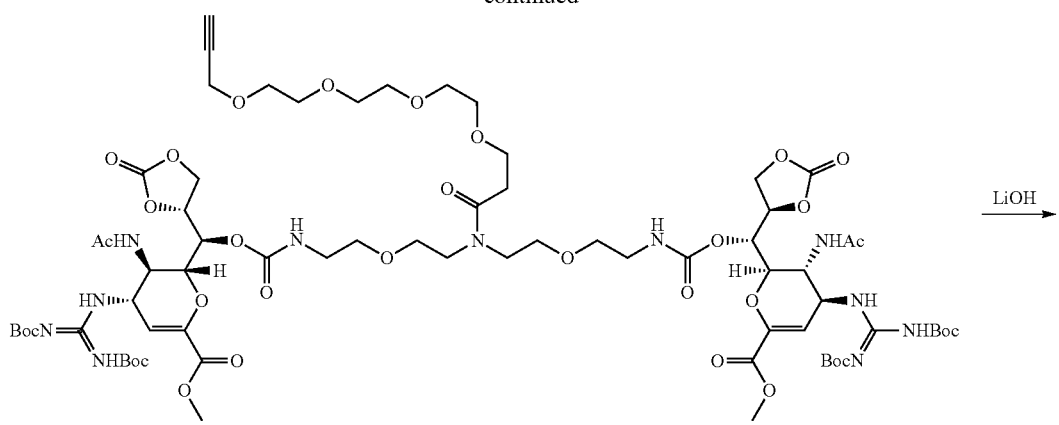
LiOH →
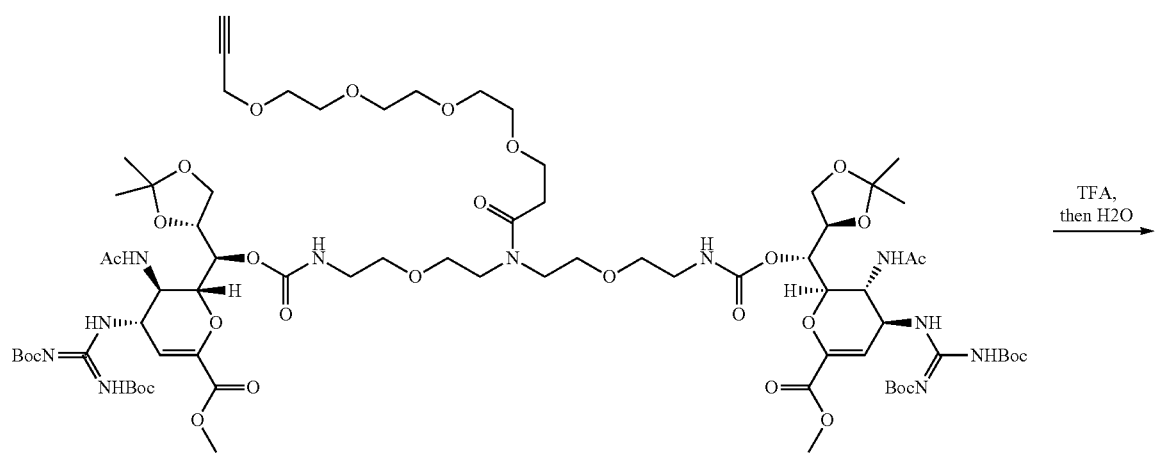
TFA, then H2O →
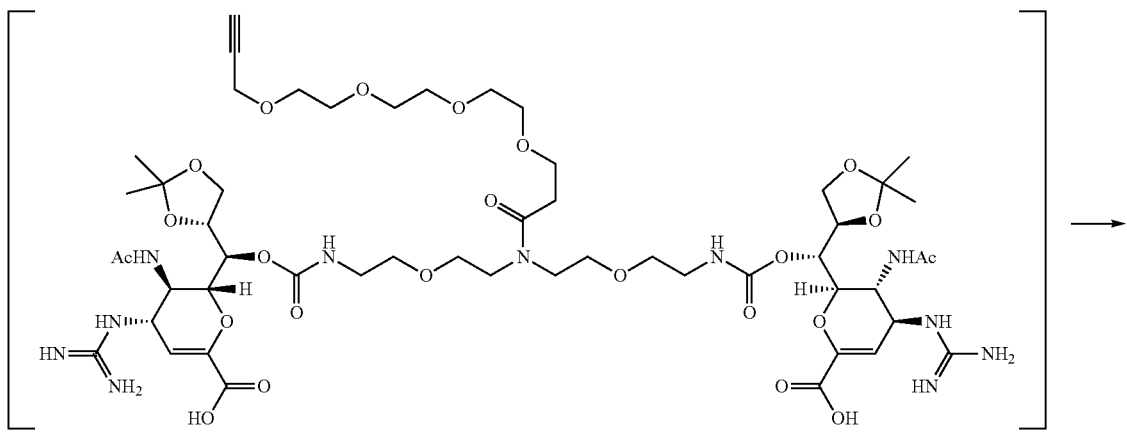

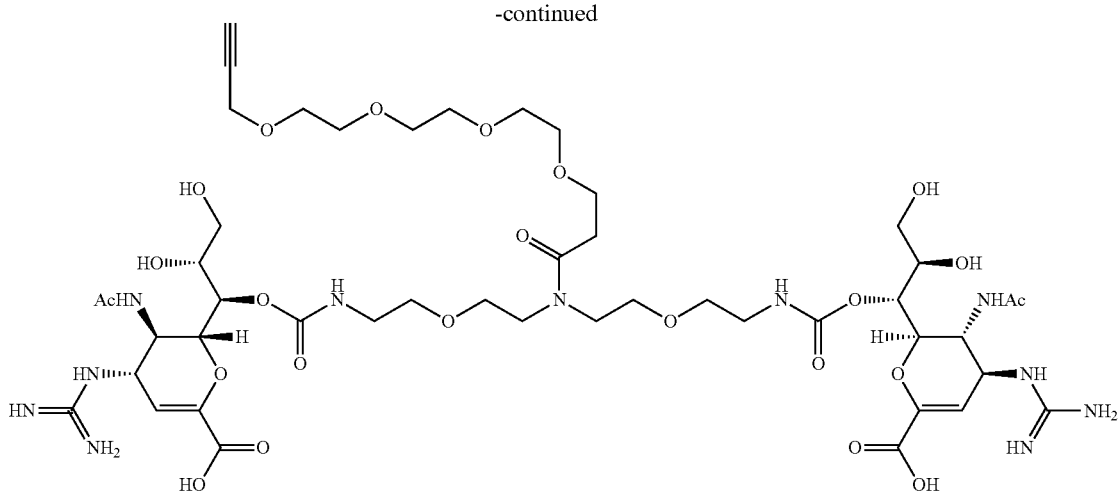

Step a.

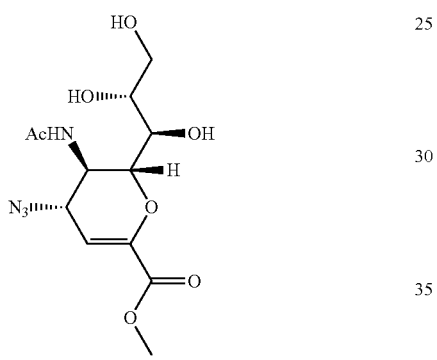

Methyl 5-acetamido-7,8,9-O-triacetyl-2,6-anhydro-4-azido-3,4,5-trideoxy-D-glycero-D-galacto-non-2-enonate (10.0 g, 22 mmol) was dissolved in 60 ml dry methanol, then treated with 20 ml sodium methoxide in methanol (0.5 M in methanol, 10 mmol) while cooling in an ice-water bath. Progress of the reaction was monitored by LCMS, which was complete after 2 hours. The pH of the reaction solution was then adjusted to a value of 5 to 6 by using Amberlite IRN-77 ion exchange resin. The mixture was filtered to remove the resin and evaporated to dryness under vacuum. The resulting oil was used for next step without further purification. Ion(s) found by LCMS: M+H=331.1.

Step b.

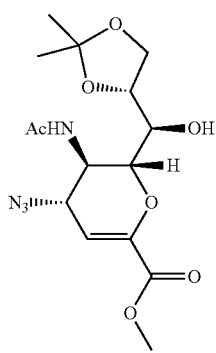 [SMILES: COC(=O)C1=C[C@H](N=[N+]=[N-])[C@@H](NC(C)=O)[C@H]([C@H](O)[C@H]2COC(C)(C)O2)O1]

To a solution of the products from the previous step in 70 ml of acetone were added 30 ml of 2,2-dimethoxypropane and p-toluenesulfonic acid 1 hydrate (400 mg, 2.0 mmol), the resulting solution was stirred at room temperature overnight. At the end of this time, sodium bicarbonate (170 mg, 2.0 mmol) was added, and the mixture was concentrated to dryness. The resulting residue was used in next step without purification. Ion(s) found by LCMS: M+H=371.2.

Step c.

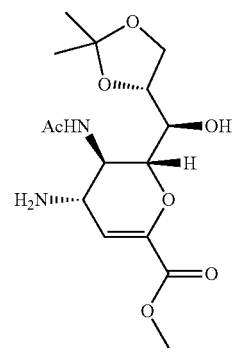 [SMILES: COC(=O)C1=C[C@H](N)[C@@H](NC(C)=O)[C@H]([C@H](O)[C@H]2COC(C)(C)O2)O1]

To a solution of material from the previous step in 60 ml of methanol was added 5.0 g of a Lindlar catalyst. The resulting mixture was flushed with hydrogen every 30 minutes and stirred for 5 hours. After complete reaction as determined by HPLC, the catalyst was filtered off through celite. The filtrate was concentrated and used in the next step without purification.

Crude product from the previous step in 60 ml THF was treated with N,N'-bis-boc-1-guanylpyrazole (9.3 g, 30.0 mmol), and DIEA (9.9 ml, 57.0 mmol). The resulting solution was stirred at room temperature until all starting material was consumed as determined by LCMS (4 h). The solution was concentrated and purified by flash chromatography eluted with 20% to 80% ethyl acetate/dichloromethane. Yield 8.8 g, 59.0% for four steps. Ion(s) found by LCMS: M+H 587.3.

Step d.

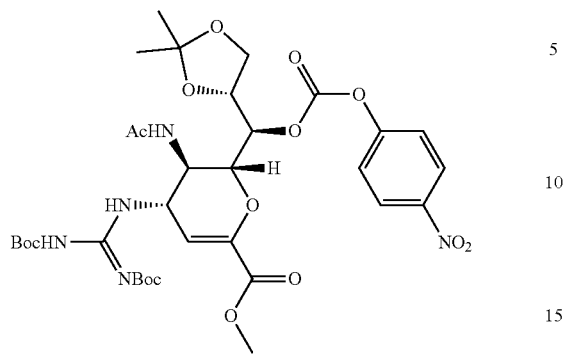

A reaction flask containing product from the previous step (6.5 g, 11 mmol) was vacuum flushed with nitrogen and dissolved in anhydrous dichloromethane (100 ml). After the solution was cooled in an ice-water bath, DMAP (4.89 g, 40 mmol) was added and stirred to dissolve, then 4-nitrophenylchloroformate (5.58 g, 28 mmol) was added in portions, while stirring at 0° C. to room temperature for 1 hour. LCMS shows starting material 1 hr so additional DMAP (1.22 g, 10 mmol) and 4-nitrophenylchloroformate (1.0 g, 5 mmol) were added. The reaction was continued for 4 more hours, then concentrated and purified by flash chromatography eluting with 20% to 80% ethyl acetate/dichloromethane. Yield 5.1 g, 59.9%. Ion found by LCMS: $[M+H]^+=752.2$.

Step e.

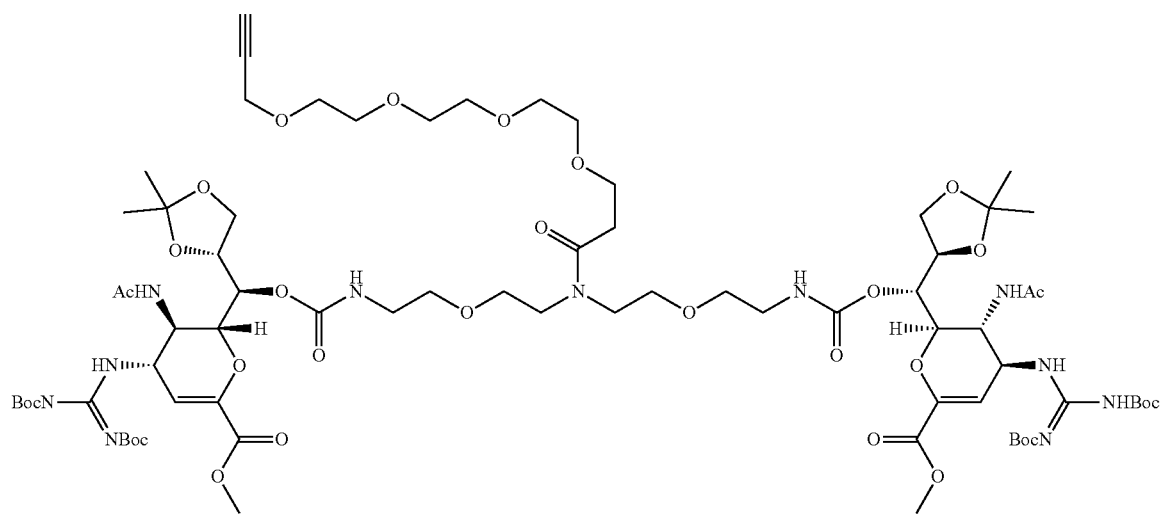

To a solution of the nitrophenyl carbonate from the previous step (1.8 g. 2.3 mmol) in anhydrous dichloromethane (20 ml) was added a mixture of central linker (0.51 g, 1.0 mmol, added in portions over 30 minutes) and DIPEA (1.4 ml, 10 mmol) in anhydrous DMF (20 ml). The reaction was stirred at room temperature overnight, then concentrated and purified by flash chromatography eluting with 0% to 10% methanol/dichloromethane. Yield 1.35 g, 80%. Ions found by LCMS: $[(M+2H)/2]^+=830.4$, $[(M-Boc+2H)/2]^+=780.4$, $[(M-2Boc+2H)/2]^+=730.4$.

Step f.

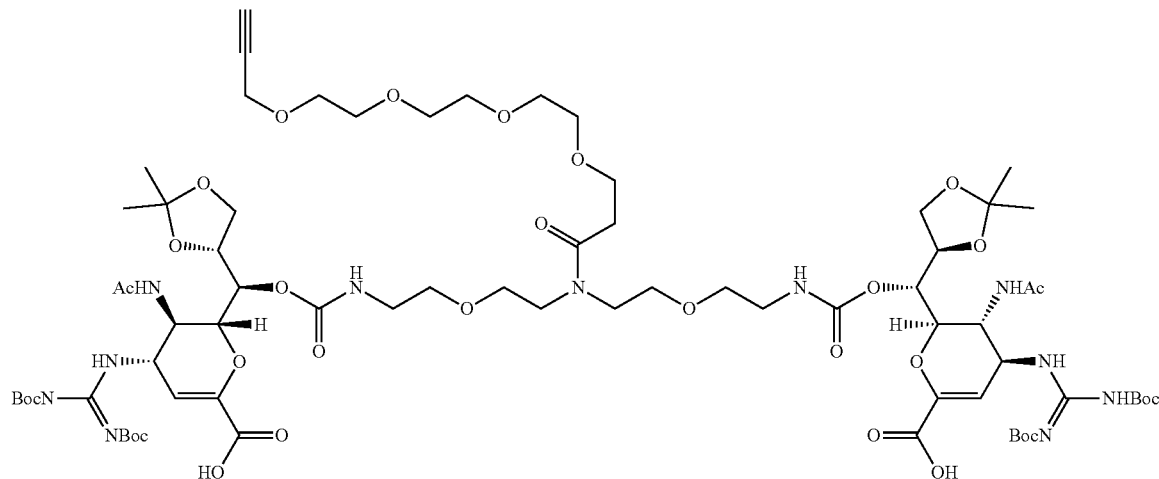

Product from the previous step (200 mg, 0.2 mmol) was dissolved into 2 ml MeOH and 2 ml THF, then treated with a solution of lithium hydroxide (24 mg, 1 mmol) dissolved in 2 ml water. The reaction was stirred for 10 min at room temperature at which time HPLC showed the reaction was complete. The pH of the reaction solution was adjusted to the value of 5 to 6 by using Amberlite IRN-77 ion exchange resin the filtered to remove the resin. The crude product was evaporated to dryness under a vacuum and used in the next step with purification. Ion(s) found by LCMS: $[(M+2H)/2]^+=815.4$, $[(M-Boc+2H)/2]^+=765.4$, $[(M-2Boc+2H)/2]^+=715.4$.

Step g.

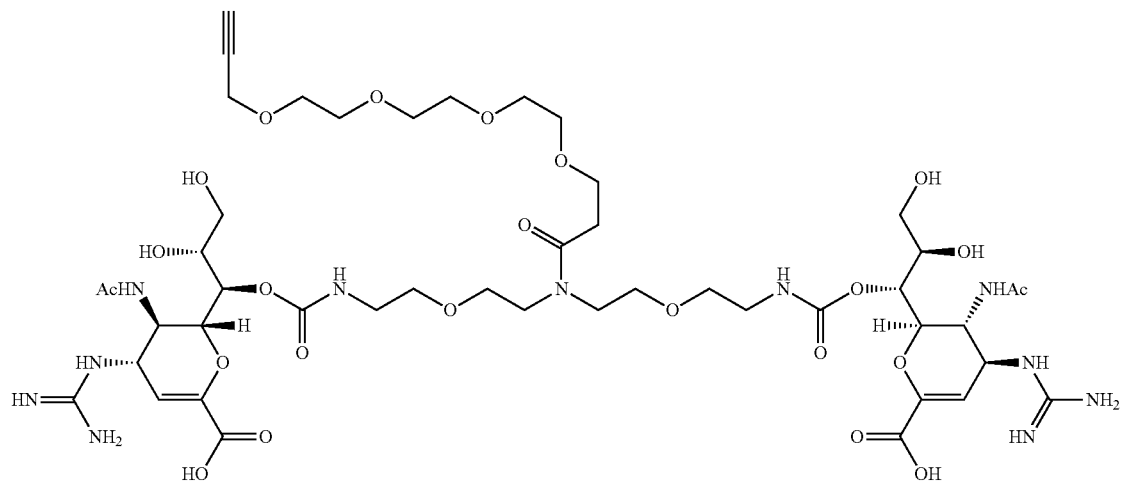 [SMILES: C#CCOCCOCCOCCOCCC(=O)N(CCOCCNC(=O)O[C@@H]([C@@H]1OC(C(=O)O)=C[C@H](NC(=N)N)[C@H]1NC(C)=O)[C@H](O)CO)CCOCCNC(=O)O[C@@H]([C@@H]1OC(C(=O)O)=C[C@H](NC(=N)N)[C@H]1NC(C)=O)[C@H](O)CO]

The product from step g (400 mg, 0.25 mmol) was dissolved into 5 ml dichloromethane and 5 ml TFA, and the resulting reaction solution was stirred at room temperature. The progress of the reaction was monitored by LCMS. After the completion of the reaction (6 h), the solution was stripped to dryness and then dissolved in 4 ml water and 4 ml acetonitrile. The resulting solution was stirred for another 2 hour at room temperature at which LCMS show complete deprotection of the acetonide protecting groups. This mixture was concentrated and purified by reverse phase liquid chromatography (RPLC) using an Isco COMBIFLASH® liquid chromatograph eluted with 5% to 40% acetonitrile/water with 0.1% TFA as the modifier. Yield 270 mg, 68.0%. Ion(s) found by LCMS: $[(M+2H)/2]^+=575.8$, $[(M+3H)/3]^+=384.2$.

Example 104. NMR Results for Int-7a, Int-7b, and Int-7c
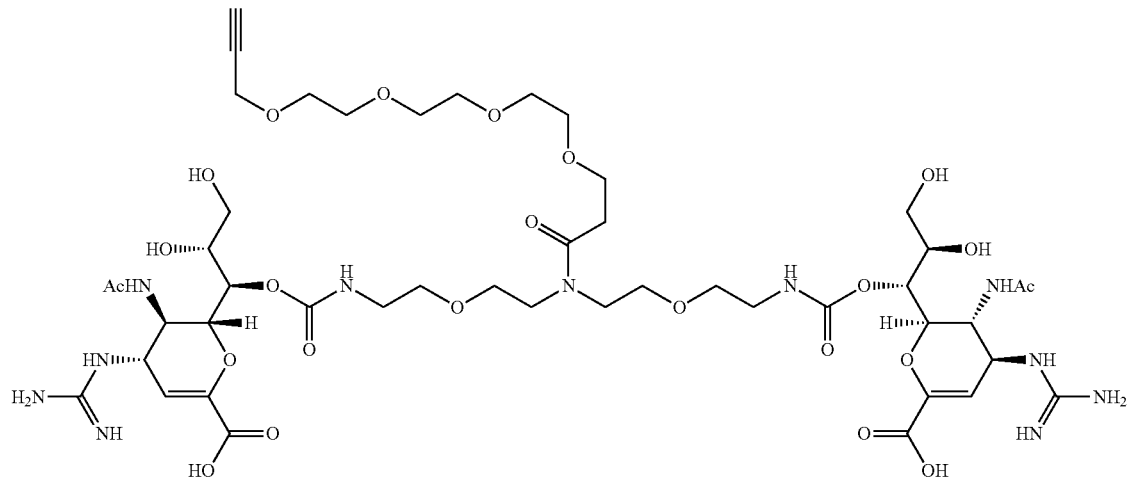
NMR of Int-7a
¹H NMR (500 MHz, Methanol-d₄) δ 5.91-5.89 (m, 2H), 5.00-4.96 (m, 2H), 4.58-4.53 (m, 2H), 4.42-4.37 (m, 2H), 4.20-4.17 (m, 6H), 4.02-3.97 (m, 2H), 3.78-3.49 (m, 28H), 3.29-3.18 (m, 4H), 2.86 (t, J=2.6 Hz, 1H), 2.85-2.72 (m, 2H), 1.96 (s, 3H), 1.95 (s, 3H).
¹³C NMR (125 MHz, MeOD) δ 171.73, 170.80, 170.29, 161.95, 156.06, 155.08, 154.99, 144.07, 143.93, 116.41, 114.10, 106.03, 105.86, 77.71, 74.46, 73.22, 68.62, 68.54, 68.50, 68.38, 68.12, 68.00, 67.94, 67.67, 67.64, 67.53, 67.20, 66.96, 65.44, 61.53, 56.17, 49.74, 49.64, 47.37, 45.17, 39.16, 39.06, 31.73, 19.96, 19.92.
¹H NMR (500 MHz, DMSO-d₆) δ: 8.28 (d, J=8.4 Hz, 2H, —NH), 7.98 (d, J=11.5 Hz, 2H, —NH), 7.78 (d, J=8.7 Hz, 2H, —NH), 7.60 (t, J=8.5 Hz, 2H, —NH), 7.20 (bs, 2H, —NH), 7.06 (bs, 2H, —NH), 5.69 (bs, 1H), 5.67 (d, J=2.4 Hz, 1H), 4.83 (dd, J=9.2, 2.2 Hz, 1H), 4.45 (dt, J=9, 2.5 Hz, 1H), 4.37 (d, J=2.2 Hz, 1H), 4.33-4.24 (m, 2H), 4.13 (d, J=2.5 Hz, 2H), 4.05-4.32 (m, 41H), 3.23 (m, 1H), 3.15-3.09 (m, 2H), 3.06-3.02 (m, 2H), 2.59 (t, J=6.7 Hz, 2H), 1.91 (s, 3H), 1.78 (s, 3H).
¹³C NMR (125 MHz, MeOD) δ: 173.19, 172.98, 172.25, 171.75, 164.26, 163.82, 157.88, 157.55, 156.51, 146.09, 107.21, 106.93, 106.59, 79.22, 76.19, 75.92, 74.72, 74.68,
NMR of Int-7b
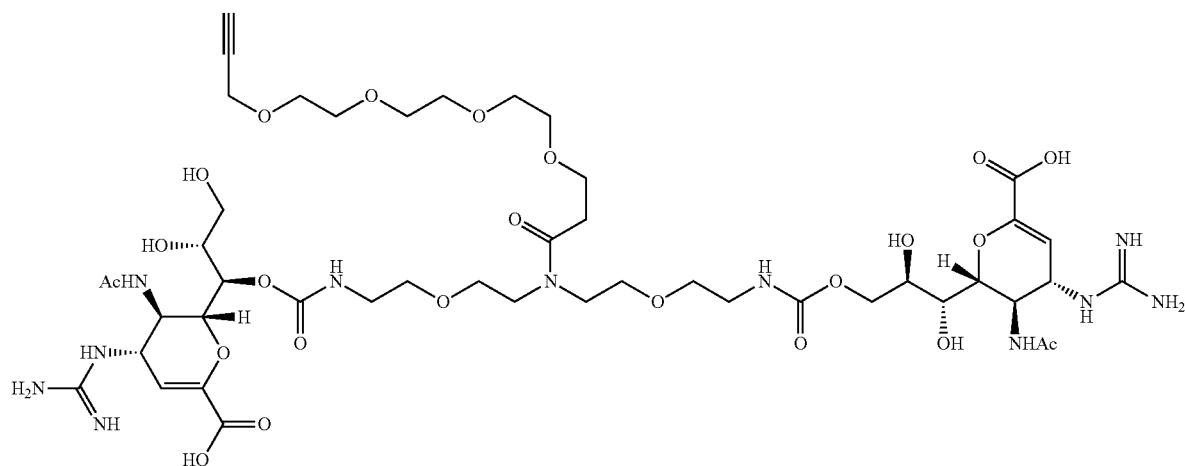
¹H NMR (500 MHz, Methanol-d₄) δ 5.91-5.87 (m, 2H), 5.04-4.95 (m, 1H), 4.58-4.48 (m, 2H), 4.45-4.37 (m, 3H), 4.20-4.10 (m, 5H), 4.08-3.98 (m, 2H), 3.79-3.44 (m, 29H), 3.29-3.18 (m, 4H), 2.88-2.70 (m, 3H), 2.02 (s, 3H), 1.96-1.94 (m, 3H).
70.12, 70.08, 70.03, 69.99, 69.92, 69.88, 69.66, 69.48, 69.12, 69.01, 68.94, 68.73, 68.69, 68.50, 68.19, 67.08, 66.93, 66.79, 63.04, 57.68, 51.24, 51.15, 50.13, 48.87, 48.72, 46.72, 46.58, 46.23, 40.64, 40.41, 33.21, 21.49, 21.45, 21.40.

NMR of Int-7c
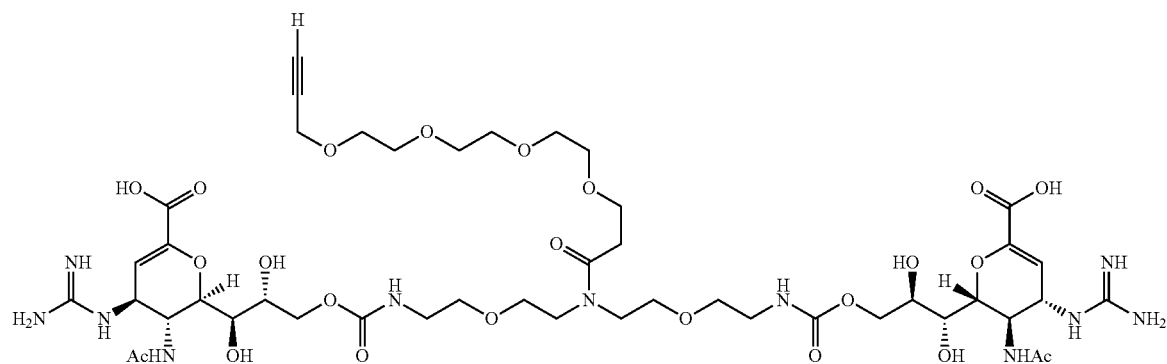
¹H NMR (500 MHz, Methanol-d₄) δ: 5.88 (d, J=2.6 Hz, 2H), 4.50 (dt, J=8.5, 2.7 Hz, 2H), 4.43 (ddd, J=9.7, 3.9, 1.5 Hz, 2H), 4.39 (dd, J=11.5, 2.4 Hz, 2H), 4.25-4.16 (m, 2H), 4.19 (d, J=2.4 Hz, 2H), 4.13 (dt, J=11.5, 5.9 Hz, 2H), 4.05 (m, 2H), 3.77 (t, J=6.2 Hz, 2H), 3.72-3.55 (m, 22H), 3.51 (m, 4H), 3.35-3.23 (m, 4H), 2.86 (t, J=2.4 Hz, 1H), 2.74 (t, J=6.2 Hz, 2H), 2.02 (s, 6H).
¹³C NMR (125 MHz, MeOD) δ:173.03, 163.76, 157.89, 157.54, 145.60, 107.21, 79.28, 76.29, 74.70, 70.11, 70.07, 70.03, 69.92, 69.70, 69.47, 68.96, 68.89, 68.72, 68.54, 68.19, 67.05, 66.75, 57.69, 50.09, 48.69, 48.08, 46.10, 40.44, 40.38, 33.23, 21.42.
Example 105. Synthesis of Int-60
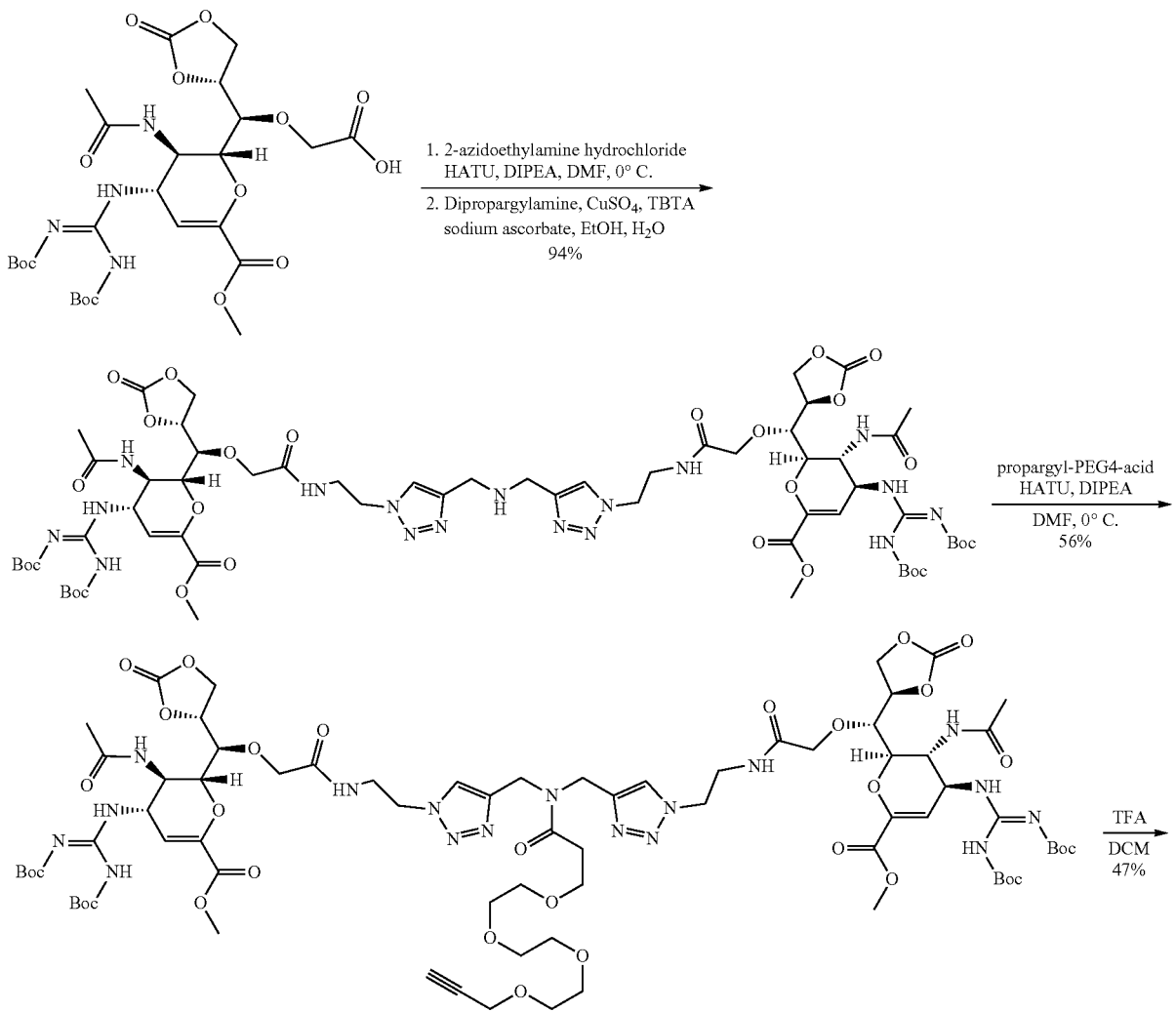

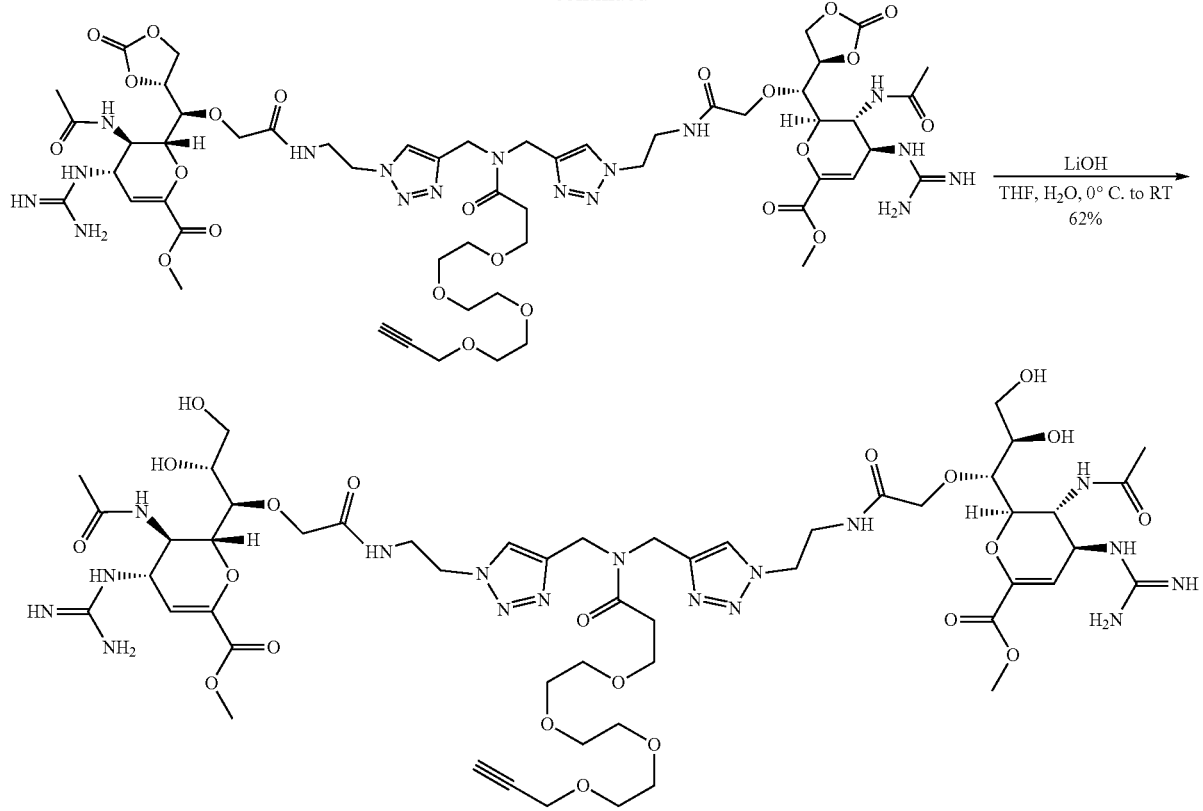

Step a.

To a 0° C. stirring solution of previously prepared Ether-zanamivir acid (1.00 g, 1.586 mmol, Example 31), 2-azido-ethylamine hydrochloride (213 mg, 1.744 mmol) and DIPEA (1.105 mL, 6.343 mmol) in DMF (8.0 mL), it was added HATU (615 mg, 1.618 mmol). The temperature was raised to ambient and stirring was continued until completion. All the volatiles were removed per vacuum techniques. The residue was taken up in ethyl acetate, washed with a 1 M aqueous solution of sulfuric acid (1×50 mL), then a saturated aqueous solution of sodium bicarbonate (3×20 mL), and brine (1×50 mL). The resulting organic layers was dried with magnesium sulfate, filtered, and all the volatiles were removed per vacuum techniques. In this way, 816 mg of the desired intermediate azide was obtained in high purity and used in the next step without any further purification. (Ion found by LCMS: [M+H]$^+$=699.2). To a stirring solution of the described crude material (816 mg, 1.168 mmol), dipropargylamine (54 mg, 0.584 mmol), tris((1-benzyl-4-triazolyl)methyl)amine (31 mg, 0.058 mmol), and sodium ascorbate (58 mg, 0.292 mmol) in ethanol (10 mL) and water (5 mL), it was added cupric sulfate (10 mg, 0.061 mmol). Upon completion, copper scavenger SiliaMetS TAAcONa (300 mg, loading 0.45 mmol/g) was added and stirring was continued for 1 h. The mixture was filtered with the aid of dichloromethane. The filtrate was washed with a saturated solution of sodium bicarbonate. The aqueous layer was additionally washed with dichloromethane (3 times). The combined organics were dried with magnesium sulfate, filtered and concentrated. The residue was purified by silica column using an Isco COMBIFLASH® liquid chromatography eluted with 0% to 100% hexanes and ethyl acetate, followed by 0% to 30% dichloromethane and. Yield 817 mg, 94% yield. Ions found by LCMS: [(M+2H)/2]$^+$=745.8, [(M+3H)/3]$^+$=497.5.

Step b.

To a 0° C. stirring solution of step a product (817 mg, 0.548 mmol), propargyl-PEG4-acid (185 mg, 0.712 mmol) and DIPEA (286 μL, 1.644 mmol) in DMF (7.0 mL), it was added HATU (212 mg, 0.544 mmol). The temperature was raised to ambient and stirring was continued until completion. All the volatiles were removed per vacuum techniques. The residue was purified by HPLC (0 to 90% methanol and water). Yield 520 mg, 56%. Ions found by LCMS: [(M+2H)/2]$^+$=866.8, [(M+3H)/3]$^+$=578.4.

Step c.

A stirring solution of step b compound (520 mg, 0.300 mmol) in 2-methyl-2-butene (0.25 mL), dichloromethane (4.0 mL) and TFA (2.0 mL) was stirred until gas evolution ceased. All the volatiles were removed per vacuum techniques. The residue was purified by HPLC (0 to 30% methanol and water, using 0.1% TFA as modifier). Yield 221 mg, 47%. Ions found by LCMS: [(M+2H)/2]$^+$=666.8, [(M+3H)/3]$^+$=444.8.

Step d.

To a 0° C. stirring solution of step c product (221 mg, 0.142 mmol) in water (3.0 mL) it was added lithium hydroxide (20 mg, 0.850 mmol). The reaction was quenched with acetic acid (120 μL), and all the volatiles were removed per vacuum techniques. The residue was purified by HPLC (0 to 20% methanol and water, using 0.1% TFA as modifier). Yield 130 mg, 62%. Ions found by LCMS: [(M+2H)/2]$^+$=626.8, [(M+3H)/3]$^+$=418.2.

Example 106. Synthesis of Conjugate 29

A solution of azido functionalized aglycosylated Fc (SEQ ID NO: 35) in pH 7.4 PBS×1 buffer solution (100 mg, 10 mL, 1.874 μmol) is added to a centrifuge tube containing a pH 7.4 PBS×1 buffer solution (10.50 mL) of alkyne derivatized small molecule (17 mg, 0.0112 mmol; Example 105, Int-60), cupric sulfate (4 mg, 0.0225 mmol), tris(3-hydroxypropyltriazolylmethyl)-amine (39 mg, 0.0900 mmol), and sodium ascorbate (7.4 mg, 0.375 mmol). The resulting mixture was gently shaken overnight. It was purified by affinity chromatography over a protein A column, followed by size exclusion chromatography (see Example 10). Maldi TOF analysis of the purified final product gave an average mass of 56938 Da (DAR=2.3). Yield 49.9 mg, 49% yield.

The nucleic acid construct encoding the Fc for conjugate 29 included a nucleic acid encoding the amino acid sequence of SEQ ID NO: 35, which includes a C-terminal lysine residue and N-terminal murine IgG signal sequence. Upon expression, the C-terminal lysine and the N-terminal murine IgG signal sequence of the Fc of conjugate 29 are proteolytically cleaved, resulting in an Fc having the sequence lacking Lys447 (e.g., lacking a C-terminal lysine residue) and the N-terminal murine IgG signal sequence. The presence or absence of a C-terminal lysine does not alter the properties of the Fc or the corresponding conjugate.

Example 107. Synthesis of Int-65

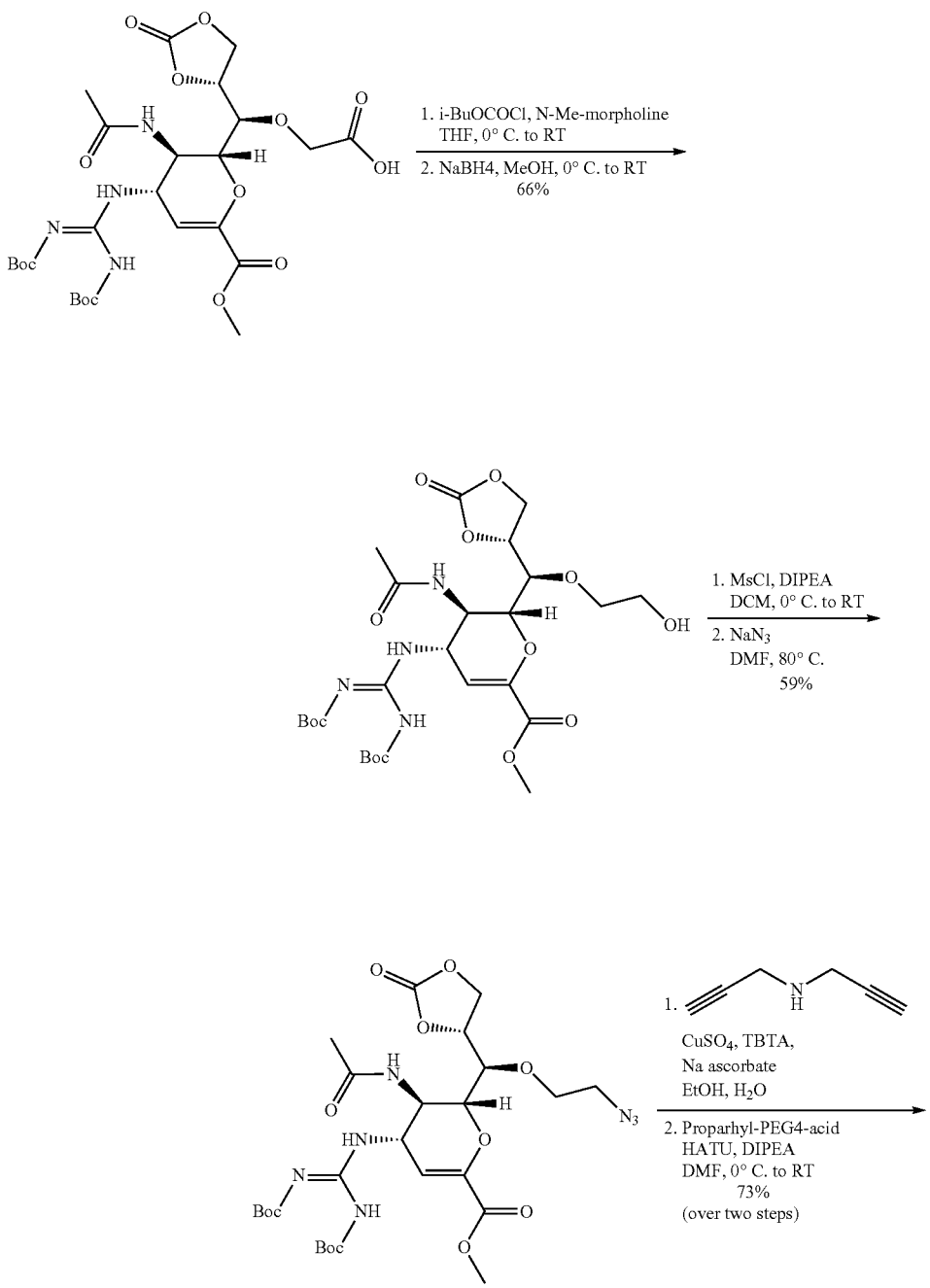

-continued

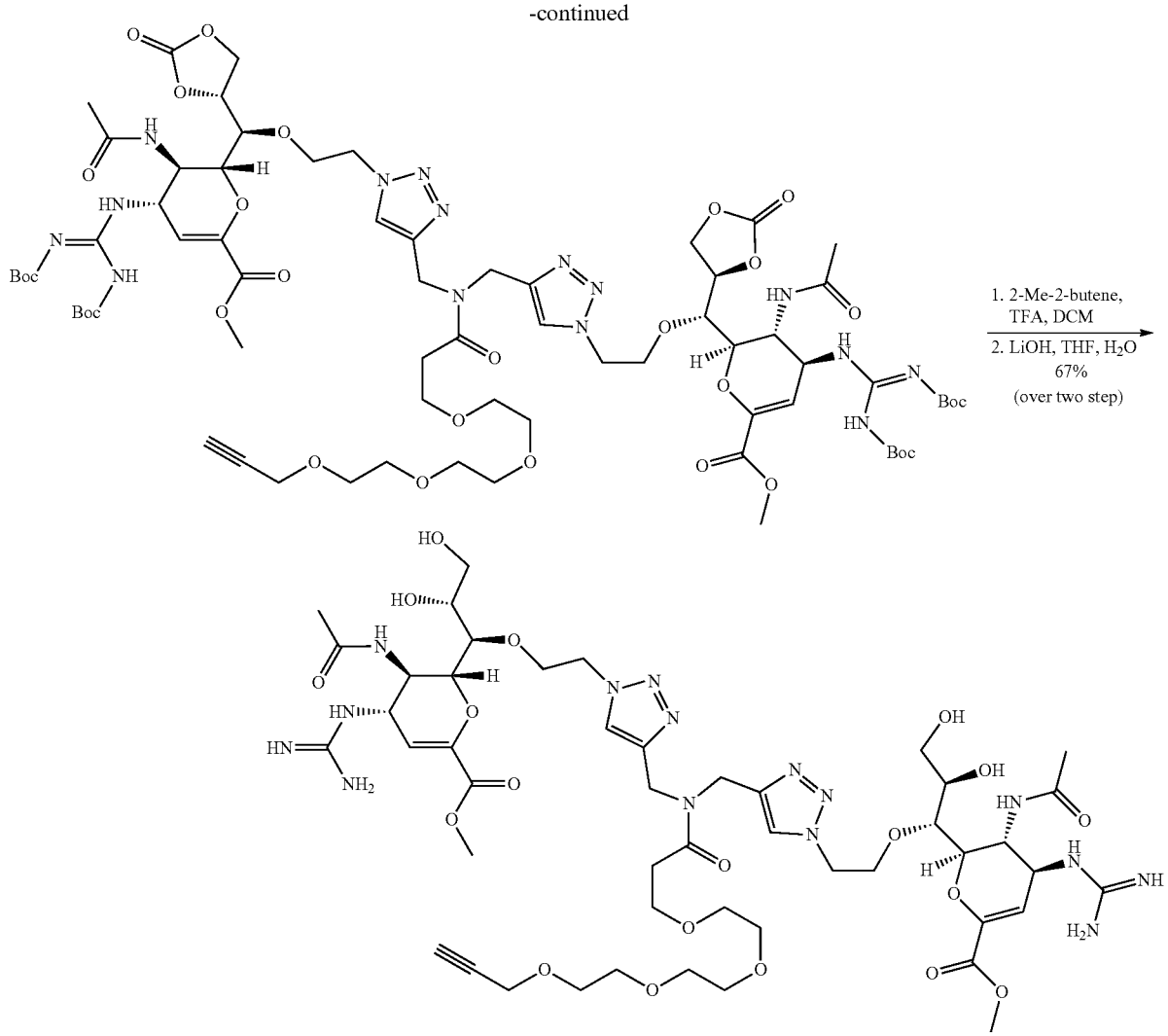

1. 2-Me-2-butene, TFA, DCM
2. LiOH, THF, H₂O
67%
(over two step)

Step a.
To a 0° C. stirring solution of previously prepared ether-zanamivir acid (2.00 g, 3.172 mmol, Example 31) and 4-methylmorpholine (0.628 mL, 5.709 mmol) in tetrahydrofuran (30 mL) it was added isobutyl chloroformate (0.617 mL, 4.7574 mmol). After 10 minutes, the temperature was increased to ambient and stirring continued for 20 minutes. The temperature was decreased back to 0° C., and sodium borohydride (360 mg, 9.515 mmol) was added in one portion, followed by dropwise addition of (10 mL) over 5 minutes. Upon completion, the reaction was quenched with acetic acid (2.860 mL, 50 mmol), and after 5 minutes the temperature was raised to ambient, while stirring was continued until gas evolution ceased. All the volatiles were evaporated and the residue was suspended in dichloromethane and filtered. The filtrate was concentrated and the residue was purified by silica column using an Isco COMBIFLASH® liquid chromatography eluted with 20% to 100% hexanes and ethyl acetate, using 3% methanol as a modifier. Yield 1.302 g, 66% yield. Ions found by LCMS: [(M+H)]⁺=617.2.

Step b.
To a 0° C. stirring solution of step a product (1.25 g, 2.027 mmol) and DIPEA (1.095 mL, 6.284 mmol) in dichloromethane (15 mL), it was added methanesulfonyl chloride (0.314 mmol, 4.054 mmol).
Upon completion, the reaction was treated with water (15 mL). The layers were separated, and the dichloromethane layer was dried with brine, then magnesium sulfate, and filtered. The solution was concentrated and the residue was dissolved in DMF (10 mL), and sodium azide (264 mg, 4.054 mmol) was added, while temperature was raised to 50° C. Completion was observed after 18 h, and all the volatiles were evaporated per vacuum techniques. The residue was purified by silica column using an Isco COMBIFLASH® liquid chromatography eluted with 20% to 100% hexanes and ethyl acetate, using 3% methanol as a modifier. Yield 767 mg, 59% yield. Ions found by LCMS: [(M+H)]⁺=642.2.

Step c.
To a stirring solution of step b product (496 mg, 0.773 mmol), dipropargylamine (36 mg, 0.386 mmol), tris((1-benzyl-4-triazolyl)methyl)amine (41 mg, 0.077 mmol), and sodium ascorbate (115 mg, 0.580 mmol) in ethanol (16 mL) and water (8 mL), it was added cupric sulfate (13 mg, 0.081 mmol). Upon completion, copper scavenger SiliaMetS TAAcONa (600 mg, loading 0.45 mmol/g) was added and stirring was continued for 1 h. The mixture was filtered with the aid of dichloromethane. The filtrate was washed with a saturated solution of sodium bicarbonate. The aqueous layer was additionally washed with dichloromethane (3 times). The combined organics were dried with magnesium sulfate, filtered and all the volatiles were evaporated per vacuum techniques. To a 0° C. stirring solution of the residue, propargyl-PEG4-acid (151 mg, 0.580 mmol)) and DIPEA (337 µL, 1.933 mmol) in DMF (10.0 mL), it was added HATU (220 mg, 0.580 mmol). The temperature was raised to ambient and stirring was continued until completion. All the volatiles were removed per vacuum techniques. The residue was purified by HPLC (0 to 90% methanol and water). Yield 457 mg, 73%. Ions found by LCMS: [(M+2H)/2]$^+$=809.8, [(M+2H-Boc)/2]$^+$=759.8.

Step d.

A stirring solution of step c compound (451 mg, 0.279 mmol) in 2-methyl-2-butene (0.25 mL), dichloromethane (4.0 mL) and TFA (2.0 mL) was stirred until gas evolution ceased. All the volatiles were removed per vacuum techniques. Ions found by LCMS: [(M+2H)/2]$^+$=609.8, [(M+3H)/3]$^+$=407.0. To a 0° C. stirring solution of the residue in tetrahydrofuran (6 mL) and water (6 mL), it was added lithium hydroxide (240 mg, 10.03 mmol). Upon completion, the reaction was quenched with acetic acid (0.638 mL, 11.14 mmol), and all the volatiles were removed per vacuum techniques. The residue was purified by HPLC (0 to 90% methanol and water, using 0.1% TFA as modifier). Yield 209 mg, 67%. Ions found by LCMS: [(M+2H)/2]$^+$=569.8, [(M+2H-Boc)/2]$^+$=380.3.

Example 108. Synthesis of Conjugate 30

A solution of azido functionalized aglycosylated Fc (Example 7, SEQ ID NO: 35) in pH 7.4 PBS×1 buffer solution (50 mg, 5 mL, 1.874 µmol) is added to a centrifuge tube containing a pH 7.4 PBS×1 buffer solution (9.50 mL) of alkyne derivatized small molecule (8.7 mg, 0.0064 mmol, Int-65), cupric sulfate (2 mg, 0.013 mmol), tris(3-hydroxypropyltriazolylmethyl)-amine (22 mg, 0.0508 mmol), and sodium ascorbate (25 mg, 0.127 mmol). The resulting mixture was gently shaken overnight. It was purified by affinity chromatography over a protein A column, followed by size exclusion chromatography (see Example 10). Maldi TOF analysis of the purified final product gave an average mass of 61548 Da (DAR=2.4). Yield 32.33 mg, 67% yield.

The nucleic acid construct encoding the Fc for conjugate 30 included a nucleic acid encoding the amino acid sequence of SEQ ID NO: 35, which includes a C-terminal lysine residue and N-terminal murine IgG signal sequence. Upon expression, the C-terminal lysine and the N-terminal murine IgG signal sequence of the Fc of conjugate 30 are proteolytically cleaved, resulting in an Fc having the sequence lacking Lys447 (e.g., lacking a C-terminal lysine residue) and the N-terminal murine IgG signal sequence. The presence or absence of a C-terminal lysine does not alter the properties of the Fc or the corresponding conjugate.

Example 109: Synthesis of p-Nitrophenyl Carbonate Zanamivir Intermediate

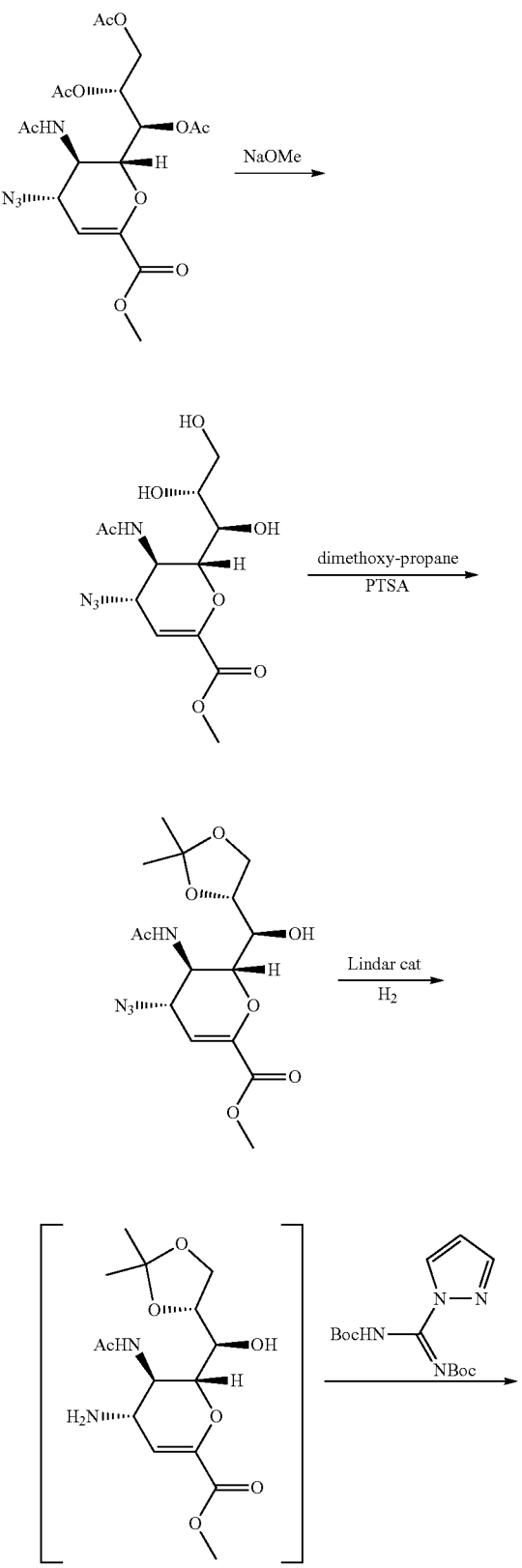

859

-continued

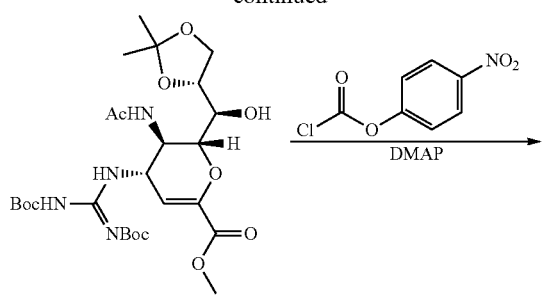

Step a.

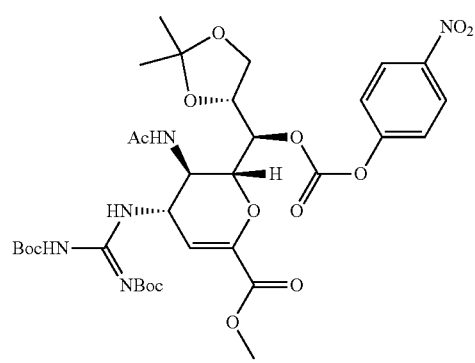

Triacetoxy-azido Zanamivir intermediate (10.0 g, 22 mmol) was dissolved in 60 ml dry methanol, then treated with 20 ml sodium methoxide in methanol (0.5 M in methanol, 10 mmol) while cooling in an ice-water bath. Progress of the reaction was monitored by LCMS, which was complete after 2 hours. The pH of the reaction solution was then adjusted to a value of 5 to 6 by using Amberlite IRN-77 ion exchange resin. The mixture was filtered to remove the resin and evaporated to dryness under vacuum. The resulting oil was used for next step without further purification. Ion(s) found by LCMS: M+H=331.1.

860

Step b.

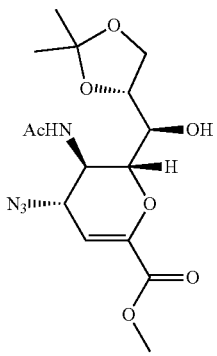 [SMILES: COC(=O)C1=C[C@H](N=[N+]=[N-])[C@@H](NC(C)=O)[C@H]([C@H](O)[C@H]2COC(C)(C)O2)O1]

To a solution of the products from the previous step in 70 ml of acetone were added 30 ml of 2,2-dimethoxypropane and p-toluenesulfonic acid 1 hydrate (400 mg, 2.0 mmol), the resulting solution was stirred at room temperature overnight. At the end of this time, sodium bicarbonate (170 mg, 2.0 mmol) was added, and the mixture was concentrated to dryness. The resulting residue was used in next step without purification. Ion(s) found by LCMS: M+H=371.2.

Steps c & d.

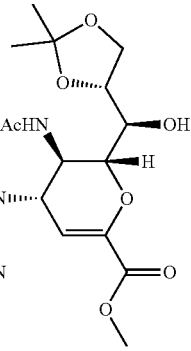

To a solution of material from the previous step in 60 ml of methanol was added 5.0 g of a Lindlar catalyst. The resulting mixture was flushed with hydrogen every 30 minutes and stirred for 5 hours. After complete reaction as determined by HPLC, the catalyst was filtered off through celite. The filtrate was concentrated and used in the next step without purification.

Crude product from the previous step in 60 ml THF was treated with N,N'-bis-boc-1-guanylpyrazole (9.3 g, 30.0 mmol), and DIEA (9.9 ml, 57.0 mmol). The resulting solution was stirred at room temperature until all starting material was consumed as determined by LCMS (4 h). The solution was concentrated and purified by flash chromatography eluted with 20% to 80% ethyl acetate/dichloromethane. Yield 8.8 g, 59.0% for four steps. Ion(s) found by LCMS: M+H 587.3.

861

Step e.

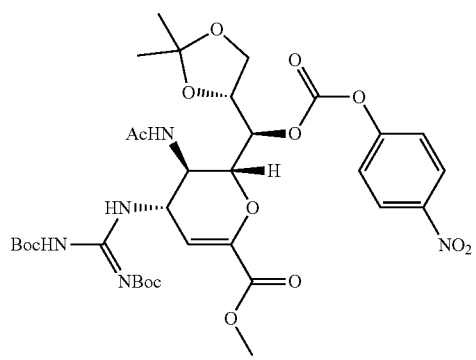

862

A reaction flask containing product from the previous step (6.5 g, 11 mmol) was vacuum flushed with nitrogen and dissolved in anhydrous dichloromethane (100 ml). After the solution was cooled in an ice-water bath, DMAP (4.89 g, 40 mmol) was added and stirred to dissolve, then 4-nitrophenylchloroformate (5.58 g, 28 mmol) was added in portions, while stirring at 0° C. to room temperature for 1 hour. LCMS shows starting material 1 hr so additional DMAP (1.22 g, 10 mmol) and 4-nitrophenylchloroformate (1.0 g, 5 mmol) were added. The reaction was continued for 4 more hours, then concentrated and purified by flash chromatography eluting with 20% to 80% ethyl acetate/dichloromethane. Yield 5.1 g, 59.9%. Ion found by LCMS: $[M+H]^+=752.2$.

Example 110. Synthesis of Int-71

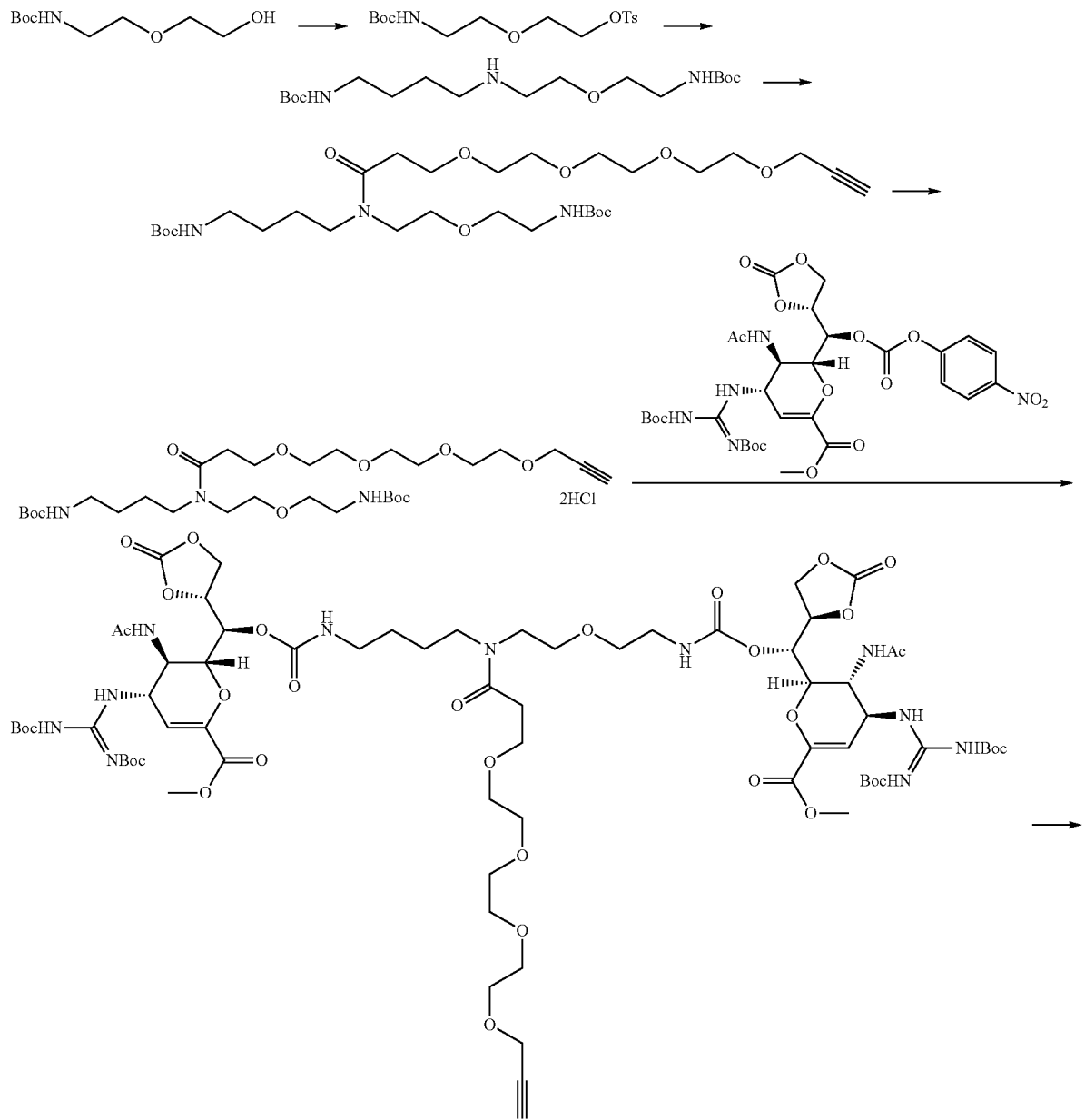

863

864

-continued

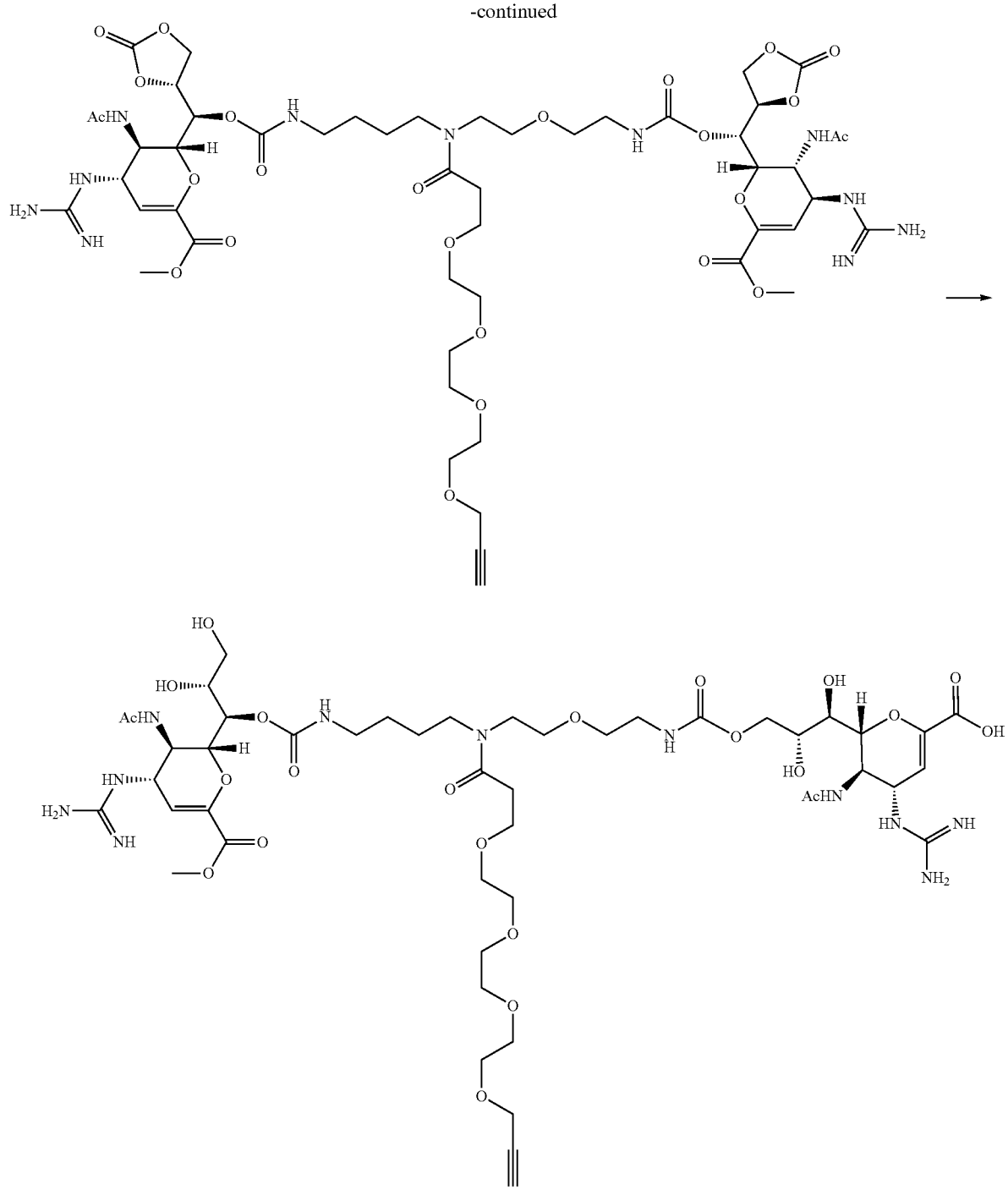

Step a.

To a solution of 2-(2-Boc-aminoethoxy) ethanol (6.15 g, 30 mmol) in anhydrous DCM (60 ml) was added DIPEA (7.8 g, 60 mmol) and DMAP (366.6 mg, 3 mmol). P-toluenesulfonyl chloride (6.86 g, 36 mmol) was then added in portions over 30 minutes. After the resulting mixture was stirred for 3 days, it was concentrated by rotary evaporation and purified by RPLC (20% to 70% acetonitrile/water). Yield 3.71 g, 34.4%. Ion found by LCMS: [M-Boc+H]$^+$= 260.

Step b.

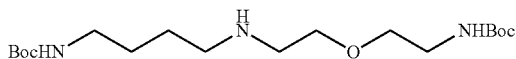 [SMILES: CC(C)(C)OC(=O)NCCCCNCCOCCNC(=O)OC(C)(C)C]

To a solution of the step-a product (2.1 g, 5.83 mmol) in anhydrous THF (10 ml) was added sodium carbonate (1.24 g, 11.7 mmol) and N-Boc-1,4-diaminobutane (1.32 g, 7 mmol). The resulting mixture was heated at 60° C. for 1 day. The salt was then filtered off, and the filtrate was concentrated by rotary evaporation. The residue was purified by RPLC (100 g, 5 to 50% acetonitrile and water). Yield 1.94 g, 88.6%. Ion found by LCMS: $[M+H]^+=376.0$.

Step c.

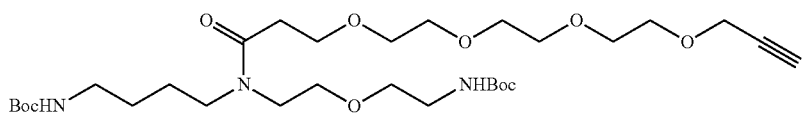 [SMILES: C#CCOCCOCCOCCOCCC(=O)N(CCCCNC(=O)OC(C)(C)C)CCOCCNC(=O)OC(C)(C)C]

To a solution of propargyl PEG-4 acid (781 mg, 3 mmol) and HATU (1.14 g, 3 mmol) in anhydrous DMF (3 ml) was added DIPEA (390 mg, 3 mmol), followed by the addition of the solution step-b product (940 mg, 2.5 mmol) and DIPEA (390 mg, 3 mmol) in anhydrous DMF (3 ml). The reaction mixture was stirred for 30 minutes, then directly purified by RPLC (5% to 80% acetonitrile and water, using 0.1% TFA as modifier). Yield 960.2 mg, 65.3%. Ion found by LCMS: $[M+H]^+=618.3$, $[M-Boc+H]^+=518.3$.

Step d.

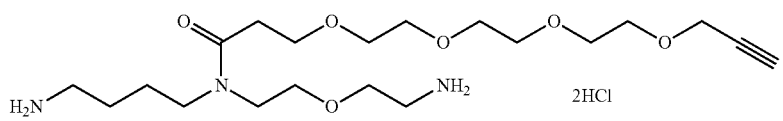 [SMILES: C#CCOCCOCCOCCOCCC(=O)N(CCCCN)CCOCCN ; "2HCl"]

The step-c product (960.2 mg, 1.63 mmol) was dissolved in anhydrous THF (6 ml). 4N HCl solution in dioxane (4 ml) was added, and the reaction mixture was stirred overnight. It was then concentrated by rotary evaporation. The residue was extracted with water (3×3 ml) and ethyl acetate (10 ml). The combined aqueous layers were lyophilized. Yield 760 mg, 95.1%. Ion found by LCMS: $[M+H]^+=418.0$.

Step e.

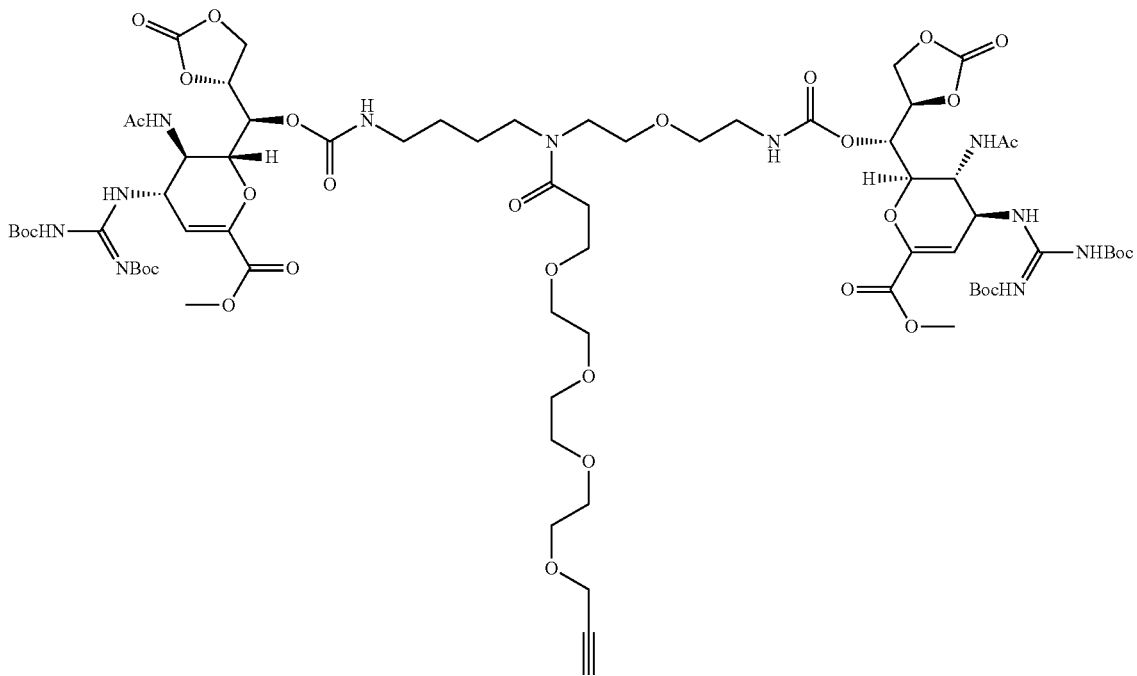

867

To a mixture of the step-d product (556.2 mg, 1.13 mmol) and DIPEA (741 mg, 5.7 mmol) in anhydrous DMF (3 ml) was added in portions p-nitrophenyl carbonate of zanamivir (1.67 g, 2.26 mmol, described in Example 109) over 20 minutes. The reaction was stirred for 1 hour, then directly purified by RPLC (30% to 90% acetonitrile/water, using 0.1% TFA as modifier). Yield 1.35 g, 74%. Ion found by LCMS: $[(M+2H)/2]^+=807.9$.

Step f.

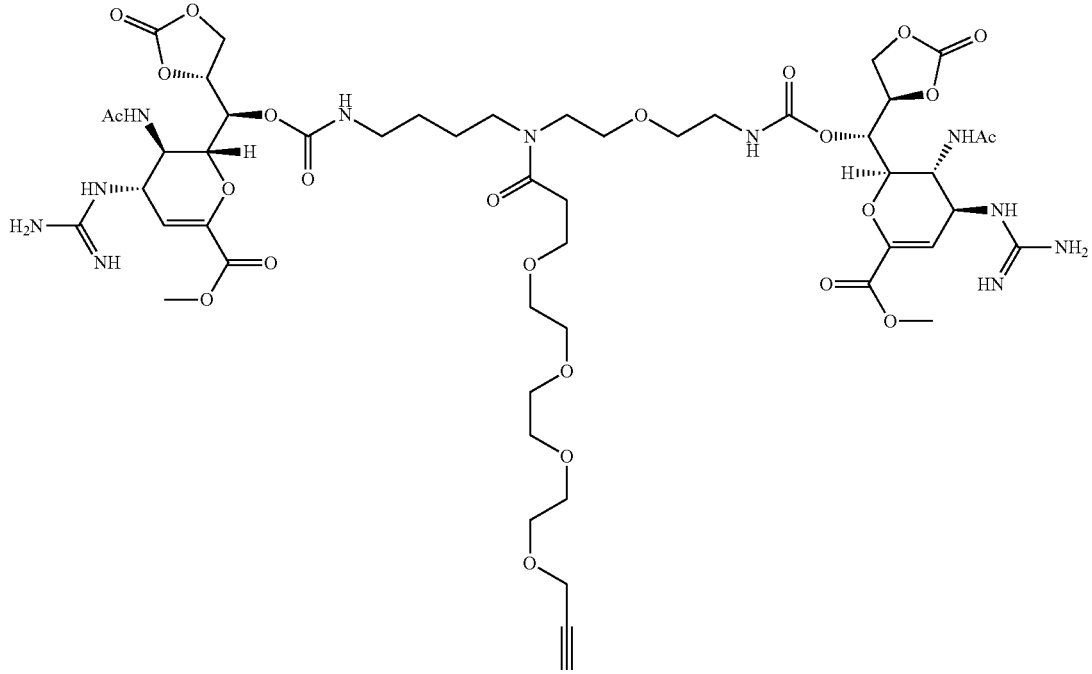 [SMILES: C#CCOCCOCCOCCOCCC(=O)N(CCCCNC(=O)O[C@@H]([C@@H]1OC(C(=O)OC)=C[C@H](NC(=N)N)[C@H]1NC(C)=O)[C@H]1COC(=O)O1)CCOCCNC(=O)O[C@@H]([C@@H]1OC(C(=O)OC)=C[C@H](NC(=N)N)[C@H]1NC(C)=O)[C@H]1COC(=O)O1]

The step-e product (1.35 g, 0.836 mmol) was dissolved in TFA (5 ml). The reaction was heated at 30° C. for 1 hour, it was directly purified by RPLC (0% to 35% acetonitrile/water, using 0.1% TFA as modifier). Yield 1.00 g, 82.9%. Ions found by LCMS: $[(M+2H)/2]^+=607.8$.

Step g.

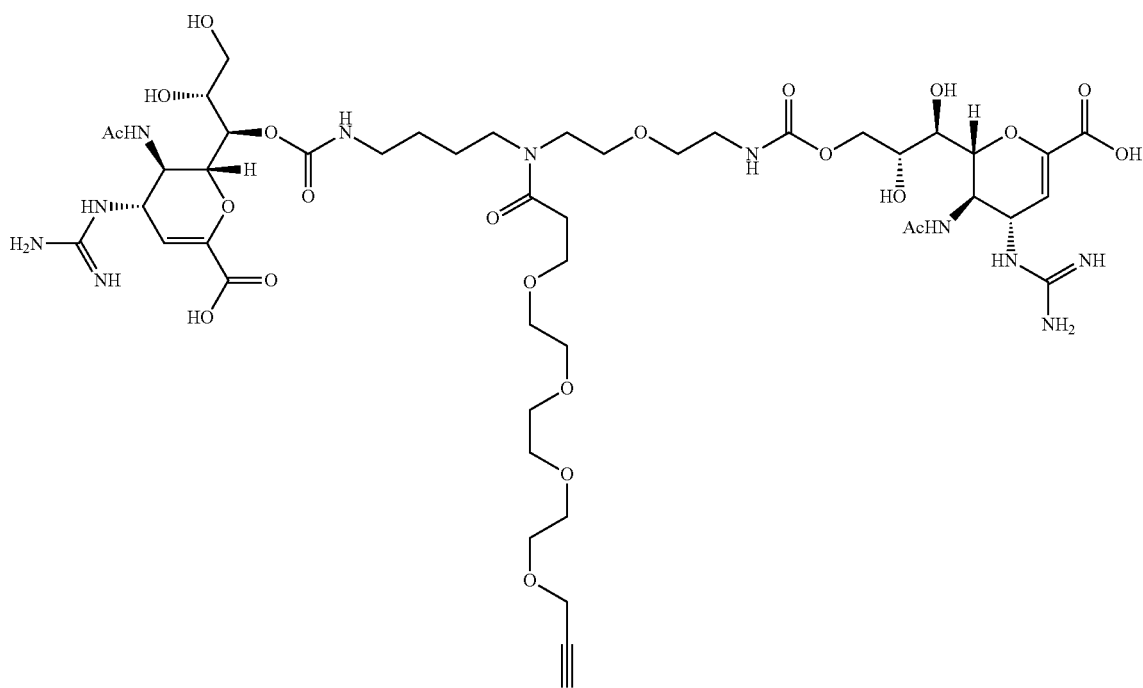 [SMILES: C#CCOCCOCCOCCOCCC(=O)N(CCCCNC(=O)O[C@@H]([C@@H]1OC(C(=O)O)=C[C@H](NC(=N)N)[C@H]1NC(C)=O)[C@H](O)CO)CCOCCNC(=O)OC[C@@H](O)[C@@H](O)[C@@H]1OC(C(=O)O)=C[C@H](NC(=N)N)[C@H]1NC(C)=O]

The step-f product (1.00 g, 0.693 mmol) was dissolved in MeOH (12 ml), then cooled in an ice-water bath. It was then treated with a solution of LiOH monohydrate (286 mg, 6.6 mmol) in water (9 ml). The resulting mixture was stirred overnight and then acidified by 4N HCl solution in dioxane (2 ml). After organic solvents were removed by rotary evaporation, the residue was purified by preparative HPLC (Isco ACCQ prep, Luna 5 µm C18(2) 100 Å LC column 100 mm×30 mm; Gradient: 0% acetonitrile/water for 2 min, then 0% to 15% acetonitrile/water over 12 min, then isocratic at 15% acetonitrile for 10 min, using 0.1% TFA). Yield 275.9 mg, 29.2%. Ions found by LCMS: $[(M+2H)/2]^+=567.8$, $[(M+3H)/3]^+=378.9$.

Example 111. Synthesis of Conjugate 31

A 15-ml sterile centrifuge tube was charged with sodium ascorbate (68.1 mg, 0.344 mmol), THPTA (14.9 mg, 0.0344 mmol), alkyne derivatized small molecule (17.5 mg, 0.00953 mmol, described in Example 110) and buffer PBS 7.4 (1 ml). After stirred by vortex to dissolve everything, Peg 4 azido Fc (50 mg, 0.0008588 mmol, described in Example 7 SEQ ID No. 18) was added followed by a solution of CuSO$_4$ (2.05 mg, 0.0129 mmol) in PBS (0.5 ml). The mixture was gently rotated for 20 hours then purified by affinity chromatography over a protein-A column, followed size exclusion chromatography. Maldi TOF analysis of the purified final product gave an average mass of 63586 Da (DAR=3.8). Yield 32.8 mg, 66% yield.

Example 112. Synthesis of Int-72

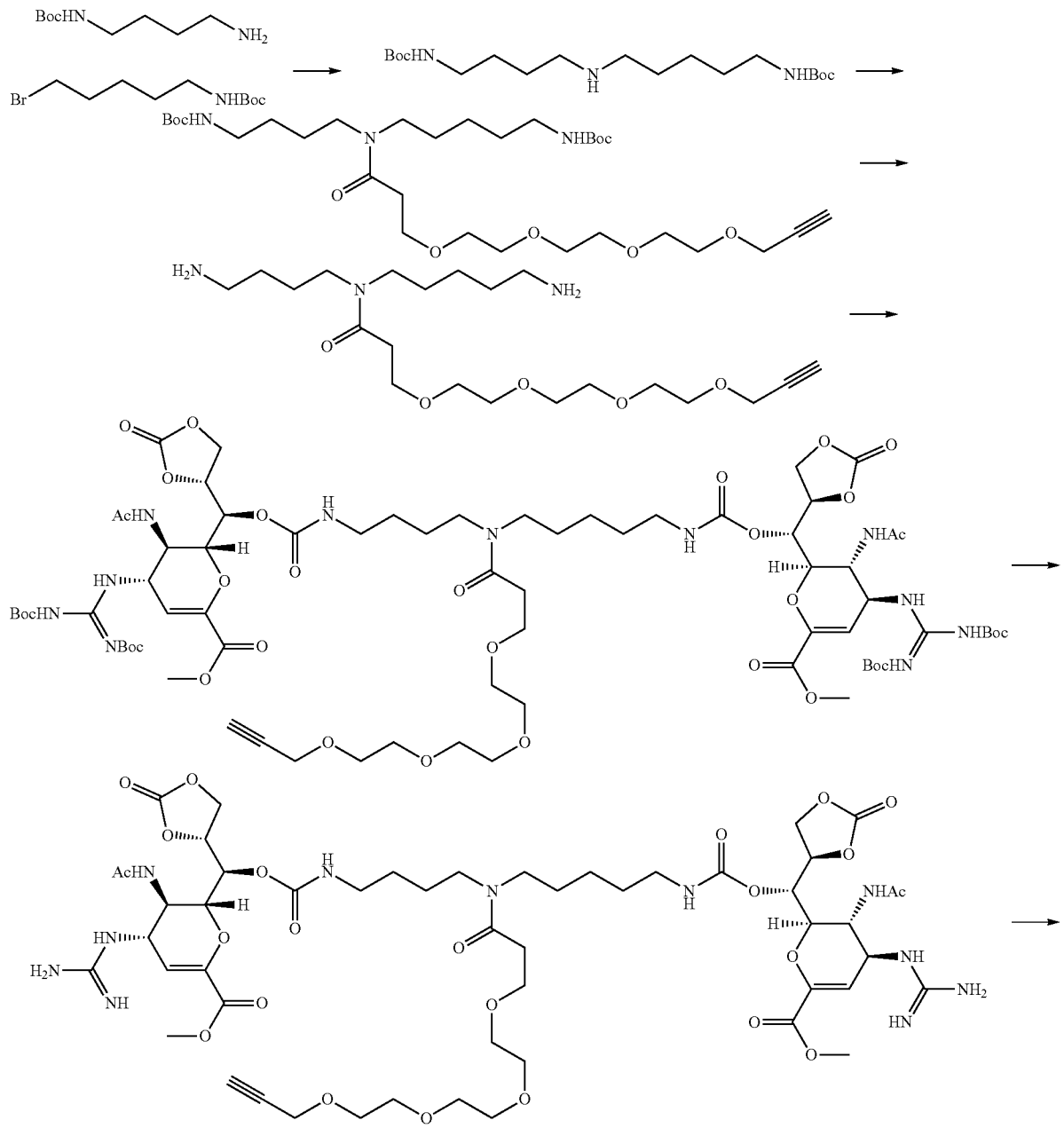

-continued

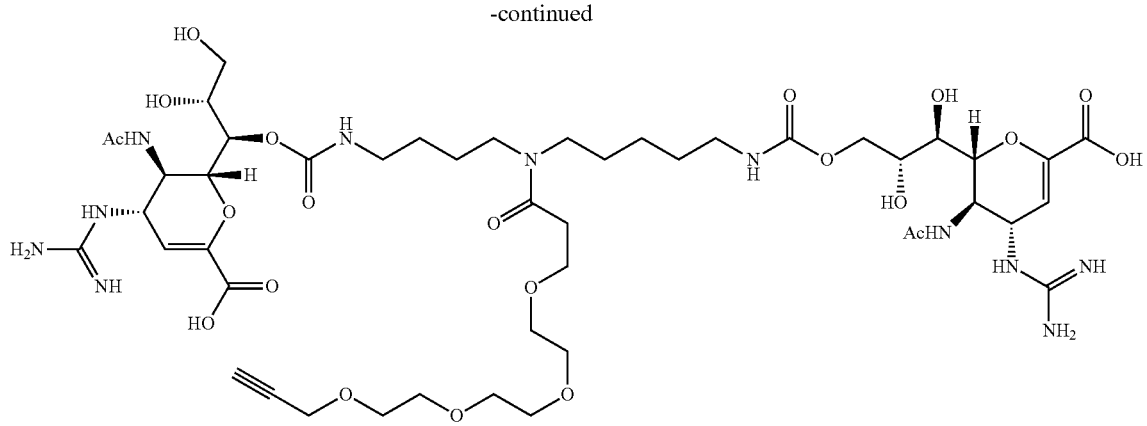

Step a.

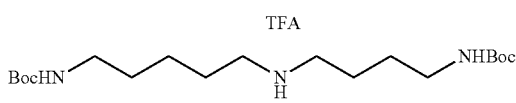

To a solution of N-Boc-1,4-diaminobutane (1.56 g, 8.28 mmol) in anhydrous DMF (7 ml) was added sodium carbonate (742 mg, 7 mmol) and 5-(Boc-amino)-1-pentylbromide (1.73 g, 6.5 mmol). The resulting mixture was heated at 50° C. for 24 hours. The salt was then filtered off, and the filtrate was concentrated by rotary evaporation. The residue was purified by RPLC (5% to 50% acetonitrile/water, using 0.1% TFA as modifier). Yield 2 g, 63.2%. Ion found by LCMS: [M+H]$^+$=374.4.

Step b.

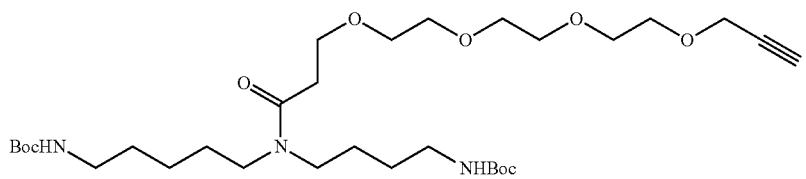 [SMILES: C#CCOCCOCCOCCOCCC(=O)N(CCCCCNC(=O)OC(C)(C)C)CCCCNC(=O)OC(C)(C)C]

To a solution of propargyl PEG-4 acid (1.3 g, 5 mmol) and HATU (2.1 g, 5.5 mmol) in anhydrous DMF (6 ml) was added DIPEA (1.3 g, 10 mmol). After 5 minutes, the reaction mixture was added to the step-a product (2 g, 4.1 mmol) and stirred for 1 hour. It was then directly purified by RPLC (5% to 80% acetonitrile/water, using 0.1% TFA as modifier). Yield 2.34 g, 95%. Ion found by LCMS: [M+H]$^+$=616.4, [M-Boc+H]=516.4.

Step c.

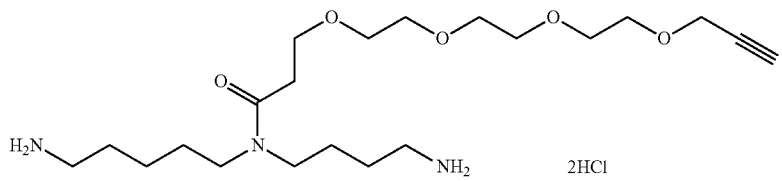 [SMILES: C#CCOCCOCCOCCOCCC(=O)N(CCCCN)CCCCCN ; "2HCl"]

The step-b product (2.34 g, 3.8 mmol) was dissolved in anhydrous THF (12 ml). 4N HCl solution in dioxane (10 ml) was added, and the reaction mixture was stirred overnight. It was then concentrated by rotary evaporation. The residue was re-dissolved in acetonitrile/water (1:1, ~16 ml), and the solution was lyophilized. The crude product was carried to the subsequent step without further purification. Yield 1.91 g, quantitative yield. Ion found by LCMS: [M+H]$^+$=416.4.

Step d.

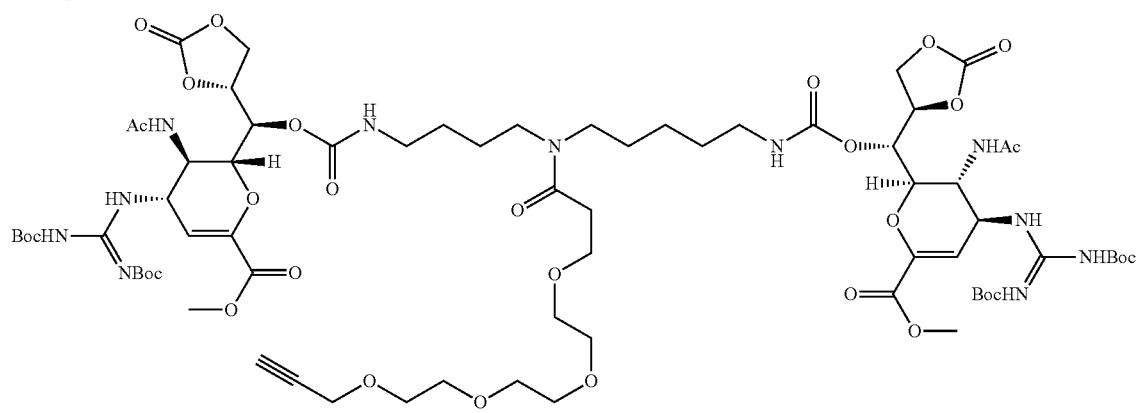

To a solution of p-nitrophenyl carbonate of zanamivir (2.25 g, 3.05 mmol, described in Example 109) in anhydrous DCM (3 ml) was added in-portions a mixture of the step-c product (610 mg, 1.249 mmol) and DIPEA (1.05 g, 8.1 mmol) in anhydrous DMF (4 ml) over 20 minutes. After stirring for 1 hour, the reaction mixture was concentrated and purified by RPLC (30% to 80% acetonitrile/water, using 0.1% TFA as modifier). Yield 1.73 g, 85.9%. Ion found by LCMS: $[(M+2H)/2]^+=806.8$, $[(M-Boc+2H)/2]^+=756.8$.

Step e.

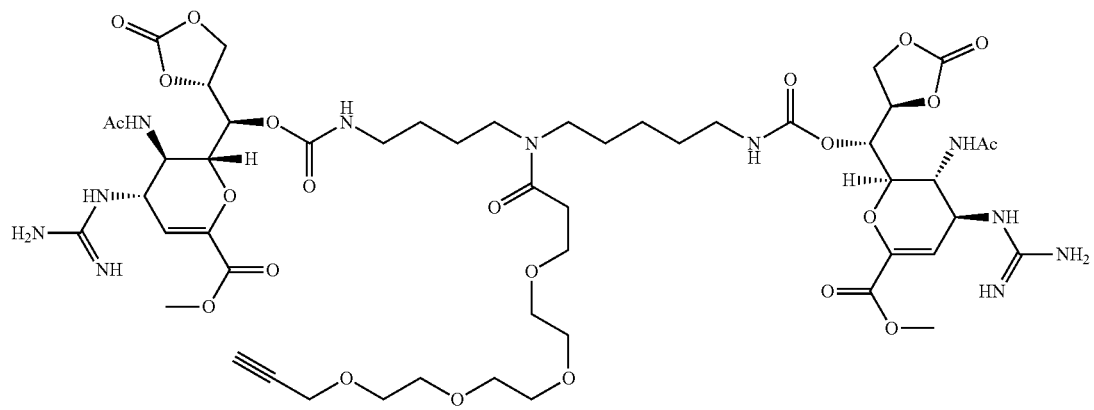 [SMILES: C#CCOCCOCCOCCOCCC(=O)N(CCCCCNC(=O)O[C@@H]([C@@H]1OC(C(=O)OC)=C[C@H](NC(=N)N)[C@H]1NC(C)=O)[C@H]1COC(=O)O1)CCCCNC(=O)O[C@@H]([C@@H]1OC(C(=O)OC)=C[C@H](NC(=N)N)[C@H]1NC(C)=O)[C@H]1COC(=O)O1]

The step-d product (1.73 g, 1.073 mmol) was dissolved in TFA (5 ml). After the solution was heated at 30° C. for 3 hours, it was directly purified by RPLC (0% to 35% acetonitrile/water, using 0.1% TFA as modifier). Yield 1.176 g, 76.1%. Ions found by LCMS: $[(M+2H)/2]^+=606.8$, $[(M+3H)/3]^+=405$.

Step f.

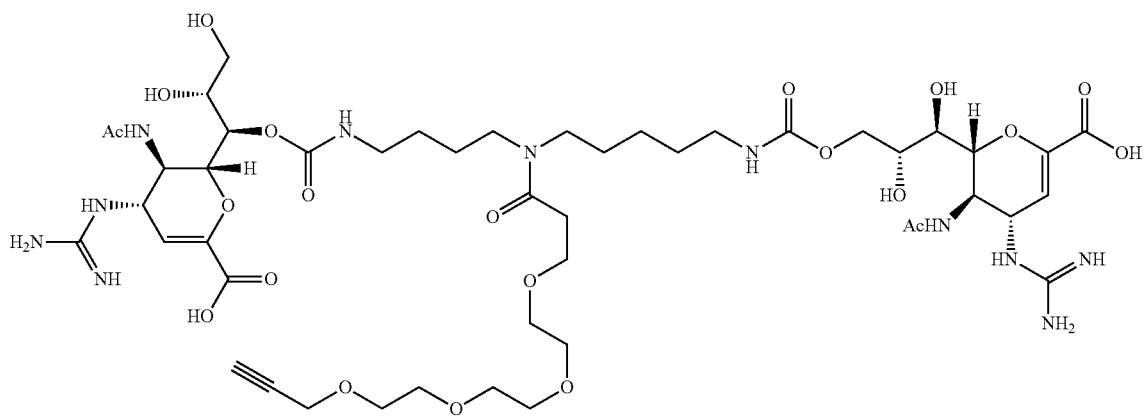 [SMILES: C#CCOCCOCCOCCOCCC(=O)N(CCCCCNC(=O)OC[C@@H](O)[C@@H](O)[C@@H]1OC(C(=O)O)=C[C@H](NC(=N)N)[C@H]1NC(C)=O)CCCCNC(=O)O[C@@H]([C@@H]1OC(C(=O)O)=C[C@H](NC(=N)N)[C@H]1NC(C)=O)[C@H](O)CO]

The step-e product (1.176 g, 0.817 mmol) was dissolved in MeOH (12 ml), and the solution was cooled in an ice-water bath. It was treated dropwise with a solution of LiOH monohydrate (344.4 mg, 8.2 mmol) in water (9 ml). The resulting mixture was stirred overnight and then acidified by 4N HCl solution in dioxane (2 ml). After organic solvents were removed by rotary evaporation, the residue was purified by preparative HPLC (Isco ACCQ prep, Luna 5 μm C18(2) 100 Å LC column 100 mm×30 mm; Gradient: 0% acetonitrile/water for 2 min, then 0% to 15% acetonitrile/water over 12 min, then isocratic at 15% acetonitrile for 10 min, using 0.1% TFA). Yield 108 mg, 9.7%. Ions found by LCMS: $[(M+2H)/2]^+=566.8$, $[(M+3H)/3]^+=378.2$.

Example 113. Synthesis of Conjugate 32

A 15-ml sterile centrifuge tube was charged with sodium ascorbate (68.1 mg, 0.344 mmol), THPTA (14.9 mg, 0.0344 mmol), product from Example 112, Int-72 (17.5 mg, 0.00953 mmol) and PBS 7.4 (1 ml). After stirring by vortex to dissolve everything, azido Fc (50 mg, 0.0008588 mmol, described in Example 7 with SEQ ID NO: 4) was added followed by a solution of $CuSO_4$ (2.05 mg, 0.0129 mmol) in PBS (0.5 ml). The mixture was rotated for 20 hours. It was purified by affinity chromatography over a protein A column, followed size exclusion chromatography. Maldi TOF analysis of the purified final product gave an average mass of 63588. Da (DAR=3.8). Yield 30.9 mg, 62% yield.

The nucleic acid construct encoding the Fc for conjugate 32 included a nucleic acid encoding the amino acid sequence of SEQ ID NO: 4, which includes a C-terminal lysine residue. Upon expression, the C-terminal lysine of the Fc of conjugate 32 is proteolytically cleaved, resulting in an Fc having the sequence lacking Lys447 (e.g., lacking a C-terminal lysine residue). The presence or absence of a C-terminal lysine does not alter the properties of the Fc or the corresponding conjugate.

Example 114. Synthesis of Int-73

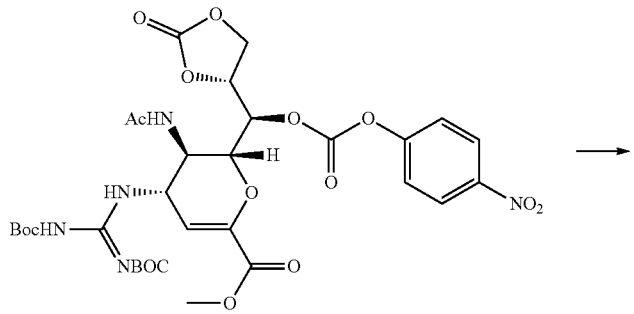

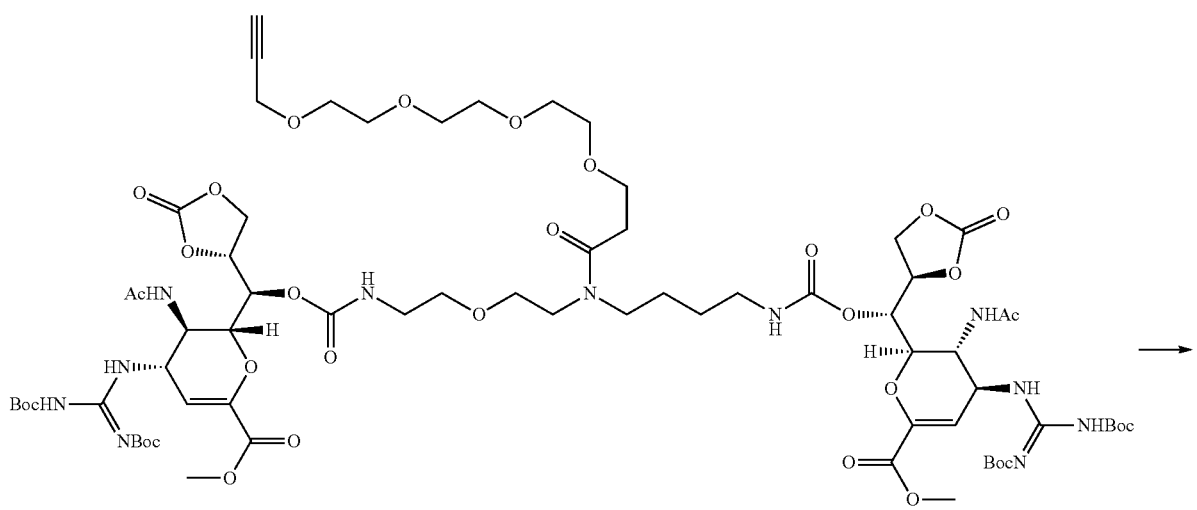

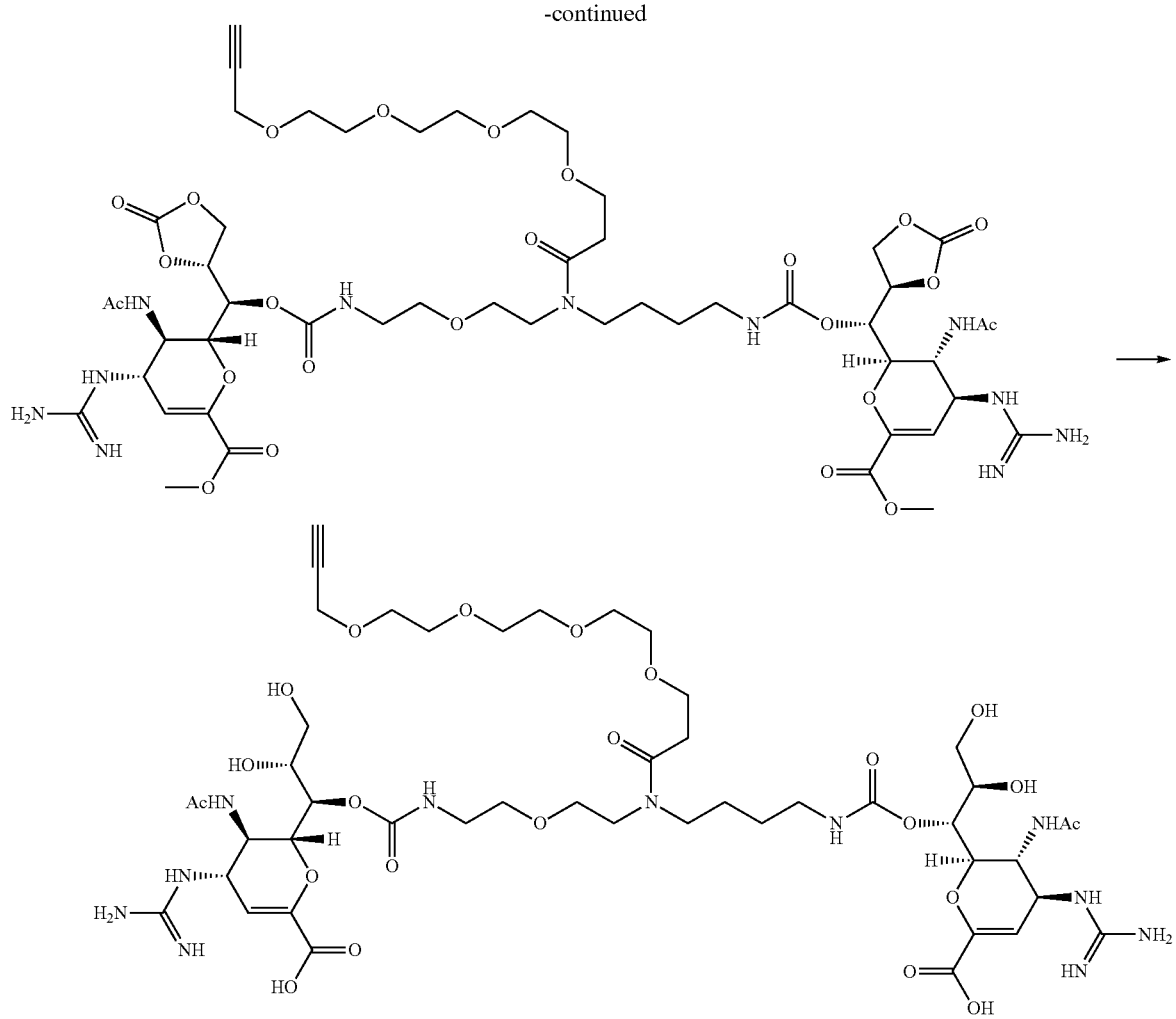

Step a.

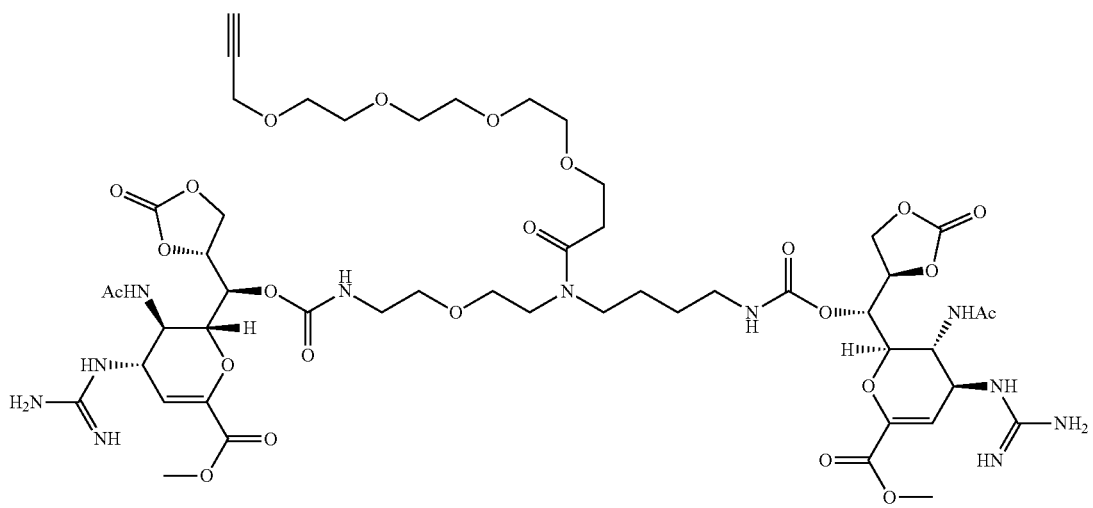

To a solution of the p-nitrophenyl carbonate of zanamivir (698.4 mg, 0.95 mmol, described in Example 109) in anhydrous DCM (2 ml) was added in-portions over 10 minutes a mixture of propargyl diamine central linker (209 mg, 0.426 mmol, described in Example 110) and DIPEA (330.8 mg, 2.56 mmol) in anhydrous DMF (2 ml). The reaction was stirred at room temperature for 1 hour. It was then concentrated and purified by RPLC (30% to 85% acetonitrile/water, no TFA modifier). Yield 531 mg, 69.2%. Ions found by LCMS: $[(M+2H)/2]^+=807.8$, $[(M-Boc+2H)/2]^+=757.8$.

Step b.

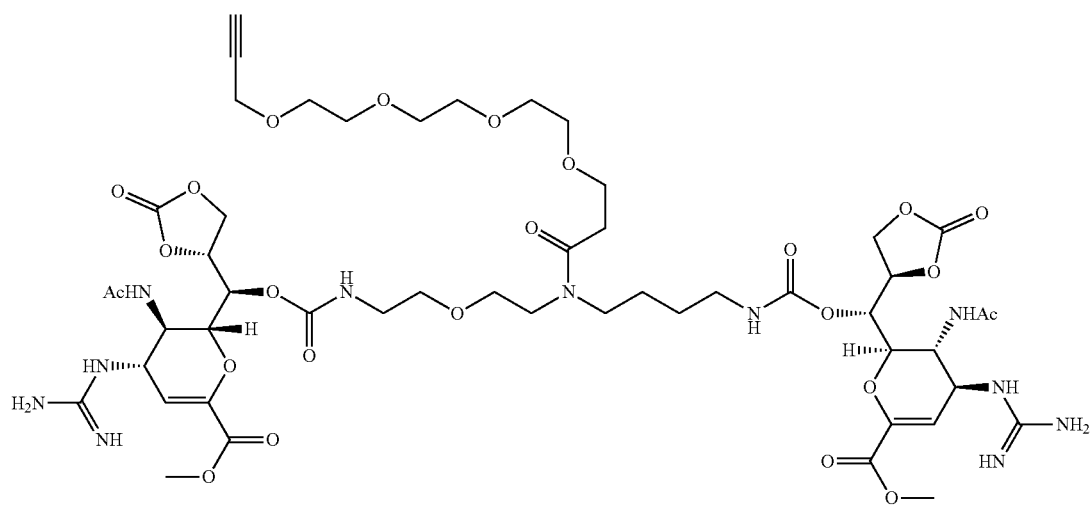 [SMILES: C#CCOCCOCCOCCOCCC(=O)N(CCCCNC(=O)O[C@@H]([C@@H]1OC(C(=O)OC)=C[C@H](NC(=N)N)[C@H]1NC(C)=O)[C@H]1COC(=O)O1)CCOCCNC(=O)O[C@@H]([C@@H]1OC(C(=O)OC)=C[C@H](NC(=N)N)[C@H]1NC(C)=O)[C@H]1COC(=O)O1]

The step-b product (531 mg, 0.329 mmol) was dissolved in DCM (1.5 ml) and TFA (1.5 ml), then stirred at 35° C. for 3 hours. It was concentrated and purified by RPLC (5% to 30% acetonitrile/water, no TFA modifier). Yield 387 mg, 97.1%. Ions found by LCMS: $[(M+2H)/2]^+=607.6$, $[(M+3H)/3]^+=405.4$.

Step c.

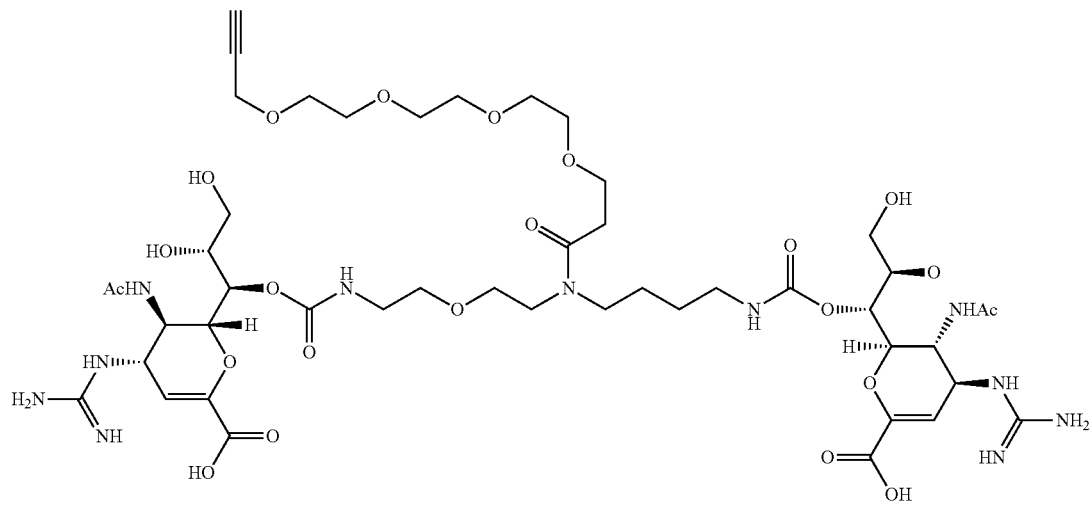 [SMILES: C#CCOCCOCCOCCOCCC(=O)N(CCCCNC(=O)O[C@@H]([C@@H]1OC(C(=O)O)=C[C@H](NC(=N)N)[C@H]1NC(C)=O)[C@H](O)CO)CCOCCNC(=O)O[C@@H]([C@@H]1OC(C(=O)O)=C[C@H](NC(=N)N)[C@H]1NC(C)=O)[C@H](O)CO]

The step-b product (121.4 mg, 0.1 mmol) was dissolved in 1.0 M NaCl solution (3 ml) and acetonitrile (1 ml). After the solution was cooled to −8° C. (salt/ice bath), 1.0 M NaOH (0.4 ml, 0.4 mmol) was added dropwise and the reaction was stirred at −14° C. to −8° C. for 6 hours. It was then neutralized with 4N HCl in dioxane solution (100 μl) and directly purified by preparative HPLC (Isco ACCQ prep, Luna μm C18(2) 100 Å LC column 100 mm×30 mm; Gradient: 0% acetonitrile/water for 2 min, then 0% to 17.8% acetonitrile/water over 12 min, then isocratic at 17.8% acetonitrile for 10 min, using 0.1% TFA). Yield 85.5 mg, 62.8%. Ions found by LCMS: $[(M+2H)/2]^+=567.8$, $[(M+3H)/3]^+=378.9$.

Example 115. Synthesis of Int-74
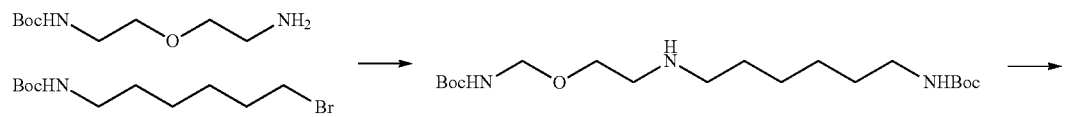
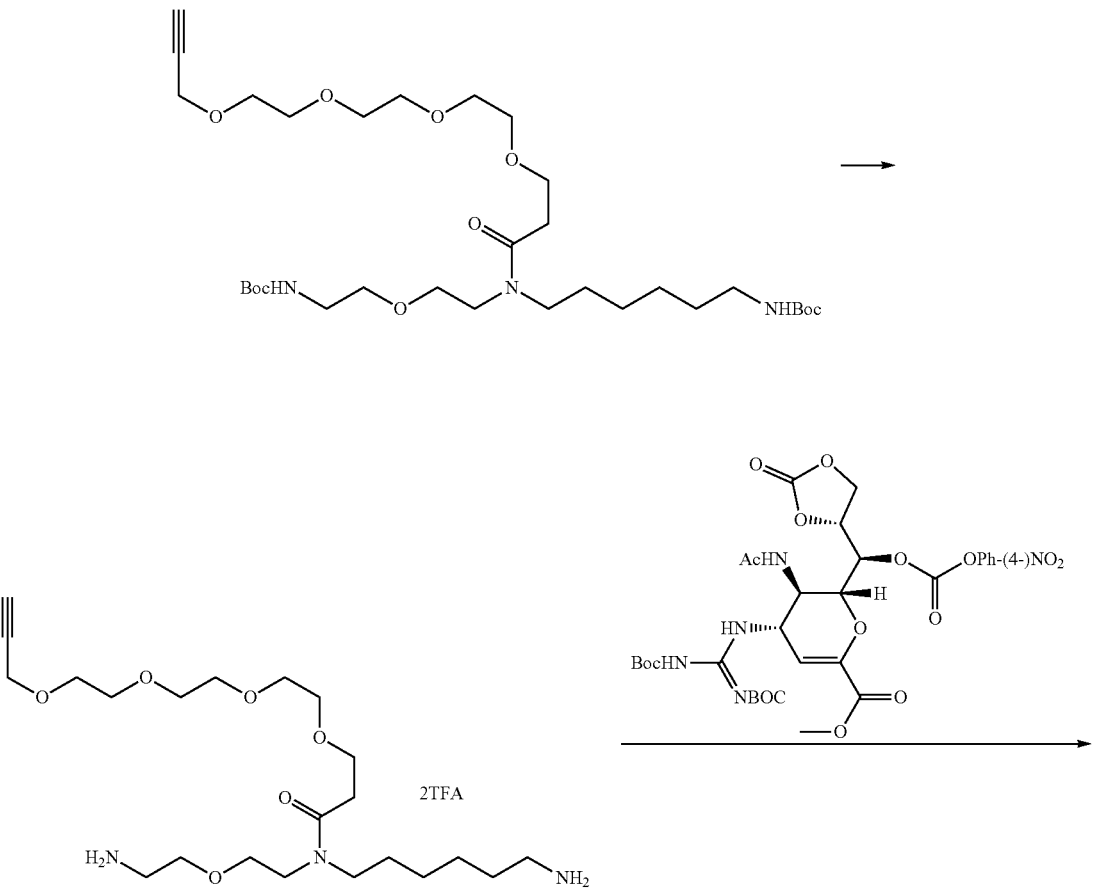
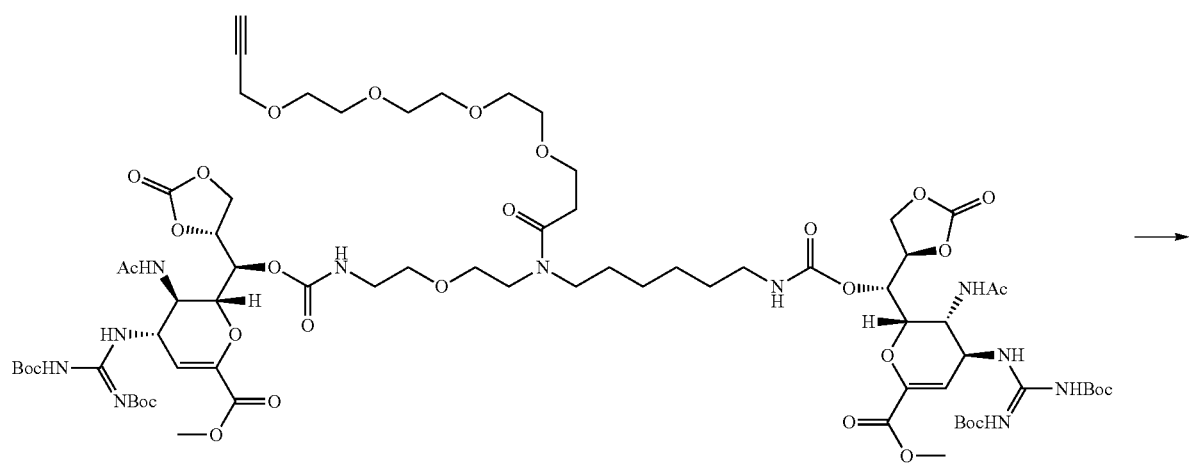

-continued

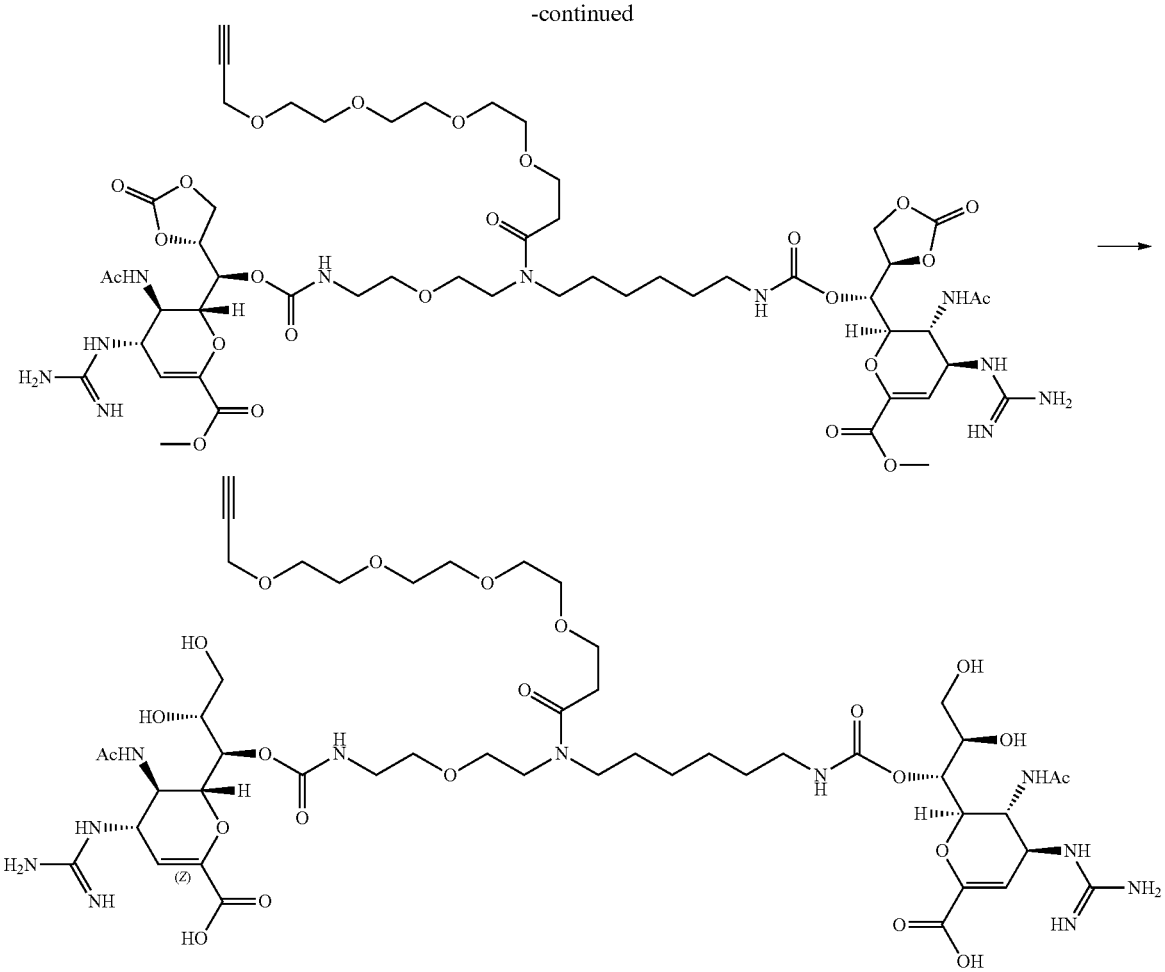

Step a.

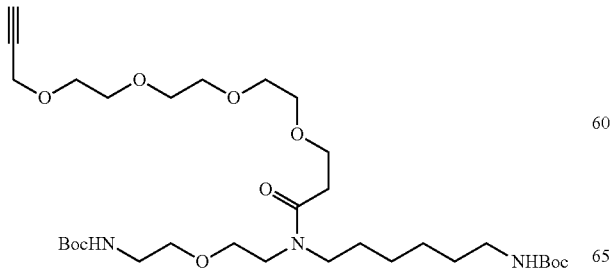

To a solution of N-Boc-2-(2-amino-ethoxy)ethylamine (1.2 g, 5 mmol) in anhydrous DMF (5 ml) was added sodium carbonate (691 mg, 5 mmol) and N-Boc-6-bromo-hexylamine (1.4 g, 5 mmol). The resulting mixture was heated at 70° C. for 24 hours. The salt was then filtered off, and the filtrate was concentrated by rotary evaporation. The residue was purified by RPLC (5% to 50% acetonitrile/water, using 0.1% TFA as modifier). Yield 444 mg, 22%. Ion found by LCMS: [M+H]$^+$=404.3.

Step b.

To a solution of propargyl PEG-4 acid (342.6 mg, 1.32 mmol) and HATU (601.5 mg, 1.58 mmol) in anhydrous DMF (2 ml) was added DIPEA (258 mg, 2 mmol). After 5 minutes, the reaction mixture was added into the step-a product (444.3 mg, 0.858 mmol) and stirred for 1 hour. It was then directly purified by RPLC (5% to 80% acetonitrile/water, using 0.1% TFA as modifier). Yield 297.1 mg, 53.6%. Ion found by LCMS: [M+H]$^+$=646.2, [M-Boc+H]$^+$=546.2.

Step c.

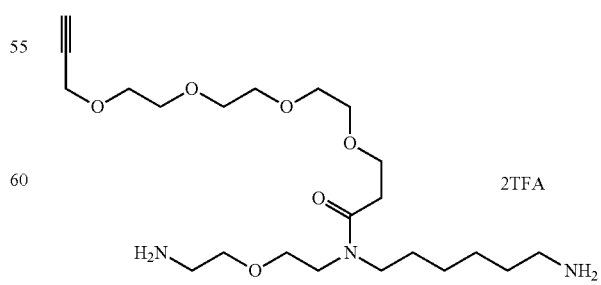

The step-b product (297.1 mg, 0.46 mmol) was dissolved in anhydrous THF (2 ml). 4N HCl solution in dioxane (4 ml)

was added, and the reaction mixture was stirred overnight. It was then concentrated by rotary evaporation and purified by preparative HPLC (5% to 50% acetonitrile/water, using 0.1% TFA as modifier). Yield 239.6 mg, 77.3%. Ion found by LCMS: [M+H]$^+$=446.2.

Step d.

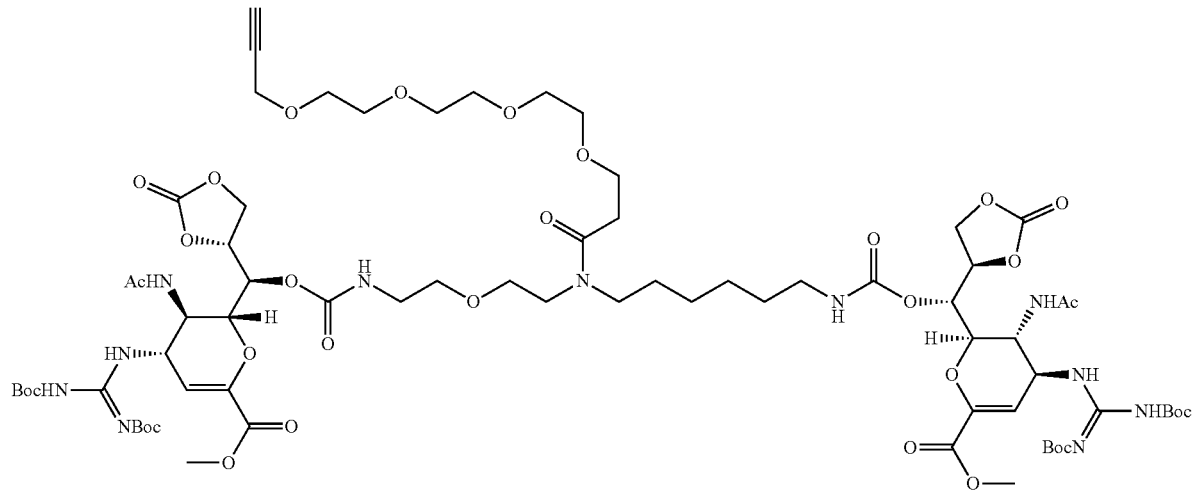

To a solution of the p-nitrophenyl carbonate of zanamivir (523.8 mg, 0.71 mmol, described in Example 109) in anhydrous DCM (2 ml) was added in portions over 10 minutes a mixture of the step-c product (239.6 mg, 0.356 mmol) and DIPEA (245.5 mg, 1.9 mmol) in anhydrous DMF (2 ml). The reaction was stirred at room temperature for 1 hour. It was then concentrated and purified by RPLC (30% to 85% acetonitrile/water, no TFA modifier). Yield 553 mg, 96.5%. Ions found by LCMS: [(M+2H)/2]$^+$=821.8, [(M-Boc+2H)/2]$^+$=771.8.

Step e.

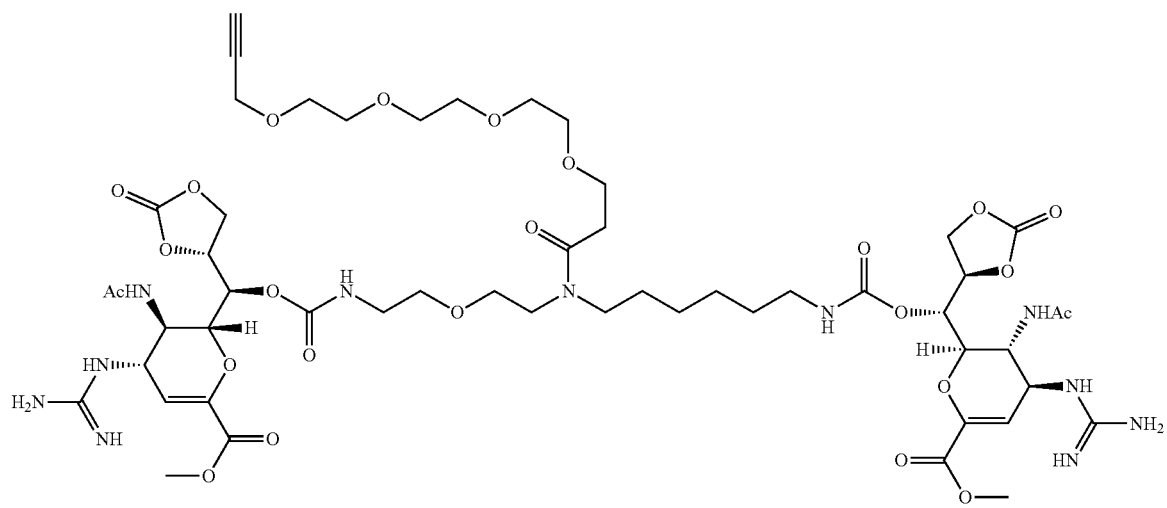 [SMILES: C#CCOCCOCCOCCOCCC(=O)N(CCCCCCNC(=O)O[C@@H]([C@@H]1OC(C(=O)OC)=C[C@H](NC(=N)N)[C@H]1NC(C)=O)[C@H]1COC(=O)O1)CCOCCNC(=O)O[C@@H]([C@@H]1OC(C(=O)OC)=C[C@H](NC(=N)N)[C@H]1NC(C)=O)[C@H]1COC(=O)O1]

The step-d product (553 mg, 0.343 mmol) was dissolved in DCM (1.5 ml) and TFA (1.5 ml), then stirred at 35° C. for 3 hours. It was concentrated and purified by RPLC (5% to 30% acetonitrile/water, no TFA modifier). Yield 424.6 mg, 99.6%. Ions found by LCMS: [(M+2H)/2]$^+$=621.6, [(M+3H)/3]$^+$=415.0.

Step f.

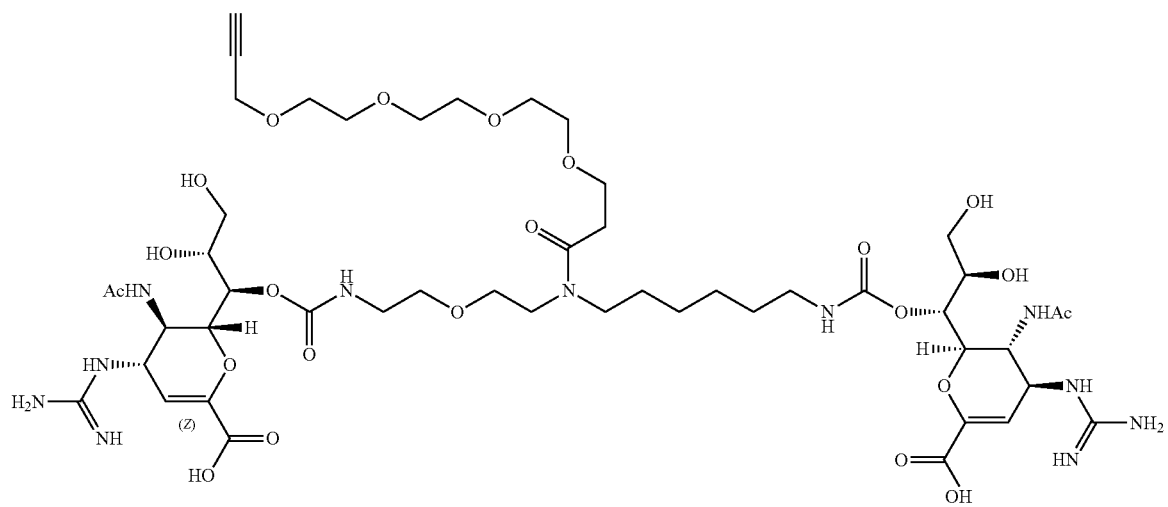

The step-e product (424.6 mg, 0342 mmol) was dissolved in 1.0 M NaCl solution (4 ml) and acetonitrile (4 ml). After the solution was cooled to −11° C. (salt/ice bath), 1.0 M NaOH (1.53 ml, 1.53 mmol) was added dropwise and the reaction was stirred at −14° C. to −8° C. for 6 hours. It was then quenched with 4N HCl in dioxane solution (375 μl) and directly purified by preparative HPLC (Isco ACCQ prep, Luna 5 μm C18(2) 100 Å $L^C$ column 100 mm×30 mm; Gradient: 0% acetonitrile/water for 2 min, then 0% to 20.9% acetonitrile/water over 13.6 min, then isocratic at 20.9% acetonitrile for 10 min, using 0.1% TFA). Yield 439 mg, 92.3%. Ions found by LCMS: $[(M+2H)/2]^+=581.8$, $[(M+3H)/3]^+=388.2$.

Example 116. Synthesis of Int-75

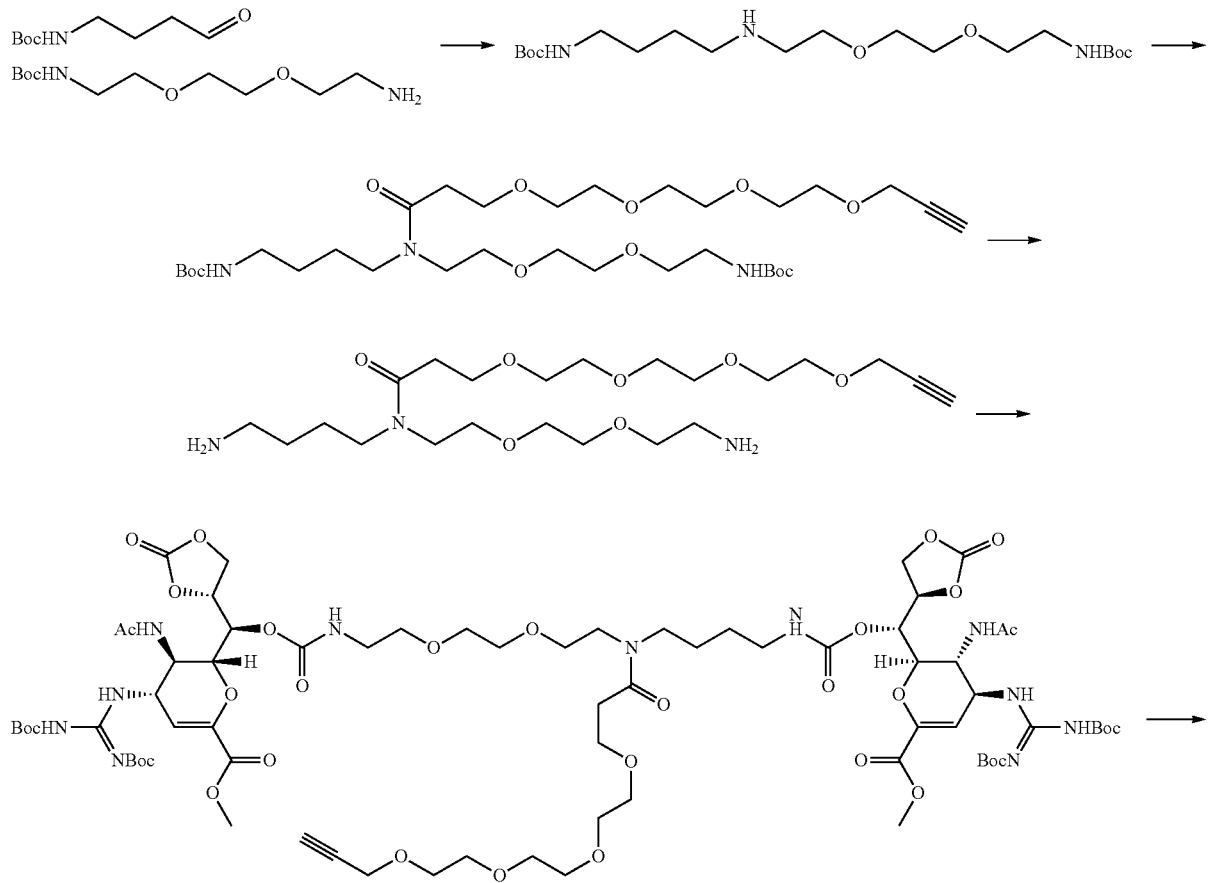

-continued

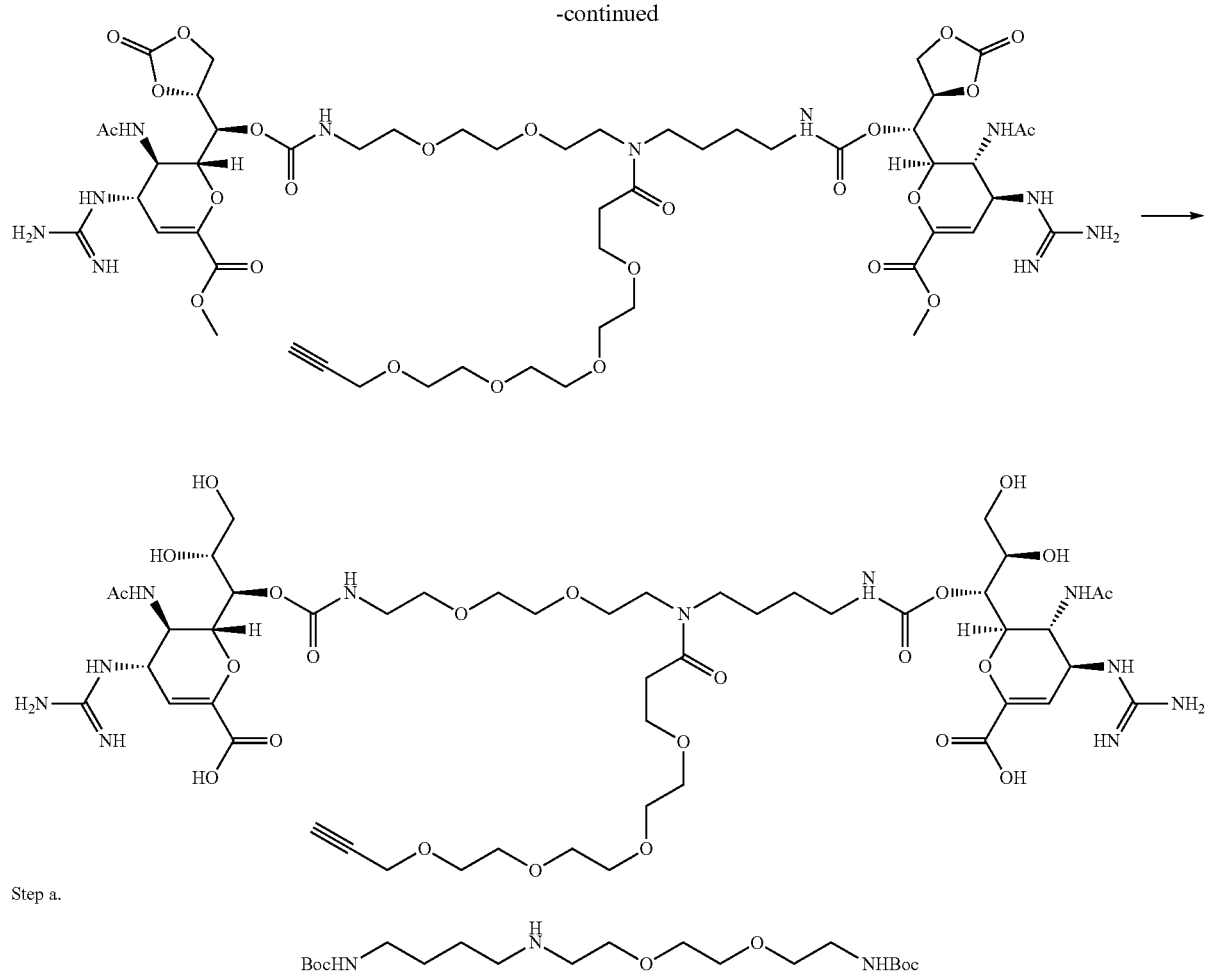

Step a.

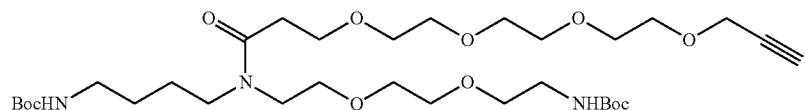 [SMILES: C#CCOCCOCCOCCOCCC(=O)N(CCCCNC(=O)OC(C)(C)C)CCOCCOCCNC(=O)OC(C)(C)C]

A mixture of tert-butyl (4-oxobutyl) carbamate (850 mg, 4.54 mg) and tert-butyl N-{2-[2-(2-aminoethoxy) ethoxy] ethyl} carbamate (1.99 g, 8 mmol) was dissolved in DCM (30 ml) and dried over $Na_2SO_4$. After filtering and concentrating, the residue was redissolved in anhydrous DCM (20 ml). Acetic acid (641 mg, 11 mmol) was added, followed by sodium triacetoxyborohydride (3.4 g, 16 mmol) in portions over 1 hour. The reaction mixture was stirred overnight, then quenched with AcOH (3 ml) and MeOH (10 ml). The mixture was filtered, and the filtrate was concentrated by rotary evaporation and purified by RPLC (5% to 45% acetonitrile and water). Yield 618 mg, 32.5%. Ion found by LCMS: $[M+H]^+$=420.4.

Step b.

This compound was prepared analogously to the step-b product of Example 115. Ions found by LCMS: $[M+H]^+$=662.4, $[M-Boc+H]^+$=562.4.

Step c.
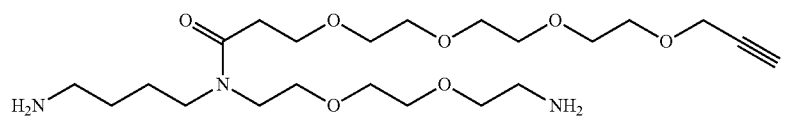 [SMILES: C#CCOCCOCCOCCOCCC(=O)N(CCCCN)CCOCCOCCN]
This compound was prepared analogously to the step-c product of Example 115. Ion found by LCMS: $[M+H]^+=462.4$.
Step d.
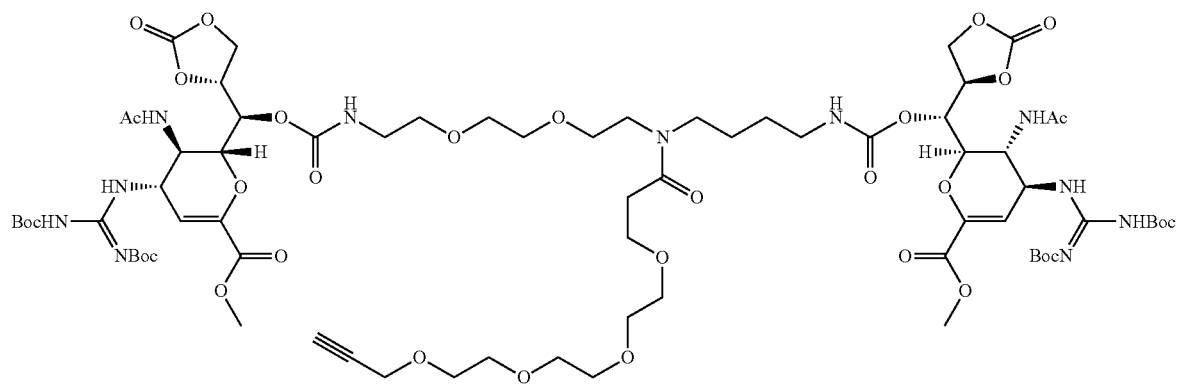
This compound was prepared analogously to the step-d product of Example 115. Ions found by LCMS: $[(M+2H)/2]^+=829.8$, $[(M-Boc+2H)/2]^+=779.8$.
Step e.
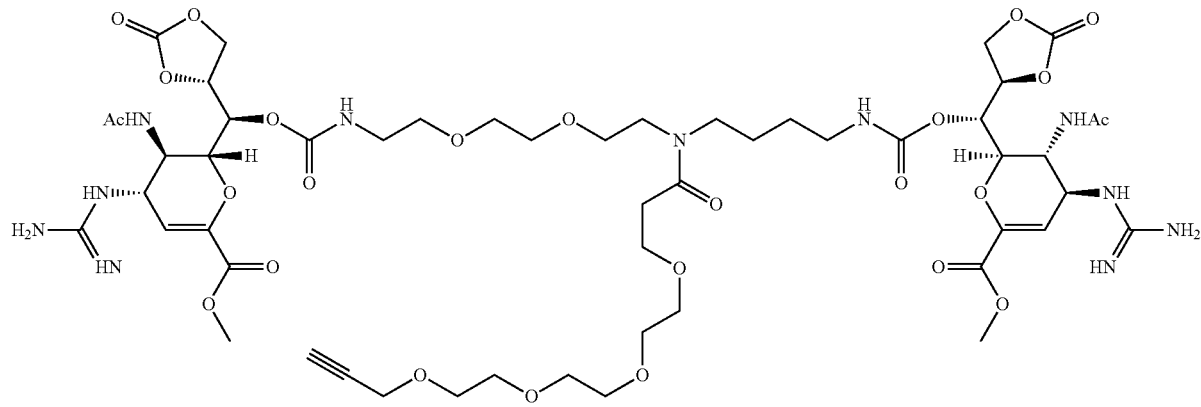 [SMILES: C#CCOCCOCCOCCOCCC(=O)N(CCCCNC(=O)O[C@@H]([C@@H]1OC(C(=O)OC)=C[C@H](NC(=N)N)[C@H]1NC(C)=O)[C@H]1COC(=O)O1)CCOCCOCCNC(=O)O[C@@H]([C@@H]1OC(C(=O)OC)=C[C@H](NC(=N)N)[C@H]1NC(C)=O)[C@H]1COC(=O)O1]
This compound was prepared analogously to the step-e product of Example 115. Ions found by LCMS: $[(M+2H)/2]^+=629.8$, $[(M+3H)/3]^+=420.2$.

Step f.
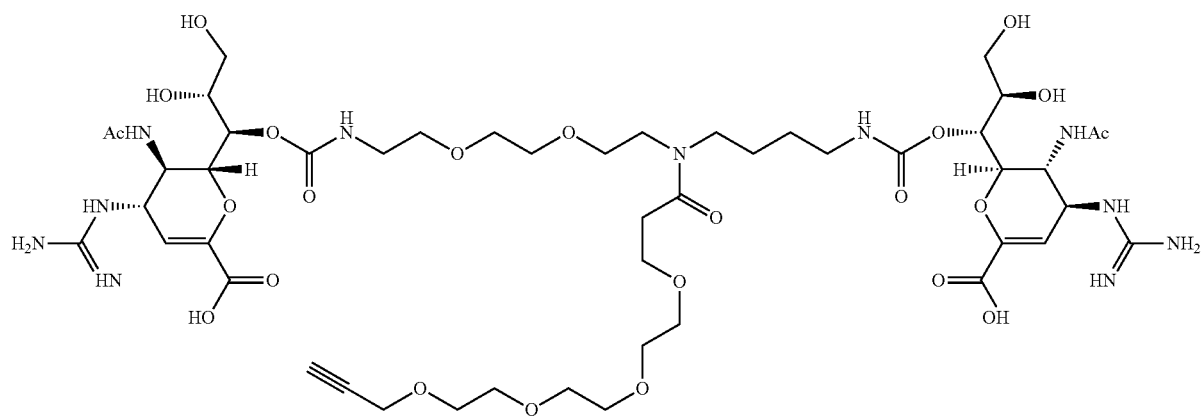 [SMILES: C#CCOCCOCCOCCOCCC(=O)N(CCCCNC(=O)O[C@@H]([C@@H]1OC(C(=O)O)=C[C@H](NC(=N)N)[C@H]1NC(C)=O)[C@H](O)CO)CCOCCOCCNC(=O)O[C@@H]([C@@H]1OC(C(=O)O)=C[C@H](NC(=N)N)[C@H]1NC(C)=O)[C@H](O)CO]
This compound was prepared analogously to the step-f product of Example 115. Ions found by LCMS: [(M+2H)/2]$^+$=598.8, [(M+3H)/3]$^+$=393.6.
Example 117. Synthesis of Int-76
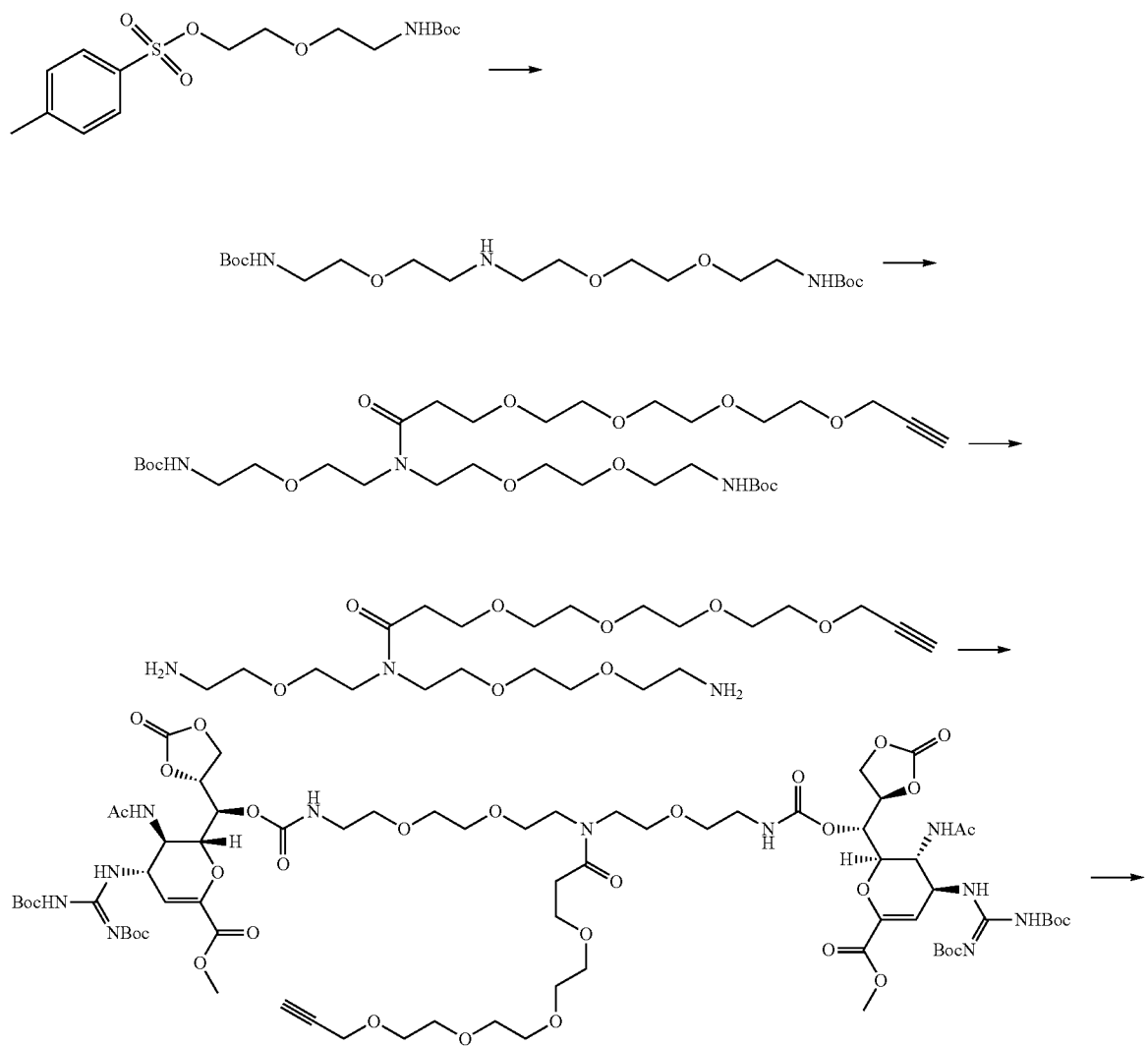

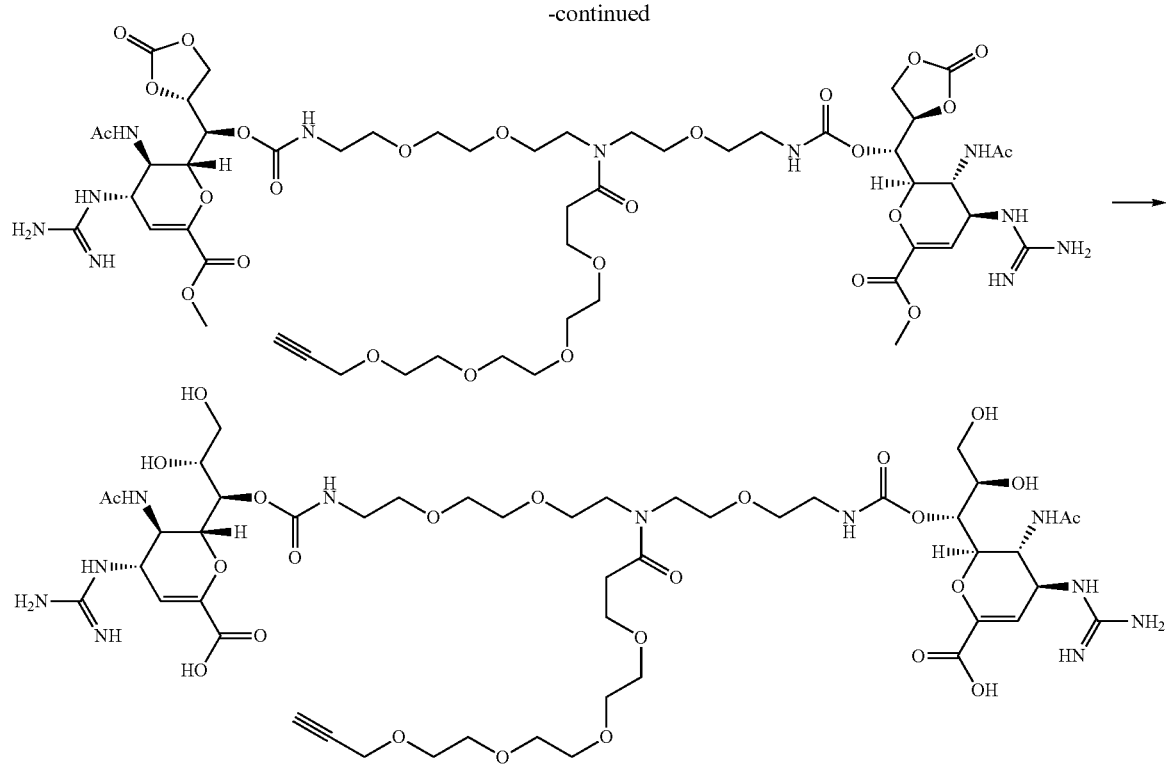

Step a.

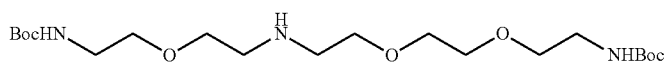

To a solution of the N-Boc-peg-1 tosylate (1.54 g, 4.28 mmol, described in Example 110) in anhydrous THF (8 ml) was added tert-butyl N-2{2-[2-(2-aminoethoxy) ethoxy] ethyl} carbamate (1.59 g, 6.42 mmol) and sodium carbonate (453.7 mg, 4.28 mmol). The resulting mixture was heated at 50° C. for 24 hours. The solid was filtered and washed with acetonitrile. The filtrate was concentrated and purified by RPLC (100 g, 5 to 90% acetonitrile and water). Yield 1.15 g, 61.7%. Ion found by LCMS: [M+H]$^+$=436.4.

Step b.

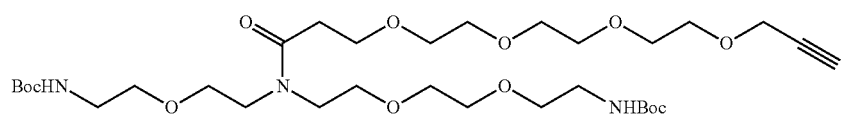 [SMILES: C#CCOCCOCCOCCOCCC(=O)N(CCOCCNC(=O)OC(C)(C)C)CCOCCOCCNC(=O)OC(C)(C)C]

This compound was prepared analogously to the product from step-b of Example 115. Ions found by LCMS: [M+H]$^+$=678.2, [M-Boc+H]$^+$=578.2.

Step c.

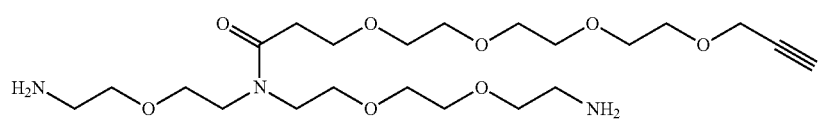 [SMILES: C#CCOCCOCCOCCOCCC(=O)N(CCOCCN)CCOCCOCCN]

This compound was prepared analogously to the product of step-c of Example 115. Ion found by LCMS: [M+H]$^+$=478.2.

Step d.

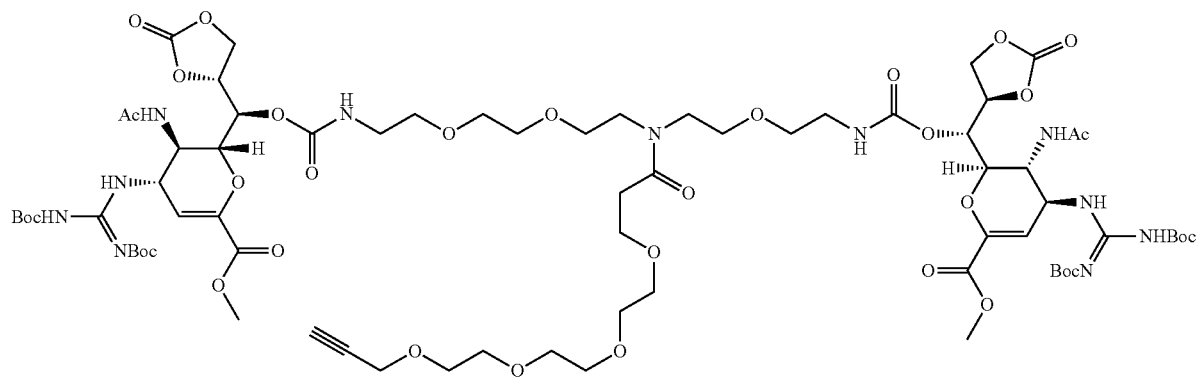

This compound was prepared analogously to the product from step-d of Example 115. Ions found by LCMS: [(M+2H)/2]$^+$=837.6, [(M-Boc+2H)/2]$^+$=767.8.

Step e.

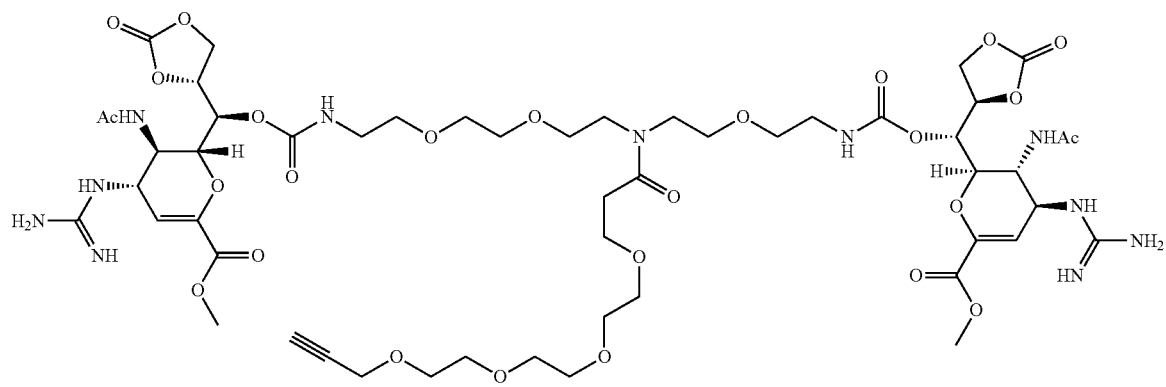 [SMILES: C#CCOCCOCCOCCOCCC(=O)N(CCOCCNC(=O)O[C@@H]([C@@H]1OC(C(=O)OC)=C[C@H](NC(=N)N)[C@H]1NC(C)=O)[C@H]1COC(=O)O1)CCOCCOCCNC(=O)O[C@@H]([C@@H]1OC(C(=O)OC)=C[C@H](NC(=N)N)[C@H]1NC(C)=O)[C@H]1COC(=O)O1]

This compound was prepared analogously to the product from step-e of Example 115. Ions found by LCMS: [(M+2H)/2]$^+$=637.5, [(M+3H)/3]$^+$=425.6.

Step f.

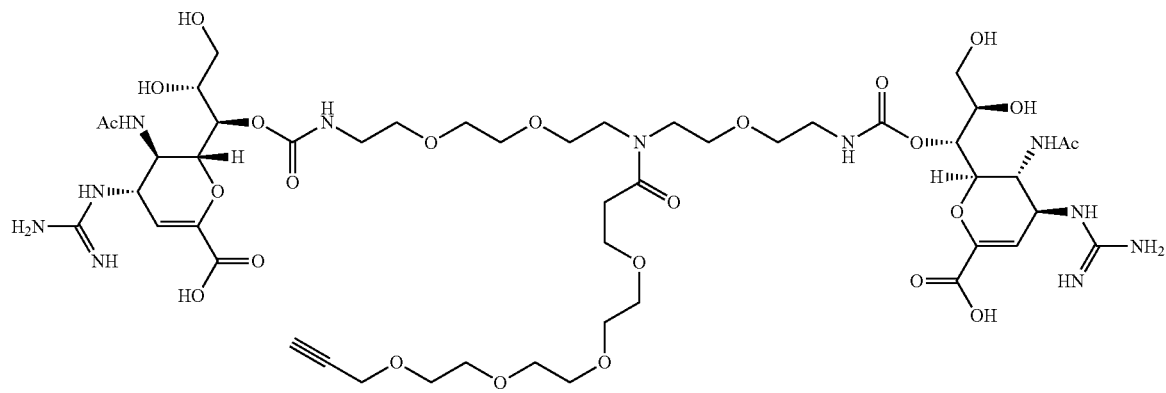 [SMILES: C#CCOCCOCCOCCOCCC(=O)N(CCOCCNC(=O)O[C@@H]([C@@H]1OC(C(=O)O)=C[C@H](NC(=N)N)[C@H]1NC(C)=O)[C@H](O)CO)CCOCCOCCNC(=O)O[C@@H]([C@@H]1OC(C(=O)O)=C[C@H](NC(=N)N)[C@H]1NC(C)=O)[C@H](O)CO]

This compound was prepared analogously to the product from step-f of Example 115. Ions found by LCMS: [(M+2H)/2]$^+$=597.8, [(M+3H)/3]$^+$=399.0.

Example 118 Synthesis of Int-67
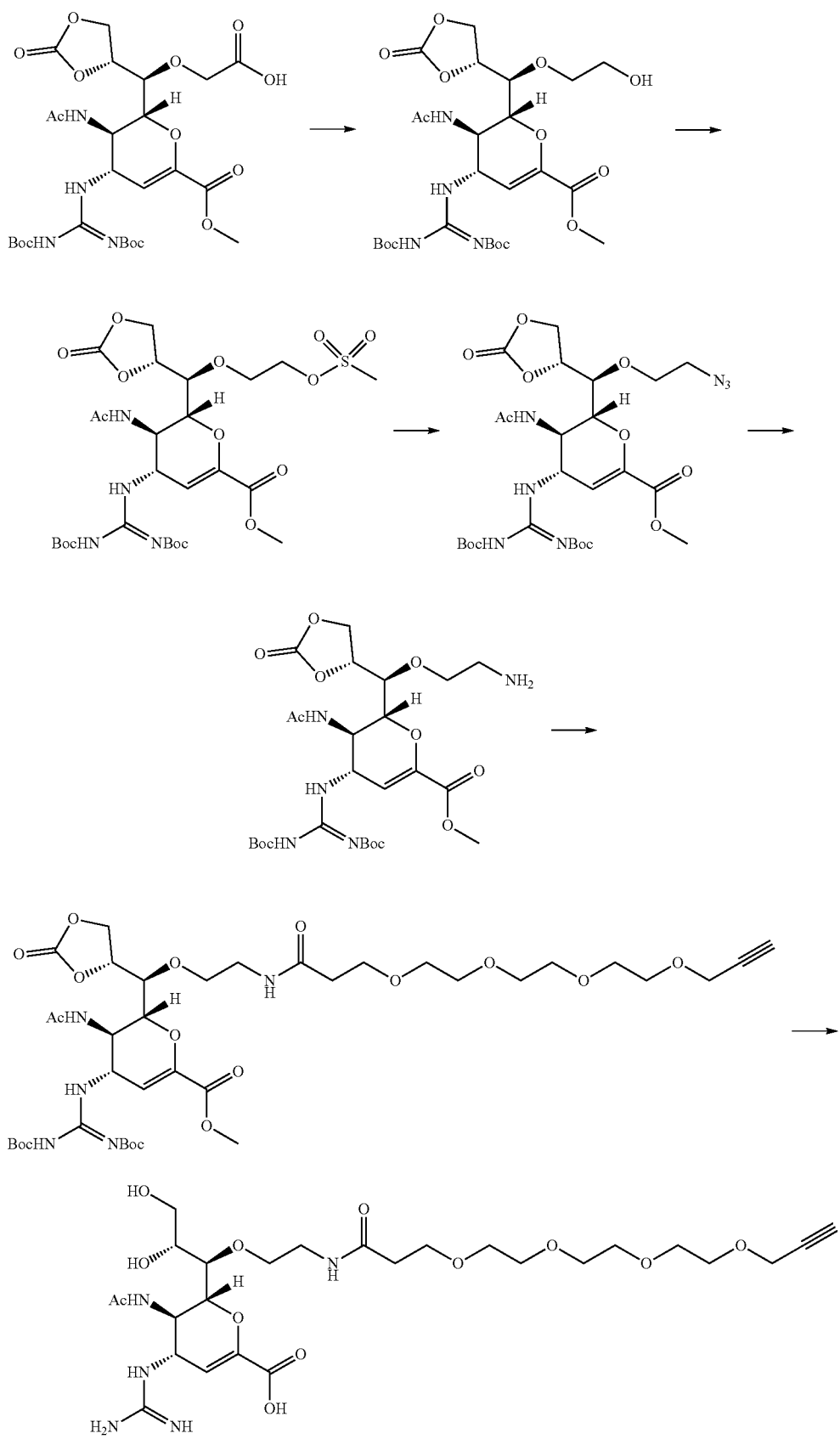

Step a.

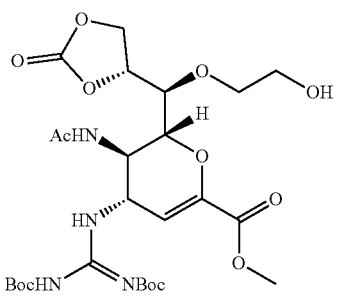

Previously prepared ether zanamivir acid starting material (0.90 g, 1.43 mmol, described in Example 22) and N-methyl morpholine (0.23 mL, 2.14 mmol) were dissolved in THF (35 mL) and cooled to 0° C. (ice water bath) under an atmosphere of nitrogen. Isobutyl chloroformate (0.24 mL, 1.85 mmol, in 2 mL DCM) was added dropwise, by way of syringe over a 5 minute period. The mixture was stirred at 0° C. for 30 minutes then 15 min at ambient temperature, and then cooled to 0° C., where sodium borohydride (540 mg, 14.3 mmol, dissolved in 5 mL of methanol) was added, dropwise over 5 minutes. The reaction was stirred for 15 minutes at which point all starting material had been consumed (by LC/MS). A few drops (~1 mL) of glacial acetic acid was added to acidify the mixture (pH~5). The mixture was diluted with ethyl acetate and water and extracted into ethyl acetate (3×). The organic layer was washed with brine, and the organic extracts were dried over sodium sulfate, and concentrated on a rotary evaporator. The crude material was purified by silica gel chromatography, dried onto celite first, and then eluted with 0%-10% methanol in DCM over 30 min. Yield 0.66 g, 75%. Ion found by LCMS: [M+H]$^+$= 617.2.

Step b.

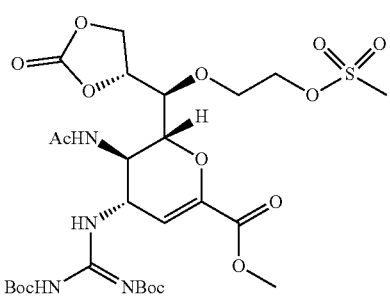

To a stirring mixture of product from the previous step (0.66 g, 1.10 mmol), in 20 mL DCM, was added triethylamine (0.30 mL, 1.3 mmol). The mixture was cooled to 0° C. (ice-water bath) under an atmosphere of nitrogen then treated with mesyl chloride (0.15 g, 1.3 mmol), dropwise over 5 minutes by way of syringe. The ice bath was removed and the reaction was stirred for 45 minutes. The reaction was quenched with saturated aqueous sodium bicarbonate, then extracted into DCM (3×). The combined organic extracts were washed with brine, dried over sodium sulfate and concentrated on the rotary evaporator. Yield 0.74 g, 99%. Ion found by LCMS: [M+H]$^+$=695.2. The intermediate was taken to the next step without purification.

Step c.

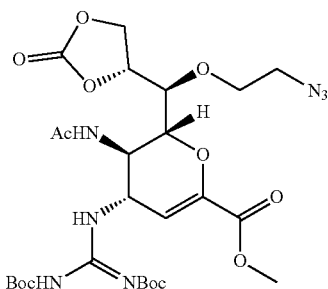

Mesylate from the previous step (0.74 g, 1.1 mmol) was stirred in DMF (5 mL) at 80° C. with 3 eq of sodium azide (0.21 g, 3.3 mmol) for 5 hours. The mixture was diluted with water, extracted into DCM (3×). The combined organic extracts were washed with brine, dried over sodium sulfate and concentrated. Yield 0.67 g, 95%. Ion found by LCMS: [M+H]$^+$=642.4. The azide was taken to the next step without purification.

Step d.

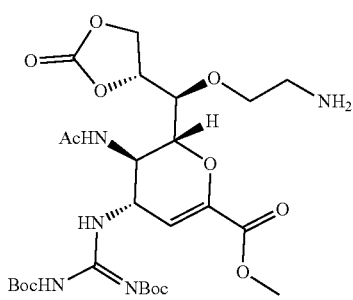

Azide from the previous step (0.67 g, 1.04 mmol) was stirred in methanol (20 mL) in the presence of Lindlar catalyst (300 mg) under 1 atmosphere of hydrogen gas for 12 hours. The mixture was filtered through celite and concentrated to afford the title compound as a clear oil. The amine was taken to the next step without purification. Yield 0.37 g, 54%, 3 steps. Ion found by LCMS: [M+H]$^+$=616.2.

Step e.

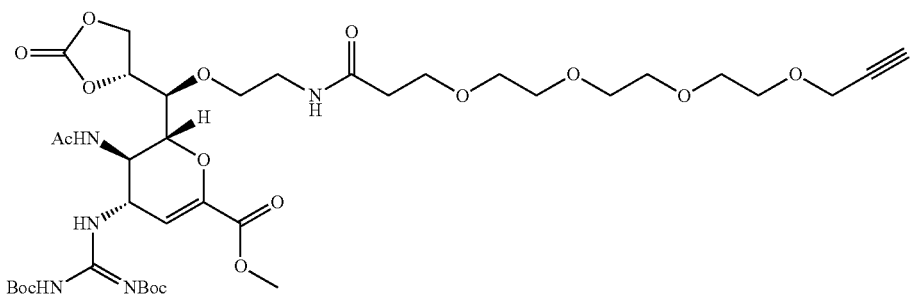

EDC (150 mg, 0.78 mmol) was added to a stirring solution of amine from the previous step (370 mg, 0.60 mmol), propargyl-peg4-carboxylic acid (188 mg, 0.72 mmol) and triethylamine (0.100 mL, 0.72 mmoL), dissolved in DMF (4 mL). The reaction was stirred for 2 hours at ambient temperature then purified directly RPLC (10%-95% acetonitrile/water, no modifier, 30 minute gradient). The pure fractions were pooled and lyophilized and taken directly to the next step. Yield 490 mg, 80%. Ion found by LC/MS: [M+H]$^+$=858.2.

Step f.

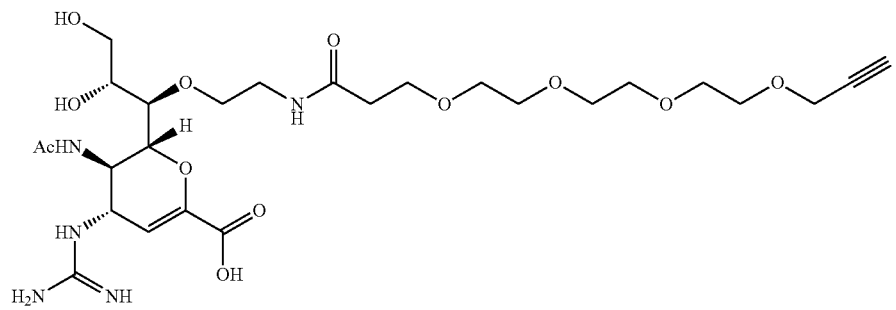 [SMILES: C#CCOCCOCCOCCOCCC(=O)NCCO[C@@H]([C@@H]1OC(C(=O)O)=C[C@H](NC(=N)N)[C@H]1NC(C)=O)[C@H](O)CO]

Product from the previous step (490 mg, 0.57 mmol) was stirred in TFA (4 mL) for 45 minutes then concentrated and azeotroped with methanol (3×) on the rotary evaporator. Ion found by LC/MS: [M+H]$^+$=658.2. The residue was stirred in 1/1 methanol/water containing LiOH (43 mg, 1.8 mmol) for 30 minutes. The reaction was neutralized with a few drops of glacial acetic acid and the volume was reduced by half on the rotary evaporator. The crude product was purified by semi-preparative HPLC (0%-75% acetonitrile/water, 0.1% TFA, 30 minute gradient). The pure fractions were pooled and lyophilized to afford the title compound. Yield 105 mg, 29%, 3 steps. Ion found by LC/MS: [M+H]$^+$=618.2.

Example 119. Synthesis of Int-68

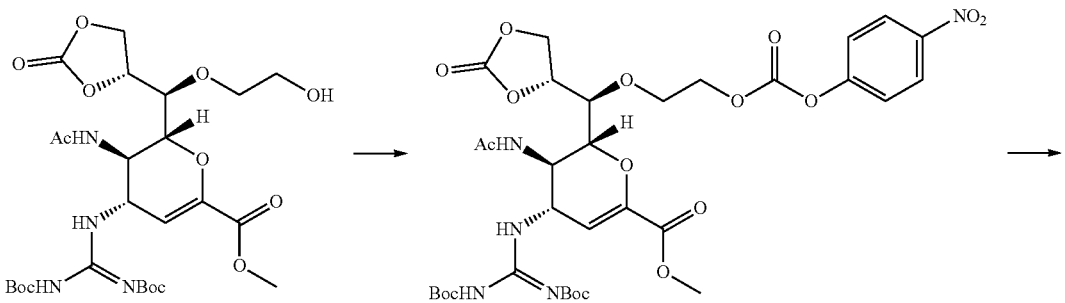

-continued

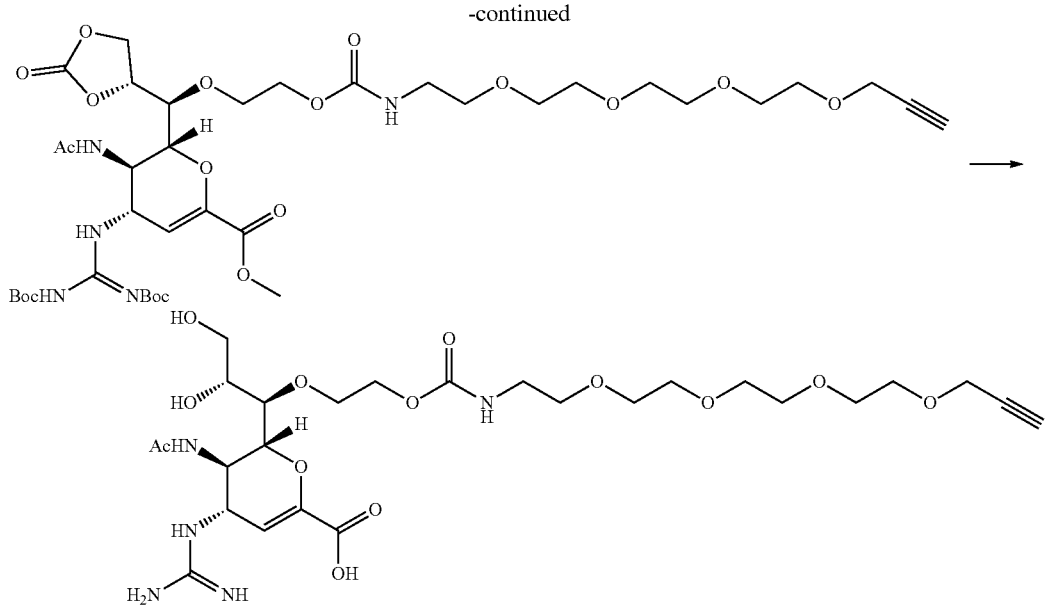

Step a.

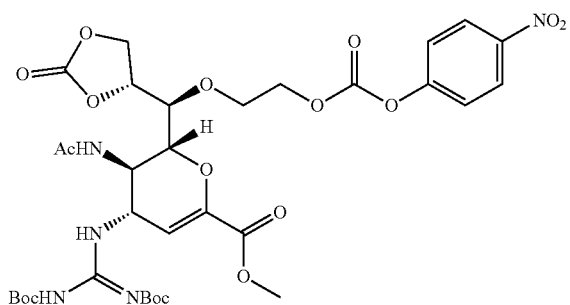

p-Nitrophenyl chloroformate (0.23 g, 1.14 mmol) was added to a stirring mixture of the primary alcohol (0.47 g, 0.76 mmol described in Example 118) and triethylamine (0.21 mL, 1.52 mmol) dissolved in DCM (15 mL, anhydrous). The reaction was stirred for 1 hour then additional trimethylamine (0.21 mL) and p-nitrophenyl chloroformate (230 mg) were added, and stirring was continued another hour, at which time the mixture was diluted with water, and extracted into DCM (3×). The combined organic extracts were washed with brine and dried over sodium sulfate. The solvent was removed by rotary evaporation. The crude residue was dissolved in DCM (3 mL), loaded onto celite and purified by silica gel chromatography (0% to 70% ethyl acetate/hexanes, 30 minute gradient). The pure fractions were pooled and concentrated to afford the title compound as a white solid. Yield 525 mg, 88%. Ion found by LCMS: [M+H]$^+$=782.2.

Step b.

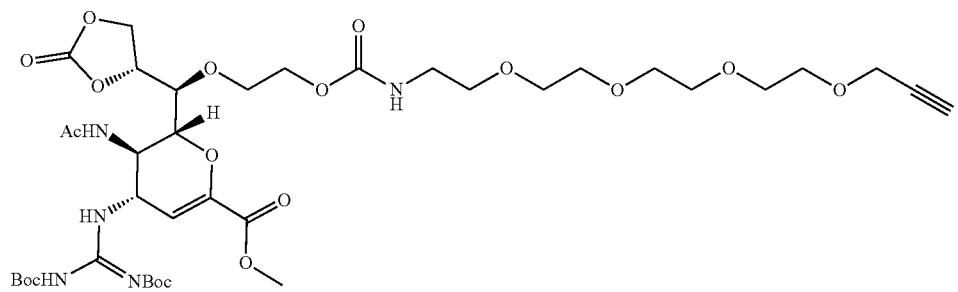

Triethylamine (0.14 mL, 0.97 mmol) was added to a stirring solution of propargyl-peg4-amine (181 mg, 0.78 mmol) in 1 mL of acetonitrile. The triethylamine/propargyl-peg4-amine mixture was added to the product from the previous step (510 mg, 0.65 mmol, in 2 mL acetonitrile) and stirred for 1 hour at which point all starting materials had been consumed. The solvent was removed on a rotary evaporator. The crude residue was purified RPLC (20-95% acetonitrile/water, 30 min gradient, no modifier). Yield 475 mg, 83%. Ion found by LC/MS: [M+H]$^+$=874.2.

Step c.

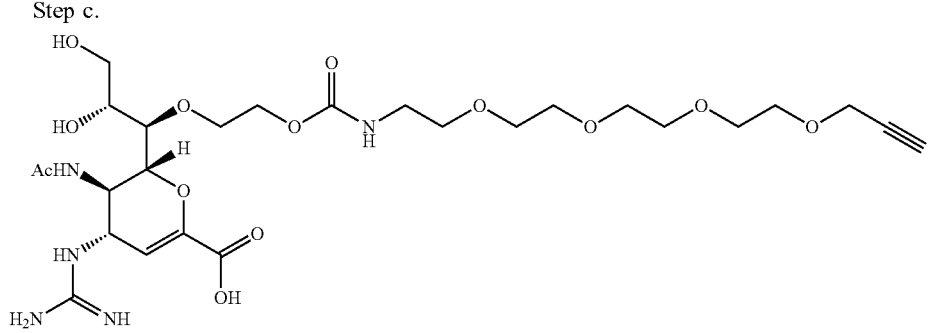

The product from the previous step (475 mg, 0.54 mmol), was stirred in TFA (5 mL) for 2 hours and then concentrated and azeotroped with methanol (3×) on a rotary evaporator. Ion found by LC/MS: [M+H]$^+$=674.2. The residue was stirred in 1:1 mixture of methanol/water containing LiOH (49 mg, 1.6 mmol) for 30 minutes. The reaction was neutralized with glacial acetic acid and then concentrated by rotary evaporation. The product was purified by semi-preparative HPLC (0%-75% acetonitrile/water, 0.1% TFA, 30 minute gradient). The pure fractions were pooled and lyophilized. Yield 204 mg, 59%. Ion found by LCMS: [M+H]$^+$=634.2.

Example 120 Synthesis of Int-77

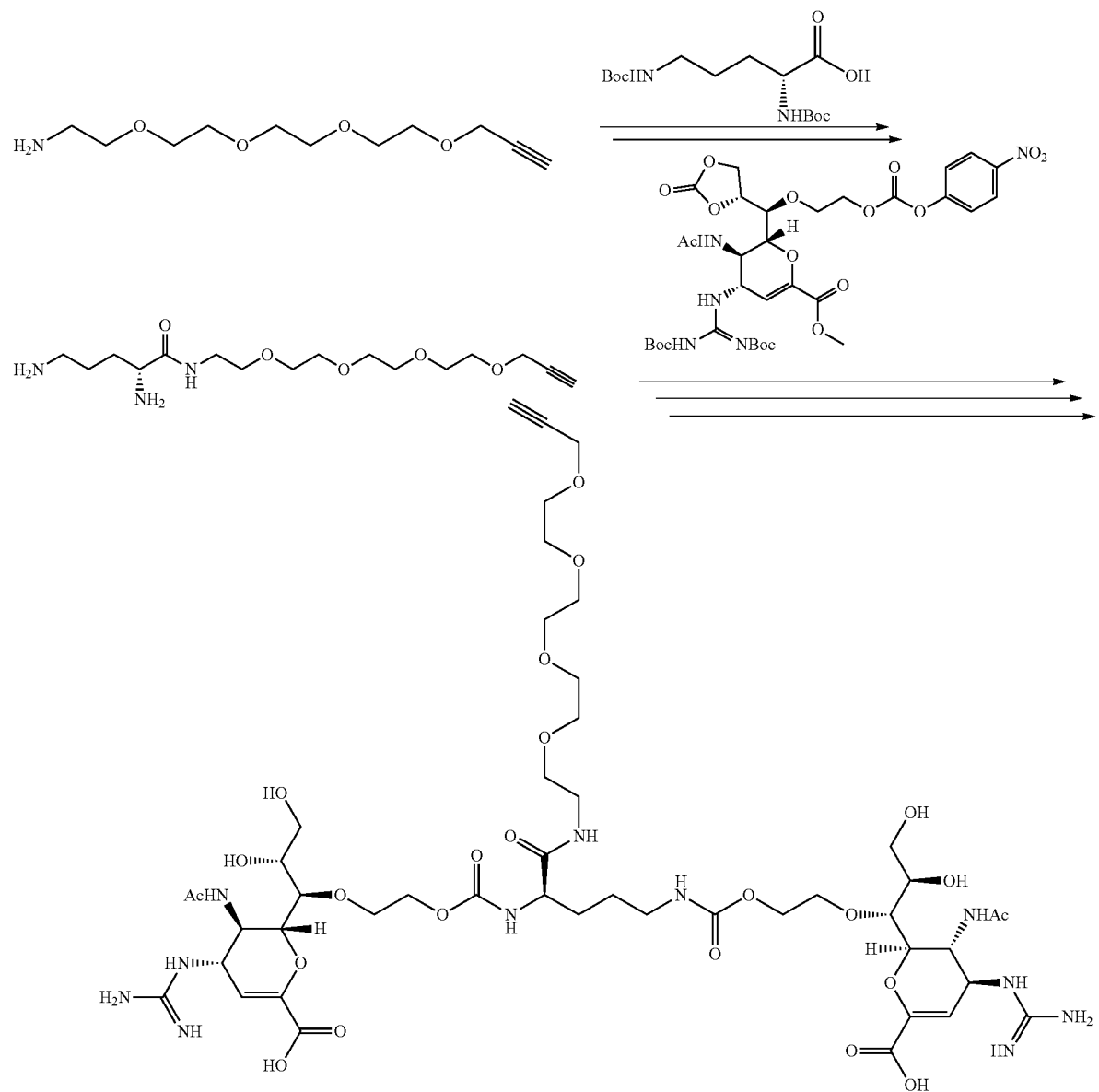

Step a.

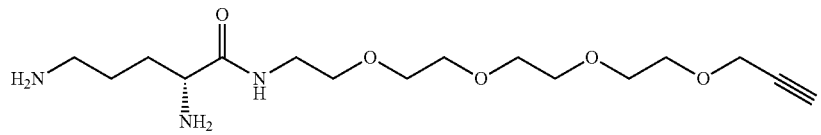

HATU (0.44 g, 1.16 mmol, in 1.5 mL of DMF) was added dropwise to a stirring solution of propargyl-peg4-amine (0.24 g, 1.05 mmol), bis-Boc-D-ornithine (0.35 g, 1.05 mmol), and triethylamine (0.59 mL, 4.21 mmol) in DMF (2 mL). The reaction was stirred for 1 hour at ambient temperature, then purified directly by RPLC (5%-90% acetonitrile/water, 0.1% TFA, 35 minute gradient). The pure fractions were pooled and lyophilized to afford the product as a viscous clear oil. Ion found by LC/MS: [M+H]$^+$=546.2.

The Boc-protected intermediate was stirred in 4N HCL in dioxane (10 mL) for 45 minutes at ambient temperature. The solvent was removed by rotary evaporation, then the resulting residue was dissolved in DI water (20 mL), frozen, and lyophilized to afford the product as a clear oil. Yield 310 mg, 70%, 2 steps. Ion found by LCMS: [M+H]$^+$=346.2.

The product from the previous step (96 mg, 0.28 mmol) and triethylamine (0.15 mL, 1.11 mmol) in acetonitrile (2 mL) were added to a stirring solution of p-nitrophenyl carbonate of zanamivir (435 mg, 0.56 mmol, described in Example 118, in 6 mL of acetonitrile), and stirred for 12 hours at ambient temperature, then 2 hours at 80° C. The solvent was removed and the crude residue was purified by RPLC (10-95% acetonitrile/water, no modifier, 35 minute gradient). The pure fractions were pooled and concentrated on a rotary evaporator. Ion found by LC/MS: [(M+2H)/2]$^+$=815.8.

This intermediate was stirred in TFA (5 mL) for 45 minutes then concentrated and dried under high vacuum. Ion found by LC/MS[(M+2H)/2]$^+$=615.8.

This TFA salt was stirred in (1/1) MeOH/DI water (5 mL) containing LiOH (27 mg, 1.11 mmol) for 30 minutes at 0° C. The mixture was acidified (~pH-5) with glacial acetic acid. The methanol was removed by rotary evaporation and the resulting residue was purified by semi-preparative HPLC (5%-70% acetonitrile/water, 0.1% TFA, 35 minute gradient). The pure fractions were pooled and lyophilized. Yield 35 mg, 11%, 3 steps. Ion found by LC/MS: [(M+2H)/2]$^+$=575.8.

Step b.

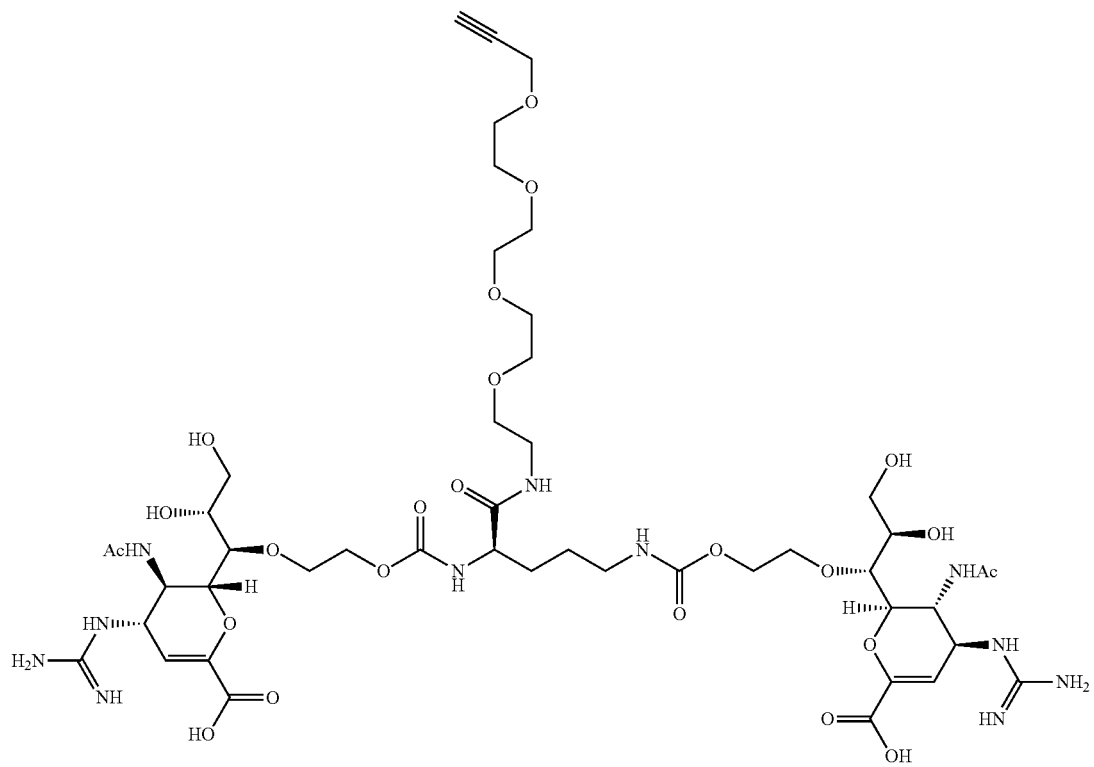 [SMILES: C#CCOCCOCCOCCOCCNC(=O)[C@@H](CCCNC(=O)OCCO[C@@H]([C@@H]1OC(C(=O)O)=C[C@H](NC(=N)N)[C@H]1NC(C)=O)[C@H](O)CO)NC(=O)OCCO[C@@H]([C@@H]1OC(C(=O)O)=C[C@H](NC(=N)N)[C@H]1NC(C)=O)[C@H](O)CO]

911
Example 121. Synthesis of Int-78
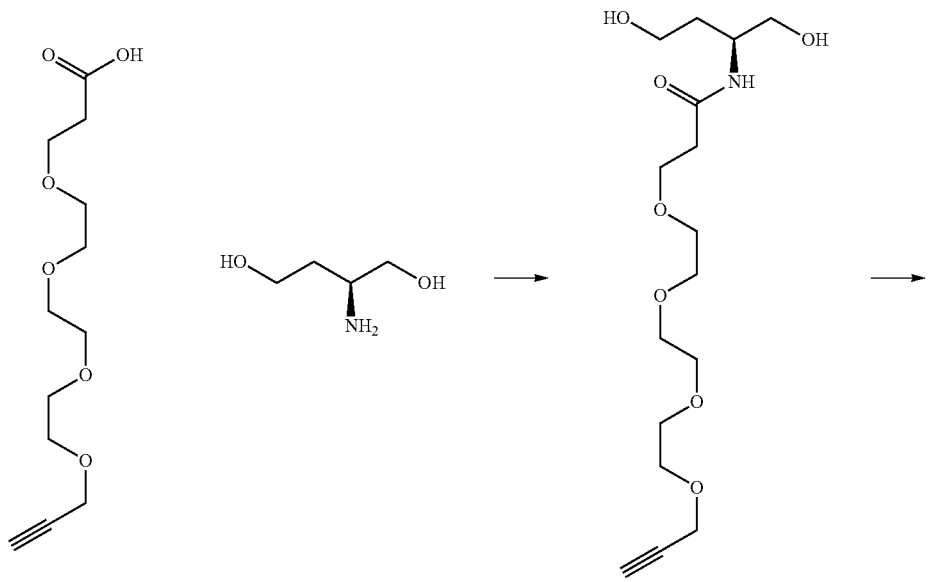
912
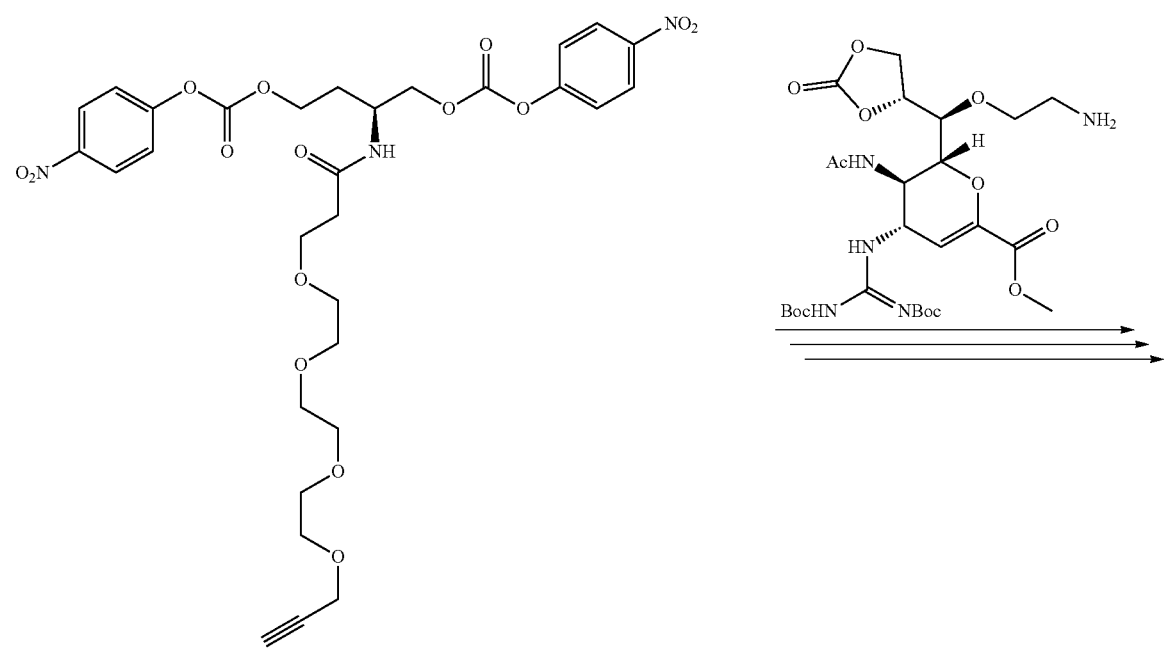

913 914

-continued

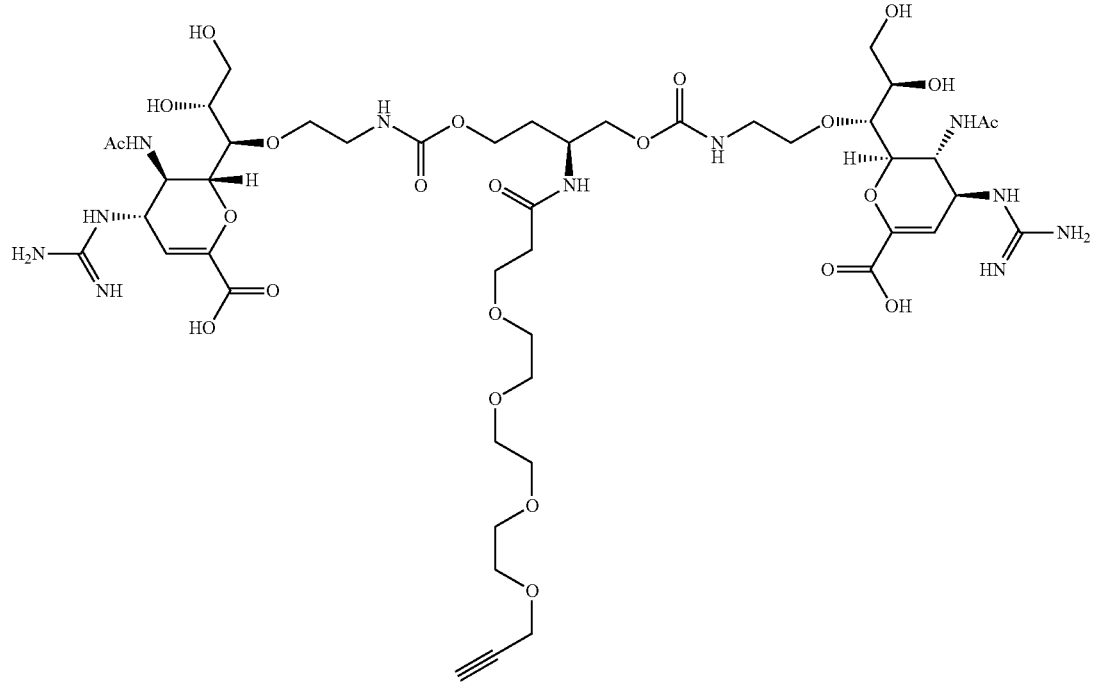

Step a.

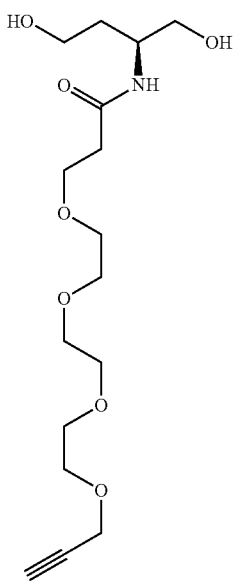

Propargyl-Peg4-acid (640 mg, 2.46 mmol), diol-HCl salt (350 mg, 2.46 mmol), EDC (471 mg, 2.46 mmol), HOBt (377 mg, 2.46 mmol), and triethylamine (249 mg, 2.46 mmol) were stirred in DMF (3 mL) at ambient temperature for 4 hours. The mixture purified directly by RPLC (0%- 80% acetonitrile/water, no modifier, 35 minute gradient). The pure fractions were pooled and concentrated to afford the product as a clear oil. Yield 580 mg, 68%. Ion found by LCMS: [M+H]$^+$=348.4.

Step b.

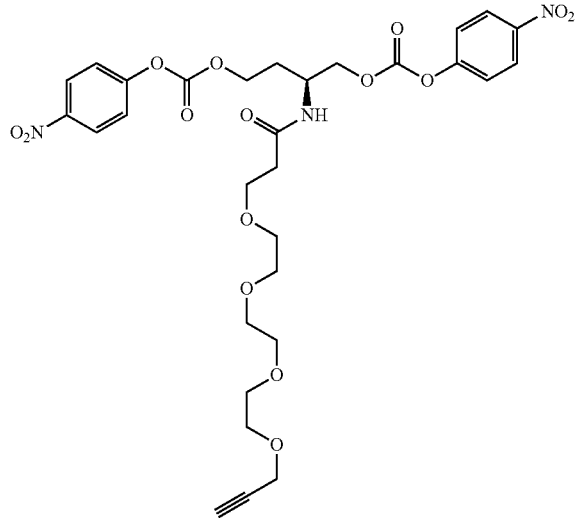 [SMILES: C#CCOCCOCCOCCOCCC(=O)N[C@@H](CCOC(=O)Oc1ccc([N+](=O)[O-])cc1)COC(=O)Oc1ccc([N+](=O)[O-])cc1]

p-Nitro-phenyl chloroformate (1.23 g, 1.25 mmol) was added to a stirring solution of product from the previous step (530 mg, 6.10 mmol) and triethylamine (925 mg, 9.15 mmol) in DCM (25 mL), then cooled to 0° C. under a nitrogen atmosphere. The mixture was stirred for 15 minutes at 0° C. and then at room temperature for 2 hours. The reaction was diluted with DI water and extracted into DCM (3×20 mL). The combined organic extracts were washed with brine and dried over sodium sulfate. The crude residue was purified by silica gel chromatography (10%-100% ethyl acetate/hexanes, 25 minute gradient) to afford the product as a white solid. Yield, 250 mg, 24%. Ion found by LCMS: $[M+H]^+=678.2$.

Step c.

Amine functionalized zanamivir (505 mg, 0.82 mmol, described in Example 118) and triethylamine (0.15 mL, 1.11 mmol) in acetonitrile (2 mL) were added to a stirring solution of the product of the previous step (220 mg, 0.37 mmol) in acetonitrile (10 mL), and stirred for 4 hours at ambient temperature. The reaction was concentrated on the rotary evaporator. The resulting residue was purified by RPLC (15%-95% acetonitrile/water, no modifier, 35 minute gradient). The pure fractions were pooled and concentrated on a rotary evaporator. Ion found by LC/MS: $[(M+2H)/2]^+=815.2$.

This intermediate was stirred in TFA (5 mL) for 45 minutes then concentrated and dried under high vac. Ion found by LC/MS: $[(M+2H)/2]^+=615.2$.

The resulting TFA salt was stirred in (1/1) MeOH/DI water (5 mL) containing LiOH (71 mg, 2.98 mmol) for 30 minutes at 0° C. The mixture was acidified (~pH-5) with glacial acetic acid. The methanol was removed by rotary evaporator and purified by semi-preparative HPLC (5%-70% acetonitrile/water, 0.1% TFA, 35 minute gradient). The pure fractions were pooled and lyophilized. Yield 125 mg, 29% for 3 steps. Ion found by LC/MS: $[(M+2H)/2]^+=575.8$.

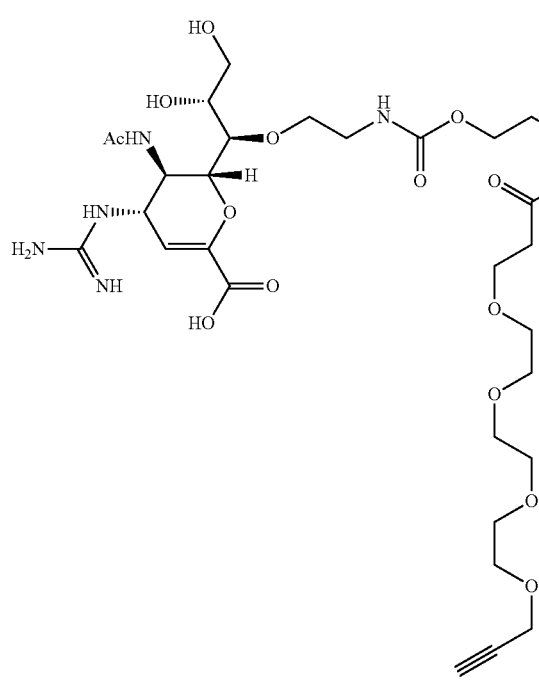
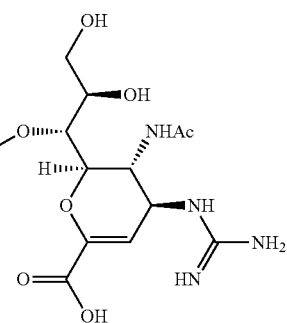

Example 122. Synthesis of Int-4a

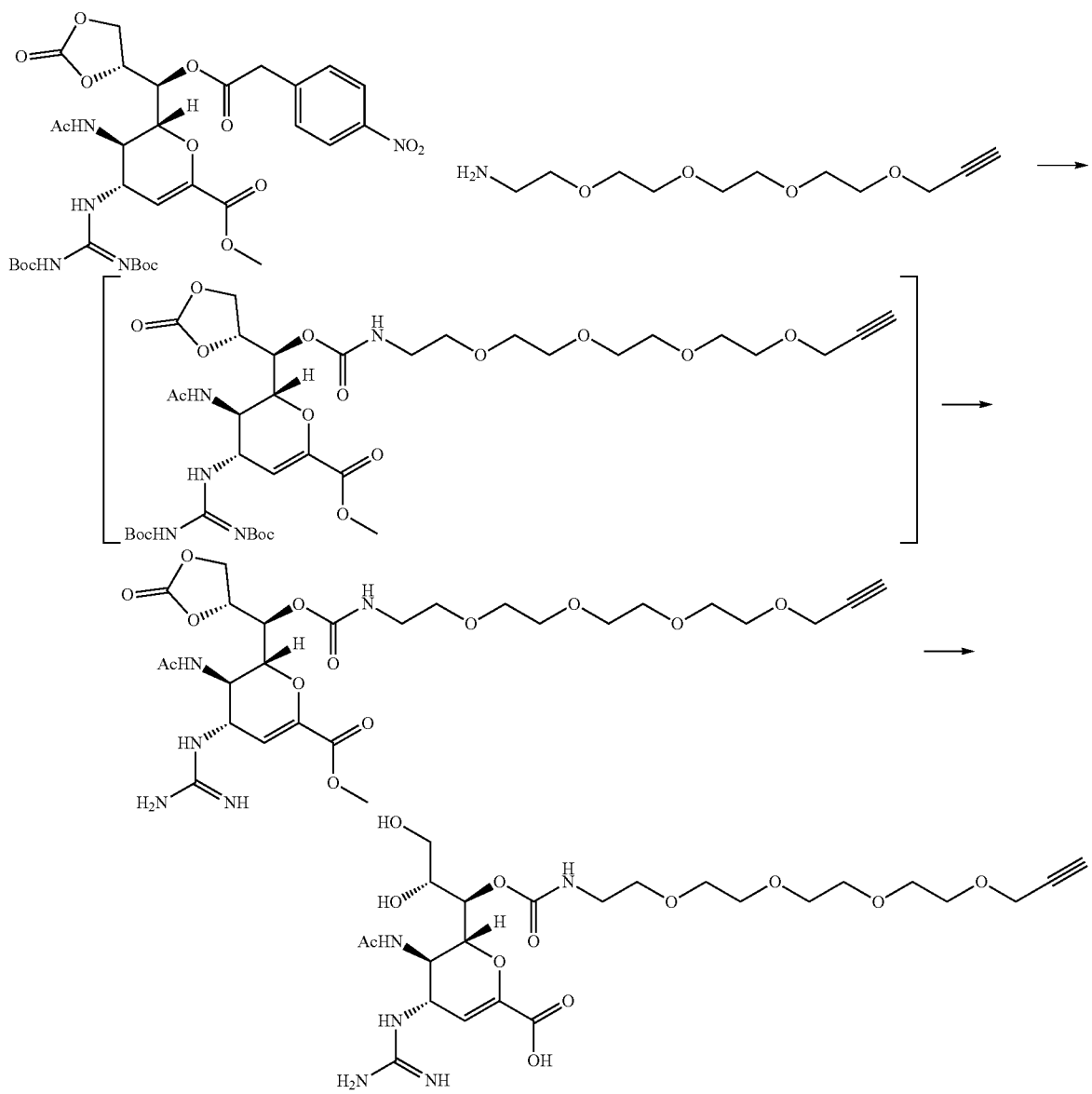

Step a.

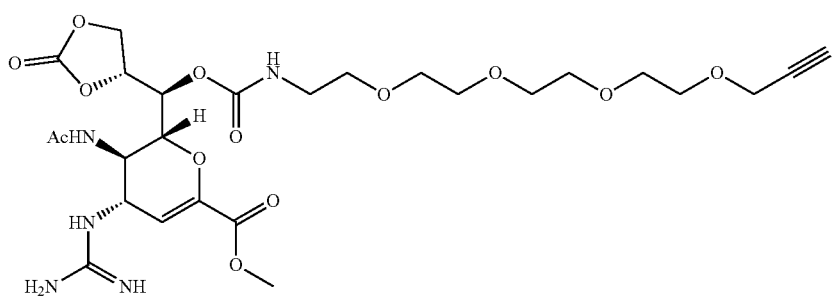

Propargyl-Peg 4-amine (165 mg, 0.71 mmol) was added to a stirring solution of p-nitrophenyl carbonate of zanamivir (350 mg, 0.47 mmol, described in Example 109) in acetonitrile (20 mL). The reaction was stirred for 1 hour at ambient temperature, then solvent was removed by rotary evaporator. The residue was purified by RPLC (10%-95% acetonitrile/ water, no modifier, 30 minute gradient). The pure fractions were pooled and lyophilized to afford the boc protected intermediate as a white solid. Ion found by LCMS: [M+H]$^+$= 830.2.

This intermediate was stirred in TFA (5 mL) at ambient temperature for 30 minutes. The solvent was removed by rotary evaporator and the residue was purified by RPLC (10%-95% acetonitrile/water, 0.1% TFA, 30 minute gradient). The pure fractions were pooled and lyophilized to afford the product as a white solid. Yield 155 mg, 52%, 2 steps. Ion found by LCMS: [M+H]$^+$=630.2.

Step b.

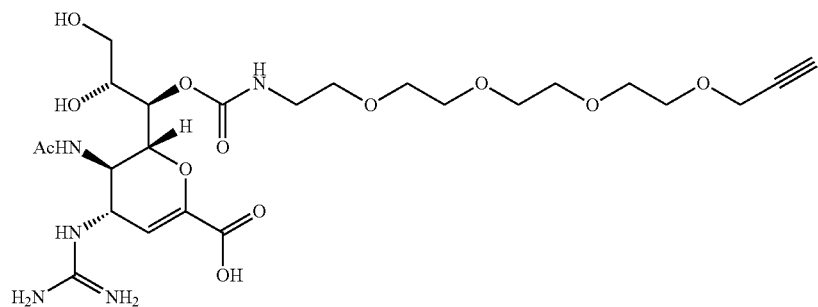 [SMILES: C#CCOCCOCCOCCOCCNC(=O)O[C@@H]([C@@H]1OC(C(=O)O)=C[C@H](NC(=N)N)[C@H]1NC(C)=O)[C@H](O)CO]

The product from the previous step (140 mg, 0.22 mmol) was stirred in a 1:3 mixture of methanol:water (8 mL) containing LiOH (21 mg, 0.89 mmol) at 0° C. for 20 minutes. The mixture was acidified with a few drops of glacial acetic acid and concentrated on a rotary evaporator. The crude material was purified by semi-preparative HPLC (5%-95% acetonitrile/water, 0.1% TFA, 30 minute gradient). The pure fractions were pooled and lyophilized to afford the product as a white solid. Yield 60 mg, 45%. Ion found by LCMS: [M+H]$^+$=590.2.

$^1$H NMR (500 MHz, Methanol-d$_4$) δ 5.86 (d, J=2.6 Hz, 1H), 4.99 (dd, J=9.0, 2.7 Hz, 1H), 4.55 (dd, J=9.7, 2.7 Hz, 1H), 4.38 (dd, J=8.6, 2.6 Hz, 1H), 4.24-4.14 (m, 1H), 4.19 (d, J=2.6 Hz, 2H), 4.02-3.98 (m, 1H), 3.74-3.59 (m, 13H), 3.54 (t, J=5.6 Hz, 2H), 3.52-3.48 (m, 1H), 3.29-3.22 (m, 2H), 2.84 (t, J=2.4 Hz, 1H), 1.96 (s, 3H).

$^{13}$C NMR (126 MHz, MeOD) δ 172.33, 163.68, 157.54, 156.58, 106.80, 79.23, 75.91, 74.56, 70.18, 70.13, 69.96, 69.87, 69.59, 69.51, 69.14, 68.74, 62.98, 57.67, 51.11, 40.54, 21.37.

Example 123. Synthesis of Int-4b

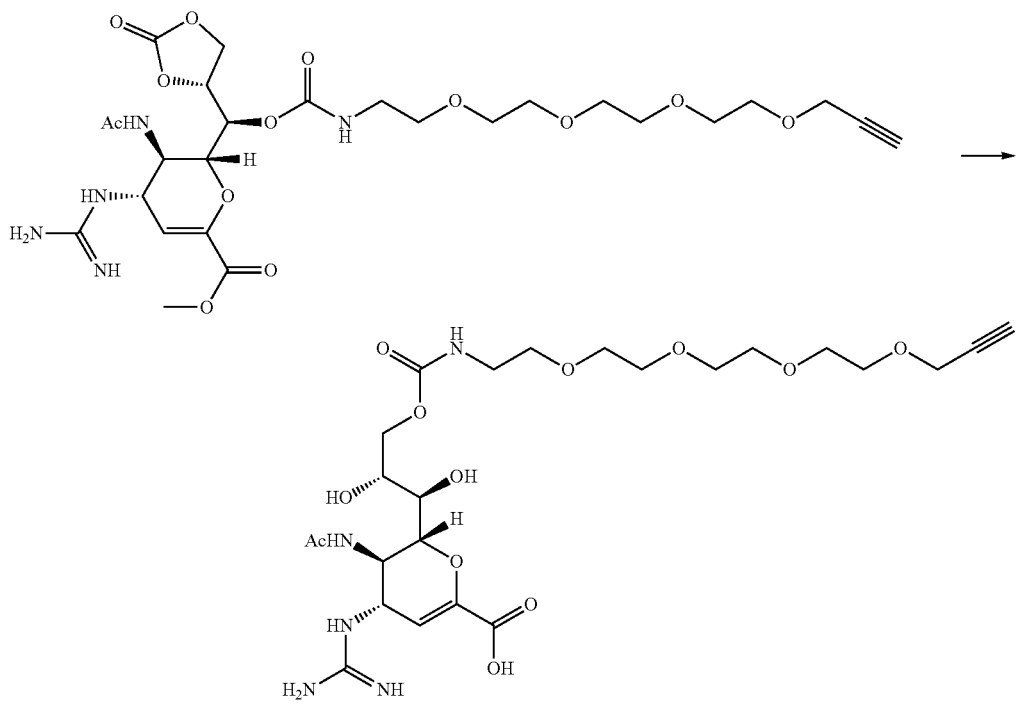

Peg functionalized intermediate (100 mg, 0.13 mmol, described in Example 122) was stirred in a 1:3 mixture of methanol:water (5 mL) containing LiOH (12 mg, 0.52 mmol) at ambient temperature for 2 hours. The mixture was acidified with glacial acetic acid and concentrated by rotary evaporator. The crude material was purified by RPLC (5-95% acetonitrile in DI water, 0.1% TFA, 30 minute gradient). The pure fractions were pooled and lyophilized to afford the product as a white solid. Yield 21 mg, 31%. Ion found by LCMS: [M+H]$^+$=590.2.

¹H NMR (Methanol-d₄) δ: 5.86 (d, J=2.6 Hz, 1H), 4.48 (dd, J=8.6, 2.7 Hz, 1H), 4.42 (dd, J=9.6, 1.4 Hz, 1H), 4.38 (d, J=12 Hz, 1H), 4.22-4.19 (m, 1H), 4.19 (d, J=2.4 Hz, 2H), 4.16-4.12 (dd, J=11.5, 6 Hz, 1H), 4.09-4.02 (m, 1H), 3.75-3.58 (m, 13H), 3.55 (t, J=5.5 Hz, 2H), 3.33-3.29 (m, 2H), 2.84 (t, J=2.4 Hz, 1H), 2.02 (s, 3H).
¹³C NMR (126 MHz, MeOD) δ 172.94, 163.82, 157.90, 157.53, 106.80, 79.23, 76.18, 74.55, 70.19, 70.13, 69.96, 69.90, 69.61, 68.96, 68.74, 68.17, 66.69, 57.67, 50.11, 40.43, 21.33.

Example 124. General Procedure for Synthesis of Azido Fc

Preparation of PEG4-azido NHS ester solution (0.050 M) in DMF/PBS: 16.75 mg of PEG4-azido NHS ester was dissolved in 0.100 mL of DMF at 0° C. and diluted to 0.837 mL by adding PBS 1× buffer at 0° C. This solution was used for preparing other PEG4-azido Fc with a variety of DAR values by adjusting the equivalents of this PEG4-azido NHS ester PBS solution.

The nucleic acid construct encoding the Fc for any conjugate described herein may include a nucleic acid encoding the amino acid sequence of an Fc including a C-terminal lysine residue and/or N-terminal murine IgG signal sequence (e.g., any one of SEQ ID NOs: 48-53). Upon expression, the C-terminal lysine and the N-terminal murine IgG signal sequence of the Fc of the conjugate are proteolytically cleaved, resulting in an Fc having the sequence lacking Lys447 (e.g., lacking a C-terminal lysine residue) and the N-terminal murine IgG signal sequence. The presence or absence of a C-terminal lysine does not alter the properties of the Fc or the corresponding conjugate.

Pretreatment of h-IgG1 Fc, SEQ ID NO: 48 (107.2 mg in 8.800 mL of pH 7.4 PBS, MW-57891 Da, 1.852 µmol): The Fc solution was transferred into four centrifugal concentrators (30,000 MWCO, 15 mL) and diluted to 15 mL with PBS×1 buffer and concentrated to a volume of ~1.5 mL. The residue was diluted 1:10 in PBS pH 7.4, and concentrated again. This wash procedure was repeated for total of four times followed by dilution to 8.80 mL.

Preparation of PEG4-azido Fc: 0.050M PEG4-azidoNHS ester PBS buffer solution (0.593 mL, 29.6 µmol, 16 equivalents) was added to above solution of h-IgG1 Fc (SEQ ID NO: 48) and the mixture was shaken rotated for 2 hours at ambient temperature. The solution was concentrated by using four centrifugal concentrators (30,000 MWCO, 15 mL) to a volume of ~1.5 mL. The crude mixture was diluted 1:10 in PBS pH 7.4, and concentrated again. This wash procedure was repeated for total of three times. The concentrated Fc-PEG4-azide was diluted to 8.80 mL with pH 7.4 PBS buffer and ready for Click conjugation. The purified material was quantified using a NANODROP™ UV visible spectrophotometer (using a calculated extinction coefficient based on the amino acid sequence of h-IgG1). Yield was quantitative after purification.

Example 125. Synthesis of Conjugate 34

A solution of azido functionalized Fc (40 mg, 2.5 mL, 0.69 µmol, described in the general preparation of azido Fc, Example 124, SEQ ID No. 18) was added to a 15 mL centrifuge tube containing alkyne derivatized small molecule (6.0 mg, 8.23 µmol, Int-67, Example 118). After gently agitating to dissolve all solids, the mixture was added to a solution of L-ascorbic acid sodium salt (54 mg, 0.27 mmol), copper (II) sulfate (0.88 mg, 5.5 µmol), and BTTA (9.4 mg, 22 µmol) in PBS 7.4 buffer (1.09 mL). The resulting mixture was gently rotated overnight. It was then purified by affinity chromatography over a protein A column, followed size exclusion chromatography (See general conjugate purification protocol). Maldi TOF analysis of the purified final product gave an average mass of 64,678 Da (DAR=7.2). Yield 24 mg, 54% yield.

Example 126. Synthesis of Conjugate 35

A solution of azido functionalized Fc (40 mg, 2.5 mL, 0.69 µmol, described in the general preparation of azido Fc, Example 124, SEQ ID No. 18) was added to a 15 mL centrifuge tube containing alkyne derivatized small molecule (6.1 mg, 8.23 µmol, Int-68 Example 119). After gently agitating to dissolve all solids, the mixture was added to solution of L-ascorbic acid sodium salt (54 mg, 0.27 mmol), copper (II) sulfate (0.88 mg, 5.5 µmol), and BTTA (9.4 mg, 22 µmol) in PBS 7.4 buffer (1.09 mL). The resulting solution was gently rotated overnight. It was then purified by affinity chromatography over a protein A column, followed size exclusion chromatography (See general conjugate purification protocol). Maldi TOF analysis of the purified final product gave an average mass of 64,830 Da (DAR=7.3). Yield 23 mg, 52% yield.

Example 127. Synthesis of Conjugate 36

A solution of azido functionalized Fc (50 mg, 2.5 mL, 0.86 µmol, described in the general preparation of azido Fc, Example 124, SEQ ID No. 18) was added to a 15 mL centrifuge tube containing alkyne derivatized small molecule (7.1 mg, 5.2 µmol, Int-77, Example 120). After gently agitating to dissolve all solids, the mixture was added to a solution of L-ascorbic acid sodium salt (68 mg, 0.34 mmol), copper (II) sulfate (1.1 mg, 6.9 µmol), and BTTA (12 mg, 27 µmol) in PBS 7.4 buffer (1.37 mL). The resulting mixture was gently rotated overnight. It was then purified by affinity chromatography over a protein A column, followed size exclusion chromatography (See general conjugate purification protocol). Maldi TOF analysis of the purified final product gave an average mass of 63,300 Da (DAR=3.6). Yield 37 mg, 73% yield.

Example 128. Synthesis of Conjugate 37

A solution of azido functionalized Fc (70 mg, 2.5 mL, 1.2 µmol, described in the general preparation of azido Fc, Example 124, SEQ ID No. 18) was added to a 15 mL centrifuge tube containing alkyne derivatized small molecule (13.3 mg, 9.6 µmol, Int 78, Example 121). After gently agitating to dissolve all solids, the mixture was added to a solution of L-ascorbic acid sodium salt (96 mg, 0.48 mmol), copper (II) sulfate (1.6 mg, 10 µmol), and BTTA (17 mg, 38 µmol) in PBS 7.4 buffer (1.92 mL). The resulting mixture was gently shaken overnight. It was then purified by affinity chromatography over a protein A column, followed size exclusion chromatography (See general conjugate purification protocol). Maldi TOF analysis of the purified final product gave an average mass of 63,574 Da (DAR=3.6). Yield 42 mg, 61% yield.

Example 129. Synthesis of Conjugate 33

Preparation of the Click reagent solution: 0.0050M CuSO₄ in PBS buffer solution: 10.0 mg CuSO₄ was dissolved in 12.53 mL PBS, then took 5.00 mL this CuSO₄ solution and added 43.1 mg BTTAA (CAS #1334179-85-9) and 247.5 mg sodium ascorbate to give the Click reagent solution (0.0050M $CuSO_4$, 0.020M BTTAA and 0.25M sodium ascorbate).

To a solution of azido functionalized Fc (104.9 mg, 8.60 mL, 18.1 µmol; Example 124, SEQ ID NO: 73 in a 15 mL centrifuge tube was added to alkyne derivatized small molecule (29.7 mg, 19.9 µmol, described in Example 100, 2.5 equivalents for each azido on the Fc). After gently agitating to dissolve all solids, the mixture was treated with the Click reagent solution(4.34 mL) of (L-ascorbic acid sodium, 0.25 M, 1086 µmol, copper (II) sulfate 0.0050M, 21.7 µmol, and BTTAA 0.020M, 86.9 µmol). The resulting mixture was gently rotated for 6 hours at ambient temperature. It was purified by affinity chromatography over a protein A column, followed size exclusion chromatography (see general conjugate purification protocol). Maldi TOF analysis of the purified final product gave an average mass of 64550 Da (DAR=4.6). Yield 90.7 mg with 98% purity. The resulting conjugate is depicted in FIG. 61.

The nucleic acid construct encoding the Fc for Conjugate 33 included a nucleic acid encoding the amino acid sequence of SEQ ID NO: 64, which includes a C-terminal lysine residue. Upon expression, the C-terminal lysine of the Fc of Conjugate 33 is proteolytically cleaved, resulting in an Fc having the sequence of SEQ ID NO: 73. The presence or absence of a C-terminal lysine does not alter the properties of the Fc or the corresponding conjugate.

Example 130. Efficacy of Conjugate 33 Against Influenza B/Brisbane/60/2008 in a Lethal Mouse Model Test articles were evaluated against a lethal Influenza B influenza infection in female BALB/c mice (Jackson Laboratories, 6-8 weeks old). The challenge virus (B/Brisbane/60/2008) is a mouse-adapted isolate capable of causing lethal infections in mice. The experiment comprised 10 groups of 5 mice each. At day 0, all mice were challenged with virus at 3× the LD95 by intranasal inoculation in a volume of 50 µl (approx. 1 E5 virus per mouse), after being anesthetized with isoflurane.

All groups received a single IV treatment of conjugate 33 (Example 129), vehicle (PBS), or Fc only control (hIgG1 Fc) two hours post viral challenge. An additional group was treated orally with oseltamivir (20 mg/kg, bid, for 5 days) starting 8 hours after viral challenge.

The study evaluated 7 different dose concentrations of conjugate 33 (10, 3, 1, 0.3, 0.1, 0.03, and 0.01 mg/kg). Mice were monitored for 2 weeks and animals exceeding 20% body weight loss, or were found moribund, were scored as a mortality. Body weights were also recorded to monitor the general health of the animals.

All mice treated with vehicle, or the Fc only control, reached mortality by Day 8 as expected. In contrast, all mice receiving conjugate 33 were fully protected after receiving single IV doses from 10 down to 0.3 mg/kg for the duration of the study (Table 48). In contrast, the oseltamivir treated group only resulted in 40% survival although the cumulative dose these mice received was 200 mg/kg over the course of the experiment. The potency of conjugate 33 was further supported by daily body weight measurements (Table 49; data only shown until the first death within a group). Mice treated with conjugate 33 at 0.3 mg/kg only demonstrated a transient loss of body weight reaching a maximum of 7%, for a single day. Collectively this study demonstrates the potency of conjugate 33 as measured by two parameters indicative of Influenza B infection (survival and body weight) against an influenza strain of the Yamagata lineage.

TABLE 48

| | | | % survival | | | | |
|---|---|---|---|---|---|---|---|
| Day post-infection | PBS | Fc (10 mg/kg) | Conjugate 33 | | | | Oseltamivir |
| | | | (10 to 0.3 mg/kg) | (0.1 mg/kg) | (0.03 mg/kg) | (0.01 mg/kg) | |
| 0 | 100 | 100 | 100 | 100 | 100 | 100 | 100 |
| 1 | 100 | 100 | 100 | 100 | 100 | 100 | 100 |
| 2 | 100 | 100 | 100 | 100 | 100 | 100 | 100 |
| 3 | 100 | 100 | 100 | 100 | 100 | 100 | 100 |
| 4 | 60 | 100 | 100 | 100 | 100 | 100 | 100 |
| 5 | 40 | 40 | 100 | 100 | 100 | 100 | 100 |
| 6 | 0 | 0 | 100 | 60 | 60 | 80 | 40 |
| 7 | 0 | 0 | 100 | 60 | 60 | 40 | 0 |
| 8 | 0 | 0 | 100 | 60 | 60 | 0 | 0 |
| 9 | 0 | 0 | 100 | 60 | 60 | 0 | 0 |
| 10 | 0 | 0 | 100 | 60 | 60 | 0 | 0 |
| 11 | 0 | 0 | 100 | 60 | 60 | 0 | 0 |
| 12 | 0 | 0 | 100 | 60 | 60 | 0 | 0 |
| 13 | 0 | 0 | 100 | 60 | 60 | 0 | 0 |
| 14 | 0 | 0 | 100 | 60 | 60 | 0 | 0 |

TABLE 49

Body weights (gm)

| Day post-infection | PBS | Fc (10 mg/kg) | Conjugate 33 (10 mg/kg) | Conjugate 33 (3 mg/kg) | Conjugate 33 (1 mg/kg) | Conjugate 33 (0.3 mg/kg) | Conjugate 33 (0.1 mg/kg) | Conjugate 33 (0.03 mg/kg) | Conjugate 33 (0.01 mg/kg) | Oseltamivir |
|---|---|---|---|---|---|---|---|---|---|---|
| 0 | 100 | 100 | 100 | 100 | 100 | 100 | 100 | 100 | 100 | 100 |
| 1 | 99 | 101 | 103 | 98 | 98 | 98 | 98 | 99 | 98 | 98 |
| 2 | 95 | 97 | 100 | 99 | 97 | 101 | 97 | 97 | 97 | 97 |
| 3 | 87 | 90 | 101 | 98 | 96 | 97 | 93 | 95 | 92 | 89 |
| 4 | 82 | 84 | 104 | 99 | 99 | 97 | 93 | 93 | 88 | 85 |
| 5 | 78 | 79 | 102 | 99 | 99 | 97 | 92 | | 84 | 79 |
| 6 | | | 98 | 96 | 98 | 93 | | | 79 | |
| 7 | | | 102 | 98 | 100 | 96 | | | | |
| 8 | | | 101 | 98 | 98 | 97 | | | | |
| 9 | | | 104 | 101 | 102 | 101 | | | | |
| 10 | | | 103 | 100 | 101 | 101 | | | | |
| 11 | | | 104 | 102 | 101 | 101 | | | | |
| 12 | | | 104 | 101 | 102 | 102 | | | | |
| 13 | | | 103 | 102 | 102 | 102 | | | | |
| 14 | | | 103 | 102 | 102 | 101 | | | | |

Example 131. Characterization of Regioisomers

Monomer and dimer intermediates may be produced as a particular regioisomer or a mixture of regioisomers. Examples 100-102 showed how to prepare Int-7 regioisomers (C7-C7, Example 100; 07-09, Example 101; C9-C9, Example 102; C7-C7 optimized, Example 103). The methods described therein can be used to separate mixtures of regioisomers of any intermediate described herein. Table 50 provides the characterization of the relative percent (%) amounts of 07 and 09 linked monomers and 07-07, C7-C9, and C9-C9 linked dimers in the previously described syntheses of the pre-conjugation intermediate.

TABLE 50

Regiosomer Analysis

| Int | Example | Monomer (M) or Dimer (D) | % C7 | % C7-C9 | % C9 |
|---|---|---|---|---|---|
| Int-2 | Example 6 | D | 95 | 5 | |
| Int-3 | Example 11 | D | 70 | 30 | |
| Int-4 | Example 13 | M | 58 | | 42 |
| Int-4a | Example 122 | M | | | 97 |
| Int-7 | Example 19 | D | 3 | 2 | 95 |
| Int-7a | Example 100 | D | 100 | | |
| Int-7b | Example 101 | D | 5 | 95 | |
| Int-7c | Example 102 | D | | | 100 |
| Int-25 | N/A | D | | 5 | 95 |
| Int-26 | N/A | D | 25 | 50 | 25 |
| Int-27 | N/A | D | 29 | 35 | 36 |
| Int-28 | N/A | D | 5 | 28 | 67 |
| Int-31 | N/A | D | 90 | | |
| Int-34 | N/A | D | 12 | 6 | 82 |
| Int-37 | N/A | M | | | 95 |
| Int-71 | Example 110 | D | 3 | 97 | |
| Int-72 | Example 112 | D | | | 100 |

Example 132. Efficacy of Conjugate 33 Subcutaneously Dosed Against Influenza A/Puerto Rico/8/34 (HI NI) in a Lethal Mouse Model Conjugate 33 was evaluated against a lethal IAV H1N1 influenza infection in female BALB/c mice (

TABLE 52

Percent survival by study day (n = 5)

| Day Post Infection | Vehicle | hIgG1 Fc (1.0 mg/kg) | Conjugate 33 (1.0 mg/kg) | Conjugate 33 (0.3 mg/kg) | Conjugate 33 (0.1 mg/kg) | Conjugate 33 (0.03 mg/kg) |
|---|---|---|---|---|---|---|
| 0 | 100 | 100 | 100 | 100 | 100 | 100 |
| 1 | 100 | 100 | 100 | 100 | 100 | 100 |
| 2 | 100 | 100 | 100 | 100 | 100 | 100 |
| 3 | 100 | 100 | 100 | 100 | 100 | 100 |
| 4 | 100 | 100 | 100 | 100 | 100 | 100 |
| 5 | 100 | 100 | 100 | 100 | 100 | 100 |
| 6 | 40 | 60 | 100 | 100 | 100 | 100 |
| 7 | 0 | 0 | 100 | 100 | 100 | 60 |
| 8 | 0 | 0 | 100 | 100 | 100 | 0 |
| 9 | 0 | 0 | 100 | 100 | 100 | 0 |
| 10 | 0 | 0 | 100 | 100 | 100 | 0 |
| 11 | 0 | 0 | 100 | 100 | 100 | 0 |
| 12 | 0 | 0 | 100 | 100 | 100 | 0 |
| 13 | 0 | 0 | 100 | 100 | 100 | 0 |
| 14 | 0 | 0 | 100 | 100 | 100 | 0 |

The potency of conjugate 33 was further supported by daily body weight measurements. As expected, mice treated with vehicle or hIgG Fc demonstrated a steady drop in body weight until it exceeded 20%, at which time they were scored as a mortality (Table 53).

In contrast to control mice, those groups receiving conjugate 33 at 1, 0.3, and 0.1 mg/kg maintained healthy body weights throughout the study and never demonstrated more than a transient body weight drop of less than 8% (0.1 ink/kg dose group, Day 8; Table 53). By both survival and body weight measurements conjugate 33 demonstrated robust protection from a lethal challenge of Influenza A/Puerto Rico/8/1934 with a single SC dose as low as 0.1 mg/kg.

TABLE 53

Body weight data (g

TABLE 54-continued

Study Design

| Test Article (DAR) | Route/Schedule | Dose [mg/kg] |
|---|---|---|
| Conjugate 33 (4.7) | SC, T + 2 h | 1 |
| Conjugate 33 (4.7) | SC, T + 2 h | 3 |
| uninfected | N/A | N/A |

For PFU determination, supernatants of lung homogenate were diluted in infection buffer ranging from $10^{-1}$ to $10^{-6}$. 100 μL of virus dilutions were added to confluent monolayer of MDCK cells in 24 well plates and incubated for 1 h at room temperature with rocking every 15 min. After removing the virus, liquid overlay media containing Avicel was added to MDCK cells. Cells were incubation at 37° C., 5% $CO_2$ for 40 h. After incubation, the media was removed and cells were stained with crystal violet to enumerate plaques and Plaque forming units (PFU) were calculated relative to weight of the lung (PFU/g lung).

For cytokine analysis, supernatants of lung homogenate were serially diluted 2-fold in 96 well plate. Cytokine levels for INF-γ, TNF-α, IL-6, MIP-1α and MCP-1 were determined by ELISA according to manufacturer's instructions (R&D Systems). After a lethal challenge with influenza in a mouse model, lung PFU burden (FIGS. 63A-63B) and lung cytokine levels were determined on day 4 post-infection (Table 55, and Table 56, respectively). Conjugate 33 demonstrated a dose-dependent log reduction in viral burden resulting in 0.7 at 0.1 mg/kg, 1.88 at 0.3 mg/kg, 3 at 1 mg/kg and 3.8 at 3 mg/kg. Oseltamivir at 5 mg/kg and 50 mg/kg had modest effects on viral burden resulting in 0.86 and 2 log reduction, respectively. Baloxavir reduced the viral burden below the limit of detection, 1e2 PFU/mL, thereby reducing the viral burden by >5.99 logs as compared to PBS control.

No biological relevant difference was observed between negative controls, PBS and hIgG1 Fc as expected.

Conjugate 33 reduces viral burden in dose dependency on day 4 post-infection challenged with influenza A in a mouse model (Table 55, FIGS. 64A-64B). Similarly, conjugate 33 demonstrated a dose-dependent fold-reduction in cytokine levels for TNF-α, IL-6, INF-γ, MCP-1, and MIP-1α (FIGS. 65A-65E, respectively) compared to uninfected control on day 4 post-infection challenged with influenza A in a mouse model (Table 56).

TABLE 55

PFU burden

| Test article [mg/kg] | PFU/g | Log reduction |
|---|---|---|
| PBS [0]PBS | 3.26E+07 | 0.0 |
| hIgG1 Fc [3] | 1.74E+07 | 0.364 |
| Oseltamivir [5] | 4.78E+06 | 0.86 |
| Oseltamivir [50] | 3.81E+05 | 2 |
| Baloxavir [30] | <1.00E+02* | >5.99* |
| conjugate 33 [0.1] | 6.85E+06 | 0.715 |
| conjugate 33 [0.3] | 5.31E+05 | 1.88 |
| conjugate 33 [1] | 3.69E+04 | 2.99 |
| conjugate 33 [3] | 5.84E+03 | 3.77 |

*Baloxavir reduced the viral burden below the limit of detection.

TABLE 56

Lung cytokine levels

| Test article [mg/kg] | INF-γ | TNF-α | IL-6 | MCP-1 | MIP-1a |
|---|---|---|---|---|---|
| PBS [0] | 1.6 | 1.4 | 4.2 | 38.6 | 18.1 |
| hIgG1 Fc [3] | 1.7 | 1.2 | 3.3 | 36.3 | 15.9 |
| Oseltamivir [5] | 1.0 | 0.8 | 1.8 | 24.0 | 6.3 |
| Oseltamivir [50] | 0.8 | 0.8 | 1.4 | 16.2 | 4.0 |
| Baloxavir [30] | 1.2 | 1.0 | 1.0 | 1.0 | 0.8 |
| conjugate 33 [0.1] | 1.1 | 0.7 | 0.8 | 19.1 | 5.6 |
| conjugate 33 [0.3] | 1.1 | 0.9 | 0.8 | 9.6 | 3.9 |
| conjugate 33 [1] | 0.9 | 0.7 | 1.1 | 5.7 | 1.7 |
| conjugate 33 [3] | 0.8 | 0.7 | 1.1 | 1.8 | 1.0 |
| Uninfected | 1 | 1 | 1 | 1 | 1 |

The highest concentration tested of conjugate 33 at 3 mg/kg demonstrated no weight loss throughout the course of infection similar to uninfected control mice (Table 57).

TABLE 57

Body weight data (% reduction)

| Test article [mg/kg] | Day 0 | Day 1 | Day 2 | Day 3 | Day 4 |
|---|---|---|---|---|---|
| PBS [0] | 0 | -3.5 | -2.86 | -10.96 | -17.32 |
| hIgG1 Fc [3] | 0 | -2.6 | -1.3 | -9.58 | -15.6 |
| Oseltamivir [5] | 0 | -2.86 | -2.42 | -8.16 | -13.88 |
| Oseltamivir [50] | 0 | -3.78 | -2.12 | -3.22 | -5.74 |
| Baloxavir [30] | 0 | -2.38 | -2.82 | -2.6 | -0.18 |
| conjugate 33 [0.1] | 0 | -3.24 | -2.32 | -10.12 | -11.46 |
| conjugate 33 [0.3] | 0 | -2.16 | 1.34 | -3.4 | -4.36 |
| conjugate 33 [1] | 0 | -1.5 | -0.9 | -1.98 | -0.9 |
| conjugate 33 [3] | 0 | -1.7 | -1.6 | -1.9 | 0.52 |
| Uninfected | 0 | 1.02 | -0.14 | -0.16 | 2.8 |

Example 134. Efficacy of Conjugate 33 Against Influenza A (H1N1) in a Lethal Severe Combined Immunodeficiency (SCID) Mouse Model Test articles were evaluated against a lethal Influenza A influenza infection in female BALB/cscid mice (Jackson Laboratories, 6-8 weeks old). The challenge virus (A/Puerto Rico/8/1934) is a mouse-adapted isolate capable of causing lethal infections in mice. The experiment comprised 11 groups of 5 mice each. At day 0, all mice were challenged with virus at 3× the LD95 by intranasal inoculation in a volume of 30 μl (approx. 1 E3 virus per mouse), after being anesthetized with a mixture of ketamine/xylazine (150 and 10 mg/kg respectively).

Groups received a single SC treatment of vehicle (PBS), hIgG1 Fc control, or conjugate 33 (3, 1, 0.3, 0.1, 0.03 mg/kg) two hours post viral challenge. A separate arm of the study consisted of 3 groups of mice treated with baloxavir marboxil (DC Chemicals, Shanghai, China) orally, twice daily, for 1 day; also starting 2 hours post viral challenge. Mice were monitored for 2 weeks and animals exceeding 20% body weight loss, or were found moribund, were scored as a mortality.

At study end (Day 14) mice receiving conjugate 33 were fully protected at all dose concentrations between 3 and 0.1 mg/kg (Table 58). Conjugate 33 only failed to protect against lethal viral challenge at the lowest tested concentration of 0.03 mg/kg. As expected, groups receiving vehicle or hIgG1 Fc were not protected. Mice treated with baloxavir were also protected, but at the significantly higher cumulative doses of 60 and 20 mg/kg, at a total dose of 6 mg/kg only 40% of mice survived to Day 14.

TABLE 58

% Survival on Day 14.

| Vehicle (PBS) | hIgG1 Fc (3.0 mg/kg) | Baloxavir | | | Conjugate 33 | | | | |
|---|---|---|---|---|---|---|---|---|---|
| | | (30 mg/kg) | (10 mg/kg) | (3.0 mg/kg) | (3.0 mg/kg) | (1.0 mg/kg) | (0.3 mg/kg) | (0.1 mg/kg) | (0.03 mg/kg) |
| 0 | 0 | 100 | 100 | 40 | 100 | 100 | 100 | 100 | 0 |

The potency of conjugate 33 in this model of severe immunodeficiency was also evident based on body weights (Table 59). The lowest concentration of conjugate providing full protection based on a mortality readout was 0.1 mg/kg. At this dose level, the greatest average weight loss for the group was transient, and resulted in less than a 5% reduction (occurring on Day 2). Furthermore the difference in body weight for groups at the 1 and 3 mg/kg dose levels showed less than a 2% difference on Day 14 compared to uninfected mice.

Collectively this data demonstrates the potency of conjugate 33 by protecting lethally challenged mice with single SC doses of conjugate as low as 0.1 mg/kg. This was accomplished in a severe model of immunodeficiency with mice completely lacking T & B immune cells, which are essential in clearing influenza infections. This data supports the use of conjugate 33 to treat immune deficient patient populations.

Test groups received a single subcutaneous (SC) treatment of conjugate 33, hIgG1 Fc control, or vehicle (PBS) 2 hours post viral challenge. The study design and dose levels are summarized in Table 60.

TABLE 60

Study design for Influenza A/California/07/2009 (H1N1) pdm study

| Group | Test article | Route/Schedule | Dose (mq/kg) | Dose volume (ml/kq) | # of mice |
|---|---|---|---|---|---|
| 1 | Vehicle | SC, T + 2 hrs. | na | 10 | 5 |
| 2 | hIgG1 Fc | SC, T + 2 hrs. | 1 | 10 | 5 |
| 3 | conjugate 33 | SC, T + 2 hrs. | 1 | 10 | 5 |
| 4 | conjugate 33 | SC, T + 2 hrs. | 0.3 | 10 | 5 |
| 5 | conjugate 33 | SC, T + 2 hrs. | 0.1 | 10 | 5 |
| 6 | conjugate 33 | SC, T + 2 hrs. | 0.03 | 10 | 5 |

TABLE 59

% Average body weight by day, (mg/kg). Data only shown until the first mortality within a group.

| Day post infection | Vehicle (PBS) | hIgG1 Fc (3 mg/kg) | Baloxavir | | | Conjugate 33 | | | | | Uninfected |
|---|---|---|---|---|---|---|---|---|---|---|---|
| | | | (30 mg/kg) | (10 mg/kg) | (3 mg/kg) | (3 mg/kg) | (1 mg/kg) | (0.3 mg/kg) | (0.1 mg/kg) | (0.003 mg/kg) | |
| 0 | 100.0 | 100.0 | 100.0 | 100.0 | 100.0 | 100.0 | 100.0 | 100.0 | 100.0 | 100.0 | 100.0 |
| 1 | 100.0 | 99.0 | 98.9 | 91.5 | 97.3 | 99.0 | 99.6 | 98.8 | 97.6 | 99.7 | 99.5 |
| 2 | 99.0 | 100.8 | 99.1 | 97.3 | 100.1 | 100.1 | 99.9 | 100.7 | 95.8 | 98.6 | 99.8 |
| 3 | 94.0 | 93.0 | 97.0 | 96.4 | 97.4 | 100.0 | 98.9 | 97.6 | 97.0 | 96.7 | 98.8 |
| 4 | 93.0 | 89.7 | 99.1 | 95.9 | 99.0 | 101.0 | 99.8 | 99.2 | 97.8 | 94.4 | 99.9 |
| 5 | 87.0 | 84.4 | 99.1 | 97.5 | 96.6 | 99.0 | 98.6 | 96.3 | 97.4 | 93.0 | 10.9 |
| 6 | 82.0 | 80.1 | 97.9 | 97.9 | 97.0 | 100.6 | 99.7 | 99.9 | 98.7 | 91.6 | 100.2 |
| 7 | 78.0 | | 98.6 | 97.0 | 97.2 | 101.9 | 99.6 | 99.6 | 98.1 | 87.0 | 101.0 |
| 8 | | | 98.6 | 96.4 | 95.4 | 100.9 | 98. | 99.2 | 98.3 | 82.2 | 100.4 |
| 9 | | | 99.6 | 95.1 | 93.1 | 100.6 | 98.4 | 100.0 | 97.0 | | 100.7 |
| 10 | | | 96.0 | 95.9 | 90.5 | 98.8 | 98.8 | 98.5 | 95.8 | | 100.2 |
| 11 | | | 97.3 | 97.3 | | 99.0 | 99.3 | 98.3 | 96.0 | | 99.7 |
| 12 | | | 98.7 | 95.8 | | 99.1 | 99.4 | 98.1 | 96.3 | | 100.4 |
| 13 | | | 98.6 | 96.8 | | 98.4 | 99.0 | 97.9 | 97.3 | | 99.7 |
| 14 | | | 97.9 | 95.9 | | 99.3 | 99.3 | 98.1 | 97.8 | | 100.5 |

Example 135. Efficacy of Conjugate 33 Subcutaneously Dosed Against Influenza A/California/07/2009 (H1N1) Pdm in a Lethal Mouse Model Conjugate 33 was evaluated against a lethal IAV H1N1 influenza infection in female BALB/c mice (Charles River Laboratories, 6-8 weeks). The challenge virus (A/California/07/2009 (H1N1) pdm) is a pandemic isolate capable of causing lethal infections in mice. The experiment comprised 6 groups of 5 mice. At day 0, all mice were challenged with virus at 3× the LD95 by intranasal inoculation in a volume of 30 μl, after being anesthetized with a mixture of ketamine/xylazine (150 and 10 mg/kg respectively). Mortality and body weights were recorded daily and any animal with a 20% loss of body weight was scored as a death.

As expected, mice receiving vehicle or the hIgG1 Fc control succumbed to infection on Days 6-7 (Table 61). However, mice treated with conjugate 33 were fully protected at 1 mg/kg, and nearly so at 0.3 (80% survival). Significant mortality with conjugate 33 was only seen at the lower dose concentrations of 0.1 and 0.03 mg/kg.

TABLE 61

Percent survival by day, (mg/kg)

| | | hIgG1 Fc | conjugate 33 | | | |
|---|---|---|---|---|---|---|
| Day | Vehicle | (1.0 mg/kg) | (1.0 mg/kg) | (0.3 mg/kg) | (0.1 mg/kg) | (0.03 mg/kg) |
| 0 | 100 | 100 | 100 | 100 | 100 | 100 |
| 1 | 100 | 100 | 100 | 100 | 100 | 100 |

TABLE 61-continued

Percent survival by day. (mg/kg)

| Day | Vehicle | hIgG1 Fc (1.0 mg/kg) | conjugate 33 (1.0 mg/kg) | (0.3 mg/kg) | (0.1 mg/kg) | (0.03 mg/kg) |
|---|---|---|---|---|---|---|
| 2 | 100 | 100 | 100 | 100 | 100 | 100 |
| 3 | 100 | 100 | 100 | 100 | 100 | 100 |
| 4 | 100 | 100 | 100 | 100 | 100 | 100 |
| 5 | 40 | 20 | 100 | 100 | 60 | 80 |
| 6 | 0 | 20 | 100 | 80 | 20 | 20 |
| 7 | 0 | 0 | 100 | 80 | 0 | 0 |
| 8 | 0 | 0 | 100 | 80 | 0 | 0 |
| 9 | 0 | 0 | 100 | 80 | 0 | 0 |
| 10 | 0 | 0 | 100 | 80 | 0 | 0 |
| 11 | 0 | 0 | 100 | 80 | 0 | 0 |
| 12 | 0 | 0 | 100 | 80 | 0 | 0 |
| 13 | 0 | 0 | 100 | 80 | 0 | 0 |
| 14 | 0 | 0 | 100 | 80 | 0 | 0 |

The potency of conjugate 33 was further supported by daily body weight measurements. As expected, mice treated with vehicle or hIgG1 Fc demonstrated a steady drop in body weight until it exceeded 20%, at which time they were scored as a mortality (Table 62).

In contrast to control mice, mice receiving conjugate 33 at 1 mg/kg only demonstrated a transient drop in bodyweight of approximately 10%, peaking on Day 3 (Table 62). By both survival and body weight measurements conjugate 33 demonstrated robust protection from a lethal challenge of Influenza A/California/07/2009 (H1N1) pdm with a single 1 mg/kg dose administered SC. Activity against the clinically relevant pandemic strain used in this study supports the utility of conjugate 33 in treating serious influenza infections.

TABLE 62

% Average body weight by day. (mg/kg). Data only shown until the first mortality within a group.

| Day post infection | Vehicle | hIgG1 Fc (1.0 mg/kg) | Conjugate 33 (1.0 mg/kg) | (0.3 mg/kg) | (0.1 mg/kg) | (0.03 mg/kg) |
|---|---|---|---|---|---|---|
| 0 | 100 | 100 | 100 | 100 | 100 | 100 |
| 1 | 99.5 | 97.9 | 96.8 | 96.7 | 98 | 98.7 |
| 2 | 97.1 | 97.2 | 99.5 | 99.2 | 98 | 98.4 |
| 3 | 86.5 | 86.0 | 89.7 | 89.6 | 87.6 | 88.8 |
| 4 | 80.3 | 80.3 | 91.6 | 88.5 | 81.3 | 81.9 |
| 5 | 76.2 | 76.6 | 92.9 | 91.0 | 76.8 | 77.9 |
| 6 | | | 94.7 | 90.5 | | |
| 7 | | | 94.2 | | | |
| 8 | | | 95.4 | | | |
| 9 | | | 98.0 | | | |
| 10 | | | 96.8 | | | |
| 11 | | | 98.8 | | | |
| 12 | | | 97.7 | | | |
| 13 | | | 100.1 | | | |
| 14 | | | 100.5 | | | |

Example 136. Efficacy of Conjugate 33 Intravenously (IV) Dosed Against Influenza A/Puerto Rico/8/1934 (H1N1) in a Lethal Mouse Model of Delayed Treatment Conjugate 33 was evaluated against a lethal influenza A (H1N1) infection in female BALB/c mice (Charles River Laboratories, 6-8 weeks). The challenge virus (A/Puerto Rico/8/1934) is a mouse-adapted isolate capable of causing lethal infections in mice. At day 0, all mice were challenged with virus at 3× the LD95 by intranasal inoculation in a volume of 30 µl, after being anesthetized with a mixture of ketamine/xylazine (150 and 10 mg/kg respectively). Mortality and body weights were recorded daily and any animal with a 20% loss of body weight was scored as a death.

The study design is detailed in Table 63, and consists of multiple arms. The control arm comprises vehicle (PBS) and hIgG1 Fc only groups, dosed 24 hours after viral challenge (an uninfected group was also part of this arm). The second arm consisted of oseltamivir dosed at 4× its humanized dose, with the initiation of treatment delayed for 24, 48, or 72 hours. The final 3 arms consisted of conjugate 33 administered as single IV doses of 10, 3, or 1 mg/kg; each being dosed on the same schedule as the oseltamivir arm above.

As expected, vehicle and hIgG1 Fc were not protective when dosed 24 hours after viral challenge and resulted in complete mortality by Day 7. In our hands, oseltamivir, even at 4× the humanized dose (200 mg/kg cumulative dose) was only partially efficacious when dosing was delayed 24 hours (Table 64; 40% survival). However, conjugate 33 was fully protective at all concentrations (10, 3, & 1 mg/kg) at the same 24 hour dose schedule.

When dosing was delayed a full 48 hours after viral challenge oseltamivir was no longer efficacious (0% survival) while conjugate 33 was 80% protective at doses of 10 and 3 mg/kg. When dosing was delayed until 72 hours, only the 10 mg/kg dose of conjugate 33 demonstrated partial protection (40%). The efficacy of conjugate 33 was also evident based on daily body weight measurements (Table 65). This was especially significant in the T+24 hours groups where less than a 3% reduction was observed for any conjugate 33 group, which was transient and occurred on Day 1. In this study, conjugate 33 is more efficacious than oseltamivir, an approved treatment for influenza.

TABLE 63

Study design

| Group | Influenza A strain | Test Article | Route, Schedule | First dose (hours) | Dose (mg/kg) | Dose volume (ml/kg) | N (balb/c) |
|---|---|---|---|---|---|---|---|
| 1 | A/PR/8/34 (H1N1) 3E2 PFU/mouse | PBS | IV, single | T + 24 | — | 5 | 5 |
| 2 | | hIgG1 Fc | IV, single | T + 24 | 10 | 5 | 5 |
| 3 | | Oseltamivir | PO, bid × 5 days | T + 24 | 20 | 10 | 5 |
| 4 | | | | T + 48 | | | |
| 5 | | | | T + 72 | | | |

TABLE 63-continued

Study design

| Group | Influenza A strain | Test Article | Route, Schedule | First dose (hours) | Dose (mg/kg) | Dose volume (ml/kg) | N (balb/c) |
|---|---|---|---|---|---|---|---|
| 6 | | Conjugate 33 | IV, single | T + 24 | 10 | 5 | 5 |
| 7 | | | | T + 48 | | | |
| 8 | | | | T + 72 | | | |
| 9 | | Conjugate 33 | IV, single | T + 24 | 3 | 5 | 5 |
| 10 | | | | T + 48 | | | |
| 11 | | | | T + 72 | | | |
| 12 | | Conjugate 33 | IV, single | T + 24 | 1 | 5 | 5 |
| 13 | | | | T + 48 | | | |
| 14 | | | | T + 72 | | | |
| 15 | | Uninfected BW control | | | | | |

TABLE 64

% Survival by day. Test article/Dose/Time of treatment initiation

| | | | Oseltamivir | | | Conjugate 33 | | | Conjugate 33 | | | Conjugate 33 | | | |
|---|---|---|---|---|---|---|---|---|---|---|---|---|---|---|---|
| Day post infection | Vehicle na T + 24 hrs. | hIgG1 Fc 10 mpk T + 24 hrs. | 20 mpk, bid × 5 T + 24 hrs. | 20 mpk, bid × 5 T + 48 hrs. | 20 mpk, bid × 5 T + 72 hrs. | 10 mpk, single T + 24 hrs. | 10 mpk, single T + 48 hrs. | 10 mpk, single T + 72 hrs. | 3 mpk, single T + 24 hrs. | 3 mpk, single T + 48 hrs. | 3 mpk, single T + 72 hrs. | 1 mpk, single T + 24 hrs. | 1 mpk, single T + 48 hrs. | 1 mpk, single T + 72 hrs. | Uninfected na na |
| 0 | 100 | 100 | 100 | 100 | 100 | 100 | 100 | 100 | 100 | 100 | 100 | 100 | 100 | 100 | 100 |
| 1 | 100 | 100 | 100 | 100 | 100 | 100 | 100 | 100 | 100 | 100 | 100 | 100 | 100 | 100 | 100 |
| 2 | 100 | 100 | 100 | 100 | 100 | 100 | 100 | 100 | 100 | 100 | 100 | 100 | 100 | 100 | 100 |
| 3 | 100 | 100 | 100 | 100 | 100 | 100 | 100 | 100 | 100 | 100 | 100 | 100 | 100 | 100 | 100 |
| 4 | 100 | 100 | 100 | 100 | 100 | 100 | 100 | 100 | 100 | 100 | 100 | 100 | 100 | 100 | 100 |
| 5 | 100 | 100 | 100 | 100 | 100 | 100 | 100 | 100 | 100 | 100 | 100 | 100 | 80 | 100 | 100 |
| 6 | 60 | 100 | 100 | 100 | 100 | 100 | 100 | 60 | 100 | 100 | 80 | 100 | 80 | 80 | 100 |
| 7 | 0 | 0 | 100 | 100 | 20 | 100 | 100 | 40 | 100 | 80 | 0 | 100 | 60 | 40 | 100 |
| 8 | 0 | 0 | 100 | 100 | 0 | 100 | 80 | 40 | 100 | 80 | 0 | 100 | 40 | 0 | 100 |
| 9 | 0 | 0 | 60 | 60 | 0 | 100 | 80 | 40 | 100 | 80 | 0 | 100 | 40 | 0 | 100 |
| 10 | 0 | 0 | 40 | 0 | 0 | 100 | 80 | 40 | 100 | 80 | 0 | 100 | 40 | 0 | 100 |
| 11 | 0 | 0 | 40 | 0 | 0 | 100 | 80 | 40 | 100 | 80 | 0 | 100 | 40 | 0 | 100 |
| 12 | 0 | 0 | 40 | 0 | 0 | 100 | 80 | 40 | 100 | 80 | 0 | 100 | 40 | 0 | 100 |
| 13 | 0 | 0 | 40 | 0 | 0 | 100 | 80 | 40 | 100 | 80 | 0 | 100 | 40 | 0 | 100 |
| 14 | 0 | 0 | 40 | 0 | 0 | 100 | 80 | 40 | 100 | 80 | 0 | 100 | 40 | 0 | 100 |

TABLE 65

Body Weight Data (gm). mpk = mg/kg. Data only shown until the first death within a group. Test article/Dose/Time of treatment initiation

| | | | Oseltamivir | | | Conjugate 33 | | | Conjugate 33 | | | Conjugate 33 | | | |
|---|---|---|---|---|---|---|---|---|---|---|---|---|---|---|---|
| Day post infection | Vehicle na T + 24 hrs. | hIgG1 Fc 10 mpk T + 24 hrs. | 20 mpk, bid × 5 T + 24 hrs. | 20 mpk, bid × 5 T + 48 hrs. | 20 mpk, bid × 5 T + 72 hrs. | 10 mpk, single T + 24 hrs. | 10 mpk, single T + 48 hrs. | 10 mpk, single T + 72 hrs. | 3 mpk, single T + 24 hrs. | 3 mpk, single T + 48 hrs. | 3 mpk, single T + 72 hrs. | 1 mpk, single T + 24 hrs. | 1 mpk, single T + 48 hrs. | 1 mpk, single T + 72 hrs. | Uninfected na na |
| 0 | 100 | 100 | 100 | 100 | 100 | 100 | 100 | 100 | 100 | 100 | 100 | 100 | 100 | 100 | 100 |
| 1 | 99.3 | 98.8 | 96.4 | 97.5 | 98.2 | 97.6 | 97.7 | 98.5 | 97.1 | 98.3 | 98.7 | 98.3 | 99.4 | 99.4 | 99.5 |
| 2 | 103.9 | 101 | 100.7 | 101.2 | 102.6 | 102.1 | 101.7 | 100.1 | 102 | 102.5 | 99.4 | 104.2 | 102 | 101.4 | 101.7 |
| 3 | 96.9 | 97.4 | 95.5 | 97.5 | 95.6 | 102.3 | 96.2 | 95.1 | 100.6 | 95.9 | 97.6 | 102.3 | 96.9 | 98.6 | 105.8 |
| 4 | 88.7 | 90.1 | 92.6 | 89.7 | 87.7 | 102.3 | 88.4 | 88.8 | 100 | 87.8 | 88.6 | 100 | 89.2 | 89.7 | 105 |
| 5 | 81.7 | 83.9 | 92.2 | 88.6 | 81.6 | 101.5 | 88.1 | 82.7 | 99 | 85.3 | 81.7 | 101.2 | 83.7 | 83.2 | 105.5 |
| 6 | 77.3 | 79.3 | 91.8 | 86 | 78.6 | 102.6 | 91.1 | 80.4 | 101.4 | 87.1 | 77.5 | 103.3 | | 78.7 | 104.9 |
| 7 | | | 87.8 | 81 | | 101.9 | 91.1 | | 102.3 | 86.1 | | 102.1 | | | 103.5 |
| 8 | | | 83.5 | 75.8 | | 101.5 | 91.3 | | 101.1 | | | 103.2 | | | 102.9 |
| 9 | | | 81.1 | | | 102.2 | | | 102.1 | | | 104.1 | | | 102.9 |
| 10 | | | | | | 102.5 | | | 101.6 | | | 105 | | | 103.3 |
| 11 | | | | | | 102.4 | | | 102.1 | | | 103.9 | | | 104.3 |
| 12 | | | | | | 100.9 | | | 101.6 | | | 103.4 | | | 102.5 |
| 13 | | | | | | 101 | | | 101.8 | | | 103.5 | | | 102.5 |
| 14 | | | | | | 102.2 | | | 103.6 | | | 104 | | | 103.1 |

Example 137. Synthesis of Conjugate 38 (Int-73), Conjugate 39 (Int-74), Conjugate 40 (Int-75), and Conjugate 41 (Int-76)

A 15-ml sterile centrifuge tube is charged with sodium ascorbate (68.3 mg, 0.345 mmol), BTTAA (11.9 mg, 0.0276 mmol), product from Examples 114 (Int-73), 115 (Int-74), 116 (Int-75), or 117 (Int-76) (0.00953 mmol) and PBS 7.4 (1 ml). The reagents were vortexed until homogeneous then mixed with azido Fc (50 mg, 0.0008624 mmol, described in Example 124, SEQ ID NO: 73) followed by a solution of $CuSO_4$ (1.1 mg, 0.0069 mmol) in water (0.5 ml). The mixture is rotated for 12 hours then purified by affinity chromatography over a protein A column, followed size exclusion chromatography. Conjugates are characterized by Maldi TOF analysis (DAR typically =4.5). Yields are typically 50%.

The nucleic acid construct encoding the Fc for conjugates 38-41 included a nucleic acid encoding the amino acid sequence of SEQ ID NO: 64, which includes a C-terminal lysine residue. Upon expression, the C-terminal lysine of the Fc of conjugates 38-41 is proteolytically cleaved, resulting in an Fc having the sequence of SEQ ID NO: 73. The presence or absence of a C-terminal lysine does not alter the properties of the Fc or the corresponding conjugate.

Example 138. Synthesis of Int-79

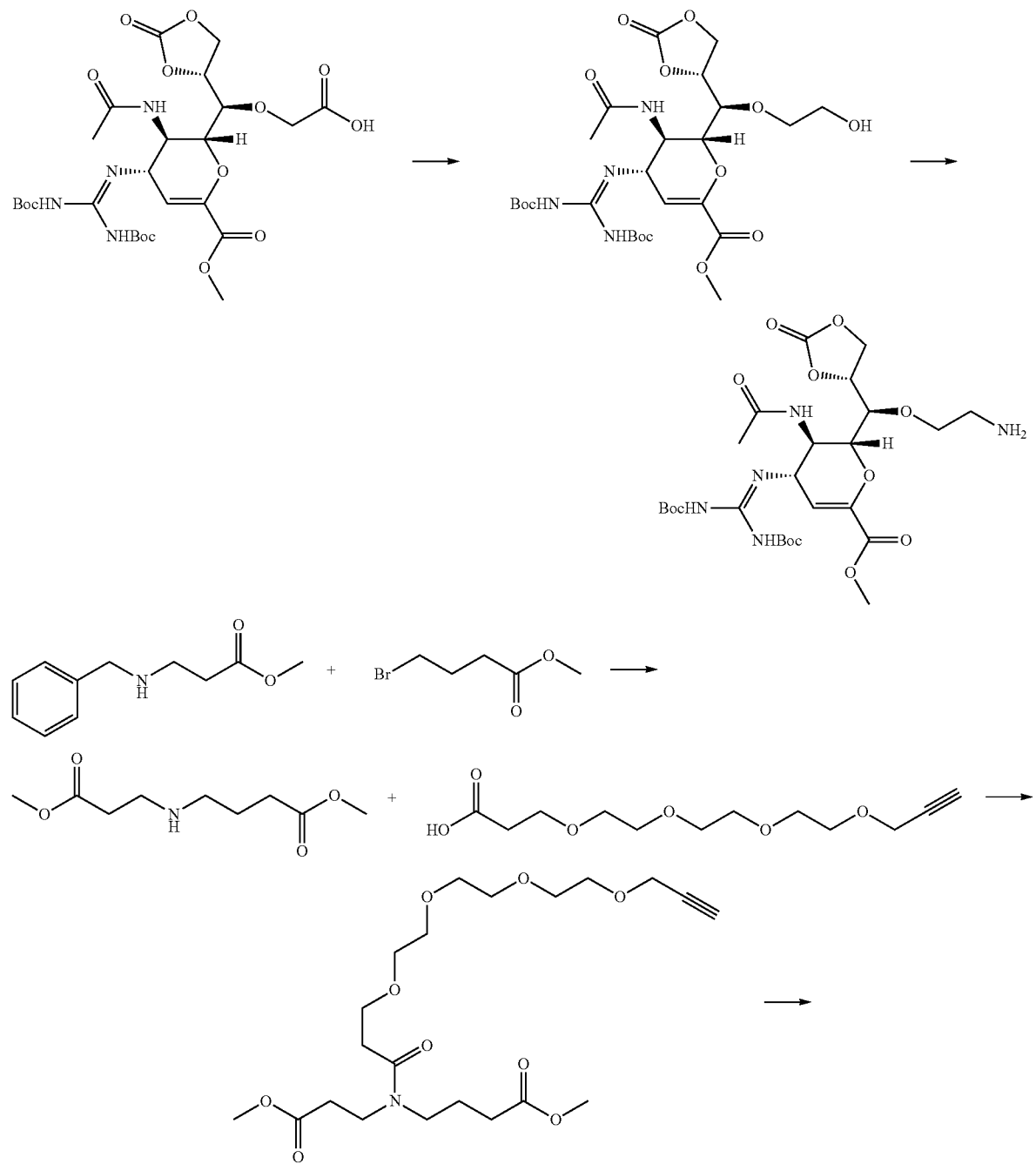

939 940
-continued
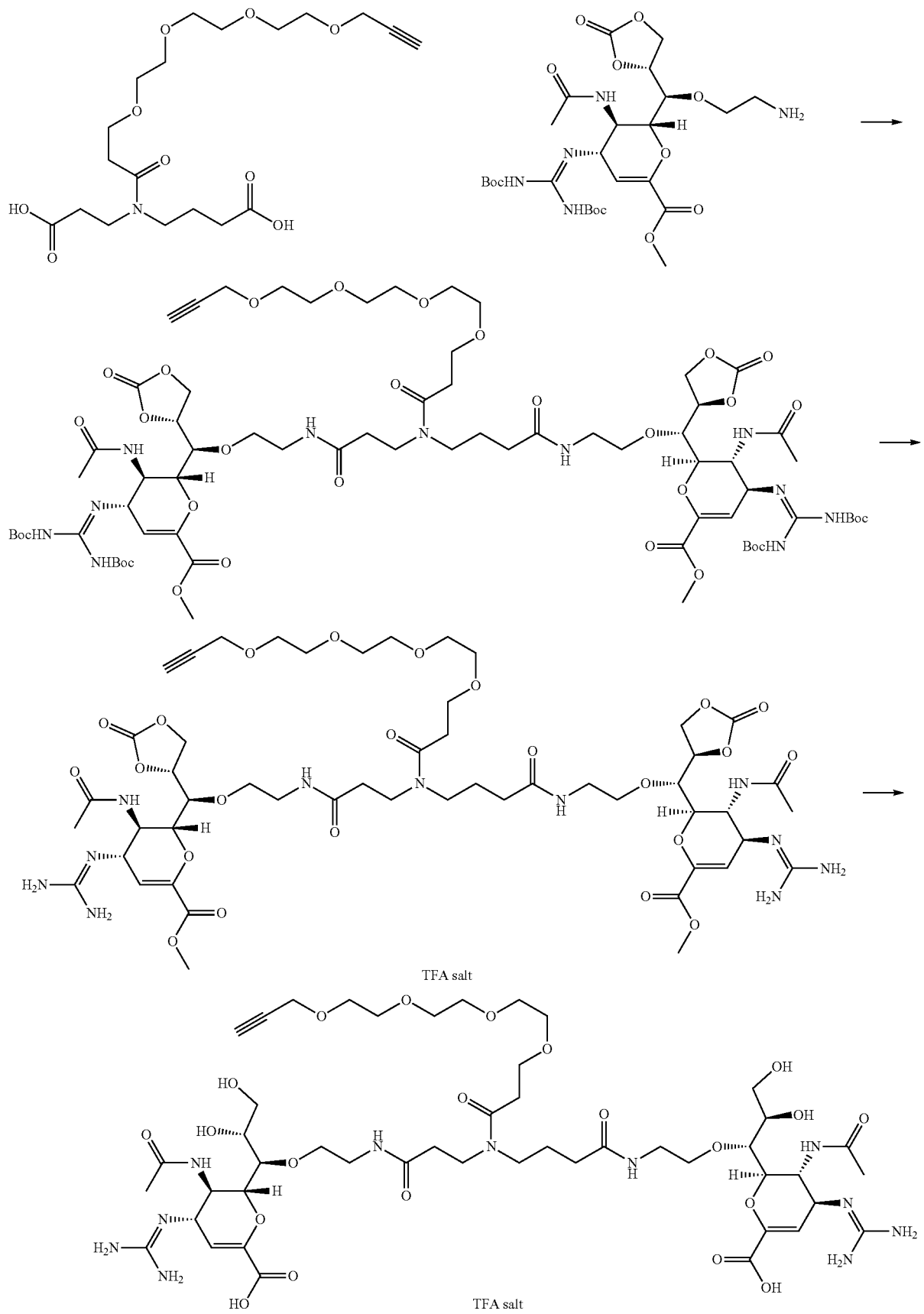
TFA salt
TFA salt

Step a.

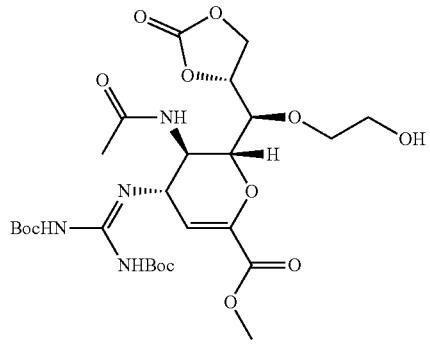

Zanamivir-ether-acid (0.90 g, 1.43 mmol, Example 31) and N-methyl morpholine (0.23 mL, 2.14 mmol) were dissolved in THF (35 mL) and cooled to 0° C. (ice water bath) under an atmosphere of nitrogen. Isobutyl chloroformate (0.24 mL, 1.85 mmol, in 2 mL DCM) was added dropwise, by way of syringe over a 5 minute period. The mixture was stirred at 0° C. for 30 minutes then 15 min at ambient temperature, and then cooled to 0° C. Sodium borohydride (540 mg, 14.3 mmol, dissolved in 5 mL of methanol) was added, dropwise over 5 minutes. The reaction was stirred for 15 minutes at which point all starting material had been consumed (by LC/MS). A few drops (~1 mL) of glacial acetic acid was added to acidify the mixture (pH-5). Dilute with ethyl acetate and water and extract into ethyl acetate (3×). The organic layer was washed with brine, and the organic extracts were dried over sodium sulfate, and concentrated on the rotary evaporator. The crude material was purified by silica gel chromatography (loaded on celite first) (0-10% methanol in DCM, 30 min). Yield 0.66 g, 75%. Ion found by LCMS: [M+H]+=617.2.

Step b.

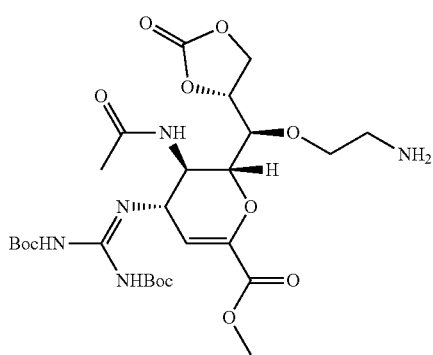 [SMILES: COC(=O)C1=C[C@H](N=C(NC(=O)OC(C)(C)C)NC(=O)OC(C)(C)C)[C@@H](NC(C)=O)[C@H]([C@H](OCCN)[C@H]2COC(=O)O2)O1]

To a stirring mixture of alcohol (0.66, 1.1 mol, in 20 mL CH$_2$Cl$_2$), was added triethylamine (0.30 mL, 1.3 mmol). The mixture was cooled to 0° C. (ice-water bath) under 1 atmosphere of nitrogen and mesyl chloride (150 mg, 1.3 mmol) was added, dropwise over 5 minutes by way of syringe. The ice bath was removed and the reaction was stirred for 45 minutes. The mixture was diluted with saturated, aqueous sodium bicarbonate, extracted into DCM (3×). The combined organic extracts were washed with brine, dried over sodium sulfate and concentrated on the rotary evaporator. Ion found by LCMS: [M+H]+=695.2. The intermediate was taken to the next step without purification.

The zanamivir mesylate was stirred in DMF at 80° C. with 3 eq of sodium azide for 5 hours. The mixture was diluted with water, extracted into DCM (3×). The combined organic extracts were washed with brine, dried over sodium sulfate and concentrated. Ion found by LCMS: [M+H]+=695.2. The azide was taken to the next step without purification.

The zanamivir azide (670 mg, 1.04 mmol) was stirred in methanol (20 mL) in the presence of Lindlar catalyst (300 mg) under 1 atmosphere of hydrogen gas for 12 hours. The mixture was filtered through celite and concentrated to afford the title compound as a clear oil. The amine was taken to the next step without purification. Yield 0.37 g, 54%, 3 steps. Ion found by LCMS: [M+H]+=616.2.

Step c.

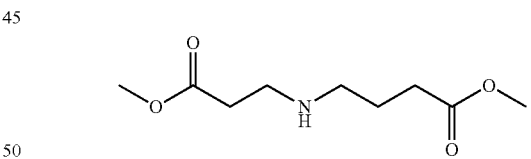

Methyl 3-(benzylamino)propanoate (1 g, 5.2 mmol), methyl 4-bromobutanoate (1.2 g, 6.2 mmol), and diisopropylethylamine (1.34 mL, 7.8 mmol) were stirred in DMF (5 mL) at 65° C. for 4 hours. Most of the solvent was removed by rotary evaporator and the crude material was purified by silica gel chromatography (Isco, 0 to 9% methanol in DCM, 30 minute gradient) to afford the benzyl protected intermediate as a clear oil. The benzyl protected intermediate was stirred in methanol (20 mL) under 1 atmosphere of hydrogen gas in the presence of 20% palladium hydroxide on carbon (300 mg) for 12 hours. The mixture was filtered through celite and concentrated to afford the title compound as a clear oil. Yield 0.72 g, 69%. Ion found by LCMS: [M+H]+=204.2.

943

Step d.

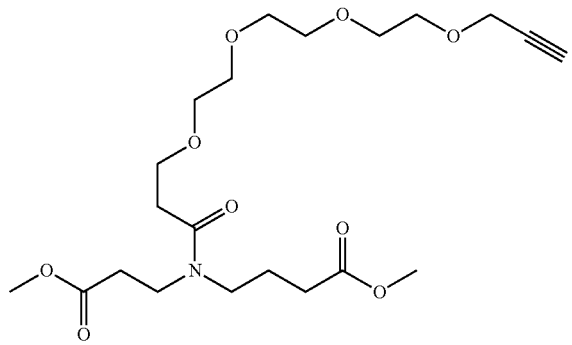 [SMILES: C#CCOCCOCCOCCOCCC(=O)N(CCCC(=O)OC)CCC(=O)OC]

The step-c product (0.70 g, 2.16 mmol), propargyl PEG-4 acid (0.63 mg, 2.38 mmol) HATU (1.26 g, 3.24 mmol) in DMF (2 mL) were stirred at room temperature following addition of DIEA (1.15 mL, 6.49 mmol). The reaction mixture was stirred for 2 hours then purified by reverse phase liquid chromatography (Isco, 5 to 50% acetonitrile and water with 0.1% TFA as modifier). Yield 840 mg, 87%. Ion found by LCMS [M+H]+=446.2.

944

Step e.

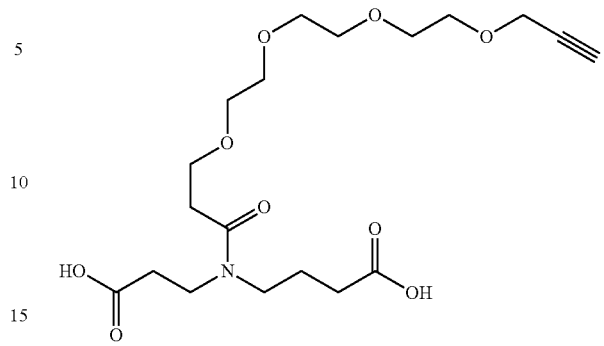

A solution of step-d product (840 mg, 1.85 mmol) and LiOH (113.1 mg, 4.72 mmol) in H$_2$O:MeOH (1:2, 9 mL) was stirred at room temperature for 2 hours. Then the reaction was acidified with TFA. The resulted solution was concentrated then purified by reverse phase liquid chromatography (Isco, 0% to 20% acetonitrile and water). Yield 454.5 mg, 59%. Ion found by LCMS [M+H]+=418.2.

Step f.

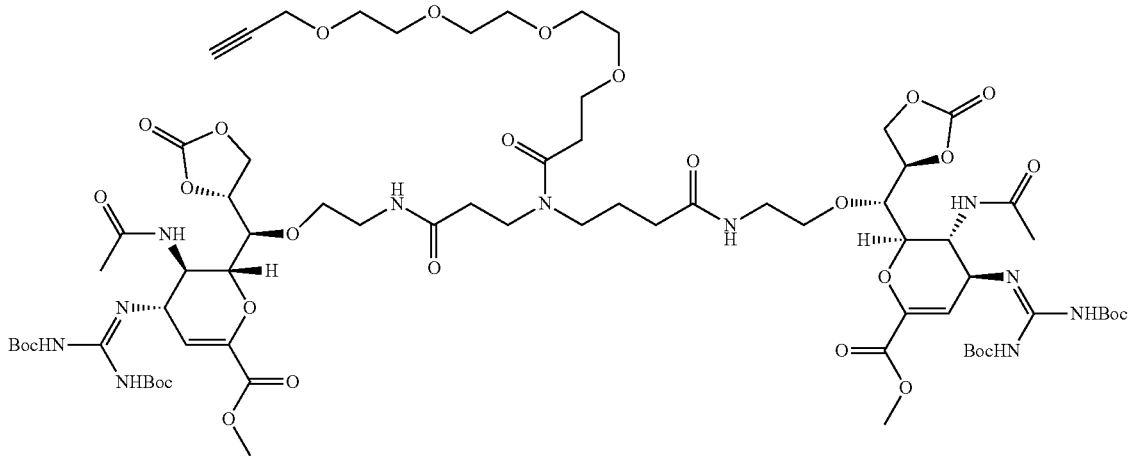 [SMILES: C#CCOCCOCCOCCOCCC(=O)N(CCCC(=O)NCCO[C@@H]([C@@H]1OC(C(=O)OC)=C[C@H](N=C(NC(=O)OC(C)(C)C)NC(=O)OC(C)(C)C)[C@H]1NC(C)=O)[C@H]1COC(=O)O1)CCC(=O)NCCO[C@@H]([C@@H]1OC(C(=O)OC)=C[C@H](N=C(NC(=O)OC(C)(C)C)NC(=O)OC(C)(C)C)[C@H]1NC(C)=O)[C@H]1COC(=O)O1]

To a solution of step-b product (334.7 mg, 0.52 mmol), step-e product (102 mg, 0.24 mmol) and HATU (273.25 mg, 0.704 mmol) in anhydrous DMF (3 mL) at room temperature was added DIEA (217 mg, 16.4 mmol). The resulting mixture was stirred for 1 hour then was purified by RPLC (20% to 100% methanol and water without modifier). Yield 206.5 mg, 55%. Ion found by LCMS [(M+2H)/2]+=806.8.

Step g.

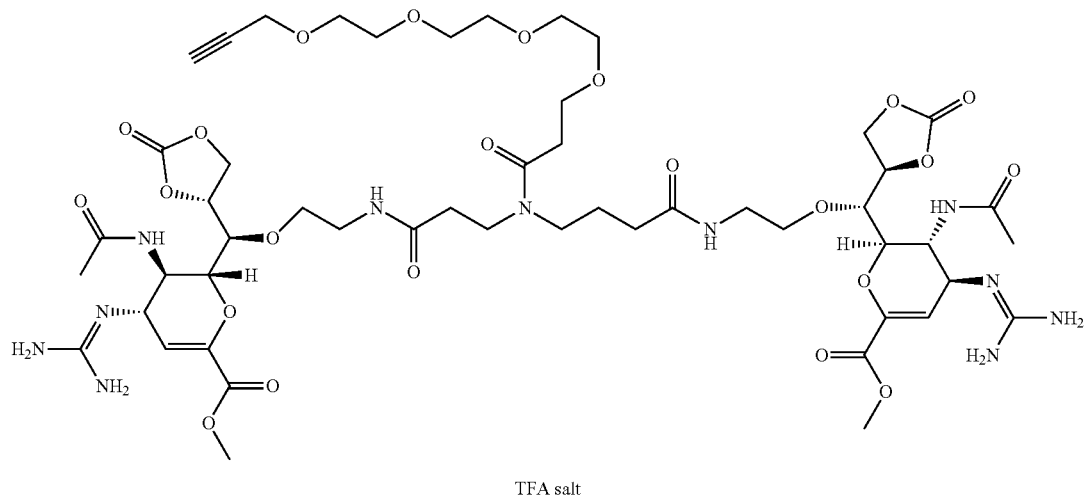 [SMILES: C#CCOCCOCCOCCOCCC(=O)N(CCCC(=O)NCCO[C@@H]([C@@H]1OC(C(=O)OC)=C[C@H](N=C(N)N)[C@H]1NC(C)=O)[C@H]1COC(=O)O1)CCC(=O)NCCO[C@@H]([C@@H]1OC(C(=O)OC)=C[C@H](N=C(N)N)[C@H]1NC(C)=O)[C@H]1COC(=O)O1]

TFA salt

The step-f product (206.5 mg, 0.128 mmol) and TFA (3 mL) in $CH_2Cl_2$ (5 mL) was stirred at room temperature overnight, then concentrated under reduced pressure. The resulting residue was purified by semi-preparative HPLC (0% to 30% acetonitrile and water with 0.1% TFA as modifier). Yield 144.5 mg, 69%. Ion found by LCMS [(M+2H)/2]+=606.8.

Step h.

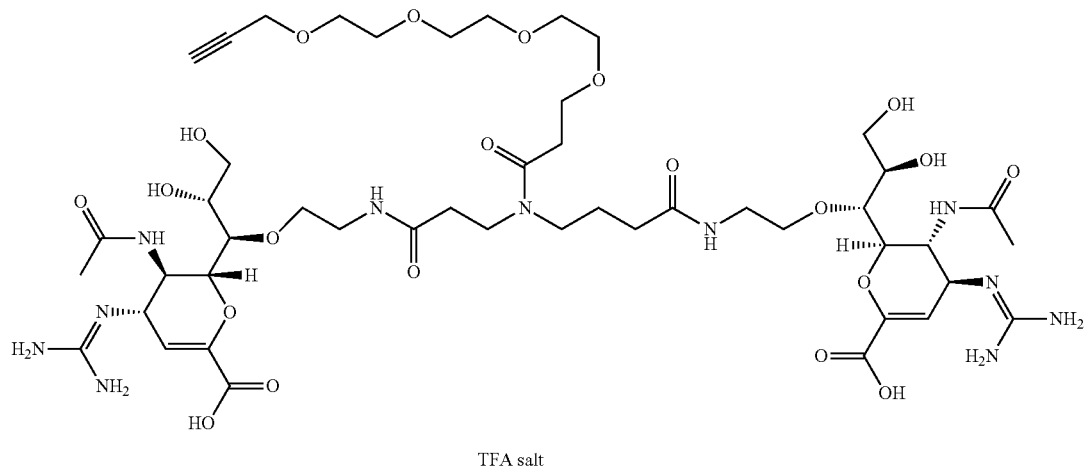 [SMILES: C#CCOCCOCCOCCOCCC(=O)N(CCCC(=O)NCCO[C@@H]([C@@H]1OC(C(=O)O)=C[C@H](N=C(N)N)[C@H]1NC(C)=O)[C@H](O)CO)CCC(=O)NCCO[C@@H]([C@@H]1OC(C(=O)O)=C[C@H](N=C(N)N)[C@H]1NC(C)=O)[C@H](O)CO]

TFA salt

To a solution of the step-g product (144.5 mg, 0.119 mmol) in MeOH (9 mL) and water (3 mL) was added LiOH (18 mg, 0.75 mmol). The resulting solution was stirred at room temperature for 1 hour, then acidified with TFA and concentrated under reduced pressure. The residue was purified by semi-preparative HPLC (0% to 25% acetonitrile and water, using 0.1% TFA as modifier). Yield 45 mg, 28%. Ions found by LCMS [(M+2H)/2]+=566.8.

Example 139. Synthesis of conjugate 42

A solution of azido functionalized Fc (50 mg, 5.4 mL, 0.859 μmol, Example 124, SEQ ID NO: 18) was added to a 10 mL centrifuge tube containing alkyne derivatized small molecule (7.87 mg, 0.057 mmol, Example 138). After gently shaking to dissolve all solids, the mixture was added to 3 mL premixed solution of L-ascorbic acid sodium (0.68 mg, 0.34 mmol, 0.25 M), copper (II) sulfate (1.1 mg, 0.0069 mmol, 0.005 M) and BTTAA (11.8 mg, 0.027 mmol, 0.02 M) in PBS 7.4 buffer. The resulting solution was gently rotated overnight. It was purified by affinity chromatography over a protein A column, followed by size exclusion chromatography (See general conjugate purification protocol). Maldi TOF analysis of the purified final product gave an average mass of 63623 Da (DAR 3.8). Yield 36.01 mg, 72%.

Example 140. Synthesis of Int-80
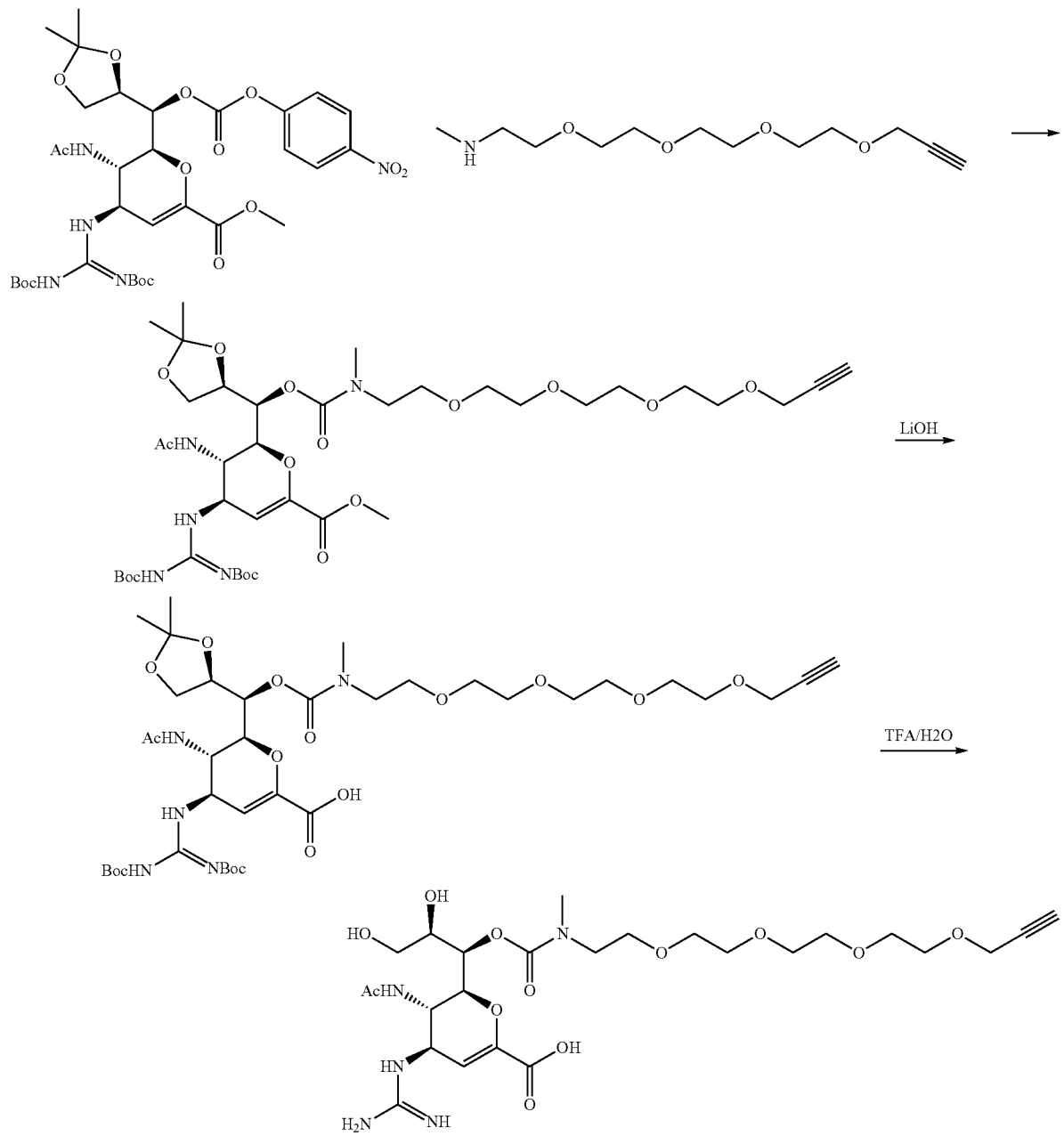
Step a.
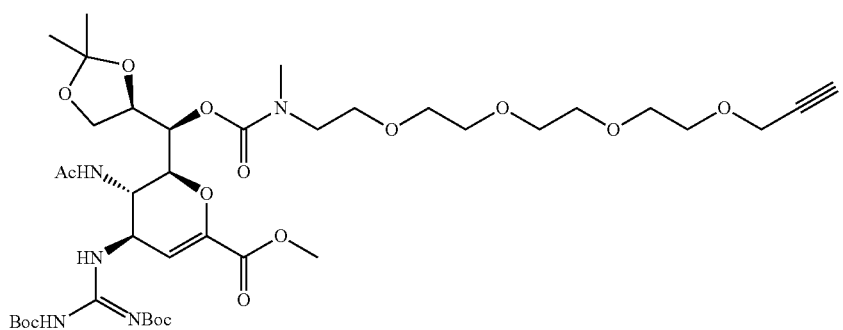

To a solution of the p-nitrophenyl carbonate of Zanamivir (0.3 g. 0.4 mmol, Example 103) in anhydrous dichloromethane (5 ml) was added a propargyl-PEG4-methylamine (0.11 g, 0.44 mmol) and DIPEA (0.14 ml, 1.0 mmol) in anhydrous DMF (5 ml). The reaction was stirred at room temperature overnight, then concentrated and purified by flash chromatography eluting with 0% to 10% methanol/dichloromethane. Yield 0.28 g, 81%. Ions found by LCMS: $(M+H)^+=858.4$, $(M-Boc)^+H^+=758.4$.

Step b.

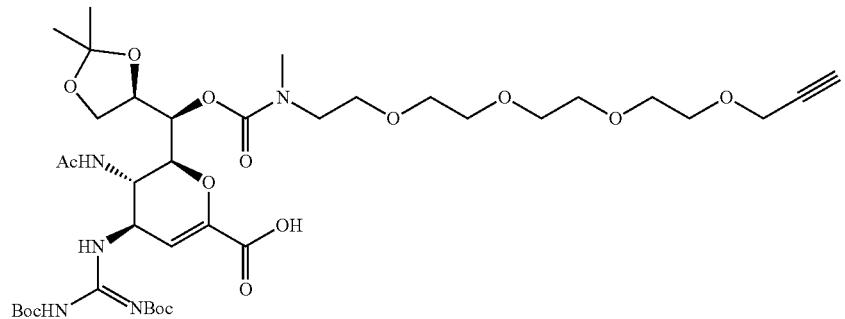

Product from the previous step (280 mg, 0.2 mmol) was dissolved into 2 ml MeOH and 2 ml THF, then treated with a solution of lithium hydroxide (24 mg, 1 mmol) dissolved in 2 ml water. The reaction was stirred for 10 min at room temperature at which time HPLC showed the reaction was complete. The pH of the reaction was adjusted to the value of 5 to 6 by using Amberlite IRN-77 ion exchange resin, then filtered to remove the resin. The crude filtrate was evaporated to dryness under a vacuum and used in the next step with purification, and the yield was quantitative. Ion(s) found by LCMS: $(M+H)^+=844.4$, $(M-Boc+H)^+=744.4$.

Step c.

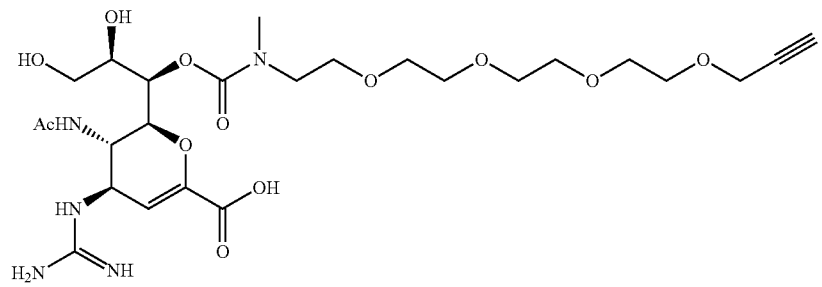 [SMILES: C#CCOCCOCCOCCOCCN(C)C(=O)O[C@@H]([C@H]1OC(C(=O)O)=C[C@@H](NC(=N)N)[C@@H]1NC(C)=O)[C@H](O)CO]

The step-b product was dissolved into 2 ml dichloromethane and 2 ml TFA, and stirred at room temperature. The progress of the reaction was monitored by LCMS. After the completion of the reaction (6 h), the solution was stripped to dryness and then dissolved in 2 ml water and 2 ml acetonitrile. The resulting solution was stirred for another 2 hour at room temperature at which time LCMS show complete deprotection of the acetonide protecting groups. This mixture was concentrated and purified by reverse phase liquid chromatography (RPLC) using an Isco COMBIFLASH® liquid chromatograph eluted with 5% to 40% acetonitrile/water with 0.1% TFA as the modifier. Yield 180 mg, 78.0%. Ion(s) found by LCMS: $(M+H)^+=604.2$.

Example 141. Stability Data for Int-80 Compared to Int-4

Int-80 (Example 140) and Int-4 (Example 13) were solubilized to 10 mg/mL in deionized water and then diluted 1:10 into 1×PBS to a final concentration of 1 mg/mL. Samples were incubated at 37° C. or 60° C. for 1 week. A 25 μL aliquot was diluted into 75 μL of water for HPLC analysis. Using a Waters Acquity H-Class UPLC with a Phenomenex Biozen PS-C18 column (150×2.1 mm, 1.6 um) a gradient of 0.1% formic acid in water to 0.1% formic acid in acetonitrile was run as follows: 5% B for 0-1 min, 5-20% B from 1-20 min. Detection was at 240 nm using a diode array detector. Int-80 had less than 1% degradation over a week at 60° C., while Int-4 showed 15% degradation over the same time period (FIG. 66)

Example 142. Synthesis of Conjugate 43

Preparation of the Click reagent solution: 0.0050M $CuSO_4$ in PBS×1 buffer solution: 10.0 mg $CuSO_4$ was dissolved in 12.53 mL PBS×1, than took 10.00 mL this $CuSO_4$ solution and added 86.1 mg BTTAA and 495.3 mg Na Ascorbate to give the Click reagent solution (0.0050M $CuSO_4$, 0.020M BTTAA and 0.25M Sodium Ascorbate).

A solution of azido functionalized Fc (78.0 mg, 4.535 mL, 1.35 μmol, Example 124, SEQ ID NO: 73) was added to a 15 mL centrifuge tube containing alkyne derivatized small molecule (13.2 mg, 8.88 μmol, Int-80, Example 140). After gently shaking to dissolve all solids, the mixture was added with 2.153 mL of above Click reagent solution of (L-ascorbic acid sodium, 0.25 M, 106.6 mg, 0.538 mmol, copper (II) sulfate 0.0050M, 1.72 mg, 0.0107 mmol, and BTTAA 0.020M, 18.5 mg, 0.0431 mmol). The resulting mixture was gently rotated for 6 hours at ambient temperature. It was purified by affinity chromatography over a protein A column, followed size exclusion chromatography (See conjugate purification protocol). Maldi TOF analysis of the purified final product gave an average mass of 64,012 Da (DAR=7.0). Yield 50.3 mg, 62% yield.

The nucleic acid construct encoding the Fc for conjugate 43 included a nucleic acid encoding the amino acid sequence of SEQ ID NO: 64, which includes a C-terminal lysine residue. Upon expression, the C-terminal lysine of the Fc of conjugate 43 is proteolytically cleaved, resulting in an Fc having the sequence of SEQ ID NO: 73. The presence or absence of a C-terminal lysine does not alter the properties of the Fc or the corresponding conjugate.

Example 143. Synthesis of Int-81

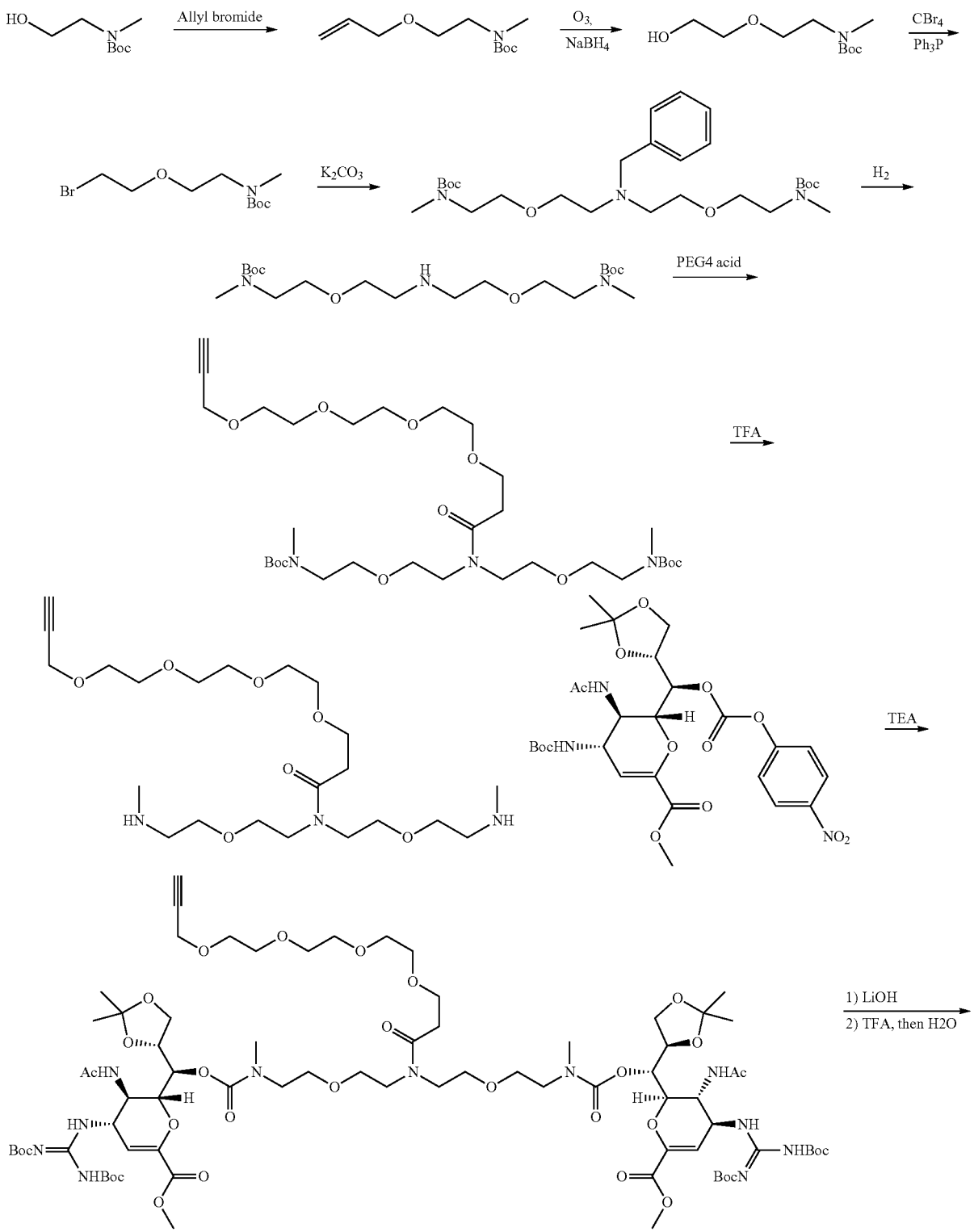

-continued

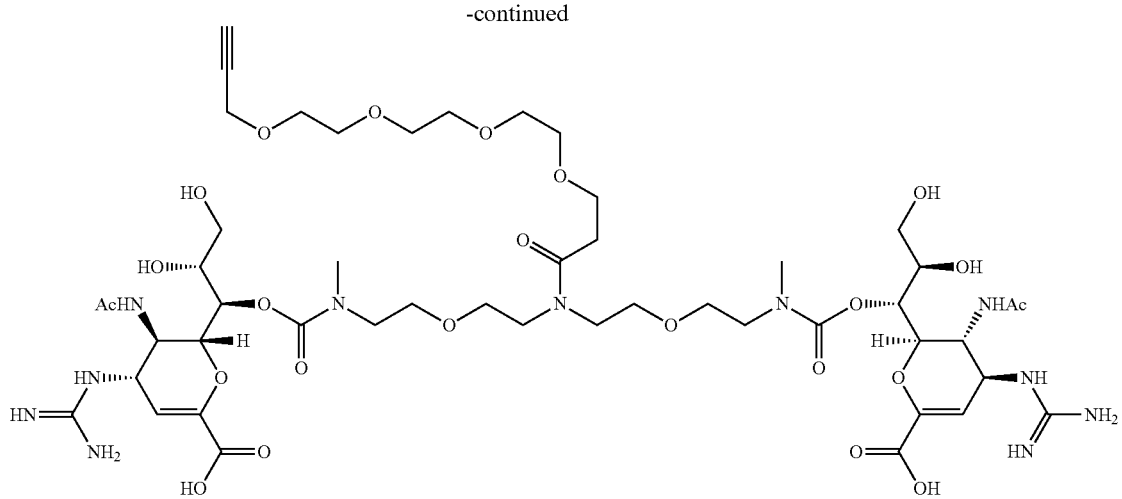

Step a.

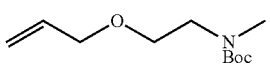

To a well-stirred solution of N-Boc-N-Me-glycinol (3.5 g, 20 mmol) in DMSO (20 mL) cooled with an ice-water bath was add allyl bromide (3.6 g, 30.0 mmol), followed by finely ground KOH powder (3.5 g, 30.0 mmol) over 15 minutes. The resulting solution was stirred for overnight at room temperature. The resulting mixture was partitioned between 5% aq. HOAc (50 mL) and ethyl acetate (200 ml). The organic layer was separated, washed with brine, dried with sodium sulfate, filtered, and concentrated, then purified by flash chromatography eluting with 10% to 80% ethyl acetate/hexane. Yield of product 4.1 g, 95%. Ion(s) found by LCMS: M+H=216.3.

Step b.

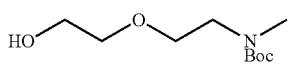

Ozone was bubbled through a solution of the compound from step a (8.0 g, 37 mmol) in MeOH (50 mL) and DCM (50 ml) at −78° C. until the appearance of a light blue color. Unreacted ozone was removed by bubbling with oxygen for 10 minutes before the addition of NaBH₄ (1.6 g, 40 mmol) in small portion over 10 minutes. After all NaBH₄ was added the mixture was gradually warmed to room temperature. The resulting solution was partitioned between ethyl acetate (100 ml) and brine (50 ml). The organic layer was separated, washed with brine, dried with sodium sulfate, filtered, concentrated to an oil, and then purified by flash chromatography eluting with 10% to 80% ethyl acetate/dichloromethane. Yield of product 5.0 g, 62%. Ion(s) found by LCMS: M+H=220.2.

Step c.

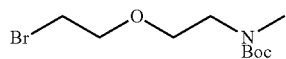

To a solution of the product (4.4 g, 20 mmol) from the previous step and CBr₄ (10.0 g, 30.0 mmol) in DCM (50 mL) at 0° C. was added PPh₃ (8.0 g, 30 mmol) slowly over 15 minutes (exothermic). During the course of the addition the internal temperature was kept below 30° C. After addition of PPh₃ the reaction was stirred overnight at room temperature. The crude reaction was concentrated to an oil then purified by normal phase chromatography, eluting with 10% ethyl acetate/hexanes to 80% ethyl acetate/hexanes. Fractions containing oil droplets on the inside of the collection tubes were combined and concentrated to a colorless oil. 4.0 g, 70.5%. Ion(s) found by LCMS: M+H=282.1.

Step d.

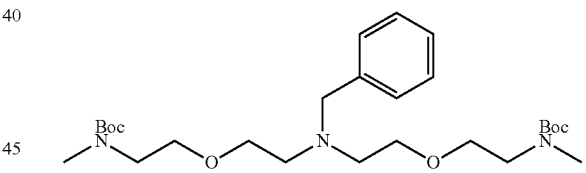

A solution of the step c product (4 g, 14 mmol), benzylamine (0.60 g, 5.7 mmol), and K₂CO₃ (2.35 g, 17 mmol) in DMF (20 mL) were heated in an oil bath at 75° C. for 8 h. The mixture was filtered, concentrated, and purified by RPLC (5% ACN/water to 100% ACN). Yield 2.1 g, 72.7%.

Step e.

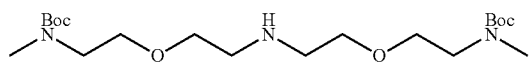

To a solution of the step-d product (1.3 g, 2.0 mmol) dissolved in CHCl₃/EtOH (1:20, 20 mL) was added 20% Pd(OH)₂/C (0.50 g). The reaction was stirred overnight under hydrogen from a balloon at ambient temperature. The reaction mixture was filtered through a Celite pad, then concentrated by way of rotary evaporator and carried to the subsequent step without further purification.

955

Step f.

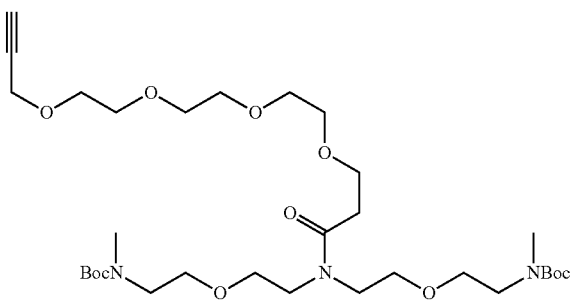 [SMILES: C#CCOCCOCCOCCOCCC(=O)N(CCOCCN(C)C(=O)OC(C)(C)C)CCOCCN(C)C(=O)OC(C)(C)C]

The step-e product was dissolved in 10 mL of DMF, then treated with propargyl PEG4 acid (0.52 g, 2.0 mmol), EDCl (0.6 g, 3.0 mmol), HOAt (0.45 g, 3 mol) and Hunig's base (0.7 mL, 5.0 mmol) at room temperature. The reaction mixture was stirred for four hours, then concentrated and purified by RPLC (10% ACN/water to 60% ACN/water). Yield 0.43 g, 65% for two steps. Ions found by LCMS: [M-Boc+H]$^+$=562.4, [M+H]$^+$=662.4.

956

Step g.

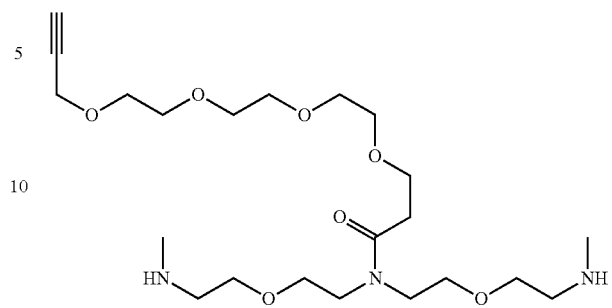

The step-d product (70 mg, 0.1 mmol) was treated with TFA (2 mL) for 2 hours at room temperature. TFA was removed by rotary evaporation, and the remaining oil was further dried under high vacuum for 12 h to give the desired product as bis-TFA salt. Yield was quantative. Ion found by LCMS: [M+H]$^+$=462.4.

Step h. 0 O$

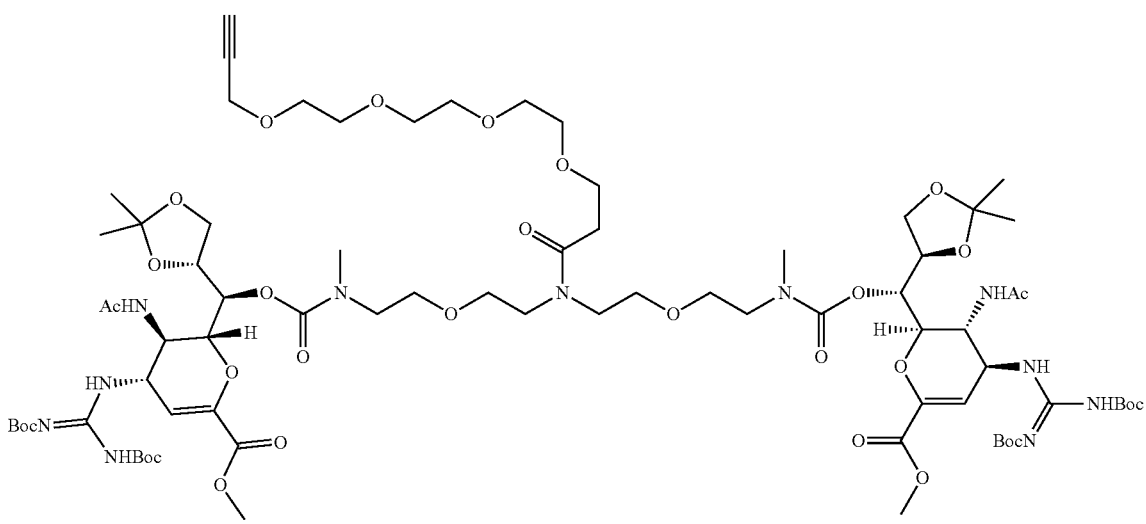

To a solution of the nitrophenyl carbonate described in the Example 109 (0.72 g. 0.95 mmol) in anhydrous DMF (5 ml) was added a mixture of the step g diamine (0.3 g, 0.43 mmol, added in portions over 30 minutes) and DIPEA (0.28 ml, 2 mmol) in anhydrous DMF (20 ml). The reaction was stirred at room temperature overnight, then concentrated and purified by flash chromatography eluting with 0% to 10% methanol/dichloromethane. Yield 0.63 g, 86%. Ions found by LCMS: [(M+2H)/2]$^+$=844.4, [(M-Boc+2H)/2]$^+$=794.4, [(M-2Boc+2H)/2]$^+$=744.4.

Step i.

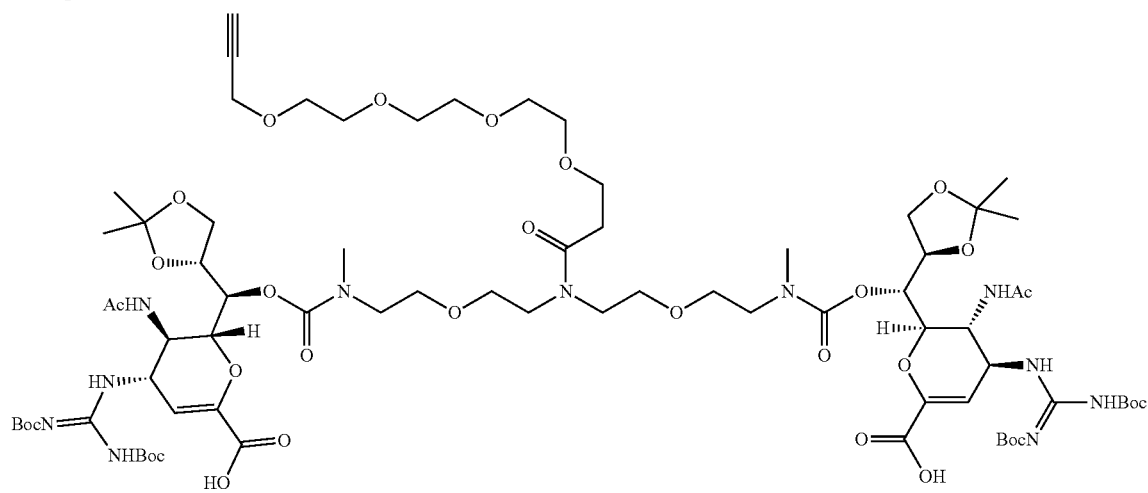

Product from the previous step (600 mg, 0.35 mmol) was dissolved into 5 ml MeOH and 5 ml THF, then treated with a solution of lithium hydroxide (48 mg, 2 mmol) dissolved in 2 ml water. The reaction was stirred for 10 min at room temperature at which time HPLC showed the reaction was complete. The pH of the reaction solution was adjusted to a value of 5 to 6 by using Amberlite IRN-77 ion exchange resin, then filtered to remove the resin. The crude product was evaporated to dryness by rotary evaporation and used in the next step with purification. Ion(s) found by LCMS: $[(M+2H)/2]^+=829.9$, $[(M-Boc+2H)/2]^+=779.4$, $[(M-2Boc+2H)/2]^+=729.4$.

Step j.

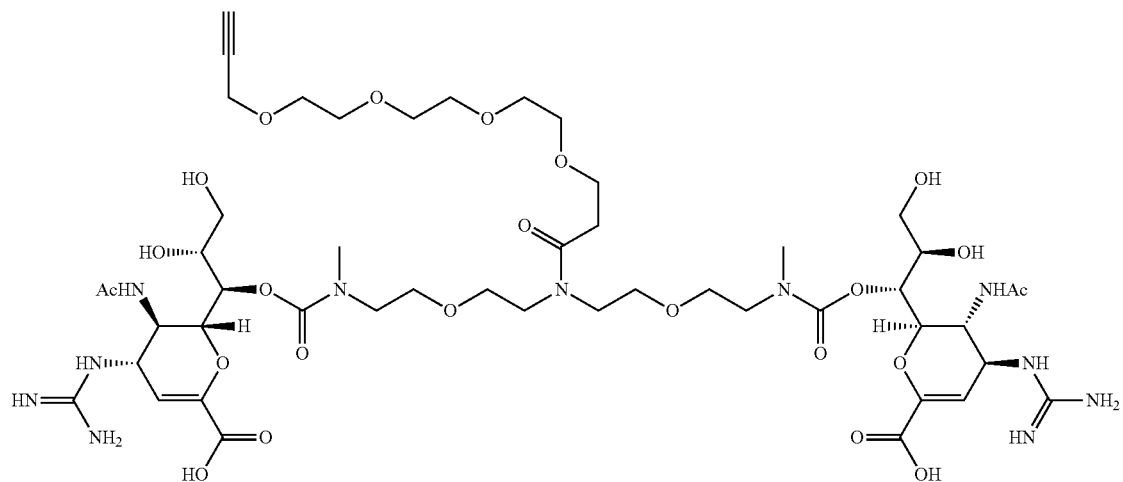 [SMILES: C#CCOCCOCCOCCOCCC(=O)N(CCOCCN(C)C(=O)O[C@@H]([C@@H]1OC(C(=O)O)=C[C@H](NC(=N)N)[C@H]1NC(C)=O)[C@H](O)CO)CCOCCN(C)C(=O)O[C@@H]([C@@H]1OC(C(=O)O)=C[C@H](NC(=N)N)[C@H]1NC(C)=O)[C@H](O)CO]

The product from step-i was dissolved into 5 ml dichloromethane and 5 ml TFA, and stirred at room temperature. The progress of the reaction was monitored by LCMS. After the completion of the reaction (6 h), the solution was stripped to dryness and then dissolved in 4 ml water and 4 ml methanol. The resulting solution was stirred for another 2 hour at room temperature at which LCMS show complete deprotection of the acetonide protecting groups. This mixture was concentrated and purified by reverse phase liquid chromatography (RPLC) using an Isco CombiFlash liquid chromatograph eluted with 5% to 40% acetonitrile/water with 0.1% TFA as the modifier. Yield 380 mg, 71.0%. Ion(s) found by LCMS: $[(M+2H)/2]^+=589.8$, $[(M+3H)/3]^+=392.5$.

Example 144. Synthesis of Int-82
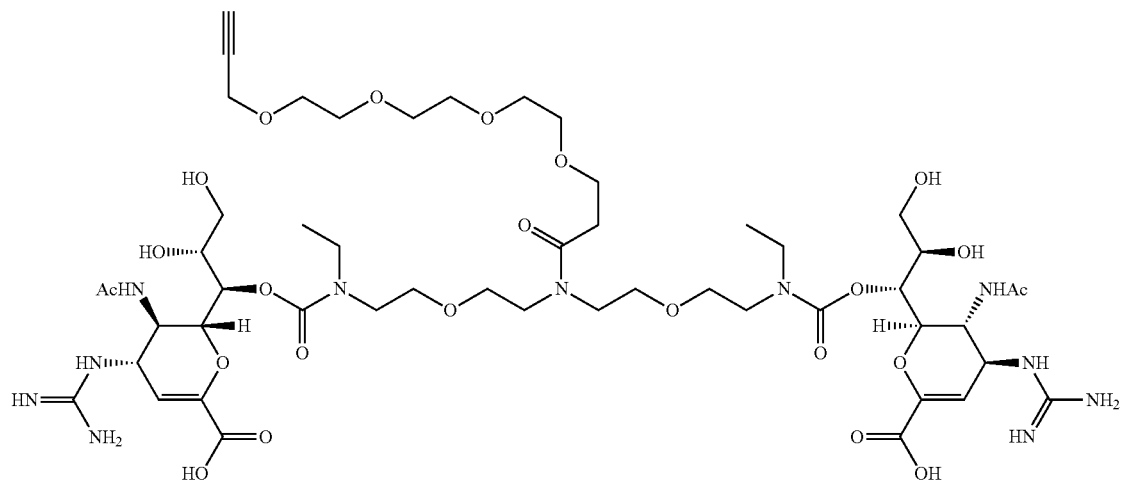 [SMILES: C#CCOCCOCCOCCOCCC(=O)N(CCOCCN(CC)C(=O)O[C@@H]([C@@H]1OC(C(=O)O)=C[C@H](NC(=N)N)[C@H]1NC(C)=O)[C@H](O)CO)CCOCCN(CC)C(=O)O[C@@H]([C@@H]1OC(C(=O)O)=C[C@H](NC(=N)N)[C@H]1NC(C)=O)[C@H](O)CO]
The title compound was prepared analogously to Example 143, Int-81, where the N-Boc-N-Me-glycinol was substituted with N-Boc-N-ethy-glycinol in the step a. Ion(s) found by LCMS: [M/2]+1=603.8, [M/3]+1=402.9.
Example 145. Synthesis of Int-83
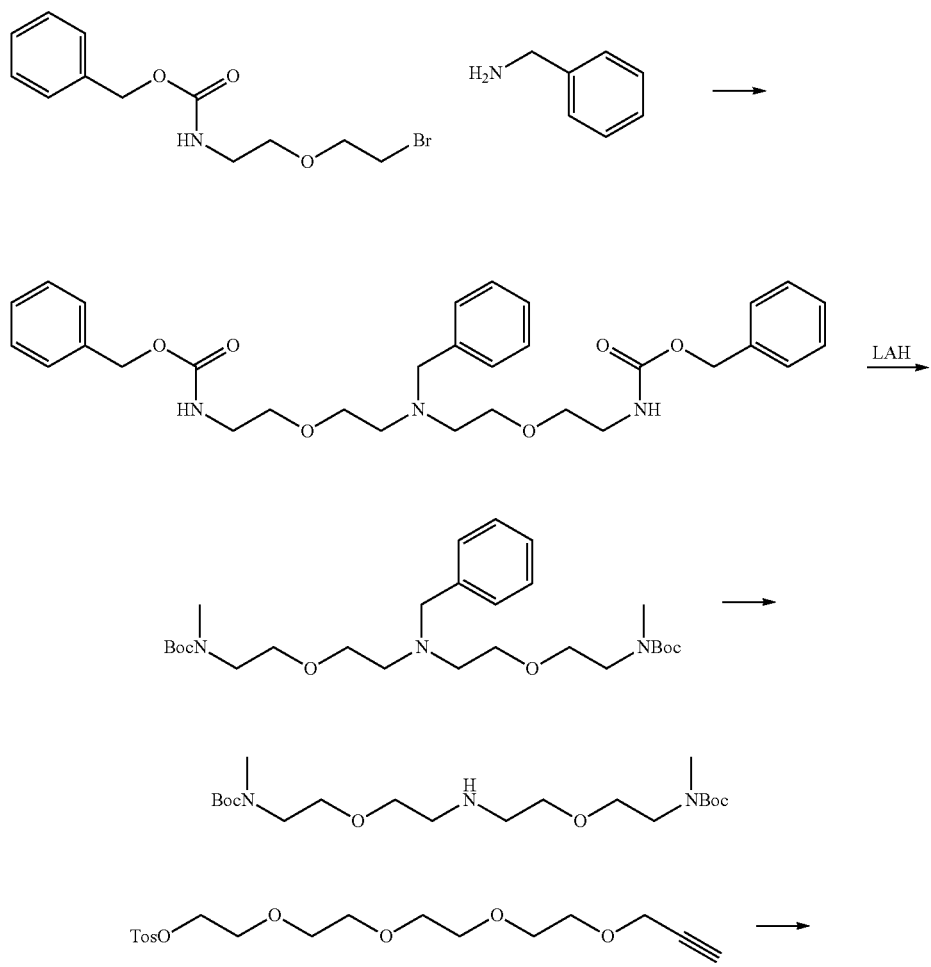

961
-continued
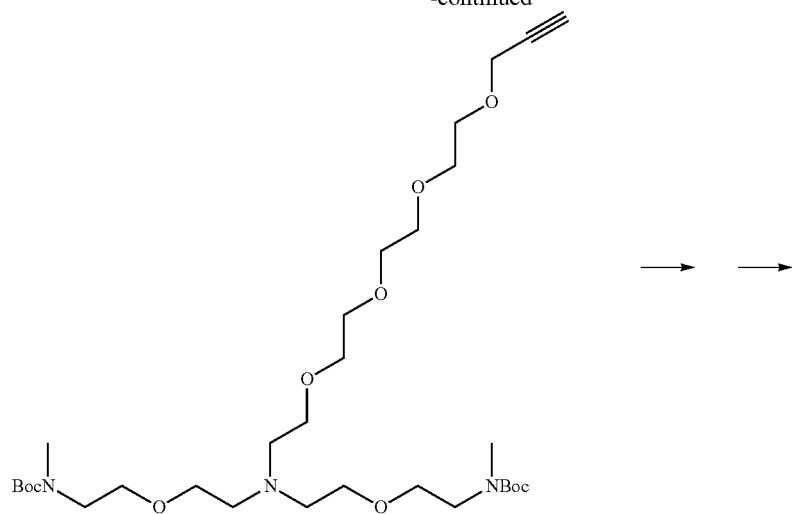
962
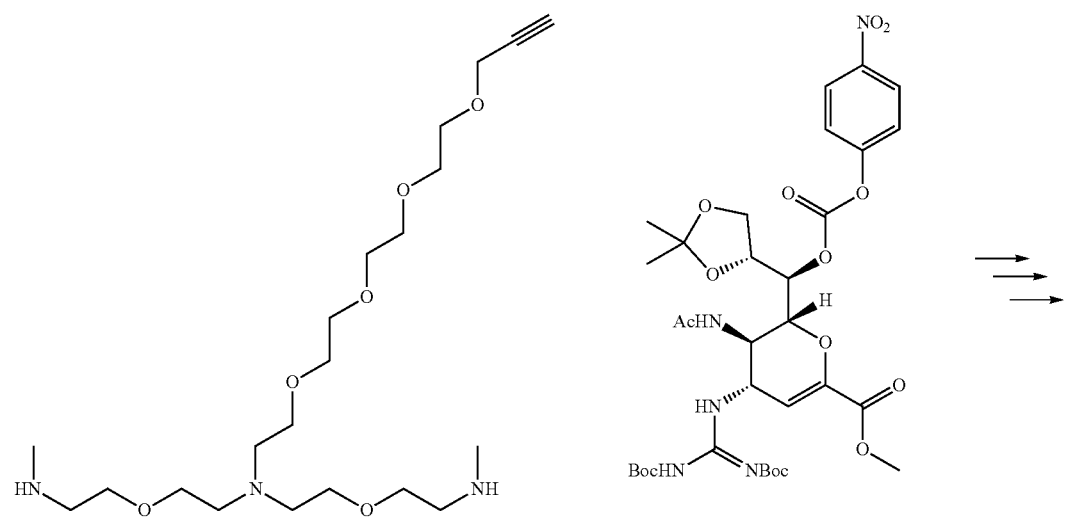

-continued

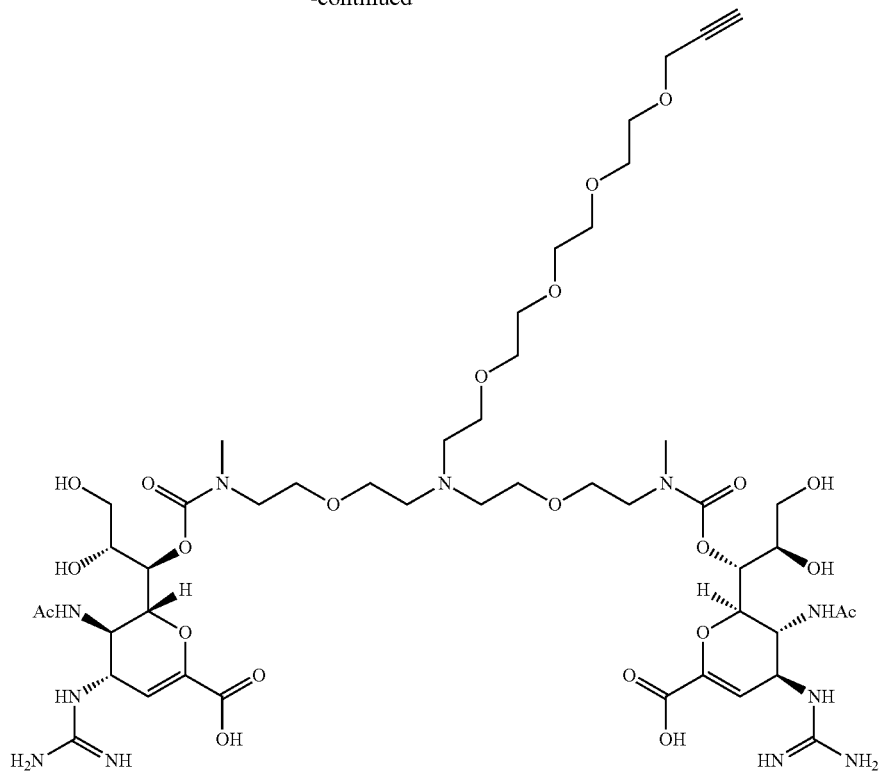

Step a.

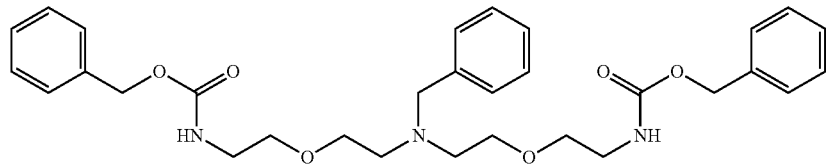 [SMILES: O=C(NCCOCCN(CCOCCNC(=O)OCc1ccccc1)Cc1ccccc1)OCc1ccccc1]

The CBZ-protected-amino-peg1-bromide (7.6 g, 25.2 mmol), benzylamine (1.1 g, 10.1 mmol), and potassium carbonate (2.8 g, 2.8 mmol) were stirred in DMF (10 mL) at 60° C. for 12 hours. The solution was concentrated on the rotary evaporator and purified by silica gel chromatography (0-10% methanol in DCM, 30 minute gradient) to afford the product as a clear viscous oil. Yield 3.2 grams, 57%. Ion found by LC/MS [M+H]+=550.2.

Step b.

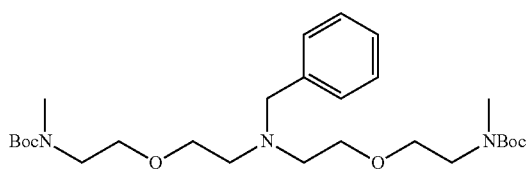 [SMILES: CN(CCOCCN(CCOCCN(C)C(=O)OC(C)(C)C)Cc1ccccc1)C(=O)OC(C)(C)C]

The product of step a (1.9 g, 3.5 mmol) was dissolved in THF (20 mL) and cooled to 0° C. by way of an ice/water bath under an atmosphere of nitrogen. LAH (6.9 ml, 13.8 mmol, 2M in THF) was added dropwise by way of syringe over a period of 10 minutes. The mixture was stirred at reflux for 2 hours then cooled to 0° C. by way of an ice/water bath. 1 mL of water was added, dropwise followed by the dropwise addition of 1 mL of aqueous (15% by weight) NaOH solution. 3 mL of water was added and the mixture was stirred for 15 minutes at which time 2 g of magnesium sulfate was added. The mixture was stirred for 10 minutes then filtered through celite, washed with 2 additional 10 ml portions of THF and the combined filtrates were concentrated by the rotary evaporator. The residue was taken up in acetonitrile (20 mL), triethylamine (1.4 g, 13.8 mmol) and boc anhydride (3.0 g, 13.8 mmol) were added. The mixture was stirred for 45 minutes, concentrated and purified by reversed phase HPLC (5-95% acetonitrile/di water, 0.1% TFA modifier, 30 minute gradient). Yield 1.4 g, 79%. Ion found by LC/MS [M+H]+=510.2.

Step c.

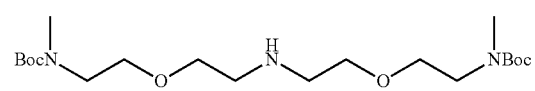 [SMILES: CN(CCOCCNCCOCCN(C)C(=O)OC(C)(C)C)C(=O)OC(C)(C)C]

The product from step b. (1 g, 1.9 mmol) of this example was stirred in methanol (25 mL) in the presence of palladium hydroxide (200 mg) under an atmosphere of hydrogen for 2 hours. The mixture was filtered through celite and concentrated to afford the product as a clear oil which was used with no further purification. Yield 0.73 g, 89%. Ion found by LC/MS [M+H]+=420.4.

Step d.

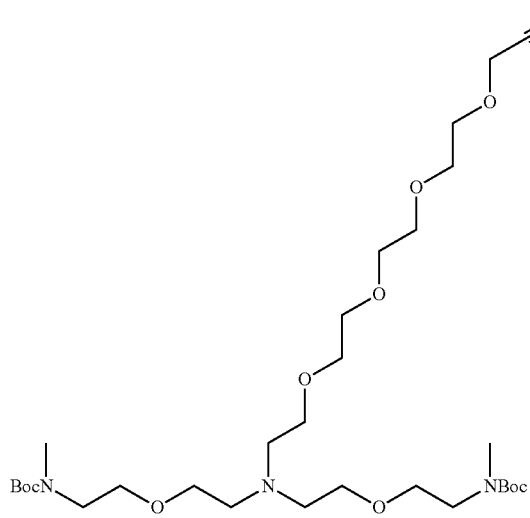

The product from step c (0.73 g, 1.7 mmol), propargyl-peg4-tosylate (0.91 g, 2.4 mmol), and diisopropylethylamine (0.76 g, 5.9 mmol) were stirred in DMF (5 mL) at 85° C. for 4 hours. The mixture was concentrated on the rotary evaporator, then purified by reversed phase HPLC (5-95% acetonitrile/DI water, 0.1% TFA modifier, 30 minute gradient) to afford the product as a clear viscous oil. Yield 0.89 g, 82%. Ion fond by LC/MS [M+H]+=634.4.

Step e.

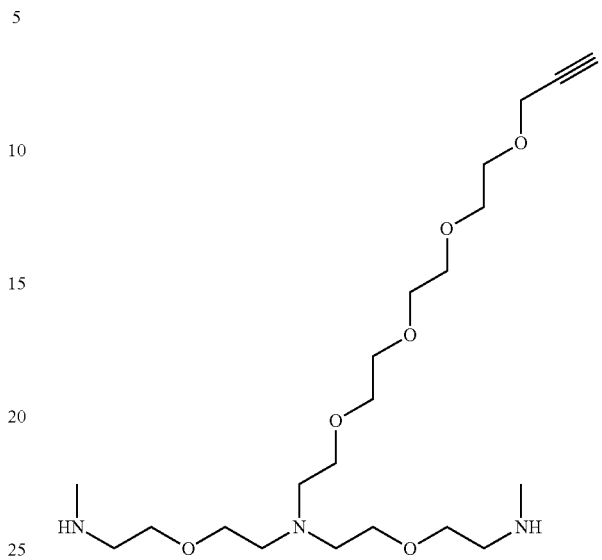

The product from step d. (0.89 g, 1.4 mml) was stirred in 4N HCl (in dioxane) for 45 minutes at ambient temperature. The mixture was concentrated on the rotary evaporator and azeotroped (3×) with benzene. The resulting residue was taken up in DI water (15 mL) frozen and lyophilized to afford the product as a clear oil, bis-HCl salt. Yield 0.65 g, 91%. Ion found by LC/MS [M+H}+=434.4.

Step f.

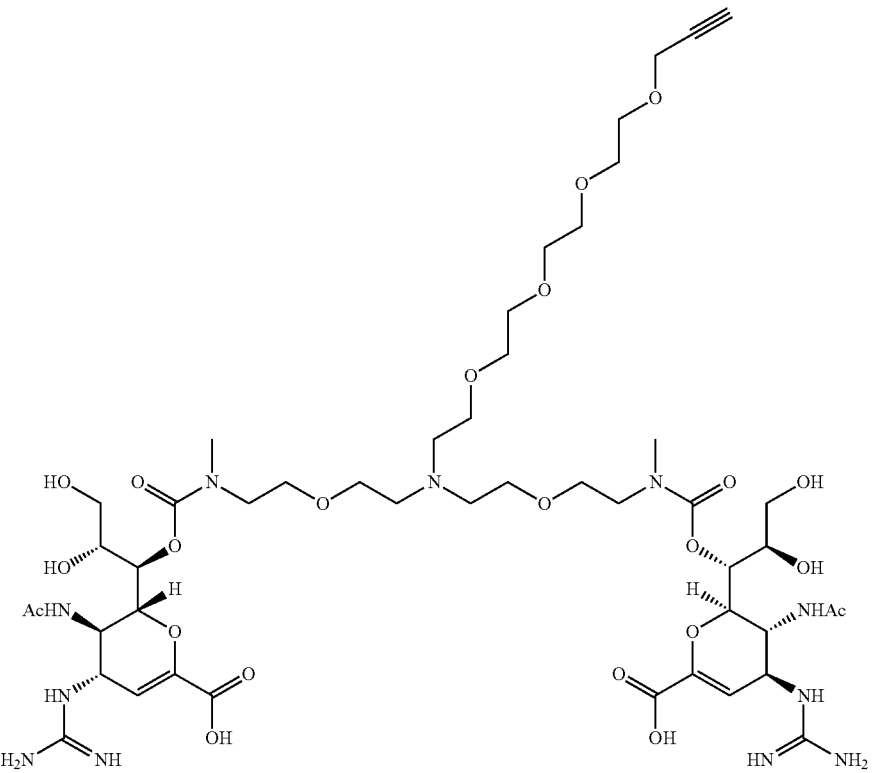 [SMILES: C#CCOCCOCCOCCOCCN(CCOCCN(C)C(=O)O[C@@H]([C@@H]1OC(C(=O)O)=C[C@H](NC(=N)N)[C@H]1NC(C)=O)[C@H](O)CO)CCOCCN(C)C(=O)O[C@@H]([C@@H]1OC(C(=O)O)=C[C@H](NC(=N)N)[C@H]1NC(C)=O)[C@H](O)CO]

The remaining four steps in the synthesis of this compound were analogous to those used in the synthesis of Example 143, Int-81. Ion(s) found by LCMS: (M+2H)/2=575.8
Example 146a. Alternate Synthesis I of Int-83
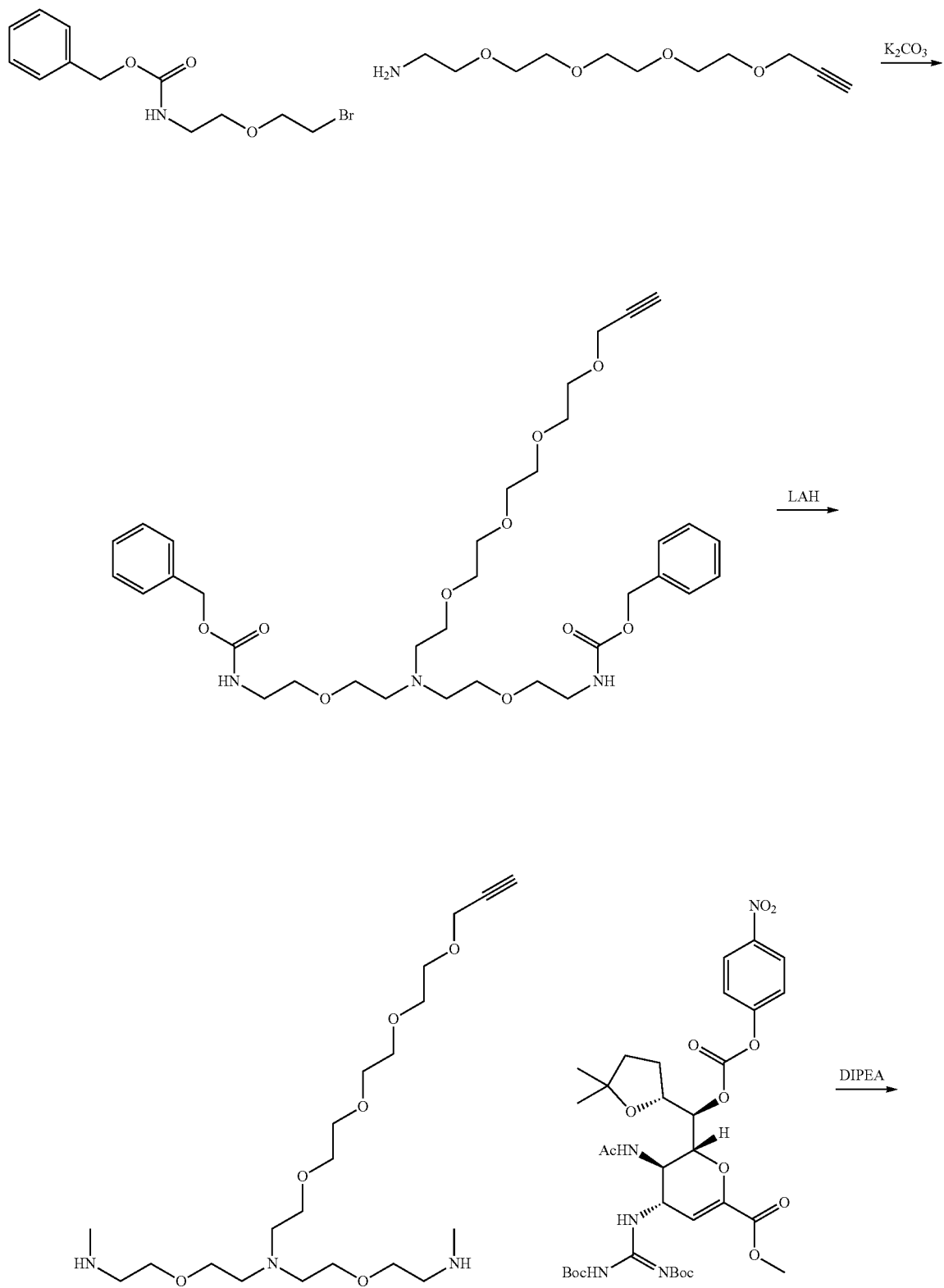

969 970
-continued
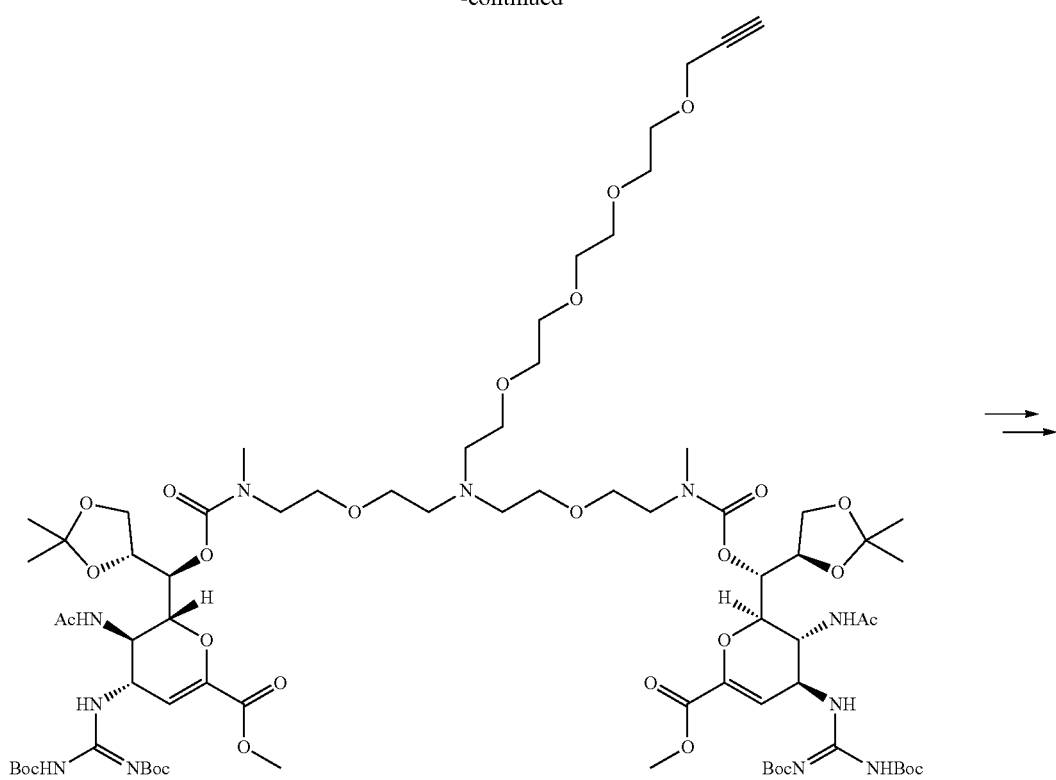
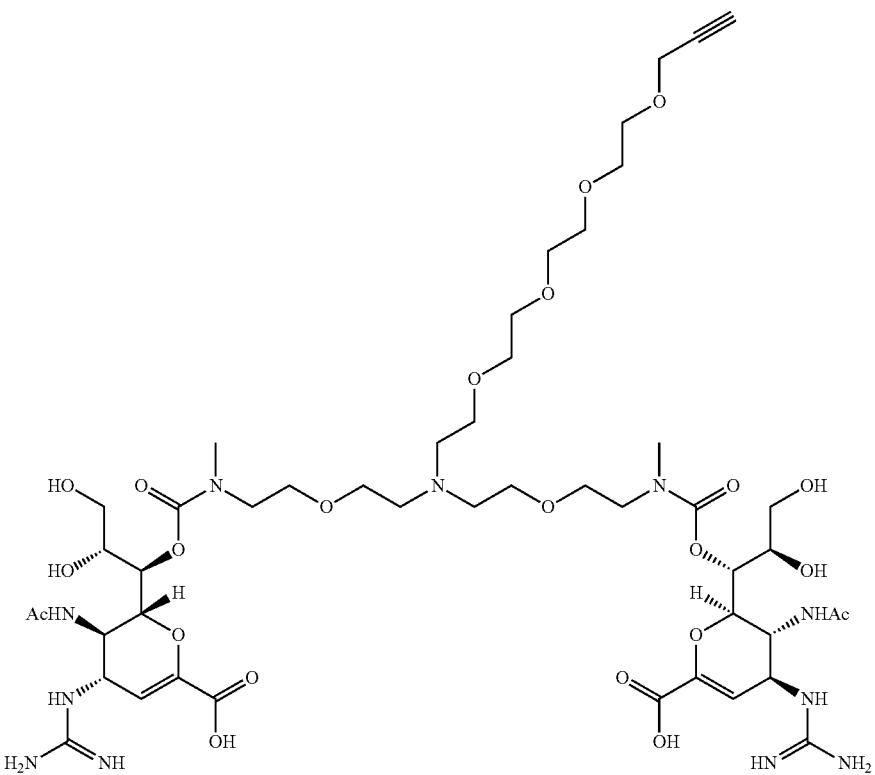

The product described in Example 145, Int-83, can be prepared alternatively using the above reaction scheme by a person skilled in the art using methods described in this patent.

Example 146b. Alternate Synthesis II of Int-83

The product described in Example 145, Int-83, can be prepared alternatively using the reaction scheme, below, by a person skilled in the art using methods described in this patent.

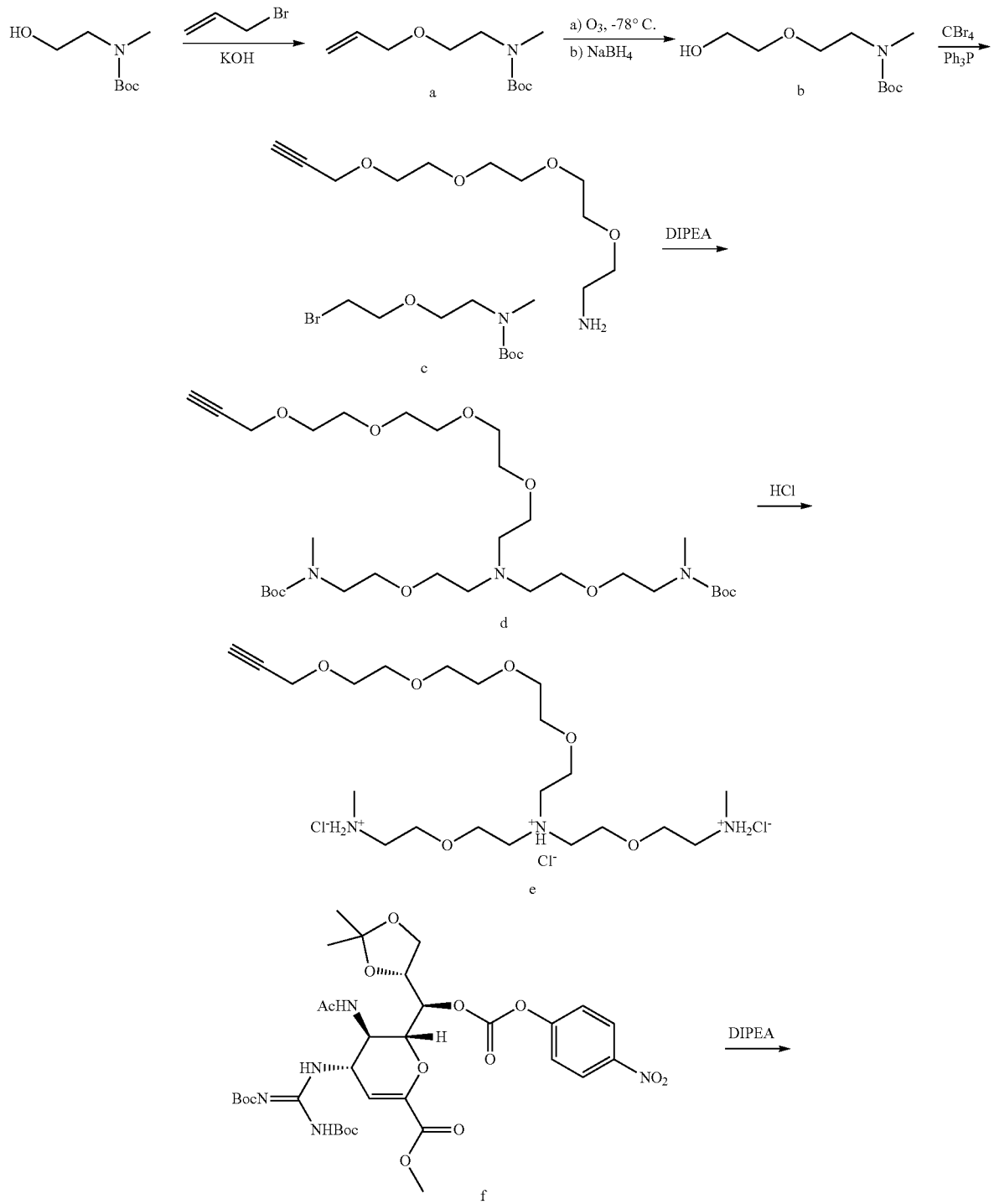

-continued

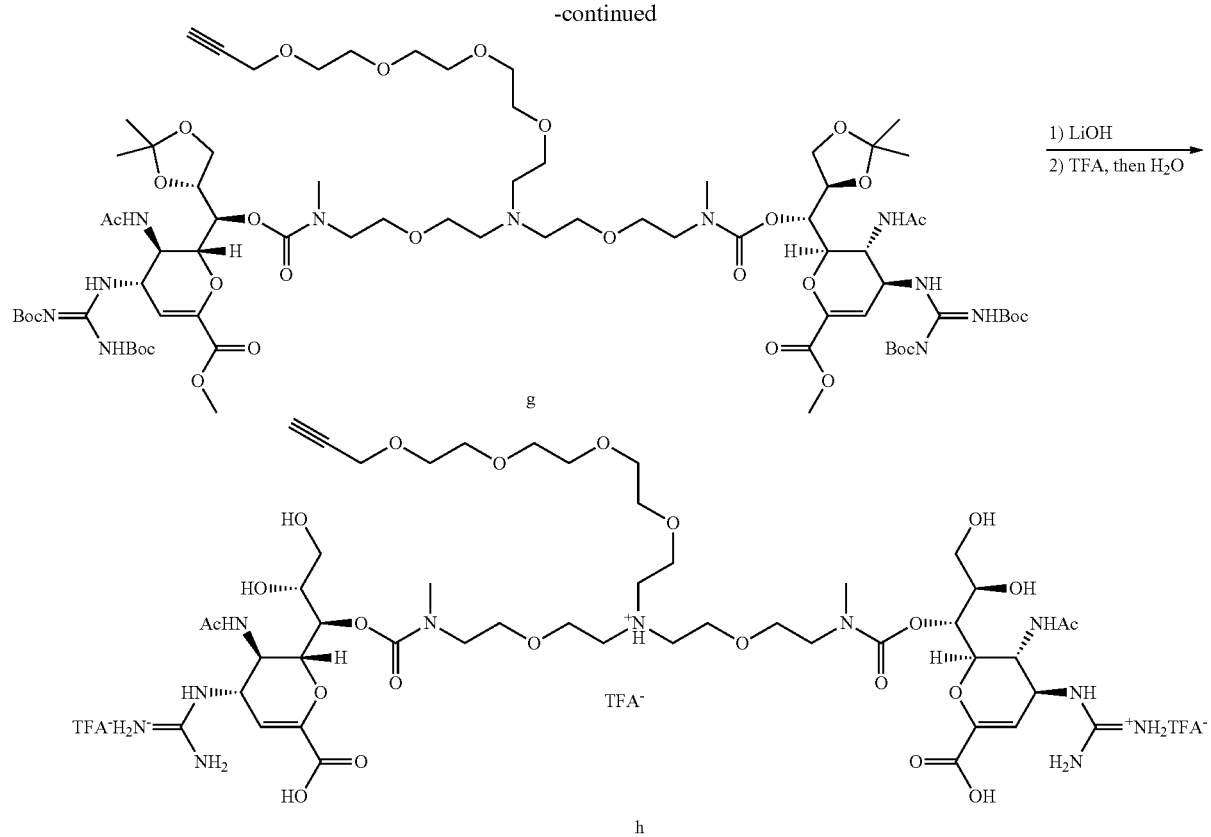

g h

Synthesis of a.

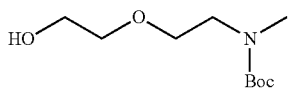

To a well-stirred solution of N-Boc-N-Me-glycinol (3.5 g, 20 mmol) in DMSO (20 mL) cooled with an ice-water bath was added allyl bromide (3.6 g, 30.0 mmol), followed by finely ground KOH powder (3.5 g, 30.0 mmol) over 15 minutes. The resulting solution was stirred overnight at room temperature. The resulting mixture was partitioned between 5% aq. HOAc (50 mL) and ethyl acetate (200 ml). The organic layer was separated, washed with brine, dried with sodium sulfate, filtered, and concentrated, then purified by flash chromatography eluting with 10% to 80% ethyl acetate/hexane. Yield of product 4.1 g, 95%. Ion found by LCMS: M+H=216.3.

Synthesis of b.

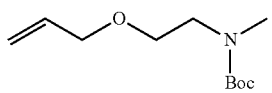

Ozone was bubbled through a solution of a (8.0 g, 37 mmol) in MeOH (50 mL) and DCM (50 ml) at −78° C. until the appearance of a light blue color. Unreacted ozone was removed by bubbling with oxygen for 10 minutes before the addition of NaBH$_4$ (1.6 g, 40 mmol) in small portions over 10 minutes. After all NaBH$_4$ was added, the mixture was gradually warmed to room temperature. The resulting solution was partitioned between ethyl acetate (100 ml) and brine (50 ml). The organic layer was separated, washed with brine, dried with sodium sulfate, filtered, concentrated to an oil, and then purified by flash chromatography eluting with 10% to 80% ethyl acetate/dichloromethane. Yield of product 5.0 g, 62%. Ion(s) found by LCMS: M+H=220.2.

Synthesis of c.

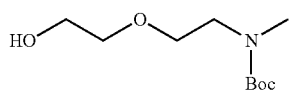

To a solution of b (4.4 g, 20 mmol) and CBr$_4$ (10.0 g, 30.0 mmol) in DCM (50 mL) cooled in an ice bath, was added PPh$_3$ (8.0 g, 30 mmol) slowly over 15 minutes (exothermic). During the course of the addition, the internal temperature was kept below 30° C. After addition of PPh$_3$ the reaction was stirred overnight at room temperature. The crude reaction was concentrated to an oil, then purified by normal phase chromatography, eluting with 10% ethyl acetate/hexanes to 80% ethyl acetate/hexanes. Fractions containing oil droplets on the inside of the collection tubes were checked by LCMS, then combined and concentrated to a colorless oil. 4.0 g, 70.5%. Ion(s) found by LCMS: M+H=282.1.

Synthesis of d.

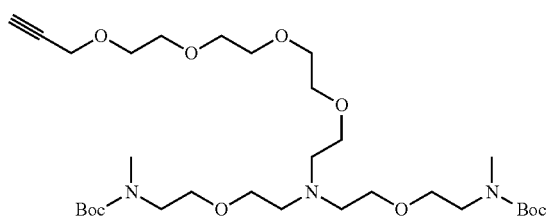 [SMILES: C#CCOCCOCCOCCOCCN(CCOCCN(C)C(=O)OC(C)(C)C)CCOCCN(C)C(=O)OC(C)(C)C]

A solution of c (4.4 g, 15.5 mmol), propargyl-PEG4-amine (1.5 g, 6.4 mmol), and DIPEA (3.3 g, 25.8 mmol) in DMF (20 mL) were heated in an oil bath at 75° C. for 18 h. The mixture was filtered, concentrated, and purified by RPLC (5% ACN/water to 100% ACN). Yield 3.85 g, 92%. LC/MS: [M+H]=634.2.

Synthesis of e.

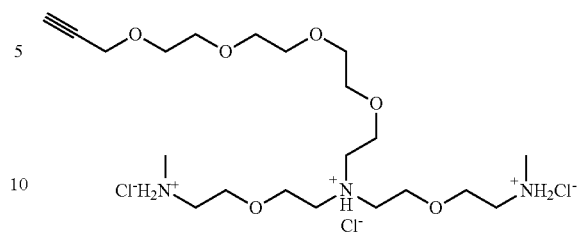

The product d (3.85, 6.1 mmol) was treated with HCl (4 N in dioxane, 15 mL) for 2 hours at room temperature. The solvent was removed by rotary evaporation, and the remaining oil was dissolved in di water (20 mL) frozen, and lyophilized to afford the product as a light yellow oil. Yield was quantitative. Ion found by LCMS: [M+H]$^+$=434.2.

Synthesis of f.

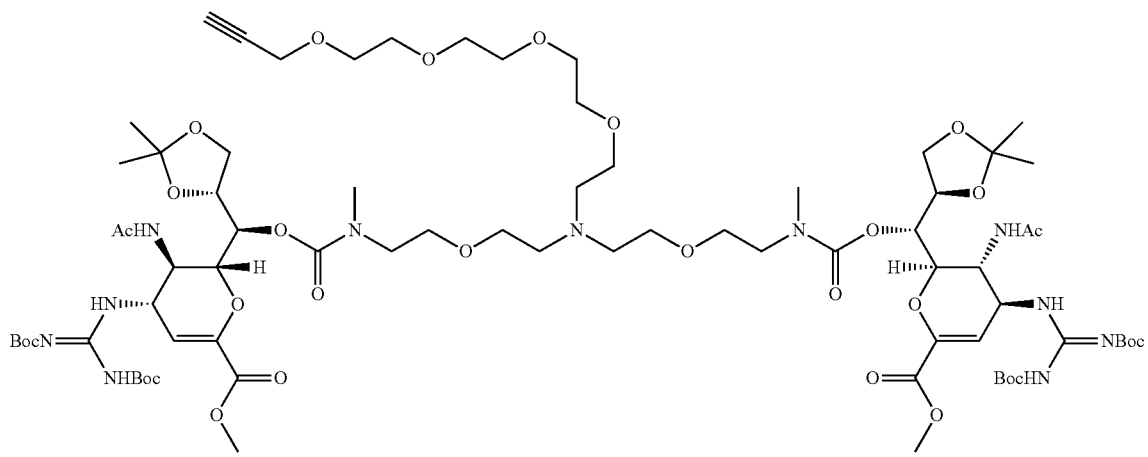

To a solution of f (0.68 g, 1.34 mmol) and DIPEA (0.87 g, 6.7 mmol) dissolved in anhydrous DMF (5 ml) was added f (2.1 g, 2.8 mmol) in portions over 1 hour. The reaction was stirred at room temperature overnight, then concentrated and purified by flash chromatography, eluting with 0% to 10% methanol/dichloromethane. Yield 1.45 g, 67%. Ion found by LCMS: [(M+2H)/2]$^+$=829.8.

Synthesis of g.

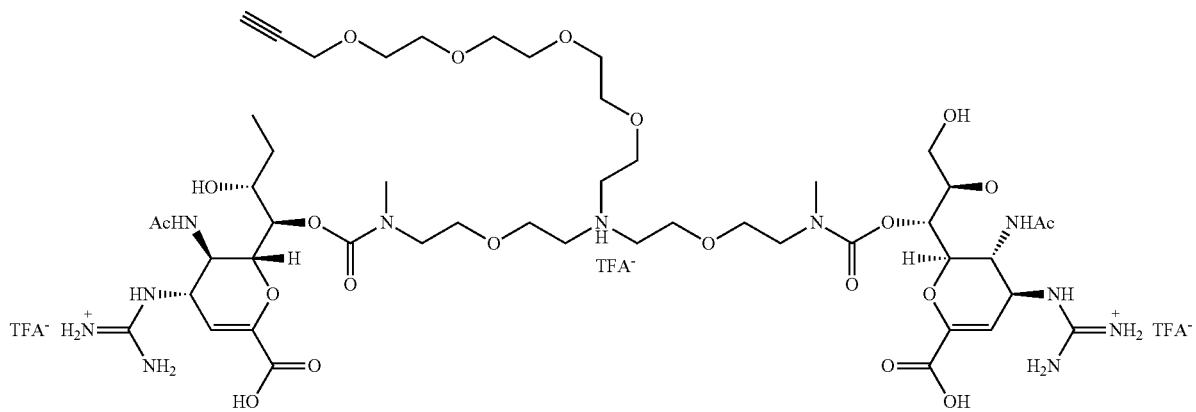 [SMILES: C#CCOCCOCCOCCOCCN(CCOCCN(C)C(=O)O[C@@H]([C@@H]1OC(C(=O)O)=C[C@H](NC(=N)N)[C@H]1NC(C)=O)[C@H](O)CC)CCOCCN(C)C(=O)O[C@@H]([C@@H]1OC(C(=O)O)=C[C@H](NC(=N)N)[C@H]1NC(C)=O)[C@H](O)CO]

The product f (1.45 g, 0.87 mmol) was dissolved into 3 ml MeOH then treated with a solution of lithium hydroxide (90 mg, 3.8 mmol) dissolved in deionized water (6 mL). The reaction was stirred for 15 minutes at room temperature at which time LCMS showed the reaction was complete. The pH of the reaction solution was adjusted to a value of 5 to 6 by using Amberlite IRN-77 ion exchange resin, then filtered to remove the resin. The filtrate was concentrated to dryness by rotary evaporation and used in the next step without further purification. Ion found by LCMS: $[(M+2H)/2]^+=815.9$.

The hydrolysis product was dissolved in dichloromethane (5 mL) and TFA (10 mL), and stirred at room temperature. The progress of the reaction was monitored by LCMS. After complete Boc-removal (~4 hours), the solution was concentrated to dryness with a rotary evaporator, and then dissolved in 8 ml water. The resulting solution was stirred for another 2 hour at room temperature at which time LCMS showed complete removal of the acetonide protecting groups. This mixture was concentrated and purified by reverse phase liquid chromatography (RPLC) using an Isco COMBI-FLASH® liquid chromatograph eluted with 5% to 40% acetonitrile/water with 0.1% TFA as the modifier. Yield for three steps 780 mg, 65.0%. Ion(s) found by LCMS: $[(M+2H)/2]^+=575.8$, $[(M+3H)/3]^+=384.8$.

Example 147. Serial Passage Experiments for Selection of Resistant Influenza Viruses To evaluate the potential for development of drug resistant mutant viral strains under selective pressure with viral inhibitors, serial passage studies were conducted with Conjugates 6 and 33, versus oseltamivir and baloxavir comparators. Serial passage studies were conducted using either A549 or MDCK cells. Passages were conducted as follows: 150,000 A549 or MDCK cells were seeded per well (12-well) in 500 μl DMEM 10% FBS, 1% PS, 1% NaPyr and 1% HEPES and incubated for approximately 24 hours. Once cells reached approximately 80% confluency, they were washed once with PBS and incubated for 2 hours in the presence of compounds or PBS alone under normal culture conditions. Test article concentrations were optimized as required for maximum virus inhibition, while maintaining enough virus production for subsequent passages. Concentrations of test articles used in the serial passage experiments are shown in FIGS. 67 and 68. Cells were then infected at an MOI of 0.01 or 0.05 (MDCK and A549 cells, respectively; 150 μl diluted in infection buffer) for 1 hour at room temperature in a buffer containing PBS, Bovine Albumin 35% and $Ca^{2+}/Mg^{2+}$, followed by removal of inoculum and washing of cells once with DMEM 1% PS, 1% NaPyr and 1% HEPES (No FBS). Cells were then Incubated for 24 hours in the presence of test articles diluted in DMEM 1% PS, 1% NaPyr, 1% HEPES and 1 μg/ml TPCK-treated trypsin. After incubation, viral supernatants were collected, and cells and debris were removed by centrifugation (5 min, 4° C., 1,400×g). S upernatants were then used to:

i Quantify viral titer by plaque assay ii Conduct a hemagglutination assay to determine if the virus escaped compound inhibition iii Re-infect freshly seeded A549 or MDCK cells in presence of compounds.

The process was repeated for 10 passages, or until resistance was observed for the oseltamivir and baloxavir controls. Once increased titers in the presence of drugs is detected for two consecutive passages, the viruses may be plaque purified. Following plaque purification, all 8 genome segments may be sequenced and compared to PBS treated control virus to detect escape mutations. Summaries of two different serial passage experiments are shown in FIGS. 67 and 68. In the experiment summarized in FIG. 67, Conjugate 6 was compared to oseltamivir and baloxavir using A549 cells infected with A/California/04/09/H1N1 pdm. Conjugate 6, baloxavir and oseltamivir were used at 0.5 nM, 0.5 nM and 200 nM, respectively. No increases in viral titer were observed for Conjugate 6 through the course of 11 passages (suggesting no emergence of resistant mutants), while baloxavir and oseltamivir titers increased to levels similar to those observed in the PBS control after passages 5 and 11, respectively. In the experiment summarized in FIG. 68, Conjugates 6 and 33 were compared to oseltamivir and baloxavir using MDCK cells infected with A/WSN/1933 H1N1. Conjugate 6, Conjugate 33, baloxavir and oseltamivir were used at 4 nM, 2 nM, 4 nM, and 50 nM, respectively. No increases in viral titer were observed for Conjugates 6 or 33 through the course of 10 passages (suggesting no emergence of resistant mutants), while baloxavir and oseltamivir titers increased to levels similar to those observed in the PBS control after passages 5 and 10, respectively.

Example 148. Synthesis of Conjugate 6a

The title conjugate is prepared analogously to Conjugate 6 (Example 20) using Int-7a (Example 100). Maldi TOF analysis of the purified final product gave an average mass of 62063. Da (DAR=2.7). Yield 175.4 mg, 50% yield.

Example 149. Synthesis of Conjugate 6b

The title conjugate is prepared analogously to Conjugate 6 (Example 20) using Int-7b (Example 101). Maldi TOF analysis of the purified final product gave an average mass of 62063. Da (DAR=2.8). Yield 175.4 mg, 50% yield.

Example 150. Synthesis of Conjugate 6c

The title conjugate is prepared analogously to Conjugate 6 (Example 20) using Int-7c (Example 102). Maldi TOF analysis of the purified final product gave an average mass of 62782. Da (DAR=3.2). Yield 175.4 mg, 50% yield.

Example 151. Synthesis of Conjugate 44

This conjugate was prepared analogously to Example 80 (Conjugate 20) by PEG4-azido-Fc (SEQ ID NO: 73, prepared as in Example 124) and Int-22 (Example 79). Maldi TOF analysis of the purified final product gave an average mass of 62,882 Da (DAR=5.6).

The nucleic acid construct encoding the Fc for Conjugate 44 included a nucleic acid encoding the amino acid sequence of SEQ ID NO: 64, which includes a C-terminal lysine residue. Upon expression, the C-terminal lysine of the Fc of Conjugate 44 is proteolytically cleaved, resulting in an Fc having the sequence of SEQ ID NO: 73. The presence or absence of a C-terminal lysine does not alter the properties of the Fc or the corresponding conjugate.

Example 152. Antibody-Dependent Cellular Cytotoxicity Assay

Conjugate 6 and Conjugate 33 were tested for antibody-dependent cellular cytotoxicity (ADCC). A monolayer of MDCK cells was infected with influenza A or influenza B strains at an MOI of 0.001-10, and incubated for 18-24 h at 37° C., in 5% $CO_2$. ADCC was determined with commercial report cell line (PROMEGA) according to manufacturer's instructions. Briefly, test articles were added at concentrations ranging from 1 to 10,000 nM to appropriate wells and incubated for 15 m at 37° C., in 5% $CO_2$. ADCC was quantified by reading luminescence. Conjugate 6 was tested against Influenza A/PR/8/1934 (H1N1), showing an MOI-dependent increase in ADCC (FIG. 69), and a dose dependent increase in ADCC at an MOI of 1 (FIG. 70). Conjugate 33 was tested against influenza A/PR/8/1934 (H1N1), influenza A/CA/07/2009 (H1N1), and influenza A/HK/1/1968 (H3N2) FIGS. 71A-71C, and influenza B/Malaysia/2506/2004 (Victoria, FIG. 72), showing an MOI-dependent increase in ADCC by conjugate 33. Conjugate 33 also showed a dose-dependent increase in ADCC against influenza A/PR/8/1934 (H1N1) at an MOI of 1 (FIG. 73A) and an MOI of 10 (FIG. 73B). The monoclonal antibody, Gedivumab (Genentech) was used as a positive control to compare receptor binding of a full length antibody to that of an Fc conjugate. Gedivumab also showed an MOI-dependent increase in ADCC when tested against influenza A/PR/8/1934 (H1N1, FIG. 74), and a dose-dependent increase in ADCC against influenza A/PR/8/1934 (H1N1) at an MOI of 1 (FIG. 75A) and an MOI of 10 (FIG. 75B).

Example 153. Antibody-Dependent Cellular Phagocytosis Assay

Conjugate 6 and Conjugate 33 were tested for cellular phagocytosis. A monolayer of MDCK cells was infected with influenza A or influenza B strains at an MOI of 0.001-10, and incubated for 18-24 h at 37° C., in 5% $CO_2$. ADCP was determined with commercial report cell line (PROMEGA) according to manufacturer's instructions. Briefly, test articles were added at concentrations ranging from 1 to 10,000 nM to appropriate wells and incubated for 15 m at 37° C., in 5% $CO_2$. ADCP was quantified by reading luminescence. Conjugate 6 was tested against Influenza A/PR/8/1934 (H1N1), showing an MOI-dependent increase in ADCP (FIG. 76), and a dose dependent increase in ADCP at an MOI of 1 (FIG. 77A) and an MOI of 10 (FIG. 77B). Conjugate 33 was tested against influenza A/PR/8/1934 (H1N1), influenza A/CA/07/2009 (H1N1), and influenza A/HK/1/1968 (H3N2) (FIGS. 78A-78C, respectively), and influenza B/Malaysia/2506/2004 (Victoria, FIG. 79), showing an MOI-dependent increase in ADCP by conjugate 33. Conjugate 33 also showed a Dose-dependent increase in ADCP against influenza A/PR/8/1934 (H1N1) at an MOI of 1 (FIG. 80A) and MOI of 10 (FIG. 80B). Gedivumab (Genentech) was used as a positive control to compare receptor binding of a full length antibody to that of an Fc conjugate. Gedivumab also showed an MOI-dependent increase in ADCP when tested against influenza A/PR/8/1934 (H1N1, FIG. 81), and a dose-dependent increase in ADCP against influenza A/PR/8/1934 (H1N1) at an MOI of 1 (FIG. 82A) and an MOI of 10 (FIG. 82B).

Example 154. Neuraminidase Inhibition with Live Influenza A Virus or Lysates of Neuraminidase Resistant Mutants Neuraminidase inhibition (NAI). Test articles were incubated with neuraminidase (Sino Biological) or with live viruses for 20 min at 37° C., 5% $CO_2$. 2'-(4-Methylumbelliferyl)-α-D-N acetylneuraminic acid substrate was added to appropriate wells and incubated for 1 h at 37° C., 5% $CO_2$. NAI was determined by reading fluorescence at 355 nm excitation/460 nm emission. Neuraminidase inhibition was determined for neuraminidase resistant mutants and for live influenza virus (Table 66, Table 67, Table 68, and Table 69).

TABLE 66

Neuraminidase inhibition with lysates of neuraminidase resistant mutants

|  | | | | | H1N1 WT $IC_{50}$ [nM] | H1N1 H275Y $IC_{50}$ [nM] | H3N2 WT $IC_{50}$ [nM] | H3N2 E119V $IC_{50}$ [nM] | H3N2 R292K $IC_{50}$ [nM] | H5N1 WT $IC_{50}$ [nM] | H7N9 WT $IC_{50}$ [nM] |
|---|---|---|---|---|---|---|---|---|---|---|---|
| Oseltamivir | N/A | N/A | N/A | N/A | 3.80 | 743.90 | 2.18 | 455.70 | 8015.00 | 15.44 | 2.95 |
| Zanamivir | N/A | N/A | N/A | N/A | 2.15 | 1.93 | 4.27 | 112.60 | 116.50 | 2.05 | 11.11 |

TABLE 66-continued

Neuraminidase inhibition with lysates of neuraminidase resistant mutants

|  |  |  |  |  | H1N1 WT IC$_{50}$ [nM] | H1N1 H275Y IC$_{50}$ [nM] | H3N2 WT IC$_{50}$ [nM] | H3N2 E119V IC$_{50}$ [nM] | H3N2 R292K IC$_{50}$ [nM] | H5N1 WT IC$_{50}$ [nM] | H7N9 WT IC$_{50}$ [nM] |
|---|---|---|---|---|---|---|---|---|---|---|---|
| Int-7a | N/A | N/A | 15 atoms | N/A | 22.58 | 9.42 | 21.11 | 679.40 | 993.60 | 17.06 | 49.04 |
| Int-7b | N/A | N/A | 15 atoms | N/A | 34.82 | 13.84 | 32.07 | 1079.00 | 1584.00 | 29.56 | 87.54 |
| Int-7b | N/A | N/A | 15 atoms | N/A | 2002.00 | 872.40 | 2914.00 | >10,000 | >10,000 | 2706.00 | 3325.00 |
| Conjugate 6a | Int-7a | 2.7 | 15 atoms | SEQ ID NO: 18 | 0.37 | 0.43 | 4.14 | 4.66 | 4.85 | 0.59 | 1.18 |
| Conjugate 6b | Int-7b | 2.8 | 15 atoms | SEQ ID NO: 18 | 0.24 | 0.30 | 2.05 | 3.67 | 7.41 | 0.54 | 0.98 |
| Conjugate 6c | Int-7c | 3.2 | 15 atoms | SEQ ID NO: 18 | 0.98 | 0.66 | 35.60 | 4423.00 | 1451.00 | 1.25 | 10.41 |
| Conjugate 33 | Int-7a | 4.5 | 15 atoms | SEQ ID NO: 73 | 1.39 | 2.61 | 13.09 | 13.21 | 17.69 | 3.51 | 5.66 |

TABLE 67

Neuraminidase inhibition with live influenza A virus

|  |  |  |  |  | A/PR/8/1934 (H1N1) IC$_{50}$ [nM] | A/Ca/7/2009 (H1N1) IC$_{50}$ [nM] | A/HK/1/1968 (H3N2) IC$_{50}$ [nM] | B/Brisbane 60/2008 (Victoria) IC$_{50}$ [nM] | B/Florida/4/2006 (Yamagata) IC$_{50}$ [nM] |
|---|---|---|---|---|---|---|---|---|---|
| Oseltamivir | N/A | N/A | N/A | N/A | 3.76 | 0.88 | 0.16 | 36.61 | 24.65 |
| Zanamivir | N/A | N/A | N/A | N/A | 0.35 | 0.28 | 0.43 | 6.74 | 3.60 |
| Int-7a | N/A | N/A | 15 atoms | N/A | 0.45 | 2.10 | 3.62 | 13.54 | 25.54 |
| Int-7b | N/A | N/A | 15 atoms | N/A | 0.98 | 3.78 | 5.57 | 16.03 | 17.26 |
| Int-7c | N/A | N/A | 15 atoms | N/A | 150.90 | 399.40 | 467.50 | 1942.00 | 5512.00 |
| Conjugate 6a | Int-7a | 2.7 | 15 atoms | SEQ ID NO: 18 | 0.22 | 0.56 | 0.41 | 2.24 | 4.65 |
| Conjugate 6b | Int-7b | 2.8 | 15 atoms | SEQ ID NO: 18 | 0.14 | 0.25 | 0.30 | 1.39 | 2.30 |
| Conjugate 6c | Int-7c | 3.2 | 15 atoms | SEQ ID NO: 18 | 0.29 | 0.35 | 0.60 | 99.08 | 44.37 |
| Conjugate 33 | Int-7a | 4.5 | 15 atoms | SEQ ID NO: 73 | 1.12 | 2.05 | 1.71 | 7.75 | 16.47 |

TABLE 68

Neuraminidase inhibition against H3N2 WT, E119V mutant or live influenza A/Ca/07/2009

| Molecule | TM | DAR | Fc | Central linker | H3N2 WT IC$_{50}$ [nM] | H3N2 E119V IC$_{50}$ [nM] | A/Ca/07/2009 pdm IC$_{50}$ [nM] |
|---|---|---|---|---|---|---|---|
| Oseltamivir | N/A | N/A | N/A | N/A | 2.873 | 150.1 | 0.7411 |
| Zanamivir | N/A | N/A | N/A | N/A | 6.302 | 35.68 | 0.8452 |
| Int-3 | N/A | N/A | N/A | 27 atom | 31.25 | 108.3 | 1.172 |
| Int-4a | N/A | N/A | N/A | N/A | 32.94 | 147.1 | 7.102 |
| Int-7a | N/A | N/A | N/A | 15 atom | 33.62 | 185.9 | 3.825 |
| Int-7c | N/A | N/A | N/A | 15 atom | 4428 | 13972 | 470.5 |
| Int-22 | N/A | N/A | N/A | N/A | 13.25 | 23.23 | 1.295 |
| Int-73 | N/A | N/A | N/A | 14 atom | 33.63 | 174.3 | 4.605 |
| Int-74 | N/A | N/A | N/A | 16 atom | 32.89 | 157.9 | 1.551 |
| Int-75 | N/A | N/A | N/A | 17 atom | 34.51 | 164 | 1.759 |
| Int-76 | N/A | N/A | N/A | 18 atom | 32.95 | 166.4 | 2.07 |
| Int-80 | N/A | N/A | N/A | N/A | 80.97 | 628.9 | 21.89 |
| Int-91 | N/A | N/A | N/A | N/A | 95.7 | 529 | 46 |
| Conjugate 6 | Int-7 | 3.3 | SEQ ID NO: 18 | 15 atom | 206.5 | 3610 | 1.366 |
| Conjugate 33 | Int-7a | 6.1 | SEQ ID NO: 73 | 15 atom | 3.051 | 2.913 | 0.2656 |
| Conjugate 33 | Int-7a | 6.8 | SEQ ID NO: 73 | 15 atom | 6.197 | 86.06 | 0.1007 |
| Conjugate 43 | Int-80 | 7.0 | SEQ ID NO: 73 | N/A | 11.28 | 11.64 | 1.231 |
| Conjugate 44 | Int-22 | 5.6 | SEQ ID NO: 73 | N/A | 6.815 | 5.816 | 0.7677 |

TABLE 69

Neuraminidase Inhibition assay [nM] with NA lysate Response

| | | | | IAV H1N1 NA Lysate | | |
|---|---|---|---|---|---|---|
| Test article | TM | DAR | Central linker | 0.1 U/mL | 1 U/mL | 10 U/mL |
| Oseltamivir | N/A | N/A | N/A | 2.162 | 19.45 | 729.9 |
| Zanamivir | N/A | N/A | N/A | 0.6719 | 7.765 | 76.53 |
| Int-7 | N/A | N/A | 15 atoms | 1958 | 12987 | >10,000 |
| Int-23 | N/A | N/A | 14 atoms | 0.2684 | 2.625 | 27.78 |
| Conjugate 6 | Int-7 | 3.3 | 15 atoms | 16.28 | 13214 | >10,000 |
| Conjugate 21 | Int-7 | 2.2 | 14 atoms | 0.5004 | 2.65 | 9.101 |

Example 155. Cytopathic Effect Assay

To measure the ability of Conjugate 6 and Conjugate 33 to protect mammalian cells from infection and destruction by influenza virus, Cytopathic effect (CPE) based microneutralization assays were conducted as discussed in Example 25, with minor variations. Briefly, a monolayer of MOCK cells was infected with influenza A or B strains at appropriate MOI varying between 0.001-1. Test articles were added at concentrations ranging between 0.1-10,000 nM and incubated for 3 days for influenza A or 5 days for influenza B at 37° C., 5% CO2. CPE was determined by crystal violet staining by reading absorbance at 595 nm. The results are shown in Table 70, Table 71, Table 72, and Table 73, below.

TABLE 70

| CPE against influenza A/PR/8/1934 (H1N1) | | | | | | | |
|---|---|---|---|---|---|---|---|
| Molecule | TM | DAR | Fc | Central linker | MOI 0.01 | MOI 0.1 $EC_{50}$ [nM] | MOI 1 |
| Oseltamivir | N/A | N/A | N/A | N/A | 3005 | >10,000 | >10,000 |
| Baloxavir | N/A | N/A | N/A | N/A | 0.4466 | 5.126 | 7.993 |
| Conjugate 6 | Int-7 | 3.3 | SEQ ID NO: 18 | 15 atom | 0.3561 | 35.52 | 1802 |
| Conjugate 33 | Int-7a | 4.5 | SEQ ID NO: 73 | 15 atom | 0.2669 | 2.458 | 77.97 |

TABLE 71

| CPE against influenza A/Ca/07/2009 (H1N1)pdm | | | | | | | |
|---|---|---|---|---|---|---|---|
| Molecule | TM | DAR | Fc | Central linker | MOI 0.01 | MOI 0.1 $EC_{50}$ [nM] | MOI 1 |
| Oseltamivir | N/A | N/A | N/A | N/A | 288.2 | >10,000 | >10,000 |
| Baloxavir | N/A | N/A | N/A | N/A | 1.439 | 3.186 | 11.3 |
| Conjugate 6 | Int-7 | 3.3 | SEQ ID NO: 18 | 15 atom | 18.13 | 513.4 | >1,000 |
| Conjugate 33 | Int-7a | 4.5 | SEQ ID NO: 73 | 15 atom | 1.845 | 39.66 | >1,000 |

TABLE 72

| CPE against influenza A/WSN/1933 (t = −1 h) | | | | | | | | | |
|---|---|---|---|---|---|---|---|---|---|
| Molecule | TM | DAR | Fc | Central linker | MOI 0.001 | MOI 0.01 | MOI 0.1 $EC_{50}$ [nM] | MOI 1 | MOI 10 |
| Oseltamivir | N/A | N/A | N/A | N/A | 3911 | >10,000 | >10,000 | >10,000 | >10,000 |
| Baloxavir | N/A | N/A | N/A | N/A | 1.261 | 3.64 | 8.306 | 8.266 | 17.1 |
| Int-7a | N/A | N/A | N/A | 15 atom | 8.704 | 13.22 | 2758 | >10,000 | >10,000 |
| Conjugate 33 | Int-7a | 4.5 | SEQ ID NO: 73 | 15 atom | 3.097 | 2.754 | 8.147 | 868.1 | >10,000 |

TABLE 73

| CPE against influenza B (t = −1 h) | | | | | | | |
|---|---|---|---|---|---|---|---|
| Molecule | TM | DAR | Fc | Central linker | B/Brisbane | B/Florida $EC_{50}$ [nM] | B/Malaysia |
| Oseltamivir | N/A | N/A | N/A | N/A | 969.1 | >10,000 | 5694 |
| Baloxavir | N/A | N/A | N/A | N/A | 240.4 | 30.57 | 2294 |

TABLE 73-continued

CPE against influenza B (t = −1 h)

| Molecule | TM | DAR | Fc | Central linker | B/Brisbane | B/Florida EC$_{50}$ [nM] | B/Malaysia |
|---|---|---|---|---|---|---|---|
| Int-7a | N/A | N/A | N/A | 15 atom | <1.93 | <1.93 | 0.8237 |
| Conjugate 33 | Int-7a | 4.5 | SEQ ID NO: 73 | 15 atom | 3.699 | 0.1946 | 10.48 |

Example 156. Synthesis of Conjugate 45

Conjugate 45 was prepared analogously to conjugate 33 (Example 129) using PEG4-azido-Fc (either SEQ ID NO: 72 (Conjugate 45a) or SEQ ID NO: 73 (Conjugate 45b), prepared as in Example 124) and Int-83 (Example 145). Maldi TOE analysis of a purified preparation of Conjugate 45b gave an average mass of 62,927 Da (OAR=4.2). The preparation of Conjugate 45a having varying DARs is also described herein (Example 199). Where the term Conjugate 45 is used, it should not be considered to be limited to any particular OAR. The resulting conjugate is depicted in FIG. 102.

The term Conjugate 45, as used herein, is meant to encompass both Conjugate 45a and Conjugate 45b. Applicant notes that SEQ ID NO: 72 (Conjugate 45a) and SEQ ID NO: 73 (Conjugate 45b) differ only in the Fc allotype, G1m(f) and G1 m(fa), respectively. The differing allotypes are expected to behave the same with respect the properties described herein.

The nucleic acid construct encoding the Fc for Conjugate 45a included a nucleic acid encoding the amino acid sequence of SEQ ID NO: 63, which includes a C-terminal lysine residue. Upon expression, the C-terminal lysine of the Fc of Conjugate 45a is proteolytically cleaved, resulting in an Fc having the sequence of SEQ ID NO: 72. Likewise, the nucleic acid construct encoding the Fc for Conjugate 45b included a nucleic acid encoding the amino acid sequence of SEQ ID NO: 64, whereas the resulting Fc has the sequence of SEQ ID NO: 73. The presence or absence of a C-terminal lysine does not alter the properties of the Fc or the corresponding conjugate.

Example 157. Efficacy of Conjugate 45b Against Influenza A (H1N1) in a Lethal Severe Combined Immunodeficiency (SCID) Mouse Model Test articles were evaluated against a lethal Influenza A influenza infection in female BALB/c scid mice (Jackson Laboratories, 6-8 weeks old). The challenge virus (A/Puerto Rico/8/1934) is a mouse-adapted isolate capable of causing lethal infections in mice. The experiment comprised 10 groups of 5 mice each. At day 0, all mice were challenged with virus at 3× the LD95 by intranasal inoculation in a volume of 30 μl (approx. 1 E3 virus per mouse), after being anesthetized with a mixture of ketamine/xylazine (150 and 10 mg/kg respectively).

Groups received a single SC treatment of vehicle (PBS), hIgG1 Fc control, or conjugate 45b two hours post viral challenge. A separate arm of the study consisted of 3 groups of mice treated with baloxavir marboxil (DC Chemicals, Shanghai, China) orally, twice daily, for 1 day; also starting 2 hours post viral challenge. The study design is outlined in Table 74. Mice were monitored for 4 weeks and animals exceeding 20% body weight loss, or were found moribund, were scored as a mortality.

TABLE 74

Study design of SCID study

| Group | Influenza strain | Test Article | Route/ Schedule | Dose (mg/ kg) | Dose volume (ml/kg) | N (balb/ c) |
|---|---|---|---|---|---|---|
| 1 | A/PR/8/34 2E2 PFU/mouse | PBS | SC, T + 2 hrs | — | 10 | 5 |
| 2 | | hIgG1 | SC, T + 2 hrs | 3 | 10 | 5 |
| 3 | | Baloxavir | PO, bid × 1 day | 10 | 10 | 5 |
| 4 | | Baloxavir | PO, bid × 1 day | 3 | 10 | 5 |
| 5 | | Conjugate 45b | SC, T + 2 hrs | 10 | 10 | 5 |
| 6 | | | SC, T + 2 hrs | 3 | 10 | 5 |
| 7 | | | SC, T + 2 hrs | 1 | 10 | 5 |
| 8 | | | SC, T + 2 hrs | 0.3 | 10 | 5 |
| 9 | | | SC, T + 2 hrs | 0.1 | 10 | 5 |
| 10 | | Uninfected BW control | | | | 5 |

At study end (Day 28) mice receiving conjugate 45b were fully protected at all dose concentrations between 10 and 0.3 mg/kg (Table 75). Conjugate 45b only failed to protect against lethal viral challenge at the lowest tested concentration of 0.1 mg/kg. As expected, groups receiving vehicle or hIgG1 Fc were not protected. Mice treated with baloxavir were also protected, but at the significantly higher cumulative doses of 20 mg/kg (80% survival), at a total dose of 6 mg/kg only 60% of mice survived to Day 28.

TABLE 75

Percent survival

| Day | Vehicle | hIgG1 Fc | Baloxavir (20) | Baloxavir (6) | Conjugate 45b (mg/kg) | | | | | Control |
| | | | | | 10 | 3 | 1 | 0.3 | 0.1 | |
|---|---|---|---|---|---|---|---|---|---|---|
| 0 | 100 | 100 | 100 | 100 | 100 | 100 | 100 | 100 | 100 | 100 |
| 1 | 100 | 100 | 100 | 100 | 100 | 100 | 100 | 100 | 100 | 100 |
| 2 | 100 | 100 | 100 | 100 | 100 | 100 | 100 | 100 | 100 | 100 |
| 3 | 100 | 100 | 100 | 100 | 100 | 100 | 100 | 100 | 100 | 100 |
| 4 | 100 | 100 | 100 | 100 | 100 | 100 | 100 | 100 | 100 | 100 |
| 5 | 100 | 100 | 100 | 100 | 100 | 100 | 100 | 100 | 100 | 100 |
| 6 | 80 | 80 | 100 | 100 | 100 | 100 | 100 | 100 | 60 | 100 |
| 7 | 20 | 20 | 100 | 100 | 100 | 100 | 100 | 100 | 100 | 100 |

TABLE 75-continued

Percent survival

| Day | Vehicle | hIgG1 Fc | Baloxavir (20) | Baloxavir (6) | Conjugate 45b (mg/kg) | | | | | Control |
|---|---|---|---|---|---|---|---|---|---|---|
| | | | | | 10 | 3 | 1 | 0.3 | 0.1 | |
| 8 | 0 | 0 | 100 | 100 | 100 | 100 | 100 | 100 | 100 | 100 |
| 9 | 0 | 0 | 100 | 100 | 100 | 100 | 100 | 100 | 100 | 100 |
| 10 | 0 | 0 | 100 | 100 | 100 | 100 | 100 | 100 | 100 | 100 |
| 11 | 0 | 0 | 100 | 100 | 100 | 100 | 100 | 100 | 100 | 100 |
| 12 | 0 | 0 | 100 | 100 | 100 | 100 | 100 | 100 | 100 | 100 |
| 13 | 0 | 0 | 100 | 100 | 100 | 100 | 100 | 100 | 100 | 100 |
| 14 | 0 | 0 | 100 | 80 | 100 | 100 | 100 | 100 | 100 | 100 |
| 15 | 0 | 0 | 100 | 80 | 100 | 100 | 100 | 100 | 100 | 100 |
| 16 | 0 | 0 | 100 | 60 | 100 | 100 | 100 | 100 | 100 | 100 |
| 17 | 0 | 0 | 100 | 60 | 100 | 100 | 100 | 100 | 100 | 100 |
| 18 | 0 | 0 | 100 | 60 | 100 | 100 | 100 | 100 | 100 | 100 |
| 19 | 0 | 0 | 100 | 60 | 100 | 100 | 100 | 100 | 100 | 100 |
| 20 | 0 | 0 | 100 | 60 | 100 | 100 | 100 | 100 | 100 | 100 |
| 21 | 0 | 0 | 100 | 60 | 100 | 100 | 100 | 100 | 100 | 100 |
| 22 | 0 | 0 | 100 | 60 | 100 | 100 | 100 | 100 | 100 | 100 |
| 23 | 0 | 0 | 100 | 60 | 100 | 100 | 100 | 100 | 80 | 100 |
| 24 | 0 | 0 | 80 | 60 | 100 | 100 | 100 | 100 | 40 | 100 |
| 25 | 0 | 0 | 80 | 60 | 100 | 100 | 100 | 100 | 20 | 100 |
| 26 | 0 | 0 | 80 | 60 | 100 | 100 | 100 | 100 | 20 | 100 |
| 27 | 0 | 0 | 80 | 60 | 100 | 100 | 100 | 100 | 0 | 100 |
| 28 | 0 | 0 | 80 | 60 | 100 | 100 | 100 | 100 | 0 | 100 |

Control = Uninfected

The potency of conjugate 45b in this model of severe immunodeficiency was also evident based on body weights (Table 76). The lowest concentration of conjugate providing full protection based on a mortality readout was 0.3 mg/kg. At this dose level, the greatest average weight loss for the group was transient, and resulted in less than a 3% reduction (occurring on Day 4). Furthermore the difference in body weight for all fully protective groups was negligible compared to uninfected mice.

TABLE 76

Percent Body Weight

| Day | Vehicle | hIgG1 Fc | Baloxavir (20) | Baloxavir (6) | Conjugate 45b (mg/kg) | | | | | Control |
|---|---|---|---|---|---|---|---|---|---|---|
| | | | | | 10 | 3 | 1 | 0.3 | 0.1 | |
| 0 | 100 | 100 | 100 | 100 | 100 | 100 | 100 | 100 | 100 | 100 |
| 1 | 99.2 | 97.6 | 93.8 | 96.9 | 95.8 | 97.4 | 98 | 99 | 98 | 101.8 |
| 2 | 101.3 | 98.7 | 98.3 | 98.1 | 96.7 | 99.5 | 96.3 | 98.3 | 102.6 | 100.8 |
| 3 | 95.4 | 94.9 | 100.3 | 98.3 | 100.6 | 97.9 | 100.9 | 99.6 | 101 | 101 |
| 4 | 92.3 | 90.1 | 103.3 | 100.8 | 100.8 | 101.3 | 102.4 | 97.5 | 99.2 | 104.6 |
| 5 | 86.5 | 84.9 | 103.2 | 100.5 | 102.2 | 102 | 102.7 | 99.8 | 99.2 | 103.3 |
| 6 | 78.8 | 78 | 100.6 | 99.7 | 101.5 | 101.5 | 101.4 | 102 | 99.2 | 103.3 |
| 7 | | | 103.6 | 100 | 103.5 | 101.8 | 100.5 | 100.7 | 101.6 | 103.7 |
| 8 | | | 104.2 | 100.2 | 103.7 | 103.1 | 100.4 | 103.3 | 102.7 | 101.7 |
| 9 | | | 101.4 | 97.3 | 103.6 | 101.5 | 100.5 | 103.1 | 102.9 | 102.1 |
| 10 | | | 100.9 | 96 | 102.8 | 100.8 | 101.8 | 104.2 | 102.7 | 101.7 |
| 11 | | | 102.3 | 98.3 | 104.2 | 103.7 | 102.4 | 104.5 | 103.3 | 103.8 |
| 12 | | | 103 | 95.3 | 105.4 | 105.9 | 103 | 105.4 | 103.8 | 103.9 |
| 13 | | | 103.5 | 93.4 | 103.6 | 105.1 | 104.1 | 105.2 | 104 | 103.9 |
| 14 | | | 102.3 | 91.8 | 103.3 | 103.6 | 103.2 | 104.8 | 102.6 | 103.1 |
| 15 | | | 102.2 | | 104.2 | 105.8 | 102.5 | 104.8 | 104.7 | 103.1 |
| 16 | | | 102.3 | | 102 | 101.9 | 104 | 104.6 | 100.1 | 102.1 |
| 17 | | | 103.3 | | 102 | 103.3 | 104.4 | 103.8 | 101.4 | 102.8 |
| 18 | | | 103.3 | | 106.4 | 105.3 | 105.8 | 105.1 | 100.4 | 104.1 |
| 19 | | | 105.4 | | 106.6 | 103.6 | 106.5 | 105.6 | 96.7 | 103.5 |
| 20 | | | 105.9 | | 105.1 | 102.1 | 105.5 | 106.3 | 92.9 | 103.8 |
| 21 | | | 106.6 | | 108.6 | 102.8 | 106.5 | 107.6 | 90.6 | 106 |
| 22 | | | 103.8 | | 109.1 | 103.1 | 105.7 | 107.3 | 86.7 | 102.1 |
| 23 | | | 102.1 | | 106.3 | 101.8 | 105.5 | 105.3 | | 99.3 |
| 24 | | | 100 | | 107.9 | 104 | 106 | 104.8 | | 103.7 |
| 25 | | | | | 108.6 | 105.3 | 104.9 | 106.1 | | 104.8 |
| 26 | | | | | 110 | 107.3 | 107.9 | 105.4 | | 105.2 |
| 27 | | | | | 109 | 106.8 | 106 | 102.1 | | 104 |
| 28 | | | | | 108.2 | 106.2 | 106.7 | 101.2 | | 104.4 |

Control = Uninfected

Collectively these data demonstrate the potency of conjugate 45b by protecting lethally challenged mice with single SC doses of conjugate as low as 0.3 mg/kg. This was accomplished in a severe model of immunodeficiency with mice completely lacking T & B immune cells, which are essential in clearing influenza infections. These data support the use of conjugate 45b to treat immune deficient patient populations.

Example 158. Efficacy of Conjugate 45b Subcutaneously Dosed Against Influenza A/Puerto Rico/8/34 (H1 N1) in a Lethal Mouse Model Conjugate 45b was evaluated against a lethal IAV H1N1 influenza infection in female BALB/c mice (Charles River Laboratories, 6-8 weeks). The challenge virus (A/Puerto Rico/8/i1934) is a mouse-adapted isolate capable of causing lethal infections in mice. The experiment comprised 7 groups of 5 mice. At day 0, all mice were challenged with virus at 3× the LD95 by intranasal inoculation in a volume of 30 μl, after being anesthetized with a mixture of ketamine/xylazine (150 and 10 mg/kg respectively). Mortality and body weights were recorded daily for 14 days and any animal with a 20% loss of body weight was scored as a death.

Test groups received a single subcutaneous (SC) treatment of conjugate 45b (1, 0.3, 0.1, 0.03, or 0.01 mg/kg), hIgG1 Fc control, or vehicle (PBS) 2 hours post viral challenge. The study design is summarized in Table 77.

TABLE 77

Study design for Influenza A/PR/8/34 (H1N1) study

| Group | Test article | Route/Schedule | Dose (mq/kq) | Dose volume (ml/kq) | # of mice |
|---|---|---|---|---|---|
| 1 | Vehicle | SC, T + 2 hrs. | na | 10 | 5 |
| 2 | hIgG1 Fc | SC, T + 2 hrs. | 1 | 10 | 5 |
| 3 | Conjugate 45b | SC, T + 2 hrs. | 1 | 10 | 5 |
| 4 |  | SC, T + 2 hrs. | 0.3 | 10 | 5 |
| 5 |  | SC, T + 2 hrs. | 0.1 | 10 | 5 |
| 6 |  | SC, T + 2 hrs. | 0.03 | 10 | 5 |
| 7 |  | SC, T + 2 hrs. | 0.01 | 10 | 5 |

As expected, mice receiving vehicle or the hIgG1 Fc control succumbed to infection on Day 6 (Table 78). However, mice treated with conjugate 45b were fully protected at 1, 0.3, and 0.1 mg/kg dose levels. Mortality with conjugate 45b was only seen at the lowest dose concentration of 0.03 and 0.01 mg/kg.

TABLE 78

Percent Survival

| Day | Vehicle | hIgG1 Fc | Conjugate 45b (mg/kg) | | | | |
| | | | 1 | 0.3 | 0.1 | 0.03 | 0.01 |
|---|---|---|---|---|---|---|---|
| 0 | 100 | 100 | 100 | 100 | 100 | 100 | 100 |
| 1 | 100 | 100 | 100 | 100 | 100 | 100 | 100 |
| 2 | 100 | 100 | 100 | 100 | 100 | 100 | 100 |
| 3 | 100 | 100 | 100 | 100 | 100 | 100 | 100 |
| 4 | 100 | 100 | 100 | 100 | 100 | 100 | 100 |
| 5 | 60 | 40 | 100 | 100 | 100 | 100 | 100 |
| 6 | 0 | 0 | 100 | 100 | 100 | 100 | 60 |
| 7 | 0 | 0 | 100 | 100 | 100 | 80 | 0 |
| 8 | 0 | 0 | 100 | 100 | 100 | 0 | 0 |
| 9 | 0 | 0 | 100 | 100 | 100 | 0 | 0 |
| 10 | 0 | 0 | 100 | 100 | 100 | 0 | 0 |
| 11 | 0 | 0 | 100 | 100 | 100 | 0 | 0 |
| 12 | 0 | 0 | 100 | 100 | 100 | 0 | 0 |
| 13 | 0 | 0 | 100 | 100 | 100 | 0 | 0 |
| 14 | 0 | 0 | 100 | 100 | 100 | 0 | 0 |

The potency of conjugate 45b was further supported by daily body weight measurements. As expected, mice treated with vehicle or hIgG1 Fc demonstrated a steady drop in body weight until it exceeded 20%, at which time they were scored as a mortality (Table 78).

In contrast to control mice, those groups receiving conjugate 45b at 1, 0.3, and 0.1 mg/kg maintained healthy body weights throughout the study and never demonstrated more than a transient body weight drop of less than 7% (0.1 mk/kg dose group, Day 7; Table 79). By both survival and body weight measurements conjugate 45b demonstrated robust protection from a lethal challenge of Influenza A/Puerto Rico/8/1934 with a single SC dose as low as 0.1 mg/kg.

TABLE 79

Percent Body Weight

| Day | Vehicle | hIgG1 Fc | Conjugate 45b (mg/kg) | | | | |
| | | | 1 | 0.3 | 0.1 | 0.03 | 0.01 |
|---|---|---|---|---|---|---|---|
| 0 | 100.0 | 100.0 | 100.0 | 100.0 | 100.0 | 100.0 | 100.0 |
| 1 | 97.0 | 98.0 | 97.7 | 96.7 | 98.2 | 98.8 | 96.2 |
| 2 | 98.6 | 99.9 | 100.8 | 101.9 | 101.0 | 100.5 | 100.4 |
| 3 | 90.7 | 92.4 | 98.8 | 98.9 | 96.7 | 93.3 | 92.0 |
| 4 | 82.1 | 83.4 | 97.7 | 97.5 | 95.1 | 87.5 | 84.7 |
| 5 | 76.2 | 76.9 | 98.4 | 96.3 | 94.7 | 87.6 | 79.3 |
| 6 | | | 102.1 | 102.4 | 99.7 | 84.1 | 76.8 |
| 7 | | | 101.8 | 103.1 | 93.8 | 78.8 | |
| 8 | | | 100.1 | 102.3 | 98.3 | | |
| 9 | | | 103.4 | 103.7 | 104.3 | | |
| 10 | | | 103.9 | 104.6 | 102.2 | | |
| 11 | | | 101.8 | 102.5 | 101.7 | | |
| 12 | | | 100.9 | 101.0 | 102.3 | | |
| 13 | | | 106.0 | 104.8 | 105.6 | | |
| 14 | | | 106.6 | 104.0 | 105.0 | | |

Example 159. Efficacy of Conjugate 45b Subcutaneously Dosed Against Influenza A/California/07/2009 (H1N1) Pdm in a Lethal Mouse Model Conjugate 45b was evaluated against a lethal IAV H1N1 influenza infection in female BALB/c mice (Charles River Laboratories, 6-8 weeks). The challenge virus (A/California/07/2009 (H1N1) pdm) is a pandemic isolate capable of causing lethal infections in mice. The experiment comprised 5 groups of 5 mice. At day 0, all mice were challenged with virus at 3× the LD95 by intranasal inoculation in a volume of 30 μl, after being anesthetized with a mixture of ketamine/xylazine (150 and 10 mg/kg respectively). Mortality and body weights were recorded daily and any animal with a 20% loss of body weight was scored as a death.

Test groups received a single subcutaneous (SC) treatment of conjugate 45b or vehicle (PBS) 2 hours post viral challenge. The study design and dose levels are summarized in Table 80.

TABLE 80

Study design for Influenza A/California/07/2009 (H1N1) pdm study

| Group | Test article | Route/Schedule | Dose (mq/kq) | Dose volume (ml/kq) | # of mice |
|---|---|---|---|---|---|
| 1 | Vehicle | SC, T + 2 hrs. | na | 10 | 5 |
| 2 | Conjugate 45b | SC, T + 2 hrs. | 3 | 10 | 5 |
| 3 | Conjugate 45b | SC, T + 2 hrs. | 1 | 10 | 5 |
| 4 | Conjugate 45b | SC, T + 2 hrs. | 0.3 | 10 | 5 |
| 5 | Conjugate 45b | SC, T + 2 hrs. | 0.1 | 10 | 5 |

As expected, mice receiving vehicle succumbed to infection by Days 7 (Table 81). However, mice treated with conjugate 45b were fully protected at concentrations as low as 0.3 mg/kg, and partially so at 0.1 mg/kg (60% survival). Achieving full protection against a highly virulent pandemic strain with a single dose of less than 1 mg/kg demonstrates the potency of conjugate 45b against clinically relevant influenza A.

TABLE 81

Percent Survival

| | | Conjugate 45b (mg/kg) | | | |
|---|---|---|---|---|---|
| Day | Vehicle | 3 | 1 | 0.3 | 0.1 |
| 0 | 100 | 100 | 100 | 100 | 100 |
| 1 | 100 | 100 | 100 | 100 | 100 |
| 2 | 100 | 100 | 100 | 100 | 100 |
| 3 | 100 | 100 | 100 | 100 | 100 |
| 4 | 100 | 100 | 100 | 100 | 100 |
| 5 | 80 | 100 | 100 | 100 | 80 |
| 6 | 40 | 100 | 100 | 100 | 80 |
| 7 | 0 | 100 | 100 | 100 | 60 |
| 8 | 0 | 100 | 100 | 100 | 60 |
| 9 | 0 | 100 | 100 | 100 | 60 |
| 10 | 0 | 100 | 100 | 100 | 60 |
| 11 | 0 | 100 | 100 | 100 | 60 |
| 12 | 0 | 100 | 100 | 100 | 60 |
| 13 | 0 | 100 | 100 | 100 | 60 |
| 14 | 0 | 100 | 100 | 100 | 60 |

The potency of conjugate 45b was further supported by daily body weight measurements. As expected, mice treated with vehicle demonstrated a steady drop in body weight until it exceeded 20%, at which time they were scored as a mortality (Table 82).

In contrast to control mice, mice receiving conjugate 45b at 3, 1, or 0.3 mg/kg only demonstrated a transient drop in bodyweight of approximately 10%, peaking on Days 3-5 (Table 82). By study end (Day 14) these mice largely recovered (or exceeded) their starting weight. By both survival and body weight measurements conjugate 45b demonstrated robust protection from a lethal challenge of Influenza A/California/07/2009 (H1N1) pdm with a single 0.3 mg/kg dose administered SC. Activity against the clinically relevant pandemic strain used in this study supports the utility of conjugate 45b in treating serious influenza infections.

TABLE 82

Percent Body Weight

| | | Conjugate 45b (mg/kg) | | | |
|---|---|---|---|---|---|
| Day | Vehicle | 3 | 1 | 0.3 | 0.1 |
| 0 | 100 | 100 | 100 | 100 | 100 |
| 1 | 96.9 | 95.9 | 97.1 | 96.3 | 96.1 |

TABLE 82-continued

Percent Body Weight

| | | Conjugate 45b (mg/kg) | | | |
|---|---|---|---|---|---|
| Day | Vehicle | 3 | 1 | 0.3 | 0.1 |
| 2 | 99.8 | 98.2 | 99.2 | 100.3 | 101.5 |
| 3 | 90 | 94.2 | 91.1 | 91.7 | 90.1 |
| 4 | 81 | 91.2 | 89.7 | 88.1 | 83.2 |
| 5 | 77.8 | 94.2 | 93.2 | 90.4 | 82.1 |
| 6 | | 97.8 | 97.4 | 92.1 | |
| 7 | | 97.6 | 96.3 | 90.3 | |
| 8 | | 98.6 | 96.4 | 91.4 | |
| 9 | | 101.3 | 98.9 | 94 | |
| 10 | | 99.3 | 98.9 | 92.8 | |
| 11 | | 100.4 | 101.7 | 95.3 | |
| 12 | | 99.5 | 100.8 | 96.7 | |
| 13 | | 100.1 | 100.9 | 97.3 | |
| 14 | | 103.3 | 103.3 | 99.9 | |

Example 160. Efficacy of Conjugate 45b Subcutaneously Dosed Against Influenza A/Hong Kong/1/1968 (H3N2) in a Lethal Mouse Model Conjugate 45b was evaluated against a lethal IAV H3N2 influenza infection in female BALB/c mice (Charles River Laboratories, 6-8 weeks). The challenge virus (A/Hong Kong/1/1968) is a mouse-adapted isolate capable of causing lethal infections in mice. The experiment comprised 3 groups of 5 mice. At day 0, all mice were challenged with virus at 3× the LD95 by intranasal inoculation in a volume of 30 µl, after being anesthetized with a mixture of ketamine/xylazine (150 and 10 mg/kg respectively). Mortality and body weights were recorded daily and any animal with a 20% loss of body weight was scored as a death.

Test groups received a single subcutaneous (SC) treatment of conjugate 45b or vehicle (PBS) 2 hours post viral challenge. The study design is summarized in Table 83.

TABLE 83

Study design for Influenza A/Hong Kong/1/1968 (H3N2) study

| Group | Test article | Route/Schedule | Dose (mq/kq) | Dose volume (ml/kq) | # of mice |
|---|---|---|---|---|---|
| 1 | Vehicle | SC, T + 2 hrs. | na | 10 | 5 |
| 2 | Conjugate 45b | SC, T + 2 hrs. | 1 | 10 | 5 |
| 3 | Conjugate 45b | SC, T + 2 hrs. | 0.3 | 10 | 5 |

As expected, mice receiving vehicle succumbed to infection by Day 7 (Table 84). However, mice treated with conjugate 45b were fully protected at 1 and 0.3 mg/kg dose levels. In this study conjugate 45b was not dosed lower than 0.3 mg/kg.

TABLE 84

Percent Survival

| | | Conjugate 45b (mg/kg) | |
|---|---|---|---|
| Day | Vehicle | 1 | 0.3 |
| 0 | 100 | 100 | 100 |
| 1 | 100 | 100 | 100 |
| 2 | 100 | 100 | 100 |
| 3 | 100 | 100 | 100 |

TABLE 84-continued

Percent Survival

| | | Conjugate 45b (mg/kg) | |
|---|---|---|---|
| Day | Vehicle | 1 | 0.3 |
| 4 | 100 | 100 | 100 |
| 5 | 40 | 100 | 100 |
| 6 | 20 | 100 | 100 |
| 7 | 0 | 100 | 100 |
| 8 | 0 | 100 | 100 |
| 9 | 0 | 100 | 100 |
| 10 | 0 | 100 | 100 |
| 11 | 0 | 100 | 100 |
| 12 | 0 | 100 | 100 |
| 13 | 0 | 100 | 100 |
| 14 | 0 | 100 | 100 |

The potency of conjugate 45b was further supported by daily body weight measurements. As expected, mice treated with vehicle demonstrated a steady drop in body weight until it exceeded 20%, at which time they were scored as a mortality (Table 85).

In contrast to control mice, those groups receiving conjugate 45b at 1 and 0.3 mg/kg maintained nearly healthy body weights throughout the study and never demonstrated more than a transient body weight drop of less than 11% before regaining nearly their starting body weight by study end (Table 85). By both survival and body weight measurements conjugate 45b demonstrated robust protection from a lethal challenge of Influenza A (H3N2) with a single SC dose as low as 0.3 mg/kg.

TABLE 85

Percent Body Weight

| | | Conjugate 45b (mg/kg) | |
|---|---|---|---|
| Day | Vehicle | 1 | 0.3 |
| 0 | 100 | 100 | 100 |
| 1 | 99.2 | 96 | 98.1 |
| 2 | 94.1 | 94.2 | 94.4 |
| 3 | 89.5 | 91 | 89.1 |
| 4 | 88.6 | 94.1 | 90.5 |
| 5 | 84.1 | 93.1 | 89.1 |
| 6 | | 96.3 | 90.6 |
| 7 | | 95 | 90.2 |
| 8 | | 97.3 | 92.8 |
| 9 | | 96.7 | 93.2 |
| 10 | | 97.8 | 94.6 |
| 11 | | 99.9 | 97.5 |
| 12 | | 98.3 | 97.4 |
| 13 | | 98.9 | 99.5 |
| 14 | | 98.6 | 100.2 |

Example 161. Efficacy of Conjugate 45b Against Influenza B (Victoria Lineage) in a Lethal Mouse Model Conjugate 45b was evaluated against a lethal Influenza B influenza infection in female BALB/c mice (Charles River Laboratories, 6-8 weeks). The challenge virus (B/Malaysia/8/1934) is a mouse-adapted isolate capable of causing lethal infections in mice. The experiment comprised 6 groups of 5 mice. At day 0, all mice were challenged with virus at 3× the LD95 by intranasal inoculation in a volume of 30 µl (approx. 1 E4 per mouse), after being anesthetized with a mixture of ketamine/xylazine (150 and 10 mg/kg respectively).

All groups received a single SC treatment, 2 hours post viral challenge of test article, vehicle (PBS), or Fc only control (hIgG1 Fc). The study evaluated concentrations of conjugate 45b at 1, 0.3, 0.1, and 0.03 mg/kg. Mice were monitored for 2 weeks and animals exceeding 20% body weight loss, or were found moribund, were scored as a mortality.

All mice treated with vehicle or the Fc only control, reached mortality by day 7. In contrast, mice receiving 1, 0.3, or 0.1 mg/kg of conjugate 45b were fully protected after receiving a single SC dose (Table 86). The potency of conjugate 45b against Influenza B was further supported by the daily body measurements (Table 87), which show a less than 5% transient drop at 0.3 mg/kg.

TABLE 86

Percent Survival

| | | | Conjugate 45b (mg/kg) | | | |
|---|---|---|---|---|---|---|
| Day | Vehicle | hIgG1 Fc (1) | 1 | 0.3 | 0.1 | 0.03 |
| 0 | 100 | 100 | 100 | 100 | 100 | 100 |
| 1 | 100 | 100 | 100 | 100 | 100 | 100 |
| 2 | 100 | 100 | 100 | 100 | 100 | 100 |
| 3 | 100 | 100 | 100 | 100 | 100 | 100 |
| 4 | 100 | 100 | 100 | 100 | 100 | 100 |
| 5 | 100 | 100 | 100 | 100 | 100 | 100 |
| 6 | 100 | 80 | 100 | 100 | 100 | 100 |
| 7 | 0 | 0 | 100 | 100 | 100 | 20 |
| 8 | 0 | 0 | 100 | 100 | 100 | 0 |
| 9 | 0 | 0 | 100 | 100 | 100 | 0 |
| 10 | 0 | 0 | 100 | 100 | 100 | 0 |
| 11 | 0 | 0 | 100 | 100 | 100 | 0 |
| 12 | 0 | 0 | 100 | 100 | 100 | 0 |
| 13 | 0 | 0 | 100 | 100 | 100 | 0 |
| 14 | 0 | 0 | 100 | 100 | 100 | 0 |

TABLE 87

Percent Body Weight

| | | | Conjugate 45b (mg/kg) | | | |
|---|---|---|---|---|---|---|
| Day | Vehicle | hIgG1 Fc (1) | 1 | 0.3 | 0.1 | 0.03 |
| 0 | 100 | 100 | 100 | 100 | 100 | 100 |
| 1 | 98.1 | 97 | 98.1 | 98.2 | 97.8 | 98.7 |
| 2 | 98.7 | 99.7 | 101.7 | 100.6 | 101.5 | 102.7 |
| 3 | 97.8 | 97.7 | 102.1 | 98.4 | 101.6 | 101.3 |
| 4 | 88 | 87.7 | 99.8 | 96.9 | 96.8 | 92 |
| 5 | 78.3 | 80.6 | 99.6 | 95.4 | 94.5 | 83.8 |
| 6 | 77.9 | 77.6 | 102.5 | 100.1 | 90.7 | 80 |
| 7 | | | 103.5 | 100.7 | 86.1 | 75.3 |
| 8 | | | 103 | 100.3 | 86.3 | |
| 9 | | | 103.2 | 101.1 | 91.5 | |
| 10 | | | 102.8 | 101 | 94 | |
| 11 | | | 101.2 | 99.7 | 94.1 | |
| 12 | | | 101.9 | 99.9 | 96.1 | |
| 13 | | | 102.9 | 101.6 | 97.6 | |
| 14 | | | 102.5 | 99.9 | 98.6 | |

Example 162. Efficacy of Conjugate 45b Against Influenza B (Yamagata Lineage) in a Lethal Mouse Model Conjugate 45b was evaluated against a lethal Influenza B influenza infection in female BALB/c mice (Charles River Laboratories, 6-8 weeks). The challenge virus (B/Florida/4/2006) is a mouse-adapted isolate capable of causing lethal infections in mice. The experiment comprised 7 groups of 5 mice. At day 0, all mice were challenged with virus at 3× the LD95 by intranasal inoculation in a volume of 30 μl (approx. 3E4 per mouse), after being anesthetized with a mixture of ketamine/xylazine (150 and 10 mg/kg respectively).

All groups received a single SC treatment, 2 hours post viral challenge of test article, vehicle (PBS), or Fc only control (hIgG1 Fc). The study evaluated concentrations of conjugate 45b from 3 to 0.03 mg/kg. Mice were monitored for 2 weeks and animals exceeding 20% body weight loss, or were found moribund, were scored as a mortality.

All mice treated with vehicle reached mortality by day 8, while the hIgG1 Fc control had 80% mortality. In contrast, mice receiving conjugate 45b were fully protected after receiving a single SC dose at all concentrations tested (Table 88).

TABLE 88

Percent Survival

| Day | Vehicle | hIgG1 Fc (1) | Conjugate 45b (mg/kg) | | | | |
|---|---|---|---|---|---|---|---|
| | | | 3 | 1 | 0.3 | 0.1 | 0.03 |
| 0 | 100 | 100 | 100 | 100 | 100 | 100 | 100 |
| 1 | 100 | 100 | 100 | 100 | 100 | 100 | 100 |
| 2 | 100 | 100 | 100 | 100 | 100 | 100 | 100 |
| 3 | 100 | 100 | 100 | 100 | 100 | 100 | 100 |
| 4 | 100 | 100 | 100 | 100 | 100 | 100 | 100 |
| 5 | 100 | 100 | 100 | 100 | 100 | 100 | 100 |
| 6 | 100 | 100 | 100 | 100 | 100 | 100 | 100 |
| 7 | 40 | 60 | 100 | 100 | 100 | 100 | 100 |
| 8 | 0 | 40 | 100 | 100 | 100 | 100 | 100 |
| 9 | 0 | 20 | 100 | 100 | 100 | 100 | 100 |
| 10 | 0 | 20 | 100 | 100 | 100 | 100 | 100 |
| 11 | 0 | 20 | 100 | 100 | 100 | 100 | 100 |
| 12 | 0 | 20 | 100 | 100 | 100 | 100 | 100 |
| 13 | 0 | 20 | 100 | 100 | 100 | 100 | 100 |
| 14 | 0 | 20 | 100 | 100 | 100 | 100 | 100 |

The potency of conjugate 45b against Influenza B (Yamagata) was further supported by the daily body measurements (Table 89), which show a less than 4% transient drop at 0.03 mg/kg, the lowest tested concentration.

TABLE 89

Percent Body Weight

| Day | Vehicle | hIgG1 Fc (1) | Conjugate 45b (mg/kg) | | | | |
|---|---|---|---|---|---|---|---|
| | | | 3 | 1 | 0.3 | 0.1 | 0.03 |
| 0 | 100 | 100 | 100 | 100 | 100 | 100 | 100 |
| 1 | 98.7 | 100.5 | 97.8 | 99.2 | 99.1 | 98.7 | 96.8 |
| 2 | 99.6 | 99.8 | 99.1 | 98.4 | 98.9 | 99.4 | 98.6 |
| 3 | 98.7 | 99.3 | 100.8 | 101.2 | 101.2 | 103.8 | 100.9 |
| 4 | 89.8 | 91 | 100.4 | 99.3 | 98.3 | 98.5 | 97.3 |
| 5 | 84.6 | 87.6 | 99.2 | 97.5 | 98 | 98.2 | 96.2 |
| 6 | 80.2 | 86.6 | 103.4 | 100.7 | 100.9 | 101.8 | 100.4 |
| 7 | 75.5 | 79.9 | 101.3 | 102.3 | 100.8 | 101.4 | 96.9 |
| 8 | | | 102.7 | 103 | 103 | 102.7 | 99.2 |
| 9 | | | 100.2 | 101.9 | 101.7 | 100 | 99 |
| 10 | | | 102.6 | 102.8 | 101.7 | 101.3 | 100.7 |
| 11 | | | 103 | 105.1 | 104.1 | 102.3 | 101.9 |
| 12 | | | 101 | 103.2 | 101.8 | 100.2 | 100.1 |
| 13 | | | 103.3 | 104.9 | 103.9 | 103.7 | 104.2 |
| 14 | | | 101.8 | 104.6 | 103.1 | 101.6 | 102.1 |

Example 163. Efficacy of Conjugate 45b Against Influenza H1N1, H3N2, and B (Victoria) in a 28-Day Mouse Prevention Model Conjugate 45b was evaluated against lethal challenge by seasonal influenza subtypes (H1N1, H3N2, and B (Victoria lineage)) in female BALB/c mice (Charles River Laboratories, 6-8 weeks). The experiment comprised 13 groups of 5 mice, except for group 6 (Vehicle, A/HK/1/68 challenge), which consisted of 4 animals. On day 0, mice were subcutaneously (SC) administered conjugate 45b at 3, 1, or 0.3 mg/kg in a single dose. Control mice were also treated by the same route with vehicle (PBS) or hIgG1 Fc only. Twenty-eight Days after administration of test article, mice were challenged intranasally with 3× the $LD_{95}$ of one of the following seasonal influenza subtypes:

A/California/07/2009 (H1N1)
A/Hong Kong/i/i968 (H3N2)
B/Malaysia/8/1934 (B; Victoria lineage)

For viral challenge mice were anesthetized with a mixture of ketamine/xylazine (150 and 10 mg/kg respectively), and the virus was given in a volume of 30 μl. Mortality and body weights were recorded daily and any animal with a 20% loss of body weight was scored as a death.

For the H1N1 arm of the study all mice treated with vehicle only succumbed to infection by Day 7. The Fc only control was also not protective, with only 20% survival at study end (Day 42, 14 days after viral challenge). Conjugate 45b however was fully protective for a month against this pandemic isolate after a single SC dose at 1 mg/kg (P=0.0020; Table 90). Even at the lowest test concentration (0.3 mg/kg) 80% of mice survived to study end. The daily body weight (BW) percent measurements further supported the efficacy of conjugate 45b in this model (Table 91), at 1 mg/kg the mice had a transient loss of 12.1% which is typical against this highly pathogenic strain, which largely recovered by study end (96.5% of the starting value).

TABLE 90

H1N1 Percent Survival

| Day | Vehicle | hIgG1 Fc (3) | Conjugate 45b (mg/kg) | | |
|---|---|---|---|---|---|
| | | | 3 | 1 | 0.3 |
| 0 | 100 | 100 | 100 | 100 | 100 |
| 1 | 100 | 100 | 100 | 100 | 100 |
| 2 | 100 | 100 | 100 | 100 | 100 |
| 3 | 100 | 100 | 100 | 100 | 100 |
| 4 | 100 | 100 | 100 | 100 | 100 |
| 5 | 100 | 40 | 100 | 100 | 100 |
| 6 | 20 | 40 | 100 | 100 | 80 |
| 7 | 0 | 20 | 100 | 100 | 80 |
| 8 | 0 | 20 | 100 | 100 | 80 |
| 9 | 0 | 20 | 100 | 100 | 80 |
| 10 | 0 | 20 | 100 | 100 | 80 |
| 11 | 0 | 20 | 100 | 100 | 80 |
| 12 | 0 | 20 | 100 | 100 | 80 |
| 13 | 0 | 20 | 100 | 100 | 80 |
| 14 | 0 | 20 | 100 | 100 | 80 |

TABLE 91

H1N1 Percent Body Weight*

| Day | Vehicle | hIgG1 Fc (3) | Conjugate 45b (mg/kg) | | |
|---|---|---|---|---|---|
| | | | 3 | 1 | 0.3 |
| 0 | 100 | 100 | 100 | 100 | 100 |
| 1 | 100.2 | 93.6 | 99.6 | 93 | 97 |
| 2 | 97.1 | 93 | 99.5 | 93 | 97.7 |
| 3 | 89.1 | 87 | 92.7 | 88.1 | 90.9 |
| 4 | 82.3 | 80.6 | 89.8 | 89.1 | 89.4 |
| 5 | 77.7 | 77.4 | 89 | 88 | 87.2 |
| 6 | | | 88.9 | 87.9 | 87 |

TABLE 91-continued

H1N1 Percent Body Weight*

| Day | Vehicle | hIgG1 Fc (3) | Conjugate 45b (mg/kg) | |
| --- | --- | --- | --- | --- |
| | | | 3 | 1 | 0.3 |
| 7 | | | 90.9 | 90.7 | |
| 8 | | | 92.1 | 90.5 | |
| 9 | | | 92.9 | 90.4 | |
| 10 | | | 96 | 92.2 | |
| 11 | | | 95.1 | 94.5 | |
| 12 | | | 94.7 | 94.3 | |
| 13 | | | 96.2 | 96.2 | |
| 14 | | | 97 | 96.5 | |

*Note, that BWs are only given until the first death occurs within a group

For the H3N2 arm of the study (A/Hong Kong/1/1968), all mice treated with vehicle only succumbed to infection by Day 8. In contrast to vehicle only treatment, all Conjugate 45b concentrations were fully protective, even at a dose level of 0.3 mg/kg (P=0.0007; Table 92). As seen with the H1N1 arm of the study, daily BW measurements further supported the efficacy of conjugate 45b against the H3N2 subtype (Table 93), at 0.3 mg/kg the mice had a transient loss of less than 11%, with BWs largely recovered by study end (98.4% of the starting value).

TABLE 92

H3N2 Percent Survival

| Day | Vehicle | Conjugate 45b (mg/kg) | | |
| --- | --- | --- | --- | --- |
| | | 3 | 1 | 0.3 |
| 0 | 100 | 100 | 100 | 100 |
| 1 | 100 | 100 | 100 | 100 |
| 2 | 100 | 100 | 100 | 100 |
| 3 | 100 | 100 | 100 | 100 |
| 4 | 100 | 100 | 100 | 100 |
| 5 | 100 | 100 | 100 | 100 |
| 6 | 100 | 100 | 100 | 100 |
| 7 | 75 | 100 | 100 | 100 |
| 8 | 0 | 100 | 100 | 100 |
| 9 | 0 | 100 | 100 | 100 |
| 10 | 0 | 100 | 100 | 100 |
| 11 | 0 | 100 | 100 | 100 |
| 12 | 0 | 100 | 100 | 100 |
| 13 | 0 | 100 | 100 | 100 |
| 14 | 0 | 100 | 100 | 100 |

TABLE 93

H3N2 Percent Body Weight

| Day | Vehicle | Conjugate 45b (mg/kg) | | |
| --- | --- | --- | --- | --- |
| | | 3 | 1 | 0.3 |
| 0 | 100 | 100 | 100 | 100 |
| 1 | 98.4 | 99.2 | 99.1 | 100 |
| 2 | 93.7 | 98.5 | 97.7 | 99.1 |
| 3 | 88.2 | 96.7 | 94.6 | 95.3 |
| 4 | 88.5 | 97.3 | 93.4 | 95.6 |
| 5 | 86.2 | 95.8 | 94 | 92.6 |
| 6 | 81.4 | 96.8 | 94.6 | 89.3 |
| 7 | 77 | 99.8 | 97.1 | 89.6 |
| 8 | | 100.3 | 97.8 | 91.5 |
| 9 | | 98.2 | 96.9 | 91.7 |
| 10 | | 101.3 | 101.2 | 96.8 |
| 11 | | 100.5 | 100.8 | 97.9 |
| 12 | | 98.6 | 99.7 | 96.5 |
| 13 | | 99.3 | 98.3 | 97 |
| 14 | | 99.7 | 100.1 | 98.4 |

The final arm of the study determined the efficacy of conjugate 45b against the Victoria lineage of influenza B. Typical to what was seen in the other arms of this study, vehicle only treated mice succumbed to infection by Day 7. Similar to the results against the H1N1 subtype, a single SC dose of 1 mg/kg was fully protective against lethal challenge by influenza B (Table 94; P=0.0031) one month after conjugate 45b administration. At the lowest test concentration (0.1 mg/kg), 60% of mice survived. As in the other arms of the study, BW data supports the potency of conjugate 45b. Against the B/Malaysia strain animals treated at 1 mg/kg showed a less than 6% transient BW loss which had recovered by study end (Table 95; 100.2%).

TABLE 94

Influenza B Percent Survival

| Day | Vehicle | Conjugate 45b (mg/kg) | | |
| --- | --- | --- | --- | --- |
| | | 3 | 1 | 0.3 |
| 0 | 100 | 100 | 100 | 100 |
| 1 | 100 | 100 | 100 | 100 |
| 2 | 100 | 100 | 100 | 100 |
| 3 | 100 | 100 | 100 | 100 |
| 4 | 100 | 100 | 100 | 100 |
| 5 | 100 | 100 | 100 | 100 |
| 6 | 60 | 100 | 100 | 100 |
| 7 | 0 | 100 | 100 | 100 |
| 8 | 0 | 100 | 100 | 40 |
| 9 | 0 | 100 | 100 | 40 |
| 10 | 0 | 100 | 100 | 40 |
| 11 | 0 | 100 | 100 | 40 |
| 12 | 0 | 100 | 100 | 40 |
| 13 | 0 | 100 | 100 | 40 |
| 14 | 0 | 100 | 100 | 40 |

TABLE 95

Influenza B Percent Body Weight

| Day | Vehicle | Conjugate 45b (mg/kg) | | |
| --- | --- | --- | --- | --- |
| | | 3 | 1 | 0.3 |
| 0 | 100 | 100 | 100 | 100 |
| 1 | 97.3 | 98.7 | 97.2 | 98.6 |
| 2 | 97.1 | 98.8 | 98.9 | 99.2 |
| 3 | 96.4 | 99.2 | 98.6 | 98.6 |
| 4 | 88.5 | 99.6 | 98.3 | 96.8 |
| 5 | 80.8 | 96.2 | 95.8 | 90 |
| 6 | 77 | 96.5 | 94.5 | 86.2 |
| 7 | | 97.8 | 95.5 | 82.8 |
| 8 | | 100.5 | 97 | 81.6 |
| 9 | | 100.1 | 97.3 | |
| 10 | | 102.3 | 99.7 | |
| 11 | | 102.3 | 100.3 | |
| 12 | | 100.7 | 98.7 | |
| 13 | | 98.7 | 98.3 | |
| 14 | | 101.6 | 100.2 | |

Example 164. In vitro plaque reduction assay

Plaque reduction assays were performed in Madin Darby Canine Kidney (MDCK) cells seeded in 24 well plates. 500,000 MDCK cells were seeded in 0.5 mL of media (DMEM) containing 10% FBS and incubated for approximately 24 hours. Dilutions of the test articles and the viruses used, H1N1 WT (A/California/12/2012) and H275Y (A/Texas/23/2012), H3N2 WT (A/Washington/12/2007) and E119V (A/Texas/12/2007), and B (B/Malaysia/2506/2004), were performed in a buffer containing PBS, Bovine Albumin 35% and $Ca^{2+}/Mg^{2+}$. Conjugate 45b and baloxavir, zanamivir oseltamivir comparators were pre-incubated with virus for 30 minutes at room temperature before adding them to the monolayers of MDCK cells after media removal and one wash with PBS. The MOI for each drug-virus combination was selected to target 30 plaques in the PBS control well. Adsorption was carried out for 1 h, the virus-test article mix was removed, and the infected cells were incubated for 48 h in the presence the test article diluted in a mixture of 1.25% Avicel, DMEM, 0.01% DEAE-dextran and 2 µg/mL of TPCK trypsin. After 48 hours the Avicel mixture was then removed and cells were fixed with paraformaldehyde and stained with 1% crystal violet to count the plaques. All drugs were tested at six concentrations, ranging from 0.3 to 100 nM. $EC_{50}$ values (nM) were calculated using GraphPad Prism software. Results are summarized in Table 96.

TABLE 96

Summary of conjugate 45b plaque reduction assay $EC_{50}$ values for WT and NA mutant influenza strains

| | $EC_{50}$ (nM) | | | | |
|---|---|---|---|---|---|
| Molecule | A/CA/ 12/2012 (H1N1) | A/TX/23/ 2012 (H1N1) H275Y | A/WA/12/ 2007 (H3N2) | A/TX/12/ 2007 (H3N2) E119V | B/Malaysia/ 2506/2004 |
| conjugate 45b | 1 | 1.2 | ≤0.3 | 1.2 | 4.1 |
| baloxavir | 4 | 1.6 | 4.8 | 3.2 | 8.4 |
| zanamivir | 35 | 93.8 | >100 | 74 | 17.3 |
| oseltamivir | >100 | >100 | 29.6 | >100 | 22.1 |

Conjugate 45b demonstrated its potent activity in plaque reduction assays against all H1N1, H3N2 and B strains tested, generating $EC_{50}$ values lower than those for all three comparator agents (Table 96). In addition, the activity of conjugate 45b was minimally impacted by the presence of oseltamivir resistance-conferring NA mutations E119V and H275Y

Example 165. Serial Passage Experiments for Selection of Resistant Influenza Viruses To evaluate the potential for development of drug resistant mutant viral strains under selective pressure with viral inhibitors, serial passage studies were conducted with conjugate 45b, versus oseltamivir and baloxavir comparators. Serial passage studies were conducted using MDCK cells. Passages were conducted as follows: 500,000 MDCK cells were seeded per well (24-well) in 500 µl DMEM 10% FBS, 1% PS, 1% NaPyr and 1% HEPES and incubated for approximately 24 hours. Once cells reached approximately 80% confluency, they were washed once with PBS and incubated for 2 hours in the presence of compounds or PBS alone under normal culture conditions. Selecting agent concentrations were optimized as required for maximum virus inhibition, while maintaining enough virus production for subsequent passages. Concentrations of conjugate 45b, baloxavir, and oseltamivir used in the serial passage experiments were 4 nM, 4 nM and 200 nM respectively. Cells were infected at an MOI of 0.01 with A/California/07/2009 H1N1 pdm for 1 hour at room temperature in a buffer containing PBS, Bovine Albumin 35% and $Ca^{2+}/Mg^{2+}$, followed by removal of inoculum and washing of cells once with DMEM 1% PS, 1% NaPyr and 1% HEPES (No FBS). Cells were then Incubated for 24 hours in the presence of selecting agents diluted in DMEM 1% PS, 1% NaPyr, 1% HEPES and 2 µg/ml TPCK-treated trypsin. After incubation, viral supernatants were collected, and cells and debris were removed by centrifugation (5 min, 4° C., 1,400×g). Supernatants were then used to:

i Quantify viral titer by plaque assay ii Conduct a hemagglutination assay to determine if the virus escaped compound inhibition iii Re-infect freshly seeded MDCK cells in presence of compounds The process was repeated for 10 passages. Once increased titers in the presence of drugs are detected the viruses may be plaque purified. Following plaque purification, all 8 genome segments may be sequenced and compared to PBS treated control virus to detect escape mutations. A summary of the serial passage is shown in figure FIG. 83. No increases in viral titer were observed for conjugate 45b through the course of 10 passages (suggesting no emergence of resistant mutants), while baloxavir and oseltamivirtiters increased to levels similar to those observed in the PBS control after passages 6 and 8 respectively.

Example 166. Cytopathic Effect Assay

To measure the ability of Conjugate 45b to protect mammalian cells from infection and destruction by influenza virus, Cytopathic effect (CPE) based microneutralization assays were conducted as discussed in Example 25, with minor variations. Briefly, a monolayer of MOCK cells was infected with influenza A or B strains at appropriate MOI varying between 0.001-1. Test articles were added at concentrations ranging between 0.1-10,000 nM and incubated for 3 days for influenza A or 5 days for influenza B at 37° C., 5% C02. CPE was determined by crystal violet staining by reading absorbance at 595 nm. The results are shown in Table 97 and Table 98 below.

TABLE 97

CPE of Conjugate 45b against Influenza A H1N1 at MOI 0.01 or MOI 0.001 (CPE [nM])

| Molecule | TM | DAR | Fc | Central linker | A/WSN/ 1933 | A/CA/07/ 2009pdm | A/CA/12/ 2012 H275 | A/Texas/23/2012 H275Y mutant |
|---|---|---|---|---|---|---|---|---|
| Oseltamivir | N/A | N/A | N/A | N/A | >10,000 | 34.2 | 107.6 | >10,000 |
| Zanamivir | N/A | N/A | N/A | N/A | N/A | 33.16 | 54.59 | 327.7 |
| Conjugate | Int-83 | 4.2 | SEQ ID 15 | atom | 3.676 | 2.964 | 0.7043 | 2.101 |

TABLE 97-continued

CPE of Conjugate 45b against Influenza A H1N1 at MOI 0.01 or MOI 0.001 (CPE [nM])

| Molecule | TM | DAR | Fc | Central linker | A/WSN/ 1933 | A/CA/07/ 2009pdm | A/CA/12/ 2012 H275 | A/Texas/23/2012 H275Y mutant |
|---|---|---|---|---|---|---|---|---|
| 45b | | | NO: 73 | | | | | |
| Baloxavir | N/A | N/A | N/A | N/A | 11.35 | 2.216 | 3.718 | 3.318 |

TABLE 98

CPE of Conjugate 45b against Influenza A H3N2 at MOI 0.01 or MOI 0.001 (CPE [nM])

| Molecule | TM | DAR | Fc | Central linker | A/HK/ 1/1968 | A/Wisconsin/ 04/2018 | A/Bethesda/ 956/2006 R292K mutant | A/Washington/ 12/2007 | A/Texas/12/2007 E119V mutant |
|---|---|---|---|---|---|---|---|---|---|
| Oseltamivir | N/A | N/A | N/A | N/A | 0.7444 | 151.1 | >10,000 | 1.908 | 351.4 |
| Zanamivir | N/A | N/A | N/A | N/A | <0.3 | 308 | 9591 | 1.968 | 2.096 |
| Conjugate 45b | Int-83 | 4.2 | SEQ ID NO: 73 | 15 atom | <0.3 | 8.99 | 54.01 | 0.04449 | 0.6594 |
| Baloxavir | N/A | N/A | N/A | N/A | 2.596 | 4.916 | 17.15 | 0.5252 | 5.602 |

Example 167. Neuraminidase Inhibition with Live Influenza A Virus or Lysates of Neuraminidase Resistant Mutants Neuraminidase inhibition (NAI). Test articles were incubated with neuraminidase (Sino Biological) or with live viruses for 20 min at 37° C., 5% $CO_2$. 2'-(4-Methylumbelliferyl)-α-D-N acetylneuraminic acid substrate was added to appropriate wells and incubated for 1 h at 37° C., 5% $CO_2$. NAI was determined by reading fluorescence at 355 nm excitation/460 nm emission. Neuraminidase inhibition was determined for neuraminidase resistant mutants and for live influenza virus (Table 99, Table100, Table101, Table102, and Table 103).

TABLE 99

NAI against live influenza A (H1N1) viruses

| Molecule | TM | DAR | Fc | Central linker | A/Ca/07/2009 (H1N1)pdm $IC_{50}$ [nM] | A/PR/8/1934 (H1N1) $IC_{50}$ [nM] | A/California/12/2012 (H1N1)pdm09 $IC_{50}$ [nM] | A/Texas/23/2012 (H1N1)pdm09 H275Y $IC_{50}$ [nM] |
|---|---|---|---|---|---|---|---|---|
| Oseltamivir | N/A | N/A | N/A | N/A | 0.9103 | 2.427 | 1.28 | 367.9 |
| Zanamivir | N/A | N/A | N/A | N/A | 0.5634 | 0.6041 | 0.8891 | 0.8505 |
| Int-83 | N/A | N/A | N/A | 15 atom | 28.59 | 4.231 | 45.08 | 26.47 |
| Conjugate 45b | Int-83 | 4.8 | SEQ ID NO: 73 | 15 atom | 0.8124 | 0.07184 | 2.527 | 1.471 |

*All live viruses tested at 1e6 PFU.

TABLE 100

NAI against live influenza A (H3N2) viruses

| Molecule | TM | DAR | Fc | Central linker | A/Wash/1/2007 (H3N2) $IC_{50}$ [nM] | A/Texas/12/2007 (H3N2) E119V $IC_{50}$ [nM] | A/Texas/71/2017 (H3N2) $IC_{50}$ [nM] | A/Bethesda/956/2006 (H3N2) R292K* $IC_{50}$ [nM] |
|---|---|---|---|---|---|---|---|---|
| Oseltamivir | N/A | N/A | N/A | N/A | 0.2086 | 114.2 | 0.9502 | 4667 |
| Zanamivir | N/A | N/A | N/A | N/A | 4.845 | 3.085 | 2.321 | 31.59 |
| Int-83 | N/A | N/A | N/A | 15 atom | 99.05 | 50.22 | 301.1 | 1147 |
| Conjugate 45b | Int-83 | 4.8 | SEQ ID NO: 73 | 15 atom | 0.0233 | 2.79 | 11.3 | 23.55 |

*All live viruses tested at 1e6 PFU (except R292K which was tested at 1e5 PFU)

TABLE 101

NAI against live influenza A (H1N1)pdm09 viruses

| Molecule | TM | DAR | Fc | Central linker | A/Illinois/08/2018 (H1N1)pdm09 I38 WT $IC_{50}$ [nM] | A/Illinois/37/2018 (H1N1)pdm09 I38L $IC_{50}$ [nM] | A/Illinois/08/2018 (H1N1)pdm09 I38T $IC_{50}$ [nM] |
|---|---|---|---|---|---|---|---|
| Oseltamivir | N/A | N/A | N/A | N/A | 0.43 | 0.71 | 0.58 |
| Zanamivir | N/A | N/A | N/A | N/A | 0.37 | 0.47 | 0.50 |
| Int-83 | N/A | N/A | N/A | 15 atom | 5.90 | 6.16 | 4.81 |
| Conjugate 45b | Int-83 | 4.8 | SEQ ID NO: 73 | 15 atom | 0.04 | 0.10 | 0.01 |

*All live viruses tested at 1e7 PFU.

TABLE 102

NAI against live influenza A (H3N2) viruses

| Molecule | TM | DAR | Fc | Central linker | A/Louisiana/50/2017 (H3N2) I38 WT $IC_{50}$ [nM] | A/Louisiana/49/2017 (H3N2) I38M $IC_{50}$ [nM] |
|---|---|---|---|---|---|---|
| Oseltamivir | N/A | N/A | N/A | N/A | 0.26 | 0.19 |
| Zanamivir | N/A | N/A | N/A | N/A | 0.48 | 0.37 |
| Int-83 | N/A | N/A | N/A | 15 atom | 47.72 | 26.09 |
| Conjugate 45b | Int-83 | 4.8 | SEQ ID NO: 73 | 15 atom | 4.58 | 5.13 |

*All live viruses tested at 1e7 PFU.

TABLE 103

NAI against influenza B viruses

| Molecule | TM | DAR | Fc | Central linker | B/Florida/4/2006 (Yamagata) $IC_{50}$ [nM] | B/Malaysia/2506/2004 (Victoria) $IC_{50}$ [nM] | B/Colorado/6/2017 (Victoria) $IC_{50}$ [nM] |
|---|---|---|---|---|---|---|---|
| Oseltamivir | N/A | N/A | N/A | N/A | 14.37 | 32.02 | 35.03 |
| Zanamivir | N/A | N/A | N/A | N/A | 4.755 | 4.147 | 5.112 |
| Int-83 | N/A | N/A | N/A | 15 atom | 275.3 | 273.1 | 124.8 |
| Conjugate 45b | Int-83 | 4.8 | SEQ ID NO: 73 | 15 atom | 2.888 | 1.514 | 19.83 |

*All live viruses tested at 1e6 PFU.

Example 168. Antibody-dependent cellular phagocytosis assay

Conjugate 45b was tested for antibody-dependent cellular phagocytosis (ADCP). A monolayer of MDCK cells was infected with influenza A or influenza B strains at an MOI of 0.001-10, and incubated for 18-24 h at 37° C., in 5% $CO_2$. ADCP was determined with commercial report cell line (PROMEGA) according to manufacturer's instructions. Briefly, test articles were added at concentrations ranging from 1 to 10,000 nM to appropriate wells and incubated for 15 m at 37° C., in 5% $CO_2$. ADCP was quantified by reading luminescence. Conjugate 45b and Fc alone (SEQ ID NO: 73, prepared analogous to Example 124) were tested against influenza A/PR/8/1934 (H1N1), influenza A/CA/07/2009 (H1N1), and influenza A/HK/1/1968 (H3N2) (Tables 104-106, respectively), and influenza B/Malaysia/2506/2004 (Victoria, Table 107), showing an MOI-dependent increase in ADCP by conjugate 45b. Conjugate 45b also showed a Dose-dependent increase in ADCP against influenza A/PR/8/1934 (H1N1), influenza A/CA/07/2009 (H1N1), and influenza A/HK/1/1968 (H3N2) at an MOI of 10 (Tables 108-110, respectively), and influenza B/Malaysia/2506/2004 (Victoria, Table 111).

TABLE 104

MOI-dependent increase in ADCP (fold induction) by Conjugate 45b against influenza A

| Influenza A/PR/8/1934 (H1N1) MOI | Fc Alone | Conjugate 45b [1 µM] |
|---|---|---|
| 0 | 1 | 1 |
| 0.1 | 1.13 | 1.8 |
| 0.3 | 1.21 | 9.95 |
| 1 | 0.96 | 13.77 |
| 3 | 1.1 | 14.94 |
| 10 | 1.05 | 13.76 |

TABLE 105

MOI-dependent increase in ADCP (fold induction) by Conjugate 45b against influenza A

| Influenza A/CA/7/2009 (H1N1)pdm MOI | Fc Alone | Conjugate 45b [1 µM] |
|---|---|---|
| 0 | 0.98 | 1.02 |
| 0.1 | 1.14 | 6.33 |

TABLE 105-continued

MOI-dependent increase in ADCP (fold induction) by
Conjugate 45b against influenza A

| Influenza A/CA/7/2009 (H1N1)pdm MOI | Fc Alone | Conjugate 45b [1 μM] |
|---|---|---|
| 0.3 | 1.03 | 22.16 |
| 1 | 0.99 | 18.27 |
| 3 | 0.93 | 19.61 |
| 10 | 1.05 | 21.11 |

TABLE 106

MOI-dependent increase in ADCP (fold induction) by
Conjugate 45b against influenza A

| Influenza A/HK/1/1968 (H3N2) MOI | Fc Alone | Conjugate 45b [1 μM] |
|---|---|---|
| 0 | 1.02 | 0.98 |
| 0.1 | 1.07 | 1.48 |
| 0.3 | 1.05 | 2.63 |
| 1 | 1.18 | 2.74 |
| 3 | 1.01 | 4.3 |
| 10 | 1.06 | 4.39 |

TABLE 107

MOI-dependent increase in ADCP (fold induction) by
Conjugate 45b against influenza B

| Influenza B/Malaysia/2506/2004 MOI | Fc Alone | Conjugate 45b [1 μM] |
|---|---|---|
| 0 | 1.07 | 0.93 |
| 0.1 | 0.98 | 1.67 |
| 0.3 | 0.99 | 6.93 |
| 1 | 1.14 | 25.86 |
| 3 | 1.11 | 34.29 |
| 10 | 1 | 30.38 |

TABLE 108

Dose-dependent increase in ADCP (fold induction) by Conjugate 45b
against influenza A at MOI 10

| Influenza A/PR/8/1934 (H1N1) [nM] | Fc Alone | Conjugate 45b |
|---|---|---|
| 0 | 0.96 | 1.04 |
| 100 | 1.22 | 3.44 |
| 300 | 1.56 | 7 |
| 1000 | 1.91 | 17.04 |
| 3000 | 2.22 | 28.54 |
| 10000 | 3.08 | 44.93 |

TABLE 109

Dose-dependent increase in ADCP (fold induction) by
Conjugate 45b against influenza A at MOI 10

| Influenza A/CA/7/2009 (H1N1)pdm [nM] | Fc Alone | Conjugate 45b |
|---|---|---|
| 0 | 0.98 | 1.02 |
| 100 | 1.64 | 2.32 |
| 300 | 1.74 | 5.41 |
| 1000 | 2.15 | 10.04 |

TABLE 109-continued

Dose-dependent increase in ADCP (fold induction) by
Conjugate 45b against influenza A at MOI 10

| Influenza A/CA/7/2009 (H1N1)pdm [nM] | Fc Alone | Conjugate 45b |
|---|---|---|
| 3000 | 2.13 | 24.28 |
| 10000 | 2.24 | 33.87 |

TABLE 110

Dose-dependent increase in ADCP (fold induction) by
Conjugate 45b against influenza A at MOI 10

| Influenza A/HK/1/1968 (H3N2) [nM] | Fc Alone | Conjugate 45b |
|---|---|---|
| 0 | 1.01 | 0.99 |
| 100 | 1.03 | 1.81 |
| 300 | 1.48 | 3.33 |
| 1000 | 2.29 | 6.09 |
| 3000 | 2.87 | 9.01 |
| 10000 | 2.11 | 9.96 |

TABLE 111

Dose-dependent increase in ADCP (fold induction) by
Conjugate 45b against influenza B/Malaysia/2506/2004 at MOI 10

| Influenza B/Malaysia/2506/2004 MOI | Fc Alone | Conjugate 45b |
|---|---|---|
| 0 | 1.15 | 0.85 |
| 100 | 1.3 | 6.67 |
| 300 | 2.09 | 26.21 |
| 1000 | 2.32 | 61.43 |
| 3000 | 3.26 | 96.95 |
| 10000 | 3.91 | 104.49 |

Example 169. Antibody-Dependent Cellular Cytotoxicity Assay

Conjugate 45b was tested for antibody-dependent cellular cytotoxicity (ADCC). A monolayer of MDCK cells was infected with influenza A or influenza B strains at an MOI of 0.001-10, and incubated for 18-24 h at 37° C., in 5% $CO_2$. ADCC was determined with commercial report cell line (PROMEGA) according to manufacturer's instructions. Briefly, test articles were added at concentrations ranging from 1 to 10,000 nM to appropriate wells and incubated for 15 m at 37° C., in 5% $CO_2$. ADCC was quantified by reading luminescence. Conjugate 45b and Fc alone (SEQ ID NO: 73, prepared analogous to Example 124) were tested against influenza A/PR/8/1934 (H1N1), influenza A/CA/07/2009 (H1N1), and influenza A/HK/1/1968 (H3N2) (Tables 112-114, respectively), and influenza B/Malaysia/2506/2004 (Victoria, Table 115), showing an MOI-dependent increase in ADCC by conjugate 45b. Conjugate 45b also showed a Dose-dependent increase in ADCC against influenza A/PR/8/1934 (H1N1), influenza A/CA/07/2009 (H1N1), and influenza A/HK/1/1968 (H3N2) at an MOI of 10 (Tables 116-118, respectively), and influenza B/Malaysia/2506/2004 (Victoria, Table 119).

TABLE 112

MOI-dependent increase in ADCC (fold induction) by Conjugate 45b against influenza A

| Influenza A/PR/8/1934 (H1N1) MOI | Fc Alone | Conjugate 45b [1 µM] |
|---|---|---|
| 0 | 0.97 | 1.03 |
| 0.1 | 1.22 | 1.54 |
| 0.3 | 1.27 | 2.27 |
| 1 | 1.47 | 4.03 |
| 3 | 1.92 | 6.14 |
| 10 | 2.34 | 11.46 |

TABLE 113

MOI-dependent increase in ADCC by Conjugate 45b against influenza A

| Influenza A/CA/7/2009 (H1N1)pdm MOI | Fc Alone | Conjugate 45b [1 µM] |
|---|---|---|
| 0 | 1.02 | 0.98 |
| 0.1 | 1.23 | 1.48 |
| 0.3 | 1.4 | 2.21 |
| 1 | 1.62 | 3.74 |
| 3 | 1.74 | 6.08 |
| 10 | 2.14 | 9.59 |

TABLE 114

MOI-dependent increase in ADCC (fold induction) by Conjugate 45b against influenza A

| Influenza A/HK/1/1968 (H3N2) MOI | Fc Alone | Conjugate 45b [1 µM] |
|---|---|---|
| 0 | 0.99 | 1.01 |
| 0.1 | 1.31 | 1.46 |
| 0.3 | 1.66 | 2.17 |
| 1 | 2.48 | 3.4 |
| 3 | 1.43 | 2.74 |
| 10 | 0.89 | 2.34 |

TABLE 115

MOI-dependent increase in ADCC (fold induction) by Conjugate 45b against influenza B

| Influenza B/Malaysia/2506/2004 MOI | Fc Alone | Conjugate 45b [1 µM] |
|---|---|---|
| 0 | 0.97 | 1.03 |
| 0.1 | 1.27 | 3.6 |
| 0.3 | 1.64 | 9.38 |
| 1 | 2.36 | 22.09 |
| 3 | 2.65 | 26.21 |
| 10 | 2.87 | 34.46 |

TABLE 116

Dose-dependent increase in ADCC (fold induction) by Conjugate 45b against influenza A at MOI 10

| Influenza A/PR/8/1934 (H1N1) [nM] | Fc Alone | Conjugate 45b |
|---|---|---|
| 0 | 0.93 | 1.07 |
| 100 | 1.12 | 1.78 |
| 300 | 1.25 | 3.8 |
| 1000 | 1.4 | 5.16 |
| 3000 | 1.19 | 7.09 |
| 10000 | 1.03 | 5.68 |

TABLE 117

Dose-dependent increase in ADCC (fold induction) by Conjugate 45b against influenza A at MOI 10

| Influenza A/CA/7/2009 (H1N1)pdm [nM] | Fc Alone | Conjugate 45b |
|---|---|---|
| 0 | 0.91 | 1.09 |
| 100 | 1.16 | 3.44 |
| 300 | 1.02 | 5.53 |
| 1000 | 1.21 | 6.18 |
| 3000 | 1.17 | 6.05 |
| 10000 | 1.15 | 5.48 |

TABLE 118

Dose-dependent increase in ADCC (fold induction) by Conjugate 45b against influenza A at MOI 10

| Influenza A/HK/1/1968 (H3N2) [nM] | Fc Alone | Conjugate 45 |
|---|---|---|
| 0 | 0.97 | 1.03 |
| 100 | 1.11 | 1.42 |
| 300 | 1.15 | 2.24 |
| 1000 | 1.11 | 2.93 |
| 3000 | 1.11 | 3.08 |
| 10000 | 1.09 | 2.67 |

TABLE 119

Dose-dependent increase in ADCC (fold induction) by Conjugate 45b against influenza B/Malaysia/2506/2004 at MOI 10

| Influenza B/Malaysia/2506/2004 MOI | Fc Alone | Conjugate 45 |
|---|---|---|
| 0 | 0.96 | 1.04 |
| 100 | 1.18 | 4.16 |
| 300 | 1.11 | 5.34 |
| 1000 | 1.18 | 15.21 |
| 3000 | 1.04 | 14.84 |
| 10000 | 1.02 | 12.11 |

Example 170. Efficacy of Conjugate 45b in Lethal Mouse Influenza Model: Study #58

Conjugate 45b was evaluated against a lethal influenza A/PR/8/1934 (3E2 PFU) in female BALB/c mice (6-8 weeks old, n=5/group). The study design is shown in Table 120. Mice were treated with test articles at t=+2 h (SC) post-infection with a single dose for Conjugate 45b or twice daily for 4 days for control agents. All mice were monitored for body weight daily. Mice were sacrificed on day 4 post-infection and both lung lobes were harvested. Lungs were homogenized to determine the viral burden and immune response. Data are shown in tables 121-123.

TABLE 120

Efficacy Study #58 design

| Group | Test article (DAR) | Route/Schedule | Dose [mg/kg] | Dose/day [mg/kg] |
|---|---|---|---|---|
| 1 | PBS | SC, T + 2 h | N/A | N/A |
| 2 | hIgG1 Fc | SC, T + 2 h | 3 | 3 |
| 3 | Oseltamivir | PO, BID × 4 | 5 | 10 |
| 4 | Oseltamivir | PO, BID × 4 | 50 | 100 |
| 5 | Baloxavir | PO, BID × 4 | 15 | 30 |
| 6 | Conjugate 45b (4.8) | SC, T + 2 h | 0.1 | 0.1 |
| 7 | Conjugate 45b (4.8) | SC, T + 2 h | 0.3 | 0.3 |
| 8 | Conjugate 45b (4.8) | SC, T + 2 h | 1 | 1 |
| 9 | Conjugate 45b (4.8) | SC, T + 2 h | 3 | 3 |
| 10 | uninfected | N/A | N/A | N/A |

TABLE 121

Viral burden on day 4 post-infection in PFU/g

| Group | Test article [mg/kg] | PFU/g | Log reduction PFU/g |
|---|---|---|---|
| 1 | PBS [0] | 1.92E+07 | 0.00 |
| 2 | hIgG1 Fc [3] | 5.12E+07 | −0.43 |
| 3 | Oseltamivir [5] | 2.86E+06 | 0.83 |
| 4 | Oseltamivir [50] | 2.66E+06 | 0.86 |
| 5 | Baloxavir [15] | BLD (<10) | N/A (>6) |
| 6 | Conjugate 45b [0.1] | 1.50E+06 | 1.11 |
| 7 | Conjugate 45b [0.3] | 1.26E+05 | 2.18 |
| 8 | Conjugate 45b [1] | 1.32E+04 | 3.16 |
| 9 | Conjugate 45b [3] | 5.00E+03 | 3.58 |
| 10 | Uninfected | BLD | N/A |

TABLE 122

Cytokine levels on day 4 post-infection

| Test article [mg/kg] | TNF-α [pg/mL] | IL-6 [pg/mL] | MCP-1 [pg/mL] | MIP-1α [pg/mL] | KC [pg/mL] |
|---|---|---|---|---|---|
| PBS [0] | 1077.2 | 1446.6 | 21219.9 | 3750.8 | 8090.4 |
| hIgG1 Fc [3] | 958.6 | 1129.5 | 20534.7 | 3545.1 | 7730.8 |
| Oseltamivir [5] | 861.6 | 714.2 | 5301.6 | 1439.8 | 3466.4 |
| Oseltamivir [50] | 501.7 | 467.1 | 4572.8 | 948.2 | 2705.5 |
| Baloxavir [15] | 522.5 | 308.7 | 338.7 | 185.6 | 392.0 |
| Conjugate 45b [0.1] | 515.3 | 470.5 | 6807.3 | 1506.5 | 2954.1 |
| Conjugate 45b [0.3] | 521.7 | 424.9 | 2957.5 | 820.1 | 1788.5 |
| Conjugate 45b [1] | 460.0 | 329.8 | 2005.2 | 451.7 | 1262.8 |
| Conjugate 45b [3] | 464.8 | 309.2 | 739.4 | 246.4 | 678.8 |
| Uninfected | 488.0 | 312.6 | 423.9 | 177.8 | 444.6 |

TABLE 123

Cytokine levels on day 4 post-infection in fold-change as compared to uninfected control

| Test article [mg/kg] | TNF-α | IL-6 | MCP-1 | MIP-1α | KC |
|---|---|---|---|---|---|
| PBS [0] | 2.21 | 4.63 | 50.06 | 21.10 | 18.20 |
| hIgG1 Fc [3] | 1.96 | 3.61 | 48.44 | 19.94 | 17.39 |
| Oseltamivir [5] | 1.77 | 2.28 | 12.51 | 8.10 | 7.80 |
| Oseltamivir [50] | 1.03 | 1.49 | 10.79 | 5.33 | 6.09 |
| Baloxavir [15] | 1.07 | 0.99 | 0.80 | 1.04 | 0.88 |
| Conjugate 45b [0.1] | 1.06 | 1.51 | 16.06 | 8.48 | 6.65 |
| Conjugate 45b [0.3] | 1.07 | 1.36 | 6.98 | 4.61 | 4.02 |
| Conjugate 45b [1] | 0.94 | 1.05 | 4.73 | 2.54 | 2.84 |
| Conjugate 45b [3] | 0.95 | 0.99 | 1.74 | 1.39 | 1.53 |
| Uninfected | 1.00 | 1.00 | 1.00 | 1.00 | 1.00 |

Example 171. Efficacy of Conjugate 45b in Lethal Mouse Influenza Model: Study #55

Conjugate 45b was evaluated against a lethal influenza A/CA/07/2009 (3E4 PFU) in female BALB/c mice (6-8 weeks old, n=5/group). The study design is shown in Table 124. Mice were treated with test articles at t=+2 h (SC) post-infection with a single dose for Conjugate 45b or twice daily for 4 days for control agents. All mice were monitored for body weight daily. Mice were sacrificed on day 4 post-infection and both lung lobes were harvested. Lungs were homogenized to determine the viral burden and immune response. Data are shown in Tables 125 and 126A-126B.

TABLE 124

Efficacy study #58: Study design

| Group | Test article (DAR) | Route/Schedule | Dose [mg/kg] | Dose/day [mg/kg] |
|---|---|---|---|---|
| 1 | PBS | SC, T + 2 h | N/A | N/A |
| 2 | hIgG1 Fc | SC, T + 2 h | 30 | 30 |
| 3 | Oseltamivir | PO, BID × 4 | 5 | 10 |
| 4 | Baloxavir | PO, BID × 4 | 15 | 30 |
| 4 | Conjugate 45b (4.8) | SC, T + 2 h | 0.3 | 0.3 |
| 6 | Conjugate 45b (4.8) | SC, T + 2 h | 1 | 1 |
| 7 | Conjugate 45b (4.8) | SC, T + 2 h | 3 | 3 |
| 8 | Conjugate 45b (4.8) | SC, T + 2 h | 30 | 30 |
| 9 | uninfected | N/A | N/A | N/A |

TABLE 125

Viral burden on day 4 post-infection in PFU/g

| Group | Test article [mg/kg] | PFU/g | Log reduction PFU/g |
|---|---|---|---|
| 1 | PBS [0] | 1.71E+07 | 0.00 |
| 2 | hIgG1 Fc [30] | 1.08E+07 | 0.20 |
| 3 | Oseltamivir [5] | 2.05E+07 | −0.08 |
| 4 | Baloxavir [15] | 1.51E+02 | 5.06 |
| 5 | Conjugate 45b [0.1] | 8.81E+06 | 0.29 |
| 6 | Conjugate 45b [0.3] | 4.25E+06 | 0.60 |
| 7 | Conjugate 45b [1] | 1.24E+05 | 2.14 |
| 8 | Conjugate 45b [3] | 3.72E+03 | 3.66 |
| 9 | uninfected | 0.00 | 0.00 |

TABLE 126A

Cytokine levels on day 4 post-infection

| Test article [mg/kg] | TNF-α [pg/mL] | IL-6 [pg/mL] | MCP-1 [pg/mL] | MIP-1α [pg/mL] | KC [pg/mL] |
|---|---|---|---|---|---|
| PBS [0] | 1409.1 | 728.1 | 10139.0 | 2439.6 | 2542.4 |
| hIgG1 Fc [30] | 1489.6 | 709.6 | 9414.3 | 2245.0 | 2212.8 |
| Oseltamivir [5] | 1260.1 | 714.2 | 8891.9 | 1454.1 | 2327.7 |
| Baloxavir [15] | 586.5 | 238.5 | 378.5 | 175.0 | 247.7 |
| Conjugate 45b [0.3] | 1211.4 | 426.2 | 4059.8 | 886.7 | 1530.2 |
| Conjugate 45b [1] | 1069.7 | 378.9 | 3874.0 | 765.3 | 1759.6 |
| Conjugate 45b [3] | 1069.6 | 427.6 | 2457.6 | 720.0 | 1478.5 |
| Conjugate 45b [30] | 662.5 | 284.2 | 1185.6 | 406.4 | 1069.3 |
| Uninfected | 523.1 | 227.3 | 247.5 | 179.6 | 293.1 |

TABLE 126B

Cytokine level on day 4 pose-infection in fold-change as compared to uninfected control

| Test article [mg/kg] | INF-γ | TNF-α | IL-6 | MCP-1 | MIP-1α | KC |
|---|---|---|---|---|---|---|
| PBS [0] | 3.39 | 2.69 | 3.20 | 40.96 | 13.59 | 8.67 |
| hIgG1 Fc [3] | 3.06 | 2.85 | 3.12 | 38.03 | 12.50 | 7.55 |
| Oseltamivir [5] | 2.44 | 2.41 | 2.59 | 35.92 | 8.10 | 7.94 |
| Baloxavir [15] | 0.94 | 1.12 | 1.05 | 1.53 | 0.97 | 0.85 |
| Conjugate 45b [0.3] | 1.98 | 2.32 | 1.87 | 16.40 | 4.94 | 5.22 |
| Conjugate 45b [1] | 1.87 | 2.04 | 1.67 | 15.65 | 4.26 | 6.00 |
| Conjugate 45b [3] | 1.85 | 2.04 | 1.88 | 9.93 | 4.01 | 5.04 |
| Conjugate 45b [30] | 1.18 | 1.27 | 1.25 | 4.79 | 2.26 | 3.65 |
| Uninfected | 1.00 | 1.00 | 1.00 | 1.00 | 1.00 | 1.00 |

Example 172. In Vitro Cross-Species Fc Receptor Binding of Conjugate 45b

Binding of Conjugate 45b to Fc gamma receptors from multiple species was performed using the ELISA method described below. Nunc Maxisorp 96-well plates were coated overnight at 4° C. with 1 μg (100 μL/well) of Conjugate 45b in carbonate buffer. Unconjugated human IgG1 Fc and isotype control antibodies were also coated overnight under the same conditions. The next day, plates were washed 5× with 300 μL/well 1×PBS pH 7.4 supplemented with 0.05% Tween 20 (PBST), then blocked with 200 μL/well of 1% BSA in PBST for 1 hr at room temperature on an orbital plate shaker. The plates were washed 5× with 300 μL/well PBST, then incubated with duplicate 2-fold serial dilutions of recombinant His-tagged Fc gamma receptor (0.5-1,000 ng; 100 μL/well) in diluent (0.5% BSA in PBS 0.025% Tween 20) for 2 hr at room temperature with shaking. Human and cynomolgus monkey FcγR1/CD64 were screened at a starting concentration of 25 ng/100 μL/well. The plates were washed 5× with 300 μL/well PBST, then incubated with 100 μL/well of mouse anti-His HRP antibody (cat no. MAB050H, R&D Systems) diluted 1:1,000 in diluent for 1 hr at room temperature with shaking. The plates were washed 8× with 300 μL/well PBST, with 1 min incubation between washes, and developed with 100 μL/well TMB substrate reagent for 5-10 min. The reaction was stopped with 100 μL/well 1 N $H_2SO_4$ and the absorbance read at 450 nm with an EnSpire multimode plate reader (PerkinElmer). Half maximal effective concentration ($EC_{50}$) was calculated with GraphPad Prism version 8 using nonlinear regression analysis (Sigmoidal, 4PL) of binding curves. Binding of Conjugate 45b to FcRn receptors from multiple species was performed essentially as described for the Fc gamma binding ELISA with the following modification. Following the blocking step, binding assays were performed in duplicate at pH 5.8, the optimal pH for FcRn binding, and pH 7.4.

Conjugate 45b bound to Fc gamma receptors from mouse, human, rat and cynomolgus monkey with comparable avidity to human IgG1 Fc (Table 127). Conjugate 45b bound immune activating Fc gamma receptors with higher avidity compared to immune inhibitory Fc gamma receptors. At pH 5.8, Conjugate 45b bound FcRn receptors from all species with equivalent avidity to human IgG1 Fc. As expected, conjugate 45b FcRn binding was reduced at pH 7.4 (Table 127).

TABLE 127

Cross-species Fc receptor binding for Conjugate 45b

| | | | $EC_{50}$ [nM] | | |
|---|---|---|---|---|---|
| Species | Fc receptor | Signal/function | Conjugate 45 | hIgG1 Fc | hIgG1 |
| Mouse | FcγR1/CD64 | Activating | 12 | 9 | 3 |
| | FcγR2B/CD32b | Inhibitory | 228 | 135 | 153 |
| | FcγR3/CD16 | Activating | >455 | >455 | >455 |
| | FcγR4/CD16-2 | Activating | 3 | 0.5 | 6E−07 |
| | FcRn pH 5.8 | IgG, albumin recycling | 6 | 6 | 5 |
| | FcRn pH 7.4 | IgG, albumin recycling | 80 | 14 | 40 |
| Human | FcγR1/CD64 | Activating | 12 | 12 | 7 |
| | FcγR2A/CD32a (R167) | Inhibitory | 334 | 193 | 144 |
| | FcγR3A/CD16a | Activating | 20 | 9 | 2 |
| | FcγR3B/CD16b | Activating | >455 | >455 | >455 |
| | FcRn pH 5.8 | IgG, albumin recycling | 49 | 49 | 44 |
| | FcRn pH 7.4 | IgG, albumin recycling | >455 | >455 | >455 |
| Rat | FcγR1/CD64 | Activating | 7 | 3 | 2 |
| | FcγR2A/CD32a | Inhibitory | >455 | >455 | 1 |
| | FcγR2B/CD32b | Inhibitory | 561 | 49 | 208 |
| | FcγR3A/CD16a | Activating | 6 | 3 | 0.008 |
| | FcRn pH 5.8 | IgG, albumin recycling | 25 | 15 | 13 |
| | FcRn pH 7.4 | IgG, albumin recycling | 104 | >230 | >230 |
| Cynomolgus monkey | FcγR1/CD64 | Activating | 24 | 18 | 0.37 |
| | FcγR2A/CD32a | Inhibitory | 1995 | 688 | 693 |
| | FγR2B/CD32b | Inhibitory | 11 | 6 | 1 |
| | FcγR3/CD16 | Activating | >320 | >320 | >320 |
| | FcRn pH 5.8 | IgG, albumin recycling | 31 | 17 | 28 |
| | FcRn pH 7.4 | IgG, albumin recycling | 88 | 32 | 78 |

Example 173. 7-Day Mouse PK Study Comparing IV, SC and IM Administration of Conjugate 45b Mouse PK studies were performed using male CD-i mice 6 weeks of age. Mice were injected IV, SC and IM with 5 mg/kg of test article (5 ml/kg dose volume). Animals were housed under standard IACUC approved housing conditions. At appropriate times animals were non-terminally bled (retro-orbital, cheek, or by tail vein) with blood collected in K₂EDTA tubes to prevent coagulation. Collected blood was centrifuged (2,000×g, for 10 minutes) and plasma withdrawn for analysis of test article concentrations over time. The plasma concentrations for Conjugate 45b at each time point were measured by sandwich ELISA as follows: Conjugate 45b molecules were captured on neuraminidase coated plates and then detected using an HRP-conjugated anti-human IgG-Fc antibody. Protein concentration was calculated in GraphPad Prism using 4PL non-linear regression of Conjugate 45b (or hIgG1 Fc) standard curves. A more detailed method description is provided above. The curves comparing Conjugate 45b are shown in FIG. 84, and the curves comparing hIgG1 Fc (SEQ ID NO: 73) are shown in FIG. 85. The Conjugate 45b plasma exposure levels for SC and IM were comparable and resulting bioavailability from either SC or IM routes were approximately 77% compared to IV administration (Tables 128-130). Conjugate 45b plasma concentrations were equivalent for all routes at approximately 24 h post-injection.

Example 174. 7-Day Mouse PK Study Comparing Dose Linearity of Conjugate 45b

Mouse PK studies were performed using male CD-1 mice 6 weeks of age. Mice were injected SC with 1, 3, 10, 30, or 100 mg/kg of test article (5 ml/kg dose volume). Animals were housed under standard IACUC approved housing conditions. At appropriate times animals were non-terminally bled (retro-orbital, cheek, or by tail vein) with blood collected in K2EDTA tubes to prevent coagulation. Collected blood was centrifuged (2,000×g, for 10 minutes) and plasma withdrawn for analysis of test article concentrations over time. The plasma concentrations for Conjugate 45b at each time point were measured by sandwich ELISA as follows: Conjugate 45b molecules were captured on neuraminidase coated plates and then detected using an HRP-conjugated anti-human IgG-Fc antibody. Protein concentration was calculated in GraphPad Prism using 4PL non-linear regression of Conjugate 45b (or hIgG1 Fc) standard curves. A more detailed method description is provided above. The curves comparing Conjugate 45b detected by NA and Fc capture are shown in FIGS. 86 and 87, respectively. In mouse, reasonable linear dose proportionality from 1 to 100 mg/kg SC administration of Conjugate 45b was observed (Table 131).

TABLE 128

Mouse PK 5 mg/kg IV administration

| Dose (mg/kg) | Route | Animal | Time (hr) 0.0833 | 1 | 3 | 5 | 24 Conc (ug/mL) | 48 | 72 | 96 | 168 |
|---|---|---|---|---|---|---|---|---|---|---|---|
| 5 | IV | Mean | 35.8 | 30.1 | 20.8 | 23 | 11.1 | 11.3 | 6.9 | 8.08 | 5.21 |

| Dose (mg/kg) | Route | Animal | Tmax (hr) | C0 (ug/mL) | Cmax (ug/mL) | AUClast (hr * ug/mL) | AUCINF_obs (hr * ug/mL) | Half-life (hr) | CI_obs (mL/min/kg) | Vss_obs (mL/kg) | Vz_obs (mL/kg) |
|---|---|---|---|---|---|---|---|---|---|---|---|
| 5 | IV | Mean | 0.0833 | 36.4 | 35.8 | 1600 | 2560 | 128 | 0.0325 | 336 | 361 |

TABLE 129

Mouse PK 5 mg/kg IM administration

| Dose (mg/kg) | Route | Animal | Time (hr) 0.25 | 1 | 3 | 5 | 24 Conc (ug/mL) | 48 | 72 | 96 | 168 | Tmax (hr) | Cmax (ug/mL) | AUClast (hr * ug/mL) | AUCINF_obs (hr * ug/mL) |
|---|---|---|---|---|---|---|---|---|---|---|---|---|---|---|---|
| 5 | IM | Mean | 0.195 | 1.44 | 3.69 | 3.83 | 8.52 | 10.9 | 7.94 | 7.35 | 5.56 | 48 | 10.9 | 1240 | 2720 |

TABLE 130

Mouse PK 5 mg/kg SC administration

| Dose (mg/kg) | Route | Animal | Time (hr) 0.25 | 1 | 3 | 5 | 24 Conc (ug/mL) | 48 | 72 | 96 | 168 | Tmax (hr) | Cmax (ug/mL) | AUClast (hr * ug/mL) | AUCINF_pred (hr * ug/mL) |
|---|---|---|---|---|---|---|---|---|---|---|---|---|---|---|---|
| 5 | SC | Mean | 0.148 | 0.387 | 3.23 | 2.55 | 8.89 | 9.29 | 9.13 | 7.49 | 5.46 | 48 | 9.29 | 1220 | 2280 |

TABLE 131

Mouse PK dose proportional from 1-100 mg/kg

| Dose (mg/kg) | Route | Animal | Time (hr) 0.25 | 0.5 | 1 | 2 | 4 Conc (ug/mL) | 24 | 96 | 120 | 168 |
|---|---|---|---|---|---|---|---|---|---|---|---|
| 1 | SC | 1 | 0.83 | Missing | 5.9 | 0.764 | 9.39 | 4.11 | 1.1 | 2.13 | 0.317 |
| 3 | SC | 3 | 0.355 | 0.0874 | 1.02 | 0.52 | 5.16 | 11.4 | 9.84 | 8.32 | 6.84 |
| 10 | SC | 10 | 1.01 | 0.879 | 1.81 | 4.65 | 15.5 | 41.3 | 18.4 | 26.7 | 15 |
| 30 | SC | 30 | 0.179 | 0.616 | 5.71 | 7.6 | 56 | 125 | 75 | 83.7 | 49.7 |
| 100 | SC | 100 | 22.4 | 72.3 | 313 | 446 | 733 | 657 | 183 | 246 | 160 |

| Dose (mg/kg) | D | Route | Dose (mg) | Tmax (hr) | Cmax (hr * ug/mL) | AUClast (hr * ug/mL) | AUCINF_pred (hr * ug/mL) |
|---|---|---|---|---|---|---|---|
| 1 | 1 | SC | 1 | 4 | 9.39 | 436 | 465 |
| 3 | 3 | SC | 3 | 24 | 11.4 | 1520 | 2900 |
| 10 | 10 | SC | 10 | 24 | 41.3 | 4280 | 6650 |
| 30 | 30 | SC | 30 | 24 | 125 | 14200 | 22300 |
| 100 | 100 | SC | 100 | 4 | 733 | 60700 | 75300 |

Example 175. 14-Day Rat PK Study Following IV or SC Administration of Conjugate 45b Rat PK studies were performed by Seventh Wave Laboratories (Maryland Heights, Mo.) using male Sprague Dawley Rats 46-49 days of age. Rats were injected IV via the tail vein with 5 mg/kg Conjugate 45b or SC with 5 or 50 mg/kg of test article (5 ml/kg dose volume) (FIGS. 88-89). Animals were housed under standard IACUC approved housing conditions. At appropriate times animals were non-terminally bled (retro-orbital, cheek, or by tail vein) with blood collected in K2EDTA tubes to prevent coagulation. Collected blood was centrifuged (2,000×g, for 10 minutes) and plasma withdrawn for analysis of test article concentrations over time (Table 132). The plasma concentrations for Conjugate 45b at each time point were measured by sandwich ELISA as follows: Conjugate 45b molecules were captured either on neuraminidase coated plates and then detected using an HRP-conjugated anti-human IgG-Fc antibody (Tables 133-134). hIgG1 was captured using anti-hIgG1 Fc antibody. Protein concentration was calculated in GraphPad Prism using 4PL non-linear regression of Conjugate 45b standard curves. A more detailed method description is provided above. The curves comparing Conjugate 45b shown in FIG. 88 demonstrate linear dose proportionality. Conjugate 45b plasma levels for IV and SC administration converge at 24 hr post injection (FIG. 89). Data are shown in Tables 135 and 136.

TABLE 132

Rat PK Study Design

| Dose/ Dose path | 10 min IV; 30 min SC | Plasma Collection Time Points |
|---|---|---|
| | | 1 h | 4 h | 8 h | 24 h | 72 h | 120 h | 168 h | 336 h |
| Group 1 (n = 3) | 5 mpk IV | X | X | X | X | X | X | X | X | X |
| Group 2 (n = 3) | 5 mpk SC | X | X | X | X | X | X | X | X | X |
| Group 3 (n = 3) | 50 mpk SC | X | X | X | X | X | X | X | X | X |

TABLE 133

H1N1 (A/CA/04/2009) NA Capture

| Time (hr) | 5 mpk IV g1.1 n1 | g1.1 n2 | g1.2 n1 | g1.2 n2 | g1.3 n1 | g1.3 n2 | 5 mpk SC g2.1 n1 | g2.1 n2 | g2.2 n1 |
|---|---|---|---|---|---|---|---|---|---|
| 10 m/30 m | 139.0184 | 116.434 | 128.9835 | 126.3728 | 99.90003 | 96.30608 | 0.336397 | 0.352108 | 0.26567 |
| 1 | 103.0288 | 107.5882 | 108.6186 | 112.708 | 80.42177 | 83.55724 | 0.601405 | 0.600861 | 0.50378 |
| 4 | 67.18744 | 70.49817 | 65.26259 | 59.96993 | 52.09719 | 60.13481 | 3.331236 | 3.577401 | 3.291326 |
| 8 | 49.96849 | 56.19489 | 56.94676 | 57.68125 | 48.90448 | 55.23444 | 9.120017 | 8.164349 | 6.224308 |
| 24 | 33.99514 | 33.83988 | 34.76042 | 33.60106 | 33.04519 | 32.52448 | 24.64741 | 22.57097 | 19.34957 |
| 72 | 24.03197 | 23.99513 | 26.1422 | 25.50985 | 23.92523 | 24.53129 | 26.81972 | 23.95593 | 19.1652 |
| 120 | 17.28743 | 17.88652 | 18.16672 | 17.61109 | 17.14011 | 16.81636 | 18.13665 | 18.07425 | 15.58847 |
| 168 | 16.37894 | 14.18949 | 15.0406 | 14.28349 | 12.29568 | 13.27299 | 16.36903 | 16.31503 | 13.37669 |
| 336 | 8.706758 | 9.475766 | 8.069783 | 8.240227 | 7.314977 | 7.120923 | 8.57262 | 8.694249 | 6.866837 |

TABLE 133-continued

H1N1 (A/CA/04/2009) NA Capture

| Time | 5 mpk SC | | | 50 mpk SC | | | | | |
|---|---|---|---|---|---|---|---|---|---|
| | g2.2 | g2.3 | | g3.1 | | g3.2 | | g3.3 | |
| (hr) | n2 | n1 | n2 | n1 | n2 | n1 | n2 | n1 | n2 |
| 10 m/30 m | 0.24961 | 0.259523 | 0.205043 | 1.111022 | 1.021191 | 2.951729 | 3.184274 | 3.78442 | 3.30374 |
| 1 | 0.53983 | 0.680512 | 0.48924 | | 2.858977 | 6.907325 | 4.617704 | 7.575 | 8.21763 |
| 4 | 3.31843 | 3.942251 | 3.945549 | 19.50094 | 17.82466 | 17.83342 | 19.84081 | 27.2367 | 27.0064 |
| 8 | 6.16066 | 7.856424 | 7.047854 | 43.56345 | 44.30664 | 55.25942 | 53.41513 | 58.2069 | 56.4707 |
| 24 | 21.3297 | 20.90625 | 23.61215 | 156.8759 | 159.158 | 210.1323 | 209.9947 | 208.024 | 181.09 |
| 72 | 23.1289 | 18.91189 | 16.60657 | 142.6993 | 137.0533 | 152.6497 | 155.1297 | 149.881 | 142.385 |
| 120 | 19.193 | 16.70847 | 16.4339 | 117.7776 | 112.064 | 136.8244 | 141.3221 | 137.704 | 132.748 |
| 168 | 14.9629 | 12.9219 | 12.3945 | 100.8302 | 116.8275 | 99.00073 | 118.0093 | 97.4236 | 96.2287 |
| 336 | 7.0874 | 7.635397 | 7.876635 | 53.87703 | 51.16129 | 57.02179 | 55.22173 | 54.121 | 59.193 |

TABLE 134 hIgG Fc Capture

| Time | 5 mpk IV | | | | | | 5 mpk SC | | |
|---|---|---|---|---|---|---|---|---|---|
| | g1.1 | | g1.2 | | g1.3 | | g2.1 | | g2.2 |
| (hr) | n1 | n2 | n1 | n2 | n1 | n2 | n1 | n2 | n1 |
| 10 m/30 m | 131.8211 | 132.2644 | 138.5205 | 124.2897 | 92.28536 | 93.95777 | 0.301641 | 0.272994 | 0.3302 |
| 1 | 105.1676 | 118.2516 | 111.4847 | 110.7111 | 83.06342 | 83.13157 | 0.492532 | 0.510306 | 0.372862 |
| 4 | 61.3296 | 59.41234 | 59.52775 | 47.35522 | 53.9032 | 61.12485 | 3.615572 | 3.792592 | 3.297844 |
| 8 | | 50.28953 | 48.15108 | 52.90292 | 48.1017 | 48.46983 | 8.261891 | 9.08554 | 6.598579 |
| 24 | 29.91591 | 30.67022 | 30.25926 | 31.29131 | 28.39885 | 29.88579 | 23.96117 | 19.31521 | 16.86928 |
| 72 | 19.38442 | 21.26014 | 20.06189 | 20.38354 | 17.46987 | 18.56471 | 19.96086 | 21.67188 | 15.66477 |
| 120 | 12.13442 | 13.49033 | 12.39415 | 11.80685 | 13.47915 | 12.68468 | 14.71684 | 15.61295 | 11.56458 |
| 168 | 14.61786 | 14.48309 | 13.2966 | 13.12374 | 12.4622 | 13.06133 | 13.73621 | 9.73 | 11.21421 |
| 336 | 8.33093 | 8.680053 | 7.88281 | 7.805351 | 6.912784 | 6.784823 | 7.736292 | 7.661658 | 6.466908 |

| Time | 5 mpk SC | | | 50 mpk SC | | | | | |
|---|---|---|---|---|---|---|---|---|---|
| | g2.2 | g2.3 | | g3.1 | | g3.2 | | g3.3 | |
| (hr) | n2 | n1 | n2 | n1 | n2 | n1 | n2 | n1 | n2 |
| 10 m/30 m | 0.58892 | 0.071346 | 0.209457 | 0.85958 | 2.600291 | 2.362582 | 2.417453 | 3.26701 | 3.24606 |
| 1 | 0.35967 | 0.267192 | 0.28284 | 2.328096 | 2.360296 | 3.618227 | 3.5931 | 7.33632 | 7.4207 |
| 4 | 3.46322 | 4.157923 | 4.501974 | 20.52563 | 19.67262 | 19.46794 | 19.46851 | 28.6829 | 31.5564 |
| 8 | 5.92739 | 8.778635 | 7.990053 | 45.29742 | 44.30181 | 54.38999 | 63.46517 | 61.1055 | 70.8567 |
| 24 | 17.6982 | 17.00515 | 18.2297 | 155.7401 | 138.399 | 200.935 | 236.9577 | 239.536 | 249.133 |
| 72 | 16.3864 | 19.15136 | 19.56853 | 152.6623 | 171.8249 | 181.134 | 173.9026 | 186.293 | 194.744 |
| 120 | 11.8629 | 14.66388 | 14.79211 | 113.865 | 103.0581 | 131.7811 | 129.7576 | 153.859 | 149.209 |
| 168 | 12.2178 | 14.54814 | 12.79694 | 94.56107 | 112.0218 | 105.5593 | 101.004 | 104.147 | 113.431 |
| 336 | 6.00365 | 7.32696 | 6.554063 | 49.96583 | 43.11898 | 58.15043 | 57.84531 | 54.516 | 49.5564 |

TABLE 135

Rat PK 5 mg/kg IV administration

| Rat Dose (mg/kg) | Time (hr) | | | | | | | | |
|---|---|---|---|---|---|---|---|---|---|
| | 0.167 | 1 | 4 | 8 | 24 | 72 | 120 | 168 | 336 |
| | | | | | Conc (ug/mL) | | | | |
| 5 | 118 | 99.3 | 62.5 | 54.2 | 33.6 | 24.7 | 17.5 | 14.2 | 8.15 |

TABLE 135-continued

Rat PK 5 mg/kg IV administration

| Rat Dose (mg/kg) | Tmax (hr) | C0 (ug/mL) | Cmas (ug/mL) | AUClast (hr * ug/mL) | AUCINF_obs (hr * ug/mL) | Half-life (hr) | CI_obs (mL/min/kg) | Vss_obs (mL/kg) | Vz_obs (mL/kg) |
|---|---|---|---|---|---|---|---|---|---|
| 5 | 0.167 | 122 | 118 | 6340 | 8690 | 199 | 0.00959 | 144 | 166 |

TABLE 136

Rat PK 5 mg/kg and 50 mg/kg SC administration

| Rat | | | Time (hr) | | | | | | | | | | | |
|---|---|---|---|---|---|---|---|---|---|---|---|---|---|---|
| | | | 0.5 | 1 | 4 | 8 | 24 | 72 | 120 | 168 | 336 | Tmax | Cmax | AUClast | AUCINF_obs |
| Dose (mg/kg) | Route | Animal | | | | | Conc (ug/mL) | | | | | (hr) | (ug/mL) | (hr * ug/mL) | (hr * ug/mL) |
| 5 | SC | Mean | 0.278 | 0.569 | 3.57 | 7.43 | 22.1 | 21.4 | 17.4 | 14.4 | 7.79 | 24 | 22.1 | 4860 | 6970 |
| 50 | SC | Mean | 2.56 | 6.04 | 21.5 | 51.9 | 188 | 147 | 130 | 105 | 55.1 | 24 | 188 | 35800 | 49800 |

Example 176. 14-Day Non-Human Primate PK Study Following SC Administration of Conjugate 45b Non-human primate (NHP) PK studies were performed by Charles River using male and female Cynomolgus monkeys 4.5-8 years old with body weights ranging from 2.5-6.5 kg. NHPs were injected SC with 5 or 20 mg/kg of test article (5 ml/kg dose volume) on day 1 and 8. Animals were housed under standard IACUC approved housing conditions. At appropriate times animals were non-terminally bled (via femoral or cephalic veins) with blood collected in K2EDTA tubes to prevent coagulation. Collected blood was centrifuged (2,000×g, for 10 minutes) and plasma withdrawn for analysis of test article concentrations over time (Table 137). The plasma concentrations for Conjugate 45b at each time point were measured by sandwich ELISA as follows: Conjugate 45b molecules were captured on neuraminidase coated plates and then detected using an HRP-conjugated anti-human IgG-Fc antibody (FIG. 90-91). Protein concentration was calculated in GraphPad Prism using 4PL nonlinear regression of Conjugate 45b standard curves. A more detailed method description is provided above. The curves comparing Conjugate 45b are shown in FIG. 92. The dose response is linear between 5 and 20 mg/kg SC. Accumulation of Conjugate 45b was observed following the second administration of Conjugate 45b on day 8.

Example 177. Efficacy of Conjugate 45b Against an Oseltamivir-Resistant Isolate in a Lethal Mouse Influenza Model Conjugate 45b was evaluated against a lethal IAV H1N1 influenza infection in female BALB/c mice (Charles River Laboratories, 6-8 weeks). The challenge virus (A/Perth/261/2009) is a mouse-adapted isolate that carries the H275Y mutation resulting in resistance to the neuraminidase inhibitor oseltamivir.

The experiment comprised 9 groups of 5 mice. At day 0, all mice were challenged with A/Perth/261/2009 (H1N1) at 2× the LD90 by intranasal inoculation in a volume of 50 µl, to mice lightly anesthetized with isoflurane. Groups 1-8 received a single treatment by SC, 2 hours post challenge. In addition to the vehicle (PBS) only group, human IgG1 (Fc alone) was included as an additional negative control. Group 9 received Oseltamivir phosphate via oral delivery, starting 8 hours post infection twice daily for 5 days (Table 138). All mice were monitored for survival (Table 139) and weight loss (Table 140) for 14 days after challenge.

Mice treated with Conjugate 45b showed 100% survival against challenge by influenza (A/Perth/261/2009) with single doses at 10, 3, 1, and 0.3 mg/kg. Furthermore, despite the small group size (n=5) these results were statistically significant relative to the vehicle control (Table 139). No mice survived to the end of the study if dosed with vehicle

TABLE 137

Monkey PK high exposures after second weekly dose

| Dose (mg/kg) | Route | Group | Animal | 0.0833 | 1 | 2 | 4 | Time (hr) 8 Conc (ug/mL) | 24 | 72 | 120 | 168 | Tmax (hr) | Cmax (hr * ug/mL) | AUClast (hr * ug/mL) |
|---|---|---|---|---|---|---|---|---|---|---|---|---|---|---|---|
| 5 | SC | D1 | Mean | blq | 1.05 | 3.62 | 9.91 | 17.9 | 22.2 | 26.1 | 23.8 | 20 | 72 | 26.1 | 3800 |
| | | D8 | Mean | 24.3 | 19.4 | 25.7 | 31 | 61 | 47.3 | 54.1 | 42.8 | 33.3 | 8 | 61 | 7740 |
| 20 | SC | D1 | Mean | blq | 10.9 | 6.77 | 28.8 | 61.9 | 101 | 107 | 71.6 | 85.1 | 72 | 107 | 14600 |
| | | D8 | Mean | 63.4 | 59.5 | 70.4 | 107 | 150 | 197 | 167 | 139 | 99.1 | 24 | 197 | 25400 |

(PBS), and only 20% survived if treated with hIgG1 Fc only. The oseltamivir group had no survivors despite treatment with a dose shown to be protective against oseltamivir-sensitive isolates previously (20 mg/kg, bid×5 days). These results confirm that the challenge virus is resistant to oseltamivir, and sensitive to Conjugate 45b.

The potency of Conjugate 45b against influenza containing the H275Y mutation was further supported by body weight data (Table 140). Groups receiving a single dose of Conjugate 45b at concentrations of 1 mg/kg or more demonstrated 3%, or less, transient weight loss which was recovered by study end.

TABLE 138

Study design

| Group n = 5 | Challenge Day 0 | Compound | Dose (mg/kg) | Treatment Route/Schedule |
|---|---|---|---|---|
| 1 | Influenza A virus (H1N1) A/Perth/261/2009 via IN route. | Vehicle (PBS) | N/A | SC, q.d. 2 hours post-challenge |
| 2 | | Fc alone | 10 | |
| 3 | | Conjugate 45b | 10 | |
| 4 | | Conjugate 45b | 3 | |
| 5 | | Conjugate 45b | 1 | |
| 6 | | Conjugate 45b | 0.3 | |
| 7 | | Conjugate 45b | 0.1 | |
| 8 | | Conjugate 45b | 0.03 | |
| 9 | | Oseltamivir (Tamiflu™) | 20 | PO, b.i.d. 8 hours after challenge for 5 days |

TABLE 139

Percent Survival

| | | Test agent (mg/kg) | | | | | | | |
|---|---|---|---|---|---|---|---|---|---|
| | | hIgG1 Fc | oseltamivir | Conjugate 45b (mg/kg) | | | | | |
| Day | Vehicle | (10) | (200) | 10 | 3 | 1 | 0.3 | 0.1 | 0.03 |
| 0 | 100 | 100 | 100 | 100 | 100 | 100 | 100 | 100 | 100 |
| 1 | 100 | 100 | 100 | 100 | 100 | 100 | 100 | 100 | 100 |
| 2 | 100 | 100 | 100 | 100 | 100 | 100 | 100 | 100 | 100 |
| 3 | 100 | 100 | 100 | 100 | 100 | 100 | 100 | 100 | 100 |
| 4 | 100 | 80 | 80 | 100 | 100 | 100 | 100 | 100 | 80 |
| 5 | 100 | 60 | 60 | 100 | 100 | 100 | 100 | 80 | 40 |
| 6 | 80 | 60 | 0 | 100 | 100 | 100 | 100 | 0 | 0 |
| 7 | 0 | 40 | 0 | 100 | 100 | 100 | 100 | 0 | 0 |
| 8 | 0 | 20 | 0 | 100 | 100 | 100 | 100 | 0 | 0 |
| 9 | 0 | 20 | 0 | 100 | 100 | 100 | 100 | 0 | 0 |
| 10 | 0 | 20 | 0 | 100 | 100 | 100 | 100 | 0 | 0 |
| 11 | 0 | 20 | 0 | 100 | 100 | 100 | 100 | 0 | 0 |
| 12 | 0 | 20 | 0 | 100 | 100 | 100 | 100 | 0 | 0 |
| 13 | 0 | 20 | 0 | 100 | 100 | 100 | 100 | 0 | 0 |
| 14 | 0 | 20 | 0 | 100 | 100 | 100 | 100 | 0 | 0 |
| Significance relative to vehicle | na | 0.665 | 0.0035 | 0.0035 | 0.0035 | 0.0035 | 0.0035 | ns | ns |

TABLE 140

Percent Body Weight (grams)

| | | Test agent (mg/kg) | | | | | | |
|---|---|---|---|---|---|---|---|---|
| | | hIgG1 Fc | oseltamivir | Conjugate 45b (mg/kg) | | | | |
| Day | Vehicle | (10) | (200) | 10 | 3 | 1 | 0.3 | 0.1 |
| 0 | 100 | 100 | 100 | 100 | 100 | 100 | 100 | 100 |
| 1 | 101 | 101 | 102 | 99 | 97 | 98 | 96 | 97 |
| 2 | 98 | 100 | 99 | 101 | 99 | 102 | 99 | 98 |
| 3 | 91 | 93 | 89 | 101 | 95 | 97 | 94 | 89 |
| 4 | 89 | 88 | 84 | 101 | 95 | 97 | 95 | 84 |
| 5 | 89 | 89 | 82 | 104 | 100 | 101 | 98 | 83 |
| 6 | 79 | 85 | 74 | 100 | 94 | 97 | 93 | 74 |
| 7 | 78 | 83 | | 105 | 100 | 102 | 97 | |
| 8 | | 84 | | 105 | 100 | 103 | 98 | |
| 9 | | 85 | | 101 | 98 | 101 | 96 | |
| 10 | | 90 | | 103 | 98 | 101 | 98 | |
| 11 | | 92 | | 102 | 98 | 101 | 97 | |
| 12 | | 99 | | 105 | 103 | 103 | 102 | |
| 13 | | 101 | | 106 | 103 | 103 | 102 | |
| 14 | | 98 | | 104 | 101 | 101 | 101 | |

Example 178. Efficacy of Conjugate 45b Against a Second Oseltamivir-Resistant Isolate in a Lethal Mouse Influenza Model In a study similar to that shown in Example 177, conjugate 45b was tested for activity against a second influenza A (H1N1) isolate carrying the H275Y mutation conferring resistance to oseltamivir. For this study the mutation was carried in A/Texas/23/2012. As before, BALB/c mice (Charles River; 6-8 weeks) were used and challenged intranasally with 2× the LD95 (5E4 pfu/mouse). Oseltamivir was dosed orally at 20 mg/kg, bid for 5 days starting 2 hours after viral challenge. All other test articles were dosed SC, as listed in Table 141. Animals were monitored for 14 days, and body weights (BW) were recorded daily. If an animal reached 20% BW loss it was recorded as a mortality.

TABLE 141

| | | | Study design | | |
|---|---|---|---|---|---|
| Group | Influenza strain | Test Article | Route/ Schedule | Dose (mg/kg) | N (balb/c) |
| 1 | A/Texas/23/2012 | PBS | SC, T + 2 hrs | — | 5 |
| 2 | pdm (H275Y) | hIgG1 | SC, T + 2 hrs | 3 | 5 |
| 3 | (H1N1) | Oseltamivir | PO, bid × 5 (T + 2 h) | 20 | 5 |
| 4 | 5E4 PFU/ | Conjugate 45b | SC, T + 2 hrs | 3 | 5 |
| 5 | mouse | Conjugate 45b | SC, T + 2 hrs | 1 | 5 |
| 6 | | Conjugate 45b | SC, T + 2 hrs | 0.3 | 5 |
| 7 | | Conjugate 45b | SC, T + 2 hrs | 0.1 | 5 |

Similar to the previous study, neither vehicle nor the hIgG1 Fc (SEQ ID NO: 73) only controls afforded protection from lethal challenge (20 and 0% survival respectively; Table 142). In contrast, groups treated with Conjugate 45b at concentrations ranging from 0.3 to 3.0 mg/kg were fully protected from lethal challenge. Furthermore, conjugate 45b at 0.1 mg/kg demonstrated partial protection, with a 60% survival rate over the 14 days of the study. However a 200 mg total dose of oseltamivir failed to protect mice from viral challenge as expected. BW data (Table 143; recorded until the first death within a group) mirrored the survival results with only transient loss of weight seen in protected groups (Conjugate 45, 0.3 to 3.0 mg/kg). The oseltamivir mutation (H275Y) tested in this study is a clinically relevant mutation which is shown by this study to be highly susceptible to Conjugate 45b.

TABLE 142

| Percent Survival | | | | | | | |
|---|---|---|---|---|---|---|---|
| | | Test agent (mg/kg) | | | | | |
| | | hIgG1 | oseltamivir | Conjugate 45b (mg/kg) | | | |
| Day | Vehicle | Fc (1) | (200) | 3 | 1 | 0.3 | 0.1 |
| 0 | 100 | 100 | 100 | 100 | 100 | 100 | 100 |
| 1 | 100 | 100 | 100 | 100 | 100 | 100 | 100 |
| 2 | 100 | 100 | 100 | 100 | 100 | 100 | 100 |
| 3 | 100 | 100 | 100 | 100 | 100 | 100 | 100 |
| 4 | 100 | 100 | 100 | 100 | 100 | 100 | 100 |
| 5 | 20 | 60 | 20 | 100 | 100 | 100 | 60 |
| 6 | 20 | 0 | 0 | 100 | 100 | 100 | 60 |
| 7 | 20 | 0 | 0 | 100 | 100 | 100 | 60 |
| 8 | 20 | 0 | 0 | 100 | 100 | 100 | 60 |
| 9 | 20 | 0 | 0 | 100 | 100 | 100 | 60 |
| 10 | 20 | 0 | 0 | 100 | 100 | 100 | 60 |
| 11 | 20 | 0 | 0 | 100 | 100 | 100 | 60 |
| 12 | 20 | 0 | 0 | 100 | 100 | 100 | 60 |
| 13 | 20 | 0 | 0 | 100 | 100 | 100 | 60 |
| 14 | 20 | 0 | 0 | 100 | 100 | 100 | 60 |

TABLE 143

| Percent Body Weight (grams) | | | | | | | |
|---|---|---|---|---|---|---|---|
| | | Test agent (mg/kg) | | | | | |
| | | hIgG1 | oseltamivir | Conjugate 45b (mg/kg) | | | |
| Day | Vehicle | Fc (1) | (200) | 3 | 1 | 0.3 | 0.1 |
| 0 | 100 | 100 | 100 | 100 | 100 | 100 | 100 |
| 1 | 100 | 99 | 97 | 99 | 98 | 97 | 98 |
| 2 | 95 | 93 | 92 | 96 | 96 | 93 | 94 |
| 3 | 88 | 85 | 84 | 93 | 90 | 85 | 86 |
| 4 | 82 | 80 | 78 | 95 | 90 | 84 | 80 |

TABLE 143-continued

| Percent Body Weight (grams) | | | | | | | |
|---|---|---|---|---|---|---|---|
| | | Test agent (mg/kg) | | | | | |
| | | hIgG1 | oseltamivir | Conjugate 45b (mg/kg) | | | |
| Day | Vehicle | Fc (1) | (200) | 3 | 1 | 0.3 | 0.1 |
| 5 | 78 | 75 | | 94 | 90 | 84 | 79 |
| 6 | | | | 96 | 94 | 85 | |
| 7 | | | | 101 | 97 | 89 | |
| 8 | | | | 100 | 96 | 88 | |
| 9 | | | | 101 | 99 | 91 | |
| 10 | | | | 99 | 99 | 91 | |
| 11 | | | | 100 | 99 | 92 | |
| 12 | | | | 101 | 99 | 94 | |
| 13 | | | | 100 | 98 | 94 | |
| 14 | | | | 103 | 101 | 99 | |

Example 179. Efficacy of Conjugate 45b Subcutaneously Dosed Against Influenza A/WSN/1933 (H1N1) in a Lethal Mouse Model Conjugate 45b was evaluated against a lethal IAV H1N1 influenza infection in female BALB/c mice (Charles River Laboratories, 6-8 weeks). The challenge virus (A/WSN/1933) is a mouse-adapted isolate capable of causing lethal infections in mice. The experiment comprised 7 groups of 5 mice. At day 0, all mice were challenged with virus at 3× the LD95 by intranasal inoculation in a volume of 30 μl (2E3 virus/mouse), after being anesthetized with a mixture of ketamine/xylazine (150 and 10 mg/kg respectively). Mortality and body weights were recorded daily for 21 days and any animal with a 20% loss of body weight was scored as a death.

Test groups received a single subcutaneous (SC) treatment of conjugate 45b at 3, 1, 0.3, 0.1, or 0.03 mg/kg, or hIgG1 Fc control, or vehicle (PBS) 2 hours post viral challenge in a dose volume of 10 ml/kg. The study design is summarized in Table 144.

TABLE 144

| Study Design | | | | | |
|---|---|---|---|---|---|
| Group | Influenza strain | Test Article | Route/ Schedule | Dose (mg/kg) | N (balb/c) |
| 1 | A/WSN/1933 | PBS | SC, T + 2 hrs | — | 5 |
| 2 | (H1N1) | hIgG1 | SC, T + 2 hrs | 1 | 5 |
| 3 | ~2E3 PFU/ | Conjugate 45b | SC, T + 2 hrs | 3 | 5 |
| 4 | mouse | Conjugate 45b | SC, T + 2 hrs | 1 | 5 |
| 5 | | Conjugate 45b | SC, T + 2 hrs | 0.3 | 5 |
| 6 | | Conjugate 45b | SC, T + 2 hrs | 0.1 | 5 |
| 7 | | Conjugate 45b | SC, T + 2 hrs | 0.03 | 5 |

As expected, mice receiving vehicle or the hIgG1 Fc control succumbed to infection on Day 7 or 8, respectively (Table 145). However, mice treated with conjugate 45b were fully protected at concentrations down to 0.3 mg/kg, and 80% protection at 0.1. Complete loss of protection by conjugate 45b was only seen at the lowest dose concentration of 0.03 mg/kg.

TABLE 145

Percent Survival

| Day | Vehicle | hIgG1 Fc | Conjugate 45b (mg/kg) | | | | |
|---|---|---|---|---|---|---|---|
| | | | 3 | 1 | 0.3 | 0.1 | 0.03 |
| 0 | 100 | 100 | 100 | 100 | 100 | 100 | 100 |
| 1 | 100 | 100 | 100 | 100 | 100 | 100 | 100 |
| 2 | 100 | 100 | 100 | 100 | 100 | 100 | 100 |
| 3 | 100 | 100 | 100 | 100 | 100 | 100 | 100 |
| 4 | 100 | 100 | 100 | 100 | 100 | 100 | 100 |
| 5 | 100 | 100 | 100 | 100 | 100 | 100 | 100 |
| 6 | 40 | 60 | 100 | 100 | 100 | 100 | 100 |
| 7 | 0 | 20 | 100 | 100 | 100 | 100 | 100 |
| 8 | 0 | 0 | 100 | 100 | 100 | 100 | 40 |
| 9 | 0 | 0 | 100 | 100 | 100 | 80 | 0 |
| 10 | 0 | 0 | 100 | 100 | 100 | 80 | 0 |
| 11 | 0 | 0 | 100 | 100 | 100 | 80 | 0 |
| 12 | 0 | 0 | 100 | 100 | 100 | 80 | 0 |
| 13 | 0 | 0 | 100 | 100 | 100 | 80 | 0 |
| 14 | 0 | 0 | 100 | 100 | 100 | 80 | 0 |

The daily body weight measurements were consistent with survival observations. As expected, mice treated with vehicle or hIgG1 Fc demonstrated a steady drop in body weight until it exceeded 20%, at which time they were scored as a mortality (Table 146).

In contrast to control mice, those groups receiving conjugate 45b at 3.1, and 0.3 mg/kg maintained healthy body weights throughout the study and never demonstrated more than a transient body weight drop of less than 3% (1 ink/kg dose group, Day 18; Table 146). By both survival and body weight measurements conjugate 45b demonstrated robust protection from a lethal challenge of Influenza A/WSN/1933 with a single SC dose as low as 0.3 mg/kg.

TABLE 146

Percent Body Weight

| Day | Vehicle | hIgG1 Fc | Conjugate 45b (mg/kg) | | | | |
|---|---|---|---|---|---|---|---|
| | | | 3 | 1 | 0.3 | 0.1 | 0.03 |
| 0 | 100 | 100 | 100 | 100 | 100 | 100 | 100 |
| 1 | 96.8 | 96.6 | 98.5 | 98.9 | 99 | 96.9 | 99.4 |
| 2 | 99.9 | 98.1 | 100.9 | 99.9 | 100.5 | 101.2 | 100.7 |
| 3 | 92 | 90.8 | 101.1 | 100.6 | 99 | 97 | 94.8 |
| 4 | 83.5 | 85.3 | 98.4 | 98.2 | 96 | 94.6 | 92.4 |
| 5 | 79.7 | 82.3 | 99 | 102.5 | 99.2 | 94.2 | 91.5 |
| 6 | 76.1 | 78.8 | 101.2 | 105.4 | 102.1 | 90.9 | 87.3 |
| 7 | | | 100 | 102.8 | 101.6 | 84.8 | 82.3 |
| 8 | | | 98.4 | 101.9 | 100.8 | 81.9 | 76 |
| 9 | | | 102.2 | 102.8 | 101.6 | 84.3 | |
| 10 | | | 101.9 | 103 | 101.7 | | |
| 11 | | | 101.3 | 102.1 | 99.5 | | |
| 12 | | | 99.5 | 99.9 | 99.3 | | |
| 13 | | | 100 | 101.8 | 101.7 | | |
| 14 | | | 102.1 | 102.3 | 102.7 | | |
| 15 | | | 99.8 | 101.6 | 101.6 | | |
| 16 | | | 100.1 | 102.1 | 103.1 | | |
| 17 | | | 98.7 | 98.7 | 100.5 | | |
| 18 | | | 99.3 | 97.8 | 99.4 | | |
| 19 | | | 98.8 | 98.3 | 100.2 | | |

TABLE 146-continued

Percent Body Weight

| Day | Vehicle | hIgG1 Fc | Conjugate 45b (mg/kg) | | | | |
|---|---|---|---|---|---|---|---|
| | | | 3 | 1 | 0.3 | 0.1 | 0.03 |
| 20 | | | 100.1 | 100.1 | 100.8 | | |
| 21 | | | 102.3 | 100.5 | 101.1 | | |

Example 180. Efficacy of Conjugate 45b Intravenously Dosed Against Influenza A/Texas/36/91 (H1N1) in a Lethal Mouse Model of Delayed Treatment Conjugate 45b was evaluated against a lethal influenza A (H1N1) infection in female BALB/c mice (Charles River Laboratories, 6-8 weeks). The challenge virus (A/Texas/36/91) is a mouse-adapted isolate capable of causing lethal infections in mice. At day 0, all mice were challenged with virus at 2× the LD95 (~75 virus/mouse) by intranasal inoculation in a volume of 50 µl, after being anesthetized with a mixture of ketamine/xylazine (150 and 10 mg/kg respectively). Mortality, clinical signs, and body weight were recorded daily for 15 days and any animal with a 20% loss of body weight was scored as a death.

The study design is detailed in Table 147, and consists of multiple arms. The control arm comprises vehicle (PBS) and hIgG1 Fc only groups, dosed 24 hours after viral challenge (an uninfected group was also part of this arm). The second arm consisted of oseltamivir dosed at 4× its humanized dose, with initiation of treatment delayed for 24, 48, 72, or 96 hours. The final arms consisted of conjugate 45b administered as a single IV doses at 1 or 3 mg/kg; each being dosed on the same schedule as the oseltamivir arm above.

As expected, vehicle and hIgG1 Fc were not protective when dosed 24 hours after viral challenge and resulted in complete mortality by Day 6. In this study, oseltamivir, at 4× the humanized dose (200 mg/kg cumulative dose) was only partially efficacious when dosing was delayed 24 hours (Table 148; 80% survival). At 48 hours post-challenge the efficacy of oseltamivir dropped even lower, with only 40% of mice surviving to study end. If oseltamivir treatment was delayed until 72 or 96 hours there was no protection.

In contrast, conjugate 45b was fully protective at 1 and 3 mg/kg when dosing was delayed 24 hours. At 48 hours post challenge the 3 mg/kg group was still fully protected, and the 1 mg/kg was nearly so, with 80% survival. At 72 hours the 1 mg/kg also showed 80% protection however, the 3 mg/kg demonstrated only 20% protection. Collectively both the 1 and 3 mg/kg conjugate 45b dose groups show superior potency to oseltamivir in this delayed treatment model as measured by survival. Notably as well, the total dose of conjugate 45b was 1 or 3 mg/kg while oseltamivir was given at 200 mg/kg.

As expected, the weight data supports the survival findings (Table 149) and in general shows conjugate 45b treated mice to have superior retention of body weight. Although not statistically significant, weight is better retained in conjugate 45b treated mice, even though the oseltamivir-treated groups received a much higher dose.

TABLE 147

Study design

| Group (n = 5) | Challenge (Day 0) | Test Article | Dose (mg/kg) | Schedule (pi) | Route | Readout |
|---|---|---|---|---|---|---|
| 1 | Influenza A virus, H1N1 strain A/TX/36/91 via IN route | Vehicle (PBS) | N/A | 24-hours | Single treatment IV | Daily weight and health score monitoring for 15 days total. (Day 0 – Day 14 pi) % Survival |
| 2 | | hIgG1 Fc | 3 | 24-hours | | |
| 3 | | Conjugate 45b | 3 | 24-hours | | |
| 4 | | | | 48-hours | | |
| 5 | | | | 72-hours | | |
| 6 | | | | 96-hours | | |
| 7 | | | 1 | 24-hours | | |
| 8 | | | | 48-hours | | |
| 9 | | | | 72-hours | | |
| 10 | | | | 96-hours | | |
| 11 | | Oseltamivir phosphate | 20 | 24-hours | PO, bid for 5 days | |
| 12 | | | | 48-hours | | |
| 13 | | | | 72-hours | | |
| 14 | | | | 96-hours | | |
| 15 | Naïve mice: untreated and uninfected | | | | | |

TABLE 148

Percent Survival

| | | | Conjugate 45b (mg/kg) 1 | | | | Conjugate 45b (mg/kg) 3 | | | | Oseltamivir (mg/kg) 20 | | | |
|---|---|---|---|---|---|---|---|---|---|---|---|---|---|---|
| Day | Vehicle | hIgG1 Fc | 24 hrs | 48 hrs | 72 hrs | 96 hrs | 24 hrs | 48 hrs | 72 hrs | 96 hrs | 24 hrs | 48 hrs | 72 hrs | 96 hrs |
| 0 | 100 | 100 | 100 | 100 | 100 | 100 | 100 | 100 | 100 | 100 | 100 | 100 | 100 | 100 |
| 1 | 100 | 100 | 100 | 100 | 100 | 100 | 100 | 100 | 100 | 100 | 100 | 100 | 100 | 100 |
| 2 | 100 | 100 | 100 | 100 | 100 | 100 | 100 | 100 | 100 | 100 | 100 | 100 | 100 | 100 |
| 3 | 100 | 100 | 100 | 100 | 100 | 100 | 100 | 100 | 100 | 100 | 100 | 100 | 100 | 100 |
| 4 | 80 | 100 | 100 | 80 | 100 | 100 | 100 | 100 | 100 | 100 | 100 | 100 | 100 | 100 |
| 5 | 20 | 60 | 100 | 80 | 80 | 40 | 100 | 100 | 20 | 60 | 100 | 100 | 60 | 0 |
| 6 | 0 | 0 | 100 | 80 | 80 | 0 | 100 | 100 | 20 | 0 | 100 | 100 | 40 | 0 |
| 7 | 0 | 0 | 100 | 80 | 80 | 0 | 100 | 100 | 20 | 0 | 100 | 60 | 0 | 0 |
| 8 | 0 | 0 | 100 | 80 | 80 | 0 | 100 | 100 | 20 | 0 | 80 | 40 | 0 | 0 |
| 9 | 0 | 0 | 100 | 80 | 80 | 0 | 100 | 100 | 20 | 0 | 80 | 40 | 0 | 0 |
| 10 | 0 | 0 | 100 | 80 | 80 | 0 | 100 | 100 | 20 | 0 | 80 | 40 | 0 | 0 |
| 11 | 0 | 0 | 100 | 80 | 80 | 0 | 100 | 100 | 20 | 0 | 80 | 40 | 0 | 0 |
| 12 | 0 | 0 | 100 | 80 | 80 | 0 | 100 | 100 | 20 | 0 | 80 | 40 | 0 | 0 |
| 13 | 0 | 0 | 100 | 80 | 80 | 0 | 100 | 100 | 20 | 0 | 80 | 40 | 0 | 0 |
| 14 | 0 | 0 | 100 | 80 | 80 | 0 | 100 | 100 | 20 | 0 | 80 | 40 | 0 | 0 |

TABLE 149

Percent Body Weight

| | | | Conjugate 45b (mg/kg) 1 | | | | Conjugate 45b (mg/kg) 3 | | | | Oseltamivir (mg/kg) 20 | | | | |
|---|---|---|---|---|---|---|---|---|---|---|---|---|---|---|---|
| Day | Vehicle | hIgG2 Fc | 24 hrs | 48 hrs | 72 hrs | 96 hrs | 24 hrs | 48 hrs | 72 hrs | 96 hrs | 24 hrs | 48 hrs | 72 hrs | 96 hrs | Naïve |
| 0 | 100 | 100 | 100 | 100 | 100 | 100 | 100 | 100 | 100 | 100 | 100 | 100 | 100 | 100 | 100 |
| 1 | 98 | 100 | 98 | 98 | 98 | 100 | 103 | 102 | 100 | 101 | 98 | 101 | 99 | 99 | 99 |
| 2 | 96 | 102 | 97 | 97 | 99 | 99 | 104 | 103 | 100 | 100 | 99 | 99 | 99 | 99 | 102 |
| 3 | 88 | 93 | 92 | 90 | 91 | 90 | 99 | 95 | 92 | 92 | 94 | 93 | 89 | 89 | 103 |
| 4 | 83 | 87 | 93 | 88 | 85 | 85 | 99 | 92 | 85 | 85 | 95 | 92 | 86 | 84 | 101 |
| 5 | 78 | 81 | 95 | 91 | 83 | 79 | 103 | 96 | 79 | 80 | 94 | 91 | 82 | 78 | 101 |
| 6 | 73 | 79 | 98 | 93 | 87 | 76 | 105 | 97 | 91 | 80 | 91 | 88 | 83 | | 103 |
| 7 | | | 100 | 95 | 87 | | 106 | 102 | 92 | | 88 | 84 | 81 | | 103 |
| 8 | | | 101 | 99 | 93 | | 108 | 105 | 99 | | 91 | 88 | | | 104 |
| 9 | | | 98 | 98 | 96 | | 103 | 103 | 100 | | 97 | 91 | | | 104 |
| 10 | | | 100 | 99 | 98 | | 105 | 105 | 100 | | 100 | 93 | | | 105 |
| 11 | | | 100 | 98 | 98 | | 103 | 105 | 100 | | 101 | 91 | | | 104 |
| 12 | | | 101 | 100 | 99 | | 104 | 107 | 99 | | 102 | 93 | | | 106 |

TABLE 149-continued

| | | Conjugate 45b (mg/kg) 1 | | | | Conjugate 45b (mg/kg) 3 | | | | Oseltamivir (mg/kg) 20 | | | | |
|---|---|---|---|---|---|---|---|---|---|---|---|---|---|---|
| Day | Vehicle | hIgG2 Fc | 24 hrs | 48 hrs | 72 hrs | 96 hrs | 24 hrs | 48 hrs | 72 hrs | 96 hrs | 24 hrs | 48 hrs | 72 hrs | 96 hrs | Naïve |
| 13 | | | 100 | 99 | 100 | | 105 | 106 | 99 | | 101 | 94 | | | 105 |
| 14 | | | 101 | 100 | 101 | | 107 | 107 | 102 | | 103 | 96 | | | 105 |

Percent Body Weight

Example 181. Safety of Conjugate 45b Evaluated in a 14-Day Cynomolgus Monkey Dose-Range Finder Toxicity Study Cynomolgus monkeys were administered either 5 mpk or 20 mpk, or 50 mpk of Conjugate 45b by subcutaneous injection on days 0 and 7 of the study. Compared with vehicle controls, no significant effects on body weight gain, organ weights, food consumption were observed at any dose tested. Plasma exposures (measured by AUC) increased proportionally with dose. These preclinical safety results are consistent with a high therapeutic index (54×), based on AUC ratios from the highest dose in the toxicology study versus AUCs required for 28-day protection from influenza infection in lethal mouse influenza models. No test article related adverse effects were observed at any dose tested. A summary of observations is provided in Table 150.

TABLE 150

Summary of 14 day dose-range finder toxicity study

| Parameter | Findings at highest dose (50 mpk), compared to vehicle |
|---|---|
| Clinical observations | No findings |
| Hematology | No change from vehicle |
| Clinical Chemistry | No change from vehicle |
| Coagulation | No change from vehicle |
| Urinalysis | No change from vehicle |
| Immunophenoytyping | No change from vehicle |
| Cytokines | No change from vehicle |
| Histopathology | No findings |

Example 182. Efficacy of Conjugate 45b Subcutaneously Dosed Against Influenza A/California/07/2009 (H1N1) Pdm in a Non-Lethal Ferret Model Influenza A infections in ferrets is generally considered to have similar pathogenesis to that seen in humans. Therefore, conjugate 45b was tested in a non-lethal ferret model challenged with influenza A/CA/07/09, and H1N1 pandemic strain of clinical relevance. Briefly, male ferrets (3-5 months old) were obtained from Tripe F farms and verified to lack antibodies against influenza A H1N1. Each ferret received either Conjugate 45b, Vehicle (PBS), or hIgG1 Fc in a single intravenous (IV) injection 24±2.0 hours prior to challenge or oseltamivir phosphate (20 mg/kg), by oral gavage starting 4±0.5 hours prior to influenza virus inoculation. Administration of oseltamivir continued twice daily (12±1.5 hours apart) for 5 days after virus inoculation. Test concentrations and the experimental design are detailed in Table 151.

Ferrets were challenged intranasally with 1 E6 infectious particles of influenza A/California/07/2009 (H1N1) in a volume of 0.5 mL after being anesthetized with ketamine (25 mg/kg) and xylazine (2 mg/kg). Animals were also anesthetized as above for administration of test articles. The duration of the study was 14 days and readouts consisted of daily body weights (BW), clinical signs, temperature, and nasal washes (0.5 mL) or throat swabs at the times listed in Table 151. Viral burden in nasal washes was determined using standard plaque assays with MDCK cells. Viral burden of throat swabs was performed using standard qPCR methods. Plasma samples were also obtained from group 6 animals (dosed with 3 mg/kg of conjugate 45b) at 5 minutes, 2, 24, 72, and 120 hours. As detailed in Table 152, control animals treated with vehicle (PBS) or Fc only began losing BW starting on Day 1 which peaked on Day 6 (10.8 and 10.1% respectively). A similar drop in BW was also seen at the lowest conjugate 45b dose (0.3 mg/kg). In contrast, ferrets treated with conjugate between 1 and 30 mg/kg showed an approximate 50% reduction in BW loss.

As predicted based on BW, conjugate 45b also demonstrated a reduction in viral burden from nasal washes, the primary site of influenza infection in ferrets (Table 153 and Table 154). The efficacy of conjugate 45b is most notably demonstrated in the Day 2 burdens in which a close to 2-Log reduction is achieved at the highest dose relative to vehicle treated animals. Furthermore, the reduction in viral titer with conjugate 45b is dose-responsive between 30 and 1 mg/kg. This trend is largely repeated in the Day 4 titers, although slightly muted because the immune system plays a greater role in non-lethal ferret models (as evident by the reduction in vehicle-treated titers between Day 2 and 4).

Based on the two primary study readouts (nasal titers and BW), collectively these data demonstrate the ability of conjugate 45b to reach the upper respiratory tract at therapeutic concentrations in an important model mirroring human disease.

TABLE 151

Study design and dosing schedule

| Group | N | Test Material | Route/ Schedule | Dose (mg/kg) | Nasal Washes | Throat Swabs |
|---|---|---|---|---|---|---|
| 1 | 5 | PBS (vehicle) | IV, single @ T-24 hrs. | — | 2, 4, 6, 8 | 2, 4, 6, 8 |
| 2 | 5 | hIgG1 Fc | IV, single @ T-24 hrs. | 30 | 2, 4, 6, 8 | — |
| 3 | 5 | Oseltamivir[1] | PO, bid × 5 days, @ −4 hrs. | 20 | 2, 4, 6, 8 | — |
| 4 | 5 | Conjugate 45b | IV, single @ T-24 hrs. | 30 | 2, 4, 6, 8 | 2, 4, 6, 8 |
| 5 | 5 | Conjugate 45b | IV, single @ T-24 hrs. | 10 | 2, 4, 6, 8 | 2, 4, 6, 8 |
| 6 | 5 | Conjugate 45b | IV, single @ T-24 hrs. | 3 | 2, 4, 6, 8 | 2, 4, 6, 8 |
| 7 | 5 | Conjugate 45b | IV, single @ T-24 hrs. | 1 | 2, 4, 6, 8 | 2, 4, 6, 8 |
| 8 | 5 | Conjugate 45b | IV, single @ T-24 hrs. | 0.3 | 2, 4, 6, 8 | — |

TABLE 152

Average Body Weight Changes by Day (% Initial)

| Group | Day 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| G1 | 0.08 | −4.34 | −5.60 | −6.15 | −7.31 | −10.80 | −9.77 | −7.61 | −7.05 | −5.67 | −5.20 | −5.53 | −4.36 | −4.23 |
| G2 | −1.90 | −6.35 | −7.19 | −7.60 | −8.02 | −10.06 | −9.71 | −9.54 | −7.71 | −6.66 | −5.94 | −6.38 | −7.32 | −4.99 |
| G3 | 1.78 | −0.39 | −0.90 | −0.14 | −0.90 | −1.78 | −1.00 | −1.19 | −2.57 | 0.04 | 0.39 | 0.10 | 0.22 | 2.15 |
| G4 | −1.59 | −4.47 | −3.26 | −3.10 | −3.81 | −5.23 | −5.34 | −5.47 | −5.51 | −5.14 | −5.12 | −4.56 | −5.23 | −4.56 |
| G5 | 0.41 | −3.45 | −2.95 | −3.33 | −2.90 | −3.65 | −4.03 | −4.00 | −4.46 | −3.29 | −3.29 | −3.89 | −3.06 | −2.69 |
| G6 | −0.51 | −6.03 | −4.55 | −3.43 | −4.19 | −5.72 | −4.99 | −5.90 | −4.81 | −4.09 | −4.23 | −2.51 | −3.33 | −2.69 |
| G7 | −0.47 | −4.76 | −5.29 | −4.43 | −5.97 | −6.10 | −5.95 | −5.33 | −4.98 | −4.27 | −4.17 | −2.85 | −4.17 | −3.39 |
| G8 | 0.10 | −5.50 | −7.74 | −8.98 | −9.76 | −11.52 | −9.16 | −8.35 | −7.73 | −6.06 | −4.63 | −4.84 | −4.53 | −4.24 |

TABLE 153

Viral Burden in Nasal Washes (Log10)

| | Day 2 | Day 4 | Day 6 | Day 8 |
|---|---|---|---|---|
| G1 | 6.12 | 4.36 | Below LOD | Below LOD |
| G2 | 6.31 | 4.42 | Below LOD | Below LOD |
| G3 | 5.80 | — | Below LOD | Below LOD |
| G4 | 4.26 | 3.12 | Below LOD | Below LOD |
| G5 | 4.34 | 3.37 | Below LOD | Below LOD |
| G6 | 5.11 | 3.44 | Below LOD | Below LOD |
| G7 | 5.62 | 3.84 | Below LOD | Below LOD |
| G8 | 6.07 | 3.56 | Below LOD | Below LOD |

TABLE 154

Change in Viral Burden Relative to Vehicle (G1) (Log 10)

| | Day 2 | Day 4 | Day 6 | Day 8 |
|---|---|---|---|---|
| G1 | 0.00 | 0.00 | na | na |
| G2 | 0.19 | 0.06 | na | na |
| G3 | −0.32 | — | na | na |
| G4 | −1.86 | −1.24 | na | na |
| G5 | −1.79 | −0.99 | na | na |
| G6 | −1.01 | −0.92 | na | na |
| G7 | −0.50 | −0.52 | na | na |
| G8 | −0.06 | −0.80 | na | na |

Temperature changes were also recorded (AM & PM) and are listed in Table 155. Temperature changes over the course of the study largely support the efficacy of conjugate 45b seen with nasal burdens and body weights. Most notably is the overall reduction in time animals show an elevated temperature upon treatment with conjugate 45b or oseltamivir, relative to vehicle treated ferrets.

In this study animals were observed daily and scored for clinical symptoms of influenza, and their severity. In this non-lethal model, sneezing was the dominant sign of illness recorded by technicians (Table 156). Relative to vehicle treated ferrets, animals treated with conjugate 45b or the positive control showed fewer instances of sneezing, which resolved quicker relative to group 1. For clarity, the 0.3 mg/kg treatment group alongside vehicle and oseltamivir groups is graphed in FIG. 96.

In this study conjugate 45b demonstrated potent activity relative to vehicle treated animals by all readouts (nasal burden, body weight, temperature, & clinical score). Importantly, conjugate 45b was more potent than significantly higher doses of oseltamivir at reducing viral burden in nasal washes, the primary readout for this study. The observed efficacy of conjugate 45b in an important model recognized as mimicking human disease supports the therapeutic potential of this candidate.

TABLE 155

Temperature changes over the study

Average Change in Degrees (° C.) by Day and time (AM/PM)

| Group | 1 (AM) | 1 (PM) | 2 (AM) | 2 (PM) | 3 (AM) | 3 (PM) | 4 (AM) | 4 (PM) | 5 (AM) | 5 (PM) | 6 (AM) | 7 (AM) | 8 (AM) | 9 (AM) | 10 (AM) | 11 (AM) | 12 (AM) | 13 (AM) | 14 (AM) |
|---|---|---|---|---|---|---|---|---|---|---|---|---|---|---|---|---|---|---|---|
| G1 | 0.8 | 0.9 | 0.2 | 0.5 | 0.8 | 0.2 | 0.1 | −1.1 | 0.5 | −0.1 | 0.5 | 0.6 | 0.0 | 0.6 | 0.2 | 0.4 | 0.5 | 0.3 | −0.4 |
| G2 | 1.2 | 0.8 | −0.3 | 0.1 | −1.1 | 0.7 | 0.5 | −0.2 | 0.0 | −0.4 | 0.8 | 0.6 | 0.5 | 0.5 | 0.0 | 0.8 | 0.5 | 0.5 | −0.4 |
| G3 | −0.4 | −0.1 | 0.8 | 0.0 | −0.6 | −0.3 | 0.5 | −1.7 | −0.3 | −0.8 | 0.2 | −0.1 | −0.2 | 0.1 | −1.2 | −0.1 | 0.4 | 0.1 | −0.1 |
| G4 | −0.9 | −0.3 | 0.6 | −0.8 | −1.4 | −0.5 | 0.2 | −1.4 | −0.9 | −1.2 | 0.3 | 0.0 | −0.4 | 0.5 | 0.3 | 0.1 | 0.1 | 0.3 | −0.8 |
| G5 | −0.2 | −0.1 | 0.7 | −0.7 | −0.8 | −0.7 | −0.4 | −1.7 | −0.1 | −1.1 | 0.2 | 0.0 | −0.2 | 0.1 | −0.2 | 0.2 | 0.1 | 0.1 | −0.4 |
| G6 | 0.1 | 0.6 | 1.1 | −0.1 | −1.2 | −0.8 | 0.7 | −0.5 | −0.7 | −0.7 | 0.8 | 0.3 | −0.4 | 0.2 | 0.4 | 0.1 | 0.1 | 0.5 | −0.5 |
| G7 | −0.3 | 0.0 | 0.8 | −0.5 | −1.8 | −0.4 | −0.3 | −1.1 | −0.6 | −0.9 | −0.4 | 0.6 | −0.1 | −0.7 | −0.2 | 0.1 | 0.3 | 0.5 | 0.1 |
| G8 | −0.1 | 0.6 | 0.8 | 0.1 | −1.6 | −0.4 | 0.3 | −0.6 | −0.2 | −1.0 | 0.0 | −0.3 | 0.1 | −0.4 | −0.2 | 0.1 | 0.1 | 0.2 | −0.1 |

TABLE 156

Clinical Scores

| | Number of animals with clinical signs per day | | | | | | | | | | | | | |
|---|---|---|---|---|---|---|---|---|---|---|---|---|---|---|
| Group | 1 | 2 | 3 | 4 | 5 | 6 | 7 | 8 | 9 | 10 | 11 | 12 | 13 | 14 |
| G1 | 0 | 3 | 2 | 2 | 3 | 2 | 4 | 4 | 2 | 3 | 3 | 0 | 2 | 0 |
| G2 | 0 | 1 | 2 | 1 | 1 | 3 | 2 | 2 | 3 | 3 | 0 | 0 | 0 | 0 |
| G3 | 0 | 0 | 2 | 2 | 1 | 1 | 2 | 1 | 0 | 1 | 0 | 0 | 1 | 0 |
| G4 | 0 | 2 | 1 | 2 | 3 | 1 | 1 | 1 | 1 | 2 | 1 | 0 | 0 | 0 |
| G5 | 0 | 2 | 2 | 2 | 2 | 0 | 0 | 1 | 1 | 1 | 0 | 0 | 0 | 0 |
| G6 | 0 | 1 | 1 | 2 | 1 | 0 | 2 | 0 | 0 | 3 | 0 | 0 | 0 | 0 |
| G7 | 0 | 2 | 2 | 1 | 1 | 2 | 3 | 1 | 1 | 1 | 0 | 1 | 0 | 0 |
| G8 | 0 | 1 | 2 | 1 | 1 | 3 | 1 | 1 | 1 | 0 | 1 | 0 | 0 | 0 |

Example 183. 5-Day PK Analysis of Conjugate 45b in Ferrets Following a Single IV Injection 3 mg/kg Ferret PK studies were performed by IIT Research Institute (IITRI) using male ferrets 3-5 months old. Ferrets (n=5) were administered conjugate 45b by a single intravenous (IV) injection at 3 mg/kg (2 mL dose volume) 24 h prior to intranasal challenge with 1×10$^6$ plaque forming units (PFU) of A/California/07/2009 (H1N1) influenza virus. Ferrets were anesthetized priorto dosing and virus challenge using a ketamine (25 mg/kg) and xylazine (2 mg/kg) mixture. Blood (~0.5-1 mL) was collected at 5 min, 2, 24, 72 and 120 hr post dosing and processed for plasma. Nasal washed (0.5 mL in PBS) were collected at days 2, 4, 6, and 8. Conjugate 45b molecules were captured on neuraminidase (NA) or Fc coated plates and then detected using an HRP-conjugated anti-human IgG-Fc antibody. Protein concentration was calculated in GraphPad Prism using 4PL non-linear regression of conjugate 45b standard curves. Mean plasma concentrations were used to calculate pharmacokinetic parameters using Phoenix WinNonlin 7.0. A more detailed method description is provided below.

In the NA-capture ELISA, Nunc Maxisorp 96-well plates (cat no. 12-565-136, ThermoFisher) were coated with 0.1 U/well NA from A/California/04/2009 (H1N1) (cat no. 11058-VNAHC, Sino Biological) in 1×KPL coating buffer (cat no 5150-0041, SeraCare). Plates were incubated at room temperature for 1 hr on an orbital plate shaker (500 rpm). Serial dilutions of plasma samples were plated and incubated at room temperature for 2 hrs with shaking (sample diluent: 0.5% BSA in PBS 0.025% Tween 20+naïve ferret plasma final concentration of 1:100; plasma was excluded from nasal wash samples). Conjugate 45b standard curves ranging from 0.230 to 500 ng/mL were run on each plate in duplicate. Following the 2 hr incubation, plates were washed 5× in 300 µL PBS with 0.05% Tween 20. Conjugate bound to NA on the plates was then probed with an HRP conjugated anti-human IgG Fc F(ab')2 (cat no. 709-036-098, Jackson) diluted 1:2,000 in sample diluent for 1 hr at room temp. Plates were then washed 8× in 300 µL PBS with 0.05% Tween 20 and developed with TMB substrate for 7-8 minutes. The reaction was stopped with 1 N $H_2SO_4$. Absorbance was read at 450 nm with an EnSpire multimode plate reader (PerkinElmer). Conjugate 45b in plasma samples was interpolated using GraphPad Prism Version 8 following nonlinear regression analysis (Sigmoidal, 4PL analysis) of the standard curves. The resulting mean plasma concentrations were then used to calculate pharmacokinetic parameters by non-compartmental analysis using Phoenix WinNonlin 7.0.

In the Fc-capture ELISA, Nunc Maxisorp 96-well plates (cat no. 12-565-136, ThermoFisher) were coated overnight at 4° C. with 0.1 µg/100 µL/well of mouse anti-human IgG (CH$_2$ domain) clone R$_{10}$Z8E9 (cat no. MCA5748G, Bio-Rad) in carbonate buffer (cat no. C3041, MilliporeSigma). Plates were washed 5× with 300 µL/well PBST and blocked with 200 µL/well 5% non-fat dry milk (cat no. 9999S, Cell Signaling Technology) in PBST for 1 hr at room temperature with shaking on an orbital plate shaker (500 rpm). Serial dilutions of plasma samples were plated and incubated at room temperature for 2 hrs with shaking (sample diluent: 2.5% non-fat dry milk in PBS 0.025% Tween 20+naïve ferret plasma final concentration of 1:100; plasma was excluded from nasal wash samples). Conjugate 45b standard curves ranging from 0.03 to 55 ng/mL were run on each plate in duplicate. Following the 2 hr incubation, plates were washed 5× with 300 µL/well PBST. Conjugate bound to Fc on the plates was then probed with 100 µL/well of HRP conjugated anti-human IgG Fc F(ab')2 (cat no. 709-036-098, Jackson Immunoresearch) diluted 1:2,000 in sample diluent for 1 hr at room temp with shaking. Plates were then washed 8× in 300 µL/well PBST and developed with 100 µL/well TMB substrate reagent (cat no. 555214, BD) for 7-8 minutes. The reaction was stopped with 100 µL/well 1N $H_2SO_4$ and the absorbance read at 450 nm with an EnSpire multimode plate reader (PerkinElmer). Conjugate 45b in plasma samples was interpolated using nonlinear regression analysis and PK parameters calculated as described above.

The PK profiles comparing conjugate 45b levels in plasma and nasal washes are shown in FIGS. 93 and 94, respectively. Similar conjugate 45b plasma exposure levels were observed for the NA- and Fc-capture ELISAs. The mean conjugate 45b ferret plasma concentration was ~10 µg/mL at day 5 following a single IV dose at 3 mg/kg. Levels in nasal washes were approximately 3-5% of levels in plasma at matched timepoints.

Example 184. Efficacy of Conjugate 45b Subcutaneously Dosed Against Influenza A/PR/8/34 (H1N1) in a High Viral Challenge Lethal Mouse Model Conjugate 45b was evaluated against a lethal IAV H1N1 influenza infection in female BALB/c mice (Charles River Laboratories, 6-8 weeks). The challenge virus (A/PR/8/34) is a mouse-adapted isolate capable of causing lethal infections in mice. The experiment comprised 10 groups of 5 mice in 2 experimental arms. At day 0, mice were challenged with virus at 2× the LD95 (1×; groups 1-5) by intranasal inoculation in a volume of 30 µl or with 50× the LD95 (25×; groups 6-10), after being anesthetized with a mixture of ketamine/xylazine (150 and 10 mg/kg respectively). Mortality and body weights were recorded daily for 14 days and any animal with a 20% loss of body weight was scored as a death. Test groups received a single subcutaneous (SC) treatment of conjugate 45b at 3, 1, 0.3, or 0.1 mg/kg 2 hours post viral challenge in a dose volume of 10 ml/kg. The study design is summarized in Table 157.

In the 1× study arm vehicle treated mice succumbed to the challenge virus on Day 6. Conjugate 45b in contrast, demonstrated exceptional potency and fully protected 1× virally challenged mice at the lowest dose (Table 158A). Body weight data (Table 159A) showed a transient loss of weight which was largely recovered by study end for all conjugate 45b treated mice.

In the groups challenged with 25× more virus (50× the LD95) mice succumbed to infection faster with 80% reaching mortality by Day 5, and 100% mortality by Day 6 (Table 158B). Mice treated with conjugate 45b were fully protected at 1 or 3 mg/kg, while the 0.3 mg/kg group had a 60% survival rate. Surprisingly, even with the greater viral challenge the 1 and 3 mg/kg treatment only showed a modest drop in body weight and ended the study with a net weight gain (Table 159B).

This study demonstrates the exceptional potency of conjugate 45b even with challenge by very high viral titers.

TABLE 157

General study design

| Group | Influenza A strain | Test Article | Route, Schedule (T + 2 hours) | Dose (mg/kg) | N |
|---|---|---|---|---|---|
| 1 | A/PR/8/34 | Vehicle (PBS) | SC, single | — | 5 |
| 2 | (H1N1) | Conjugate 45b | SC, single | 3 | 5 |
| 3 | 3E2 | Conjugate 45b | SC, single | 1 | 5 |
| 4 | PFU/mouse | Conjugate 45b | SC, single | 0.3 | 5 |
| 5 | via IN | Conjugate 45b | SC, single | 0.1 | 5 |
| 6 | A/PR/8/34 | Vehicle (PBS) | SC, single | — | 5 |
| 7 | (H1N1) | Conjugate 45b | SC, single | 3 | 5 |
| 8 | 7.5E3 | Conjugate 45b | SC, single | 1 | 5 |
| 9 | PFU/mouse | Conjugate 45b | SC, single | 0.3 | 5 |
| 10 | via IN | Conjugate 45b | SC, single | 0.1 | 5 |

TABLE 158A

Percent Survival (1x challenge)

| | | Conjugate 45b (mg/kg) | | |
|---|---|---|---|---|
| Day | Vehicle | 3 | 1 | 0.3 | 0.1 |
| 0 | 100 | 100 | 100 | 100 | 100 |
| 1 | 100 | 100 | 100 | 100 | 100 |
| 2 | 100 | 100 | 100 | 100 | 100 |
| 3 | 100 | 100 | 100 | 100 | 100 |
| 4 | 100 | 100 | 100 | 100 | 100 |
| 5 | 100 | 100 | 100 | 100 | 100 |
| 6 | 0 | 100 | 100 | 100 | 100 |
| 7 | 0 | 100 | 100 | 100 | 100 |
| 8 | 0 | 100 | 100 | 100 | 100 |
| 9 | 0 | 100 | 100 | 100 | 100 |
| 10 | 0 | 100 | 100 | 100 | 100 |
| 11 | 0 | 100 | 100 | 100 | 100 |
| 12 | 0 | 100 | 100 | 100 | 100 |
| 13 | 0 | 100 | 100 | 100 | 100 |
| 14 | 0 | 100 | 100 | 100 | 100 |

TABLE 158B

Percent Survival (25x challenge)

| | | Conjugate 45b (mg/kg) | | |
|---|---|---|---|---|
| Day | Vehicle | 3 | 1 | 0.3 | 0.1 |
| 0 | 100 | 100 | 100 | 100 | 100 |
| 1 | 100 | 100 | 100 | 100 | 100 |
| 2 | 100 | 100 | 100 | 100 | 100 |
| 3 | 100 | 100 | 100 | 100 | 100 |
| 4 | 100 | 100 | 100 | 100 | 100 |
| 5 | 20 | 100 | 100 | 80 | 60 |
| 6 | 0 | 100 | 100 | 60 | 0 |
| 7 | 0 | 100 | 100 | 60 | 0 |
| 8 | 0 | 100 | 100 | 60 | 0 |
| 9 | 0 | 100 | 100 | 60 | 0 |
| 10 | 0 | 100 | 100 | 60 | 0 |
| 11 | 0 | 100 | 100 | 60 | 0 |
| 12 | 0 | 100 | 100 | 60 | 0 |
| 13 | 0 | 100 | 100 | 60 | 0 |
| 14 | 0 | 100 | 100 | 60 | 0 |

TABLE 159A

Percent Body Weight (1x challenge)

| | | Conjugate 45b (mg/kg) | | |
|---|---|---|---|---|
| Day | Vehicle | 3 | 1 | 0.3 | 0.1 |
| 0 | 100 | 100 | 100 | 100 | 100 |
| 1 | 98.5 | 97.5 | 96.1 | 96.6 | 98.2 |
| 2 | 99.6 | 98.2 | 99.9 | 97.5 | 100 |
| 3 | 92.8 | 97.4 | 98.6 | 95.8 | 96.8 |
| 4 | 85.7 | 98.7 | 98.9 | 93.7 | 90.4 |
| 5 | 79 | 98.4 | 100.1 | 95.6 | 92.4 |
| 6 | | 99.5 | 99.2 | 96.7 | 91.4 |
| 7 | | 100.7 | 101.3 | 98.9 | 88.5 |
| 8 | | 97.8 | 99.2 | 96.9 | nd |
| 9 | | 102.9 | 103.2 | 100.7 | 92.1 |
| 10 | | 101.4 | 101.4 | 99.7 | 95.9 |
| 11 | | 100.9 | 101.5 | 99.6 | 96.7 |
| 12 | | 102.1 | 104.5 | 100.9 | 98.8 |
| 13 | | 102.7 | 102.6 | 101.8 | 99.3 |
| 14 | | 101.9 | 103.4 | 101.1 | 98.6 | nd = not done

TABLE 159B

Percent Body Weight (25x challenge)

| | | Conjugate 45b (mg/kg) | | |
|---|---|---|---|---|
| Day | Vehicle | 3 | 1 | 0.3 | 0.1 |
| 0 | 100 | 100 | 100 | 100 | 100 |
| 1 | 97.2 | 96.6 | 97.4 | 97.6 | 98.6 |
| 2 | 95 | 99.6 | 100.9 | 98 | 98.7 |
| 3 | nd | nd | nd | nd | nd |
| 4 | 79.9 | 98.5 | 90.3 | 82.8 | 82.5 |
| 5 | 75.7 | 100.3 | 91.5 | 82.7 | 76.7 |
| 6 | | 100.2 | 96.4 | | |
| 7 | | 102.2 | 99.1 | | |
| 8 | | 99.5 | 97.5 | | |
| 9 | | 104.3 | 103 | | |
| 10 | | 103.5 | 102.2 | | |
| 11 | | 102.9 | 103.4 | | |
| 12 | | 105.5 | 106.1 | | |
| 13 | | 105.8 | 105.1 | | |
| 14 | | 103.9 | 106 | | | nd = not done

Example 185. Activity of Conjugate 45b Against High Path Influenza A (H5N1, H7N9) in a Cytopathic Effects (CPE) Assay An in vitro assay to determine the potency of conjugate 45b was conducted against BSL-3 (high path) influenza A, and generally followed standard procedures. Briefly, different concentrations of test articles were mixed with virus (approximately 250 $TC_{ID50}$) and allowed to incubate at 35° C. for one hour. After incubation, the mixture was added to an 80-90% confluent monolayer of MDCK cells. After a 90 minute incubation, cells were washed and the test article was re-applied. The monolayer was subsequently overlaid with carboxymethylcellulose to minimize viral spreading and was allowed to incubate for two days. After two days of culture, cells were washed with PBS and fixed with 10% formalin. After fixation the MDCK monolayer was permeabilized with Triton X-100 and immunostained with a mouse mAb against influenza nucleoprotein. Monolayers were read, and the stained area per well was calculated to determine $EC_{50/100}$ values.

The results of the study are summarized in Table 160 and demonstrate the potency of conjugate 45b against highly pathogenic strains with pandemic potential. Importantly, conjugate 45b generated $IC_{50}$ values at, or below, 17 nM against four H5N1 and one H7N9 isolate. In contrast, oseltamivir and zanamivir demonstrated incomplete coverage of the high path strains in this panel. Most notably was their lack of activity against the important H7N9 isolate. Conjugate 45b, however, was highly potent against this isolate (0.5 nM). These results suggest that the potential of conjugate 45b to treat pandemics caused by highly-virulent influenza to be superior to that of oseltamivir and zanamivir, and roughly equal to baloxavir.

TABLE 160

In vitro activity of conjugate 45b against high path influenza isolates.

| Influenza type | HA/NA Type | IC50 for viral replication (in nM) Conjugate 45b | Conjugate 6 | Oseltamivir | Baloxavir | Zanamivir |
|---|---|---|---|---|---|---|
| A/Vietnam/1194/2004 | H5N1 (clade 1) | 5.3 | 0.5 | 168.7 | 1.7 | 16.9 |
| A/Indonesia/05/2005 | H5N1 (clade 2.1) | 16.9 | 0.5 | ≥300 | 1.7 | 16.9 |
| A/Turkey/turkey/1/2005 | H5N1 (clade 2.2) | 1.7 | 0.5 | 168.7 | 1.7 | 5.3 |
| A/Hong Kong/156/ | H5N1 (clade 0) | 0.5 | 1.7 | ≥300 | 1.7 | 53.3 |
| A/Anhui/1/2013 | H7N9 | 0.5 | 0.2 | ≥300 | 5.3 | ≥300 |
| A/Netherlands/602/2009 | H1N1* | 1.7 | 0.5 | ≥300 | 1.7 | ≥300 |

*Seasonal comparator

Example 186. 8-Day PK Analysis of Conjugate 45b in Ferret Nasal Washes Following a Single IV Injection at 30, 10, 3, 1 or 0.3 mg/kg Ferret PK studies were performed by IIT Research Institute (IITRI) using male ferrets 3-5 months old. Ferrets (n=5) were administered conjugate 45b by a single intravenous (IV) injection at 30, 10, 3, 1 or 0.3 mg/kg (2 mL dose volume) 24 h prior to intranasal challenge with $1\times10^6$ plaque forming units (PFU) of A/California/07/2009 (H1N1) influenza virus. Ferrets were anesthetized prior to dosing and virus challenge using a ketamine (25 mg/kg) and xylazine (2 mg/kg) mixture. Nasal washes were collected at days 2, 4, 6 and 8 post challenge by anesthetizing animals with ketamine (25 mg/kg) and xylazine (2 mg/kg), injecting 0.5 mL of sterile PBS supplemented with penicillin (100 U/mL), streptomycin (100 μg/mL) and gentamycin (50 μg/mL) into each nostril, and collecting the expelled fluid into a specimen cup. The volume of recovered nasal wash was recorded and the concentration of conjugate 45b determined by Fc capture ELISA. Conjugate 45b molecules were captured either on neuraminidase coated plates or anti-hIgG1 antibody coated plates and then detected using an HRP-conjugated anti-human IgG-Fc antibody. hIgG1 was captured using anti-hIgG1 Fc antibody.

Briefly, Nunc Maxisorp 96-well plates (cat no. 12-565-136, ThermoFisher) were coated overnight at 4° C. with 0.1 μg/100 μL/well of mouse anti-human IgG ($CH_2$ domain) clone $R_{10}$Z8E9 (cat no. MCA5748G, BioRad) in carbonate buffer (cat no. C3041, MilliporeSigma). Plates were washed 5× with 300 μL/well PBST and blocked with 200 μL/well 5% non-fat dry milk (cat no. 9999S, Cell Signaling Technology) in PBST for 1 hr at room temperature with shaking on an orbital plate shaker (500 rpm). Nasal wash samples were initially diluted 1:10 in matrix-matched diluent (1:10 dilution of nasal wash from naïve animals in PBS with 0.5% BSA and 0.025% Tween 20), then 3-fold serially diluted and 100 μL/well added to plates and incubated at room temperature for 2 hr with shaking. Standard curves for conjugate 45b, ranging from 0.03 to 55 ng/mL, were run on each plate in duplicate. Following the 2 hr incubation, plates were washed 5× with 300 μL/well PBST. Conjugate 45b bound to Fc on the plates was then probed with 100 μL/well of HRP conjugated anti-human IgG Fc F(ab')2 (cat no. 709-036-098, Jackson Immunoresearch) diluted 1:2,000 in sample diluent for 1 hr at room temp with shaking. Plates were then washed 8× in 300 μL/well PBST and developed with 100 μL/well TMB substrate reagent (cat no. 555214, BD) for 7-8 minutes. The reaction was stopped with 100 μL/well 1 N $H_2SO_4$ and the absorbance read at 450 nm with an ENSPIRE® multimode plate reader (PerkinElmer). Conjugate 45b in ferret nasal wash samples was interpolated using GraphPad Prism Version 8 following nonlinear regression analysis (Sigmoidal, 4PL analysis) of the standard curves. The PK profiles comparing conjugate 45b in ferret nasal washes are shown in FIG. 94 and FIG. 95. A dose proportional increase in conjugate 45b ferret nasal wash levels was observed between 0.3 and 30 mg/kg IV. The 8-day time point for the 0.3 mg/kg cohort was below the limit of Fc capture detection (1 ng/mL).

Example 187. Efficacy of Conjugate 45b Against Influenza A (HI NI) in a Lethal Mouse Influenza Model, Dosed by Three Different Routes Conjugate 45b was evaluated against a lethal IAV H1N1 influenza infection in female BALB/c mice (Charles River Laboratories, 6-8 weeks). The challenge virus (A/California/07/2009) is a pandemic isolate capable of causing lethal infections in mice. The experiment comprised 10 groups of 5 mice. At day 0, all mice were challenged with virus at 3× the $LD_{95}$ (~3E4 virus/mouse) by intranasal inoculation in a volume of 30 μl after being lightly anesthetized with ketamine/xylazine (100 and 10 mg/kg respectively). Groups received a single treatment of conjugate 45b or vehicle (PBS), 2 hours after challenge, either intravenously (IV), intramuscular (IM), or subcutaneously (SC) (Table 160). Mortality and body weight (BW) were monitored daily for 14 days. Any mouse losing more than 20% BW was scored as a mortality.

TABLE 160

General study design

| Group | Influenza A strain | Test Article | Route, Schedule (T + 2 hrs.) | Dose (mg/kg) | N |
|---|---|---|---|---|---|
| 1 | A/CA/07/09 | Vehicle (PBS) | IV, single | — | 5 |
| 2 | (H1N1) | Conjugate 45b | IV, single | 1 | 5 |
| 3 | 3E4 PFU/ | Conjugate 45b | IV, single | 0.3 | 5 |
| 4 | mouse | Conjugate 45b | IV, single | 0.1 | 5 |
| 5 | via IN | Conjugate 45b | IM, single | 1 | 5 |
| 6 | | Conjugate 45b | IM, single | 0.3 | 5 |
| 7 | | Conjugate 45b | IM, single | 0.1 | 5 |
| 8 | | Conjugate 45b | SC, single | 1 | 5 |
| 9 | | Conjugate 45b | SC, single | 0.3 | 5 |
| 10 | | Conjugate 45b | SC, single | 0.1 | 5 |

In order to determine the potency of Conjugate 45b by different dose routes, matching concentrations of conjugate (1, 0.3, and 0.1 mg/kg) were dosed either IV, IM, or SC. As measured by survival, all dose routes were 100% efficacious by any dose route at 0.1 mg/kg, which previously was determined to be the lowest effective dose when conjugate 45b was dosed SC (Table 161). However, mice treated with vehicle reached 80% mortality by Day 6. When measured by survival, these data demonstrate the equivalent potency of conjugate 45b regardless of dose route.

TABLE 161

Percent survival

| | | Conjugate 45b (Dose Route) (mg/kg) | | | | | | | |
|---|---|---|---|---|---|---|---|---|---|
| | | IV | | | IM | | | SC | | |
| Day | Vehicle | 1 | 0.3 | 0.1 | 1 | 0.3 | 0.1 | 1 | 0.3 | 0.1 |
| 0 | 100 | 100 | 100 | 100 | 100 | 100 | 100 | 100 | 100 | 100 |
| 1 | 100 | 100 | 100 | 100 | 100 | 100 | 100 | 100 | 100 | 100 |
| 2 | 100 | 100 | 100 | 100 | 100 | 100 | 100 | 100 | 100 | 100 |
| 3 | 100 | 100 | 100 | 100 | 100 | 100 | 100 | 100 | 100 | 100 |
| 4 | 100 | 100 | 100 | 100 | 100 | 100 | 100 | 100 | 100 | 100 |
| 5 | 100 | 100 | 100 | 100 | 100 | 100 | 100 | 100 | 100 | 100 |
| 6 | 20 | 100 | 100 | 100 | 100 | 100 | 100 | 100 | 100 | 100 |
| 7 | 20 | 100 | 100 | 100 | 100 | 100 | 100 | 100 | 100 | 100 |
| 8 | 20 | 100 | 100 | 100 | 100 | 100 | 100 | 100 | 100 | 100 |
| 9 | 20 | 100 | 100 | 100 | 100 | 100 | 100 | 100 | 100 | 100 |
| 10 | 20 | 100 | 100 | 100 | 100 | 100 | 100 | 100 | 100 | 100 |
| 11 | 20 | 100 | 100 | 100 | 100 | 100 | 100 | 100 | 100 | 100 |
| 12 | 20 | 100 | 100 | 100 | 100 | 100 | 100 | 100 | 100 | 100 |
| 13 | 20 | 100 | 100 | 100 | 100 | 100 | 100 | 100 | 100 | 100 |
| 14 | 20 | 100 | 100 | 100 | 100 | 100 | 100 | 100 | 100 | 100 |

Body weight data strongly supports the survival data demonstrating that conjugate 45b is highly potent by either dose route (Table 162). As typical for this highly virulent pandemic isolate, mice showed a BW loss of approximately 10% around Day 3 or 4. Strikingly, the difference in BW between the same dose concentrations varied only minimally by dose route (see italics, Table 162). BW data from this study further supports the conclusion that conjugate 45b is efficacious regardless of dose route.

TABLE 162

Percent body weight*

| | | Conjugate 45b (Dose Route) (mg/kg) | | | | | | | | |
|---|---|---|---|---|---|---|---|---|---|---|
| | | IV | | | IM | | | SC | | |
| Day | Vehicle | 1 | 0.3 | 0.1 | 1 | 0.3 | 0.1 | 1 | 0.3 | 0.1 |
| 0 | 100 | 100 | 100 | 100 | 100 | 100 | 100 | 100 | 100 | 100 |
| 1 | 96.3 | 96.6 | 98.5 | 96.9 | 97.6 | 98 | 100 | 100.3 | 99.9 | 101.1 |
| 2 | 96.8 | 100.7 | 100.7 | 100.3 | 101.8 | 100.2 | 100.9 | 101.9 | 101.3 | 101.4 |
| 3 | 87.7 | 91.4 | *90.8* | 91.9 | 92.3 | 91.3 | 90.4 | 93.1 | 90.8 | 90.7 |
| 4 | 82.8 | 94.3 | 91.1 | 89.8 | 94.5 | 91.4 | *89* | 91.3 | *88* | 88.4 |
| 5 | 80.8 | 97.5 | 94.2 | 92.2 | 96.6 | 93.5 | 93.1 | 95.1 | 90 | 89.5 |
| 6 | 78.9 | 97.4 | 95.5 | 93.2 | 96.8 | 95.2 | 94.8 | 96.8 | 90.6 | 90.1 |
| 7 | | 100.1 | 97.5 | 96.8 | 99.7 | 96.7 | 96.7 | 96.9 | 95 | 92.9 |
| 8 | | 98.5 | 97 | 95.1 | 98.4 | 94.9 | 96.4 | 97.1 | 94.8 | 93.2 |
| 9 | | 99.8 | 96.8 | 95.7 | 98.5 | 94.8 | 95.7 | 96.6 | 93.8 | 93.3 |
| 10 | | 99.3 | 97.3 | 95.5 | 98.7 | 94.8 | 97.7 | 95.2 | 94.8 | 93.9 |
| 11 | | 103.4 | 100.8 | 101.4 | 103.3 | 100.1 | 101.1 | 100.2 | 99.4 | 98.1 |
| 12 | | 102.3 | 100.4 | 100.3 | 101.7 | 99.4 | 100.5 | 99.1 | 98.2 | 98 |
| 13 | | 102.2 | 100 | 99.8 | 101.4 | 99.5 | 101.1 | 99 | 98.7 | 98.4 |
| 14 | | 103.6 | 101.8 | 100.4 | 102.5 | 101.2 | 102.7 | 101.9 | 100.4 | 99.9 |

*Data are group average until first mortality in group

By two different readouts conjugate 45b was found to be equally efficacious if dosed by IV, SC, or IM dose routes. The dose route flexibility of conjugate 45b is a significant advantage, allowing for different formulations and dose routes for hospital and outpatient settings if necessary.

Example 188 Synthesis of Conjugate 46

Preparation of the Click reagent solution: 0.0050M $CuSO_4$ in PBS buffer solution: 10.0 mg $CuSO_4$ was dissolved in 12.53 mL PBS, then took 5.00 mL this $CuSO_4$ solution and added 43.1 mg BTTAA (CAS #1334179-85-9) and 247.5 mg sodium ascorbate to give the Click reagent solution (0.0050M $CuSO_4$, 0.020M BTTAA and 0.25M sodium ascorbate).

To a solution of azido functionalized Fc (65.5 mg, 10.0 mL, 1.13 μmol, azido DAR-5.9, SEQ ID NO: 76) in a 15 mL centrifuge tube was added to alkyne derivatized small molecule (22.7 mg, 15.2 μmol, described in Int-83. Example 145, 3.0 equivalents per each azido of the Fc). After gently agitating to dissolve all solids, the mixture was treated with the Click reagent solution (1.80 mL). The resulting mixture was gently rotated for 12 hours at ambient temperature. It was purified by affinity chromatography over a protein A column, followed size exclusion chromatography (see general conjugate purification protocol). Maldi TOF analysis of the purified final product gave an average mass of 66,420 Da (DAR=5.8). Yield 57 mg with 98% purity. The resulting conjugate is depicted in FIG. 102.

Applicant notes that Conjugate 46 may alternately be prepared using an Fc domain having the amino acid sequence of SEQ ID NO: 77, corresponding to a difference in Fc allotype. The differing allotypes are expected to behave the same with respect the properties described herein.

Applicant further notes that the nucleic acid construct encoding the Fc for Conjugate 46 included a nucleic acid encoding the amino acid sequence of SEQ ID NO: 67, which includes a C-terminal lysine residue. Upon expression, the C-terminal lysine of the Fc of Conjugate 46 is proteolytically cleaved, resulting in an Fc having the sequence of SEQ ID NO: 76. The presence or absence of a C-terminal lysine does not alter the properties of the Fc or the corresponding conjugate.

Example 189. 30-Day Comparative Non-Human Primate PK Study Following IV Administration of Conjugate 45b and Conjugate 46

Non-human primate (NHP) PK studies were performed by BTS Research (San Diego, Calif.) using male and female cynomolgus monkeys 5-9 years old with body weights ranging from 3.5-8.5 kg. NHPs were injected IV with 2 mg/kg of test article (0.4 mL/kg dose volume). Animals were housed under standard IACUC approved housing conditions. At appropriate times animals were non-terminally bled (via femoral or cephalic veins) with blood collected in K2EDTA tubes to prevent coagulation. Collected blood was centrifuged (2,000×g, for 10 minutes) and plasma withdrawn for analysis of test article concentrations over time (Table 163). The plasma concentrations for Conjugate 45b and Conjugate 46 at each time point were measured by sandwich ELISA. Briefly, test articles were captured on Fc-coated plates and then detected using a HRP-conjugated anti-human IgG-Fc antibody. Protein concentrations were calculated in GraphPad Prism using 4PL non-linear regression of Conjugate 45b or Conjugate 46 standard curves. A more detailed method description is provided above. The curves comparing Conjugate 45b and Conjugate 46 are shown in FIG. 97. Conjugate 46 demonstrates a significantly improved terminal half-life of ~45 days compared with ~10 days for Conjugate 45b. AUCs for Conjugate 46 are 2× greater than the AUCs for Conjugate 45b (Table 163).

TABLE 163

Monkey PK, Conjugate 45b vs. Conjugate 46

| Dose (mg/kg) | Route | Conjugate | | 0.25 | 4 | 8 | 24 | 72 | 120 | 168 | 240 | 336 | 672 | Tmax (hr) | Cmax (ug/mL) | AUClast (hr * ug/mL) | Half-life (hr) |
|---|---|---|---|---|---|---|---|---|---|---|---|---|---|---|---|---|---|
| | | | | | | | | Conc (ug/mL) | | | | | | | | | |
| 2 | IV | Conjugate 45b | Mean | 32.6 | 24.8 | 20.1 | 14.1 | 9.97 | 7.61 | 6.33 | 4.47 | 3.62 | 1.47 | 0.25 | 32.6 | 3450 | 249 |
| 2 | IV | Conjugate 46 | Mean | 35.4 | 29 | 25.7 | 20.5 | 15.1 | 13 | 11.2 | 10.4 | 8.71 | 7.97 | 0.25 | 35.4 | 7210 | 1080 |

Example 190. Activity of Conjugate 45b and Standard of Care Comparators Against Influenza A Seasonal, Pandemic, and Drug-Resistant Strains in a Cytopathic Effects (CPE) Assay An in vitro assay to determine the potency of conjugate 45b compared to controls of Oseltamivir, Zanamivir, and Baloxavir was conducted as performed in Example 166, and generally followed standard procedures. Data are shown in Tables 164-167.

TABLE 164

CPE against influenza A/CA/07/2009 (H1N1) pdm in MDCK SIAT1 cells

| Molecule | MOI 0.001 EC$_{50}$ [nM] | MOI 0.01 EC$_{50}$ [nM] |
|---|---|---|
| Oseltamivir | 18.54 | 34.2 |
| Zanamivir | 16.321 | 33.16 |
| Conjugate 45b | 0.8355 | 2.964 |
| Baloxavir | <0.3 | 2.216 |

TABLE 165

CPE against influenza A WT and H275Y mutant (H1N1) in MDCK SIAT1 cells

| EC$_{50}$ [nM] | Influenza A/ California/12/2012 (H1N1) | | Influenza A/ Texas/23/2012 (H1N1) H275Y | |
|---|---|---|---|---|
| Molecule | MOI 0.001 | MOI 0.01 | MOI 0.001 | MOI 0.01 |
| Oseltamivir | 107.6 | 1653 | >10,000 | >10,000 |
| Zanamivir | 54.59 | 558.1 | 327.7 | >10,000 |
| Conjugate 45b | 0.7043 | 20.1 | 2.101 | 81.86 |
| Baloxavir | 3.718 | 4.924 | 3.318 | 21.24 |

TABLE 166

CPE against influenza A WT and E119V mutant (H3N2) in MDCK SIAT1 cells

| Cytopathic Effect EC$_{50}$ [nM] | Influenza A/Washington/ 12/2007 (H3N2) | | Influenza A/Texas/ 12/2007 (H3N2) E119V | |
|---|---|---|---|---|
| Molecule | MOI 0.001 | MOI 0.01 | MOI 0.001 | MOI 0.01 |
| Oseltamivir | N/A | 12.39 | 96.04 | >10,000 |
| Zanamivir | N/A | 29.57 | 50.17 | 940.1 |
| Conjugate 45b | N/A | 0.0637 | 1.193 | 43.12 |
| Baloxavir | N/A | 0.9758 | 5.196 | 27.87 |

TABLE 167

CPE [nM] against influenza B at MOI 0.01

| Molecule | TM | DAR | Fc | Central linker | B/Florida/4/2006 | B/Brisbane/60/2008 | B/Malaysia/2506/2004 | B/Colorado/6/2017 |
|---|---|---|---|---|---|---|---|---|
| Oseltamivir | N/A | N/A | N/A | N/A | 1203 | 1568 | 735.7 | >10,000 |
| Zanamivir | N/A | N/A | N/A | N/A | 61.57 | 607.9 | 360.7 | 2746 |
| Conjugate 45b | Int–83 | 4.2 | SEQ ID NO: 73 | 15 atom | 10.78 | 7.291 | 6.252 | 25.93 |
| Baloxavir | N/A | N/A | N/A | N/A | 20.95 | 46.84 | 61.33 | 100.9 |

Example 191. 14-Day Mouse PK Study Comparing Plasma and Epithelial Lining Fluid (ELF) Concentrations of Conjugate 45b Female BALB/c mice from Charles River Laboratories were allowed to acclimate for 5 days prior to study commencement. Animals were housed 3-6 per cage with free access to food and water. All procedures were performed to NeoSome IACUC policies and guidelines. Mice were injected subcutaneously (SC) with 20 mg/kg of test article (10 mL/kg dose volume). At selected time points, 3 mice were euthanized by $CO_2$ inhalation. Blood was collected through cardiac puncture into K2EDTA tubes for plasma retention. Following blood collection, a bronchoalveolar lavage (BAL) was performed by exposing the trachea, inserting a 23G tubing adaptor, and performing 2×0.5 mL flushes with sterile 1×PBS pH 7.4. The recovered fluid volume was recorded and retained. Once the BAL procedure was complete, the lungs were removed, weighed and stored at –80° C. Aliquots of the plasma and BAL fluid (BALF) were decanted prior to –80° C. storage of the samples for use in a urea quantification assay. The collected BALF was centrifuged at 12,000 RPM for 5 minutes at room temperature to pellet the alveolar macrophages with both the pellet and supernatant stored at –80° C. until shipment to sponsor. The plasma concentrations for conjugate 45b at each time point were measured by indirect ELISA as described in detail above. Briefly, conjugate 45b molecules were captured on neuraminidase (NA) coated plates and then detected using a HRP-conjugated anti-human IgG Fcγ specific F(ab')2. The same ELISA was performed on BALF harvested as described above. Conjugate 45b plasma concentrations were calculated in GraphPad Prism using 4PL non-linear regression of conjugate 45b standard curves. ELF volume and conjugate 45b concentration in ELF was determined using urea as a dilution marker as described previously (Rennard et al., 1986 *J Appl Physiol* 60:532-538). The curves comparing conjugate 45b to ELF levels are shown in FIG. 98. By 2 h post injection, conjugate 45b epithelial lining fluid (ELF) levels are ~60% of plasma exposure levels (AUCs) across the rest of the time course indicating nearly immediate partitioning of conjugate 45b from plasma to the ELF in the lung (FIG. 98, Table 168).

TABLE 168

Conjugate 45b plasma and ELF levels in mice over 2 weeks.

| Group | Time (hr) 1 | 2 | 4 | 8 | 24 | 48 | 72 | 120 | 168 | 336 Conc (ug/mL) | Tmax (hr) | Cmax (ug/mL) | AUClast (hr * ug/mL) |
|---|---|---|---|---|---|---|---|---|---|---|---|---|---|
| ELF | 5.61 | 29.9 | 70.6 | 98.4 | 149 | 105 | 94.2 | 49.5 | 47.4 | 16.1 | 24 | 149 | 19000 |
| Plasma | 30.7 | 63.9 | 110 | 180 | 197 | 178 | 144 | 104 | 87 | 29.4 | 24 | 197 | 32500 |

Example 192. 7-Day Mouse PK Study Comparing IV, SC and IM Administration of Conjugate 45b in SCID Mice Mouse PK studies were performed using male severe combined immunodeficient (SCID) mice 6 weeks of age which lack an adaptive immune system. Mice were injected IV, SC or IM with 5 mg/kg of test article (10 mL/kg dose volume). Animals were housed under standard IACUC approved housing conditions. At appropriate times animals were non-terminally bled (retro-orbital, cheek, or by tail vein) with blood collected in K2EDTA tubes to prevent coagulation. Collected blood was centrifuged (2,000×g, for 10 minutes) and plasma withdrawn for analysis of test article concentrations overtime. The plasma concentrations for conjugate 45b at each time point were measured by ELISA as described in detail above. Briefly, conjugate 45b molecules were captured on neuraminidase (NA) coated plates and then detected using a HRP-conjugated anti-human IgG Fcγ specific $F(ab')_2$. For the Fc capture ELISA, hIgG1 was captured using an anti-hIgG1 Fc antibody and then detected using a HRP-conjugated anti-human IgG Fcγ specific $F(ab')_2$. Protein concentration was calculated in GraphPad Prism using 4PL non-linear regression of conjugate 45b standard curves. The curves comparing conjugate 45b PK profiles in SCID mice over 7 days are shown in FIGS. 99-100. The conjugate 45b plasma exposure levels for SC and IM were comparable and the resulting bioavailability from either SC or IM routes were approximately 77% compared to IV administration. Conjugate 45b plasma concentrations were equivalent for all dose routes at approximately 24 h post-injection.

Example 193. 7-Day Mouse PK Study Comparing SC Administration of Conjugate 45b Vs Conjugate 46

Mouse PK studies were performed using male CD-1 mice 6 weeks of age. Mice were injected SC with 10 mg/kg of test article (10 mL/kg dose volume). Animals were housed under standard IACUC approved housing conditions. At appropriate times animals were non-terminally bled (retro-orbital, cheek, or by tail vein) with blood collected in K2EDTA tubes to prevent coagulation. Collected blood was centrifuged (2,000×g, for 10 minutes) and plasma withdrawn for analysis of test article concentrations over time. The plasma concentrations for conjugate 45b at each time point were measured by indirect ELISA as described in detail above. Briefly, conjugate 45b molecules were captured on neuraminidase (NA) coated plates and then detected using a HRP-conjugated anti-human IgG Fcγ specific F(ab')$_2$. Protein concentration was calculated in GraphPad Prism using 4PL non-linear regression of conjugate 45b standard curves. The curves comparing the 7-day PK profiles of conjugate 45b and conjugate 46 are shown in FIG. 101. The plasma exposure levels for conjugate 46 were approximately 50% greater than for conjugate 46. Compared to WT human IgG1, the half-life of human IgG1 YTE Fc variant is known to be reduced in mice due to enhanced mouse FcRn binding at neutral pH, which negates the improved binding to mouse FcRn at acidic pH (Dall'Acqua et al. 2002 J Immunol 169:5171-5180).

Example 194. Combination Treatment of Conjugate 45b and Baloxavir

Cytopathic effect (CPE). A monolayer of MOCK Siat1 cells was infected with influenza A subtypes at appropriate MOI varying between 0.01-1. Conjugate 45b was tested alone or in combination with standard of care agent, e.g. baloxavir, at concentrations ranging between 1-1,000 nM and incubated for 3 days for influenza A at 37° C., 5% $CO_2$. CPE was determined by crystal violet staining by reading absorbance at 595 nm. Data are shown in Tables 169-172. When used in combination with baloxavir, conjugate 45b is effective at inhibiting viral replication at significantly lower concentrations than when used alone (with reductions in $EC_{50}$s of >10-fold), even when baloxavir is present at concentrations below its $EC_{50}$.

TABLE 169

Variation in Conjugate 45b $EC_{50}$ in the presence of fixed concentrations of baloxavir in CPE versus influenza A/CA/07/2009(H1N1) pdm in MDCK SIAT cells at MOI 0.01

| Molecule | Baloxavir [nM] | MOI 0.01 $EC_{50}$ [nM] |
| --- | --- | --- |
| Conjugate 45 | 0 | 7.369 |
| | 1 | 0.7347 |
| | 2 | <0.39 |
| | 4 | <0.39 |
| | 8 | <0.39 |
| | 16 | <0.39 |
| | 32 | <0.39 |
| | 64 | <0.39 |

$EC_{50}$ of Baloxavir alone = 2.41 nM

TABLE 170

Variation in Conjugate 45b $EC_{50}$ in the presence of fixed concentrations of baloxavir in CPE assays versus influenza A/CA/07/2009(H1N1) pdm in MDCK SIAT cells at MOI 0.1

| Molecule | Baloxavir [nM] | MOI 0.1 $EC_{50}$ [nM] |
| --- | --- | --- |
| Conjugate 45b | 0 | >100 (405.5) |
| | 1 | 9.169 |
| | 2 | 4.671 |
| | 4 | <0.39 |
| | 8 | <0.39 |
| | 16 | <0.39 |
| | 32 | <0.39 |
| | 64 | <0.39 |

$EC_{50}$ of Baloxavir alone = 7.95 nM

TABLE 171

Variation in Conjugate 45b $EC_{50}$ in the presence of fixed concentrations of baloxavir in CPE assays influenza A/Texas/71/2017 (H3N2) pdm in MDCK SIAT cells at MOI 0.01

| Molecule | Baloxavir [nM] | MOI 0.01 $EC_{50}$ [nM] |
| --- | --- | --- |
| Conjugate 45b | 0 | 45.93 |
| | 1 | 5.242 |
| | 2 | 2.429 |
| | 4 | 0.8822 |
| | 8 | 0.2175 |
| | 16 | 0.02432 |
| | 32 | 0.04907 |
| | 64 | 0.1346 |

$EC_{50}$ of Baloxavir alone = 8.238 nM

TABLE 172

Variation in Conjugate 45b EC50 in the presence of fixed concentrations of baloxavir in CPE assays versus influenza A/Texas/71/2017 (H3N2) pdm in MDCK SIAT cells at MOI 0.1

| Molecule | Baloxavir [nM] | MOI 0.1 $EC_{50}$ [nM] |
| --- | --- | --- |
| Conjugate 45b | 0 | 30015 |
| | 1 | 105 |
| | 2 | 100.9 |
| | 4 | 10.17 |
| | 8 | <0.39 |
| | 16 | <0.39 |
| | 32 | <0.39 |
| | 64 | <0.39 |

$EC_{50}$ of Baloxavir alone = 17.31 nM

Example 195. Synthesis of Int-91
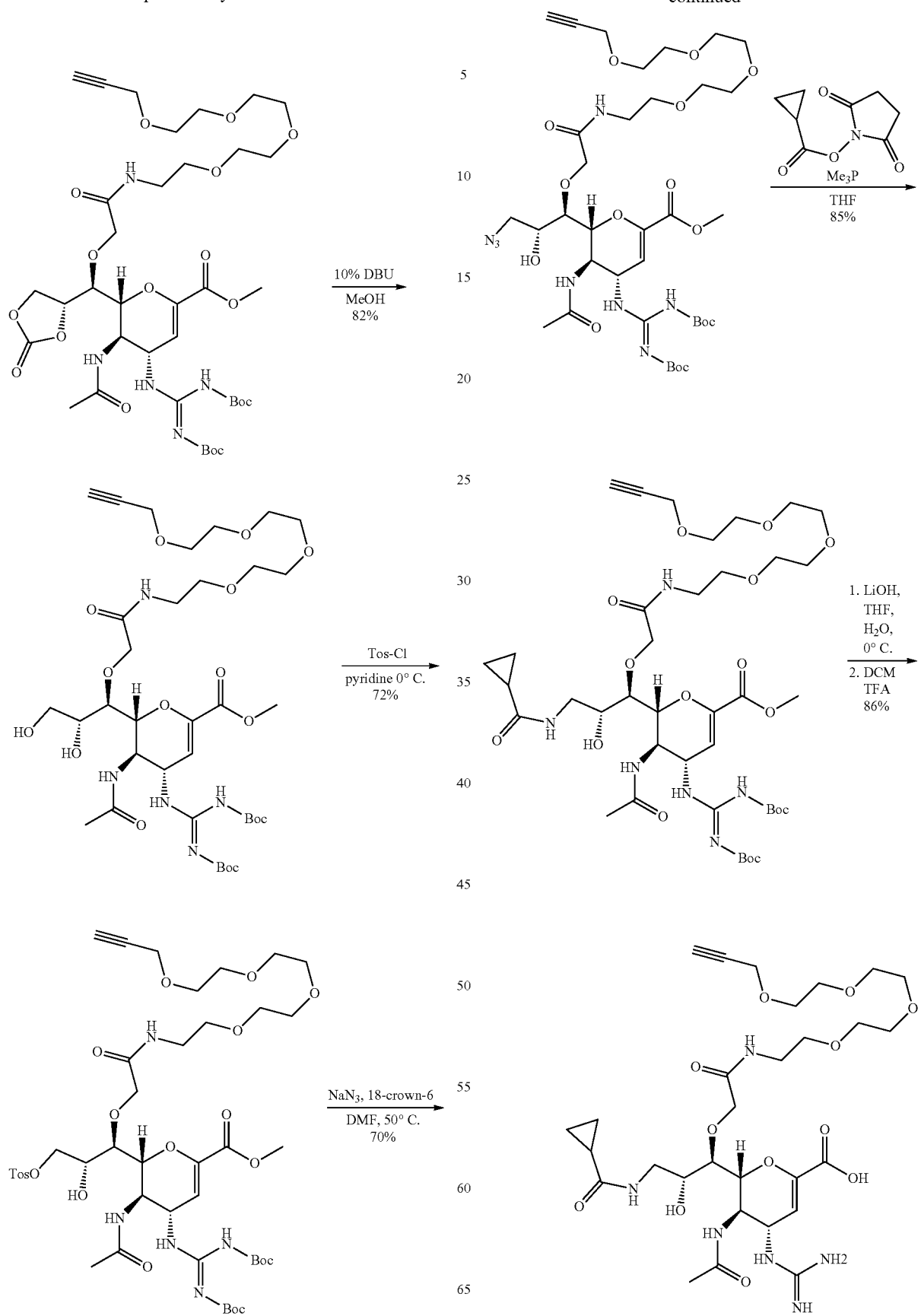

Step a.

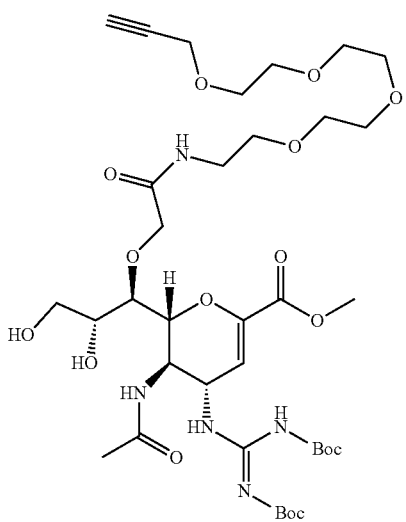

To a 0° C. stirring solution of the previously prepared-zanamivir derivative (1.993 g, 2.362 mmol, Int-22 described in Example 79) in methanol (30 mL) it was added DBU (2.4 mL). The temperature was raised to ambient and after 1 h the reaction evolved exclusively to the desired product. All the volatiles were removed by rotatory evaporation. The residue was purified by silica column using an Isco CombiFlash liquid chromatography eluted with 0% to 30% methanol and dichloromethane. Yield 1.584 g, 82%. Ions found by LCMS: $[(M+H+Na)]^+=840.0$, $[(M+H)]^+=818.2$.

Step b.

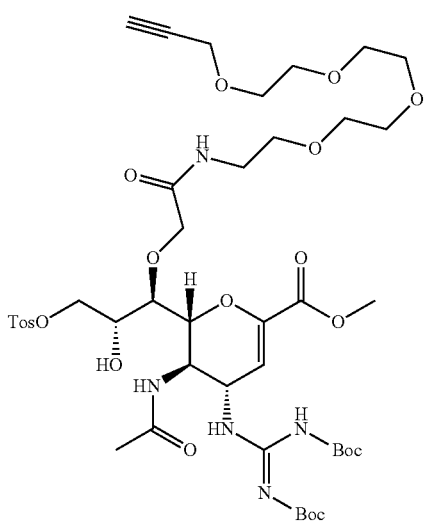

To a 0° C. stirring solution of step a product (500 mg, 0.611 mmol) in pyridine (15.0 mL) it was added tosyl chloride (146 mg, 0.764 mmol) 5.0 mL of dichloromethane) over 1 hour with the aid of a syringe pump. Upon full consumption of tosyl chloride (HPLC monitoring) an equal aliquot of tosyl chloride was added in the same fashion, and this addition was repeated an additional two times (total equivalents of tosyl chloride at the end of the reaction was 5). The reaction was quenched with methanol (0.5 mL), and all the volatiles were removed by rotatory evaporation. The residue was purified by silica column using an Isco COMBIFLASH® liquid chromatography eluted with 0% to 30% methanol and dichloromethane. Yield 0.429 g, 72%. Ions found by LCMS: $[(M+H)]^+=972.2$.

Step c.

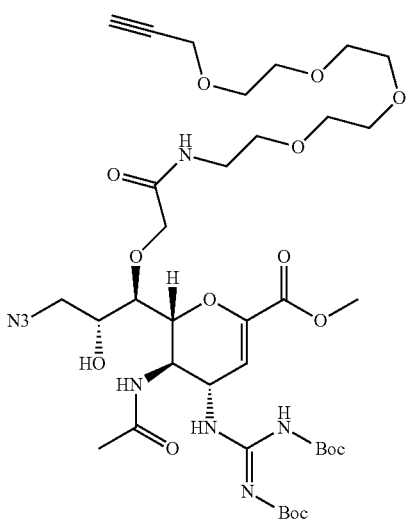 [SMILES: C#CCOCCOCCOCCOCCNC(=O)CO[C@@H]([C@@H]1OC(C(=O)OC)=C[C@H](N/C(=N/C(=O)OC(C)(C)C)NC(=O)OC(C)(C)C)[C@H]1NC(C)=O)[C@H](O)CN=[N+]=[N-]]

To a stirring solution of step b product (547 mg, 0.563 mmol) in DMF (5.0 mL) was added 18-crown-6 (59 mg, 0.225 mmol), and sodium azide (183 mg, 2.814 mmol), then the temperature was raised to 50° C. Upon completion of the reaction by LCMS, all volatiles were removed by rotatory evaporation. The residue was purified by silica column using an Isco COMBIFLASH® liquid chromatography eluted with 0% to 30% methanol and dichloromethane. Yield 0.333 g, 70%. Ions found by LCMS: $[(M+H)]^+=843.2$.

Step d.

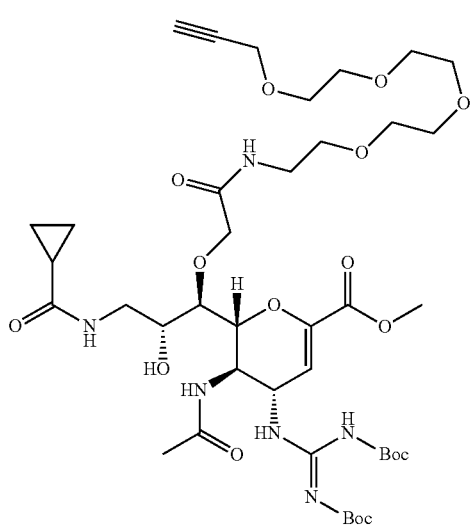 [SMILES: C#CCOCCOCCOCCOCCNC(=O)CO[C@@H]([C@@H]1OC(C(=O)OC)=C[C@H](N/C(=N/C(=O)OC(C)(C)C)NC(=O)OC(C)(C)C)[C@H]1NC(C)=O)[C@H](O)CNC(=O)C1CC1]

To a stirring solution of step c product (548 mg, 0.650 mmol) in THF (8.0 mL) it was added N-hydroxysuccinimidyl ester of cyclopropane acid (237 mg, 1.300 mmol) and trimethylphosphine (133 μL, 1.300 mmol). Upon completion by LCMS, all the volatiles were removed by rotatory evaporation. The residue was purified by silica column using an Isco COMBIFLASH® liquid chromatography eluted with 0% to 50% methanol and dichloromethane. Yield 0.488 g, 85%. Ions found by LCMS: [(M+H)]⁺=885.2.

Step e.

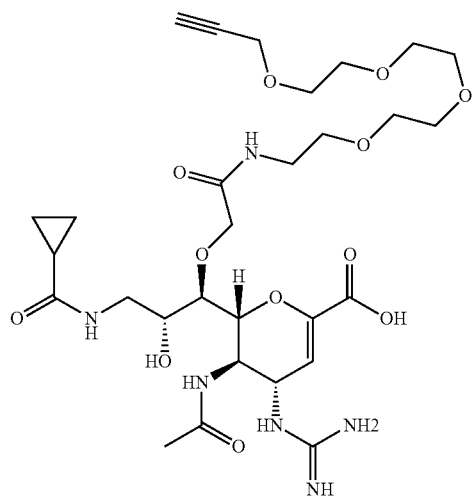 [SMILES: C#CCOCCOCCOCCOCCNC(=O)CO[C@@H]([C@@H]1OC(C(=O)O)=C[C@H](NC(=N)N)[C@H]1NC(C)=O)[C@H](O)CNC(=O)C1CC1]

To a 0° C. stirring solution of step d product (488 mg, 0.551 mmol) in tetrahydrofuran and water (2.0 mL) was added lithium hydroxide (14 mg, 0.606 mmol). Upon completion by LCMS, amberlite IRN-77 was added until pH was found acidic. The mixture was filtered with the aid of ethyl acetate, and the resin was discarded. All the volatiles were removed by rotatory evaporation and the crude material was dissolved in dichloromethane (4.0 mL) and TFA (2.0 mL). Upon completion, all the volatiles were evaporated by rotatory evaporation. The residue was purified by HPLC (0 to 40% methanol and water, using 0.1% TFA as modifier). Yield 370 mg, 86%. Ions found by LCMS: [(M+H)]⁺=671.2.

Example 196. Synthesis of Conjugate 47

A solution of azido functionalized Fc (50 mg, 5.0 mL, 0.862 μmol, SEQ ID NO: 73, DAR-7.0) was added to a 40 mL centrifuge tube containing alkyne functionalized small molecule (6.1 mg, 7.760 μmol, Int-91, prepared as described in Example 195). After gently shaking to dissolve all solids, it was added a solution of L-ascorbic acid sodium (12.3 mg, 62.08 μmol), copper (II) sulfate (2.5 mg, 15.52 μmol), and BTTAA (26.7 mg, 62.08 μmol) in PBS 7.4 buffer (6.984 mL). The resulting mixture was gently shaken overnight. It was purified by affinity chromatography over a protein A column, followed size exclusion chromatography (see general conjugate purification protocol provided herein). Maldi TOF analysis of the purified final product gave an average mass of 64,423 Da (DAR=6.9). Yield 35.3 mg, 70% yield.

The nucleic acid construct encoding the Fc for Conjugate 47 included a nucleic acid encoding the amino acid sequence of SEQ ID NO: 64, which includes a C-terminal lysine residue. Upon expression, the C-terminal lysine of the Fc of Conjugate 47 is proteolytically cleaved, resulting in an Fc having the sequence of SEQ ID NO: 73. The presence or absence of a C-terminal lysine does not alter the properties of the Fc or the corresponding conjugate.

Example 197. Synthesis of carbamate Int-92

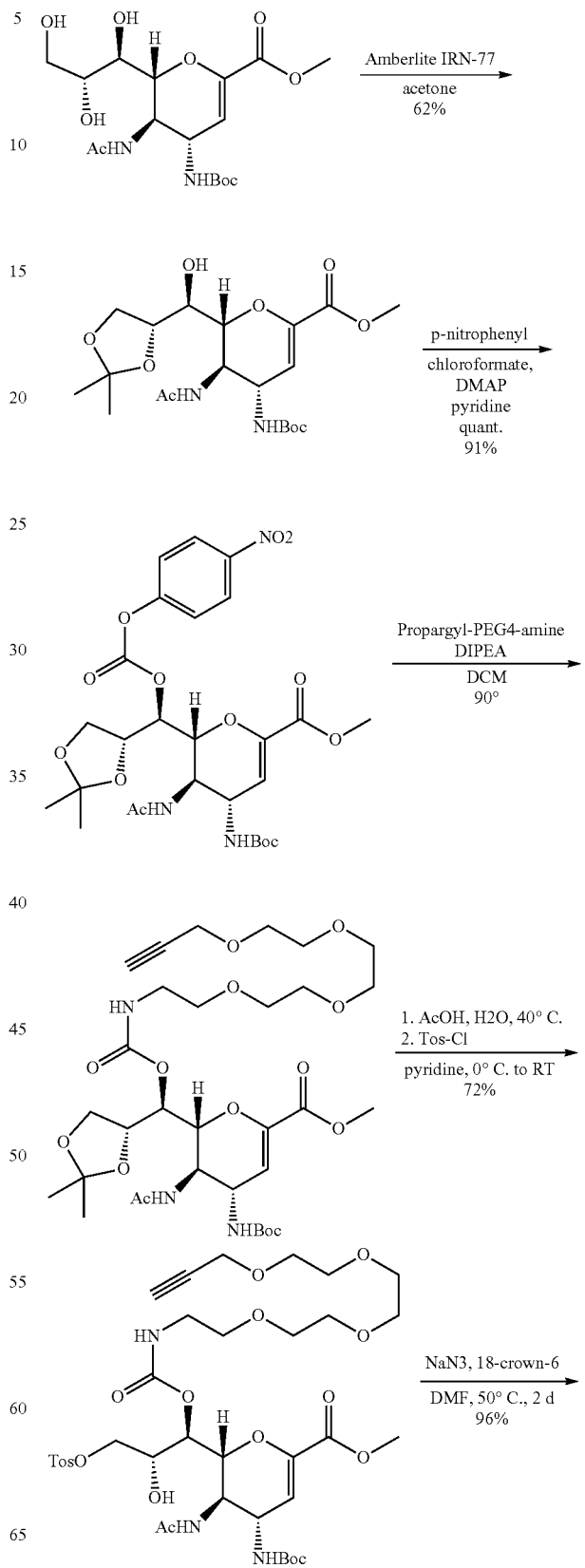

1053
-continued

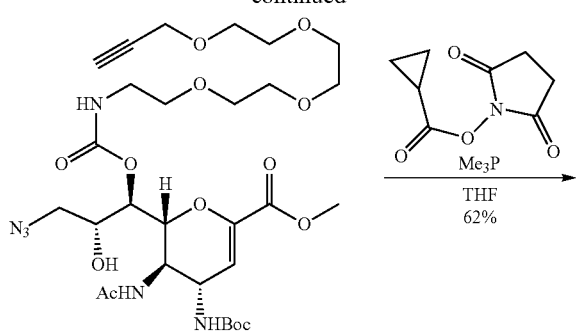 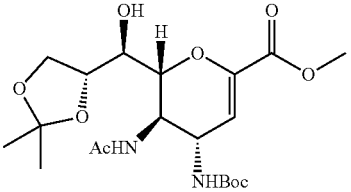

1054
-continued

Step a.

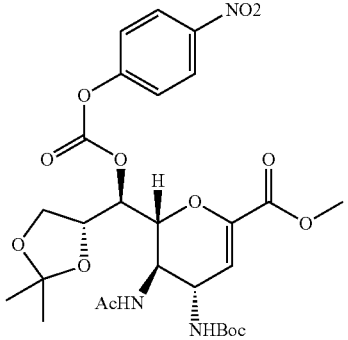

Intermediate prepared as described at Example 21 (5.15 g, 12.74 mmol) was dissolved in acetone (100 mL). Amberlite IRN-77 acidic resin was added, bringing the pH to ~4, when measured with pH paper. The reaction was heated until all starting material was consumed. Upon cooling, the reaction was filtered, and the filtrate was concentrated by rotatory evaporation. The residue was purified by silica column using an Isco COMBIFLASH® liquid chromatography eluted with 0% to 30% methanol and dichloromethane. Yield 3.535 g, 62%. Ions found by LCMS: $[(M+H+Na)]^+=467.2$, $[(M+H-t-Bu)]^+=389.2$, $[(M+H-Boc)]^+=345.2$.

Step b.

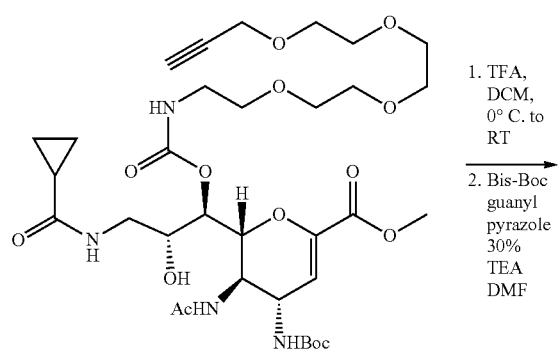

1. TFA, DCM, 0° C. to RT
2. Bis-Boc guanyl pyrazole 30% TEA DMF

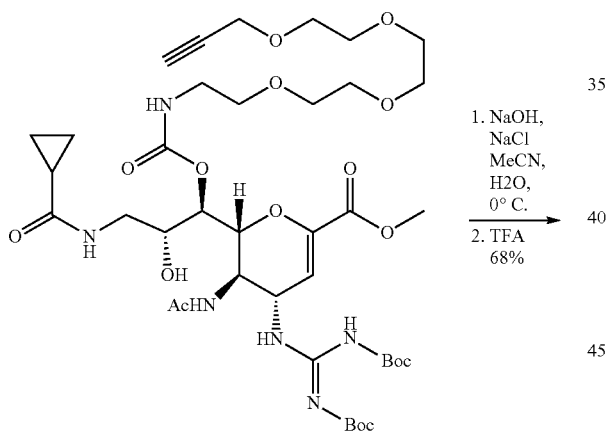

1. NaOH, NaCl MeCN, H2O, 0° C.
2. TFA 68%

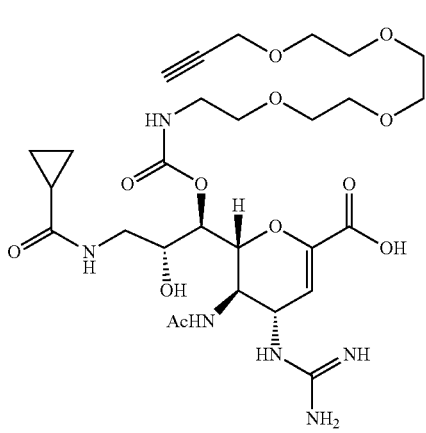

To a stirring solution of step a product (3.258 g, 7.391 mmol) and p-nitrophenol chloroformate (2.979 g, 14.78 mmol) in pyridine (80 mL), was added DMAP (1.806 g, 14.78 mmol). After 18 h, additional p-nitrophenol chloroformate (1.490 g, 7.391 mmol) and DMAP (0.903 g, 7.391 mmol) were added. Upon reaction completion, all the volatiles were removed by rotatory evaporation. The residue was taken up in DCM (250 mL), and filtered. The filtrate was washed with a 2 N solution of sulfuric acid (3×100 mL), then a saturated solution of sodium bicarbonate (3×100 mL). The organics were dried with brine (200 mL), then magnesium sulfate, filtered, and concentrated. The residue was purified by silica column using an Isco COMBIFLASH® liquid chromatography eluted with 0% to 100% acetone and hexanes. Yield 4.122 g, 91%. Ions found by LCMS: $[(M+H+Na)]^+=632.1$, $[(M+H)]^+=554.0$, $[(M+H-Boc)]^+=510.2$.

Step c.

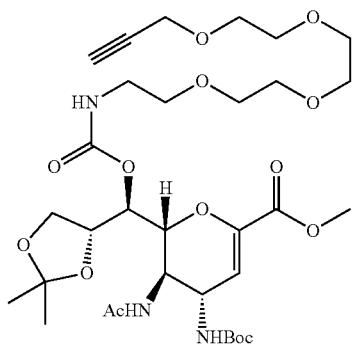

To a 0° C. stirring solution of step b product (4.00 g, 6.562 mmol) and DIPEA (2.400 mL, 13.78 mmol) in DCM (40 mL), was added propargyl-PEG4-amine. The temperature was raised to ambient and stirring was continued until complete by LCMS. All the volatiles were removed by rotatory evaporation. The residue was purified by silica column using an Isco COMBIFLASH® liquid chromatography eluted with 0% to 50% methanol and dichloromethane. Yield 4.130 g, 90%. Ions found by LCMS: $[(M+H+Na)]^+=724.1$, $[(M+H-Boc)]^+=602.2$.

Step d.

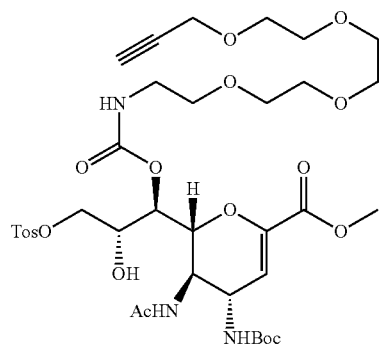

The product from step c (4.13 g, 5.885 mmol) was dissolved in acetic acid (24 mL) and water (12 mL), then stirred until complete conversion was observed by LCMS. The reaction was concentrated by rotatory evaporation. To a stirring solution of this residue (4.60 g, 5.340 mmol) in pyridine (150 mL) was slowly added a solution of Tosyl-Cl (1.392 g, 7.299 mmol) in DCM (10 mL) by syringe pump. Upon consumption of the Tos-Cl, and additional amount (1.392 g, 7.299 mmol) was added. Upon complete conversion of the starting material, all the volatiles were removed by rotatory evaporation. The residue was purified by silica column using an Isco COMBIFLASH® liquid chromatography eluted with 0% to 50% methanol and dichloromethane. Yield 3.380 g, 71%. Ions found by LCMS: $[(M+H+Na)]^+=838.0$, $[(M+H-Boc)]^+=716.2$.

Step e.

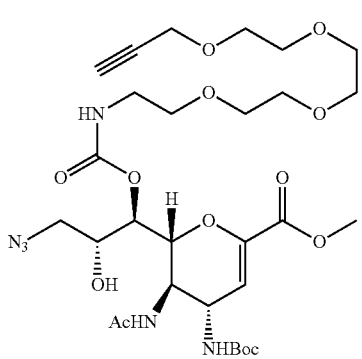 [SMILES: C#CCOCCOCCOCCOCCNC(=O)O[C@@H]([C@@H]1OC(C(=O)OC)=C[C@H](NC(=O)OC(C)(C)C)[C@H]1NC(C)=O)[C@H](O)CN=[N+]=[N-]]

To a stirring solution of the step d tosylate (3.280 g, 4.020 mmol) in DMF (30 mL) was added 18-crown-6 (425 mg, 1.608 mmol), and sodium azide (1.307 g, 20.10 mmol), then the temperature was raised to 50° C. Upon completion by LCMS, all the volatiles were evaporated by rotatory evaporation. The residue was purified by silica column using an Isco COMBIFLASH® liquid chromatography eluted with 0% to 50% methanol and dichloromethane. Yield 2.651 g, 96%. Ions found by LCMS: $[(M+H+Na)]^+=709.2$, $[(M+H-Boc)]^+=587.2$.

Step f.

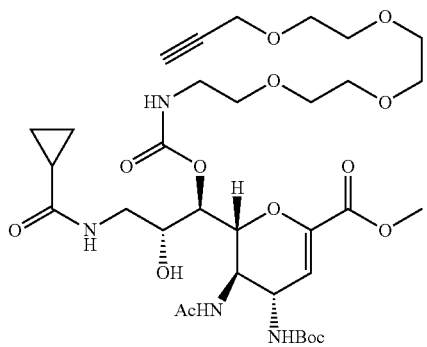 [SMILES: C#CCOCCOCCOCCOCCNC(=O)O[C@@H]([C@@H]1OC(C(=O)OC)=C[C@H](NC(=O)OC(C)(C)C)[C@H]1NC(C)=O)[C@H](O)CNC(=O)C1CC1]

To a stirring solution of step e product (2.649 mg, 3.858 mmol) in THF (20 mL) was added N-hydroxysuccinimidyl ester of cyclopropane acid (1.413 g, 7.715 mmol) and trimethylphosphine (795 µL, 7.715 mmol). Upon completion of the reaction by LCMS, all the volatiles were evaporated by rotatory evaporation. The residue was purified by silica column using an Isco COMBIFLASH® liquid chromatography eluted with 0% to 50% methanol and dichloromethane. Yield 1.744 g, 62%. Ions found by LCMS: $[(M+H)]^+=729.2$.

Step g.

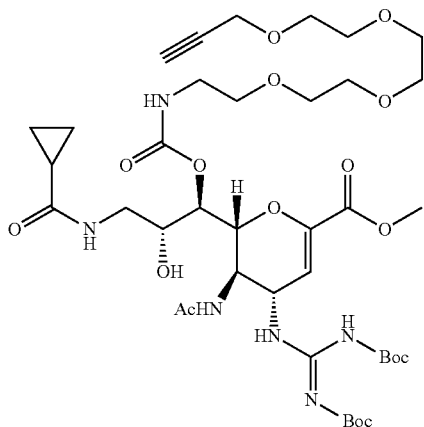 [SMILES: C#CCOCCOCCOCCOCCNC(=O)O[C@@H]([C@@H]1OC(C(=O)OC)=C[C@H](N/C(=N/C(=O)OC(C)(C)C)NC(=O)OC(C)(C)C)[C@H]1NC(C)=O)[C@H](O)CNC(=O)C1CC1]

To a 0° C. stirring solution of step f product (1.744 g, 2.393 mmol) in DCM (15 mL) was added TFA (15 mL), then the temperature was raised to ambient. Upon consumption of all starting material, volatiles were removed by rotatory evaporation. LCMS analysis of this crude showed [(M+H)]$^+$=629.2. This material was taken up in a 0° C. stirring solution of DIPEA (7.502 mL, 43.07 mmol) in DCM (15 mL), and treated with bis-Boc-p-nitrophenol chloroformate (817 mg, 2.632 mmol). Upon consumption of the starting material, all the volatiles were removed by rotatory evaporation. The residue was purified by silica column using an Isco COMBIFLASH® liquid chromatography eluted with 0% to 50% methanol and dichloromethane. Yield 631 mg, 30%. Ions found by LCMS: [(M+H)]$^+$=871.2.

Step h.

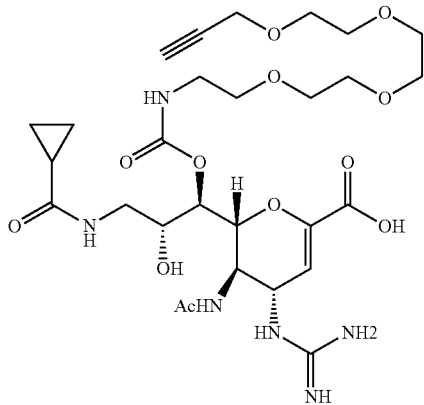 [SMILES: C#CCOCCOCCOCCOCCNC(=O)O[C@@H]([C@@H]1OC(C(=O)O)=C[C@H](NC(=N)N)[C@H]1NC(C)=O)[C@H](O)CNC(=O)C1CC1]

To a 0° C. stirring solution of step g product (315 mg, 0.362 mmol) in acetonitrile (4.0 mL) and 1.0 M solution of NaCl in water (8 mL), it was added a 1.0 M solution of NaOH in water (15 mg, 380 µL, 0.380 mmol). Stirring was continued overnight, while the temperature was gently allowed to reach ambient. The reaction was quenched with acetic acid (100 µL) and all the volatiles were removed by rotatory evaporation. The residue was suspended in DCM:MeOH=9:1 and filtered. All the volatiles were removed by rotatory evaporation. LCMS analysis of this crude material showed a major peak with the desired [(M+H)]$^+$=857.2. The residue was dissolved in DCM (3.0 mL) and TFA (3.0 mL) to remove the boc groups. Upon completion by LCMS, all the volatiles were removed by rotatory evaporation. The residue was purified by HPLC (0 to 40% methanol and water, using 0.1% TFA as modifier). Yield 370 mg, 86%. Ions found by LCMS: [(M+H)]$^+$=657.2.

Example 198. Synthesis of Conjugate 48

A solution of azido functionalized Fc (33.3 mg, 3.33 mL, 0.576 µmol, SEQ ID NO: 73; DAR-7.0) was added to a 50 mL centrifuge tube containing alkyne functionalized small molecule (6.1 mg, 7.760 µmol, Int-92 prepared as described in Example 197). After gently shaking to dissolve all solids, this solution was added to a solution of L-ascorbic acid sodium (8.6 mg, 11.21 µmol), copper (II) sulfate (2.5 mg, 15.52 µmol), and BTTAA (26.7 mg, 62.08 µmol) in PBS 7.4 buffer (6.984 mL). The resulting solution was gently rotated overnight. It was purified by affinity chromatography over a protein A column, followed size exclusion chromatography (see general conjugate purification protocol described herein). Maldi TOF analysis of the purified final product gave an average mass of 63,734 Da (DAR=6.2). Yield 35.3 mg, 63% yield.

The nucleic acid construct encoding the Fc for conjugate 48 included a nucleic acid encoding the amino acid sequence of SEQ ID NO: 64, which includes a C-terminal lysine residue. Upon expression, the C-terminal lysine of the Fc of conjugate 48 is proteolytically cleaved, resulting in an Fc having the sequence of SEQ ID NO: 73. The presence or absence of a C-terminal lysine does not alter the properties of the Fc or the corresponding conjugate.

Example 199. The Effects of DAR on Neuraminidase Inhibition

Neuraminidase Inhibition (NAI)

Test articles were incubated with live viruses at designated PFU/mL for 20 min at 37° C., 5% $CO_2$. NA-Fluor substrate was added to appropriate wells and incubated for 1 h at 37° C., 5% $CO_2$. NAI was determined by reading fluorescence at 355 nm excitation/460 nm emission. The % NAI was calculated using the formula: % NAI=(1−(FI$_{virus\ with\ TA}$−FI$_{no\ virus}$))/(FI$_{virus\ only}$−FI$_{no\ virus}$)×100. IC$_{50}$ was calculated using non-linear regression analysis software in GraphPad Prism.

Conjugate 45a demonstrated DAR-dependent increased activity reaching maximal activity at DAR 3.3 or greater against influenza A/PR/8/1934 (H1N1) (Table 173).

The A/Bethesda/956/2006 (H3N2) R$_{292}$K mutant showed resistance to oseltamivir and showed decreased susceptibility against zanamivir. Conjugate 45a did not shift against this mutant and demonstrated DAR-dependent increased activity reaching maximal activity at DAR 3.3 or greater against influenza (Table 173).

TABLE 173

Summary $IC_{50}$ for Conjugate 110 against influenza A (H1N1) and (H3N2) subtype

| Test article | DAR | $IC_{50}$ [nM] A/PR/8/1934 (H1N1) | $IC_{50}$ [nM] A/Bethesda/956/2006 (H3N2) R292K |
|---|---|---|---|
| Oseltamivir | N/A | 5.276 | >1,000 |
| Zanamivir | N/A | 1.072 | 20.79 |
| Int-83 | N/A | 11.48 | 510.6 |
| Conjugate 45a | 0.4 | 23.61 | 78.79 |
| Conjugate 45a | 1 | 12.25 | 29.31 |
| Conjugate 45a | 3.3 | 2.772 | 4.166 |
| Conjugate 45a | 4.7 | 2.706 | 3.13 |

TABLE 173-continued

Summary IC$_{50}$ for Conjugate 110 against influenza
A (H1N1) and (H3N2) subtype

| Test article | DAR | IC$_{50}$ [nM] A/PR/8/1934 (H1N1) | IC$_{50}$ [nM] A/Bethesda/956/2006 (H3N2) R292K |
|---|---|---|---|
| Conjugate 45a | 5.1 | 3.259 | 3.583 |
| Conjugate 45a | 7.3 | 3.098 | 2.509 |

Example 200. Secondary Infection Mouse Models

Secondary Bacterial Infection Model with MRSA.

Efficacy studies were conducted in 6-8 week old female BALB/c mice (Charles River) challenged intranasally with 3E3 PFU/mouse (sub-lethal) of A/CA/07/2009 (H1N1)pdm (Virapur, Lot #E1020A1). Conjugate 45b or human IgG1 Fc controls was administered as a single subcutaneous (SC) dose 2 h post-challenge at 0.3-3 mg/kg. On day 6 post-infection, mice were challenged intranasally with sub-lethal dose of methicillin-resistant *Staphylococcus aureus* (MRSA) TCH1516 at 5E7 colony forming units (CFU) (FIG. 104).

For bacterial lung burden determination, mice were sacrificed by $CO_2$ and both lung lobes were harvested to determine bacterial burden at 24 h post-infection with MRSA. Lungs were homogenized with 1 mm silica beads in 1 mL PBS using a MagNA Lyser (Roche). Homogenization was carried out at 6,000 rpm for 60 s and chilled on ice for 5 min in-between runs. For CFU determination, lung homogenates were serially 10-fold diluted in PBS and plated onto LA plates. CFU were calculated relative to weight of the lung (CFU/g lung). For survival studies the general health status of animals was monitored and body weights (BW) recorded daily for 14 days. Moribund or animals exhibiting >20% of body weight (BW) loss, were recorded as a mortality. Survival, BW curves, and statistical analysis were performed with GraphPad Prism (version 6.07).

Conjugate 45b demonstrated protection against bacterial superinfection mouse model with sub-lethal challenge of influenza A/CA/07/2009 (H1N1)pdm followed by sub-lethal infection with MRSA. Cumulatively, the two sublethal infections resulted in 100% mortality in mice that were treated with hIgG1 Fc (FIG. 105A). Conjugate 45b treatment at 0.3 or 3 mg/kg—to prevent disease with influenza—resulted in 100% survival of mice. Conjugate 45b demonstrated reduction of bacterial burden in the lung as compared to hIgG1 Fc at 24 h after challenge with MRSA (FIG. 105B). The bacterial burden following conjugate 45b treatment was comparable to the burden observed in mice that were only challenged with MRSA.

These data demonstrate the potential for conjugate 45b in mitigating complications from infection with influenza such as *S. aureus* superinfection that contribute to mortality associated with influenza infection.

Secondary Bacterial Infection Model with *Streptococcus pneumoniae*

Efficacy studies were conducted in 6-8 week old female BALB/c mice (Charles River) challenged intranasally with 3E1 PFU/mouse (sub-lethal) of A/CA/07/2009 (H1N1)pdm (Virapur, Lot #1512B4) (FIG. 106). Conjugate 45b or human IgG1 Fc controls was administered as a single subcutaneously (SC) dose 2 h post-challenge at 0.3 mg/kg. On day 6 post-infection, mice were challenged intranasally with sub-lethal dose of *Streptococcus pneumoniae* (SPN) strain 6301 at 1 E5 CFU. The general health of animals was monitored and BW recorded daily for 14 days. Moribund, or animals exhibiting >20% or more of BW loss, were recorded as a mortality. Survival, BW curves, and statistical analysis were performed with GraphPad Prism (version 6.07).

Conjugate 45b demonstrated protection against bacterial superinfection mouse model with sub-lethal challenge of influenza A/CA/07/2009 (H1N1)pdm followed by sub-lethal infection with SPN. Cumulatively, the two sublethal infections resulted in 100% death in mice that were treated with hIgG1 Fc. Conjugate 45b treatment at 0.3 mg/kg—to prevent disease with influenza—resulted in 100% survival of mice demonstrating the potential for conjugate 45b in mitigating complications from infection with influenza against the most common cause of bacterial superinfection, *S. pneumoniae* (FIG. 107). Bacterial superinfection significantly contributes to mortality associated with influenza.

Example 201. Dosing Optimization Study for Conjugate 45a Treatment of an A/Vietnam/1203/2004 (H5N1) Virus Infection in BALB/c Mice Female 18-20 g BALB/c mice were obtained from Charles River Laboratories (Wilmington, Mass.) for this experiment. The mice were quarantined for 6 days before use and maintained on Teklad Rodent Diet (Harlan Teklad) and tap water at the Laboratory Animal Research Center of Utah State University.

Highly pathogenic avian influenza A/Vietnam/1203/2004 (H5N1), was obtained from the Centers for Disease Control (Atlanta, Ga.). Viral propagation was done in Madin-Darby canine kidney (MDCK) cells (American Type Culture Collection, Manassas, Va.). Parent virus was passaged once to prepare a challenge pool. The challenge pool was then titrated in MDCK cells before use.

Animal numbers and study groups are described in Table 174. Groups of mice were treated by the sub-cutaneous (sc) injection with 0.3, 1, 3, and 10 mg/kg doses of conjugate 45a on a single occasion, either 7 days before virus infection, or 4 hours after virus infection. Oseltamivir (10 mg/kg), used as a positive control for the virus challenge dose, was administered by oral gavage twice daily, beginning 4 hours post-infection. Unconjugated Fc, used as placebo, was administered in a similar manner to conjugate 45a. In addition, three non-treated control mice were maintained for weight comparison.

For influenza virus challenge, mice were anesthetized by i.p. injection of ketamine/xylazine (50 mg/kg/5 mg/kg) prior to challenge by the intranasal route with approximately 5 plaque forming units (1× $LD_{90}$) of virus per mouse in a 90 μm inoculum volume.

Mice were weighed prior to treatment and then every other day thereafter to assess the effects of treatment on ameliorating weight loss due to virus infection. All mice were observed for morbidity and mortality through day 21.

Kaplan-Meier survival curves were generated and compared by the Log-rank (Mantel-Cox) test followed by pairwise comparison using the Gehan-Breslow-Wilcoxon test in Prism 8.3 (GraphPad Software Inc.). Mean body weights were analyzed by one-way analysis of variance (ANOVA) followed by Tukey's multiple comparison tests using Prism 8.3.

TABLE 174

Dosing Optimization Study for Efficacy

| No./Cage | Group No. | Infected Y or N | Compound | Dosage | Treatment Schedule | Observations/Testing |
|---|---|---|---|---|---|---|
| 10 | 1 | Yes | conjugate 45a | 10 mg/kg | Once, 7 days pre-infection | Observed for weight loss and mortality through day 21 |
| 10 | 3 | Yes | conjugate 45a | 3 mg/kg | | |
| 10 | 5 | Yes | conjugate 45a | 1 mg/kg | | |
| 10 | 7 | Yes | conjugate 45a | 0.3 mg/kg | | |
| 10 | 9 | Yes | Placebo (unconjugated Fc, SEQ ID NO: 72) | — | Once, 4 h post-infection | |
| 10 | 11 | Yes | conjugate 45a | 10 mg/kg | | |
| 10 | 13 | Yes | conjugate 45a | 3 mg/kg | | |
| 10 | 15 | Yes | conjugate 45a | 1 mg/kg | | |
| 10 | 17 | Yes | conjugate 45a | 0.3 mg/kg | | |
| 10 | 19 | Yes | Oseltamivir | 30 mg/kg/day | b.i.d. × 5 d, beg 4 h post-infection | |
| 3 | 2 | No | Untreated mice observed for normal weight gain | | | |

Following treatment with conjugate 45a at 7 days before virus infection, 100% protection was observed for the 10 mg/kg dose, 80% protection for the 0.3 and 3 mg/kg doses, and 70% protection for the 1 mg/kg dose (FIG. 108A). 30% survival in the placebo group is unusual, so the 1 mg/kg dose did not provide significant protection. In addition, all doses provided significant protection from weight loss (FIG. 108B).

Following treatment with conjugate 45a at 4 hours after virus infection, 100% protection was observed for the 1, 3, and 10 mg/kg doses, and 70% protection for the 0.3 mg/kg dose (FIG. 109A). Due to the 30% survival observed in the placebo group, the 0.3 mg/kg dose did not provide significant protection. In addition, all doses provided significant protection from weight loss (FIG. 109B).

Example 202. Enzyme-Linked Lectin Assay (ELLA)

The ELLA assay was conducted as reported in Gao et al. (*J. Vis. Exp*. Doi:10.3791/54573, 2016) with minor modifications. Briefly, Nunc Maxisorp 96-well plates (ThermoFisher) were coated with 2.5 μg fetuin (Sigma-Aldrich) in 1×KPL coating buffer (SeraCare) overnight at 4° C. The next day, plates were washed with PBS at pH 7.4 supplemented with 0.05% Tween 20 (PBST). Test articles were tested at 0.001-1000 nM and added in 50 μL/well. Influenza virus was added at 1 e5-1e6 PFU/well in 50 μL/well. Plates were incubated for 16-18 h at 37° C., 5% $CO_2$. After washing plates, peanut agglutinin conjugated to HRP (PNA-HRP) at 0.13 μg for 2 h, washed again and developed with 100 μL/well TMB substrate (BD) for 3-5 min. The reaction was stopped with 100 μL/well 1 N $H_2SO_4$. Absorbance was read at 450 nm with an EnSpire multimode plate reader. $IC_{50}$ was calculated with GraphPad Prism version 8 using non-linear regression analysis (Dose-response (Inhibition)).

Conjugate 45b demonstrated increased potency as compared to oseltamivir or zanamivir in ELLA with $IC_{50}$ between against representative influenza A and B strains (Table 175).

TABLE 175

Activity of conjugate 45b in enzyme-linked lectin assay (ELLA) against influenza A and B ($IC_{50}$)

| Influenza Strain | Subtype/lineage | Conjugate 45b [nM] | hIgG1 Fc [nM] | Oseltamivir [nM] | Zanamivir [nM] |
|---|---|---|---|---|---|
| A/PR/8/1934 | H1N1 | 0.11 | >1,000 | 25.4 | 3.8 |
| A/CA/7/2009 | H1N1pdm | 0.02 | >1,000 | 0.99 | 0.09 |
| A/Hong Kong/1/1968 | H3N2 | 0.003 | >1,000 | 0.07 | 0.24 |
| B/Florida/4/2006 | Yamagata | 0.02 | >1,000 | 1.00 | 0.09 |
| B/Malaysia/2506/2004 | Victoria | 0.15 | >1,000 | 3.2 | 9.3 |

Example 203. Conjugate 45b Attributes that Allow for Potential Multivalent Binding to Influenza Virus Neuraminidase Conjugate 45b comprises a chemically and biologically stable conjugate of Int-83 with an N-terminally extended hIgG1 Fc domain (SEQ ID NO: 73). As shown in FIG. 110B, Int-83 includes zanamivir dimers that are symmetrically fused through methyl carbamate moieties on the C7-hydroxyl of zanamivir to a flexible 15 Å central-linker that spaces the zanamivir monomers by approximately 18 Å. Multiple copies of the Int-83 are conjugated to surface exposed lysine residues on the Fc domain through a 32-atom flexible polyethylene glycol (PEG)-based cross-linker, which projects them out from the surface of the Fc by 35-40 Å when the linker is fully extended (FIG. 1101B). Specific solvent-exposed lysine residues were sites for conjugation (FIG. 110B). The average ratio of Int-83 to Fc used in Conjugate 45b was 4.5:1. Synthesis of conjugate 45b is described in Example 156. The spatial distribution of preferred sites for conjugation (FIG. 110B) coupled with the length and flexibility of the cross-linker allow, in principle, for conjugate 45b to simultaneously interact with multiple NA active sites within a tetramer (ca. or 70 Å, respectively, FIG. 110A). Additionally, the spacing of Int-83 in conjugate 45b allows for bridging of NA active sites across neighboring NA tetramers on the same virion (25-30 Å), or across two virions (16 Å).

Universal Activity, and Low Resistance Potential of Conjugate 45b In Vitro

We investigated the intrinsic antiviral activity of conjugate 45b in the absence of immune engagement using a standard neuraminidase inhibition (NAI) assay that employs a small molecule substrate. Conjugate 45b demonstrated potent activity against influenza A and B with median $IC_{50}$ of 1.7 nM against influenza A H1N1 strains (n=7, ranging from 1.1 nM to 4.8 nM), 4.2 nM against influenza A H3N2 strains (n=6, ranging from 0.3 nM to 14.9 nM) and 4.4 nM against influenza B strains (n=6, ranging from 1.0 nM to 20.7 nM), respectively (Table 176). In general, conjugate 45b performed similarly to zanamivir and oseltamivir, but was more potent than oseltamivir versus influenza B strains (Table 176). Importantly, conjugate 45b $IC_{50}$s did not shift against clinically relevant variants with reduced susceptibility to approved neuraminidase inhibitors. The activity of conjugate 45b was 1.7 nM against H275Y in H1N1 subtype, 2.6 nM E119V, 1.2 nM $R_{292}K$ in H3N2 subtype or 6.7 nM $R_{152}K$ in B type. Oseltamivir or zanamivir lost up to >100-fold or >10-fold in potency, respectively, against these variants (Table 177). Conjugate 45b retained potent activity against cell lysates from H5N1 and H7N9 viruses, with $IC_{50}$s of 1.9 nM and 1.2 nM, respectively (Table 178). Oseltamivir and zanamivir had comparable activity versus H5N1, but oseltamivir and zanamivir lost activity against H7N9 with $IC_{50}$s of >1 μM or >100 nM, respectively (Table 178).

Next, we tested the activity of conjugate 45b in an enzyme-linked lectin assay (ELLA) in which a large glycoprotein is used as the substrate. The presentation of sialic acid (Sia) in the ELLA assay is more similar to NA substrate presentation on the surface of a cell. As a result, access to the substrate is more limited and NA activity in the ELLA assay has been shown to be influenced by factors that block access to the NA active site (Chen Y. Q., et al., *J. Virol.* 93: doi.1i0.1128/JVI.01526-18, 2019). Interestingly, compared with the NA inhibition results using a small molecule substrate as described above, the activity of conjugate 45b was enhanced (>1 Ox) versus zanamivir and oseltamivir against influenza A/PR/8/1934 (H1N1) (Table 179). With conjugate 45b, steric hindrance of adjacent intra- or inter-NA tetramer NA active sites by the Fc domain, or multivalent target engagement causing viral aggregation may have contributed to the enhancements in potency observed in the ELLA assay.

TABLE 176

Universal, broad-spectrum activity of conjugate 45b against influenza A (H1N1), (H3N2) and B (Yamagata and Victoria lineage) in neuraminidase inhibition (median $IC_{50}$) and cell-based cytopathic effect assay (median $EC_{50}$).

| Molecule | type/subtype | $IC_{50}$ [nM] | $EC_{50}$ [nM] |
|---|---|---|---|
| Conjugate 45b | A (H1N1) | 1.7 | 1.9 |
| | A (H3N2) | 4.2 | 0.9 |
| | B | 4.4 | 7.4 |
| Oseltamivir | A (H1N1) | 2.2 | 2414 |
| | A (H3N2) | 0.4 | 8185 |
| | B | 37.7 | 758.5 |
| Zanamivir | A (H1N1) | 1.0 | 1093 |
| | A (H3N2) | 1.3 | >10,000 |
| | B | 6.3 | 80.2 |

TABLE 177

Activity of conjugate 45b against variants with reduced susceptibility in neuraminidase inhibition ($IC_{50}$)

| Live influenza strain | Variant | subtype/ lineage | Conjugate 45b [nM] | Oseltamivir [nM] | Zanamivir [nM] |
|---|---|---|---|---|---|
| A/Texas/ 23/2012 | H275Y | H1N1pdm09 | 1.7 | 507.1 | 1.1 |
| A/Texas/ 12/2007 | E119V | H3N2 | 2.6 | 148.9 | 3.8 |
| A/Bethesda/ 956/2006 | R292K | H3N2 | 1.2 | >1000 | 22.18 |
| B/Memphis/ 20/1996 | R152K | Yamagata | 6.7 | >1000 | 125.5 |

TABLE 178

Activity of conjugate 45b against cell lysate from influenza A H5N1 and H7N9 in neuraminidase inhibition ($IC_{50}$)

| NA cell lysate from | subtype/ lineage | Conjugate 45b [nM] | Oseltamivir [nM] | Zanamivir [nM] |
|---|---|---|---|---|
| A/Anhui/1/2005 | H5N1 | 1.9 | 3.7 | 0.6 |
| A/Shanghai/1/2013 | H7N9 | 1.2 | >1,000 | 100.4 |

TABLE 179

Broad-spectrum activity of conjugate 45b against influenza A and B in CPE ($EC_{50}$).

| Influenza strain | subtype/ lineage | Conjugate 45b [nM] | Oseltamivir [nM] | Zanamivir [nM] |
|---|---|---|---|---|
| A/WSN/1933 | H1N1 | 0.2059 | 51.36 | 29.12 |
| A/PR/8/1934 | H1N1 | 0.782 | 1461 | 7581 |
| A/PR/8/1934 (mouse-adapted) | H1N1 | 32.49 | >10,000 | not tested |
| A/CA/7/2009 | H1N1pdm | 2.964 | 34.2 | 33.16 |
| A/CA/12/2012 | H1N1pdm09 | 0.4931 | >10,000 | 1093 |
| A/Texas/23/2012 H275Y | H1N1pdm09 | 2.886 | >10,000 | >10,000 |
| A/Illinois/08/ 2018 | H1N1pdm09 | 9.584 | 3366 | 4278 |
| A/Illinois/37/ 2018 I38L | H1N1pdm09 | 0.4304 | 200.4 | 179.1 |
| A/Illinois/08/ 2018 I38T | H1N1pdm09 | 1.35 | >10,000 | >10,000 |
| A/Hong Kong/ 1/1968 (mouse-adapted) | H3N2 | 36.57 | 6369 | not tested |
| A/Texas/71/2017 | H3N2 | 0.3748 | >10,000 | >10,000 |
| A/Washington/ 01/2007 | H3N2 | 0.04449 | 1.908 | 1.968 |
| A/Texas/12/ 2007 E119V | H3N2 | 0.6594 | 351.4 | 2.096 |
| A/Louisiana/ 50/2017 | H3N2 | 1.41 | >10,000 | >10,000 |
| A/Louisiana/49/ 2017 I38M | H3N2 | 0.606 | >10,000 | 4815 |
| A/Bethesda/956/ 2006 R292K | H3N2 | 20.1 | 1653 | 558.1 |
| B/Florida/4/2006 | Yamagata | 12.8 | 1030 | 76.89 |
| B/Brisbane/ 60/2008 | Victoria | 6.288 | 487 | 254.2 |
| B/Malaysia/ 2506/2004 | Victoria | 1.512 | 471.2 | 83.52 |
| B/Colorado/ 6/2017 | Victoria | 8.485 | 4480 | 56.98 |

Even greater discrimination between conjugate 45b and zanamivir and oseltamivir was observed in cell-based cytopathic effect (CPE) assays. Conjugate 45b demonstrated potent activity against influenza A and B types with median $EC_{50}$s of 1.3 nM for influenza A H1N1 strains (n=6, ranging from 0.43 nM to 32.4 nM), 0.9 nM for influenza A H3N2 strains (n=4, ranging from 0.04 nM to 36.6 nM) and 7.4 nM for influenza B strains (n=4, ranging from 1.5 nM to 12.8 nM), respectively in MOCK SIAT1 or for mouse-adapted influenza strains in MOCK cells (Table 179). Notably, conjugate 45b was 3 logs more active than oseltamivir and zanamivir against some of the influenza strains tested (Table 176). When conjugate 45b was tested against high-pathogenicity strains in cell-based microneutralization assays, $EC_{50}$s for conjugate 45b were 1.7 nM versus H5N1 strains (n=4) and 5.3 nM versus an H7N9 strain (n=1) (Table 180). The $CC_{50}$ for conjugate 45b in MDCK-SIAT1 or MOCK cells was >10,000 nM (data not shown). Therefore, the calculated selectivity index (SI) for conjugate 45b in cell-based assay was >1,000× for influenza A and B types.

TABLE 180

Broad-spectrum activity of conjugate 45b against high-pathogenic influenza A (H5N1) and (H7N9) in microneutralization ($IC_{50}$).

| Influenza strain | subtype/ lineage | Conjugate 45b [nM] | Oseltamivir [nM] | Zanamivir [nM] |
| --- | --- | --- | --- | --- |
| A/Vietnam/1194/2004 | H5N1 | 1.7 | 168.7 | 16.9 |
| A/Indonesia/05/2005 | H5N1 | 1.7 | >300 | 16.9 |
| A/turkey/Turkey/1/2005 | H5N1 | 1.7 | 168.7 | 5.3 |
| A/Hong Kong/156/97 | H5N1 | 1.7 | >300 | 53.3 |
| A/Anhui/1/2013 | H7N9 | 5.3 | >300 | >300 |
| A/Netherlands/602/2009* | H1N1pdm09 | 1.7 | >300 | >300 |

*Pandemic control influenza A strain

In addition to CPE assays, serial passage experiments were conducted using MDCK cells infected with influenza A/CA/07/2009 (H1N1)pdm to compare the resistance potential of conjugate 45b to the two commercially dominant influenza antivirals, oseltamivir and baloxivir. Conjugate 45b had a superior resistance profile to both comparators and demonstrated no reduction in antiviral activity throughout the 10 passage of the experiment. Baloxivir and oseltamivir antiviral activity was reduced to that of the drug free control after 6 and 8 passages, respectively. Sequencing of the viral genomes from drug-resistant viral plaques in the later oseltamivir passages showed that resistance was conferred by an NA active-site mutation (E 119K) that has been observed in the clinic (REF).

Immune Cell Engagement by Conjugate 45b

Human IgG1 Fc domain was selected as the protein carrier for conjugate 45b, because it is the most activating human antibody IgG isotype with the longest circulating half-life. Despite utilizing a heterogeneous lysine conjugation strategy with conjugate 45b, we observed similar Fcγ receptor binding to all human and murine Fcγ receptors tested with conjugate 45b compared to the unconjugated Fc control and human IgG1 (FIGS. 111A-111H). In functional assays, conjugate 45b induced potent antibody-dependent cellular cytotoxicity (ADCC) in MOI (FIG. 111I) and dose-dependency against influenza A/PR/8/1934 (H1N1) infected MDCK Slat1 cells (FIG. 111J). Thus, conjugate 45b can bind to Fcγ receptors and functionally engage immune cells.

Conjugate 45b is Highly Effective in Multiple Lethal Influenza Challenge Models

The potency and antiviral spectrum of conjugate 45b observed in vitro translated to efficacy in animal infection models. Single, 0.3 mg/kg or lower subcutaneous (SC) doses of conjugate 45b were fully protective in lethal mouse challenge models against A/CA/07/2009 (H1N1)pdm, A/WSN/1933 (H1N1), A/CA/12/2012 (H1 Ni)pdm09, A/Texas/23/2012 (H1 Ni)pdm09 H275Y variant, A/Hong Kong/1/1968 (H3N2), B/Florida/4/2006 (Yamagata) and B/Malaysia/2506/2004 (Victoria) (FIGS. 112A-112H). Treatment with conjugate 45b often resulted in only limited, transient body weight loss following minimal protective dose (FIGS. 113A-113H). When tested against the avian pandemic strain A/Vietnam/1203/2004 (H5N1) in mice, conjugate 45b demonstrated 70% protection at 0.3 mg/kg and 100% protection at 1 mg/kg or higher (FIG. 112I). Oseltamivir at 6× the humanized dose in mice was only 90% protective (FIG. 112I).

To better quantify conjugate 45b efficacy, and to compare its performance with oseltamivir, viral load and cytokine levels in lung were measured 4 days post-infection following a lethal challenge model with mouse-adapted influenza A/PR/8/1934 (H1N1). In this model, the minimal protective dose of conjugate 45b was 0.1 mg/kg (SC) (FIG. 112A) and was accompanied by transient body-weight (BW) loss of ca. 5% (FIG. 113A). Conjugate 45b demonstrated dose-dependent reduction in lung viral burden (PFU/g in lung tissue) of 1.06 logs at 0.1 mg/kg, 2.12 logs 0.3 mg/kg and 3.17 logs at 1 mg/kg and 3.63 logs at 3 mg/kg as determined by plaque assay. By comparison, oseltamivir dosed at the human equivalent (5 mg/kg) dose (BID x 4 days) or at 10× the human equivalent dose (50 mg/kg) (BID×4 days) showed no dose response, and resulted in moderate viral load reductions of ca. 0.8 log. Interestingly, the two oseltamivir doses tested led to different survival outcomes. Oseltamivir at 5 mg/kg or 50 mg/kg dosed for 5 days BID resulted in 0% survival or 80%, respectively (FIGS. 114A-114B).

To understand the effectiveness of conjugate 45b in reducing a potentially harmful immune response that could lead to lung damage, levels of specific inflammatory and lung injury cytokines were measured at the same time point. Conjugate 45b effectively reduced levels in a dose-dependent manner, with all cytokines measured approaching levels similar to uninfected controls at the 3 mg/kg dose (FIGS. 112K-112L and FIGS. 115A-115C. Overall, the magnitude of cytokine reduction induced by conjugate 45b was more pronounced than afforded by treatment with the human equivalent dose of oseltamivir for all cytokines tested and was superior for KC, MIP-1a, MCP-1 when compared to mice treated at 10× human equivalent dose of oseltamivir (FIGS. 112K-112L and FIGS. 115A-115C). These data demonstrate that conjugate 45b induces potent, dose-dependent reduction in viral burden that correlated with reductions in cytokine levels in the lung by conjugate 45b that was not observed with oseltamivir.

The impact of dosing route on efficacy was evaluated for conjugate 45b. In a lethal challenge model using mice against A/CA/07/2009 (H1N1)pdm, conjugate 45b was fully protective at 0.1 mg/kg following intravenous (IV), intramuscular (IM) or SC administration (FIGS. 116A-116B). When comparing plasma levels in mice following IV, IM or SC dosing, the plasma levels of conjugate 45b were comparable after 24 h as determined by an enzyme-linked immunosorbent (ELISA) assay. Of note, two different ELISA capture methods were used to measure conjugate 45b levels in plasma—one that utilized an anti-human Fc capture antibody to measure Fc levels, and one that utilized viral NA for capture to detect intact conjugate (FIGS. 116C-116D). The plasma levels of conjugate 45b measured by both methods were identical within experimental error, demonstrating that conjugate 45b is a stable as an intact conjugate in vivo.

Conjugate 45b is Highly Effective in Immune-Compromised Hosts

High-risk groups for severe infections with influenza and complications from influenza infection include the elderly and immune-compromised. To determine the effectiveness of conjugate 45b in an immune-compromised background, we determined the efficacy of conjugate 45b in severely combined immune-deficiency (SCID) mice, which lack mature T-cells and B-cells and are complement-deficient. Conjugate 45b demonstrated full protection with single 0.3 mg/kg dose in SCID mice infected with A/CA/07/2009 (H1N1)pdm (FIG. 112M), which is the same protective dose for immune-competent mice.

Taken together, these results highlight the potential of conjugate 45b to provide universal influenza protection in healthy and high-risk populations.

Conjugate 45b Demonstrates a Long-Duration of Action in Prevention Models

Pharmacokinetic (PK) profiling, prophylactic efficacy and preclinical toxicology studies further highlight the potential for use of conjugate 45b as a durable, long-acting agent for universal influenza prevention. The half-life of conjugate 45b was determined after a single IV administration in mouse and cynomolgus monkey and ranges from 5-10 days in 1- and 4-week PK studies, respectively. These results are typical for mABs and is supported by comparable binding curves of conjugate 45b, hIgG1 Fc and full-length human IgG1 isotype control antibody to murine, cynomolgus monkey, and human FcRn in pH-dependency (FIGS. 117A-117C). Conjugate 45b exhibits dose-linear PK in mice across a wide dose range from 1-100 mg/kg (FIG. 118A). In mouse model, conjugate 45b establishes a rapid equilibrium between plasma and lung, allowing for a rapid onset of action for treatment indications, and distributes to epithelial lining fluid (ELF) at high levels (FIG. 118B). High levels of conjugate 45b in ELF appeared rapidly and were sustained at ca. 60% of plasma levels (FIG. 118B).

To assess conjugate 45b efficacy in a prevention setting, and determine target plasma levels necessary for protection in lethal influenza challenge models, mice were dosed 28 days prior to infection. A single SC dose of 1 mg/kg conferred full protection against influenza A/CA/07/2009 (H1N1)pdm, A/HK/1/1968 (H3N2), B/Malaysia/2506/2004 (Victoria) and B/Florida/4/2006 (Yamagata) (FIGS. 118C-118F). The corresponding conjugate 45b plasma level necessary for protection, measured at the time of infection, was 0.5 µg/mL (8 nM, data not shown). Multi-species PK and the target plasma level of conjugate 45b required for protection will be used to estimate human doses necessary for long-term prevention in humans, and was used to estimate therapeutic margins for conjugate 45b in preclinical toxicology studies. In a two-week dose-range finding toxicity study conducted in cynomolgus monkeys no adverse events were observed at highest dose tested (20 mg/kg). The therapeutic index (TI) based on plasma exposure ratios in the 20 mg/kg dosed monkeys and the 1 mg/kg dosed mice is >50 (Tables 181 and 182). This safety margin, coupled with allometric scaling incorporating the high potency and sustained exposures of conjugate 45b (data not shown), suggest that one to two doses, protection for an entire influenza season with conjugate 45b is achievable in humans.

TABLE 181

Dose-proportionality of conjugate 45b in mice

| Test article | Dose [mg/kg] | $T_{max}$ [h] | $C_{max}$ [µg/mL] | AUC [h × µg/mL] |
| --- | --- | --- | --- | --- |
| Conjugate 45b | 1 | 4 | 9.39 | 436 |
| | 3 | 24 | 11.4 | 1520 |
| | 10 | 24 | 41.3 | 4280 |
| | 30 | 24 | 125 | 14200 |
| | 100 | 4 | 733 | 60700 |

TABLE 182

Dose-proportionality of conjugate 45b in cynomolgus monkeys

| Test article | Day | Dose [mg/kg] | $T_{max}$ [h] | $C_{max}$ [µg/mL] | AUC [h × µg/mL] |
| --- | --- | --- | --- | --- | --- |
| Conjugate 45b | 1 | 5 | 72 | 26.1 | 3800 |
| | 8 | 5 | 8 | 61 | 7740 |
| | 1 | 20 | 72 | 107 | 14600 |
| | 8 | 20 | 24 | 197 | 25400 |

In the cynomolgus monkey toxicology study, following 2 weekly SC doses at 5 or 20 mg/kg, no adverse effect on BW, clinical chemistry, hematology, coagulation, cytokines, or urinalysis were observed (data not shown).

Example 204. Determination of Optimal Drug-to-Antibody Ratio (DAR) of Conjugate 45a Against Influenza A (H1N1) in a Lethal Mouse Influenza Model DAR variants of Conjugate 45a were evaluated in a lethal H1N1 influenza infection model in female BALB/c mice (Charles River Laboratories, 6-8 weeks). The challenge virus (A/Puerto Rico/8/1934) is a mouse-adapted isolate capable of causing lethal infections in mice. The experiment comprised 2 study arms with a total of 25 groups of 5 mice. At day 0, all mice were challenged with virus at 3× the $LD_{95}$ (~2E4 virus/mouse) by intranasal inoculation in a volume of 30 µl after being lightly anesthetized with ketamine/xylazine (100 and 10 mg/kg respectively). Groups received a single treatment of conjugate 45a, DAR variant of conjugate 45a, Fc only, or vehicle (PBS), 2 hours after viral challenge by intramuscular (IM) administration. Conjugate 45a variants were tested with average DARs of 0.4, 1.0, 3.3, 4.7, 5.1, or 7.3. Mortality and body weight (BW) were monitored daily for 14 days. Any mouse losing more than 20% BW was scored as a mortality. The experimental outline for each study arm is summarized in Tables 183 and 184.

TABLE 183

Low average DAR arm study design

| Group | Influenza A strain (IN challenge) | Test Article | DAR | Route, Schedule | Dose (mg/kg) | Cmpd prep Dose volume ml/kg | Cmpd prep mg/ml | Cmpd prep Vol needed (ml) | N |
|---|---|---|---|---|---|---|---|---|---|
| 1 | A/PR/8/34 | Vehicle (PBS) | — | IM, single, T + 2 h | — | 5 | — | 1 | 5 |
| 2 | (H1N1) | Fc alone | — | IM, single, T + 2 h | 0.3 | 5 | 0.06 | 1 | 5 |
| 3 | 3E2 | Conjugate 45a | 0.4 | IM, single, T + 2 h | 0.3 | 5 | 0.06 | 1 | 5 |
| 4 | PFU/mouse | Conjugate 45a | 0.4 | IM, single, T + 2 h | 0.1 | 5 | 0.02 | 1 | 5 |
| 5 | | Conjugate 45a | 0.4 | IM, single, T + 2 h | 0.03 | 5 | 0.006 | 1 | 5 |
| 6 | | Conjugate 45a | 1 | IM, single, T + 2 h | 0.3 | 5 | 0.06 | 1 | 5 |
| 7 | | Conjugate 45a | 1 | IM, single, T + 2 h | 0.1 | 5 | 0.02 | 1 | 5 |
| 8 | | Conjugate 45a | 1 | IM, single, T + 2 h | 0.03 | 5 | 0.006 | 1 | 5 |
| 9 | | Conjugate 45a | 3.3 | IM, single, T + 2 h | 0.3 | 5 | 0.06 | 1 | 5 |
| 10 | | Conjugate 45a | 3.3 | IM, single, T + 2 h | 0.1 | 5 | 0.02 | 1 | 5 |
| 11 | | Conjugate 45a | 3.3 | IM, single, T + 2 h | 0.03 | 5 | 0.006 | 1 | 5 |
| 12 | | Conjugate 45a | 4.7 | IM, single, T + 2 h | 0.3 | 5 | 0.06 | 1 | 5 |
| 13 | | Conjugate 45a | 4.7 | IM, single, T + 2 h | 0.1 | 5 | 0.02 | 1 | 5 |
| 14 | | Conjugate 45a | 4.7 | IM, single, T + 2 h | 0.03 | 5 | 0.006 | 1 | 5 |

TABLE 184

High DAR arm study design

| Group | Influenza A strain (IN challenge) | Test Article | DAR | Route, Schedule | Dose (mg/kg) | Cmpd prep Dose volume ml/kg | Cmpd prep mg/ml | Cmpd prep Vol needed (ml) | N |
|---|---|---|---|---|---|---|---|---|---|
| 1 | A/PR/8/34 | Vehicle (PBS) | — | IM, single, T + 2 h | — | 5 | — | 1 | 5 |
| 2 | (H1N1) | Fc alone | — | IM, single, T + 2 h | 0.3 | 5 | 0.06 | 1 | 5 |
| 3 | 3E2 | Conjugate 45a | 4.7 | IM, single, T + 2 h | 0.3 | 5 | 0.06 | 1 | 5 |
| 4 | PFU/mouse | Conjugate 45a | 4.7 | IM, single, T + 2 h | 0.1 | 5 | 0.02 | 1 | 5 |
| 5 | | Conjugate 45a | 4.7 | IM, single, T + 2 h | 0.03 | 5 | 0.006 | 1 | 5 |
| 6 | | Conjugate 45a | 5.1 | IM, single, T + 2 h | 0.3 | 5 | 0.06 | 1 | 5 |
| 7 | | Conjugate 45a | 5.1 | IM, single, T + 2 h | 0.1 | 5 | 0.02 | 1 | 5 |
| 8 | | Conjugate 45a | 5.1 | IM, single, T + 2 h | 0.03 | 5 | 0.006 | 1 | 5 |
| 9 | | Conjugate 45a | 7.3 | IM, single, T + 2 h | 0.3 | 5 | 0.06 | 1 | 5 |
| 10 | | Conjugate 45a | 7.3 | IM, single, T + 2 h | 0.1 | 5 | 0.02 | 1 | 5 |
| 11 | | Conjugate 45a | 7.3 | IM, single, T + 2 h | 0.03 | 5 | 0.006 | 1 | 5 |

In the first study arm, variants with an average DAR of 0.4, 1.0, 3.3, or 4.7 were run at concentrations of 0.03, 0.1, and 0.3 mg/kg (single IM administration at T+2 h relative to viral challenge). In this study vehicle (PBS) treated mice succumbed to infection by Day 7, and those treated with Fc only (SEQ ID NO: 72) reached mortality on Day 6 (Table 185). In contrast, conjugate 45a variants with average DARs of 1.0, 3.3, and 4.7 were fully protected at the highest dose concentration (0.3 mg/kg). Only the 0.4 average DAR conjugate failed to offer protection, with mice reaching mortality by Day 9, indicating it had the lowest potency average DAR of the conjugates tested. At the next lowest conjugate dose (0.1 mg/kg) only mice treated with conjugates having an average DAR of 3.3 or 4.7 were fully protected. The two lower average DAR conjugates (0.4 and 1.0) reached mortality on Day 7 and 9, respectively, at this dose. In the final dose group (0.03 mg/kg) only the conjugate 45a variant with an average DAR of 4.7 demonstrated any potency (80% survival). Based on mortality data a clear trend was evident in this study arm, with increasing average DAR resulting in increasing potency.

BW data for arm 1 study groups supported the trends seen in the mortality data (Table 186). For example, in the 0.3 mg/kg dose groups, conjugate 45a variants with average DARs of 1.0, 3.3, and 4.7 were all protective based on mortality, but mice receiving the 1.0 average DAR variant had greater BW loss than the higher average DAR constructs. This resulted in the loss of protection by the 1.0 average DAR variant when the dose was lowered to 0.1 mg/kg. Similarly, at 0.1 mg/kg mice receiving the 3.3 average DAR variant were protected from lethal challenge based on mortality, but had greater BW loss than the animals treated with the 4.7 average DAR variant. By both study readouts (mortality and BW), greater potency was seen with increasing average DAR.

TABLE 185

Mortality data (% survival) for arm 1.

| | | | Average DAR | | | | | | | | | | |
|---|---|---|---|---|---|---|---|---|---|---|---|---|---|
| | | | 0.4 | | | 1.0 | | | 3.3 | | | 4.7 | | |
| Day post challenge | Vehicle (PBS) | Fc alone (0.3 mpk) | (0.3 mpk) | (0.1 mpk) | (0.03 mpk) | (0.3 mpk) | (0.1 mpk) | (0.03 mpk) | (0.3 mpk) | (0.1 mpk) | (0.03 mpk) | (0.3 mpk) | (0.1 mpk) | (0.03 mpk) |
| 0 | 100 | 100 | 100 | 100 | 100 | 100 | 100 | 100 | 100 | 100 | 100 | 100 | 100 | 100 |
| 1 | 100 | 100 | 100 | 100 | 100 | 100 | 100 | 100 | 100 | 100 | 100 | 100 | 100 | 100 |
| 2 | 100 | 100 | 100 | 100 | 100 | 100 | 100 | 100 | 100 | 100 | 100 | 100 | 100 | 100 |
| 3 | 100 | 100 | 100 | 100 | 100 | 100 | 100 | 100 | 100 | 100 | 100 | 100 | 100 | 100 |
| 4 | 100 | 100 | 100 | 100 | 100 | 100 | 100 | 100 | 100 | 100 | 100 | 100 | 100 | 100 |
| 5 | 80 | 100 | 100 | 100 | 100 | 100 | 100 | 100 | 100 | 100 | 100 | 100 | 100 | 100 |
| 6 | 40 | 0 | 100 | 60 | 80 | 100 | 100 | 80 | 100 | 100 | 100 | 100 | 100 | 100 |
| 7 | 0 | | 40 | 0 | 0 | 100 | 80 | 0 | 100 | 100 | 80 | 100 | 100 | 100 |
| 8 | | | 20 | | | 100 | 20 | | 100 | 100 | 60 | 100 | 100 | 100 |
| 9 | | | 0 | | | 100 | 0 | | 100 | 100 | 20 | 100 | 100 | 80 |
| 10 | | | | | | 100 | | | 100 | 100 | 0 | 100 | 100 | 80 |
| 11 | | | | | | 100 | | | 100 | 100 | | 100 | 100 | 80 |
| 12 | | | | | | 100 | | | 100 | 100 | | 100 | 100 | 80 |
| 13 | | | | | | 100 | | | 100 | 100 | | 100 | 100 | 80 |
| 14 | | | | | | 100 | | | 100 | 100 | | 100 | 100 | 80 |

TABLE 186

BW data for arm 1. Average group BW until the first death within a group.

| | | Fc alone | Average DAR | | | | | | | | | | | |
|---|---|---|---|---|---|---|---|---|---|---|---|---|---|---|
| | | | 0.4 | | | 1.0 | | | 3.3 | | | 4.7 | | |
| Day post challenge | Vehicle (PBS) | (0.3 mpk) | (0.3 mpk) | (0.1 mpk) | (0.03 mpk) | (0.3 mpk) | (0.1 mpk) | (0.03 mpk) | (0.3 mpk) | (0.1 mpk) | (0.03 mpk) | (0.3 mpk) | (0.1 mpk) | (0.03 mpk) |
| 0 | 100 | 100 | 100 | 100 | 100 | 100 | 100 | 100 | 100 | 100 | 100 | 100 | 100 | 100 |
| 1 | 96.9 | 98.8 | 98.2 | 97.9 | 97.7 | 98 | 97.6 | 97.9 | 97 | 97.1 | 99.9 | 97.7 | 97.8 | 99.8 |
| 2 | 100 | 101.9 | 101.2 | 100.3 | 99.8 | 99.9 | 99.6 | 100.9 | 101.8 | 99.2 | 102.9 | 102.4 | 100.9 | 100.7 |
| 3 | 93.1 | 93.4 | 96.8 | 95 | 98.3 | 96.3 | 96.6 | 94.3 | 100.1 | 97.7 | 98.1 | 101.3 | 98.2 | 99.4 |
| 4 | 83.6 | 83.3 | 89 | 84.7 | 88.1 | 91.6 | 88.8 | 86.3 | 99.7 | 93.9 | 92 | 100.9 | 95 | 97.2 |
| 5 | 79.9 | 80 | 86.3 | 81.8 | 84.2 | 95.6 | 89.1 | 82.9 | 101.1 | 96.3 | 91.8 | 100.4 | 97.4 | 98.9 |
| 6 | | | 81.8 | 76.9 | 77.5 | 95.7 | 84.5 | 77.4 | 102.3 | 96.6 | 88.8 | 103.5 | 99.9 | 97.5 |
| 7 | | | 76.8 | | | 91.4 | 78.9 | | 103.6 | 92.3 | 82.4 | 105 | 100.8 | 91.3 |
| 8 | | | | | | 95.7 | | | 104.5 | 92.9 | | 103.9 | 101.3 | 85.3 |
| 9 | | | | | | 97.2 | | | 104.2 | 96.4 | | 103.9 | 103.4 | 83.9 |
| 10 | | | | | | 98.5 | | | 105 | 98.2 | | 107.8 | 104.3 | |
| 11 | | | | | | 98.2 | | | 104.7 | 99.8 | | 106.8 | 103.5 | |
| 12 | | | | | | 98.9 | | | 105.1 | 102.9 | | 108.7 | 104.5 | |
| 13 | | | | | | 99.7 | | | 107.2 | 104.3 | | 110.5 | 106.1 | |
| 14 | | | | | | 99.9 | | | 105.8 | 103.6 | | 109 | 104.7 | |

In arm 2 of the study, conjugate 45a variants with average DARs of 4.7, 5.1, and 7.3 were evaluated at the same dose levels as arm 1 (0.3, 0.1, and 0.03 mg/kg). In contrast to the results seen in arm 1, increasing average DAR above 4.7 did not increase the potency of conjugate 45a. All three DAR variants were of approximate equal potency based on mortality and BW (Tables 187 and 188, respectively). Only slight differences were seen in these higher DAR constructs which were within the normal experimental error seen in efficacy models (note the slightly faster time to death for vehicle treated animals in arm 2). The later point includes the observation that the 4.7 average DAR conjugate was protective in the first arm at 0.03 mg/kg, but not in arm 2. Collectively the results of both study arms show a distinct increase in potency up to an average DAR of 4.7, but then further increases in average DAR do not translate into greater potency. Therefore, an average DAR of 4.7 is the minimum average DAR which achieves the maximum potency of conjugate 45a.

TABLE 187

Mortality data (% survival) for arm 2

| Day post challenge | Vehicle (PBS) | Fc Alone (0.3 mpk) | DAR 4.7 (0.3 mpk) | DAR 4.7 (0.1 mpk) | DAR 4.7 (0.03 mpk) | DAR 5.1 (0.3 mpk) | DAR 5.1 (0.1 mpk) | DAR 5.1 (0.03 mpk) | DAR 7.3 (0.3 mpk) | DAR 7.3 (0.1 mpk) | DAR 7.3 (0.03 mpk) |
|---|---|---|---|---|---|---|---|---|---|---|---|
| 0 | 100 | 100 | 100 | 100 | 100 | 100 | 100 | 100 | 100 | 100 | 100 |
| 1 | 100 | 100 | 100 | 100 | 100 | 100 | 100 | 100 | 100 | 100 | 100 |
| 2 | 100 | 100 | 100 | 100 | 100 | 100 | 100 | 100 | 100 | 100 | 100 |
| 3 | 100 | 100 | 100 | 100 | 100 | 100 | 100 | 100 | 100 | 100 | 100 |
| 4 | 100 | 100 | 100 | 100 | 100 | 100 | 100 | 100 | 100 | 100 | 100 |
| 5 | 40 | 100 | 100 | 100 | 100 | 100 | 100 | 100 | 100 | 100 | 100 |
| 6 | 0 | 40 | 100 | 100 | 100 | 100 | 100 | 100 | 100 | 100 | 100 |
| 7 |   | 0 | 100 | 100 | 60 | 100 | 100 | 80 | 100 | 100 | 100 |
| 8 |   |   | 100 | 100 | 60 | 100 | 100 | 40 | 100 | 100 | 80 |
| 9 |   |   | 100 | 100 | 40 | 100 | 100 | 20 | 100 | 100 | 40 |
| 10 |   |   | 100 | 100 | 0 | 100 | 80 | 0 | 100 | 100 | 0 |
| 11 |   |   | 100 | 100 |   | 100 | 80 |   | 100 | 100 |   |
| 12 |   |   | 100 | 100 |   | 100 | 80 |   | 100 | 100 |   |
| 13 |   |   | 100 | 100 |   | 100 | 80 |   | 100 | 100 |   |
| 14 |   |   | 100 | 100 |   | 100 | 80 |   | 100 | 100 |   |

TABLE 188

BW data for arm 2: Average group BW until the first death within a group

| Day post challenge | Vehicle (PBS) | Fc Alone (0.3 mpk) | DAR 4.7 (0.3 mpk) | DAR 4.7 (0.1 mpk) | DAR 4.7 (0.03 mpk) | DAR 5.1 (0.3 mpk) | DAR 5.1 (0.1 mpk) | DAR 5.1 (0.03 mpk) | DAR 7.3 (0.3 mpk) | DAR 7.3 (0.1 mpk) | DAR 7.3 (0.03 mpk) |
|---|---|---|---|---|---|---|---|---|---|---|---|
| 0 | 100 | 100 | 100 | 100 | 100 | 100 | 100 | 100 | 100 | 100 | 100 |
| 1 | 99.5 | 98.4 | 98.4 | 98.3 | 98.2 | 98.1 | 98.5 | 98.6 | 99.4 | 96.5 | 99.4 |
| 2 | 98.7 | 100.3 | 99.9 | 100.5 | 99.3 | 97.7 | 98.5 | 101.3 | 100.2 | 102 | 99.1 |
| 3 | 93.7 | 95.8 | 99.8 | 100.7 | 99.3 | 101.1 | 99.7 | 100.8 | 100.7 | 100.9 | 100.3 |
| 4 | 81 | 84.9 | 99.6 | 99 | 93.2 | 98 | 95.4 | 93.5 | 100.1 | 99.9 | 97.4 |
| 5 | 77.7 | 81.2 | 100 | 98.8 | 91.5 | 98.5 | 97.1 | 91 | 96.7 | 99.7 | 93.7 |
| 6 |   | 76.9 | 100 | 98.9 | 86 | 99.9 | 95.6 | 85.9 | 100.3 | 99.2 | 88.6 |
| 7 |   |   | 102.5 | 100.5 | 81.6 | 102 | 88.8 | 82.9 | 103.4 | 97.8 | 85.3 |
| 8 |   |   | 102.8 | 100.8 |   | 103.3 | 87.8 |   | 103.5 | 98.8 |   |
| 9 |   |   | 101.9 | 103.3 |   | 104.9 | 89.4 |   | 104.5 | 102.3 |   |
| 10 |   |   | 103.6 | 105.4 |   | 105.6 | 95.3 |   | 106.4 | 105 |   |
| 11 |   |   | 103.4 | 104 |   | 105.1 |   |   | 106.2 | 103.9 |   |
| 12 |   |   | 104 | 104 |   | 104.5 |   |   | 105.4 | 104.2 |   |
| 13 |   |   | 103.8 | 104 |   | 105.1 |   |   | 104.9 | 103.1 |   |
| 14 |   |   | 102.3 | 102.5 |   | 102.8 |   |   | 103.1 | 103.1 |   |

Example 205. Determination of Conjugate 45a Potency Against an Influenza A Pandemic Strain (A/California/12/2012; H1N1) in a Lethal Mouse Model Conjugate 45a was evaluated in a lethal H1N1 influenza infection model in female BALB/c mice (Charles River Laboratories, 6-8 weeks). The challenge virus (A/CA/12/2012) is a pandemic isolate capable of causing lethal infections in mice. The experiment was comprised of 7 groups, with 5 mice per group. At day 0, all mice were challenged with virus at 3× the $LD_{95}$ (3E4 virus/mouse) by intranasal inoculation in a volume of 30 µl after being lightly anesthetized with ketamine/xylazine(100 and 10 mg/kg respectively). Groups received a single treatment of conjugate 45a, hIgG1 Fc, or vehicle (PBS), 2 hours after viral challenge by intramuscular (IM) administration (right flank). Conjugate 45a was tested at concentrations of 3, 1, 0.3, 0.1, and 0.03 mg/kg. Mortality and body weight (BW) were monitored daily for 21 days. Any mouse losing more than 20% BW was scored as a mortality. The experimental outline is summarized in Table 189.

TABLE 189

Study outline

| Group | Test Article | Route/ Schedule | Dose (mg/ kg) | Dose volume (ml/kg) | mg/ml | Volume needed (ml) | N (balb/ c) |
|---|---|---|---|---|---|---|---|
| 1 | PBS | IM, T + 2 hrs | — | 5 | — | 1 | 5 |
| 2 | Fc alone | IM, T + 2 hrs | 3 | 5 | 0.6 | 1 | 5 |
| 3 | Conjugate | IM, T + 2 hrs | 3 | 5 | 0.6 | 1 | 5 |
| 4 | 45 a | IM, T + 2 hrs | 1 | 5 | 0.2 | 1 | 5 |
| 5 |  | IM, T + 2 hrs | 0.3 | 5 | 0.06 | 1 | 5 |
| 6 |  | IM, T + 2 hrs | 0.1 | 5 | 0.02 | 1 | 5 |
| 7 |  | IM, T + 2 hrs | 0.03 | 5 | 0.006 | 1 | 5 |

In this study a single IM administration of Conjugate 45a fully protected mice from lethal challenge by a pandemic seasonal (H1N1) influenza isolate at 0.3, 1, and 3 mg/kg (Table 190). Additionally, partial protection was seen (relative to vehicle) in the two lowest dose groups (0.1 and 0.03 mg/kg) with 60 and 20% survival, respectively. In contrast, vehicle treated animals succumbed to infection by Day 8, while hIgG1 Fc only treated animals reached 80% mortality. The potency of Conjugate 45a was also supported by BW data. Mice treated with fully protective doses (3, 1, and 0.3 mg/kg) displayed transient BW loss around Day 3-5, before steadily recovering BW through the end of the study (Day 21) (Table 191). Collectively this study demonstrated the potency of Conjugate 45a, by both mortality and BW readouts, against an important pandemic influenza isolate.

TABLE 190

Percent survival

| Day Post Challenge | Vehicle (PBS) | hIgG1 Fc (3 mpk) | Conjugate 45 a | | | | |
|---|---|---|---|---|---|---|---|
|  |  |  | (3 mpk) | (1 mpk) | (0.3 mpk) | (0.1 mpk) | (0.03 mpk) |
| 0 | 100 | 100 | 100 | 100 | 100 | 100 | 100 |
| 1 | 100 | 100 | 100 | 100 | 100 | 100 | 100 |
| 2 | 100 | 100 | 100 | 100 | 100 | 100 | 100 |
| 3 | 100 | 100 | 100 | 100 | 100 | 100 | 100 |
| 4 | 100 | 100 | 100 | 100 | 100 | 100 | 100 |
| 5 | 40 | 60 | 100 | 100 | 100 | 60 | 20 |
| 6 | 20 | 20 | 100 | 100 | 100 | 60 | 20 |
| 7 | 20 | 20 | 100 | 100 | 100 | 60 | 20 |
| 8 | 0 | 20 | 100 | 100 | 100 | 60 | 20 |
| 9 |  | 20 | 100 | 100 | 100 | 60 | 20 |
| 10 |  | 20 | 100 | 100 | 100 | 60 | 20 |
| 11 |  | 20 | 100 | 100 | 100 | 60 | 20 |
| 12 |  | 20 | 100 | 100 | 100 | 60 | 20 |
| 13 |  | 20 | 100 | 100 | 100 | 60 | 20 |
| 14 |  | 20 | 100 | 100 | 100 | 60 | 20 |
| 15 |  | 20 | 100 | 100 | 100 | 60 | 20 |
| 16 |  | 20 | 100 | 100 | 100 | 60 | 20 |
| 17 |  | 20 | 100 | 100 | 100 | 60 | 20 |
| 18 |  | 20 | 100 | 100 | 100 | 60 | 20 |
| 19 |  | 20 | 100 | 100 | 100 | 60 | 20 |
| 20 |  | 20 | 100 | 100 | 100 | 60 | 20 |
| 21 |  | 20 | 100 | 100 | 100 | 60 | 20 |

TABLE 191

Average body weight loss (%), until first death within a group

| Day Post Challenge | Vehicle (PBS) | hIgG1 Fc (3 mpk) | Conjugate 45 a | | | | |
|---|---|---|---|---|---|---|---|
|  |  |  | (3 mpk) | (1 mpk) | (0.3 mpk) | (0.1 mpk) | (0.03 mpk) |
| 0 | 100 | 100 | 100 | 100 | 100 | 100 | 100 |
| 1 | 97.8 | 99 | 96.8 | 97.9 | 97.1 | 99.8 | 98.4 |
| 2 | 91.6 | 92 | 96 | 93.8 | 91.8 | 90.8 | 91 |
| 3 | 84.5 | 86.9 | 93.5 | 92.2 | 87.1 | 84.7 | 84.3 |
| 4 | 80.4 | 82.5 | 95.8 | 92.3 | 88.1 | 80.1 | 80.3 |
| 5 | 76.5 | 77.6 | 95.2 | 90.6 | 86.9 | 78.2 | 76.6 |
| 6 |  |  | 98.2 | 94.5 | 89.7 |  |  |
| 7 |  |  | 97.7 | 92.8 | 89.9 |  |  |
| 8 |  |  | 98.6 | 94.1 | 91.4 |  |  |
| 9 |  |  | 98.3 | 96.8 | 92.7 |  |  |
| 10 |  |  | 99.7 | 98.2 | 95 |  |  |
| 11 |  |  | 102.8 | 100.3 | 98.7 |  |  |
| 12 |  |  | 99.6 | 99 | 96.2 |  |  |
| 13 |  |  | 101.4 | 101.8 | 97.5 |  |  |
| 14 |  |  | 101.5 | 100.8 | 96.4 |  |  |
| 15 |  |  | 100.8 | 99.1 | 96.6 |  |  |
| 16 |  |  | 100.4 | 101.4 | 97.7 |  |  |
| 17 |  |  | 102.7 | 103.9 | 100.1 |  |  |
| 18 |  |  | 102.4 | 102.5 | 98.6 |  |  |
| 19 |  |  | 103.9 | 103.9 | 100.9 |  |  |
| 20 |  |  | 104.6 | 104.1 | 100.3 |  |  |
| 21 |  |  | 104 | 103.9 | 99.5 |  |  |

Example 206. Efficacy of Conjugate 45b in Combination with Baloxavir Against Influenza A (H1N1) in a Lethal Mouse Influenza Model Conjugate 45b was evaluated against a lethal IAV H1N1 influenza infection in female BALB/c mice (Charles River Laboratories, 6-8 weeks). The challenge virus (A/California/ 07/2009) is a pandemic isolate capable of causing lethal infections in mice. The experiment comprised 11 groups of 5 mice. At day 0, all mice were challenged with virus at 3× the $LD_{95}$ (~3E4 virus/mouse) by intranasal inoculation in a volume of 30 µl after being lightly anesthetized with ketamine/xylazine (100 and 10 mg/kg respectively). Groups received treatment with vehicle, conjugate 45b, baloxavir marboxil (DC Chemicals, cat no DC111056; suspended in 0.5% methyl cellulose), or a combination (2 hours after challenge). Baloxavir was dosed orally (PO), twice daily for 3 days and conjugate 45b was administered subcutaneously (SC) as a single dose (Table 192). Mortality and body weight (BW) were monitored daily for 14 days. Any mouse losing more than 20% BW was scored as a mortality.

TABLE 192

Study Design

| Group | Influenza A strain | Test Article | Route, Schedule (T + 2 hours) | Dose (mg/kg) | N |
|---|---|---|---|---|---|
| 1 | A/CA/07/09 | Vehicle (PBS) | SC, single | — | 5 |
| 2 | (H1N1) | conjugate 45b | SC, single | 0.01 | 5 |
| 3 | 3E4 PFU/ | conjugate 45b | SC, single | 0.03 | 5 |
| 4 | mouse | conjugate 45b | SC, single | 0.1 | 5 |
| 5 | via IN | conjugate 45b | SC, single | 0.3 | 5 |
| 6 | | Baloxavir | PO, bid × 3 days | 1 | 5 |
| 7 | | Baloxavir | PO, bid × 3 days | 3 | 5 |
| 8 | | Baloxavir | PO, bid × 3 days | 10 | 5 |
| 9 | | Baloxavir conjugate 45b | PO, bid × 3 days SC, single | 3 0.01 | 5 5 |
| 10 | | Baloxavir conjugate 45b | PO, bid × 3 days SC, single | 3 0.03 | 5 5 |
| 11 | | Baloxavir conjugate 45b | PO, bid × 3 days SC, single | 3 0.1 | 5 5 |

In order to determine the potency of conjugate 45b and baloxavir separately the dose range was determined for each molecule. For conjugate 45b doses of 0.1 and 0.3 mg/kg were protective while 0.01 and 0.03 were not based on survival (Table 193). For baloxavir doses of 1 and 3 mg/kg were able to delay, but not prevent death by Day 14. In contrast, a 10 mg/kg dose of baloxavir was 80% protective.

For combination studies the mid-range dose of baloxavir (3 mg/kg) was dosed in conjunction with conjugate 45b at 0.01, 0.03, and 0.1 mg/kg (groups 9-11). As shown in Table 193, neither conjugate 45b at 0.03 mg/kg or baloxavir at 3 mg/kg are protective individually. However, significantly, in combination they demonstrated 80% protection over the course of the study (group 10).

TABLE 193

% Survival

| Day | Vehicle | conjugate 45 b (mg/kg) (SC, single) | | | | Baloxavir (mg/kg) (PO, bid x3 days) | | | conjugate 45 b / Baloxavir Combo (mg/kg) | | |
|---|---|---|---|---|---|---|---|---|---|---|---|
| | | 0.01 | 0.03 | 0.1 | 0.3 | 1 | 3 | 10 | 0.01 / 3 | 0.03 / 3 | 0.1 / 3 |
| 0 | 100 | 100 | 100 | 100 | 100 | 100 | 100 | 100 | 100 | 100 | 100 |
| 1 | 100 | 100 | 100 | 100 | 100 | 100 | 100 | 100 | 100 | 100 | 100 |
| 2 | 100 | 100 | 100 | 100 | 100 | 100 | 100 | 100 | 100 | 100 | 100 |
| 3 | 100 | 100 | 100 | 100 | 100 | 100 | 100 | 100 | 100 | 100 | 100 |
| 4 | 100 | 100 | 100 | 100 | 100 | 100 | 100 | 100 | 100 | 100 | 100 |
| 5 | 20 | 60 | 60 | 100 | 100 | 100 | 100 | 100 | 100 | 100 | 100 |
| 6 | 0 | 20 | 40 | 100 | 100 | 100 | 100 | 100 | 100 | 100 | 100 |
| 7 | 0 | 20 | 20 | 100 | 100 | 100 | 100 | 100 | 100 | 100 | 100 |
| 8 | 0 | 0 | 0 | 100 | 100 | 100 | 80 | 100 | 100 | 100 | 100 |
| 9 | 0 | 0 | 0 | 100 | 100 | 40 | 0 | 100 | 0 | 80 | 100 |
| 10 | 0 | 0 | 0 | 100 | 100 | 0 | 0 | 80 | 0 | 80 | 100 |
| 11 | 0 | 0 | 0 | 100 | 100 | 0 | 0 | 80 | 0 | 80 | 100 |
| 12 | 0 | 0 | 0 | 100 | 100 | 0 | 0 | 80 | 0 | 80 | 100 |
| 13 | 0 | 0 | 0 | 100 | 100 | 0 | 0 | 80 | 0 | 80 | 100 |
| 14 | 0 | 0 | 0 | 100 | 100 | 0 | 0 | 80 | 0 | 80 | 100 |

Body weight data further illustrates the enhanced active of the two molecules administered in combination (Table 194). When dosed at 0.1/3 mg/kg (conjugate 45b/baloxavir) a dramatic reduction in BW loss is observed. Conjugate 45b dosed at 0.1 mg/kg by itself is protective but animals demonstrate an 18.8% drop in BW on Day 4. However, this dose administered with a non-protective dose of baloxavir (3 mg/kg) reduces the maximum BW loss to 4.5% (group 11).

TABLE 194

% Body Weight

| Day | Vehicle | conjugate 45 b (mg/kg) (SC, single) | | | | Baloxavir (mg/kg) (PO bid x3 days) | | | conjugate 45 b / Baloxavir Combo (mg/kg) | | |
|---|---|---|---|---|---|---|---|---|---|---|---|
| | | 0.01 | 0.03 | 0.1 | 0.3 | 1 | 3 | 10 | 0.01 / 3 | 0.03 / 3 | 0.1 / 3 |
| 0 | 100 | 100 | 100 | 100 | 100 | 100 | 100 | 100 | 100 | 100 | 100 |
| 1 | 96.9 | 97.9 | 97 | 97.7 | 99.8 | 99.2 | 97.1 | 95.9 | 97.5 | 96.7 | 96.8 |
| 2 | 94.3 | 96.8 | 95.2 | 97.3 | 99.3 | 99.8 | 99 | 101.8 | 98.9 | 95.4 | 98 |

TABLE 194-continued

| | % Body Weight | | | | | | | | | | |
|---|---|---|---|---|---|---|---|---|---|---|---|
| | conjugate 45 b (mg/kg) (SC, single) | | | | Baloxavir (mg/kg) (PO bid x3 days) | | | | conjugate 45 b / Baloxavir Combo (mg/kg) | | |
| Day | Vehicle | 0.01 | 0.03 | 0.1 | 0.3 | 1 | 3 | 10 | 0.01 / 3 | 0.03 / 3 | 0.1 / 3 |
| 3 | 85.4 | 86.3 | 85.5 | 85.5 | 88.4 | 90.3 | 92.1 | 97.4 | 94 | 93.2 | 95.5 |
| 4 | 78.9 | 79.8 | 79.8 | 81.2 | 86 | 90.5 | 92.5 | 98 | 94.2 | 92.7 | 95.5 |
| 5 | 77.2 | 78.7 | 79.3 | 81.6 | 95.3 | 94.6 | 97.3 | 100.8 | 99.1 | 96.9 | 100 |
| 6 | | | | 83.9 | 98.6 | 91.1 | 89.9 | 98.9 | 93.3 | 94.3 | 99.2 |
| 7 | | | | 85.8 | 99.1 | 84.6 | 83.3 | 91.1 | 85.6 | 87.8 | 100.4 |
| 8 | | | | 87.9 | 99.6 | 79.5 | 77.9 | 86.9 | 79.4 | 83.9 | 99.8 |
| 9 | | | | 90 | 99.1 | 75.7 | | 86.4 | 74.8 | 85.2 | 102.4 |
| 10 | | | | 89.2 | 99.9 | | | 88.2 | | | 100.4 |
| 11 | | | | 92.8 | 99.9 | | | | | | 101 |
| 12 | | | | 97.7 | 100.8 | | | | | | 100.9 |
| 13 | | | | 98.7 | 101.8 | | | | | | 100.3 |
| 14 | | | | 101 | 101.4 | | | | | | 102.1 |

In this important study two different groups demonstrated enhanced potency of conjugate 45b with the co-administration of baloxavir. Also, not to be overlooked is the critical observation that the two compounds do not inhibit the activity of each other. The observation that the reverse is true, and the combination is more effective is a benefit that would likely translate into the clinic.

Example 207. Alternate Synthesis of Conjugate 45a

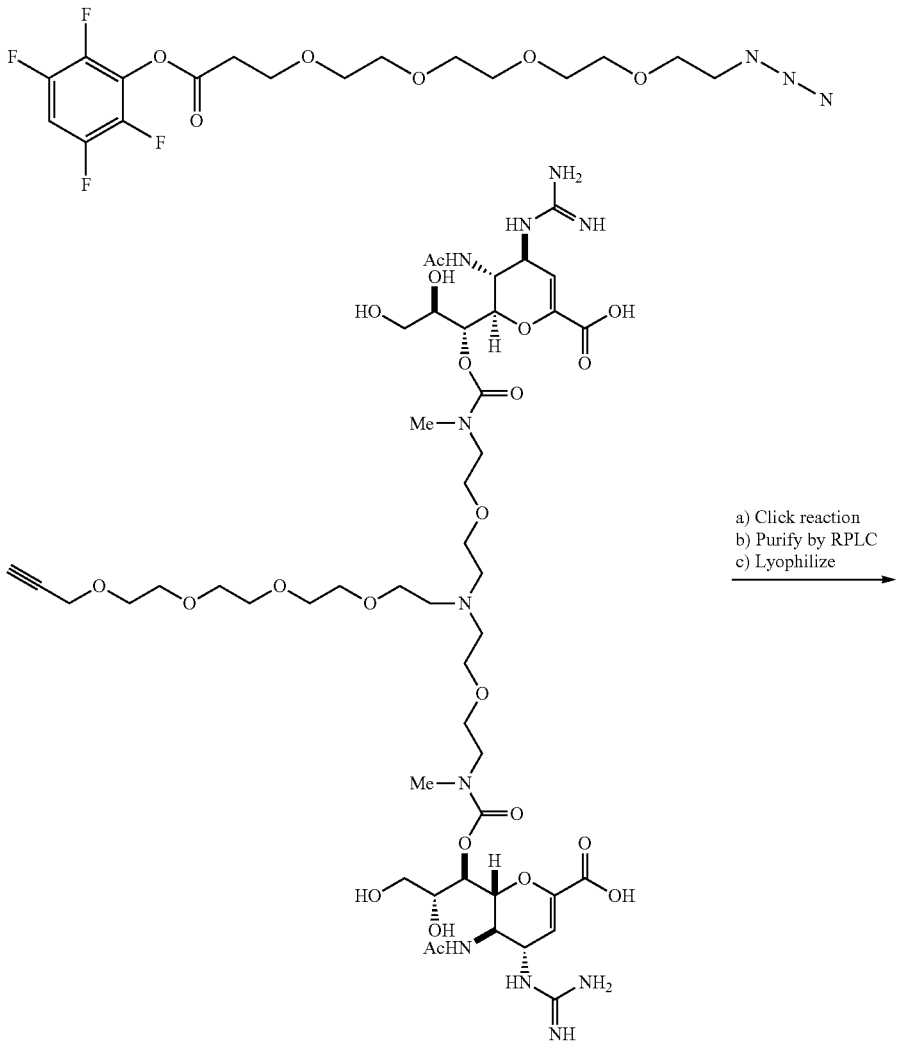

1081
1082
-continued
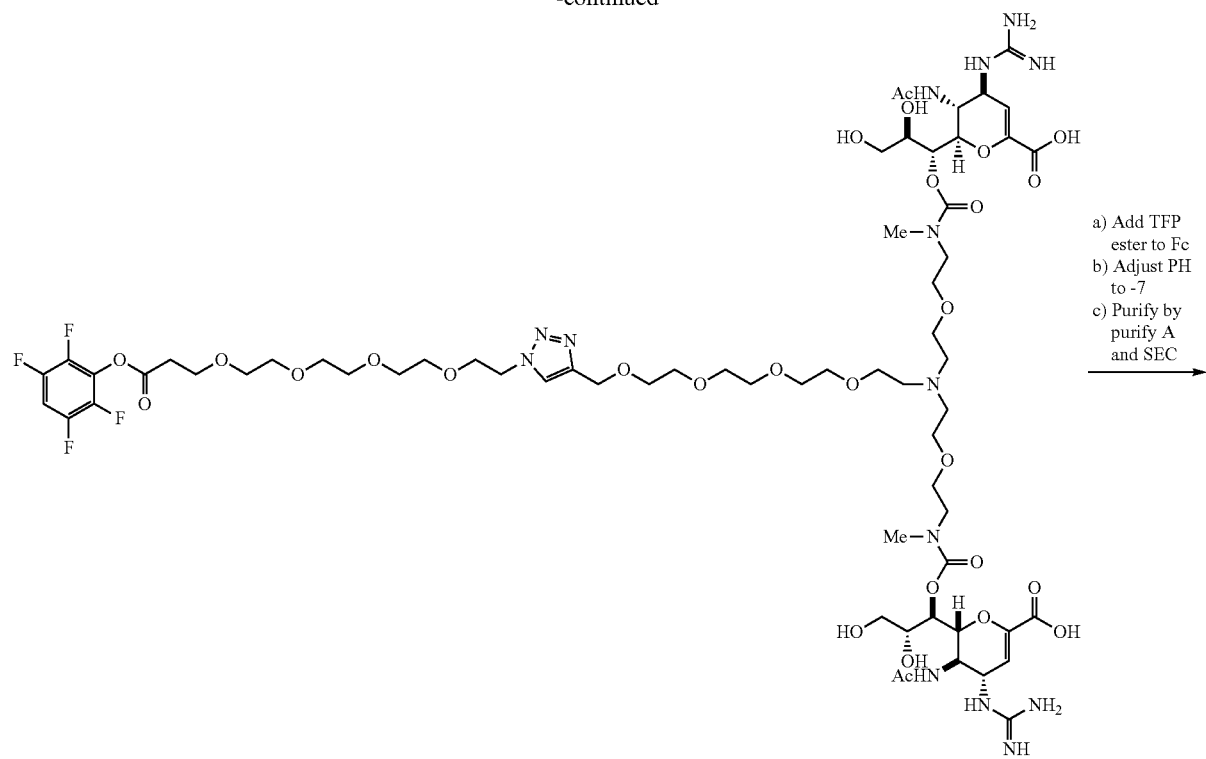
a) Add TFP ester to Fc
b) Adjust PH to ~7
c) Purify by purify A and SEC
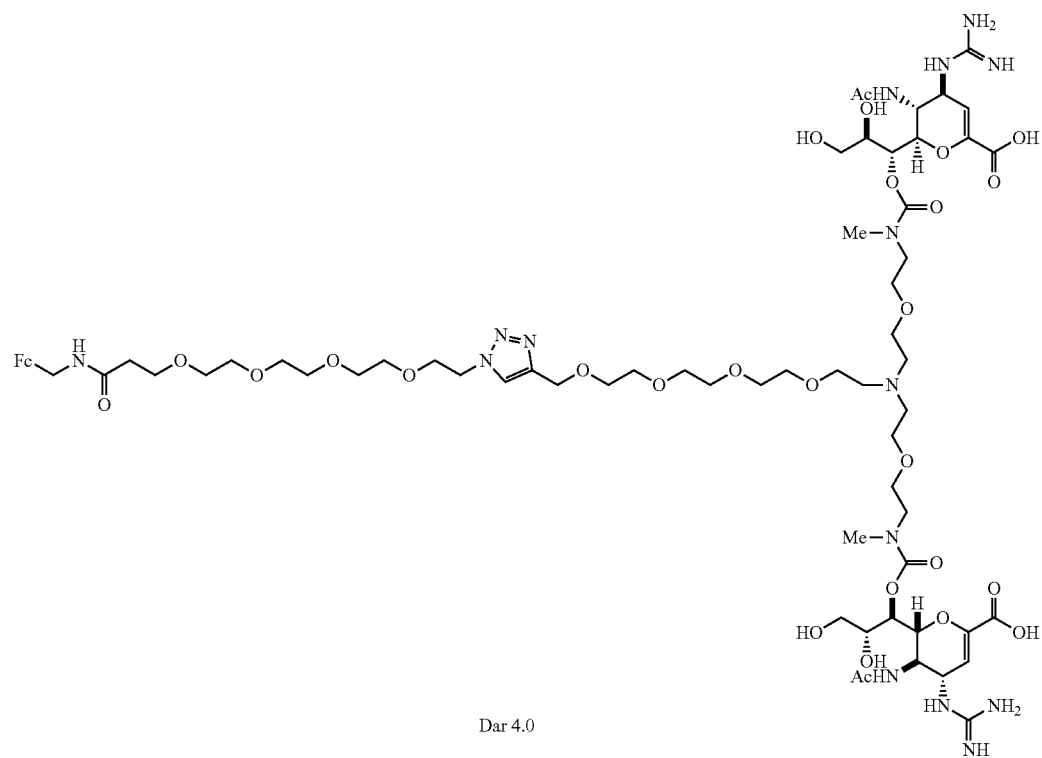
Dar 4.0

Step a.

-continued

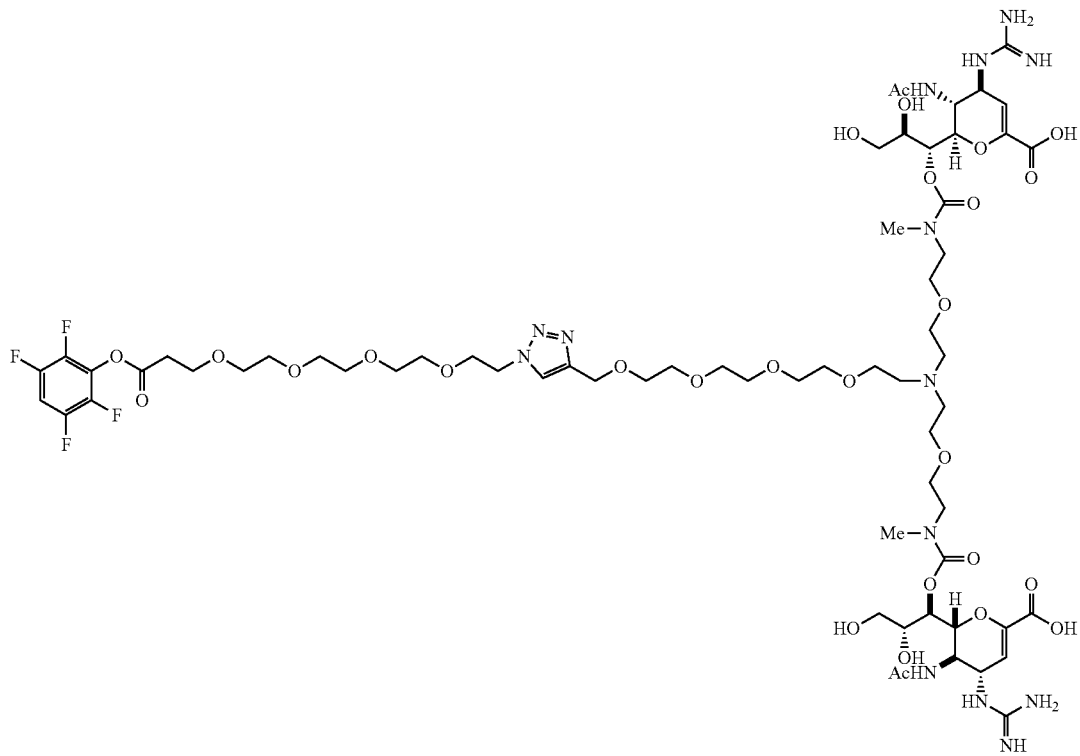

A solution of azido-PEG4-TFP ester (0.1 g, 0.067 mmol) and alkyne functionalized dimer (0.0383 g, 0.0871 mmol) in DMF (2.0 mL), were treated with a solution of copper(II) sulfate (0.0027 g, 0.0168 mmol), sodium ascorbate (0.0133 g, 0.067 mmol), and THPTA (0.0116 g, 0.027 mmol) at room temperature, in water (1.5 mL). The reaction was then vacuum flushed with nitrogen 3× and stirred under an atmosphere of nitrogen. LCMS after 30 min shows complete consumption of starting material. The reaction was acidified with 400 µL of acetic acid, and then purified directly by reverse phase chromatography eluting with a gradient of 5% to 100% acetonitrile/water with 0.1% TFA. The product containing fractions were combined, frozen, and lyophilized overnight. Yield of triple TFA salt was 69%. Ion(s) found by LCMS: $(M+2H)^{+2}=795.4$, $(M+3H)^{+3}=530.8$, $(M+4H)^{+4}=398.4$.

Step b.

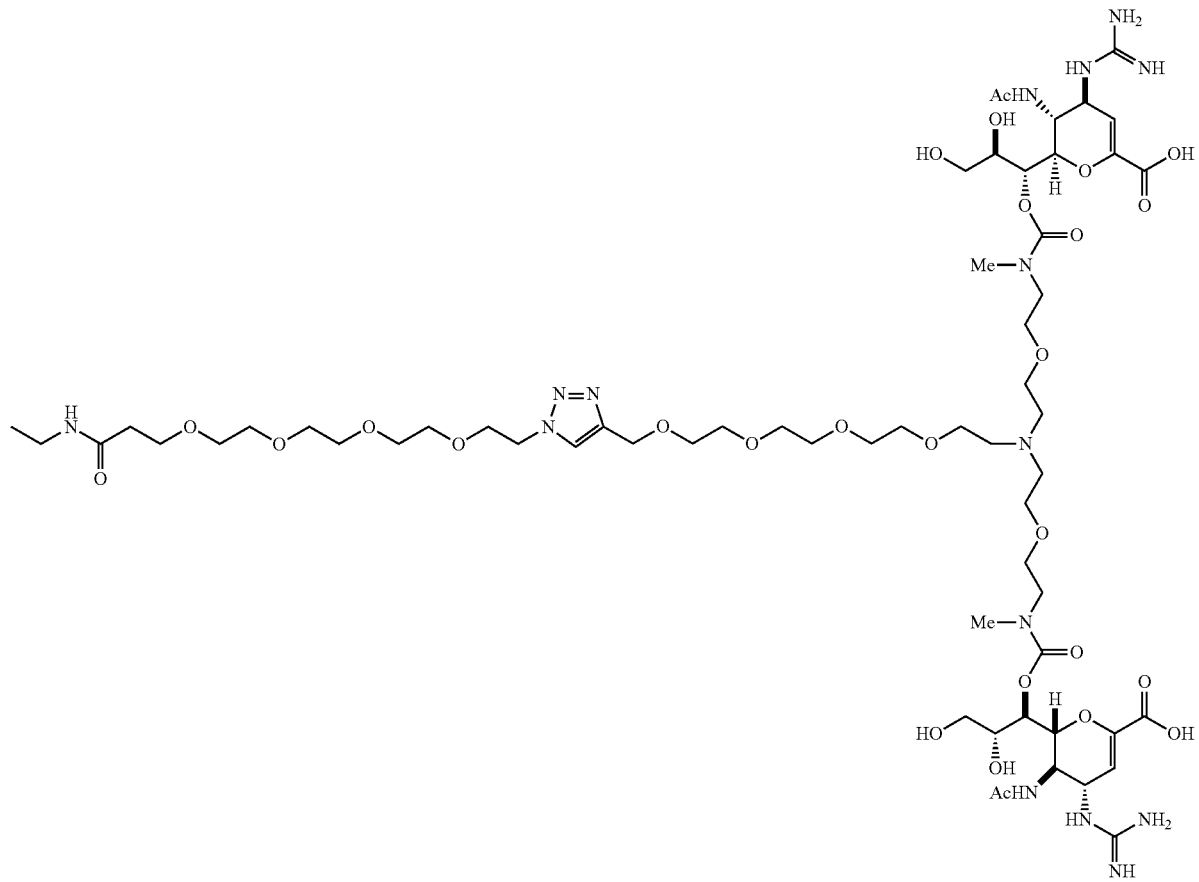

A solution of Fc (0.100 g in 5.2 mL, 1.717 µmol, MW=58,218, SEQ ID NO: 72) in pH=7.4 PBS buffer was treated with solid TFP ester (0.0273 g, 17.17 µmol) from the previous step. The pH was adjusted to ~7.0 with borate buffer (120 µL, 1 M, pH 8.5) then was gently rocked at room temperature. Maldi TOF after 1.5 hr shows an average DAR of 3.3, which did not change upon further mixing. After 24 hr additional TFP ester (0.0073 g, 4.6 µmol) was added and rocking was continued for another 3 h. The crude conjugate was purified Protein A and SEC according to general purification methods. Total yield after Protein A was ~83%, and after SEC ~77%. Maldi TOF of the purified conjugate showed an average mass of 63,574, which equates to an average DAR of 4.0.

The alternate synthesis described in Example 207 is advantageous at it avoids exposing the Fc to copper+2 and sodium ascorbate, leading to a cleaner crude conjugate that is 98.9% pure by analytical SEC after protein A purification alone. At this level of purity it may be possible to eliminate the SEC purification which is time very consuming and costly. Initial by attempts with an azido-PEG4-NHS ester were only partially successful because the NHS ester is too reactive to be purified, and the crude click reaction mixture had to be mixed with the Fc, thus necessitating copper removal and high molecular weight aggregate removal (from exposure to sodium ascorbate). Also this approach did not generate DAR's greater than 2. Subsequent attempts using a less reactive active ester (TFP tetrafluorophenol) that is stable enough to withstand reverse phase purification and lyophilization, allows the click reaction with azido TFP ester to be done separate from the Fc, purified, and then mixed with the Fc. In Example 207 an average DAR of 4.0 was achieved and higher DARs are possible by adding more of the TFP ester.

The nucleic acid construct encoding the Fc for Conjugate 45a included a nucleic acid encoding the amino acid sequence of SEQ ID NO: 63, which includes a C-terminal lysine residue. Upon expression, the C-terminal lysine of the Fc of Conjugate 45a is proteolytically cleaved, resulting in an Fc having the sequence of SEQ ID NO: 72. The presence or absence of a C-terminal lysine does not alter the properties of the Fc or the corresponding conjugate.

Example 208. Efficacy of Conjugate 45a in Combination with Baloxavir Against Influenza A (H1N1) in a Lethal Mouse Influenza Model (Confirmation Study)

Conjugate 45a was evaluated in combination with baloxavir marboxil (BXM) against a lethal IAV H1N1 influenza infection in female BALB/c mice (Charles River Laboratories, 6-8 weeks). This was a follow up to Example 206 which tested the same combination in an initial experiment, but used a subcutaneous dose route for conjugate 45a instead of intramuscular (IM), which was used in the present study. The challenge virus (A/California/07/2009) is a pandemic isolate capable of causing lethal infections in mice. The experiment comprised 8 groups of 5 mice. At day 0, all mice were challenged with virus at 3× the $LD_{95}$ (3E4 virus/mouse) by intranasal inoculation in a volume of 30 μl after being lightly anesthetized with ketamine/xylazine(100 and 10 mg/kg respectively). Groups received treatment with vehicle, hIgG1 Fc only, conjugate 45a, BXM (DC Chemicals, cat no DC11056; suspended in 0.5% methyl cellulose), or a combination (2 hours after challenge). BXM was dosed orally (PO), twice daily for 3 days and conjugate 45a was administered by IM as a single dose (Table 195). Mortality and body weight (BW) was monitored daily for 21 days. Any mouse losing more than 20% BW on 2 consecutive days was scored as a mortality.

TABLE 195

Study design for conjugate 45a and BXM combination study

| Group | Influenza A strain | Test Article | Route, Schedule (T + 2 hours) | Dose (mg/kg) | N |
|---|---|---|---|---|---|
| 1 | A/CA/07/09 | Vehicle (PBS) | IM, single | — | 5 |
| 2 | (H1N1) | hIgG1 Fc | IM, single | 0.1 | 5 |
| 3 | 3E4 | Conjugate 45a | IM, single | 0.03 | 5 |
| 4 | PFU/mouse via | Conjugate 45a | IM, single | 0.1 | 5 |
| 5 | IN | BXM | PO, bid × 3 days | 3 | 5 |
| 6 | | BXM | PO, bid × 3 days | 10 | 5 |
| 7 | | BXM | PO, bid × 3 days | 3 | 5 |
| | | Conjugate 45a | IM, single | 0.03 | 5 |
| 8 | | BXM | PO, bid × 3 days | 3 | 5 |
| | | Conjugate 45a | IM, single | 0.1 | 5 |

In order to determine the potency of conjugate 45a and BXM separately the dose range was determined for each molecule. For conjugate 45a a dose of 0.1 mg/kg was protective, while a 0.03 mg/kg dose was not based on survival (Table 196). For BXM, the group receiving 10 mg/kg (bid×3 days) was protected, while those receiving 3 mg/kg with the same dose schedule were not. Groups administered vehicle or hIgG1 Fc only were not protected. The combination of conjugate 45a (0.1 mg/kg) with BXM (3 mg/kg) was also fully protected as expected based on the above results.

Group 7 animals received sub-efficacious levels of both conjugate 45a (0.03 mg/kg) and BXM (3 mg/kg) in combination. Although neither test article was significantly protective when administered individually, in combination they were fully protective (Table 196). Animals in group 7 also only displayed transient BW lose which did not exceed 5.2% (Day 3) (Table 197). By study end this group had exceeded its starting BW reaching 106.3% of initial BW on Day 21. In addition to not exhibiting any antagonistic effects between conjugate 45a and BXM, the opposite was found, suggesting an added benefit of co-treatment with these two therapeutics.

TABLE 196

% Survival for Study Groups

| | Controls | | Conjugate 45 a | | Baloxavir (mg/kg) | | Conjugate 45 a / Baloxavir Combo (mg/kg) | |
|---|---|---|---|---|---|---|---|---|
| | Vehicle | hIgG1 Fc (0.1 mg/kg) | (mg/kg) (IM, single) | | (PO, bid x3 days) | | | |
| Day | | | 0.03 | 0.1 | 3 | 10 | 0.03 / 3 | 0.1 / 3 |
| 0 | 100 | 100 | 100 | 100 | 100 | 100 | 100 | 100 |
| 1 | 100 | 100 | 100 | 100 | 100 | 100 | 100 | 100 |
| 2 | 100 | 100 | 100 | 100 | 100 | 100 | 100 | 100 |
| 3 | 100 | 100 | 100 | 100 | 100 | 100 | 100 | 100 |
| 4 | 100 | 100 | 80 | 100 | 100 | 100 | 100 | 100 |
| 5 | 80 | 60 | 60 | 100 | 100 | 100 | 100 | 100 |
| 6 | 80 | 20 | 20 | 100 | 100 | 100 | 100 | 100 |
| 7 | 60 | 0 | 20 | 100 | 100 | 100 | 100 | 100 |
| 8 | 0 | | 20 | 100 | 60 | 100 | 100 | 100 |
| 9 | | | 20 | 100 | 0 | 100 | 100 | 100 |
| 10 | | | 20 | 100 | | 100 | 100 | 100 |
| 11 | | | 20 | 100 | | 100 | 100 | 100 |
| 12 | | | 20 | 100 | | 100 | 100 | 100 |
| 13 | | | 20 | 100 | | 100 | 100 | 100 |
| 14 | | | 20 | 100 | | 100 | 100 | 100 |
| 15 | | | 20 | 100 | | 100 | 100 | 100 |
| 16 | | | 20 | 100 | | 100 | 100 | 100 |
| 17 | | | 20 | 100 | | 100 | 100 | 100 |
| 18 | | | 20 | 100 | | 100 | 100 | 100 |
| 19 | | | 20 | 100 | | 100 | 100 | 100 |
| 20 | | | 20 | 100 | | 100 | 100 | 100 |
| 21 | | | 20 | 100 | | 100 | 100 | 100 |

TABLE 197

Average Body Weight by Day (group average; until 1st death in a group)

| | Controls | | Conjugate | | Baloxavir | | Conjugate 45 a / Baloxavir Combo (mg/kg) | |
|---|---|---|---|---|---|---|---|---|
| | Vehicle | hIgG1 Fc (0.1 mg/kg) | 45 a (mg/kg) (IM, single) | | (mg/kg) (PO bid x3 days) | | | |
| Day | | | 0.03 | 0.1 | 3 | 10 | 0.03 / 3 | 0.1 / 3 |
| 0 | 100 | 100 | 100 | 100 | 100 | 100 | 100 | 100 |
| 1 | 102.1 | 100.2 | 99.9 | 99.6 | 97.9 | 97.9 | 100.3 | 100 |
| 2 | 94.9 | 94.3 | 93.3 | 95 | 90.5 | 98.7 | 99.9 | 99.6 |
| 3 | 85 | 84.2 | 83.1 | 83.7 | 88.5 | 94.6 | 94.8 | 94.3 |
| 4 | 81.3 | 79.6 | 79.7 | 81.4 | 90.7 | 95.8 | 96.9 | 96.1 |
| 5 | 82.4 | 80.1 | 82.3 | 88.3 | 95.3 | 99.4 | 100.9 | 100.4 |
| 6 | | | | 91.1 | 87.7 | 96.7 | 99 | 99.2 |
| 7 | | | | 91.7 | 81 | 89.6 | 96.8 | 98.5 |
| 8 | | | | 96.9 | 76.7 | 90.9 | 101.6 | 101.9 |
| 9 | | | | 95.7 | | 92.6 | 99.1 | 99 |
| 10 | | | | 99.4 | | 98.2 | 101.7 | 102.3 |
| 11 | | | | 98.6 | | 95.8 | 98.7 | 100.3 |
| 12 | | | | 98.4 | | 96.8 | 100.7 | 99.9 |
| 13 | | | | 101 | | 99.5 | 102.9 | 101.1 |
| 14 | | | | 102.3 | | 99.2 | 103.7 | 103.6 |
| 15 | | | | 101.2 | | 97.8 | 102.1 | 100.2 |
| 16 | | | | 102.8 | | 99.5 | 103.1 | 102.8 |
| 17 | | | | 101.9 | | 98.3 | 102.7 | 101.1 |
| 18 | | | | 102.3 | | 97.1 | 101.7 | 100.1 |
| 19 | | | | 103.9 | | 98.9 | 101.6 | 100.6 |
| 20 | | | | 103.9 | | 98.9 | 104.5 | 102.6 |
| 21 | | | | 107 | | 101.2 | 106.3 | 103.8 |

Example 209. Determination of Conjugate 45a Potency Against a Component of the 2020-2021 Northern Hemisphere Quadrivalent Vaccine (A/Hawaii/70/2019Pdm; H1N1) in a Lethal Mouse Model Conjugate 45a was evaluated in a lethal H1N1 influenza infection model in female BALB/c mice (Charles River Laboratories, 6-8 weeks). The challenge virus (A/Hawaii/70/2019) is a pandemic H1N1 isolate capable of causing lethal infections in mice. It is also a recommended component of the 2020-2021 northern hemisphere quadrivalent vaccine.

The experiment was comprised of 9 groups, with 5 mice per group. At day 0, all mice were challenged with virus at 2× the $LD_{95}$ (2E3 virus/mouse) by intranasal inoculation in a volume of 30 μl after being anesthetized with ketamine/xylazine (100 and 10 mg/kg respectively). Groups received a single treatment of Conjugate 45a, hIgG1 Fc, or vehicle (PBS), 2 hours after viral challenge by intramuscular (IM, 5 ml/kg dose volume) administration (right flank). Conjugate 45a was tested at concentrations of 3, 1, 0.3, 0.1, 0.03, and 0.01 mg/kg. An uninfected group was also included in the study as a control. Mortality and body weight (BW) was monitored daily for 21 days. Any mouse maintaining a 20% BW loss on two consecutive days was scored as a mortality. The experimental outline is summarized in Table 198.

In this study a single IM administration of conjugate 45a fully protected mice from lethal challenge by A/HA/70/2019 (H1N1) at 0.3, 1, and 3 mg/kg (Table 199). The potency of Conjugate 45a at these dose levels was significant compared to vehicle treated animals (P=0.0031). Vehicle and hIgG1 Fc treated animals in contrast reached 100% mortality on Day 5. Partial protection was also seen in the 0.1 and 0.03 mg/kg dose groups (60 and 20% survival respectively), but was not statistically significant compared to vehicle treated animals. Collectively the survival data demonstrated that conjugate 45a is potent against this important influenza isolate and a clear dose response was evident in the lower dose groups (FIG. 119).

The potency of conjugate 45a was also supported by BW data. Mice treated with fully protective doses (3, 1, and 0.3 mg/kg) displayed transient BW loss on Day 3 (Maximum of 12% BW loss at a conjugate 45a dose of 0.3 mg/kg), before steadily recovering BW through the end of the study (Day 21) (Table 200). BW trends mirrored the survival outcome of the study and supported the efficacy of the conjugate against this H1N1 isolate.

Collectively this study demonstrated the potency of conjugate 45a, by both mortality and BW readouts, against an important pandemic influenza isolate. As A/HA/70/2019 has been selected for inclusion in the 2020 northern hemisphere vaccine it is considered a clinically relevant isolate and a threat to public health. The potency of conjugate 45a against this pandemic strain with a single IM dose of 0.3 mg/kg supports its continued development as a therapeutic against influenza.

TABLE 198

Outline of conjugate 45 a potency against A/HA/70/2019 study

| Group | Influenza A strain (IN challenge) | Test Article | Route, Schedule | Dose (mg/kg) | Dose volume (ml/kg) | Number of mice |
|---|---|---|---|---|---|---|
| 1 | Uninfected | Vehicle (PBS) | IM, single, T + 2 h | — | 5 | 5 |
| 2 | A/HA/ 70/2019 | Vehicle (PBS) | IM, single, T + 2 h | — | 5 | 5 |
| 3 | (H1N1) ~2E3 pfu/ml | hIgG1 Fc (SEQ ID NO: 72) | IM, single, T + 2 h | 0.3 | 5 | 5 |
| 4 | | Conjugate 45a | IM, single, T + 2 h | 3 | 5 | 5 |
| 5 | | Conjugate 45a | IM, single, T + 2 h | 1 | 5 | 5 |
| 6 | | Conjugate 45a | IM, single, T + 2 h | 0.3 | 5 | 5 |
| 7 | | Conjugate 45a | IM, single, T + 2 h | 0.1 | 5 | 5 |
| 8 | | Conjugate 45a | IM, single, T + 2 h | 0.03 | 5 | 5 |
| 9 | | Conjugate 45a | IM, single, T + 2 h | 0.01 | 5 | 5 |

TABLE 199

% Survival of animals by group and date

| | Controls | | | Conjugate 45 a (mg/kg) (IM, single) | | | | | |
|---|---|---|---|---|---|---|---|---|---|
| Day | Uninfected | Vehicle | hIgG1 Fc (0.3 mg/kg) (SEQ ID NO: 72) | 3 | 1 | 0.3 | 0.1 | 0.03 | 0.01 |
| 0 | 100 | 100 | 100 | 100 | 100 | 100 | 100 | 100 | 100 |
| 1 | 100 | 100 | 100 | 100 | 100 | 100 | 100 | 100 | 100 |
| 2 | 100 | 100 | 100 | 100 | 100 | 100 | 100 | 100 | 100 |
| 3 | 100 | 100 | 100 | 100 | 100 | 100 | 100 | 100 | 100 |
| 4 | 100 | 60 | 60 | 100 | 100 | 100 | 100 | 100 | 80 |
| 5 | 100 | 0 | 0 | 100 | 100 | 100 | 60 | 20 | 60 |
| 6 | 100 | | | 100 | 100 | 100 | 60 | 20 | 60 |
| 7 | 100 | | | 100 | 100 | 100 | 60 | 20 | 40 |
| 8 | 100 | | | 100 | 100 | 100 | 60 | 20 | 0 |
| 9 | 100 | | | 100 | 100 | 100 | 60 | 20 | |
| 10 | 100 | | | 100 | 100 | 100 | 60 | 20 | |
| 11 | 100 | | | 100 | 100 | 100 | 60 | 20 | |
| 12 | 100 | | | 100 | 100 | 100 | 60 | 20 | |
| 13 | 100 | | | 100 | 100 | 100 | 60 | 20 | |
| 14 | 100 | | | 100 | 100 | 100 | 60 | 20 | |
| 15 | 100 | | | 100 | 100 | 100 | 60 | 20 | |
| 16 | 100 | | | 100 | 100 | 100 | 60 | 20 | |
| 17 | 100 | | | 100 | 100 | 100 | 60 | 20 | |
| 18 | 100 | | | 100 | 100 | 100 | 60 | 20 | |
| 19 | 100 | | | 100 | 100 | 100 | 60 | 20 | |
| 20 | 100 | | | 100 | 100 | 100 | 60 | 20 | |
| 21 | 100 | | | 100 | 100 | 100 | 60 | 20 | |

TABLE 200

% Average Body Weight by Day (group average; until 1st death within a group)

| | Controls | | Conjugate 45 a | | | | | |
|---|---|---|---|---|---|---|---|---|
| | | hIgG1 Fc | (mg/kg) (IM, single) | | | | | |
| Day | Uninfected | Vehicle | (0.3 mg/kg) | 3 | 1 | 0.3 | 0.1 | 0.03 | 0.01 |
| 0 | 100 | 100 | 100 | 100 | 100 | 100 | 100 | 100 | 100 |
| 1 | 100.8 | 97.9 | 97.2 | 98.6 | 98.4 | 98.1 | 98.5 | 98.4 | 99.2 |
| 2 | 103.2 | 93.9 | 94.3 | 100.3 | 98.9 | 96.5 | 96.3 | 95.9 | 95.5 |
| 3 | 100.9 | 84.3 | 84.8 | 94.1 | 92.6 | 88 | 85.8 | 86.2 | 84.1 |
| 4 | 103.4 | | 78.2 | 95.1 | 95.3 | 88.2 | 84.1 | 81.3 | 81.2 |
| 5 | 103.1 | | | 97.5 | 96.2 | 91.5 | 82.7 | 77 | |
| 6 | 105.5 | | | 100.3 | 99.2 | 96.3 | | | |
| 7 | 104.4 | | | 99.6 | 99.1 | 95.6 | | | |
| 8 | 105.1 | | | 102.2 | 102.4 | 100.5 | | | |
| 9 | 104.7 | | | 100.7 | 100.7 | 99.9 | | | |
| 10 | 103.9 | | | 101.6 | 100.9 | 100.2 | | | |
| 11 | 106.8 | | | 102.3 | 101.7 | 100.9 | | | |
| 12 | 108.7 | | | 102.8 | 103.4 | 101.9 | | | |
| 13 | 105.7 | | | 102.1 | 102.3 | 101.5 | | | |
| 14 | 108.7 | | | 102.9 | 104.7 | 103.8 | | | |
| 15 | 110.15 | | | 103.1 | 104 | 102.8 | | | |
| 16 | 106.5 | | | 100.9 | 101.5 | 99.5 | | | |
| 17 | 105.5 | | | 100.7 | 101 | 100.3 | | | |
| 18 | 106.1 | | | 100.6 | 101.6 | 100.5 | | | |
| 19 | 107.7 | | | 100.9 | 103 | 101.5 | | | |
| 20 | 107.2 | | | 99.9 | 102.5 | 101.5 | | | |
| 21 | 107.6 | | | 102.5 | 102.8 | 104.2 | | | |

Example 210. Efficacy of Conjugate 45a Against Influenza A/Puerto Rico/8/1934 (H1N1) in a 4-Week Lethal Mouse Model Conjugate 45a was evaluated against a lethal IAV H1N1 influenza infection in female BALB/c mice (Charles River Laboratories, 6-8 weeks). The challenge virus (A/Puerto Rico/8/1934) is a mouse-adapted isolate capable of causing lethal infections in mice. The experiment comprised 7 groups of 5 mice. At day 0, all mice were challenged with virus at 3× the LD95 by intranasal (IN) inoculation in a volume of 30 µl, after being anesthetized with a mixture of ketamine/xylazine (150 and 10 mg/kg respectively). The only exception was group 1 which consisted of uninfected mice used as a body weight (BW) control. Mortality and BW were recorded daily for 28 days and any animal with a cumulative 20% loss of weight for 2 consecutive days was scored as a death.

Test groups received a single intramuscular (IM) injection, 2 hours post viral challenge of conjugate 45a (0.01 to 0.3 mg/kg), hIgG1 Fc only (0.3 mg/kg, SEQ ID NO: 72), or vehicle (PBS). Injections were in the thigh muscle of the right hind limb at a dose volume of 5 ml/kg.

TABLE 201

Study outline

| Group | Influenza A | Test Article | Route, Schedule | Dose (mg/kg) | N |
|---|---|---|---|---|---|
| 1 | Uninfected | Vehicle (PBS) | IM, single, T + 2 h | — | 5 |
| 2 | A/PR/8/34 | Vehicle (PBS) | IM, single, T + 2 h | — | 5 |
| 3 | (H1N1) | hIgG1 Fc | IM, single, T + 2 h | 0.3 | 5 |
| 4 | 3E2 | Conjugate 45a | IM, single, T + 2 h | 0.3 | 5 |
| 5 | PFU/mouse | Conjugate 45a | IM, single, T + 2 h | 0.1 | 5 |
| 6 | | Conjugate 45a | IM, single, T + 2 h | 0.03 | 5 |
| 7 | | Conjugate 45a | IM, single, T + 2 h | 0.01 | 5 |

Animals treated with vehicle only began to reach mortality on Day 5, with 100% mortality by Day 7. Similarly, mice treated with hIgG1 Fc only (which lacks the antiviral moiety of the conjugate) had fully succumbed to infection on Day 7 (FIG. 120 and Table 202). In contrast, groups receiving conjugate 45a at 0.1 and 0.3 mg/kg were fully protected until study end on Day 28. Relative to vehicle only treated mice this difference in survival was statistically significant (P=0.0020 for both groups by the Log-rank (Mantel-Cox) test). Conjugate 45a administered at dose levels of 0.01 and 0.03 mg/kg however were sub-efficacious, with mice reaching 100% mortality on Days 8 and 7 respectively (FIG. 120 and Table 202).

TABLE 202

% Survival of Study Groups by Day

| | Controls | | | Conjugate 45 a (mg/kg) | | | |
|---|---|---|---|---|---|---|---|
| | | | hIgG1 Fc | | | | |
| Day | Uninfected | Vehicle | (0.3 mg/kg) | 0.3 | 0.1 | 0.03 | 0.01 |
| 0 | 100 | 100 | 100 | 100 | 100 | 100 | 100 |
| 1 | 100 | 100 | 100 | 100 | 100 | 100 | 100 |
| 2 | 100 | 100 | 100 | 100 | 100 | 100 | 100 |
| 3 | 100 | 100 | 100 | 100 | 100 | 100 | 100 |
| 4 | 100 | 100 | 100 | 100 | 100 | 100 | 100 |
| 5 | 100 | 80 | 100 | 100 | 100 | 100 | 100 |
| 6 | 100 | 20 | 40 | 100 | 100 | 80 | 80 |
| 7 | 100 | 0 | 0 | 100 | 100 | 0 | 20 |
| 8 | 100 | | | 100 | 100 | | 0 |
| 9 | 100 | | | 100 | 100 | | |
| 10 | 100 | | | 100 | 100 | | |
| 11 | 100 | | | 100 | 100 | | |
| 12 | 100 | | | 100 | 100 | | |
| 13 | 100 | | | 100 | 100 | | |
| 14 | 100 | | | 100 | 100 | | |
| 15 | 100 | | | 100 | 100 | | |
| 16 | 100 | | | 100 | 100 | | |

TABLE 202-continued

% Survival of Study Groups by Day

| | Controls | | | Conjugate 45 a (mg/kg) | | | |
|---|---|---|---|---|---|---|---|
| Day | Uninfected | Vehicle | hIgG1 Fc (0.3 mg/kg) | 0.3 | 0.1 | 0.03 | 0.01 |
| 17 | 100 | | | | 100 | 100 | |
| 18 | 100 | | | | 100 | 100 | |
| 19 | 100 | | | | 100 | 100 | |
| 20 | 100 | | | | 100 | 100 | |
| 21 | 100 | | | | 100 | 100 | |
| 22 | 100 | | | | 100 | 100 | |
| 23 | 100 | | | | 100 | 100 | |
| 24 | 100 | | | | 100 | 100 | |
| 25 | 100 | | | | 100 | 100 | |
| 26 | 100 | | | | 100 | 100 | |
| 27 | 100 | | | | 100 | 100 | |
| 28 | 100 | | | | 100 | 100 | |

In addition to survival, BW was also monitored daily throughout the study. Uninfected mice (group 1) steadily gained BW reaching 108.7% of their starting BW by study end, indicating the general good health of test animals (Table 203). In contrast, negative control groups (2 and 3) began losing BW on Day 1 until the first animal in each group reached mortality on Day 5 and 6 respectively. After the first death within a group BW values were not recorded because the group becomes a biased population.

Mice treated with a protective dose of conjugate 45a (groups 4 and 5) only displayed a transient BW loss of less than 5%. By study end both of these groups exceeded their starting BW (105.9 and 108.7% respectively). As expected, mice receiving a sub-protective dose of conjugate 45a (groups 6 and 7) showed a steady loss of weight until the animals began reaching mortality.

Collectively this data shows the potency of conjugate 45a against lethal challenge by influenza A (H1N1). Significantly, protection was achieved by a single IM injection of less than 1 mg/kg. Lastly, animals were followed for a full 4-weeks after viral challenge indicating that protected animals had most likely full cleared the infection.

TABLE 203

% Average Body Weight by Day (group average; until 1st death within a group)

| | Controls | | | Conjugate 45 a (mg/kg) (IM, single) | | | |
|---|---|---|---|---|---|---|---|
| Day | Uninfected | Vehicle | hIgG1 Fc (0.3 mg/kg) | 0.3 | 0.1 | 0.03 | 0.01 |
| 0 | 100 | 100 | 100 | 100 | 100 | 100 | 100 |
| 1 | 100.5 | 98.1 | 97.7 | 96 | 98.7 | 98.5 | 98.2 |
| 2 | 101.3 | 97.8 | 98.3 | 96.5 | 99 | 100.4 | 98.4 |
| 3 | 102 | 92.1 | 92.7 | 97.2 | 98.3 | 94.6 | 94.4 |
| 4 | 103.2 | 84.3 | 85.1 | 97.4 | 95.3 | 89.2 | 87.7 |
| 5 | 106.5 | | 80.8 | 101.2 | 102.3 | 89.1 | 83.9 |
| 6 | 104.9 | | 74.7 | 99.7 | 98.6 | 81.4 | 77.9 |
| 7 | 106.8 | | | 102.6 | 101.3 | | |
| 8 | 108.3 | | | 102.3 | 102.7 | | |
| 9 | 103.6 | | | 99.6 | 101.7 | | |
| 10 | 108.4 | | | 103.9 | 105.4 | | |
| 11 | 105.1 | | | 100.5 | 102.4 | | |
| 12 | 108 | | | 103.8 | 107.1 | | |
| 13 | 107.7 | | | 102.9 | 105.1 | | |
| 14 | 106.3 | | | 102.9 | 105.3 | | |
| 15 | 106.6 | | | 103.4 | 105.9 | | |

TABLE 203-continued

% Average Body Weight by Day (group average; until 1st death within a group)

| | Controls | | | Conjugate 45 a (mg/kg) (IM, single) | | | |
|---|---|---|---|---|---|---|---|
| Day | Uninfected | Vehicle | hIgG1 Fc (0.3 mg/kg) | 0.3 | 0.1 | 0.03 | 0.01 |
| 16 | 104.2 | | | 101.2 | 102.9 | | |
| 17 | 104.9 | | | 101.2 | 103.9 | | |
| 18 | 107 | | | 103.9 | 106.9 | | |
| 19 | 107.3 | | | 104.3 | 106.1 | | |
| 20 | 105.6 | | | 103 | 105.7 | | |
| 21 | 104.7 | | | 103 | 105.6 | | |
| 22 | 108.5 | | | 106.8 | 107.8 | | |
| 23 | 106.8 | | | 103.5 | 106 | | |
| 24 | 106.4 | | | 101.4 | 107.7 | | |
| 25 | 106.1 | | | 103.2 | 107 | | |
| 26 | 109.3 | | | 106.1 | 109.4 | | |
| 27 | 108 | | | 105.1 | 107.8 | | |
| 28 | 108.7 | | | 105.9 | 108.7 | | |

Example 211. Efficacy of Conjugate 45a and Oseltamivir Against Influenza H1N1 A/CA/12/2012 and A/PR/8/1934 in a Lethal Mouse Model Conjugate 45a and oseltamivir were evaluated against lethal challenge by two influenza H1N1 subtypes (A/PR/8/34 and A/CA12/12) in female BALB/c mice (Charles River Laboratories, 6-8 weeks). The experiment comprised 10 groups of 5 mice split into two experimental arms (Table 204). At T+2 h, mice were intramuscularly (IM) administered conjugate 45a at 0.3 mg/kg in a single dose. Also at T+2 h mice were orally administered oseltamivir at 5 or 50 mg/kg, twice daily for 5 days. Control mice were treated IM with vehicle (PBS) or hIgG1 Fc only. Two hours prior to compound administration mice were intranasally challenged with 3× the LD95 of A/PR/8/34 (3E2 pfu) or A/CA/12/12 (3E4 pfu). For viral challenge mice were anesthetized with a mixture of ketamine/xylazine (150 and 10 mg/kg respectively), and the virus was given in a volume of 30 µl. Mortality and body weights (BW) were recorded daily for 14 days and any animal with a 20% loss of BW was scored as a death.

Against A/PR/8/34 challenge mice treated with vehicle or Fc only (SEQ ID NO: 72) succumbed to infection by day 7, while those administered Conjugate 45a at 0.3 mg/kg were fully protected (Table 205). For oseltamivir treated animals, a 50 mg/kg dose was 80% protective while a dose of 5 mg/kg only delayed death until day 10. Against A/CA/12/12 vehicle and Fc control animals reached 100% mortality by day 6, and once again, a 0.3 mg/kg dose of Conjugate 45a was fully protective. In contrast, oseltamivir was unprotective at 5 mg/kg, and even the 50 mg/kg dose group only had 40% survival. BW data for both study arms supported the mortality findings (Tables 205-208).

Collectively this data demonstrates superior activity by a single 0.3 mg/kg dose of conjugate is superior to oseltamivir, even when the latter is dosed at 5 or 50 mg/kg twice daily for 5 days.

TABLE 204

Study design

| Group | Influenza A strain (IN challenge) | Test Article | DAR | Route, Schedule | Dose (mg/kg) | Dose volume ml/kg | Cmpd prep mg/ml | Vol needed (ml) | N |
|---|---|---|---|---|---|---|---|---|---|
| 1 | A/PR/8/34 (H1N1) 3E2 PFU/mouse | Vehicle (PBS) | — | IM, single, T + 2 h | — | 5 | — | 1 | 5 |
| 2 | | Fc only | — | IM, single, T + 2 h | 0.3 | 5 | 0.06 | 1 | 5 |
| 3 | | Conjugate 45a | 4.6 | IM, single, T + 2 h | 0.3 | 5 | 0.06 | 1 | 5 |
| 4 | | Oseltamivir | — | PO, bid × 5 days | 5 | 10 | 0.5 | 14 | 5 |
| 5 | | Oseltamivir | — | PO, bid × 5 days | 50 | 10 | 5 | 14 | 5 |
| | | | | Arm II | | | | | |
| 6 | A/CA/12/12 (H1N1) 3E4 PFU/mouse | Vehicle (PBS) | — | IM, single, T + 2 h | — | 5 | — | 1 | 5 |
| 7 | | Fc only | — | IM, single, T + 2 h | 0.3 | 5 | 0.06 | 1 | 5 |
| 8 | | Conjugate 45a | 4.6 | IM, single, T + 2 h | 0.3 | 5 | 0.06 | 1 | 5 |
| 9 | | Oseltamivir | — | PO, bid × 5 days | 5 | 10 | 0.5 | 14 | 5 |
| 10 | | Oseltamivir | — | PO, bid × 5 days | 50 | 10 | 5 | 14 | 5 |

TABLE 205

% Survival of A/PR/8/34

| Day post challenge | Vehicle (PBS) | Fc only (0.3 mpk) | Conjugate 45a (0.3 mpk) | Oseltamivir (5 mpk) | Oseltamivir (50 mpk) |
|---|---|---|---|---|---|
| 0 | 100 | 100 | 100 | 100 | 100 |
| 1 | 100 | 100 | 100 | 100 | 100 |
| 2 | 100 | 100 | 100 | 100 | 100 |
| 3 | 100 | 100 | 100 | 100 | 100 |
| 4 | 100 | 100 | 100 | 100 | 100 |
| 5 | 100 | 100 | 100 | 100 | 100 |
| 6 | 0 | 60 | 100 | 100 | 100 |
| 7 | | 0 | 100 | 100 | 100 |
| 8 | | | 100 | 60 | 100 |
| 9 | | | 100 | 40 | 100 |
| 10 | | | 100 | 0 | 80 |
| 11 | | | 100 | | 80 |
| 12 | | | 100 | | 80 |
| 13 | | | 100 | | 80 |
| 14 | | | 100 | | 80 |

TABLE 206

% Survival of A/CA/12/2012 challenged mice.

| Day post challenge | Vehicle (PBS) | Fc only (0.3 mpk) | Conjugate 45a (0.3 mpk) | Oseltamivir (5 mpk) | Oseltamivir (50 mpk) |
|---|---|---|---|---|---|
| 0 | 100 | 100 | 100 | 100 | 100 |
| 1 | 100 | 100 | 100 | 100 | 100 |
| 2 | 100 | 100 | 100 | 100 | 100 |
| 3 | 100 | 100 | 100 | 100 | 100 |
| 4 | 80 | 100 | 100 | 100 | 100 |
| 5 | 0 | 20 | 100 | 20 | 40 |
| 6 | | 0 | 100 | 20 | 40 |
| 7 | | | 100 | 20 | 40 |
| 8 | | | 100 | 0 | 40 |
| 9 | | | 100 | | 40 |
| 10 | | | 100 | | 40 |
| 11 | | | 100 | | 40 |
| 12 | | | 100 | | 40 |
| 13 | | | 100 | | 40 |
| 14 | | | 100 | | 40 |

TABLE 207

Average % BW of A/PR/8/34 challenged mice, until the first death within a group

| Day post challenge | Vehicle (PBS) | Fc only (0.3 mpk) | Conjugate 45a (0.3 mpk) | Oseltamivir (5 mpk) | Oseltamivir (50 mpk) |
|---|---|---|---|---|---|
| 0 | 100 | 100 | 100 | 100 | 100 |
| 1 | 98.9 | 100.2 | 99.6 | 98.5 | 98.6 |
| 2 | 102 | 104.2 | 102.5 | 100.7 | 99.2 |
| 3 | 94.7 | 97.1 | 100.6 | 99.4 | 100.3 |
| 4 | 85.8 | 88.8 | 100.9 | 93.5 | 97.9 |
| 5 | 78.9 | 81.5 | 99 | 88.5 | 90.5 |
| 6 | 74.9 | 77.6 | 102 | 90 | 96 |
| 7 | | | 104 | 84.5 | 89.7 |
| 8 | | | 103.9 | 79.4 | 84.2 |
| 9 | | | 104.6 | | 86.3 |
| 10 | | | 105.4 | | 90.3 |
| 11 | | | 103.4 | | |
| 12 | | | 103.9 | | |
| 13 | | | 104.3 | | |
| 14 | | | 106.3 | | |

TABLE 208

Average % BW of A/CA/12/2012 challenged mice, until the first death within a group

| Day post challenge | Vehicle (PBS) | Fc only (0.3 mpk) | Conjugate 45a (0.3 mpk) | Oseltamivir (5 mpk) | Oseltamivir (50 mpk) |
|---|---|---|---|---|---|
| 0 | 100 | 100 | 100 | 100 | 100 |
| 1 | 99.6 | 97.6 | 100.2 | 98.3 | 98.9 |
| 2 | 92.2 | 90.6 | 91.2 | 92.9 | 93.5 |
| 3 | 85.4 | 83.5 | 86.7 | 86.4 | 86.3 |
| 4 | 78 | 77.9 | 85.5 | 80.9 | 82.2 |
| 5 | | | 87.2 | 76.2 | 78.7 |
| 6 | | | 90.7 | | |
| 7 | | | 94.2 | | |
| 8 | | | 96.3 | | |
| 9 | | | 97.8 | | |
| 10 | | | 100 | | |
| 11 | | | 98.6 | | |
| 12 | | | 98.1 | | |

TABLE 208-continued

Average % BW of A/CA/12/2012 challenged mice, until the first death within a group

| Day post challenge | Vehicle (PBS) | Fc only (0.3 mpk) | Conjugate 45a (0.3 mpk) | Oseltamivir (5 mpk) | Oseltamivir (50 mpk) |
|---|---|---|---|---|---|
| 13 |  |  | 98.5 |  |  |
| 14 |  |  | 100.4 |  |  |

Example 212. Efficacy of Conjugate 45a Against Influenza B/Florida/4/2006 (Yamagata) in a 28-Day Mouse Prevention Model Conjugate 45a was evaluated against lethal challenge by an influenza B seasonal influenza subtype (B/Florida/4/2006) in female BALB/c mice (Charles River Laboratories, 6-8 weeks). The experiment comprised 7 groups of 5 mice. On day 0, mice were subcutaneously (SC) administered conjugate 45a at 3, 1, 0.3, 0.01, or 0.3 mg/kg in a single dose. Control mice were also treated by the same route with vehicle (PBS) or hIgG1 Fc only. Twenty-eight Days after administration of test article, mice were challenged intranasally with 3× the $LD_{95}$ of B/Florida. A summary of the experimental design is provided in Table 209. For viral challenge mice were anesthetized with a mixture of ketamine/xylazine (150 and 10 mg/kg respectively), and the virus was given in a volume of 30 µl. Mortality and body weights (BW) were recorded daily for 21 days and any animal with a 20% loss of body weight was scored as a death.

Mice treated with vehicle only reached mortality by day 7, while those treated with the Fc only negative control succumbed to infection by day 8 (Table 210). In contrast, those receiving conjugate 45a at 1 or 3 mg/kg were fully protected over the course of the study. Group 4 animals which were treated at 0.3 mg/kg also demonstrated 80% survival. At a dose concentration of 0.1 mg/kg survival dropped to 40%, and at 0.03 mg/kg no protection was afforded by conjugate 45a. BW data (Table 211) mirrored the mortality results and mice receiving a fully protective dose (1 and 3 mg/kg) showed less than a transient 5% drop in BW on day 4, before recovering their starting BW.

Collectively, these data support the robust potency of conjugate 45a against in important seasonal subtype of influenza. It also demonstrates the utility of conjugate 45a as a long-term preventative against influenza.

TABLE 209

General study design

| Group | Influenza B strain (IN challenge) | Test Article | DAR | Route, Schedule | Dose (mg/kg) | Dose timing | Dose volume ml/kg | Cmpd prep mg/ml | Vol needed (ml) | N |
|---|---|---|---|---|---|---|---|---|---|---|
| 1 | B/FL/4/2006 | Vehicle (PBS) | — | SC, single | — | T − 28 Days | 10 | — | 1.5 | 5 |
| 2 | (Yamagata) | Fc only | — | SC, single | 3 | T − 28 Days | 10 | 0.3 | 1.5 | 5 |
| 3 | 5E4 | Conjugate 45a | 4.7 | SC, single | 3 | T − 28 Days | 10 | 0.3 | 1.5 | 5 |
| 4 | PFU/mouse | Conjugate 45a | 4.7 | SC, single | 1 | T − 28 Days | 10 | 0.1 | 1.5 | 5 |
| 5 |  | Conjugate 45a | 4.7 | SC, single | 0.3 | T − 28 Days | 10 | 0.03 | 1.5 | 5 |
| 6 |  | Conjugate 45a | 4.7 | SC, single | 0.1 | T − 28 Days | 10 | 0.01 | 1.5 | 5 |
| 7 |  | Conjugate 45a | 4.7 | SC, single | 0.03 | T − 28 Days | 10 | 0.003 | 1.5 | 5 |

TABLE 210

% Survival for study groups

| Day Post Infection | Vehicle (PBS) | Fc only (3 mpk) | Conjugate 45a (3 mpk) | Conjugate 45a (1 mpk) | Conjugate 45a (0.3 mpk) | Conjugate 45a (0.1 mpk) | Conjugate 45a (0.03 mpk) |
|---|---|---|---|---|---|---|---|
| 0 | 100 | 100 | 100 | 100 | 100 | 100 | 100 |
| 1 | 100 | 100 | 100 | 100 | 100 | 100 | 100 |
| 2 | 100 | 100 | 100 | 100 | 100 | 100 | 100 |
| 3 | 100 | 100 | 100 | 100 | 100 | 100 | 100 |
| 4 | 100 | 100 | 100 | 100 | 100 | 100 | 100 |
| 5 | 100 | 100 | 100 | 100 | 100 | 100 | 100 |
| 6 | 60 | 100 | 100 | 100 | 100 | 100 | 100 |
| 7 | 0 | 20 | 100 | 100 | 80 | 80 | 80 |
| 8 |  | 0 | 100 | 100 | 80 | 40 | 0 |
| 9 |  |  | 100 | 100 | 80 | 40 |  |
| 10 |  |  | 100 | 100 | 80 | 40 |  |
| 11 |  |  | 100 | 100 | 80 | 40 |  |
| 12 |  |  | 100 | 100 | 80 | 40 |  |
| 13 |  |  | 100 | 100 | 80 | 40 |  |
| 14 |  |  | 100 | 100 | 80 | 40 |  |
| 15 |  |  | 100 | 100 | 80 | 40 |  |
| 16 |  |  | 100 | 100 | 80 | 40 |  |
| 17 |  |  | 100 | 100 | 80 | 40 |  |
| 18 |  |  | 100 | 100 | 80 | 40 |  |
| 19 |  |  | 100 | 100 | 80 | 40 |  |

TABLE 210-continued

% Survival for study groups

| Day Post Infection | Vehicle (PBS) | Fc only (3 mpk) | Conjugate 45a (3 mpk) | Conjugate 45a (1 mpk) | Conjugate 45a (0.3 mpk) | Conjugate 45a (0.1 mpk) | Conjugate 45a (0.03 mpk) |
|---|---|---|---|---|---|---|---|
| 20 | | | 100 | 100 | 80 | 40 | |
| 21 | | | 100 | 100 | 80 | 40 | |

TABLE 211

Average % daily BWs until the first death within a group

| Day Post Infection | Vehicle (PBS) | Fc only (3 mpk) | Conjugate 45a (3 mpk) | Conjugate 45a (1 mpk) | Conjugate 45a (0.3 mpk) | Conjugate 45a (0.1 mpk) | Conjugate 45a (0.03 mpk) |
|---|---|---|---|---|---|---|---|
| 0 | 100 | 100 | 100 | 100 | 100 | 100 | 100 |
| 1 | 97 | 94.9 | 97.1 | 98.3 | 96.9 | 96.9 | 97.2 |
| 2 | 97.8 | 96.3 | 97.7 | 98.5 | 99.5 | 97.9 | 98.9 |
| 3 | 93.9 | 94.3 | 99.9 | 100.9 | 99.7 | 97.6 | 98.8 |
| 4 | 84.5 | 85.3 | 95.8 | 95.8 | 90.9 | 88.9 | 89.3 |
| 5 | 81.4 | 83.1 | 102 | 99.4 | 95.1 | 90.6 | 87.5 |
| 6 | 76.5 | 78.2 | 101.1 | 99.8 | 91.9 | 85.9 | 81.9 |
| 7 | | | 98.7 | 97.9 | 87 | 79.5 | 76 |
| 8 | | | 99.6 | 97.9 | 88 | | |
| 9 | | | 99.6 | 99 | | | |
| 10 | | | 99.9 | 100.2 | | | |
| 11 | | | 101.9 | 100.7 | | | |
| 12 | | | 99.5 | 99.4 | | | |
| 13 | | | 100 | 99.4 | | | |
| 14 | | | 99.4 | 101 | | | |
| 15 | | | 98 | 97 | | | |
| 16 | | | 100 | 99.4 | | | |
| 17 | | | 97.5 | 98.2 | | | |
| 18 | | | 99.4 | 100.4 | | | |
| 19 | | | 98.8 | 100.9 | | | |
| 20 | | | 100.8 | 101.9 | | | |
| 21 | | | 100 | 100.1 | | | |

Example 213. Fc-Mediated Immune Contribution of Conjugate 45a

Efficacy studies were conducted in 6-8 weeks female BALB/c mice (Charles River) or Fcer1g$^{-/-}$ model 583 (Taconic) challenged intranasally with 3E2 PFU/mouse (3× the LD9s) of mouse-adapted influenza A/Puerto Rico/8/1934 (H1N1) or with 3e4 PFU/mouse of influenza A/CA/07/2009 (H1N1)pdm. AVCs or controls—human IgG1 Fc or PBS—were administered as a single dose administered subcutaneously (SC) or intramuscular (IM) as indicated 2 h post-challenge at 0.03-3 mg/kg. Body weights (BW) were recorded daily. Mortality is defined as body weight loss of greater 20% for two consecutive days or when animals are moribund.

For viral burden and cytokine analysis, at 4 days post-infection, mice were sacrificed by $CO_2$ and both lung lobes were harvested. Lungs were homogenized with 1 mm silica beads in 1 mL PBS using a MagNA Lyser (Roche). Homogenization was carried out at 6,000 rpm for 60 s and chilled on ice for 5 min in-between runs. After lung homogenization tubes were centrifuged for 10 min at 600×g and supernatant was transferred into new tube. For PFU determination, supernatants of lung homogenate were diluted in infection buffer ranging from $10^{-1}$ to $10^{-6}$. 100 µL of virus dilutions were added to confluent monolayer of MDCK cells in 24 well plates and incubated for 1 h at room temperature with rocking every 15 min. After removing the virus, liquid overlay media containing Avicel was added to MDCK cells. Cells were incubation at 37° C., 5% $CO_2$ for 40 h. After incubation, the media was removed and cells were stained with crystal violet to enumerate plaques. and plaque forming units (PFU) were calculated relative to weight of the lung (PFU/g lung). For cytokine analysis, supernatants of lung homogenate were serially diluted 2-fold in 96 well plate. Cytokine levels for IL-6, MIP-1ca and MCP-1 were determined by ELISA according to manufacturer's instructions (R&D Systems).

Conjugate 45a at 0.03 mg/kg or higher dose was fully protective against a lethal challenge with influenza A/CA/07/2009 (H1N1)pdm in Balb/C (WT) and Fcer1g$^{-/-}$ (KO) mice (see Table 212) suggesting that the protection of conjugate 45a is independent of Fc-mediated immune contribution.

TABLE 212

Efficacy of Conjugate 45a in Balb/C mice (WT) or Fcer1g$^{-/-}$ (KO) mice against influenza A/CA/07/2009 (H1N1)pdm.

| Test article [mg/kg] | Dose route | Mouse background | % Survival |
|---|---|---|---|
| hIgG1 Fc [1] | IM | WT | 0 |
| conjugate 45a [0.03] | IM | WT | 100 |
| conjugate 45a [0.1] | IM | WT | 100 |
| conjugate 45a [0.3] | IM | WT | 100 |
| conjugate 45a [1] | IM | WT | 100 |
| hIgG1 Fc [1] | IM | KO | 0 |
| conjugate 45a [0.03] | IM | KO | 100 |

TABLE 212-continued

Efficacy of Conjugate 45a in Balb/C mice (WT) or Fcer1g$^{-/-}$ (KO) mice against influenza A/CA/07/2009 (H1N1)pdm.

| Test article [mg/kg] | Dose route | Mouse background | % Survival |
|---|---|---|---|
| conjugate 45a [0.1] | IM | KO | 100 |
| conjugate 45a [0.3] | IM | KO | 100 |
| conjugate 45a [1] | IM | KO | 100 |

Conjugate 45a at 0.1 mg/kg or higher dose was fully protective against a lethal challenge with influenza A/PR/8/1934 (H1N1) in Balb/C mice (see Table 213). To determine the immune contribution in WT Balb/c mice, a version of conjugate 45a on an aglycosylated Fc mutant (N297A), conjugate 49 (e.g., an Fc comprising SEQ ID NO: 72 further comprising an N297A mutation), was made. This Fc mutant is known to result in largely abrogated immune effector function. conjugate 49 was also protective at 0.1 mg/kg suggesting that the protection conferred by conjugate 45a is independent of Fc-mediated immune contribution. To determine if the efficacy of conjugate 45a can be enhanced by increased Fc-mediated immune effector function, a conjugate 45a version was conjugated to an Fc comprising a DE (S239D/1332E) mutation (e.g., an Fc comprising SEQ ID NO: 72 further comprising an S239D/1332E mutation), conjugate 50. Conjugate 50 was fully protective at 0.1 mg/kg or higher dose, which is comparable to activity of conjugate 45a. However, following treatment with conjugate 50 at 0.03 mg/kg, one mouse survived. Thus, the activity of conjugate 45a at DAR 4.5 is independent of Fc-mediated immune contribution.

TABLE 213

Efficacy of AVCs against influenza A/PR/8/1934 (H1N1) in Balb/C mice (WT).

| Test article [mg/kg] | Dose route | Fc | % Survival |
|---|---|---|---|
| hIgG1 Fc [1] | IM | WT | 0 |
| conjugate 45a [0.01] | IM | WT | 0 |
| conjugate 45a [0.03] | IM | WT | 0 |
| conjugate 45a [0.1] | IM | WT | 100 |
| conjugate 45a [0.3] | IM | WT | 100 |
| conjugate 49 [0.01] | IM | N297A | 0 |
| conjugate 49 [0.03] | IM | N297A | 0 |
| conjugate 49 [0.1] | IM | N297A | 100 |
| conjugate 49 [0.3] | IM | N297A | 100 |
| conjugate 49 [1] | IM | N297A | 100 |
| conjugate 50 [0.01] | IM | S239D/I332E | 0 |
| conjugate 50 [0.03] | IM | S239D/I332E | 20 |
| conjugate 50 [0.1] | IM | S239D/I332E | 100 |
| conjugate 50 [0.3] | IM | S239D/I332E | 100 |

After a lethal challenge with influenza in a mouse model, lung PFU burden and lung cytokine levels were determined on day 4 post-infection. Conjugate 45a and conjugate 49 demonstrated a dose-dependent log reduction in viral burden to comparable levels (see table 214). Conjugate 50 demonstrated higher reduction in viral burden at 0.1 mg/kg between 0.96 or 0.83 logs higher as for conjugate 45a or conjugate 49, respectively. No biological relevant difference was observed between negative controls, PBS and hIgG1 Fc as expected.

TABLE 214

Viral burden reduction by conjugates on day 4 post-infection challenged with influenza A/PR/8/1934 (H1N1) in a mouse model.

| Test article [mg/kg] | Dose route | PFU/g | Log reduction |
|---|---|---|---|
| PBS | SC | 2.19E + 07 | 0.00 |
| hIgG1 Fc [3] | SC | 2.85E + 07 | −0.11 |
| conjugate 45a [0.03] | SC | 1.84E + 07 | 0.07 |
| conjugate 45a [0.1] | SC | 6.34E + 06 | 0.54 |
| conjugate 45a [0.3] | SC | 2.63E + 05 | 1.92 |
| conjugate 45a [1] | SC | 9.99E + 03 | 3.34 |
| conjugate 45a [3] | SC | 1.53E + 03 | 4.16 |
| conjugate 49 [0.03] | SC | 9.06E + 06 | 0.38 |
| conjugate 49 [0.1] | SC | 4.68E + 06 | 0.67 |
| conjugate 49 [0.3] | SC | 1.36E + 05 | 2.21 |
| conjugate 49 [1] | SC | 4.57E + 04 | 2.68 |
| conjugate 49 [3] | SC | 5.89E + 03 | 3.57 |
| conjugate 50 [0.1] | SC | 6.40E + 05 | 1.53 |

Similarly, conjugate 45a and conjugate 49 reduced cytokines, IL-6, MIP-1a, MOP-1, in dose-dependency to similar levels (see table 215). As for conjugate 50 at 0.1 mg/kg slightly lower levels for IL-6 and MIP-1a, but comparable levels were observed, conjugate 50 at 0.1 mg/kg showed markedly increased MOP-1 levels as compared to conjugate 45a and conjugate 49. No biological relevant difference was observed between negative controls, PBS and hIgG1 Fc as expected. Table 215: Cytokine levels in fold-change versus uninfected control for IL-6, MIP-1ac and MOP-i on dy 4 post-infection challenged with influenza A in a mouse model.

TABLE 215

Cytokine levels in fold-change versus uninfected control for IL-6, MIP-1α and MCP-1 on day 4 post-infection challenged with influenza A in a mouse model.

| Test article [mg/kg] | IL-6 | MCP-1 | MIP-1α |
|---|---|---|---|
| PBS | 4.4 | 30.0 | 13.7 |
| hIgG1 Fc [3] | 4.6 | 31.9 | 15.4 |
| conjugate 45a [0.03] | 3.1 | 14.8 | 14.3 |
| conjugate 45a [0.1] | 2.5 | 10.2 | 7.1 |
| conjugate 45a [0.3] | 2.1 | 3.2 | 3.7 |
| conjugate 45a [1] | 2.0 | 1.2 | 2.2 |
| conjugate 45a [3] | 2.0 | 1.2 | 2.1 |
| conjugate 49 [0.03] | 2.3 | 19.4 | 10.6 |
| conjugate 49 [0.1] | 2.4 | 11.1 | 5.7 |
| conjugate 49 [0.3] | 2.9 | 10.7 | 5.0 |
| conjugate 49 [1] | 2.5 | 4.7 | 2.4 |
| conjugate 49 [3] | 2.3 | 4.5 | 2.2 |
| conjugate 50 [0.1] | 1.9 | 25.6 | 4.9 |
| Uninfected | 1.0 | 1.0 | 1.0 |

Example 214. Efficacy of Conjugate 45a Against Influenza 2020-2021 Vaccine Strains Neuraminidase Inhibition (NAI)

NAI activity was determined using the commercial NA-Fluor kit. Briefly, live viruses were adjusted to 1e5 PFU/mL and added to appropriate wells in 96 well plate (black). Test articles were added at concentrations ranging from 0.001 to 1,000 nM to appropriate wells. Virus and test article were incubated for 20-30 min at 37° C., 5% $CO_2$. Next, NA substrate was added to each well and incubated for 1 h at 37° C., 5% $CO_2$. NAI was determined by reading fluorescence at 355 nm excitation/460 nm emission. $IC_{50}$ was calculated with GraphPad Prism version 8 using nonlinear regression analysis (Dose-response (Inhibition)).

Conjugate 45a demonstrated comparable potency by $IC_{50}$ as compared to oseltamivir or zanamivir in NAI against influenza vaccine strains 2020-21 for Northern Hemisphere (Table 216).

TABLE 216

Activity of conjugate 45a in neuraminidase inhibition (NAI) assay against influenza vaccine strains 2020-21 for Northern Hemisphere ($IC_{50}$)

| influenza strain | subtype/ lineage | conjugate 45a [nM] | Oseltamivir [nM] | Zanamivir [nM] |
|---|---|---|---|---|
| A/Hawaii/70/2019 | H1N1pdm09 | 0.21 | 0.32 | 0.26 |
| A/Hong Kong/2671/2019 | H3N2 | 4.8 | 0.76 | 1.05 |
| B/Phuket/3073/2013 | Yamagata | 4.58 | 24.44 | 2.78 |
| B/Washington/02/2019 | Victoria | 3.11 | 16.71 | 2.3 |

Enzyme-Linked Lectin Assay (ELLA).

Nunc Maxisorp 96-well plates (ThermoFisher) were coated with 2.5 μg fetuin (Sigma-Aldrich) in 1×KPL coating buffer (SeraCare) overnight at 4° C. The next day, plates were washed with PBS at pH 7.4 supplemented with 0.05% Tween 20 (PBST). Test articles were tested at 0.001-1000 nM and added in 50 μL/well. Influenza virus was added at 5e4-5e5 PFU/mL in 50 μL/well. Plates were incubated for 16-18 h at 37° C., 5% $CO_2$. After washing plates, peanut agglutinin conjugated to HRP (PNA-HRP) was added at 0.13 μg in 100 uL buffer for 2 h, washed again and developed with 100 μL/well TMB substrate (BD) for 3-5 min. The reaction was stopped with 100 μL/well 1 N $H_2SO_4$. Absorbance was read at 450 nm with an EnSpire multimode plate reader. $IC_{50}$ was calculated with GraphPad Prism version 8 using nonlinear regression analysis (Dose-response (Inhibition)).

Conjugate 45a demonstrated increased potency by $IC_{50}$ as compared to oseltamivir or zanamivir in NAI against influenza vaccine strains 2020-21 for Northern Hemisphere (Table 217).

TABLE 217

Activity of conjugate 45a in enzyme-linked lectin assay (ELLA) against influenza vaccine strains 2020-21 for Northern Hemisphere ($IC_{50}$)

| influenza strain | subtype/ lineage | conjugate 45a [nM] | hIgG1 Fc [nM] | Oseltamivir [nM] | Zanamivir [nM] |
|---|---|---|---|---|---|
| A/Hawaii/70/2019 | H1N1pdm09 | 0.2 | >1,000 | 5.9 | 2.7 |
| A/Hong Kong/2671/2019 | H3N2 | 0.1 | >1,000 | 0.3 | 0.4 |
| B/Phuket/3073/2013 | Yamagata | 2.8 | >1,000 | 28.8 | 9 |
| B/Washington/02/2019 | Victoria | 3.9 | >1,000 | 47.9 | 6.6 |

Plaque Reduction Assay (PRA).

Test articles ranging from 0.3 to 100 nM were incubated with virus were pre-incubated in buffer containing 0.28% bovine serum albumin and $Ca^{2+}/Mg^{2+}$ in PBS for 30 min at room temperature (RT). A confluent monolayers of Madin Darby Canine Kidney (MDCK) cells in 24 well plate were washed once with PBS. After incubation of test article and virus, both were added to MDCK cells. The MOI for each drug-virus combination was selected to target 30 plaques in the PBS control well. Virus and test article were removed after 1 h and the infected cells were incubated for 48 h at 35° C. in the presence the test article diluted in a mixture of 1.25% Avicel, DMEM, 0.01% DEAE- dextran and 2 μg/mL of TPCK trypsin. After 48 h the Avicel mixture was removed, cells were fixed with paraformaldehyde and stained with 1% crystal violet to count the plaques. $EC_{50}$ was calculated with GraphPad Prism version 8 using nonlinear regression analysis (Dose-response (Inhibition)).

Conjugate 45a demonstrated increased potency by $EC_{50}$ as compared to oseltamivir, zanamivir or baloxavir in PRA against influenza vaccine strains 2020-21 for Northern Hemisphere (Table 218).

TABLE 218

Activity of conjugate 45a in plaque reduction assay (PRA) against influenza vaccine strains 2020-21 for Northern Hemisphere ($EC_{50}$)

| influenza strain | subtype/ lineage | conjugate 45a [nM] | Oseltamivir [nM] | Zanamivir [nM] | Baloxavir [nM] |
|---|---|---|---|---|---|
| A/Hawaii/70/2019 | H1N1pdm09 | 0.14 | 7.08 | 3.69 | 10.3 |
| B/Phuket/3073/2013 | Yamagata | 2.61 | 28.5 | 13.9 | 30.96 |
| B/Washington/02/2019 | Victoria | 7.46 | 28.72 | 9.77 | 18.27 |

Cytopathic Effect (CPE).

A confluent monolayer of MDCK Siat1 cells in 96 well plate was incubated with test articles at concentrations ranging between 0.01-10,000 nM. After 1 h incubation at RT, influenza virus was added at MOI 0.01. After an additional 1 h incubation at RT, plates were incubated for 3 days for influenza A or 5 days for influenza B at 37° C., 5% $CO_2$. CPE was determined by crystal violet staining by reading absorbance at 595 nm. $EC_{50}$ was calculated with GraphPad Prism version 8 using nonlinear regression analysis (Dose-response (Inhibition)).

Conjugate 45a demonstrated increased potency by $EC_{50}$ as compared to oseltamivir, zanamivir or baloxavir in PRA against influenza vaccine strains 2020-21 for Northern Hemisphere (Table 219).

TABLE 219

Activity of conjugate 45a in cytopathic effect (CPE) assay against
influenza vaccine strains 2020-21 for Northern Hemisphere ($EC_{50}$)

| influenza strain | subtype/ lineage | conjugate 45a [nM] | Oseltamivir [nM] | Zanamivir [nM] | Baloxavir [nM] |
|---|---|---|---|---|---|
| A/Hawaii/70/2019 | H1N1pdm09 | 1.65 | 326.6 | 686.2 | 11.1 |
| A/Hong Kong/2671/2019 | H3N2 | 0.38 | 7.7 | 170 | 1 |
| B/Phuket/3073/2013 | Yamagata | 0.33 | 27.6 | 5.2 | 10.01 |
| B/Washington/02/2019 | Victoria | 1.06 | 1028 | 1.93 | 9.98 |

Example 215. Efficacy of Conjugate 45a (*Protein a Column Purified and *Protein a Column Flow-Through) Against Influenza A/Puerto Rico/8/1934 (H1N1) in a Lethal Mouse Model Conjugate 45a (protein A purified) and *conjugate 45a (protein A column flow-through) were evaluated against a lethal IAV H1N1 influenza infection in female BALB/c mice (Charles River Laboratories, 6-8 weeks). The challenge virus (A/Puerto Rico/8/1934) is a mouse-adapted isolate capable of causing lethal infections in mice. The experiment comprised 13 groups of 5 mice and the purpose was to evaluate the relative potency between the three test agents. At day 0, all mice were challenged with virus at 3× the LD95 (5E2 pfu) by intranasal (IN) inoculation in a volume of 30 µl, after being anesthetized with a mixture of ketamine/xylazine (150 and 10 mg/kg respectively). Group 1 consisted of control mice treated with vehicle only, the remaining groups received one of the conjugates at doses ranging from 0.01 to 0.3 mg/kg. Mortality and body weights (BW) were recorded daily for 14 days and any animal with a cumulative 20% loss of weight for 2 consecutive days was scored as a death.

Test groups received a single intramuscular (IM) injection, 2 hours post viral challenge of test article (study outline is detailed in Table 220). Injections were in the thigh muscle of the right hind limb at a dose volume of 5 ml/kg.

TABLE 220

Study outline for Conjugate 45a process development study

| Group | Influenza A strain (IN challenge) | Test Article | Route, Schedule | Dose (mg/kg) | N |
|---|---|---|---|---|---|
| 1 | A/PR/8/34 (H1N1) 5E2 PFU/mouse | Vehicle (PBS) | IM, single, T + 2 h | — | 5 |
| 2 | | Conjugate 45a (protein A column purified) | IM, single, T + 2 h | 0.3 | 5 |
| 3 | | | IM, single, T + 2 h | 0.1 | 5 |
| 4 | | | IM, single, T + 2 h | 0.03 | 5 |
| 5 | | | IM, single, T + 2 h | 0.01 | 5 |
| 6 | | *Conjugate 45a (protein A column flow-through) | IM, single, T + 2 h | 0.3 | 5 |
| 7 | | | IM, single, T + 2 h | 0.1 | 5 |
| 8 | | | IM, single, T + 2 h | 0.03 | 5 |
| 9 | | | IM, single, T + 2 h | 0.01 | 5 |

Animals treated with vehicle only began to reach mortality on Day 6, with 100% mortality by Day 8 (FIG. 121 and Table 221). In contrast, both conjugates (e.g., protein A column purified conjugate 45a and protein A column flow-through *conjugate 45a) were fully protective at 0.1 and 0.3 mg/kg through study end (Day 14). At the two lowest test concentrations (0.03 and 0.01 mg/kg), no, or partial protection was seen (40 and 0% for Conjugate 45a, respectively; 80 and 40% for *Conjugate 45a). However the differences between conjugates at 0.03 and 0.01 mg/kg was not statistically significant (Log-rank Mantel-Cox test) and probably represents normal experimental variation from very low test concentrations.

TABLE 221

% survival by group and day (mg/kg)

| Day | Vehicle (PBS) | Conjugate 45a (0.3) | Conjugate 45a (0.1) | Conjugate 45a (0.03) | Conjugate 45a (0.01) | *Conjugate 45a (0.3) | *Conjugate 45a (0.1) | *Conjugate 45a (0.03) | *Conjugate 45a (0.01) |
|---|---|---|---|---|---|---|---|---|---|
| 0 | 100 | 100 | 100 | 100 | 100 | 100 | 100 | 100 | 100 |
| 1 | 100 | 100 | 100 | 100 | 100 | 100 | 100 | 100 | 100 |
| 2 | 100 | 100 | 100 | 100 | 100 | 100 | 100 | 100 | 100 |
| 3 | 100 | 100 | 100 | 100 | 100 | 100 | 100 | 100 | 100 |
| 4 | 100 | 100 | 100 | 100 | 100 | 100 | 100 | 100 | 100 |
| 5 | 100 | 100 | 100 | 100 | 100 | 100 | 100 | 100 | 100 |
| 6 | 80 | 100 | 100 | 100 | 100 | 100 | 100 | 100 | 100 |
| 7 | 20 | 100 | 100 | 100 | 100 | 100 | 100 | 100 | 100 |
| 8 | 0 | 100 | 100 | 100 | 40 | 100 | 100 | 100 | 80 |
| 9 | | 100 | 100 | 40 | 0 | 100 | 100 | 80 | 40 |
| 10 | | 100 | 100 | 40 | | 100 | 100 | 80 | 40 |
| 11 | | 100 | 100 | 40 | | 100 | 100 | 80 | 40 |
| 12 | | 100 | 100 | 40 | | 100 | 100 | 80 | 40 |
| 13 | | 100 | 100 | 40 | | 100 | 100 | 80 | 40 |
| 14 | | 100 | 100 | 40 | | 100 | 100 | 80 | 40 |

Conjugate 45a purified using a protein A column;
*Conjugate 45a from protein A column flowthrough (e.g., conjugate that did not bind to protein A)

Body weight (BW) data (Table 222) was also evaluated for all dose groups. As expected, BW data largely reflected survival data with all fully protective doses with any conjugate demonstrating transient loss before recovery by study end. In these dose groups the average BW on Day 14 was 100% or greater. Collectively this data demonstrates the potency of all 3 conjugates against lethal challenge by influenza A (H1N1). Significantly, protection was achieved by a single IM injection of 0.1 mg/kg. By the conditions evaluated in this study Conjugates 45a and *Conjugate 45a (e.g., conjugate that did not bind to protein A column) demonstrated comparable potency.

vehicle only, and group 2 animals were dosed with Fc only (hIgG1 Fc), the remaining groups received one of the conjugates at doses ranging from 1 to 0.03 mg/kg. Mortality and body weights (BW) were recorded daily for 14 days and any animal with a cumulative 20% loss of weight for 2 consecutive days was scored as a death.

Survival data is presented in Table 224 and shows control animals (groups 1 and 2) reached full mortality on Day 6 as expected. In contrast, mice receiving either conjugate at 1.0 or 0.3 mg/kg were fully protected through study end (Day 21). At the lowest dose concentration (0.03 mg/kg) no significant protection was evident for either conjugate. How-

TABLE 222

% BW of animals by group and day (mg/kg)
(Data shown until the first death within a group)

| Day | Vehicle (PBS) | Conjugate 45a (0.3) | Conjugate 45a (0.1) | Conjugate 45a (0.03) | Conjugate 45a (0.01) | *Conjugate 45a (0.3) | *Conjugate 45a (0.1) | *Conjugate 45a (0.03) | *Conjugate 45a (0.01) |
|---|---|---|---|---|---|---|---|---|---|
| 0 | 100 | 100 | 100 | 100 | 100 | 100 | 100 | 100 | 100 |
| 1 | 99.5 | 100.5 | 99 | 100.1 | 99.2 | 99 | 98 | 99.3 | 99.3 |
| 2 | 98.4 | 101.8 | 99.8 | 98.6 | 101 | 101.4 | 97.1 | 100.7 | 99 |
| 3 | 93.3 | 103.1 | 99.4 | 98 | 98.6 | 101.9 | 98.3 | 100.8 | 99.2 |
| 4 | 87.7 | 101.5 | 94.4 | 94.1 | 92.7 | 103 | 97.9 | 98.8 | 93.5 |
| 5 | 82.2 | 97.8 | 96 | 92.3 | 90 | 99.6 | 95.2 | 97 | 89.4 |
| 6 | 78.6 | 101.6 | 99.2 | 91.8 | 86.5 | 99.8 | 97.7 | 99.1 | 91.9 |
| 7 |  | 102.7 | 99.6 | 86.7 | 81.1 | 102.1 | 98.7 | 93.3 | 84 |
| 8 |  | 104.3 | 103.1 | 83.9 | 76.4 | 104.6 | 101.7 | 92.4 | 79.9 |
| 9 |  | 102.2 | 100.3 | 80.4 |  | 102.4 | 97.7 | 93.1 |  |
| 10 |  | 99.2 | 100.8 |  |  | 102.5 | 98.4 |  |  |
| 11 |  | 105 | 103.2 |  |  | 104.8 | 100.1 |  |  |
| 12 |  | 105.1 | 101.8 |  |  | 103.8 | 101.1 |  |  |
| 13 |  | 103.8 | 102 |  |  | 102.9 | 100.8 |  |  |
| 14 |  | 105.1 | 103.8 |  |  | 102.4 | 101.1 |  |  |

Conjugate 45a purified using a protein A column;
*Conjugate 45a from protein A column flow-through (e.g., conjugate that did not bind to protein A)

Example 216. Comparison of Conjugates 45a and 46 in a Humanized Mouse Model (FcRn) Against Influenza A/California/07/2009Pdm (H1N1) in a Lethal Infection Study Conjugates 45a and 46 were evaluated against a lethal IAV H1N1 influenza infection in female B6.Cg-Fcgrttm1 Dcr Tg(FCGRT)32Dcr/DcrJ mice (6-8 weeks old; Jackson Labs #014565). These mice express the human neonatal receptor (FcRn) which is an essential factor in the prolonged half-life of antibodies or Fc containing therapeutics. Conjugate 46 contains the YTE Fc mutation which has been shown to extend half-life in humans and cynomolgus monkeys. Although the YTE mutation is silent in wild-type mice, it is permissive in transgenic murine species expressing FcRn. Therefore we evaluated the relative efficacy of Conjugates 45a and 46 which are identical except for the presence of the YTE mutation in the latter, to determine if prolonged half-life offered a potency advantage in a Day –7 prevention model.

The challenge virus (A/California/07/2009) is an H1N1 pandemic isolate capable of causing lethal infections in mice. The experiment comprised 10 groups of 5 mice (Table 223). Seven days prior to viral challenge mice were administered a single dose of test article by intramuscular (IM) injection into the thigh muscle of the right hind limb at a dose volume of 5 ml/kg. At day 0, all mice were challenged with virus at 3× the LD95 (3E4 pfu) by intranasal (IN) inoculation in a volume of 30 μl, after being anesthetized with a mixture of ketamine/xylazine (150 and 10 mg/kg respectively). Group 1 consisted of control mice treated with ever, at 0.1 mg/kg a relative difference in potency between Conjugates 45a and 46 was apparent. Conjugate 45a containing a wild-type Fc sequence was not significantly more potent than vehicle or Fc only dosed animals, while Conjugate 46 treated animals were (80% survival; P=0.0016 relative to vehicle) (FIG. 122). These data suggest the YTE mutation of Conjugate 46 offers a potency advantage over Conjugate 45a, likely due to prolonged half-life. BW data for all study groups is listed in Table 225 and supports the survival data.

Collectively this study demonstrates an increase in potency of conjugate 46, relative to conjugate 45a. As both conjugates have identical targeting moieties it follows that the improvement in efficacy of conjugate 46 is due to the YTE mutation. This conclusion is supported by plasma levels of both conjugates collected from study animals (0.1 mg/kg dose groups) the day prior to viral challenge (Conjugate 45a, 0.09 μg/ml; Conjugate 46, 0.48 μg/ml). The higher plasma levels of Conjugate 46 at the time of viral challenge resulted in superior protection relative to Conjugate 45a.

TABLE 223

General protocol outline for FcRn mouse study

| Group | Influenza A strain (IN challenge) | Test Article | Route, Schedule | Dose (mg/kg) | Dose timing | N |
|---|---|---|---|---|---|---|
| 1 | A/CA/–7/09 ~3E4 | Vehicle(PBS) | IM, single | — | T – 7 Days | 5 |
| 2 |  | hIgG1 Fc |  | 1 |  |  |

TABLE 223-continued

General protocol outline for FcRn mouse study

| Group | Influenza A strain (IN challenge) | Test Article | Route, Schedule | Dose (mg/kg) | Dose timing | N |
|---|---|---|---|---|---|---|
| 3 | PFU/mouse | Conjugate 45a | | 1 | | |
| 4 | | Conjugate 45a | | 0.3 | | |
| 5 | | Conjugate 45a | | 0.1 | | |
| 6 | | Conjugate 45a | | 0.03 | | |
| 7 | | Conjugate 46 | | 1 | | |
| 8 | | Conjugate 46 | | 0.3 | | |
| 9 | | Conjugate 46 | | 0.1 | | |
| 10 | | Conjugate 46 | | 0.03 | | |

TABLE 224

% survival by group and day (mg/kg)

| Day | Vehicle (PBS) | hIgG1 Fc | Conjugate 45a (1) | Conjugate 45a (0.3) | Conjugate 45a (0.1) | Conjugate 45a (0.03) | Conjugate 46 (1) | Conjugate 46 (0.3) | Conjugate 46 (0.1) | Conjugate 46 (0.03) |
|---|---|---|---|---|---|---|---|---|---|---|
| 0 | 100 | 100 | 100 | 100 | 100 | 100 | 100 | 100 | 100 | 100 |
| 1 | 100 | 100 | 100 | 100 | 100 | 100 | 100 | 100 | 100 | 100 |
| 2 | 100 | 100 | 100 | 100 | 100 | 100 | 100 | 100 | 100 | 100 |
| 3 | 100 | 100 | 100 | 100 | 100 | 100 | 100 | 100 | 100 | 100 |
| 4 | 100 | 80 | 100 | 100 | 100 | 100 | 100 | 100 | 100 | 100 |
| 5 | 20 | 60 | 100 | 100 | 100 | 100 | 100 | 100 | 100 | 100 |
| 6 | 0 | 0 | 100 | 100 | 80 | 80 | 100 | 100 | 100 | 20 |
| 7 | | | 100 | 100 | 60 | 20 | 100 | 100 | 100 | 0 |
| 8 | | | 100 | 100 | 20 | 20 | 100 | 100 | 80 | |
| 9 | | | 100 | 100 | 20 | 20 | 100 | 100 | 80 | |
| 10 | | | 100 | 100 | 20 | 20 | 100 | 100 | 80 | |
| 11 | | | 100 | 100 | 20 | 20 | 100 | 100 | 80 | |
| 12 | | | 100 | 100 | 20 | 20 | 100 | 100 | 80 | |
| 13 | | | 100 | 100 | 20 | 20 | 100 | 100 | 80 | |
| 14 | | | 100 | 100 | 20 | 20 | 100 | 100 | 80 | |
| 15 | | | 100 | 100 | 20 | 20 | 100 | 100 | 80 | |
| 16 | | | 100 | 100 | 20 | 20 | 100 | 100 | 80 | |
| 17 | | | 100 | 100 | 20 | 20 | 100 | 100 | 80 | |
| 18 | | | 100 | 100 | 20 | 20 | 100 | 100 | 80 | |
| 19 | | | 100 | 100 | 20 | 20 | 100 | 100 | 80 | |
| 20 | | | 100 | 100 | 20 | 20 | 100 | 100 | 80 | |
| 21 | | | 100 | 100 | 20 | 20 | 100 | 100 | 80 | |

TABLE 225

% BW of animals by group and day (mg/kg). *Data shown until the first death within a group

| Day Post Infection | Vehicle (PBS) | hIgG1 Fc | Conjugate 45a (1) | Conjugate 45a (0.3) | Conjugate 45a (0.1) | Conjugate 45a (0.03) | Conjugate 46 (1) | Conjugate 46 (0.3) | Conjugate 46 (0.1) | Conjugate 46 (0.03) |
|---|---|---|---|---|---|---|---|---|---|---|
| 0 | 100 | 100 | 100 | 100 | 100 | 100 | 100 | 100 | 100 | 100 |
| 1 | 97.2 | 97.7 | 97.8 | 100.4 | 99.4 | 98 | 96.9 | 100.8 | 99.4 | 98.6 |
| 2 | 89.5 | 90.7 | 96.7 | 95.6 | 94 | 92.8 | 96.3 | 100.7 | 94.3 | 91.8 |
| 3 | 82.9 | 83.8 | 98.7 | 91.9 | 86.8 | 88.3 | 97.8 | 95.2 | 86.5 | 85.4 |
| 4 | 79 | 80.1 | 100.9 | 93.3 | 84.4 | 85.3 | 97.7 | 97.1 | 86.5 | 83.5 |
| 5 | 75.1 | | 98.5 | 91.9 | 81.8 | 84 | 96.7 | 97.3 | 84.6 | 79.3 |
| 6 | | | 102 | 93.7 | 80.4 | 82.2 | 97.8 | 101.4 | 84.4 | 76.7 |
| 7 | | | 99.5 | 94.1 | | | 97.2 | 99.9 | 82.5 | |
| 8 | | | 99.8 | 94.5 | | | 98.3 | 100.8 | 84.8 | |
| 9 | | | 98.8 | | | | 98.3 | 102.4 | | |
| 10 | | | 99.3 | | | | 97.2 | 103.1 | | |
| 11 | | | 103.9 | | | | 101.4 | 103.5 | | |
| 12 | | | 103.8 | | | | 99.8 | 103.2 | | |
| 13 | | | 102.1 | | | | 100.2 | 102.8 | | |
| 14 | | | 103.8 | | | | 104.3 | 104.9 | | |
| 15 | | | 103.8 | | | | 102.1 | 106.2 | | |
| 16 | | | 101.9 | | | | 100 | 101.9 | | |
| 17 | | | 101.2 | | | | 102.3 | 103.6 | | |
| 18 | | | 101.9 | | | | 103.6 | 104.5 | | |
| 19 | | | 102.3 | | | | 104.3 | 104 | | |
| 20 | | | 102.4 | | | | 102.3 | 105.5 | | |
| 21 | | | 104.2 | | | | 102 | 106.9 | | |

Example 217. Efficacy of Conjugate 45a in an Influenza A (H1N1) Mouse Model Designed to Mimic the Early-Stage Pathogenies of Human Infections Previous examples provided in this patent have utilized a model in which mice are heavily sedated with ketamine/xylazine (150 and 10 mg/kg respectively) during viral challenge. After intranasal (IN) viral challenge (3× the LD9s in 30 µl) mice are kept on their backs until recovery (approx. 30 min). This enhances drainage of virus into the lungs (lower respiratory tract or LRT) generating a robust and very reproducible screening model for anti-influenza therapeutics. However, it does not replicate the natural infection process in which generally fewer viral particles are seeded into the upper respiratory tract (URT) of humans. This study was designed to more closely mimic the natural infection process by seeding virus into the URT, and investigating two different challenge inoculums.

This study utilized female BALB/c mice (Charles River Laboratories, 6-8 weeks) which were challenged with influenza A/California/07/2009 (H1N1), a pandemic isolate capable of causing lethal infections in mice, at 3E4 (3× the $LD_{95}$) and 3E3 pfu/mouse. The viral challenge was done on isoflurane (3%) anesthetized mice by IN inoculation with a volume of 30 µl. The experiment comprised 13 groups of mice and the general study design is shown in Table 226. Three days prior to viral challenge mice were administered a single IM (thigh muscle) dose of Conjugate 45a between 0.001 and 0.3 mg/kg. Negative controls animals were treated with PBS only. One group was also "sham infected" using PBS instead of virus. Mortality and BW were recorded daily for 14 days and any animal with a cumulative 20% loss of weight for 2 consecutive days was scored as a death.

Survival results from the study are summarized in Table 227. At both viral concentrations (3E3 and 3E4 pfu/mouse) vehicle treated mice were not fully protected from mortality as expected. The 3E3 PBS group reached 100% mortality compared to 60% at 3E4. Although counter-intuitive this is likely the result of normal experimental variation in URT models. Importantly, Conjugate 45a was fully protective against challenge with 3E4 pfu down to a single IM dose of 0.03 mg/kg. In the 3E3 arm, Conjugate 45a offered full protection with a single 0.01 mg/kg dose (P=0.0031 to vehicle). The remarkable protection afforded by conjugate 45a based on a survival endpoint indicates superior PK and activity in the URT of mice.

BW data for study animals is tabulated in Table 228 and mirrors the results of the survival data. The lowest fully protective dose (0.03 mg/kg) group only displayed transient weight loss compared to sham (PBS) infected mice and terminal BWs (Day 14) were within 1.5% of each other in the 3E4 challenge arm. For the 3E3 arm the lowest protective dose (0.01 mg/kg) was within ~5% of sham infected animals at study end.

Collectively this study indicates Conjugate 45a has exceptional exposure in the URTs of mice and is extremely effective at preventing the spread of virus into the LRT, where lethal infections occur. Furthermore, conservation of BW in treated mice and lack of obvious clinical symptoms indicates Conjugate 45a has the potential to act as a superior preventative against Influenza A.

TABLE 226

General study outline

| Group | Influenza A strain | Test Article | Virus challenge (IN) | Route, Schedule | Dose (mg/kg) | Dose volume (ml/kg) | N |
|---|---|---|---|---|---|---|---|
| 1 | Sham infection | Vehicle (PBS) | PBS | IM, single, T – 72 h | — | — | 5 |
| 2 | A/CA/07/09 (H1N1) | Vehicle (PBS) | 3.00E+04 | IM, single, T – 72 h | — | 5 | |
| 3 | | Conjugate 45a | | IM, single, T – 72 h | 0.3 | | |
| 4 | | | | IM, single, T – 72 h | 0.1 | | |
| 5 | | | | IM, single, T – 72 h | 0.03 | | |
| 6 | | | | IM, single, T – 72 h | 0.01 | | |
| 7 | | | | IM, single, T – 72 h | 0.003 | | |
| 8 | | Vehicle (PBS) | 3.00E+03 | IM, single, T – 72 h | — | | |
| 9 | | Conjugate 45a | | IM, single, T – 72 h | 0.1 | | |
| 10 | | | | IM, single, T – 72 h | 0.03 | | |
| 11 | | | | IM, single, T – 72 h | 0.01 | | |
| 12 | | | | IM, single, T – 72 h | 0.003 | | |
| 13 | | | | IM, single, T – 72 h | 0.001 | | |

TABLE 227

Percent survival of groups by day

| Day Post Infection | Sham (PBS) infection | Conjugate 45a (mg/kg) · 3E4 pfu/mouse challenge groups | | | | | | Conjugate 45a (mg/kg) · 3E3 pfu/mouse challenge groups | | | | | |
|---|---|---|---|---|---|---|---|---|---|---|---|---|---|
| | | Vehicle (PBS) | 0.3 mg/kg | 0.1 mg/kg | 0.03 mg/kg | 0.01 mg/kg | 0.003 mg/kg | Vehicle (PBS) | 0.1 mg/kg | 0.03 mg/kg | 0.01 mg/kg | 0.003 mg/kg | 0.001 mg/kg |
| 0 | 100 | 100 | 100 | 100 | 100 | 100 | 100 | 100 | 100 | 100 | 100 | 100 | 100 |
| 1 | 100 | 100 | 100 | 100 | 100 | 100 | 100 | 100 | 100 | 100 | 100 | 100 | 100 |
| 2 | 100 | 100 | 100 | 100 | 100 | 100 | 100 | 100 | 100 | 100 | 100 | 100 | 100 |
| 3 | 100 | 100 | 100 | 100 | 100 | 100 | 100 | 100 | 100 | 100 | 100 | 100 | 100 |
| 4 | 100 | 100 | 100 | 100 | 100 | 100 | 100 | 100 | 100 | 100 | 100 | 100 | 100 |
| 5 | 100 | 100 | 100 | 100 | 100 | 100 | 100 | 100 | 100 | 100 | 100 | 100 | 100 |

TABLE 227-continued

Percent survival of groups by day

| Day Post Infection | Sham (PBS) infection | Vehicle (PBS) | Conjugate 45a (mg/kg) · 3E4 pfu/mouse challenge groups | | | | | Vehicle (PBS) | Conjugate 45a (mg/kg) · 3E3 pfu/mouse challenge groups | | | | |
|---|---|---|---|---|---|---|---|---|---|---|---|---|---|
| | | | 0.3 mg/kg | 0.1 mg/kg | 0.03 mg/kg | 0.01 mg/kg | 0.003 mg/kg | | 0.1 mg/kg | 0.03 mg/kg | 0.01 mg/kg | 0.003 mg/kg | 0.001 mg/kg |
| 6 | 100 | 60 | 100 | 100 | 100 | 60 | 60 | 100 | 100 | 100 | 100 | 100 | 100 |
| 7 | 100 | 60 | 100 | 100 | 100 | 60 | 20 | 60 | 100 | 100 | 100 | 100 | 80 |
| 8 | 100 | 60 | 100 | 100 | 100 | 60 | 20 | 0 | 100 | 100 | 100 | 80 | 80 |
| 9 | 100 | 60 | 100 | 100 | 100 | 60 | 20 | | 100 | 100 | 100 | 80 | 80 |
| 10 | 100 | 60 | 100 | 100 | 100 | 60 | 20 | | 100 | 100 | 100 | 80 | 80 |

TABLE 228

Percent starting BW of animals by group and day. *Data shown until the first death within a group

| Day Post Infection | Sham (PBS) infection | Vehicle (PBS) (3E4) | Conjugate 45a (mg/kg) · 3E4 pfu/mouse challenge groups | | | | | Vehicle (PBS) (3E3) | Conjugate 45a (mg/kg) · 3E3 pfu/mouse challenge groups | | | | |
|---|---|---|---|---|---|---|---|---|---|---|---|---|---|
| | | | 0.3 mg/kg | 0.1 mg/kg | 0.03 mg/kg | 0.01 mg/kg | 0.003 mg/kg | | 0.1 mg/kg | 0.03 mg/kg | 0.01 mg/kg | 0.003 mg/kg | 0.001 mg/kg |
| 0 | 100 | 100 | 100 | 100 | 100 | 100 | 100 | 100 | 100 | 100 | 100 | 100 | 100 |
| 1 | 101.5 | 103.4 | 103.2 | 102.2 | 104.6 | 101.3 | 102.3 | 104.7 | 100.7 | 102.8 | 103.9 | 99.8 | 101.9 |
| 2 | 98.6 | 99.1 | 100.5 | 100.6 | 102.3 | 97.2 | 100 | 100.8 | 98.5 | 100.9 | 101.7 | 96.8 | 99.4 |
| 3 | 101.1 | 92.4 | 99.5 | 98.9 | 97.4 | 92.3 | 92.6 | 95.4 | 99.1 | 99.8 | 97.7 | 94.6 | 97.2 |
| 4 | 104.2 | 89 | 100.3 | 99.2 | 96.2 | 88.1 | 87.3 | 89.6 | 101.6 | 97.9 | 97.9 | 88.8 | 94 |
| 5 | 104.2 | 87.3 | 102.1 | 101.6 | 95.7 | 86 | 82.4 | 84.7 | 101.7 | 98.2 | 96.2 | 86.4 | 90.9 |
| 6 | 104.6 | 85.2 | 104.3 | 103.9 | 94.6 | 83 | | 81 | 102.5 | 97.1 | 92.9 | 84 | 84.3 |
| 7 | 105.1 | 82.1 | 103.5 | 104.7 | 97.2 | | | 76.1 | 102.7 | 94.5 | 87.4 | 79.5 | 81.8 |
| 8 | 105.2 | | 106.9 | 100.8 | 98.7 | | | | 102.7 | 99.2 | 90 | 83 | |
| 9 | 103.9 | | 104.3 | 104.1 | 99.8 | | | | 101.2 | 98.8 | 93.3 | | |
| 10 | 105.4 | | 106.6 | 105.9 | 103.9 | | | | 104.8 | 100.9 | 99.8 | | |

Example 218. Efficacy of Conjugate 45a Against Influenza A/California/07/2009 (H1N1) by Dose Route in a Delayed Treatment Mouse Model Conjugate 45a was evaluated against a lethal influenza A (H1N1) infection in female BALB/c mice (Charles River Laboratories, 6-8 weeks). The challenge virus (A/California/07/2009) is a pandemic isolate capable of causing lethal infections in mice. The experiment comprised 7 groups of 5 mice. The general study design is shown in Table 229, briefly: On day 0 all mice were challenged with virus at 2-3× the LD95 by intranasal (IN) inoculation in a volume of 30 μl, after being anesthetized with a mixture of ketamine/xylazine (150 and 10 mg/kg respectively). Test groups received a single intramuscular (IM) or intravenous (IV) injection, 24 hours post viral challenge of conjugate 45a (0.03 to 0.3 mg/kg) or vehicle (PBS). IM Injections were in the thigh muscle of the right hind limb at a dose volume of 10 ml/kg. IV injections were administered into the tail vein at the same dose volume. Mortality and BW were recorded daily for 14 days and any animal with a cumulative 20% loss of weight for 2 consecutive days was scored as a death.

Survival results from the study are summarized in Table 230. Mice treated with vehicle (PBS) rapidly began to lose BW after challenge, reaching 100% mortality on Day 5. Animals receiving Conjugate 45a at a dose of 0.3 mg/kg by IV (group 2) or IM (group 5) were fully protected through study end (Day 14). Both groups also displayed similar BW trends, with a transient loss of weight before recovering, and eventually exceeding, their initial BW by study end (Table 231).

At the lowest Conjugate 45a dose tested (0.03 mg/kg) all mice succumbed to infection by Day 6 regardless of dose route. The intermediate dose groups (0.1 mg/kg) demonstrated 40% survival when dosed by IV, and was not protective (0% survival) when dosed by IM. This difference however was not statistically significant (P=0.0993). Collectively this study demonstrated the potency of Conjugate 45a against an important pandemic isolate of influenza A (H1N1) with a single IV or IM dose of less than 1 mg/kg. Importantly, efficacy was comparable between both dose routes indicating the ability of Conjugate 45a to be used in an outpatient setting (IM dosing). Lastly, Conjugate 45a was fully protective even though dosing was delayed for 24 hours, allowing the initial viral inoculum time to establish/propagate. This suggests Conjugate 45a may have therapeutic use as both a preventative and a therapeutic.

TABLE 229

General study outline

| Group | Influenza A strain | Test Article | Route, Schedule (T + 24 hours) | Dose (mg/kg) | ml/kg | N |
|---|---|---|---|---|---|---|
| 1 | A/CA/07/09 (3E4 pfu/mouse) | Vehicle (PBS) | IV, single, T + 24 | — | 10 | 5 |
| 2 | | Conjugate 45a | IV, single, T + 24 | 0.3 | 10 | 5 |
| 3 | | | IV, single, T + 24 | 0.1 | 10 | 5 |

TABLE 229-continued

General study outline

| Group | Influenza A strain | Test Article | Route, Schedule (T + 24 hours) | Dose (mg/kg) | ml/kg | N |
|---|---|---|---|---|---|---|
| 4 | | | IV, single, T + 24 | 0.03 | 10 | 5 |
| 5 | | | IM, single, T + 24 | 0.3 | 10 | 5 |
| 6 | | | IM, single, T + 24 | 0.1 | 10 | 5 |
| 7 | | | IM, single, T + 24 | 0.03 | 10 | 5 |

TABLE 230

Percent survival by group and day (mg/kg) (dose route)

| Day | Vehicle (PBS) | Conjugate 45a (0.3) (IV) | Conjugate 45a (0.1) (IV) | Conjugate 45a (0.03) (IV) | Conjugate 45a (0.3) (IM) | Conjugate 45a (0.1) (IM) | Conjugate 45a (0.03) (IM) |
|---|---|---|---|---|---|---|---|
| 0 | 100 | 100 | 100 | 100 | 100 | 100 | 100 |
| 1 | 100 | 100 | 100 | 100 | 100 | 100 | 100 |
| 2 | 100 | 100 | 100 | 100 | 100 | 100 | 100 |
| 3 | 100 | 100 | 100 | 100 | 100 | 100 | 100 |
| 4 | 100 | 100 | 100 | 100 | 100 | 100 | 100 |
| 5 | 0 | 100 | 80 | 20 | 100 | 40 | 60 |
| 6 | | 100 | 40 | 0 | 100 | 0 | 0 |
| 7 | | 100 | 40 | | 100 | | |
| 8 | | 100 | 40 | | 100 | | |
| 9 | | 100 | 40 | | 100 | | |
| 10 | | 100 | 40 | | 100 | | |
| 11 | | 100 | 40 | | 100 | | |
| 12 | | 100 | 40 | | 100 | | |
| 13 | | 100 | 40 | | 100 | | |
| 14 | | 100 | 40 | | 100 | | |

TABLE 231

Percent Starting BW of animals by group and day (mg/kg) (dose route). *Data shown until the first death within a group.

| Day Post Challenge | Vehicle (PBS) | Conjugate 45a (0.3) (IV) | Conjugate 45a (0.1) (IV) | Conjugate 45a (0.03) (IV) | Conjugate 45a (0.3) (IM) | Conjugate 45a (0.1) (IM) | Conjugate 45a (0.03) (IM) |
|---|---|---|---|---|---|---|---|
| 0 | 100 | 100 | 100 | 100 | 100 | 100 | 100 |
| 1 | 97.5 | 99.5 | 96.9 | 99.1 | 98.6 | 97.2 | 97.6 |
| 2 | 95.1 | 99.4 | 96 | 94 | 97.1 | 95.5 | 95 |
| 3 | 86.6 | 94.5 | 89.9 | 86.8 | 89.7 | 88.8 | 89.1 |
| 4 | 79.9 | 93 | 82.6 | 79.2 | 89.1 | 80.8 | 81.2 |
| 5 | 74.6 | 94.7 | 81 | 74.6 | 92.1 | 76.4 | 75.7 |
| 6 | | 97.4 | | | 94.3 | | |
| 7 | | 99.3 | | | 97.1 | | |
| 8 | | 101.9 | | | 98.7 | | |
| 9 | | 102 | | | 101.7 | | |
| 10 | | 105 | | | 103.6 | | |
| 11 | | 103.3 | | | 100.9 | | |
| 12 | | 102.4 | | | 101.2 | | |
| 13 | | 105.9 | | | 102.8 | | |
| 14 | | 104.2 | | | 101.6 | | |

Example 219. A Single-Dose Subcutaneous Rangefinding Study and Single-Dose Toxicity and Toxicokinetic (2-Week Exposure) Study of Conjugate 45a in Sprague-Dawley Rats The purpose of this study, was to evaluate the tolerability in male and female rats then toxicity and toxicokinetics (TK) of conjugate 45a when administered as a single subcutaneous (SC) dose to male Sprague Dawley rats.

This study consisted of two phases; Phase 1 tolerability (Groups 1-3) and Phase 2 toxicology (Groups 4-7) and satellite TK (Groups 8-10). Each treatment group in Phase 1 was comprised of one female and one male Sprague Dawley rat. Phase 1 rats were administered either 100 mg/kg conjugate 45a(Group 1), 200 mg/kg conjugate 45a(Group 2), or 400 mg/kg conjugate 45a(Group 3) on a single day via SC injection at a dose volume of 5 mL/kg (5 mL×2 sites for Group 3, mid-scapular and dorsal lumbar). Each Phase 2 toxicology group (Groups 4-7) was comprised of five male Sprague Dawley rats. Each Phase 2 satellite TK group (Groups 8-10) was comprised of four male Sprague Dawley rats. Based on the tolerability in Phase 1, Phase 2 rats were administered either PBS (Group 4), 50 mg/kg conjugate 45a(Groups 5 and 8), 150 mg/kg conjugate 45a(Groups 6 and 9), or 400 mg/kg conjugate 45a (Groups 7 and 10) on a single day via SC injection at a dose volume of 5 mL/kg (5 mL×2 sites for Group 3, mid-scapular and dorsal lumbar for Groups 7 and 10).

Clinical observations for Phase 1 were recorded twice daily on Days 1-3 and detailed observations were recorded at randomization. Clinical observations for Phase 2 were recorded twice daily on Days 1-15 and detailed observations were recorded on Day 1 (prior to dosing) and on Day 14. Body weight measurements were recorded at randomization and pre-dose for Phase 1. Body weight measurements for Phase 2 were recorded at randomization, on Day 1, Day 3, Day 7, Day 14, and on Day prior to necropsy. Food consumption measurements for Phase 2 were recorded on Days 1, 4, 7, 10, 12, and 14. Plasma samples were collected from satellite TK rats (Groups 8-10) at 0.5, 1, 2, 4, 8, 24, 72, 120, 168, 240, and 336 hours post-dose for analysis of systemic exposure to conjugate 45a. Urine samples were collected from toxicology rats (Groups 4-7) for 24 hours from Day 14 to Day 15. Blood samples for the evaluation of hematology, chemistry, and coagulation endpoints were collected on Day from toxicology rats (Groups 4-7). Following blood sample collections, necropsy was conducted on toxicology rats (Groups 4-7). Protocol-specified tissues were collected and evaluated grossly, select organs were weighed, and tissues were fixed for microscopic evaluation. Tissues were subsequently processed and evaluated microscopically.

Tolerability:

Based on the absence of test article-related abnormal observations, administration of conjugate 45aat <400 mg/kg as a single subcutaneous injection (at either one or two sites on each dosing day) was well tolerated for up to 3 days in male and female Sprague Dawley rats.

Toxicokinetics:

Conjugate 45aplasma levels were maintained over the 2-week exposure period and were comparable between the neuraminidase (NA)-capture and the Fc-capture assays. This observation suggested that the intact molecule (containing at least 1 target moiety linked to the Fc group) remained stable after dose administration in vivo. Mean plasma exposures appeared to increase approximately dose-proportionally from 50 to 400 mg/kg.

Toxicology:

Based on the absence of test article-related changes in body weight, food consumption, clinical observations, organ weights, hematologic parameters, clinical chemistry, macroscopic findings and microscopic findings, administration of conjugate 45a at <400 mg/kg as a single subcutaneous injection (high dose administered across two sites) was well tolerated for up to 14 days in male Sprague Dawley rats. This dose corresponded to mean AUC0-inf values of 312,000 and 319,000 μg·hr/mL and mean Cmax values of 1150 and 974 μg/mL for NA-capture and Fc-capture assays, respectively.

Example 220. A Single-Dose Subcutaneous Rangefinding Study and Single-Dose Toxicity and Toxicokinetic (2-Week Exposure) Study of Conjugate 45a in Sprague-Dawley Rats The purpose of this study was to evaluate the tolerability in male and female rats, then toxicity and toxicokinetics of Conjugate 45a when administered as a single subcutaneous (SC) dose to male Sprague Dawley Rats. Male animals in Phase 2 were administered 50, 150, or 400 mg/kg/dose conjugate 45a.

All study animals survived to scheduled sacrifice. There were no test article-related changes in organ weights, hematologic parameters, clinical chemistry, macroscopic findings and microscopic findings. Recorded microscopic findings were present at a similar incidence in control animals and test article exposed groups, or were considered to represent incidental "background" findings that are seen commonly in rats of this strain and age.

NUMBERED EMBODIMENTS

1. A conjugate described by any one of formulas (D-I), (M-I), (1), or (2):

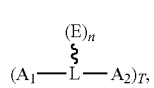
(D-I)

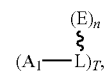
(M-I)

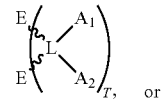
(1)

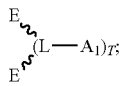
(2)

wherein each $A_1$ and each $A_2$ is independently described by formula (A-I)-(A-XII):

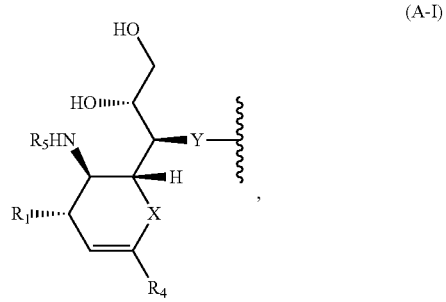
(A-I)

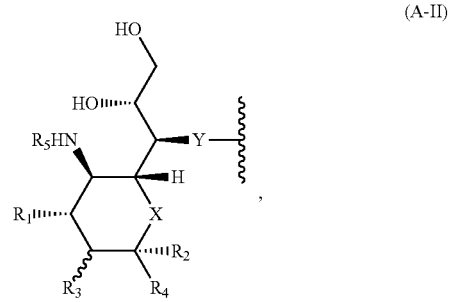
(A-II)

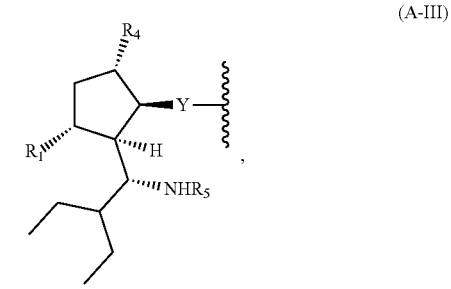
(A-III)

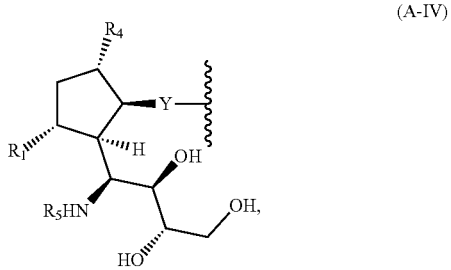
(A-IV)

(A-V)
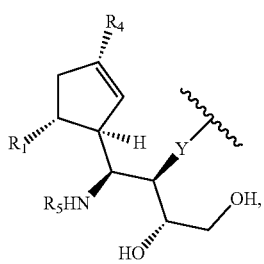
(A-VI)
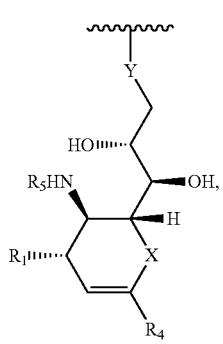
(A-VII)
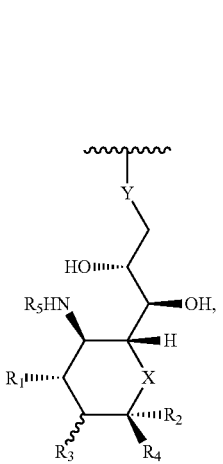
(A-VIII)
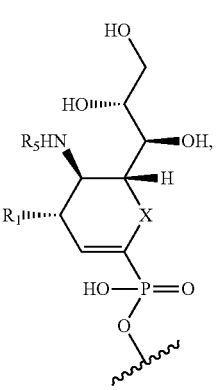
(A-IX)
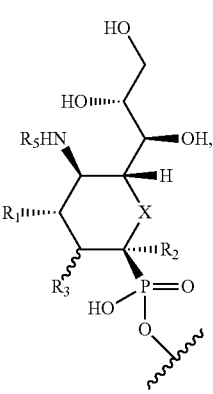
(A-X)
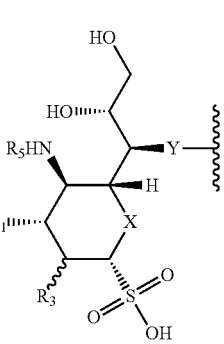
(A-XI)
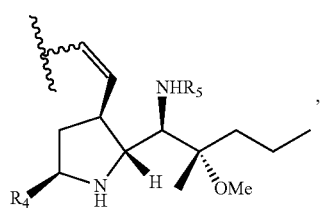
(A-XII)
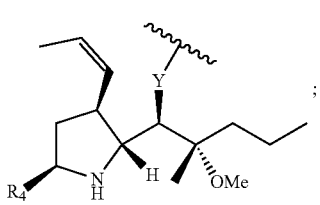
wherein $R_1$ is selected from —OH, —NH$_2$, —NHC(=NH)NH$_2$, and —NHC(=NH)NHR$_6$;
$R_2$ and $R_3$ are each independently selected from —H, —OH, —F, —Cl, and —Br;
$R_4$ is selected from —CO$_2$H, —P(=O)(OH)$_2$, —SO$_3$H;
$R_5$ is selected from —COCH$_3$, —COCF$_3$, —SO$_2$CH$_3$;
X is selected from —O— and —S—;
Y is selected from:
 , 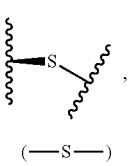 , 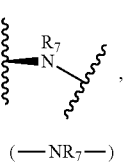 ,
(—O—)    (—S—)    (—NR$_7$—)

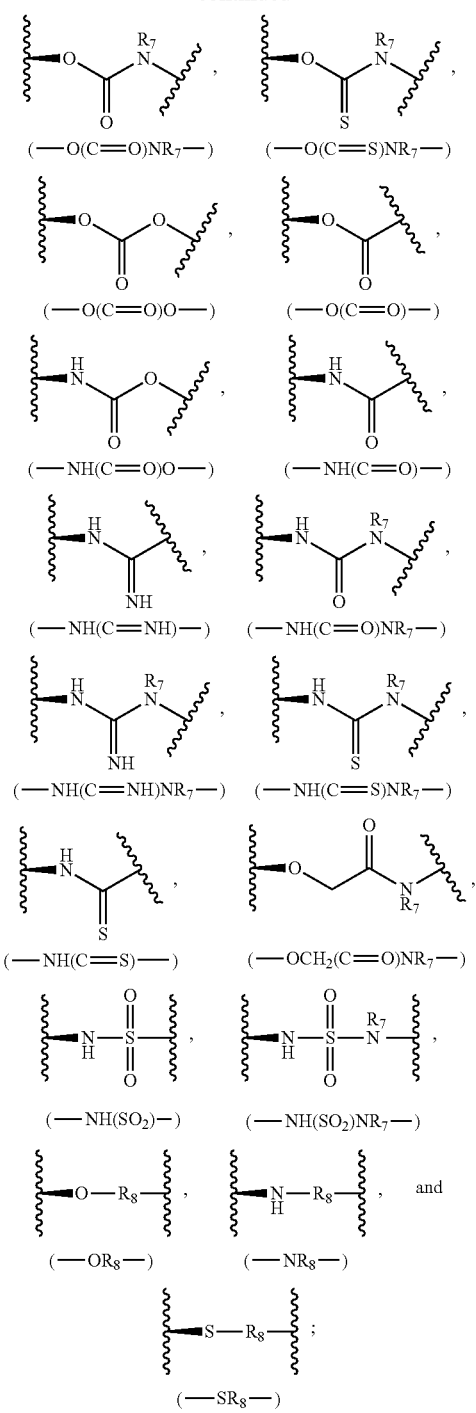
$R_6$ is selected from
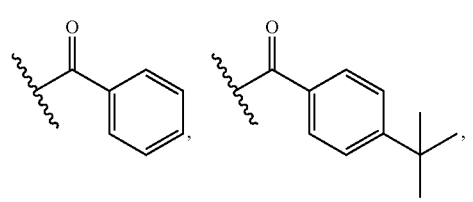
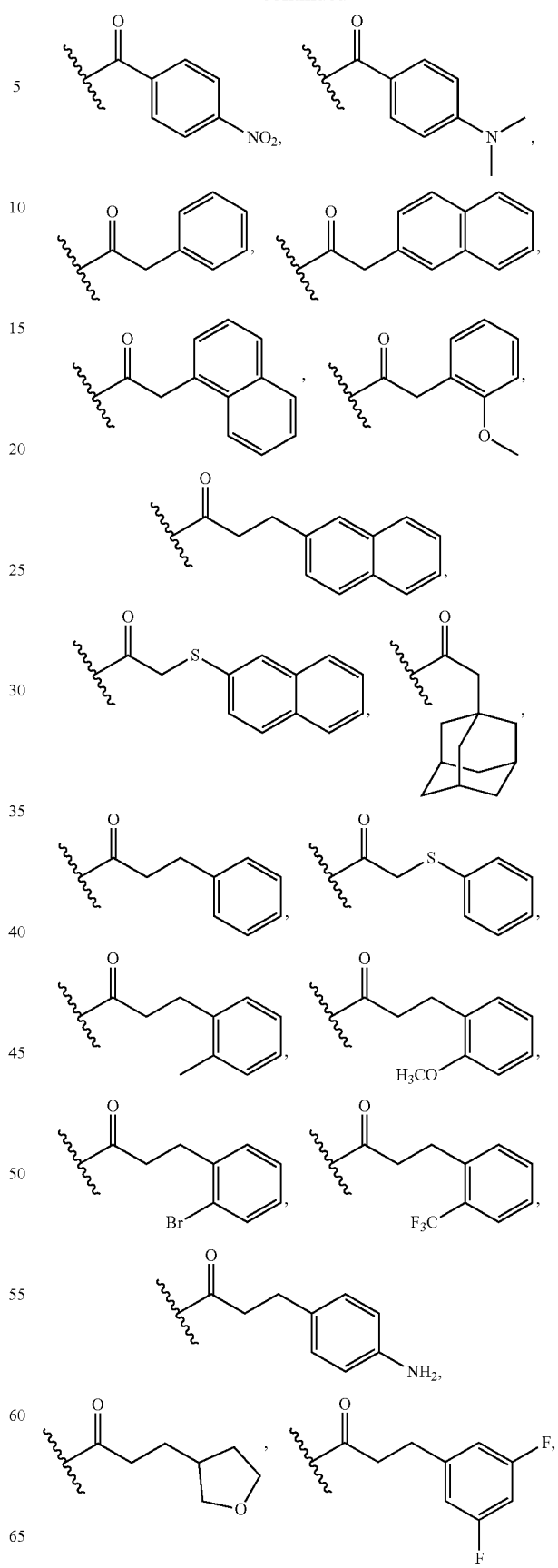

-continued

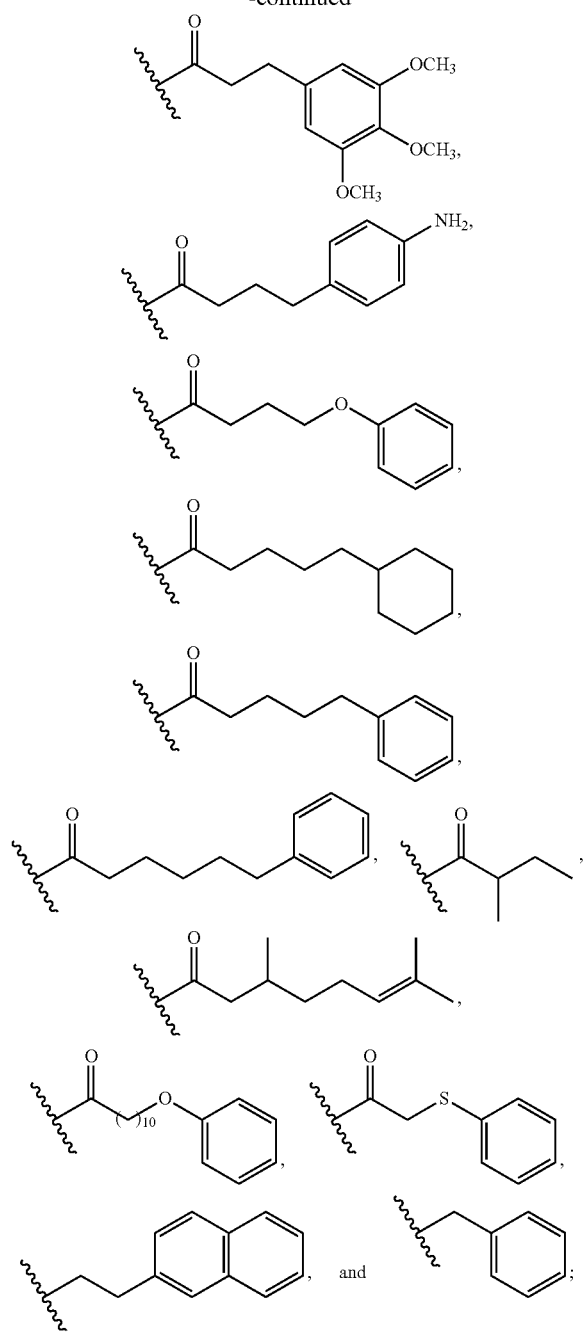

$R_7$ is selected from H, C1-C20 alkyl, C3-C20 cycloalkyl, C3-C20 heterocycloalkyl; C5-C15 aryl, and C2-C15 heteroaryl;

$R_8$ is selected from C3-C20 heterocycloalkyl, C5-C15 aryl, and C2-C15 heteroaryl;

n is 1 or 2;

each E comprises an Fc domain monomer, an albumin protein, an albumin protein-binding peptide, or an Fc-binding peptide;

L is a linker covalently attached to E and to each Y of each $A_1$ or each $A_1$ and $A_2$;

T is an integer from 1 to 20, and each squiggly line in formulas (D-I), (M-I), (1), or (2) indicates that L is covalently attached to each E;

or a pharmaceutically acceptable salt thereof.

2. The conjugate of embodiment 1, wherein the conjugate is described by formula (D-I): $(A_1\text{-L A}_2)$ T (D-I)

(D-I)

wherein each $A_1$ and each $A_2$ is independently selected from any one of formulas (A-I)-(A-XII);

each E comprises an Fc domain monomer, an albumin protein, an albumin protein-binding peptide, or an Fc-binding peptide;

n is 1 or 2;

T is an integer from 1 to 20; and the squiggly line connected to the E indicates that each $A_1$-L-$A_2$ is covalently attached to E, or a pharmaceutically acceptable salt thereof.

3. The conjugate of embodiment 2, wherein each $A_1$ and each $A_2$ is independently selected from any one of formulas (A-I), (A-II), (A-VI), or (A-VII);

each E comprises an Fc domain monomer, an albumin protein, an albumin protein-binding peptide, or an Fc-binding peptide;

n is 1 or 2;

T is an integer from 1 to 20; and the squiggly line connected to the E indicates that each $A_1$-L-$A_2$ is covalently attached to E, or a pharmaceutically acceptable salt thereof.

4. The conjugate of embodiment 3, wherein each $A_1$ and each $A_2$ is described by formula (A-I) or a pharmaceutically acceptable salt thereof.

5. The conjugate of any one of embodiments 1-4, wherein the conjugate is described by formula (D-II):

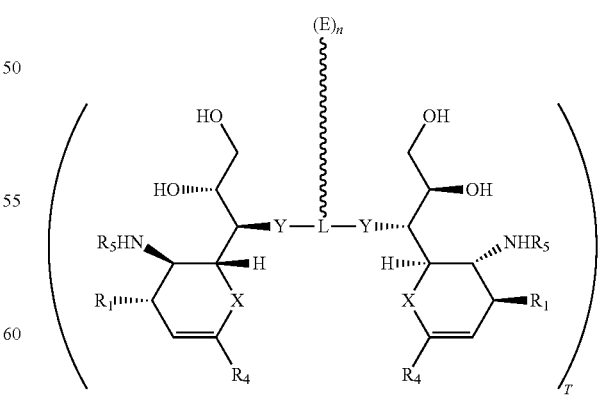

(D-II)

or a pharmaceutically acceptable salt thereof.

6. The conjugate of embodiment 5, wherein the conjugate is described by formula (D-I1-1):

(D-II-1)

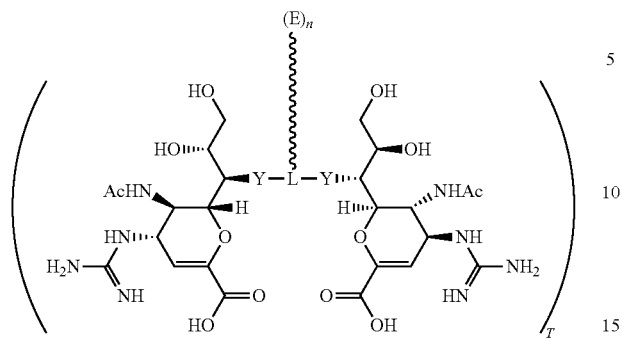

or a pharmaceutically acceptable salt thereof.
7. The conjugate of embodiment 6, wherein the conjugate is described by formula (D-II-2):

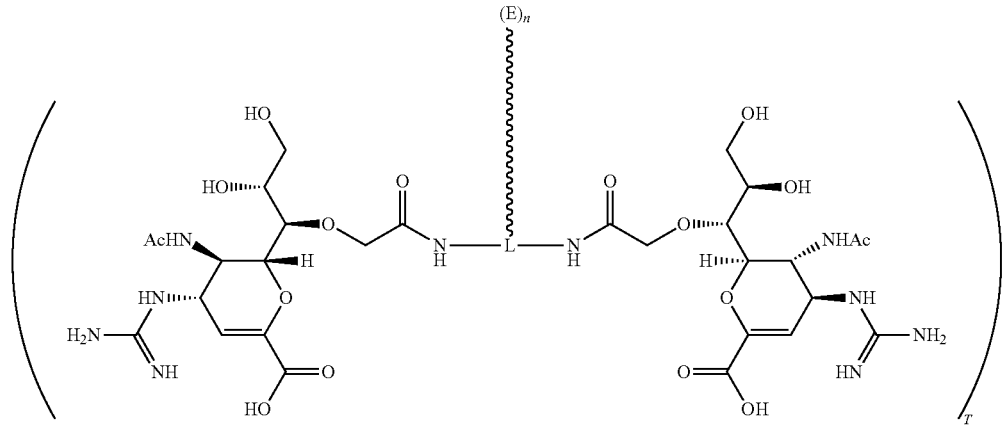

or a pharmaceutically acceptable salt thereof.
8. The conjugate of embodiment 7, wherein the conjugate is described by formula (D-II-3):

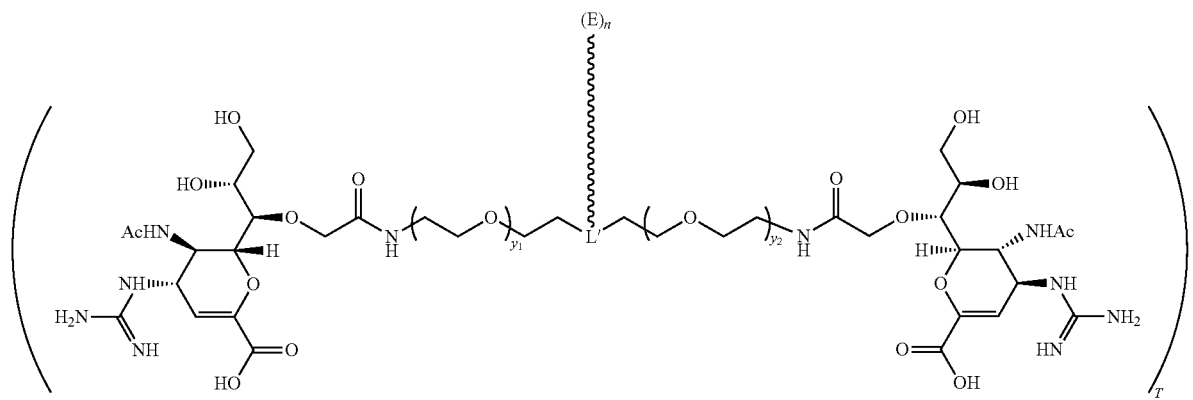

wherein L' is the remainder of L, and
$y_1$ and $y_2$ are each independently an integer from 1-20,
or a pharmaceutically acceptable salt thereof.

9. The conjugate of embodiment 8, wherein L' is a nitrogen atom.
10. The conjugate of embodiment 9 wherein the conjugate has the structure selected from
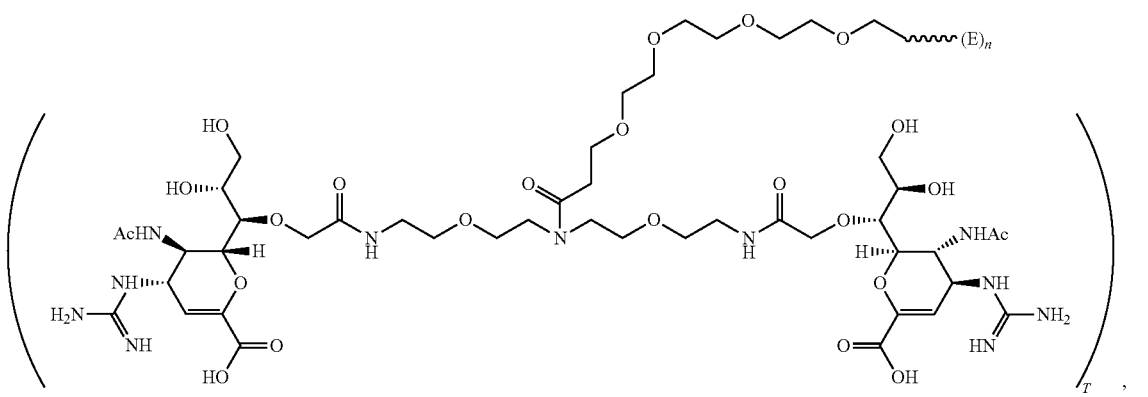
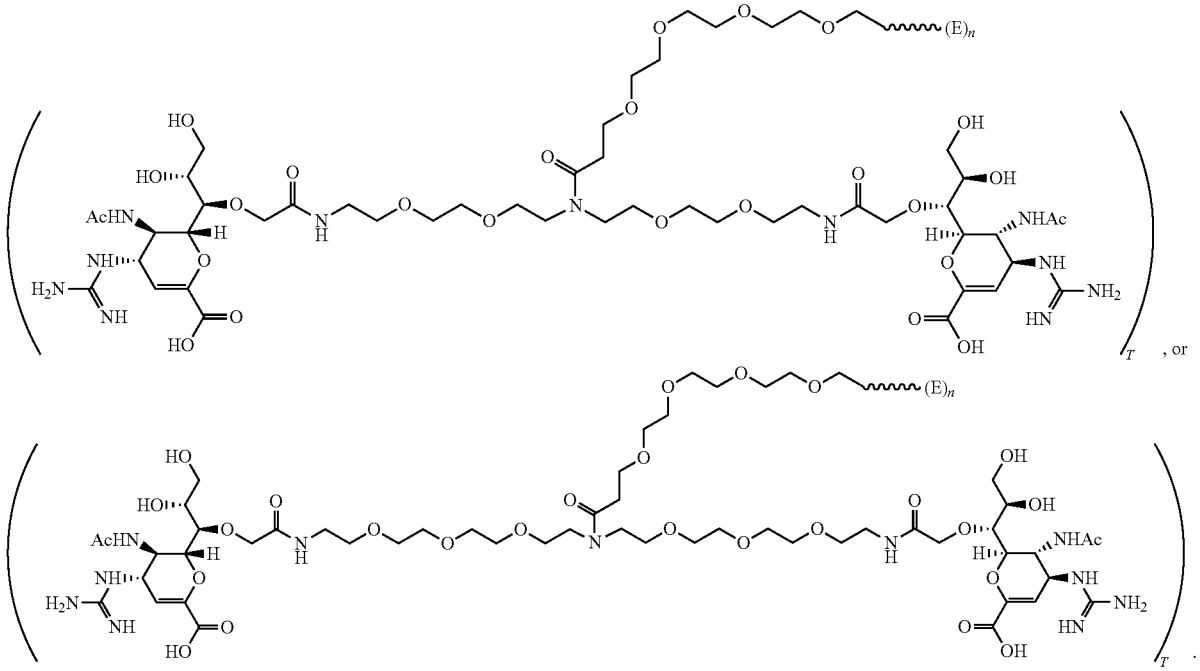
11. The conjugate of embodiment 6, wherein the conjugate is described by formula (D-II-4):
(D-II-4)
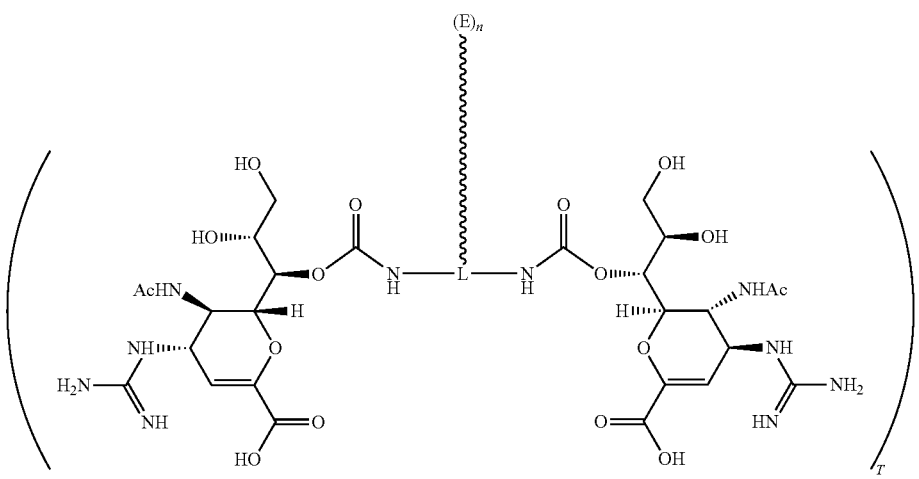
or a pharmaceutically acceptable salt thereof.

12. The conjugate of embodiment 11, wherein the conjugate is described by formula (D-II-5):
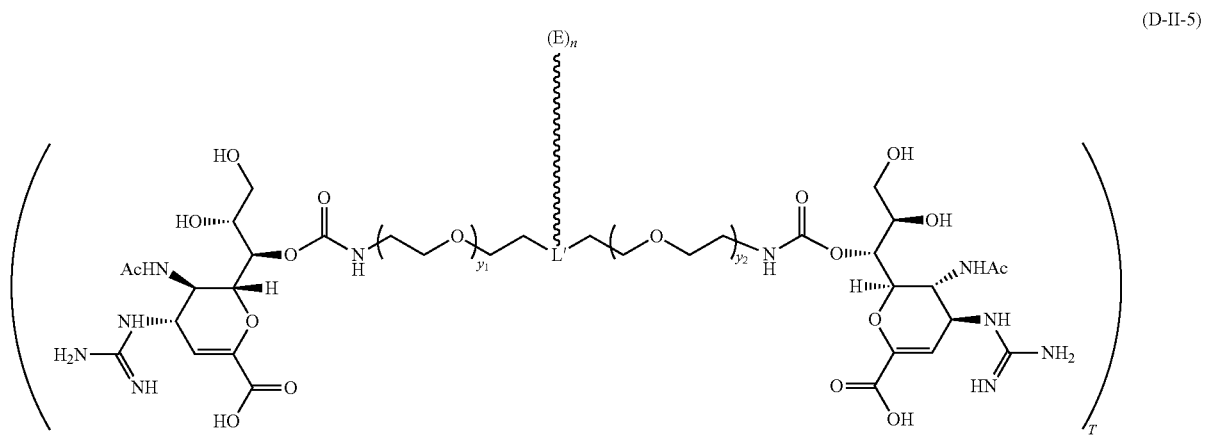
wherein L' is the remainder of L, and
y₁ and y₂ are each independently an integer from 1-20,
or a pharmaceutically acceptable salt thereof.
13. The conjugate of embodiment 12, wherein L' is a nitrogen atom.
14. The conjugate of embodiment 13, wherein the conjugate has the structure selected from
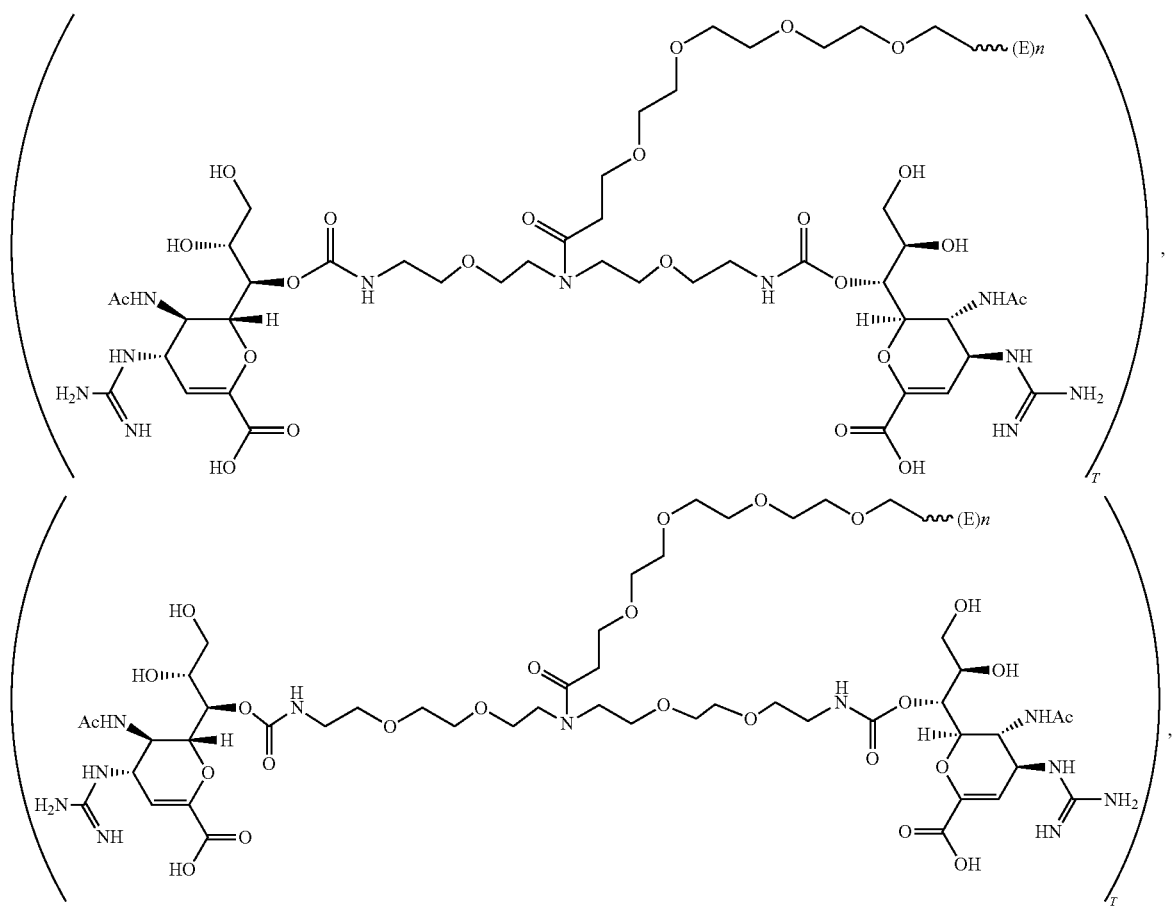
or

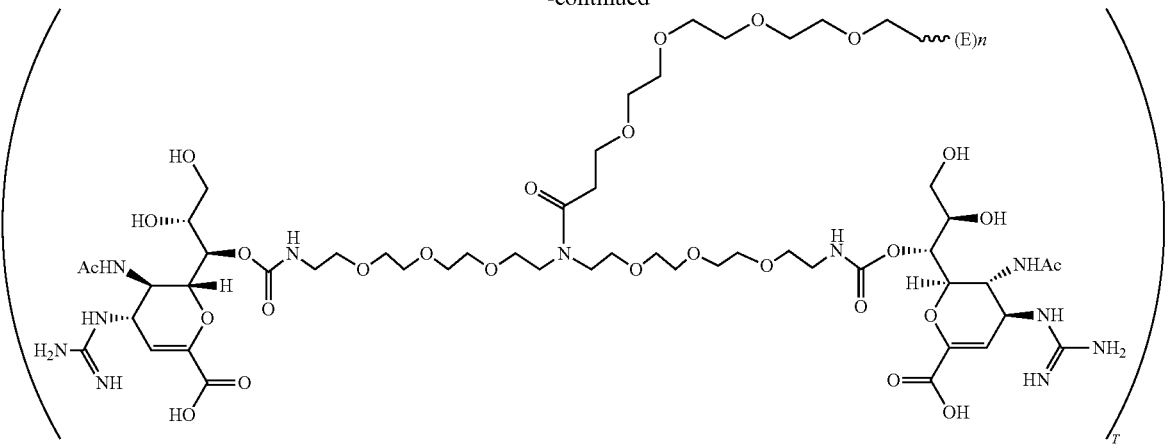
15. The conjugate of embodiment 11, wherein the conjugate has the structure of
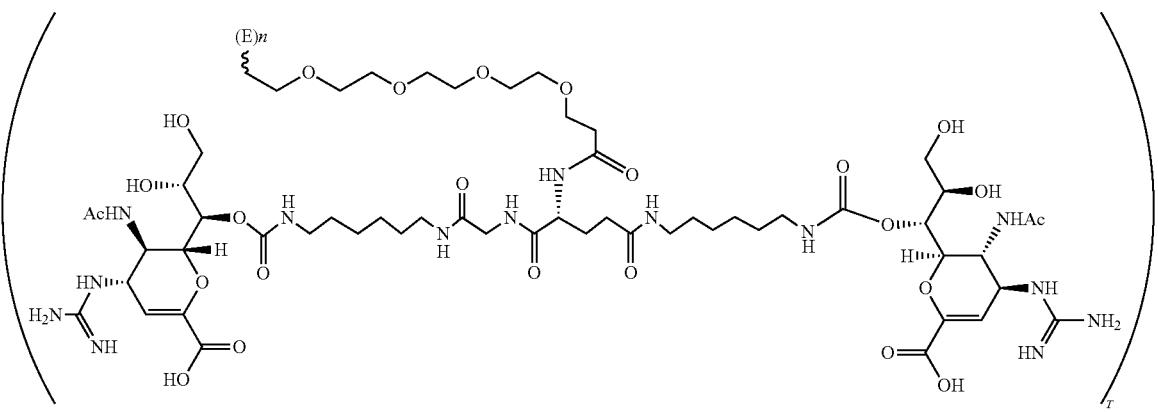
or a pharmaceutically acceptable salt thereof.
16. The conjugate of embodiment 6, wherein the conjugate is described by formula (D-II-6):
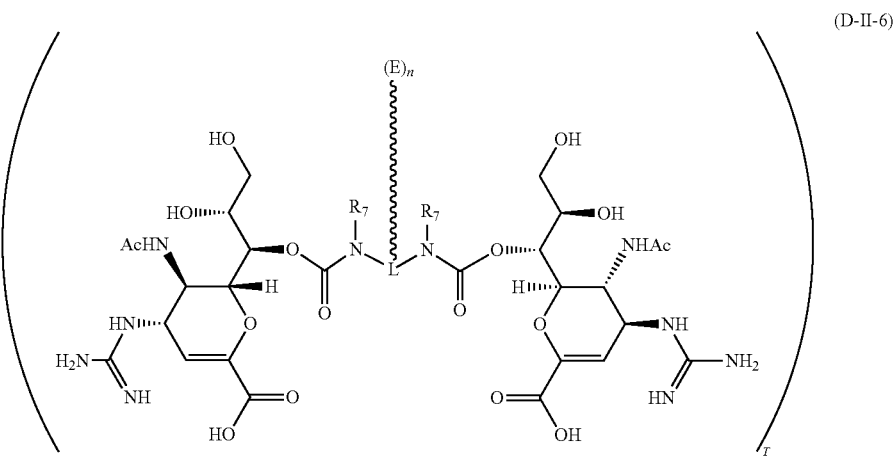
wherein $R_7$ is selected from H, C1-C20 alkyl, C3-C20 cycloalkyl, C3-C20 heterocycloalkyl; C5-C15 aryl, and C2-C15 heteroaryl;
or a pharmaceutically acceptable salt thereof.

17. The conjugate of embodiment 16, wherein $R_7$ is selected from C1-C20 alkyl, C3-C20 cycloalkyl, C3-C20 heterocycloalkyl; C5-C15 aryl, and C2-C15 heteroaryl.

18. The conjugate of embodiment 16 or 17, wherein $R_7$ is selected from methyl, ethyl, propyl, or butyl.

19. The conjugate of any one of embodiments 16-18, wherein the conjugate is described by formula (D-II-7):

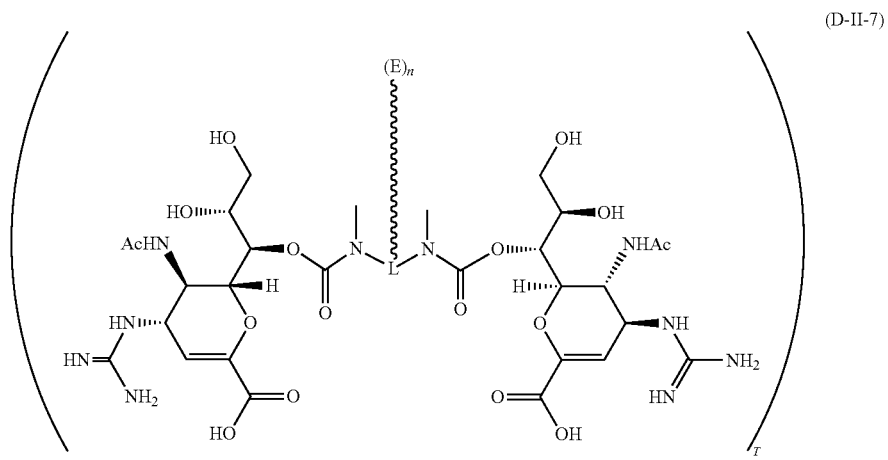

(D-II-7)

or a pharmaceutically acceptable salt thereof.

20. The conjugate of embodiment 19, wherein the conjugate is described by formula (D-II-8):

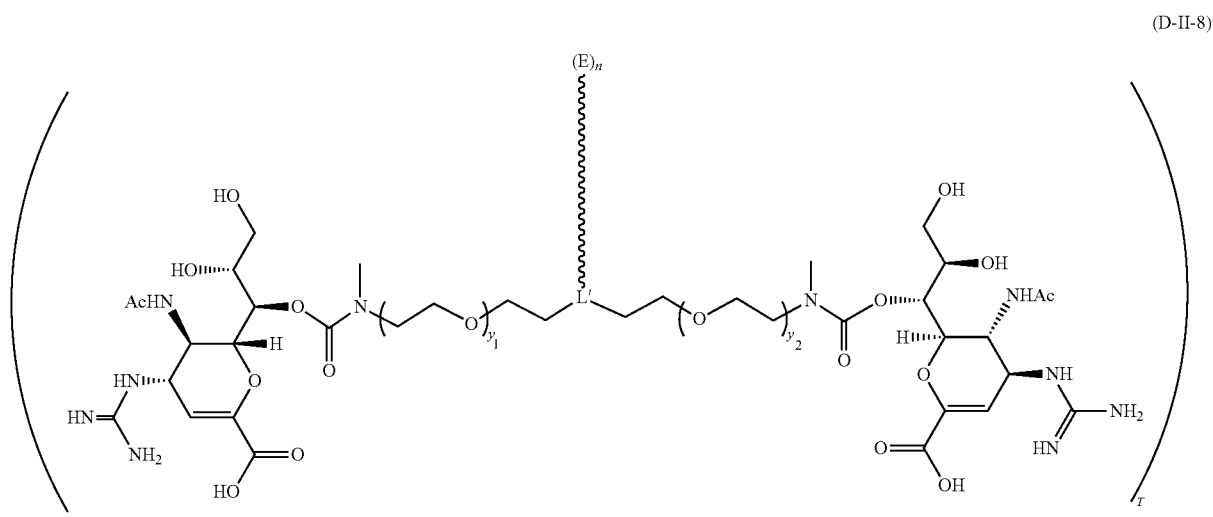

(D-II-8)

wherein L' is the remainder of L, and $y_1$ and $y_2$ are each independently an integer from 1-20, or a pharmaceutically acceptable salt thereof.

21. The conjugate of embodiment 20, wherein the conjugate has the structure of:

1135
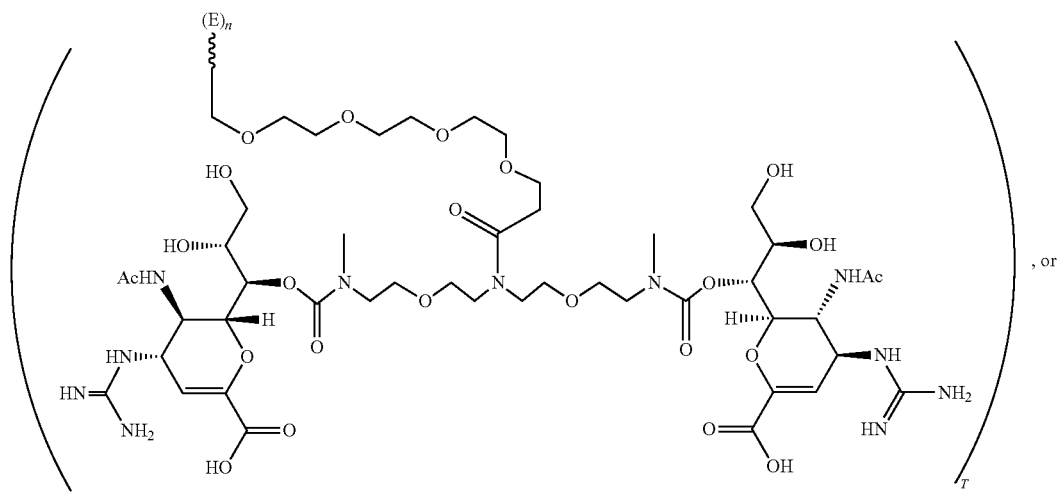
, or
1136
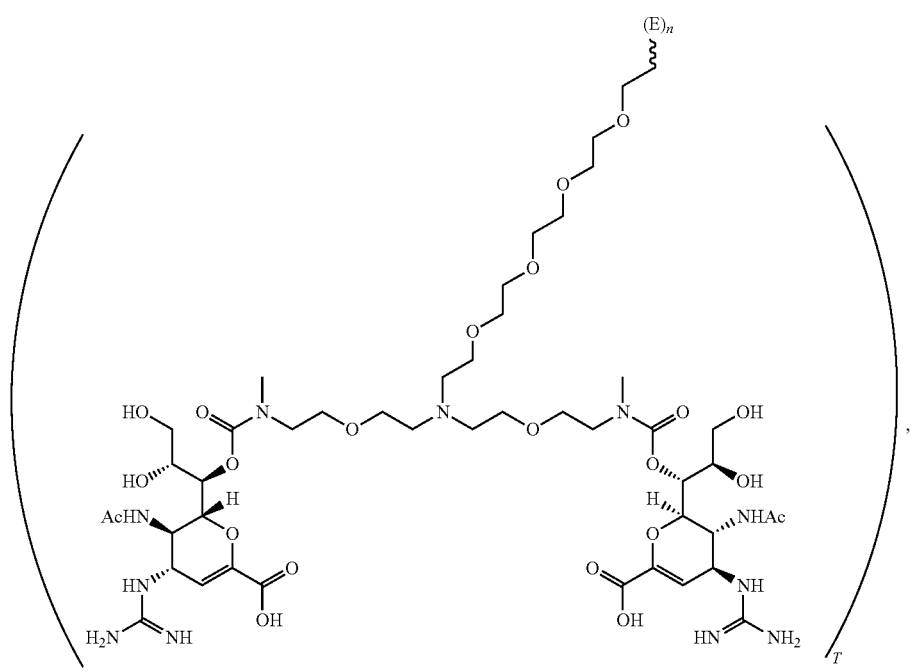
,
or a pharmaceutically acceptable salt thereof.

22. The conjugate of embodiment 21, wherein the conjugate is described by
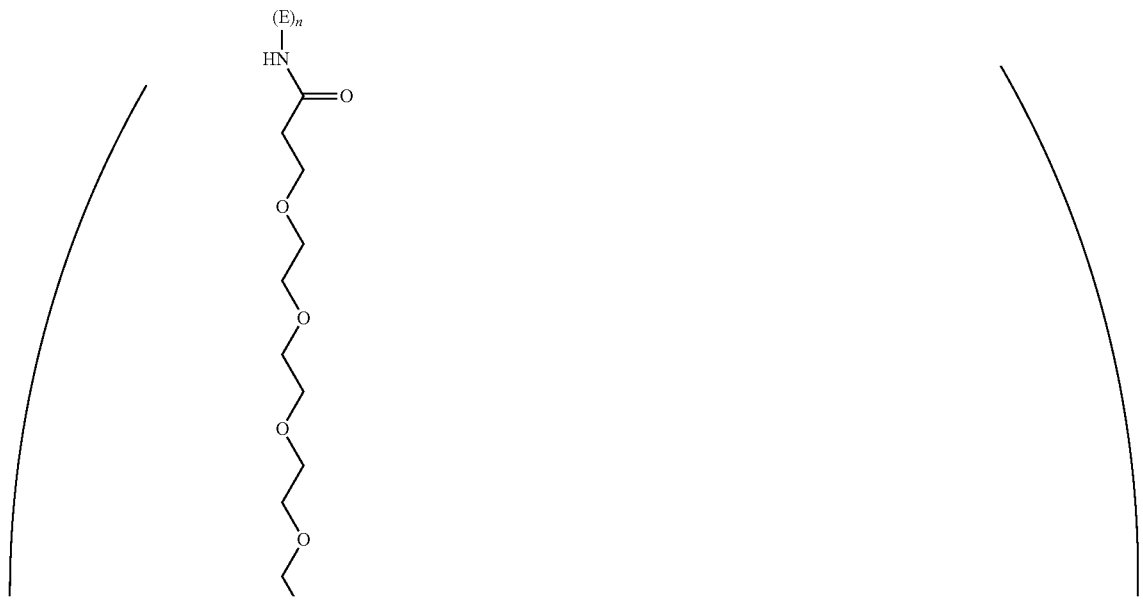
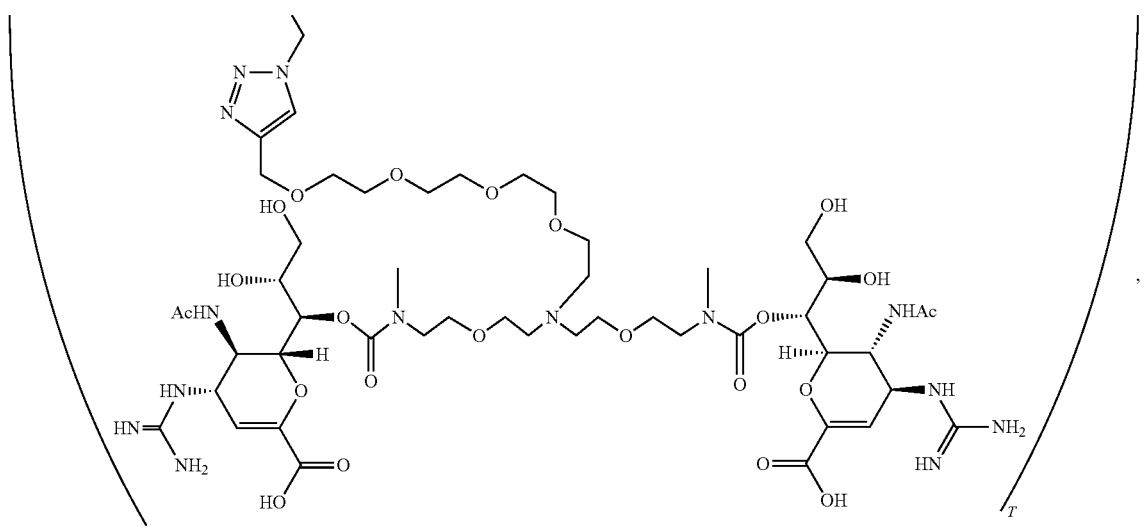
or a pharmaceutically acceptable salt thereof.
23. The conjugate of any one of embodiments 16-18, wherein the conjugate is described by formula (D-II-9):

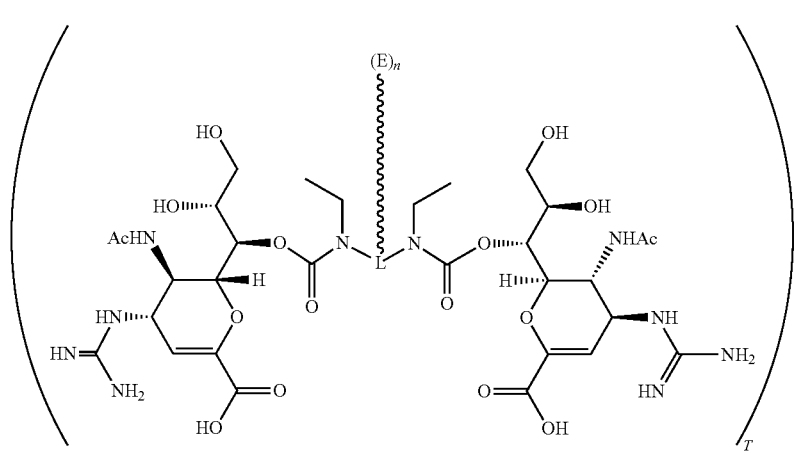
(D-II-9)
or a pharmaceutically acceptable salt thereof.
24. The conjugate of embodiment 23, wherein the conjugate is described by formula (D-I1-10):
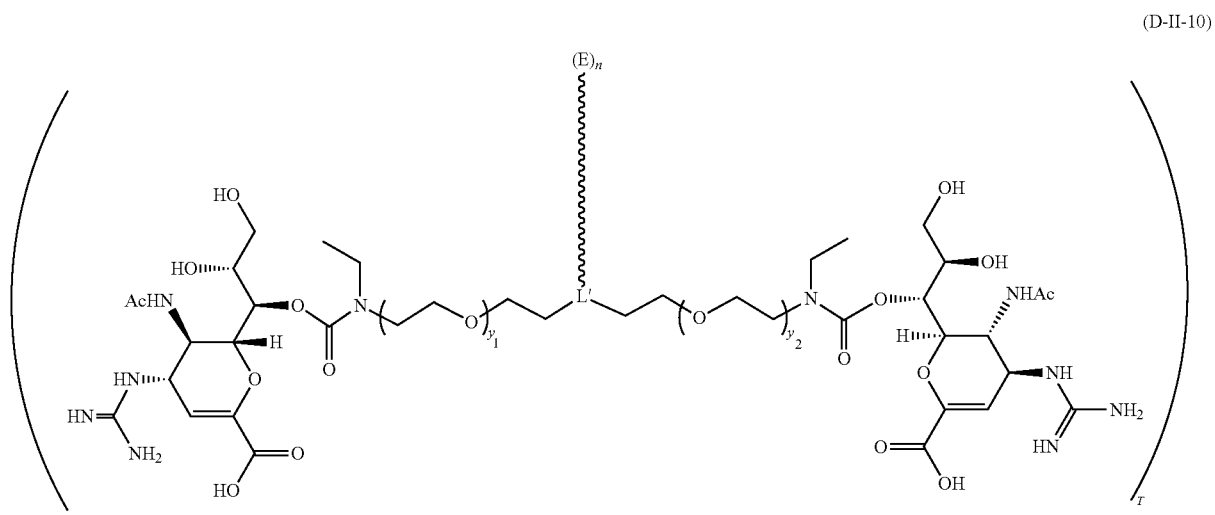
(D-II-10)
wherein L' is the remainder of L, and
$y_1$ and $y_2$ are each independently an integer from 1-20,
or a pharmaceutically acceptable salt thereof.
25. The conjugate of embodiment 24, wherein the conjugate has the structure of

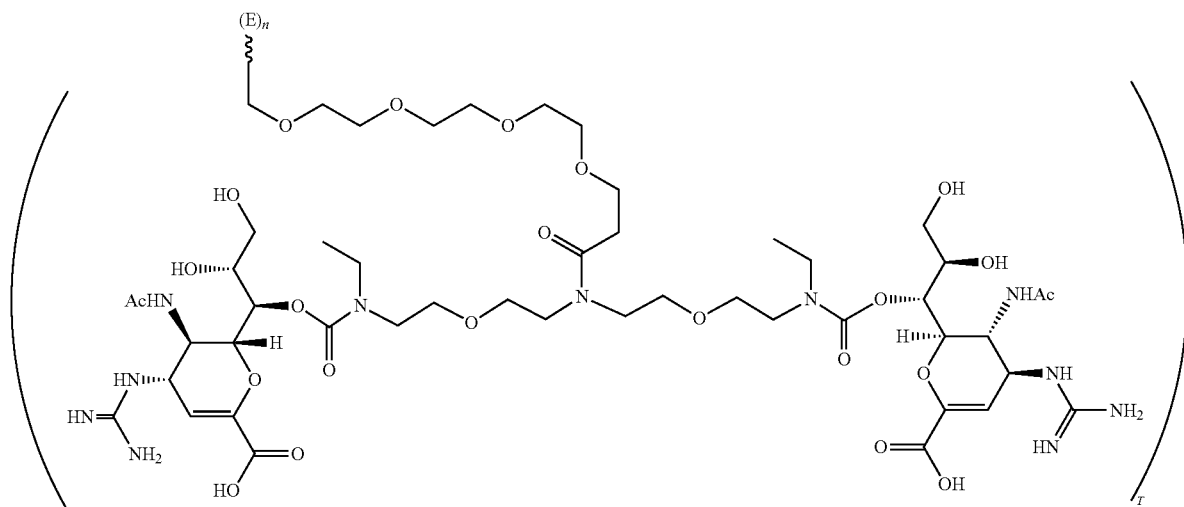

or a pharmaceutically acceptable salt thereof.

26. The conjugate of embodiment 2 or 3, wherein the conjugate is described by formula (D-III):

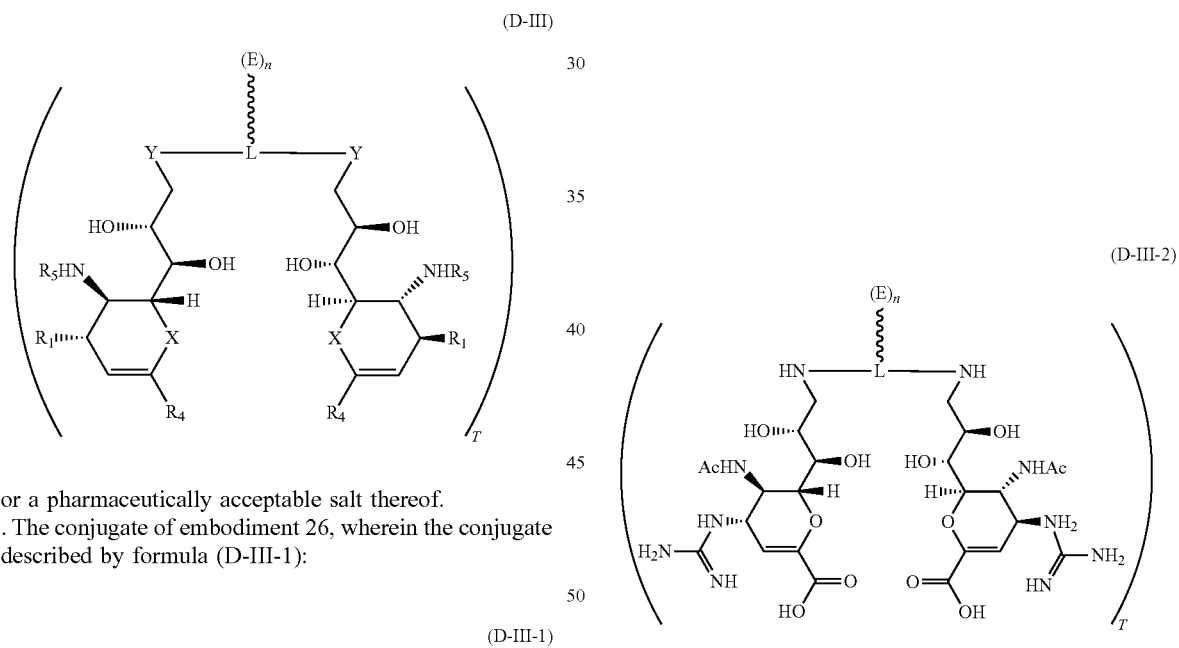

or a pharmaceutically acceptable salt thereof.

27. The conjugate of embodiment 26, wherein the conjugate is described by formula (D-III-1):

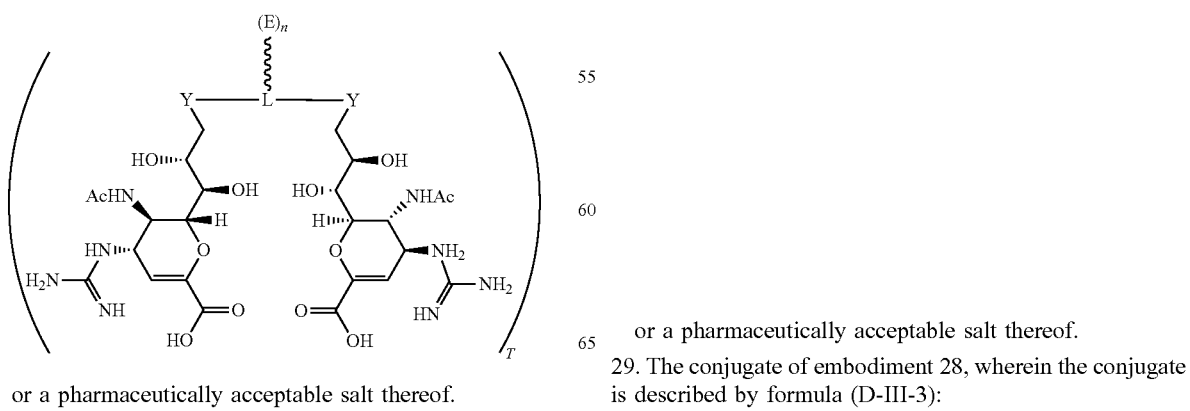

or a pharmaceutically acceptable salt thereof.

28. The conjugate of embodiment 27, wherein the conjugate is described by formula (D-III-2):

(D-III-2)

or a pharmaceutically acceptable salt thereof.

29. The conjugate of embodiment 28, wherein the conjugate is described by formula (D-III-3):

(D-III-3)
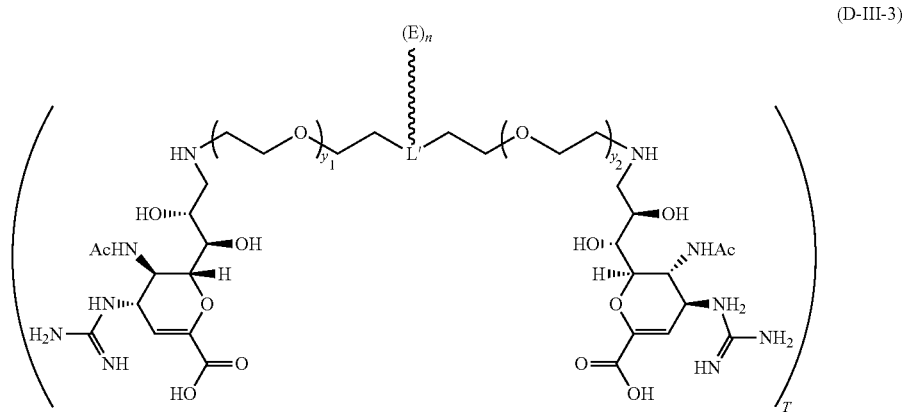
wherein L' is the remainder of L, and
y₁ and y₂ are each independently an integer from 1-20,
or a pharmaceutically acceptable salt thereof.
30. The conjugate of embodiment 27, wherein the conjugate is described by formula (D-III-4):
(D-III-4)
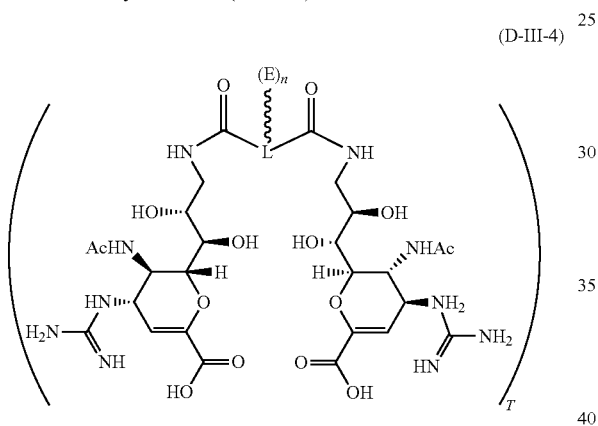
or a pharmaceutically acceptable salt thereof.
31. The conjugate of embodiment 30, wherein the conjugate is described by formula (D-III-5):
(D-III-5)
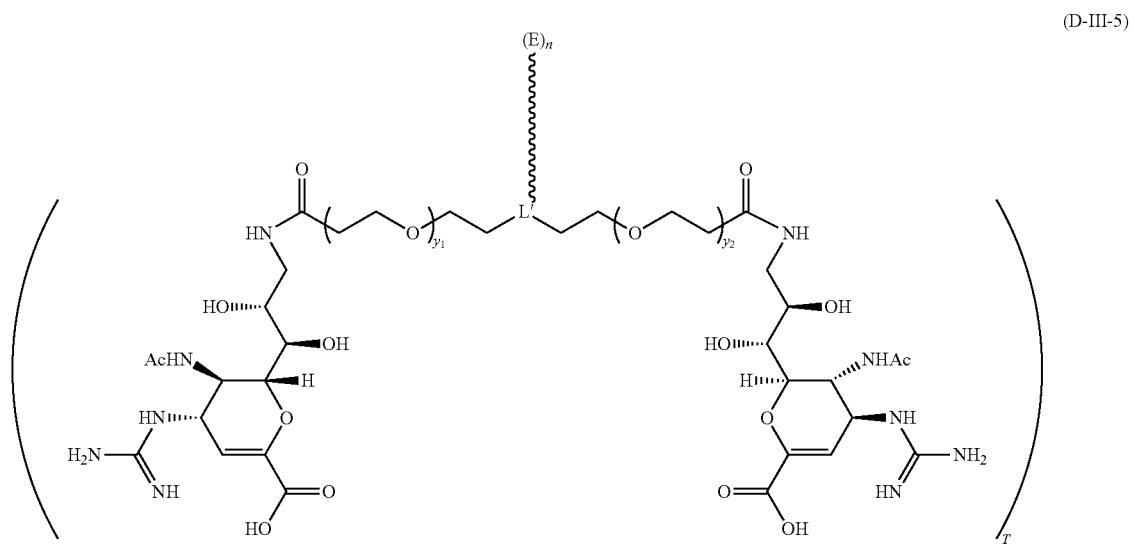

wherein L' is the remainder of L, and
$y_1$ and $y_2$ are each independently an integer from 1-20,
or a pharmaceutically acceptable salt thereof.

32. The conjugate of embodiment 27, wherein the conjugate is described by formula (D-III-6):

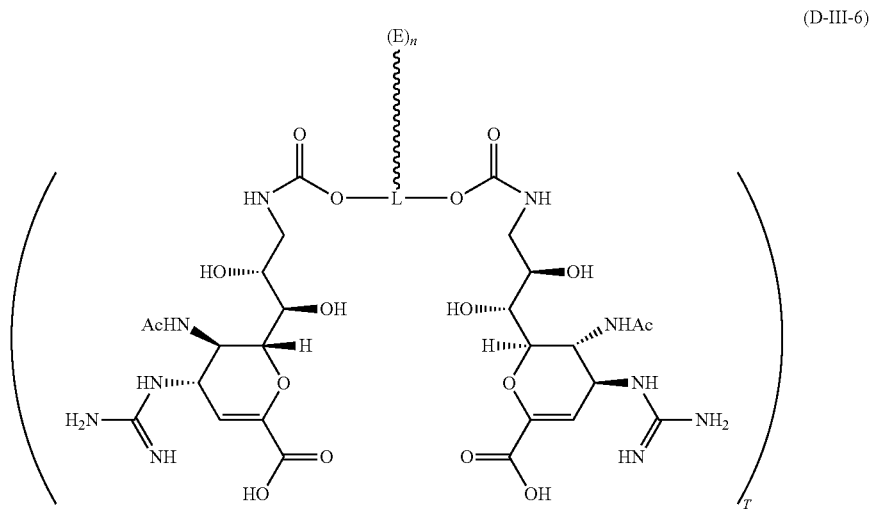

(D-III-6)

or a pharmaceutically acceptable salt thereof.

33. The conjugate of embodiment 32, wherein the conjugate is described by formula (D-III-7):

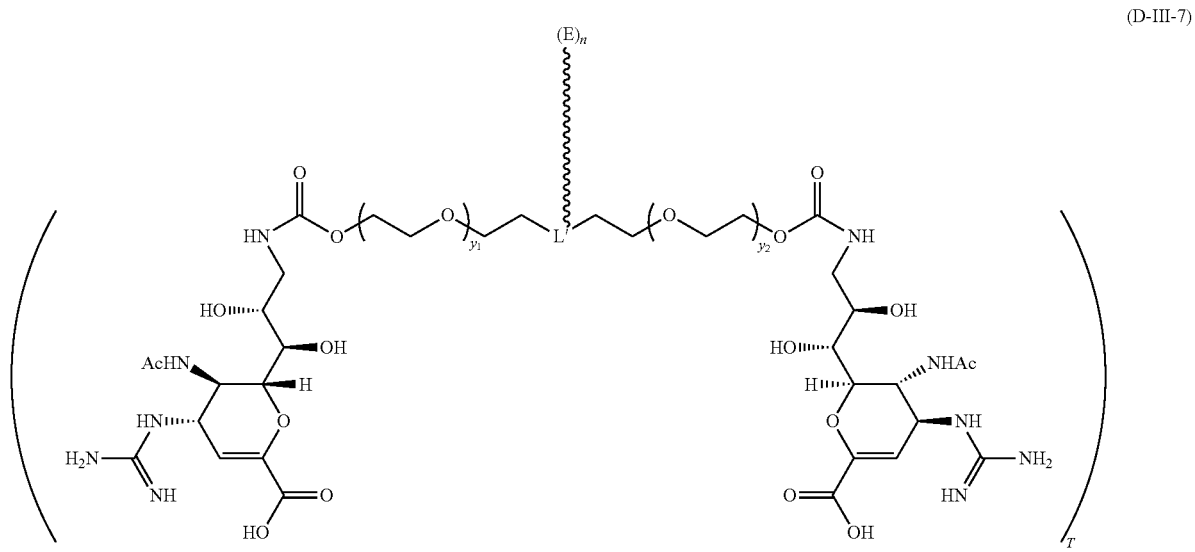

(D-III-7)

wherein L' is the remainder of L, and
$y_1$ and $y_2$ are each independently an integer from 1-20,
or a pharmaceutically acceptable salt thereof.

34. The conjugate of embodiment 27, wherein the conjugate is described by formula (D-III-8):

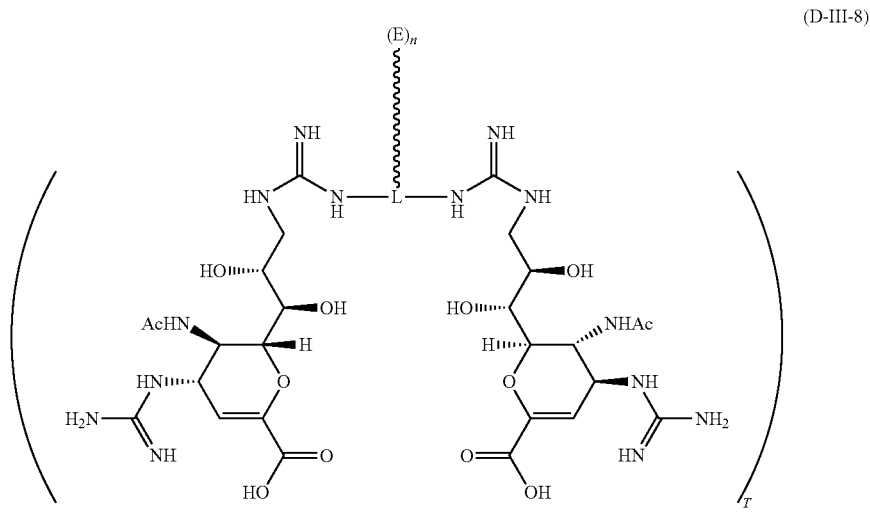
(D-III-8)
or a pharmaceutically acceptable salt thereof.
35. The conjugate of embodiment 34, wherein the conjugate is described by formula (D-III-9):
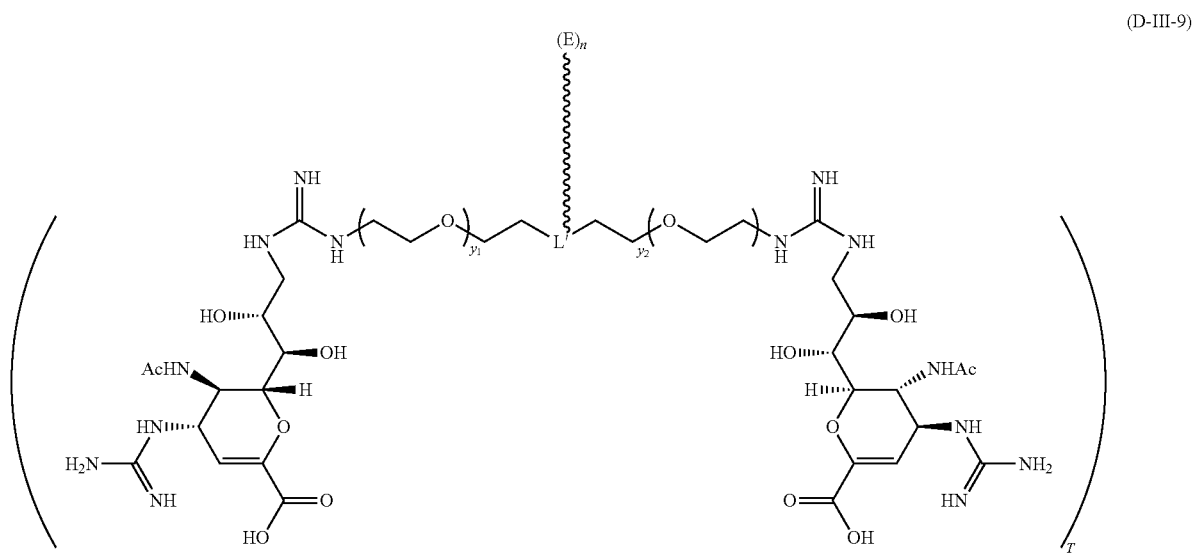
(D-III-9)
wherein L' is the remainder of L, and
$y_1$ and $y_2$ are each independently an integer from 1-20,
or a pharmaceutically acceptable salt thereof.
36. The conjugate of embodiment 2, wherein the conjugate is described by formula (D-IV):

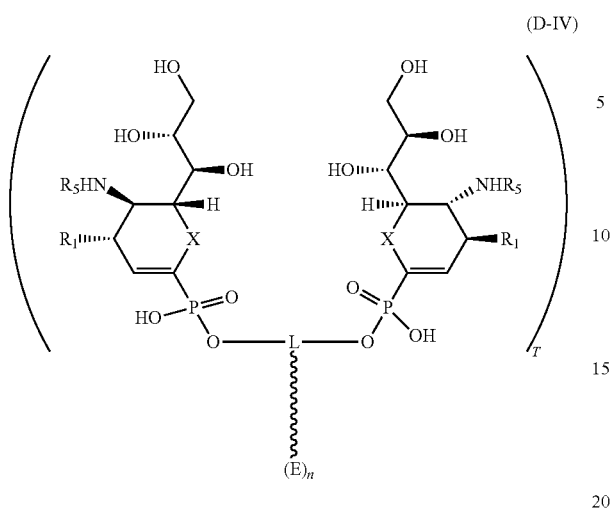
(D-IV)
or a pharmaceutically acceptable salt thereof.
37. The conjugate of embodiment 36, wherein the conjugate is described by formula (D-IV-1):
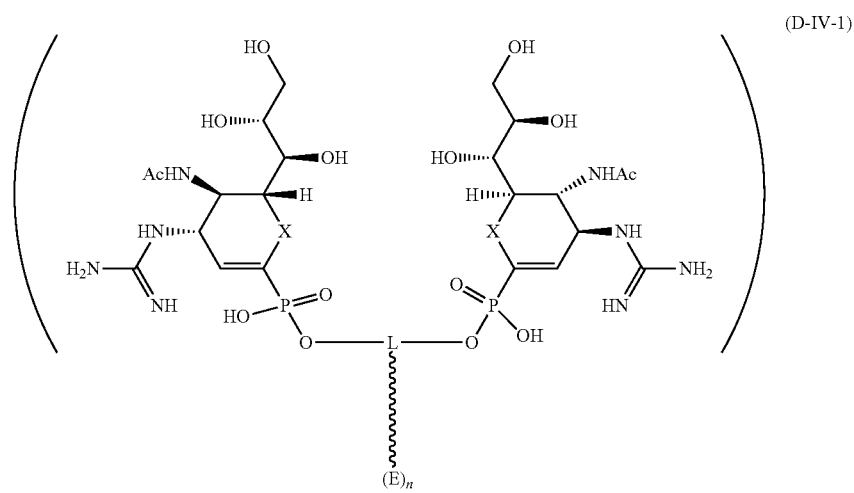
(D-IV-1)
or a pharmaceutically acceptable salt thereof.
38. The conjugate of embodiment 37, wherein the conjugate is described by formula (D-IV-2):

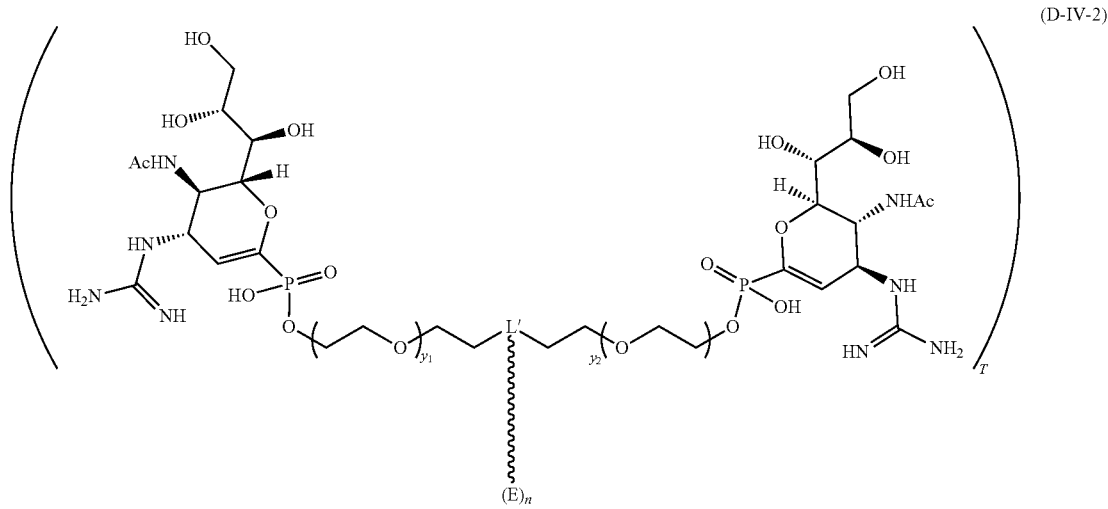

(D-IV-2)

wherein L' is the remainder of L, and
$y_1$ and $y_2$ are each independently an integer from 1-20, or a pharmaceutically acceptable salt thereof.

39. The conjugate of embodiment 2 or 3, wherein the conjugate is described by formula (D-V): Y-L-Y.

40. The conjugate of embodiment 39, wherein the conjugate is described by formula (D-V-1):

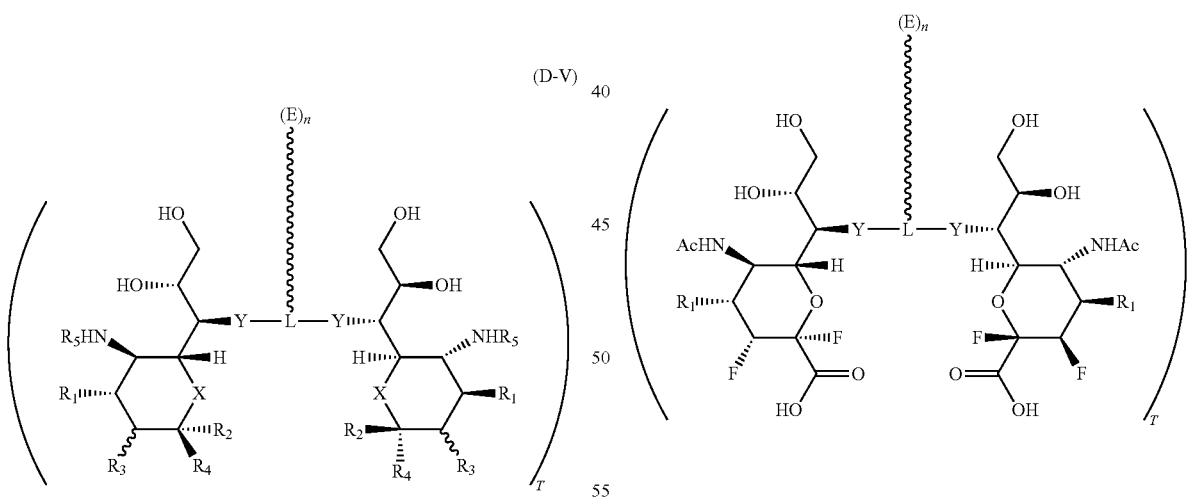

(D-V)

(D-V-1)

or a pharmaceutically acceptable salt thereof.

or a pharmaceutically acceptable salt thereof.

41. The conjugate of embodiment 40, wherein the conjugate is described by formula (D-V-2):

(D-V-2)

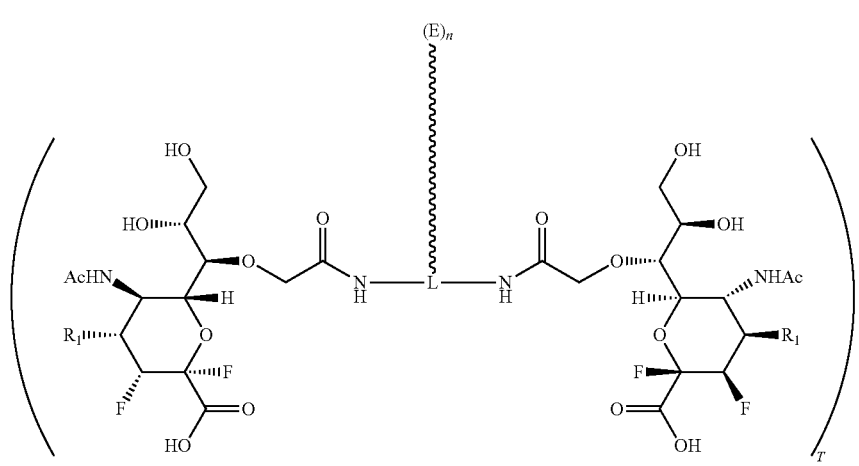

or a pharmaceutically acceptable salt thereof.

42. The conjugate of embodiment 41, wherein the conjugate is described by formula (D-V-3):

(D-V-3)

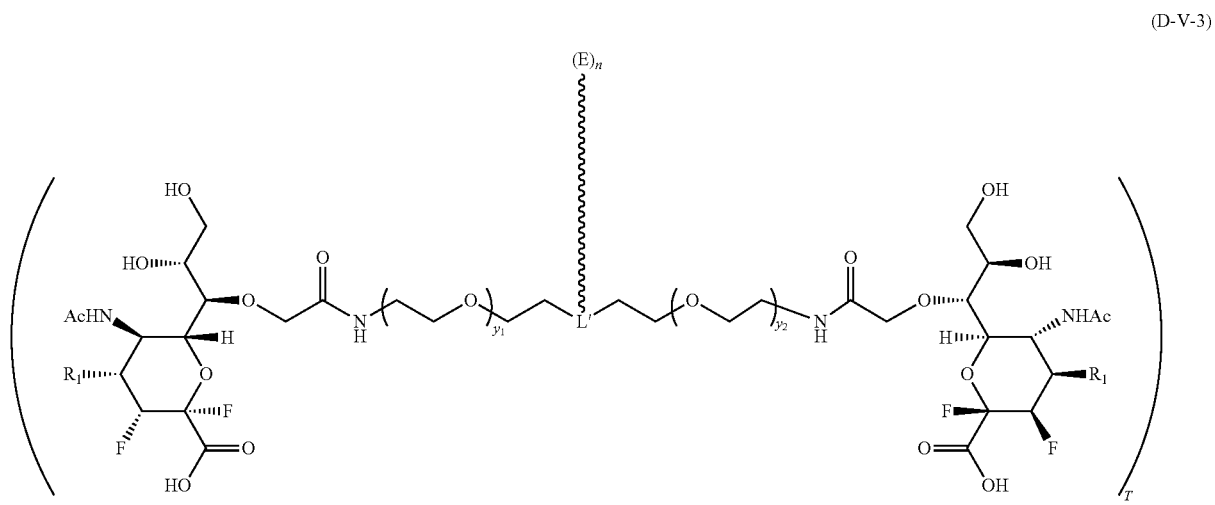

wherein L' is the remainder of L, and $y_1$ and $y_2$ are each independently an integer from 1-20, or a pharmaceutically acceptable salt thereof.

43. The conjugate of embodiment 42, wherein L' is a nitrogen atom.

44. The conjugate of embodiment 42, wherein $y_1$ and $y_2$ are each 1, $y_1$ and $y_2$ are each 2, or $y_1$ and $y_2$ are each 3.

45. The conjugate of embodiment 40, wherein the conjugate is described by formula (D-V-4):

(D-V-4)

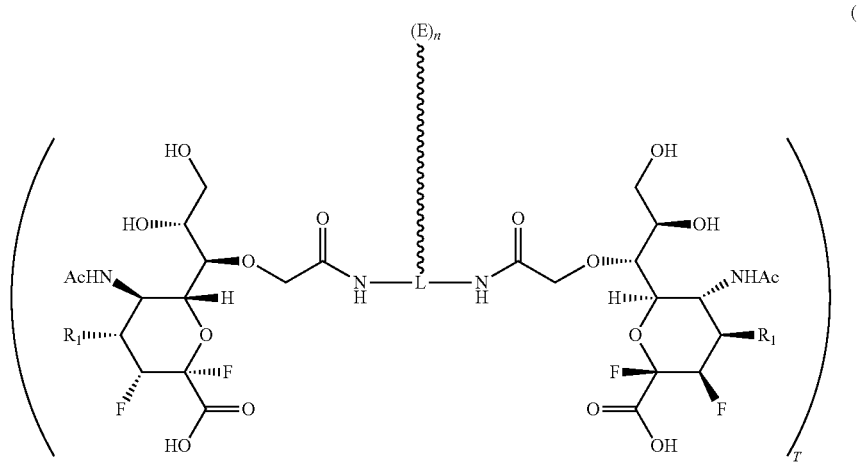

or a pharmaceutically acceptable salt thereof.

46. The conjugate of embodiment 45, wherein the conjugate is described by formula (D-V-5):

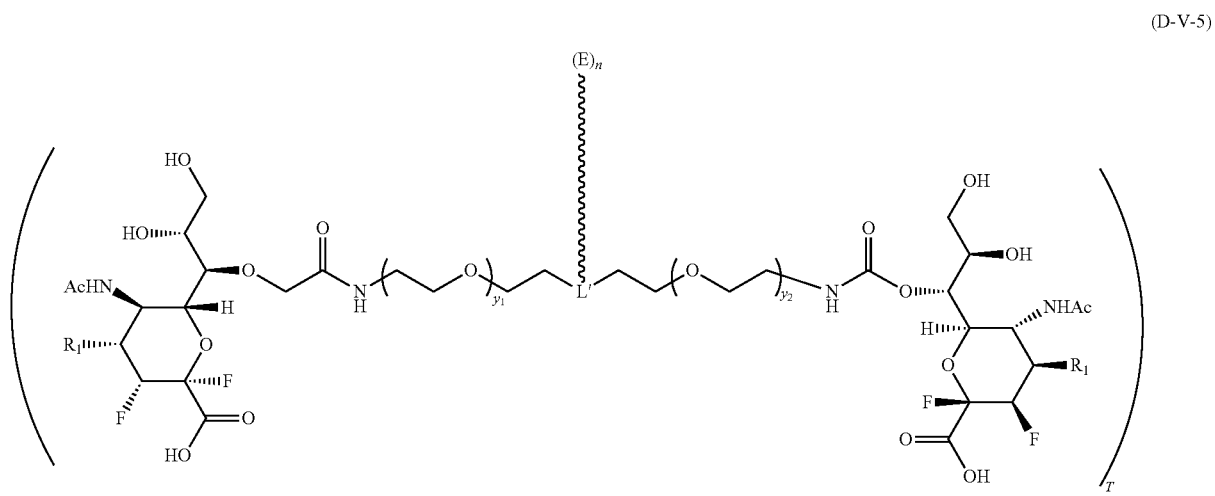

(D-V-5)

wherein L' is the remainder of L, and $y_1$ and $y_2$ are each independently an integer from 1-20, or a pharmaceutically acceptable salt thereof.

47. The conjugate of embodiment 46, wherein L' is a nitrogen atom.

48. The conjugate of embodiment 46, wherein $y_1$ and $y_2$ are each 1, $y_1$ and $y_2$ are each 2, or $y_1$ and $y_2$ are each 3.

49. The conjugate of embodiment 39, wherein the conjugate is described by formula (D-V-6):

(D-V-6)
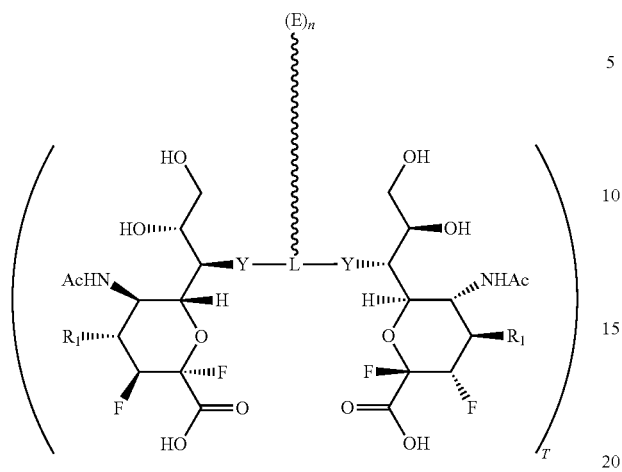
or a pharmaceutically acceptable salt thereof.
50. The conjugate of embodiment 49, wherein the conjugate is described by formula (D-V-7):
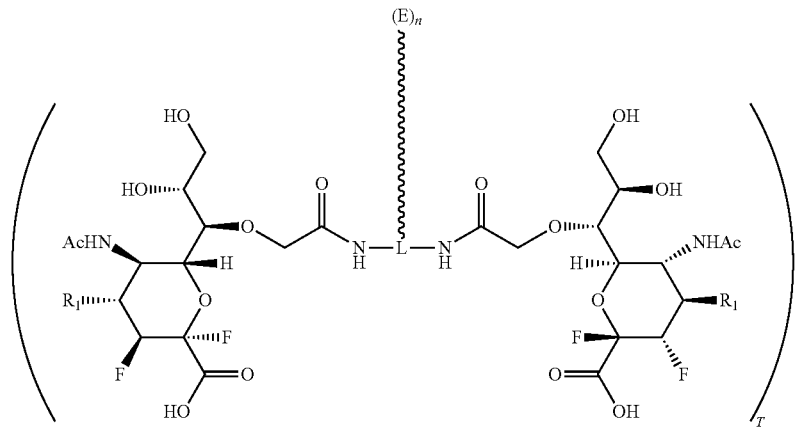
or a pharmaceutically acceptable salt thereof.
51. The conjugate of embodiment 50, wherein the conjugate is described by formula (D-V-8):

(D-V-8)

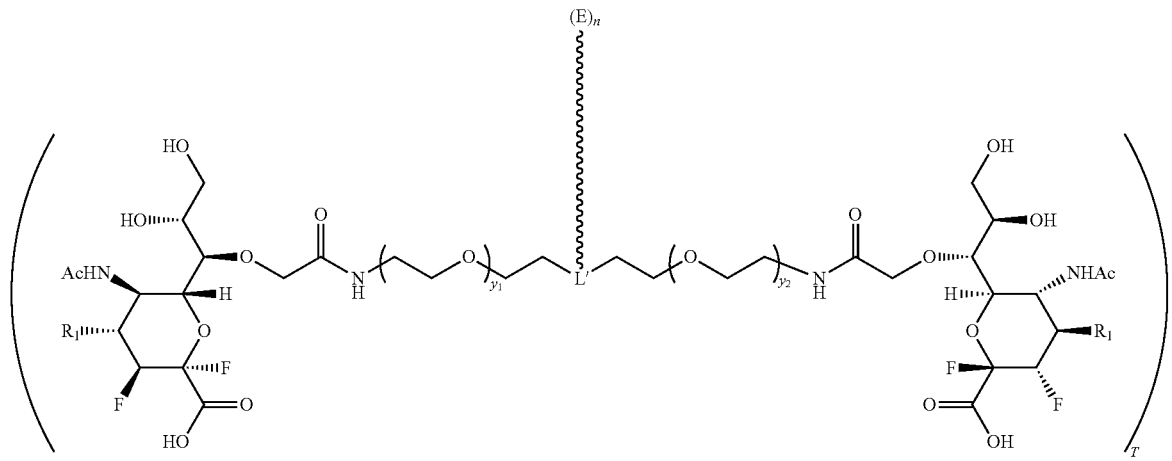

wherein L' is the remainder of L, and
y₁ and y₂ are each independently an integer from 1-20,
or a pharmaceutically acceptable salt thereof.

52. The conjugate of embodiment 51, wherein L' is a nitrogen atom.

53. The conjugate of embodiment 51, wherein $y_1$ and $y_2$ are each 1, $y_1$ and $y_2$ are each 2, or $y_1$ and $y_2$ are each 3.

54. The conjugate of embodiment 49, wherein the conjugate is described by formula (D-V-9):

(D-V-9)

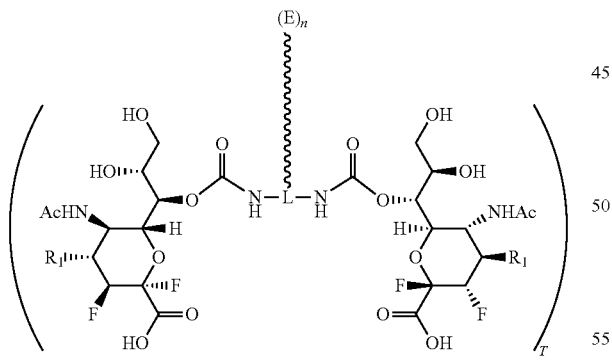

or a pharmaceutically acceptable salt thereof.

55. The conjugate of embodiment 51, wherein the conjugate is described by formula (D-V-10):

(D-V-10)

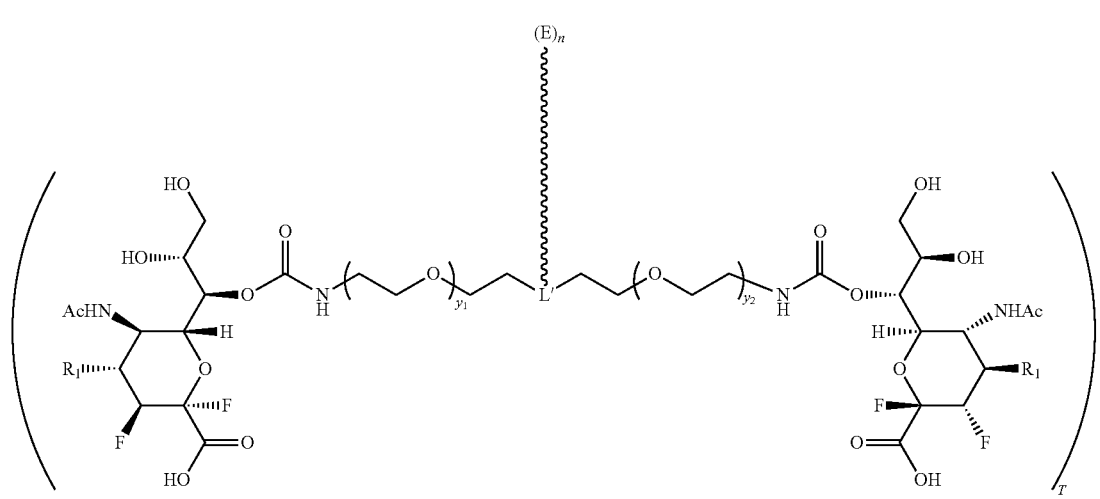

wherein L' is the remainder of L, and $y_1$ and $y_2$ are each independently an integer from 1-20, or a pharmaceutically acceptable salt thereof.

56. The conjugate of embodiment 55, wherein L' is a nitrogen atom.

57. The conjugate of embodiment 56, wherein $y_1$ and $y_2$ are each 1, $y_1$ and $y_2$ are each 2, or $y_1$ and $y_2$ are each 3.

58. The conjugate of embodiment 2 or 3, wherein the conjugate is described by formula (D-VI):

59. The conjugate of embodiment 58, wherein the conjugate is described by formula (D-VI-1):

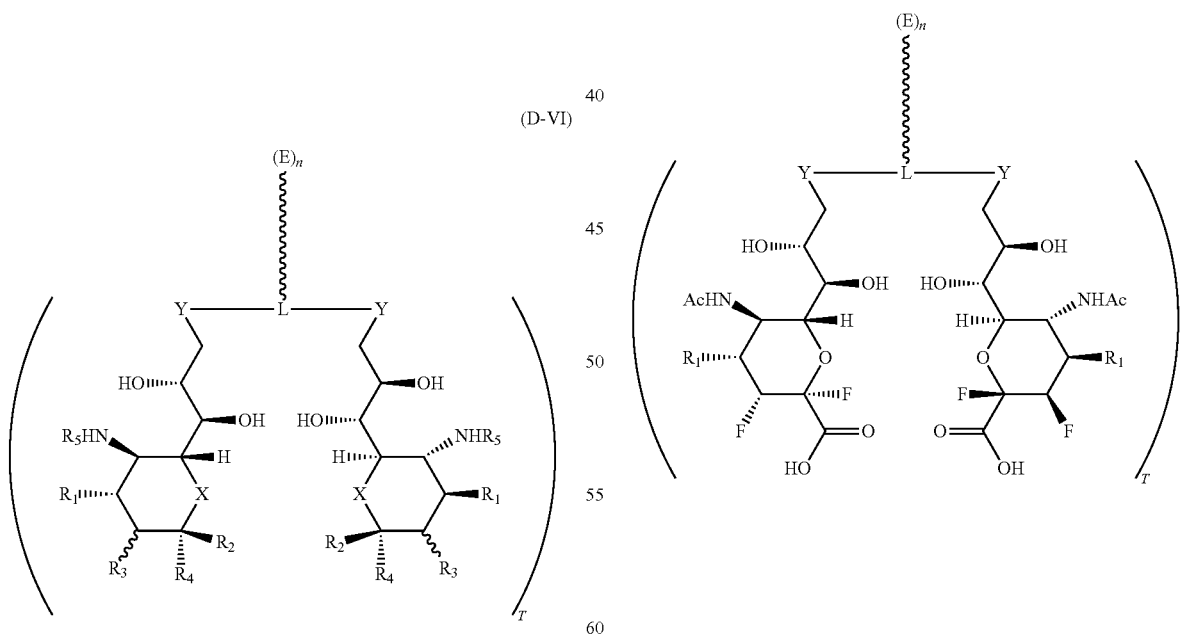

or a pharmaceutically acceptable salt thereof.

or a pharmaceutically acceptable salt thereof.

60. The conjugate of embodiment 59, wherein the conjugate is described by formula (D-VI-2):

wherein L' is the remainder of L, and
$y_1$ and $y_2$ are each independently an integer from 1-20,
or a pharmaceutically acceptable salt thereof.

62. The conjugate of embodiment 59, wherein the conjugate is described by formula (D-VI-4):
or a pharmaceutically acceptable salt thereof.

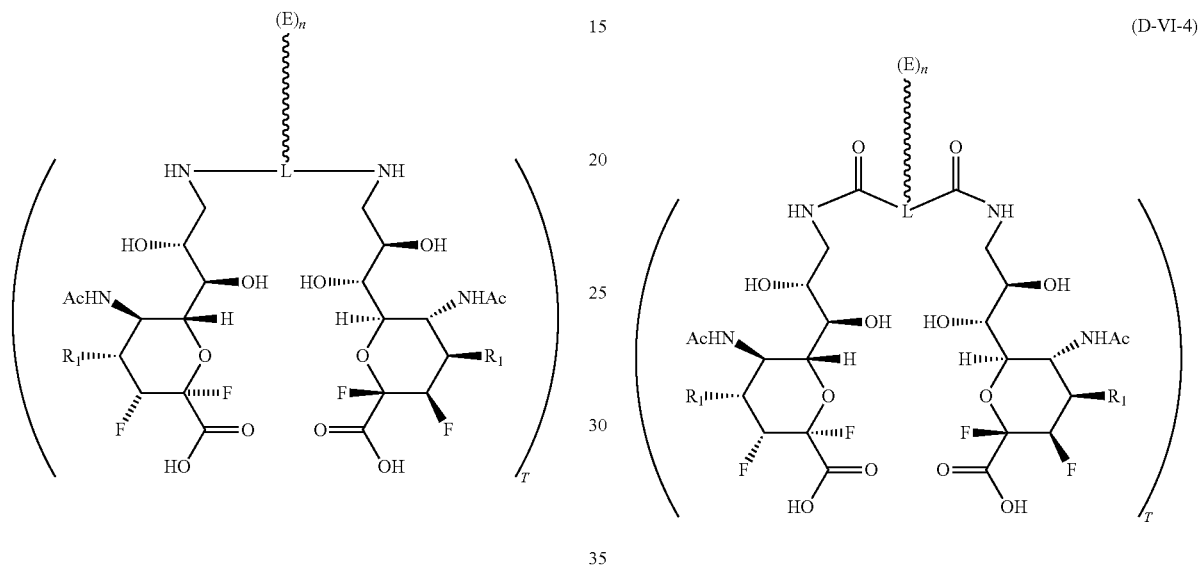

(D-VI-2)

(D-VI-4)

or a pharmaceutically acceptable salt thereof.

61. The conjugate of embodiment 60, wherein the conjugate is described by formula (D-VI-3):

63. The conjugate of embodiment 62, wherein the conjugate is described by formula (D-VI-5):

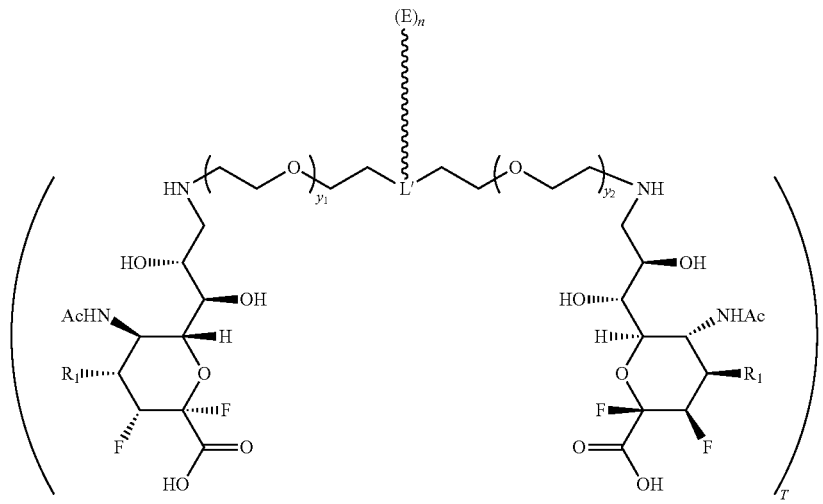

(D-VI-3)

(D-VI-5)
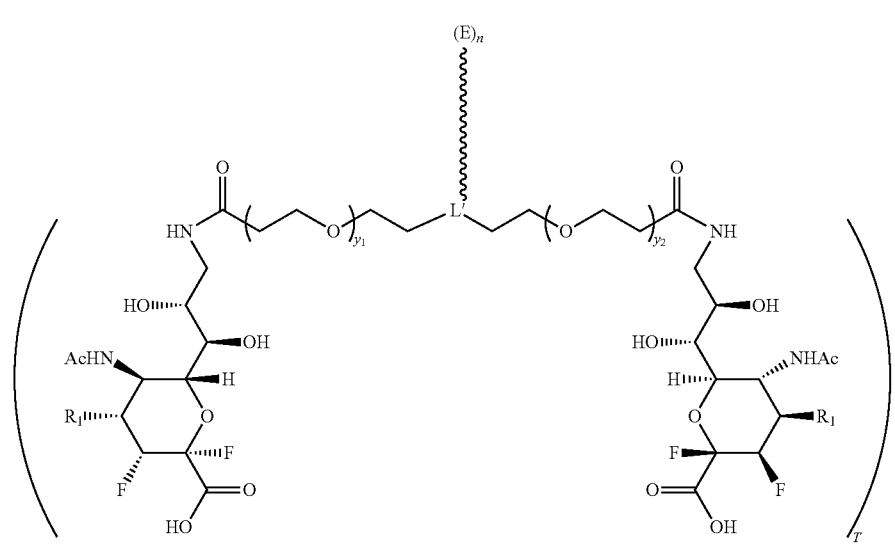
wherein L' is the remainder of L, and
$y_1$ and $y_2$ are each independently an integer from 1-20,
or a pharmaceutically acceptable salt thereof.
64. The conjugate of embodiment 59, wherein the conjugate is described by formula (D-VI-6):
(D-VI-6)
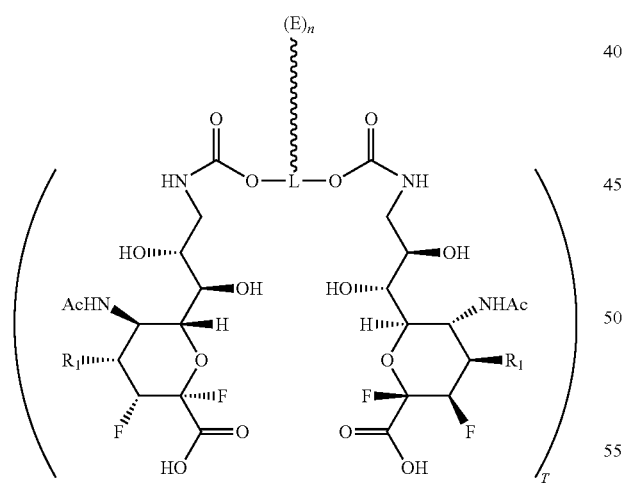
or a pharmaceutically acceptable salt thereof.
65. The conjugate of embodiment 64, wherein the conjugate is described by formula (D-VI-7):

(D-VI-7)
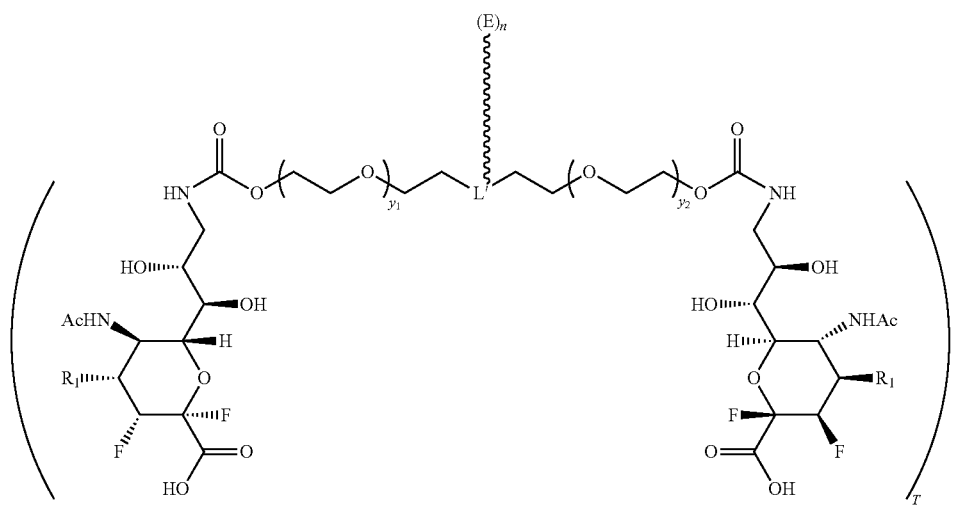
wherein L' is the remainder of L, and
$y_1$ and $y_2$ are each independently an integer from 1-20,
or a pharmaceutically acceptable salt thereof.
66. The conjugate of embodiment 59, wherein the conjugate is described by formula (D-VI-8):
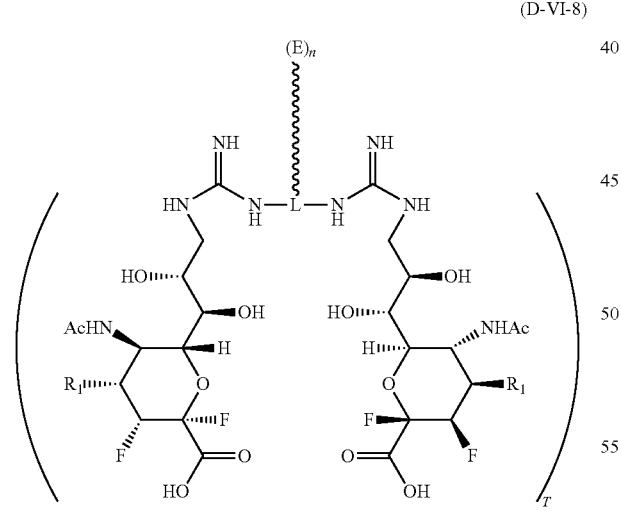
(D-VI-8)
or a pharmaceutically acceptable salt thereof.
67. The conjugate of embodiment 66, wherein the conjugate is described by formula (D-VI-9):

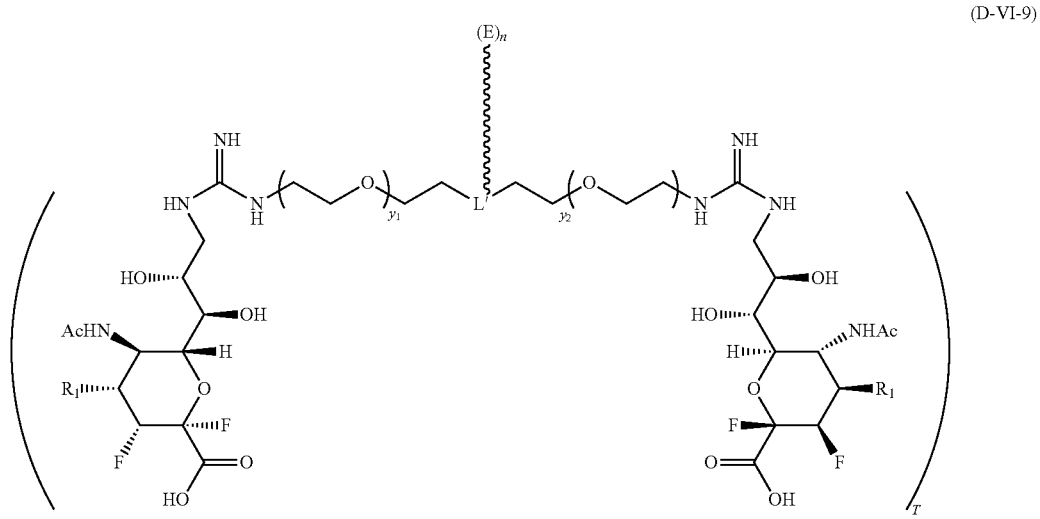

(D-VI-9)

wherein L' is the remainder of L, and $y_1$ and $y_2$ are each independently an integer from 1-20, or a pharmaceutically acceptable salt thereof.

68. The conjugate of embodiment 2 or 3, wherein the conjugate is described by formula (D-VII):

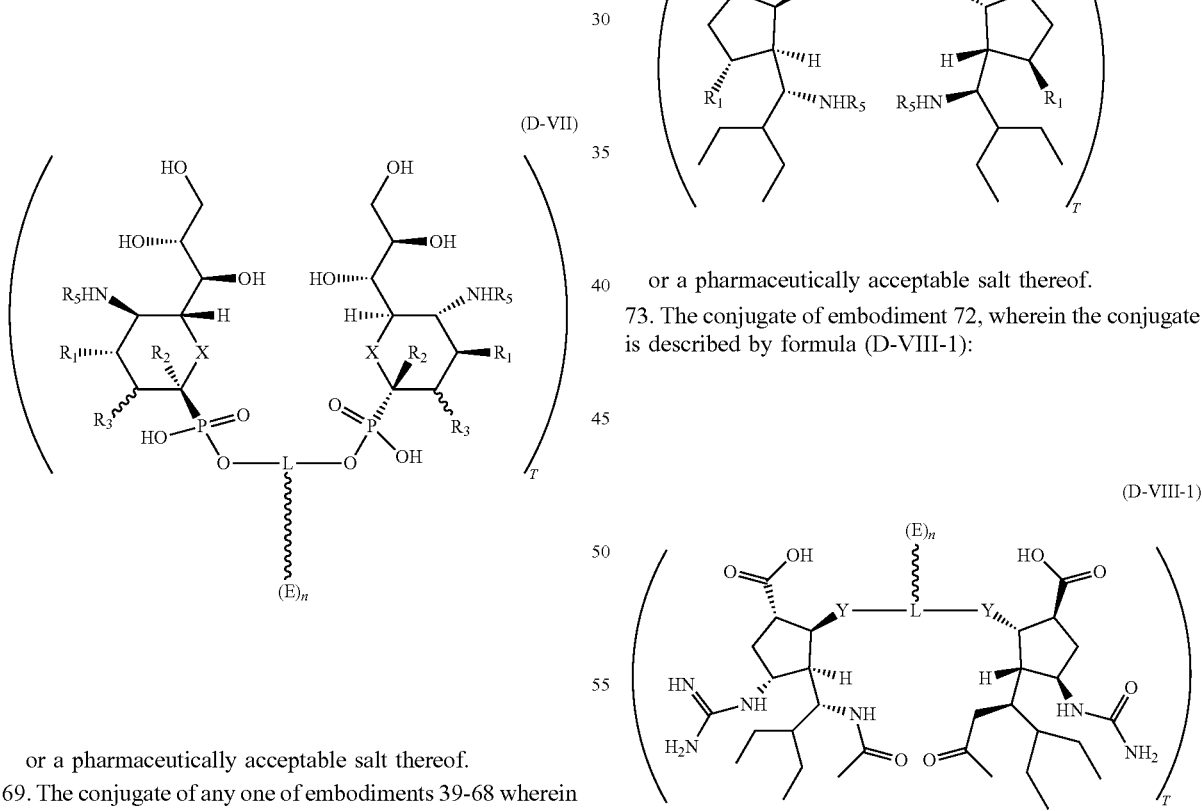

or a pharmaceutically acceptable salt thereof.

69. The conjugate of any one of embodiments 39-68 wherein $R_1$ is —OH.

70. The conjugate of any one of embodiments 39-68 wherein $R_1$ is —$NH_2$.

71. The conjugate of any one of embodiments 39-68 wherein $R_1$ is —NHC(=NH)$NH_2$.

72. The conjugate of embodiment 2, wherein the conjugate is described by formula (D-VIII):

or a pharmaceutically acceptable salt thereof.

73. The conjugate of embodiment 72, wherein the conjugate is described by formula (D-VIII-1):

or a pharmaceutically acceptable salt thereof.

74. The conjugate of embodiment 73, wherein the conjugate is described by formula (D-VIII-2):

(D-VIII-2)

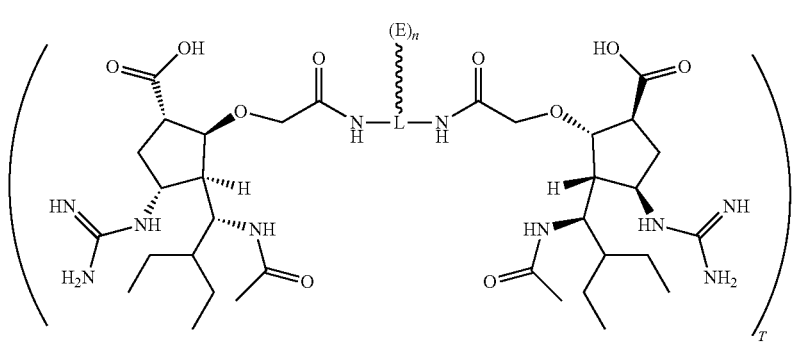

or a pharmaceutically acceptable salt thereof.
75. The conjugate of embodiment 74, wherein the conjugate is described by formula (D-VIII-3):

(D-VIII-3)

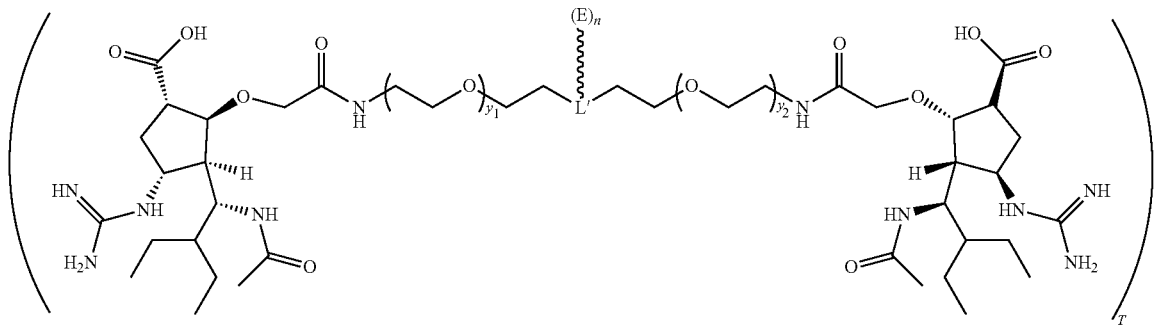

wherein L' is the remainder of L, and
$y_1$ and $y_2$ are each independently an integer from 1-20,
or a pharmaceutically acceptable salt thereof.
76. The conjugate of embodiment 75, wherein L' is a nitrogen atom.
77. The conjugate of embodiment 75, wherein the conjugate has the structure selected from

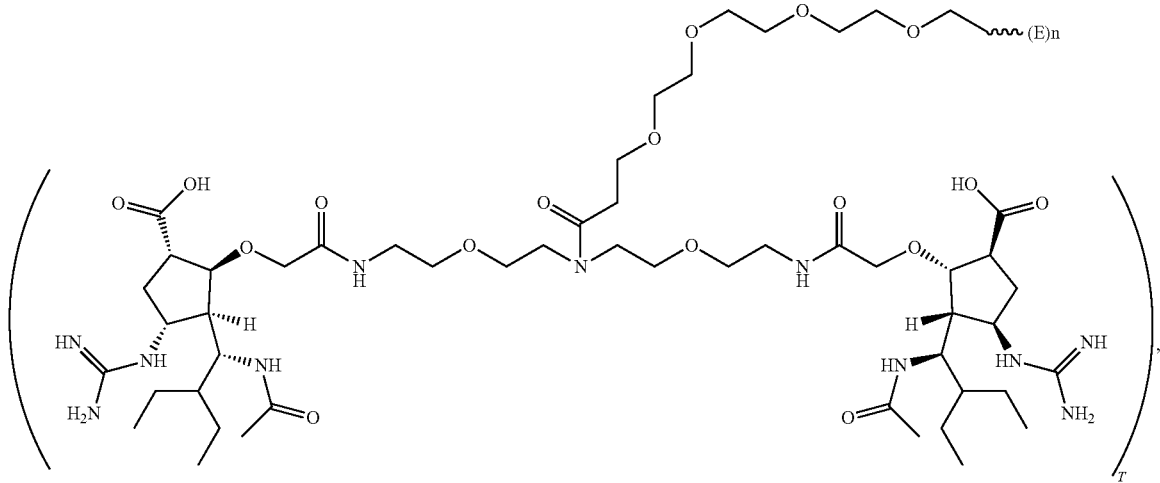

-continued
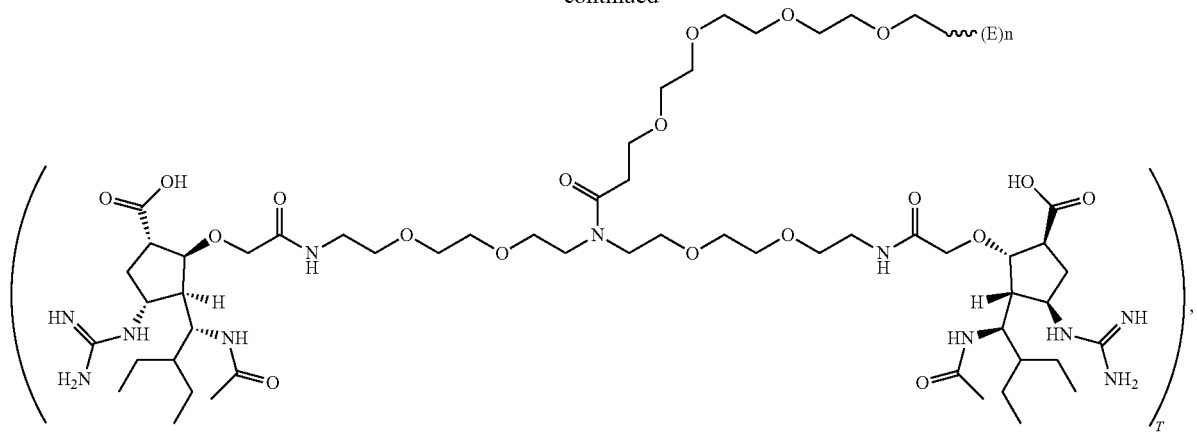
or
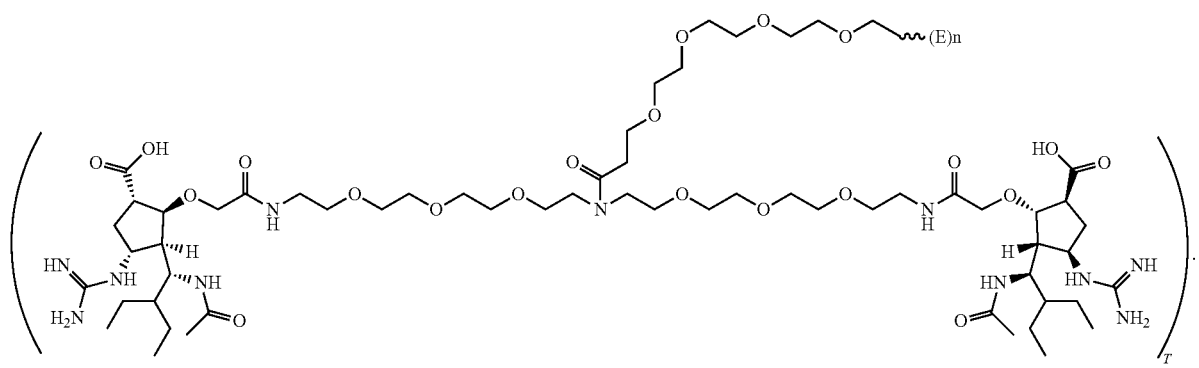
78. The conjugate of embodiment 73, wherein the conjugate is described by formula (D-VIII-4):
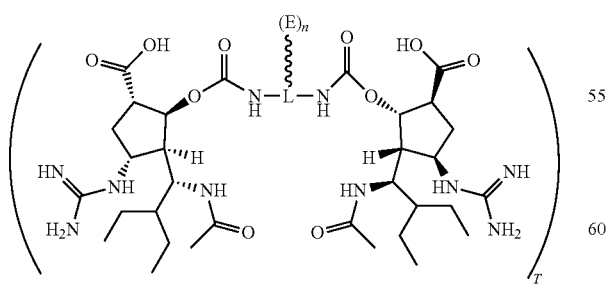
(D-VIII-4)
or a pharmaceutically acceptable salt thereof.
79. The conjugate of embodiment 78, wherein the conjugate is described by formula (D-VIII-5):

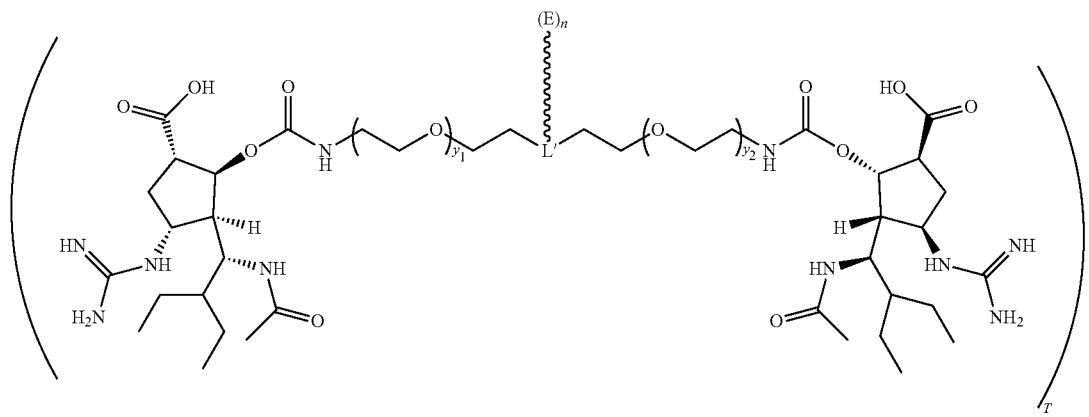
(D-VIII-5)
wherein L' is the remainder of L, and
$y_1$ and $y_2$ are each independently an integer from 1-20,
or a pharmaceutically acceptable salt thereof.
80. The conjugate of embodiment 79, wherein L' is a nitrogen atom.
81. The conjugate of embodiment 79, wherein the conjugate has the structure selected from
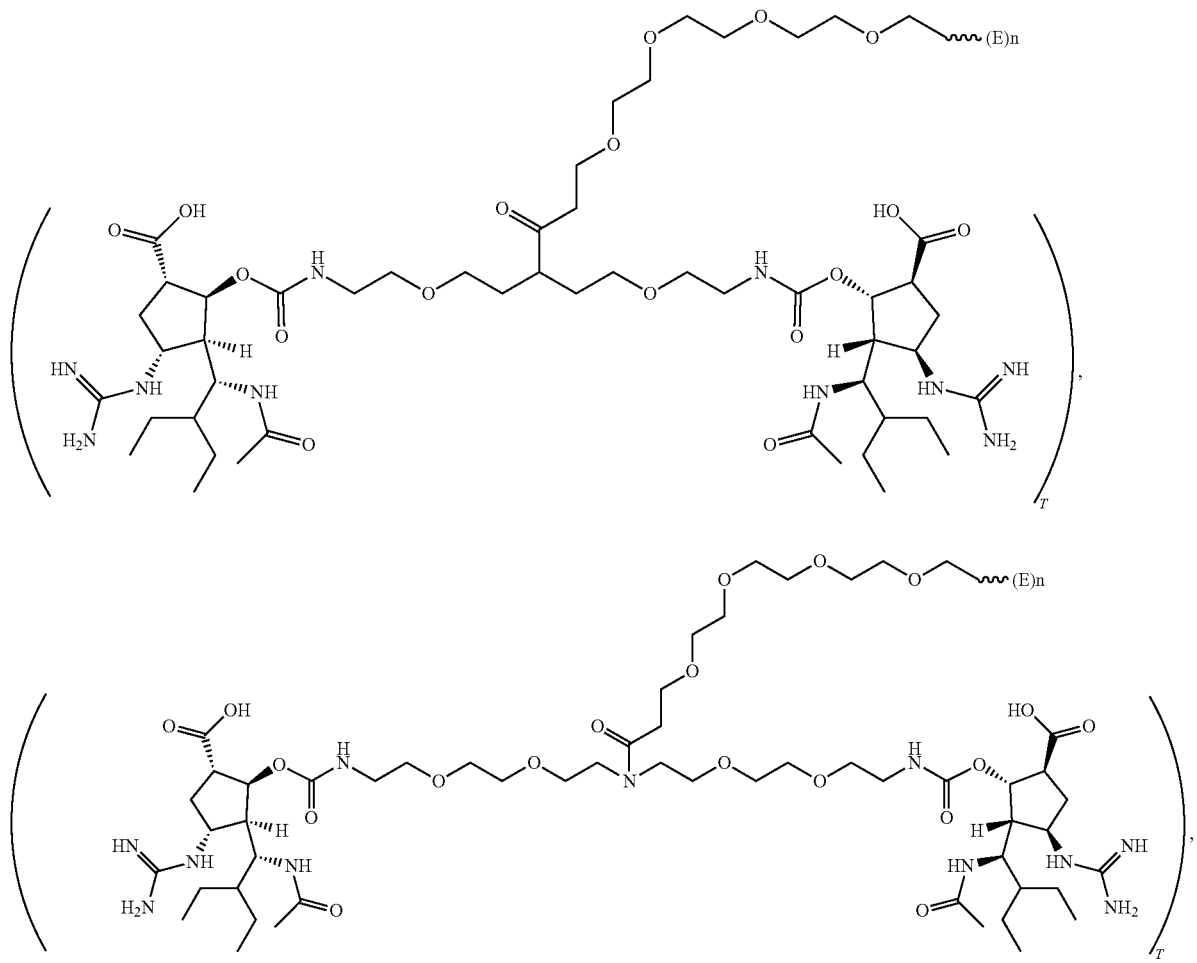
or -continued
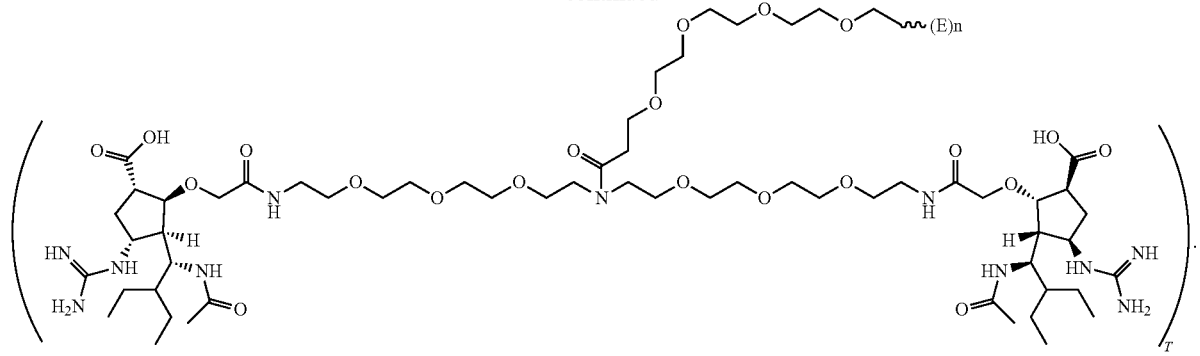
82. The conjugate of embodiment 78, wherein the conjugate is described by the structure of
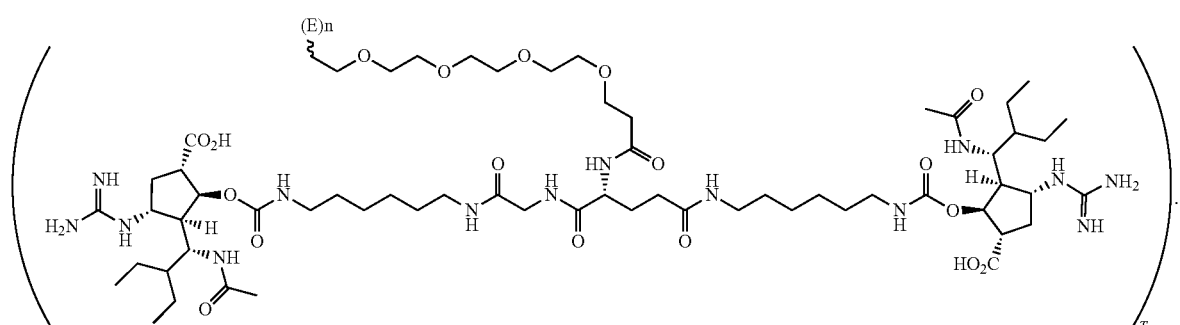
83. The conjugate of embodiment 73, wherein the conjugate is described by formula (D-VIII-6):
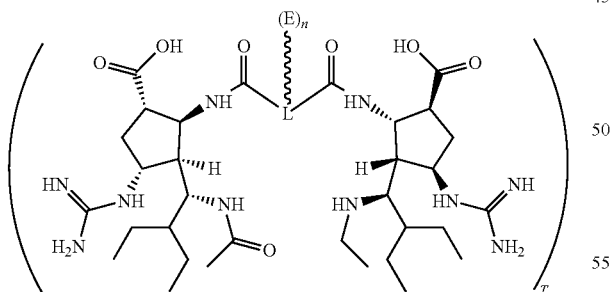
(D-VIII-6)
or a pharmaceutically acceptable salt thereof.
84. The conjugate of embodiment 83, wherein the conjugate is described by formula (D-VIII-7):

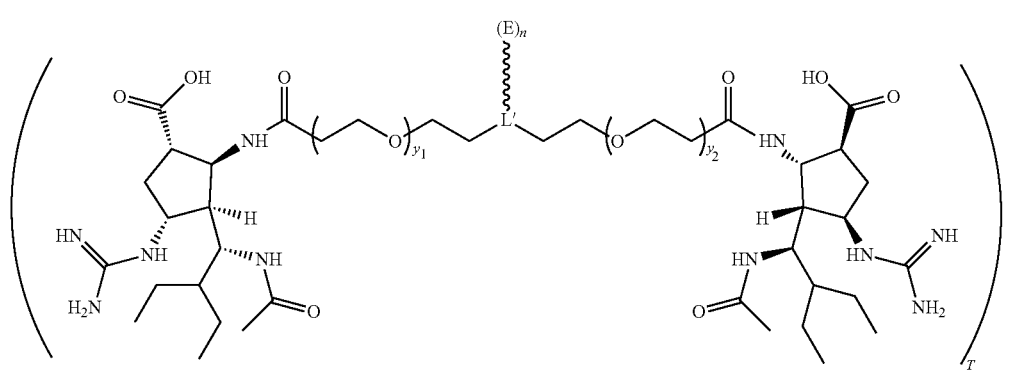

wherein L' is the remainder of L, and
$y_1$ and $y_2$ are each independently an integer from 1-20,
or a pharmaceutically acceptable salt thereof.

85. The conjugate of embodiment 73, wherein the conjugate is described by formula (D-VIII-8):

wherein L' is the remainder of L, and
$y_1$ and $y_2$ are each independently an integer from 1-20,
or a pharmaceutically acceptable salt thereof.

87. The conjugate of embodiment 72, wherein the conjugate is described by formula (D-VIII-10):

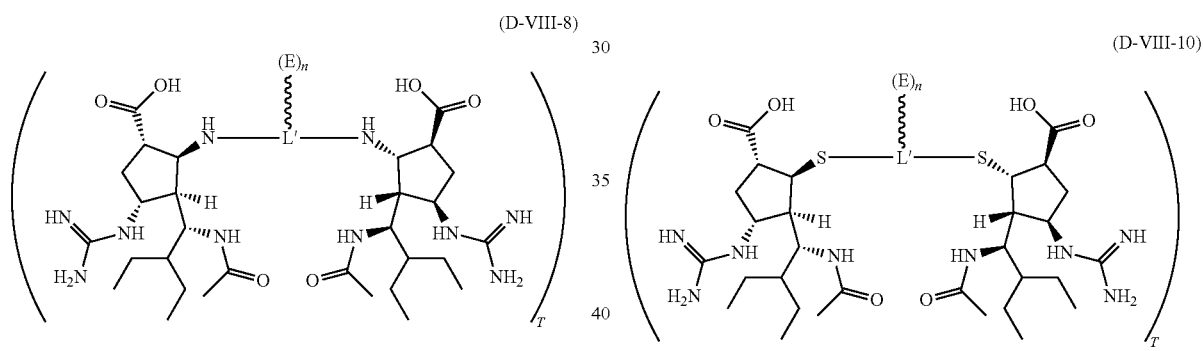

or a pharmaceutically acceptable salt thereof.

86. The conjugate of embodiment 85, wherein the conjugate is described by formula (D-VIII-9):

or a pharmaceutically acceptable salt thereof.

88. The conjugate of embodiment 87, wherein the conjugate is described by formula (D-VIII-11):

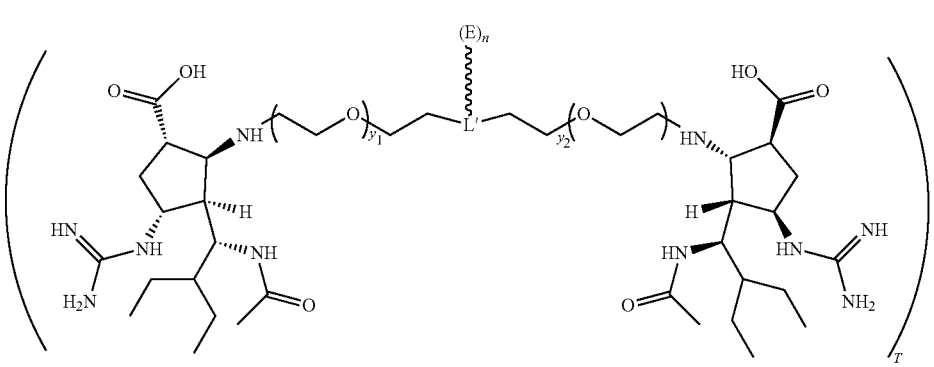

(D-VIII-11)

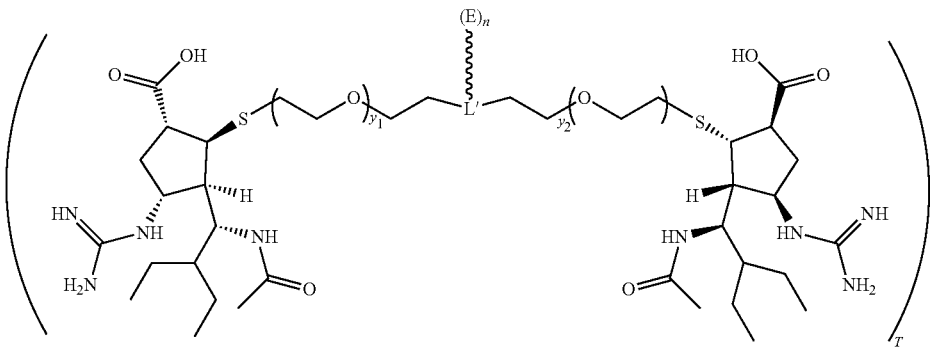

wherein L' is the remainder of L, and
y$_1$ and y$_2$ are each independently an integer from 1-20,
or a pharmaceutically acceptable salt thereof.

89. The conjugate of embodiment 2, wherein the conjugate is described by formula (D-IX):

(D-IX)

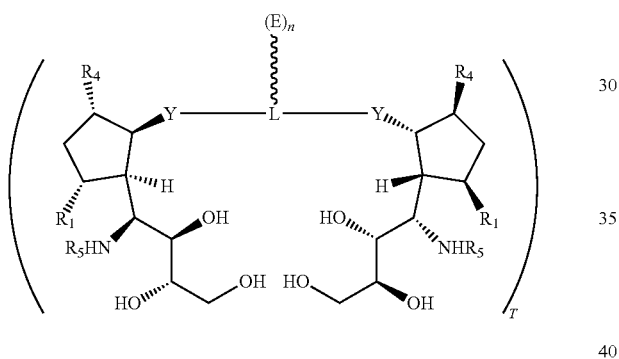

or a pharmaceutically acceptable salt thereof.

90. The conjugate of embodiment 89, wherein the conjugate is described by formula (D-IX-1):

(D-IX-1)

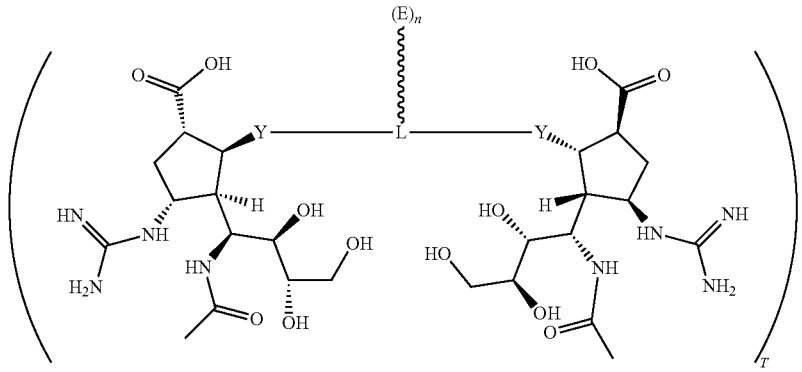

or a pharmaceutically acceptable salt thereof.

91. The conjugate of embodiment 90, wherein the conjugate is described by formula (D-IX-2):

(D-IX-2)

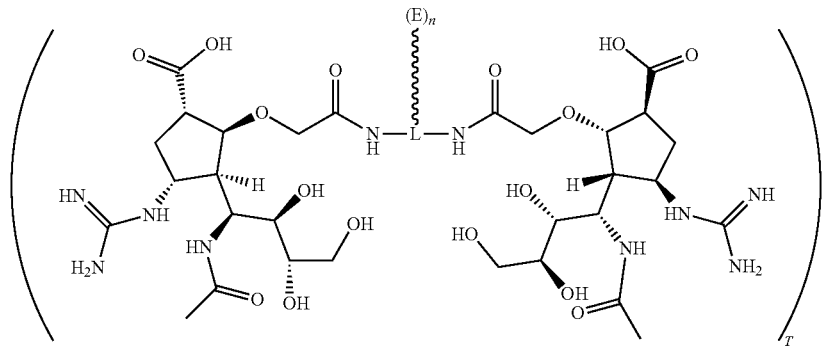

or a pharmaceutically acceptable salt thereof.
92. The conjugate of embodiment 90, wherein the conjugate is described by formula (D-IX-3):

(D-IX-3)

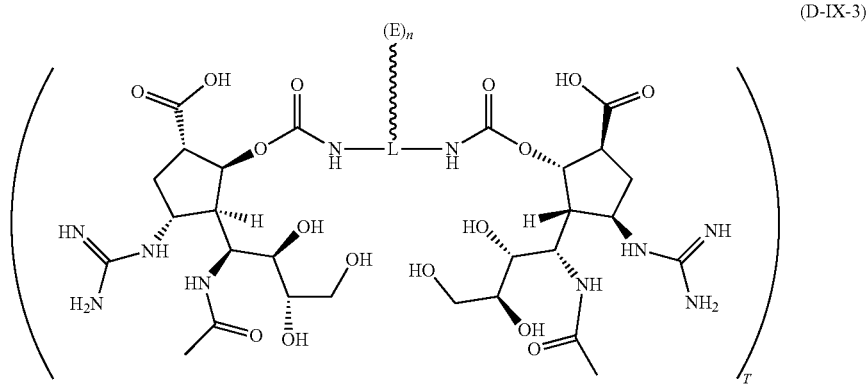

or a pharmaceutically acceptable salt thereof.
93. The conjugate of embodiment 90, wherein the conjugate is described by formula (D-IX-4):

(D-IX-4)

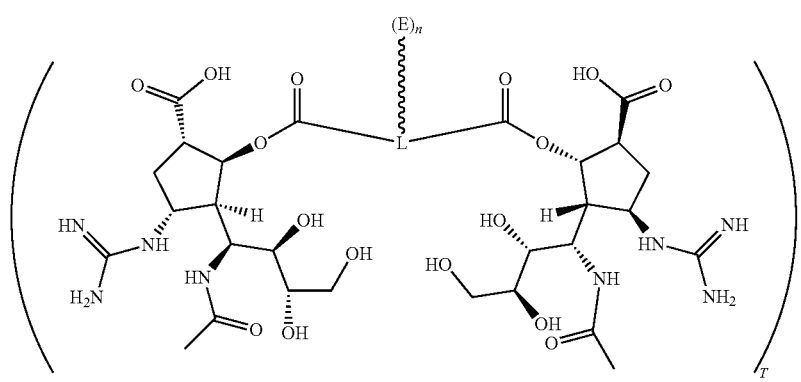

or a pharmaceutically acceptable salt thereof.
94. The conjugate of embodiment 90, wherein the conjugate is described by formula (D-IX-5):

(D-IX-5)

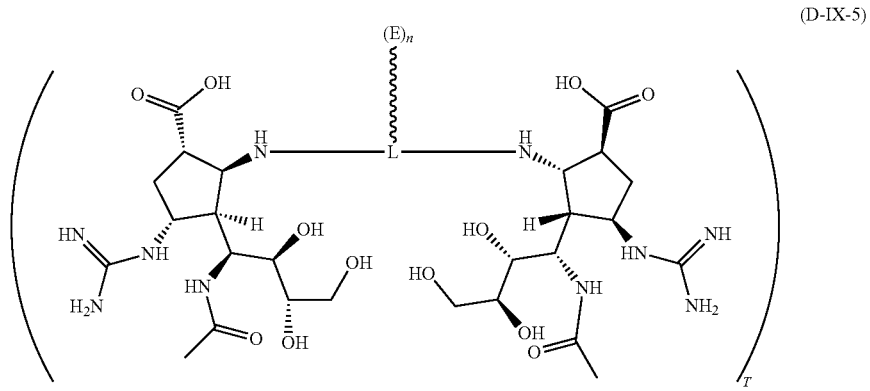

or a pharmaceutically acceptable salt thereof.
95. The conjugate of embodiment 90, wherein the conjugate is described by formula (D-IX-6):

(D-IX-6)

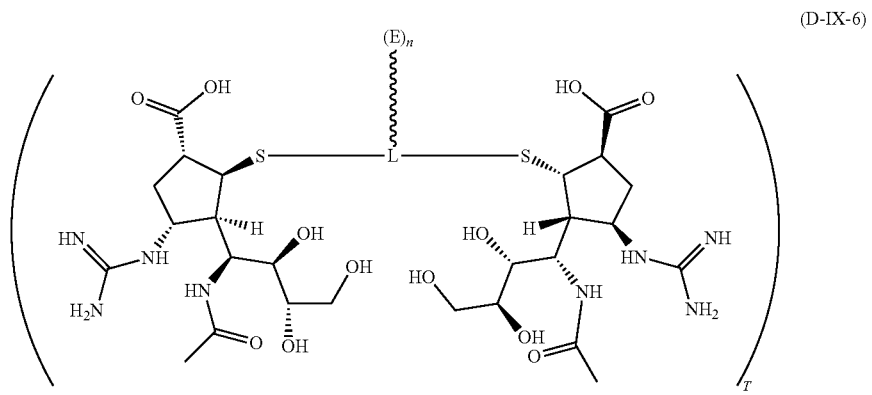

or a pharmaceutically acceptable salt thereof.
96. The conjugate of embodiment 2, wherein the conjugate is described by formula (D-X):

(D-X)

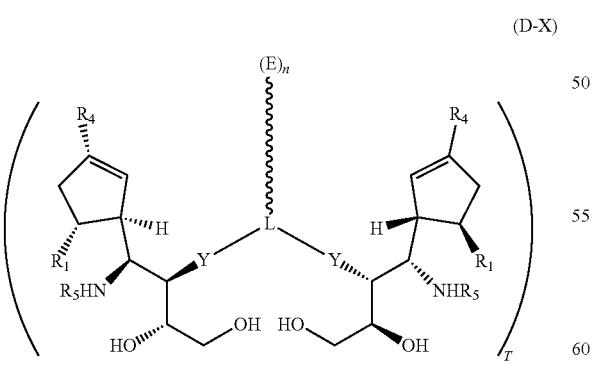

or a pharmaceutically acceptable salt thereof.
97. The conjugate of embodiment 96, wherein the conjugate is described by formula (D-X-1):

(D-X-1)

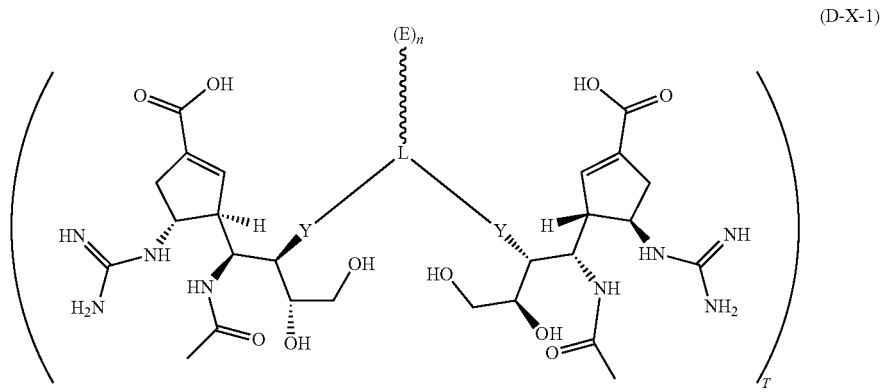

or a pharmaceutically acceptable salt thereof.
98. The conjugate of embodiment 97, wherein the conjugate is described by formula (D-X-2):

(D-X-2)

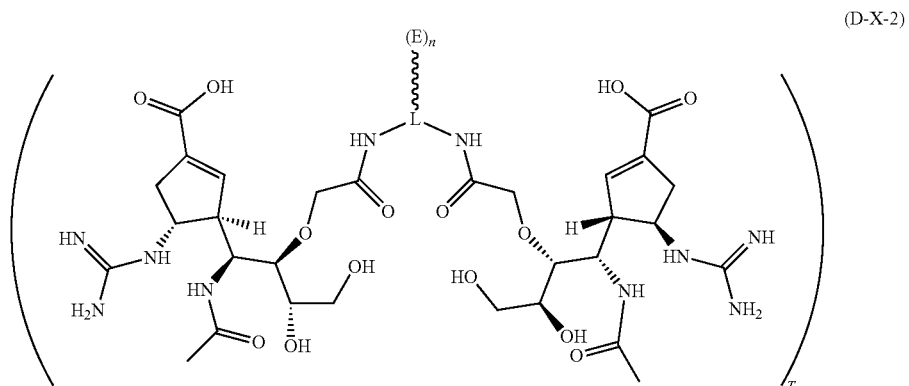

or a pharmaceutically acceptable salt thereof.
99. The conjugate of embodiment 97, wherein the conjugate is described by formula (D-X-3):

(D-X-3)

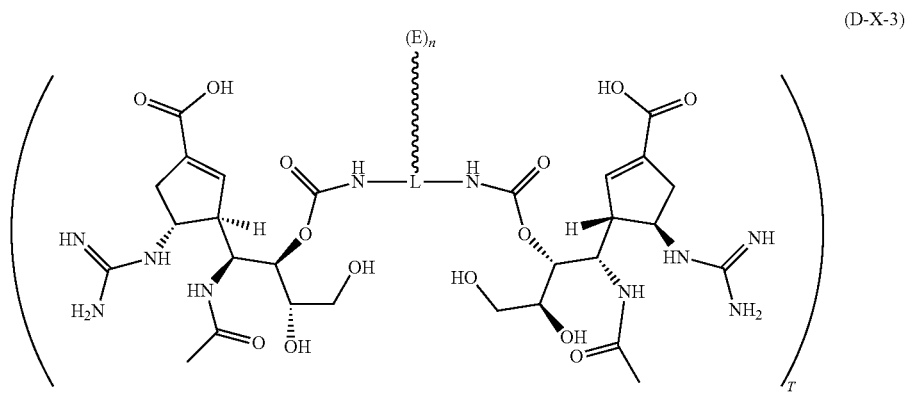

or a pharmaceutically acceptable salt thereof.
100. The conjugate of any one of embodiments 1-99, wherein L or L' comprises one or more optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, optionally substituted C2-C15 heteroarylene, O, S, NR$^i$, P, carbonyl, thiocarbonyl, sulfonyl, phosphate, phosphoryl, or imino, wherein R$^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl.

101. The conjugate of embodiment 100, wherein the backbone of L or L' consists of one or more optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, optionally substituted C2-C15 heteroarylene, O, S, $NR^i$, P, carbonyl, thiocarbonyl, sulfonyl, phosphate, phosphoryl, or imino, wherein $R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl.

102. The conjugate of embodiment 100 or 101, wherein L or L' is oxo substituted.

103. The conjugate of any one of embodiments 1-102, wherein the backbone of L or L' comprises no more than 250 atoms.

104. The conjugate of any one of embodiments 1-103, wherein L or L' is capable of forming an amide, a carbamate, a sulfonyl, or a urea linkage.

105. The conjugate of any one of embodiments 1-99, wherein L or L' is a bond.

106. The conjugate of any one of embodiments 1-99, wherein L or L' is an atom.

107. The conjugate of any one of embodiments 1-106, wherein each L is described by formula (D-L-I):

(D-L-I)

wherein $L^A$ is described by formula $G^{A1}$-$(Z^{A1})_{g1}$—$(Y^{A1})_{h1}$—$(Z^{A2})_{i1}$—$(Y^{A2})_{j1}$—$(Z^{A3})_{k1}$—$(Y^{A3})_{l1}$—$(Z^{A4})_{m1}$—$(Y^{A4})_{n1}$—$(Z^{A5})_{o1}$-$G^{A2}$;

$L^B$ is described by formula $G^{B1}$-$(Z^{B1})_{g2}$—$(Y^{B1})_{h2}$—$(Z^{B2})_{i2}$—$(Y^{B2})_{j2}$—$(Z^{B3})_{k2}$—$(Y^{B3})_{l2}$—$(Z^{B4})_{m2}$—$(Y^{B4})_{n2}$—$(Z^{B5})_{o2}$-$G^{B2}$;

$L^C$ is described by formula $G^{C1}$-$(Z^{C1})_{g3}$—$(Y^{C1})_{h3}$—$(Z^{C2})_{i3}$—$(Y^{C2})_{j3}$—$(Z^{C3})_{k3}$—$(Y^{C3})_{l3}$—$(Z^{C4})_{m3}$—$(Y^{C4})_{n3}$—$(Z^{C5})_{o3}$-$G^{C2}$;

$G^{A1}$ is a bond attached to Q;

$G^{A2}$ is a bond attached to A1;

$G^{B1}$ is a bond attached to Q;

$G^{B2}$ is a bond attached to A2;

$G^{G1}$ is a bond attached to Q;

$G^{C2}$ is a bond attached to E or a functional group capable of reacting with a functional group conjugated to E (e.g., maleimide and cysteine, amine and activated carboxylic acid, thiol and maleimide, activated sulfonic acid and amine, isocyanate and amine, azide and alkyne, and alkene and tetrazine);

each of $Z^{A1}$, $Z^{A2}$, $Z^{A3}$, $Z^{A4}$, $Z^{A5}$, $Z^{B1}$, $Z^{B2}$, $Z^{B3}$, $Z^{B4}$, $Z^{B5}$, $Z^{C1}$, $Z^{C2}$, $Z^{C3}$, $Z^{C4}$, and $Z^{C5}$ is, independently, optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, or optionally substituted C2-C15 heteroarylene;

each of $Y^{A1}$, $Y^{A2}$, $Y^{A3}$, $Y^{A4}$, $Y^{B1}$, $Y^{B2}$, $Y^{B3}$, $Y^{B4}$, $Y^{C1}$, $Y^{C2}$, $Y^{C3}$ and $Y^{C4}$ is, independently, O, S, $NR^i$, P, carbonyl, thiocarbonyl, sulfonyl, phosphate, phosphoryl, or imino;

$R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl; each of g1, h1, i1, j1, k1, l1, m1, n1, o1, g2, h2, i2, j2, k2, l2, m2, n2, o2, g3, h3, i3, j3, k3, l3, m3, n3, and o3 is, independently, 0 or 1;

Q is a nitrogen atom, optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, or optionally substituted C2-C15 heteroarylene.

108. The conjugate of embodiment 107, wherein L is selected from

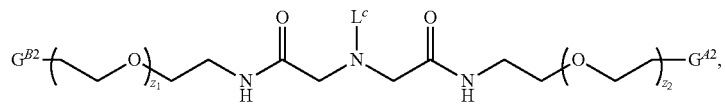
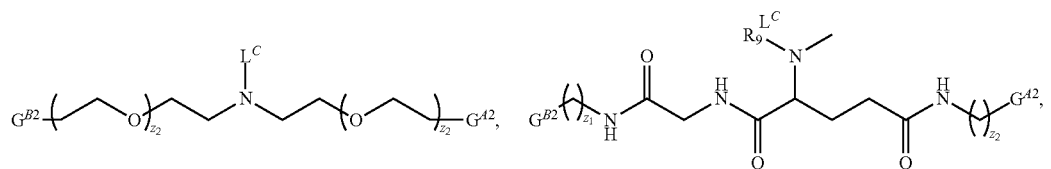
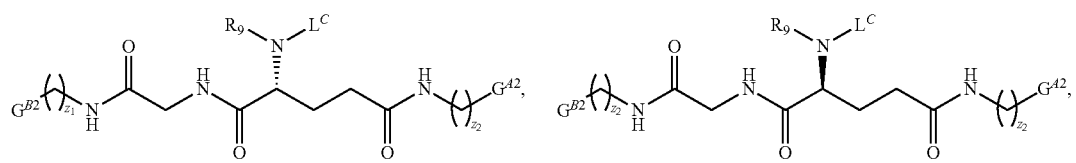
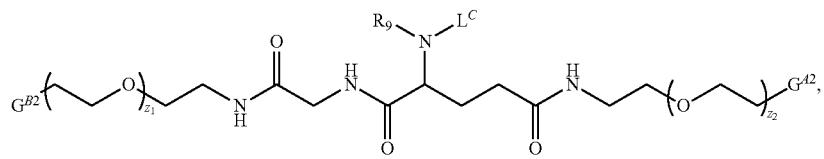
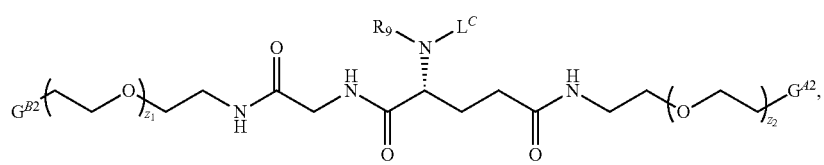
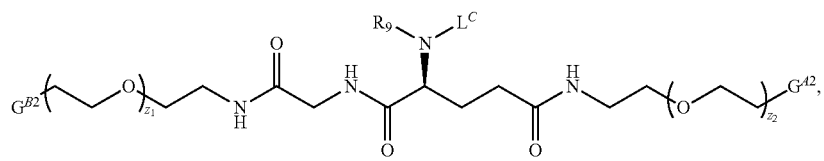
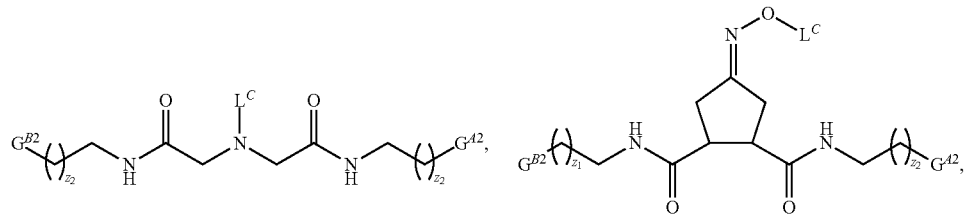
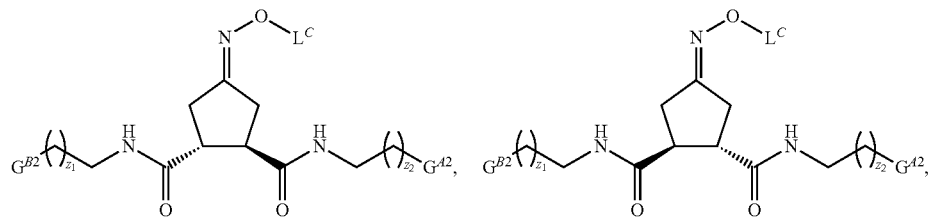
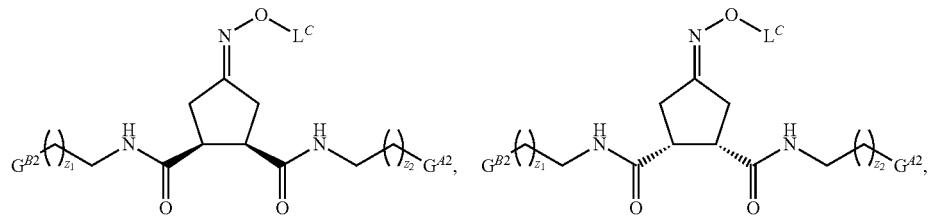

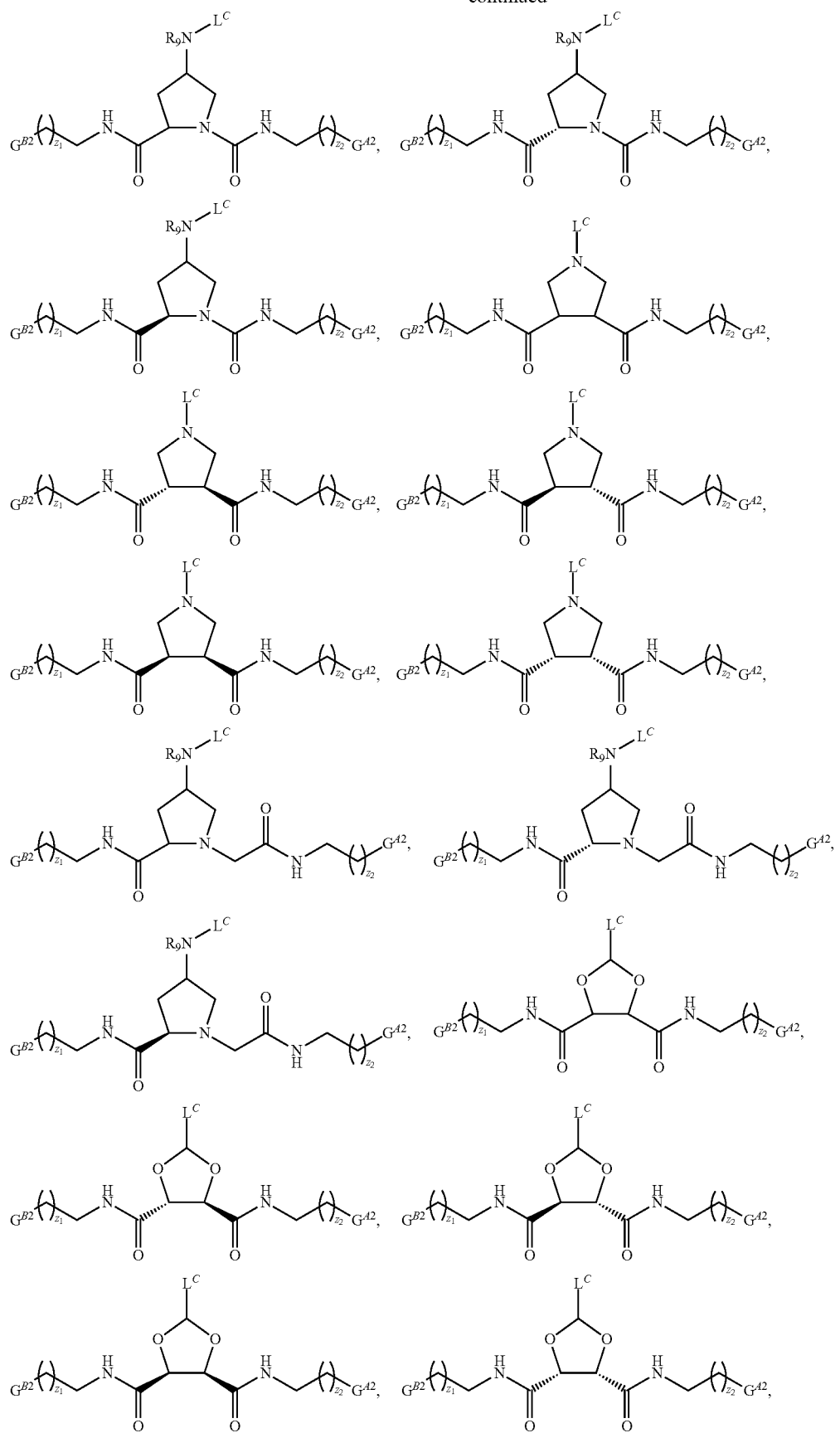

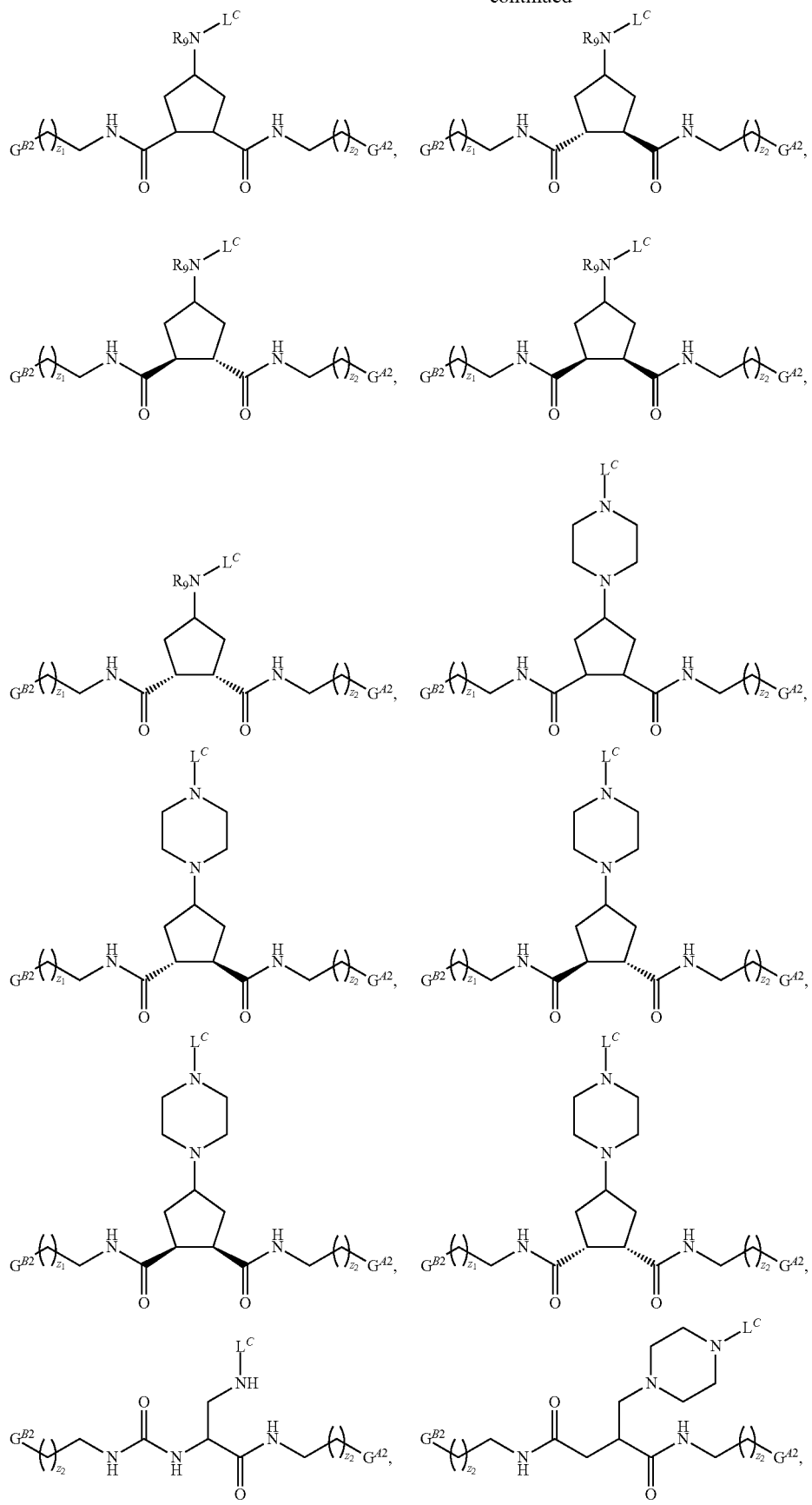

1197 1198
-continued
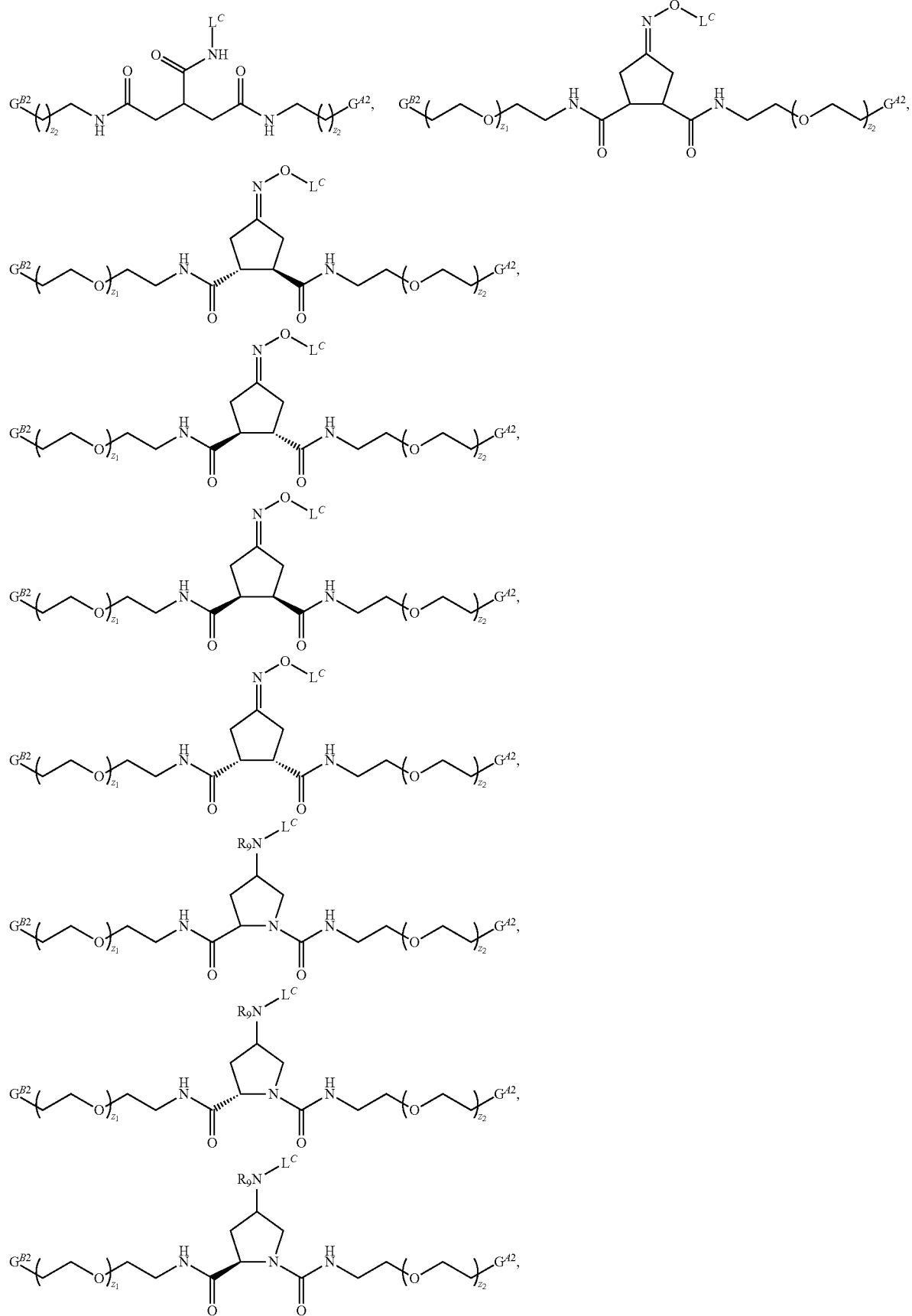

-continued
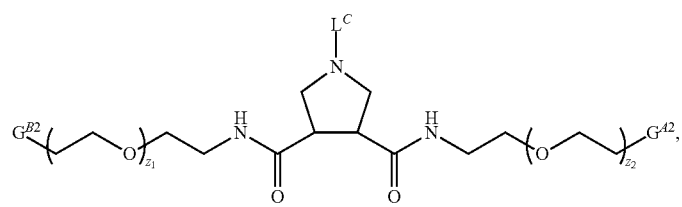
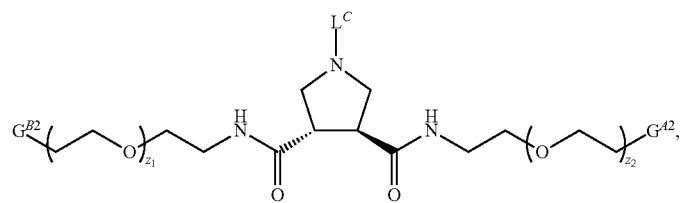
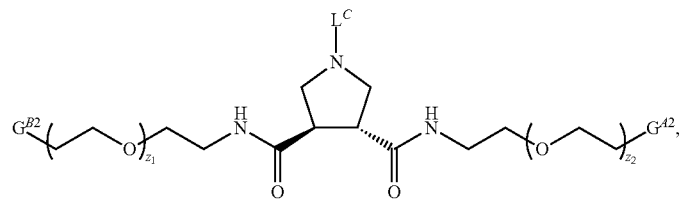
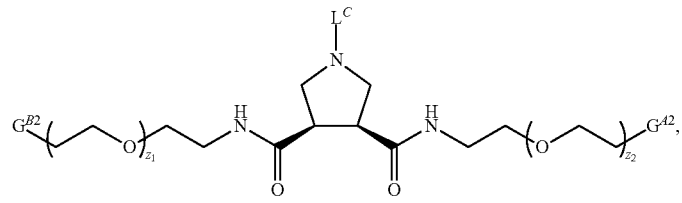
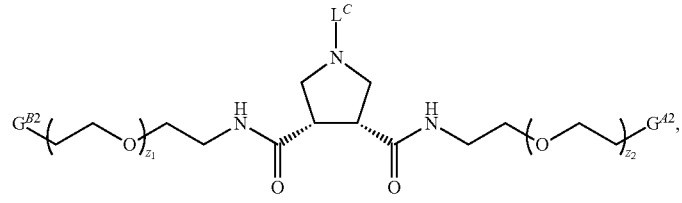
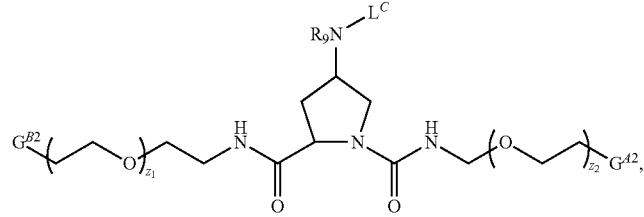
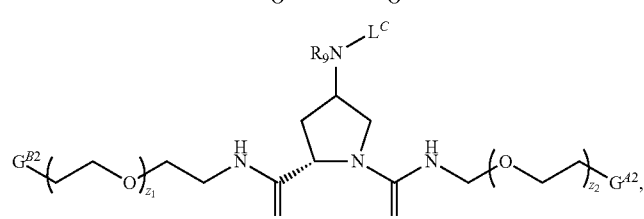
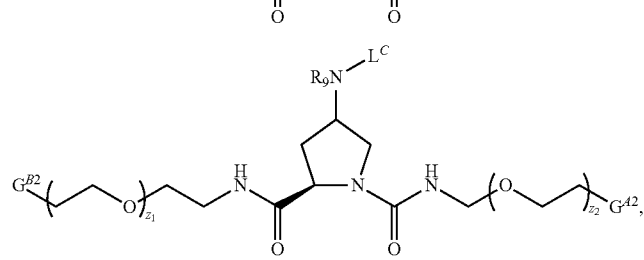

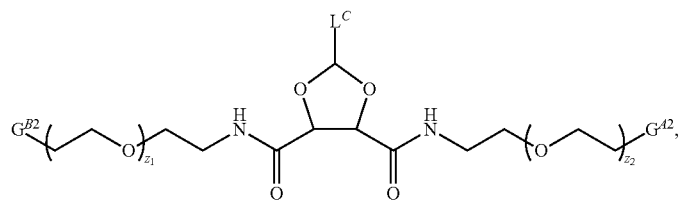
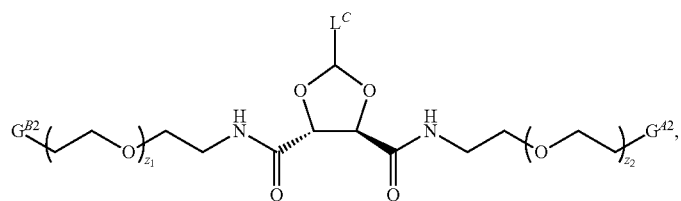
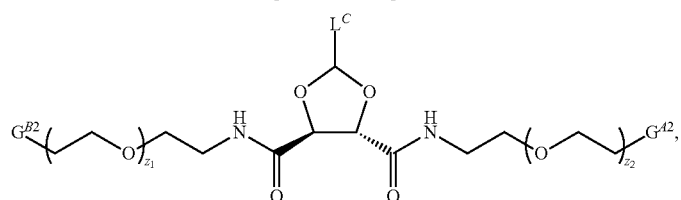
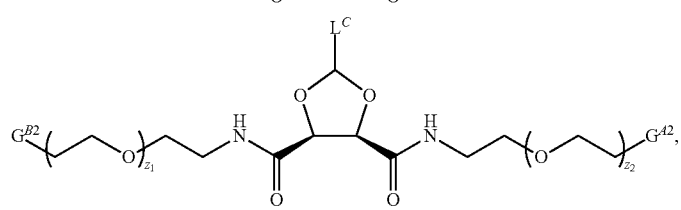
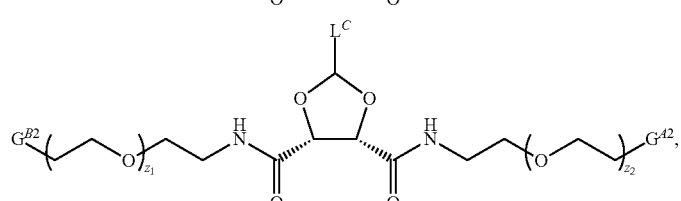
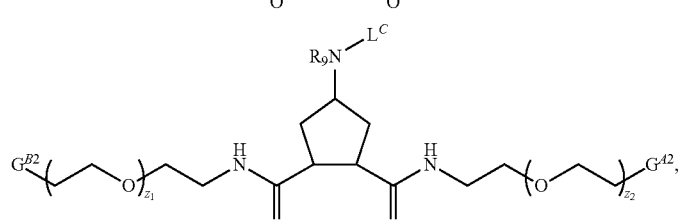
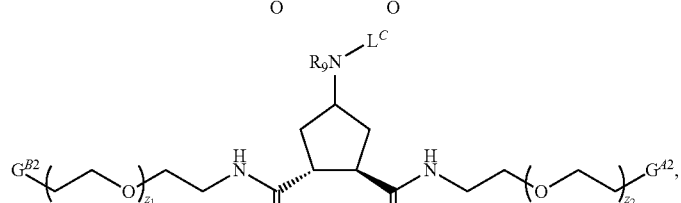
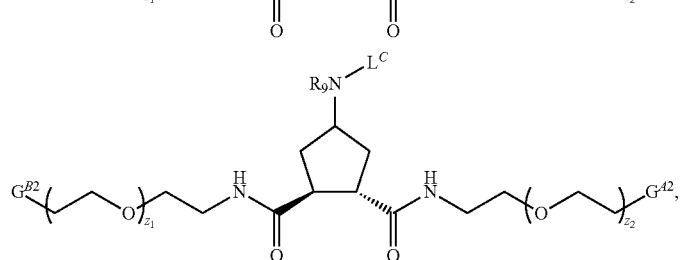

-continued
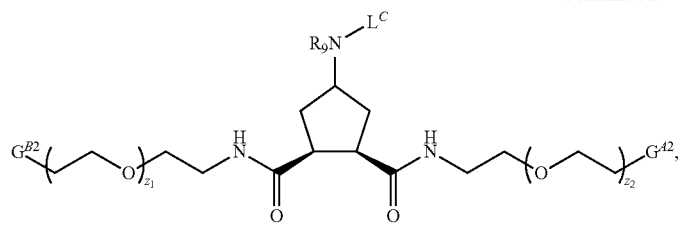
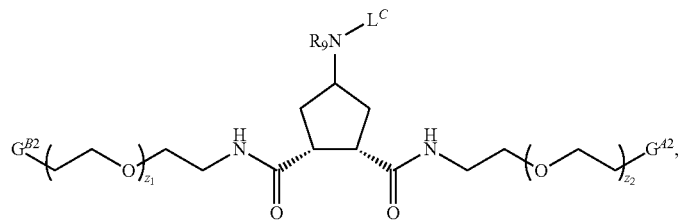
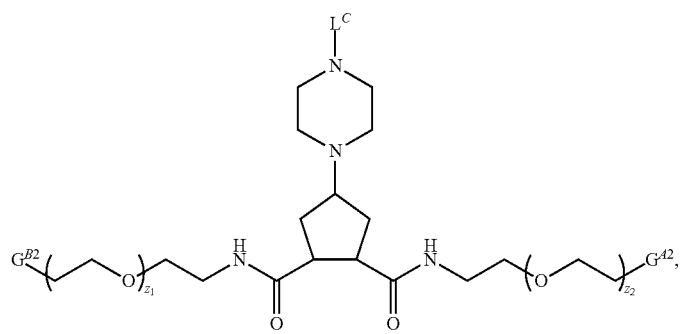
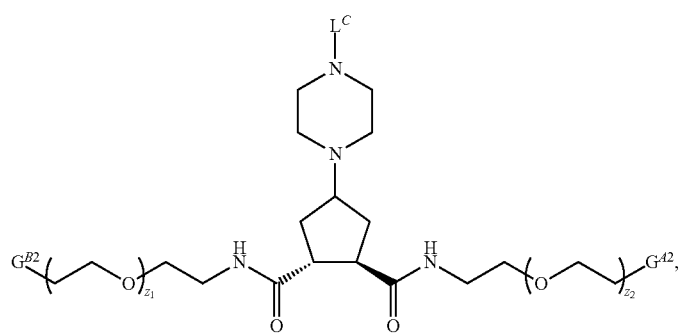
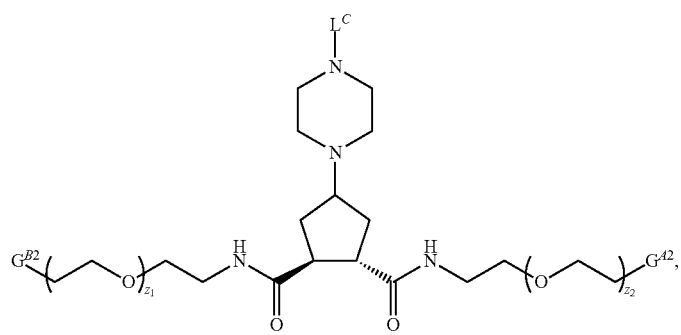

-continued
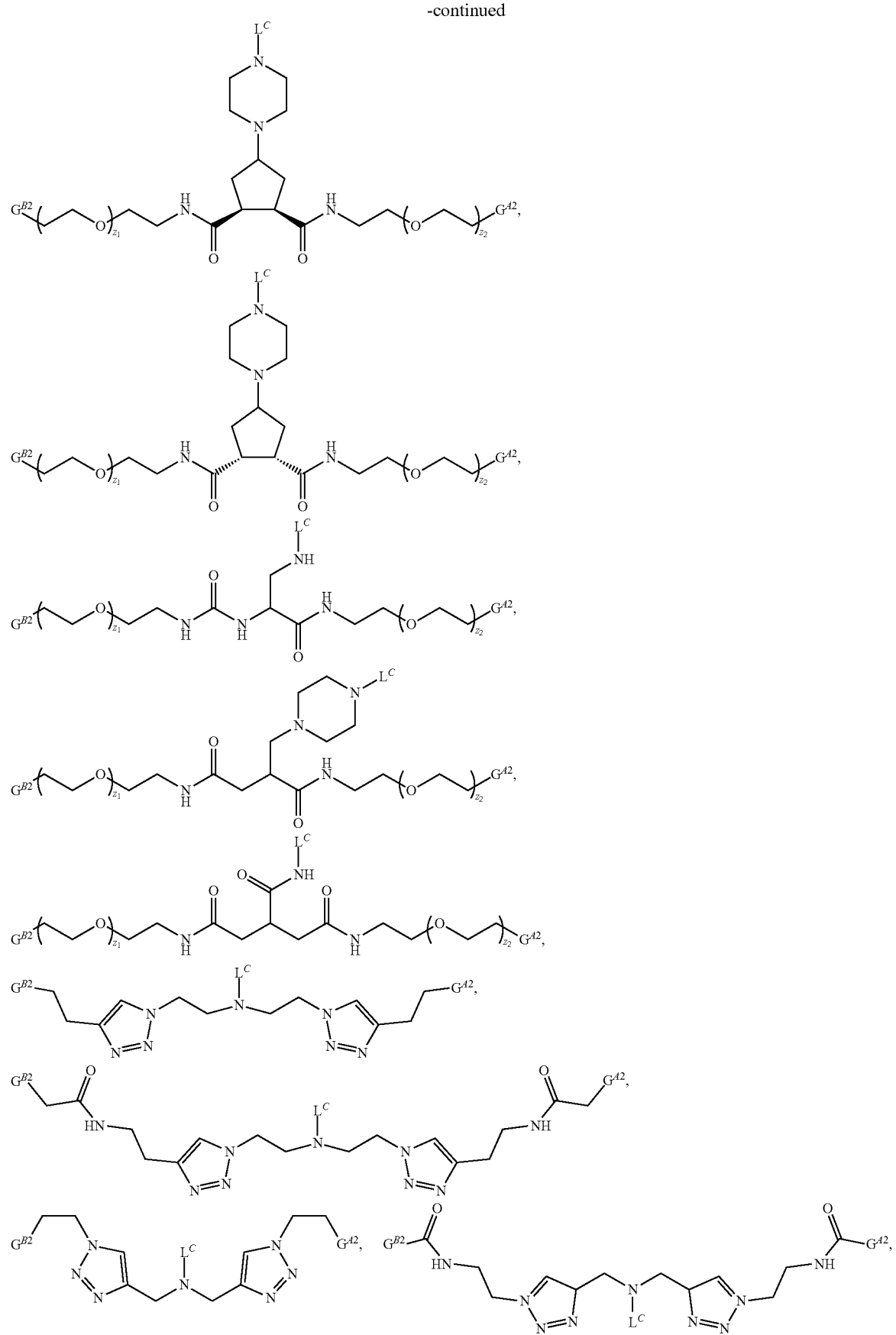

-continued
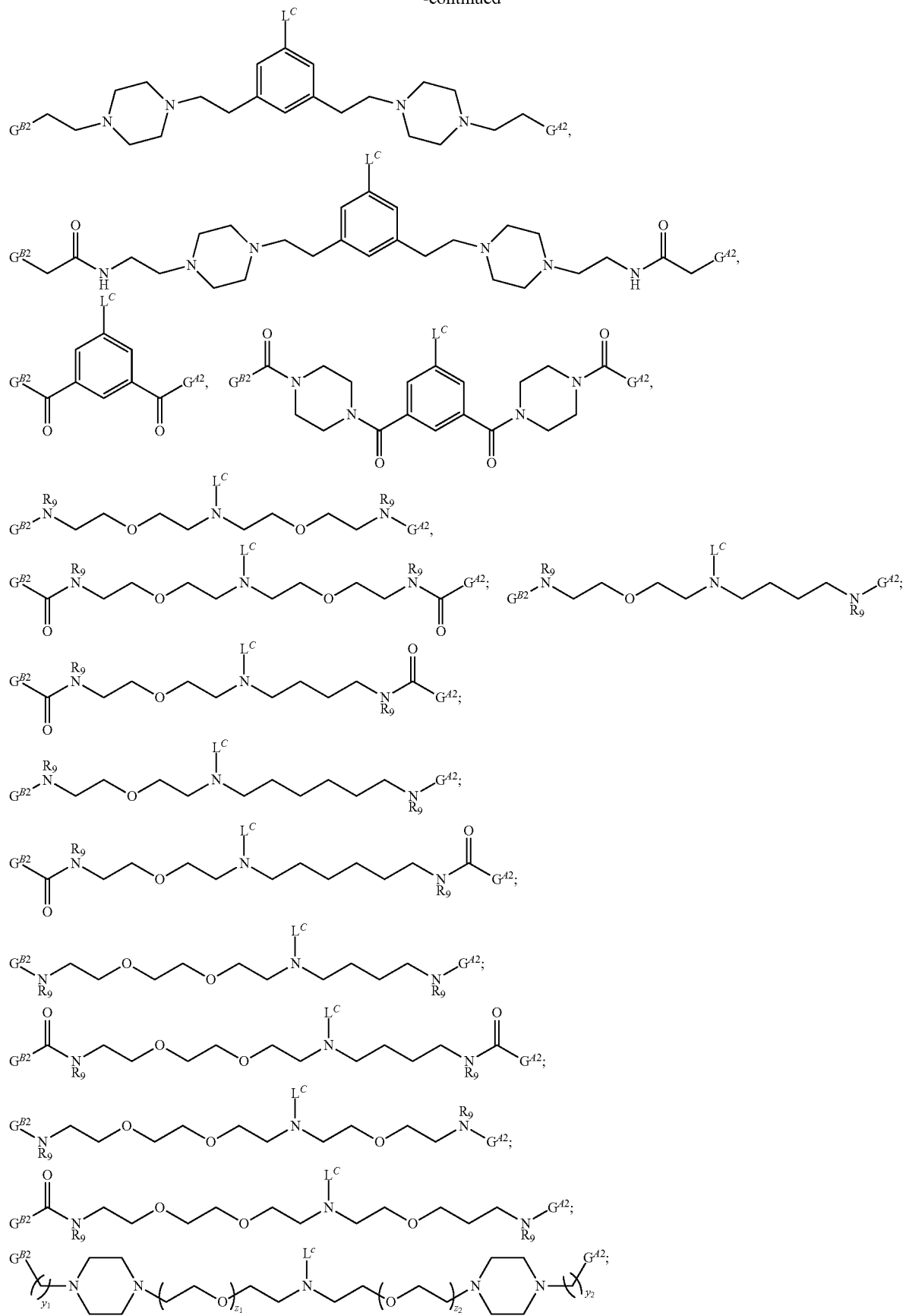

-continued

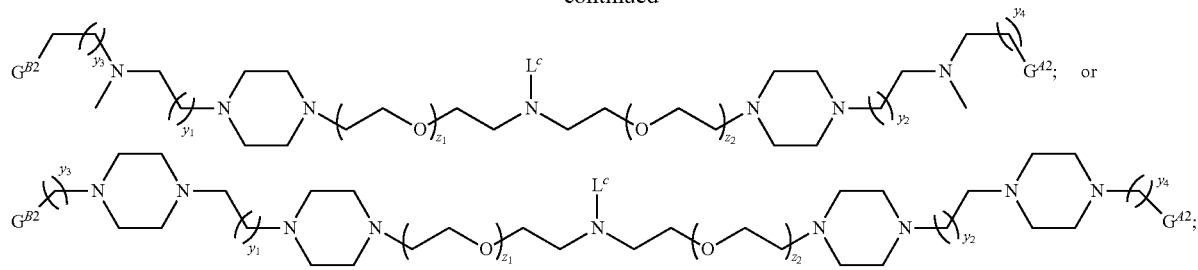

wherein $z_1$ and $z_2$ are each, independently, and integer from 1 to 20; and $R_9$ is selected from H, C1-C20 alkyl, C3-C20 cycloalkyl, C3-C20 heterocycloalkyl; C5-C15 aryl, and C2-C15 heteroaryl.

109. The conjugate of embodiment 108, wherein Y is:

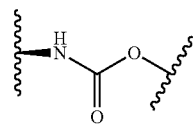

(—NH(C=O)O—) and L is:

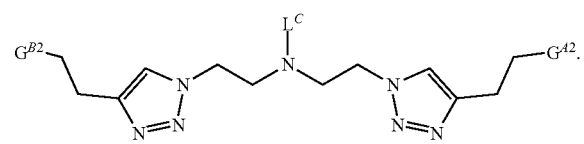

110. The conjugate of embodiment 108, wherein Y is:

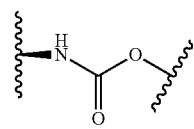

(—NH(C=O)O—) and L is:

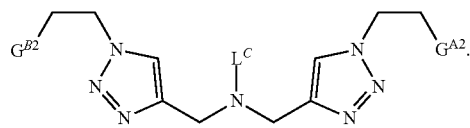

111. The conjugate of embodiment 108, wherein Y is:

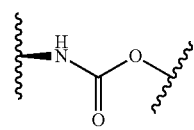

(—NH(C=O)O—) and L is:

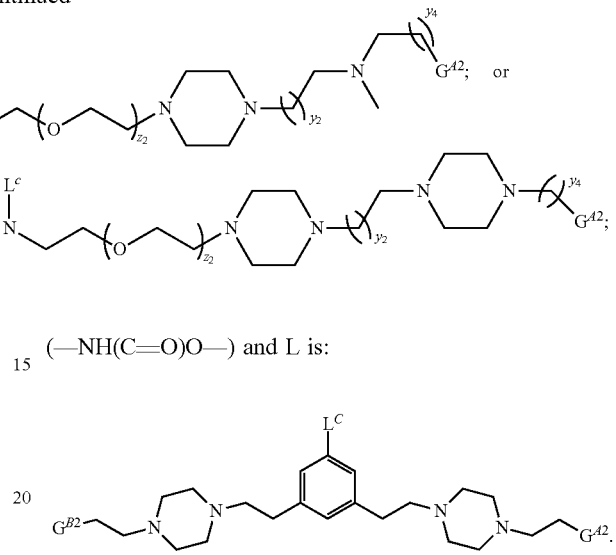

112. The conjugate of embodiment 108, wherein Y is:

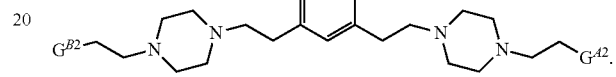

( —O— )

and L is:

113. The conjugate of embodiment 1, wherein the conjugate is described by formula (M-I):

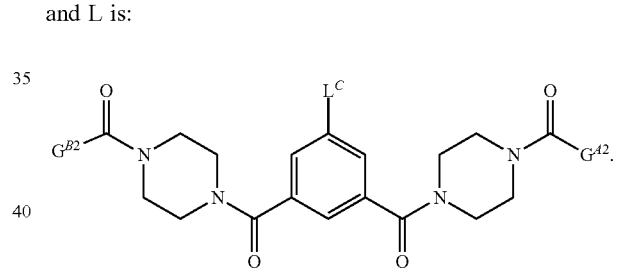

wherein each $A_1$ is independently selected from any one of formulas (A-I)-(A-XII);
each E comprises an Fc domain monomer, an albumin protein, an albumin protein-binding peptide, or an Fc-binding peptide;
n is 1 or 2;
T is an integer from 1 to 20; and
L is a linker covalently attached to each of E and $A_1$, the squiggly line connected to the E indicates that each $A_1$-L is covalently attached to E;
or a pharmaceutically acceptable salt thereof.

114. The conjugate of embodiment 113, wherein each $A_1$ is independently selected from any one of formulas (A-I), (A-II), (A-VI), or (A-VII);

each E comprises an Fc domain monomer, an albumin protein, an albumin
protein-binding peptide, or an Fc-binding peptide, and
the squiggly line connected to the E indicates that each $A_1$-L is covalently attached to E;
or a pharmaceutically acceptable salt thereof.

115. The conjugate of embodiment 114, wherein each $A_1$ is independently selected from formula (A-I).

116. The conjugate of embodiment 115, wherein the conjugate is described by formula (M-II):

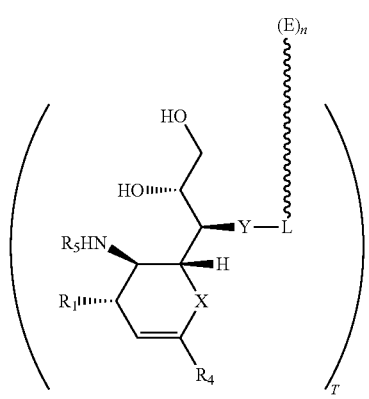

(M-II)

or a pharmaceutically acceptable salt thereof.

117. The conjugate of embodiment 116, wherein the conjugate is described by formula (M-II-1):

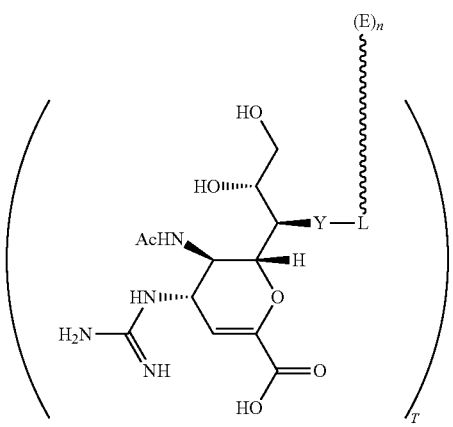

(M-II-1)

or a pharmaceutically acceptable salt thereof.

118. The conjugate of embodiment 117, wherein the conjugate is described by formula (M-II-2):

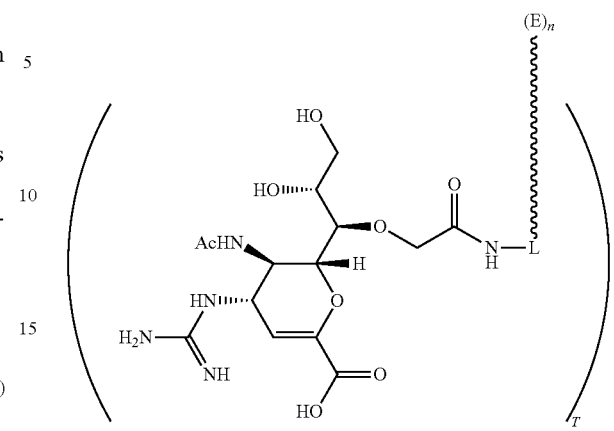

(M-II-2)

or a pharmaceutically acceptable salt thereof.

119. The conjugate of embodiment 118, wherein the conjugate is described by formula (M-II-3):

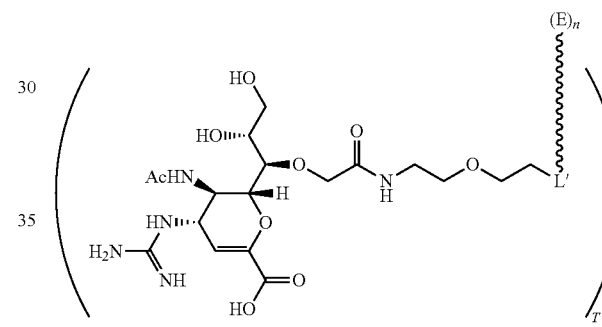

(M-II-3)

wherein L' is the remainder of L, and
$y_1$ is an integer from 1-20,
or a pharmaceutically acceptable salt thereof.

120. The conjugate of embodiment 119, wherein the conjugate is described by formula (M-II-4):

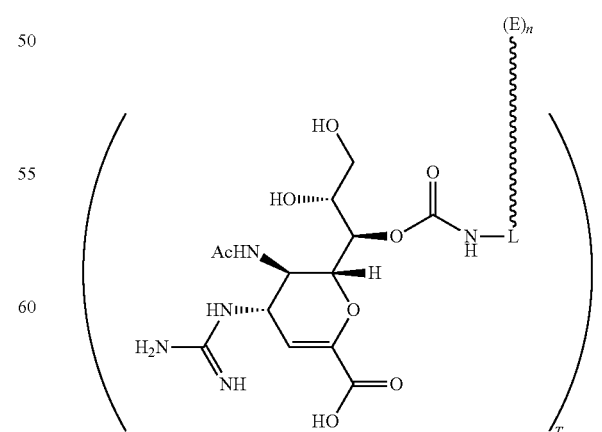

(M-II-4)

or a pharmaceutically acceptable salt thereof.

121. The conjugate of embodiment 120, wherein the conjugate is described by formula (M-II-5):

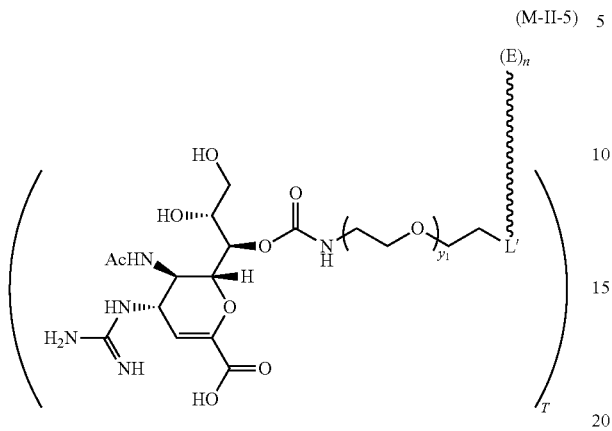

wherein L' is the remainder of L, and
$y_1$ is an integer from 1-20,
or a pharmaceutically acceptable salt thereof.

122. The conjugate of embodiment 121, wherein the conjugate has the structure of

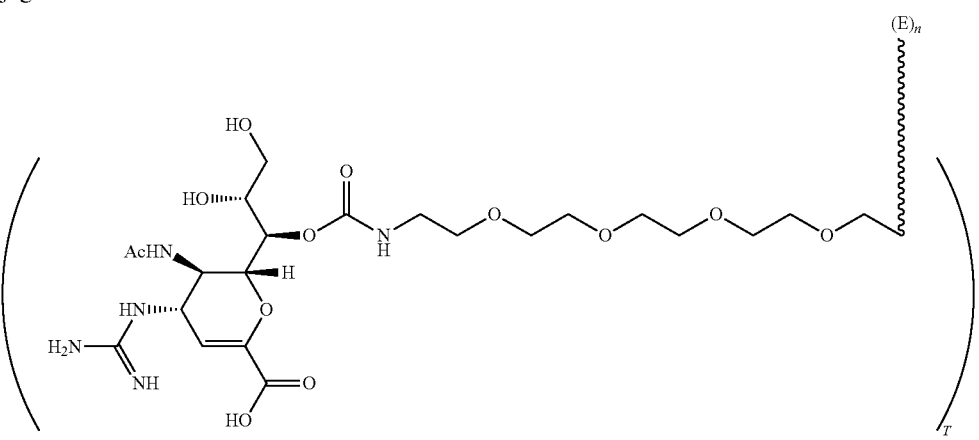

or a pharmaceutically acceptable salt thereof.

123. The conjugate of embodiment 116, wherein the conjugate is described by formula (M-II-6):

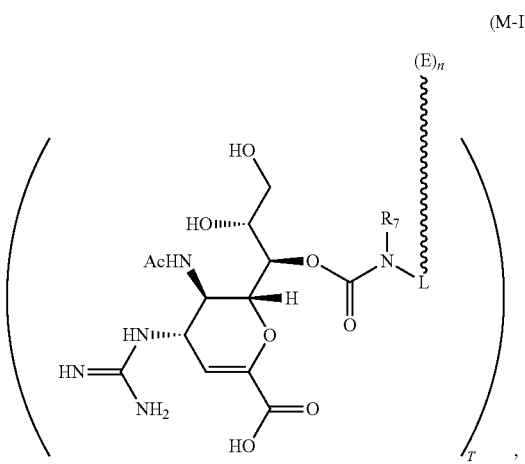

wherein $R_7$ is selected from H, C1-C20 alkyl, C3-C20 cycloalkyl, C3-C20 heterocycloalkyl; C5-C15 aryl, and C2-C15 heteroaryl;

or a pharmaceutically acceptable salt thereof.

124. The conjugate of embodiment 123, wherein $R_7$ is selected from C1-C20 alkyl, C3-C20 cycloalkyl, C3-C20 heterocycloalkyl; C5-C15 aryl, and C2-C15 heteroaryl.

125. The conjugate of embodiment 123 or 124, wherein $R_7$ is selected from methyl, ethyl, propyl, or butyl.

126. The conjugate of any one of embodiments 123-125, wherein the conjugate is described by formula (M-II-7):

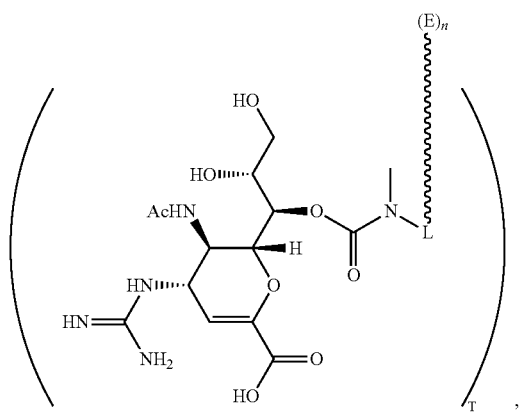

(M-II-7)

or a pharmaceutically acceptable salt thereof.

127. The conjugate of embodiment 126, wherein the conjugate is described by formula (M-II-8):

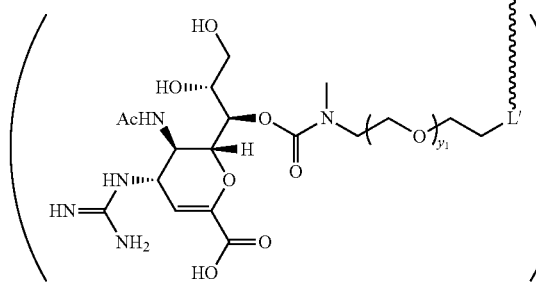

(M-II-8)

wherein L' is the remainder of L, and
$y_1$ is an integer from 1-20,
or a pharmaceutically acceptable salt thereof.

128. The conjugate of embodiment 127, wherein the conjugate has the structure of

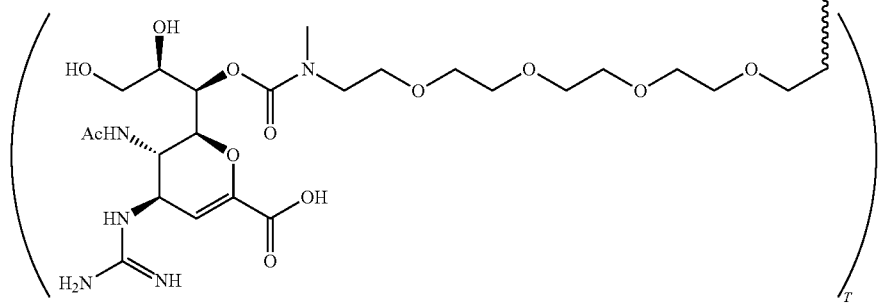

or a pharmaceutically acceptable salt thereof.

129. The conjugate of embodiment 127, wherein the conjugate is described by the formula (M-II-9):

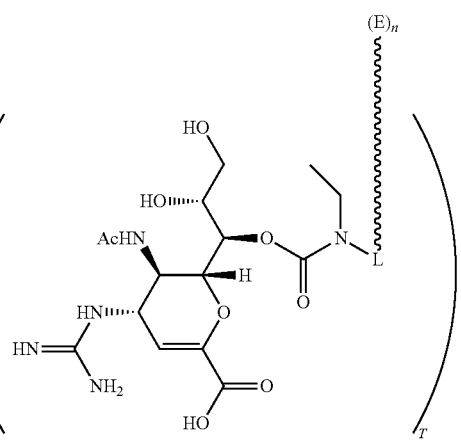

(M-II-9)

or a pharmaceutically acceptable salt thereof.

130. The conjugate of embodiment 129, wherein the conjugate is described by the formula (M-II-10):

(M-II-10)

wherein L' is the remainder of L, and
$y_1$ is an integer from 1-20,
or a pharmaceutically acceptable salt thereof.

131. The conjugate of embodiment 130, wherein the conjugate has the structure

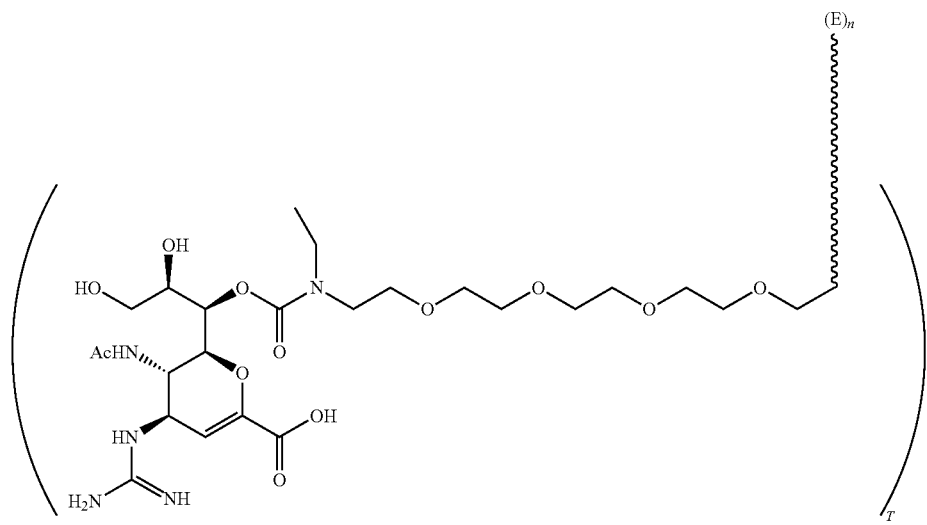

or a pharmaceutically acceptable salt thereof.

132. The conjugate of embodiment 113 or 114, wherein the conjugate is described by formula (M-III):

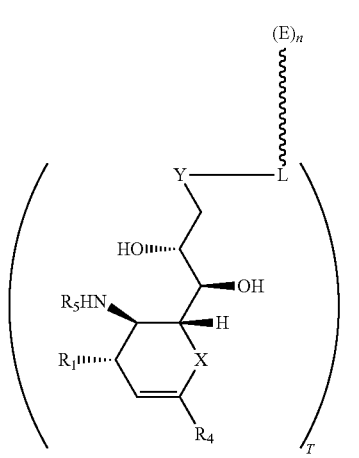

(M-III)

or a pharmaceutically acceptable salt thereof.

133. The conjugate of embodiment 132, wherein the conjugate is described by formula (M-III-1):

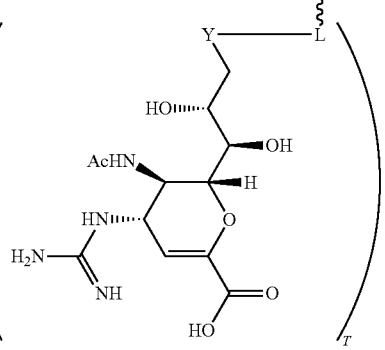

(M-III-1)

or a pharmaceutically acceptable salt thereof.

134. The conjugate of embodiment 133, wherein the conjugate is described by formula (M-III-2):

(M-III-2)

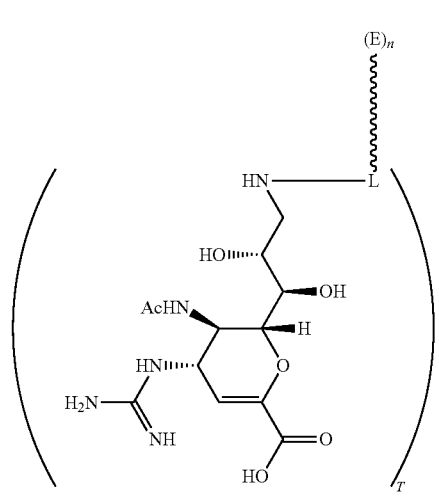

or a pharmaceutically acceptable salt thereof.

135. The conjugate of embodiment 134, wherein the conjugate is described by formula (M-III-3):

(M-III-4)

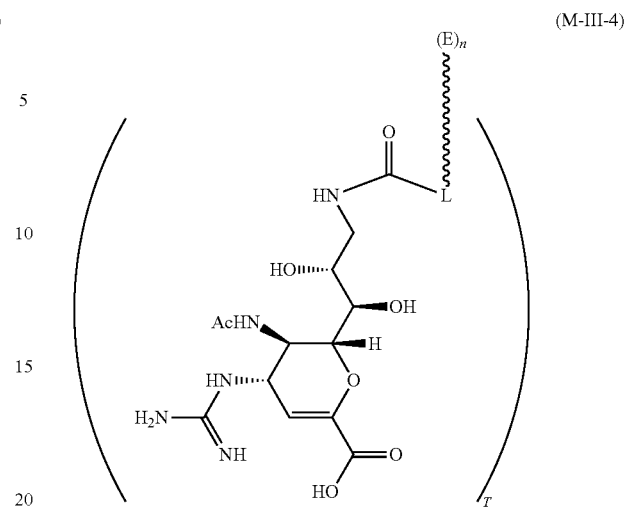

or a pharmaceutically acceptable salt thereof.

137. The conjugate of embodiment 136, wherein the conjugate is described by formula (M-III-5):

(M-III-3)

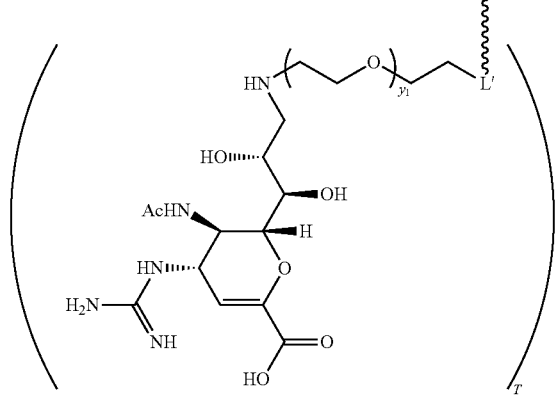

wherein L' is the remainder of L, and $y_1$ and $y_2$ are each independently an integer from 1-20, or a pharmaceutically acceptable salt thereof.

136. The conjugate of embodiment 133, wherein the conjugate is described by formula (M-III-4):

(M-III-5)

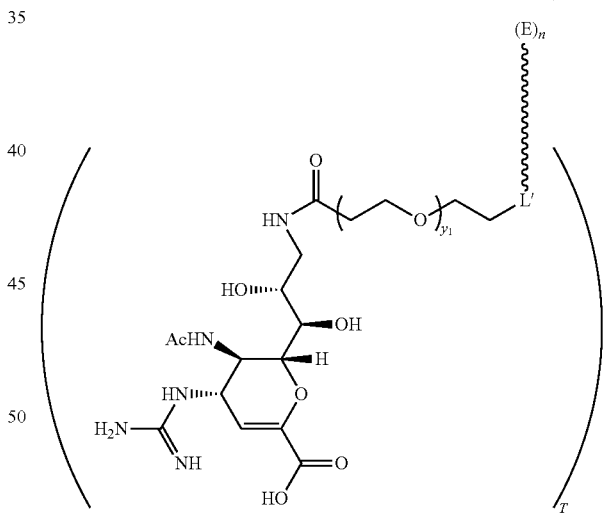

wherein L' is the remainder of L, and $y_1$ and $y_2$ are each independently an integer from 1-20, or a pharmaceutically acceptable salt thereof.

138. The conjugate of embodiment 133, wherein the conjugate is described by formula (M-III-6):

(M-III-6)

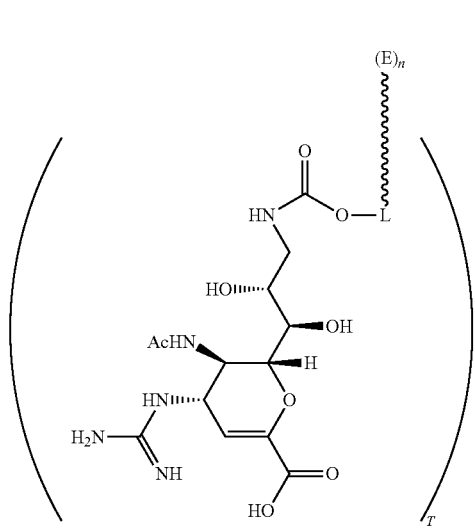

or a pharmaceutically acceptable salt thereof.
139. The conjugate of embodiment 138, wherein the conjugate is described by formula (M-III-7):

(M-III-8)

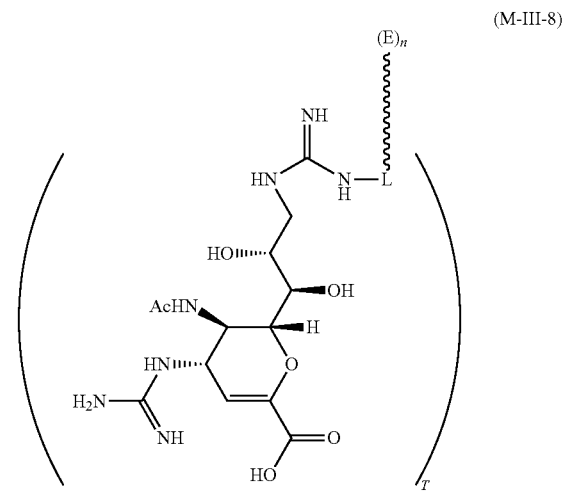

or a pharmaceutically acceptable salt thereof.
141. The conjugate of embodiment 140, wherein the conjugate is described by formula (M-III-9):

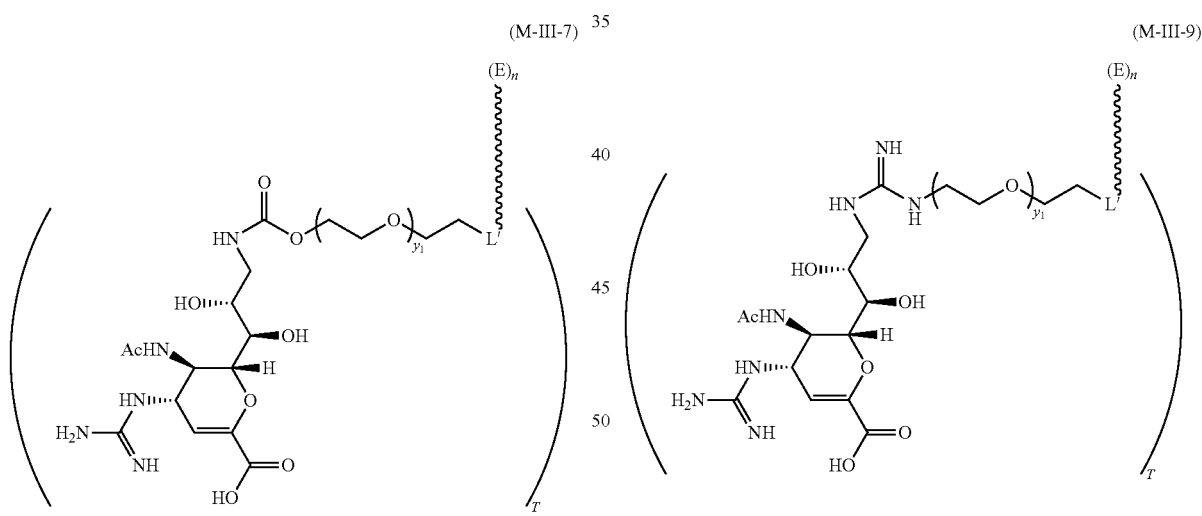

wherein L' is the remainder of L, and
$y_1$ and $y_2$ are each independently an integer from 1-20,
or a pharmaceutically acceptable salt thereof.
140. The conjugate of embodiment 133, wherein the conjugate is described by formula (M-III-8):

wherein L' is the remainder of L, and
$y_1$ and $y_2$ are each independently an integer from 1-20,
or a pharmaceutically acceptable salt thereof.
142. The conjugate of embodiment 113, wherein the conjugate is described by formula (M-IV):

(M-IV)

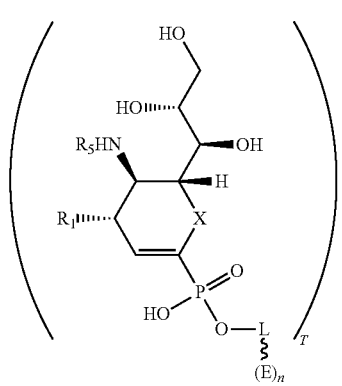

or a pharmaceutically acceptable salt thereof.
143. The conjugate of embodiment 142, wherein the conjugate is described by formula (M-IV-1):

(M-IV-1)

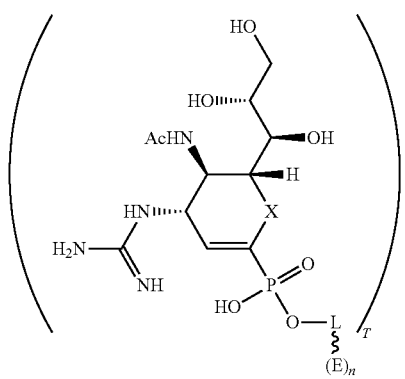

or a pharmaceutically acceptable salt thereof.
144. The conjugate of embodiment 143, wherein the conjugate is described by formula (M-IV-2):

(M-IV-2)

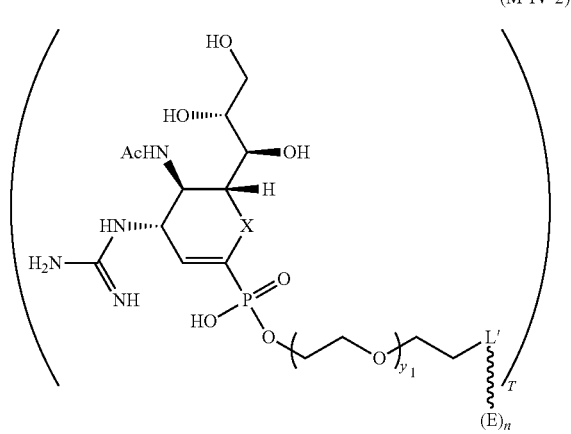

wherein L' is the remainder of L, and
$y_1$ and $y_2$ are each independently an integer from 1-20,
or a pharmaceutically acceptable salt thereof.
145. The conjugate of embodiment 113 or 114, wherein the conjugate is described by formula (M-V):

(M-V)

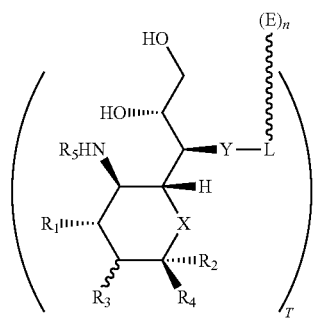

or a pharmaceutically acceptable salt thereof.
146. The conjugate of embodiment 145, wherein the conjugate is described by formula (M-V-1):

(M-V-1)

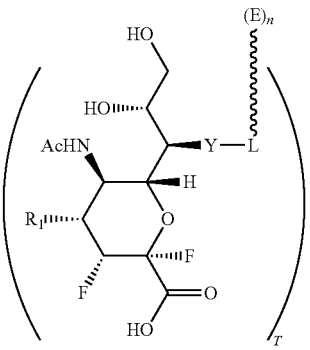

or a pharmaceutically acceptable salt thereof.
147. The conjugate of embodiment 146, wherein the conjugate is described by formula (M-V-2):

or a pharmaceutically acceptable salt thereof.

(M-V-2)

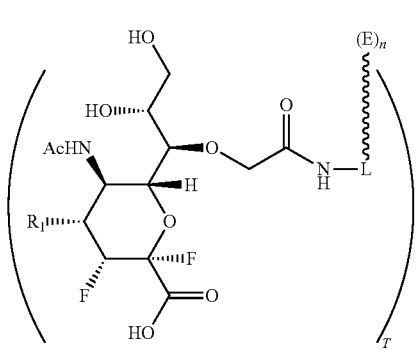

148. The conjugate of embodiment 147, wherein the conjugate is described by formula (M-V-3):

(M-V-3)

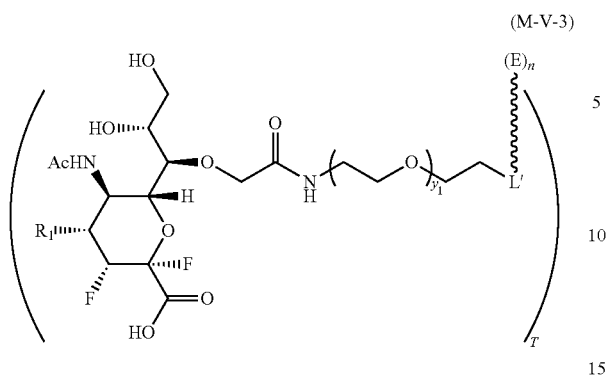

wherein L' is the remainder of L, and
$y_1$ is an integer from 1-20,
or a pharmaceutically acceptable salt thereof.

149. The conjugate of embodiment 148, wherein the conjugate is described by formula (M-V-4):

(M-V-4)

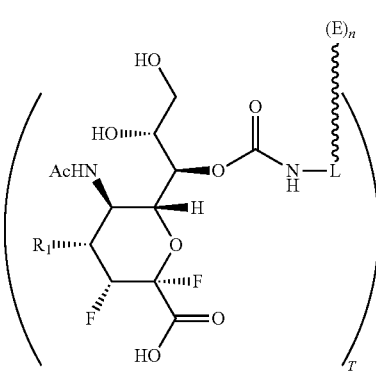

or a pharmaceutically acceptable salt thereof.

150. The conjugate of embodiment 149, wherein the conjugate is described by formula (M-V-5):

(M-V-5)

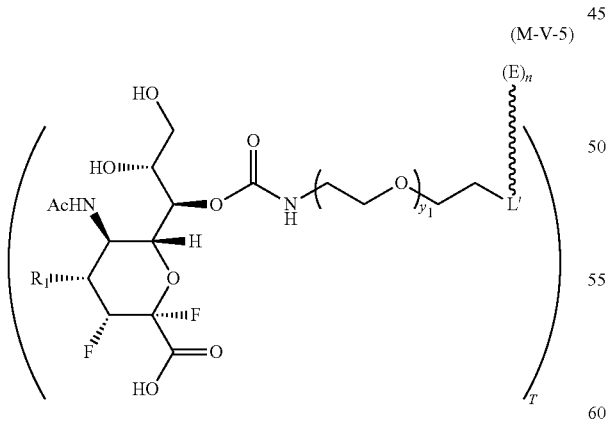

wherein L' is the remainder of L, and
$y_1$ is an integer from 1-20,
or a pharmaceutically acceptable salt thereof.

151. The conjugate of embodiment 145, wherein the conjugate is described by formula (M-V-6):

(M-V-6)

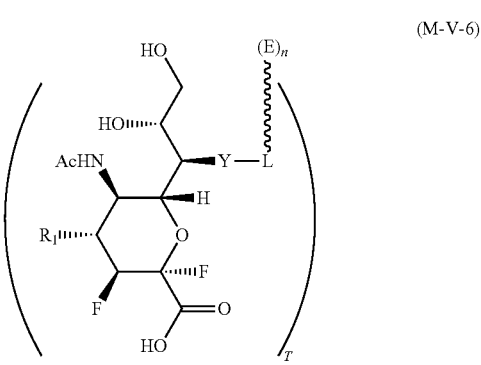

or a pharmaceutically acceptable salt thereof.

152. The conjugate of embodiment 151, wherein the conjugate is described by formula (M-V-7):

(M-V-7)

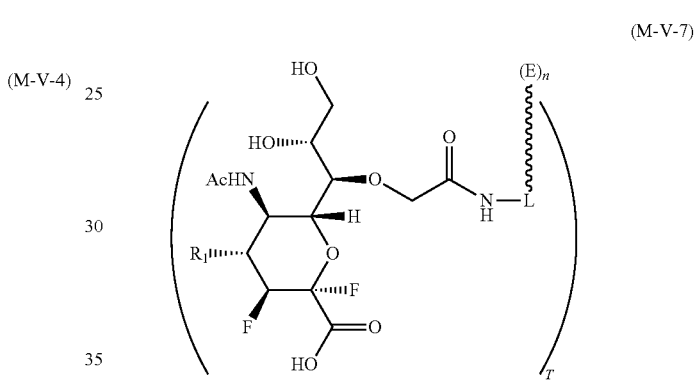

or a pharmaceutically acceptable salt thereof.

153. The conjugate of embodiment 152, wherein the conjugate is described by formula (M-V-8):

(M-V-8)

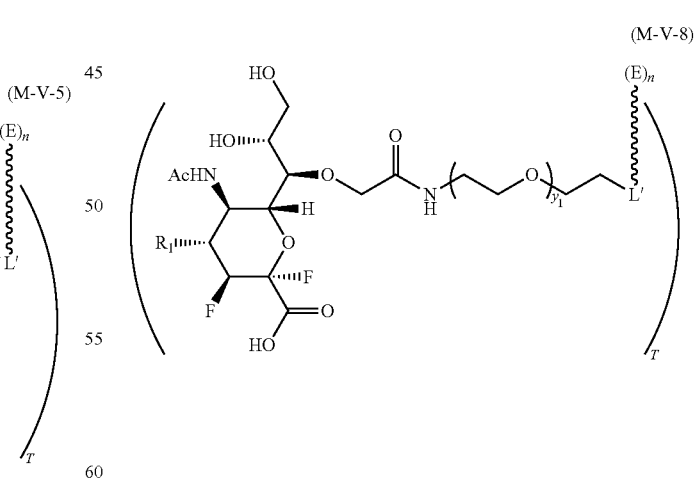

wherein L' is the remainder of L, and
$y_1$ is an integer from 1-20,
or a pharmaceutically acceptable salt thereof.

154. The conjugate of embodiment 151, wherein the conjugate is described by formula (M-V-9):

(M-V-9)

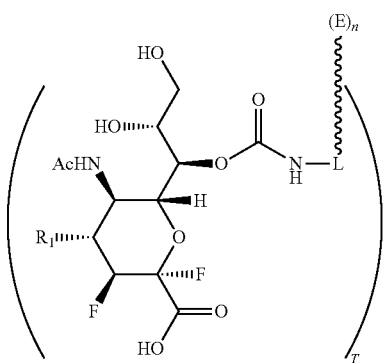

or a pharmaceutically acceptable salt thereof.

155. The conjugate of embodiment 154, wherein the conjugate is described by formula (M-V-10):

(M-V-10)

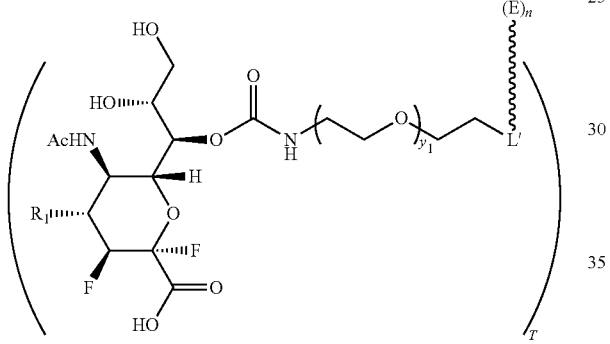

wherein L' is the remainder of L, and $y_1$ is an integer from 1-20, or a pharmaceutically acceptable salt thereof.

156. The conjugate of embodiment 113 or 114, wherein the conjugate is described by formula (M-VI):

(M-VI)

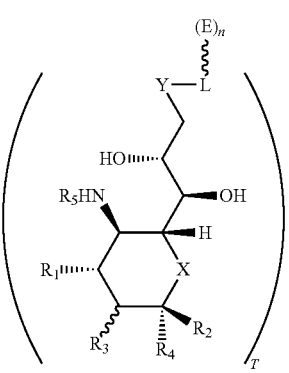

or a pharmaceutically acceptable salt thereof.

157. The conjugate of embodiment 156, wherein the conjugate is described by formula (M-VI-1):

(M-VI-1)

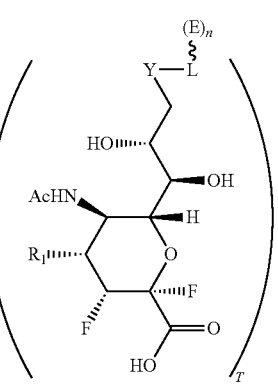

or a pharmaceutically acceptable salt thereof.

158. The conjugate of embodiment 157, wherein the conjugate is described by formula (M-VI-2):

(M-VI-2)

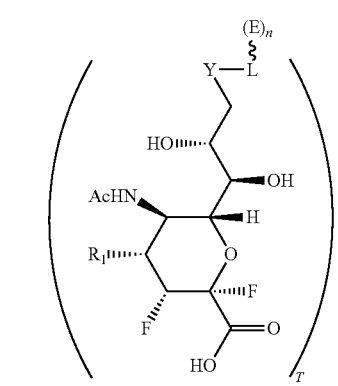

or a pharmaceutically acceptable salt thereof.

159. The conjugate of embodiment 158, wherein the conjugate is described by formula (M-VI-3):

(M-VI-3)

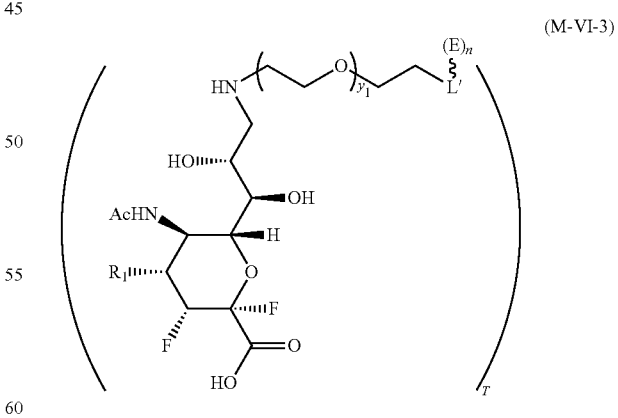

wherein L' is the remainder of L, and $y_1$ and $y_2$ are each independently an integer from 1-20, or a pharmaceutically acceptable salt thereof.

160. The conjugate of embodiment 157, wherein the conjugate is described by formula (M-VI-4):

(M-VI-4)

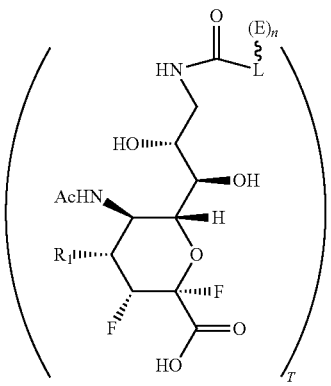

or a pharmaceutically acceptable salt thereof.
161. The conjugate of embodiment 160, wherein the conjugate is described by formula (M-VI-5):

(M-VI-5)

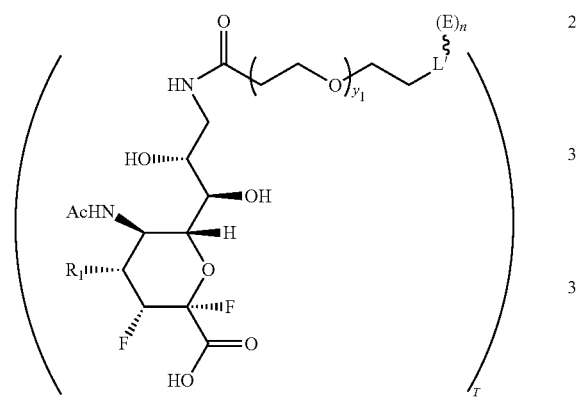

wherein L' is the remainder of L, and
$y_1$ and $y_2$ are each independently an integer from 1-20,
or a pharmaceutically acceptable salt thereof.
162. The conjugate of embodiment 157, wherein the conjugate is described by formula (M-VI-6):

(M-VI-6)

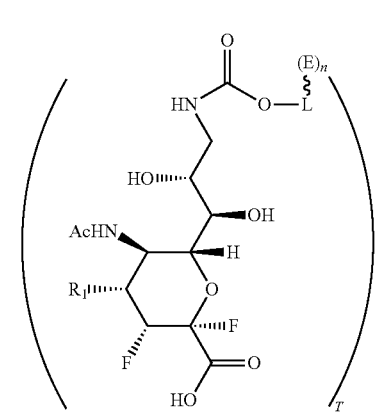

or a pharmaceutically acceptable salt thereof.
163. The conjugate of embodiment 162, wherein the conjugate is described by formula (M-VI-7):

(M-VI-7)

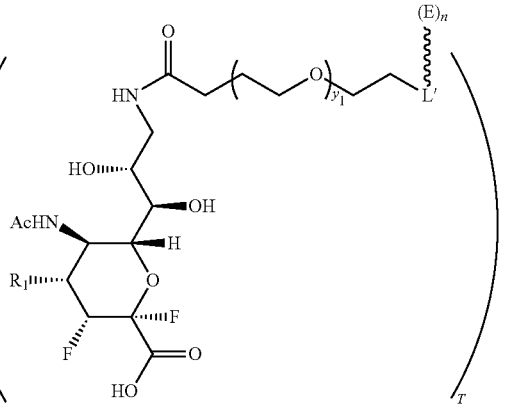

wherein L' is the remainder of L, and
$y_1$ and $y_2$ are each independently an integer from 1-20,
or a pharmaceutically acceptable salt thereof.
164. The conjugate of embodiment 157, wherein the conjugate is described by formula (M-VI-8):

(M-VI-8)

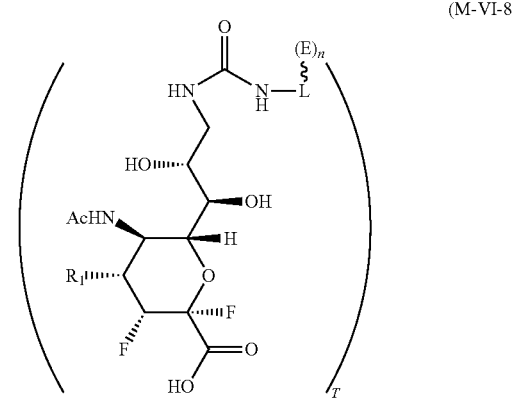

or a pharmaceutically acceptable salt thereof.
165. The conjugate of embodiment 164, wherein the conjugate is described by formula (M-VI-9):

(M-VI-9)

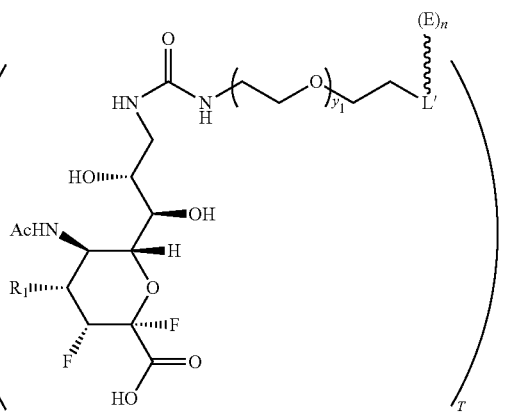

wherein L' is the remainder of L, and
$y_1$ and $y_2$ are each independently an integer from 1-20,
or a pharmaceutically acceptable salt thereof.

166. The conjugate of embodiment 113, wherein the conjugate is described by formula (M-VII):

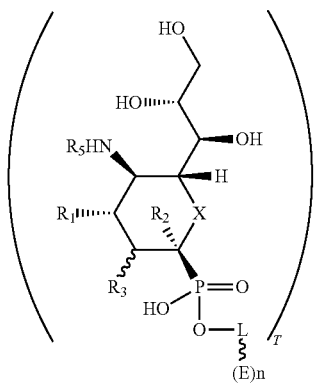

(M-VII)

or a pharmaceutically acceptable salt thereof.

167. The conjugate of any one of embodiments 113-166 wherein $R_1$ is OH.

168. The conjugate of any one of embodiments 113-166 wherein R, is $NH_2$.

169. The conjugate of any one of embodiments 113-166 wherein $R_1$ is —NHC(=NH)$NH_2$.

170. The conjugate of embodiment 113, wherein the conjugate is described by formula (M-VIII):

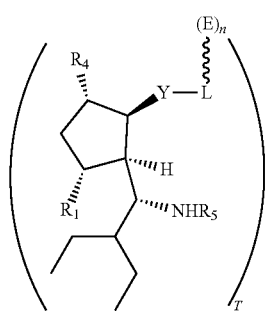

(M-VIII)

or a pharmaceutically acceptable salt thereof.

171. The conjugate of embodiment 170, wherein the conjugate is described by formula (M-VIII-1):

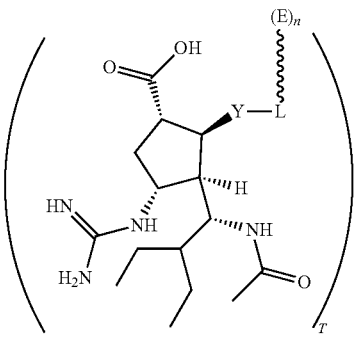

(M-VIII-1)

or a pharmaceutically acceptable salt thereof.

172. The conjugate of embodiment 171, wherein the conjugate is described by formula (M-VIII-2):

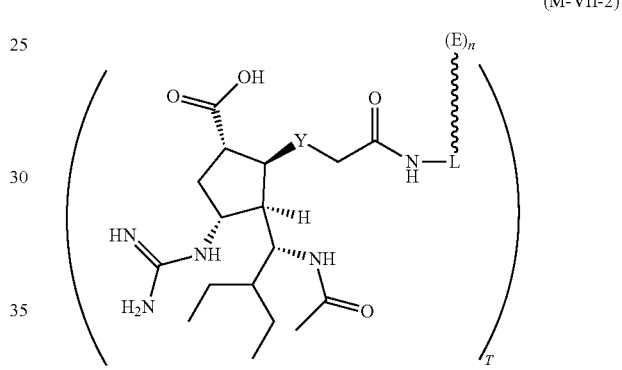

(M-VII-2)

or a pharmaceutically acceptable salt thereof.

173. The conjugate of embodiment 172, wherein the conjugate is described by formula (M-VIII-3):

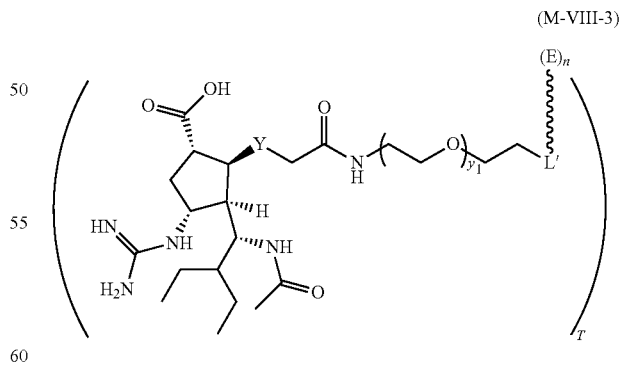

(M-VIII-3)

wherein L' is the remainder of L, and $y_1$ is an integer from 1-20, or a pharmaceutically acceptable salt thereof.

174. The conjugate of embodiment 173, wherein the conjugate is described by formula (M-VIII-4):

(M-VIII-4)

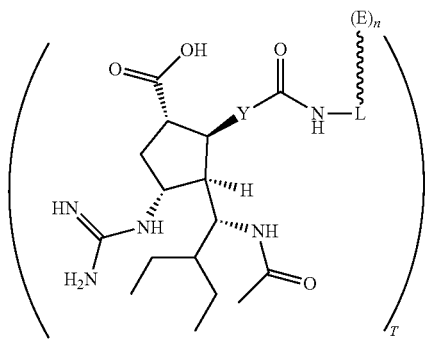

or a pharmaceutically acceptable salt thereof.
175. The conjugate of embodiment 174, wherein the conjugate is described by formula (M-VIII-5):

(M-VIII-5)

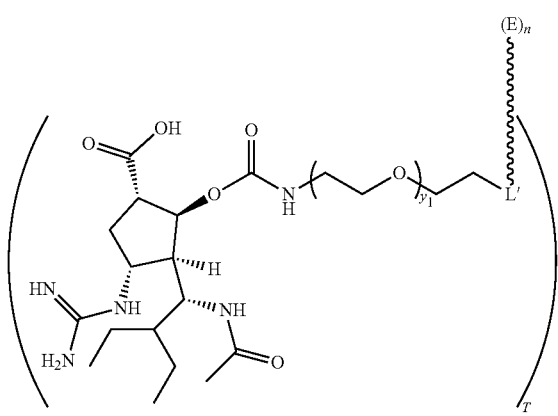

wherein L' is the remainder of L, and
$y_1$ is an integer from 1-20,
or a pharmaceutically acceptable salt thereof.
176. The conjugate of embodiment 175, wherein the conjugate has the structure of:

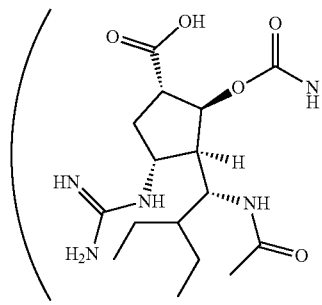

or a pharmaceutically acceptable salt thereof.

177. The conjugate of embodiment 171, wherein the conjugate is described by formula (M-VIII-6):

(M-VIII-6)

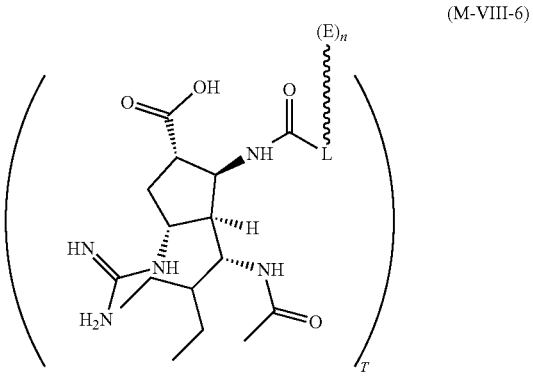

or a pharmaceutically acceptable salt thereof.
178. The conjugate of embodiment 177, wherein the conjugate is described by formula (M-VIII-7):

(M-VIII-7)

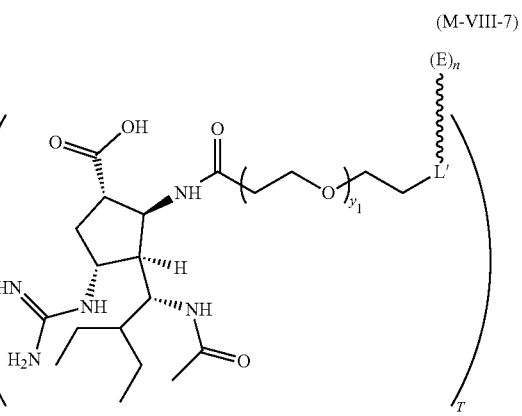

wherein L' is the remainder of L, and
$y_1$ and $y_2$ are each independently an integer from 1-20,
or a pharmaceutically acceptable salt thereof.
179. The conjugate of embodiment 171, wherein the conjugate is described by formula (M-VIII-8):

(M-VIII-8)

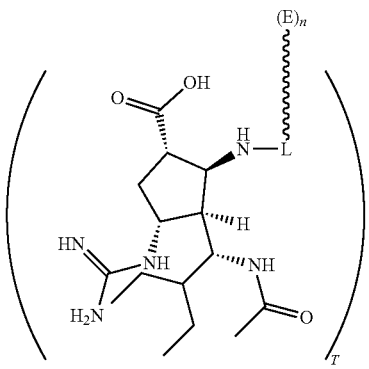

or a pharmaceutically acceptable salt thereof.
180. The conjugate of embodiment 179, wherein the conjugate is described by formula (M-VIII-9):

(M-VIII-9)

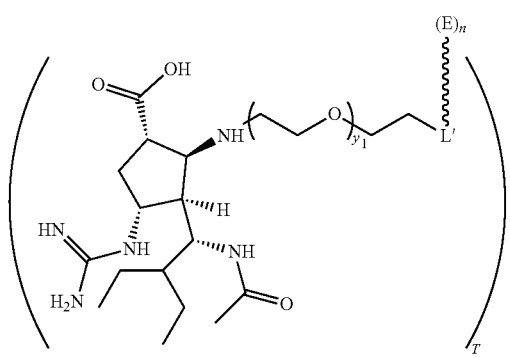

wherein L' is the remainder of L, and
$y_1$ and $y_2$ are each independently an integer from 1-20,
or a pharmaceutically acceptable salt thereof.
181. The conjugate of embodiment 180, wherein the conjugate is described by formula (M-VIII-10):

(M-VIII-10)

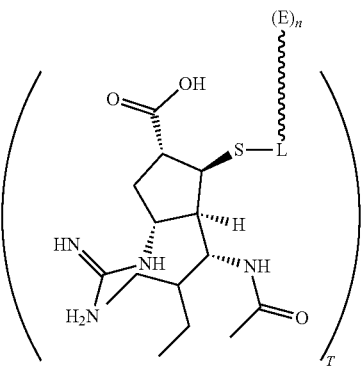

or a pharmaceutically acceptable salt thereof.
182. The conjugate of embodiment 181, wherein the conjugate is described by formula (M-VIII-11):

(M-VIII-11)

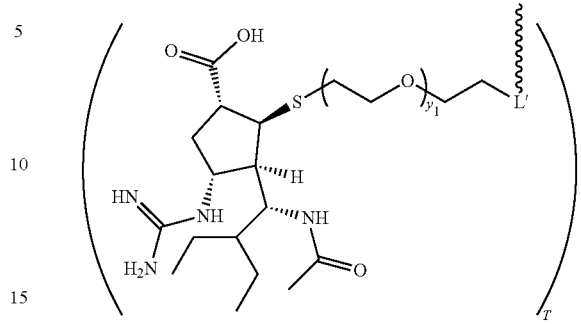

wherein L' is the remainder of L, and
$y_1$ and $y_2$ are each independently an integer from 1-20,
or a pharmaceutically acceptable salt thereof.
183. The conjugate of embodiment 113, wherein the conjugate is described by formula (M-IX):

(M-IX)

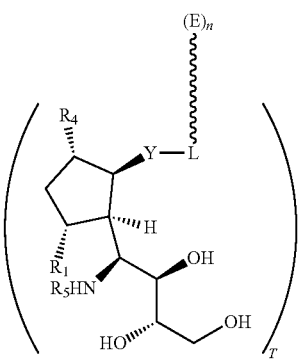

or a pharmaceutically acceptable salt thereof.
184. The conjugate of embodiment 183, wherein the conjugate is described by formula (M-IX-1):

(M-IX-1)

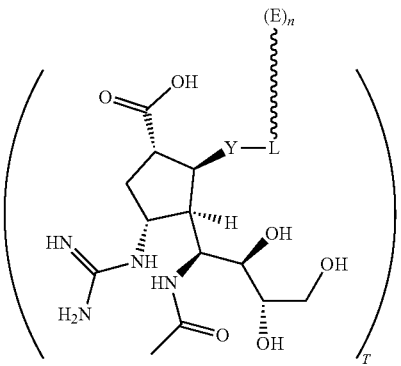

or a pharmaceutically acceptable salt thereof.
185. The conjugate of embodiment 184, wherein the conjugate is described by formula (M-IX-2):

(M-IX-2)

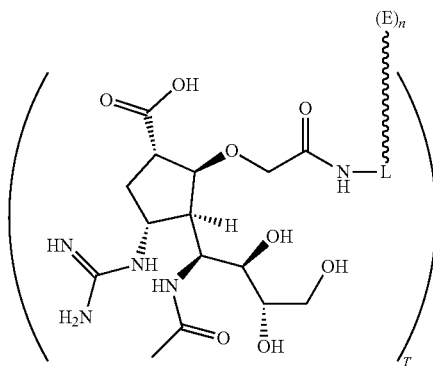

or a pharmaceutically acceptable salt thereof.

186. The conjugate of embodiment 184, wherein the conjugate is described by formula (M-IX-3):

(M-IX-3)

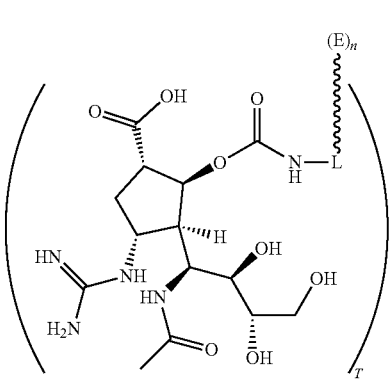

or a pharmaceutically acceptable salt thereof.

187. The conjugate of embodiment 184, wherein the conjugate is described by formula (M-IX-4):

(M-IX-4)

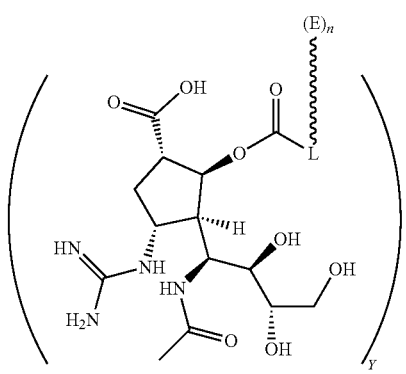

or a pharmaceutically acceptable salt thereof.

188. The conjugate of embodiment 184, wherein the conjugate is described by formula (M-IX-5):

(M-IX-5)

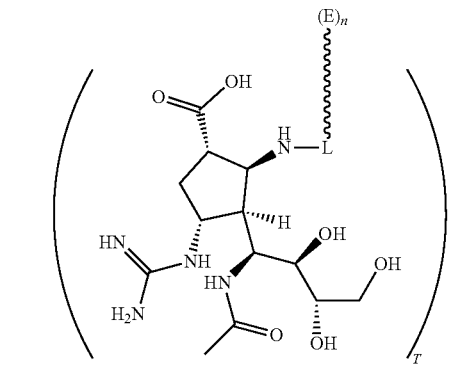

or a pharmaceutically acceptable salt thereof.

189. The conjugate of embodiment 184, wherein the conjugate is described by formula (M-IX-6):

(M-IX-6)

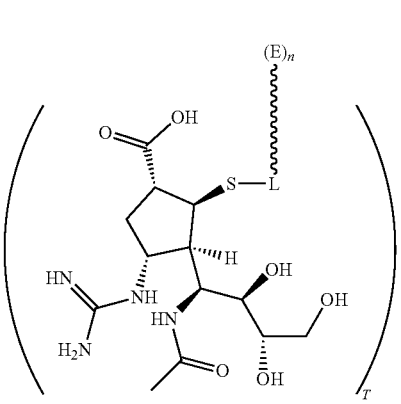

or a pharmaceutically acceptable salt thereof.

190. The conjugate of embodiment 113, wherein the conjugate is described by formula (M-X):

(M-X)

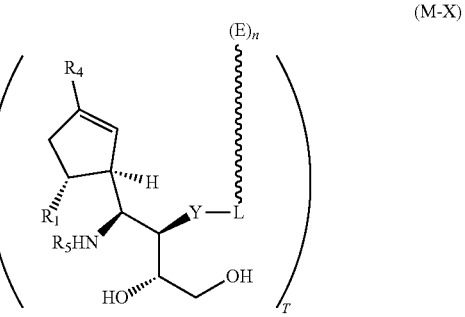

or a pharmaceutically acceptable salt thereof.

191. The conjugate of embodiment 190, wherein the conjugate is described by formula (M-X-1):

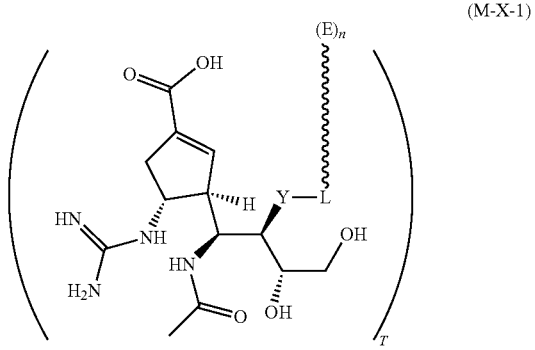

(M-X-1)

or a pharmaceutically acceptable salt thereof.

192. The conjugate of embodiment 191, wherein the conjugate is described by formula (M-X-2):

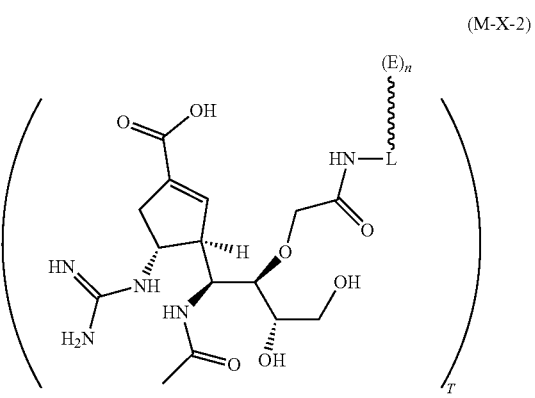

(M-X-2)

or a pharmaceutically acceptable salt thereof.

193. The conjugate of embodiment 190, wherein the conjugate is described by formula (M-X-3):

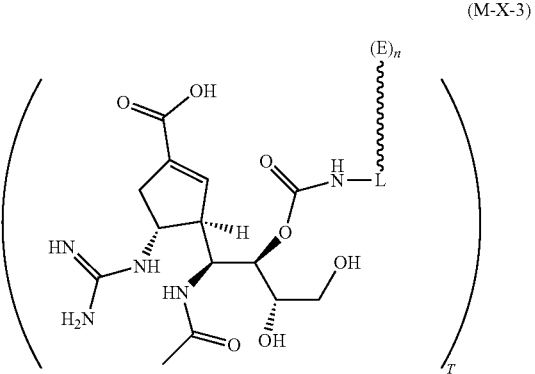

(M-X-3)

or a pharmaceutically acceptable salt thereof.

194. The conjugate of any one of embodiments 113-193, wherein L or L' comprises one or more optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, optionally substituted C2-C15 heteroarylene, O, S, $NR^i$, P, carbonyl, thiocarbonyl, sulfonyl, phosphate, phosphoryl, or imino, wherein $R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl.

195. The conjugate of embodiment 194, wherein the backbone of L or L' consists of one or more optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, optionally substituted C2-C15 heteroarylene, O, S, $NR^i$, P, carbonyl, thiocarbonyl, sulfonyl, phosphate, phosphoryl, or imino, wherein $R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl.

196. The conjugate of embodiment 194 or 195, wherein L or L' is oxo substituted.

197. The conjugate of any one of embodiments 113-196, wherein the backbone of L or L' comprises no more than 250 atoms.

198. The conjugate of any one of embodiments 113-197, wherein L or L' is capable of forming an amide, a carbamate, a sulfonyl, or a urea linkage.

199. The conjugate of any one of embodiments 113-193, wherein L or L' is a bond.

200. The conjugate of any one of embodiments 113-193, wherein L or L' is an atom.

201. The conjugate of any one of embodiments 113-200, wherein each L is described by formula (M-L-I):

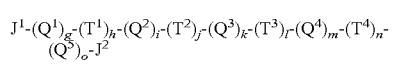

wherein $J^1$ is a bond attached $A_1$;

$J^2$ is a bond attached to E or a functional group capable of reacting with a functional group conjugated to E (e.g., maleimide and cysteine, amine and activated carboxylic acid, thiol and maleimide, activated sulfonic acid and amine, isocyanate and amine, azide and alkyne, and alkene and tetrazine);

each of $Q^1$, $Q^2$, $Q^3$, $Q^4$ and $Q^5$ is, independently, optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, or optionally substituted C2-C15 heteroarylene;

each of $T^1$, $T^2$, $T^3$, $T^4$ is, independently, O, S, $NR^i$, P, carbonyl, thiocarbonyl, sulfonyl, phosphate, phosphoryl, or imino;

$R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl; and each of g, h, i, j, k, l, m, n, and o is, independently, 0 or 1.

202. The conjugate of any one of embodiments 1-201, wherein $R_1$ is —NHC(=NH)NH$_2$.

203. The conjugate of any one of embodiments 1-202, wherein $R_2$ is —F.

204. The conjugate of any one of embodiments 1-203, wherein $R_3$ is —F.

205. The conjugate of any one of embodiments 1-204, wherein $R_4$ is —CO$_2$H.

206. The conjugate of any one of embodiments 1-205, wherein $R_5$ is —COCH$_3$.

207. The conjugate of any one of embodiment 1-206, wherein the squiggly line connected to E indicates that the L of each $A_1$-L or each $A_1$-L-$A_2$ is covalently attached to a nitrogen atom of a solvent-exposed lysine of E.

208. The conjugate of any one of embodiment 1-206, wherein the squiggly line connected to E indicates that the L of each $A_1$-L or each $A_1$-L-$A_2$ L is covalently attached to a sulfur atom of a solvent-exposed cysteine of E.

209. The conjugate of any one of embodiments 1-208, wherein each E is an Fc domain monomer.

210. The conjugate of embodiment 209, wherein n is 2, and each E dimerizes to form an Fc domain.

211. The conjugate of any one of embodiments 2-4, wherein n is 2, each E is an Fc domain monomer, each E dimerizes to form an Fc domain, and the conjugate is described by formula (D-I-1):

(D-I-1)

wherein J is an Fc domain; and

T is an integer from 1 to 20, or a pharmaceutically acceptable salt thereof.

212. The conjugate of embodiment 211, wherein the conjugate has the structure of

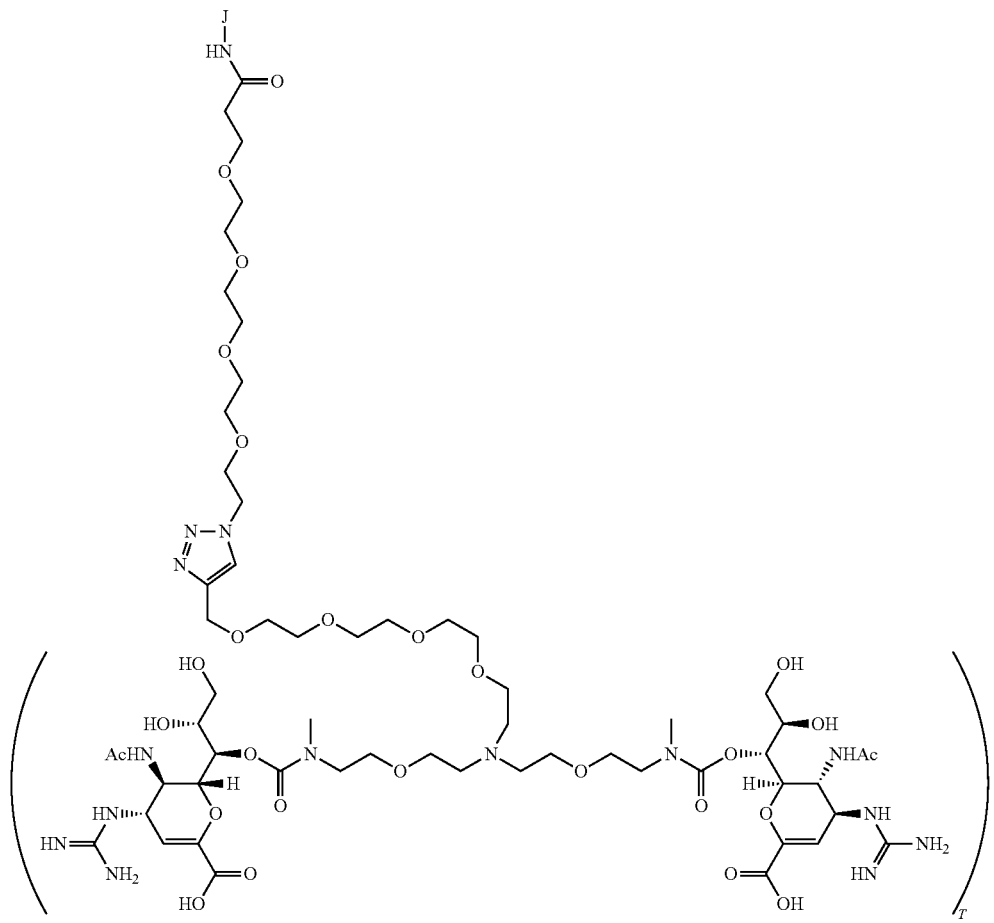

or a pharmaceutically acceptable salt thereof.

213. The conjugate of embodiment any one of embodiments 113-115, wherein n is 2, each E is an Fc domain monomer, each E dimerizes to form an Fc domain, and the conjugate is described by formula (M-I-1)

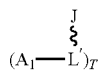
(M-I-1)

wherein J is an Fc domain; and
T is an integer from 1 to 20,
or a pharmaceutically acceptable salt thereof.

214. The conjugate of any one of embodiments 209-213, wherein each E comprises an amino acid sequence at least 95% identical to the sequence of any one of SEQ ID NOs: 1-138.

215. The conjugate of embodiment 214, wherein each E comprises and amino acid sequence at least 95% identical to the sequence of any one of SEQ ID NO: 62, SEQ ID NO: 63, SEQ ID NO: 64, SEQ ID NO: 67, SEQ ID NO: 68, SEQ ID NO: 72, SEQ ID NO: 73, SEQ ID NO: 76, SEQ ID NO: 77, SEQ ID NO: 80, SEQ ID NO: 81, SEQ ID NO: 82, SEQ ID NO: 85, SEQ ID NO: 86, SEQ ID NO: 90, SEQ ID NO: 91, SEQ ID NO: 94, SEQ ID NO: 95.

216. The conjugate of embodiment 215, wherein each E comprises the amino acid sequence of SEQ ID NO: 62.

217. The conjugate of embodiment 215, wherein each E comprises the amino acid sequence of SEQ ID NO: 63.

218. The conjugate of embodiment 215, wherein each E comprises the amino acid sequence of SEQ ID NO: 64.

219. The conjugate of embodiment 215, wherein each E comprises the amino acid sequence of SEQ ID NO: 67.

220. The conjugate of embodiment 215, wherein each E comprises the amino acid sequence of SEQ ID NO: 68.

221. The conjugate of embodiment 215, wherein each E comprises the amino acid sequence of SEQ ID NO: 72.

222. The conjugate of embodiment 215, wherein each E comprises the amino acid sequence of SEQ ID NO: 73.

223. The conjugate of embodiment 215, wherein each E comprises the amino acid sequence of SEQ ID NO: 76.

224. The conjugate of embodiment 215, wherein each E comprises the amino acid sequence of SEQ ID NO: 77.

225. The conjugate of embodiment 215, wherein each E comprises the amino acid sequence of SEQ ID NO: 80.

226. The conjugate of embodiment 215, wherein each E comprises the amino acid sequence of SEQ ID NO: 81.

227. The conjugate of embodiment 215, wherein each E comprises the amino acid sequence of SEQ ID NO: 82.

228. The conjugate of embodiment 215, wherein each E comprises the amino acid sequence of SEQ ID NO: 85.

229. The conjugate of embodiment 215, wherein each E comprises the amino acid sequence of SEQ ID NO: 86.

230. The conjugate of embodiment 215, wherein each E comprises the amino acid sequence of SEQ ID NO: 90.

231. The conjugate of embodiment 215, wherein each E comprises the amino acid sequence of SEQ ID NO: 91.
232. The conjugate of embodiment 215, wherein each E comprises the amino acid sequence of SEQ ID NO: 94.
233. The conjugate of embodiment 215, wherein each E comprises the amino acid sequence of SEQ ID NO: 95.
234. The conjugate of any one of embodiments 209-233, wherein T is 1, 2, 3, 4, 5, 6, 7, 8, 9, or 10.
235. A population of conjugates of any one of embodiments 209-233, wherein the average value of T is 1 to 10.
236. The population of conjugates of embodiment 235, wherein the average value of T is 1 to 5.
237. The population of conjugates of embodiment 235, wherein the average value of T is 3 to 7.
238. The population of conjugates of embodiment 236 or 237, wherein the average value of T is 3.5 to 5.5.
239. The population of conjugates of embodiment 236 or 237, wherein the average value of T is about 4.5.
240. The population of conjugates of embodiment 235, wherein the average value of T is 5 to 10.
241. A pharmaceutical composition comprising a conjugate of any of embodiments 1-234, or a population of conjugates of embodiments 235-240, or a pharmaceutically acceptable salt thereof, and a pharmaceutically acceptable excipient.
242. A method for the treatment of a subject having a viral infection or presumed to have a viral infection, the method comprising administering to the subject an effective amount of a conjugate or composition of any one of embodiments 1-241.
243. A method for the prophylactic treatment of a viral infection in a subject in need thereof, the method comprising administering to the subject an effective amount of a conjugate or composition of any one of embodiments 1-241.
244. The method of embodiment 242 or 243, wherein the viral infection is caused by influenza virus or parainfluenza virus.
245. The method of any one of embodiments 242-244, wherein the viral infection is influenza virus A, B, or C, or parainfluenza virus.
246. The method of any one of embodiments 242-245, wherein the subject is immunocompromised.
247. The method of any one of embodiments 242-246, wherein the subject has been diagnosed with humoral immune deficiency, T cell deficiency, neutropenia, asplenia, or complement deficiency.
248. The method of any one of embodiments 242-247, wherein the subject is being treated or is about to be treated with an immunosuppressive therapy.
249. The method of any one of embodiments 242-248, wherein said subject has been diagnosed with a disease which causes immunosuppression.
250. The method of embodiment 249, wherein the disease is cancer or acquired immunodeficiency syndrome.
251. The method of embodiment 250, wherein the cancer is leukemia, lymphoma, or multiple myeloma.
252. The method of any one of embodiments 242-251, wherein the subject has undergone or is about to undergo hematopoietic stem cell transplantation.
253. The method of any one of embodiments 242-252, wherein the subject has undergone or is about to undergo an organ transplant.
254. The method of any one of embodiments 242-253, wherein the subject has or is at risk of developing a secondary infection.
255. A method of preventing a secondary infection in a subject diagnosed with an influenza infection, wherein the method includes administering to the subject the conjugate or composition of any one of embodiments 1-241.
256. The method of embodiments 254 or 255, wherein the secondary infection is a respiratory infection.
257. The method of any one of embodiments 254-256, wherein the secondary infection is associated with pneumonia.
258. The method of any one of embodiments 254-257, wherein the secondary infection is a bacterial infection, a viral infection, or a fungal infection.
259. The method of embodiment 258, wherein the secondary infection is a bacterial infection.
260. The method of embodiment 259, wherein the bacterial infection is a methicillin-resistant *Staphylococcus aureus* (MRSA), *Streptococcus pneumoniae, Pseudomonas aeruginosa,* or *Haemophilus influenzae* infection.
261. The method of embodiment 260, wherein the bacterial infection is MRSA.
262. The method of embodiment 260, wherein the bacterial infection is *S. pneumoniae.*
263. The method of any one of embodiments 242-262 wherein the conjugate of composition is administered intramuscularly, intravenously, intradermally, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctival, intravesicularlly, mucosally, intrapericardially, intraumbilically, intraocularally, orally, locally, by inhalation, by injection, or by infusion.
264. The method of any one of embodiments 242-263, wherein the subject is treated with a second therapeutic agent.
265. The method of embodiment 264, wherein the second therapeutic agent is an antiviral agent.
266. The method of embodiment 264, wherein the antiviral agent is selected from pimovidir, oseltamivir, zanamivir, peramivir, laninamivir, amantadine, or rimantadine.
267. The method of embodiment 266, wherein the second therapeutic agent is an antiviral vaccine.
268. The method of embodiment 267, wherein the antiviral vaccine elicits an immune response in the subject against influenza virus A, B, or C, or parainfluenza virus.
269. The method of embodiment 265, wherein the antiviral agent is baloxavir.
270. The method of embodiment 265, wherein the conjugate and baloxavir are administered sequentially.
271. The method of embodiment 265, wherein the conjugate and baloxavir are administered simultaneously.
272. The method of any one of embodiments 242-271, wherein conjugate is described by formula (D-II-6).
273. The method of embodiment 272, wherein $R_7$ is selected from C1-C20 alkyl, C3-C20 cycloalkyl, C3-C20 heterocycloalkyl; C5-C15 aryl, and C2-C15 heteroaryl.
274. The method of embodiment 272 or 273, wherein $R_7$ is selected from methyl, ethyl, propyl, or butyl.
275. The method of embodiments 272-274, wherein the conjugate is described by formula (D-II-7).
276. The method of any one of embodiments 242-275, wherein each E has a sequence at least 95% identical to the sequence of any one of SEQ ID NOs: 63-68.
277. The method of any one of embodiments 242-275, wherein each E has a sequence at least 95% identical to the sequence of SEQ ID NO: 63, SEQ ID NO: 64, SEQ ID NO: 72, or SEQ ID NO: 73.

278. The method of any one of embodiments 242-275, wherein each E has a sequence at least 95% identical to the sequence of SEQ ID NO: 67, SEQ ID NO: 68, SEQ ID NO: 76, or SEQ ID NO: 77.

279. The method of any one of embodiments 242-275, wherein the conjugate is conjugate 45 or conjugate 46.

280. A method for treating or preventing a viral infection in a subject, the method comprising administering to the subject:
  a) a conjugate or composition of any one of embodiments 1-241; and
  b) a second therapeutic agent.

281. The method of embodiment 280, wherein conjugate is administered to the subject after the subject has a viral infection, is presumed to have a viral infection, or has been exposed to a virus.

282. The method of embodiment 280, wherein the conjugate is administered to the subject prophylactically.

283. The method of any one of embodiments 278-282, wherein the second therapeutic agent is administered to the subject after the subject has a viral infection, is presumed to have a viral infection, or has been exposed to the virus.

284. The method of any one of embodiments 278-283, wherein the second therapeutic agent is administered to the subject prophylactically.

285. The method of any one of embodiments 278-284, wherein the second therapeutic agent is administered within 2 days of the conjugate.

286. The method of any one of embodiments 278-285, wherein the second therapeutic agent is an antiviral agent.

287. The method of embodiment 286, wherein the antiviral agent is pimovidir, oseltamivir, zanamivir, peramivir, laninamivir, amantadine, baloxavir marboxil, baloxavir acid, rimantadine, or a pharmaceutically acceptable salt thereof.

288. The method of embodiment 287, wherein the antiviral agent is baloxavir marboxil, baloxavir acid, or a pharmaceutically acceptable salt thereof.

289. The method of any one of embodiments 288, wherein the baloxavir marboxil, baloxavir acid, or a pharmaceutically acceptable salt thereof, is administered in an amount between 20 mg and 90 mg.

290. The method of embodiment 286, wherein the baloxavir marboxil, baloxavir acid, or a pharmaceutically acceptable salt thereof, is administered orally.

291. The method of embodiment 289 or 290, wherein the baloxavir marboxil, baloxavir acid, or a pharmaceutically acceptable salt thereof, is administered as a single dose.

292. The method of embodiment 289 or 290, wherein the baloxavir marboxil, baloxavir acid, or a pharmaceutically acceptable salt thereof, is administered as more than one dose.

293. The method of any one of embodiments 289-292, wherein the baloxavir marboxil, baloxavir acid, or a pharmaceutically acceptable salt thereof, is administered in an amount between 20 mg and 40 mg.

294. The method of any one of embodiments 289-292, wherein the baloxavir marboxil, baloxavir acid, or a pharmaceutically acceptable salt thereof, is administered in an amount between 30 and 80 mg.

295. The method of embodiment any one of embodiments 278-294, wherein the conjugate is described by formula (D-II-6).

296. The method of embodiment 295, wherein $R_7$ is selected from C1-C20 alkyl, C3-C20 cycloalkyl, C3-C20 heterocycloalkyl; C5-C15 aryl, and C2-C15 heteroaryl.

297. The method of embodiment 295 or 296, wherein $R_7$ is selected from methyl, ethyl, propyl, or butyl.

298. The method of any one of embodiments 295-297, wherein the conjugate is described by formula (D-11-7).

299. The method of any one of embodiments 280-298, wherein each E has a sequence at least 95% identical to the sequence of any one of SEQ ID NOs: 63-68.

300. The method of embodiment 299, wherein each E has a sequence at least 95% identical to the sequence of SEQ ID NO: 63, SEQ ID NO: 64, SEQ ID NO: 72, or SEQ ID NO: 73.

301. The method of embodiment 300, wherein each E has a sequence at least 95% identical to the sequence of SEQ ID NO: 67, SEQ ID NO: 68, SEQ ID NO: 76, or SEQ ID NO: 77.

302. The method of any one of embodiments 280-298, wherein the conjugate is conjugate 45 or conjugate 46.

303. The method of any one of embodiments 280-302, wherein the conjugate is administered intramuscularly, intravenously, intradermally, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctival, intravesicularly, mucosally, intrapericardially, intraumbilically, intraocularally, orally, locally, by inhalation, by injection, or by infusion.

304. The method of embodiment 303, wherein the conjugate is administered intravenously.

305. The method of embodiment 303, wherein the conjugate is administered subcutaneously.

306. The method of embodiment 303, wherein the conjugate is administered intramuscularly.

307. The method of any one of embodiments 280-306, wherein the viral infection is caused by an influenza virus or a parainfluenza virus.

308. The method of embodiment 307, wherein the virus is influenza virus A, B, or C, or parainfluenza virus.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims. All publications, patents, and patent applications mentioned in the above specification are hereby incorporated by reference to the same extent as if each individual publication, patent or patent application was specifically and individually indicated to be incorporated by reference in its entirety.

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

The invention claimed is:
1. A conjugate described by formula (D-II-6):

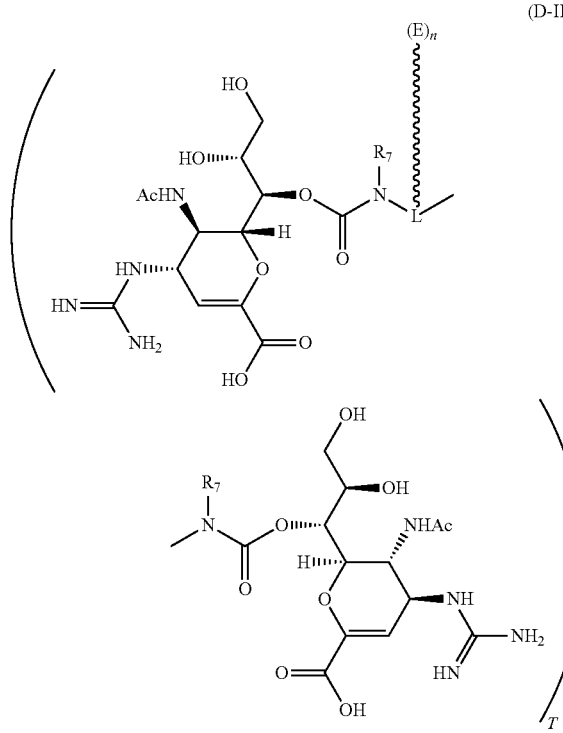

(D-II-6)

wherein each E comprises an Fc domain monomer;

n is 1 or 2;

T is an integer from 1 to 20;

L is a linker;

$R_7$ is selected from C1-C20 alkyl; and the squiggly line indicates that L is covalently attached to E;

or a pharmaceutically acceptable salt thereof.

2. The conjugate of claim 1, wherein the squiggly line indicates that L is covalently attached to a nitrogen atom of a solvent-exposed lysine of E.

3. The conjugate of claim 1, wherein the squiggly line indicates that L is covalently attached to a sulfur atom of a solvent-exposed cysteine of E.

4. The conjugate of claim 1, wherein n is 2, and the two Es dimerize with each other to form an Fc domain.

5. The conjugate of claim 1, wherein T is 1, 2, 3, 4, 5, 6, 7, 8, 9, or 10.

6. A population of conjugates of claim 1, wherein the average value of T is 1 to 10.

7. The conjugate of claim 1, wherein $R_7$ is methyl, ethyl, propyl, or butyl.

8. The conjugate of claim 7, wherein the conjugate is described by formula (D-II-7):

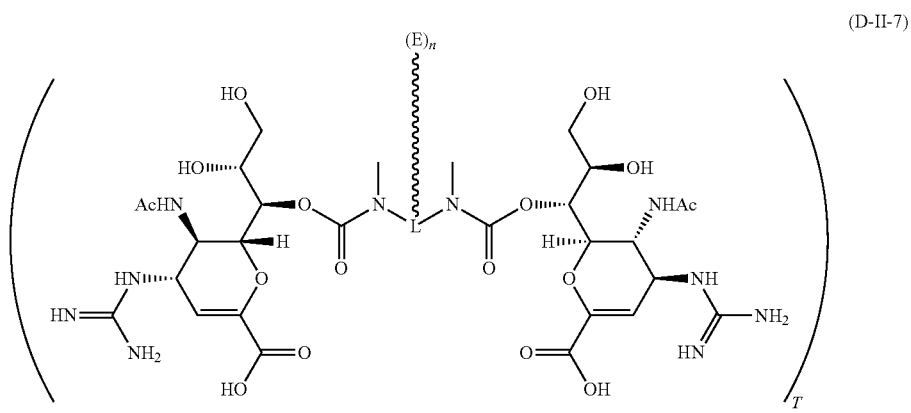

(D-II-7)

or a pharmaceutically acceptable salt thereof.

9. The conjugate of claim 8, wherein the conjugate is described by formula (D-II-8):

(D-II-8)
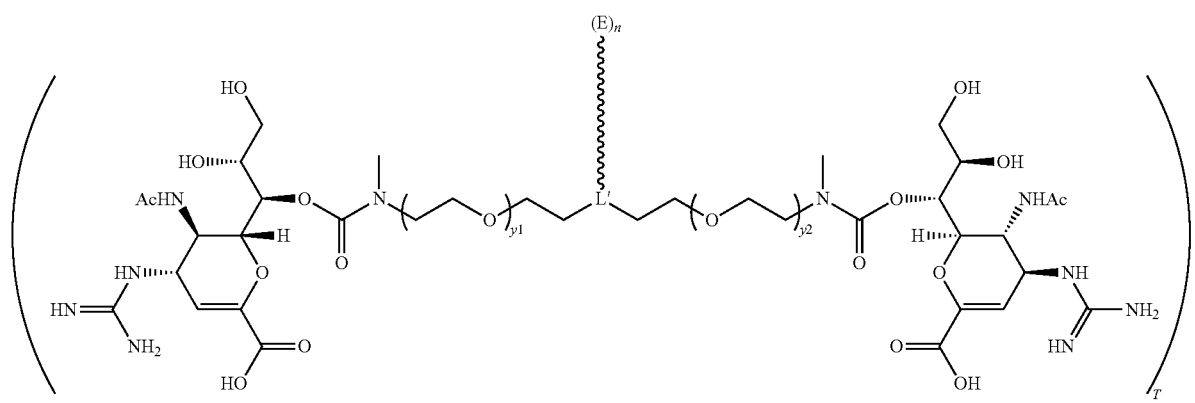
wherein L' is the remainder of L, and
$y_1$ and $y_2$ are each independently an integer from 1-20,
or a pharmaceutically acceptable salt thereof.
10. The conjugate of claim 9, wherein the conjugate has the structure of:
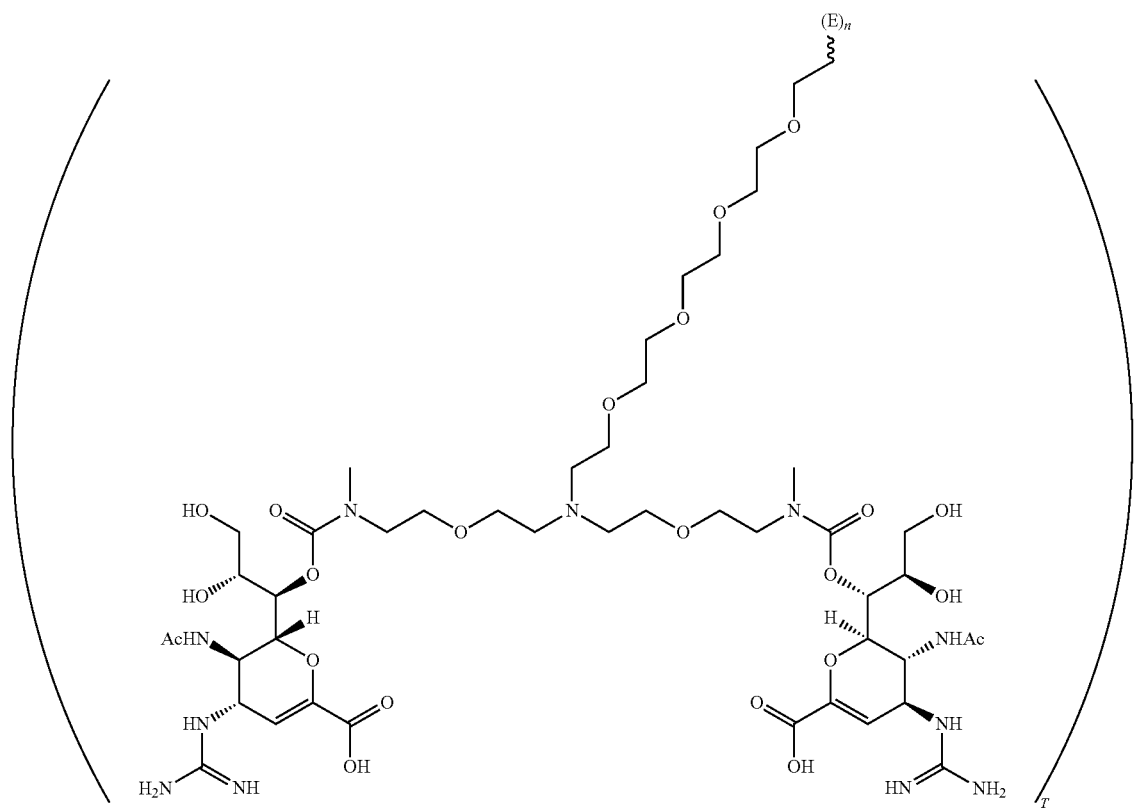
or a pharmaceutically acceptable salt thereof.
11. The conjugate of claim 10, wherein the conjugate has the structure of:

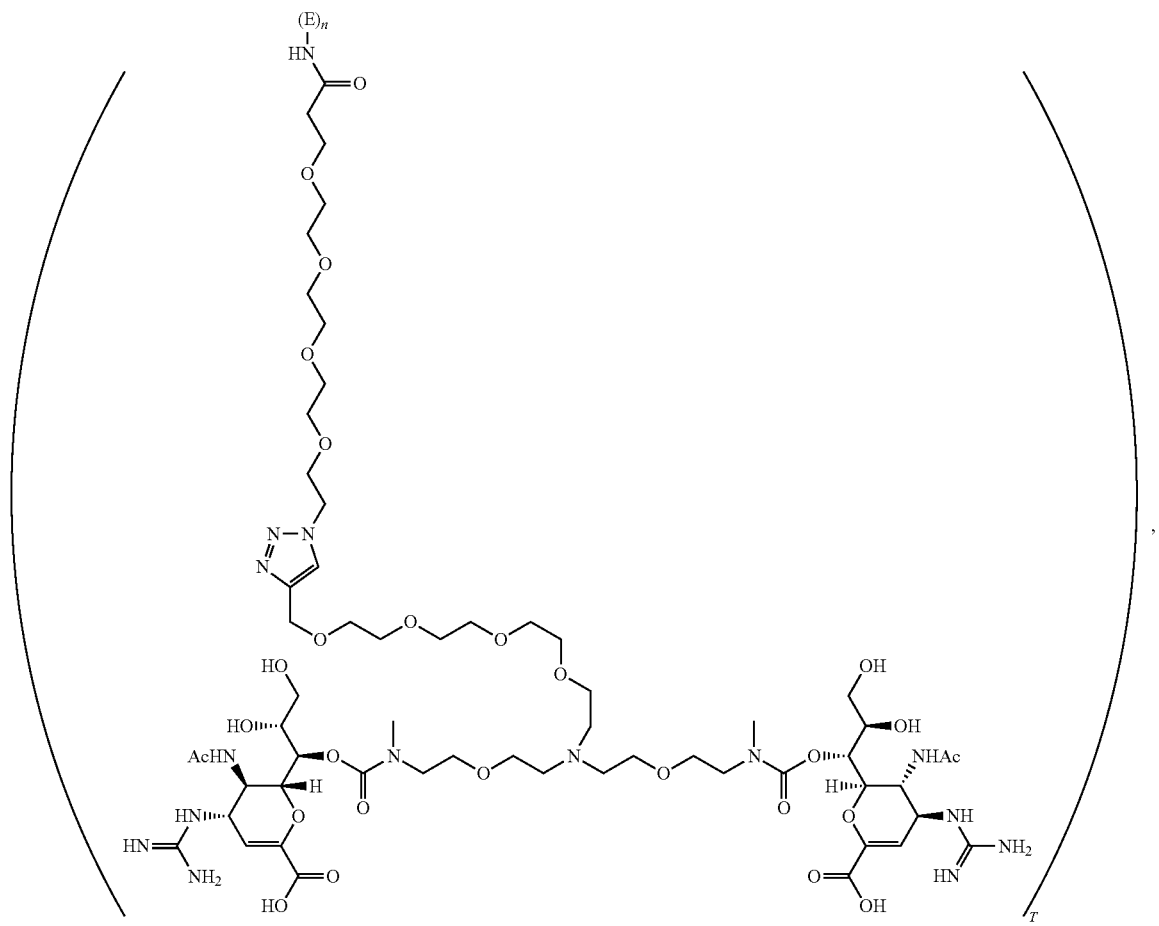

or a pharmaceutically acceptable salt thereof.

12. The conjugate of claim 11, wherein n is 2, and the two Es dimerize with each other to form an Fc domain.

13. The conjugate of claim 11, wherein T is 1, 2, 3, 4, 5, 6, 7, 8, 9, or 10.

14. A population of conjugates of claim 11, wherein the average value of T is 1 to 10.

15. The conjugate of claim 1, wherein each E comprises an amino acid sequence independently selected from of any one of SEQ ID NOs: 1-138.

16. The conjugate of claim 1, wherein each E comprises an amino acid sequence independently selected from any one of SEQ ID NO: 72, SEQ ID NO: 73, SEQ ID NO: 76, and SEQ ID NO: 77.

17. The conjugate of claim 16, wherein each E comprises an amino acid sequence of SEQ ID NO: 72.

18. The conjugate of claim 16, wherein each E comprises an amino acid sequence of SEQ ID NO: 73.

19. The conjugate of claim 16, wherein each E comprises an amino acid sequence of SEQ ID NO: 76.

20. The conjugate of claim 16, wherein each E comprises an amino acid sequence of SEQ ID NO: 77.

21. A conjugate described by the structure:

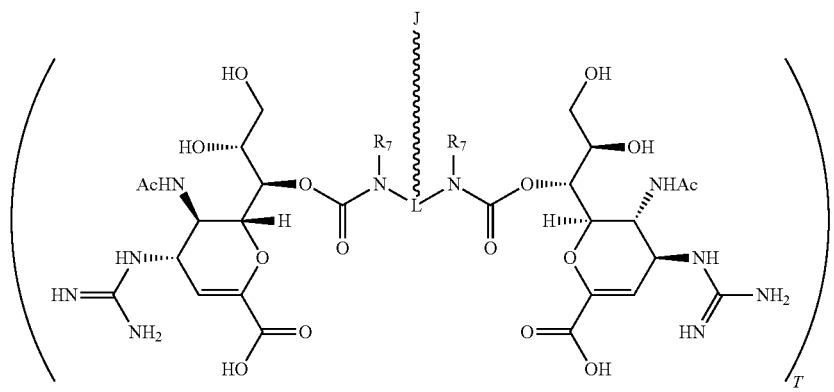

wherein J is an Fc domain comprising two Fc domain monomers,
T is an integer from 1 to 20,
L is a linker;
$R_7$ is selected from C1-C20 alkyl; and
the squiggly line indicates that L is covalently attached to J;
or a pharmaceutically acceptable salt thereof.

22. The conjugate of claim 21, wherein the squiggly line indicates that L is covalently attached to a nitrogen atom of a solvent-exposed lysine of J.

23. The conjugate of claim 21, wherein the squiggly line indicates that L is covalently attached to a sulfur atom of a solvent-exposed cysteine of J.

24. The conjugate of claim 21, wherein $R_7$ is methyl, ethyl, propyl, or butyl.

25. The conjugate of claim 21, wherein T is an integer from 1 to 10.

26. The conjugate of claim 21, wherein the conjugate has the structure of:

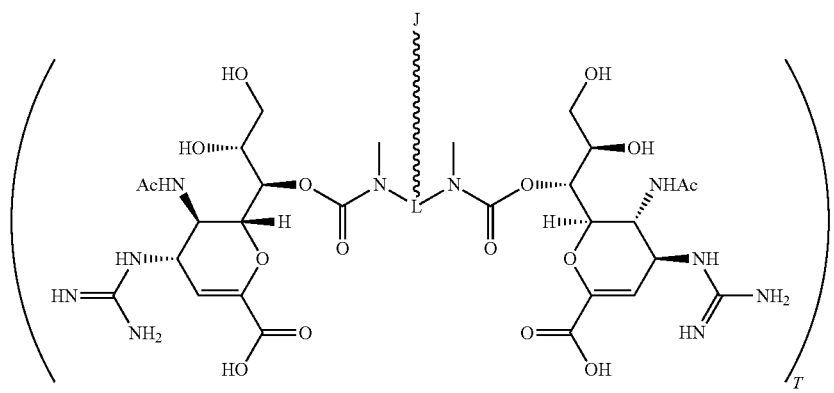

or a pharmaceutically acceptable salt thereof.

27. The conjugate of claim 26, wherein the conjugate has the structure of:

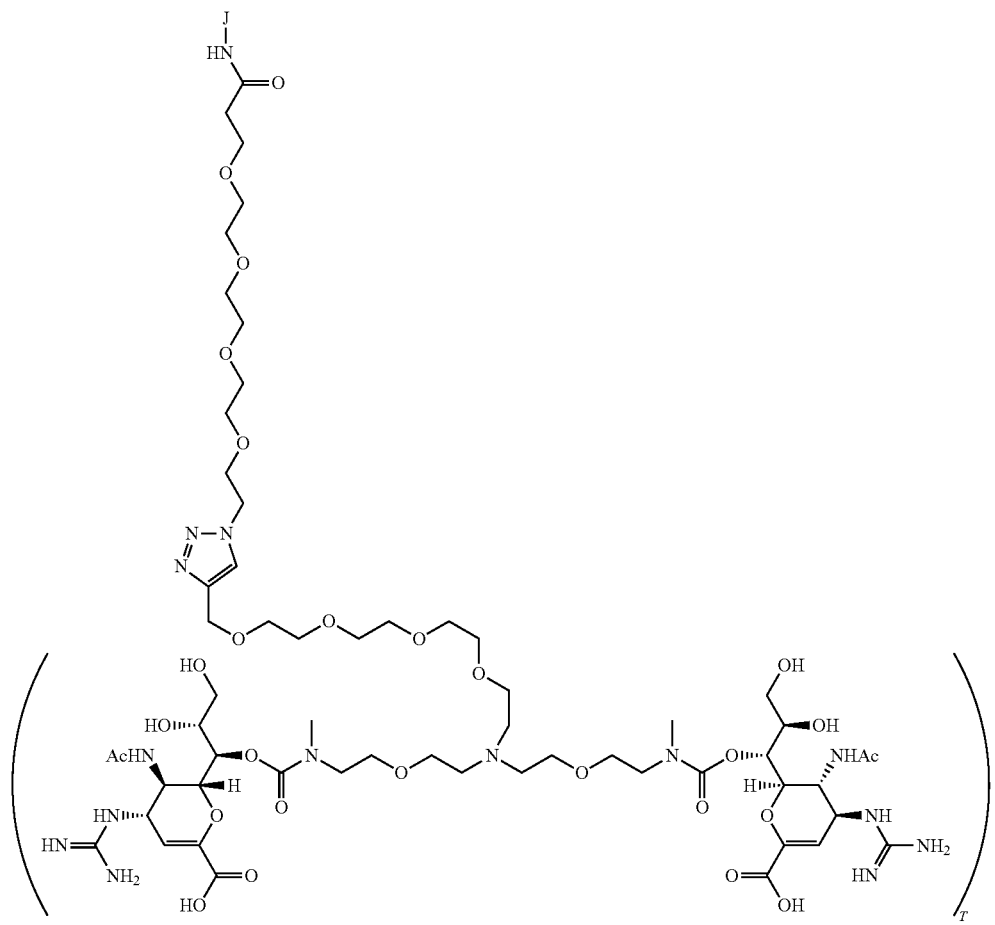

or a pharmaceutically acceptable salt thereof.

28. The conjugate of claim 27, wherein each Fc domain monomer comprises an amino acid sequence independently selected from any one of SEQ ID NOs: 1-138.

29. The conjugate of claim 28, wherein each Fc domain monomer comprises an amino acid sequence independently selected from any one of SEQ ID NO: 72, SEQ ID NO: 73, SEQ ID NO: 76, and SEQ ID NO: 77.

30. The conjugate of claim 29, wherein each Fc domain monomer comprises an amino acid sequence of SEQ ID NO: 72.

31. The conjugate of claim 29, wherein each Fc domain monomer comprises an amino acid sequence of SEQ ID NO: 73.

32. The conjugate of claim 29, wherein each Fc domain monomer comprises an amino acid sequence of SEQ ID NO: 76.

33. The conjugate of claim 29, wherein each Fc domain monomer comprises an amino acid sequence of SEQ ID NO: 77.

34. The conjugate of 27, wherein T is an integer from 1 to 10.

35. A population of conjugates of claim 27, wherein the average value of T is 1 to 10.

* * * * *

SEQUENCE LISTING

<160> NUMBER OF SEQ ID NOS: 167

<210> SEQ ID NO 1
<211> LENGTH: 252
<212> TYPE: PRT
<213> ORGANISM: Artificial Sequence
<220> FEATURE:
<223> OTHER INFORMATION: Synthetic Construct

<400> SEQUENCE: 1

Met Tyr Arg Met Gln Leu Leu Ser Cys Ile Ala Leu Ser Leu Ala Leu
1               5                   10                  15

Val Thr Asn Ser Pro Arg Gly Pro Thr Ile Lys Pro Cys Pro Pro Cys
            20                  25                  30

Lys Cys Pro Ala Pro Asn Leu Leu Gly Gly Pro Ser Val Phe Ile Phe
        35                  40                  45

Pro Pro Lys Ile Lys Asp Val Leu Met Ile Ser Leu Ser Pro Ile Val
    50                  55                  60

Thr Cys Val Val Val Asp Val Ser Glu Asp Asp Pro Asp Val Gln Ile
65                  70                  75                  80

Ser Trp Phe Val Asn Asn Val Glu Val His Thr Ala Gln Thr Gln Thr
                85                  90                  95

His Arg Glu Asp Tyr Asn Ser Thr Leu Arg Val Val Ser Ala Leu Pro
            100                 105                 110

Ile Gln His Gln Asp Trp Met Ser Gly Lys Glu Phe Lys Cys Lys Val
        115                 120                 125

Asn Asn Lys Asp Leu Pro Ala Pro Ile Glu Arg Thr Ile Ser Lys Pro
130                 135                 140

Lys Gly Ser Val Arg Ala Pro Gln Val Tyr Val Leu Pro Pro Pro Glu
145                 150                 155                 160

Glu Glu Met Thr Lys Lys Gln Val Thr Leu Thr Cys Met Val Thr Asp
                165                 170                 175

Phe Met Pro Glu Asp Ile Tyr Val Glu Trp Thr Asn Asn Gly Lys Thr
            180                 185                 190

Glu Leu Asn Tyr Lys Asn Thr Glu Pro Val Leu Asp Ser Asp Gly Ser
        195                 200                 205

Tyr Phe Met Tyr Ser Lys Leu Arg Val Glu Lys Lys Asn Trp Val Glu
    210                 215                 220

Arg Asn Ser Tyr Ser Cys Ser Val Val His Glu Gly Leu His Asn His
225                 230                 235                 240

His Thr Thr Lys Ser Phe Ser Arg Thr Pro Gly Lys
                245                 250

<210> SEQ ID NO 2
<211> LENGTH: 232
<212> TYPE: PRT
<213> ORGANISM: Mus musculus

<400> SEQUENCE: 2

Pro Arg Gly Pro Thr Ile Lys Pro Cys Pro Pro Cys Lys Cys Pro Ala
1               5                   10                  15

Pro Asn Leu Leu Gly Gly Pro Ser Val Phe Ile Phe Pro Pro Lys Ile
            20                  25                  30

Lys Asp Val Leu Met Ile Ser Leu Ser Pro Ile Val Thr Cys Val Val
        35                  40                  45

Val Asp Val Ser Glu Asp Asp Pro Asp Val Gln Ile Ser Trp Phe Val
    50                  55                  60

```
Asn Asn Val Glu Val His Thr Ala Gln Thr Gln Thr His Arg Glu Asp
 65                  70                  75                  80

Tyr Asn Ser Thr Leu Arg Val Val Ser Ala Leu Pro Ile Gln His Gln
                 85                  90                  95

Asp Trp Met Ser Gly Lys Glu Phe Lys Cys Lys Val Asn Asn Lys Asp
            100                 105                 110

Leu Pro Ala Pro Ile Glu Arg Thr Ile Ser Lys Pro Lys Gly Ser Val
            115                 120                 125

Arg Ala Pro Gln Val Tyr Val Leu Pro Pro Glu Glu Met Thr
130                 135                 140

Lys Lys Gln Val Thr Leu Thr Cys Met Val Thr Asp Phe Met Pro Glu
145                 150                 155                 160

Asp Ile Tyr Val Glu Trp Thr Asn Asn Gly Lys Thr Glu Leu Asn Tyr
                165                 170                 175

Lys Asn Thr Glu Pro Val Leu Asp Ser Asp Gly Ser Tyr Phe Met Tyr
            180                 185                 190

Ser Lys Leu Arg Val Glu Lys Lys Asn Trp Val Glu Arg Asn Ser Tyr
            195                 200                 205

Ser Cys Ser Val Val His Glu Gly Leu His Asn His Thr Thr Lys
210                 215                 220

Ser Phe Ser Arg Thr Pro Gly Lys
225                 230

<210> SEQ ID NO 3
<211> LENGTH: 251
<212> TYPE: PRT
<213> ORGANISM: Artificial Sequence
<220> FEATURE:
<223> OTHER INFORMATION: Synthetic Construct

<400> SEQUENCE: 3

Met Tyr Arg Met Gln Leu Leu Ser Cys Ile Ala Leu Ser Leu Ala Leu
  1               5                  10                  15

Val Thr Asn Ser Met Val Arg Ser Asp Lys Thr His Thr Cys Pro Pro
                 20                  25                  30

Cys Pro Ala Pro Glu Leu Leu Gly Gly Pro Ser Val Phe Leu Phe Pro
             35                  40                  45

Pro Lys Pro Lys Asp Thr Leu Met Ile Ser Arg Thr Pro Glu Val Thr
         50                  55                  60

Cys Val Val Val Asp Val Ser His Glu Asp Pro Glu Val Lys Phe Asn
 65                  70                  75                  80

Trp Tyr Val Asp Gly Val Glu Val His Asn Ala Lys Thr Lys Pro Arg
                 85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
            115                 120                 125

Asn Lys Ala Leu Pro Ala Pro Ile Glu Lys Thr Ile Ser Lys Ala Lys
130                 135                 140

Gly Gln Pro Arg Glu Pro Gln Val Tyr Thr Leu Pro Pro Ser Arg Glu
145                 150                 155                 160

Glu Met Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190
```

```
Asn Asn Tyr Lys Thr Thr Pro Pro Val Leu Asp Ser Asp Gly Ser Phe
            195                 200                 205
Phe Leu Tyr Ser Lys Leu Thr Val Asp Lys Ser Arg Trp Gln Gln Gly
    210                 215                 220
Asn Val Phe Ser Cys Ser Val Met His Glu Ala Leu His Asn His Tyr
225                 230                 235                 240
Thr Gln Lys Ser Leu Ser Leu Ser Pro Gly Lys
            245                 250
```

<210> SEQ ID NO 4
<211> LENGTH: 231
<212> TYPE: PRT
<213> ORGANISM: Artificial Sequence
<220> FEATURE:
<223> OTHER INFORMATION: Synthetic Construct

<400> SEQUENCE: 4

```
Met Val Arg Ser Asp Lys Thr His Thr Cys Pro Pro Cys Pro Ala Pro
1               5                   10                  15
Glu Leu Leu Gly Gly Pro Ser Val Phe Leu Phe Pro Pro Lys Pro Lys
            20                  25                  30
Asp Thr Leu Met Ile Ser Arg Thr Pro Glu Val Thr Cys Val Val Val
        35                  40                  45
Asp Val Ser His Glu Asp Pro Glu Val Lys Phe Asn Trp Tyr Val Asp
    50                  55                  60
Gly Val Glu Val His Asn Ala Lys Thr Lys Pro Arg Glu Glu Gln Tyr
65                  70                  75                  80
Asn Ser Thr Tyr Arg Val Val Ser Val Leu Thr Val Leu His Gln Asp
                85                  90                  95
Trp Leu Asn Gly Lys Glu Tyr Lys Cys Lys Val Ser Asn Lys Ala Leu
            100                 105                 110
Pro Ala Pro Ile Glu Lys Thr Ile Ser Lys Ala Lys Gly Gln Pro Arg
        115                 120                 125
Glu Pro Gln Val Tyr Thr Leu Pro Pro Ser Arg Glu Glu Met Thr Lys
    130                 135                 140
Asn Gln Val Ser Leu Thr Cys Leu Val Lys Gly Phe Tyr Pro Ser Asp
145                 150                 155                 160
Ile Ala Val Glu Trp Glu Ser Asn Gly Gln Pro Glu Asn Asn Tyr Lys
                165                 170                 175
Thr Thr Pro Pro Val Leu Asp Ser Asp Gly Ser Phe Phe Leu Tyr Ser
            180                 185                 190
Lys Leu Thr Val Asp Lys Ser Arg Trp Gln Gln Gly Asn Val Phe Ser
        195                 200                 205
Cys Ser Val Met His Glu Ala Leu His Asn His Tyr Thr Gln Lys Ser
    210                 215                 220
Leu Ser Leu Ser Pro Gly Lys
225                 230
```

<210> SEQ ID NO 5
<211> LENGTH: 258
<212> TYPE: PRT
<213> ORGANISM: Artificial Sequence
<220> FEATURE:
<223> OTHER INFORMATION: Synthetic Construct

<400> SEQUENCE: 5

```
Met Tyr Arg Met Gln Leu Leu Ser Cys Ile Ala Leu Ser Leu Ala Leu
```

```
  1               5                   10                  15
Val Thr Asn Ser Pro Arg Gly Pro Thr Ile Lys Pro Cys Pro Pro Cys
                 20                  25                  30
Lys Cys Pro Ala Pro Asn Leu Leu Gly Gly Pro Ser Val Phe Ile Phe
                 35                  40                  45
Pro Pro Lys Ile Lys Asp Val Leu Met Ile Ser Leu Ser Pro Ile Val
 50                  55                  60
Thr Cys Val Val Val Asp Val Ser Glu Asp Pro Asp Val Gln Ile
 65                  70                  75                  80
Ser Trp Phe Val Asn Asn Val Glu Val His Thr Ala Gln Thr Gln Thr
                 85                  90                  95
His Arg Glu Asp Tyr Asn Ser Thr Leu Arg Val Val Ser Ala Leu Pro
                100                 105                 110
Ile Gln His Gln Asp Trp Met Ser Gly Lys Glu Phe Lys Cys Lys Val
                115                 120                 125
Asn Asn Lys Asp Leu Pro Ala Pro Ile Glu Arg Thr Ile Ser Lys Pro
                130                 135                 140
Lys Gly Ser Val Arg Ala Pro Gln Val Tyr Val Leu Pro Pro Pro Glu
145                 150                 155                 160
Glu Glu Met Thr Lys Lys Gln Val Thr Leu Thr Cys Met Val Thr Asp
                165                 170                 175
Phe Met Pro Glu Asp Ile Tyr Val Glu Trp Thr Asn Asn Gly Lys Thr
                180                 185                 190
Glu Leu Asn Tyr Lys Asn Thr Glu Pro Val Leu Asp Ser Asp Gly Ser
                195                 200                 205
Tyr Phe Met Tyr Ser Lys Leu Arg Val Glu Lys Lys Asn Trp Val Glu
                210                 215                 220
Arg Asn Ser Tyr Ser Cys Ser Val Val His Glu Gly Leu His Asn His
225                 230                 235                 240
His Thr Thr Lys Ser Phe Ser Arg Thr Pro Gly Lys His His His His
                245                 250                 255
His His

<210> SEQ ID NO 6
<211> LENGTH: 238
<212> TYPE: PRT
<213> ORGANISM: Artificial Sequence
<220> FEATURE:
<223> OTHER INFORMATION: Synthetic Construct

<400> SEQUENCE: 6

Pro Arg Gly Pro Thr Ile Lys Pro Cys Pro Pro Cys Lys Cys Pro Ala
 1               5                  10                  15
Pro Asn Leu Leu Gly Gly Pro Ser Val Phe Ile Phe Pro Pro Lys Ile
                 20                  25                  30
Lys Asp Val Leu Met Ile Ser Leu Ser Pro Ile Val Thr Cys Val Val
                 35                  40                  45
Val Asp Val Ser Glu Asp Asp Pro Asp Val Gln Ile Ser Trp Phe Val
                 50                  55                  60
Asn Asn Val Glu Val His Thr Ala Gln Thr Gln Thr His Arg Glu Asp
 65                  70                  75                  80
Tyr Asn Ser Thr Leu Arg Val Val Ser Ala Leu Pro Ile Gln His Gln
                 85                  90                  95
Asp Trp Met Ser Gly Lys Glu Phe Lys Cys Lys Val Asn Asn Lys Asp
                100                 105                 110
```

```
Leu Pro Ala Pro Ile Glu Arg Thr Ile Ser Lys Pro Lys Gly Ser Val
        115                 120                 125

Arg Ala Pro Gln Val Tyr Val Leu Pro Pro Glu Glu Met Thr
    130                 135                 140

Lys Lys Gln Val Thr Leu Thr Cys Met Val Thr Asp Phe Met Pro Glu
145                 150                 155                 160

Asp Ile Tyr Val Glu Trp Thr Asn Asn Gly Lys Thr Glu Leu Asn Tyr
                165                 170                 175

Lys Asn Thr Glu Pro Val Leu Asp Ser Asp Gly Ser Tyr Phe Met Tyr
                180                 185                 190

Ser Lys Leu Arg Val Glu Lys Lys Asn Trp Val Glu Arg Asn Ser Tyr
                195                 200                 205

Ser Cys Ser Val Val His Glu Gly Leu His Asn His His Thr Thr Lys
        210                 215                 220

Ser Phe Ser Arg Thr Pro Gly Lys His His His His His
225                 230                 235

<210> SEQ ID NO 7
<211> LENGTH: 257
<212> TYPE: PRT
<213> ORGANISM: Artificial Sequence
<220> FEATURE:
<223> OTHER INFORMATION: Synthetic Construct

<400> SEQUENCE: 7

Met Tyr Arg Met Gln Leu Leu Ser Cys Ile Ala Leu Ser Leu Ala Leu
1               5                   10                  15

Val Thr Asn Ser Met Val Arg Ser Asp Lys Thr His Thr Cys Pro Pro
                20                  25                  30

Cys Pro Ala Pro Glu Leu Leu Gly Gly Pro Ser Val Phe Leu Phe Pro
            35                  40                  45

Pro Lys Pro Lys Asp Thr Leu Met Ile Ser Arg Thr Pro Glu Val Thr
        50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Thr Tyr Arg Val Val Ser Val Leu Thr Val
                100                 105                 110

Leu His Gln Asp Trp Leu Asn Gly Lys Glu Tyr Lys Cys Lys Val Ser
            115                 120                 125

Asn Lys Ala Leu Pro Ala Pro Ile Glu Lys Thr Ile Ser Lys Ala Lys
        130                 135                 140

Gly Gln Pro Arg Glu Pro Gln Val Tyr Thr Leu Pro Pro Ser Arg Glu
145                 150                 155                 160

Glu Met Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
                180                 185                 190

Asn Asn Tyr Lys Thr Thr Pro Pro Val Leu Asp Ser Asp Gly Ser Phe
            195                 200                 205

Phe Leu Tyr Ser Lys Leu Thr Val Asp Lys Ser Arg Trp Gln Gln Gly
        210                 215                 220

Asn Val Phe Ser Cys Ser Val Met His Glu Ala Leu His Asn His Tyr
225                 230                 235                 240
```

Thr Gln Lys Ser Leu Ser Leu Ser Pro Gly Lys His His His His
                245                 250                 255

His

<210> SEQ ID NO 8
<211> LENGTH: 237
<212> TYPE: PRT
<213> ORGANISM: Artificial Sequence
<220> FEATURE:
<223> OTHER INFORMATION: Synthetic Construct

<400> SEQUENCE: 8

Met Val Arg Ser Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
                20                  25                  30

Asp Thr Leu Met Ile Ser Arg Thr Pro Glu Val Thr Cys Val Val Val
            35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys His His His His His
225                 230                 235

<210> SEQ ID NO 9
<211> LENGTH: 262
<212> TYPE: PRT
<213> ORGANISM: Artificial Sequence
<220> FEATURE:
<223> OTHER INFORMATION: Synthetic Construct

<400> SEQUENCE: 9

Met Tyr Arg Met Gln Leu Leu Ser Cys Ile Ala Leu Ser Leu Ala Leu
1               5                   10                  15

Val Thr Asn Ser Met Val Arg Ser Asp Lys Thr His Thr Cys Pro Pro
                20                  25                  30

Cys Pro Pro Cys Lys Cys Pro Ala Pro Glu Leu Leu Gly Gly Pro Ser
            35                  40                  45

```
Val Phe Leu Phe Pro Pro Lys Pro Lys Asp Thr Leu Met Ile Ser Arg
    50                  55                  60

Thr Pro Glu Val Thr Cys Val Val Val Asp Val Ser His Glu Asp Pro
65                  70                  75                  80

Glu Val Lys Phe Asn Trp Tyr Val Asp Gly Val Glu Val His Asn Ala
                85                  90                  95

Lys Thr Lys Pro Arg Glu Glu Gln Tyr Asn Ser Thr Tyr Arg Val Val
            100                 105                 110

Ser Val Leu Thr Val Leu His Gln Asp Trp Leu Asn Gly Lys Glu Tyr
        115                 120                 125

Lys Cys Lys Val Ser Asn Lys Ala Leu Pro Ala Pro Ile Glu Lys Thr
    130                 135                 140

Ile Ser Lys Ala Lys Gly Gln Pro Arg Glu Pro Gln Val Tyr Thr Leu
145                 150                 155                 160

Pro Pro Ser Arg Glu Glu Met Thr Lys Asn Gln Val Ser Leu Thr Cys
                165                 170                 175

Leu Val Lys Gly Phe Tyr Pro Ser Asp Ile Ala Val Glu Trp Glu Ser
            180                 185                 190

Asn Gly Gln Pro Glu Asn Asn Tyr Lys Thr Thr Pro Pro Val Leu Asp
        195                 200                 205

Ser Asp Gly Ser Phe Phe Leu Tyr Ser Lys Leu Thr Val Asp Lys Ser
    210                 215                 220

Arg Trp Gln Gln Gly Asn Val Phe Ser Cys Ser Val Met His Glu Ala
225                 230                 235                 240

Leu His Asn His Tyr Thr Gln Lys Ser Leu Ser Leu Ser Pro Gly Lys
                245                 250                 255

His His His His His His
            260

<210> SEQ ID NO 10
<211> LENGTH: 242
<212> TYPE: PRT
<213> ORGANISM: Artificial Sequence
<220> FEATURE:
<223> OTHER INFORMATION: Synthetic Construct

<400> SEQUENCE: 10

Met Val Arg Ser Asp Lys Thr His Thr Cys Pro Pro Cys Pro Pro Cys
1               5                   10                  15

Lys Cys Pro Ala Pro Glu Leu Leu Gly Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Ser His Glu Asp Pro Glu Val Lys Phe
    50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Ala
        115                 120                 125

Lys Gly Gln Pro Arg Glu Pro Gln Val Tyr Thr Leu Pro Pro Ser Arg
    130                 135                 140
```

```
Glu Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Asp Ser Asp Gly Ser
            180                 185                 190

Phe Phe Leu Tyr Ser Lys Leu Thr Val Asp Lys Ser Arg Trp Gln Gln
        195                 200                 205

Gly Asn Val Phe Ser Cys Ser Val Met His Glu Ala Leu His Asn His
    210                 215                 220

Tyr Thr Gln Lys Ser Leu Ser Leu Ser Pro Gly Lys His His His His
225                 230                 235                 240

His His

<210> SEQ ID NO 11
<211> LENGTH: 236
<212> TYPE: PRT
<213> ORGANISM: Artificial Sequence
<220> FEATURE:
<223> OTHER INFORMATION: Synthetic Construct

<400> SEQUENCE: 11

Met Val Arg Ser Asp Lys Thr His Thr Cys Pro Pro Cys Pro Pro Cys
1               5                   10                  15

Lys Cys Pro Ala Pro Glu Leu Leu Gly Gly Pro Ser Val Phe Leu Phe
                20                  25                  30

Pro Pro Lys Pro Lys Asp Thr Leu Met Ile Ser Arg Thr Pro Glu Val
            35                  40                  45

Thr Cys Val Val Val Asp Val Ser His Glu Asp Pro Glu Val Lys Phe
        50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Ala
        115                 120                 125

Lys Gly Gln Pro Arg Glu Pro Gln Val Tyr Thr Leu Pro Pro Ser Arg
130                 135                 140

Glu Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Asp Ser Asp Gly Ser
            180                 185                 190

Phe Phe Leu Tyr Ser Lys Leu Thr Val Asp Lys Ser Arg Trp Gln Gln
        195                 200                 205

Gly Asn Val Phe Ser Cys Ser Val Met His Glu Ala Leu His Asn His
    210                 215                 220

Tyr Thr Gln Lys Ser Leu Ser Leu Ser Pro Gly Lys
225                 230                 235

<210> SEQ ID NO 12
<211> LENGTH: 258
```

```
<212> TYPE: PRT
<213> ORGANISM: Artificial Sequence
<220> FEATURE:
<223> OTHER INFORMATION: Synthetic Construct

<400> SEQUENCE: 12

Met Tyr Arg Met Gln Leu Leu Ser Cys Ile Ala Leu Ser Leu Ala Leu
1               5                   10                  15

Val Thr Asn Ser Pro Arg Gly Pro Thr Ile Lys Pro Cys Pro Pro Cys
            20                  25                  30

Lys Cys Pro Ala Pro Asn Leu Leu Gly Gly Pro Ser Val Phe Ile Phe
        35                  40                  45

Pro Pro Lys Ile Lys Asp Val Leu Met Ile Ser Leu Ser Pro Ile Val
50                  55                  60

Thr Cys Val Val Val Asp Val Ser Glu Asp Asp Pro Asp Val Gln Ile
65                  70                  75                  80

Ser Trp Phe Val Asn Asn Val Glu Val His Thr Ala Gln Thr Gln Thr
                85                  90                  95

His Arg Glu Asp Tyr Ala Ser Thr Leu Arg Val Val Ser Ala Leu Pro
            100                 105                 110

Ile Gln His Gln Asp Trp Met Ser Gly Lys Glu Phe Lys Cys Lys Val
        115                 120                 125

Asn Asn Lys Asp Leu Pro Ala Pro Ile Glu Arg Thr Ile Ser Lys Pro
130                 135                 140

Lys Gly Ser Val Arg Ala Pro Gln Val Tyr Val Leu Pro Pro Pro Glu
145                 150                 155                 160

Glu Glu Met Thr Lys Lys Gln Val Thr Leu Thr Cys Met Val Thr Asp
                165                 170                 175

Phe Met Pro Glu Asp Ile Tyr Val Glu Trp Thr Asn Asn Gly Lys Thr
            180                 185                 190

Glu Leu Asn Tyr Lys Asn Thr Glu Pro Val Leu Asp Ser Asp Gly Ser
        195                 200                 205

Tyr Phe Met Tyr Ser Lys Leu Arg Val Glu Lys Lys Asn Trp Val Glu
210                 215                 220

Arg Asn Ser Tyr Ser Cys Ser Val Val His Glu Gly Leu His Asn His
225                 230                 235                 240

His Thr Thr Lys Ser Phe Ser Arg Thr Pro Gly Lys His His His His
                245                 250                 255

His His

<210> SEQ ID NO 13
<211> LENGTH: 238
<212> TYPE: PRT
<213> ORGANISM: Artificial Sequence
<220> FEATURE:
<223> OTHER INFORMATION: Synthetic Construct

<400> SEQUENCE: 13

Pro Arg Gly Pro Thr Ile Lys Pro Cys Pro Pro Cys Lys Cys Pro Ala
1               5                   10                  15

Pro Asn Leu Leu Gly Gly Pro Ser Val Phe Ile Phe Pro Pro Lys Ile
            20                  25                  30

Lys Asp Val Leu Met Ile Ser Leu Ser Pro Ile Val Thr Cys Val Val
        35                  40                  45

Val Asp Val Ser Glu Asp Asp Pro Asp Val Gln Ile Ser Trp Phe Val
50                  55                  60
```

```
Asn Asn Val Glu Val His Thr Ala Gln Thr Gln Thr His Arg Glu Asp
 65                  70                  75                  80

Tyr Ala Ser Thr Leu Arg Val Val Ser Ala Leu Pro Ile Gln His Gln
                 85                  90                  95

Asp Trp Met Ser Gly Lys Glu Phe Lys Cys Lys Val Asn Asn Lys Asp
            100                 105                 110

Leu Pro Ala Pro Ile Glu Arg Thr Ile Ser Lys Pro Lys Gly Ser Val
        115                 120                 125

Arg Ala Pro Gln Val Tyr Val Leu Pro Pro Glu Glu Met Thr
    130                 135                 140

Lys Lys Gln Val Thr Leu Thr Cys Met Val Thr Asp Phe Met Pro Glu
145                 150                 155                 160

Asp Ile Tyr Val Glu Trp Thr Asn Asn Gly Lys Thr Glu Leu Asn Tyr
                165                 170                 175

Lys Asn Thr Glu Pro Val Leu Asp Ser Asp Gly Ser Tyr Phe Met Tyr
            180                 185                 190

Ser Lys Leu Arg Val Glu Lys Lys Asn Trp Val Glu Arg Asn Ser Tyr
        195                 200                 205

Ser Cys Ser Val Val His Glu Gly Leu His Asn His Thr Thr Lys
    210                 215                 220

Ser Phe Ser Arg Thr Pro Gly Lys His His His His His His
225                 230                 235

<210> SEQ ID NO 14
<211> LENGTH: 257
<212> TYPE: PRT
<213> ORGANISM: Artificial Sequence
<220> FEATURE:
<223> OTHER INFORMATION: Synthetic Construct

<400> SEQUENCE: 14

Met Tyr Arg Met Gln Leu Leu Ser Cys Ile Ala Leu Ser Leu Ala Leu
1               5                   10                  15

Val Thr Asn Ser Met Val Arg Ser Asp Lys Thr His Thr Cys Pro Pro
                20                  25                  30

Cys Pro Ala Pro Glu Leu Leu Gly Gly Pro Ser Val Phe Leu Phe Pro
            35                  40                  45

Pro Lys Pro Lys Asp Thr Leu Met Ile Ser Arg Thr Pro Glu Val Thr
        50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Ala Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ala Pro Ile Glu Lys Thr Ile Ser Lys Ala Lys
130                 135                 140

Gly Gln Pro Arg Glu Pro Gln Val Tyr Thr Leu Pro Pro Ser Arg Glu
145                 150                 155                 160

Glu Met Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190
```

```
Asn Asn Tyr Lys Thr Thr Pro Pro Val Leu Asp Ser Asp Gly Ser Phe
            195                 200                 205

Phe Leu Tyr Ser Lys Leu Thr Val Asp Lys Ser Arg Trp Gln Gln Gly
            210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys His His His His His
            245                 250                 255

His
```

```
<210> SEQ ID NO 15
<211> LENGTH: 237
<212> TYPE: PRT
<213> ORGANISM: Artificial Sequence
<220> FEATURE:
<223> OTHER INFORMATION: Synthetic Construct

<400> SEQUENCE: 15

Met Val Arg Ser Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Ala Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys His His His His His
225                 230                 235
```

```
<210> SEQ ID NO 16
<211> LENGTH: 252
<212> TYPE: PRT
<213> ORGANISM: Artificial Sequence
<220> FEATURE:
<223> OTHER INFORMATION: Synthetic Construct

<400> SEQUENCE: 16
```

Met Lys Trp Val Thr Phe Ile Ser Leu Leu Phe Leu Phe Ser Ser Ala
1               5                   10                  15

Tyr Ser Ile Ser Ala Met Val Arg Ser Asp Lys Thr His Thr Cys Pro
                20                  25                  30

Pro Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250

<210> SEQ ID NO 17
<211> LENGTH: 266
<212> TYPE: PRT
<213> ORGANISM: Artificial Sequence
<220> FEATURE:
<223> OTHER INFORMATION: Synthetic Construct

<400> SEQUENCE: 17

Met Lys Trp Val Thr Phe Ile Ser Leu Leu Phe Leu Phe Ser Ser Ala
1               5                   10                  15

Tyr Ser Ile Ser Ala Met Val Arg Ser Asp Lys Thr His Thr Cys Pro
                20                  25                  30

Pro Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
        50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
            115                 120                 125

Ser Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Gly Gly Gly Gly Ser
                245                 250                 255

Glu Gln Lys Leu Ile Ser Glu Glu Asp Leu
            260                 265

<210> SEQ ID NO 18
<211> LENGTH: 248
<212> TYPE: PRT
<213> ORGANISM: Artificial Sequence
<220> FEATURE:
<223> OTHER INFORMATION: Synthetic Construct

<400> SEQUENCE: 18

Ile Ser Ala Met Val Arg Ser Asp Lys Thr His Thr Cys Pro Pro Cys
1               5                   10                  15

Pro Ala Pro Glu Leu Leu Gly Gly Pro Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser His Glu Asp Pro Glu Val Lys Phe Asn Trp
    50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Glu Glu
    130                 135                 140

Met Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

-continued

Val Phe Ser Cys Ser Val Met His Glu Ala Leu His Asn His Tyr Thr
    210                 215                 220

Gln Lys Ser Leu Ser Leu Ser Pro Gly Gly Gly Gly Ser Glu Gln
225                 230                 235                 240

Lys Leu Ile Ser Glu Glu Asp Leu
                245

<210> SEQ ID NO 19
<211> LENGTH: 252
<212> TYPE: PRT
<213> ORGANISM: Artificial Sequence
<220> FEATURE:
<223> OTHER INFORMATION: Synthetic Construct

<400> SEQUENCE: 19

Met Lys Trp Val Thr Phe Ile Ser Leu Leu Phe Leu Phe Ser Ser Ala
1               5                   10                  15

Tyr Ser Ile Ser Ala Met Val Arg Ser Asp Lys Thr His Thr Cys Pro
                20                  25                  30

Pro Cys Pro Ala Pro Glu Leu Leu Gly Gly Pro Ser Val Phe Leu Phe
            35                  40                  45

Pro Pro Lys Pro Ser Asp Thr Leu Met Ile Ser Arg Thr Pro Glu Val
        50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250

<210> SEQ ID NO 20
<211> LENGTH: 234
<212> TYPE: PRT
<213> ORGANISM: Artificial Sequence
<220> FEATURE:
<223> OTHER INFORMATION: Synthetic Construct

<400> SEQUENCE: 20

Ile Ser Ala Met Val Arg Ser Asp Lys Thr His Thr Cys Pro Pro Cys
1               5                   10                  15

Pro Ala Pro Glu Leu Leu Gly Gly Pro Ser Val Phe Leu Phe Pro Pro
            20                  25                  30

Lys Pro Ser Asp Thr Leu Met Ile Ser Arg Thr Pro Glu Val Thr Cys
        35                  40                  45

Val Val Val Asp Val Ser His Glu Asp Pro Glu Val Lys Phe Asn Trp
 50                  55                  60

Tyr Val Asp Gly Val Glu Val His Asn Ala Lys Thr Lys Pro Arg Glu
65                   70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Glu Glu
130                 135                 140

Met Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
210                 215                 220

Gln Lys Ser Leu Ser Leu Ser Pro Gly Lys
225                 230

<210> SEQ ID NO 21
<211> LENGTH: 266
<212> TYPE: PRT
<213> ORGANISM: Artificial Sequence
<220> FEATURE:
<223> OTHER INFORMATION: Synthetic Construct

<400> SEQUENCE: 21

Met Lys Trp Val Thr Phe Ile Ser Leu Leu Phe Leu Phe Ser Ser Ala
1               5                   10                  15

Tyr Ser Ile Ser Ala Met Val Arg Ser Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Ser Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
130                 135                 140

```
Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Gly Gly Gly Gly Ser
                245                 250                 255

Glu Gln Lys Leu Ile Ser Glu Glu Asp Leu
            260                 265

<210> SEQ ID NO 22
<211> LENGTH: 248
<212> TYPE: PRT
<213> ORGANISM: Artificial Sequence
<220> FEATURE:
<223> OTHER INFORMATION: Synthetic Construct

<400> SEQUENCE: 22

Ile Ser Ala Met Val Arg Ser Asp Lys Thr His Thr Cys Pro Pro Cys
1               5                   10                  15

Pro Ala Pro Glu Leu Leu Gly Gly Pro Ser Val Phe Leu Phe Pro Pro
                20                  25                  30

Lys Pro Ser Asp Thr Leu Met Ile Ser Arg Thr Pro Glu Val Thr Cys
            35                  40                  45

Val Val Val Asp Val Ser His Glu Asp Pro Glu Val Lys Phe Asn Trp
        50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Glu Glu
    130                 135                 140

Met Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
    210                 215                 220

Gln Lys Ser Leu Ser Leu Ser Pro Gly Gly Gly Gly Gly Ser Glu Gln
225                 230                 235                 240
```

```
Lys Leu Ile Ser Glu Glu Asp Leu
                245

<210> SEQ ID NO 23
<211> LENGTH: 266
<212> TYPE: PRT
<213> ORGANISM: Artificial Sequence
<220> FEATURE:
<223> OTHER INFORMATION: Synthetic Construct

<400> SEQUENCE: 23

Met Lys Trp Val Thr Phe Ile Ser Leu Leu Phe Leu Phe Ser Ser Ala
1               5                   10                  15

Tyr Ser Ile Ser Ala Met Val Arg Ser Asp Lys Thr His Thr Cys Pro
                20                  25                  30

Pro Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
        50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Ala Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Gly Gly Gly Gly Ser
                245                 250                 255

Glu Gln Lys Leu Ile Ser Glu Glu Asp Leu
            260                 265

<210> SEQ ID NO 24
<211> LENGTH: 248
<212> TYPE: PRT
<213> ORGANISM: Artificial Sequence
<220> FEATURE:
<223> OTHER INFORMATION: Synthetic Construct

<400> SEQUENCE: 24

Ile Ser Ala Met Val Arg Ser Asp Lys Thr His Thr Cys Pro Cys Pro
1               5                   10                  15

Pro Ala Pro Glu Leu Leu Gly Gly Pro Ser Val Phe Leu Phe Pro Pro
```

```
                20                  25                  30
Lys Pro Lys Asp Thr Leu Met Ile Ser Arg Thr Pro Glu Val Thr Cys
            35                  40                  45

Val Val Val Asp Val Ser His Glu Asp Pro Glu Val Lys Phe Asn Trp
 50                  55                  60

Tyr Val Asp Gly Val Glu Val His Asn Ala Lys Thr Lys Pro Arg Glu
 65                  70                  75                  80

Glu Gln Tyr Ala Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Glu Glu
    130                 135                 140

Met Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
    210                 215                 220

Gln Lys Ser Leu Ser Leu Ser Pro Gly Gly Gly Gly Ser Glu Gln
225                 230                 235                 240

Lys Leu Ile Ser Glu Glu Asp Leu
                245

<210> SEQ ID NO 25
<211> LENGTH: 266
<212> TYPE: PRT
<213> ORGANISM: Artificial Sequence
<220> FEATURE:
<223> OTHER INFORMATION: Synthetic Construct

<400> SEQUENCE: 25

Met Lys Trp Val Thr Phe Ile Ser Leu Leu Phe Leu Phe Ser Ser Ala
 1               5                  10                  15

Tyr Ser Ile Ser Ala Met Val Arg Ser Asp Lys Thr His Thr Cys Pro
                20                  25                  30

Pro Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
        50                  55                  60

Thr Cys Val Val Val Asp Val Ser His Glu Asp Pro Glu Val Lys Phe
 65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu Ala Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
```

```
             130                 135                 140
Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
                195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn Ala
225                 230                 235                 240

Tyr Thr Gln Lys Ser Leu Ser Leu Ser Pro Gly Gly Gly Gly Gly Ser
                245                 250                 255

Glu Gln Lys Leu Ile Ser Glu Glu Asp Leu
                260                 265

<210> SEQ ID NO 26
<211> LENGTH: 248
<212> TYPE: PRT
<213> ORGANISM: Artificial Sequence
<220> FEATURE:
<223> OTHER INFORMATION: Synthetic Construct

<400> SEQUENCE: 26

Ile Ser Ala Met Val Arg Ser Asp Lys Thr His Thr Cys Pro Pro Cys
1               5                   10                  15

Pro Ala Pro Glu Leu Leu Gly Gly Pro Ser Val Phe Leu Phe Pro Pro
                20                  25                  30

Lys Pro Lys Asp Thr Leu Met Ile Ser Arg Thr Pro Glu Val Thr Cys
            35                  40                  45

Val Val Val Asp Val Ser His Glu Asp Pro Glu Val Lys Phe Asn Trp
    50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

Ala Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Glu Glu
    130                 135                 140

Met Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn Ala Tyr Thr
    210                 215                 220

Gln Lys Ser Leu Ser Leu Ser Pro Gly Gly Gly Gly Gly Ser Glu Gln
```

```
               225                 230                 235                 240

Lys Leu Ile Ser Glu Glu Asp Leu
                245
```

<210> SEQ ID NO 27
<211> LENGTH: 266
<212> TYPE: PRT
<213> ORGANISM: Artificial Sequence
<220> FEATURE:
<223> OTHER INFORMATION: Synthetic Construct

<400> SEQUENCE: 27

```
Met Lys Trp Val Thr Phe Ile Ser Leu Leu Phe Leu Phe Ser Ser Ala
1               5                   10                  15

Tyr Ser Ile Ser Ala Met Val Arg Ser Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Gly Gly Gly Gly Ser
                245                 250                 255

Glu Gln Phe Leu Ile Ser Glu Glu Asp Leu
            260                 265
```

<210> SEQ ID NO 28
<211> LENGTH: 248
<212> TYPE: PRT
<213> ORGANISM: Artificial Sequence
<220> FEATURE:
<223> OTHER INFORMATION: Synthetic Construct

<400> SEQUENCE: 28

```
Ile Ser Ala Met Val Arg Ser Asp Lys Thr His Thr Cys Pro Pro Cys
1               5                   10                  15
```

Pro Ala Pro Glu Leu Leu Gly Gly Pro Ser Val Phe Leu Phe Pro Pro
             20                  25                  30

Lys Pro Lys Asp Thr Leu Met Ile Ser Arg Thr Pro Glu Val Thr Cys
         35                  40                  45

Val Val Val Asp Val Ser His Glu Asp Pro Glu Val Lys Phe Asn Trp
 50                  55                  60

Tyr Val Asp Gly Val Glu Val His Asn Ala Lys Thr Lys Pro Arg Glu
 65                  70                  75                  80

Glu Gln Tyr Asn Ser Thr Tyr Arg Val Val Ser Val Leu Thr Val Leu
             85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Glu Glu
    130                 135                 140

Met Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
210                 215                 220

Gln Lys Ser Leu Ser Leu Ser Pro Gly Gly Gly Gly Ser Glu Gln
225                 230                 235                 240

Phe Leu Ile Ser Glu Glu Asp Leu
                245

<210> SEQ ID NO 29
<211> LENGTH: 266
<212> TYPE: PRT
<213> ORGANISM: Artificial Sequence
<220> FEATURE:
<223> OTHER INFORMATION: Synthetic Construct

<400> SEQUENCE: 29

Met Lys Trp Val Thr Phe Ile Ser Leu Leu Phe Leu Phe Ser Ser Ala
 1                   5                  10                  15

Tyr Ser Ile Ser Ala Met Val Arg Ser Asp Lys Thr His Thr Cys Pro
             20                  25                  30

Pro Cys Pro Ala Pro Glu Leu Leu Gly Gly Pro Ser Val Phe Leu Phe
         35                  40                  45

Pro Pro Lys Pro Lys Asp Thr Leu Met Ile Ser Arg Thr Pro Glu Val
 50                  55                  60

Thr Cys Val Val Val Asp Val Ser His Glu Asp Pro Glu Val Lys Phe
 65                  70                  75                  80

Asn Trp Tyr Val Asp Gly Val Glu Val His Asn Ala Lys Thr Lys Pro
             85                  90                  95

Arg Glu Glu Gln Tyr Ala Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

```
Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Gly Gly Gly Ser
                245                 250                 255

Glu Gln Phe Leu Ile Ser Glu Glu Asp Leu
            260                 265
```

<210> SEQ ID NO 30
<211> LENGTH: 248
<212> TYPE: PRT
<213> ORGANISM: Artificial Sequence
<220> FEATURE:
<223> OTHER INFORMATION: Synthetic Construct

<400> SEQUENCE: 30

```
Ile Ser Ala Met Val Arg Ser Asp Lys Thr His Thr Cys Pro Pro Cys
1               5                   10                  15

Pro Ala Pro Glu Leu Leu Gly Gly Pro Ser Val Phe Leu Phe Pro Pro
                20                  25                  30

Lys Pro Lys Asp Thr Leu Met Ile Ser Arg Thr Pro Glu Val Thr Cys
            35                  40                  45

Val Val Val Asp Val Ser His Glu Asp Pro Glu Val Lys Phe Asn Trp
        50                  55                  60

Tyr Val Asp Gly Val Glu Val His Asn Ala Lys Thr Lys Pro Arg Glu
65                  70                  75                  80

Glu Gln Tyr Ala Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Glu Glu
    130                 135                 140

Met Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
    210                 215                 220
```

Gln Lys Ser Leu Ser Leu Ser Pro Gly Gly Gly Gly Ser Glu Gln
225                 230                 235                 240

Phe Leu Ile Ser Glu Glu Asp Leu
                245

<210> SEQ ID NO 31
<211> LENGTH: 259
<212> TYPE: PRT
<213> ORGANISM: Artificial Sequence
<220> FEATURE:
<223> OTHER INFORMATION: Synthetic Construct

<400> SEQUENCE: 31

Met Lys Trp Val Thr Phe Ile Ser Leu Leu Phe Leu Phe Ser Ser Ala
1               5                   10                  15

Tyr Ser Asp Lys Thr His Thr Cys Pro Pro Cys Pro Ala Pro Glu Leu
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Lys Phe Asn Trp Tyr Val Asp Gly Val
65                  70                  75                  80

Glu Val His Asn Ala Lys Thr Lys Pro Arg Glu Glu Gln Tyr Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
        115                 120                 125

Pro Ile Glu Lys Thr Ile Ser Lys Ala Lys Gly Gln Pro Arg Glu Pro
    130                 135                 140

Gln Val Tyr Thr Leu Pro Pro Ser Arg Asp Glu Leu Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Pro Gly Gly Gly Gly Ser Glu Gln Phe Leu Ile Ser Glu
                245                 250                 255

Glu Asp Leu

<210> SEQ ID NO 32
<211> LENGTH: 245
<212> TYPE: PRT
<213> ORGANISM: Artificial Sequence
<220> FEATURE:
<223> OTHER INFORMATION: Synthetic Construct

<400> SEQUENCE: 32

Met Lys Trp Val Thr Phe Ile Ser Leu Leu Phe Leu Phe Ser Ser Ala
1               5                   10                  15

```
Tyr Ser Asp Lys Thr His Thr Cys Pro Pro Cys Pro Ala Pro Glu Leu
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
50                  55                  60

Ser His Glu Asp Pro Glu Val Lys Phe Asn Trp Tyr Val Asp Gly Val
65                  70                  75                  80

Glu Val His Asn Ala Lys Thr Lys Pro Arg Glu Glu Gln Tyr Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
        115                 120                 125

Pro Ile Glu Lys Thr Ile Ser Lys Ala Lys Gly Gln Pro Arg Glu Pro
    130                 135                 140

Gln Val Tyr Thr Leu Pro Pro Ser Arg Asp Glu Leu Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Pro Gly Lys
                245

<210> SEQ ID NO 33
<211> LENGTH: 231
<212> TYPE: PRT
<213> ORGANISM: Artificial Sequence
<220> FEATURE:
<223> OTHER INFORMATION: Synthetic Construct

<400> SEQUENCE: 33

Met Val Arg Ser Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Tyr Ile Thr Arg Glu Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125
```

```
Glu Pro Gln Val Tyr Thr Leu Pro Pro Ser Arg Glu Met Thr Lys
130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
210                 215                 220

Leu Ser Leu Ser Pro Gly Lys
225                 230

<210> SEQ ID NO 34
<211> LENGTH: 250
<212> TYPE: PRT
<213> ORGANISM: Artificial Sequence
<220> FEATURE:
<223> OTHER INFORMATION: Synthetic Construct

<400> SEQUENCE: 34

Met Lys Trp Val Thr Phe Ile Ser Leu Leu Phe Leu Phe Ser Ser Ala
1               5                   10                  15

Tyr Ser Glu Pro Lys Ser Ser Asp Lys Thr His Thr Cys Pro Pro Cys
                20                  25                  30

Pro Ala Pro Glu Leu Leu Gly Gly Pro Ser Val Phe Leu Phe Pro Pro
            35                  40                  45

Lys Pro Lys Asp Thr Leu Met Ile Ser Arg Thr Pro Glu Val Thr Cys
50                  55                  60

Val Val Val Asp Val Ser His Glu Asp Pro Glu Val Lys Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
        115                 120                 125

Lys Ala Leu Pro Ala Pro Ile Glu Lys Thr Ile Ser Lys Ala Lys Gly
130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250
```

```
<210> SEQ ID NO 35
<211> LENGTH: 245
<212> TYPE: PRT
<213> ORGANISM: Artificial Sequence
<220> FEATURE:
<223> OTHER INFORMATION: Synthetic Construct

<400> SEQUENCE: 35

Met Gly Trp Ser Cys Ile Ile Leu Phe Leu Val Ala Thr Ala Thr Gly
1               5                   10                  15

Val His Ser Lys Thr His Thr Cys Pro Pro Cys Pro Ala Pro Glu Leu
                20                  25                  30

Leu Gly Gly Pro Ser Val Phe Leu Phe Pro Pro Lys Pro Lys Asp Thr
            35                  40                  45

Leu Met Ile Ser Arg Thr Pro Glu Val Thr Cys Val Val Val Asp Val
        50                  55                  60

Ser His Glu Asp Pro Glu Val Lys Phe Asn Trp Tyr Val Asp Gly Val
65                  70                  75                  80

Glu Val His Asn Ala Lys Thr Lys Pro Arg Glu Glu Gln Tyr Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
        115                 120                 125

Pro Ile Glu Lys Thr Ile Ser Lys Ala Lys Gly Gln Pro Arg Glu Pro
130                 135                 140

Gln Val Tyr Thr Leu Pro Pro Ser Arg Asp Glu Leu Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
        210                 215                 220

Val Met His Glu Ala Leu His Asn His Tyr Thr Gln Lys Ser Leu Ser
225                 230                 235                 240

Leu Ser Pro Gly Lys
                245

<210> SEQ ID NO 36
<211> LENGTH: 226
<212> TYPE: PRT
<213> ORGANISM: Artificial Sequence
<220> FEATURE:
<223> OTHER INFORMATION: Synthetic Construct

<400> SEQUENCE: 36

Lys Thr His Thr Cys Pro Pro Cys Pro Ala Pro Glu Leu Leu Gly Gly
1               5                   10                  15

Pro Ser Val Phe Leu Phe Pro Pro Lys Pro Lys Asp Thr Leu Tyr Ile
                20                  25                  30

Thr Arg Glu Pro Glu Val Thr Cys Val Val Val Asp Val Ser His Glu
            35                  40                  45

Asp Pro Glu Val Lys Phe Asn Trp Tyr Val Asp Gly Val Glu Val His
        50                  55                  60
```

```
Asn Ala Lys Thr Lys Pro Arg Glu Glu Gln Tyr Asn Ser Thr Tyr Arg
 65                  70                  75                  80

Val Val Ser Val Leu Thr Val Leu His Gln Asp Trp Leu Asn Gly Lys
                 85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Asp Glu Leu Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
225

<210> SEQ ID NO 37
<211> LENGTH: 226
<212> TYPE: PRT
<213> ORGANISM: Artificial Sequence
<220> FEATURE:
<223> OTHER INFORMATION: Synthetic Construct

<400> SEQUENCE: 37

Lys Thr His Thr Cys Pro Pro Cys Pro Ala Pro Glu Leu Leu Gly Gly
  1               5                  10                  15

Pro Ser Val Phe Leu Phe Pro Pro Lys Pro Lys Asp Thr Leu Met Ile
                 20                  25                  30

Ser Arg Thr Pro Glu Val Thr Cys Val Val Val Asp Val Ser His Glu
            35                  40                  45

Asp Pro Glu Val Lys Phe Asn Trp Tyr Val Asp Gly Val Glu Val His
        50                  55                  60

Asn Ala Lys Thr Lys Pro Arg Glu Glu Gln Tyr Asn Ser Thr Tyr Arg
 65                  70                  75                  80

Val Val Ser Val Leu Thr Val Leu His Gln Asp Trp Leu Asn Gly Lys
                 85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Asp Glu Leu Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190
```

Lys Ser Arg Trp Gln Gln Gly Asn Val Phe Ser Cys Ser Val Leu His
        195                 200                 205

Glu Ala Leu His Ser His Tyr Thr Gln Lys Ser Leu Ser Leu Ser Pro
    210                 215                 220

Gly Lys
225

<210> SEQ ID NO 38
<211> LENGTH: 259
<212> TYPE: PRT
<213> ORGANISM: Artificial Sequence
<220> FEATURE:
<223> OTHER INFORMATION: Synthetic Construct

<400> SEQUENCE: 38

Met Lys Trp Val Thr Phe Ile Ser Leu Leu Phe Leu Phe Ser Ser Ala
1               5                   10                  15

Tyr Ser Asp Lys Thr His Thr Cys Pro Pro Cys Pro Ala Pro Glu Leu
            20                  25                  30

Leu Gly Gly Pro Ser Val Phe Leu Phe Pro Pro Lys Pro Lys Asp Thr
        35                  40                  45

Leu Tyr Ile Thr Arg Glu Pro Glu Val Thr Cys Val Val Val Asp Val
    50                  55                  60

Ser His Glu Asp Pro Glu Val Lys Phe Asn Trp Tyr Val Asp Gly Val
65                  70                  75                  80

Glu Val His Asn Ala Lys Thr Lys Pro Arg Glu Glu Gln Tyr Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
        115                 120                 125

Pro Ile Glu Lys Thr Ile Ser Lys Ala Lys Gly Gln Pro Arg Glu Pro
    130                 135                 140

Gln Val Tyr Thr Leu Pro Pro Ser Arg Asp Glu Leu Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Pro Gly Gly Gly Gly Ser Glu Gln Lys Leu Ile Ser Glu
                245                 250                 255

Glu Asp Leu

<210> SEQ ID NO 39
<211> LENGTH: 226
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature

```
<222> LOCATION: (32)..(32)
<223> OTHER INFORMATION: Xaa is Met or Tyr
<220> FEATURE:
<221> NAME/KEY: misc_feature
<222> LOCATION: (34)..(34)
<223> OTHER INFORMATION: Xaa is Ser or Thr
<220> FEATURE:
<221> NAME/KEY: misc_feature
<222> LOCATION: (36)..(36)
<223> OTHER INFORMATION: Xaa is Thr or Glu
<220> FEATURE:
<221> NAME/KEY: misc_feature
<222> LOCATION: (136)..(136)
<223> OTHER INFORMATION: Xaa is Asp or Glu
<220> FEATURE:
<221> NAME/KEY: misc_feature
<222> LOCATION: (138)..(138)
<223> OTHER INFORMATION: Xaa is Leu or Met
<220> FEATURE:
<221> NAME/KEY: misc_feature
<222> LOCATION: (208)..(208)
<223> OTHER INFORMATION: Xaa is Met or Leu
<220> FEATURE:
<221> NAME/KEY: misc_feature
<222> LOCATION: (214)..(214)
<223> OTHER INFORMATION: Xaa is Asn or Ser
<220> FEATURE:
<221> NAME/KEY: misc_feature
<222> LOCATION: (265)..(265)
<223> OTHER INFORMATION: Xaa is Asn or Ser

<400> SEQUENCE: 39

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Xaa
            20                  25                  30

Ile Xaa Arg Xaa Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Xaa Glu Xaa Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Xaa
        195                 200                 205

His Glu Ala Leu His Xaa His Tyr Thr Gln Lys Ser Leu Ser Leu Ser
    210                 215                 220

Pro Gly
225
```

```
<210> SEQ ID NO 40
<211> LENGTH: 226
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (136)..(136)
<223> OTHER INFORMATION: Xaa is Asp or Glu
<220> FEATURE:
<221> NAME/KEY: misc_feature
<222> LOCATION: (138)..(138)
<223> OTHER INFORMATION: Xaa is Leu or Met

<400> SEQUENCE: 40

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Xaa Glu Xaa Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 41
<211> LENGTH: 226
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (136)..(136)
<223> OTHER INFORMATION: Xaa is Asp or Glu
<220> FEATURE:
<221> NAME/KEY: misc_feature
<222> LOCATION: (138)..(138)
<223> OTHER INFORMATION: Xaa is Leu or Met

<400> SEQUENCE: 41
```

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Xaa Glu Xaa Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly
225

<210> SEQ ID NO 42
<211> LENGTH: 226
<212> TYPE: PRT
<213> ORGANISM: Artificial Sequence
<220> FEATURE:
<223> OTHER INFORMATION: Synthetic Construct

<400> SEQUENCE: 42

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125
```

```
Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly
225

<210> SEQ ID NO 43
<211> LENGTH: 226
<212> TYPE: PRT
<213> ORGANISM: Artificial Sequence
<220> FEATURE:
<223> OTHER INFORMATION: Synthetic Construct

<400> SEQUENCE: 43

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
                20                  25                  30

Ile Thr Arg Glu Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly
225

<210> SEQ ID NO 44
```

```
<211> LENGTH: 226
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (136)..(136)
<223> OTHER INFORMATION: Xaa is Asp or Glu
<220> FEATURE:
<221> NAME/KEY: misc_feature
<222> LOCATION: (138)..(138)
<223> OTHER INFORMATION: Xaa is Leu or Met

<400> SEQUENCE: 44

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Xaa Glu Xaa Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Leu
        195                 200                 205

His Glu Ala Leu His Ser His Tyr Thr Gln Lys Ser Leu Ser Leu Ser
    210                 215                 220

Pro Gly
225

<210> SEQ ID NO 45
<211> LENGTH: 226
<212> TYPE: PRT
<213> ORGANISM: Artificial Sequence
<220> FEATURE:
<223> OTHER INFORMATION: Synthetic Construct

<400> SEQUENCE: 45

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45
```

```
Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Leu
        195                 200                 205

His Glu Ala Leu His Ser His Tyr Thr Gln Lys Ser Leu Ser Leu Ser
    210                 215                 220

Pro Gly
225

<210> SEQ ID NO 46
<211> LENGTH: 226
<212> TYPE: PRT
<213> ORGANISM: Artificial Sequence
<220> FEATURE:
<223> OTHER INFORMATION: Synthetic Construct

<400> SEQUENCE: 46

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
             20                  25                  30

Ile Ser Arg Thr Pro Glu Val Thr Cys Val Val Val Asp Val Ser His
         35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

-continued

```
Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Leu
        195                 200                 205

His Glu Ala Leu His Ser His Tyr Thr Gln Lys Ser Leu Ser Leu Ser
    210                 215                 220

Pro Gly
225

<210> SEQ ID NO 47
<211> LENGTH: 265
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (71)..(71)
<223> OTHER INFORMATION: Xaa is Met or Tyr
<220> FEATURE:
<221> NAME/KEY: misc_feature
<222> LOCATION: (73)..(73)
<223> OTHER INFORMATION: Xaa is Ser or Thr
<220> FEATURE:
<221> NAME/KEY: misc_feature
<222> LOCATION: (75)..(75)
<223> OTHER INFORMATION: Xaa is Thr or Glu
<220> FEATURE:
<221> NAME/KEY: misc_feature
<222> LOCATION: (175)..(175)
<223> OTHER INFORMATION: Xaa is Asp or Glu
<220> FEATURE:
<221> NAME/KEY: misc_feature
<222> LOCATION: (177)..(177)
<223> OTHER INFORMATION: Xaa is Leu or Met
<220> FEATURE:
<221> NAME/KEY: misc_feature
<222> LOCATION: (247)..(247)
<223> OTHER INFORMATION: Xaa is Met or Leu
<220> FEATURE:
<221> NAME/KEY: misc_feature
<222> LOCATION: (253)..(253)
<223> OTHER INFORMATION: Xaa is Asn or Ser

<400> SEQUENCE: 47

Met Gly Trp Ser Cys Ile Ile Leu Phe Leu Val Ala Thr Ala Thr Gly
1               5                   10                  15

Val His Ser Asn Val Asn His Lys Pro Ser Asn Thr Lys Val Asp Lys
            20                  25                  30

Lys Val Glu Pro Lys Ser Ser Asp Lys Thr His Thr Cys Pro Pro Cys
        35                  40                  45

Pro Ala Pro Glu Leu Leu Gly Gly Pro Ser Val Phe Leu Phe Pro Pro
    50                  55                  60

Lys Pro Lys Asp Thr Leu Xaa Ile Xaa Arg Xaa Pro Glu Val Thr Cys
65                  70                  75                  80

Val Val Val Asp Val Ser His Glu Asp Pro Glu Val Lys Phe Asn Trp
                85                  90                  95

Tyr Val Asp Gly Val Glu Val His Asn Ala Lys Thr Lys Pro Arg Glu
            100                 105                 110

Glu Gln Tyr Asn Ser Thr Tyr Arg Val Val Ser Val Leu Thr Val Leu
        115                 120                 125

His Gln Asp Trp Leu Asn Gly Lys Glu Tyr Lys Cys Lys Val Ser Asn
    130                 135                 140

Lys Ala Leu Pro Ala Pro Ile Glu Lys Thr Ile Ser Lys Ala Lys Gly
```

```
145                 150                 155                 160
Gln Pro Arg Glu Pro Gln Val Tyr Thr Leu Pro Pro Ser Arg Xaa Glu
                165                 170                 175

Xaa Thr Lys Asn Gln Val Ser Leu Thr Cys Leu Val Lys Gly Phe Tyr
                180                 185                 190

Pro Ser Asp Ile Ala Val Glu Trp Glu Ser Asn Gly Gln Pro Glu Asn
                195                 200                 205

Asn Tyr Lys Thr Thr Pro Pro Val Leu Asp Ser Asp Gly Ser Phe Phe
                210                 215                 220

Leu Tyr Ser Lys Leu Thr Val Asp Lys Ser Arg Trp Gln Gln Gly Asn
225                 230                 235                 240

Val Phe Ser Cys Ser Val Xaa His Glu Ala Leu His Xaa His Tyr Thr
                245                 250                 255

Gln Lys Ser Leu Ser Leu Ser Pro Gly
                260                 265

<210> SEQ ID NO 48
<211> LENGTH: 266
<212> TYPE: PRT
<213> ORGANISM: Artificial Sequence
<220> FEATURE:
<223> OTHER INFORMATION: Synthetic Construct

<400> SEQUENCE: 48

Met Gly Trp Ser Cys Ile Ile Leu Phe Leu Val Ala Thr Ala Thr Gly
1               5                   10                  15

Val His Ser Asn Val Asn His Lys Pro Ser Asn Thr Lys Val Asp Lys
                20                  25                  30

Lys Val Glu Pro Lys Ser Ser Asp Lys Thr His Thr Cys Pro Pro Cys
            35                  40                  45

Pro Ala Pro Glu Leu Leu Gly Gly Pro Ser Val Phe Leu Phe Pro Pro
        50                  55                  60

Lys Pro Lys Asp Thr Leu Met Ile Ser Arg Thr Pro Glu Val Thr Cys
65                  70                  75                  80

Val Val Val Asp Val Ser His Glu Asp Pro Glu Val Lys Phe Asn Trp
                85                  90                  95

Tyr Val Asp Gly Val Glu Val His Asn Ala Lys Thr Lys Pro Arg Glu
                100                 105                 110

Glu Gln Tyr Asn Ser Thr Tyr Arg Val Val Ser Val Leu Thr Val Leu
            115                 120                 125

His Gln Asp Trp Leu Asn Gly Lys Glu Tyr Lys Cys Lys Val Ser Asn
130                 135                 140

Lys Ala Leu Pro Ala Pro Ile Glu Lys Thr Ile Ser Lys Ala Lys Gly
145                 150                 155                 160

Gln Pro Arg Glu Pro Gln Val Tyr Thr Leu Pro Pro Ser Arg Asp Glu
                165                 170                 175

Leu Thr Lys Asn Gln Val Ser Leu Thr Cys Leu Val Lys Gly Phe Tyr
                180                 185                 190

Pro Ser Asp Ile Ala Val Glu Trp Glu Ser Asn Gly Gln Pro Glu Asn
                195                 200                 205

Asn Tyr Lys Thr Thr Pro Pro Val Leu Asp Ser Asp Gly Ser Phe Phe
                210                 215                 220

Leu Tyr Ser Lys Leu Thr Val Asp Lys Ser Arg Trp Gln Gln Gly Asn
225                 230                 235                 240

Val Phe Ser Cys Ser Val Met His Glu Ala Leu His Asn His Tyr Thr
```

```
                        245                 250                 255
Gln Lys Ser Leu Ser Leu Ser Pro Gly Lys
                260                 265

<210> SEQ ID NO 49
<211> LENGTH: 266
<212> TYPE: PRT
<213> ORGANISM: Artificial Sequence
<220> FEATURE:
<223> OTHER INFORMATION: Synthetic Construct

<400> SEQUENCE: 49

Met Gly Trp Ser Cys Ile Ile Leu Phe Leu Val Ala Thr Ala Thr Gly
1               5                   10                  15

Val His Ser Asn Val Asn His Lys Pro Ser Asn Thr Lys Val Asp Lys
            20                  25                  30

Lys Val Glu Pro Lys Ser Ser Asp Lys Thr His Thr Cys Pro Pro Cys
        35                  40                  45

Pro Ala Pro Glu Leu Leu Gly Gly Pro Ser Val Phe Leu Phe Pro Pro
    50                  55                  60

Lys Pro Lys Asp Thr Leu Met Ile Ser Arg Thr Pro Glu Val Thr Cys
65                  70                  75                  80

Val Val Val Asp Val Ser His Glu Asp Pro Glu Val Lys Phe Asn Trp
                85                  90                  95

Tyr Val Asp Gly Val Glu Val His Asn Ala Lys Thr Lys Pro Arg Glu
            100                 105                 110

Glu Gln Tyr Asn Ser Thr Tyr Arg Val Val Ser Val Leu Thr Val Leu
        115                 120                 125

His Gln Asp Trp Leu Asn Gly Lys Glu Tyr Lys Cys Lys Val Ser Asn
    130                 135                 140

Lys Ala Leu Pro Ala Pro Ile Glu Lys Thr Ile Ser Lys Ala Lys Gly
145                 150                 155                 160

Gln Pro Arg Glu Pro Gln Val Tyr Thr Leu Pro Pro Ser Arg Glu Glu
                165                 170                 175

Met Thr Lys Asn Gln Val Ser Leu Thr Cys Leu Val Lys Gly Phe Tyr
            180                 185                 190

Pro Ser Asp Ile Ala Val Glu Trp Glu Ser Asn Gly Gln Pro Glu Asn
        195                 200                 205

Asn Tyr Lys Thr Thr Pro Pro Val Leu Asp Ser Asp Gly Ser Phe Phe
    210                 215                 220

Leu Tyr Ser Lys Leu Thr Val Asp Lys Ser Arg Trp Gln Gln Gly Asn
225                 230                 235                 240

Val Phe Ser Cys Ser Val Met His Glu Ala Leu His Asn His Tyr Thr
                245                 250                 255

Gln Lys Ser Leu Ser Leu Ser Pro Gly Lys
                260                 265

<210> SEQ ID NO 50
<211> LENGTH: 266
<212> TYPE: PRT
<213> ORGANISM: Artificial Sequence
<220> FEATURE:
<223> OTHER INFORMATION: Synthetic Construct

<400> SEQUENCE: 50

Met Gly Trp Ser Cys Ile Ile Leu Phe Leu Val Ala Thr Ala Thr Gly
1               5                   10                  15
```

Val His Ser Asn Val Asn His Lys Pro Ser Asn Thr Lys Val Asp Lys
            20                  25                  30

Lys Val Glu Pro Lys Ser Ser Asp Lys Thr His Thr Cys Pro Pro Cys
            35                  40                  45

Pro Ala Pro Glu Leu Leu Gly Gly Pro Ser Val Phe Leu Phe Pro Pro
        50                  55                  60

Lys Pro Lys Asp Thr Leu Met Ile Ser Arg Thr Pro Glu Val Thr Cys
65                  70                  75                  80

Val Val Val Asp Val Ser His Glu Asp Pro Glu Val Lys Phe Asn Trp
                85                  90                  95

Tyr Val Asp Gly Val Glu Val His Asn Ala Lys Thr Lys Pro Arg Glu
            100                 105                 110

Glu Gln Tyr Asn Ser Thr Tyr Arg Val Val Ser Val Leu Thr Val Leu
        115                 120                 125

His Gln Asp Trp Leu Asn Gly Lys Glu Tyr Lys Cys Lys Val Ser Asn
    130                 135                 140

Lys Ala Leu Pro Ala Pro Ile Glu Lys Thr Ile Ser Lys Ala Lys Gly
145                 150                 155                 160

Gln Pro Arg Glu Pro Gln Val Tyr Thr Leu Pro Pro Ser Arg Asp Glu
                165                 170                 175

Leu Thr Lys Asn Gln Val Ser Leu Thr Cys Leu Val Lys Gly Phe Tyr
            180                 185                 190

Pro Ser Asp Ile Ala Val Glu Trp Glu Ser Asn Gly Gln Pro Glu Asn
        195                 200                 205

Asn Tyr Lys Thr Thr Pro Pro Val Leu Asp Ser Asp Gly Ser Phe Phe
    210                 215                 220

Leu Tyr Ser Lys Leu Thr Val Asp Lys Ser Arg Trp Gln Gln Gly Asn
225                 230                 235                 240

Val Phe Ser Cys Ser Val Leu His Glu Ala Leu His Ser His Tyr Thr
                245                 250                 255

Gln Lys Ser Leu Ser Leu Ser Pro Gly Lys
            260                 265

<210> SEQ ID NO 51
<211> LENGTH: 266
<212> TYPE: PRT
<213> ORGANISM: Artificial Sequence
<220> FEATURE:
<223> OTHER INFORMATION: Synthetic Construct

<400> SEQUENCE: 51

Met Gly Trp Ser Cys Ile Ile Leu Phe Leu Val Ala Thr Ala Thr Gly
1               5                   10                  15

Val His Ser Asn Val Asn His Lys Pro Ser Asn Thr Lys Val Asp Lys
            20                  25                  30

Lys Val Glu Pro Lys Ser Ser Asp Lys Thr His Thr Cys Pro Pro Cys
        35                  40                  45

Pro Ala Pro Glu Leu Leu Gly Gly Pro Ser Val Phe Leu Phe Pro Pro
        50                  55                  60

Lys Pro Lys Asp Thr Leu Met Ile Ser Arg Thr Pro Glu Val Thr Cys
65                  70                  75                  80

Val Val Val Asp Val Ser His Glu Asp Pro Glu Val Lys Phe Asn Trp
                85                  90                  95

Tyr Val Asp Gly Val Glu Val His Asn Ala Lys Thr Lys Pro Arg Glu
            100                 105                 110

```
Glu Gln Tyr Asn Ser Thr Tyr Arg Val Val Ser Val Leu Thr Val Leu
                115                 120                 125

His Gln Asp Trp Leu Asn Gly Lys Glu Tyr Lys Cys Lys Val Ser Asn
            130                 135                 140

Lys Ala Leu Pro Ala Pro Ile Glu Lys Thr Ile Ser Lys Ala Lys Gly
145                 150                 155                 160

Gln Pro Arg Glu Pro Gln Val Tyr Thr Leu Pro Pro Ser Arg Glu Glu
                165                 170                 175

Met Thr Lys Asn Gln Val Ser Leu Thr Cys Leu Val Lys Gly Phe Tyr
            180                 185                 190

Pro Ser Asp Ile Ala Val Glu Trp Glu Ser Asn Gly Gln Pro Glu Asn
                195                 200                 205

Asn Tyr Lys Thr Thr Pro Pro Val Leu Asp Ser Asp Gly Ser Phe Phe
            210                 215                 220

Leu Tyr Ser Lys Leu Thr Val Asp Lys Ser Arg Trp Gln Gln Gly Asn
225                 230                 235                 240

Val Phe Ser Cys Ser Val Leu His Glu Ala Leu His Ser His Tyr Thr
                245                 250                 255

Gln Lys Ser Leu Ser Leu Ser Pro Gly Lys
            260                 265
```

<210> SEQ ID NO 52
<211> LENGTH: 266
<212> TYPE: PRT
<213> ORGANISM: Artificial Sequence
<220> FEATURE:
<223> OTHER INFORMATION: Synthetic Construct

<400> SEQUENCE: 52

```
Met Gly Trp Ser Cys Ile Ile Leu Phe Leu Val Ala Thr Ala Thr Gly
1               5                   10                  15

Val His Ser Asn Val Asn His Lys Pro Ser Asn Thr Lys Val Asp Lys
            20                  25                  30

Lys Val Glu Pro Lys Ser Ser Asp Lys Thr His Thr Cys Pro Pro Cys
            35                  40                  45

Pro Ala Pro Glu Leu Leu Gly Gly Pro Ser Val Phe Leu Phe Pro Pro
            50                  55                  60

Lys Pro Lys Asp Thr Leu Tyr Ile Thr Arg Glu Pro Glu Val Thr Cys
65                  70                  75                  80

Val Val Val Asp Val Ser His Glu Asp Pro Glu Val Lys Phe Asn Trp
                85                  90                  95

Tyr Val Asp Gly Val Glu Val His Asn Ala Lys Thr Lys Pro Arg Glu
            100                 105                 110

Glu Gln Tyr Asn Ser Thr Tyr Arg Val Val Ser Val Leu Thr Val Leu
                115                 120                 125

His Gln Asp Trp Leu Asn Gly Lys Glu Tyr Lys Cys Lys Val Ser Asn
            130                 135                 140

Lys Ala Leu Pro Ala Pro Ile Glu Lys Thr Ile Ser Lys Ala Lys Gly
145                 150                 155                 160

Gln Pro Arg Glu Pro Gln Val Tyr Thr Leu Pro Pro Ser Arg Asp Glu
                165                 170                 175

Leu Thr Lys Asn Gln Val Ser Leu Thr Cys Leu Val Lys Gly Phe Tyr
            180                 185                 190

Pro Ser Asp Ile Ala Val Glu Trp Glu Ser Asn Gly Gln Pro Glu Asn
                195                 200                 205
```

Asn Tyr Lys Thr Thr Pro Pro Val Leu Asp Ser Asp Gly Ser Phe Phe
    210                 215                 220

Leu Tyr Ser Lys Leu Thr Val Asp Lys Ser Arg Trp Gln Gln Gly Asn
225                 230                 235                 240

Val Phe Ser Cys Ser Val Met His Glu Ala Leu His Asn His Tyr Thr
                245                 250                 255

Gln Lys Ser Leu Ser Leu Ser Pro Gly Lys
            260                 265

<210> SEQ ID NO 53
<211> LENGTH: 266
<212> TYPE: PRT
<213> ORGANISM: Artificial Sequence
<220> FEATURE:
<223> OTHER INFORMATION: Synthetic Construct

<400> SEQUENCE: 53

Met Gly Trp Ser Cys Ile Ile Leu Phe Leu Val Ala Thr Ala Thr Gly
1               5                   10                  15

Val His Ser Asn Val Asn His Lys Pro Ser Asn Thr Lys Val Asp Lys
                20                  25                  30

Lys Val Glu Pro Lys Ser Ser Asp Lys Thr His Thr Cys Pro Pro Cys
            35                  40                  45

Pro Ala Pro Glu Leu Leu Gly Gly Pro Ser Val Phe Leu Phe Pro Pro
        50                  55                  60

Lys Pro Lys Asp Thr Leu Tyr Ile Thr Arg Glu Pro Glu Val Thr Cys
65                  70                  75                  80

Val Val Val Asp Val Ser His Glu Asp Pro Glu Val Lys Phe Asn Trp
                85                  90                  95

Tyr Val Asp Gly Val Glu Val His Asn Ala Lys Thr Lys Pro Arg Glu
            100                 105                 110

Glu Gln Tyr Asn Ser Thr Tyr Arg Val Val Ser Val Leu Thr Val Leu
        115                 120                 125

His Gln Asp Trp Leu Asn Gly Lys Glu Tyr Lys Cys Lys Val Ser Asn
130                 135                 140

Lys Ala Leu Pro Ala Pro Ile Glu Lys Thr Ile Ser Lys Ala Lys Gly
145                 150                 155                 160

Gln Pro Arg Glu Pro Gln Val Tyr Thr Leu Pro Pro Ser Arg Glu Glu
                165                 170                 175

Met Thr Lys Asn Gln Val Ser Leu Thr Cys Leu Val Lys Gly Phe Tyr
            180                 185                 190

Pro Ser Asp Ile Ala Val Glu Trp Glu Ser Asn Gly Gln Pro Glu Asn
        195                 200                 205

Asn Tyr Lys Thr Thr Pro Pro Val Leu Asp Ser Asp Gly Ser Phe Phe
    210                 215                 220

Leu Tyr Ser Lys Leu Thr Val Asp Lys Ser Arg Trp Gln Gln Gly Asn
225                 230                 235                 240

Val Phe Ser Cys Ser Val Met His Glu Ala Leu His Asn His Tyr Thr
                245                 250                 255

Gln Lys Ser Leu Ser Leu Ser Pro Gly Lys
            260                 265

<210> SEQ ID NO 54
<211> LENGTH: 267
<212> TYPE: PRT
<213> ORGANISM: Artificial Sequence
<220> FEATURE:

<223> OTHER INFORMATION: Synthetic Construct

<400> SEQUENCE: 54

```
Met Gly Trp Ser Cys Ile Ile Leu Phe Leu Val Ala Thr Ala Thr Gly
1               5                   10                  15

Val His Ser Ile Ser Ala Met Val Arg Ser Asp Lys Thr His Thr Cys
                20                  25                  30

Pro Pro Cys Pro Ala Pro Glu Leu Leu Gly Gly Pro Ser Val Phe Leu
            35                  40                  45

Phe Pro Pro Lys Pro Lys Asp Thr Leu Met Ile Ser Arg Thr Pro Glu
        50                  55                  60

Val Thr Cys Val Val Val Asp Val Ser His Glu Asp Pro Glu Val Lys
65                  70                  75                  80

Phe Asn Trp Tyr Val Asp Gly Val Glu Val His Asn Ala Lys Thr Lys
                85                  90                  95

Pro Arg Glu Glu Gln Tyr Asn Ser Thr Tyr Arg Val Val Ser Val Leu
            100                 105                 110

Thr Val Leu His Gln Asp Trp Leu Asn Gly Lys Glu Tyr Lys Cys Lys
        115                 120                 125

Val Ser Asn Lys Ala Leu Pro Ala Pro Ile Glu Lys Thr Ile Ser Lys
    130                 135                 140

Ala Lys Gly Gln Pro Arg Glu Pro Gln Val Tyr Thr Leu Pro Pro Ser
145                 150                 155                 160

Arg Glu Glu Met Thr Lys Asn Gln Val Ser Leu Thr Cys Leu Val Lys
                165                 170                 175

Gly Phe Tyr Pro Ser Asp Ile Ala Val Glu Trp Glu Ser Asn Gly Gln
            180                 185                 190

Pro Glu Asn Asn Tyr Lys Thr Thr Pro Pro Val Leu Asp Ser Asp Gly
        195                 200                 205

Ser Phe Phe Leu Tyr Ser Lys Leu Thr Val Asp Lys Ser Arg Trp Gln
    210                 215                 220

Gln Gly Asn Val Phe Ser Cys Ser Val Leu His Glu Ala Leu His Ser
225                 230                 235                 240

His Tyr Thr Gln Lys Ser Leu Ser Leu Ser Pro Gly Gly Gly Gly Gly
                245                 250                 255

Ser Glu Gln Lys Leu Ile Ser Glu Glu Asp Leu
            260                 265
```

<210> SEQ ID NO 55
<211> LENGTH: 267
<212> TYPE: PRT
<213> ORGANISM: Artificial Sequence
<220> FEATURE:
<223> OTHER INFORMATION: Synthetic Construct

<400> SEQUENCE: 55

```
Met Gly Trp Ser Cys Ile Ile Leu Phe Leu Val Ala Thr Ala Thr Gly
1               5                   10                  15

Val His Ser Ile Ser Ala Met Val Arg Ser Asp Lys Thr His Thr Cys
                20                  25                  30

Pro Pro Cys Pro Ala Pro Glu Leu Leu Gly Gly Pro Ser Val Phe Leu
            35                  40                  45

Phe Pro Pro Lys Pro Lys Asp Thr Leu Met Ile Ser Arg Thr Pro Glu
        50                  55                  60

Val Thr Cys Val Val Val Asp Val Ser His Glu Asp Pro Glu Val Lys
65                  70                  75                  80
```

```
Phe Asn Trp Tyr Val Asp Gly Val Glu Val His Asn Ala Lys Thr Lys
                85                  90                  95

Pro Arg Glu Glu Gln Tyr Asn Ser Thr Tyr Arg Val Val Ser Val Leu
            100                 105                 110

Thr Val Leu His Gln Asp Trp Leu Asn Gly Lys Glu Tyr Lys Cys Lys
        115                 120                 125

Val Ser Asn Lys Ala Leu Pro Ala Pro Ile Glu Lys Thr Ile Ser Lys
    130                 135                 140

Ala Lys Gly Gln Pro Arg Glu Pro Gln Val Tyr Thr Leu Pro Pro Ser
145                 150                 155                 160

Arg Asp Glu Leu Thr Lys Asn Gln Val Ser Leu Thr Cys Leu Val Lys
                165                 170                 175

Gly Phe Tyr Pro Ser Asp Ile Ala Val Glu Trp Glu Ser Asn Gly Gln
            180                 185                 190

Pro Glu Asn Asn Tyr Lys Thr Thr Pro Pro Val Leu Asp Ser Asp Gly
        195                 200                 205

Ser Phe Phe Leu Tyr Ser Lys Leu Thr Val Asp Lys Ser Arg Trp Gln
    210                 215                 220

Gln Gly Asn Val Phe Ser Cys Ser Val Leu His Glu Ala Leu His Ser
225                 230                 235                 240

His Tyr Thr Gln Lys Ser Leu Ser Leu Ser Pro Gly Gly Gly Gly Gly
                245                 250                 255

Ser Glu Gln Lys Leu Ile Ser Glu Glu Asp Leu
                260                 265

<210> SEQ ID NO 56
<211> LENGTH: 267
<212> TYPE: PRT
<213> ORGANISM: Artificial Sequence
<220> FEATURE:
<223> OTHER INFORMATION: Synthetic Construct

<400> SEQUENCE: 56

Met Gly Trp Ser Cys Ile Ile Leu Phe Leu Val Ala Thr Ala Thr Gly
1               5                   10                  15

Val His Ser Ile Ser Ala Met Val Arg Ser Asp Lys Thr His Thr Cys
            20                  25                  30

Pro Pro Cys Pro Ala Pro Glu Leu Leu Gly Gly Pro Ser Val Phe Leu
        35                  40                  45

Phe Pro Pro Lys Pro Lys Asp Thr Leu Tyr Ile Thr Arg Glu Pro Glu
    50                  55                  60

Val Thr Cys Val Val Val Asp Val Ser His Glu Asp Pro Glu Val Lys
65                  70                  75                  80

Phe Asn Trp Tyr Val Asp Gly Val Glu Val His Asn Ala Lys Thr Lys
                85                  90                  95

Pro Arg Glu Glu Gln Tyr Asn Ser Thr Tyr Arg Val Val Ser Val Leu
            100                 105                 110

Thr Val Leu His Gln Asp Trp Leu Asn Gly Lys Glu Tyr Lys Cys Lys
        115                 120                 125

Val Ser Asn Lys Ala Leu Pro Ala Pro Ile Glu Lys Thr Ile Ser Lys
    130                 135                 140

Ala Lys Gly Gln Pro Arg Glu Pro Gln Val Tyr Thr Leu Pro Pro Ser
145                 150                 155                 160

Arg Glu Glu Met Thr Lys Asn Gln Val Ser Leu Thr Cys Leu Val Lys
                165                 170                 175
```

```
Gly Phe Tyr Pro Ser Asp Ile Ala Val Glu Trp Glu Ser Asn Gly Gln
            180                 185                 190

Pro Glu Asn Asn Tyr Lys Thr Thr Pro Pro Val Leu Asp Ser Asp Gly
        195                 200                 205

Ser Phe Phe Leu Tyr Ser Lys Leu Thr Val Asp Lys Ser Arg Trp Gln
    210                 215                 220

Gln Gly Asn Val Phe Ser Cys Ser Val Met His Glu Ala Leu His Asn
225                 230                 235                 240

His Tyr Thr Gln Lys Ser Leu Ser Leu Ser Pro Gly Gly Gly Gly Gly
                245                 250                 255

Ser Glu Gln Lys Leu Ile Ser Glu Glu Asp Leu
            260                 265

<210> SEQ ID NO 57
<211> LENGTH: 267
<212> TYPE: PRT
<213> ORGANISM: Artificial Sequence
<220> FEATURE:
<223> OTHER INFORMATION: Synthetic Construct

<400> SEQUENCE: 57

Met Gly Trp Ser Cys Ile Ile Leu Phe Leu Val Ala Thr Ala Thr Gly
1               5                   10                  15

Val His Ser Ile Ser Ala Met Val Arg Ser Asp Lys Thr His Thr Cys
            20                  25                  30

Pro Pro Cys Pro Ala Pro Glu Leu Leu Gly Gly Pro Ser Val Phe Leu
        35                  40                  45

Phe Pro Pro Lys Pro Lys Asp Thr Leu Tyr Ile Thr Arg Glu Pro Glu
    50                  55                  60

Val Thr Cys Val Val Val Asp Val Ser His Glu Asp Pro Glu Val Lys
65                  70                  75                  80

Phe Asn Trp Tyr Val Asp Gly Val Glu Val His Asn Ala Lys Thr Lys
                85                  90                  95

Pro Arg Glu Glu Gln Tyr Asn Ser Thr Tyr Arg Val Val Ser Val Leu
            100                 105                 110

Thr Val Leu His Gln Asp Trp Leu Asn Gly Lys Glu Tyr Lys Cys Lys
        115                 120                 125

Val Ser Asn Lys Ala Leu Pro Ala Pro Ile Glu Lys Thr Ile Ser Lys
    130                 135                 140

Ala Lys Gly Gln Pro Arg Glu Pro Gln Val Tyr Thr Leu Pro Pro Ser
145                 150                 155                 160

Arg Asp Glu Leu Thr Lys Asn Gln Val Ser Leu Thr Cys Leu Val Lys
                165                 170                 175

Gly Phe Tyr Pro Ser Asp Ile Ala Val Glu Trp Glu Ser Asn Gly Gln
            180                 185                 190

Pro Glu Asn Asn Tyr Lys Thr Thr Pro Pro Val Leu Asp Ser Asp Gly
        195                 200                 205

Ser Phe Phe Leu Tyr Ser Lys Leu Thr Val Asp Lys Ser Arg Trp Gln
    210                 215                 220

Gln Gly Asn Val Phe Ser Cys Ser Val Met His Glu Ala Leu His Asn
225                 230                 235                 240

His Tyr Thr Gln Lys Ser Leu Ser Leu Ser Pro Gly Gly Gly Gly Gly
                245                 250                 255

Ser Glu Gln Lys Leu Ile Ser Glu Glu Asp Leu
            260                 265
```

<210> SEQ ID NO 58
<211> LENGTH: 275
<212> TYPE: PRT
<213> ORGANISM: Artificial Sequence
<220> FEATURE:
<223> OTHER INFORMATION: Synthetic Construct

<400> SEQUENCE: 58

```
Met Gly Trp Ser Cys Ile Ile Leu Phe Leu Val Ala Thr Ala Thr Gly
1               5                   10                  15

Val His Ser Glu Pro Lys Ser Ser Asp Lys Thr His Thr Cys Pro Pro
            20                  25                  30

Cys Pro Ala Pro Glu Leu Leu Gly Gly Pro Ser Val Phe Leu Phe Pro
        35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ala Pro Ile Glu Lys Thr Ile Ser Lys Ala Lys
    130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
    210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Gly Gly Gly Ser Gln
                245                 250                 255

Arg Asn Pro Arg Leu Arg Leu Ile Arg Arg His Pro Thr Leu Arg Ile
            260                 265                 270

Pro Pro Ile
        275
```

<210> SEQ ID NO 59
<211> LENGTH: 275
<212> TYPE: PRT
<213> ORGANISM: Artificial Sequence
<220> FEATURE:
<223> OTHER INFORMATION: Synthetic Construct

<400> SEQUENCE: 59

```
Met Gly Trp Ser Cys Ile Ile Leu Phe Leu Val Ala Thr Ala Thr Gly
1               5                   10                  15

Val His Ser Glu Pro Lys Ser Ser Asp Lys Thr His Thr Cys Pro Pro
```

```
                20                  25                  30

Cys Pro Ala Pro Glu Leu Leu Gly Gly Pro Ser Val Phe Leu Phe Pro
             35                  40                  45

Pro Lys Pro Lys Asp Thr Leu Met Ile Ser Arg Thr Pro Glu Val Thr
 50                  55                  60

Cys Val Val Asp Val Ser His Glu Asp Pro Glu Val Lys Phe Asn
 65                  70                  75                  80

Trp Tyr Val Asp Gly Val Glu Val His Asn Ala Lys Thr Lys Pro Arg
                 85                  90                  95

Glu Glu Gln Tyr Asn Ser Thr Tyr Arg Val Val Ser Val Leu Thr Val
                100                 105                 110

Leu His Gln Asp Trp Leu Asn Gly Lys Glu Tyr Lys Cys Lys Val Ser
            115                 120                 125

Asn Lys Ala Leu Pro Ala Pro Ile Glu Lys Thr Ile Ser Lys Ala Lys
130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
210                 215                 220

Asn Val Phe Ser Cys Ser Val Leu His Glu Ala Leu His Ser His Tyr
225                 230                 235                 240

Thr Gln Lys Ser Leu Ser Leu Ser Pro Gly Gly Gly Gly Ser Gln
                245                 250                 255

Arg Asn Pro Arg Leu Arg Leu Ile Arg Arg His Pro Thr Leu Arg Ile
            260                 265                 270

Pro Pro Ile
        275

<210> SEQ ID NO 60
<211> LENGTH: 247
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (20)..(20)
<223> OTHER INFORMATION: Glx is Cys or Ser
<220> FEATURE:
<221> NAME/KEY: misc_feature
<222> LOCATION: (52)..(52)
<223> OTHER INFORMATION: Xaa is Met or Tyr
<220> FEATURE:
<221> NAME/KEY: misc_feature
<222> LOCATION: (54)..(54)
<223> OTHER INFORMATION: Xaa is Ser or Thr
<220> FEATURE:
<221> NAME/KEY: misc_feature
<222> LOCATION: (56)..(56)
<223> OTHER INFORMATION: Xaa is Thr or Glu
<220> FEATURE:
<221> NAME/KEY: misc_feature
<222> LOCATION: (156)..(156)
<223> OTHER INFORMATION: Xaa is Asp or Glu
<220> FEATURE:
<221> NAME/KEY: misc_feature
```

<222> LOCATION: (158)..(158)
<223> OTHER INFORMATION: Xaa is Leu or Met
<220> FEATURE:
<221> NAME/KEY: misc_feature
<222> LOCATION: (228)..(228)
<223> OTHER INFORMATION: Xaa is Met or Leu
<220> FEATURE:
<221> NAME/KEY: misc_feature
<222> LOCATION: (234)..(234)
<223> OTHER INFORMATION: Xaa is Asn or Ser

<400> SEQUENCE: 60

Asn Val Asn His Lys Pro Ser Asn Thr Lys Val Asp Lys Lys Val Glu
1               5                   10                  15

Pro Lys Ser Glx Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Xaa Ile Xaa Arg Xaa Pro Glu Val Thr Cys Val Val Val
    50                  55                  60

Asp Val Ser His Glu Asp Pro Glu Val Lys Phe Asn Trp Tyr Val Asp
65              70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Xaa Glu Xaa Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Xaa His Glu Ala Leu His Xaa His Tyr Thr Gln Lys Ser
225                 230                 235                 240

Leu Ser Leu Ser Pro Gly Lys
                245

<210> SEQ ID NO 61
<211> LENGTH: 247
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (52)..(52)
<223> OTHER INFORMATION: Xaa is Met or Tyr
<220> FEATURE:
<221> NAME/KEY: misc_feature
<222> LOCATION: (54)..(54)
<223> OTHER INFORMATION: Xaa is Ser or Thr
<220> FEATURE:
<221> NAME/KEY: misc_feature
<222> LOCATION: (56)..(56)

<223> OTHER INFORMATION: Xaa is Ser or Thr
<220> FEATURE:
<221> NAME/KEY: misc_feature
<222> LOCATION: (156)..(156)
<223> OTHER INFORMATION: Xaa is Asp or Glu
<220> FEATURE:
<221> NAME/KEY: misc_feature
<222> LOCATION: (158)..(158)
<223> OTHER INFORMATION: Xaa is Leu or Met
<220> FEATURE:
<221> NAME/KEY: misc_feature
<222> LOCATION: (228)..(228)
<223> OTHER INFORMATION: Xaa is Met or Leu
<220> FEATURE:
<221> NAME/KEY: misc_feature
<222> LOCATION: (234)..(234)
<223> OTHER INFORMATION: Xaa is Asn or Ser

<400> SEQUENCE: 61

Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Xaa Ile Xaa Arg Xaa Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Xaa Glu Xaa Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Xaa His Glu Ala Leu His Xaa His Tyr Thr Gln Lys Ser
225                 230                 235                 240

Leu Ser Leu Ser Pro Gly Lys
                245

<210> SEQ ID NO 62
<211> LENGTH: 247
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (156)..(156)
<223> OTHER INFORMATION: Xaa is Asp or Glu
<220> FEATURE:
<221> NAME/KEY: misc_feature
<222> LOCATION: (158)..(158)
<223> OTHER INFORMATION: Xaa is Leu or Met

<400> SEQUENCE: 62

Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Xaa Glu Xaa Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys
                245

<210> SEQ ID NO 63
<211> LENGTH: 247
<212> TYPE: PRT
<213> ORGANISM: Artificial Sequence
<220> FEATURE:
<223> OTHER INFORMATION: Synthetic Construct

<400> SEQUENCE: 63

Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

```
Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys
                245

<210> SEQ ID NO 64
<211> LENGTH: 247
<212> TYPE: PRT
<213> ORGANISM: Artificial Sequence
<220> FEATURE:
<223> OTHER INFORMATION: Synthetic Construct

<400> SEQUENCE: 64

Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190
```

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
        210                 215                 220

Cys Ser Val Met His Glu Ala Leu His Asn His Tyr Thr Gln Lys Ser
225                 230                 235                 240

Leu Ser Leu Ser Pro Gly Lys
            245

<210> SEQ ID NO 65
<211> LENGTH: 247
<212> TYPE: PRT
<213> ORGANISM: Artificial Sequence
<220> FEATURE:
<223> OTHER INFORMATION: Synthetic Construct

<400> SEQUENCE: 65

Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Leu His Glu Ala Leu His Ser His Tyr Thr Gln Lys Ser
225                 230                 235                 240

Leu Ser Leu Ser Pro Gly Lys
            245

<210> SEQ ID NO 66
<211> LENGTH: 247
<212> TYPE: PRT
<213> ORGANISM: Artificial Sequence
<220> FEATURE:
<223> OTHER INFORMATION: Synthetic Construct -continued

<400> SEQUENCE: 66

```
Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Leu His Glu Ala Leu His Ser His Tyr Thr Gln Lys Ser
225                 230                 235                 240

Leu Ser Leu Ser Pro Gly Lys
                245
```

```
<210> SEQ ID NO 67
<211> LENGTH: 247
<212> TYPE: PRT
<213> ORGANISM: Artificial Sequence
<220> FEATURE:
<223> OTHER INFORMATION: Synthetic Construct
```

<400> SEQUENCE: 67

```
Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Tyr Ile Thr Arg Glu Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
```

```
            100                 105                 110
Trp Leu Asn Gly Lys Glu Tyr Lys Cys Lys Val Ser Asn Lys Ala Leu
            115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys
                245

<210> SEQ ID NO 68
<211> LENGTH: 247
<212> TYPE: PRT
<213> ORGANISM: Artificial Sequence
<220> FEATURE:
<223> OTHER INFORMATION: Synthetic Construct

<400> SEQUENCE: 68

Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Tyr Ile Thr Arg Glu Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
            115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
```

-continued

```
                210                 215                 220
Cys Ser Val Met His Glu Ala Leu His Asn His Tyr Thr Gln Lys Ser
225                 230                 235                 240

Leu Ser Leu Ser Pro Gly Lys
                245

<210> SEQ ID NO 69
<211> LENGTH: 246
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (19)..(19)
<223> OTHER INFORMATION: Glx is Cys or Ser
<220> FEATURE:
<221> NAME/KEY: misc_feature
<222> LOCATION: (52)..(52)
<223> OTHER INFORMATION: Xaa is Met or Tyr
<220> FEATURE:
<221> NAME/KEY: misc_feature
<222> LOCATION: (54)..(54)
<223> OTHER INFORMATION: Xaa is Ser or Thr
<220> FEATURE:
<221> NAME/KEY: misc_feature
<222> LOCATION: (56)..(56)
<223> OTHER INFORMATION: Xaa is Thr or Glu
<220> FEATURE:
<221> NAME/KEY: misc_feature
<222> LOCATION: (156)..(156)
<223> OTHER INFORMATION: Xaa is Asp or Glu
<220> FEATURE:
<221> NAME/KEY: misc_feature
<222> LOCATION: (158)..(158)
<223> OTHER INFORMATION: Xaa is Leu or Met
<220> FEATURE:
<221> NAME/KEY: misc_feature
<222> LOCATION: (228)..(228)
<223> OTHER INFORMATION: Xaa is Met or Leu
<220> FEATURE:
<221> NAME/KEY: misc_feature
<222> LOCATION: (234)..(234)
<223> OTHER INFORMATION: Xaa is Asn or Ser

<400> SEQUENCE: 69

Asn Val Asn His Lys Pro Ser Asn Thr Lys Val Asp Lys Lys Val Glu
1               5                   10                  15

Pro Lys Ser Glx Asp Lys Thr His Thr Cys Pro Pro Cys Pro Ala Pro
                20                  25                  30

Glu Leu Leu Gly Gly Pro Ser Val Phe Leu Phe Pro Pro Lys Pro Lys
            35                  40                  45

Asp Thr Leu Xaa Ile Xaa Arg Xaa Pro Glu Val Thr Cys Val Val Val
        50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Xaa Glu Xaa Thr Lys
145                 150                 155                 160
```

```
Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Xaa His Glu Ala Leu His Xaa His Tyr Thr Gln Lys Ser
225             230                 235                 240

Leu Ser Leu Ser Pro Gly
                245

<210> SEQ ID NO 70
<211> LENGTH: 246
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (52)..(52)
<223> OTHER INFORMATION: Xaa is Met or Tyr
<220> FEATURE:
<221> NAME/KEY: misc_feature
<222> LOCATION: (54)..(54)
<223> OTHER INFORMATION: Xaa is Ser or Thr
<220> FEATURE:
<221> NAME/KEY: misc_feature
<222> LOCATION: (56)..(56)
<223> OTHER INFORMATION: Xaa is Thr or Glu
<220> FEATURE:
<221> NAME/KEY: misc_feature
<222> LOCATION: (156)..(156)
<223> OTHER INFORMATION: Xaa is Asp or Glu
<220> FEATURE:
<221> NAME/KEY: misc_feature
<222> LOCATION: (158)..(158)
<223> OTHER INFORMATION: Xaa is Leu or Met
<220> FEATURE:
<221> NAME/KEY: misc_feature
<222> LOCATION: (228)..(228)
<223> OTHER INFORMATION: Xaa is Met or Leu
<220> FEATURE:
<221> NAME/KEY: misc_feature
<222> LOCATION: (234)..(234)
<223> OTHER INFORMATION: Xaa is Asn or Ser

<400> SEQUENCE: 70

Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Xaa Ile Xaa Arg Xaa Pro Glu Val Thr Cys Val Val Val
    50                  55                  60

Asp Val Ser His Glu Asp Pro Glu Val Lys Phe Asn Trp Tyr Val Asp
65              70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
```

```
            115                 120                 125
Pro Ala Pro Ile Glu Lys Thr Ile Ser Lys Ala Lys Gly Gln Pro Arg
        130                 135                 140

Glu Pro Gln Val Tyr Thr Leu Pro Pro Ser Arg Xaa Glu Xaa Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
210                 215                 220

Cys Ser Val Xaa His Glu Ala Leu His Xaa His Tyr Thr Gln Lys Ser
225                 230                 235                 240

Leu Ser Leu Ser Pro Gly
                245

<210> SEQ ID NO 71
<211> LENGTH: 246
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (156)..(156)
<223> OTHER INFORMATION: Xaa is Asp or Glu
<220> FEATURE:
<221> NAME/KEY: misc_feature
<222> LOCATION: (158)..(158)
<223> OTHER INFORMATION: Xaa is is Leu or Met

<400> SEQUENCE: 71

Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Xaa Glu Xaa Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190
```

```
Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
        210                 215                 220

Cys Ser Val Met His Glu Ala Leu His Asn His Tyr Thr Gln Lys Ser
225                 230                 235                 240

Leu Ser Leu Ser Pro Gly
                245

<210> SEQ ID NO 72
<211> LENGTH: 246
<212> TYPE: PRT
<213> ORGANISM: Artificial Sequence
<220> FEATURE:
<223> OTHER INFORMATION: Synthetic Construct

<400> SEQUENCE: 72

Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
        210                 215                 220

Cys Ser Val Met His Glu Ala Leu His Asn His Tyr Thr Gln Lys Ser
225                 230                 235                 240

Leu Ser Leu Ser Pro Gly
                245

<210> SEQ ID NO 73
<211> LENGTH: 246
<212> TYPE: PRT
<213> ORGANISM: Artificial Sequence
<220> FEATURE:
<223> OTHER INFORMATION: Synthetic Construct
```

<400> SEQUENCE: 73

Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly
                245

<210> SEQ ID NO 74
<211> LENGTH: 246
<212> TYPE: PRT
<213> ORGANISM: Artificial Sequence
<220> FEATURE:
<223> OTHER INFORMATION: Synthetic Construct

<400> SEQUENCE: 74

Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp

```
                    100                 105                 110
Trp Leu Asn Gly Lys Glu Tyr Lys Cys Lys Val Ser Asn Lys Ala Leu
            115                 120                 125

Pro Ala Pro Ile Glu Lys Thr Ile Ser Lys Ala Lys Gly Gln Pro Arg
        130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
                215                 220

Cys Ser Val Leu His Glu Ala Leu His Ser His Tyr Thr Gln Lys Ser
225                 230                 235                 240

Leu Ser Leu Ser Pro Gly
                245

<210> SEQ ID NO 75
<211> LENGTH: 246
<212> TYPE: PRT
<213> ORGANISM: Artificial Sequence
<220> FEATURE:
<223> OTHER INFORMATION: Synthetic Construct

<400> SEQUENCE: 75

Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
                20                  25                  30

Glu Leu Leu Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
        50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
```

```
                    210                 215                 220
Cys Ser Val Leu His Glu Ala Leu His Ser His Tyr Thr Gln Lys Ser
225                 230                 235                 240

Leu Ser Leu Ser Pro Gly
                245

<210> SEQ ID NO 76
<211> LENGTH: 246
<212> TYPE: PRT
<213> ORGANISM: Artificial Sequence
<220> FEATURE:
<223> OTHER INFORMATION: Synthetic Construct

<400> SEQUENCE: 76

Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
                20                  25                  30

Glu Leu Leu Gly Gly Pro Ser Val Phe Leu Phe Pro Pro Lys Pro Lys
            35                  40                  45

Asp Thr Leu Tyr Ile Thr Arg Glu Pro Glu Val Thr Cys Val Val Val
        50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly
                245

<210> SEQ ID NO 77
<211> LENGTH: 246
<212> TYPE: PRT
<213> ORGANISM: Artificial Sequence
<220> FEATURE:
<223> OTHER INFORMATION: Synthetic Construct

<400> SEQUENCE: 77

Asn Val Asn His Lys Pro Ser Asn Thr Lys Val Asp Lys Lys Val Glu
1               5                   10                  15
```

```
Pro Lys Ser Ser Asp Lys Thr His Thr Cys Pro Pro Cys Pro Ala Pro
             20                  25                  30

Glu Leu Leu Gly Gly Pro Ser Val Phe Leu Phe Pro Pro Lys Pro Lys
         35                  40                  45

Asp Thr Leu Tyr Ile Thr Arg Glu Pro Glu Val Thr Cys Val Val Val
     50                  55                  60

Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                 85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly
                245

<210> SEQ ID NO 78
<211> LENGTH: 246
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (19)..(19)
<223> OTHER INFORMATION: Glx is Cys or Ser
<220> FEATURE:
<221> NAME/KEY: misc_feature
<222> LOCATION: (51)..(51)
<223> OTHER INFORMATION: Xaa is Met or Tyr
<220> FEATURE:
<221> NAME/KEY: misc_feature
<222> LOCATION: (53)..(53)
<223> OTHER INFORMATION: Xaa is Ser or Thr
<220> FEATURE:
<221> NAME/KEY: misc_feature
<222> LOCATION: (55)..(55)
<223> OTHER INFORMATION: Xaa is Thr or Glu
<220> FEATURE:
<221> NAME/KEY: misc_feature
<222> LOCATION: (155)..(155)
<223> OTHER INFORMATION: Xaa is Asp or Glu
<220> FEATURE:
<221> NAME/KEY: misc_feature
<222> LOCATION: (157)..(157)
<223> OTHER INFORMATION: Xaa is Leu or Met
<220> FEATURE:
<221> NAME/KEY: misc_feature
<222> LOCATION: (227)..(227)
```

<223> OTHER INFORMATION: Xaa is Met or Leu
<220> FEATURE:
<221> NAME/KEY: misc_feature
<222> LOCATION: (233)..(233)
<223> OTHER INFORMATION: Xaa is Asn or Ser

<400> SEQUENCE: 78

```
Val Asn His Lys Pro Ser Asn Thr Lys Val Asp Lys Lys Val Glu Pro
1               5                   10                  15

Lys Ser Glx Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Xaa Ile Xaa Arg Xaa Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Xaa Glu Xaa Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Xaa His Glu Ala Leu His Xaa His Tyr Thr Gln Lys Ser Leu
225                 230                 235                 240

Ser Leu Ser Pro Gly Lys
                245
```

<210> SEQ ID NO 79
<211> LENGTH: 246
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (51)..(51)
<223> OTHER INFORMATION: Xaa is Met or Tyr
<220> FEATURE:
<221> NAME/KEY: misc_feature
<222> LOCATION: (53)..(53)
<223> OTHER INFORMATION: Xaa is Ser or Thr
<220> FEATURE:
<221> NAME/KEY: misc_feature
<222> LOCATION: (55)..(55)
<223> OTHER INFORMATION: Xaa is Thr or Glu
<220> FEATURE:
<221> NAME/KEY: misc_feature
<222> LOCATION: (155)..(155)
<223> OTHER INFORMATION: Xaa is Asp or Glu

```
<220> FEATURE:
<221> NAME/KEY: misc_feature
<222> LOCATION: (157)..(157)
<223> OTHER INFORMATION: Xaa is Leu or Met
<220> FEATURE:
<221> NAME/KEY: misc_feature
<222> LOCATION: (227)..(227)
<223> OTHER INFORMATION: Xaa is Met or Leu
<220> FEATURE:
<221> NAME/KEY: misc_feature
<222> LOCATION: (233)..(233)
<223> OTHER INFORMATION: Xaa is Asn or Ser

<400> SEQUENCE: 79

Val Asn His Lys Pro Ser Asn Thr Lys Val Asp Lys Lys Val Glu Pro
1               5                   10                  15

Lys Ser Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Xaa Ile Xaa Arg Xaa Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Xaa Glu Xaa Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Xaa His Glu Ala Leu His Xaa His Tyr Thr Gln Lys Ser Leu
225                 230                 235                 240

Ser Leu Ser Pro Gly Lys
                245

<210> SEQ ID NO 80
<211> LENGTH: 246
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (155)..(155)
<223> OTHER INFORMATION: Xaa is Asp or Glu
<220> FEATURE:
<221> NAME/KEY: misc_feature
<222> LOCATION: (157)..(157)
<223> OTHER INFORMATION: Xaa is Leu or Met
```

-continued

```
<400> SEQUENCE: 80

Val Asn His Lys Pro Ser Asn Thr Lys Val Asp Lys Lys Val Glu Pro
1               5                   10                  15

Lys Ser Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Xaa Glu Xaa Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245

<210> SEQ ID NO 81
<211> LENGTH: 246
<212> TYPE: PRT
<213> ORGANISM: Artificial Sequence
<220> FEATURE:
<223> OTHER INFORMATION: Synthetic Construct

<400> SEQUENCE: 81

Val Asn His Lys Pro Ser Asn Thr Lys Val Asp Lys Lys Val Glu Pro
1               5                   10                  15

Lys Ser Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
```

-continued

```
                100                 105                 110
Leu Asn Gly Lys Glu Tyr Lys Cys Lys Val Ser Asn Lys Ala Leu Pro
            115                 120                 125

Ala Pro Ile Glu Lys Thr Ile Ser Lys Ala Lys Gly Gln Pro Arg Glu
        130                 135                 140

Pro Gln Val Tyr Thr Leu Pro Pro Ser Arg Glu Met Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245

<210> SEQ ID NO 82
<211> LENGTH: 246
<212> TYPE: PRT
<213> ORGANISM: Artificial Sequence
<220> FEATURE:
<223> OTHER INFORMATION: Synthetic Construct

<400> SEQUENCE: 82

Val Asn His Lys Pro Ser Asn Thr Lys Val Asp Lys Lys Val Glu Pro
1               5                   10                  15

Lys Ser Ser Asp Lys Thr His Thr Cys Pro Pro Cys Pro Ala Pro Glu
                20                  25                  30

Leu Leu Gly Gly Pro Ser Val Phe Leu Phe Pro Pro Lys Pro Lys Asp
            35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
```

```
            210                 215                 220
Ser Val Met His Glu Ala Leu His Asn His Tyr Thr Gln Lys Ser Leu
225                 230                 235                 240

Ser Leu Ser Pro Gly Lys
                245

<210> SEQ ID NO 83
<211> LENGTH: 246
<212> TYPE: PRT
<213> ORGANISM: Artificial Sequence
<220> FEATURE:
<223> OTHER INFORMATION: Synthetic Construct

<400> SEQUENCE: 83

Val Asn His Lys Pro Ser Asn Thr Lys Val Asp Lys Lys Val Glu Pro
1               5                   10                  15

Lys Ser Ser Asp Lys Thr His Thr Cys Pro Pro Cys Pro Ala Pro Glu
                20                  25                  30

Leu Leu Gly Gly Pro Ser Val Phe Leu Phe Pro Pro Lys Pro Lys Asp
            35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Leu His Glu Ala Leu His Ser His Tyr Thr Gln Lys Ser Leu
225                 230                 235                 240

Ser Leu Ser Pro Gly Lys
                245

<210> SEQ ID NO 84
<211> LENGTH: 246
<212> TYPE: PRT
<213> ORGANISM: Artificial Sequence
<220> FEATURE:
<223> OTHER INFORMATION: Synthetic Construct

<400> SEQUENCE: 84

Val Asn His Lys Pro Ser Asn Thr Lys Val Asp Lys Lys Val Glu Pro
1               5                   10                  15
```

```
Lys Ser Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
 50                  55                  60

Val Ser His Glu Asp Pro Glu Val Lys Phe Asn Trp Tyr Val Asp Gly
 65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
                100                 105                 110

Leu Asn Gly Lys Glu Tyr Lys Cys Lys Val Ser Asn Lys Ala Leu Pro
            115                 120                 125

Ala Pro Ile Glu Lys Thr Ile Ser Lys Ala Lys Gly Gln Pro Arg Glu
        130                 135                 140

Pro Gln Val Tyr Thr Leu Pro Pro Ser Arg Glu Glu Met Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
210                 215                 220

Ser Val Leu His Glu Ala Leu His Ser His Tyr Thr Gln Lys Ser Leu
225                 230                 235                 240

Ser Leu Ser Pro Gly Lys
                245

<210> SEQ ID NO 85
<211> LENGTH: 246
<212> TYPE: PRT
<213> ORGANISM: Artificial Sequence
<220> FEATURE:
<223> OTHER INFORMATION: Synthetic Construct

<400> SEQUENCE: 85

Val Asn His Lys Pro Ser Asn Thr Lys Val Asp Lys Lys Val Glu Pro
1               5                   10                  15

Lys Ser Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Tyr Ile Thr Arg Glu Pro Glu Val Thr Cys Val Val Val Asp
 50                  55                  60

Val Ser His Glu Asp Pro Glu Val Lys Phe Asn Trp Tyr Val Asp Gly
 65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
                100                 105                 110

Leu Asn Gly Lys Glu Tyr Lys Cys Lys Val Ser Asn Lys Ala Leu Pro
            115                 120                 125
```

```
Ala Pro Ile Glu Lys Thr Ile Ser Lys Ala Lys Gly Gln Pro Arg Glu
130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245

<210> SEQ ID NO 86
<211> LENGTH: 246
<212> TYPE: PRT
<213> ORGANISM: Artificial Sequence
<220> FEATURE:
<223> OTHER INFORMATION: Synthetic Construct

<400> SEQUENCE: 86

Val Asn His Lys Pro Ser Asn Thr Lys Val Asp Lys Lys Val Glu Pro
1               5                   10                  15

Lys Ser Ser Asp Lys Thr His Thr Cys Pro Pro Cys Pro Ala Pro Glu
                20                  25                  30

Leu Leu Gly Gly Pro Ser Val Phe Leu Phe Pro Pro Lys Pro Lys Asp
            35                  40                  45

Thr Leu Tyr Ile Thr Arg Glu Pro Glu Val Thr Cys Val Val Val Asp
        50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
                100                 105                 110

Leu Asn Gly Lys Glu Tyr Lys Cys Lys Val Ser Asn Lys Ala Leu Pro
            115                 120                 125

Ala Pro Ile Glu Lys Thr Ile Ser Lys Ala Lys Gly Gln Pro Arg Glu
130                 135                 140

Pro Gln Val Tyr Thr Leu Pro Pro Ser Arg Glu Glu Met Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240
```

Ser Leu Ser Pro Gly Lys
            245

<210> SEQ ID NO 87
<211> LENGTH: 245
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (19)..(19)
<223> OTHER INFORMATION: Glx is Cys or Ser
<220> FEATURE:
<221> NAME/KEY: misc_feature
<222> LOCATION: (51)..(51)
<223> OTHER INFORMATION: Xaa is Met or Tyr
<220> FEATURE:
<221> NAME/KEY: misc_feature
<222> LOCATION: (53)..(53)
<223> OTHER INFORMATION: Xaa is Ser or Thr
<220> FEATURE:
<221> NAME/KEY: misc_feature
<222> LOCATION: (55)..(55)
<223> OTHER INFORMATION: Xaa is Thr or Glu
<220> FEATURE:
<221> NAME/KEY: misc_feature
<222> LOCATION: (155)..(155)
<223> OTHER INFORMATION: Xaa is Asp or Glu
<220> FEATURE:
<221> NAME/KEY: misc_feature
<222> LOCATION: (157)..(157)
<223> OTHER INFORMATION: Xaa is Leu or Met
<220> FEATURE:
<221> NAME/KEY: misc_feature
<222> LOCATION: (227)..(227)
<223> OTHER INFORMATION: Xaa is Met or Leu
<220> FEATURE:
<221> NAME/KEY: misc_feature
<222> LOCATION: (233)..(233)
<223> OTHER INFORMATION: Xaa is Asn or Ser

<400> SEQUENCE: 87

Val Asn His Lys Pro Ser Asn Thr Lys Val Asp Lys Lys Val Glu Pro
1               5                   10                  15

Lys Ser Glx Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Xaa Ile Xaa Arg Xaa Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Xaa Glu Xaa Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr

```
                   180                 185                 190
Thr Pro Pro Val Leu Asp Ser Asp Gly Ser Phe Phe Leu Tyr Ser Lys
            195                 200                 205

Leu Thr Val Asp Lys Ser Arg Trp Gln Gln Gly Asn Val Phe Ser Cys
        210                 215                 220

Ser Val Xaa His Glu Ala Leu His Xaa His Tyr Thr Gln Lys Ser Leu
225                 230                 235                 240

Ser Leu Ser Pro Gly
            245

<210> SEQ ID NO 88
<211> LENGTH: 245
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (51)..(51)
<223> OTHER INFORMATION: Xaa is Met or Tyr
<220> FEATURE:
<221> NAME/KEY: misc_feature
<222> LOCATION: (53)..(53)
<223> OTHER INFORMATION: Xaa is Ser or Thr
<220> FEATURE:
<221> NAME/KEY: misc_feature
<222> LOCATION: (55)..(55)
<223> OTHER INFORMATION: Xaa is Thr or Glu
<220> FEATURE:
<221> NAME/KEY: misc_feature
<222> LOCATION: (155)..(155)
<223> OTHER INFORMATION: Xaa is Asp or Glu
<220> FEATURE:
<221> NAME/KEY: misc_feature
<222> LOCATION: (157)..(157)
<223> OTHER INFORMATION: Xaa is Leu or Met
<220> FEATURE:
<221> NAME/KEY: misc_feature
<222> LOCATION: (227)..(227)
<223> OTHER INFORMATION: Xaa is Met or Leu
<220> FEATURE:
<221> NAME/KEY: misc_feature
<222> LOCATION: (233)..(233)
<223> OTHER INFORMATION: Xaa is Asn or Ser

<400> SEQUENCE: 88

Val Asn His Lys Pro Ser Asn Thr Lys Val Asp Lys Lys Val Glu Pro
1               5                   10                  15

Lys Ser Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Xaa Ile Xaa Arg Xaa Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140
```

```
Pro Gln Val Tyr Thr Leu Pro Pro Ser Arg Xaa Glu Xaa Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
                195                 200                 205

Leu Thr Val Asp Lys Ser Arg Trp Gln Gln Gly Asn Val Phe Ser Cys
        210                 215                 220

Ser Val Xaa His Glu Ala Leu His Xaa His Tyr Thr Gln Lys Ser Leu
225                 230                 235                 240

Ser Leu Ser Pro Gly
                245

<210> SEQ ID NO 89
<211> LENGTH: 245
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (155)..(155)
<223> OTHER INFORMATION: Xaa is Asp or Glu
<220> FEATURE:
<221> NAME/KEY: misc_feature
<222> LOCATION: (157)..(157)
<223> OTHER INFORMATION: Xaa is Leu or Met

<400> SEQUENCE: 89

Val Asn His Lys Pro Ser Asn Thr Lys Val Asp Lys Lys Val Glu Pro
1               5                   10                  15

Lys Ser Ser Asp Lys Thr His Thr Cys Pro Pro Cys Pro Ala Pro Glu
                20                  25                  30

Leu Leu Gly Gly Pro Ser Val Phe Leu Phe Pro Pro Lys Pro Lys Asp
            35                  40                  45

Thr Leu Met Ile Ser Arg Thr Pro Glu Val Thr Cys Val Val Val Asp
        50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Xaa Glu Xaa Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
                195                 200                 205

Leu Thr Val Asp Lys Ser Arg Trp Gln Gln Gly Asn Val Phe Ser Cys
```

```
                210                 215                 220
Ser Val Met His Glu Ala Leu His Asn His Tyr Thr Gln Lys Ser Leu
225                 230                 235                 240

Ser Leu Ser Pro Gly
                245

<210> SEQ ID NO 90
<211> LENGTH: 245
<212> TYPE: PRT
<213> ORGANISM: Artificial Sequence
<220> FEATURE:
<223> OTHER INFORMATION: Synthetic Construct

<400> SEQUENCE: 90

Val Asn His Lys Pro Ser Asn Thr Lys Val Asp Lys Lys Val Glu Pro
1               5                   10                  15

Lys Ser Ser Asp Lys Thr His Thr Cys Pro Pro Cys Pro Ala Pro Glu
                20                  25                  30

Leu Leu Gly Gly Pro Ser Val Phe Leu Phe Pro Pro Lys Pro Lys Asp
            35                  40                  45

Thr Leu Met Ile Ser Arg Thr Pro Glu Val Thr Cys Val Val Val Asp
50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Glu Glu Met Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly
                245

<210> SEQ ID NO 91
<211> LENGTH: 245
<212> TYPE: PRT
<213> ORGANISM: Artificial Sequence
<220> FEATURE:
<223> OTHER INFORMATION: Synthetic Construct

<400> SEQUENCE: 91

Val Asn His Lys Pro Ser Asn Thr Lys Val Asp Lys Lys Val Glu Pro
1               5                   10                  15
```

```
Lys Ser Ser Asp Lys Thr His Thr Cys Pro Pro Cys Pro Ala Pro Glu
                20                  25                  30

Leu Leu Gly Gly Pro Ser Val Phe Leu Phe Pro Pro Lys Pro Lys Asp
            35                  40                  45

Thr Leu Met Ile Ser Arg Thr Pro Glu Val Thr Cys Val Val Val Asp
 50                  55                  60

Val Ser His Glu Asp Pro Glu Val Lys Phe Asn Trp Tyr Val Asp Gly
 65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
                100                 105                 110

Leu Asn Gly Lys Glu Tyr Lys Cys Lys Val Ser Asn Lys Ala Leu Pro
            115                 120                 125

Ala Pro Ile Glu Lys Thr Ile Ser Lys Ala Lys Gly Gln Pro Arg Glu
        130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
210                 215                 220

Ser Val Met His Glu Ala Leu His Asn His Tyr Thr Gln Lys Ser Leu
225                 230                 235                 240

Ser Leu Ser Pro Gly
            245

<210> SEQ ID NO 92
<211> LENGTH: 245
<212> TYPE: PRT
<213> ORGANISM: Artificial Sequence
<220> FEATURE:
<223> OTHER INFORMATION: Synthetic Construct

<400> SEQUENCE: 92

Val Asn His Lys Pro Ser Asn Thr Lys Val Asp Lys Lys Val Glu Pro
 1               5                  10                  15

Lys Ser Ser Asp Lys Thr His Thr Cys Pro Pro Cys Pro Ala Pro Glu
                20                  25                  30

Leu Leu Gly Gly Pro Ser Val Phe Leu Phe Pro Pro Lys Pro Lys Asp
            35                  40                  45

Thr Leu Met Ile Ser Arg Thr Pro Glu Val Thr Cys Val Val Val Asp
 50                  55                  60

Val Ser His Glu Asp Pro Glu Val Lys Phe Asn Trp Tyr Val Asp Gly
 65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
                100                 105                 110

Leu Asn Gly Lys Glu Tyr Lys Cys Lys Val Ser Asn Lys Ala Leu Pro
            115                 120                 125
```

```
Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Leu His Glu Ala Leu His Ser His Tyr Thr Gln Lys Ser Leu
225                 230                 235                 240

Ser Leu Ser Pro Gly
                245

<210> SEQ ID NO 93
<211> LENGTH: 245
<212> TYPE: PRT
<213> ORGANISM: Artificial Sequence
<220> FEATURE:
<223> OTHER INFORMATION: Synthetic Construct

<400> SEQUENCE: 93

Val Asn His Lys Pro Ser Asn Thr Lys Val Asp Lys Val Glu Pro
1               5                   10                  15

Lys Ser Ser Asp Lys Thr His Thr Cys Pro Pro Cys Pro Ala Pro Glu
                20                  25                  30

Leu Leu Gly Gly Pro Ser Val Phe Leu Phe Pro Pro Lys Pro Lys Asp
            35                  40                  45

Thr Leu Met Ile Ser Arg Thr Pro Glu Val Thr Cys Val Val Val Asp
        50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
                100                 105                 110

Leu Asn Gly Lys Glu Tyr Lys Cys Lys Val Ser Asn Lys Ala Leu Pro
            115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Glu Glu Met Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Leu His Glu Ala Leu His Ser His Tyr Thr Gln Lys Ser Leu
225                 230                 235                 240
```

Ser Leu Ser Pro Gly
            245

<210> SEQ ID NO 94
<211> LENGTH: 245
<212> TYPE: PRT
<213> ORGANISM: Artificial Sequence
<220> FEATURE:
<223> OTHER INFORMATION: Synthetic Construct

<400> SEQUENCE: 94

Val Asn His Lys Pro Ser Asn Thr Lys Val Asp Lys Lys Val Glu Pro
1               5                   10                  15

Lys Ser Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Tyr Ile Thr Arg Glu Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly
            245

<210> SEQ ID NO 95
<211> LENGTH: 245
<212> TYPE: PRT
<213> ORGANISM: Artificial Sequence
<220> FEATURE:
<223> OTHER INFORMATION: Synthetic Construct

<400> SEQUENCE: 95

Val Asn His Lys Pro Ser Asn Thr Lys Val Asp Lys Lys Val Glu Pro
1               5                   10                  15

Lys Ser Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

```
Thr Leu Tyr Ile Thr Arg Glu Pro Glu Val Thr Cys Val Val Asp
    50                  55                  60
Val Ser His Glu Asp Pro Glu Val Lys Phe Asn Trp Tyr Val Asp Gly
 65                  70                  75                  80
Val Glu Val His Asn Ala Lys Thr Lys Pro Arg Glu Glu Gln Tyr Asn
                 85                  90                  95
Ser Thr Tyr Arg Val Val Ser Val Leu Thr Val Leu His Gln Asp Trp
            100                 105                 110
Leu Asn Gly Lys Glu Tyr Lys Cys Lys Val Ser Asn Lys Ala Leu Pro
        115                 120                 125
Ala Pro Ile Glu Lys Thr Ile Ser Lys Ala Lys Gly Gln Pro Arg Glu
    130                 135                 140
Pro Gln Val Tyr Thr Leu Pro Pro Ser Arg Glu Glu Met Thr Lys Asn
145                 150                 155                 160
Gln Val Ser Leu Thr Cys Leu Val Lys Gly Phe Tyr Pro Ser Asp Ile
                165                 170                 175
Ala Val Glu Trp Glu Ser Asn Gly Gln Pro Glu Asn Asn Tyr Lys Thr
            180                 185                 190
Thr Pro Pro Val Leu Asp Ser Asp Gly Ser Phe Phe Leu Tyr Ser Lys
        195                 200                 205
Leu Thr Val Asp Lys Ser Arg Trp Gln Gln Gly Asn Val Phe Ser Cys
    210                 215                 220
Ser Val Met His Glu Ala Leu His Asn His Tyr Thr Gln Lys Ser Leu
225                 230                 235                 240

Ser Leu Ser Pro Gly
            245

<210> SEQ ID NO 96
<211> LENGTH: 247
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa is Asn or absent
<220> FEATURE:
<221> NAME/KEY: misc_feature
<222> LOCATION: (20)..(20)
<223> OTHER INFORMATION: Glx is Cys or Ser
<220> FEATURE:
<221> NAME/KEY: misc_feature
<222> LOCATION: (52)..(52)
<223> OTHER INFORMATION: Xaa is Met or Tyr
<220> FEATURE:
<221> NAME/KEY: misc_feature
<222> LOCATION: (54)..(54)
<223> OTHER INFORMATION: Xaa is Ser or Thr
<220> FEATURE:
<221> NAME/KEY: misc_feature
<222> LOCATION: (56)..(56)
<223> OTHER INFORMATION: Xaa is Thr or Glu
<220> FEATURE:
<221> NAME/KEY: misc_feature
<222> LOCATION: (97)..(97)
<223> OTHER INFORMATION: Xaa is Asn or Ala
<220> FEATURE:
<221> NAME/KEY: misc_feature
<222> LOCATION: (109)..(109)
<223> OTHER INFORMATION: Xaa is Leu or Asp
<220> FEATURE:
<221> NAME/KEY: misc_feature
<222> LOCATION: (111)..(111)
<223> OTHER INFORMATION: Xaa is Gln or His
```

<220> FEATURE:
<221> NAME/KEY: misc_feature
<222> LOCATION: (156)..(156)
<223> OTHER INFORMATION: Xaa is Asp or Glu
<220> FEATURE:
<221> NAME/KEY: misc_feature
<222> LOCATION: (158)..(158)
<223> OTHER INFORMATION: Xaa is Leu or Met
<220> FEATURE:
<221> NAME/KEY: misc_feature
<222> LOCATION: (228)..(228)
<223> OTHER INFORMATION: Xaa is Met or Leu
<220> FEATURE:
<221> NAME/KEY: misc_feature
<222> LOCATION: (234)..(234)
<223> OTHER INFORMATION: Xaa is Asn or Ser
<220> FEATURE:
<221> NAME/KEY: misc_feature
<222> LOCATION: (247)..(247)
<223> OTHER INFORMATION: Xaa is Lys or absent

<400> SEQUENCE: 96

Xaa Val Asn His Lys Pro Ser Asn Thr Lys Val Asp Lys Lys Val Glu
1               5                   10                  15

Pro Lys Ser Glx Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Xaa Ile Xaa Arg Xaa Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Xaa Ser Thr Tyr Arg Val Val Ser Val Leu Thr Val Xaa His Xaa Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Xaa Glu Xaa Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Xaa His Glu Ala Leu His Xaa His Tyr Thr Gln Lys Ser
225                 230                 235                 240

Leu Ser Leu Ser Pro Gly Xaa
                245

<210> SEQ ID NO 97
<211> LENGTH: 247
<212> TYPE: PRT
<213> ORGANISM: Artificial Sequence
<220> FEATURE:
<223> OTHER INFORMATION: Synthetic Construct
<220> FEATURE:

```
<221> NAME/KEY: misc_feature
<222> LOCATION: (1)..(1)
<223> OTHER INFORMATION: Xaa is Asn or absent
<220> FEATURE:
<221> NAME/KEY: misc_feature
<222> LOCATION: (97)..(97)
<223> OTHER INFORMATION: Xaa is Asn or Ala
<220> FEATURE:
<221> NAME/KEY: misc_feature
<222> LOCATION: (109)..(109)
<223> OTHER INFORMATION: Xaa i sLeu or Asp
<220> FEATURE:
<221> NAME/KEY: misc_feature
<222> LOCATION: (111)..(111)
<223> OTHER INFORMATION: Xaa is Gln or His
<220> FEATURE:
<221> NAME/KEY: misc_feature
<222> LOCATION: (156)..(156)
<223> OTHER INFORMATION: Xaa is Asp or Glu
<220> FEATURE:
<221> NAME/KEY: misc_feature
<222> LOCATION: (158)..(158)
<223> OTHER INFORMATION: Xaa is Leu or Met
<220> FEATURE:
<221> NAME/KEY: misc_feature
<222> LOCATION: (234)..(234)
<223> OTHER INFORMATION: Xaa is Asn or Ser
<220> FEATURE:
<221> NAME/KEY: misc_feature
<222> LOCATION: (247)..(247)
<223> OTHER INFORMATION: Xaa is Lys or absent

<400> SEQUENCE: 97

Xaa Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Xaa Ser Thr Tyr Arg Val Val Ser Val Leu Thr Val Xaa His Xaa Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
130                 135                 140

Glu Pro Gln Val Tyr Thr Leu Pro Pro Ser Arg Xaa Glu Xaa Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
210                 215                 220

Cys Ser Val Met His Glu Ala Leu His Xaa His Tyr Thr Gln Lys Ser
225                 230                 235                 240
```

```
Leu Ser Leu Ser Pro Gly Xaa
                245

<210> SEQ ID NO 98
<211> LENGTH: 247
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa is Asn or absent
<220> FEATURE:
<221> NAME/KEY: misc_feature
<222> LOCATION: (97)..(97)
<223> OTHER INFORMATION: Xaa is Asn or Ala
<220> FEATURE:
<221> NAME/KEY: misc_feature
<222> LOCATION: (156)..(156)
<223> OTHER INFORMATION: Xaa is Asp or Glu
<220> FEATURE:
<221> NAME/KEY: misc_feature
<222> LOCATION: (158)..(158)
<223> OTHER INFORMATION: Xaa is Leu or Met
<220> FEATURE:
<221> NAME/KEY: misc_feature
<222> LOCATION: (247)..(247)
<223> OTHER INFORMATION: Xaa is Lys or absent

<400> SEQUENCE: 98

Xaa Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Xaa Ser Thr Tyr Arg Val Val Ser Val Leu Thr Val Asp His His Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Xaa Glu Xaa Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Ser His Tyr Thr Gln Lys Ser
225                 230                 235                 240

Leu Ser Leu Ser Pro Gly Xaa
                245
```

```
<210> SEQ ID NO 99
<211> LENGTH: 247
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (97)..(97)
<223> OTHER INFORMATION: Xaa is Asn or Ala
<220> FEATURE:
<221> NAME/KEY: misc_feature
<222> LOCATION: (156)..(156)
<223> OTHER INFORMATION: Xaa is Asp or Glu
<220> FEATURE:
<221> NAME/KEY: misc_feature
<222> LOCATION: (158)..(158)
<223> OTHER INFORMATION: Xaa is Leu or Met

<400> SEQUENCE: 99
```

| Asn | Val | Asn | His | Lys | Pro | Ser | Asn | Thr | Lys | Val | Asp | Lys | Lys | Val | Glu |
|---|---|---|---|---|---|---|---|---|---|---|---|---|---|---|---|
| 1 | | | | 5 | | | | | 10 | | | | | 15 | |

| Pro | Lys | Ser | Ser | Asp | Lys | Thr | His | Thr | Cys | Pro | Pro | Cys | Pro | Ala | Pro |
|---|---|---|---|---|---|---|---|---|---|---|---|---|---|---|---|
| | | | 20 | | | | | 25 | | | | | 30 | | |

| Glu | Leu | Leu | Gly | Gly | Pro | Ser | Val | Phe | Leu | Phe | Pro | Pro | Lys | Pro | Lys |
|---|---|---|---|---|---|---|---|---|---|---|---|---|---|---|---|
| | | | 35 | | | | | 40 | | | | | 45 | | |

| Asp | Thr | Leu | Met | Ile | Ser | Arg | Thr | Pro | Glu | Val | Thr | Cys | Val | Val | Val |
|---|---|---|---|---|---|---|---|---|---|---|---|---|---|---|---|
| | 50 | | | | | 55 | | | | | 60 | | | | |

| Asp | Val | Ser | His | Glu | Asp | Pro | Glu | Val | Lys | Phe | Asn | Trp | Tyr | Val | Asp |
|---|---|---|---|---|---|---|---|---|---|---|---|---|---|---|---|
| 65 | | | | | 70 | | | | | 75 | | | | | 80 |

| Gly | Val | Glu | Val | His | Asn | Ala | Lys | Thr | Lys | Pro | Arg | Glu | Glu | Gln | Tyr |
|---|---|---|---|---|---|---|---|---|---|---|---|---|---|---|---|
| | | | | 85 | | | | | 90 | | | | | 95 | |

| Xaa | Ser | Thr | Tyr | Arg | Val | Val | Ser | Val | Leu | Thr | Val | Asp | His | His | Asp |
|---|---|---|---|---|---|---|---|---|---|---|---|---|---|---|---|
| | | | 100 | | | | | 105 | | | | | 110 | | |

| Trp | Leu | Asn | Gly | Lys | Glu | Tyr | Lys | Cys | Lys | Val | Ser | Asn | Lys | Ala | Leu |
|---|---|---|---|---|---|---|---|---|---|---|---|---|---|---|---|
| | | | 115 | | | | | 120 | | | | | 125 | | |

| Pro | Ala | Pro | Ile | Glu | Lys | Thr | Ile | Ser | Lys | Ala | Lys | Gly | Gln | Pro | Arg |
|---|---|---|---|---|---|---|---|---|---|---|---|---|---|---|---|
| | 130 | | | | | 135 | | | | | 140 | | | | |

| Glu | Pro | Gln | Val | Tyr | Thr | Leu | Pro | Pro | Ser | Arg | Xaa | Glu | Xaa | Thr | Lys |
|---|---|---|---|---|---|---|---|---|---|---|---|---|---|---|---|
| 145 | | | | | 150 | | | | | 155 | | | | | 160 |

| Asn | Gln | Val | Ser | Leu | Thr | Cys | Leu | Val | Lys | Gly | Phe | Tyr | Pro | Ser | Asp |
|---|---|---|---|---|---|---|---|---|---|---|---|---|---|---|---|
| | | | | 165 | | | | | 170 | | | | | 175 | |

| Ile | Ala | Val | Glu | Trp | Glu | Ser | Asn | Gly | Gln | Pro | Glu | Asn | Asn | Tyr | Lys |
|---|---|---|---|---|---|---|---|---|---|---|---|---|---|---|---|
| | | | 180 | | | | | 185 | | | | | 190 | | |

| Thr | Thr | Pro | Pro | Val | Leu | Asp | Ser | Asp | Gly | Ser | Phe | Phe | Leu | Tyr | Ser |
|---|---|---|---|---|---|---|---|---|---|---|---|---|---|---|---|
| | | | 195 | | | | | 200 | | | | | 205 | | |

| Lys | Leu | Thr | Val | Asp | Lys | Ser | Arg | Trp | Gln | Gln | Gly | Asn | Val | Phe | Ser |
|---|---|---|---|---|---|---|---|---|---|---|---|---|---|---|---|
| | 210 | | | | | 215 | | | | | 220 | | | | |

| Cys | Ser | Val | Met | His | Glu | Ala | Leu | His | Ser | His | Tyr | Thr | Gln | Lys | Ser |
|---|---|---|---|---|---|---|---|---|---|---|---|---|---|---|---|
| 225 | | | | | 230 | | | | | 235 | | | | | 240 |

| Leu | Ser | Leu | Ser | Pro | Gly | Lys |
|---|---|---|---|---|---|---|
| | | | | 245 | | |

```
<210> SEQ ID NO 100
<211> LENGTH: 247
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: misc_feature
<222> LOCATION: (156)..(156)
<223> OTHER INFORMATION: Xaa is Asp or Glu
<220> FEATURE:
<221> NAME/KEY: misc_feature
<222> LOCATION: (158)..(158)
<223> OTHER INFORMATION: Xaa is Leu or Met

<400> SEQUENCE: 100
```

Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Asp His His Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Xaa Glu Xaa Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Ser His Tyr Thr Gln Lys Ser
225                 230                 235                 240

Leu Ser Leu Ser Pro Gly Lys
                245

```
<210> SEQ ID NO 101
<211> LENGTH: 247
<212> TYPE: PRT
<213> ORGANISM: Artificial Sequence
<220> FEATURE:
<223> OTHER INFORMATION: Synthetic Construct

<400> SEQUENCE: 101
```

Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val

```
            50                  55                  60
Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                 85                  90                  95

Asn Ser Thr Tyr Arg Val Val Ser Val Leu Thr Val Asp His His Asp
                100                 105                 110

Trp Leu Asn Gly Lys Glu Tyr Lys Cys Lys Val Ser Asn Lys Ala Leu
                115                 120                 125

Pro Ala Pro Ile Glu Lys Thr Ile Ser Lys Ala Lys Gly Gln Pro Arg
            130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
        210                 215                 220

Cys Ser Val Met His Glu Ala Leu His Ser His Tyr Thr Gln Lys Ser
225                 230                 235                 240

Leu Ser Leu Ser Pro Gly Lys
                245

<210> SEQ ID NO 102
<211> LENGTH: 247
<212> TYPE: PRT
<213> ORGANISM: Artificial Sequence
<220> FEATURE:
<223> OTHER INFORMATION: Synthetic Construct

<400> SEQUENCE: 102

Asn Val Asn His Lys Pro Ser Asn Thr Lys Val Asp Lys Lys Val Glu
 1               5                  10                  15

Pro Lys Ser Ser Asp Lys Thr His Thr Cys Pro Pro Cys Pro Ala Pro
                20                  25                  30

Glu Leu Leu Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
 50                  55                 60

Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                 85                  90                  95

Asn Ser Thr Tyr Arg Val Val Ser Val Leu Thr Val Asp His His Asp
                100                 105                 110

Trp Leu Asn Gly Lys Glu Tyr Lys Cys Lys Val Ser Asn Lys Ala Leu
                115                 120                 125

Pro Ala Pro Ile Glu Lys Thr Ile Ser Lys Ala Lys Gly Gln Pro Arg
            130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
```

165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Ser His Tyr Thr Gln Lys Ser
225                 230                 235                 240

Leu Ser Leu Ser Pro Gly Lys
                245

<210> SEQ ID NO 103
<211> LENGTH: 246
<212> TYPE: PRT
<213> ORGANISM: Artificial Sequence
<220> FEATURE:
<223> OTHER INFORMATION: Synthetic Construct

<400> SEQUENCE: 103

Val Asn His Lys Pro Ser Asn Thr Lys Val Asp Lys Lys Val Glu Pro
1               5                   10                  15

Lys Ser Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Asp His His Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Ser His Tyr Thr Gln Lys Ser Leu
225                 230                 235                 240

Ser Leu Ser Pro Gly Lys
                245

<210> SEQ ID NO 104
<211> LENGTH: 246
<212> TYPE: PRT

<213> ORGANISM: Artificial Sequence
<220> FEATURE:
<223> OTHER INFORMATION: Synthetic Construct

<400> SEQUENCE: 104

```
Val Asn His Lys Pro Ser Asn Thr Lys Val Asp Lys Lys Val Glu Pro
1               5                   10                  15
Lys Ser Ser Asp Lys Thr His Thr Cys Pro Pro Cys Pro Ala Pro Glu
            20                  25                  30
Leu Leu Gly Gly Pro Ser Val Phe Leu Phe Pro Pro Lys Pro Lys Asp
        35                  40                  45
Thr Leu Met Ile Ser Arg Thr Pro Glu Val Thr Cys Val Val Val Asp
    50                  55                  60
Val Ser His Glu Asp Pro Glu Val Lys Phe Asn Trp Tyr Val Asp Gly
65                  70                  75                  80
Val Glu Val His Asn Ala Lys Thr Lys Pro Arg Glu Glu Gln Tyr Asn
                85                  90                  95
Ser Thr Tyr Arg Val Val Ser Val Leu Thr Val Asp His His Asp Trp
            100                 105                 110
Leu Asn Gly Lys Glu Tyr Lys Cys Lys Val Ser Asn Lys Ala Leu Pro
        115                 120                 125
Ala Pro Ile Glu Lys Thr Ile Ser Lys Ala Lys Gly Gln Pro Arg Glu
    130                 135                 140
Pro Gln Val Tyr Thr Leu Pro Pro Ser Arg Glu Glu Met Thr Lys Asn
145                 150                 155                 160
Gln Val Ser Leu Thr Cys Leu Val Lys Gly Phe Tyr Pro Ser Asp Ile
                165                 170                 175
Ala Val Glu Trp Glu Ser Asn Gly Gln Pro Glu Asn Asn Tyr Lys Thr
            180                 185                 190
Thr Pro Pro Val Leu Asp Ser Asp Gly Ser Phe Phe Leu Tyr Ser Lys
        195                 200                 205
Leu Thr Val Asp Lys Ser Arg Trp Gln Gln Gly Asn Val Phe Ser Cys
    210                 215                 220
Ser Val Met His Glu Ala Leu His Ser His Tyr Thr Gln Lys Ser Leu
225                 230                 235                 240
Ser Leu Ser Pro Gly Lys
                245
```

<210> SEQ ID NO 105
<211> LENGTH: 247
<212> TYPE: PRT
<213> ORGANISM: Artificial Sequence
<220> FEATURE:
<223> OTHER INFORMATION: Synthetic Construct

<400> SEQUENCE: 105

```
Asn Val Asn His Lys Pro Ser Asn Thr Lys Val Asp Lys Lys Val Glu
1               5                   10                  15
Pro Lys Ser Ser Asp Lys Thr His Thr Cys Pro Pro Cys Pro Ala Pro
            20                  25                  30
Glu Leu Leu Gly Gly Pro Ser Val Phe Leu Phe Pro Pro Lys Pro Lys
        35                  40                  45
Asp Thr Leu Met Ile Ser Arg Thr Pro Glu Val Thr Cys Val Val Val
    50                  55                  60
Asp Val Ser His Glu Asp Pro Glu Val Lys Phe Asn Trp Tyr Val Asp
65                  70                  75                  80
```

```
Gly Val Glu Val His Asn Ala Lys Thr Lys Pro Arg Glu Glu Gln Tyr
                85                  90                  95

Asn Ser Thr Tyr Arg Val Val Ser Val Leu Thr Val Asp His His Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Ser His Tyr Thr Gln Lys Ser
225                 230                 235                 240

Leu Ser Leu Ser Pro Gly Lys
                245

<210> SEQ ID NO 106
<211> LENGTH: 247
<212> TYPE: PRT
<213> ORGANISM: Artificial Sequence
<220> FEATURE:
<223> OTHER INFORMATION: Synthetic Construct

<400> SEQUENCE: 106

Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Asp His His Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190
```

-continued

```
Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Ser His Tyr Thr Gln Lys Ser
225                 230                 235                 240

Leu Ser Leu Ser Pro Gly Lys
                245

<210> SEQ ID NO 107
<211> LENGTH: 245
<212> TYPE: PRT
<213> ORGANISM: Artificial Sequence
<220> FEATURE:
<223> OTHER INFORMATION: Synthetic Construct

<400> SEQUENCE: 107

Val Asn His Lys Pro Ser Asn Thr Lys Val Asp Lys Lys Val Glu Pro
1               5                   10                  15

Lys Ser Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Asp His His Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Ser His Tyr Thr Gln Lys Ser Leu
225                 230                 235                 240

Ser Leu Ser Pro Gly
                245

<210> SEQ ID NO 108
<211> LENGTH: 245
<212> TYPE: PRT
<213> ORGANISM: Artificial Sequence
<220> FEATURE:
<223> OTHER INFORMATION: Synthetic Construct

<400> SEQUENCE: 108
```

```
Val Asn His Lys Pro Ser Asn Thr Lys Val Asp Lys Val Glu Pro
1               5                   10                  15

Lys Ser Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
                35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Asp His His Asp Trp
                100                 105                 110

Leu Asn Gly Lys Glu Tyr Lys Cys Lys Val Ser Asn Lys Ala Leu Pro
                115                 120                 125

Ala Pro Ile Glu Lys Thr Ile Ser Lys Ala Lys Gly Gln Pro Arg Glu
            130                 135                 140

Pro Gln Val Tyr Thr Leu Pro Pro Ser Arg Glu Glu Met Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
            195                 200                 205

Leu Thr Val Asp Lys Ser Arg Trp Gln Gln Gly Asn Val Phe Ser Cys
    210                 215                 220

Ser Val Met His Glu Ala Leu His Ser His Tyr Thr Gln Lys Ser Leu
225                 230                 235                 240

Ser Leu Ser Pro Gly
                245

<210> SEQ ID NO 109
<211> LENGTH: 247
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (156)..(156)
<223> OTHER INFORMATION: Xaa is Asp or Glu
<220> FEATURE:
<221> NAME/KEY: misc_feature
<222> LOCATION: (158)..(158)
<223> OTHER INFORMATION: Xaa is Leu or Met

<400> SEQUENCE: 109

Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
                20                  25                  30

Glu Leu Leu Gly Gly Pro Ser Val Phe Leu Phe Pro Pro Lys Pro Lys
                35                  40                  45

Asp Thr Leu Met Ile Ser Arg Thr Pro Glu Val Thr Cys Val Val Val
    50                  55                  60
```

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Ala Ser Thr Tyr Arg Val Val Ser Val Leu Thr Val Asp His His Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Xaa Glu Xaa Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Ser His Tyr Thr Gln Lys Ser
225                 230                 235                 240

Leu Ser Leu Ser Pro Gly Lys
                245

<210> SEQ ID NO 110
<211> LENGTH: 247
<212> TYPE: PRT
<213> ORGANISM: Artificial Sequence
<220> FEATURE:
<223> OTHER INFORMATION: Synthetic Construct

<400> SEQUENCE: 110

Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
                20                  25                  30

Glu Leu Leu Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
        50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Ala Ser Thr Tyr Arg Val Val Ser Val Leu Thr Val Asp His His Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

-continued

```
Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Ser His Tyr Thr Gln Lys Ser
225                 230                 235                 240

Leu Ser Leu Ser Pro Gly Lys
                245

<210> SEQ ID NO 111
<211> LENGTH: 247
<212> TYPE: PRT
<213> ORGANISM: Artificial Sequence
<220> FEATURE:
<223> OTHER INFORMATION: Synthetic Construct

<400> SEQUENCE: 111

Asn Val Asn His Lys Pro Ser Asn Thr Lys Val Asp Lys Lys Val Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Ala Ser Thr Tyr Arg Val Val Ser Val Leu Thr Val Asp His His Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Ser His Tyr Thr Gln Lys Ser
225                 230                 235                 240

Leu Ser Leu Ser Pro Gly Lys
                245

<210> SEQ ID NO 112
<211> LENGTH: 246
<212> TYPE: PRT
<213> ORGANISM: Artificial Sequence
<220> FEATURE:
```

<223> OTHER INFORMATION: Synthetic Construct

<400> SEQUENCE: 112

```
Val Asn His Lys Pro Ser Asn Thr Lys Val Asp Lys Lys Val Glu Pro
1               5                   10                  15

Lys Ser Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Ala
                85                  90                  95

Ser Thr Tyr Arg Val Val Ser Val Leu Thr Val Asp His His Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Ser His Tyr Thr Gln Lys Ser Leu
225                 230                 235                 240

Ser Leu Ser Pro Gly Lys
                245
```

<210> SEQ ID NO 113
<211> LENGTH: 246
<212> TYPE: PRT
<213> ORGANISM: Artificial Sequence
<220> FEATURE:
<223> OTHER INFORMATION: Synthetic Construct

<400> SEQUENCE: 113

```
Val Asn His Lys Pro Ser Asn Thr Lys Val Asp Lys Lys Val Glu Pro
1               5                   10                  15

Lys Ser Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Ala
                85                  90                  95
```

-continued

```
Ser Thr Tyr Arg Val Val Ser Val Leu Thr Val Asp His His Asp Trp
            100                 105                 110
Leu Asn Gly Lys Glu Tyr Lys Cys Lys Val Ser Asn Lys Ala Leu Pro
        115                 120                 125
Ala Pro Ile Glu Lys Thr Ile Ser Lys Ala Lys Gly Gln Pro Arg Glu
    130                 135                 140
Pro Gln Val Tyr Thr Leu Pro Pro Ser Arg Glu Glu Met Thr Lys Asn
145                 150                 155                 160
Gln Val Ser Leu Thr Cys Leu Val Lys Gly Phe Tyr Pro Ser Asp Ile
                165                 170                 175
Ala Val Glu Trp Glu Ser Asn Gly Gln Pro Glu Asn Asn Tyr Lys Thr
            180                 185                 190
Thr Pro Pro Val Leu Asp Ser Asp Gly Ser Phe Phe Leu Tyr Ser Lys
        195                 200                 205
Leu Thr Val Asp Lys Ser Arg Trp Gln Gln Gly Asn Val Phe Ser Cys
    210                 215                 220
Ser Val Met His Glu Ala Leu His Ser His Tyr Thr Gln Lys Ser Leu
225                 230                 235                 240
Ser Leu Ser Pro Gly Lys
                245

<210> SEQ ID NO 114
<211> LENGTH: 247
<212> TYPE: PRT
<213> ORGANISM: Artificial Sequence
<220> FEATURE:
<223> OTHER INFORMATION: Synthetic Construct

<400> SEQUENCE: 114

Asn Val Asn His Lys Pro Ser Asn Thr Lys Val Asp Lys Lys Val Glu
1               5                   10                  15
Pro Lys Ser Ser Asp Lys Thr His Thr Cys Pro Pro Cys Pro Ala Pro
            20                  25                  30
Glu Leu Leu Gly Gly Pro Ser Val Phe Leu Phe Pro Pro Lys Pro Lys
        35                  40                  45
Asp Thr Leu Met Ile Ser Arg Thr Pro Glu Val Thr Cys Val Val Val
    50                  55                  60
Asp Val Ser His Glu Asp Pro Glu Val Lys Phe Asn Trp Tyr Val Asp
65                  70                  75                  80
Gly Val Glu Val His Asn Ala Lys Thr Lys Pro Arg Glu Glu Gln Tyr
                85                  90                  95
Ala Ser Thr Tyr Arg Val Val Ser Val Leu Thr Val Asp His His Asp
            100                 105                 110
Trp Leu Asn Gly Lys Glu Tyr Lys Cys Lys Val Ser Asn Lys Ala Leu
        115                 120                 125
Pro Ala Pro Ile Glu Lys Thr Ile Ser Lys Ala Lys Gly Gln Pro Arg
    130                 135                 140
Glu Pro Gln Val Tyr Thr Leu Pro Pro Ser Arg Asp Glu Leu Thr Lys
145                 150                 155                 160
Asn Gln Val Ser Leu Thr Cys Leu Val Lys Gly Phe Tyr Pro Ser Asp
                165                 170                 175
Ile Ala Val Glu Trp Glu Ser Asn Gly Gln Pro Glu Asn Asn Tyr Lys
            180                 185                 190
Thr Thr Pro Pro Val Leu Asp Ser Asp Gly Ser Phe Phe Leu Tyr Ser
        195                 200                 205
```

```
Lys Leu Thr Val Asp Lys Ser Arg Trp Gln Gln Gly Asn Val Phe Ser
        210                 215                 220
Cys Ser Val Met His Glu Ala Leu His Ser His Tyr Thr Gln Lys Ser
225                 230                 235                 240
Leu Ser Leu Ser Pro Gly Lys
                245

<210> SEQ ID NO 115
<211> LENGTH: 247
<212> TYPE: PRT
<213> ORGANISM: Artificial Sequence
<220> FEATURE:
<223> OTHER INFORMATION: Synthetic Construct

<400> SEQUENCE: 115

Asn Val Asn His Lys Pro Ser Asn Thr Lys Val Asp Lys Lys Val Glu
1               5                   10                  15
Pro Lys Ser Ser Asp Lys Thr His Thr Cys Pro Pro Cys Pro Ala Pro
            20                  25                  30
Glu Leu Leu Gly Gly Pro Ser Val Phe Leu Phe Pro Pro Lys Pro Lys
        35                  40                  45
Asp Thr Leu Met Ile Ser Arg Thr Pro Glu Val Thr Cys Val Val Val
    50                  55                  60
Asp Val Ser His Glu Asp Pro Glu Val Lys Phe Asn Trp Tyr Val Asp
65                  70                  75                  80
Gly Val Glu Val His Asn Ala Lys Thr Lys Pro Arg Glu Glu Gln Tyr
                85                  90                  95
Ala Ser Thr Tyr Arg Val Val Ser Val Leu Thr Val Asp His His Asp
            100                 105                 110
Trp Leu Asn Gly Lys Glu Tyr Lys Cys Lys Val Ser Asn Lys Ala Leu
        115                 120                 125
Pro Ala Pro Ile Glu Lys Thr Ile Ser Lys Ala Lys Gly Gln Pro Arg
    130                 135                 140
Glu Pro Gln Val Tyr Thr Leu Pro Pro Ser Arg Glu Glu Met Thr Lys
145                 150                 155                 160
Asn Gln Val Ser Leu Thr Cys Leu Val Lys Gly Phe Tyr Pro Ser Asp
                165                 170                 175
Ile Ala Val Glu Trp Glu Ser Asn Gly Gln Pro Glu Asn Asn Tyr Lys
            180                 185                 190
Thr Thr Pro Pro Val Leu Asp Ser Asp Gly Ser Phe Phe Leu Tyr Ser
        195                 200                 205
Lys Leu Thr Val Asp Lys Ser Arg Trp Gln Gln Gly Asn Val Phe Ser
    210                 215                 220
Cys Ser Val Met His Glu Ala Leu His Ser His Tyr Thr Gln Lys Ser
225                 230                 235                 240
Leu Ser Leu Ser Pro Gly Lys
                245

<210> SEQ ID NO 116
<211> LENGTH: 245
<212> TYPE: PRT
<213> ORGANISM: Artificial Sequence
<220> FEATURE:
<223> OTHER INFORMATION: Synthetic Construct

<400> SEQUENCE: 116

Val Asn His Lys Pro Ser Asn Thr Lys Val Asp Lys Lys Val Glu Pro
```

-continued

```
              1               5                  10                 15
            Lys Ser Ser Asp Lys Thr His Thr Cys Pro Pro Cys Pro Ala Pro Glu
                            20                  25                 30

Leu Leu Gly Gly Pro Ser Val Phe Leu Phe Pro Pro Lys Pro Lys Asp
                            35                  40                 45

Thr Leu Met Ile Ser Arg Thr Pro Glu Val Thr Cys Val Val Val Asp
                            50                  55                 60

Val Ser His Glu Asp Pro Glu Val Lys Phe Asn Trp Tyr Val Asp Gly
             65                 70                  75                 80

Val Glu Val His Asn Ala Lys Thr Lys Pro Arg Glu Glu Gln Tyr Ala
                            85                  90                 95

Ser Thr Tyr Arg Val Val Ser Val Leu Thr Val Asp His His Asp Trp
                            100                 105                110

Leu Asn Gly Lys Glu Tyr Lys Cys Lys Val Ser Asn Lys Ala Leu Pro
                            115                 120                125

Ala Pro Ile Glu Lys Thr Ile Ser Lys Ala Lys Gly Gln Pro Arg Glu
                            130                 135                140

Pro Gln Val Tyr Thr Leu Pro Pro Ser Arg Asp Glu Leu Thr Lys Asn
            145                 150                 155                160

Gln Val Ser Leu Thr Cys Leu Val Lys Gly Phe Tyr Pro Ser Asp Ile
                            165                 170                175

Ala Val Glu Trp Glu Ser Asn Gly Gln Pro Glu Asn Asn Tyr Lys Thr
                            180                 185                190

Thr Pro Pro Val Leu Asp Ser Asp Gly Ser Phe Phe Leu Tyr Ser Lys
                            195                 200                205

Leu Thr Val Asp Lys Ser Arg Trp Gln Gln Gly Asn Val Phe Ser Cys
                            210                 215                220

Ser Val Met His Glu Ala Leu His Ser His Tyr Thr Gln Lys Ser Leu
            225                 230                 235                240

Ser Leu Ser Pro Gly
                            245
```

<210> SEQ ID NO 117
<211> LENGTH: 245
<212> TYPE: PRT
<213> ORGANISM: Artificial Sequence
<220> FEATURE:
<223> OTHER INFORMATION: Synthetic Construct

<400> SEQUENCE: 117

```
            Val Asn His Lys Pro Ser Asn Thr Lys Val Asp Lys Lys Val Glu Pro
             1               5                  10                 15

Lys Ser Ser Asp Lys Thr His Thr Cys Pro Pro Cys Pro Ala Pro Glu
                            20                  25                 30

Leu Leu Gly Gly Pro Ser Val Phe Leu Phe Pro Pro Lys Pro Lys Asp
                            35                  40                 45

Thr Leu Met Ile Ser Arg Thr Pro Glu Val Thr Cys Val Val Val Asp
                            50                  55                 60

Val Ser His Glu Asp Pro Glu Val Lys Phe Asn Trp Tyr Val Asp Gly
             65                 70                  75                 80

Val Glu Val His Asn Ala Lys Thr Lys Pro Arg Glu Glu Gln Tyr Ala
                            85                  90                 95

Ser Thr Tyr Arg Val Val Ser Val Leu Thr Val Asp His His Asp Trp
                            100                 105                110

Leu Asn Gly Lys Glu Tyr Lys Cys Lys Val Ser Asn Lys Ala Leu Pro
```

```
              115                 120                 125
Ala Pro Ile Glu Lys Thr Ile Ser Lys Ala Lys Gly Gln Pro Arg Glu
    130                 135                 140

Pro Gln Val Tyr Thr Leu Pro Pro Ser Arg Glu Glu Met Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Ser His Tyr Thr Gln Lys Ser Leu
225                 230                 235                 240

Ser Leu Ser Pro Gly
                245

<210> SEQ ID NO 118
<211> LENGTH: 247
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa is Asn or absent
<220> FEATURE:
<221> NAME/KEY: misc_feature
<222> LOCATION: (97)..(97)
<223> OTHER INFORMATION: Xaa is Asn or Ala
<220> FEATURE:
<221> NAME/KEY: misc_feature
<222> LOCATION: (109)..(109)
<223> OTHER INFORMATION: Xaa is Leu or Asp
<220> FEATURE:
<221> NAME/KEY: misc_feature
<222> LOCATION: (111)..(111)
<223> OTHER INFORMATION: Xaa is Gln or His
<220> FEATURE:
<221> NAME/KEY: misc_feature
<222> LOCATION: (156)..(156)
<223> OTHER INFORMATION: Xaa is Asp or Glu
<220> FEATURE:
<221> NAME/KEY: misc_feature
<222> LOCATION: (158)..(158)
<223> OTHER INFORMATION: Xaa is Leu or Met
<220> FEATURE:
<221> NAME/KEY: misc_feature
<222> LOCATION: (234)..(234)
<223> OTHER INFORMATION: Xaa is Asn or Ser
<220> FEATURE:
<221> NAME/KEY: misc_feature
<222> LOCATION: (247)..(247)
<223> OTHER INFORMATION: Xaa is Lys or absent

<400> SEQUENCE: 118

Xaa Val Asn His Lys Pro Ser Asn Thr Lys Val Asp Lys Lys Val Glu
1               5                   10                  15

Pro Lys Ser Cys Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60
```

```
Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                 85                  90                  95

Xaa Ser Thr Tyr Arg Val Val Ser Val Leu Thr Val Xaa His Xaa Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Xaa Glu Xaa Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Xaa His Tyr Thr Gln Lys Ser
225                 230                 235                 240

Leu Ser Leu Ser Pro Gly Xaa
                245

<210> SEQ ID NO 119
<211> LENGTH: 247
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa is Asn or absent
<220> FEATURE:
<221> NAME/KEY: misc_feature
<222> LOCATION: (97)..(97)
<223> OTHER INFORMATION: Xaa is Asn or Ala
<220> FEATURE:
<221> NAME/KEY: misc_feature
<222> LOCATION: (156)..(156)
<223> OTHER INFORMATION: Xaa is Asp or Glu
<220> FEATURE:
<221> NAME/KEY: misc_feature
<222> LOCATION: (158)..(158)
<223> OTHER INFORMATION: Xaa is Leu or Met
<220> FEATURE:
<221> NAME/KEY: misc_feature
<222> LOCATION: (247)..(247)
<223> OTHER INFORMATION: Xaa is Lys or absent

<400> SEQUENCE: 119

Xaa Val Asn His Lys Pro Ser Asn Thr Lys Val Asp Lys Lys Val Glu
 1               5                  10                  15

Pro Lys Ser Cys Asp Lys Thr His Thr Cys Pro Pro Cys Pro Ala Pro
             20                  25                  30

Glu Leu Leu Gly Gly Pro Ser Val Phe Leu Phe Pro Pro Lys Pro Lys
         35                  40                  45

Asp Thr Leu Met Ile Ser Arg Thr Pro Glu Val Thr Cys Val Val Val
     50                  55                  60
```

```
Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                 85                  90                  95

Xaa Ser Thr Tyr Arg Val Val Ser Val Leu Thr Val Asp His His Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
130                 135                 140

Glu Pro Gln Val Tyr Thr Leu Pro Pro Ser Arg Xaa Glu Xaa Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
210                 215                 220

Cys Ser Val Met His Glu Ala Leu His Ser His Tyr Thr Gln Lys Ser
225                 230                 235                 240

Leu Ser Leu Ser Pro Gly Xaa
                245

<210> SEQ ID NO 120
<211> LENGTH: 247
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (97)..(97)
<223> OTHER INFORMATION: Xaa is Asn or Ala
<220> FEATURE:
<221> NAME/KEY: misc_feature
<222> LOCATION: (156)..(156)
<223> OTHER INFORMATION: Xaa is Asp or Glu
<220> FEATURE:
<221> NAME/KEY: misc_feature
<222> LOCATION: (158)..(158)
<223> OTHER INFORMATION: Xaa is Leu or Met

<400> SEQUENCE: 120

Asn Val Asn His Lys Pro Ser Asn Thr Lys Val Asp Lys Lys Val Glu
 1               5                  10                  15

Pro Lys Ser Cys Asp Lys Thr His Thr Cys Pro Pro Cys Pro Ala Pro
             20                  25                  30

Glu Leu Leu Gly Gly Pro Ser Val Phe Leu Phe Pro Pro Lys Pro Lys
         35                  40                  45

Asp Thr Leu Met Ile Ser Arg Thr Pro Glu Val Thr Cys Val Val Val
     50                  55                  60

Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                 85                  90                  95

Xaa Ser Thr Tyr Arg Val Val Ser Val Leu Thr Val Asp His His Asp
            100                 105                 110
```

```
Trp Leu Asn Gly Lys Glu Tyr Lys Cys Lys Val Ser Asn Lys Ala Leu
            115                 120                 125

Pro Ala Pro Ile Glu Lys Thr Ile Ser Lys Ala Lys Gly Gln Pro Arg
130                 135                 140

Glu Pro Gln Val Tyr Thr Leu Pro Pro Ser Arg Xaa Glu Xaa Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
            195                 200                 205

Lys Leu Thr Val Asp Lys Ser Arg Trp Gln Gln Gly Asn Val Phe Ser
    210                 215                 220

Cys Ser Val Met His Glu Ala Leu His Ser His Tyr Thr Gln Lys Ser
225                 230                 235                 240

Leu Ser Leu Ser Pro Gly Lys
                245

<210> SEQ ID NO 121
<211> LENGTH: 247
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (156)..(156)
<223> OTHER INFORMATION: Xaa is Asp or Glu
<220> FEATURE:
<221> NAME/KEY: misc_feature
<222> LOCATION: (158)..(158)
<223> OTHER INFORMATION: Xaa is Leu or Met

<400> SEQUENCE: 121

Asn Val Asn His Lys Pro Ser Asn Thr Lys Val Asp Lys Lys Val Glu
1               5                   10                  15

Pro Lys Ser Cys Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Asp His His Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
130                 135                 140

Glu Pro Gln Val Tyr Thr Leu Pro Pro Ser Arg Xaa Glu Xaa Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
```

```
                180                 185                 190

Thr Thr Pro Pro Val Leu Asp Ser Asp Gly Ser Phe Phe Leu Tyr Ser
            195                 200                 205

Lys Leu Thr Val Asp Lys Ser Arg Trp Gln Gln Gly Asn Val Phe Ser
        210                 215                 220

Cys Ser Val Met His Glu Ala Leu His Ser His Tyr Thr Gln Lys Ser
225                 230                 235                 240

Leu Ser Leu Ser Pro Gly Lys
                245

<210> SEQ ID NO 122
<211> LENGTH: 247
<212> TYPE: PRT
<213> ORGANISM: Artificial Sequence
<220> FEATURE:
<223> OTHER INFORMATION: Synthetic Construct

<400> SEQUENCE: 122

Asn Val Asn His Lys Pro Ser Asn Thr Lys Val Asp Lys Lys Val Glu
1               5                   10                  15

Pro Lys Ser Cys Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Asp His His Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Ser His Tyr Thr Gln Lys Ser
225                 230                 235                 240

Leu Ser Leu Ser Pro Gly Lys
                245

<210> SEQ ID NO 123
<211> LENGTH: 247
<212> TYPE: PRT
<213> ORGANISM: Artificial Sequence
<220> FEATURE:
<223> OTHER INFORMATION: Synthetic Construct
```

<400> SEQUENCE: 123

| | | | | | | | | | | | | |
|---|---|---|---|---|---|---|---|---|---|---|---|---|
|Asn|Val|Asn|His|Lys|Pro|Ser|Asn|Thr|Lys|Val|Asp|Lys|Lys|Val|Glu
|1| | | |5| | | | |10| | | | |15| |

Pro Lys Ser Cys Asp Lys Thr His Thr Cys Pro Pro Cys Pro Ala Pro
                20                  25                  30

Glu Leu Leu Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
     50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Asp His His Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Ser His Tyr Thr Gln Lys Ser
225                 230                 235                 240

Leu Ser Leu Ser Pro Gly Lys
                245

<210> SEQ ID NO 124
<211> LENGTH: 246
<212> TYPE: PRT
<213> ORGANISM: Artificial Sequence
<220> FEATURE:
<223> OTHER INFORMATION: Synthetic Construct

<400> SEQUENCE: 124

Val Asn His Lys Pro Ser Asn Thr Lys Val Asp Lys Lys Val Glu Pro
1               5                   10                  15

Lys Ser Cys Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

```
Ser Thr Tyr Arg Val Val Ser Val Leu Thr Val Asp His His Asp Trp
                100                 105                 110

Leu Asn Gly Lys Glu Tyr Lys Cys Lys Val Ser Asn Lys Ala Leu Pro
            115                 120                 125

Ala Pro Ile Glu Lys Thr Ile Ser Lys Ala Lys Gly Gln Pro Arg Glu
        130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
210                 215                 220

Ser Val Met His Glu Ala Leu His Ser His Tyr Thr Gln Lys Ser Leu
225                 230                 235                 240

Ser Leu Ser Pro Gly Lys
                245

<210> SEQ ID NO 125
<211> LENGTH: 246
<212> TYPE: PRT
<213> ORGANISM: Artificial Sequence
<220> FEATURE:
<223> OTHER INFORMATION: Synthetic Construct

<400> SEQUENCE: 125

Val Asn His Lys Pro Ser Asn Thr Lys Val Asp Lys Lys Val Glu Pro
1               5                   10                  15

Lys Ser Cys Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Asp His His Asp Trp
                100                 105                 110

Leu Asn Gly Lys Glu Tyr Lys Cys Lys Val Ser Asn Lys Ala Leu Pro
            115                 120                 125

Ala Pro Ile Glu Lys Thr Ile Ser Lys Ala Lys Gly Gln Pro Arg Glu
        130                 135                 140

Pro Gln Val Tyr Thr Leu Pro Pro Ser Arg Glu Met Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205
```

-continued

Leu Thr Val Asp Lys Ser Arg Trp Gln Gln Gly Asn Val Phe Ser Cys
    210                 215                 220

Ser Val Met His Glu Ala Leu His Ser His Tyr Thr Gln Lys Ser Leu
225                 230                 235                 240

Ser Leu Ser Pro Gly Lys
            245

<210> SEQ ID NO 126
<211> LENGTH: 247
<212> TYPE: PRT
<213> ORGANISM: Artificial Sequence
<220> FEATURE:
<223> OTHER INFORMATION: Synthetic Construct

<400> SEQUENCE: 126

Asn Val Asn His Lys Pro Ser Asn Thr Lys Val Asp Lys Lys Val Glu
1               5                   10                  15

Pro Lys Ser Cys Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Asp His His Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Ser His Tyr Thr Gln Lys Ser
225                 230                 235                 240

Leu Ser Leu Ser Pro Gly Lys
                245

<210> SEQ ID NO 127
<211> LENGTH: 247
<212> TYPE: PRT
<213> ORGANISM: Artificial Sequence
<220> FEATURE:
<223> OTHER INFORMATION: Synthetic Construct

<400> SEQUENCE: 127

Asn Val Asn His Lys Pro Ser Asn Thr Lys Val Asp Lys Lys Val Glu
1               5                   10                  15

-continued

```
Pro Lys Ser Cys Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
 50                  55                  60

Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Asp His His Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Ser His Tyr Thr Gln Lys Ser
225                 230                 235                 240

Leu Ser Leu Ser Pro Gly Lys
                245
```

<210> SEQ ID NO 128
<211> LENGTH: 245
<212> TYPE: PRT
<213> ORGANISM: Artificial Sequence
<220> FEATURE:
<223> OTHER INFORMATION: Synthetic Construct

<400> SEQUENCE: 128

```
Val Asn His Lys Pro Ser Asn Thr Lys Val Asp Lys Lys Val Glu Pro
 1               5                  10                  15

Lys Ser Cys Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
 65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Asp His His Asp Trp
            100                 105                 110

Leu Asn Gly Lys Glu Tyr Lys Cys Lys Val Ser Asn Lys Ala Leu Pro
        115                 120                 125
```

```
Ala Pro Ile Glu Lys Thr Ile Ser Lys Ala Lys Gly Gln Pro Arg Glu
            130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
                195                 200                 205

Leu Thr Val Asp Lys Ser Arg Trp Gln Gln Gly Asn Val Phe Ser Cys
            210                 215                 220

Ser Val Met His Glu Ala Leu His Ser His Tyr Thr Gln Lys Ser Leu
225                 230                 235                 240

Ser Leu Ser Pro Gly
                245

<210> SEQ ID NO 129
<211> LENGTH: 245
<212> TYPE: PRT
<213> ORGANISM: Artificial Sequence
<220> FEATURE:
<223> OTHER INFORMATION: Synthetic Construct

<400> SEQUENCE: 129

Val Asn His Lys Pro Ser Asn Thr Lys Val Asp Lys Lys Val Glu Pro
1               5                   10                  15

Lys Ser Cys Asp Lys Thr His Thr Cys Pro Pro Cys Pro Ala Pro Glu
                20                  25                  30

Leu Leu Gly Gly Pro Ser Val Phe Leu Phe Pro Pro Lys Pro Lys Asp
            35                  40                  45

Thr Leu Met Ile Ser Arg Thr Pro Glu Val Thr Cys Val Val Val Asp
        50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Asp His His Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
            130                 135                 140

Pro Gln Val Tyr Thr Leu Pro Pro Ser Arg Glu Met Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
                195                 200                 205

Leu Thr Val Asp Lys Ser Arg Trp Gln Gln Gly Asn Val Phe Ser Cys
            210                 215                 220

Ser Val Met His Glu Ala Leu His Ser His Tyr Thr Gln Lys Ser Leu
225                 230                 235                 240
```

Ser Leu Ser Pro Gly
            245

<210> SEQ ID NO 130
<211> LENGTH: 247
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (156)..(156)
<223> OTHER INFORMATION: Xaa is Asp or Glu
<220> FEATURE:
<221> NAME/KEY: misc_feature
<222> LOCATION: (158)..(158)
<223> OTHER INFORMATION: Xaa is Leu or Met

<400> SEQUENCE: 130

Asn Val Asn His Lys Pro Ser Asn Thr Lys Val Asp Lys Lys Val Glu
1               5                   10                  15

Pro Lys Ser Cys Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Ala Ser Thr Tyr Arg Val Val Ser Val Leu Thr Val Asp His His Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Xaa Glu Xaa Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Ser His Tyr Thr Gln Lys Ser
225                 230                 235                 240

Leu Ser Leu Ser Pro Gly Lys
            245

<210> SEQ ID NO 131
<211> LENGTH: 247
<212> TYPE: PRT
<213> ORGANISM: Artificial Sequence
<220> FEATURE:
<223> OTHER INFORMATION: Synthetic Construct

<400> SEQUENCE: 131

Asn Val Asn His Lys Pro Ser Asn Thr Lys Val Asp Lys Val Glu
1               5                   10                  15

Pro Lys Ser Cys Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
        50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Ala Ser Thr Tyr Arg Val Val Ser Val Leu Thr Val Asp His His Asp
                100                 105                 110

Trp Leu Asn Gly Lys Glu Tyr Lys Cys Lys Val Ser Asn Lys Ala Leu
            115                 120                 125

Pro Ala Pro Ile Glu Lys Thr Ile Ser Lys Ala Lys Gly Gln Pro Arg
        130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
                180                 185                 190

Thr Thr Pro Pro Val Leu Asp Ser Asp Gly Ser Phe Phe Leu Tyr Ser
            195                 200                 205

Lys Leu Thr Val Asp Lys Ser Arg Trp Gln Gln Gly Asn Val Phe Ser
        210                 215                 220

Cys Ser Val Met His Glu Ala Leu His Ser His Tyr Thr Gln Lys Ser
225                 230                 235                 240

Leu Ser Leu Ser Pro Gly Lys
            245

<210> SEQ ID NO 132
<211> LENGTH: 247
<212> TYPE: PRT
<213> ORGANISM: Artificial Sequence
<220> FEATURE:
<223> OTHER INFORMATION: Synthetic Construct

<400> SEQUENCE: 132

Asn Val Asn His Lys Pro Ser Asn Thr Lys Val Asp Lys Val Glu
1               5                   10                  15

Pro Lys Ser Cys Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
        50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Ala Ser Thr Tyr Arg Val Val Ser Val Leu Thr Val Asp His His Asp
                100                 105                 110

```
Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Ser His Tyr Thr Gln Lys Ser
225                 230                 235                 240

Leu Ser Leu Ser Pro Gly Lys
                245

<210> SEQ ID NO 133
<211> LENGTH: 246
<212> TYPE: PRT
<213> ORGANISM: Artificial Sequence
<220> FEATURE:
<223> OTHER INFORMATION: Synthetic Construct

<400> SEQUENCE: 133

Val Asn His Lys Pro Ser Asn Thr Lys Val Asp Lys Lys Val Glu Pro
1               5                   10                  15

Lys Ser Cys Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Ala
                85                  90                  95

Ser Thr Tyr Arg Val Val Ser Val Leu Thr Val Asp His His Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220
```

```
Ser Val Met His Glu Ala Leu His Ser His Tyr Thr Gln Lys Ser Leu
225                 230                 235                 240

Ser Leu Ser Pro Gly Lys
                245

<210> SEQ ID NO 134
<211> LENGTH: 246
<212> TYPE: PRT
<213> ORGANISM: Artificial Sequence
<220> FEATURE:
<223> OTHER INFORMATION: Synthetic Construct

<400> SEQUENCE: 134

Val Asn His Lys Pro Ser Asn Thr Lys Val Asp Lys Val Glu Pro
1               5                   10                  15

Lys Ser Cys Asp Lys Thr His Thr Cys Pro Pro Cys Pro Ala Pro Glu
                20                  25                  30

Leu Leu Gly Gly Pro Ser Val Phe Leu Phe Pro Pro Lys Pro Lys Asp
            35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Ala
                85                  90                  95

Ser Thr Tyr Arg Val Val Ser Val Leu Thr Val Asp His His Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Glu Glu Met Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Ser His Tyr Thr Gln Lys Ser Leu
225                 230                 235                 240

Ser Leu Ser Pro Gly Lys
                245

<210> SEQ ID NO 135
<211> LENGTH: 247
<212> TYPE: PRT
<213> ORGANISM: Artificial Sequence
<220> FEATURE:
<223> OTHER INFORMATION: Synthetic Construct

<400> SEQUENCE: 135

Asn Val Asn His Lys Pro Ser Asn Thr Lys Val Asp Lys Lys Val Glu
1               5                   10                  15

Pro Lys Ser Cys Asp Lys Thr His Thr Cys Pro Pro Cys Pro Ala Pro
```

-continued

```
                20                  25                  30

Glu Leu Leu Gly Gly Pro Ser Val Phe Leu Phe Pro Lys Pro Lys
            35                  40                  45

Asp Thr Leu Met Ile Ser Arg Thr Pro Glu Val Thr Cys Val Val Val
 50                  55                  60

Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                85                  90                  95

Ala Ser Thr Tyr Arg Val Val Ser Val Leu Thr Val Asp His His Asp
            100                 105                 110

Trp Leu Asn Gly Lys Glu Tyr Lys Cys Lys Val Ser Asn Lys Ala Leu
            115                 120                 125

Pro Ala Pro Ile Glu Lys Thr Ile Ser Lys Ala Lys Gly Gln Pro Arg
130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
            195                 200                 205

Lys Leu Thr Val Asp Lys Ser Arg Trp Gln Gln Gly Asn Val Phe Ser
            210                 215                 220

Cys Ser Val Met His Glu Ala Leu His Ser His Tyr Thr Gln Lys Ser
225                 230                 235                 240

Leu Ser Leu Ser Pro Gly Lys
                245
```

<210> SEQ ID NO 136
<211> LENGTH: 247
<212> TYPE: PRT
<213> ORGANISM: Artificial Sequence
<220> FEATURE:
<223> OTHER INFORMATION: Synthetic Construct

<400> SEQUENCE: 136

```
Asn Val Asn His Lys Pro Ser Asn Thr Lys Val Asp Lys Lys Val Glu
 1               5                  10                  15

Pro Lys Ser Cys Asp Lys Thr His Thr Cys Pro Pro Cys Pro Ala Pro
                20                  25                  30

Glu Leu Leu Gly Gly Pro Ser Val Phe Leu Phe Pro Lys Pro Lys
            35                  40                  45

Asp Thr Leu Met Ile Ser Arg Thr Pro Glu Val Thr Cys Val Val Val
 50                  55                  60

Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                85                  90                  95

Ala Ser Thr Tyr Arg Val Val Ser Val Leu Thr Val Asp His His Asp
            100                 105                 110

Trp Leu Asn Gly Lys Glu Tyr Lys Cys Lys Val Ser Asn Lys Ala Leu
            115                 120                 125

Pro Ala Pro Ile Glu Lys Thr Ile Ser Lys Ala Lys Gly Gln Pro Arg
```

```
            130                 135                 140
Glu Pro Gln Val Tyr Thr Leu Pro Pro Ser Arg Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
                180                 185                 190

Thr Thr Pro Pro Val Leu Asp Ser Asp Gly Ser Phe Phe Leu Tyr Ser
            195                 200                 205

Lys Leu Thr Val Asp Lys Ser Arg Trp Gln Gln Gly Asn Val Phe Ser
        210                 215                 220

Cys Ser Val Met His Glu Ala Leu His Ser His Tyr Thr Gln Lys Ser
225                 230                 235                 240

Leu Ser Leu Ser Pro Gly Lys
                245

<210> SEQ ID NO 137
<211> LENGTH: 245
<212> TYPE: PRT
<213> ORGANISM: Artificial Sequence
<220> FEATURE:
<223> OTHER INFORMATION: Synthetic Construct

<400> SEQUENCE: 137

Val Asn His Lys Pro Ser Asn Thr Lys Val Asp Lys Lys Val Glu Pro
1               5                   10                  15

Lys Ser Cys Asp Lys Thr His Thr Cys Pro Pro Cys Pro Ala Pro Glu
                20                  25                  30

Leu Leu Gly Gly Pro Ser Val Phe Leu Phe Pro Pro Lys Pro Lys Asp
            35                  40                  45

Thr Leu Met Ile Ser Arg Thr Pro Glu Val Thr Cys Val Val Val Asp
        50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Ala
                85                  90                  95

Ser Thr Tyr Arg Val Val Ser Val Leu Thr Val Asp His His Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Ser His Tyr Thr Gln Lys Ser Leu
225                 230                 235                 240

Ser Leu Ser Pro Gly
```

<210> SEQ ID NO 138
<211> LENGTH: 245
<212> TYPE: PRT
<213> ORGANISM: Artificial Sequence
<220> FEATURE:
<223> OTHER INFORMATION: Synthetic Construct

<400> SEQUENCE: 138

```
Val Asn His Lys Pro Ser Asn Thr Lys Val Asp Lys Lys Val Glu Pro
1               5                   10                  15
Lys Ser Cys Asp Lys Thr His Thr Cys Pro Pro Cys Pro Ala Pro Glu
            20                  25                  30
Leu Leu Gly Gly Pro Ser Val Phe Leu Phe Pro Pro Lys Pro Lys Asp
        35                  40                  45
Thr Leu Met Ile Ser Arg Thr Pro Glu Val Thr Cys Val Val Val Asp
    50                  55                  60
Val Ser His Glu Asp Pro Glu Val Lys Phe Asn Trp Tyr Val Asp Gly
65                  70                  75                  80
Val Glu Val His Asn Ala Lys Thr Lys Pro Arg Glu Glu Gln Tyr Ala
                85                  90                  95
Ser Thr Tyr Arg Val Val Ser Val Leu Thr Val Asp His His Asp Trp
            100                 105                 110
Leu Asn Gly Lys Glu Tyr Lys Cys Lys Val Ser Asn Lys Ala Leu Pro
        115                 120                 125
Ala Pro Ile Glu Lys Thr Ile Ser Lys Ala Lys Gly Gln Pro Arg Glu
    130                 135                 140
Pro Gln Val Tyr Thr Leu Pro Pro Ser Arg Glu Glu Met Thr Lys Asn
145                 150                 155                 160
Gln Val Ser Leu Thr Cys Leu Val Lys Gly Phe Tyr Pro Ser Asp Ile
                165                 170                 175
Ala Val Glu Trp Glu Ser Asn Gly Gln Pro Glu Asn Asn Tyr Lys Thr
            180                 185                 190
Thr Pro Pro Val Leu Asp Ser Asp Gly Ser Phe Phe Leu Tyr Ser Lys
        195                 200                 205
Leu Thr Val Asp Lys Ser Arg Trp Gln Gln Gly Asn Val Phe Ser Cys
    210                 215                 220
Ser Val Met His Glu Ala Leu His Ser His Tyr Thr Gln Lys Ser Leu
225                 230                 235                 240
Ser Leu Ser Pro Gly
                245
```

<210> SEQ ID NO 139
<211> LENGTH: 585
<212> TYPE: PRT
<213> ORGANISM: Homo sapiens

<400> SEQUENCE: 139

```
Asp Ala His Lys Ser Glu Val Ala His Arg Phe Lys Asp Leu Gly Glu
1               5                   10                  15
Glu Asn Phe Lys Ala Leu Val Leu Ile Ala Phe Ala Gln Tyr Leu Gln
            20                  25                  30
Gln Cys Pro Phe Glu Asp His Val Lys Leu Val Asn Glu Val Thr Glu
        35                  40                  45
Phe Ala Lys Thr Cys Val Ala Asp Glu Ser Ala Glu Asn Cys Asp Lys
    50                  55                  60
```

-continued

```
Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480
```

```
Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 140
<211> LENGTH: 591
<212> TYPE: PRT
<213> ORGANISM: Homo sapiens

<400> SEQUENCE: 140

Arg Gly Val Phe Arg Arg Asp Ala His Lys Ser Glu Val Ala His Arg
1               5                   10                  15

Phe Lys Asp Leu Gly Glu Glu Asn Phe Lys Ala Leu Val Leu Ile Ala
            20                  25                  30

Phe Ala Gln Tyr Leu Gln Gln Cys Pro Phe Glu Asp His Val Lys Leu
        35                  40                  45

Val Asn Glu Val Thr Glu Phe Ala Lys Thr Cys Val Ala Asp Glu Ser
    50                  55                  60

Ala Glu Asn Cys Asp Lys Ser Leu His Thr Leu Phe Gly Asp Lys Leu
65                  70                  75                  80

Cys Thr Val Ala Thr Leu Arg Glu Thr Tyr Gly Glu Met Ala Asp Cys
                85                  90                  95

Cys Ala Lys Gln Glu Pro Glu Arg Asn Glu Cys Phe Leu Gln His Lys
            100                 105                 110

Asp Asp Asn Pro Asn Leu Pro Arg Leu Val Arg Pro Glu Val Asp Val
        115                 120                 125

Met Cys Thr Ala Phe His Asp Asn Glu Glu Thr Phe Leu Lys Lys Tyr
    130                 135                 140

Leu Tyr Glu Ile Ala Arg Arg His Pro Tyr Phe Tyr Ala Pro Glu Leu
145                 150                 155                 160

Leu Phe Phe Ala Lys Arg Tyr Lys Ala Ala Phe Thr Glu Cys Cys Gln
                165                 170                 175

Ala Ala Asp Lys Ala Ala Cys Leu Leu Pro Lys Leu Asp Glu Leu Arg
            180                 185                 190

Asp Glu Gly Lys Ala Ser Ser Ala Lys Gln Arg Leu Lys Cys Ala Ser
        195                 200                 205

Leu Gln Lys Phe Gly Glu Arg Ala Phe Lys Ala Trp Ala Val Ala Arg
    210                 215                 220

Leu Ser Gln Arg Phe Pro Lys Ala Glu Phe Ala Glu Val Ser Lys Leu
225                 230                 235                 240

Val Thr Asp Leu Thr Lys Val His Thr Glu Cys Cys His Gly Asp Leu
                245                 250                 255

Leu Glu Cys Ala Asp Asp Arg Ala Asp Leu Ala Lys Tyr Ile Cys Glu
            260                 265                 270
```

Asn Gln Asp Ser Ile Ser Ser Lys Leu Lys Glu Cys Cys Glu Lys Pro
                275                 280                 285

Leu Leu Glu Lys Ser His Cys Ile Ala Glu Val Glu Asn Asp Glu Met
            290                 295                 300

Pro Ala Asp Leu Pro Ser Leu Ala Ala Asp Phe Val Glu Ser Lys Asp
305                 310                 315                 320

Val Cys Lys Asn Tyr Ala Glu Ala Lys Asp Val Phe Leu Gly Met Phe
                325                 330                 335

Leu Tyr Glu Tyr Ala Arg Arg His Pro Asp Tyr Ser Val Val Leu Leu
            340                 345                 350

Leu Arg Leu Ala Lys Thr Tyr Glu Thr Thr Leu Glu Lys Cys Cys Ala
        355                 360                 365

Ala Ala Asp Pro His Glu Cys Tyr Ala Lys Val Phe Asp Glu Phe Lys
    370                 375                 380

Pro Leu Val Glu Glu Pro Gln Asn Leu Ile Lys Gln Asn Cys Glu Leu
385                 390                 395                 400

Phe Glu Gln Leu Gly Glu Tyr Lys Phe Gln Asn Ala Leu Leu Val Arg
                405                 410                 415

Tyr Thr Lys Lys Val Pro Gln Val Ser Thr Pro Thr Leu Val Glu Val
            420                 425                 430

Ser Arg Asn Leu Gly Lys Val Gly Ser Lys Cys Cys Lys His Pro Glu
        435                 440                 445

Ala Lys Arg Met Pro Cys Ala Glu Asp Tyr Leu Ser Val Val Leu Asn
    450                 455                 460

Gln Leu Cys Val Leu His Glu Lys Thr Pro Val Ser Asp Arg Val Thr
465                 470                 475                 480

Lys Cys Cys Thr Glu Ser Leu Val Asn Arg Arg Pro Cys Phe Ser Ala
                485                 490                 495

Leu Glu Val Asp Glu Thr Tyr Val Pro Lys Glu Phe Asn Ala Glu Thr
            500                 505                 510

Phe Thr Phe His Ala Asp Ile Cys Thr Leu Ser Glu Lys Glu Arg Gln
        515                 520                 525

Ile Lys Lys Gln Thr Ala Leu Val Glu Leu Val Lys His Lys Pro Lys
    530                 535                 540

Ala Thr Lys Glu Gln Leu Lys Ala Val Met Asp Asp Phe Ala Ala Phe
545                 550                 555                 560

Val Glu Lys Cys Cys Lys Ala Asp Asp Lys Glu Thr Cys Phe Ala Glu
                565                 570                 575

Glu Gly Lys Lys Leu Val Ala Ala Ser Gln Ala Ala Leu Gly Leu
            580                 585                 590

<210> SEQ ID NO 141
<211> LENGTH: 590
<212> TYPE: PRT
<213> ORGANISM: Mus musculus

<400> SEQUENCE: 141

Arg Gly Val Phe Arg Arg Glu Ala His Lys Ser Glu Ile Ala His Arg
1               5                   10                  15

Tyr Asn Asp Leu Gly Glu Gln His Phe Lys Gly Leu Val Leu Ile Ala
            20                  25                  30

Phe Ser Gln Tyr Leu Gln Lys Cys Ser Tyr Asp Glu His Ala Lys Leu
        35                  40                  45

Val Gln Glu Val Thr Asp Phe Ala Lys Thr Cys Val Ala Asp Glu Ser

```
              50                  55                  60
Ala Ala Asn Cys Asp Lys Ser Leu His Thr Leu Phe Gly Asp Lys Leu
65                  70                  75                  80

Cys Ala Ile Pro Asn Leu Arg Glu Asn Tyr Gly Glu Leu Ala Asp Cys
                    85                  90                  95

Cys Thr Lys Gln Glu Pro Glu Arg Asn Glu Cys Phe Leu Gln His Lys
                100                 105                 110

Asp Asp Asn Pro Ser Leu Pro Pro Phe Glu Arg Pro Glu Ala Glu Ala
                115                 120                 125

Met Cys Thr Ser Phe Lys Glu Asn Pro Thr Thr Phe Met Gly His Tyr
                130                 135                 140

Leu His Glu Val Ala Arg Arg His Pro Tyr Phe Tyr Ala Pro Glu Leu
145                 150                 155                 160

Leu Tyr Tyr Ala Glu Gln Tyr Asn Glu Ile Leu Thr Gln Cys Cys Ala
                165                 170                 175

Glu Ala Asp Lys Glu Ser Cys Leu Thr Pro Lys Leu Asp Gly Val Lys
                180                 185                 190

Glu Lys Ala Leu Val Ser Ser Val Arg Gln Arg Met Lys Cys Ser Ser
                195                 200                 205

Met Gln Lys Phe Gly Glu Arg Ala Phe Lys Ala Trp Ala Val Ala Arg
210                 215                 220

Leu Ser Gln Thr Phe Pro Asn Ala Asp Phe Ala Glu Ile Thr Lys Leu
225                 230                 235                 240

Ala Thr Asp Leu Thr Lys Val Asn Lys Glu Cys Cys His Gly Asp Leu
                245                 250                 255

Leu Glu Cys Ala Asp Asp Arg Ala Glu Leu Ala Lys Tyr Met Cys Glu
                260                 265                 270

Asn Gln Ala Thr Ile Ser Ser Lys Leu Gln Thr Cys Cys Asp Lys Pro
                275                 280                 285

Leu Leu Lys Lys Ala His Cys Leu Ser Glu Val Glu His Asp Thr Met
                290                 295                 300

Pro Ala Asp Leu Pro Ala Ile Ala Ala Asp Phe Val Glu Asp Gln Glu
305                 310                 315                 320

Val Cys Lys Asn Tyr Ala Glu Ala Lys Asp Val Phe Leu Gly Thr Phe
                325                 330                 335

Leu Tyr Glu Tyr Ser Arg Arg His Pro Asp Tyr Ser Val Ser Leu Leu
                340                 345                 350

Leu Arg Leu Ala Lys Lys Tyr Glu Ala Thr Leu Glu Lys Cys Cys Ala
                355                 360                 365

Glu Ala Asn Pro Pro Ala Cys Tyr Gly Thr Val Leu Ala Glu Phe Gln
                370                 375                 380

Pro Leu Val Glu Glu Pro Lys Asn Leu Val Lys Thr Asn Cys Asp Leu
385                 390                 395                 400

Tyr Glu Lys Leu Gly Glu Tyr Gly Phe Gln Asn Ala Ile Leu Val Arg
                405                 410                 415

Tyr Thr Gln Lys Ala Pro Gln Val Ser Thr Pro Thr Leu Val Glu Ala
                420                 425                 430

Ala Arg Asn Leu Gly Arg Val Gly Thr Lys Cys Cys Thr Leu Pro Glu
                435                 440                 445

Asp Gln Arg Leu Pro Cys Val Glu Asp Tyr Leu Ser Ala Ile Leu Asn
                450                 455                 460

Arg Val Cys Leu Leu His Glu Lys Thr Pro Val Ser Glu His Val Thr
465                 470                 475                 480
```

-continued

```
Lys Cys Cys Ser Gly Ser Leu Val Glu Arg Arg Pro Cys Phe Ser Ala
            485                 490                 495

Leu Thr Val Asp Glu Thr Tyr Val Pro Lys Glu Phe Lys Ala Glu Thr
        500                 505                 510

Phe Thr Phe His Ser Asp Ile Cys Thr Leu Pro Glu Lys Glu Lys Gln
    515                 520                 525

Ile Lys Lys Gln Thr Ala Leu Ala Glu Leu Val Lys His Lys Pro Lys
530                 535                 540

Ala Thr Ala Glu Gln Leu Lys Thr Val Met Asp Asp Phe Ala Gln Phe
545                 550                 555                 560

Leu Asp Thr Cys Cys Lys Ala Ala Asp Lys Asp Thr Cys Phe Ser Thr
                565                 570                 575

Glu Gly Pro Asn Leu Val Thr Arg Cys Lys Asp Ala Leu Ala
                580                 585                 590

<210> SEQ ID NO 142
<211> LENGTH: 330
<212> TYPE: PRT
<213> ORGANISM: Homo sapiens

<400> SEQUENCE: 142

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
```

```
              260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
            325                 330

<210> SEQ ID NO 143
<211> LENGTH: 326
<212> TYPE: PRT
<213> ORGANISM: Homo sapiens

<400> SEQUENCE: 143

Ala Ser Thr Lys Gly Pro Ser Val Phe Pro Leu Ala Pro Cys Ser Arg
1               5                  10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
            100                 105                 110
Pro Val Ala Gly Pro Ser Val Phe Leu Phe Pro Pro Lys Pro Lys Asp
    115                 120                 125
Thr Leu Met Ile Ser Arg Thr Pro Glu Val Thr Cys Val Val Val Asp
130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
    195                 200                 205
Ala Pro Ile Glu Lys Thr Ile Ser Lys Thr Lys Gly Gln Pro Arg Glu
210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ser Val Glu Trp Glu Ser Asn Gly Gln Pro Glu Asn Asn Tyr Lys Thr
            260                 265                 270
Thr Pro Pro Met Leu Asp Ser Asp Gly Ser Phe Phe Leu Tyr Ser Lys
    275                 280                 285
Leu Thr Val Asp Lys Ser Arg Trp Gln Gln Gly Asn Val Phe Ser Cys
290                 295                 300
```

Ser Val Met His Glu Ala Leu His Asn His Tyr Thr Gln Lys Ser Leu
305                 310                 315                 320

Ser Leu Ser Pro Gly Lys
                325

<210> SEQ ID NO 144
<211> LENGTH: 377
<212> TYPE: PRT
<213> ORGANISM: Homo sapiens

<400> SEQUENCE: 144

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

```
Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 145
<211> LENGTH: 327
<212> TYPE: PRT
<213> ORGANISM: Homo sapiens

<400> SEQUENCE: 145

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

```
<210> SEQ ID NO 146
<211> LENGTH: 6
<212> TYPE: PRT
<213> ORGANISM: Artificial Sequence
<220> FEATURE:
<223> OTHER INFORMATION: Synthetic Construct

<400> SEQUENCE: 146

His His His His His His
1               5

<210> SEQ ID NO 147
<211> LENGTH: 20
<212> TYPE: PRT
<213> ORGANISM: Artificial Sequence
<220> FEATURE:
<223> OTHER INFORMATION: Synthetic Construct

<400> SEQUENCE: 147

Met Tyr Arg Met Gln Leu Leu Ser Cys Ile Ala Leu Ser Leu Ala Leu
1               5                   10                  15

Val Thr Asn Ser
            20

<210> SEQ ID NO 148
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (18)..(20)
<223> OTHER INFORMATION: Xaa can be any naturally occurring amino acid

<400> SEQUENCE: 148

Xaa Xaa Cys Xaa Xaa Xaa Xaa Xaa Cys Xaa Xaa Phe Cys Xaa Asp Trp
1               5                   10                  15

Pro Xaa Xaa Xaa Ser Cys
            20

<210> SEQ ID NO 149
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(6)
<223> OTHER INFORMATION: Xaa can be any naturally occurring amino acid

<400> SEQUENCE: 149

Val Cys Tyr Xaa Xaa Xaa Ile Cys Phe
```

```
<210> SEQ ID NO 150
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 150

Cys Tyr Xaa Pro Gly Xaa Cys
1               5

<210> SEQ ID NO 151
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 151

Asp Xaa Cys Leu Pro Xaa Trp Gly Cys Leu Trp
1               5                   10

<210> SEQ ID NO 152
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 152

Trp Cys Asp Xaa Xaa Leu Xaa Ala Xaa Asp Leu Cys
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
```

```
<223> OTHER INFORMATION: Xaa can be any naturally occurring amino acid

<400> SEQUENCE: 153

Asp Leu Val Xaa Leu Gly Leu Glu Cys Trp
1               5                   10

<210> SEQ ID NO 154
<211> LENGTH: 11
<212> TYPE: PRT
<213> ORGANISM: Artificial Sequence
<220> FEATURE:
<223> OTHER INFORMATION: Synthetic Construct

<400> SEQUENCE: 154

Asp Leu Cys Leu Arg Asp Trp Gly Cys Leu Trp
1               5                   10

<210> SEQ ID NO 155
<211> LENGTH: 11
<212> TYPE: PRT
<213> ORGANISM: Artificial Sequence
<220> FEATURE:
<223> OTHER INFORMATION: Synthetic Construct

<400> SEQUENCE: 155

Asp Ile Cys Leu Pro Arg Trp Gly Cys Leu Trp
1               5                   10

<210> SEQ ID NO 156
<211> LENGTH: 15
<212> TYPE: PRT
<213> ORGANISM: Artificial Sequence
<220> FEATURE:
<223> OTHER INFORMATION: Synthetic Construct

<400> SEQUENCE: 156

Met Glu Asp Ile Cys Leu Pro Arg Trp Gly Cys Leu Trp Gly Asp
1               5                   10                  15

<210> SEQ ID NO 157
<211> LENGTH: 20
<212> TYPE: PRT
<213> ORGANISM: Artificial Sequence
<220> FEATURE:
<223> OTHER INFORMATION: Synthetic Construct

<400> SEQUENCE: 157

Gln Arg Leu Met Glu Asp Ile Cys Leu Pro Arg Trp Gly Cys Leu Trp
1               5                   10                  15

Glu Asp Asp Glu
            20

<210> SEQ ID NO 158
<211> LENGTH: 20
<212> TYPE: PRT
<213> ORGANISM: Artificial Sequence
<220> FEATURE:
<223> OTHER INFORMATION: Synthetic Construct

<400> SEQUENCE: 158

Gln Gly Leu Ile Gly Asp Ile Cys Leu Pro Arg Trp Gly Cys Leu Trp
1               5                   10                  15

Gly Arg Ser Val
            20
```

```
<210> SEQ ID NO 159
<211> LENGTH: 21
<212> TYPE: PRT
<213> ORGANISM: Artificial Sequence
<220> FEATURE:
<223> OTHER INFORMATION: Synthetic Construct

<400> SEQUENCE: 159

Gln Gly Leu Ile Gly Asp Ile Cys Leu Pro Arg Trp Gly Cys Leu Trp
1               5                   10                  15

Gly Arg Ser Val Lys
            20

<210> SEQ ID NO 160
<211> LENGTH: 15
<212> TYPE: PRT
<213> ORGANISM: Artificial Sequence
<220> FEATURE:
<223> OTHER INFORMATION: Synthetic Construct

<400> SEQUENCE: 160

Glu Asp Ile Cys Leu Pro Arg Trp Gly Cys Leu Trp Glu Asp Asp
1               5                   10                  15

<210> SEQ ID NO 161
<211> LENGTH: 18
<212> TYPE: PRT
<213> ORGANISM: Artificial Sequence
<220> FEATURE:
<223> OTHER INFORMATION: Synthetic Construct

<400> SEQUENCE: 161

Arg Leu Met Glu Asp Ile Cys Leu Pro Arg Trp Gly Cys Leu Trp Glu
1               5                   10                  15

Asp Asp

<210> SEQ ID NO 162
<211> LENGTH: 16
<212> TYPE: PRT
<213> ORGANISM: Artificial Sequence
<220> FEATURE:
<223> OTHER INFORMATION: Synthetic Construct

<400> SEQUENCE: 162

Met Glu Asp Ile Cys Leu Pro Arg Trp Gly Cys Leu Trp Glu Asp Asp
1               5                   10                  15

<210> SEQ ID NO 163
<211> LENGTH: 15
<212> TYPE: PRT
<213> ORGANISM: Artificial Sequence
<220> FEATURE:
<223> OTHER INFORMATION: Synthetic Construct

<400> SEQUENCE: 163

Met Glu Asp Ile Cys Leu Pro Arg Trp Gly Cys Leu Trp Glu Asp
1               5                   10                  15
```

<210> SEQ ID NO 164
<211> LENGTH: 18
<212> TYPE: PRT
<213> ORGANISM: Artificial Sequence
<220> FEATURE:
<223> OTHER INFORMATION: Synthetic Construct

<400> SEQUENCE: 164

Arg Leu Met Glu Asp Ile Cys Leu Ala Arg Trp Gly Cys Leu Trp Glu
1               5                   10                  15

Asp Asp

<210> SEQ ID NO 165
<211> LENGTH: 20
<212> TYPE: PRT
<213> ORGANISM: Artificial Sequence
<220> FEATURE:
<223> OTHER INFORMATION: Synthetic Construct

<400> SEQUENCE: 165

Glu Val Arg Ser Phe Cys Thr Arg Trp Pro Ala Glu Lys Ser Cys Lys
1               5                   10                  15

Pro Leu Arg Gly
            20

<210> SEQ ID NO 166
<211> LENGTH: 20
<212> TYPE: PRT
<213> ORGANISM: Artificial Sequence
<220> FEATURE:
<223> OTHER INFORMATION: Synthetic Construct

<400> SEQUENCE: 166

Arg Ala Pro Glu Ser Phe Val Cys Tyr Trp Glu Thr Ile Cys Phe Glu
1               5                   10                  15

Arg Ser Glu Gln
            20

<210> SEQ ID NO 167
<211> LENGTH: 11
<212> TYPE: PRT
<213> ORGANISM: Artificial Sequence
<220> FEATURE:
<223> OTHER INFORMATION: Synthetic Construct

<400> SEQUENCE: 167

Glu Met Cys Tyr Phe Pro Gly Ile Cys Trp Met
1               5                   10